(12) United States Patent
Nichols et al.

(10) Patent No.: US 12,721,901 B2
(45) Date of Patent: Sep. 1, 2026

(54) ANTIGEN-BINDING PROTEIN CONSTRUCTS AND USES THEREOF

(71) Applicant: Mythic Therapeutics, Inc., Waltham, MA (US)

(72) Inventors: Alexander J. Nichols, Lincoln, MA (US); Brian P. Fiske, Cambridge, MA (US); Nimish Gera, Waltham, MA (US)

(73) Assignee: Mythic Therapeutics, Inc.

( * ) Notice: Subject to any disclaimer, the term of this patent is extended or adjusted under 35 U.S.C. 154(b) by 966 days.

(21) Appl. No.: 17/641,495

(22) PCT Filed: Sep. 11, 2020

(86) PCT No.: PCT/US2020/050402
§ 371 (c)(1),
(2) Date: Mar. 9, 2022

(87) PCT Pub. No.: WO2021/050871
PCT Pub. Date: Mar. 18, 2021

(65) Prior Publication Data
US 2022/0306751 A1 Sep. 29, 2022

Related U.S. Application Data

(60) Provisional application No. 62/900,113, filed on Sep. 13, 2019.

(51) Int. Cl.
*A61K 47/68* (2017.01)
*A61K 39/00* (2006.01)
*A61P 35/00* (2006.01)
*C07K 16/28* (2006.01)

(52) U.S. Cl.
CPC .... *A61K 47/6849* (2017.08); *A61K 47/68031* (2023.08); *A61K 47/68035* (2023.08); *A61P 35/00* (2018.01); *C07K 16/2866* (2013.01); *A61K 2039/505* (2013.01); *C07K 2317/33* (2013.01); *C07K 2317/73* (2013.01);
(Continued)

(58) Field of Classification Search
None
See application file for complete search history.

(56) References Cited

U.S. PATENT DOCUMENTS 7,612,181 B2 11/2009 Wu et al.
8,088,376 B2 1/2012 Chamberlain et al.
8,258,268 B2 9/2012 Wu et al.
(Continued)

FOREIGN PATENT DOCUMENTS

EP 2552955 5/2017
KR 10-2018-0025865 3/2018
(Continued)

OTHER PUBLICATIONS

Hutmacher et al. Development of a novel fully-human anti-CD-123 antibody to target acute myeloid leukemia. Leukemia Research 84 (2019) 106178 (Year: 2019).*
(Continued)

*Primary Examiner* — Amy E Juedes
*Assistant Examiner* — Hilary Ann Petrash
(74) *Attorney, Agent, or Firm* — Fish & Richardson P.C.

(57) ABSTRACT

Provided herein are antigen-binding protein constructs and uses of the same.

21 Claims, 273 Drawing Sheets

Specification includes a Sequence Listing.

(52) U.S. Cl.
CPC ...... *C07K 2317/77* (2013.01); *C07K 2317/92* (2013.01); *C07K 2317/94* (2013.01)

(56) References Cited

U.S. PATENT DOCUMENTS

| | | | |
|---|---|---|---|
| 8,394,925 B2 | 3/2013 | Chamberlain et al. | |
| 8,586,714 B2 | 11/2013 | Ghayur et al. | |
| 8,716,450 B2 | 5/2014 | Ghayur et al. | |
| 8,722,855 B2 | 5/2014 | Ghayur et al. | |
| 8,735,546 B2 | 5/2014 | Ghayur et al. | |
| 8,822,645 B2 | 9/2014 | Ghayur et al. | |
| 10,077,313 B2 * | 9/2018 | Kovtun ............ | A61K 47/68035 |
| 10,336,818 B2 | 7/2019 | Chamberlain et al. | |
| 2013/0243775 A1 | 9/2013 | Papadopoulos et al. | |
| 2016/0082114 A1 | 3/2016 | Chari et al. | |
| 2017/0007715 A1 | 1/2017 | Andreev et al. | |
| 2017/0191055 A1 | 7/2017 | Short et al. | |
| 2018/0208658 A1 | 7/2018 | Liu et al. | |
| 2019/0024078 A1 | 1/2019 | Short et al. | |
| 2019/0330357 A1 | 10/2019 | Lerchen et al. | |

FOREIGN PATENT DOCUMENTS

| | | |
|---|---|---|
| WO | WO 2011/111007 | 9/2011 |
| WO | WO 2011/122011 | 10/2011 |
| WO | WO 2013/138400 | 9/2013 |
| WO | WO 2017/134197 | 8/2017 |
| WO | WO 2017/216028 | 12/2017 |
| WO | WO 2018/044619 | 3/2018 |
| WO | WO 2018/098258 | 5/2018 |
| WO | WO 2018/136455 | 7/2018 |
| WO | WO 2019/060718 | 3/2019 |

OTHER PUBLICATIONS

Ritchie et al. Implications of receptor-mediated endocytosis and intracellular trafficking dynamics in the development of antibody srug conjugates. mAbs, vol. 5, Iss 1, pp. 13-21, DOI: 10.4161/mabs.22854 (Year: 2012).*

Murthy et al. Interleukin-3 Down-Regulates Its Own Receptor. Blood, vol. 73, No. 5, 1989: pp. 1180-1187. DOI: 10.1182/blood.V73.5.1180.1180 (Year: 1989).*

Murtaugh et al. A Combinatorial Histidine Scanning Library Approach to Engineer Highly pH-Dependent Protein Switches. Protein Science, 2011, 20: 1619-1631, DOI: 10.1002/pro.696 (Year: 2011).*

Bovin et al. (2015) De novo isolation of antibodies with pH-dependent binding properties. mAbs 7:2, pp. 294-302, DOI: 10.1080/19420862.2015.1006993 (Year: 2015).*

Igawa et al. (2010) Antibody recycling by engineered pH-dependent antigen binding improves the duration of antigen neutralization. Nature Biotechnology vol. 28, No. 11, DOI: 10.1038/nbt.1691 (Year: 2010).*

Riggers et al. (2012) Increasing Serum Half-life and Extending Cholesterol Lowering in Vivo by Engineering Antibody with pH-sensitive Binding to PCSK9. Journal of Biological Chemistry, vol. 287, Iss: 14, pp. 11090-11097, DOI: 10.1074/jbc.M111.319764 (Year: 2012).*

Rouet et al. Fully Human VH single domains that rival the stability and cleft recognition of camelid antibodies. The Journal of Biological Chemistry (2015) vol. 290, No. 19, pp. 11905-11917, DOI: 10.1074/jbc.M111.319764 (Year: 2015).*

Holt et al. Domain antibodies: proteins for therapy. Trends in biotechnology (2003) vol. 21, No. 11, pp. 484-490, doi:10.1016/j.tibtech.2003.08.007 (Year: 2003).*

Kapingidza et al. 2020. Antigen-Antibody Complexes. Vertebrate and Invertebrate Respiratory Proteins, Lipoproteins and other Body Fluid, CH 19, pp. 465-484 (Year: 2020).*

Culang et al. (2013) The structural basis of antibody-antigen recognition. Front. In Immun. 2013. vol. 4, Article 302, pp. 1-13. DOI:10.3389/fimmu.2013.00302 (Year: 2013).*

Clark et al. Influence of canonical structure determining residues on antibody affinity and stability. Journal of Structural Biology 185 (2014) 223-227, DOI: 10.1016/j.jsb.2013.08.009 (Year: 2014).*

Brown et al. Tolerance to Single, but Not Multiple, Amino Acid Replacements in Antibody VH, CDR2. J Immunol (1996) 156 (9): 3285-3291, DOI: 10.4049/jimmunol.156.9.3285 (Year: 1996).*

Steeland et al. Nanobodies as therapeutics: big opportunities for small antibodies. Drug Discover Today. vol. 21, No. 7, 2016 p. 1076-1113 (Year: 2016).*

Abdiche et al., "Exploring blocking assays using Octet, ProteOn, and Biacore biosensors," Analytical Biochemistry, Mar. 15, 2009, 386(2):172-180.

Bonvin et al., "De novo isolation of antibodies with pH-dependent binding properties," mAbs, 2015, 7(2):294-302.

Borrok et al., "pH-dependent Binding Engineering Reveals an FcRn Affinity Threshold That Governs IgG Recycling," The Journal of Biological Chemistry, Feb. 13, 2015, 290(7):4282-4290.

broadinstitute.org [online], "Cancer Cell Line Encyclopedia," Jul. 2021, retrieved on May 23, 2023, retrieved from URL <https://sites.broadinstitute.org/ccle>, 6 pages.

Carter et al., "Antibody-drug conjugates for cancer therapy," The Cancer Journal, May 2008, 14(3):154-169.

Catcott et al., "Microscale screening of antibody libraries as maytansinoid antibody-drug conjugates," mAbs, 2016, 8(3):513-523.

Chandna, "Single-cell gel electrophoresis assay monitors precise kinetics of DNA fragmentation induced during programmed cell death," Cytometry Part A, Oct. 2004, 61A(2):127-133.

Chari, "Targeted cancer therapy: conferring specificity to cytotoxic drugs," Accounts of Chemical Research, Jan. 2008, 41(1):98-107.

Cromie et al., "Nanobodies and their Use in GPCR Drug Discovery," Current Topics in Medicinal Chemistry, 2015, 15(24):2543-2557.

De Genst et al., "Antibody repertoire development in camelids," Developmental & Comparative Immunology, 2006, 30:187-198.

De Meyer et al., "Nanobody-based products as research and diagnostic tools," Trends in Biotechnology, May 2014, 32(5):263-270.

DiGiammarino et al., "Design and Generation of DVD-Ig™ Molecules for Dual-Specific Targeting," Methods in Molecular Biology, Therapeutic Proteins, 2012, 899:145-156.

Fischer et al., "The assay design used for measurement of therapeutic antibody concentrations can affect pharmacokinetic parameters," mAbs, 2012, 4(5):623-631.

Garber, "Bispecific antibodies rise again," Nature Reviews Drug Discovery, 2014, 13:799-801.

Gera et al., "Design of pH Sensitive Binding Proteins from the Hyperthermophilic Sso7D Scaffold," PLoS One, Nov. 2012, 7(11): e48928.

Gupta et al., "Preclinical pharmacokinetics of MHAA4549A, a human monoclonal antibody to influenza A virus, and the prediction of its efficacious clinical dose for the treatment of patients hospitalized with influenza A," mAbs, 2016, 8(5):991-997.

Huang et al., "Assessment of histone H2AX phosphorylation induced by DNA topoisomerase I and II inhibitors topotecan and mitoxantrone and by the DNA cross-linking agent cisplatin," Cytometry Part A, Apr. 2004, 58A(2):99-110.

Igawa et al., "pH-dependent antigen-binding antibodies as a novel therapeutic modality," Biochimica et Biophysica Acta (BBA)—Proteins and Proteomics, Nov. 201, 1844(11):1943-1950.

International Preliminary Report on Patentability in International Appln. No. PCT/US2020/050402, mailed on Mar. 24, 2022, 12 pages.

International Search Report and Written Opinion in International Appln. No. PCT/US2020/050402, mailed on Nov. 26, 2020, 15 pages.

Jakob et al., "Structure reveals function of the dual variable domain immunoglobulin (DVD-Ig™) molecule," mAbs, May 1, 2013, 5(3):358-363.

Jamur et al., "Permeabilization of cell membranes," Immunocytochemical Methods and Protocols, Methods in Molecular Biology, 2010, 588:63-66.

Kijanka et al., "Nanobody-based cancer therapy of solid tumors," Nanomedicine, 2015, 10(1):161-174.

(56) References Cited

OTHER PUBLICATIONS

Kovaleva et al., "Shark variable new antigen receptor biologics—a novel technology platform for therapeutic drug development," Expert Opinion on Biological Therapy, 2014, 14(10):1527-1539.
Kovtun et al., "A CD123-targeting antibody-drug conjugate, IMGN632, designed to eradicate AML while sparing normal bone marrow cells," Blood Advances, Apr. 24, 2018, 2(8):848-858.
Krah et al., "Single-domain antibodies for biomedical applications," Immunopharmacology and Immunotoxicology, 2016, 38(1):21-28.
Labrijn et al., "Controlled Fab-arm exchange for the generation of stable bispecific IgG1," Nature Protocols, Oct. 2014, 9(10):2450-2463.
Lefranc, "The IMGT unique numbering for immunoglobulins, T-cell receptors, and Ig-like domains," Immunologist, 1999, 7(4):132-136.
Li et al., "A Biparatopic HER2-Targeting Antibody-Drug Conjugate Induces Tumor Regression in Primary Models Refractory to or Ineligible for HER2-Targeted Therapy," Cancer Cell, Jan. 2016, 29(1):117-129.
Li et al., "Characterization of SGN-CD123A, A Potent CD123-Directed Antibody-Drug Conjugate for Acute Myeloid Leukemia," Molecular Cancer Research, Nov. 2017, 17(2):554-564.
Lu et al., "Linkers Having a Crucial Role in Antibody-Drug Conjugates," International Journal of Molecular Sciences, 2016, 17(4):561.
Mahmutefendic et al., "Segregation of open Major Histocompatibility Class I conformers at the plasma membrane and during endosomal trafficking reveals conformation-based sorting in the endosomal system," The International Journal of Biochemistry & Cell Biology, Apr. 2011, 43(4):504-515.
McCombs et al., "Antibody drug conjugates: design and selection of linker, payload and conjugation chemistry," The AAPS Journal, Mar. 2015, 17(2):339-351.
Mendoza et al., "Inhibition of Ligand-mediated HER2 Activation in Androgen-independent Prostate Cancer," Cancer Research, Oct. 1, 2002, 62(19):5485-5488.
Mujic-Delic et al., "GPCR-targeting nanobodies: attractive research tools, diagnostics, and therapeutics," Trends in Pharmacological Sciences, May 2014, 35(5):247-255.
Muyldermans et al., "Recognition of antigens by single-domain antibody fragments: the superfluous luxury of paired domains," Trends in Biochemical Sciences, Apr. 1, 2001, 26(4):230-235.
Muyldermans, "Nanobodies: natural single-domain antibodies," Annual Review of Biochemistry, 2013, 82:775-797.
Muyldermans, "Single domain camel antibodies: current status," Reviews in Molecular Biotechnology, Jun. 2001, 74(4):277-302.
Oflazoglu et al., "Potent anticarcinoma activity of the humanized anti-CD70 antibody h1F6 conjugated to the tubulin inhibitor auristatin via an uncleavable linker," Clinical Cancer Research, Oct. 1, 2008, 14(19):6171-6180.
Promega Corp., "CellTiter-Glo® Luminescent Cell Viability Assay," Technical Bulletin TB288, Jan. 2023, retrieved on Jun. 9, 2023, retrieved from URL <https://www.promega.com/-/media/files/resources/protocols/technical-bulletins/0/celltiter-glo-luminescent-cell-viability-assay-protocol.pdf>, 14 pages.
Rahbarizadeh et al., "Nanobody; an old concept and new vehicle for immunotargeting," Immunological Investigations, 2011, 40(3):299-338.
Sanderson et al., "In vivo Drug-Linker Stability of an Anti-CD30 Dipeptide-Linked Auristatin Immunoconjugate," Clin. Cancer Res., Jan. 15, 2005, 11(2 Pt 1):843-852.
Schneider et al., "Quantification of human Alu sequences by real-time PCR—an improved method to measure therapeutic efficacy of anti-metastatic drugs in human xenotransplants," Clinical & Experimental Metastasis, Nov. 2002, 19(7):571-582.
Singh et al., "Measurement and Mathematical Characterization of Cell-Level Pharmacokinetics of Antibody-Drug Conjugates: A Case Study with Trastuzumab-vc-MMAE," Drug Metabolism and Disposition, Nov. 2017, 45(11):1120-1132.
Sorkin et al., "Quantitative Analysis of Endocytosis and Turnover of Epidermal Growth Factor (EGF) and EGF Receptor," Current Protocols in Cell Biology, Mar. 1, 2010, 15.14.1-15.14.20.
Spiess et al., "Alternative molecular formats and therapeutic applications for bispecific antibodies," Molecular Immunology, Oct. 2015, 67(2 Pt A):95-106.
Tiberghien et al., "Design and Synthesis of Tesirine, a Clinical Antibody-Drug Conjugate Pyrrolobenzodiazepine Dimer Payload," ACS Medicinal Chemistry Letters, Nov. 2016, 7(11):983-987.
Vainshtein et al., "Quantitative measurement of the target-mediated internalization kinetics of biopharmaceuticals," Pharmaceutical Research, Jan. 2015, 32(1):286-299.
Van Audenhove et al., "Nanobodies as Versatile Tools to Understand, Diagnose, Visualize and Treat Cancer," EBioMedicine, Jun. 2016, 8:40-48.
Van Bockstaele et al., "The development of nanobodies for therapeutic applications," Current Opinion in Investigational Drugs, Nov. 2009, 10(11):1212-1224.
Vincke et al., "Introduction to heavy chain antibodies and derived Nanobodies," Methods in Molecular Biology, 2012, 911:15-26.
Wasolowski et al., "Single domain antibodies: promising experimental and therapeutic tools in infection and immunity," Medical Microbiology and Immunology, Aug. 2009, 198(3):157-174.
Wiley et al., "The role of tyrosine kinase activity in endocytosis, compartmentation, and down-regulation of the epidermal growth factor receptor," Journal of Biological Chemistry, Jun. 15, 1991, 266(17):11083-11094.
Wustner, "Steady State Analysis and Experimental Validation of a Model for Hepatic High-Density Lipoprotein Transport," Traffic, Jun. 2006, 7(6):699-715.

* cited by examiner

| | Heavy | Light | CDRH1 | CDRH2 | CDRH3 | CDRL1 | CDRL2 | CDRL3 |
|---|---|---|---|---|---|---|---|---|
| MYT1251 (IMGN632) | 1 | 2 | 3 | 4 | 5 | 6 | 7 | 8 |
| MYT1252 | 13 | 2 | | | | | | |
| MYT1253 | 14 | 2 | | | | | | |
| MYT1254 | 15 | 2 | | | | | | |
| MYT1255 | 16 | 2 | | | | | | |
| MYT1256 | 17 | 2 | | | | | | |
| MYT1257 | 18 | 2 | | | | | | |
| MYT1258 | 19 | 2 | | | | | | |
| MYT1259 | 20 | 2 | | | | | | |
| MYT1260 | 21 | 2 | | | | | | |
| MYT1261 | 22 | 2 | | | | | | |
| MYT1262 | 23 | 2 | | | | | | |
| MYT1263 | 24 | 2 | | | | | | |
| MYT1264 | 25 | 2 | | | | | | |
| MYT1265 | 26 | 2 | | | | | | |
| MYT1266 | 27 | 2 | | | | | | |
| MYT1267 | 28 | 2 | | | | | | |
| MYT1268 | 29 | 2 | | | | | | |
| MYT1269 | 30 | 2 | | | | | | |
| MYT1270 | 31 | 2 | | | | | | |
| MYT1271 | 32 | 2 | | | | | | |
| MYT1272 | 33 | 2 | | | | | | |
| MYT1273 | 34 | 2 | | | | | | |
| MYT1274 | 35 | 2 | | | | | | |
| MYT1275 | 36 | 2 | | | | | | |
| MYT1276 | 37 | 2 | | | | | | |
| MYT1277 | 38 | 2 | | | | | | |
| MYT1278 | 39 | 2 | | | | | | |
| MYT1279 | 40 | 2 | | | | | | |
| MYT1280 | 41 | 2 | | | | | | |
| MYT1281 | 42 | 2 | | | | | | |
| MYT1282 | 43 | 2 | | | | | | |
| MYT1283 | 44 | 2 | | | | | | |
| MYT1284 | 45 | 2 | | | | | | |
| MYT1285 | 46 | 2 | | | | | | |
| MYT1286 | 47 | 2 | | | | | | |
| MYT1287 | 48 | 2 | | | | | | |
| MYT1288 | 49 | 2 | | | | | | |
| MYT1289 | 50 | 2 | | | | | | |
| MYT1290 | 51 | 2 | | | | | | |
| MYT1291 | 52 | 2 | | | | | | |
| MYT1292 | 53 | 2 | | | | | | |

FIG. 3

| | Heavy | Light | CDRH1 | CDRH2 | CDRH3 | CDRL1 | CDRL2 | CDRL3 |
|---|---|---|---|---|---|---|---|---|
| MYT1251 (IMGN632) | 1 | 2 | 3 | 4 | 5 | 6 | 7 | 8 |
| MYT2773 | 1 | 54 | | | | | | |
| MYT2774 | 1 | 55 | | | | | | |
| MYT2775 | 1 | 56 | | | | | | |
| MYT2776 | 1 | 57 | | | | | | |
| MYT2777 | 1 | 58 | | | | | | |
| MYT2778 | 1 | 59 | | | | | | |
| MYT2779 | 1 | 60 | | | | | | |
| MYT2780 | 1 | 61 | | | | | | |
| MYT2781 | 1 | 62 | | | | | | |
| MYT2782 | 1 | 63 | | | | | | |
| MYT2783 | 1 | 64 | | | | | | |
| MYT2784 | 1 | 65 | | | | | | |
| MYT2785 | 1 | 66 | | | | | | |
| MYT2786 | 1 | 67 | | | | | | |
| MYT2787 | 1 | 68 | | | | | | |
| MYT2788 | 1 | 69 | | | | | | |
| MYT2789 | 1 | 70 | | | | | | |
| MYT2790 | 1 | 71 | | | | | | |
| MYT2791 | 1 | 72 | | | | | | |
| MYT2792 | 1 | 73 | | | | | | |
| MYT2793 | 1 | 74 | | | | | | |
| MYT2794 | 1 | 75 | | | | | | |
| MYT2795 | 1 | 76 | | | | | | |
| MYT2796 | 1 | 77 | | | | | | |
| MYT2797 | 1 | 78 | | | | | | |
| MYT2798 | 1 | 79 | | | | | | |
| MYT2799 | 1 | 80 | | | | | | |

FIG. 6

| | Heavy | Light | CDRH1 | CDRH2 | CDRH3 | CDRL1 | CDRL2 | CDRL3 |
|---|---|---|---|---|---|---|---|---|
| MYT1251 (IMGN632) | 1 | 2 | 3 | 4 | 5 | 6 | 7 | 8 |
| MYT2753 | 81 | 2 | | | | | | |
| MYT2754 | 82 | 2 | | | | | | |
| MYT2755 | 83 | 2 | | | | | | |
| MYT2756 | 84 | 2 | | | | | | |
| MYT2757 | 85 | 2 | | | | | | |
| MYT2758 | 86 | 2 | | | | | | |
| MYT2759 | 87 | 2 | | | | | | |
| MYT2760 | 88 | 2 | | | | | | |
| MYT2761 | 89 | 2 | | | | | | |
| MYT2762 | 90 | 2 | | | | | | |
| MYT2763 | 91 | 2 | | | | | | |
| MYT2764 | 92 | 2 | | | | | | |
| MYT2765 | 93 | 2 | | | | | | |
| MYT2766 | 94 | 2 | | | | | | |
| MYT2767 | 95 | 2 | | | | | | |
| MYT2768 | 96 | 2 | | | | | | |
| MYT2769 | 97 | 2 | | | | | | |
| MYT2770 | 98 | 2 | | | | | | |
| MYT2771 | 99 | 2 | | | | | | |
| MYT2772 | 100 | 2 | | | | | | |

FIG. 9

| | Heavy | Light | CDRH1 | CDRH2 | CDRH3 | CDRL1 | CDRL2 | CDRL3 |
|---|---|---|---|---|---|---|---|---|
| MYT1251 (IMGN632) | 1 | 2 | 3 | 4 | 5 | 6 | 7 | 8 |
| MYT3552 | 14 | 64 | | | | | | |
| MYT3553 | 22 | 64 | | | | | | |
| MYT3554 | 48 | 64 | | | | | | |
| MYT3555 | 50 | 64 | | | | | | |
| MYT3556 | 52 | 64 | | | | | | |
| MYT3557 | 81 | 64 | | | | | | |
| MYT3558 | 83 | 64 | | | | | | |
| MYT3559 | 85 | 64 | | | | | | |
| MYT3560 | 86 | 64 | | | | | | |
| MYT3561 | 87 | 64 | | | | | | |
| MYT3562 | 88 | 64 | | | | | | |
| MYT3563 | 89 | 64 | | | | | | |
| MYT3564 | 91 | 64 | | | | | | |
| MYT3565 | 94 | 64 | | | | | | |
| MYT3566 | 95 | 64 | | | | | | |
| MYT3567 | 96 | 64 | | | | | | |
| MYT3568 | 100 | 64 | | | | | | |
| MYT3569 | 14 | 70 | | | | | | |
| MYT3570 | 22 | 70 | | | | | | |
| MYT3571 | 48 | 70 | | | | | | |
| MYT3572 | 50 | 70 | | | | | | |
| MYT3573 | 52 | 70 | | | | | | |
| MYT3574 | 81 | 70 | | | | | | |
| MYT3575 | 83 | 70 | | | | | | |
| MYT3576 | 85 | 70 | | | | | | |
| MYT3577 | 86 | 70 | | | | | | |
| MYT3578 | 87 | 70 | | | | | | |
| MYT3579 | 88 | 70 | | | | | | |
| MYT3580 | 89 | 70 | | | | | | |
| MYT3581 | 91 | 70 | | | | | | |
| MYT3582 | 94 | 70 | | | | | | |
| MYT3583 | 95 | 70 | | | | | | |
| MYT3584 | 96 | 70 | | | | | | |
| MYT3585 | 100 | 70 | | | | | | |
| MYT3586 | 14 | 74 | | | | | | |
| MYT3587 | 22 | 74 | | | | | | |
| MYT3588 | 48 | 74 | | | | | | |
| MYT3589 | 50 | 74 | | | | | | |
| MYT3590 | 52 | 74 | | | | | | |
| MYT3591 | 81 | 74 | | | | | | |
| MYT3592 | 83 | 74 | | | | | | |
| MYT3593 | 85 | 74 | | | | | | |
| MYT3594 | 86 | 74 | | | | | | |
| MYT3595 | 87 | 74 | | | | | | |
| MYT3596 | 88 | 74 | | | | | | |
| MYT3597 | 89 | 74 | | | | | | |
| MYT3598 | 91 | 74 | | | | | | |
| MYT3599 | 94 | 74 | | | | | | |
| MYT3600 | 95 | 74 | | | | | | |
| MYT3601 | 96 | 74 | | | | | | |
| MYT3602 | 100 | 74 | | | | | | |

FIG. 12

| | Heavy | Light | CDRH1 | CDRH2 | CDRH3 | CDRL1 | CDRL2 | CDRL3 |
|---|---|---|---|---|---|---|---|---|
| MYT1413 | 101 | 102 | 103 | 104 | 105 | 106 | 107 | 108 |
| MYT1414 | 109 | 102 | | | | | | |
| MYT1415 | 110 | 102 | | | | | | |
| MYT1416 | 111 | 102 | | | | | | |
| MYT1417 | 112 | 102 | | | | | | |
| MYT1418 | 113 | 102 | | | | | | |
| MYT1419 | 114 | 102 | | | | | | |
| MYT1420 | 115 | 102 | | | | | | |
| MYT1421 | 116 | 102 | | | | | | |
| MYT1422 | 117 | 102 | | | | | | |
| MYT1423 | 118 | 102 | | | | | | |
| MYT1424 | 119 | 102 | | | | | | |
| MYT1425 | 120 | 102 | | | | | | |
| MYT1426 | 121 | 102 | | | | | | |
| MYT1427 | 122 | 102 | | | | | | |
| MYT1428 | 123 | 102 | | | | | | |
| MYT1429 | 124 | 102 | | | | | | |
| MYT1430 | 125 | 102 | | | | | | |
| MYT1431 | 126 | 102 | | | | | | |
| MYT1432 | 127 | 102 | | | | | | |
| MYT1433 | 128 | 102 | | | | | | |
| MYT1434 | 129 | 102 | | | | | | |
| MYT1435 | 130 | 102 | | | | | | |
| MYT1436 | 131 | 102 | | | | | | |
| MYT1437 | 132 | 102 | | | | | | |
| MYT1438 | 133 | 102 | | | | | | |
| MYT1439 | 134 | 102 | | | | | | |
| MYT1440 | 135 | 102 | | | | | | |
| MYT1441 | 136 | 102 | | | | | | |
| MYT1442 | 137 | 102 | | | | | | |
| MYT1443 | 138 | 102 | | | | | | |
| MYT1444 | 139 | 102 | | | | | | |
| MYT1445 | 140 | 102 | | | | | | |
| MYT1446 | 141 | 102 | | | | | | |
| MYT1447 | 142 | 102 | | | | | | |
| MYT1448 | 143 | 102 | | | | | | |
| MYT1449 | 144 | 102 | | | | | | |
| MYT1450 | 145 | 102 | | | | | | |
| MYT1451 | 146 | 102 | | | | | | |
| MYT1452 | 147 | 102 | | | | | | |
| MYT1453 | 148 | 102 | | | | | | |

FIG. 15

| | Heavy | Light | CDRH1 | CDRH2 | CDRH3 | CDRL1 | CDRL2 | CDRL3 |
|---|---|---|---|---|---|---|---|---|
| MYT5440 (TPP-8988) | 149 | 150 | 151 | 152 | 153 | 154 | 155 | 156 |
| MYT5441 | 157 | 150 | | | | | | |
| MYT5442 | 158 | 150 | | | | | | |
| MYT5443 | 159 | 150 | | | | | | |
| MYT5444 | 160 | 150 | | | | | | |
| MYT5445 | 161 | 150 | | | | | | |
| MYT5446 | 162 | 150 | | | | | | |
| MYT5447 | 163 | 150 | | | | | | |
| MYT5448 | 164 | 150 | | | | | | |
| MYT5449 | 165 | 150 | | | | | | |
| MYT5450 | 166 | 150 | | | | | | |
| MYT5451 | 167 | 150 | | | | | | |
| MYT5452 | 168 | 150 | | | | | | |
| MYT5453 | 169 | 150 | | | | | | |
| MYT5454 | 170 | 150 | | | | | | |
| MYT5455 | 171 | 150 | | | | | | |
| MYT5456 | 172 | 150 | | | | | | |
| MYT5457 | 173 | 150 | | | | | | |
| MYT5458 | 174 | 150 | | | | | | |
| MYT5459 | 175 | 150 | | | | | | |
| MYT5460 | 176 | 150 | | | | | | |
| MYT5461 | 177 | 150 | | | | | | |
| MYT5462 | 178 | 150 | | | | | | |
| MYT5463 | 179 | 150 | | | | | | |
| MYT5464 | 180 | 150 | | | | | | |
| MYT5465 | 181 | 150 | | | | | | |
| MYT5466 | 182 | 150 | | | | | | |
| MYT5467 | 183 | 150 | | | | | | |
| MYT5468 | 184 | 150 | | | | | | |
| MYT5469 | 185 | 150 | | | | | | |
| MYT5470 | 186 | 150 | | | | | | |
| MYT5471 | 187 | 150 | | | | | | |
| MYT5472 | 188 | 150 | | | | | | |
| MYT5473 | 189 | 150 | | | | | | |
| MYT5474 | 190 | 150 | | | | | | |
| MYT5475 | 191 | 150 | | | | | | |
| MYT5476 | 192 | 150 | | | | | | |
| MYT5477 | 193 | 150 | | | | | | |
| MYT5478 | 194 | 150 | | | | | | |
| MYT5479 | 195 | 150 | | | | | | |
| MYT5480 | 196 | 150 | | | | | | |
| MYT5481 | 197 | 150 | | | | | | |

FIG. 18

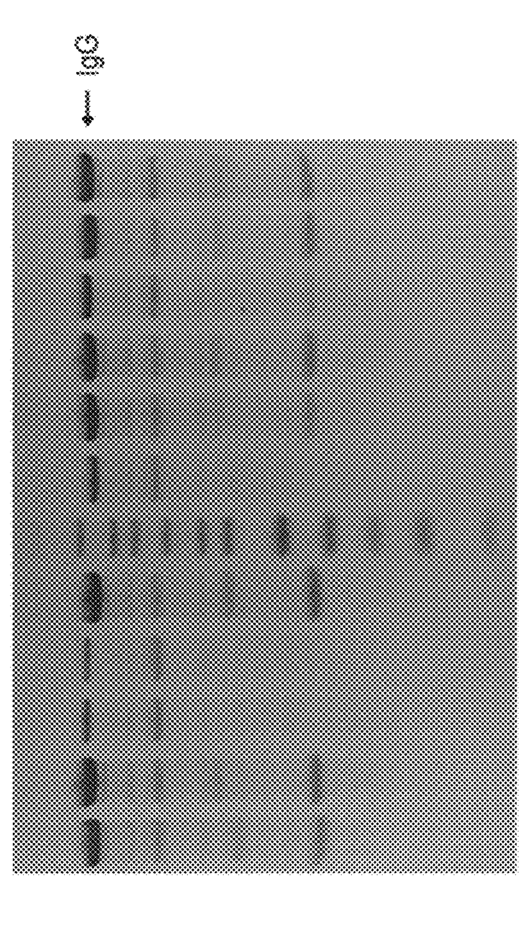
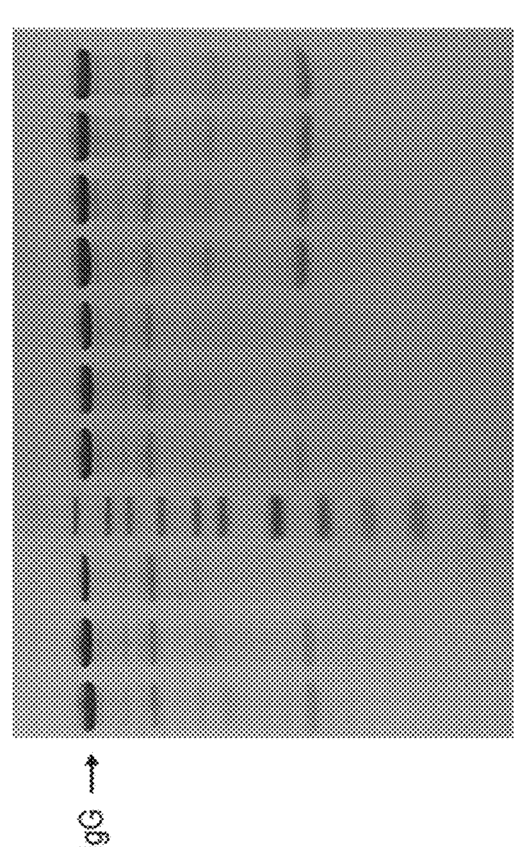
FIG. 19
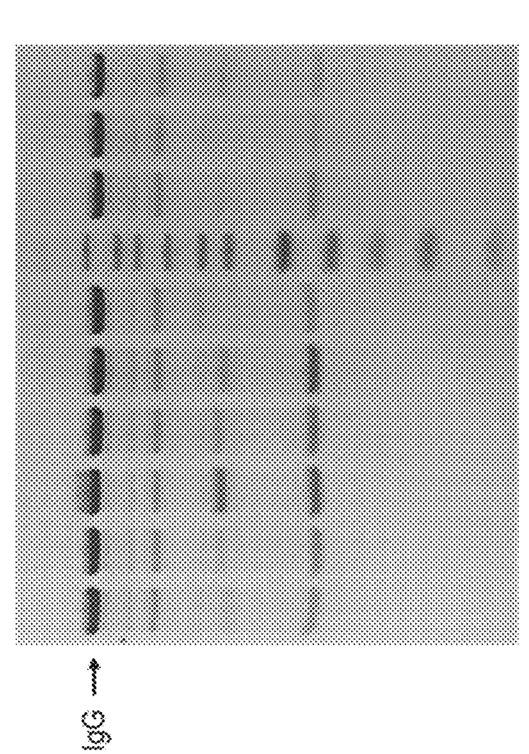

| | Heavy | Light | CDRH1 | CDRH2 | CDRH3 | CDRL1 | CDRL2 | CDRL3 |
|---|---|---|---|---|---|---|---|---|
| MYT5440 (TPP-8988) | 149 | 150 | 151 | 152 | 153 | 154 | 155 | 156 |
| MYT5482 | 149 | 198 | | | | | | |
| MYT5483 | 149 | 199 | | | | | | |
| MYT5484 | 149 | 200 | | | | | | |
| MYT5485 | 149 | 201 | | | | | | |
| MYT5486 | 149 | 202 | | | | | | |
| MYT5487 | 149 | 203 | | | | | | |
| MYT5488 | 149 | 204 | | | | | | |
| MYT5489 | 149 | 205 | | | | | | |
| MYT5490 | 149 | 206 | | | | | | |
| MYT5491 | 149 | 207 | | | | | | |
| MYT5492 | 149 | 208 | | | | | | |
| MYT5493 | 149 | 209 | | | | | | |
| MYT5494 | 149 | 210 | | | | | | |
| MYT5495 | 149 | 211 | | | | | | |
| MYT5496 | 149 | 212 | | | | | | |
| MYT5497 | 149 | 213 | | | | | | |
| MYT5498 | 149 | 214 | | | | | | |
| MYT5499 | 149 | 215 | | | | | | |
| MYT5500 | 149 | 216 | | | | | | |
| MYT5501 | 149 | 217 | | | | | | |
| MYT5502 | 149 | 218 | | | | | | |
| MYT5503 | 149 | 219 | | | | | | |
| MYT5504 | 149 | 220 | | | | | | |
| MYT5505 | 149 | 221 | | | | | | |
| MYT5506 | 149 | 222 | | | | | | |
| MYT5507 | 149 | 223 | | | | | | |
| MYT5508 | 149 | 224 | | | | | | |
| MYT5509 | 149 | 225 | | | | | | |
| MYT5510 | 149 | 226 | | | | | | |
| MYT5511 | 149 | 227 | | | | | | |

FIG. 21

SEQUENCE LISTING

```
<160> NUMBER OF SEQ ID NOS: 227

<210> SEQ ID NO 1
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of IMGN632 IgG"

<400> SEQUENCE: 1

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser Ser
            20                  25                  30

Ile Met His Trp Val Arg Gln Ala Pro Gly Gln Gly Leu Glu Trp Ile
        35                  40                  45

Gly Tyr Ile Lys Pro Tyr Asn Asp Gly Thr Lys Tyr Asn Glu Lys Phe
    50                  55                  60

Lys Gly Arg Ala Thr Leu Thr Ser Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Gly Asn Asp Tyr Tyr Asp Thr Met Asp Tyr Trp Gly
            100                 105                 110

Gln Gly Thr Leu Val Thr Val Ser Ser
        115                 120


<210> SEQ ID NO 2
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of IMGN632 IgG"

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Ser Tyr
```

```
            20                  25                  30

Leu Ser Trp Phe Gln Gln Lys Pro Gly Lys Ala Pro Lys Thr Leu Ile
        35                  40                  45

Tyr Arg Val Asn Arg Leu Val Asp Gly Val Pro Ser Arg Phe Ser Gly
    50                  55                  60

Ser Gly Ser Gly Asn Asp Tyr Thr Leu Thr Ile Ser Ser Leu Gln Pro
65                  70                  75                  80

Glu Asp Phe Ala Thr Tyr Tyr Cys Leu Gln Tyr Asp Ala Phe Pro Tyr
                85                  90                  95

Thr Phe Gly Gln Gly Thr Lys Val Glu Ile Lys
            100                 105


<210> SEQ ID NO 3
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Heavy Chain CDR1 of IMGN632"

<400> SEQUENCE: 3

Gly Tyr Ile Phe Thr Ser Ser Ile Met His
1               5                   10


<210> SEQ ID NO 4
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Heavy Chain CDR2 of IMGN632"

<400> SEQUENCE: 4

Tyr Ile Lys Pro Tyr Asn Asp Gly Thr Lys Tyr Asn Glu Lys Phe Lys
1               5                   10                  15

Gly


<210> SEQ ID NO 5
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Heavy Chain CDR3 of IMGN632"

<400> SEQUENCE: 5

Ala Arg Glu Gly Gly Asn Asp Tyr Tyr Asp Thr Met Asp Tyr
1               5                   10


<210> SEQ ID NO 6
<211> LENGTH: 11
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Light Chain CDR1 of IMGN632"

<400> SEQUENCE: 6

Arg Ala Ser Gln Asp Ile Asn Ser Tyr Leu Ser
1               5                   10


<210> SEQ ID NO 7
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Light Chain CDR2 of IMGN632"

<400> SEQUENCE: 7

Arg Val Asn Arg Leu Val Asp
1               5


<210> SEQ ID NO 8
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Light Chain CDR3 of IMGN632"

<400> SEQUENCE: 8

Leu Gln Tyr Asp Ala Phe Pro Tyr Thr
1               5


<210> SEQ ID NO 9
<211> LENGTH: 360
<212> TYPE: PRT
<213> ORGANISM: Homo sapiens
<220> FEATURE:
<221> NAME/KEY: source
<223> OTHER INFORMATION: /note="Mature Human CD123"

<400> SEQUENCE: 9

Thr Lys Glu Asp Pro Asn Pro Pro Ile Thr Asn Leu Arg Met Lys Ala
1               5                   10                  15

Lys Ala Gln Gln Leu Thr Trp Asp Leu Asn Arg Asn Val Thr Asp Ile
            20                  25                  30

Glu Cys Val Lys Asp Ala Asp Tyr Ser Met Pro Ala Val Asn Asn Ser
        35                  40                  45

Tyr Cys Gln Phe Gly Ala Ile Ser Leu Cys Glu Val Thr Asn Tyr Thr
    50                  55                  60

Val Arg Val Ala Asn Pro Pro Phe Ser Thr Trp Ile Leu Phe Pro Glu
65                  70                  75                  80

Asn Ser Gly Lys Pro Trp Ala Gly Ala Glu Asn Leu Thr Cys Trp Ile
                85                  90                  95

His Asp Val Asp Phe Leu Ser Cys Ser Trp Ala Val Gly Pro Gly Ala
            100                 105                 110
```

```
Pro Ala Asp Val Gln Tyr Asp Leu Tyr Leu Asn Val Ala Asn Arg Arg
        115                 120                 125

Gln Gln Tyr Glu Cys Leu His Tyr Lys Thr Asp Ala Gln Gly Thr Arg
    130                 135                 140

Ile Gly Cys Arg Phe Asp Asp Ile Ser Arg Leu Ser Ser Gly Ser Gln
145                 150                 155                 160

Ser Ser His Ile Leu Val Arg Gly Arg Ser Ala Ala Phe Gly Ile Pro
                165                 170                 175

Cys Thr Asp Lys Phe Val Val Phe Ser Gln Ile Glu Ile Leu Thr Pro
            180                 185                 190

Pro Asn Met Thr Ala Lys Cys Asn Lys Thr His Ser Phe Met His Trp
        195                 200                 205

Lys Met Arg Ser His Phe Asn Arg Lys Phe Arg Tyr Glu Leu Gln Ile
    210                 215                 220

Gln Lys Arg Met Gln Pro Val Ile Thr Glu Gln Val Arg Asp Arg Thr
225                 230                 235                 240

Ser Phe Gln Leu Leu Asn Pro Gly Thr Tyr Thr Val Gln Ile Arg Ala
                245                 250                 255

Arg Glu Arg Val Tyr Glu Phe Leu Ser Ala Trp Ser Thr Pro Gln Arg
            260                 265                 270

Phe Glu Cys Asp Gln Glu Glu Gly Ala Asn Thr Arg Ala Trp Arg Thr
        275                 280                 285

Ser Leu Leu Ile Ala Leu Gly Thr Leu Leu Ala Leu Val Cys Val Phe
    290                 295                 300

Val Ile Cys Arg Arg Tyr Leu Val Met Gln Arg Leu Phe Pro Arg Ile
305                 310                 315                 320

Pro His Met Lys Asp Pro Ile Gly Asp Ser Phe Gln Asn Asp Lys Leu
                325                 330                 335

Val Val Trp Glu Ala Gly Lys Ala Gly Leu Glu Glu Cys Leu Val Thr
            340                 345                 350

Glu Val Gln Val Val Gln Lys Thr
        355                 360


<210> SEQ ID NO 10
<211> LENGTH: 1080
<212> TYPE: DNA
<213> ORGANISM: Homo sapiens
<220> FEATURE:
<221> NAME/KEY: source
<223> OTHER INFORMATION: /note="cDNA Encoding Mature Human CD123"

<400> SEQUENCE: 10

acgaaggaag atccaaaccc accaatcacg aacctaagga tgaaagcaaa ggctcagcag      60

ttgacctggg accttaacag aaatgtgacc gatatcgagt gtgttaaaga cgccgactat     120

tctatgccgg cagtgaacaa tagctattgc cagtttggag caatttcctt atgtgaagtg     180

accaactaca ccgtccgagt ggccaaccca ccattctcca cgtggatcct cttccctgag     240

aacagtggga agccttgggc aggtgcggag aatctgacct gctggattca tgacgtggat     300

ttcttgagct gcagctgggc ggtaggcccg ggggccccgg cggacgtcca gtacgacctg     360

tacttgaacg ttgccaacag gcgtcaacag tacgagtgtc ttcactacaa aacggatgct     420

cagggaacac gtatcgggtg tcgtttcgat gacatctctc gactctccag cggttctcaa     480

agttcccaca tcctggtgcg gggcaggagc gcagccttcg gtatcccctg cacagataag     540

tttgtcgtct tttcacagat tgagatatta actccaccca acatgactgc aaagtgtaat     600
```

```
aagacacatt cctttatgca ctggaaaatg agaagtcatt tcaatcgcaa atttcgctat    660

gagcttcaga tacaaaagag aatgcagcct gtaatcacag aacaggtcag agacagaacc    720

tccttccagc tactcaatcc tggaacgtac acagtacaaa taagagcccg ggaaagagtg    780

tatgaattct tgagcgcctg gagcaccccc cagcgcttcg agtgcgacca ggaggagggc    840

gcaaacacac gtgcctggcg gacgtcgctg ctgatcgcgc tggggacgct gctggccctg    900

gtctgtgtct tcgtgatctg cagaaggtat ctggtgatgc agagactctt tccccgcatc    960

cctcacatga aagaccccat cggtgacagc ttccaaaacg acaagctggt ggtctgggag   1020

gcgggcaaag ccggcctgga ggagtgtctg gtgactgaag tacaggtcgt gcagaaaact   1080
```

```
<210> SEQ ID NO 11
<211> LENGTH: 287
<212> TYPE: PRT
<213> ORGANISM: Homo sapiens
<220> FEATURE:
<221> NAME/KEY: source
<223> OTHER INFORMATION: /note="Extracellular Domain of CD123"

<400> SEQUENCE: 11

Thr Lys Glu Asp Pro Asn Pro Pro Ile Thr Asn Leu Arg Met Lys Ala
1               5                   10                  15

Lys Ala Gln Gln Leu Thr Trp Asp Leu Asn Arg Asn Val Thr Asp Ile
            20                  25                  30

Glu Cys Val Lys Asp Ala Asp Tyr Ser Met Pro Ala Val Asn Asn Ser
        35                  40                  45

Tyr Cys Gln Phe Gly Ala Ile Ser Leu Cys Glu Val Thr Asn Tyr Thr
    50                  55                  60

Val Arg Val Ala Asn Pro Pro Phe Ser Thr Trp Ile Leu Phe Pro Glu
65                  70                  75                  80

Asn Ser Gly Lys Pro Trp Ala Gly Ala Glu Asn Leu Thr Cys Trp Ile
                85                  90                  95

His Asp Val Asp Phe Leu Ser Cys Ser Trp Ala Val Gly Pro Gly Ala
            100                 105                 110

Pro Ala Asp Val Gln Tyr Asp Leu Tyr Leu Asn Val Ala Asn Arg Arg
        115                 120                 125

Gln Gln Tyr Glu Cys Leu His Tyr Lys Thr Asp Ala Gln Gly Thr Arg
    130                 135                 140

Ile Gly Cys Arg Phe Asp Asp Ile Ser Arg Leu Ser Ser Gly Ser Gln
145                 150                 155                 160

Ser Ser His Ile Leu Val Arg Gly Arg Ser Ala Ala Phe Gly Ile Pro
                165                 170                 175

Cys Thr Asp Lys Phe Val Val Phe Ser Gln Ile Glu Ile Leu Thr Pro
            180                 185                 190

Pro Asn Met Thr Ala Lys Cys Asn Lys Thr His Ser Phe Met His Trp
        195                 200                 205

Lys Met Arg Ser His Phe Asn Arg Lys Phe Arg Tyr Glu Leu Gln Ile
    210                 215                 220

Gln Lys Arg Met Gln Pro Val Ile Thr Glu Gln Val Arg Asp Arg Thr
225                 230                 235                 240

Ser Phe Gln Leu Leu Asn Pro Gly Thr Tyr Thr Val Gln Ile Arg Ala
                245                 250                 255

Arg Glu Arg Val Tyr Glu Phe Leu Ser Ala Trp Ser Thr Pro Gln Arg
            260                 265                 270
```

```
Phe Glu Cys Asp Gln Glu Glu Gly Ala Asn Thr Arg Ala Trp Arg
        275                 280                 285


<210> SEQ ID NO 12
<211> LENGTH: 861
<212> TYPE: DNA
<213> ORGANISM: Homo sapiens
<220> FEATURE:
<221> NAME/KEY: source
<223> OTHER INFORMATION: /note="cDNA Encoding Extracellular Domain of
      CD123"

<400> SEQUENCE: 12

acgaaggaag atccaaaccc accaatcacg aacctaagga tgaaagcaaa ggctcagcag      60

ttgacctggg accttaacag aaatgtgacc gatatcgagt gtgttaaaga cgccgactat     120

tctatgccgg cagtgaacaa tagctattgc cagtttggag caatttcctt atgtgaagtg     180

accaactaca ccgtccgagt ggccaaccca ccattctcca cgtggatcct cttccctgag     240

aacagtggga agccttgggc aggtgcggag aatctgacct gctggattca tgacgtggat     300

ttcttgagct gcagctgggc ggtaggcccg gggccccccg cggacgtcca gtacgacctg     360

tacttgaacg ttgccaacag gcgtcaacag tacgagtgtc ttcactacaa aacggatgct     420

cagggaacac gtatcgggtg tcgtttcgat gacatctctc gactctccag cggttctcaa     480

agttcccaca tcctggtgcg gggcaggagc gcagccttcg gtatcccctg cacagataag     540

tttgtcgtct tttcacagat tgagatatta actccaccca acatgactgc aaagtgtaat     600

aagacacatt cctttatgca ctggaaaatg agaagtcatt tcaatcgcaa atttcgctat     660

gagcttcaga tacaaaagag aatgcagcct gtaatcacag aacaggtcag agacagaacc     720

tccttccagc tactcaatcc tggaacgtac acagtacaaa taagagcccg ggaaagagtg     780

tatgaattct tgagcgcctg gagcaccccc cagcgcttcg agtgcgacca ggaggagggc     840

gcaaacacac gtgcctggcg g                                                861


<210> SEQ ID NO 13
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of IMGN632 IgG histidine
      scanning variant #1"

<400> SEQUENCE: 13

Gln Val Gln Leu Val Gln Ser Gly Ala Glu Val Lys Lys Pro Gly Ala
1               5                   10                  15

Ser Val Lys Val Ser Cys Lys Ala Ser His Tyr Ile Phe Thr Ser Ser
            20                  25                  30

Ile Met His Trp Val Arg Gln Ala Pro Gly Gln Gly Leu Glu Trp Ile
        35                  40                  45

Gly Tyr Ile Lys Pro Tyr Asn Asp Gly Thr Lys Tyr Asn Glu Lys Phe
    50                  55                  60

Lys Gly Arg Ala Thr Leu Thr Ser Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

```
Ala Arg Glu Gly Gly Asn Asp Tyr Tyr Asp Thr Met Asp Tyr Trp Gly
            100                 105                 110

Gln Gly Thr Leu Val Thr Val Ser Ser
        115                 120


<210> SEQ ID NO 14
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of IMGN632 IgG histidine
      scanning variant #2"

<400> SEQUENCE: 14

Gln Val Gln Leu Val Gln Ser Gly Ala Glu Val Lys Lys Pro Gly Ala
1               5                   10                  15

Ser Val Lys Val Ser Cys Lys Ala Ser Gly His Ile Phe Thr Ser Ser
            20                  25                  30

Ile Met His Trp Val Arg Gln Ala Pro Gly Gln Gly Leu Glu Trp Ile
        35                  40                  45

Gly Tyr Ile Lys Pro Tyr Asn Asp Gly Thr Lys Tyr Asn Glu Lys Phe
    50                  55                  60

Lys Gly Arg Ala Thr Leu Thr Ser Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Gly Asn Asp Tyr Tyr Asp Thr Met Asp Tyr Trp Gly
            100                 105                 110

Gln Gly Thr Leu Val Thr Val Ser Ser
        115                 120


<210> SEQ ID NO 15
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of IMGN632 IgG histidine
      scanning variant #3"

<400> SEQUENCE: 15

Gln Val Gln Leu Val Gln Ser Gly Ala Glu Val Lys Lys Pro Gly Ala
1               5                   10                  15

Ser Val Lys Val Ser Cys Lys Ala Ser Gly Tyr His Phe Thr Ser Ser
            20                  25                  30

Ile Met His Trp Val Arg Gln Ala Pro Gly Gln Gly Leu Glu Trp Ile
        35                  40                  45

Gly Tyr Ile Lys Pro Tyr Asn Asp Gly Thr Lys Tyr Asn Glu Lys Phe
    50                  55                  60

Lys Gly Arg Ala Thr Leu Thr Ser Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

```
Ala Arg Glu Gly Gly Asn Asp Tyr Tyr Asp Thr Met Asp Tyr Trp Gly
            100                 105                 110

Gln Gly Thr Leu Val Thr Val Ser Ser
        115                 120


<210> SEQ ID NO 16
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of IMGN632 IgG histidine
      scanning variant #4"

<400> SEQUENCE: 16

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile His Thr Ser Ser
            20                  25                  30

Ile Met His Trp Val Arg Gln Ala Pro Gly Gln Gly Leu Glu Trp Ile
        35                  40                  45

Gly Tyr Ile Lys Pro Tyr Asn Asp Gly Thr Lys Tyr Asn Glu Lys Phe
    50                  55                  60

Lys Gly Arg Ala Thr Leu Thr Ser Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Gly Asn Asp Tyr Tyr Asp Thr Met Asp Tyr Trp Gly
            100                 105                 110

Gln Gly Thr Leu Val Thr Val Ser Ser
        115                 120


<210> SEQ ID NO 17
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of IMGN632 IgG histidine
      scanning variant #5"

<400> SEQUENCE: 17

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe His Ser Ser
            20                  25                  30

Ile Met His Trp Val Arg Gln Ala Pro Gly Gln Gly Leu Glu Trp Ile
        35                  40                  45

Gly Tyr Ile Lys Pro Tyr Asn Asp Gly Thr Lys Tyr Asn Glu Lys Phe
    50                  55                  60

Lys Gly Arg Ala Thr Leu Thr Ser Asp Arg Ser Thr Ser Thr Ala Tyr
65                  70                  75                  80

Met Glu Leu Ser Ser Leu Arg Ser Glu Asp Thr Ala Val Tyr Tyr Cys
```

```
                85                  90                  95

Ala Arg Glu Gly Gly Asn Asp Tyr Tyr Asp Thr Met Asp Tyr Trp Gly
            100                 105                 110

Gln Gly Thr Leu Val Thr Val Ser Ser
        115                 120


<210> SEQ ID NO 18
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of IMGN632 IgG histidine
      scanning variant #6"

<400> SEQUENCE: 18

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr His Ser
            20                  25                  30

Ile Met His Trp Val Arg Gln Ala Pro Gly Gln Gly Leu Glu Trp Ile
        35                  40                  45

Gly Tyr Ile Lys Pro Tyr Asn Asp Gly Thr Lys Tyr Asn Glu Lys Phe
    50                  55                  60

Lys Gly Arg Ala Thr Leu Thr Ser Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Gly Asn Asp Tyr Tyr Asp Thr Met Asp Tyr Trp Gly
            100                 105                 110

Gln Gly Thr Leu Val Thr Val Ser Ser
        115                 120


<210> SEQ ID NO 19
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of IMGN632 IgG histidine
      scanning variant #7"

<400> SEQUENCE: 19

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser His
            20                  25                  30

Ile Met His Trp Val Arg Gln Ala Pro Gly Gln Gly Leu Glu Trp Ile
        35                  40                  45

Gly Tyr Ile Lys Pro Tyr Asn Asp Gly Thr Lys Tyr Asn Glu Lys Phe
    50                  55                  60

Lys Gly Arg Ala Thr Leu Thr Ser Asp Arg Ser Thr Ser Thr Ala Tyr
65                  70                  75                  80
```

```
Met Glu Leu Ser Ser Leu Arg Ser Glu Asp Thr Ala Val Tyr Tyr Cys
                85                  90                  95

Ala Arg Glu Gly Gly Asn Asp Tyr Tyr Asp Thr Met Asp Tyr Trp Gly
            100                 105                 110

Gln Gly Thr Leu Val Thr Val Ser Ser
        115                 120
```

<210> SEQ ID NO 20
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="Heavy Chain of IMGN632 IgG histidine scanning variant #8"

<400> SEQUENCE: 20

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser Ser
            20                  25                  30

His Met His Trp Val Arg Gln Ala Pro Gly Gln Gly Leu Glu Trp Ile
        35                  40                  45

Gly Tyr Ile Lys Pro Tyr Asn Asp Gly Thr Lys Tyr Asn Glu Lys Phe
    50                  55                  60

Lys Gly Arg Ala Thr Leu Thr Ser Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Gly Asn Asp Tyr Tyr Asp Thr Met Asp Tyr Trp Gly
            100                 105                 110

Gln Gly Thr Leu Val Thr Val Ser Ser
        115                 120
```

<210> SEQ ID NO 21
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="Heavy Chain of IMGN632 IgG histidine scanning variant #9"

<400> SEQUENCE: 21

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser Ser
            20                  25                  30

Ile His His Trp Val Arg Gln Ala Pro Gly Gln Gly Leu Glu Trp Ile
        35                  40                  45

Gly Tyr Ile Lys Pro Tyr Asn Asp Gly Thr Lys Tyr Asn Glu Lys Phe
    50                  55                  60

Lys Gly Arg Ala Thr Leu Thr Ser Asp Arg Ser Thr Ser Thr Ala Tyr
65                  70                  75                  80
```

Met Glu Leu Ser Ser Leu Arg Ser Glu Asp Thr Ala Val Tyr Tyr Cys
85 90 95

Ala Arg Glu Gly Gly Asn Asp Tyr Tyr Asp Thr Met Asp Tyr Trp Gly
100 105 110

Gln Gly Thr Leu Val Thr Val Ser Ser
115 120

<210> SEQ ID NO 22
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="Heavy Chain of IMGN632 IgG histidine scanning variant #10"

<400> SEQUENCE: 22

Gln Val Gln Leu Val Gln Ser Gly Ala Glu Val Lys Lys Pro Gly Ala
1 5 10 15

Ser Val Lys Val Ser Cys Lys Ala Ser Gly Tyr Ile Phe Thr Ser Ser
20 25 30

Ile Met Ala Trp Val Arg Gln Ala Pro Gly Gln Gly Leu Glu Trp Ile
35 40 45

Gly Tyr Ile Lys Pro Tyr Asn Asp Gly Thr Lys Tyr Asn Glu Lys Phe
50 55 60

Lys Gly Arg Ala Thr Leu Thr Ser Asp Arg Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Glu Gly Gly Asn Asp Tyr Tyr Asp Thr Met Asp Tyr Trp Gly
100 105 110

Gln Gly Thr Leu Val Thr Val Ser Ser
115 120

<210> SEQ ID NO 23
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="Heavy Chain of IMGN632 IgG histidine scanning variant #11"

<400> SEQUENCE: 23

Gln Val Gln Leu Val Gln Ser Gly Ala Glu Val Lys Lys Pro Gly Ala
1 5 10 15

Ser Val Lys Val Ser Cys Lys Ala Ser Gly Tyr Ile Phe Thr Ser Ser
20 25 30

Ile Met His Trp Val Arg Gln Ala Pro Gly Gln Gly Leu Glu Trp Ile
35 40 45

Gly His Ile Lys Pro Tyr Asn Asp Gly Thr Lys Tyr Asn Glu Lys Phe
50 55 60

Lys Gly Arg Ala Thr Leu Thr Ser Asp Arg Ser Thr Ser Thr Ala Tyr

```
65                  70                  75                  80

Met Glu Leu Ser Ser Leu Arg Ser Glu Asp Thr Ala Val Tyr Tyr Cys
                85                  90                  95

Ala Arg Glu Gly Gly Asn Asp Tyr Tyr Asp Thr Met Asp Tyr Trp Gly
            100                 105                 110

Gln Gly Thr Leu Val Thr Val Ser Ser
        115                 120


<210> SEQ ID NO 24
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of IMGN632 IgG histidine
      scanning variant #12"

<400> SEQUENCE: 24

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser Ser
            20                  25                  30

Ile Met His Trp Val Arg Gln Ala Pro Gly Gln Gly Leu Glu Trp Ile
        35                  40                  45

Gly Tyr His Lys Pro Tyr Asn Asp Gly Thr Lys Tyr Asn Glu Lys Phe
    50                  55                  60

Lys Gly Arg Ala Thr Leu Thr Ser Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Gly Asn Asp Tyr Tyr Asp Thr Met Asp Tyr Trp Gly
            100                 105                 110

Gln Gly Thr Leu Val Thr Val Ser Ser
        115                 120


<210> SEQ ID NO 25
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of IMGN632 IgG histidine
      scanning variant #13"

<400> SEQUENCE: 25

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser Ser
            20                  25                  30

Ile Met His Trp Val Arg Gln Ala Pro Gly Gln Gly Leu Glu Trp Ile
        35                  40                  45

Gly Tyr Ile His Pro Tyr Asn Asp Gly Thr Lys Tyr Asn Glu Lys Phe
    50                  55                  60
```

```
Lys Gly Arg Ala Thr Leu Thr Ser Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Gly Asn Asp Tyr Tyr Asp Thr Met Asp Tyr Trp Gly
            100                 105                 110

Gln Gly Thr Leu Val Thr Val Ser Ser
        115                 120


<210> SEQ ID NO 26
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of IMGN632 IgG histidine
      scanning variant #14"

<400> SEQUENCE: 26

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser Ser
            20                  25                  30

Ile Met His Trp Val Arg Gln Ala Pro Gly Gln Gly Leu Glu Trp Ile
        35                  40                  45

Gly Tyr Ile Lys His Tyr Asn Asp Gly Thr Lys Tyr Asn Glu Lys Phe
    50                  55                  60

Lys Gly Arg Ala Thr Leu Thr Ser Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Gly Asn Asp Tyr Tyr Asp Thr Met Asp Tyr Trp Gly
            100                 105                 110

Gln Gly Thr Leu Val Thr Val Ser Ser
        115                 120


<210> SEQ ID NO 27
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of IMGN632 IgG histidine
      scanning variant #15"

<400> SEQUENCE: 27

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser Ser
            20                  25                  30

Ile Met His Trp Val Arg Gln Ala Pro Gly Gln Gly Leu Glu Trp Ile
        35                  40                  45

Gly Tyr Ile Lys Pro His Asn Asp Gly Thr Lys Tyr Asn Glu Lys Phe
    50                  55                  60
```

```
Lys Gly Arg Ala Thr Leu Thr Ser Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Gly Asn Asp Tyr Tyr Asp Thr Met Asp Tyr Trp Gly
            100                 105                 110

Gln Gly Thr Leu Val Thr Val Ser Ser
        115                 120


<210> SEQ ID NO 28
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of IMGN632 IgG histidine
      scanning variant #16"

<400> SEQUENCE: 28

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser Ser
            20                  25                  30

Ile Met His Trp Val Arg Gln Ala Pro Gly Gln Gly Leu Glu Trp Ile
        35                  40                  45

Gly Tyr Ile Lys Pro Tyr His Asp Gly Thr Lys Tyr Asn Glu Lys Phe
    50                  55                  60

Lys Gly Arg Ala Thr Leu Thr Ser Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Gly Asn Asp Tyr Tyr Asp Thr Met Asp Tyr Trp Gly
            100                 105                 110

Gln Gly Thr Leu Val Thr Val Ser Ser
        115                 120


<210> SEQ ID NO 29
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of IMGN632 IgG histidine
      scanning variant #17"

<400> SEQUENCE: 29

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser Ser
            20                  25                  30

Ile Met His Trp Val Arg Gln Ala Pro Gly Gln Gly Leu Glu Trp Ile
        35                  40                  45

Gly Tyr Ile Lys Pro Tyr Asn His Gly Thr Lys Tyr Asn Glu Lys Phe
```

```
    50                  55                  60

Lys Gly Arg Ala Thr Leu Thr Ser Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Gly Asn Asp Tyr Tyr Asp Thr Met Asp Tyr Trp Gly
            100                 105                 110

Gln Gly Thr Leu Val Thr Val Ser Ser
        115                 120


<210> SEQ ID NO 30
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of IMGN632 IgG histidine
      scanning variant #18"

<400> SEQUENCE: 30

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser Ser
            20                  25                  30

Ile Met His Trp Val Arg Gln Ala Pro Gly Gln Gly Leu Glu Trp Ile
        35                  40                  45

Gly Tyr Ile Lys Pro Tyr Asn Asp His Thr Lys Tyr Asn Glu Lys Phe
    50                  55                  60

Lys Gly Arg Ala Thr Leu Thr Ser Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Gly Asn Asp Tyr Tyr Asp Thr Met Asp Tyr Trp Gly
            100                 105                 110

Gln Gly Thr Leu Val Thr Val Ser Ser
        115                 120


<210> SEQ ID NO 31
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of IMGN632 IgG histidine
      scanning variant #19"

<400> SEQUENCE: 31

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser Ser
            20                  25                  30

Ile Met His Trp Val Arg Gln Ala Pro Gly Gln Gly Leu Glu Trp Ile
        35                  40                  45
```

```
Gly Tyr Ile Lys Pro Tyr Asn Asp Gly His Lys Tyr Asn Glu Lys Phe
    50                  55                  60

Lys Gly Arg Ala Thr Leu Thr Ser Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Gly Asn Asp Tyr Tyr Asp Thr Met Asp Tyr Trp Gly
            100                 105                 110

Gln Gly Thr Leu Val Thr Val Ser Ser
        115                 120


<210> SEQ ID NO 32
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of IMGN632 IgG histidine
      scanning variant #20"

<400> SEQUENCE: 32

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser Ser
            20                  25                  30

Ile Met His Trp Val Arg Gln Ala Pro Gly Gln Gly Leu Glu Trp Ile
        35                  40                  45

Gly Tyr Ile Lys Pro Tyr Asn Asp Gly Thr His Tyr Asn Glu Lys Phe
    50                  55                  60

Lys Gly Arg Ala Thr Leu Thr Ser Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Gly Asn Asp Tyr Tyr Asp Thr Met Asp Tyr Trp Gly
            100                 105                 110

Gln Gly Thr Leu Val Thr Val Ser Ser
        115                 120


<210> SEQ ID NO 33
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of IMGN632 IgG histidine
      scanning variant #21"

<400> SEQUENCE: 33

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser Ser
            20                  25                  30

Ile Met His Trp Val Arg Gln Ala Pro Gly Gln Gly Leu Glu Trp Ile
        35                  40                  45
```

```
Gly Tyr Ile Lys Pro Tyr Asn Asp Gly Thr Lys His Asn Glu Lys Phe
    50                  55                  60

Lys Gly Arg Ala Thr Leu Thr Ser Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Gly Asn Asp Tyr Tyr Asp Thr Met Asp Tyr Trp Gly
            100                 105                 110

Gln Gly Thr Leu Val Thr Val Ser Ser
        115                 120


<210> SEQ ID NO 34
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of IMGN632 IgG histidine
      scanning variant #22"

<400> SEQUENCE: 34

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser Ser
            20                  25                  30

Ile Met His Trp Val Arg Gln Ala Pro Gly Gln Gly Leu Glu Trp Ile
        35                  40                  45

Gly Tyr Ile Lys Pro Tyr Asn Asp Gly Thr Lys Tyr His Glu Lys Phe
    50                  55                  60

Lys Gly Arg Ala Thr Leu Thr Ser Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Gly Asn Asp Tyr Tyr Asp Thr Met Asp Tyr Trp Gly
            100                 105                 110

Gln Gly Thr Leu Val Thr Val Ser Ser
        115                 120


<210> SEQ ID NO 35
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of IMGN632 IgG histidine
      scanning variant #23"

<400> SEQUENCE: 35

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser Ser
            20                  25                  30

Ile Met His Trp Val Arg Gln Ala Pro Gly Gln Gly Leu Glu Trp Ile
```

```
        35                  40                  45

Gly Tyr Ile Lys Pro Tyr Asn Asp Gly Thr Lys Tyr Asn His Lys Phe
    50                  55                  60

Lys Gly Arg Ala Thr Leu Thr Ser Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Gly Asn Asp Tyr Tyr Asp Thr Met Asp Tyr Trp Gly
            100                 105                 110

Gln Gly Thr Leu Val Thr Val Ser Ser
        115                 120


<210> SEQ ID NO 36
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of IMGN632 IgG histidine
      scanning variant #24"

<400> SEQUENCE: 36

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser Ser
            20                  25                  30

Ile Met His Trp Val Arg Gln Ala Pro Gly Gln Gly Leu Glu Trp Ile
        35                  40                  45

Gly Tyr Ile Lys Pro Tyr Asn Asp Gly Thr Lys Tyr Asn Glu His Phe
    50                  55                  60

Lys Gly Arg Ala Thr Leu Thr Ser Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Gly Asn Asp Tyr Tyr Asp Thr Met Asp Tyr Trp Gly
            100                 105                 110

Gln Gly Thr Leu Val Thr Val Ser Ser
        115                 120


<210> SEQ ID NO 37
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of IMGN632 IgG histidine
      scanning variant #25"

<400> SEQUENCE: 37

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser Ser
            20                  25                  30
```

```
Ile Met His Trp Val Arg Gln Ala Pro Gly Gln Gly Leu Glu Trp Ile
        35                  40                  45

Gly Tyr Ile Lys Pro Tyr Asn Asp Gly Thr Lys Tyr Asn Glu Lys His
    50                  55                  60

Lys Gly Arg Ala Thr Leu Thr Ser Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Gly Asn Asp Tyr Tyr Asp Thr Met Asp Tyr Trp Gly
            100                 105                 110

Gln Gly Thr Leu Val Thr Val Ser Ser
        115                 120


<210> SEQ ID NO 38
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of IMGN632 IgG histidine
      scanning variant #26"

<400> SEQUENCE: 38

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser Ser
            20                  25                  30

Ile Met His Trp Val Arg Gln Ala Pro Gly Gln Gly Leu Glu Trp Ile
        35                  40                  45

Gly Tyr Ile Lys Pro Tyr Asn Asp Gly Thr Lys Tyr Asn Glu Lys Phe
    50                  55                  60

His Gly Arg Ala Thr Leu Thr Ser Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Gly Asn Asp Tyr Tyr Asp Thr Met Asp Tyr Trp Gly
            100                 105                 110

Gln Gly Thr Leu Val Thr Val Ser Ser
        115                 120


<210> SEQ ID NO 39
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of IMGN632 IgG histidine
      scanning variant #27"

<400> SEQUENCE: 39

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser Ser
            20                  25                  30
```

```
Ile Met His Trp Val Arg Gln Ala Pro Gly Gln Gly Leu Glu Trp Ile
        35                  40                  45

Gly Tyr Ile Lys Pro Tyr Asn Asp Gly Thr Lys Tyr Asn Glu Lys Phe
    50                  55                  60

Lys His Arg Ala Thr Leu Thr Ser Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Gly Asn Asp Tyr Tyr Asp Thr Met Asp Tyr Trp Gly
            100                 105                 110

Gln Gly Thr Leu Val Thr Val Ser Ser
        115                 120


<210> SEQ ID NO 40
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of IMGN632 IgG histidine
      scanning variant #28"

<400> SEQUENCE: 40

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser Ser
            20                  25                  30

Ile Met His Trp Val Arg Gln Ala Pro Gly Gln Gly Leu Glu Trp Ile
        35                  40                  45

Gly Tyr Ile Lys Pro Tyr Asn Asp Gly Thr Lys Tyr Asn Glu Lys Phe
    50                  55                  60

Lys Gly Arg Ala Thr Leu Thr Ser Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

His Arg Glu Gly Gly Asn Asp Tyr Tyr Asp Thr Met Asp Tyr Trp Gly
            100                 105                 110

Gln Gly Thr Leu Val Thr Val Ser Ser
        115                 120


<210> SEQ ID NO 41
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of IMGN632 IgG histidine
      scanning variant #29"

<400> SEQUENCE: 41

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser Ser
```

```
            20                  25                  30

Ile Met His Trp Val Arg Gln Ala Pro Gly Gln Gly Leu Glu Trp Ile
        35                  40                  45

Gly Tyr Ile Lys Pro Tyr Asn Asp Gly Thr Lys Tyr Asn Glu Lys Phe
    50                  55                  60

Lys Gly Arg Ala Thr Leu Thr Ser Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala His Glu Gly Gly Asn Asp Tyr Tyr Asp Thr Met Asp Tyr Trp Gly
            100                 105                 110

Gln Gly Thr Leu Val Thr Val Ser Ser
        115                 120


<210> SEQ ID NO 42
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of IMGN632 IgG histidine
      scanning variant #30"

<400> SEQUENCE: 42

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser Ser
            20                  25                  30

Ile Met His Trp Val Arg Gln Ala Pro Gly Gln Gly Leu Glu Trp Ile
        35                  40                  45

Gly Tyr Ile Lys Pro Tyr Asn Asp Gly Thr Lys Tyr Asn Glu Lys Phe
    50                  55                  60

Lys Gly Arg Ala Thr Leu Thr Ser Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Gly Gly Asn Asp Tyr Tyr Asp Thr Met Asp Tyr Trp Gly
            100                 105                 110

Gln Gly Thr Leu Val Thr Val Ser Ser
        115                 120


<210> SEQ ID NO 43
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of IMGN632 IgG histidine
      scanning variant #31"

<400> SEQUENCE: 43

Gln Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Ile Phe Thr Ser Ser
            20                  25                  30

Ile Met His Trp Val Arg Gln Ala Pro Gly Gln Gly Leu Glu Trp Ile
        35                  40                  45

Gly Tyr Ile Lys Pro Tyr Asn Asp Gly Thr Lys Tyr Asn Glu Lys Phe
    50                  55                  60

Lys Gly Arg Ala Thr Leu Thr Ser Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu His Gly Asn Asp Tyr Tyr Asp Thr Met Asp Tyr Trp Gly
            100                 105                 110

Gln Gly Thr Leu Val Thr Val Ser Ser
        115                 120


<210> SEQ ID NO 44
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of IMGN632 IgG histidine
      scanning variant #32"

<400> SEQUENCE: 44

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser Ser
            20                  25                  30

Ile Met His Trp Val Arg Gln Ala Pro Gly Gln Gly Leu Glu Trp Ile
        35                  40                  45

Gly Tyr Ile Lys Pro Tyr Asn Asp Gly Thr Lys Tyr Asn Glu Lys Phe
    50                  55                  60

Lys Gly Arg Ala Thr Leu Thr Ser Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly His Asn Asp Tyr Tyr Asp Thr Met Asp Tyr Trp Gly
            100                 105                 110

Gln Gly Thr Leu Val Thr Val Ser Ser
        115                 120


<210> SEQ ID NO 45
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of IMGN632 IgG histidine
      scanning variant #33"

<400> SEQUENCE: 45

Gln Val Gln Leu Val Gln Ser Gly Ala Glu Val Lys Lys Pro Gly Ala
1               5                   10                  15
```

Ser Val Lys Val Ser Cys Lys Ala Ser Gly Tyr Ile Phe Thr Ser Ser
20 25 30

Ile Met His Trp Val Arg Gln Ala Pro Gly Gln Gly Leu Glu Trp Ile
35 40 45

Gly Tyr Ile Lys Pro Tyr Asn Asp Gly Thr Lys Tyr Asn Glu Lys Phe
50 55 60

Lys Gly Arg Ala Thr Leu Thr Ser Asp Arg Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Glu Gly Gly His Asp Tyr Tyr Asp Thr Met Asp Tyr Trp Gly
100 105 110

Gln Gly Thr Leu Val Thr Val Ser Ser
115 120

<210> SEQ ID NO 46
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="Heavy Chain of IMGN632 IgG histidine scanning variant #34"

<400> SEQUENCE: 46

Gln Val Gln Leu Val Gln Ser Gly Ala Glu Val Lys Lys Pro Gly Ala
1 5 10 15

Ser Val Lys Val Ser Cys Lys Ala Ser Gly Tyr Ile Phe Thr Ser Ser
20 25 30

Ile Met His Trp Val Arg Gln Ala Pro Gly Gln Gly Leu Glu Trp Ile
35 40 45

Gly Tyr Ile Lys Pro Tyr Asn Asp Gly Thr Lys Tyr Asn Glu Lys Phe
50 55 60

Lys Gly Arg Ala Thr Leu Thr Ser Asp Arg Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Glu Gly Gly Asn His Tyr Tyr Asp Thr Met Asp Tyr Trp Gly
100 105 110

Gln Gly Thr Leu Val Thr Val Ser Ser
115 120

<210> SEQ ID NO 47
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="Heavy Chain of IMGN632 IgG histidine scanning variant #35"

<400> SEQUENCE: 47

Gln Val Gln Leu Val Gln Ser Gly Ala Glu Val Lys Lys Pro Gly Ala

```
1               5                   10                  15

Ser Val Lys Val Ser Cys Lys Ala Ser Gly Tyr Ile Phe Thr Ser Ser
            20                  25                  30

Ile Met His Trp Val Arg Gln Ala Pro Gly Gln Gly Leu Glu Trp Ile
        35                  40                  45

Gly Tyr Ile Lys Pro Tyr Asn Asp Gly Thr Lys Tyr Asn Glu Lys Phe
    50                  55                  60

Lys Gly Arg Ala Thr Leu Thr Ser Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Gly Asn Asp His Tyr Asp Thr Met Asp Tyr Trp Gly
            100                 105                 110

Gln Gly Thr Leu Val Thr Val Ser Ser
        115                 120


<210> SEQ ID NO 48
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of IMGN632 IgG histidine
      scanning variant #36"

<400> SEQUENCE: 48

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser Ser
            20                  25                  30

Ile Met His Trp Val Arg Gln Ala Pro Gly Gln Gly Leu Glu Trp Ile
        35                  40                  45

Gly Tyr Ile Lys Pro Tyr Asn Asp Gly Thr Lys Tyr Asn Glu Lys Phe
    50                  55                  60

Lys Gly Arg Ala Thr Leu Thr Ser Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Gly Asn Asp Tyr His Asp Thr Met Asp Tyr Trp Gly
            100                 105                 110

Gln Gly Thr Leu Val Thr Val Ser Ser
        115                 120


<210> SEQ ID NO 49
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of IMGN632 IgG histidine
      scanning variant #37"

<400> SEQUENCE: 49
```

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser Ser
            20                  25                  30

Ile Met His Trp Val Arg Gln Ala Pro Gly Gln Gly Leu Glu Trp Ile
        35                  40                  45

Gly Tyr Ile Lys Pro Tyr Asn Asp Gly Thr Lys Tyr Asn Glu Lys Phe
    50                  55                  60

Lys Gly Arg Ala Thr Leu Thr Ser Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Gly Asn Asp Tyr Tyr His Thr Met Asp Tyr Trp Gly
            100                 105                 110

Gln Gly Thr Leu Val Thr Val Ser Ser
        115                 120
```

<210> SEQ ID NO 50
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="Heavy Chain of IMGN632 IgG histidine scanning variant #38"

<400> SEQUENCE: 50

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser Ser
            20                  25                  30

Ile Met His Trp Val Arg Gln Ala Pro Gly Gln Gly Leu Glu Trp Ile
        35                  40                  45

Gly Tyr Ile Lys Pro Tyr Asn Asp Gly Thr Lys Tyr Asn Glu Lys Phe
    50                  55                  60

Lys Gly Arg Ala Thr Leu Thr Ser Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Gly Asn Asp Tyr Tyr Asp His Met Asp Tyr Trp Gly
            100                 105                 110

Gln Gly Thr Leu Val Thr Val Ser Ser
        115                 120
```

<210> SEQ ID NO 51
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="Heavy Chain of IMGN632 IgG histidine scanning variant #39"

<400> SEQUENCE: 51

Gln Val Gln Leu Val Gln Ser Gly Ala Glu Val Lys Lys Pro Gly Ala
1 5 10 15

Ser Val Lys Val Ser Cys Lys Ala Ser Gly Tyr Ile Phe Thr Ser Ser
20 25 30

Ile Met His Trp Val Arg Gln Ala Pro Gly Gln Gly Leu Glu Trp Ile
35 40 45

Gly Tyr Ile Lys Pro Tyr Asn Asp Gly Thr Lys Tyr Asn Glu Lys Phe
50 55 60

Lys Gly Arg Ala Thr Leu Thr Ser Asp Arg Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Glu Gly Gly Asn Asp Tyr Tyr Asp Thr His Asp Tyr Trp Gly
100 105 110

Gln Gly Thr Leu Val Thr Val Ser Ser
115 120

<210> SEQ ID NO 52
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="Heavy Chain of IMGN632 IgG histidine scanning variant #40"

<400> SEQUENCE: 52

Gln Val Gln Leu Val Gln Ser Gly Ala Glu Val Lys Lys Pro Gly Ala
1 5 10 15

Ser Val Lys Val Ser Cys Lys Ala Ser Gly Tyr Ile Phe Thr Ser Ser
20 25 30

Ile Met His Trp Val Arg Gln Ala Pro Gly Gln Gly Leu Glu Trp Ile
35 40 45

Gly Tyr Ile Lys Pro Tyr Asn Asp Gly Thr Lys Tyr Asn Glu Lys Phe
50 55 60

Lys Gly Arg Ala Thr Leu Thr Ser Asp Arg Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Glu Gly Gly Asn Asp Tyr Tyr Asp Thr Met His Tyr Trp Gly
100 105 110

Gln Gly Thr Leu Val Thr Val Ser Ser
115 120

<210> SEQ ID NO 53
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="Heavy Chain of IMGN632 IgG histidine scanning variant #41"

<400> SEQUENCE: 53

Gln Val Gln Leu Val Gln Ser Gly Ala Glu Val Lys Lys Pro Gly Ala
1 5 10 15

Ser Val Lys Val Ser Cys Lys Ala Ser Gly Tyr Ile Phe Thr Ser Ser
20 25 30

Ile Met His Trp Val Arg Gln Ala Pro Gly Gln Gly Leu Glu Trp Ile
35 40 45

Gly Tyr Ile Lys Pro Tyr Asn Asp Gly Thr Lys Tyr Asn Glu Lys Phe
50 55 60

Lys Gly Arg Ala Thr Leu Thr Ser Asp Arg Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Glu Gly Gly Asn Asp Tyr Tyr Asp Thr Met Asp His Trp Gly
100 105 110

Gln Gly Thr Leu Val Thr Val Ser Ser
115 120

<210> SEQ ID NO 54
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="Light Chain of IMGN632 IgG histidine scanning variant #1"

<400> SEQUENCE: 54

Asp Ile Gln Met Thr Gln Ser Pro Ser Ser Leu Ser Ala Ser Val Gly
1 5 10 15

Asp Arg Val Thr Ile Thr Cys His Ala Ser Gln Asp Ile Asn Ser Tyr
20 25 30

Leu Ser Trp Phe Gln Gln Lys Pro Gly Lys Ala Pro Lys Thr Leu Ile
35 40 45

Tyr Arg Val Asn Arg Leu Val Asp Gly Val Pro Ser Arg Phe Ser Gly
50 55 60

Ser Gly Ser Gly Asn Asp Tyr Thr Leu Thr Ile Ser Ser Leu Gln Pro
65 70 75 80

Glu Asp Phe Ala Thr Tyr Tyr Cys Leu Gln Tyr Asp Ala Phe Pro Tyr
85 90 95

Thr Phe Gly Gln Gly Thr Lys Val Glu Ile Lys
100 105

<210> SEQ ID NO 55
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="Light Chain of IMGN632 IgG histidine scanning variant #2"

<400> SEQUENCE: 55

```
Asp Ile Gln Met Thr Gln Ser Pro Ser Ser Leu Ser Ala Ser Val Gly
1               5                   10                  15

Asp Arg Val Thr Ile Thr Cys Arg His Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg Val Asn Arg Leu Val Asp Gly Val Pro Ser Arg Phe Ser Gly
    50                  55                  60

Ser Gly Ser Gly Asn Asp Tyr Thr Leu Thr Ile Ser Ser Leu Gln Pro
65                  70                  75                  80

Glu Asp Phe Ala Thr Tyr Tyr Cys Leu Gln Tyr Asp Ala Phe Pro Tyr
                85                  90                  95

Thr Phe Gly Gln Gly Thr Lys Val Glu Ile Lys
            100                 105


<210> SEQ ID NO 56
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of IMGN632 IgG histidine
      scanning variant #3"

<400> SEQUENCE: 56

Asp Ile Gln Met Thr Gln Ser Pro Ser Ser Leu Ser Ala Ser Val Gly
1               5                   10                  15

Asp Arg Val Thr Ile Thr Cys Arg Ala His Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg Val Asn Arg Leu Val Asp Gly Val Pro Ser Arg Phe Ser Gly
    50                  55                  60

Ser Gly Ser Gly Asn Asp Tyr Thr Leu Thr Ile Ser Ser Leu Gln Pro
65                  70                  75                  80

Glu Asp Phe Ala Thr Tyr Tyr Cys Leu Gln Tyr Asp Ala Phe Pro Tyr
                85                  90                  95

Thr Phe Gly Gln Gly Thr Lys Val Glu Ile Lys
            100                 105


<210> SEQ ID NO 57
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of IMGN632 IgG histidine
      scanning variant #4"

<400> SEQUENCE: 57

Asp Ile Gln Met Thr Gln Ser Pro Ser Ser Leu Ser Ala Ser Val Gly
1               5                   10                  15

Asp Arg Val Thr Ile Thr Cys Arg Ala Ser His Asp Ile Asn Ser Tyr
            20                  25                  30
```

```
Leu Ser Trp Phe Gln Gln Lys Pro Gly Lys Ala Pro Lys Thr Leu Ile
        35                  40                  45

Tyr Arg Val Asn Arg Leu Val Asp Gly Val Pro Ser Arg Phe Ser Gly
    50                  55                  60

Ser Gly Ser Gly Asn Asp Tyr Thr Leu Thr Ile Ser Ser Leu Gln Pro
65                  70                  75                  80

Glu Asp Phe Ala Thr Tyr Tyr Cys Leu Gln Tyr Asp Ala Phe Pro Tyr
                85                  90                  95

Thr Phe Gly Gln Gly Thr Lys Val Glu Ile Lys
            100                 105


<210> SEQ ID NO 58
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of IMGN632 IgG histidine
      scanning variant #5"

<400> SEQUENCE: 58

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln His Ile Asn Ser Tyr
            20                  25                  30

Leu Ser Trp Phe Gln Gln Lys Pro Gly Lys Ala Pro Lys Thr Leu Ile
        35                  40                  45

Tyr Arg Val Asn Arg Leu Val Asp Gly Val Pro Ser Arg Phe Ser Gly
    50                  55                  60

Ser Gly Ser Gly Asn Asp Tyr Thr Leu Thr Ile Ser Ser Leu Gln Pro
65                  70                  75                  80

Glu Asp Phe Ala Thr Tyr Tyr Cys Leu Gln Tyr Asp Ala Phe Pro Tyr
                85                  90                  95

Thr Phe Gly Gln Gly Thr Lys Val Glu Ile Lys
            100                 105


<210> SEQ ID NO 59
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of IMGN632 IgG histidine
      scanning variant #6"

<400> SEQUENCE: 59

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp His Asn Ser Tyr
            20                  25                  30

Leu Ser Trp Phe Gln Gln Lys Pro Gly Lys Ala Pro Lys Thr Leu Ile
        35                  40                  45

Tyr Arg Val Asn Arg Leu Val Asp Gly Val Pro Ser Arg Phe Ser Gly
```

```
    50                  55                  60

Ser Gly Ser Gly Asn Asp Tyr Thr Leu Thr Ile Ser Ser Leu Gln Pro
65                  70                  75                  80

Glu Asp Phe Ala Thr Tyr Tyr Cys Leu Gln Tyr Asp Ala Phe Pro Tyr
                85                  90                  95

Thr Phe Gly Gln Gly Thr Lys Val Glu Ile Lys
            100                 105


<210> SEQ ID NO 60
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of IMGN632 IgG histidine
      scanning variant #7"

<400> SEQUENCE: 60

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile His Ser Tyr
            20                  25                  30

Leu Ser Trp Phe Gln Gln Lys Pro Gly Lys Ala Pro Lys Thr Leu Ile
        35                  40                  45

Tyr Arg Val Asn Arg Leu Val Asp Gly Val Pro Ser Arg Phe Ser Gly
    50                  55                  60

Ser Gly Ser Gly Asn Asp Tyr Thr Leu Thr Ile Ser Ser Leu Gln Pro
65                  70                  75                  80

Glu Asp Phe Ala Thr Tyr Tyr Cys Leu Gln Tyr Asp Ala Phe Pro Tyr
                85                  90                  95

Thr Phe Gly Gln Gly Thr Lys Val Glu Ile Lys
            100                 105


<210> SEQ ID NO 61
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of IMGN632 IgG histidine
      scanning variant #8"

<400> SEQUENCE: 61

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn His Tyr
            20                  25                  30

Leu Ser Trp Phe Gln Gln Lys Pro Gly Lys Ala Pro Lys Thr Leu Ile
        35                  40                  45

Tyr Arg Val Asn Arg Leu Val Asp Gly Val Pro Ser Arg Phe Ser Gly
    50                  55                  60

Ser Gly Ser Gly Asn Asp Tyr Thr Leu Thr Ile Ser Ser Leu Gln Pro
65                  70                  75                  80
```

```
Glu Asp Phe Ala Thr Tyr Tyr Cys Leu Gln Tyr Asp Ala Phe Pro Tyr
                85                  90                  95

Thr Phe Gly Gln Gly Thr Lys Val Glu Ile Lys
            100                 105


<210> SEQ ID NO 62
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of IMGN632 IgG histidine
      scanning variant #9"

<400> SEQUENCE: 62

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Ser His
            20                  25                  30

Leu Ser Trp Phe Gln Gln Lys Pro Gly Lys Ala Pro Lys Thr Leu Ile
        35                  40                  45

Tyr Arg Val Asn Arg Leu Val Asp Gly Val Pro Ser Arg Phe Ser Gly
    50                  55                  60

Ser Gly Ser Gly Asn Asp Tyr Thr Leu Thr Ile Ser Ser Leu Gln Pro
65                  70                  75                  80

Glu Asp Phe Ala Thr Tyr Tyr Cys Leu Gln Tyr Asp Ala Phe Pro Tyr
                85                  90                  95

Thr Phe Gly Gln Gly Thr Lys Val Glu Ile Lys
            100                 105


<210> SEQ ID NO 63
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of IMGN632 IgG histidine
      scanning variant #10"

<400> SEQUENCE: 63

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Ser Tyr
            20                  25                  30

His Ser Trp Phe Gln Gln Lys Pro Gly Lys Ala Pro Lys Thr Leu Ile
        35                  40                  45

Tyr Arg Val Asn Arg Leu Val Asp Gly Val Pro Ser Arg Phe Ser Gly
    50                  55                  60

Ser Gly Ser Gly Asn Asp Tyr Thr Leu Thr Ile Ser Ser Leu Gln Pro
65                  70                  75                  80

Glu Asp Phe Ala Thr Tyr Tyr Cys Leu Gln Tyr Asp Ala Phe Pro Tyr
                85                  90                  95

Thr Phe Gly Gln Gly Thr Lys Val Glu Ile Lys
            100                 105
```

<210> SEQ ID NO 64
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="Light Chain of IMGN632 IgG histidine scanning variant #11"

<400> SEQUENCE: 64

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Ser Tyr
            20                  25                  30

Leu His Trp Phe Gln Gln Lys Pro Gly Lys Ala Pro Lys Thr Leu Ile
        35                  40                  45

Tyr Arg Val Asn Arg Leu Val Asp Gly Val Pro Ser Arg Phe Ser Gly
    50                  55                  60

Ser Gly Ser Gly Asn Asp Tyr Thr Leu Thr Ile Ser Ser Leu Gln Pro
65                  70                  75                  80

Glu Asp Phe Ala Thr Tyr Tyr Cys Leu Gln Tyr Asp Ala Phe Pro Tyr
                85                  90                  95

Thr Phe Gly Gln Gly Thr Lys Val Glu Ile Lys
            100                 105
```

<210> SEQ ID NO 65
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="Light Chain of IMGN632 IgG histidine scanning variant #12"

<400> SEQUENCE: 65

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr His Val Asn Arg Leu Val Asp Gly Val Pro Ser Arg Phe Ser Gly
    50                  55                  60

Ser Gly Ser Gly Asn Asp Tyr Thr Leu Thr Ile Ser Ser Leu Gln Pro
65                  70                  75                  80

Glu Asp Phe Ala Thr Tyr Tyr Cys Leu Gln Tyr Asp Ala Phe Pro Tyr
                85                  90                  95

Thr Phe Gly Gln Gly Thr Lys Val Glu Ile Lys
            100                 105
```

<210> SEQ ID NO 66
<211> LENGTH: 107
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of IMGN632 IgG histidine
      scanning variant #13"

<400> SEQUENCE: 66

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg His Asn Arg Leu Val Asp Gly Val Pro Ser Arg Phe Ser Gly
    50                  55                  60

Ser Gly Ser Gly Asn Asp Tyr Thr Leu Thr Ile Ser Ser Leu Gln Pro
65                  70                  75                  80

Glu Asp Phe Ala Thr Tyr Tyr Cys Leu Gln Tyr Asp Ala Phe Pro Tyr
                85                  90                  95

Thr Phe Gly Gln Gly Thr Lys Val Glu Ile Lys
            100                 105


<210> SEQ ID NO 67
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of IMGN632 IgG histidine
      scanning variant #14"

<400> SEQUENCE: 67

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg Val His Arg Leu Val Asp Gly Val Pro Ser Arg Phe Ser Gly
    50                  55                  60

Ser Gly Ser Gly Asn Asp Tyr Thr Leu Thr Ile Ser Ser Leu Gln Pro
65                  70                  75                  80

Glu Asp Phe Ala Thr Tyr Tyr Cys Leu Gln Tyr Asp Ala Phe Pro Tyr
                85                  90                  95

Thr Phe Gly Gln Gly Thr Lys Val Glu Ile Lys
            100                 105


<210> SEQ ID NO 68
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

```
<220> FEATURE:
<221> NAME/KEY: source
<223> OTHER INFORMATION: /note="Light Chain of IMGN632 IgG histidine
      scanning variant #15"

<400> SEQUENCE: 68

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg Val Asn His Leu Val Asp Gly Val Pro Ser Arg Phe Ser Gly
    50                  55                  60

Ser Gly Ser Gly Asn Asp Tyr Thr Leu Thr Ile Ser Ser Leu Gln Pro
65                  70                  75                  80

Glu Asp Phe Ala Thr Tyr Tyr Cys Leu Gln Tyr Asp Ala Phe Pro Tyr
                85                  90                  95

Thr Phe Gly Gln Gly Thr Lys Val Glu Ile Lys
            100                 105


<210> SEQ ID NO 69
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of IMGN632 IgG histidine
      scanning variant #16"

<400> SEQUENCE: 69

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg Val Asn Arg His Val Asp Gly Val Pro Ser Arg Phe Ser Gly
    50                  55                  60

Ser Gly Ser Gly Asn Asp Tyr Thr Leu Thr Ile Ser Ser Leu Gln Pro
65                  70                  75                  80

Glu Asp Phe Ala Thr Tyr Tyr Cys Leu Gln Tyr Asp Ala Phe Pro Tyr
                85                  90                  95

Thr Phe Gly Gln Gly Thr Lys Val Glu Ile Lys
            100                 105


<210> SEQ ID NO 70
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of IMGN632 IgG histidine
      scanning variant #17"
```

```
<400> SEQUENCE: 70

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg Val Asn Arg Leu His Asp Gly Val Pro Ser Arg Phe Ser Gly
    50                  55                  60

Ser Gly Ser Gly Asn Asp Tyr Thr Leu Thr Ile Ser Ser Leu Gln Pro
65                  70                  75                  80

Glu Asp Phe Ala Thr Tyr Tyr Cys Leu Gln Tyr Asp Ala Phe Pro Tyr
                85                  90                  95

Thr Phe Gly Gln Gly Thr Lys Val Glu Ile Lys
            100                 105


<210> SEQ ID NO 71
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of IMGN632 IgG histidine
      scanning variant #18"

<400> SEQUENCE: 71

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg Val Asn Arg Leu Val His Gly Val Pro Ser Arg Phe Ser Gly
    50                  55                  60

Ser Gly Ser Gly Asn Asp Tyr Thr Leu Thr Ile Ser Ser Leu Gln Pro
65                  70                  75                  80

Glu Asp Phe Ala Thr Tyr Tyr Cys Leu Gln Tyr Asp Ala Phe Pro Tyr
                85                  90                  95

Thr Phe Gly Gln Gly Thr Lys Val Glu Ile Lys
            100                 105


<210> SEQ ID NO 72
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of IMGN632 IgG histidine
      scanning variant #19"

<400> SEQUENCE: 72

Asp Ile Gln Met Thr Gln Ser Pro Ser Ser Leu Ser Ala Ser Val Gly
1               5                   10                  15
```

```
Asp Arg Val Thr Ile Thr Cys Arg Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg Val Asn Arg Leu Val Asp Gly Val Pro Ser Arg Phe Ser Gly
    50                  55                  60

Ser Gly Ser Gly Asn Asp Tyr Thr Leu Thr Ile Ser Ser Leu Gln Pro
65                  70                  75                  80

Glu Asp Phe Ala Thr Tyr Tyr Cys His Gln Tyr Asp Ala Phe Pro Tyr
                85                  90                  95

Thr Phe Gly Gln Gly Thr Lys Val Glu Ile Lys
            100                 105


<210> SEQ ID NO 73
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of IMGN632 IgG histidine
      scanning variant #20"

<400> SEQUENCE: 73

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg Val Asn Arg Leu Val Asp Gly Val Pro Ser Arg Phe Ser Gly
    50                  55                  60

Ser Gly Ser Gly Asn Asp Tyr Thr Leu Thr Ile Ser Ser Leu Gln Pro
65                  70                  75                  80

Glu Asp Phe Ala Thr Tyr Tyr Cys Leu His Tyr Asp Ala Phe Pro Tyr
                85                  90                  95

Thr Phe Gly Gln Gly Thr Lys Val Glu Ile Lys
            100                 105


<210> SEQ ID NO 74
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of IMGN632 IgG histidine
      scanning variant #21"

<400> SEQUENCE: 74

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45
```

```
Tyr Arg Val Asn Arg Leu Val Asp Gly Val Pro Ser Arg Phe Ser Gly
    50                  55                  60

Ser Gly Ser Gly Asn Asp Tyr Thr Leu Thr Ile Ser Ser Leu Gln Pro
65                  70                  75                  80

Glu Asp Phe Ala Thr Tyr Tyr Cys Leu Gln His Asp Ala Phe Pro Tyr
                85                  90                  95

Thr Phe Gly Gln Gly Thr Lys Val Glu Ile Lys
            100                 105
```

<210> SEQ ID NO 75
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="Light Chain of IMGN632 IgG histidine scanning variant #22"

<400> SEQUENCE: 75

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg Val Asn Arg Leu Val Asp Gly Val Pro Ser Arg Phe Ser Gly
    50                  55                  60

Ser Gly Ser Gly Asn Asp Tyr Thr Leu Thr Ile Ser Ser Leu Gln Pro
65                  70                  75                  80

Glu Asp Phe Ala Thr Tyr Tyr Cys Leu Gln Tyr His Ala Phe Pro Tyr
                85                  90                  95

Thr Phe Gly Gln Gly Thr Lys Val Glu Ile Lys
            100                 105
```

<210> SEQ ID NO 76
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="Light Chain of IMGN632 IgG histidine scanning variant #23"

<400> SEQUENCE: 76

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg Val Asn Arg Leu Val Asp Gly Val Pro Ser Arg Phe Ser Gly
    50                  55                  60

Ser Gly Ser Gly Asn Asp Tyr Thr Leu Thr Ile Ser Ser Leu Gln Pro
```

```
65                  70                  75                  80

Glu Asp Phe Ala Thr Tyr Tyr Cys Leu Gln Tyr Asp His Phe Pro Tyr
                85                  90                  95

Thr Phe Gly Gln Gly Thr Lys Val Glu Ile Lys
            100                 105


<210> SEQ ID NO 77
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of IMGN632 IgG histidine
      scanning variant #24"

<400> SEQUENCE: 77

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg Val Asn Arg Leu Val Asp Gly Val Pro Ser Arg Phe Ser Gly
    50                  55                  60

Ser Gly Ser Gly Asn Asp Tyr Thr Leu Thr Ile Ser Ser Leu Gln Pro
65                  70                  75                  80

Glu Asp Phe Ala Thr Tyr Tyr Cys Leu Gln Tyr Asp Ala His Pro Tyr
                85                  90                  95

Thr Phe Gly Gln Gly Thr Lys Val Glu Ile Lys
            100                 105


<210> SEQ ID NO 78
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of IMGN632 IgG histidine
      scanning variant #25"

<400> SEQUENCE: 78

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg Val Asn Arg Leu Val Asp Gly Val Pro Ser Arg Phe Ser Gly
    50                  55                  60

Ser Gly Ser Gly Asn Asp Tyr Thr Leu Thr Ile Ser Ser Leu Gln Pro
65                  70                  75                  80

Glu Asp Phe Ala Thr Tyr Tyr Cys Leu Gln Tyr Asp Ala Phe His Tyr
                85                  90                  95
```

```
Thr Phe Gly Gln Gly Thr Lys Val Glu Ile Lys
            100                 105


<210> SEQ ID NO 79
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of IMGN632 IgG histidine
      scanning variant #26"

<400> SEQUENCE: 79

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg Val Asn Arg Leu Val Asp Gly Val Pro Ser Arg Phe Ser Gly
    50                  55                  60

Ser Gly Ser Gly Asn Asp Tyr Thr Leu Thr Ile Ser Ser Leu Gln Pro
65                  70                  75                  80

Glu Asp Phe Ala Thr Tyr Tyr Cys Leu Gln Tyr Asp Ala Phe Pro His
                85                  90                  95

Thr Phe Gly Gln Gly Thr Lys Val Glu Ile Lys
            100                 105


<210> SEQ ID NO 80
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of IMGN632 IgG histidine
      scanning variant #27"

<400> SEQUENCE: 80

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg Val Asn Arg Leu Val Asp Gly Val Pro Ser Arg Phe Ser Gly
    50                  55                  60

Ser Gly Ser Gly Asn Asp Tyr Thr Leu Thr Ile Ser Ser Leu Gln Pro
65                  70                  75                  80

Glu Asp Phe Ala Thr Tyr Tyr Cys Leu Gln Tyr Asp Ala Phe Pro Tyr
                85                  90                  95

His Phe Gly Gln Gly Thr Lys Val Glu Ile Lys
            100                 105


<210> SEQ ID NO 81
```

```
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain Combinations of IMGN632 IgG
      histidine scanning variant #1"

<400> SEQUENCE: 81

Gln Val Gln Leu Val Gln Ser Gly Ala Glu Val Lys Lys Pro Gly Ala
1               5                   10                  15

Ser Val Lys Val Ser Cys Lys Ala Ser Gly His Ile Phe Thr Ser Ser
            20                  25                  30

Ile Met Ala Trp Val Arg Gln Ala Pro Gly Gln Gly Leu Glu Trp Ile
        35                  40                  45

Gly Tyr Ile Lys Pro Tyr Asn Asp Gly Thr Lys Tyr Asn Glu Lys Phe
    50                  55                  60

Lys Gly Arg Ala Thr Leu Thr Ser Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Gly Asn Asp Tyr Tyr Asp Thr Met Asp Tyr Trp Gly
            100                 105                 110

Gln Gly Thr Leu Val Thr Val Ser Ser
        115                 120


<210> SEQ ID NO 82
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain Combinations of IMGN632 IgG
      histidine scanning variant #2"

<400> SEQUENCE: 82

Gln Val Gln Leu Val Gln Ser Gly Ala Glu Val Lys Lys Pro Gly Ala
1               5                   10                  15

Ser Val Lys Val Ser Cys Lys Ala Ser Gly His Ile Phe Thr Ser Ser
            20                  25                  30

Ile Met His Trp Val Arg Gln Ala Pro Gly Gln Gly Leu Glu Trp Ile
        35                  40                  45

Gly Tyr Ile Lys Pro Tyr Asn Asp Gly Thr Lys Tyr Asn Glu Lys Phe
    50                  55                  60

Lys Gly Arg Ala Thr Leu Thr Ser Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Gly Asn Asp Tyr His Asp Thr Met Asp Tyr Trp Gly
            100                 105                 110

Gln Gly Thr Leu Val Thr Val Ser Ser
        115                 120
```

```
<210> SEQ ID NO 83
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain Combinations of IMGN632 IgG
      histidine scanning variant #3"

<400> SEQUENCE: 83

Gln Val Gln Leu Val Gln Ser Gly Ala Glu Val Lys Lys Pro Gly Ala
1               5                   10                  15

Ser Val Lys Val Ser Cys Lys Ala Ser Gly His Ile Phe Thr Ser Ser
            20                  25                  30

Ile Met His Trp Val Arg Gln Ala Pro Gly Gln Gly Leu Glu Trp Ile
        35                  40                  45

Gly Tyr Ile Lys Pro Tyr Asn Asp Gly Thr Lys Tyr Asn Glu Lys Phe
    50                  55                  60

Lys Gly Arg Ala Thr Leu Thr Ser Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Gly Asn Asp Tyr Tyr Asp His Met Asp Tyr Trp Gly
            100                 105                 110

Gln Gly Thr Leu Val Thr Val Ser Ser
        115                 120


<210> SEQ ID NO 84
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain Combinations of IMGN632 IgG
      histidine scanning variant #4"

<400> SEQUENCE: 84

Gln Val Gln Leu Val Gln Ser Gly Ala Glu Val Lys Lys Pro Gly Ala
1               5                   10                  15

Ser Val Lys Val Ser Cys Lys Ala Ser Gly His Ile Phe Thr Ser Ser
            20                  25                  30

Ile Met His Trp Val Arg Gln Ala Pro Gly Gln Gly Leu Glu Trp Ile
        35                  40                  45

Gly Tyr Ile Lys Pro Tyr Asn Asp Gly Thr Lys Tyr Asn Glu Lys Phe
    50                  55                  60

Lys Gly Arg Ala Thr Leu Thr Ser Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Gly Asn Asp Tyr Tyr Asp Thr Met His Tyr Trp Gly
            100                 105                 110

Gln Gly Thr Leu Val Thr Val Ser Ser
        115                 120
```

<210> SEQ ID NO 85
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="Heavy Chain Combinations of IMGN632 IgG histidine scanning variant #5"

<400> SEQUENCE: 85

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser Ser
            20                  25                  30

Ile Met Ala Trp Val Arg Gln Ala Pro Gly Gln Gly Leu Glu Trp Ile
        35                  40                  45

Gly Tyr Ile Lys Pro Tyr Asn Asp Gly Thr Lys Tyr Asn Glu Lys Phe
    50                  55                  60

Lys Gly Arg Ala Thr Leu Thr Ser Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Gly Asn Asp Tyr His Asp Thr Met Asp Tyr Trp Gly
            100                 105                 110

Gln Gly Thr Leu Val Thr Val Ser Ser
        115                 120
```

<210> SEQ ID NO 86
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="Heavy Chain Combinations of IMGN632 IgG histidine scanning variant #6"

<400> SEQUENCE: 86

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser Ser
            20                  25                  30

Ile Met Ala Trp Val Arg Gln Ala Pro Gly Gln Gly Leu Glu Trp Ile
        35                  40                  45

Gly Tyr Ile Lys Pro Tyr Asn Asp Gly Thr Lys Tyr Asn Glu Lys Phe
    50                  55                  60

Lys Gly Arg Ala Thr Leu Thr Ser Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Gly Asn Asp Tyr Tyr Asp His Met Asp Tyr Trp Gly
            100                 105                 110

Gln Gly Thr Leu Val Thr Val Ser Ser
        115                 120
```

<210> SEQ ID NO 87
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="Heavy Chain Combinations of IMGN632 IgG histidine scanning variant #7"

<400> SEQUENCE: 87

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser Ser
            20                  25                  30

Ile Met Ala Trp Val Arg Gln Ala Pro Gly Gln Gly Leu Glu Trp Ile
        35                  40                  45

Gly Tyr Ile Lys Pro Tyr Asn Asp Gly Thr Lys Tyr Asn Glu Lys Phe
    50                  55                  60

Lys Gly Arg Ala Thr Leu Thr Ser Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Gly Asn Asp Tyr Tyr Asp Thr Met His Tyr Trp Gly
            100                 105                 110

Gln Gly Thr Leu Val Thr Val Ser Ser
        115                 120
```

<210> SEQ ID NO 88
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="Heavy Chain Combinations of IMGN632 IgG histidine scanning variant #8"

<400> SEQUENCE: 88

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser Ser
            20                  25                  30

Ile Met His Trp Val Arg Gln Ala Pro Gly Gln Gly Leu Glu Trp Ile
        35                  40                  45

Gly Tyr Ile Lys Pro Tyr Asn Asp Gly Thr Lys Tyr Asn Glu Lys Phe
    50                  55                  60

Lys Gly Arg Ala Thr Leu Thr Ser Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Gly Asn Asp Tyr His Asp His Met Asp Tyr Trp Gly
            100                 105                 110

Gln Gly Thr Leu Val Thr Val Ser Ser
```

115 120

<210> SEQ ID NO 89
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="Heavy Chain Combinations of IMGN632 IgG histidine scanning variant #9"

<400> SEQUENCE: 89

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser Ser
            20                  25                  30

Ile Met His Trp Val Arg Gln Ala Pro Gly Gln Gly Leu Glu Trp Ile
        35                  40                  45

Gly Tyr Ile Lys Pro Tyr Asn Asp Gly Thr Lys Tyr Asn Glu Lys Phe
    50                  55                  60

Lys Gly Arg Ala Thr Leu Thr Ser Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Gly Asn Asp Tyr His Asp Thr Met His Tyr Trp Gly
            100                 105                 110

Gln Gly Thr Leu Val Thr Val Ser Ser
        115                 120
```

<210> SEQ ID NO 90
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="Heavy Chain Combinations of IMGN632 IgG histidine scanning variant #10"

<400> SEQUENCE: 90

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser Ser
            20                  25                  30

Ile Met His Trp Val Arg Gln Ala Pro Gly Gln Gly Leu Glu Trp Ile
        35                  40                  45

Gly Tyr Ile Lys Pro Tyr Asn Asp Gly Thr Lys Tyr Asn Glu Lys Phe
    50                  55                  60

Lys Gly Arg Ala Thr Leu Thr Ser Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Gly Asn Asp Tyr Tyr Asp His Met His Tyr Trp Gly
            100                 105                 110
```

```
Gln Gly Thr Leu Val Thr Val Ser Ser
        115                 120


<210> SEQ ID NO 91
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain Combinations of IMGN632 IgG
      histidine scanning variant #11"

<400> SEQUENCE: 91

Gln Val Gln Leu Val Gln Ser Gly Ala Glu Val Lys Lys Pro Gly Ala
1               5                   10                  15

Ser Val Lys Val Ser Cys Lys Ala Ser Gly His Ile Phe Thr Ser Ser
            20                  25                  30

Ile Met Ala Trp Val Arg Gln Ala Pro Gly Gln Gly Leu Glu Trp Ile
        35                  40                  45

Gly Tyr Ile Lys Pro Tyr Asn Asp Gly Thr Lys Tyr Asn Glu Lys Phe
    50                  55                  60

Lys Gly Arg Ala Thr Leu Thr Ser Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Gly Asn Asp Tyr His Asp Thr Met Asp Tyr Trp Gly
            100                 105                 110

Gln Gly Thr Leu Val Thr Val Ser Ser
        115                 120


<210> SEQ ID NO 92
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain Combinations of IMGN632 IgG
      histidine scanning variant #12"

<400> SEQUENCE: 92

Gln Val Gln Leu Val Gln Ser Gly Ala Glu Val Lys Lys Pro Gly Ala
1               5                   10                  15

Ser Val Lys Val Ser Cys Lys Ala Ser Gly His Ile Phe Thr Ser Ser
            20                  25                  30

Ile Met Ala Trp Val Arg Gln Ala Pro Gly Gln Gly Leu Glu Trp Ile
        35                  40                  45

Gly Tyr Ile Lys Pro Tyr Asn Asp Gly Thr Lys Tyr Asn Glu Lys Phe
    50                  55                  60

Lys Gly Arg Ala Thr Leu Thr Ser Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Gly Asn Asp Tyr Tyr Asp His Met Asp Tyr Trp Gly
            100                 105                 110
```

Gln Gly Thr Leu Val Thr Val Ser Ser
115 120

<210> SEQ ID NO 93
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="Heavy Chain Combinations of IMGN632 IgG histidine scanning variant #13"

<400> SEQUENCE: 93

Gln Val Gln Leu Val Gln Ser Gly Ala Glu Val Lys Lys Pro Gly Ala
1 5 10 15

Ser Val Lys Val Ser Cys Lys Ala Ser Gly His Ile Phe Thr Ser Ser
20 25 30

Ile Met Ala Trp Val Arg Gln Ala Pro Gly Gln Gly Leu Glu Trp Ile
35 40 45

Gly Tyr Ile Lys Pro Tyr Asn Asp Gly Thr Lys Tyr Asn Glu Lys Phe
50 55 60

Lys Gly Arg Ala Thr Leu Thr Ser Asp Arg Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Glu Gly Gly Asn Asp Tyr Tyr Asp Thr Met His Tyr Trp Gly
100 105 110

Gln Gly Thr Leu Val Thr Val Ser Ser
115 120

<210> SEQ ID NO 94
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="Heavy Chain Combinations of IMGN632 IgG histidine scanning variant #14"

<400> SEQUENCE: 94

Gln Val Gln Leu Val Gln Ser Gly Ala Glu Val Lys Lys Pro Gly Ala
1 5 10 15

Ser Val Lys Val Ser Cys Lys Ala Ser Gly His Ile Phe Thr Ser Ser
20 25 30

Ile Met His Trp Val Arg Gln Ala Pro Gly Gln Gly Leu Glu Trp Ile
35 40 45

Gly Tyr Ile Lys Pro Tyr Asn Asp Gly Thr Lys Tyr Asn Glu Lys Phe
50 55 60

Lys Gly Arg Ala Thr Leu Thr Ser Asp Arg Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Glu Gly Gly Asn Asp Tyr His Asp His Met Asp Tyr Trp Gly

```
            100                 105                 110

Gln Gly Thr Leu Val Thr Val Ser Ser
        115                 120


<210> SEQ ID NO 95
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain Combinations of IMGN632 IgG
      histidine scanning variant #15"

<400> SEQUENCE: 95

Gln Val Gln Leu Val Gln Ser Gly Ala Glu Val Lys Lys Pro Gly Ala
1               5                   10                  15

Ser Val Lys Val Ser Cys Lys Ala Ser Gly His Ile Phe Thr Ser Ser
            20                  25                  30

Ile Met His Trp Val Arg Gln Ala Pro Gly Gln Gly Leu Glu Trp Ile
        35                  40                  45

Gly Tyr Ile Lys Pro Tyr Asn Asp Gly Thr Lys Tyr Asn Glu Lys Phe
    50                  55                  60

Lys Gly Arg Ala Thr Leu Thr Ser Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Gly Asn Asp Tyr His Asp Thr Met His Tyr Trp Gly
            100                 105                 110

Gln Gly Thr Leu Val Thr Val Ser Ser
        115                 120


<210> SEQ ID NO 96
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain Combinations of IMGN632 IgG
      histidine scanning variant #16"

<400> SEQUENCE: 96

Gln Val Gln Leu Val Gln Ser Gly Ala Glu Val Lys Lys Pro Gly Ala
1               5                   10                  15

Ser Val Lys Val Ser Cys Lys Ala Ser Gly His Ile Phe Thr Ser Ser
            20                  25                  30

Ile Met His Trp Val Arg Gln Ala Pro Gly Gln Gly Leu Glu Trp Ile
        35                  40                  45

Gly Tyr Ile Lys Pro Tyr Asn Asp Gly Thr Lys Tyr Asn Glu Lys Phe
    50                  55                  60

Lys Gly Arg Ala Thr Leu Thr Ser Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

```
Ala Arg Glu Gly Gly Asn Asp Tyr Tyr Asp His Met His Tyr Trp Gly
            100                 105                 110

Gln Gly Thr Leu Val Thr Val Ser Ser
        115                 120


<210> SEQ ID NO 97
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain Combinations of IMGN632 IgG
      histidine scanning variant #17"

<400> SEQUENCE: 97

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser Ser
            20                  25                  30

Ile Met Ala Trp Val Arg Gln Ala Pro Gly Gln Gly Leu Glu Trp Ile
        35                  40                  45

Gly Tyr Ile Lys Pro Tyr Asn Asp Gly Thr Lys Tyr Asn Glu Lys Phe
    50                  55                  60

Lys Gly Arg Ala Thr Leu Thr Ser Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Gly Asn Asp Tyr His Asp His Met Asp Tyr Trp Gly
            100                 105                 110

Gln Gly Thr Leu Val Thr Val Ser Ser
        115                 120


<210> SEQ ID NO 98
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain Combinations of IMGN632 IgG
      histidine scanning variant #18"

<400> SEQUENCE: 98

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser Ser
            20                  25                  30

Ile Met Ala Trp Val Arg Gln Ala Pro Gly Gln Gly Leu Glu Trp Ile
        35                  40                  45

Gly Tyr Ile Lys Pro Tyr Asn Asp Gly Thr Lys Tyr Asn Glu Lys Phe
    50                  55                  60

Lys Gly Arg Ala Thr Leu Thr Ser Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

```
Ala Arg Glu Gly Gly Asn Asp Tyr His Asp Thr Met His Tyr Trp Gly
            100                 105                 110

Gln Gly Thr Leu Val Thr Val Ser Ser
        115                 120


<210> SEQ ID NO 99
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain Combinations of IMGN632 IgG
      histidine scanning variant #19"

<400> SEQUENCE: 99

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser Ser
            20                  25                  30

Ile Met Ala Trp Val Arg Gln Ala Pro Gly Gln Gly Leu Glu Trp Ile
        35                  40                  45

Gly Tyr Ile Lys Pro Tyr Asn Asp Gly Thr Lys Tyr Asn Glu Lys Phe
    50                  55                  60

Lys Gly Arg Ala Thr Leu Thr Ser Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Gly Asn Asp Tyr Tyr Asp His Met His Tyr Trp Gly
            100                 105                 110

Gln Gly Thr Leu Val Thr Val Ser Ser
        115                 120


<210> SEQ ID NO 100
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain Combinations of IMGN632 IgG
      histidine scanning variant #20"

<400> SEQUENCE: 100

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser Ser
            20                  25                  30

Ile Met His Trp Val Arg Gln Ala Pro Gly Gln Gly Leu Glu Trp Ile
        35                  40                  45

Gly Tyr Ile Lys Pro Tyr Asn Asp Gly Thr Lys Tyr Asn Glu Lys Phe
    50                  55                  60

Lys Gly Arg Ala Thr Leu Thr Ser Asp Arg Ser Thr Ser Thr Ala Tyr
65                  70                  75                  80

Met Glu Leu Ser Ser Leu Arg Ser Glu Asp Thr Ala Val Tyr Tyr Cys
```

```
                85                  90                  95

Ala Arg Glu Gly Gly Asn Asp Tyr His Asp His Met His Tyr Trp Gly
            100                 105                 110

Gln Gly Thr Leu Val Thr Val Ser Ser
        115                 120


<210> SEQ ID NO 101
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of SGN-CD123A IgG"

<400> SEQUENCE: 101

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Asp Tyr
            20                  25                  30

Tyr Met Lys Trp Val Lys Gln Ala Pro Gly Gln Gly Leu Glu Trp Ile
        35                  40                  45

Gly Asp Ile Ile Pro Ser Asn Gly Ala Thr Phe Tyr Asn Gln Lys Phe
    50                  55                  60

Lys Gly Lys Ala Thr Leu Thr Val Asp Arg Ser Ile Ser Thr Ala Tyr
65                  70                  75                  80

Met His Leu Asn Arg Leu Arg Ser Asp Asp Thr Ala Val Tyr Tyr Cys
                85                  90                  95

Thr Arg Ser His Leu Leu Arg Ala Ser Trp Phe Ala Tyr Trp Gly Gln
            100                 105                 110

Gly Thr Leu Val Thr Val Ser Ser
        115                 120


<210> SEQ ID NO 102
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of SGN-CD123A IgG"

<400> SEQUENCE: 102

Asp Phe Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Lys Asn Tyr Leu Thr Trp Tyr Leu Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95
```

```
Asp Tyr Ser Tyr Pro Tyr Thr Phe Gly Gln Gly Thr Lys Leu Glu Ile
            100                 105                 110

Lys


<210> SEQ ID NO 103
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Heavy Chain CDR1 of SGN-CD123A"

<400> SEQUENCE: 103

Gly Tyr Thr Phe Thr Asp Tyr Tyr Met Lys
1               5                   10


<210> SEQ ID NO 104
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Heavy Chain CDR2 of SGN-CD123A"

<400> SEQUENCE: 104

Asp Ile Ile Pro Ser Asn Gly Ala Thr Phe Tyr Asn Gln Lys Phe Lys
1               5                   10                  15

Gly


<210> SEQ ID NO 105
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Heavy Chain CDR3 of SGN-CD123A"

<400> SEQUENCE: 105

Thr Arg Ser His Leu Leu Arg Ala Ser Trp Phe Ala Tyr
1               5                   10


<210> SEQ ID NO 106
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Light Chain CDR1 of SGN-CD123A"

<400> SEQUENCE: 106

Lys Ser Ser Gln Ser Leu Leu Asn Ser Gly Asn Gln Lys Asn Tyr Leu
1               5                   10                  15
```

Thr

<210> SEQ ID NO 107
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: source
<223> OTHER INFORMATION: /note="Light Chain CDR2 of SGN-CD123A"

<400> SEQUENCE: 107

```
Trp Ala Ser Thr Arg Glu Ser
1               5
```

<210> SEQ ID NO 108
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: source
<223> OTHER INFORMATION: /note="Light Chain CDR3 of SGN-CD123A"

<400> SEQUENCE: 108

```
Gln Asn Asp Tyr Ser Tyr Pro Tyr Thr
1               5
```

<210> SEQ ID NO 109
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="Heavy Chain of SGN-CD123A IgG histidine scanning variant #1"

<400> SEQUENCE: 109

```
Gln Val Gln Leu Val Gln Ser Gly Ala Glu Val Lys Lys Pro Gly Ala
1               5                   10                  15

Ser Val Lys Met Ser Cys Lys Ala Ser His Tyr Thr Phe Thr Asp Tyr
            20                  25                  30

Tyr Met Lys Trp Val Lys Gln Ala Pro Gly Gln Gly Leu Glu Trp Ile
        35                  40                  45

Gly Asp Ile Ile Pro Ser Asn Gly Ala Thr Phe Tyr Asn Gln Lys Phe
    50                  55                  60

Lys Gly Lys Ala Thr Leu Thr Val Asp Arg Ser Ile Ser Thr Ala Tyr
65                  70                  75                  80

Met His Leu Asn Arg Leu Arg Ser Asp Asp Thr Ala Val Tyr Tyr Cys
                85                  90                  95

Thr Arg Ser His Leu Leu Arg Ala Ser Trp Phe Ala Tyr Trp Gly Gln
            100                 105                 110

Gly Thr Leu Val Thr Val Ser Ser
        115                 120
```

<210> SEQ ID NO 110
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="Heavy Chain of SGN-CD123A IgG histidine scanning variant #2"

<400> SEQUENCE: 110

```
Gln Val Gln Leu Val Gln Ser Gly Ala Glu Val Lys Lys Pro Gly Ala
1               5                   10                  15

Ser Val Lys Met Ser Cys Lys Ala Ser Gly His Thr Phe Thr Asp Tyr
            20                  25                  30

Tyr Met Lys Trp Val Lys Gln Ala Pro Gly Gln Gly Leu Glu Trp Ile
        35                  40                  45

Gly Asp Ile Ile Pro Ser Asn Gly Ala Thr Phe Tyr Asn Gln Lys Phe
    50                  55                  60

Lys Gly Lys Ala Thr Leu Thr Val Asp Arg Ser Ile Ser Thr Ala Tyr
65                  70                  75                  80

Met His Leu Asn Arg Leu Arg Ser Asp Asp Thr Ala Val Tyr Tyr Cys
                85                  90                  95

Thr Arg Ser His Leu Leu Arg Ala Ser Trp Phe Ala Tyr Trp Gly Gln
            100                 105                 110

Gly Thr Leu Val Thr Val Ser Ser
        115                 120
```

<210> SEQ ID NO 111
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="Heavy Chain of SGN-CD123A IgG histidine scanning variant #3"

<400> SEQUENCE: 111

```
Gln Val Gln Leu Val Gln Ser Gly Ala Glu Val Lys Lys Pro Gly Ala
1               5                   10                  15

Ser Val Lys Met Ser Cys Lys Ala Ser Gly Tyr His Phe Thr Asp Tyr
            20                  25                  30

Tyr Met Lys Trp Val Lys Gln Ala Pro Gly Gln Gly Leu Glu Trp Ile
        35                  40                  45

Gly Asp Ile Ile Pro Ser Asn Gly Ala Thr Phe Tyr Asn Gln Lys Phe
    50                  55                  60

Lys Gly Lys Ala Thr Leu Thr Val Asp Arg Ser Ile Ser Thr Ala Tyr
65                  70                  75                  80

Met His Leu Asn Arg Leu Arg Ser Asp Asp Thr Ala Val Tyr Tyr Cys
                85                  90                  95

Thr Arg Ser His Leu Leu Arg Ala Ser Trp Phe Ala Tyr Trp Gly Gln
            100                 105                 110

Gly Thr Leu Val Thr Val Ser Ser
        115                 120
```

<210> SEQ ID NO 112
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="Heavy Chain of SGN-CD123A IgG histidine scanning variant #4"

<400> SEQUENCE: 112

```
Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr His Thr Asp Tyr
            20                  25                  30

Tyr Met Lys Trp Val Lys Gln Ala Pro Gly Gln Gly Leu Glu Trp Ile
        35                  40                  45

Gly Asp Ile Ile Pro Ser Asn Gly Ala Thr Phe Tyr Asn Gln Lys Phe
    50                  55                  60

Lys Gly Lys Ala Thr Leu Thr Val Asp Arg Ser Ile Ser Thr Ala Tyr
65                  70                  75                  80

Met His Leu Asn Arg Leu Arg Ser Asp Asp Thr Ala Val Tyr Tyr Cys
                85                  90                  95

Thr Arg Ser His Leu Leu Arg Ala Ser Trp Phe Ala Tyr Trp Gly Gln
            100                 105                 110

Gly Thr Leu Val Thr Val Ser Ser
        115                 120
```

<210> SEQ ID NO 113
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="Heavy Chain of SGN-CD123A IgG histidine scanning variant #5"

<400> SEQUENCE: 113

```
Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe His Asp Tyr
            20                  25                  30

Tyr Met Lys Trp Val Lys Gln Ala Pro Gly Gln Gly Leu Glu Trp Ile
        35                  40                  45

Gly Asp Ile Ile Pro Ser Asn Gly Ala Thr Phe Tyr Asn Gln Lys Phe
    50                  55                  60

Lys Gly Lys Ala Thr Leu Thr Val Asp Arg Ser Ile Ser Thr Ala Tyr
65                  70                  75                  80

Met His Leu Asn Arg Leu Arg Ser Asp Asp Thr Ala Val Tyr Tyr Cys
                85                  90                  95

Thr Arg Ser His Leu Leu Arg Ala Ser Trp Phe Ala Tyr Trp Gly Gln
            100                 105                 110

Gly Thr Leu Val Thr Val Ser Ser
```

115 120

<210> SEQ ID NO 114
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="Heavy Chain of SGN-CD123A IgG histidine scanning variant #6"

<400> SEQUENCE: 114

```
Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr His Tyr
            20                  25                  30

Tyr Met Lys Trp Val Lys Gln Ala Pro Gly Gln Gly Leu Glu Trp Ile
        35                  40                  45

Gly Asp Ile Ile Pro Ser Asn Gly Ala Thr Phe Tyr Asn Gln Lys Phe
    50                  55                  60

Lys Gly Lys Ala Thr Leu Thr Val Asp Arg Ser Ile Ser Thr Ala Tyr
65                  70                  75                  80

Met His Leu Asn Arg Leu Arg Ser Asp Asp Thr Ala Val Tyr Tyr Cys
                85                  90                  95

Thr Arg Ser His Leu Leu Arg Ala Ser Trp Phe Ala Tyr Trp Gly Gln
            100                 105                 110

Gly Thr Leu Val Thr Val Ser Ser
        115                 120
```

<210> SEQ ID NO 115
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="Heavy Chain of SGN-CD123A IgG histidine scanning variant #7"

<400> SEQUENCE: 115

```
Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Asp His
            20                  25                  30

Tyr Met Lys Trp Val Lys Gln Ala Pro Gly Gln Gly Leu Glu Trp Ile
        35                  40                  45

Gly Asp Ile Ile Pro Ser Asn Gly Ala Thr Phe Tyr Asn Gln Lys Phe
    50                  55                  60

Lys Gly Lys Ala Thr Leu Thr Val Asp Arg Ser Ile Ser Thr Ala Tyr
65                  70                  75                  80

Met His Leu Asn Arg Leu Arg Ser Asp Asp Thr Ala Val Tyr Tyr Cys
                85                  90                  95

Thr Arg Ser His Leu Leu Arg Ala Ser Trp Phe Ala Tyr Trp Gly Gln
            100                 105                 110
```

```
Gly Thr Leu Val Thr Val Ser Ser
        115                 120


<210> SEQ ID NO 116
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of SGN-CD123A IgG histidine
      scanning variant #8"

<400> SEQUENCE: 116

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Asp Tyr
            20                  25                  30

His Met Lys Trp Val Lys Gln Ala Pro Gly Gln Gly Leu Glu Trp Ile
        35                  40                  45

Gly Asp Ile Ile Pro Ser Asn Gly Ala Thr Phe Tyr Asn Gln Lys Phe
    50                  55                  60

Lys Gly Lys Ala Thr Leu Thr Val Asp Arg Ser Ile Ser Thr Ala Tyr
65                  70                  75                  80

Met His Leu Asn Arg Leu Arg Ser Asp Asp Thr Ala Val Tyr Tyr Cys
                85                  90                  95

Thr Arg Ser His Leu Leu Arg Ala Ser Trp Phe Ala Tyr Trp Gly Gln
            100                 105                 110

Gly Thr Leu Val Thr Val Ser Ser
        115                 120


<210> SEQ ID NO 117
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of SGN-CD123A IgG histidine
      scanning variant #9"

<400> SEQUENCE: 117

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Asp Tyr
            20                  25                  30

Tyr His Lys Trp Val Lys Gln Ala Pro Gly Gln Gly Leu Glu Trp Ile
        35                  40                  45

Gly Asp Ile Ile Pro Ser Asn Gly Ala Thr Phe Tyr Asn Gln Lys Phe
    50                  55                  60

Lys Gly Lys Ala Thr Leu Thr Val Asp Arg Ser Ile Ser Thr Ala Tyr
65                  70                  75                  80

Met His Leu Asn Arg Leu Arg Ser Asp Asp Thr Ala Val Tyr Tyr Cys
                85                  90                  95

Thr Arg Ser His Leu Leu Arg Ala Ser Trp Phe Ala Tyr Trp Gly Gln
            100                 105                 110
```

```
Gly Thr Leu Val Thr Val Ser Ser
        115                 120


<210> SEQ ID NO 118
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of SGN-CD123A IgG histidine
      scanning variant #10"

<400> SEQUENCE: 118

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Asp Tyr
            20                  25                  30

Tyr Met His Trp Val Lys Gln Ala Pro Gly Gln Gly Leu Glu Trp Ile
        35                  40                  45

Gly Asp Ile Ile Pro Ser Asn Gly Ala Thr Phe Tyr Asn Gln Lys Phe
    50                  55                  60

Lys Gly Lys Ala Thr Leu Thr Val Asp Arg Ser Ile Ser Thr Ala Tyr
65                  70                  75                  80

Met His Leu Asn Arg Leu Arg Ser Asp Asp Thr Ala Val Tyr Tyr Cys
                85                  90                  95

Thr Arg Ser His Leu Leu Arg Ala Ser Trp Phe Ala Tyr Trp Gly Gln
            100                 105                 110

Gly Thr Leu Val Thr Val Ser Ser
        115                 120


<210> SEQ ID NO 119
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of SGN-CD123A IgG histidine
      scanning variant #11"

<400> SEQUENCE: 119

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Asp Tyr
            20                  25                  30

Tyr Met Lys Trp Val Lys Gln Ala Pro Gly Gln Gly Leu Glu Trp Ile
        35                  40                  45

Gly His Ile Ile Pro Ser Asn Gly Ala Thr Phe Tyr Asn Gln Lys Phe
    50                  55                  60

Lys Gly Lys Ala Thr Leu Thr Val Asp Arg Ser Ile Ser Thr Ala Tyr
65                  70                  75                  80

Met His Leu Asn Arg Leu Arg Ser Asp Asp Thr Ala Val Tyr Tyr Cys
                85                  90                  95

Thr Arg Ser His Leu Leu Arg Ala Ser Trp Phe Ala Tyr Trp Gly Gln
```

```
            100                 105                 110

Gly Thr Leu Val Thr Val Ser Ser
        115                 120


<210> SEQ ID NO 120
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of SGN-CD123A IgG histidine
      scanning variant #12"

<400> SEQUENCE: 120

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Asp Tyr
            20                  25                  30

Tyr Met Lys Trp Val Lys Gln Ala Pro Gly Gln Gly Leu Glu Trp Ile
        35                  40                  45

Gly Asp His Ile Pro Ser Asn Gly Ala Thr Phe Tyr Asn Gln Lys Phe
    50                  55                  60

Lys Gly Lys Ala Thr Leu Thr Val Asp Arg Ser Ile Ser Thr Ala Tyr
65                  70                  75                  80

Met His Leu Asn Arg Leu Arg Ser Asp Asp Thr Ala Val Tyr Tyr Cys
                85                  90                  95

Thr Arg Ser His Leu Leu Arg Ala Ser Trp Phe Ala Tyr Trp Gly Gln
            100                 105                 110

Gly Thr Leu Val Thr Val Ser Ser
        115                 120


<210> SEQ ID NO 121
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of SGN-CD123A IgG histidine
      scanning variant #13"

<400> SEQUENCE: 121

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Asp Tyr
            20                  25                  30

Tyr Met Lys Trp Val Lys Gln Ala Pro Gly Gln Gly Leu Glu Trp Ile
        35                  40                  45

Gly Asp Ile His Pro Ser Asn Gly Ala Thr Phe Tyr Asn Gln Lys Phe
    50                  55                  60

Lys Gly Lys Ala Thr Leu Thr Val Asp Arg Ser Ile Ser Thr Ala Tyr
65                  70                  75                  80

Met His Leu Asn Arg Leu Arg Ser Asp Asp Thr Ala Val Tyr Tyr Cys
                85                  90                  95
```

```
Thr Arg Ser His Leu Leu Arg Ala Ser Trp Phe Ala Tyr Trp Gly Gln
            100                 105                 110

Gly Thr Leu Val Thr Val Ser Ser
        115                 120


<210> SEQ ID NO 122
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of SGN-CD123A IgG histidine
      scanning variant #14"

<400> SEQUENCE: 122

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Asp Tyr
            20                  25                  30

Tyr Met Lys Trp Val Lys Gln Ala Pro Gly Gln Gly Leu Glu Trp Ile
        35                  40                  45

Gly Asp Ile Ile His Ser Asn Gly Ala Thr Phe Tyr Asn Gln Lys Phe
    50                  55                  60

Lys Gly Lys Ala Thr Leu Thr Val Asp Arg Ser Ile Ser Thr Ala Tyr
65                  70                  75                  80

Met His Leu Asn Arg Leu Arg Ser Asp Asp Thr Ala Val Tyr Tyr Cys
                85                  90                  95

Thr Arg Ser His Leu Leu Arg Ala Ser Trp Phe Ala Tyr Trp Gly Gln
            100                 105                 110

Gly Thr Leu Val Thr Val Ser Ser
        115                 120


<210> SEQ ID NO 123
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of SGN-CD123A IgG histidine
      scanning variant #15"

<400> SEQUENCE: 123

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Asp Tyr
            20                  25                  30

Tyr Met Lys Trp Val Lys Gln Ala Pro Gly Gln Gly Leu Glu Trp Ile
        35                  40                  45

Gly Asp Ile Ile Pro His Asn Gly Ala Thr Phe Tyr Asn Gln Lys Phe
    50                  55                  60

Lys Gly Lys Ala Thr Leu Thr Val Asp Arg Ser Ile Ser Thr Ala Tyr
65                  70                  75                  80

Met His Leu Asn Arg Leu Arg Ser Asp Asp Thr Ala Val Tyr Tyr Cys
                85                  90                  95
```

```
Thr Arg Ser His Leu Leu Arg Ala Ser Trp Phe Ala Tyr Trp Gly Gln
            100                 105                 110

Gly Thr Leu Val Thr Val Ser Ser
        115                 120


<210> SEQ ID NO 124
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of SGN-CD123A IgG histidine
      scanning variant #16"

<400> SEQUENCE: 124

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Asp Tyr
            20                  25                  30

Tyr Met Lys Trp Val Lys Gln Ala Pro Gly Gln Gly Leu Glu Trp Ile
        35                  40                  45

Gly Asp Ile Ile Pro Ser His Gly Ala Thr Phe Tyr Asn Gln Lys Phe
    50                  55                  60

Lys Gly Lys Ala Thr Leu Thr Val Asp Arg Ser Ile Ser Thr Ala Tyr
65                  70                  75                  80

Met His Leu Asn Arg Leu Arg Ser Asp Asp Thr Ala Val Tyr Tyr Cys
                85                  90                  95

Thr Arg Ser His Leu Leu Arg Ala Ser Trp Phe Ala Tyr Trp Gly Gln
            100                 105                 110

Gly Thr Leu Val Thr Val Ser Ser
        115                 120


<210> SEQ ID NO 125
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of SGN-CD123A IgG histidine
      scanning variant #17"

<400> SEQUENCE: 125

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Asp Tyr
            20                  25                  30

Tyr Met Lys Trp Val Lys Gln Ala Pro Gly Gln Gly Leu Glu Trp Ile
        35                  40                  45

Gly Asp Ile Ile Pro Ser Asn His Ala Thr Phe Tyr Asn Gln Lys Phe
    50                  55                  60

Lys Gly Lys Ala Thr Leu Thr Val Asp Arg Ser Ile Ser Thr Ala Tyr
65                  70                  75                  80

Met His Leu Asn Arg Leu Arg Ser Asp Asp Thr Ala Val Tyr Tyr Cys
```

```
                85                  90                  95

Thr Arg Ser His Leu Leu Arg Ala Ser Trp Phe Ala Tyr Trp Gly Gln
            100                 105                 110

Gly Thr Leu Val Thr Val Ser Ser
        115                 120


<210> SEQ ID NO 126
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of SGN-CD123A IgG histidine
      scanning variant #18"

<400> SEQUENCE: 126

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Asp Tyr
            20                  25                  30

Tyr Met Lys Trp Val Lys Gln Ala Pro Gly Gln Gly Leu Glu Trp Ile
        35                  40                  45

Gly Asp Ile Ile Pro Ser Asn Gly His Thr Phe Tyr Asn Gln Lys Phe
    50                  55                  60

Lys Gly Lys Ala Thr Leu Thr Val Asp Arg Ser Ile Ser Thr Ala Tyr
65                  70                  75                  80

Met His Leu Asn Arg Leu Arg Ser Asp Asp Thr Ala Val Tyr Tyr Cys
                85                  90                  95

Thr Arg Ser His Leu Leu Arg Ala Ser Trp Phe Ala Tyr Trp Gly Gln
            100                 105                 110

Gly Thr Leu Val Thr Val Ser Ser
        115                 120


<210> SEQ ID NO 127
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of SGN-CD123A IgG histidine
      scanning variant #19"

<400> SEQUENCE: 127

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Asp Tyr
            20                  25                  30

Tyr Met Lys Trp Val Lys Gln Ala Pro Gly Gln Gly Leu Glu Trp Ile
        35                  40                  45

Gly Asp Ile Ile Pro Ser Asn Gly Ala His Phe Tyr Asn Gln Lys Phe
    50                  55                  60

Lys Gly Lys Ala Thr Leu Thr Val Asp Arg Ser Ile Ser Thr Ala Tyr
65                  70                  75                  80
```

```
Met His Leu Asn Arg Leu Arg Ser Asp Asp Thr Ala Val Tyr Tyr Cys
                85                  90                  95

Thr Arg Ser His Leu Leu Arg Ala Ser Trp Phe Ala Tyr Trp Gly Gln
            100                 105                 110

Gly Thr Leu Val Thr Val Ser Ser
        115                 120


<210> SEQ ID NO 128
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of SGN-CD123A IgG histidine
      scanning variant #20"

<400> SEQUENCE: 128

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Asp Tyr
            20                  25                  30

Tyr Met Lys Trp Val Lys Gln Ala Pro Gly Gln Gly Leu Glu Trp Ile
        35                  40                  45

Gly Asp Ile Ile Pro Ser Asn Gly Ala Thr His Tyr Asn Gln Lys Phe
    50                  55                  60

Lys Gly Lys Ala Thr Leu Thr Val Asp Arg Ser Ile Ser Thr Ala Tyr
65                  70                  75                  80

Met His Leu Asn Arg Leu Arg Ser Asp Asp Thr Ala Val Tyr Tyr Cys
                85                  90                  95

Thr Arg Ser His Leu Leu Arg Ala Ser Trp Phe Ala Tyr Trp Gly Gln
            100                 105                 110

Gly Thr Leu Val Thr Val Ser Ser
        115                 120


<210> SEQ ID NO 129
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of SGN-CD123A IgG histidine
      scanning variant #21"

<400> SEQUENCE: 129

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Asp Tyr
            20                  25                  30

Tyr Met Lys Trp Val Lys Gln Ala Pro Gly Gln Gly Leu Glu Trp Ile
        35                  40                  45

Gly Asp Ile Ile Pro Ser Asn Gly Ala Thr Phe His Asn Gln Lys Phe
    50                  55                  60

Lys Gly Lys Ala Thr Leu Thr Val Asp Arg Ser Ile Ser Thr Ala Tyr
65                  70                  75                  80
```

```
Met His Leu Asn Arg Leu Arg Ser Asp Asp Thr Ala Val Tyr Tyr Cys
                85                  90                  95

Thr Arg Ser His Leu Leu Arg Ala Ser Trp Phe Ala Tyr Trp Gly Gln
            100                 105                 110

Gly Thr Leu Val Thr Val Ser Ser
        115                 120
```

<210> SEQ ID NO 130
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="Heavy Chain of SGN-CD123A IgG histidine scanning variant #22"

<400> SEQUENCE: 130

```
Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Asp Tyr
            20                  25                  30

Tyr Met Lys Trp Val Lys Gln Ala Pro Gly Gln Gly Leu Glu Trp Ile
        35                  40                  45

Gly Asp Ile Ile Pro Ser Asn Gly Ala Thr Phe Tyr His Gln Lys Phe
    50                  55                  60

Lys Gly Lys Ala Thr Leu Thr Val Asp Arg Ser Ile Ser Thr Ala Tyr
65                  70                  75                  80

Met His Leu Asn Arg Leu Arg Ser Asp Asp Thr Ala Val Tyr Tyr Cys
                85                  90                  95

Thr Arg Ser His Leu Leu Arg Ala Ser Trp Phe Ala Tyr Trp Gly Gln
            100                 105                 110

Gly Thr Leu Val Thr Val Ser Ser
        115                 120
```

<210> SEQ ID NO 131
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="Heavy Chain of SGN-CD123A IgG histidine scanning variant #23"

<400> SEQUENCE: 131

```
Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Asp Tyr
            20                  25                  30

Tyr Met Lys Trp Val Lys Gln Ala Pro Gly Gln Gly Leu Glu Trp Ile
        35                  40                  45

Gly Asp Ile Ile Pro Ser Asn Gly Ala Thr Phe Tyr Asn His Lys Phe
    50                  55                  60

Lys Gly Lys Ala Thr Leu Thr Val Asp Arg Ser Ile Ser Thr Ala Tyr
```

```
65                  70                  75                  80

Met His Leu Asn Arg Leu Arg Ser Asp Asp Thr Ala Val Tyr Tyr Cys
                85                  90                  95

Thr Arg Ser His Leu Leu Arg Ala Ser Trp Phe Ala Tyr Trp Gly Gln
            100                 105                 110

Gly Thr Leu Val Thr Val Ser Ser
        115                 120


<210> SEQ ID NO 132
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of SGN-CD123A IgG histidine
      scanning variant #24"

<400> SEQUENCE: 132

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Asp Tyr
            20                  25                  30

Tyr Met Lys Trp Val Lys Gln Ala Pro Gly Gln Gly Leu Glu Trp Ile
        35                  40                  45

Gly Asp Ile Ile Pro Ser Asn Gly Ala Thr Phe Tyr Asn Gln His Phe
    50                  55                  60

Lys Gly Lys Ala Thr Leu Thr Val Asp Arg Ser Ile Ser Thr Ala Tyr
65                  70                  75                  80

Met His Leu Asn Arg Leu Arg Ser Asp Asp Thr Ala Val Tyr Tyr Cys
                85                  90                  95

Thr Arg Ser His Leu Leu Arg Ala Ser Trp Phe Ala Tyr Trp Gly Gln
            100                 105                 110

Gly Thr Leu Val Thr Val Ser Ser
        115                 120


<210> SEQ ID NO 133
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of SGN-CD123A IgG histidine
      scanning variant #25"

<400> SEQUENCE: 133

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Asp Tyr
            20                  25                  30

Tyr Met Lys Trp Val Lys Gln Ala Pro Gly Gln Gly Leu Glu Trp Ile
        35                  40                  45

Gly Asp Ile Ile Pro Ser Asn Gly Ala Thr Phe Tyr Asn Gln Lys His
    50                  55                  60
```

```
Lys Gly Lys Ala Thr Leu Thr Val Asp Arg Ser Ile Ser Thr Ala Tyr
65                  70                  75                  80

Met His Leu Asn Arg Leu Arg Ser Asp Asp Thr Ala Val Tyr Tyr Cys
                85                  90                  95

Thr Arg Ser His Leu Leu Arg Ala Ser Trp Phe Ala Tyr Trp Gly Gln
            100                 105                 110

Gly Thr Leu Val Thr Val Ser Ser
        115                 120


<210> SEQ ID NO 134
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of SGN-CD123A IgG histidine
      scanning variant #26"

<400> SEQUENCE: 134

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Asp Tyr
            20                  25                  30

Tyr Met Lys Trp Val Lys Gln Ala Pro Gly Gln Gly Leu Glu Trp Ile
        35                  40                  45

Gly Asp Ile Ile Pro Ser Asn Gly Ala Thr Phe Tyr Asn Gln Lys Phe
    50                  55                  60

His Gly Lys Ala Thr Leu Thr Val Asp Arg Ser Ile Ser Thr Ala Tyr
65                  70                  75                  80

Met His Leu Asn Arg Leu Arg Ser Asp Asp Thr Ala Val Tyr Tyr Cys
                85                  90                  95

Thr Arg Ser His Leu Leu Arg Ala Ser Trp Phe Ala Tyr Trp Gly Gln
            100                 105                 110

Gly Thr Leu Val Thr Val Ser Ser
        115                 120


<210> SEQ ID NO 135
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of SGN-CD123A IgG histidine
      scanning variant #27"

<400> SEQUENCE: 135

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Asp Tyr
            20                  25                  30

Tyr Met Lys Trp Val Lys Gln Ala Pro Gly Gln Gly Leu Glu Trp Ile
        35                  40                  45

Gly Asp Ile Ile Pro Ser Asn Gly Ala Thr Phe Tyr Asn Gln Lys Phe
    50                  55                  60
```

```
Lys His Lys Ala Thr Leu Thr Val Asp Arg Ser Ile Ser Thr Ala Tyr
65                  70                  75                  80

Met His Leu Asn Arg Leu Arg Ser Asp Asp Thr Ala Val Tyr Tyr Cys
                85                  90                  95

Thr Arg Ser His Leu Leu Arg Ala Ser Trp Phe Ala Tyr Trp Gly Gln
            100                 105                 110

Gly Thr Leu Val Thr Val Ser Ser
        115                 120


<210> SEQ ID NO 136
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of SGN-CD123A IgG histidine
      scanning variant #28"

<400> SEQUENCE: 136

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Asp Tyr
            20                  25                  30

Tyr Met Lys Trp Val Lys Gln Ala Pro Gly Gln Gly Leu Glu Trp Ile
        35                  40                  45

Gly Asp Ile Ile Pro Ser Asn Gly Ala Thr Phe Tyr Asn Gln Lys Phe
    50                  55                  60

Lys Gly Lys Ala Thr Leu Thr Val Asp Arg Ser Ile Ser Thr Ala Tyr
65                  70                  75                  80

Met His Leu Asn Arg Leu Arg Ser Asp Asp Thr Ala Val Tyr Tyr Cys
                85                  90                  95

His Arg Ser His Leu Leu Arg Ala Ser Trp Phe Ala Tyr Trp Gly Gln
            100                 105                 110

Gly Thr Leu Val Thr Val Ser Ser
        115                 120


<210> SEQ ID NO 137
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of SGN-CD123A IgG histidine
      scanning variant #29"

<400> SEQUENCE: 137

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Asp Tyr
            20                  25                  30

Tyr Met Lys Trp Val Lys Gln Ala Pro Gly Gln Gly Leu Glu Trp Ile
        35                  40                  45

Gly Asp Ile Ile Pro Ser Asn Gly Ala Thr Phe Tyr Asn Gln Lys Phe
```

```
    50                  55                  60

Lys Gly Lys Ala Thr Leu Thr Val Asp Arg Ser Ile Ser Thr Ala Tyr
65                  70                  75                  80

Met His Leu Asn Arg Leu Arg Ser Asp Asp Thr Ala Val Tyr Tyr Cys
                85                  90                  95

Thr His Ser His Leu Leu Arg Ala Ser Trp Phe Ala Tyr Trp Gly Gln
            100                 105                 110

Gly Thr Leu Val Thr Val Ser Ser
        115                 120


<210> SEQ ID NO 138
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of SGN-CD123A IgG histidine
      scanning variant #30"

<400> SEQUENCE: 138

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Asp Tyr
            20                  25                  30

Tyr Met Lys Trp Val Lys Gln Ala Pro Gly Gln Gly Leu Glu Trp Ile
        35                  40                  45

Gly Asp Ile Ile Pro Ser Asn Gly Ala Thr Phe Tyr Asn Gln Lys Phe
    50                  55                  60

Lys Gly Lys Ala Thr Leu Thr Val Asp Arg Ser Ile Ser Thr Ala Tyr
65                  70                  75                  80

Met His Leu Asn Arg Leu Arg Ser Asp Asp Thr Ala Val Tyr Tyr Cys
                85                  90                  95

Thr Arg His His Leu Leu Arg Ala Ser Trp Phe Ala Tyr Trp Gly Gln
            100                 105                 110

Gly Thr Leu Val Thr Val Ser Ser
        115                 120


<210> SEQ ID NO 139
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of SGN-CD123A IgG histidine
      scanning variant #31"

<400> SEQUENCE: 139

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Asp Tyr
            20                  25                  30

Tyr Met Lys Trp Val Lys Gln Ala Pro Gly Gln Gly Leu Glu Trp Ile
        35                  40                  45
```

```
Gly Asp Ile Ile Pro Ser Asn Gly Ala Thr Phe Tyr Asn Gln Lys Phe
    50                  55                  60

Lys Gly Lys Ala Thr Leu Thr Val Asp Arg Ser Ile Ser Thr Ala Tyr
65                  70                  75                  80

Met His Leu Asn Arg Leu Arg Ser Asp Asp Thr Ala Val Tyr Tyr Cys
                85                  90                  95

Thr Arg Ser Ala Leu Leu Arg Ala Ser Trp Phe Ala Tyr Trp Gly Gln
            100                 105                 110

Gly Thr Leu Val Thr Val Ser Ser
        115                 120
```

<210> SEQ ID NO 140
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="Heavy Chain of SGN-CD123A IgG histidine scanning variant #32"

<400> SEQUENCE: 140

```
Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Asp Tyr
            20                  25                  30

Tyr Met Lys Trp Val Lys Gln Ala Pro Gly Gln Gly Leu Glu Trp Ile
        35                  40                  45

Gly Asp Ile Ile Pro Ser Asn Gly Ala Thr Phe Tyr Asn Gln Lys Phe
    50                  55                  60

Lys Gly Lys Ala Thr Leu Thr Val Asp Arg Ser Ile Ser Thr Ala Tyr
65                  70                  75                  80

Met His Leu Asn Arg Leu Arg Ser Asp Asp Thr Ala Val Tyr Tyr Cys
                85                  90                  95

Thr Arg Ser His His Leu Arg Ala Ser Trp Phe Ala Tyr Trp Gly Gln
            100                 105                 110

Gly Thr Leu Val Thr Val Ser Ser
        115                 120
```

<210> SEQ ID NO 141
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="Heavy Chain of SGN-CD123A IgG histidine scanning variant #33"

<400> SEQUENCE: 141

```
Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Asp Tyr
            20                  25                  30

Tyr Met Lys Trp Val Lys Gln Ala Pro Gly Gln Gly Leu Glu Trp Ile
        35                  40                  45
```

```
Gly Asp Ile Ile Pro Ser Asn Gly Ala Thr Phe Tyr Asn Gln Lys Phe
    50                  55                  60

Lys Gly Lys Ala Thr Leu Thr Val Asp Arg Ser Ile Ser Thr Ala Tyr
65                  70                  75                  80

Met His Leu Asn Arg Leu Arg Ser Asp Asp Thr Ala Val Tyr Tyr Cys
                85                  90                  95

Thr Arg Ser His Leu His Arg Ala Ser Trp Phe Ala Tyr Trp Gly Gln
            100                 105                 110

Gly Thr Leu Val Thr Val Ser Ser
        115                 120


<210> SEQ ID NO 142
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of SGN-CD123A IgG histidine
      scanning variant #34"

<400> SEQUENCE: 142

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Asp Tyr
            20                  25                  30

Tyr Met Lys Trp Val Lys Gln Ala Pro Gly Gln Gly Leu Glu Trp Ile
        35                  40                  45

Gly Asp Ile Ile Pro Ser Asn Gly Ala Thr Phe Tyr Asn Gln Lys Phe
    50                  55                  60

Lys Gly Lys Ala Thr Leu Thr Val Asp Arg Ser Ile Ser Thr Ala Tyr
65                  70                  75                  80

Met His Leu Asn Arg Leu Arg Ser Asp Asp Thr Ala Val Tyr Tyr Cys
                85                  90                  95

Thr Arg Ser His Leu Leu His Ala Ser Trp Phe Ala Tyr Trp Gly Gln
            100                 105                 110

Gly Thr Leu Val Thr Val Ser Ser
        115                 120


<210> SEQ ID NO 143
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of SGN-CD123A IgG histidine
      scanning variant #35"

<400> SEQUENCE: 143

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Asp Tyr
            20                  25                  30

Tyr Met Lys Trp Val Lys Gln Ala Pro Gly Gln Gly Leu Glu Trp Ile
```

```
        35                  40                  45

Gly Asp Ile Ile Pro Ser Asn Gly Ala Thr Phe Tyr Asn Gln Lys Phe
    50                  55                  60

Lys Gly Lys Ala Thr Leu Thr Val Asp Arg Ser Ile Ser Thr Ala Tyr
65                  70                  75                  80

Met His Leu Asn Arg Leu Arg Ser Asp Asp Thr Ala Val Tyr Tyr Cys
                85                  90                  95

Thr Arg Ser His Leu Leu Arg His Ser Trp Phe Ala Tyr Trp Gly Gln
            100                 105                 110

Gly Thr Leu Val Thr Val Ser Ser
        115                 120


<210> SEQ ID NO 144
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of SGN-CD123A IgG histidine
      scanning variant #36"

<400> SEQUENCE: 144

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Asp Tyr
            20                  25                  30

Tyr Met Lys Trp Val Lys Gln Ala Pro Gly Gln Gly Leu Glu Trp Ile
        35                  40                  45

Gly Asp Ile Ile Pro Ser Asn Gly Ala Thr Phe Tyr Asn Gln Lys Phe
    50                  55                  60

Lys Gly Lys Ala Thr Leu Thr Val Asp Arg Ser Ile Ser Thr Ala Tyr
65                  70                  75                  80

Met His Leu Asn Arg Leu Arg Ser Asp Asp Thr Ala Val Tyr Tyr Cys
                85                  90                  95

Thr Arg Ser His Leu Leu Arg Ala His Trp Phe Ala Tyr Trp Gly Gln
            100                 105                 110

Gly Thr Leu Val Thr Val Ser Ser
        115                 120


<210> SEQ ID NO 145
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of SGN-CD123A IgG histidine
      scanning variant #37"

<400> SEQUENCE: 145

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Asp Tyr
            20                  25                  30
```

```
Tyr Met Lys Trp Val Lys Gln Ala Pro Gly Gln Gly Leu Glu Trp Ile
        35                  40                  45

Gly Asp Ile Ile Pro Ser Asn Gly Ala Thr Phe Tyr Asn Gln Lys Phe
    50                  55                  60

Lys Gly Lys Ala Thr Leu Thr Val Asp Arg Ser Ile Ser Thr Ala Tyr
65                  70                  75                  80

Met His Leu Asn Arg Leu Arg Ser Asp Asp Thr Ala Val Tyr Tyr Cys
                85                  90                  95

Thr Arg Ser His Leu Leu Arg Ala Ser His Phe Ala Tyr Trp Gly Gln
            100                 105                 110

Gly Thr Leu Val Thr Val Ser Ser
        115                 120


<210> SEQ ID NO 146
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of SGN-CD123A IgG histidine
      scanning variant #38"

<400> SEQUENCE: 146

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Asp Tyr
            20                  25                  30

Tyr Met Lys Trp Val Lys Gln Ala Pro Gly Gln Gly Leu Glu Trp Ile
        35                  40                  45

Gly Asp Ile Ile Pro Ser Asn Gly Ala Thr Phe Tyr Asn Gln Lys Phe
    50                  55                  60

Lys Gly Lys Ala Thr Leu Thr Val Asp Arg Ser Ile Ser Thr Ala Tyr
65                  70                  75                  80

Met His Leu Asn Arg Leu Arg Ser Asp Asp Thr Ala Val Tyr Tyr Cys
                85                  90                  95

Thr Arg Ser His Leu Leu Arg Ala Ser Trp His Ala Tyr Trp Gly Gln
            100                 105                 110

Gly Thr Leu Val Thr Val Ser Ser
        115                 120


<210> SEQ ID NO 147
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of SGN-CD123A IgG histidine
      scanning variant #39"

<400> SEQUENCE: 147

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Asp Tyr
            20                  25                  30
```

```
Tyr Met Lys Trp Val Lys Gln Ala Pro Gly Gln Gly Leu Glu Trp Ile
        35                  40                  45

Gly Asp Ile Ile Pro Ser Asn Gly Ala Thr Phe Tyr Asn Gln Lys Phe
    50                  55                  60

Lys Gly Lys Ala Thr Leu Thr Val Asp Arg Ser Ile Ser Thr Ala Tyr
65                  70                  75                  80

Met His Leu Asn Arg Leu Arg Ser Asp Asp Thr Ala Val Tyr Tyr Cys
                85                  90                  95

Thr Arg Ser His Leu Leu Arg Ala Ser Trp Phe His Tyr Trp Gly Gln
            100                 105                 110

Gly Thr Leu Val Thr Val Ser Ser
        115                 120


<210> SEQ ID NO 148
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of SGN-CD123A IgG histidine
      scanning variant #40"

<400> SEQUENCE: 148

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Thr Phe Thr Asp Tyr
            20                  25                  30

Tyr Met Lys Trp Val Lys Gln Ala Pro Gly Gln Gly Leu Glu Trp Ile
        35                  40                  45

Gly Asp Ile Ile Pro Ser Asn Gly Ala Thr Phe Tyr Asn Gln Lys Phe
    50                  55                  60

Lys Gly Lys Ala Thr Leu Thr Val Asp Arg Ser Ile Ser Thr Ala Tyr
65                  70                  75                  80

Met His Leu Asn Arg Leu Arg Ser Asp Asp Thr Ala Val Tyr Tyr Cys
                85                  90                  95

Thr Arg Ser His Leu Leu Arg Ala Ser Trp Phe Ala His Trp Gly Gln
            100                 105                 110

Gly Thr Leu Val Thr Val Ser Ser
        115                 120


<210> SEQ ID NO 149
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of TPP-8988 IgG"

<400> SEQUENCE: 149

Glu Val Gln Leu Leu Glu Ser Gly Gly Gly Leu Val Gln Pro Gly Gly
1               5                   10                  15

Ser Leu Arg Leu Ser Cys Ala Val Ser Asp Tyr Ser Ile Thr Ser Gly
            20                  25                  30
```

```
Tyr Tyr Trp Asn Trp Ile Arg Gln Ala Pro Gly Lys Lys Leu Glu Trp
        35                  40                  45

Met Gly Tyr Ile Ser Tyr Asp Gly Ser Asn Asn Tyr Asn Pro Ser Leu
    50                  55                  60

Lys Asn Gly Arg Ile Thr Ile Ser Arg Asp Thr Ser Lys Asn Thr Phe
65                  70                  75                  80

Tyr Leu Gln Met Asn Ser Leu Arg Ala Glu Asp Thr Ala Val Tyr Tyr
                85                  90                  95

Cys Ala Arg Gly Glu Gly Phe Tyr Phe Asp Ser Trp Gly Gln Gly Thr
            100                 105                 110

Leu Val Thr Val Ser Ser
        115
```

```
<210> SEQ ID NO 150
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of TPP-8988 IgG"

<400> SEQUENCE: 150

Glu Ile Val Leu Thr Gln Ser Pro Gly Thr Leu Ser Leu Ser Pro Gly
1               5                   10                  15

Glu Arg Ala Thr Leu Ser Cys Lys Ser Ser Gln Ser Leu Phe Phe Gly
            20                  25                  30

Ser Thr Gln Lys Asn Tyr Leu Ala Trp Tyr Gln Gln Lys Pro Gly Gln
        35                  40                  45

Ala Pro Arg Leu Leu Ile Tyr Trp Ala Ser Thr Arg Glu Ser Gly Ile
    50                  55                  60

Pro Asp Arg Phe Ser Gly Ser Gly Ser Gly Thr Asp Phe Thr Leu Thr
65                  70                  75                  80

Ile Ser Arg Leu Glu Pro Glu Asp Phe Ala Val Tyr Tyr Cys Gln Gln
                85                  90                  95

Tyr Tyr Asn Tyr Pro Trp Thr Phe Gly Gln Gly Thr Lys Leu Glu Ile
            100                 105                 110

Lys
```

```
<210> SEQ ID NO 151
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Heavy Chain CDR1 of TPP-8988"

<400> SEQUENCE: 151

Ala Val Ser Asp Tyr Ser Ile Thr Ser Gly Tyr Tyr Trp Asn
1               5                   10
```

```
<210> SEQ ID NO 152
<211> LENGTH: 17
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Heavy Chain CDR2 of TPP-8988"

<400> SEQUENCE: 152

Tyr Ile Ser Tyr Asp Gly Ser Asn Asn Tyr Asn Pro Ser Leu Lys Asn
1               5                   10                  15

Gly


<210> SEQ ID NO 153
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Heavy Chain CDR3 of TPP-8988"

<400> SEQUENCE: 153

Ala Arg Gly Glu Gly Phe Tyr Phe Asp Ser
1               5                   10


<210> SEQ ID NO 154
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Light Chain CDR1 of TPP-8988"

<400> SEQUENCE: 154

Gln Ser Leu Phe Phe Gly Ser Thr Gln Lys Asn Tyr Leu Ala
1               5                   10


<210> SEQ ID NO 155
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="Light Chain CDR2 of TPP-8988"

<400> SEQUENCE: 155

Trp Ala Ser Thr Arg Glu Ser
1               5


<210> SEQ ID NO 156
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<220> FEATURE:
<221> NAME/KEY: source
<223> OTHER INFORMATION: /note="Light Chain CDR3 of TPP-8988"

<400> SEQUENCE: 156

Gln Gln Tyr Tyr Asn Tyr Pro Trp Thr
1 5

<210> SEQ ID NO 157
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="Heavy Chain of TPP-8988 IgG histidine scanning variant #1"

<400> SEQUENCE: 157

Glu Val Gln Leu Leu Glu Ser Gly Gly Gly Leu Val Gln Pro Gly Gly
1 5 10 15

Ser Leu Arg Leu Ser Cys His Val Ser Asp Tyr Ser Ile Thr Ser Gly
20 25 30

Tyr Tyr Trp Asn Trp Ile Arg Gln Ala Pro Gly Lys Lys Leu Glu Trp
35 40 45

Met Gly Tyr Ile Ser Tyr Asp Gly Ser Asn Asn Tyr Asn Pro Ser Leu
50 55 60

Lys Asn Gly Arg Ile Thr Ile Ser Arg Asp Thr Ser Lys Asn Thr Phe
65 70 75 80

Tyr Leu Gln Met Asn Ser Leu Arg Ala Glu Asp Thr Ala Val Tyr Tyr
85 90 95

Cys Ala Arg Gly Glu Gly Phe Tyr Phe Asp Ser Trp Gly Gln Gly Thr
100 105 110

Leu Val Thr Val Ser Ser
115

<210> SEQ ID NO 158
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="Heavy Chain of TPP-8988 IgG histidine scanning variant #2"

<400> SEQUENCE: 158

Glu Val Gln Leu Leu Glu Ser Gly Gly Gly Leu Val Gln Pro Gly Gly
1 5 10 15

Ser Leu Arg Leu Ser Cys Ala His Ser Asp Tyr Ser Ile Thr Ser Gly
20 25 30

Tyr Tyr Trp Asn Trp Ile Arg Gln Ala Pro Gly Lys Lys Leu Glu Trp
35 40 45

Met Gly Tyr Ile Ser Tyr Asp Gly Ser Asn Asn Tyr Asn Pro Ser Leu
50 55 60

Lys Asn Gly Arg Ile Thr Ile Ser Arg Asp Thr Ser Lys Asn Thr Phe
65 70 75 80

```
Tyr Leu Gln Met Asn Ser Leu Arg Ala Glu Asp Thr Ala Val Tyr Tyr
                85                  90                  95

Cys Ala Arg Gly Glu Gly Phe Tyr Phe Asp Ser Trp Gly Gln Gly Thr
            100                 105                 110

Leu Val Thr Val Ser Ser
        115


<210> SEQ ID NO 159
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of TPP-8988 IgG histidine
      scanning variant #3"

<400> SEQUENCE: 159

Glu Val Gln Leu Leu Glu Ser Gly Gly Gly Leu Val Gln Pro Gly Gly
1               5                   10                  15

Ser Leu Arg Leu Ser Cys Ala Val His Asp Tyr Ser Ile Thr Ser Gly
            20                  25                  30

Tyr Tyr Trp Asn Trp Ile Arg Gln Ala Pro Gly Lys Lys Leu Glu Trp
        35                  40                  45

Met Gly Tyr Ile Ser Tyr Asp Gly Ser Asn Asn Tyr Asn Pro Ser Leu
    50                  55                  60

Lys Asn Gly Arg Ile Thr Ile Ser Arg Asp Thr Ser Lys Asn Thr Phe
65                  70                  75                  80

Tyr Leu Gln Met Asn Ser Leu Arg Ala Glu Asp Thr Ala Val Tyr Tyr
                85                  90                  95

Cys Ala Arg Gly Glu Gly Phe Tyr Phe Asp Ser Trp Gly Gln Gly Thr
            100                 105                 110

Leu Val Thr Val Ser Ser
        115


<210> SEQ ID NO 160
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of TPP-8988 IgG histidine
      scanning variant #4"

<400> SEQUENCE: 160

Glu Val Gln Leu Leu Glu Ser Gly Gly Gly Leu Val Gln Pro Gly Gly
1               5                   10                  15

Ser Leu Arg Leu Ser Cys Ala Val Ser His Tyr Ser Ile Thr Ser Gly
            20                  25                  30

Tyr Tyr Trp Asn Trp Ile Arg Gln Ala Pro Gly Lys Lys Leu Glu Trp
        35                  40                  45

Met Gly Tyr Ile Ser Tyr Asp Gly Ser Asn Asn Tyr Asn Pro Ser Leu
    50                  55                  60

Lys Asn Gly Arg Ile Thr Ile Ser Arg Asp Thr Ser Lys Asn Thr Phe
```

65 70 75 80

Tyr Leu Gln Met Asn Ser Leu Arg Ala Glu Asp Thr Ala Val Tyr Tyr
85 90 95

Cys Ala Arg Gly Glu Gly Phe Tyr Phe Asp Ser Trp Gly Gln Gly Thr
100 105 110

Leu Val Thr Val Ser Ser
115

<210> SEQ ID NO 161
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="Heavy Chain of TPP-8988 IgG histidine scanning variant #5"

<400> SEQUENCE: 161

Glu Val Gln Leu Leu Glu Ser Gly Gly Gly Leu Val Gln Pro Gly Gly
1 5 10 15

Ser Leu Arg Leu Ser Cys Ala Val Ser Asp His Ser Ile Thr Ser Gly
20 25 30

Tyr Tyr Trp Asn Trp Ile Arg Gln Ala Pro Gly Lys Lys Leu Glu Trp
35 40 45

Met Gly Tyr Ile Ser Tyr Asp Gly Ser Asn Asn Tyr Asn Pro Ser Leu
50 55 60

Lys Asn Gly Arg Ile Thr Ile Ser Arg Asp Thr Ser Lys Asn Thr Phe
65 70 75 80

Tyr Leu Gln Met Asn Ser Leu Arg Ala Glu Asp Thr Ala Val Tyr Tyr
85 90 95

Cys Ala Arg Gly Glu Gly Phe Tyr Phe Asp Ser Trp Gly Gln Gly Thr
100 105 110

Leu Val Thr Val Ser Ser
115

<210> SEQ ID NO 162
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="Heavy Chain of TPP-8988 IgG histidine scanning variant #6"

<400> SEQUENCE: 162

Glu Val Gln Leu Leu Glu Ser Gly Gly Gly Leu Val Gln Pro Gly Gly
1 5 10 15

Ser Leu Arg Leu Ser Cys Ala Val Ser Asp Tyr His Ile Thr Ser Gly
20 25 30

Tyr Tyr Trp Asn Trp Ile Arg Gln Ala Pro Gly Lys Lys Leu Glu Trp
35 40 45

Met Gly Tyr Ile Ser Tyr Asp Gly Ser Asn Asn Tyr Asn Pro Ser Leu
50 55 60

```
Lys Asn Gly Arg Ile Thr Ile Ser Arg Asp Thr Ser Lys Asn Thr Phe
65                  70                  75                  80

Tyr Leu Gln Met Asn Ser Leu Arg Ala Glu Asp Thr Ala Val Tyr Tyr
                85                  90                  95

Cys Ala Arg Gly Glu Gly Phe Tyr Phe Asp Ser Trp Gly Gln Gly Thr
            100                 105                 110

Leu Val Thr Val Ser Ser
        115


<210> SEQ ID NO 163
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of TPP-8988 IgG histidine
      scanning variant #7"

<400> SEQUENCE: 163

Glu Val Gln Leu Leu Glu Ser Gly Gly Gly Leu Val Gln Pro Gly Gly
1               5                   10                  15

Ser Leu Arg Leu Ser Cys Ala Val Ser Asp Tyr Ser His Thr Ser Gly
            20                  25                  30

Tyr Tyr Trp Asn Trp Ile Arg Gln Ala Pro Gly Lys Lys Leu Glu Trp
        35                  40                  45

Met Gly Tyr Ile Ser Tyr Asp Gly Ser Asn Asn Tyr Asn Pro Ser Leu
    50                  55                  60

Lys Asn Gly Arg Ile Thr Ile Ser Arg Asp Thr Ser Lys Asn Thr Phe
65                  70                  75                  80

Tyr Leu Gln Met Asn Ser Leu Arg Ala Glu Asp Thr Ala Val Tyr Tyr
                85                  90                  95

Cys Ala Arg Gly Glu Gly Phe Tyr Phe Asp Ser Trp Gly Gln Gly Thr
            100                 105                 110

Leu Val Thr Val Ser Ser
        115


<210> SEQ ID NO 164
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of TPP-8988 IgG histidine
      scanning variant #8"

<400> SEQUENCE: 164

Glu Val Gln Leu Leu Glu Ser Gly Gly Gly Leu Val Gln Pro Gly Gly
1               5                   10                  15

Ser Leu Arg Leu Ser Cys Ala Val Ser Asp Tyr Ser Ile His Ser Gly
            20                  25                  30

Tyr Tyr Trp Asn Trp Ile Arg Gln Ala Pro Gly Lys Lys Leu Glu Trp
        35                  40                  45

Met Gly Tyr Ile Ser Tyr Asp Gly Ser Asn Asn Tyr Asn Pro Ser Leu
    50                  55                  60
```

```
Lys Asn Gly Arg Ile Thr Ile Ser Arg Asp Thr Ser Lys Asn Thr Phe
65                  70                  75                  80

Tyr Leu Gln Met Asn Ser Leu Arg Ala Glu Asp Thr Ala Val Tyr Tyr
                85                  90                  95

Cys Ala Arg Gly Glu Gly Phe Tyr Phe Asp Ser Trp Gly Gln Gly Thr
            100                 105                 110

Leu Val Thr Val Ser Ser
        115


<210> SEQ ID NO 165
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of TPP-8988 IgG histidine
      scanning variant #9"

<400> SEQUENCE: 165

Glu Val Gln Leu Leu Glu Ser Gly Gly Gly Leu Val Gln Pro Gly Gly
1               5                   10                  15

Ser Leu Arg Leu Ser Cys Ala Val Ser Asp Tyr Ser Ile Thr His Gly
            20                  25                  30

Tyr Tyr Trp Asn Trp Ile Arg Gln Ala Pro Gly Lys Lys Leu Glu Trp
        35                  40                  45

Met Gly Tyr Ile Ser Tyr Asp Gly Ser Asn Asn Tyr Asn Pro Ser Leu
    50                  55                  60

Lys Asn Gly Arg Ile Thr Ile Ser Arg Asp Thr Ser Lys Asn Thr Phe
65                  70                  75                  80

Tyr Leu Gln Met Asn Ser Leu Arg Ala Glu Asp Thr Ala Val Tyr Tyr
                85                  90                  95

Cys Ala Arg Gly Glu Gly Phe Tyr Phe Asp Ser Trp Gly Gln Gly Thr
            100                 105                 110

Leu Val Thr Val Ser Ser
        115


<210> SEQ ID NO 166
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of TPP-8988 IgG histidine
      scanning variant #10"

<400> SEQUENCE: 166

Glu Val Gln Leu Leu Glu Ser Gly Gly Gly Leu Val Gln Pro Gly Gly
1               5                   10                  15

Ser Leu Arg Leu Ser Cys Ala Val Ser Asp Tyr Ser Ile Thr Ser His
            20                  25                  30

Tyr Tyr Trp Asn Trp Ile Arg Gln Ala Pro Gly Lys Lys Leu Glu Trp
        35                  40                  45

Met Gly Tyr Ile Ser Tyr Asp Gly Ser Asn Asn Tyr Asn Pro Ser Leu
```

```
    50                  55                  60

Lys Asn Gly Arg Ile Thr Ile Ser Arg Asp Thr Ser Lys Asn Thr Phe
65                  70                  75                  80

Tyr Leu Gln Met Asn Ser Leu Arg Ala Glu Asp Thr Ala Val Tyr Tyr
                85                  90                  95

Cys Ala Arg Gly Glu Gly Phe Tyr Phe Asp Ser Trp Gly Gln Gly Thr
            100                 105                 110

Leu Val Thr Val Ser Ser
        115


<210> SEQ ID NO 167
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of TPP-8988 IgG histidine
      scanning variant #11"

<400> SEQUENCE: 167

Glu Val Gln Leu Leu Glu Ser Gly Gly Gly Leu Val Gln Pro Gly Gly
1               5                   10                  15

Ser Leu Arg Leu Ser Cys Ala Val Ser Asp Tyr Ser Ile Thr Ser Gly
            20                  25                  30

His Tyr Trp Asn Trp Ile Arg Gln Ala Pro Gly Lys Lys Leu Glu Trp
        35                  40                  45

Met Gly Tyr Ile Ser Tyr Asp Gly Ser Asn Asn Tyr Asn Pro Ser Leu
    50                  55                  60

Lys Asn Gly Arg Ile Thr Ile Ser Arg Asp Thr Ser Lys Asn Thr Phe
65                  70                  75                  80

Tyr Leu Gln Met Asn Ser Leu Arg Ala Glu Asp Thr Ala Val Tyr Tyr
                85                  90                  95

Cys Ala Arg Gly Glu Gly Phe Tyr Phe Asp Ser Trp Gly Gln Gly Thr
            100                 105                 110

Leu Val Thr Val Ser Ser
        115


<210> SEQ ID NO 168
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of TPP-8988 IgG histidine
      scanning variant #12"

<400> SEQUENCE: 168

Glu Val Gln Leu Leu Glu Ser Gly Gly Gly Leu Val Gln Pro Gly Gly
1               5                   10                  15

Ser Leu Arg Leu Ser Cys Ala Val Ser Asp Tyr Ser Ile Thr Ser Gly
            20                  25                  30

Tyr His Trp Asn Trp Ile Arg Gln Ala Pro Gly Lys Lys Leu Glu Trp
        35                  40                  45
```

```
Met Gly Tyr Ile Ser Tyr Asp Gly Ser Asn Asn Tyr Asn Pro Ser Leu
    50                  55                  60

Lys Asn Gly Arg Ile Thr Ile Ser Arg Asp Thr Ser Lys Asn Thr Phe
65                  70                  75                  80

Tyr Leu Gln Met Asn Ser Leu Arg Ala Glu Asp Thr Ala Val Tyr Tyr
                85                  90                  95

Cys Ala Arg Gly Glu Gly Phe Tyr Phe Asp Ser Trp Gly Gln Gly Thr
            100                 105                 110

Leu Val Thr Val Ser Ser
        115


<210> SEQ ID NO 169
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of TPP-8988 IgG histidine
      scanning variant #13"

<400> SEQUENCE: 169

Glu Val Gln Leu Leu Glu Ser Gly Gly Gly Leu Val Gln Pro Gly Gly
1               5                   10                  15

Ser Leu Arg Leu Ser Cys Ala Val Ser Asp Tyr Ser Ile Thr Ser Gly
            20                  25                  30

Tyr Tyr His Asn Trp Ile Arg Gln Ala Pro Gly Lys Lys Leu Glu Trp
        35                  40                  45

Met Gly Tyr Ile Ser Tyr Asp Gly Ser Asn Asn Tyr Asn Pro Ser Leu
    50                  55                  60

Lys Asn Gly Arg Ile Thr Ile Ser Arg Asp Thr Ser Lys Asn Thr Phe
65                  70                  75                  80

Tyr Leu Gln Met Asn Ser Leu Arg Ala Glu Asp Thr Ala Val Tyr Tyr
                85                  90                  95

Cys Ala Arg Gly Glu Gly Phe Tyr Phe Asp Ser Trp Gly Gln Gly Thr
            100                 105                 110

Leu Val Thr Val Ser Ser
        115


<210> SEQ ID NO 170
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of TPP-8988 IgG histidine
      scanning variant #14"

<400> SEQUENCE: 170

Glu Val Gln Leu Leu Glu Ser Gly Gly Gly Leu Val Gln Pro Gly Gly
1               5                   10                  15

Ser Leu Arg Leu Ser Cys Ala Val Ser Asp Tyr Ser Ile Thr Ser Gly
            20                  25                  30

Tyr Tyr Trp His Trp Ile Arg Gln Ala Pro Gly Lys Lys Leu Glu Trp
        35                  40                  45
```

```
Met Gly Tyr Ile Ser Tyr Asp Gly Ser Asn Asn Tyr Asn Pro Ser Leu
    50                  55                  60

Lys Asn Gly Arg Ile Thr Ile Ser Arg Asp Thr Ser Lys Asn Thr Phe
65                  70                  75                  80

Tyr Leu Gln Met Asn Ser Leu Arg Ala Glu Asp Thr Ala Val Tyr Tyr
                85                  90                  95

Cys Ala Arg Gly Glu Gly Phe Tyr Phe Asp Ser Trp Gly Gln Gly Thr
            100                 105                 110

Leu Val Thr Val Ser Ser
        115


<210> SEQ ID NO 171
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of TPP-8988 IgG histidine
      scanning variant #15"

<400> SEQUENCE: 171

Glu Val Gln Leu Leu Glu Ser Gly Gly Gly Leu Val Gln Pro Gly Gly
1               5                   10                  15

Ser Leu Arg Leu Ser Cys Ala Val Ser Asp Tyr Ser Ile Thr Ser Gly
            20                  25                  30

Tyr Tyr Trp Asn Trp Ile Arg Gln Ala Pro Gly Lys Lys Leu Glu Trp
        35                  40                  45

Met Gly His Ile Ser Tyr Asp Gly Ser Asn Asn Tyr Asn Pro Ser Leu
    50                  55                  60

Lys Asn Gly Arg Ile Thr Ile Ser Arg Asp Thr Ser Lys Asn Thr Phe
65                  70                  75                  80

Tyr Leu Gln Met Asn Ser Leu Arg Ala Glu Asp Thr Ala Val Tyr Tyr
                85                  90                  95

Cys Ala Arg Gly Glu Gly Phe Tyr Phe Asp Ser Trp Gly Gln Gly Thr
            100                 105                 110

Leu Val Thr Val Ser Ser
        115


<210> SEQ ID NO 172
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of TPP-8988 IgG histidine
      scanning variant #16"

<400> SEQUENCE: 172

Glu Val Gln Leu Leu Glu Ser Gly Gly Gly Leu Val Gln Pro Gly Gly
1               5                   10                  15

Ser Leu Arg Leu Ser Cys Ala Val Ser Asp Tyr Ser Ile Thr Ser Gly
            20                  25                  30

Tyr Tyr Trp Asn Trp Ile Arg Gln Ala Pro Gly Lys Lys Leu Glu Trp
```

```
        35                  40                  45

Met Gly Tyr His Ser Tyr Asp Gly Ser Asn Asn Tyr Asn Pro Ser Leu
    50                  55                  60

Lys Asn Gly Arg Ile Thr Ile Ser Arg Asp Thr Ser Lys Asn Thr Phe
65                  70                  75                  80

Tyr Leu Gln Met Asn Ser Leu Arg Ala Glu Asp Thr Ala Val Tyr Tyr
                85                  90                  95

Cys Ala Arg Gly Glu Gly Phe Tyr Phe Asp Ser Trp Gly Gln Gly Thr
            100                 105                 110

Leu Val Thr Val Ser Ser
        115


<210> SEQ ID NO 173
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of TPP-8988 IgG histidine
      scanning variant #17"

<400> SEQUENCE: 173

Glu Val Gln Leu Leu Glu Ser Gly Gly Gly Leu Val Gln Pro Gly Gly
1               5                   10                  15

Ser Leu Arg Leu Ser Cys Ala Val Ser Asp Tyr Ser Ile Thr Ser Gly
            20                  25                  30

Tyr Tyr Trp Asn Trp Ile Arg Gln Ala Pro Gly Lys Lys Leu Glu Trp
        35                  40                  45

Met Gly Tyr Ile His Tyr Asp Gly Ser Asn Asn Tyr Asn Pro Ser Leu
    50                  55                  60

Lys Asn Gly Arg Ile Thr Ile Ser Arg Asp Thr Ser Lys Asn Thr Phe
65                  70                  75                  80

Tyr Leu Gln Met Asn Ser Leu Arg Ala Glu Asp Thr Ala Val Tyr Tyr
                85                  90                  95

Cys Ala Arg Gly Glu Gly Phe Tyr Phe Asp Ser Trp Gly Gln Gly Thr
            100                 105                 110

Leu Val Thr Val Ser Ser
        115


<210> SEQ ID NO 174
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of TPP-8988 IgG histidine
      scanning variant #18"

<400> SEQUENCE: 174

Glu Val Gln Leu Leu Glu Ser Gly Gly Gly Leu Val Gln Pro Gly Gly
1               5                   10                  15

Ser Leu Arg Leu Ser Cys Ala Val Ser Asp Tyr Ser Ile Thr Ser Gly
            20                  25                  30
```

```
Tyr Tyr Trp Asn Trp Ile Arg Gln Ala Pro Gly Lys Lys Leu Glu Trp
        35                  40                  45

Met Gly Tyr Ile Ser His Asp Gly Ser Asn Asn Tyr Asn Pro Ser Leu
    50                  55                  60

Lys Asn Gly Arg Ile Thr Ile Ser Arg Asp Thr Ser Lys Asn Thr Phe
65                  70                  75                  80

Tyr Leu Gln Met Asn Ser Leu Arg Ala Glu Asp Thr Ala Val Tyr Tyr
                85                  90                  95

Cys Ala Arg Gly Glu Gly Phe Tyr Phe Asp Ser Trp Gly Gln Gly Thr
            100                 105                 110

Leu Val Thr Val Ser Ser
        115


<210> SEQ ID NO 175
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of TPP-8988 IgG histidine
      scanning variant #19"

<400> SEQUENCE: 175

Glu Val Gln Leu Leu Glu Ser Gly Gly Gly Leu Val Gln Pro Gly Gly
1               5                   10                  15

Ser Leu Arg Leu Ser Cys Ala Val Ser Asp Tyr Ser Ile Thr Ser Gly
            20                  25                  30

Tyr Tyr Trp Asn Trp Ile Arg Gln Ala Pro Gly Lys Lys Leu Glu Trp
        35                  40                  45

Met Gly Tyr Ile Ser Tyr His Gly Ser Asn Asn Tyr Asn Pro Ser Leu
    50                  55                  60

Lys Asn Gly Arg Ile Thr Ile Ser Arg Asp Thr Ser Lys Asn Thr Phe
65                  70                  75                  80

Tyr Leu Gln Met Asn Ser Leu Arg Ala Glu Asp Thr Ala Val Tyr Tyr
                85                  90                  95

Cys Ala Arg Gly Glu Gly Phe Tyr Phe Asp Ser Trp Gly Gln Gly Thr
            100                 105                 110

Leu Val Thr Val Ser Ser
        115


<210> SEQ ID NO 176
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of TPP-8988 IgG histidine
      scanning variant #20"

<400> SEQUENCE: 176

Glu Val Gln Leu Leu Glu Ser Gly Gly Gly Leu Val Gln Pro Gly Gly
1               5                   10                  15

Ser Leu Arg Leu Ser Cys Ala Val Ser Asp Tyr Ser Ile Thr Ser Gly
            20                  25                  30
```

```
Tyr Tyr Trp Asn Trp Ile Arg Gln Ala Pro Gly Lys Lys Leu Glu Trp
        35                  40                  45

Met Gly Tyr Ile Ser Tyr Asp His Ser Asn Asn Tyr Asn Pro Ser Leu
    50                  55                  60

Lys Asn Gly Arg Ile Thr Ile Ser Arg Asp Thr Ser Lys Asn Thr Phe
65                  70                  75                  80

Tyr Leu Gln Met Asn Ser Leu Arg Ala Glu Asp Thr Ala Val Tyr Tyr
                85                  90                  95

Cys Ala Arg Gly Glu Gly Phe Tyr Phe Asp Ser Trp Gly Gln Gly Thr
            100                 105                 110

Leu Val Thr Val Ser Ser
        115


<210> SEQ ID NO 177
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of TPP-8988 IgG histidine
      scanning variant #21"

<400> SEQUENCE: 177

Glu Val Gln Leu Leu Glu Ser Gly Gly Gly Leu Val Gln Pro Gly Gly
1               5                   10                  15

Ser Leu Arg Leu Ser Cys Ala Val Ser Asp Tyr Ser Ile Thr Ser Gly
            20                  25                  30

Tyr Tyr Trp Asn Trp Ile Arg Gln Ala Pro Gly Lys Lys Leu Glu Trp
        35                  40                  45

Met Gly Tyr Ile Ser Tyr Asp Gly His Asn Asn Tyr Asn Pro Ser Leu
    50                  55                  60

Lys Asn Gly Arg Ile Thr Ile Ser Arg Asp Thr Ser Lys Asn Thr Phe
65                  70                  75                  80

Tyr Leu Gln Met Asn Ser Leu Arg Ala Glu Asp Thr Ala Val Tyr Tyr
                85                  90                  95

Cys Ala Arg Gly Glu Gly Phe Tyr Phe Asp Ser Trp Gly Gln Gly Thr
            100                 105                 110

Leu Val Thr Val Ser Ser
        115


<210> SEQ ID NO 178
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of TPP-8988 IgG histidine
      scanning variant #22"

<400> SEQUENCE: 178

Glu Val Gln Leu Leu Glu Ser Gly Gly Gly Leu Val Gln Pro Gly Gly
1               5                   10                  15

Ser Leu Arg Leu Ser Cys Ala Val Ser Asp Tyr Ser Ile Thr Ser Gly
```

```
            20                  25                  30

Tyr Tyr Trp Asn Trp Ile Arg Gln Ala Pro Gly Lys Lys Leu Glu Trp
        35                  40                  45

Met Gly Tyr Ile Ser Tyr Asp Gly Ser His Asn Tyr Asn Pro Ser Leu
    50                  55                  60

Lys Asn Gly Arg Ile Thr Ile Ser Arg Asp Thr Ser Lys Asn Thr Phe
65                  70                  75                  80

Tyr Leu Gln Met Asn Ser Leu Arg Ala Glu Asp Thr Ala Val Tyr Tyr
                85                  90                  95

Cys Ala Arg Gly Glu Gly Phe Tyr Phe Asp Ser Trp Gly Gln Gly Thr
            100                 105                 110

Leu Val Thr Val Ser Ser
        115


<210> SEQ ID NO 179
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of TPP-8988 IgG histidine
      scanning variant #23"

<400> SEQUENCE: 179

Glu Val Gln Leu Leu Glu Ser Gly Gly Gly Leu Val Gln Pro Gly Gly
1               5                   10                  15

Ser Leu Arg Leu Ser Cys Ala Val Ser Asp Tyr Ser Ile Thr Ser Gly
            20                  25                  30

Tyr Tyr Trp Asn Trp Ile Arg Gln Ala Pro Gly Lys Lys Leu Glu Trp
        35                  40                  45

Met Gly Tyr Ile Ser Tyr Asp Gly Ser Asn His Tyr Asn Pro Ser Leu
    50                  55                  60

Lys Asn Gly Arg Ile Thr Ile Ser Arg Asp Thr Ser Lys Asn Thr Phe
65                  70                  75                  80

Tyr Leu Gln Met Asn Ser Leu Arg Ala Glu Asp Thr Ala Val Tyr Tyr
                85                  90                  95

Cys Ala Arg Gly Glu Gly Phe Tyr Phe Asp Ser Trp Gly Gln Gly Thr
            100                 105                 110

Leu Val Thr Val Ser Ser
        115


<210> SEQ ID NO 180
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of TPP-8988 IgG histidine
      scanning variant #24"

<400> SEQUENCE: 180

Glu Val Gln Leu Leu Glu Ser Gly Gly Gly Leu Val Gln Pro Gly Gly
1               5                   10                  15
```

```
Ser Leu Arg Leu Ser Cys Ala Val Ser Asp Tyr Ser Ile Thr Ser Gly
            20                  25                  30

Tyr Tyr Trp Asn Trp Ile Arg Gln Ala Pro Gly Lys Lys Leu Glu Trp
        35                  40                  45

Met Gly Tyr Ile Ser Tyr Asp Gly Ser Asn Asn His Asn Pro Ser Leu
    50                  55                  60

Lys Asn Gly Arg Ile Thr Ile Ser Arg Asp Thr Ser Lys Asn Thr Phe
65                  70                  75                  80

Tyr Leu Gln Met Asn Ser Leu Arg Ala Glu Asp Thr Ala Val Tyr Tyr
                85                  90                  95

Cys Ala Arg Gly Glu Gly Phe Tyr Phe Asp Ser Trp Gly Gln Gly Thr
            100                 105                 110

Leu Val Thr Val Ser Ser
        115


<210> SEQ ID NO 181
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of TPP-8988 IgG histidine
      scanning variant #25"

<400> SEQUENCE: 181

Glu Val Gln Leu Leu Glu Ser Gly Gly Gly Leu Val Gln Pro Gly Gly
1               5                   10                  15

Ser Leu Arg Leu Ser Cys Ala Val Ser Asp Tyr Ser Ile Thr Ser Gly
            20                  25                  30

Tyr Tyr Trp Asn Trp Ile Arg Gln Ala Pro Gly Lys Lys Leu Glu Trp
        35                  40                  45

Met Gly Tyr Ile Ser Tyr Asp Gly Ser Asn Asn Tyr His Pro Ser Leu
    50                  55                  60

Lys Asn Gly Arg Ile Thr Ile Ser Arg Asp Thr Ser Lys Asn Thr Phe
65                  70                  75                  80

Tyr Leu Gln Met Asn Ser Leu Arg Ala Glu Asp Thr Ala Val Tyr Tyr
                85                  90                  95

Cys Ala Arg Gly Glu Gly Phe Tyr Phe Asp Ser Trp Gly Gln Gly Thr
            100                 105                 110

Leu Val Thr Val Ser Ser
        115


<210> SEQ ID NO 182
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of TPP-8988 IgG histidine
      scanning variant #26"

<400> SEQUENCE: 182

Glu Val Gln Leu Leu Glu Ser Gly Gly Gly Leu Val Gln Pro Gly Gly
1               5                   10                  15
```

```
Ser Leu Arg Leu Ser Cys Ala Val Ser Asp Tyr Ser Ile Thr Ser Gly
            20                  25                  30

Tyr Tyr Trp Asn Trp Ile Arg Gln Ala Pro Gly Lys Lys Leu Glu Trp
        35                  40                  45

Met Gly Tyr Ile Ser Tyr Asp Gly Ser Asn Asn Tyr Asn His Ser Leu
    50                  55                  60

Lys Asn Gly Arg Ile Thr Ile Ser Arg Asp Thr Ser Lys Asn Thr Phe
65                  70                  75                  80

Tyr Leu Gln Met Asn Ser Leu Arg Ala Glu Asp Thr Ala Val Tyr Tyr
                85                  90                  95

Cys Ala Arg Gly Glu Gly Phe Tyr Phe Asp Ser Trp Gly Gln Gly Thr
            100                 105                 110

Leu Val Thr Val Ser Ser
        115


<210> SEQ ID NO 183
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of TPP-8988 IgG histidine
      scanning variant #27"

<400> SEQUENCE: 183

Glu Val Gln Leu Leu Glu Ser Gly Gly Gly Leu Val Gln Pro Gly Gly
1               5                   10                  15

Ser Leu Arg Leu Ser Cys Ala Val Ser Asp Tyr Ser Ile Thr Ser Gly
            20                  25                  30

Tyr Tyr Trp Asn Trp Ile Arg Gln Ala Pro Gly Lys Lys Leu Glu Trp
        35                  40                  45

Met Gly Tyr Ile Ser Tyr Asp Gly Ser Asn Asn Tyr Asn Pro His Leu
    50                  55                  60

Lys Asn Gly Arg Ile Thr Ile Ser Arg Asp Thr Ser Lys Asn Thr Phe
65                  70                  75                  80

Tyr Leu Gln Met Asn Ser Leu Arg Ala Glu Asp Thr Ala Val Tyr Tyr
                85                  90                  95

Cys Ala Arg Gly Glu Gly Phe Tyr Phe Asp Ser Trp Gly Gln Gly Thr
            100                 105                 110

Leu Val Thr Val Ser Ser
        115


<210> SEQ ID NO 184
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of TPP-8988 IgG histidine
      scanning variant #28"

<400> SEQUENCE: 184

Glu Val Gln Leu Leu Glu Ser Gly Gly Gly Leu Val Gln Pro Gly Gly
```

```
1               5                   10                  15

Ser Leu Arg Leu Ser Cys Ala Val Ser Asp Tyr Ser Ile Thr Ser Gly
            20                  25                  30

Tyr Tyr Trp Asn Trp Ile Arg Gln Ala Pro Gly Lys Lys Leu Glu Trp
        35                  40                  45

Met Gly Tyr Ile Ser Tyr Asp Gly Ser Asn Asn Tyr Asn Pro Ser His
    50                  55                  60

Lys Asn Gly Arg Ile Thr Ile Ser Arg Asp Thr Ser Lys Asn Thr Phe
65                  70                  75                  80

Tyr Leu Gln Met Asn Ser Leu Arg Ala Glu Asp Thr Ala Val Tyr Tyr
                85                  90                  95

Cys Ala Arg Gly Glu Gly Phe Tyr Phe Asp Ser Trp Gly Gln Gly Thr
            100                 105                 110

Leu Val Thr Val Ser Ser
        115


<210> SEQ ID NO 185
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of TPP-8988 IgG histidine
      scanning variant #29"

<400> SEQUENCE: 185

Glu Val Gln Leu Leu Glu Ser Gly Gly Gly Leu Val Gln Pro Gly Gly
1               5                   10                  15

Ser Leu Arg Leu Ser Cys Ala Val Ser Asp Tyr Ser Ile Thr Ser Gly
            20                  25                  30

Tyr Tyr Trp Asn Trp Ile Arg Gln Ala Pro Gly Lys Lys Leu Glu Trp
        35                  40                  45

Met Gly Tyr Ile Ser Tyr Asp Gly Ser Asn Asn Tyr Asn Pro Ser Leu
    50                  55                  60

His Asn Gly Arg Ile Thr Ile Ser Arg Asp Thr Ser Lys Asn Thr Phe
65                  70                  75                  80

Tyr Leu Gln Met Asn Ser Leu Arg Ala Glu Asp Thr Ala Val Tyr Tyr
                85                  90                  95

Cys Ala Arg Gly Glu Gly Phe Tyr Phe Asp Ser Trp Gly Gln Gly Thr
            100                 105                 110

Leu Val Thr Val Ser Ser
        115


<210> SEQ ID NO 186
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of TPP-8988 IgG histidine
      scanning variant #30"

<400> SEQUENCE: 186
```

```
Glu Val Gln Leu Leu Glu Ser Gly Gly Gly Leu Val Gln Pro Gly Gly
1               5                   10                  15

Ser Leu Arg Leu Ser Cys Ala Val Ser Asp Tyr Ser Ile Thr Ser Gly
            20                  25                  30

Tyr Tyr Trp Asn Trp Ile Arg Gln Ala Pro Gly Lys Lys Leu Glu Trp
        35                  40                  45

Met Gly Tyr Ile Ser Tyr Asp Gly Ser Asn Asn Tyr Asn Pro Ser Leu
    50                  55                  60

Lys His Gly Arg Ile Thr Ile Ser Arg Asp Thr Ser Lys Asn Thr Phe
65                  70                  75                  80

Tyr Leu Gln Met Asn Ser Leu Arg Ala Glu Asp Thr Ala Val Tyr Tyr
                85                  90                  95

Cys Ala Arg Gly Glu Gly Phe Tyr Phe Asp Ser Trp Gly Gln Gly Thr
            100                 105                 110

Leu Val Thr Val Ser Ser
        115
```

<210> SEQ ID NO 187
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="Heavy Chain of TPP-8988 IgG histidine scanning variant #31"

<400> SEQUENCE: 187

```
Glu Val Gln Leu Leu Glu Ser Gly Gly Gly Leu Val Gln Pro Gly Gly
1               5                   10                  15

Ser Leu Arg Leu Ser Cys Ala Val Ser Asp Tyr Ser Ile Thr Ser Gly
            20                  25                  30

Tyr Tyr Trp Asn Trp Ile Arg Gln Ala Pro Gly Lys Lys Leu Glu Trp
        35                  40                  45

Met Gly Tyr Ile Ser Tyr Asp Gly Ser Asn Asn Tyr Asn Pro Ser Leu
    50                  55                  60

Lys Asn His Arg Ile Thr Ile Ser Arg Asp Thr Ser Lys Asn Thr Phe
65                  70                  75                  80

Tyr Leu Gln Met Asn Ser Leu Arg Ala Glu Asp Thr Ala Val Tyr Tyr
                85                  90                  95

Cys Ala Arg Gly Glu Gly Phe Tyr Phe Asp Ser Trp Gly Gln Gly Thr
            100                 105                 110

Leu Val Thr Val Ser Ser
        115
```

<210> SEQ ID NO 188
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="Heavy Chain of TPP-8988 IgG histidine scanning variant #32"

<400> SEQUENCE: 188

```
Glu Val Gln Leu Leu Glu Ser Gly Gly Gly Leu Val Gln Pro Gly Gly
1               5                   10                  15

Ser Leu Arg Leu Ser Cys Ala Val Ser Asp Tyr Ser Ile Thr Ser Gly
            20                  25                  30

Tyr Tyr Trp Asn Trp Ile Arg Gln Ala Pro Gly Lys Lys Leu Glu Trp
        35                  40                  45

Met Gly Tyr Ile Ser Tyr Asp Gly Ser Asn Asn Tyr Asn Pro Ser Leu
    50                  55                  60

Lys Asn Gly Arg Ile Thr Ile Ser Arg Asp Thr Ser Lys Asn Thr Phe
65                  70                  75                  80

Tyr Leu Gln Met Asn Ser Leu Arg Ala Glu Asp Thr Ala Val Tyr Tyr
                85                  90                  95

Cys His Arg Gly Glu Gly Phe Tyr Phe Asp Ser Trp Gly Gln Gly Thr
            100                 105                 110

Leu Val Thr Val Ser Ser
        115


<210> SEQ ID NO 189
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of TPP-8988 IgG histidine
      scanning variant #33"

<400> SEQUENCE: 189

Glu Val Gln Leu Leu Glu Ser Gly Gly Gly Leu Val Gln Pro Gly Gly
1               5                   10                  15

Ser Leu Arg Leu Ser Cys Ala Val Ser Asp Tyr Ser Ile Thr Ser Gly
            20                  25                  30

Tyr Tyr Trp Asn Trp Ile Arg Gln Ala Pro Gly Lys Lys Leu Glu Trp
        35                  40                  45

Met Gly Tyr Ile Ser Tyr Asp Gly Ser Asn Asn Tyr Asn Pro Ser Leu
    50                  55                  60

Lys Asn Gly Arg Ile Thr Ile Ser Arg Asp Thr Ser Lys Asn Thr Phe
65                  70                  75                  80

Tyr Leu Gln Met Asn Ser Leu Arg Ala Glu Asp Thr Ala Val Tyr Tyr
                85                  90                  95

Cys Ala His Gly Glu Gly Phe Tyr Phe Asp Ser Trp Gly Gln Gly Thr
            100                 105                 110

Leu Val Thr Val Ser Ser
        115


<210> SEQ ID NO 190
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Heavy Chain of TPP-8988 IgG histidine
      scanning variant #34"
```

<400> SEQUENCE: 190

```
Glu Val Gln Leu Leu Glu Ser Gly Gly Gly Leu Val Gln Pro Gly Gly
1               5                   10                  15

Ser Leu Arg Leu Ser Cys Ala Val Ser Asp Tyr Ser Ile Thr Ser Gly
            20                  25                  30

Tyr Tyr Trp Asn Trp Ile Arg Gln Ala Pro Gly Lys Lys Leu Glu Trp
        35                  40                  45

Met Gly Tyr Ile Ser Tyr Asp Gly Ser Asn Asn Tyr Asn Pro Ser Leu
    50                  55                  60

Lys Asn Gly Arg Ile Thr Ile Ser Arg Asp Thr Ser Lys Asn Thr Phe
65                  70                  75                  80

Tyr Leu Gln Met Asn Ser Leu Arg Ala Glu Asp Thr Ala Val Tyr Tyr
                85                  90                  95

Cys Ala Arg His Glu Gly Phe Tyr Phe Asp Ser Trp Gly Gln Gly Thr
            100                 105                 110

Leu Val Thr Val Ser Ser
        115
```

<210> SEQ ID NO 191
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="Heavy Chain of TPP-8988 IgG histidine scanning variant #35"

<400> SEQUENCE: 191

```
Glu Val Gln Leu Leu Glu Ser Gly Gly Gly Leu Val Gln Pro Gly Gly
1               5                   10                  15

Ser Leu Arg Leu Ser Cys Ala Val Ser Asp Tyr Ser Ile Thr Ser Gly
            20                  25                  30

Tyr Tyr Trp Asn Trp Ile Arg Gln Ala Pro Gly Lys Lys Leu Glu Trp
        35                  40                  45

Met Gly Tyr Ile Ser Tyr Asp Gly Ser Asn Asn Tyr Asn Pro Ser Leu
    50                  55                  60

Lys Asn Gly Arg Ile Thr Ile Ser Arg Asp Thr Ser Lys Asn Thr Phe
65                  70                  75                  80

Tyr Leu Gln Met Asn Ser Leu Arg Ala Glu Asp Thr Ala Val Tyr Tyr
                85                  90                  95

Cys Ala Arg Gly His Gly Phe Tyr Phe Asp Ser Trp Gly Gln Gly Thr
            100                 105                 110

Leu Val Thr Val Ser Ser
        115
```

<210> SEQ ID NO 192
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="Heavy Chain of TPP-8988 IgG histidine scanning variant #36"

<400> SEQUENCE: 192

```
Glu Val Gln Leu Leu Glu Ser Gly Gly Gly Leu Val Gln Pro Gly Gly
1               5                   10                  15

Ser Leu Arg Leu Ser Cys Ala Val Ser Asp Tyr Ser Ile Thr Ser Gly
            20                  25                  30

Tyr Tyr Trp Asn Trp Ile Arg Gln Ala Pro Gly Lys Lys Leu Glu Trp
        35                  40                  45

Met Gly Tyr Ile Ser Tyr Asp Gly Ser Asn Asn Tyr Asn Pro Ser Leu
    50                  55                  60

Lys Asn Gly Arg Ile Thr Ile Ser Arg Asp Thr Ser Lys Asn Thr Phe
65                  70                  75                  80

Tyr Leu Gln Met Asn Ser Leu Arg Ala Glu Asp Thr Ala Val Tyr Tyr
                85                  90                  95

Cys Ala Arg Gly Glu His Phe Tyr Phe Asp Ser Trp Gly Gln Gly Thr
            100                 105                 110

Leu Val Thr Val Ser Ser
        115
```

<210> SEQ ID NO 193
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="Heavy Chain of TPP-8988 IgG histidine scanning variant #37"

<400> SEQUENCE: 193

```
Glu Val Gln Leu Leu Glu Ser Gly Gly Gly Leu Val Gln Pro Gly Gly
1               5                   10                  15

Ser Leu Arg Leu Ser Cys Ala Val Ser Asp Tyr Ser Ile Thr Ser Gly
            20                  25                  30

Tyr Tyr Trp Asn Trp Ile Arg Gln Ala Pro Gly Lys Lys Leu Glu Trp
        35                  40                  45

Met Gly Tyr Ile Ser Tyr Asp Gly Ser Asn Asn Tyr Asn Pro Ser Leu
    50                  55                  60

Lys Asn Gly Arg Ile Thr Ile Ser Arg Asp Thr Ser Lys Asn Thr Phe
65                  70                  75                  80

Tyr Leu Gln Met Asn Ser Leu Arg Ala Glu Asp Thr Ala Val Tyr Tyr
                85                  90                  95

Cys Ala Arg Gly Glu Gly His Tyr Phe Asp Ser Trp Gly Gln Gly Thr
            100                 105                 110

Leu Val Thr Val Ser Ser
        115
```

<210> SEQ ID NO 194
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="Heavy Chain of TPP-8988 IgG histidine scanning variant #38"

<400> SEQUENCE: 194

```
Glu Val Gln Leu Leu Glu Ser Gly Gly Gly Leu Val Gln Pro Gly Gly
1               5                   10                  15

Ser Leu Arg Leu Ser Cys Ala Val Ser Asp Tyr Ser Ile Thr Ser Gly
            20                  25                  30

Tyr Tyr Trp Asn Trp Ile Arg Gln Ala Pro Gly Lys Lys Leu Glu Trp
        35                  40                  45

Met Gly Tyr Ile Ser Tyr Asp Gly Ser Asn Asn Tyr Asn Pro Ser Leu
    50                  55                  60

Lys Asn Gly Arg Ile Thr Ile Ser Arg Asp Thr Ser Lys Asn Thr Phe
65                  70                  75                  80

Tyr Leu Gln Met Asn Ser Leu Arg Ala Glu Asp Thr Ala Val Tyr Tyr
                85                  90                  95

Cys Ala Arg Gly Glu Gly Phe His Phe Asp Ser Trp Gly Gln Gly Thr
            100                 105                 110

Leu Val Thr Val Ser Ser
        115
```

<210> SEQ ID NO 195
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="Heavy Chain of TPP-8988 IgG histidine scanning variant #39"

<400> SEQUENCE: 195

```
Glu Val Gln Leu Leu Glu Ser Gly Gly Gly Leu Val Gln Pro Gly Gly
1               5                   10                  15

Ser Leu Arg Leu Ser Cys Ala Val Ser Asp Tyr Ser Ile Thr Ser Gly
            20                  25                  30

Tyr Tyr Trp Asn Trp Ile Arg Gln Ala Pro Gly Lys Lys Leu Glu Trp
        35                  40                  45

Met Gly Tyr Ile Ser Tyr Asp Gly Ser Asn Asn Tyr Asn Pro Ser Leu
    50                  55                  60

Lys Asn Gly Arg Ile Thr Ile Ser Arg Asp Thr Ser Lys Asn Thr Phe
65                  70                  75                  80

Tyr Leu Gln Met Asn Ser Leu Arg Ala Glu Asp Thr Ala Val Tyr Tyr
                85                  90                  95

Cys Ala Arg Gly Glu Gly Phe Tyr His Asp Ser Trp Gly Gln Gly Thr
            100                 105                 110

Leu Val Thr Val Ser Ser
        115
```

<210> SEQ ID NO 196
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="Heavy Chain of TPP-8988 IgG histidine scanning variant #40"

<400> SEQUENCE: 196

```
Glu Val Gln Leu Leu Glu Ser Gly Gly Gly Leu Val Gln Pro Gly Gly
1               5                   10                  15

Ser Leu Arg Leu Ser Cys Ala Val Ser Asp Tyr Ser Ile Thr Ser Gly
            20                  25                  30

Tyr Tyr Trp Asn Trp Ile Arg Gln Ala Pro Gly Lys Lys Leu Glu Trp
        35                  40                  45

Met Gly Tyr Ile Ser Tyr Asp Gly Ser Asn Asn Tyr Asn Pro Ser Leu
    50                  55                  60

Lys Asn Gly Arg Ile Thr Ile Ser Arg Asp Thr Ser Lys Asn Thr Phe
65                  70                  75                  80

Tyr Leu Gln Met Asn Ser Leu Arg Ala Glu Asp Thr Ala Val Tyr Tyr
                85                  90                  95

Cys Ala Arg Gly Glu Gly Phe Tyr Phe His Ser Trp Gly Gln Gly Thr
            100                 105                 110

Leu Val Thr Val Ser Ser
        115
```

<210> SEQ ID NO 197
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="Heavy Chain of TPP-8988 IgG histidine scanning variant #41"

<400> SEQUENCE: 197

```
Glu Val Gln Leu Leu Glu Ser Gly Gly Gly Leu Val Gln Pro Gly Gly
1               5                   10                  15

Ser Leu Arg Leu Ser Cys Ala Val Ser Asp Tyr Ser Ile Thr Ser Gly
            20                  25                  30

Tyr Tyr Trp Asn Trp Ile Arg Gln Ala Pro Gly Lys Lys Leu Glu Trp
        35                  40                  45

Met Gly Tyr Ile Ser Tyr Asp Gly Ser Asn Asn Tyr Asn Pro Ser Leu
    50                  55                  60

Lys Asn Gly Arg Ile Thr Ile Ser Arg Asp Thr Ser Lys Asn Thr Phe
65                  70                  75                  80

Tyr Leu Gln Met Asn Ser Leu Arg Ala Glu Asp Thr Ala Val Tyr Tyr
                85                  90                  95

Cys Ala Arg Gly Glu Gly Phe Tyr Phe Asp His Trp Gly Gln Gly Thr
            100                 105                 110

Leu Val Thr Val Ser Ser
        115
```

<210> SEQ ID NO 198
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:

```
<221> NAME/KEY: source
<223> OTHER INFORMATION: /note="Light Chain of TPP-8988 IgG histidine
      scanning variant #1"

<400> SEQUENCE: 198

Glu Ile Val Leu Thr Gln Ser Pro Gly Thr Leu Ser Leu Ser Pro Gly
1               5                   10                  15

Glu Arg Ala Thr Leu Ser Cys Lys Ser Ser His Ser Leu Phe Phe Gly
            20                  25                  30

Ser Thr Gln Lys Asn Tyr Leu Ala Trp Tyr Gln Gln Lys Pro Gly Gln
        35                  40                  45

Ala Pro Arg Leu Leu Ile Tyr Trp Ala Ser Thr Arg Glu Ser Gly Ile
    50                  55                  60

Pro Asp Arg Phe Ser Gly Ser Gly Ser Gly Thr Asp Phe Thr Leu Thr
65                  70                  75                  80

Ile Ser Arg Leu Glu Pro Glu Asp Phe Ala Val Tyr Tyr Cys Gln Gln
                85                  90                  95

Tyr Tyr Asn Tyr Pro Trp Thr Phe Gly Gln Gly Thr Lys Leu Glu Ile
            100                 105                 110

Lys


<210> SEQ ID NO 199
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of TPP-8988 IgG histidine
      scanning variant #2"

<400> SEQUENCE: 199

Glu Ile Val Leu Thr Gln Ser Pro Gly Thr Leu Ser Leu Ser Pro Gly
1               5                   10                  15

Glu Arg Ala Thr Leu Ser Cys Lys Ser Ser Gln His Leu Phe Phe Gly
            20                  25                  30

Ser Thr Gln Lys Asn Tyr Leu Ala Trp Tyr Gln Gln Lys Pro Gly Gln
        35                  40                  45

Ala Pro Arg Leu Leu Ile Tyr Trp Ala Ser Thr Arg Glu Ser Gly Ile
    50                  55                  60

Pro Asp Arg Phe Ser Gly Ser Gly Ser Gly Thr Asp Phe Thr Leu Thr
65                  70                  75                  80

Ile Ser Arg Leu Glu Pro Glu Asp Phe Ala Val Tyr Tyr Cys Gln Gln
                85                  90                  95

Tyr Tyr Asn Tyr Pro Trp Thr Phe Gly Gln Gly Thr Lys Leu Glu Ile
            100                 105                 110

Lys


<210> SEQ ID NO 200
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
```

<223> OTHER INFORMATION: /note="Light Chain of TPP-8988 IgG histidine scanning variant #3"

<400> SEQUENCE: 200

```
Glu Ile Val Leu Thr Gln Ser Pro Gly Thr Leu Ser Leu Ser Pro Gly
1               5                   10                  15

Glu Arg Ala Thr Leu Ser Cys Lys Ser Ser Gln Ser His Phe Phe Gly
            20                  25                  30

Ser Thr Gln Lys Asn Tyr Leu Ala Trp Tyr Gln Gln Lys Pro Gly Gln
        35                  40                  45

Ala Pro Arg Leu Leu Ile Tyr Trp Ala Ser Thr Arg Glu Ser Gly Ile
    50                  55                  60

Pro Asp Arg Phe Ser Gly Ser Gly Ser Gly Thr Asp Phe Thr Leu Thr
65                  70                  75                  80

Ile Ser Arg Leu Glu Pro Glu Asp Phe Ala Val Tyr Tyr Cys Gln Gln
                85                  90                  95

Tyr Tyr Asn Tyr Pro Trp Thr Phe Gly Gln Gly Thr Lys Leu Glu Ile
            100                 105                 110

Lys
```

<210> SEQ ID NO 201
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="Light Chain of TPP-8988 IgG histidine scanning variant #4"

<400> SEQUENCE: 201

```
Glu Ile Val Leu Thr Gln Ser Pro Gly Thr Leu Ser Leu Ser Pro Gly
1               5                   10                  15

Glu Arg Ala Thr Leu Ser Cys Lys Ser Ser Gln Ser Leu His Phe Gly
            20                  25                  30

Ser Thr Gln Lys Asn Tyr Leu Ala Trp Tyr Gln Gln Lys Pro Gly Gln
        35                  40                  45

Ala Pro Arg Leu Leu Ile Tyr Trp Ala Ser Thr Arg Glu Ser Gly Ile
    50                  55                  60

Pro Asp Arg Phe Ser Gly Ser Gly Ser Gly Thr Asp Phe Thr Leu Thr
65                  70                  75                  80

Ile Ser Arg Leu Glu Pro Glu Asp Phe Ala Val Tyr Tyr Cys Gln Gln
                85                  90                  95

Tyr Tyr Asn Tyr Pro Trp Thr Phe Gly Gln Gly Thr Lys Leu Glu Ile
            100                 105                 110

Lys
```

<210> SEQ ID NO 202
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="Light Chain of TPP-8988 IgG histidine scanning variant #5"

<400> SEQUENCE: 202

```
Glu Ile Val Leu Thr Gln Ser Pro Gly Thr Leu Ser Leu Ser Pro Gly
1               5                   10                  15

Glu Arg Ala Thr Leu Ser Cys Lys Ser Ser Gln Ser Leu Phe His Gly
            20                  25                  30

Ser Thr Gln Lys Asn Tyr Leu Ala Trp Tyr Gln Gln Lys Pro Gly Gln
        35                  40                  45

Ala Pro Arg Leu Leu Ile Tyr Trp Ala Ser Thr Arg Glu Ser Gly Ile
    50                  55                  60

Pro Asp Arg Phe Ser Gly Ser Gly Ser Gly Thr Asp Phe Thr Leu Thr
65                  70                  75                  80

Ile Ser Arg Leu Glu Pro Glu Asp Phe Ala Val Tyr Tyr Cys Gln Gln
                85                  90                  95

Tyr Tyr Asn Tyr Pro Trp Thr Phe Gly Gln Gly Thr Lys Leu Glu Ile
            100                 105                 110

Lys
```

<210> SEQ ID NO 203
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="Light Chain of TPP-8988 IgG histidine scanning variant #6"

<400> SEQUENCE: 203

```
Glu Ile Val Leu Thr Gln Ser Pro Gly Thr Leu Ser Leu Ser Pro Gly
1               5                   10                  15

Glu Arg Ala Thr Leu Ser Cys Lys Ser Ser Gln Ser Leu Phe Phe His
            20                  25                  30

Ser Thr Gln Lys Asn Tyr Leu Ala Trp Tyr Gln Gln Lys Pro Gly Gln
        35                  40                  45

Ala Pro Arg Leu Leu Ile Tyr Trp Ala Ser Thr Arg Glu Ser Gly Ile
    50                  55                  60

Pro Asp Arg Phe Ser Gly Ser Gly Ser Gly Thr Asp Phe Thr Leu Thr
65                  70                  75                  80

Ile Ser Arg Leu Glu Pro Glu Asp Phe Ala Val Tyr Tyr Cys Gln Gln
                85                  90                  95

Tyr Tyr Asn Tyr Pro Trp Thr Phe Gly Gln Gly Thr Lys Leu Glu Ile
            100                 105                 110

Lys
```

<210> SEQ ID NO 204
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="Light Chain of TPP-8988 IgG histidine scanning variant #7"

<400> SEQUENCE: 204

```
Glu Ile Val Leu Thr Gln Ser Pro Gly Thr Leu Ser Leu Ser Pro Gly
1               5                   10                  15

Glu Arg Ala Thr Leu Ser Cys Lys Ser Ser Gln Ser Leu Phe Phe Gly
            20                  25                  30

His Thr Gln Lys Asn Tyr Leu Ala Trp Tyr Gln Gln Lys Pro Gly Gln
        35                  40                  45

Ala Pro Arg Leu Leu Ile Tyr Trp Ala Ser Thr Arg Glu Ser Gly Ile
    50                  55                  60

Pro Asp Arg Phe Ser Gly Ser Gly Ser Gly Thr Asp Phe Thr Leu Thr
65                  70                  75                  80

Ile Ser Arg Leu Glu Pro Glu Asp Phe Ala Val Tyr Tyr Cys Gln Gln
                85                  90                  95

Tyr Tyr Asn Tyr Pro Trp Thr Phe Gly Gln Gly Thr Lys Leu Glu Ile
            100                 105                 110

Lys
```

<210> SEQ ID NO 205
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="Light Chain of TPP-8988 IgG histidine scanning variant #8"

<400> SEQUENCE: 205

```
Glu Ile Val Leu Thr Gln Ser Pro Gly Thr Leu Ser Leu Ser Pro Gly
1               5                   10                  15

Glu Arg Ala Thr Leu Ser Cys Lys Ser Ser Gln Ser Leu Phe Phe Gly
            20                  25                  30

Ser His Gln Lys Asn Tyr Leu Ala Trp Tyr Gln Gln Lys Pro Gly Gln
        35                  40                  45

Ala Pro Arg Leu Leu Ile Tyr Trp Ala Ser Thr Arg Glu Ser Gly Ile
    50                  55                  60

Pro Asp Arg Phe Ser Gly Ser Gly Ser Gly Thr Asp Phe Thr Leu Thr
65                  70                  75                  80

Ile Ser Arg Leu Glu Pro Glu Asp Phe Ala Val Tyr Tyr Cys Gln Gln
                85                  90                  95

Tyr Tyr Asn Tyr Pro Trp Thr Phe Gly Gln Gly Thr Lys Leu Glu Ile
            100                 105                 110

Lys
```

<210> SEQ ID NO 206
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="Light Chain of TPP-8988 IgG histidine scanning variant #9"

<400> SEQUENCE: 206

Glu Ile Val Leu Thr Gln Ser Pro Gly Thr Leu Ser Leu Ser Pro Gly
1 5 10 15

Glu Arg Ala Thr Leu Ser Cys Lys Ser Ser Gln Ser Leu Phe Phe Gly
20 25 30

Ser Thr His Lys Asn Tyr Leu Ala Trp Tyr Gln Gln Lys Pro Gly Gln
35 40 45

Ala Pro Arg Leu Leu Ile Tyr Trp Ala Ser Thr Arg Glu Ser Gly Ile
50 55 60

Pro Asp Arg Phe Ser Gly Ser Gly Ser Gly Thr Asp Phe Thr Leu Thr
65 70 75 80

Ile Ser Arg Leu Glu Pro Glu Asp Phe Ala Val Tyr Tyr Cys Gln Gln
85 90 95

Tyr Tyr Asn Tyr Pro Trp Thr Phe Gly Gln Gly Thr Lys Leu Glu Ile
100 105 110

Lys

<210> SEQ ID NO 207
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="Light Chain of TPP-8988 IgG histidine scanning variant #10"

<400> SEQUENCE: 207

Glu Ile Val Leu Thr Gln Ser Pro Gly Thr Leu Ser Leu Ser Pro Gly
1 5 10 15

Glu Arg Ala Thr Leu Ser Cys Lys Ser Ser Gln Ser Leu Phe Phe Gly
20 25 30

Ser Thr Gln His Asn Tyr Leu Ala Trp Tyr Gln Gln Lys Pro Gly Gln
35 40 45

Ala Pro Arg Leu Leu Ile Tyr Trp Ala Ser Thr Arg Glu Ser Gly Ile
50 55 60

Pro Asp Arg Phe Ser Gly Ser Gly Ser Gly Thr Asp Phe Thr Leu Thr
65 70 75 80

Ile Ser Arg Leu Glu Pro Glu Asp Phe Ala Val Tyr Tyr Cys Gln Gln
85 90 95

Tyr Tyr Asn Tyr Pro Trp Thr Phe Gly Gln Gly Thr Lys Leu Glu Ile
100 105 110

Lys

<210> SEQ ID NO 208
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="Light Chain of TPP-8988 IgG histidine scanning variant #11"

<400> SEQUENCE: 208

```
Glu Ile Val Leu Thr Gln Ser Pro Gly Thr Leu Ser Leu Ser Pro Gly
1               5                   10                  15

Glu Arg Ala Thr Leu Ser Cys Lys Ser Ser Gln Ser Leu Phe Phe Gly
            20                  25                  30

Ser Thr Gln Lys His Tyr Leu Ala Trp Tyr Gln Gln Lys Pro Gly Gln
        35                  40                  45

Ala Pro Arg Leu Leu Ile Tyr Trp Ala Ser Thr Arg Glu Ser Gly Ile
    50                  55                  60

Pro Asp Arg Phe Ser Gly Ser Gly Ser Gly Thr Asp Phe Thr Leu Thr
65                  70                  75                  80

Ile Ser Arg Leu Glu Pro Glu Asp Phe Ala Val Tyr Tyr Cys Gln Gln
                85                  90                  95

Tyr Tyr Asn Tyr Pro Trp Thr Phe Gly Gln Gly Thr Lys Leu Glu Ile
            100                 105                 110

Lys
```

<210> SEQ ID NO 209
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="Light Chain of TPP-8988 IgG histidine scanning variant #12"

<400> SEQUENCE: 209

```
Glu Ile Val Leu Thr Gln Ser Pro Gly Thr Leu Ser Leu Ser Pro Gly
1               5                   10                  15

Glu Arg Ala Thr Leu Ser Cys Lys Ser Ser Gln Ser Leu Phe Phe Gly
            20                  25                  30

Ser Thr Gln Lys Asn His Leu Ala Trp Tyr Gln Gln Lys Pro Gly Gln
        35                  40                  45

Ala Pro Arg Leu Leu Ile Tyr Trp Ala Ser Thr Arg Glu Ser Gly Ile
    50                  55                  60

Pro Asp Arg Phe Ser Gly Ser Gly Ser Gly Thr Asp Phe Thr Leu Thr
65                  70                  75                  80

Ile Ser Arg Leu Glu Pro Glu Asp Phe Ala Val Tyr Tyr Cys Gln Gln
                85                  90                  95

Tyr Tyr Asn Tyr Pro Trp Thr Phe Gly Gln Gly Thr Lys Leu Glu Ile
            100                 105                 110

Lys
```

<210> SEQ ID NO 210
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="Light Chain of TPP-8988 IgG histidine scanning variant #13"

<400> SEQUENCE: 210

```
Glu Ile Val Leu Thr Gln Ser Pro Gly Thr Leu Ser Leu Ser Pro Gly
1               5                   10                  15

Glu Arg Ala Thr Leu Ser Cys Lys Ser Ser Gln Ser Leu Phe Phe Gly
            20                  25                  30

Ser Thr Gln Lys Asn Tyr His Ala Trp Tyr Gln Gln Lys Pro Gly Gln
        35                  40                  45

Ala Pro Arg Leu Leu Ile Tyr Trp Ala Ser Thr Arg Glu Ser Gly Ile
    50                  55                  60

Pro Asp Arg Phe Ser Gly Ser Gly Ser Gly Thr Asp Phe Thr Leu Thr
65                  70                  75                  80

Ile Ser Arg Leu Glu Pro Glu Asp Phe Ala Val Tyr Tyr Cys Gln Gln
                85                  90                  95

Tyr Tyr Asn Tyr Pro Trp Thr Phe Gly Gln Gly Thr Lys Leu Glu Ile
            100                 105                 110

Lys
```

<210> SEQ ID NO 211
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="Light Chain of TPP-8988 IgG histidine scanning variant #14"

<400> SEQUENCE: 211

```
Glu Ile Val Leu Thr Gln Ser Pro Gly Thr Leu Ser Leu Ser Pro Gly
1               5                   10                  15

Glu Arg Ala Thr Leu Ser Cys Lys Ser Ser Gln Ser Leu Phe Phe Gly
            20                  25                  30

Ser Thr Gln Lys Asn Tyr Leu His Trp Tyr Gln Gln Lys Pro Gly Gln
        35                  40                  45

Ala Pro Arg Leu Leu Ile Tyr Trp Ala Ser Thr Arg Glu Ser Gly Ile
    50                  55                  60

Pro Asp Arg Phe Ser Gly Ser Gly Ser Gly Thr Asp Phe Thr Leu Thr
65                  70                  75                  80

Ile Ser Arg Leu Glu Pro Glu Asp Phe Ala Val Tyr Tyr Cys Gln Gln
                85                  90                  95

Tyr Tyr Asn Tyr Pro Trp Thr Phe Gly Gln Gly Thr Lys Leu Glu Ile
            100                 105                 110

Lys
```

<210> SEQ ID NO 212
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="Light Chain of TPP-8988 IgG histidine scanning variant #15"

<400> SEQUENCE: 212

```
Glu Ile Val Leu Thr Gln Ser Pro Gly Thr Leu Ser Leu Ser Pro Gly
```

```
1               5                   10                  15

Glu Arg Ala Thr Leu Ser Cys Lys Ser Ser Gln Ser Leu Phe Phe Gly
            20                  25                  30

Ser Thr Gln Lys Asn Tyr Leu Ala Trp Tyr Gln Gln Lys Pro Gly Gln
        35                  40                  45

Ala Pro Arg Leu Leu Ile Tyr His Ala Ser Thr Arg Glu Ser Gly Ile
    50                  55                  60

Pro Asp Arg Phe Ser Gly Ser Gly Ser Gly Thr Asp Phe Thr Leu Thr
65                  70                  75                  80

Ile Ser Arg Leu Glu Pro Glu Asp Phe Ala Val Tyr Tyr Cys Gln Gln
                85                  90                  95

Tyr Tyr Asn Tyr Pro Trp Thr Phe Gly Gln Gly Thr Lys Leu Glu Ile
            100                 105                 110

Lys


<210> SEQ ID NO 213
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of TPP-8988 IgG histidine
      scanning variant #16"

<400> SEQUENCE: 213

Glu Ile Val Leu Thr Gln Ser Pro Gly Thr Leu Ser Leu Ser Pro Gly
1               5                   10                  15

Glu Arg Ala Thr Leu Ser Cys Lys Ser Ser Gln Ser Leu Phe Phe Gly
            20                  25                  30

Ser Thr Gln Lys Asn Tyr Leu Ala Trp Tyr Gln Gln Lys Pro Gly Gln
        35                  40                  45

Ala Pro Arg Leu Leu Ile Tyr Trp His Ser Thr Arg Glu Ser Gly Ile
    50                  55                  60

Pro Asp Arg Phe Ser Gly Ser Gly Ser Gly Thr Asp Phe Thr Leu Thr
65                  70                  75                  80

Ile Ser Arg Leu Glu Pro Glu Asp Phe Ala Val Tyr Tyr Cys Gln Gln
                85                  90                  95

Tyr Tyr Asn Tyr Pro Trp Thr Phe Gly Gln Gly Thr Lys Leu Glu Ile
            100                 105                 110

Lys


<210> SEQ ID NO 214
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of TPP-8988 IgG histidine
      scanning variant #17"

<400> SEQUENCE: 214

Glu Ile Val Leu Thr Gln Ser Pro Gly Thr Leu Ser Leu Ser Pro Gly
1               5                   10                  15
```

```
Glu Arg Ala Thr Leu Ser Cys Lys Ser Ser Gln Ser Leu Phe Phe Gly
            20                  25                  30

Ser Thr Gln Lys Asn Tyr Leu Ala Trp Tyr Gln Gln Lys Pro Gly Gln
        35                  40                  45

Ala Pro Arg Leu Leu Ile Tyr Trp Ala His Thr Arg Glu Ser Gly Ile
    50                  55                  60

Pro Asp Arg Phe Ser Gly Ser Gly Ser Gly Thr Asp Phe Thr Leu Thr
65                  70                  75                  80

Ile Ser Arg Leu Glu Pro Glu Asp Phe Ala Val Tyr Tyr Cys Gln Gln
                85                  90                  95

Tyr Tyr Asn Tyr Pro Trp Thr Phe Gly Gln Gly Thr Lys Leu Glu Ile
            100                 105                 110

Lys
```

<210> SEQ ID NO 215
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="Light Chain of TPP-8988 IgG histidine scanning variant #18"

<400> SEQUENCE: 215

```
Glu Ile Val Leu Thr Gln Ser Pro Gly Thr Leu Ser Leu Ser Pro Gly
1               5                   10                  15

Glu Arg Ala Thr Leu Ser Cys Lys Ser Ser Gln Ser Leu Phe Phe Gly
            20                  25                  30

Ser Thr Gln Lys Asn Tyr Leu Ala Trp Tyr Gln Gln Lys Pro Gly Gln
        35                  40                  45

Ala Pro Arg Leu Leu Ile Tyr Trp Ala Ser His Arg Glu Ser Gly Ile
    50                  55                  60

Pro Asp Arg Phe Ser Gly Ser Gly Ser Gly Thr Asp Phe Thr Leu Thr
65                  70                  75                  80

Ile Ser Arg Leu Glu Pro Glu Asp Phe Ala Val Tyr Tyr Cys Gln Gln
                85                  90                  95

Tyr Tyr Asn Tyr Pro Trp Thr Phe Gly Gln Gly Thr Lys Leu Glu Ile
            100                 105                 110

Lys
```

<210> SEQ ID NO 216
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="Light Chain of TPP-8988 IgG histidine scanning variant #19"

<400> SEQUENCE: 216

```
Glu Ile Val Leu Thr Gln Ser Pro Gly Thr Leu Ser Leu Ser Pro Gly
1               5                   10                  15
```

```
Glu Arg Ala Thr Leu Ser Cys Lys Ser Ser Gln Ser Leu Phe Phe Gly
            20                  25                  30

Ser Thr Gln Lys Asn Tyr Leu Ala Trp Tyr Gln Gln Lys Pro Gly Gln
        35                  40                  45

Ala Pro Arg Leu Leu Ile Tyr Trp Ala Ser Thr His Glu Ser Gly Ile
    50                  55                  60

Pro Asp Arg Phe Ser Gly Ser Gly Ser Gly Thr Asp Phe Thr Leu Thr
65                  70                  75                  80

Ile Ser Arg Leu Glu Pro Glu Asp Phe Ala Val Tyr Tyr Cys Gln Gln
                85                  90                  95

Tyr Tyr Asn Tyr Pro Trp Thr Phe Gly Gln Gly Thr Lys Leu Glu Ile
            100                 105                 110

Lys


<210> SEQ ID NO 217
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of TPP-8988 IgG histidine
      scanning variant #20"

<400> SEQUENCE: 217

Glu Ile Val Leu Thr Gln Ser Pro Gly Thr Leu Ser Leu Ser Pro Gly
1               5                   10                  15

Glu Arg Ala Thr Leu Ser Cys Lys Ser Ser Gln Ser Leu Phe Phe Gly
            20                  25                  30

Ser Thr Gln Lys Asn Tyr Leu Ala Trp Tyr Gln Gln Lys Pro Gly Gln
        35                  40                  45

Ala Pro Arg Leu Leu Ile Tyr Trp Ala Ser Thr Arg His Ser Gly Ile
    50                  55                  60

Pro Asp Arg Phe Ser Gly Ser Gly Ser Gly Thr Asp Phe Thr Leu Thr
65                  70                  75                  80

Ile Ser Arg Leu Glu Pro Glu Asp Phe Ala Val Tyr Tyr Cys Gln Gln
                85                  90                  95

Tyr Tyr Asn Tyr Pro Trp Thr Phe Gly Gln Gly Thr Lys Leu Glu Ile
            100                 105                 110

Lys


<210> SEQ ID NO 218
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of TPP-8988 IgG histidine
      scanning variant #21"

<400> SEQUENCE: 218

Glu Ile Val Leu Thr Gln Ser Pro Gly Thr Leu Ser Leu Ser Pro Gly
1               5                   10                  15

Glu Arg Ala Thr Leu Ser Cys Lys Ser Ser Gln Ser Leu Phe Phe Gly
```

```
            20                  25                  30

Ser Thr Gln Lys Asn Tyr Leu Ala Trp Tyr Gln Gln Lys Pro Gly Gln
        35                  40                  45

Ala Pro Arg Leu Leu Ile Tyr Trp Ala Ser Thr Arg Glu His Gly Ile
    50                  55                  60

Pro Asp Arg Phe Ser Gly Ser Gly Ser Gly Thr Asp Phe Thr Leu Thr
65                  70                  75                  80

Ile Ser Arg Leu Glu Pro Glu Asp Phe Ala Val Tyr Tyr Cys Gln Gln
                85                  90                  95

Tyr Tyr Asn Tyr Pro Trp Thr Phe Gly Gln Gly Thr Lys Leu Glu Ile
            100                 105                 110

Lys


<210> SEQ ID NO 219
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of TPP-8988 IgG histidine
      scanning variant #22"

<400> SEQUENCE: 219

Glu Ile Val Leu Thr Gln Ser Pro Gly Thr Leu Ser Leu Ser Pro Gly
1               5                   10                  15

Glu Arg Ala Thr Leu Ser Cys Lys Ser Ser Gln Ser Leu Phe Phe Gly
            20                  25                  30

Ser Thr Gln Lys Asn Tyr Leu Ala Trp Tyr Gln Gln Lys Pro Gly Gln
        35                  40                  45

Ala Pro Arg Leu Leu Ile Tyr Trp Ala Ser Thr Arg Glu Ser Gly Ile
    50                  55                  60

Pro Asp Arg Phe Ser Gly Ser Gly Ser Gly Thr Asp Phe Thr Leu Thr
65                  70                  75                  80

Ile Ser Arg Leu Glu Pro Glu Asp Phe Ala Val Tyr Tyr Cys His Gln
                85                  90                  95

Tyr Tyr Asn Tyr Pro Trp Thr Phe Gly Gln Gly Thr Lys Leu Glu Ile
            100                 105                 110

Lys


<210> SEQ ID NO 220
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of TPP-8988 IgG histidine
      scanning variant #23"

<400> SEQUENCE: 220

Glu Ile Val Leu Thr Gln Ser Pro Gly Thr Leu Ser Leu Ser Pro Gly
1               5                   10                  15

Glu Arg Ala Thr Leu Ser Cys Lys Ser Ser Gln Ser Leu Phe Phe Gly
            20                  25                  30
```

```
Ser Thr Gln Lys Asn Tyr Leu Ala Trp Tyr Gln Gln Lys Pro Gly Gln
        35                  40                  45

Ala Pro Arg Leu Leu Ile Tyr Trp Ala Ser Thr Arg Glu Ser Gly Ile
    50                  55                  60

Pro Asp Arg Phe Ser Gly Ser Gly Ser Gly Thr Asp Phe Thr Leu Thr
65                  70                  75                  80

Ile Ser Arg Leu Glu Pro Glu Asp Phe Ala Val Tyr Tyr Cys Gln His
                85                  90                  95

Tyr Tyr Asn Tyr Pro Trp Thr Phe Gly Gln Gly Thr Lys Leu Glu Ile
            100                 105                 110

Lys


<210> SEQ ID NO 221
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of TPP-8988 IgG histidine
      scanning variant #24"

<400> SEQUENCE: 221

Glu Ile Val Leu Thr Gln Ser Pro Gly Thr Leu Ser Leu Ser Pro Gly
1               5                   10                  15

Glu Arg Ala Thr Leu Ser Cys Lys Ser Ser Gln Ser Leu Phe Phe Gly
            20                  25                  30

Ser Thr Gln Lys Asn Tyr Leu Ala Trp Tyr Gln Gln Lys Pro Gly Gln
        35                  40                  45

Ala Pro Arg Leu Leu Ile Tyr Trp Ala Ser Thr Arg Glu Ser Gly Ile
    50                  55                  60

Pro Asp Arg Phe Ser Gly Ser Gly Ser Gly Thr Asp Phe Thr Leu Thr
65                  70                  75                  80

Ile Ser Arg Leu Glu Pro Glu Asp Phe Ala Val Tyr Tyr Cys Gln Gln
                85                  90                  95

His Tyr Asn Tyr Pro Trp Thr Phe Gly Gln Gly Thr Lys Leu Glu Ile
            100                 105                 110

Lys


<210> SEQ ID NO 222
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of TPP-8988 IgG histidine
      scanning variant #25"

<400> SEQUENCE: 222

Glu Ile Val Leu Thr Gln Ser Pro Gly Thr Leu Ser Leu Ser Pro Gly
1               5                   10                  15

Glu Arg Ala Thr Leu Ser Cys Lys Ser Ser Gln Ser Leu Phe Phe Gly
            20                  25                  30
```

```
Ser Thr Gln Lys Asn Tyr Leu Ala Trp Tyr Gln Gln Lys Pro Gly Gln
        35                  40                  45

Ala Pro Arg Leu Leu Ile Tyr Trp Ala Ser Thr Arg Glu Ser Gly Ile
    50                  55                  60

Pro Asp Arg Phe Ser Gly Ser Gly Ser Gly Thr Asp Phe Thr Leu Thr
65                  70                  75                  80

Ile Ser Arg Leu Glu Pro Glu Asp Phe Ala Val Tyr Tyr Cys Gln Gln
                85                  90                  95

Tyr His Asn Tyr Pro Trp Thr Phe Gly Gln Gly Thr Lys Leu Glu Ile
            100                 105                 110

Lys
```

<210> SEQ ID NO 223
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="Light Chain of TPP-8988 IgG histidine scanning variant #26"

<400> SEQUENCE: 223

```
Glu Ile Val Leu Thr Gln Ser Pro Gly Thr Leu Ser Leu Ser Pro Gly
1               5                   10                  15

Glu Arg Ala Thr Leu Ser Cys Lys Ser Ser Gln Ser Leu Phe Phe Gly
            20                  25                  30

Ser Thr Gln Lys Asn Tyr Leu Ala Trp Tyr Gln Gln Lys Pro Gly Gln
        35                  40                  45

Ala Pro Arg Leu Leu Ile Tyr Trp Ala Ser Thr Arg Glu Ser Gly Ile
    50                  55                  60

Pro Asp Arg Phe Ser Gly Ser Gly Ser Gly Thr Asp Phe Thr Leu Thr
65                  70                  75                  80

Ile Ser Arg Leu Glu Pro Glu Asp Phe Ala Val Tyr Tyr Cys Gln Gln
                85                  90                  95

Tyr Tyr His Tyr Pro Trp Thr Phe Gly Gln Gly Thr Lys Leu Glu Ile
            100                 105                 110

Lys
```

<210> SEQ ID NO 224
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: source
<223> OTHER INFORMATION: /note="Light Chain of TPP-8988 IgG histidine scanning variant #27"

<400> SEQUENCE: 224

```
Glu Ile Val Leu Thr Gln Ser Pro Gly Thr Leu Ser Leu Ser Pro Gly
1               5                   10                  15

Glu Arg Ala Thr Leu Ser Cys Lys Ser Ser Gln Ser Leu Phe Phe Gly
            20                  25                  30

Ser Thr Gln Lys Asn Tyr Leu Ala Trp Tyr Gln Gln Lys Pro Gly Gln
```

```
        35                  40                  45

Ala Pro Arg Leu Leu Ile Tyr Trp Ala Ser Thr Arg Glu Ser Gly Ile
    50                  55                  60

Pro Asp Arg Phe Ser Gly Ser Gly Ser Gly Thr Asp Phe Thr Leu Thr
65                  70                  75                  80

Ile Ser Arg Leu Glu Pro Glu Asp Phe Ala Val Tyr Tyr Cys Gln Gln
                85                  90                  95

Tyr Tyr Asn His Pro Trp Thr Phe Gly Gln Gly Thr Lys Leu Glu Ile
            100                 105                 110

Lys


<210> SEQ ID NO 225
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of TPP-8988 IgG histidine
      scanning variant #28"

<400> SEQUENCE: 225

Glu Ile Val Leu Thr Gln Ser Pro Gly Thr Leu Ser Leu Ser Pro Gly
1               5                   10                  15

Glu Arg Ala Thr Leu Ser Cys Lys Ser Ser Gln Ser Leu Phe Phe Gly
            20                  25                  30

Ser Thr Gln Lys Asn Tyr Leu Ala Trp Tyr Gln Gln Lys Pro Gly Gln
        35                  40                  45

Ala Pro Arg Leu Leu Ile Tyr Trp Ala Ser Thr Arg Glu Ser Gly Ile
    50                  55                  60

Pro Asp Arg Phe Ser Gly Ser Gly Ser Gly Thr Asp Phe Thr Leu Thr
65                  70                  75                  80

Ile Ser Arg Leu Glu Pro Glu Asp Phe Ala Val Tyr Tyr Cys Gln Gln
                85                  90                  95

Tyr Tyr Asn Tyr His Trp Thr Phe Gly Gln Gly Thr Lys Leu Glu Ile
            100                 105                 110

Lys


<210> SEQ ID NO 226
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of TPP-8988 IgG histidine
      scanning variant #29"

<400> SEQUENCE: 226

Glu Ile Val Leu Thr Gln Ser Pro Gly Thr Leu Ser Leu Ser Pro Gly
1               5                   10                  15

Glu Arg Ala Thr Leu Ser Cys Lys Ser Ser Gln Ser Leu Phe Phe Gly
            20                  25                  30

Ser Thr Gln Lys Asn Tyr Leu Ala Trp Tyr Gln Gln Lys Pro Gly Gln
        35                  40                  45
```

```
Ala Pro Arg Leu Leu Ile Tyr Trp Ala Ser Thr Arg Glu Ser Gly Ile
    50                  55                  60

Pro Asp Arg Phe Ser Gly Ser Gly Ser Gly Thr Asp Phe Thr Leu Thr
65                  70                  75                  80

Ile Ser Arg Leu Glu Pro Glu Asp Phe Ala Val Tyr Tyr Cys Gln Gln
                85                  90                  95

Tyr Tyr Asn Tyr Pro His Thr Phe Gly Gln Gly Thr Lys Leu Glu Ile
            100                 105                 110

Lys


<210> SEQ ID NO 227
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Light Chain of TPP-8988 IgG histidine
      scanning variant #30"

<400> SEQUENCE: 227

Glu Ile Val Leu Thr Gln Ser Pro Gly Thr Leu Ser Leu Ser Pro Gly
1               5                   10                  15

Glu Arg Ala Thr Leu Ser Cys Lys Ser Ser Gln Ser Leu Phe Phe Gly
            20                  25                  30

Ser Thr Gln Lys Asn Tyr Leu Ala Trp Tyr Gln Gln Lys Pro Gly Gln
        35                  40                  45

Ala Pro Arg Leu Leu Ile Tyr Trp Ala Ser Thr Arg Glu Ser Gly Ile
    50                  55                  60

Pro Asp Arg Phe Ser Gly Ser Gly Ser Gly Thr Asp Phe Thr Leu Thr
65                  70                  75                  80

Ile Ser Arg Leu Glu Pro Glu Asp Phe Ala Val Tyr Tyr Cys Gln Gln
                85                  90                  95

Tyr Tyr Asn Tyr Pro Trp His Phe Gly Gln Gly Thr Lys Leu Glu Ile
            100                 105                 110

Lys
```

ANTIGEN-BINDING PROTEIN CONSTRUCTS AND USES THEREOF

CROSS-REFERENCE TO RELATED APPLICATIONS

This application is a National Stage Application under 35 U.S.C. § 371 of International Patent Application No. PCT/US2020/050402, filed on Sep. 11, 2020, which claims priority to U.S. Provisional Patent Application Ser. No. 62/900,113, filed on Sep. 13, 2019. The contents of these applications are incorporated herein by reference in their entirety.

TECHNICAL FIELD

The present disclosure relates to the field of biotechnology, and more specifically, to antigen-binding molecules.

BACKGROUND

Antibody-drug-conjugates have been designed to combat a variety of diseases. One particular advantage of this approach is the ability for antibody-drug conjugates to have cytostatic or cytotoxic effects. Despite years of development, improved antibody-drug conjugates are desired.

SUMMARY

The present invention is based on the concept that antigen-binding protein constructs can be generated that display enhanced efficacy (e.g., one or more of an increase (e.g., a detectable increase) in toxin liberation in a target mammalian cell, an increase (e.g., a detectable increase) in target mammalian cell killing, and an increase (e.g., a detectable increase) in endolysosomal delivery).

Provided herein are pharmaceutical compositions including an effective amount of an antigen-binding protein construct (ABPC) including: a first antigen-binding domain that is capable of specifically binding CD123 or an epitope of CD123 presented on the surface of a target mammalian cell, where: (a) the dissociation rate of the first antigen-binding domain at a pH of about 4.0 to about 6.5 is faster than the dissociation rate at a pH of about 7.0 to about 8.0; or (b) the dissociation constant ($K_D$) of the first antigen-binding domain at a pH of about 4.0 to about 6.5 is greater than the $K_D$ at a pH of about 7.0 to about 8.0.

In some embodiments of any of the pharmaceutical compositions described herein, the ABPC is degraded in the target mammalian cell following internalization of the ABPC by the target mammalian cell.

In some embodiments of any of the pharmaceutical compositions described herein, the ABPC includes a conjugated toxin, radioisotope, drug, or small molecule.

Also provided herein are pharmaceutical compositions including an effective amount of an antigen-binding protein construct (ABPC) including: a first antigen-binding domain that is capable of specifically binding CD123 or an epitope of CD123 presented on the surface of a target mammalian cell; and a conjugated toxin, radioisotope, drug, or small molecule, where: (a) the dissociation rate of the first antigen-binding domain at a pH of about 4.0 to about 6.5 is faster than the dissociation rate at a pH of about 7.0 to about 8.0; or the dissociation constant ($K_D$) of the first antigen-binding domain at a pH of about 4.0 to about 6.5 is greater than the $K_D$ at a pH of about 7.0 to about 8.0; and (b) the composition provides for one or more of: an increase in toxin liberation in the target mammalian cell as compared to a composition including the same amount of a control ABPC; an increase in target mammalian cell killing as compared to a composition including the same amount of a control ABPC; and an increase in endolysosomal delivery in the target mammalian cell as compared to a composition including the same amount of a control ABPC.

In some embodiments of any of the pharmaceutical compositions described herein, the first antigen-binding domain includes one of (a) through (c): (a) a heavy chain variable domain of IMGN632 with one or more amino acids substituted with a histidine, where the heavy chain variable domain of IMGN632 includes SEQ ID NO: 1; and/or a light chain variable domain of IMGN632 with one or more amino acids substituted with a histidine, where the light chain variable domain of IMGN632 includes SEQ ID NO: 2; (b) a heavy chain variable domain of SGN-CD123A with one or more amino acids substituted with a histidine, where the heavy chain variable domain of SGN-CD123A includes SEQ ID NO: 101; and/or a light chain variable domain of SGN-CD123A with one or more amino acids substituted with a histidine, where the light chain variable domain of SGN-CD123A includes SEQ ID NO: 102; and (c) a heavy chain variable domain of TPP-8988 with one or more amino acids substituted with a histidine, where the heavy chain variable domain of TPP-8988 includes SEQ ID NO: 149; and/or a light chain variable domain of TPP-8988 with one or more amino acids substituted with a histidine, where the light chain variable domain of TPP-8988 includes SEQ ID NO: 150.

In some embodiments of any of the pharmaceutical compositions described herein, the first CD123-binding domain includes one of (a) through (c): (a) a heavy chain variable domain including a CDR1, a CDR2, and a CDR3 of SEQ ID NOs: 3-5, respectively, with collectively a total of one or more amino acid positions in SEQ ID NOs: 3-5 substituted with a histidine; and/or a light chain variable domain including a CDR1, a CDR2, and a CDR3 of SEQ ID NOs: 6-8, respectively, with collectively a total of one or more amino acid positions in SEQ ID NOs: 6-8 substituted with a histidine; (b) a heavy chain variable domain including a CDR1, a CDR2, and a CDR3 of SEQ ID NOs: 103-105, respectively, with collectively a total of one or more amino acid positions in SEQ ID NOs: 103-105 substituted with a histidine; and/or a light chain variable domain including a CDR1, a CDR2, and a CDR3 of SEQ ID NOs: 106-108, respectively, with collectively a total of one or more amino acid positions in SEQ ID NOs: 106-108 substituted with a histidine; and (c) a heavy chain variable domain including a CDR1, a CDR2, and a CDR3 of SEQ ID NOs: 151-153, respectively, with collectively a total of one or more amino acid positions in SEQ ID NOs: 151-153 substituted with a histidine; and/or a light chain variable domain including a CDR1, a CDR2, and a CDR3 of SEQ ID NOs: 154-156, respectively, with collectively a total of one or more amino acid positions in SEQ ID NOs: 154-156 substituted with a histidine.

In some embodiments of any of the pharmaceutical compositions described herein, the first antigen-binding domain includes one of (a) through (c): (a) a heavy chain variable domain that is at least 90% identical to SEQ ID NO: 1, where the heavy chain variable domain includes a histidine at one or more positions in SEQ ID NO: 1 selected from the group consisting of: 27, 28, 29, 30, 33, 53, 97, 103, 104, 105, 106, 107, 108, and 109; and/or a light chain variable domain that is at least 90% identical to SEQ ID NO: 2, where the light chain variable domain includes a histidine at one or more positions in SEQ ID NO: 2 selected from the group consisting of: 34, 55, 91, 94, 95, and 96; (b) a heavy chain variable domain that is at least 90% identical to SEQ ID NO: 101, where the heavy chain variable domain includes a histidine at one or more positions in SEQ ID NO: 101 selected from the group consisting of: 26, 27, 32, 33, 35, 52, 57, 58, 59, 104, and 105; and a light chain variable domain that is at least 90% identical to SEQ ID NO: 102; and (c) a heavy chain variable domain that is at least 90% identical to SEQ ID NO: 149, where the heavy chain variable domain includes a histidine at one or more positions in SEQ ID NO: 149 selected from the group consisting of: 32, 34, 35, 36, 51, 53, 54, 98, 99, 100, 101, 103, and 104; and/or a light chain variable domain that is at least 90% identical to SEQ ID NO: 150, where the light chain variable domain includes a histidine at one or more positions in SEQ ID NO: 150 selected from the group consisting of 29, 30, 31, 32, 33, 34, 38, 56, 95, 96, 97, 101, and 102.

In some embodiments of any of the pharmaceutical compositions described herein, the first antigen-binding domain includes one of (a) through (c): (a) a light chain variable domain of SEQ ID NO: 2, SEQ ID NO: 64, SEQ ID NO: 70, SEQ ID NO: 74, SEQ ID NO: 77, SEQ ID NO: 78, or SEQ ID NO: 79 and/or a heavy chain variable domain of SEQ ID NO: 1, SEQ ID NO: 14, SEQ ID NO: 15, SEQ ID NO: 16, SEQ ID NO: 17, SEQ ID NO: 20, SEQ ID NO: 22, SEQ ID NO: 26, SEQ ID NO: 40, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, or SEQ ID NO: 100, where the first antigen-binding domain does not comprise (i) a light chain variable domain of SEQ ID NO: 2 and a heavy chain variable domain of SEQ ID NO: 1; (ii) a light chain variable domain of SEQ ID NO: 2 and heavy chain variable domain that is not one of SEQ ID NOs: 14-17, 20, 22, 26, 40, 46-52, or 81-100; or (iii) a heavy chain variable domain of SEQ ID NO: 1 and a light chain variable domain that is not one of SEQ ID NOs: 64, 70, 74, or 77-79; (b) a light chain variable domain of SEQ ID NO: 102, and/or a heavy chain variable domain of SEQ ID NO: 101, SEQ ID NO: 109, SEQ ID NO: 110, SEQ ID NO: 115, SEQ ID NO: 116, SEQ ID NO: 118, SEQ ID NO: 121, SEQ ID NO: 126, SEQ ID NO: 127, SEQ ID NO: 128, SEQ ID NO: 143, or SEQ ID NO: 144, where the first antigen-binding domain does not comprise (i) a light chain variable domain of SEQ ID NO: 102 and a heavy chain variable domain of SEQ ID NO: 101; or (ii) a light chain variable domain of SEQ ID NO: 102 and heavy chain variable domain that is not one of SEQ ID NOs: 109, 110, 115, 116, 118, 121, 126-128, 143, or 144; and (c) a light chain variable domain of SEQ ID NO: 150, SEQ ID NO: 200, SEQ ID NO: 201, SEQ ID NO: 202, SEQ ID NO: 203, SEQ ID NO: 204, SEQ ID NO: 205, SEQ ID NO: 209, SEQ ID NO: 212, SEQ ID NO: 219, SEQ ID NO: 220, SEQ ID NO: 221, SEQ ID NO: 225, or SEQ ID NO: 226, and/or a heavy chain variable domain of SEQ ID NO: 149, SEQ ID NO: 166, SEQ ID NO: 168, SEQ ID NO: 169, SEQ ID NO: 170, SEQ ID NO: 171, SEQ ID NO: 173, SEQ ID NO: 174, SEQ ID NO: 188, SEQ ID NO: 189, SEQ ID NO: 190, SEQ ID NO: 191, SEQ ID NO: 193, or SEQ ID NO: 194, where the first antigen-binding domain does not comprise (i) a light chain variable domain of SEQ ID NO: 150 and a heavy chain variable domain of SEQ ID NO: 149; (ii) a light chain variable domain of SEQ ID NO: 150 and heavy chain variable domain that is not one of SEQ ID NOs: 166, 168-171, 173, 174, 188-191, 193, or 194; or (iii) a heavy chain variable domain of SEQ ID NO: 149 and a light chain variable domain that is not one of SEQ ID NOs: 200-205, 209, 212, 219-221, 225, or 226.

In some embodiments of any of the pharmaceutical compositions described herein, the composition provides for: an increase in toxin liberation in the target mammalian cell as compared to a composition including the same amount of a control ABPC; and/or an increase in target mammalian cell killing as compared to a composition including the same amount of a control ABPC.

In some embodiments of any of the pharmaceutical compositions described herein, the composition provides for an increase in endolysosomal delivery in the target mammalian cell as compared to a composition including the same amount of a control ABPC.

In some embodiments of any of the pharmaceutical compositions described herein, the composition: results in a less of a reduction in the level of CD123 presented on the surface of the target mammalian cell as compared to a composition including the same amount of a control ABPC; or does not result in a detectable reduction in the level of CD123 presented on the surface of the target mammalian cell.

In some embodiments of any of the pharmaceutical compositions described herein, the target mammalian cell is a cancer cell. In some embodiments of any of the pharmaceutical compositions described herein, the ABPC is cytotoxic or cytostatic to the target mammalian cell.

In some embodiments of any of the pharmaceutical compositions described herein, the ABPC is: cross-reactive with a non-human primate CD123 and human CD123; or cross-reactive with a non-human primate CD123, a human CD123, and one or both of rat CD123 and a mouse CD123.

In some embodiments of any of the pharmaceutical compositions described herein, the ABPC includes a single polypeptide. In some embodiments of any of the pharmaceutical compositions described herein, the antigen-binding domain is selected from the group consisting of: a VH domain, a VHH domain, a VNAR domain, and a scFv. In some embodiments of any of the pharmaceutical compositions described herein, the ABPC includes two or more polypeptides. In some embodiments of any of the pharmaceutical compositions described herein, the ABPC is an antibody.

In some embodiments of any of the pharmaceutical compositions described herein, the half-life of the ABPC in vivo is decreased as compared to the half-life of a control ABPC in vivo.

In some embodiments of any of the pharmaceutical compositions described herein, the ABPC includes a second antigen-binding domain.

Also provided herein are an antigen-binding protein constructs (ABPCs) including: a first antigen-binding domain that is capable of specifically binding CD123 or an epitope of CD123 presented on the surface of a target mammalian cell, where: (a) the dissociation rate of the first antigen-binding domain at a pH of about 4.0 to about 6.5 is faster than the dissociation rate at a pH of about 7.0 to about 8.0; or (b) the dissociation constant ($K_D$) of the first antigen-binding domain at a pH of about 4.0 to about 6.5 is greater than the $K_D$ at a pH of about 7.0 to about 8.0.

In some embodiments of any of the ABPCs described herein, the target mammalian cell following internalization of the ABPC by the target mammalian cell.

In some embodiments of any of the ABPCs described herein, the ABPC includes a conjugated toxin, radioisotope, drug, or small molecule.

Also provided herein are an antigen-binding protein constructs (ABPCs) including: a first antigen-binding domain that is capable of specifically binding CD123 or an epitope of CD123 presented on the surface of a target mammalian cell; and a conjugated toxin, radioisotope, drug, or small molecule, where: (a) the dissociation rate of the first antigen-binding domain at a pH of about 4.0 to about 6.5 is faster than the dissociation rate at a pH of about 7.0 to about 8.0; or the dissociation constant ($K_D$) of the first antigen-binding domain at a pH of about 4.0 to about 6.5 is greater than the $K_D$ at a pH of about 7.0 to about 8.0; and (b) the composition provides for one or more of: an increase in toxin liberation in the target mammalian cell as compared to a composition including the same amount of a control ABPC; an increase in target mammalian cell killing as compared to a composition including the same amount of a control ABPC; and an increase in endolysosomal delivery in the target mammalian cell as compared to a composition including the same amount of a control ABPC.

In some embodiments of any of the ABPCs described herein, the first antigen-binding domain includes one of (a) through (c): (a) a heavy chain variable domain of IMGN632 with one or more amino acids substituted with a histidine, where the heavy chain variable domain of IMGN632 includes SEQ ID NO: 1; and/or a light chain variable domain of IMGN632 with one or more amino acids substituted with a histidine, where the light chain variable domain of IMGN632 includes SEQ ID NO: 2; (b) a heavy chain variable domain of SGN-CD123A with one or more amino acids substituted with a histidine, where the heavy chain variable domain of SGN-CD123A includes SEQ ID NO: 101; and/or a light chain variable domain of SGN-CD123A with one or more amino acids substituted with a histidine, where the light chain variable domain of SGN-CD123A includes SEQ ID NO: 102; and (c) a heavy chain variable domain of TPP-8988 with one or more amino acids substituted with a histidine, where the heavy chain variable domain of TPP-8988 includes SEQ ID NO: 149; and/or a light chain variable domain of TPP-8988 with one or more amino acids substituted with a histidine, where the light chain variable domain of TPP-8988 includes SEQ ID NO: 150.

In some embodiments of any of the ABPCs described herein, the first CD123-binding domain includes one of (a) through (c): (a) a heavy chain variable domain including a CDR1, a CDR2, and a CDR3 of SEQ ID NOs: 3-5, respectively, with collectively a total of one or more amino acid positions in SEQ ID NOs: 3-5 substituted with a histidine; and/or a light chain variable domain including a CDR1, a CDR2, and a CDR3 of SEQ ID NOs: 6-8, respectively, with collectively a total of one or more amino acid positions in SEQ ID NOs: 6-8 substituted with a histidine; (b) a heavy chain variable domain including a CDR1, a CDR2, and a CDR3 of SEQ ID NOs: 103-105, respectively, with collectively a total of one or more amino acid positions in SEQ ID NOs: 103-105 substituted with a histidine; and/or a light chain variable domain including a CDR1, a CDR2, and a CDR3 of SEQ ID NOs: 106-108, respectively, with collectively a total of one or more amino acid positions in SEQ ID NOs: 106-108 substituted with a histidine; and (c) a heavy chain variable domain including a CDR1, a CDR2, and a CDR3 of SEQ ID NOs: 151-153, respectively, with collectively a total of one or more amino acid positions in SEQ ID NOs: 151-153 substituted with a histidine; and/or a light chain variable domain including a CDR1, a CDR2, and a CDR3 of SEQ ID NOs: 154-156, respectively, with collectively a total of one or more amino acid positions in SEQ ID NOs: 154-156 substituted with a histidine.

In some embodiments of any of the ABPCs described herein, the first antigen-binding domain includes one of (a) through (c): (a) a heavy chain variable domain that is at least 90% identical to SEQ ID NO: 1, where the heavy chain variable domain includes a histidine at one or more positions in SEQ ID NO: 1 selected from the group consisting of: 27, 28, 29, 30, 33, 53, 97, 103, 104, 105, 106, 107, 108, and 109; and/or a light chain variable domain that is at least 90% identical to SEQ ID NO: 2, where the light chain variable domain includes a histidine at one or more positions in SEQ ID NO: 2 selected from the group consisting of: 34, 55, 91, 94, 95, and 96; (b) a heavy chain variable domain that is at least 90% identical to SEQ ID NO: 101, where the heavy chain variable domain includes a histidine at one or more positions in SEQ ID NO: 101 selected from the group consisting of: 26, 27, 32, 33, 35, 52, 57, 58, 59, 104, and 105; and a light chain variable domain that is at least 90% identical to SEQ ID NO: 102; and (c) a heavy chain variable domain that is at least 90% identical to SEQ ID NO: 149, where the heavy chain variable domain includes a histidine at one or more positions in SEQ ID NO: 149 selected from the group consisting of: 32, 34, 35, 36, 51, 53, 54, 98, 99, 100, 101, 103, and 104; and/or a light chain variable domain that is at least 90% identical to SEQ ID NO: 150, where the light chain variable domain includes a histidine at one or more positions in SEQ ID NO: 150 selected from the group consisting of 29, 30, 31, 32, 33, 34, 38, 56, 95, 96, 97, 101, and 102.

In some embodiments of any of the ABPCs described herein, the first antigen-binding domain includes one of (a) through (c): (a) a light chain variable domain of SEQ ID NO: 2, SEQ ID NO: 64, SEQ ID NO: 70, SEQ ID NO: 74, SEQ ID NO: 77, SEQ ID NO: 78, or SEQ ID NO: 79 and/or a heavy chain variable domain of SEQ ID NO: 1, SEQ ID NO: 14, SEQ ID NO: 15, SEQ ID NO: 16, SEQ ID NO: 17, SEQ ID NO: 20, SEQ ID NO: 22, SEQ ID NO: 26, SEQ ID NO: 40, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, or SEQ ID NO: 100, where the first antigen-binding domain does not comprise (i) a light chain variable domain of SEQ ID NO: 2 and a heavy chain variable domain of SEQ ID NO: 1; (ii) a light chain variable domain of SEQ ID NO: 2 and heavy chain variable domain that is not one of SEQ ID NOs: 14-17, 20, 22, 26, 40, 46-52, or 81-100; or (iii) a heavy chain variable domain of SEQ ID NO: 1 and a light chain variable domain that is not one of SEQ ID NOs: 64, 70, 74, or 77-79; (b) a light chain variable domain of SEQ ID NO: 102, and/or a heavy chain variable domain of SEQ ID NO: 101, SEQ ID NO: 109, SEQ ID NO: 110, SEQ ID NO: 115, SEQ ID NO: 116, SEQ ID NO: 118, SEQ ID NO: 121, SEQ ID NO: 126, SEQ ID NO: 127, SEQ ID NO: 128, SEQ ID NO: 143, or SEQ ID NO: 144, where the first antigen-binding domain does not comprise (i) a light chain variable domain of SEQ ID NO: 102 and a heavy chain variable domain of SEQ ID NO: 101; or (ii) a light chain variable domain of SEQ ID NO: 102 and heavy chain variable domain that is not one of SEQ ID NOs: 109, 110, 115, 116, 118, 121, 126-128, 143, or 144; and (c) a light chain variable domain of SEQ ID NO: 150, SEQ ID NO: 200, SEQ ID NO: 201, SEQ ID NO: 202, SEQ ID NO: 203, SEQ ID NO: 204, SEQ ID NO: 205, SEQ ID NO: 209, SEQ ID NO: 212, SEQ ID NO: 219, SEQ ID NO: 220, SEQ ID NO: 221, SEQ ID NO: 225, or SEQ ID NO: 226, and/or a heavy chain variable domain of SEQ ID NO: 149, SEQ ID NO: 166, SEQ ID NO: 168, SEQ ID NO: 169, SEQ ID NO: 170, SEQ ID NO: 171, SEQ ID NO: 173, SEQ ID NO: 174, SEQ ID NO: 188, SEQ ID NO: 189, SEQ ID NO: 190, SEQ ID NO: 191, SEQ ID NO: 193, or SEQ ID NO: 194, where the first antigen-binding domain does not comprise (i) a light chain variable domain of SEQ ID NO: 150 and a heavy chain variable domain of SEQ ID NO: 149; (ii) a light chain variable domain of SEQ ID NO: 150 and heavy chain variable domain that is not one of SEQ ID NOs: 166, 168-171, 173, 174, 188-191, 193, or 194; or (iii) a heavy chain variable domain of SEQ ID NO: 149 and a light chain variable domain that is not one of SEQ ID NOs: 200-205, 209, 212, 219-221, 225, or 226.

In some embodiments of any of the ABPCs described herein, a composition including the ABPC provides for: an increase in toxin liberation in the target mammalian cell as compared to a composition including the same amount of a control ABPC; and/or an increase in target mammalian cell killing as compared to a composition including the same amount of a control ABPC.

In some embodiments of any of the ABPCs described herein, a composition including the ABPC provides for an increase in endolysosomal delivery in the target mammalian cell as compared to a composition including the same amount of a control ABPC.

In some embodiments of any of the ABPCs described herein, a composition including the ABPC: results in a less of a reduction in the level of CD123 presented on the surface of the target mammalian cell as compared to a composition including the same amount of a control ABPC; or does not result in a detectable reduction in the level of CD123 presented on the surface of the target mammalian cell.

In some embodiments of any of the ABPCs described herein, the target mammalian cell is a cancer cell. In some embodiments of any of the ABPCs described herein, the ABPC is cytotoxic or cytostatic to the target mammalian cell.

In some embodiments of any of the ABPCs described herein, the ABPC is: cross-reactive with a non-human primate CD123 and human CD123; or cross-reactive with a non-human primate CD123, a human CD123, and one or both of rat CD123 and a mouse CD123.

In some embodiments of any of the ABPCs described herein, the ABPC includes a single polypeptide. In some embodiments of any of the ABPCs described herein, the antigen-binding domain is selected from the group consisting of: a VH domain, a VHH domain, a VNAR domain, and a scFv. In some embodiments of any of the ABPCs described herein, the ABPC includes two or more polypeptides. In some embodiments of any of the ABPCs described herein, the ABPC is an antibody.

In some embodiments of any of the ABPCs described herein, the half-life of the ABPC in vivo is decreased as compared to the half-life of a control ABPC in vivo.

In some embodiments of any of the ABPCs described herein, the ABPC includes a second antigen-binding domain.

Also provided herein are kits including at least one dose of the pharmaceutical composition of any one of the pharmaceutical compositions described herein or any one of the ABPCs described herein.

Also provided herein are methods of treating a cancer characterized by having a population of cancer cells that have CD123 or an epitope of CD123 presented on their surface, the method including: administering a therapeutically effective amount of any of the pharmaceutical compositions described herein or any one of the ABPCs described herein of any to a subject identified as having a cancer characterized by having the population of cancer cells.

Also provided herein are methods of reducing the volume of a tumor in a subject, where the tumor is characterized by having a population of cancer cells that have CD123 or an epitope of CD123 presented on their surface, the method including: administering a therapeutically effective amount of any one of the pharmaceutical compositions described herein or any one of the ABPCs described herein to a subject identified as having a cancer characterized by having the population of cancer cells.

Also provided herein are methods of inducing cell death in a cancer cell in a subject, where the cancer cell has CD123 or an epitope of CD123 presented on its surface, where the method includes: administering a therapeutically effective amount of any one of the pharmaceutical compositions or any one of the ABPCs described herein to a subject identified as having a cancer characterized by having a population of the cancer cells.

Also provided herein are methods of decreasing the risk of developing a metastasis or decreasing the risk of developing an additional metastasis in a subject having a cancer, where the cancer is characterized by having a population of cancer cells that have CD123 or an epitope of CD123 presented on their surface the method including: administering a therapeutically effective amount of any one of the pharmaceutical compositions described herein or any one of the ABPCs described herein to a subject identified as having a cancer characterized by having the population of cancer cells.

An "antigen-binding domain" is one or more protein domain(s) (e.g., formed from amino acids from a single polypeptide or formed from amino acids from two or more polypeptides (e.g., the same or different polypeptides) that is capable of specifically binding to one or more different antigen(s). In some examples, an antigen-binding domain can bind to an antigen or epitope with specificity and affinity similar to that of naturally-occurring antibodies. In some embodiments, the antigen-binding domain can be an antibody or a fragment thereof. In some embodiments, an antigen-binding domain can include an alternative scaffold. Non-limiting examples of antigen-binding domains are described herein. Additional examples of antigen-binding domains are known in the art. In some examples, an antigen-binding domain can bind to a single antigen.

The term "antibody" is used herein in its broadest sense and includes certain types of immunoglobulin molecules that include one or more antigen-binding domains that specifically bind to an antigen or epitope. An antibody specifically includes, e.g., intact antibodies (e.g., intact immunoglobulins, e.g., human IgG (e.g., human IgG1, human IgG2, human IgG3, human IgG4)), antibody fragments, and multi-specific antibodies. One example of an antigen-binding domain is an antigen-binding domain formed by a VH-VL dimer. Additional examples of an antibody are described herein. Additional examples of an antibody are known in the art.

The phrase "endosomal/lysosomal pathway" refers to a network of endosomes (early endosomes, multi-vesicular bodies, late endosomes, and lysosomes) in the cytoplasm of a mammalian cell, wherein molecules internalized through cell-mediated internalization processes, e.g., pinocytosis, micropinocytosis, receptor-mediated endocytosis, and/or phagocytosis, are sorted.

Once the endosomes in the endosomal/lysosomal pathway are purified or isolated, assays for a target protein (e.g., an antigen-binding protein construct described herein) can be performed using methods known in the art (ELISA, Western blot, immunofluorescence, and immunoprecipitation followed by an assay for protein concentration), and can be used to determine the concentration or relative level of the target protein in the endosomes. Alternatively, endosomes in the endosomal/lysosomal pathway can be imaged using immunofluorescence microscopy using an detectably-labelled antibody (e.g., a fluorophore-labelled, a dye-labelled, or a GFP-labelled antibody, e.g., CellLight™ Early Endosome-GFP) that specifically binds to a characteristic protein present in the endosomes (e.g., EEA1 for early endosomes) and a fluorophore-labelled antibody that specifically binds to the protein of interest (e.g., an antigen-binding protein construct), and the level of the target protein in the endosomes can be determined by quantitation of the overlap in the fluorescence emissions of the two different antibodies.

The phrase "endolysosomal delivery" refers to rate of accumulation over time or the total accumulation at a specific timepoint of an antigen-binding protein construct (e.g., any of the antigen-binding protein constructs described herein) in the endosomal/lysosomal pathway in a mammalian cell (e.g., any of the exemplary target mammalian cells described herein).

An exemplary method to calculate the increase in endolysosomal delivery of a pH engineered ABPC variant as compared to its corresponding starting ABPC from cellular fluorescence data is to measure the ratio of the variant's mean fluorescence intensity minus the mean fluorescence intensity of a non-binding IgG control, then all divided by the variant's corresponding starting ABPC's mean fluorescence intensity minus the mean fluorescence intensity of the IgG control.

An exemplary assay for measuring endolysosomal delivery of any of the ABPCs described herein include those which involve labeling of an ABPC with a fluorescent dye, followed by incubation of the labeled ABPC with cells and measurement of cellular fluorescence as an indicator of endolysosomal delivery of the ABPC (e.g., as described generally in Wustner, *Traffic* 7(6):699-715, 2006). Alternatively, pH-sensitive dyes which preferentially fluoresce at acidic pH but not neutral pH can be used to label any of the ABPCs described herein, which can then be incubated with cells and the cellular fluorescence measured as an indicator of delivery of the ABPC into acidic endolysosomal compartments.

The term "population" when used before a noun means two or more of the specific noun. For example, the phrase "a population of cancer cells" means "two or more cancer cells." Non-limiting examples of cancer cells are described herein.

The phrase "cytostatic to a cell" refers to a direct or indirect decrease in the proliferation (cell division) of the cell (e.g., a cancer cell) in vivo or in vitro. When an agent is cytostatic to a cell, the agent can, e.g., directly or indirectly result in cell cycle arrest of the cell (e.g., a cancer cell). In some examples, an agent that is cytostatic to a cell can reduce the number of cells in a population of the cells that are in S phase (as compared to the number of cells in a population of the cells that are in S phase prior to contact with the agent). In some examples, an agent that is cytostatic to a cell can reduce the percentage of the cells in S phase by at least 20%, at least 40%, at least 60%, or at least 80% (e.g., as compared to the percentage of cells in a population of the cells that are in S phase prior to contact with the agent).

The phrase "cytotoxic to a cell" refers to the inducement, directly or indirectly, in the death (e.g., necrosis or apoptosis) of the cell (e.g., a mammalian cell, e.g., a cancer cell).

"Affinity" refers to the strength of the sum total of non-covalent interactions between an antigen-binding site and its binding partner (e.g., an antigen or epitope). Unless indicated otherwise, as used herein, "affinity" refers to intrinsic binding affinity, which reflects a 1:1 interaction between members of an antigen-binding domain and an antigen or epitope. The affinity of a molecule X for its partner Y can be represented by the dissociation equilibrium constant ($K_D$). Affinity can be measured by common methods known in the art, including those described herein. Affinity can be determined, for example, using surface plasmon resonance (SPR) technology (e.g., BIACORE®) or biolayer interferometry (e.g., FORTEBIO®). Additional methods for determining the affinity for an antigen-binding domain and its corresponding antigen or epitope are known in the art.

The term "epitope" means a portion of an antigen that is specifically bound by an antigen-binding domain through a set of physical interactions between: (i) all monomers (e.g. individual amino acid residues, sugar side chains, and post-translationally modified amino acid residues) on the portion of the antigen-binding domain that specifically binds the antigen and (ii) all monomers (e.g. individual amino acid residues, sugar side chains, post-translationally modified amino acid residues) on the portion of the antigen that is specifically bound by the antigen-binding domain. Epitopes can, e.g., consist of surface-accessible amino acid residues, sugar side chains, phosphorylated amino acid residues, methylated amino acid residues, and/or acetylated amino acid residues and may have specific three-dimensional structural characteristics, as well as specific charge characteristics. Conformational and non-conformational epitopes are distinguished in that binding to the former, but not the latter, may be lost in the presence of denaturing solvents. In some embodiments, an epitope is defined by a linear amino acid sequence of at least about 3 to 6 amino acids, or about 10 to 15 amino acids. In some embodiments, an epitope refers to a portion of a full-length protein or a portion thereof that is defined by a three-dimensional structure (e.g., protein folding). In some embodiments, an epitope is defined by a discontinuous amino acid sequence that is brought together via protein folding. In some embodiments, an epitope is defined by a discontinuous amino acid sequence that is brought together by quaternary structure (e.g., a cleft formed by the interaction of two different polypeptide chains). The amino acid sequences between the residues that define the epitope may not be critical to three-dimensional structure of the epitope. A conformational epitope may be determined and screened using assays that compare binding of antigen-binding protein construct to a denatured version of the antigen, such that a linear epitope is generated. An epitope may include amino acid residues that are directly involved in the binding, and other amino acid residues, which are not directly involved in the binding.

Methods for identifying an epitope to which an antigen-binding domain specifically binds are known in the art, e.g., structure-based analysis (e.g. X-ray crystallography, NMR, and/or electron microscopy) (e.g. on the antigen and/or the antigen-antigen binding domain complex) and/or mutagenesis-based analysis (e.g. alanine scanning mutagenesis, glycine scanning mutagenesis, and homology scanning mutagenesis) wherein mutants are measured in a binding assay with a binding partner, many of which are known in the art.

The term "paratope" means a portion of an antigen-binding domain that specifically binds to an antigen through a set of physical interactions between: (i) all monomers (e.g. individual amino acid residues, sugar side chains, posttranslationally modified amino acid residues) on the portion of the antigen-binding domain that specifically binds the antigen and (ii) all monomers (e.g. individual amino acid residues, sugar side chains, posttranslationally modified amino acid residues) on the portion of the antigen that is specifically bound by the antigen-binding domain. Paratopes can, e.g. consist of surface-accessible amino acid residues and may have specific three-dimensional structural characteristics, as well as specific charge characteristics. In some embodiments, a paratope refers to a portion of a full-length antigen-binding domain or a portion thereof that is defined by a three-dimensional structure (e.g., protein folding). In some embodiments, a paratope is defined by a discontinuous amino acid sequence that is brought together via protein folding. In some embodiments, an epitope is defined by a discontinuous amino acid sequence that is brought together by quaternary structure (e.g., a cleft formed by the interaction of two different polypeptide chains). The amino acid sequences between the residues that define the paratope may not be critical to three-dimensional structure of the paratope. A paratope may comprise amino acid residues that are directly involved in the binding, and other amino acid residues, which are not directly involved in the binding.

Methods for identifying a paratope to which an antigen-binding domain specifically binds are known in the art, e.g., structure-based analysis (e.g., X-ray crystallography, NMR, and/or electron microscopy) (e.g. on the antigen-binding domain, and/or the antigen binding domain-antigen complex), and/or mutagenesis-based analysis (e.g., alanine scanning mutagenesis, glycine scanning mutagenesis, and homology scanning mutagenesis) wherein mutants are measured in a binding assay with a binding partner, many of which are known in the art.

The phrase "present on the surface of a mammalian cell" means (1) an antigen that physically attached to or at least partially embedded in the plasma membrane of a mammalian cell (e.g., a transmembrane protein, a peripheral membrane protein, a lipid-anchored protein (e.g., a GPI-anchor), an N-myristoylated protein, or a S-palmitoylated protein) or (2) an antigen that is stably bound to its cognate receptor, where the cognate receptor is physically attached to the plasma membrane of a mammalian cell (e.g., a ligand bound to its cognate receptor, where the cognate receptor is physically attached to the plasma membrane). Non-limiting methods for determining the presence of antigen on the surface of a mammalian cell include fluorescence-activated cell sorting (FACS), immunohistochemistry, cell-fractionation assays and Western blotting.

The phrase "control ABPC" or "control antigen-binding protein construct" means (i) an ABPC that is capable of specifically binding to CD123 or an epitope of CD123 presented on the surface of a mammalian cell (e.g., a target mammalian cell), where one or both of the following is true: (a) the dissociation rate of the first antigen-binding domain at a pH of about 4.0 to about 6.5 (e.g., any of the subranges of this range described herein) is no more than 3-fold (e.g., no more than 2.8-fold, no more than 2.6-fold, no more than 2.5-fold, no more than 2.4-fold, no more than 2.2-fold, no more than 2.0-fold, no more than 1.8-fold, no more than 1.6-fold, no more than 1.5-fold, no more than 1.4-fold, no more than 1.2-fold, no more than 1.0-fold, no more than 0.8-fold, no more than 0.6-fold, no more than 0.5-fold, no more than 0.4-fold, no more than 0.3-fold no more than 0.2-fold, or no more than 0.1-fold) faster than the dissociation rate at a pH of about 7.0 to about 8.0 (e.g., any of the subranges of this range described herein); or (b) the dissociation constant ($K_D$) of the first antigen-binding domain at a pH of about 4.0 to about 6.5 (e.g., any of the subranges of this range described herein) is no more than 3-fold (e.g., no more than 2.8-fold, no more than 2.6-fold, no more than 2.5-fold, no more than 2.4-fold, no more than 2.2-fold, no more than 2.0-fold, no more than 1.8-fold, no more than 1.6-fold, no more than 1.5-fold, no more than 1.4-fold, no more than 1.2-fold, no more than 1.0-fold, no more than 0.8-fold, no more than 0.6-fold, no more than 0.5-fold, no more than 0.4-fold, no more than 0.3-fold no more than 0.2-fold, or no more than 0.1-fold) greater than the $K_D$ at a pH of about 7.0 to about 8.0 (e.g., any of the subranges of this range described herein); and/or (ii) IMGN632; and/or (iii) SGN-CD123A; and/or TPP-8988.

The term "extracellular space" means the liquid exterior to the plasma membrane of a mammalian cell. When a mammalian cell is in vitro, the extracellular space can be a liquid culture medium. When a mammalian cell is in vivo, the extracellular space can be, e.g., plasma, serum, blood, interstitial fluid, or lymph.

The term "endolysosomal space" means the fluid encapsulated by the vesicles and organelles that make-up the endosomal/lysosomal pathway in a mammalian cell.

The phrase "a reduced level" or "a decreased level" can be a reduction or decrease of at least a 1% (e.g., at least 2%, at least 4%, at least 6%, at least 8%, at least 10%, at least 12%, at least 14%, at least 16%, at least 18%, at least 20%, at least 22%, at least 24%, at least 26%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%) reduction as compared to a reference level or value.

The term "cell killing potency" refers to the ability of an agent (e.g., any of the ABPCs described herein) to induce, directly or indirectly, the apoptosis and/or necrosis of a mammalian cell (e.g., a cancer cell), measured as a rate over time or at a relevant timepoint. Methods for determining the cell killing potency of a cell are known in the art (e.g., trypan blue staining, microscopy, fluorescence-assisted cell sorting, and assays to detect markers of apoptosis (e.g., Annexin V)). In non-limiting examples, cell killing potency can be measured, e.g., by cell killing at a single concentration of an agent, by the IC50 of the agent (i.e. the concentration of the agent whereby half the maximal cell killing potency is achieved), or by the ratio of an agent's dissociation constant $K_D$ on mammalian cells divided by its IC50. In some non-limiting examples, the IC50s and/or the $K_D$ ratios described herein are compared to those of a control ABPC (as defined herein), and, optionally, demonstrate that the ABPCs described herein have a higher cell killing potency as compared to the control ABPC.

The term "toxin liberation" refers to the ability of a mammalian cell (e.g., a non-cancerous mammalian cell or a cancer cell) to internalize (e.g., via pinocytosis and/or receptor-mediated endocytosis) any of the ABPCs described herein (e.g., any of ABPCs or control ABPCs described herein) that are conjugated to a toxin, and subsequently release the toxin conjugated to the ABPC, measured as a rate over time or at a specific timepoint. Toxin liberation can be assessed using a variety of different exemplary assays, e.g., ELISA, immunofluorescence, cell killing assays, cell cycle arrest assays, DNA damage assays, mass spectrometry, HPLC, and/or an isotope-labeled toxin.

The phrase "target cell" or "target mammalian cell" or "mammalian target cell" means a mammalian cell that has at least one CD123 present on its surface. In some examples, a mammalian target cell can be a cancer cell. In some embodiments of a target mammalian cell can have a total of about 1 to about 10,000,000, about 1 to about 9,000,000, about 1 to about 8,000,000, about 1 to about 7,000,000, about 1 to about 6,000,000, about 1 to about 5,000,000, about 1 to about 4,000,000, about 1 to about 3,000,000, about 1 to about 2,000,000, about 1 to about 1,000,000, about 1 to about 800,000, about 1 to about 600,000, about 1 to about 400,000, about 1 to about 200,000, about 1 to about 100,000, about 1 to about 80,000, about 1 to about 80,000, about 1 to about 75,000, about 1 to about 70,000, about 1 to about 65,000, about 1 to about 60,000, about 1 to about 55,000, about 1 to about 50,000, about 1 to about 45,000, about 1 to about 40,000, about 1 to about 35,000, about 1 to about 30,000, about 1 to about 25,000, about 1 to about 20,000, about 1 to about 15,000, about 1 to about 10,000, about 1 to about 7,500, about 1 to about 5,000, about 1 to about 4,000, about 1 to about 3,000, about 1 to about 2,000, about 1 to about 1,000, about 1 to about 500, about 1 to about 100, about 1 to about 50, about 1 to about 10, about 10 to about 10,000,000, about 10 to about 9,000,000, about 10 to about 8,000,000, about 10 to about 7,000,000, about 10 to about 6,000,000, about 10 to about 5,000,000, about 10 to about 4,000,000, about 10 to about 3,000,000, about 10 to about 2,000,000, about 10 to about 1,000,000, about 10 to about 800,000, about 10 to about 600,000, about 10 to about 400,000, about 10 to about 200,000, about 10 to about 100,000, about 10 to about 80,000, about 10 to about 80,000, about 10 to about 75,000, about 10 to about 70,000, about 10 to about 65,000, about 10 to about 60,000, about 10 to about 55,000, about 10 to about 50,000, about 10 to about 45,000, about 10 to about 40,000, about 10 to about 35,000, about 10 to about 30,000, about 10 to about 25,000, about 10 to about 20,000, about 10 to about 15,000, about 10 to about 10,000, about 10 to about 7,500, about 10 to about 5,000, about 10 to about 4,000, about 10 to about 3,000, about 10 to about 2,000, about 10 to about 1,000, about 10 to about 500, about 10 to about 100, about 10 to about 50, about 50 to about 10,000,000, about 50 to about 9,000,000, about 50 to about 8,000,000, about 50 to about 7,000,000, about 50 to about 6,000,000, about 50 to about 5,000,000, about 50 to about 4,000,000, about 50 to about 3,000,000, about 50 to about 2,000,000, about 50 to about 1,000,000, about 50 to about 800,000, about 50 to about 600,000, about 50 to about 400,000, about 50 to about 200,000, about 50 to about 100,000, about 50 to about 80,000, about 50 to about 80,000, about 50 to about 75,000, about 50 to about 70,000, about 50 to about 65,000, about 50 to about 60,000, about 50 to about 55,000, about 50 to about 50,000, about 50 to about 45,000, about 50 to about 40,000, about 50 to about 35,000, about 50 to about 30,000, about 50 to about 25,000, about 50 to about 20,000, about 50 to about 15,000, about 50 to about 10,000, about 50 to about 7,500, about 50 to about 5,000, about 50 to about 4,000, about 50 to about 3,000, about 50 to about 2,000, about 50 to about 1,000, about 50 to about 500, about 50 to about 100, about 100 to about 10,000,000, about 100 to about 9,000,000, about 100 to about 8,000,000, about 100 to about 7,000,000, about 100 to about 6,000,000, about 100 to about 5,000,000, about 100 to about 4,000,000, about 100 to about 3,000,000, about 100 to about 2,000,000, about 100 to about 1,000,000, about 100 to about 800,000, about 100 to about 600,000, about 100 to about 400,000, about 100 to about 200,000, about 100 to about 100,000, about 100 to about 80,000, about 100 to about 75,000, about 100 to about 70,000, about 100 to about 65,000, about 100 to about 60,000, about 100 to about 55,000, about 100 to about 50,000, about 100 to about 45,000, about 100 to about 40,000, about 100 to about 35,000, about 100 to about 30,000, about 100 to about 25,000, about 100 to about 20,000, about 100 to about 15,000, about 100 to about 10,000, about 100 to about 7,500, about 100 to about 5,000, about 100 to about 4,000, about 100 to about 3,000, about 100 to about 2,000, about 100 to about 1,000, about 100 to about 500, about 500 to about 10,000,000, about 500 to about 9,000,000, about 500 to about 8,000,000, about 500 to about 7,000,000, about 500 to about 6,000,000, about 500 to about 5,000,000, about 500 to about 4,000,000, about 500 to about 3,000,000, about 500 to about 2,000,000, about 500 to about 1,000,000, about 500 to about 800,000, about 500 to about 600,000, about 500 to about 400,000, about 500 to about 200,000, about 500 to about 100,000, about 500 to about 80,000, about 500 to about 75,000, about 500 to about 70,000, about 500 to about 65,000, about 500 to about 60,000, about 500 to about 55,000, about 500 to about 50,000, about 500 to about 45,000, about 500 to about 40,000, about 500 to about 35,000, about 500 to about 30,000, about 500 to about 25,000, about 500 to about 20,000, about 500 to about 15,000, about 500 to about 10,000, about 500 to about 7,500, about 500 to about 5,000, about 500 to about 4,000, about 500 to about 3,000, about 500 to about 2,000, about 500 to about 1,000, about 1,000 to about 10,000,000, about 1,000 to about 9,000,000, about 1,000 to about 8,000,000, about 1,000 to about 7,000,000, about 1,000 to about 6,000,000, about 1,000 to about 5,000, 000, about 1,000 to about 4,000,000, about 1,000 to about 3,000,000, about 1,000 to about 2,000,000, about 1,000 to about 1,000,000, about 1,000 to about 800,000, about 1,000 to about 600,000, about 1,000 to about 400,000, about 1,000 to about 200,000, about 1,000 to about 100,000, about 1,000 to about 80,000, about 1,000 to about 75,000, about 1,000 to about 70,000, about 1,000 to about 65,000, about 1,000 to about 60,000, about 1,000 to about 55,000, about 1,000 to about 50,000, about 1,000 to about 45,000, about 1,000 to about 40,000, about 1,000 to about 35,000, about 1,000 to about 30,000, about 1,000 to about 25,000, about 1,000 to about 20,000, about 1,000 to about 15,000, about 1,000 to about 10,000, about 1,000 to about 7,500, about 1,000 to about 5,000, about 1,000 to about 4,000, about 1,000 to about 3,000, about 1,000 to about 2,000, about 2,000 to about 10,000,000, about 2,000 to about 9,000,000, about 2,000 to about 8,000,000, about 2,000 to about 7,000,000, about 2,000 to about 6,000,000, about 2,000 to about 5,000, 000, about 2,000 to about 4,000,000, about 2,000 to about 3,000,000, about 2,000 to about 2,000,000, about 2,000 to about 1,000,000, about 2,000 to about 800,000, about 2,000 to about 600,000, about 2,000 to about 400,000, about 2,000 to about 200,000, about 2,000 to about 100,000, about 2,000 to about 80,000, about 2,000 to about 75,000, about 2,000 to about 70,000, about 2,000 to about 65,000, about 2,000 to about 60,000, about 2,000 to about 55,000, about 2,000 to about 50,000, about 2,000 to about 45,000, about 2,000 to about 40,000, about 2,000 to about 35,000, about 2,000 to about 30,000, about 2,000 to about 25,000, about 2,000 to about 20,000, about 2,000 to about 15,000, about 2,000 to about 10,000, about 2,000 to about 7,500, about 2,000 to about 5,000, about 2,000 to about 4,000, about 2,000 to about 3,000, about 3,000 to about 10,000,000, about 3,000 to about 9,000,000, about 3,000 to about 8,000,000, about 3,000 to about 7,000,000, about 3,000 to about 6,000,000, about 3,000 to about 5,000,000, about 3,000 to about 4,000,000, about 3,000 to about 3,000,000, about 3,000 to about 2,000,000, about 3,000 to about 1,000,000, about 3,000 to about 800,000, about 3,000 to about 600,000, about 3,000 to about 400,000, about 3,000 to about 200,000, about 3,000 to about 100,000, about 3,000 to about 80,000, about 3,000 to about 75,000, about 3,000 to about 70,000, about 3,000 to about 65,000, about 3,000 to about 60,000, about 3,000 to about 55,000, about 3,000 to about 50,000, about 3,000 to about 45,000, about 3,000 to about 40,000, about 3,000 to about 35,000, about 3,000 to about 30,000, about 3,000 to about 25,000, about 3,000 to about 20,000, about 3,000 to about 15,000, about 3,000 to about 10,000, about 3,000 to about 7,500, about 3,000 to about 5,000, about 3,000 to about 4,000, about 4,000 to about 10,000,000, about 4,000 to about 9,000,000, about 4,000 to about 8,000,000, about 4,000 to about 7,000,000, about 4,000 to about 6,000,000, about 4,000 to about 5,000,000, about 4,000 to about 4,000,000, about 4,000 to about 3,000,000, about 4,000 to about 2,000,000, about 4,000 to about 1,000,000, about 4,000 to about 800,000, about 4,000 to about 600,000, about 4,000 to about 400,000, about 4,000 to about 200,000, about 4,000 to about 100,000, about 4,000 to about 80,000, about 4,000 to about 75,000, about 4,000 to about 70,000, about 4,000 to about 65,000, about 4,000 to about 60,000, about 4,000 to about 55,000, about 4,000 to about 50,000, about 4,000 to about 45,000, about 4,000 to about 40,000, about 4,000 to about 35,000, about 4,000 to about 30,000, about 4,000 to about 25,000, about 4,000 to about 20,000, about 4,000 to about 15,000, about 4,000 to about 10,000, about 4,000 to about 7,500, about 4,000 to about 5,000, about 5,000 to about 10,000,000, about 5,000 to about 9,000,000, about 5,000 to about 8,000,000, about 5,000 to about 7,000,000, about 5,000 to about 6,000,000, about 5,000 to about 5,000,000, about 5,000 to about 4,000,000, about 5,000 to about 3,000,000, about 5,000 to about 2,000,000, about 5,000 to about 1,000,000, about 5,000 to about 800,000, about 5,000 to about 600,000, about 5,000 to about 400,000, about 5,000 to about 200,000, about 5,000 to about 100,000, about 5,000 to about 80,000, about 5,000 to about 75,000, about 5,000 to about 70,000, about 5,000 to about 65,000, about 5,000 to about 60,000, about 5,000 to about 55,000, about 5,000 to about 50,000, about 5,000 to about 45,000, about 5,000 to about 40,000, about 5,000 to about 35,000, about 5,000 to about 30,000, about 5,000 to about 25,000, about 5,000 to about 20,000, about 5,000 to about 15,000, about 5,000 to about 10,000, about 5,000 to about 7,500, about 7,500 to about 10,000,000, about 7,500 to about 9,000,000, about 7,500 to about 8,000,000, about 7,500 to about 7,000,000, about 7,500 to about 6,000,000, about 7,500 to about 5,000,000, about 7,500 to about 4,000,000, about 7,500 to about 3,000,000, about 7,500 to about 2,000,000, about 7,500 to about 1,000,000, about 7,500 to about 800,000, about 7,500 to about 600,000, about 7,500 to about 400,000, about 7,500 to about 200,000, about 7,500 to about 100,000, about 7,500 to about 80,000, about 7,500 to about 75,000, about 7,500 to about 70,000, about 7,500 to about 65,000, about 7,500 to about 60,000, about 7,500 to about 55,000, about 7,500 to about 50,000, about 7,500 to about 45,000, about 7,500 to about 40,000, about 7,500 to about 35,000, about 7,500 to about 30,000, about 7,500 to about 25,000, about 7,500 to about 20,000, about 7,500 to about 15,000, about 7,500 to about 10,000, about 10,000 to about 10,000,000, about 10,000 to about 9,000,000, about 10,000 to about 8,000,000, about 10,000 to about 7,000,000, about 10,000 to about 6,000,000, about 10,000 to about 5,000,000, about 10,000 to about 4,000,000, about 10,000 to about 3,000,000, about 10,000 to about 2,000,000, about 10,000 to about 1,000,000, about 10,000 to about 800,000, about 10,000 to about 600,000, about 10,000 to about 400,000, about 10,000 to about 200,000, about 10,000 to about 100,000, about 10,000 to about 80,000, about 10,000 to about 75,000, about 10,000 to about 70,000, about 10,000 to about 65,000, about 10,000 to about 60,000, about 10,000 to about 55,000, about 10,000 to about 50,000, about 10,000 to about 45,000, about 10,000 to about 40,000, about 10,000 to about 35,000, about 10,000 to about 30,000, about 10,000 to about 25,000, about 10,000 to about 20,000, about 10,000 to about 15,000, about 15,000 to about 10,000,000, about 15,000 to about 9,000,000, about 15,000 to about 8,000,000, about 15,000 to about 7,000,000, about 15,000 to about 6,000,000, about 15,000 to about 5,000,000, about 15,000 to about 4,000,000, about 15,000 to about 3,000,000, about 15,000 to about 2,000,000, about 15,000 to about 1,000,000, about 15,000 to about 800,000, about 15,000 to about 600,000, about 15,000 to about 400,000, about 15,000 to about 200,000, about 15,000 to about 100,000, about 15,000 to about 80,000, about 15,000 to about 75,000, about 15,000 to about 70,000, about 15,000 to about 65,000, about 15,000 to about 60,000, about 15,000 to about 55,000, about 15,000 to about 50,000, about 15,000 to about 45,000, about 15,000 to about 40,000, about 15,000 to about 35,000, about 15,000 to about 30,000, about 15,000 to about 25,000, about 15,000 to about 20,000, about 20,000 to about 10,000,000, about 20,000 to about 9,000,000, about 20,000 to about 8,000,000, about 20,000 to about 7,000,000, about 20,000 to about 6,000,000, about 20,000 to about 5,000,000, about 20,000 to about 4,000,000, about 20,000 to about 3,000,000, about 20,000 to about 2,000,000, about 20,000 to about 1,000,000, about 20,000 to about 800,000, about 20,000 to about 600,000, about 20,000 to about 400,000, about 20,000 to about 200,000, about 20,000 to about 100,000, about 20,000 to about 80,000, about 20,000 to about 75,000, about 20,000 to about 70,000, about 20,000 to about 65,000, about 210,000 to about 60,000, about 20,000 to about 55,000, about 20,000 to about 50,000, about 20,000 to about 45,000, about 20,000 to about 40,000, about 20,000 to about 35,000, about 20,000 to about 30,000, about 20,000 to about 25,000, about 25,000 to about 10,000,000, about 25,000 to about 9,000,000, about 25,000 to about 8,000,000, about 25,000 to about 7,000,000, about 25,000 to about 6,000,000, about 25,000 to about 5,000,000, about 25,000 to about 4,000,000, about 25,000 to about 3,000,000, about 25,000 to about 2,000,000, about 25,000 to about 1,000,000, about 25,000 to about 800,000, about 25,000 to about 600,000, about 25,000 to about 400,000, about 25,000 to about 200,000, about 25,000 to about 100,000, about 25,000 to about 80,000, about 25,000 to about 75,000, about 25,000 to about 70,000, about 25,000 to about 65,000, about 25,000 to about 60,000, about 25,000 to about 55,000, about 25,000 to about 50,000, about 25,000 to about 45,000, about 25,000 to about 40,000, about 25,000 to about 35,000, about 25,000 to about 30,000, about 30,000 to about 10,000,000, about 30,000 to about 9,000,000, about 30,000 to about 8,000,000, about 30,000 to about 7,000,000, about 30,000 to about 6,000,000, about 30,000 to about 5,000,000, about 30,000 to about 4,000,000, about 30,000 to about 3,000,000, about 30,000 to about 2,000,000, about 30,000 to about 1,000,000, about 30,000 to about 800,000, about 30,000 to about 600,000, about 30,000 to about 400,000, about 30,000 to about 200,000, about 30,000 to about 100,000, about 30,000 to about 80,000, about 30,000 to about 75,000, about 30,000 to about 70,000, about 30,000 to about 65,000, about 30,000 to about 60,000, about 30,000 to about 55,000, about 30,000 to about 50,000, about 30,000 to about 45,000, about 30,000 to about 40,000, about 30,000 to about 35,000, about 35,000 to about 10,000,000, about 35,000 to about 9,000,000, about 35,000 to about 8,000,000, about 35,000 to about 7,000,000, about 35,000 to about 6,000,000, about 35,000 to about 5,000,000, about 35,000 to about 4,000,000, about 35,000 to about 3,000,000, about 35,000 to about 2,000,000, about 35,000 to about 1,000,000, about 35,000 to about 800,000, about 35,000 to about 600,000, about 35,000 to about 400,000, about 35,000 to about 200,000, about 35,000 to about 100,000, about 35,000 to about 80,000, about 35,000 to about 75,000, about 35,000 to about 70,000, about 35,000 to about 65,000, about 35,000 to about 60,000, about 35,000 to about 55,000, about 35,000 to about 50,000, about 35,000 to about 45,000, about 35,000 to about 40,000, about 40,000 to about 10,000,000, about 40,000 to about 9,000,000, about 40,000 to about 8,000,000, about 40,000 to about 7,000,000, about 40,000 to about 6,000,000, about 40,000 to about 5,000,000, about 40,000 to about 4,000,000, about 40,000 to about 3,000,000, about 40,000 to about 2,000,000, about 40,000 to about 1,000,000, about 40,000 to about 800,000, about 40,000 to about 600,000, about 40,000 to about 400,000, about 40,000 to about 200,000, about 40,000 to about 100,000, about 40,000 to about 80,000, about 40,000 to about 75,000, about 40,000 to about 70,000, about 40,000 to about 65,000, about 40,000 to about 60,000, about 40,000 to about 55,000, about 40,000 to about 50,000, about 40,000 to about 45,000, about 45,000 to about 10,000,000, about 45,000 to about 9,000,000, about 45,000 to about 8,000,000, about 45,000 to about 7,000,000, about 45,000 to about 6,000,000, about 45,000 to about 5,000,000, about 45,000 to about 4,000,000, about 45,000 to about 3,000,000, about 45,000 to about 2,000,000, about 45,000 to about 1,000,000, about 45,000 to about 800,000, about 45,000 to about 600,000, about 45,000 to about 400,000, about 45,000 to about 200,000, about 45,000 to about 100,000, about 45,000 to about 80,000, about 45,000 to about 75,000, about 45,000 to about 70,000, about 45,000 to about 65,000, about 45,000 to about 60,000, about 45,000 to about 55,000, about 45,000 to about 50,000, about 50,000 to about 10,000,000, about 50,000 to about 9,000,000, about 50,000 to about 8,000,000, about 50,000 to about 7,000,000, about 50,000 to about 6,000,000, about 50,000 to about 5,000,000, about 50,000 to about 4,000,000, about 50,000 to about 3,000,000, about 50,000 to about 2,000,000, about 50,000 to about 1,000,000, about 50,000 to about 800,000, about 50,000 to about 600,000, about 50,000 to about 400,000, about 50,000 to about 200,000, about 50,000 to about 100,000, about 50,000 to about 80,000, about 50,000 to about 75,000, about 50,000 to about 70,000, about 50,000 to about 65,000, about 50,000 to about 60,000, about 50,000 to about 55,000, about 55,000 to about 10,000,000, about 55,000 to about 9,000,000, about 55,000 to about 8,000,000, about 55,000 to about 7,000,000, about 55,000 to about 6,000,000, about 55,000 to about 5,000,000, about 55,000 to about 4,000,000, about 55,000 to about 3,000,000, about 55,000 to about 2,000,000, about 55,000 to about 1,000,000, about 55,000 to about 800,000, about 55,000 to about 600,000, about 55,000 to about 400,000, about 55,000 to about 200,000, about 55,000 to about 100,000, about 55,000 to about 80,000, about 55,000 to about 75,000, about 55,000 to about 70,000, about 55,000 to about 65,000, about 55,000 to about 60,000, about 60,000 to about 10,000,000, about 60,000 to about 9,000,000, about 60,000 to about 8,000,000, about 60,000 to about 7,000,000, about 60,000 to about 6,000,000, about 60,000 to about 5,000,000, about 60,000 to about 4,000,000, about 60,000 to about 3,000,000, about 60,000 to about 2,000,000, about 60,000 to about 1,000,000, about 60,000 to about 800,000, about 60,000 to about 600,000, about 60,000 to about 400,000, about 60,000 to about 200,000, about 60,000 to about 100,000, about 60,000 to about 80,000, about 60,000 to about 75,000, about 60,000 to about 70,000, about 60,000 to about 65,000, about 65,000 to about 10,000,000, about 65,000 to about 9,000,000, about 65,000 to about 8,000,000, about 65,000 to about 7,000,000, about 65,000 to about 6,000,000, about 65,000 to about 5,000,000, about 65,000 to about 4,000,000, about 65,000 to about 3,000,000, about 65,000 to about 2,000,000, about 65,000 to about 1,000,000, about 65,000 to about 800,000, about 65,000 to about 600,000, about 65,000 to about 400,000, about 65,000 to about 200,000, about 65,000 to about 100,000, about 65,000 to about 80,000, about 65,000 to about 75,000, about 65,000 to about 70,000, about 70,000 to about 10,000,000, about 70,000 to about 9,000,000, about 70,000 to about 8,000,000, about 70,000 to about 7,000,000, about 70,000 to about 6,000,000, about 70,000 to about 5,000,000, about 70,000 to about 4,000,000, about 70,000 to about 3,000,000, about 70,000 to about 2,000,000, about 70,000 to about 1,000,000, about 70,000 to about 800,000, about 70,000 to about 600,000, about 70,000 to about 400,000, about 70,000 to about 200,000, about 70,000 to about 100,000, about 70,000 to about 90,000, about 70,000 to about 80,000, about 80,000 to about 10,000,000, about 80,000 to about 9,000,000, about 80,000 to about 8,000,000, about 80,000 to about 7,000,000, about 80,000 to about 6,000,000, about 80,000 to about 5,000,000, about 80,000 to about 4,000,000, about 80,000 to about 3,000,000, about 80,000 to about 2,000,000, about 80,000 to about 1,000,000, about 80,000 to about 800,000, about 80,000 to about 600,000, about 80,000 to about 400,000, about 80,000 to about 200,000, about 80,000 to about 100,000, about 80,000 to about 90,000, about 90,000 to about 10,000,000, about 90,000 to about 9,000,000, about 90,000 to about 8,000,000, about 90,000 to about 7,000,000, about 90,000 to about 6,000,000, about 90,000 to about 5,000,000, about 90,000 to about 4,000,000, about 90,000 to about 3,000,000, about 90,000 to about 2,000,000, about 90,000 to about 1,000,000, about 90,000 to about 800,000, about 90,000 to about 600,000, about 90,000 to about 400,000, about 90,000 to about 200,000, about 90,000 to about 100,000, about 100,000 to about 10,000,000, about 100,000 to about 9,000,000, about 100,000 to about 8,000,000, about 100,000 to about 7,000,000, about 100,000 to about 6,000,000, about 100,000 to about 5,000,000, about 100,000 to about 4,000,000, about 100,000 to about 3,000,000, about 100,000 to about 2,000,000, about 100,000 to about 1,000,000, about 100,000 to about 800,000, about 100,000 to about 600,000, about 100,000 to about 400,000, about 100,000 to about 200,000, about 200,000 to about 10,000,000, about 200,000 to about 9,000,000, about 200,000 to about 8,000,000, about 200,000 to about 7,000,000, about 200,000 to about 6,000,000, about 200,000 to about 5,000,000, about 200,000 to about 4,000,000, about 200,000 to about 3,000,000, about 200,000 to about 2,000,000, about 200,000 to about 1,000,000, about 200,000 to about 800,000, about 200,000 to about 600,000, about 200,000 to about 400,000, about 400,000 to about 10,000,000, about 400,000 to about 9,000,000, about 400,000 to about 8,000,000, about 400,000 to about 7,000,000, about 400,000 to about 6,000,000, about 400,000 to about 5,000,000, about 400,000 to about 4,000,000, about 400,000 to about 3,000,000, about 400,000 to about 2,000,000, about 400,000 to about 1,000,000, about 400,000 to about 800,000, about 400,000 to about 600,000, about 600,000 to about 10,000,000, about 600,000 to about 9,000,000, about 600,000 to about 8,000,000, about 600,000 to about 7,000,000, about 600,000 to about 6,000,000, about 600,000 to about 5,000,000, about 600,000 to about 4,000,000, about 600,000 to about 3,000,000, about 600,000 to about 2,000,000, about 600,000 to about 1,000,000, about 600,000 to about 800,000, about 800,000 to about 10,000,000, about 800,000 to about 9,000,000, about 800,000 to about 8,000,000, about 800,000 to about 7,000,000, about 800,000 to about 6,000,000, about 800,000 to about 5,000,000, about 800,000 to about 4,000,000, about 800,000 to about 3,000,000, about 800,000 to about 2,000,000, about 800,000 to about 1,000,000, about 1,000,000 to about 10,000,000, about 1,000,000 to about 9,000,000, about 1,000,000 to about 8,000,000, about 1,000,000 to about 7,000,000, about 1,000,000 to about 6,000,000, about 1,000,000 to about 5,000,000, about 1,000,000 to about 4,000,000, about 1,000,000 to about 3,000,000, about 1,000,000 to about 2,000,000, about 2,000,000 to about 10,000,000, about 2,000,000 to about 9,000,000, about 2,000,000 to about 8,000,000, about 2,000,000 to about 7,000,000, about 2,000,000 to about 6,000,000, about 2,000,000 to about 5,000,000, about 2,000,000 to about 4,000,000, about 2,000,000 to about 3,000,000, about 3,000,000 to about 10,000,000, about 3,000,000 to about 9,000,000, about 3,000,000 to about 8,000,000, about 3,000,000 to about 7,000,000, about 3,000,000 to about 6,000,000, about 3,000,000 to about 5,000,000, about 3,000,000 to about 4,000,000, about 4,000,000 to about 10,000,000, about 4,000,000 to about 9,000,000, about 4,000,000 to about 8,000,000, about 4,000,000 to about 7,000,000, about 4,000,000 to about 6,000,000, about 4,000,000 to about 5,000,000, about 5,000,000 to about 10,000,000, about 5,000,000 to about 9,000,000, about 5,000,000 to about 8,000,000, about 5,000,000 to about 7,000,000, about 5,000,000 to about 6,000,000, about 6,000,000 to about 10,000,000, about 6,000,000 to about 9,000,000, about 6,000,000 to about 8,000,000, about 6,000,000 to about 7,000,000, about 7,000,000 to about 10,000,000, about 7,000,000 to about 9,000,000, about 7,000,000 to about 8,000,000, about 8,000,000 to about 10,000,000, about 8,000,000 to about 9,000,000, or about 9,000,000 to about 10,000,000 of the CD123 on present on the plasma membrane of the target mammalian cell.

The phrase "antigen density" means the number of CD123 present on the surface of a target mammalian cell or the average number of CD123 on the surface of a population of particular type of target mammalian cells. It can be measured, e.g., using the Quantibright bead kit or radiolabel (e.g., BD Biosciences PE Phycoerythrin Fluorescence Quantitation Kit, catalog #340495).

The phrase "amino acid substituted with a histidine" means the substitution of an amino acid residue that is not histidine in a reference polypeptide sequence with a histidine. Non-limiting methods for substituting an amino acid residue in a reference polypeptide with a histidine are described herein. Additional methods for substituting an amino acid residue in a reference polypeptide with a histidine are known in the art.

The phrase "amino acid substituted with an alanine" means the substitution of an amino acid residue that is a histidine in a reference polypeptide sequence with an alanine. Non-limiting methods for substituting a histidine in a reference polypeptide with an alanine are described herein. Additional methods for substituting an histidine in a reference polypeptide with an alanine are known in the art.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

BRIEF DESCRIPTION OF DRAWINGS

FIG. 3: Construct identifier to SEQ ID NO correspondence table. Constructs, heavy chain histidine scanning and alanine scanning variants, are listed in the first column of the table, SEQ ID NOs are listed and correspond to constructs on the left and the appropriate heavy chain and/or light chain categories along the top.

FIG. 6: Construct identifier to SEQ ID NO correspondence table. Constructs, light chain histidine scanning and alanine scanning variants, are listed in the first column of the table, SEQ ID NOs are listed and correspond to constructs on the left and the appropriate heavy chain and/or light chain categories along the top.

FIG. 9: Construct identifier to SEQ ID NO correspondence table. Constructs, heavy chain combinations histidine scanning and alanine scanning variants, are listed in the first column of the table, SEQ ID NOs are listed and correspond to constructs on the left and the appropriate heavy chain and/or light chain categories along the top.

FIG. 12: Construct identifier to SEQ ID NO correspondence table. Constructs, paired heavy and light chain variants, combining light chain histidine and alanine scanning variants with heavy chain histidine and alanine scanning variants or heavy chain combination histidine scanning and alanine scanning variants, are listed in the first column of the table, SEQ ID NOs are listed and correspond to constructs on the left and the appropriate heavy chain and/or light chain categories along the top.

FIG. 15: Construct identifier to SEQ ID NO correspondence table. Constructs, heavy chain histidine scanning and alanine scanning variants, are listed in the first column of the table, SEQ ID NOs are listed and correspond to constructs on the left and the appropriate heavy chain and/or light chain categories along the top.

FIG. 18: Construct identifier to SEQ ID NO correspondence table. Constructs, heavy chain histidine scanning and alanine scanning variants, are listed in the first column of the table, SEQ ID NOs are listed and correspond to constructs on the left and the appropriate heavy chain and/or light chain categories along the top.

FIG. 19: SDS PAGE for TPP-8988 histidine scanning and alanine scanning. Expi293 cell culture supernatants post-harvest were loaded on non-reduced SDS PAGE gels to confirm expression of TPP-8988 and histidine scanning and alanine scanning variants. Arrows show the corresponding size for an IgG on a non-reduced SDS PAGE gel. MYT5482-MYT5511 are TPP-8988 light chain histidine scanning and alanine scanning variants.

FIG. 21: Construct identifier to SEQ ID NO correspondence table. Constructs, light chain histidine scanning and alanine scanning variants, are listed in the first column of the table, SEQ ID NOs are listed and correspond to constructs on the left and the appropriate heavy chain and/or light chain categories along the top.

FIG. 22*a* shows MYT1251 (IMGN632) with an IC50 of 0.034 nM, FIG. 22*b* shows MYT2758 with an IC50 of 0.051 nM.

FIG. 24: Downregulation of CD123 expression by anti-CD123a mAbs. Anti-CD123 mAbs were assayed for their ability to downregulate expression of CD123 on EOL-1 (CD123+) cells. FIG. 24*a* shows the continuous exposure condition while

DETAILED DESCRIPTION

Figure 1:
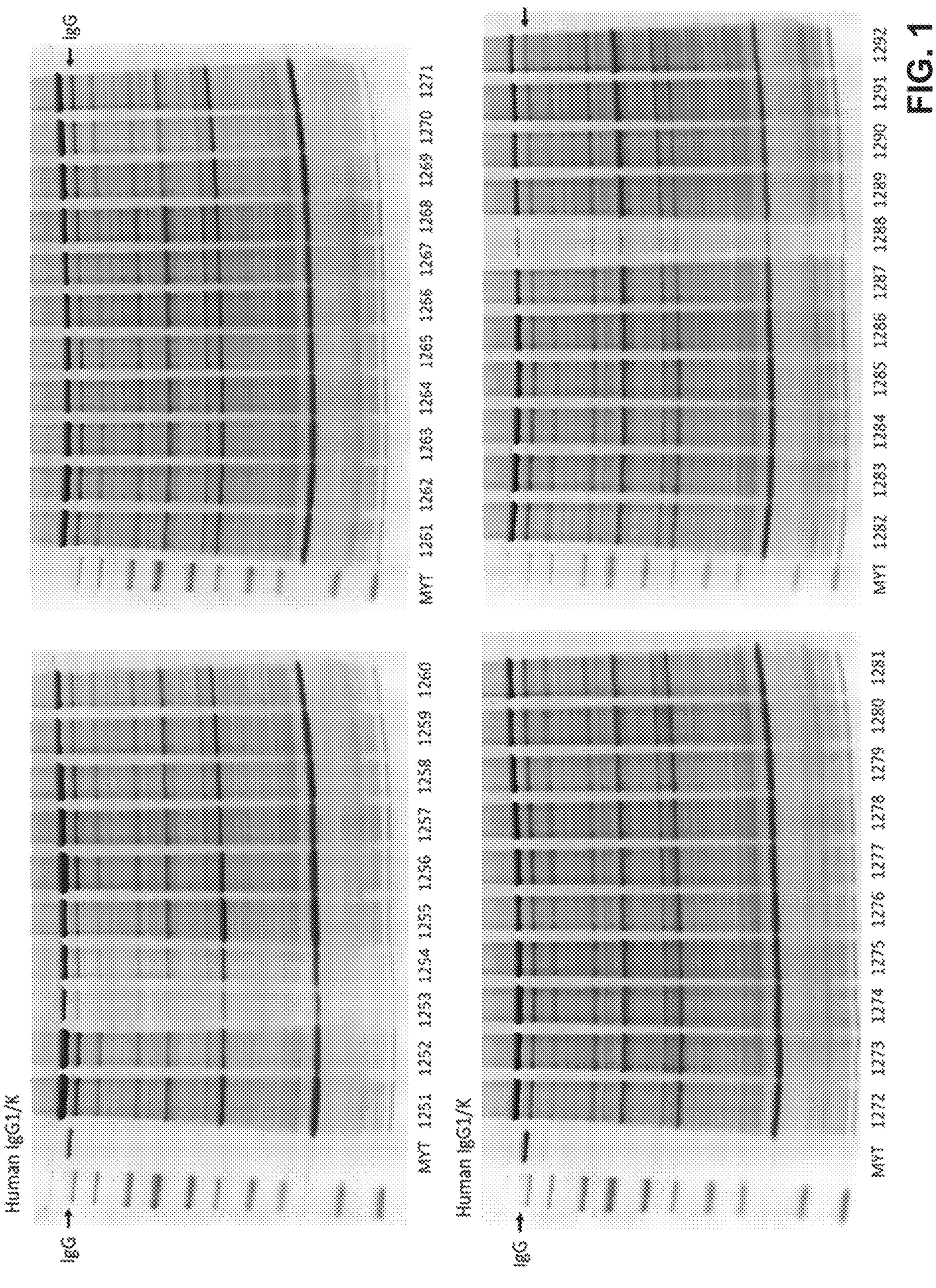
FIG. 1: SDS PAGE for IMGN632 histidine scanning and alanine scanning. Expi293 cell culture supernatants post-harvest were loaded on non-reduced SDS PAGE gels to confirm expression of IMGN632 and histidine scanning and alanine scanning variants. Arrows show the corresponding size for an IgG on a non-reduced SDS PAGE gel. MYT1251 is IMGN632 and the rest of the lanes (MYT1252-MYT1292) are IMGN632 heavy chain histidine scanning and alanine scanning variants.
Figure 2A:
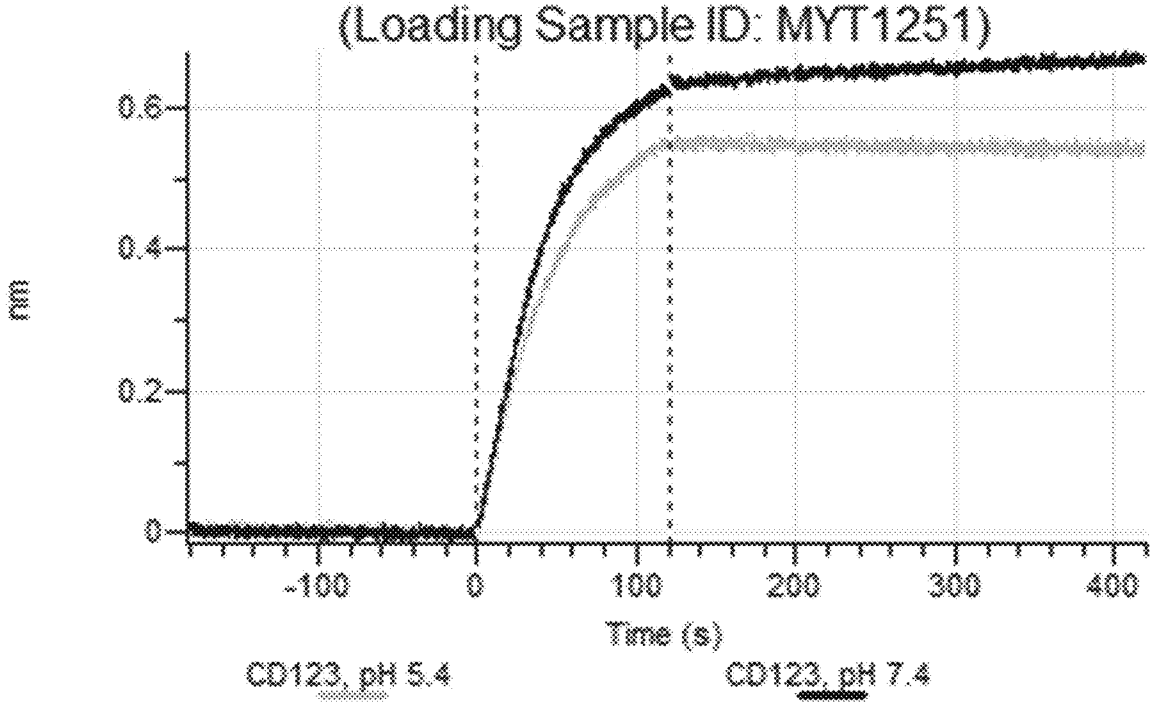
FIGS. 2*a* to 2*ap*: Binding of IMGN632 starting ABPC and histidine scanning and alanine scanning variants to CD123 by biolayer interferometry. MYT1251 (IMGN632) and MYT1252-MYT1292, heavy chain histidine scanning and alanine scanning variants, were captured on anti-human Fc biosensors and associated with CD123 at low pH or high pH, as specified in the figures.
Figure 2B:
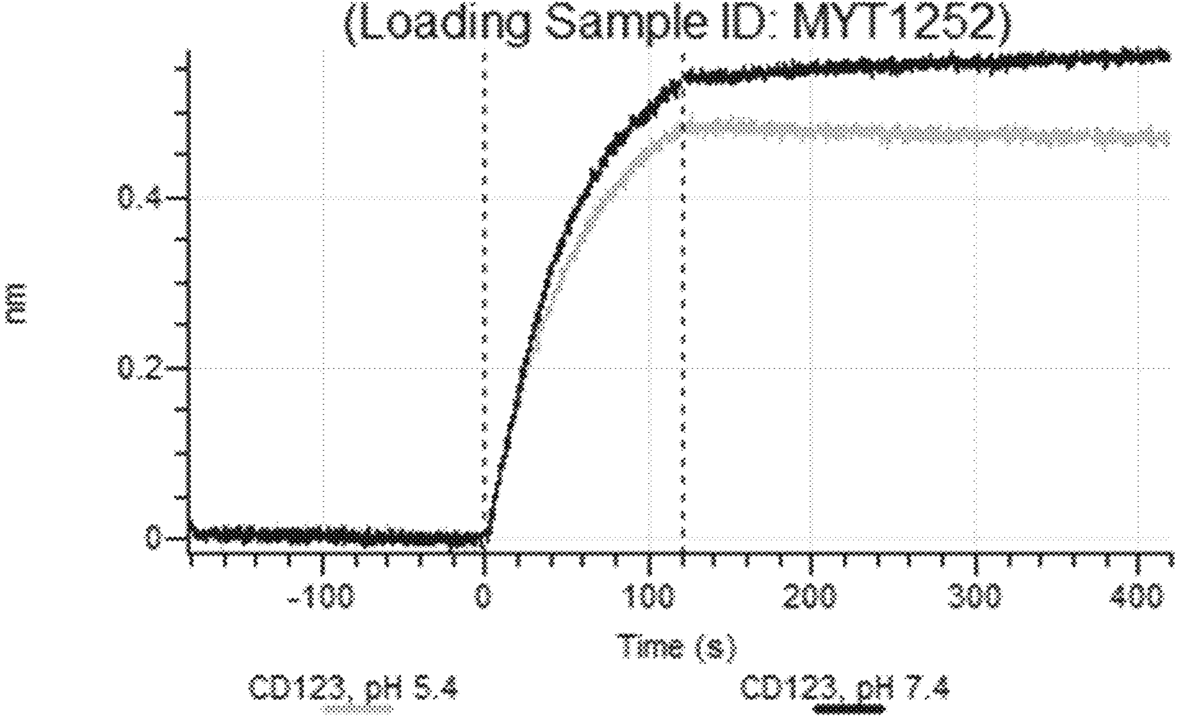
Figure 2C:
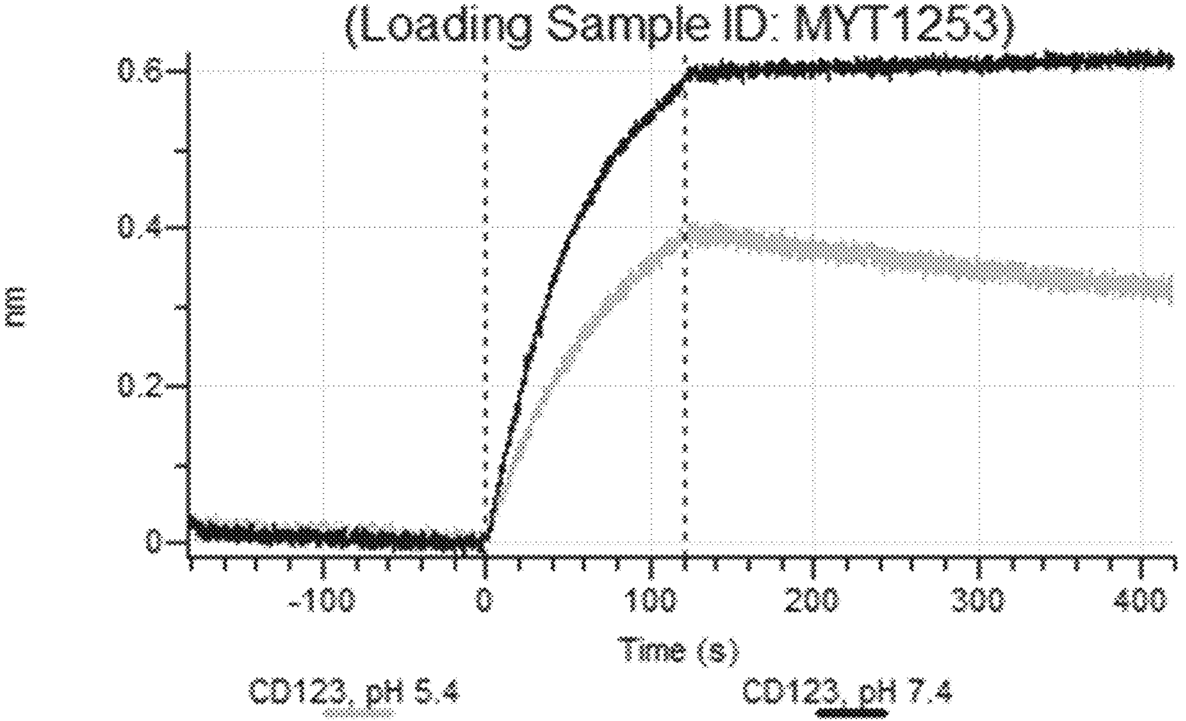
Figure 2D:
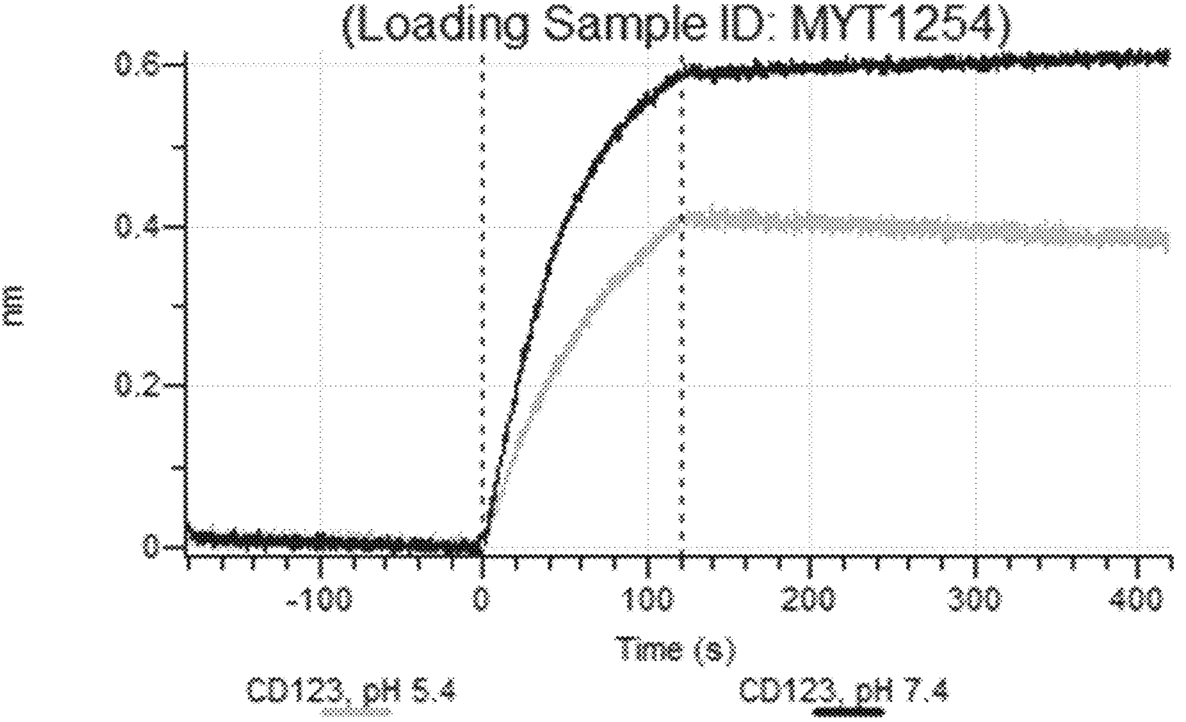
Figure 2E:
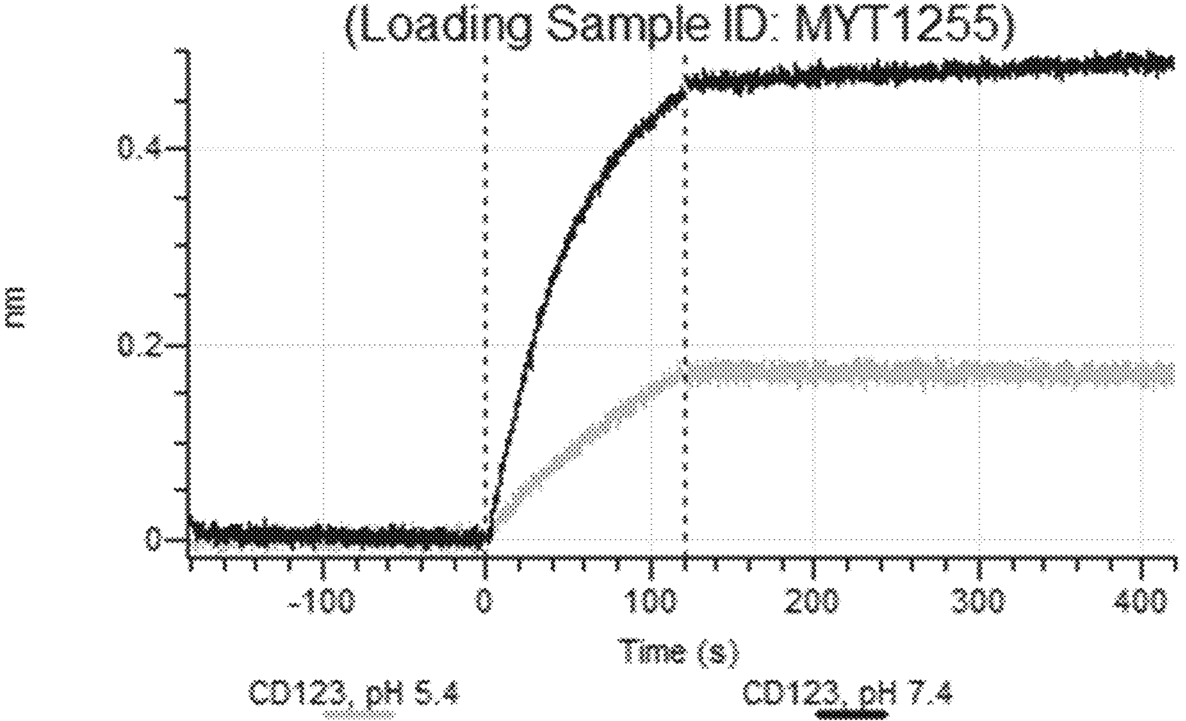
Figure 2F:
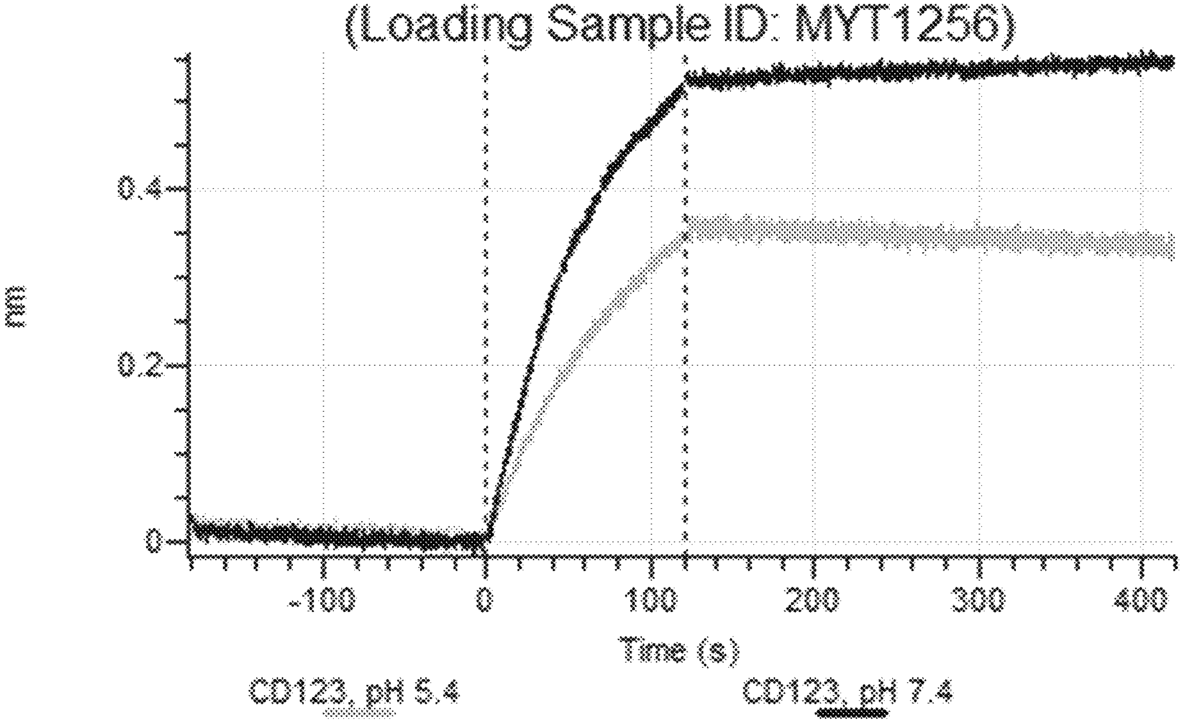
Figure 2G:
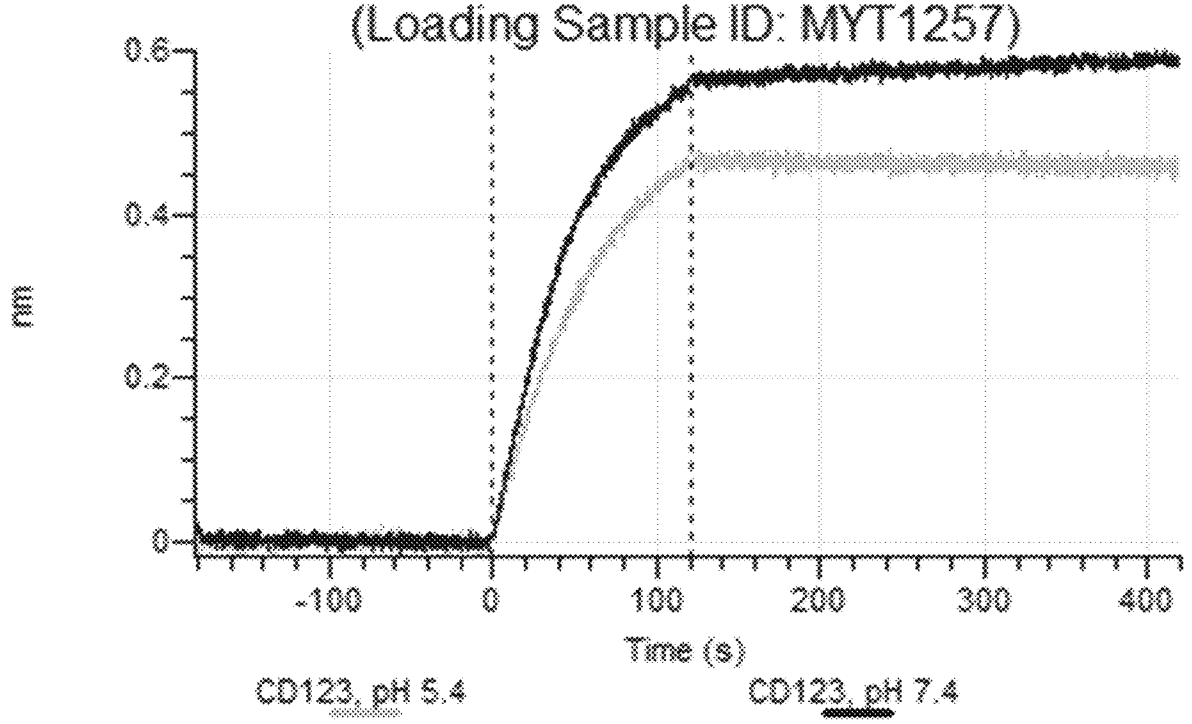
Figure 2H:
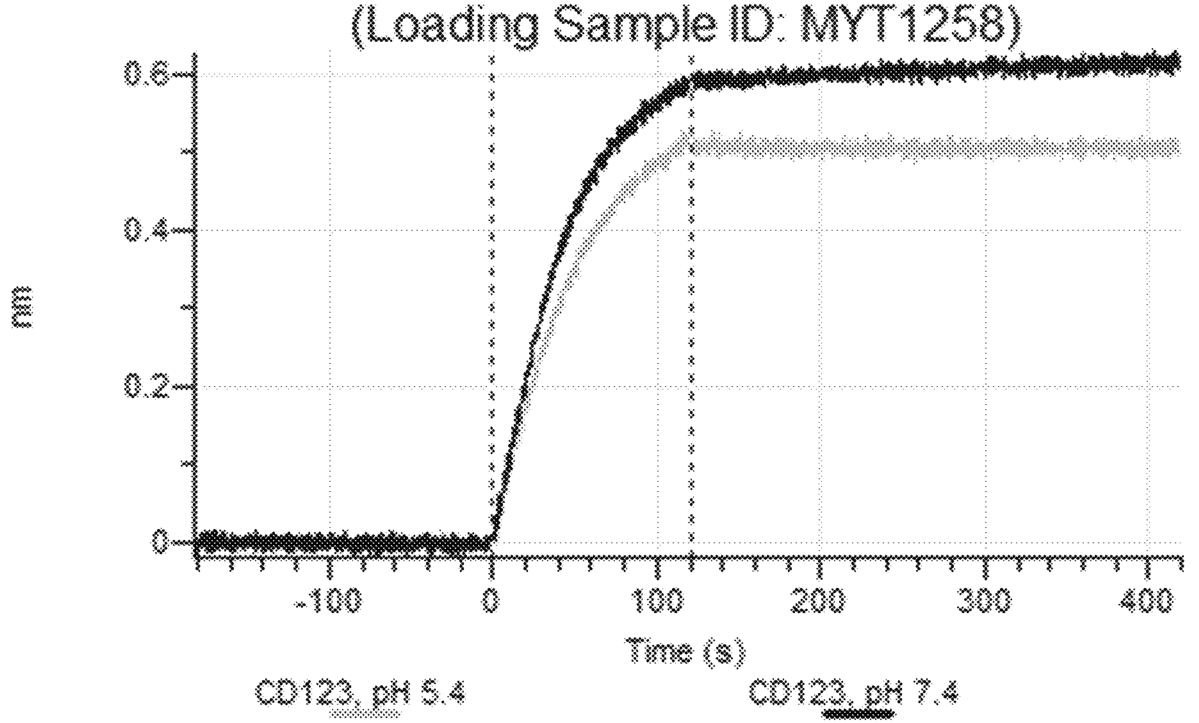
Figure 2I:
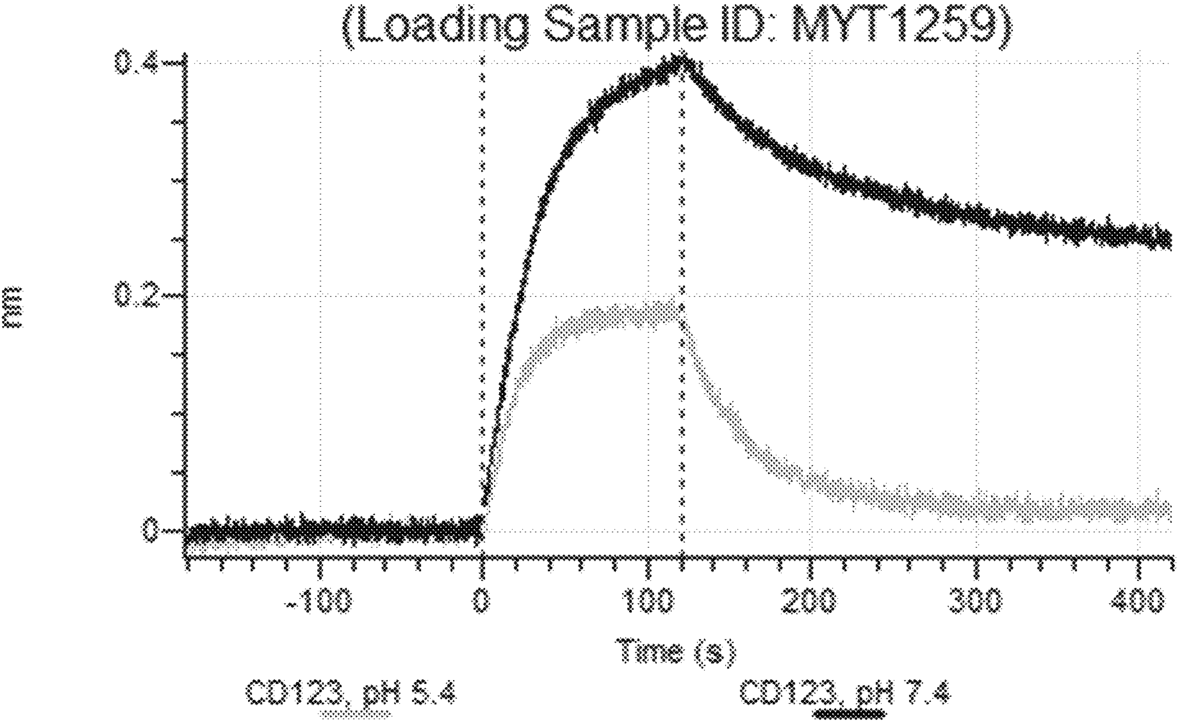
Figure 2J:
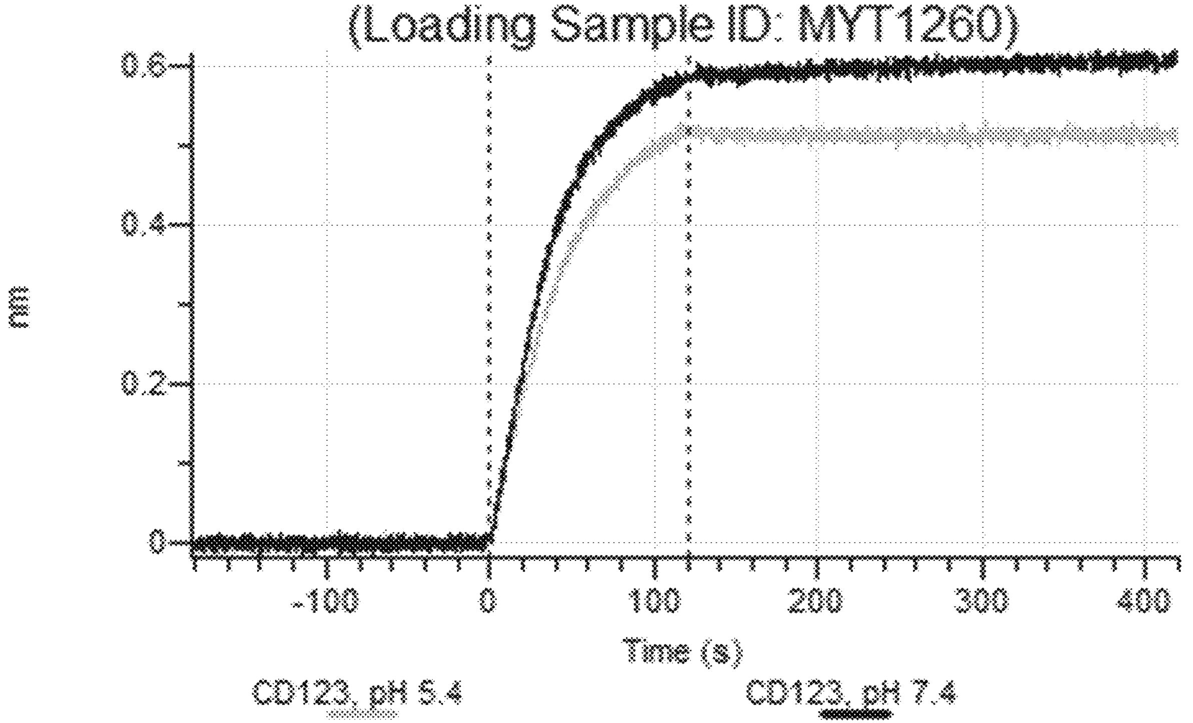
Figure 2K:
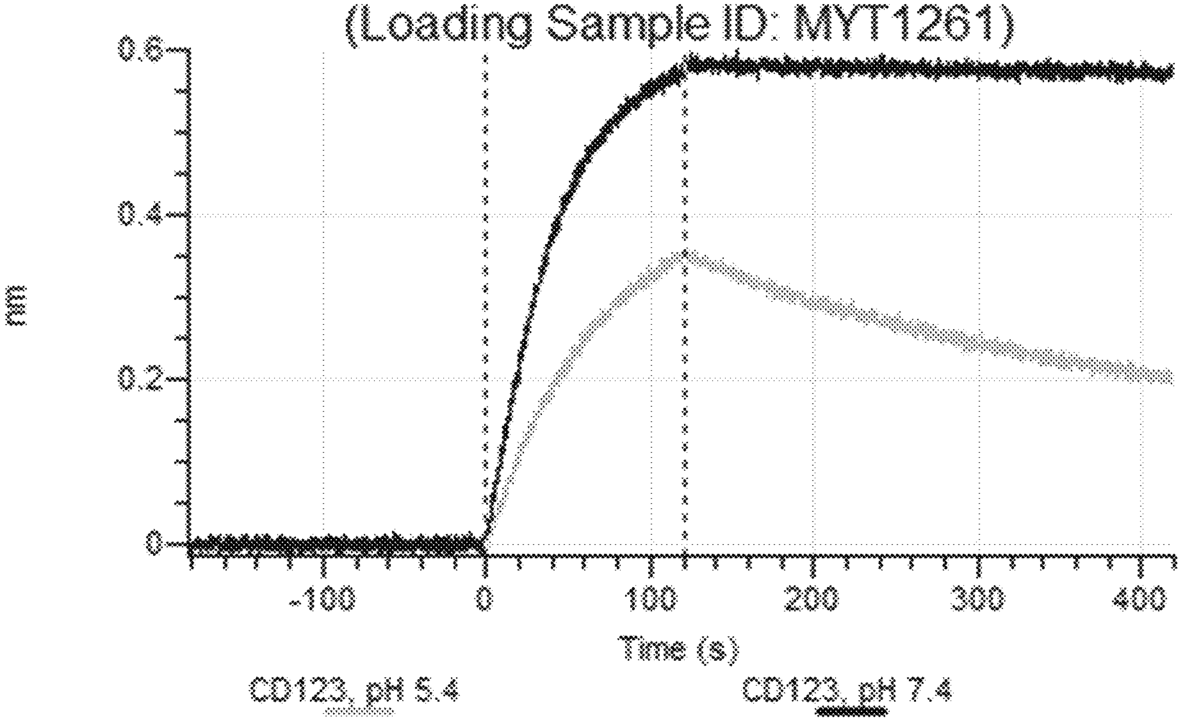
Figure 2L:
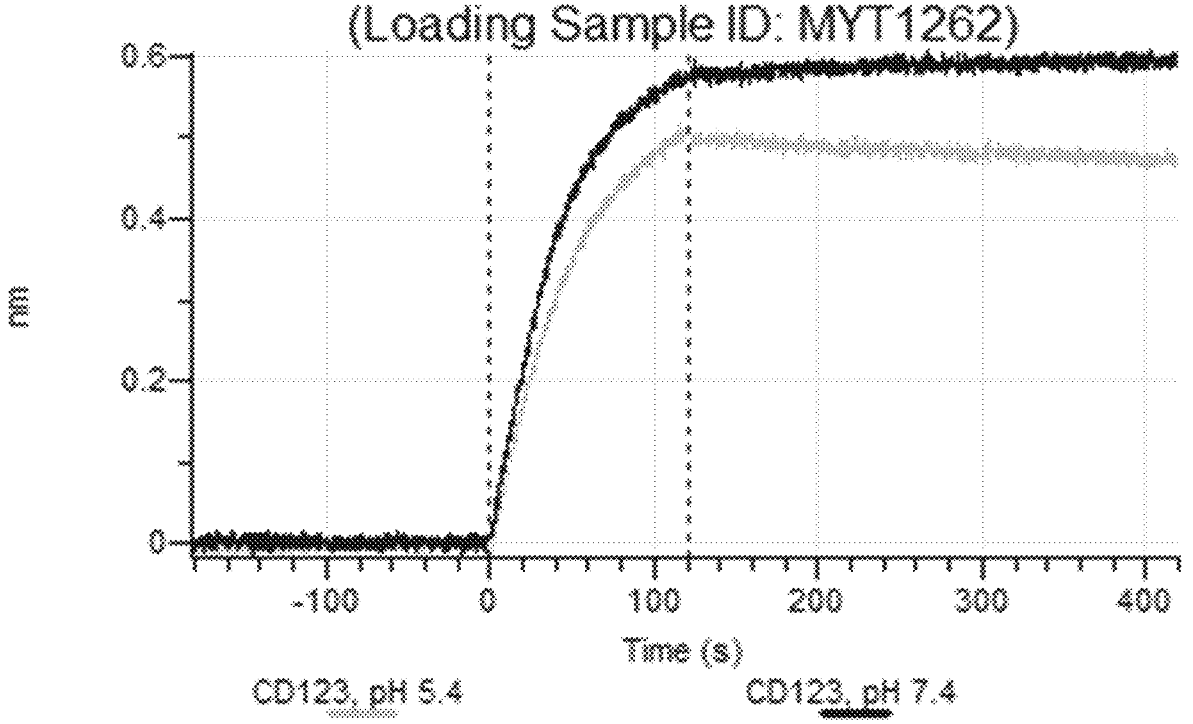
Figure 2M:
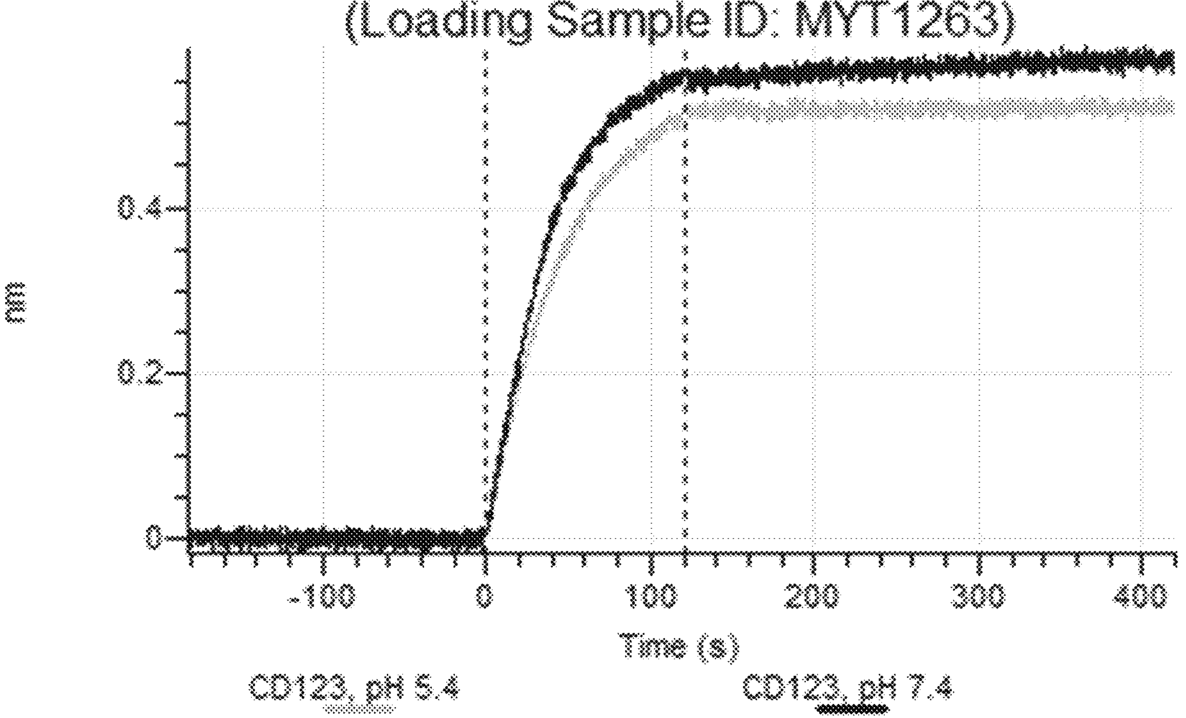
Figure 2N:
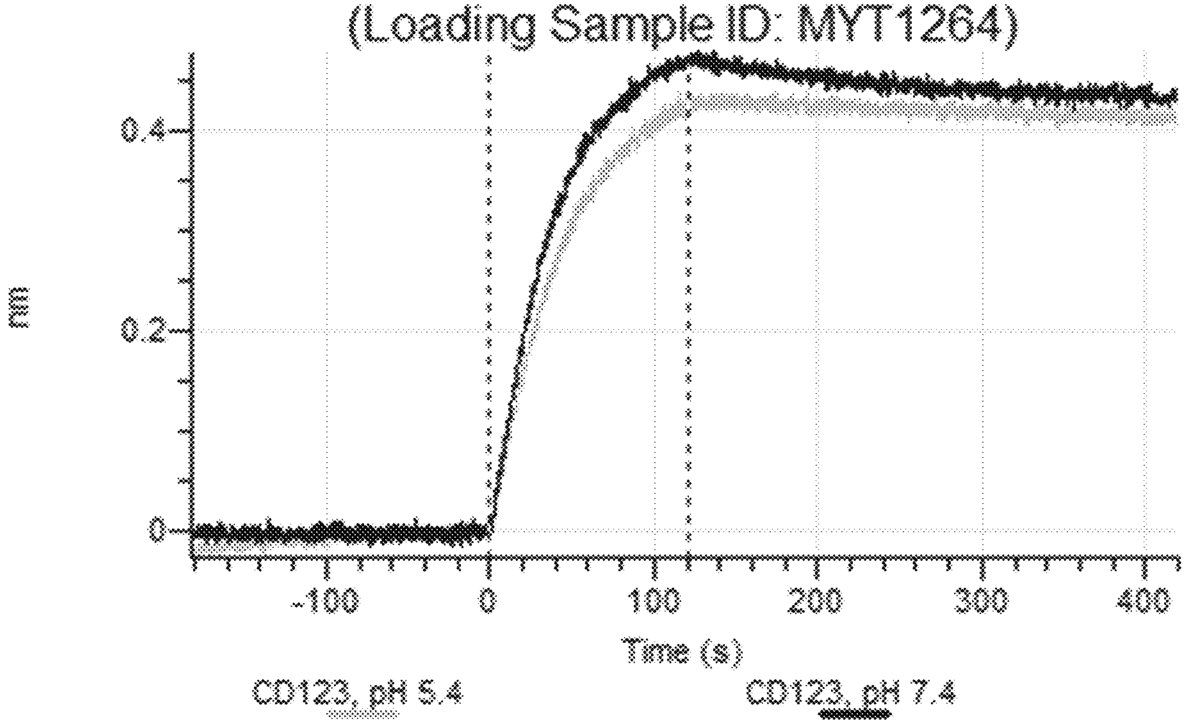
Figure 2O:
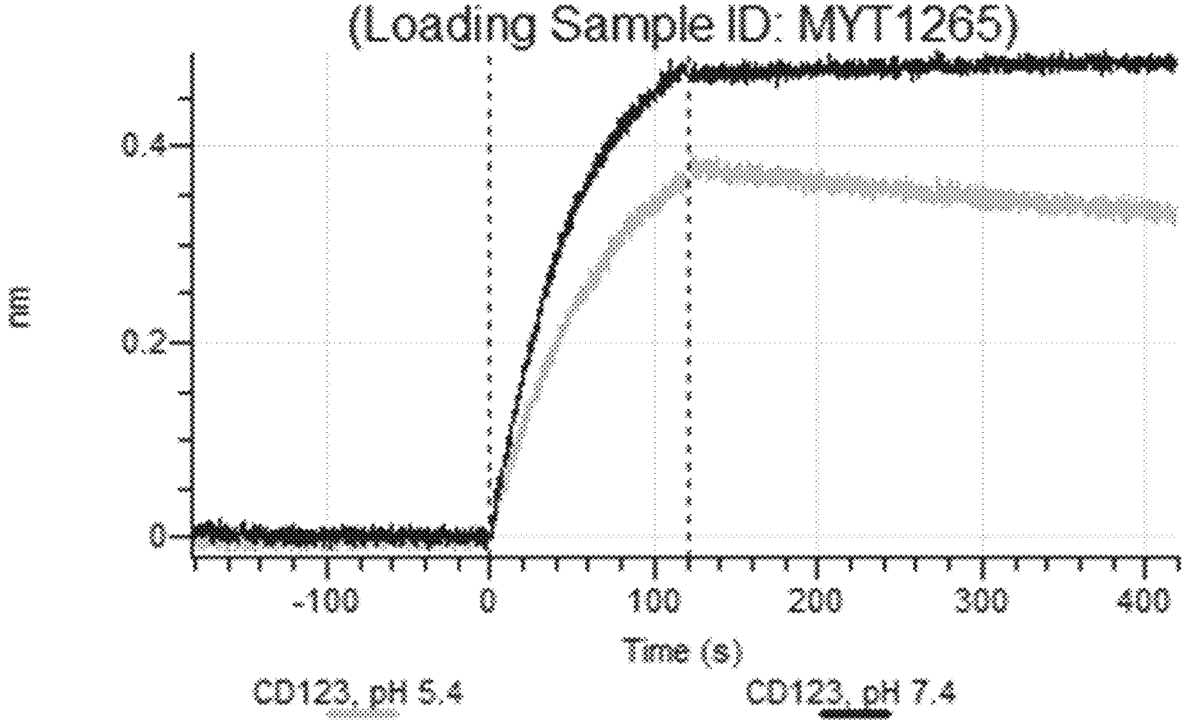
Figure 2P:
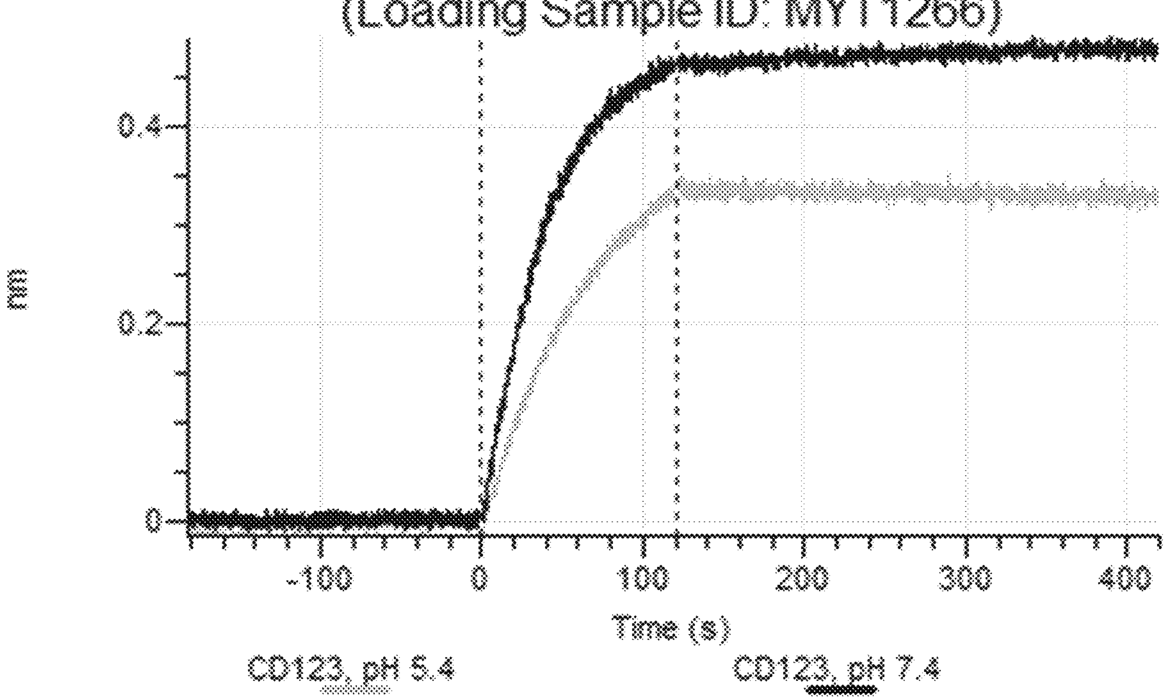
Figure 2Q:
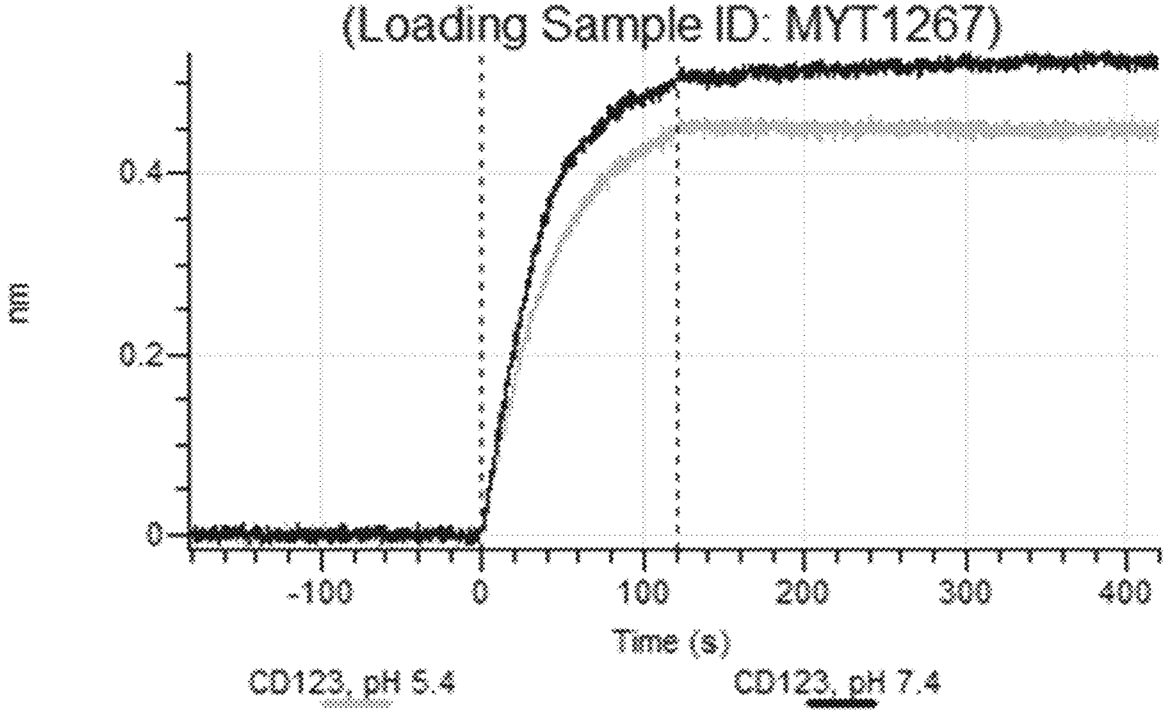
Figure 2R:
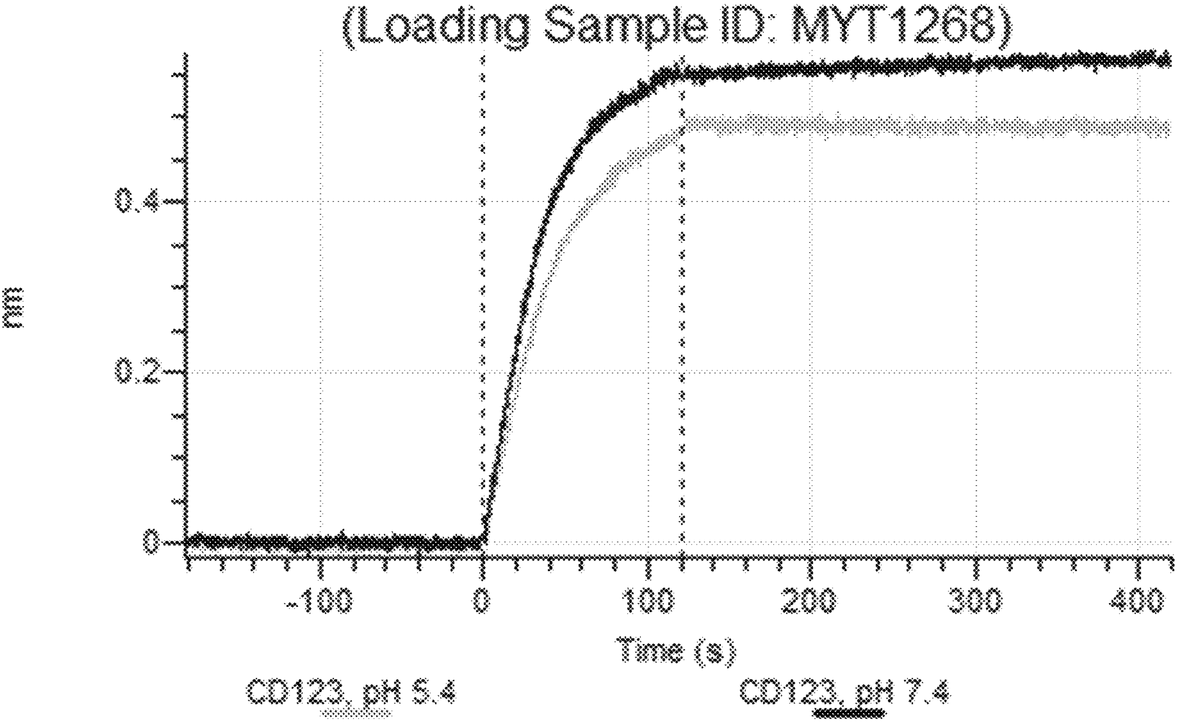
Figure 2S:
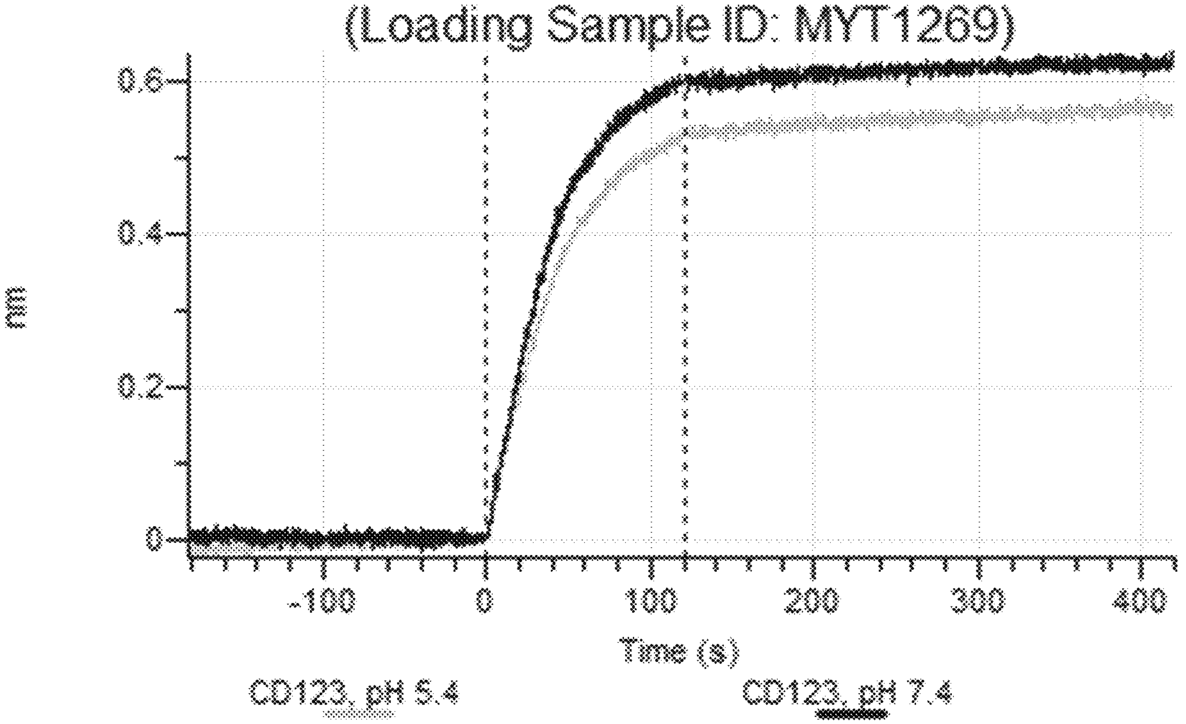
Figure 2T:
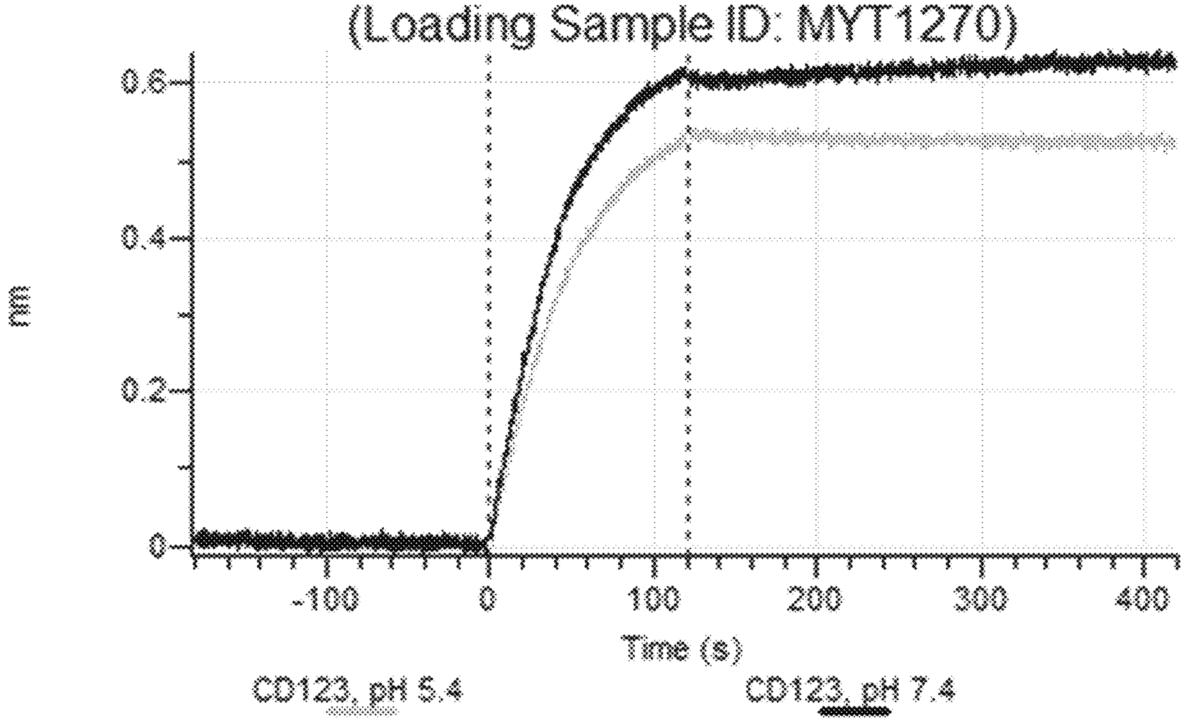
Figure 2U:
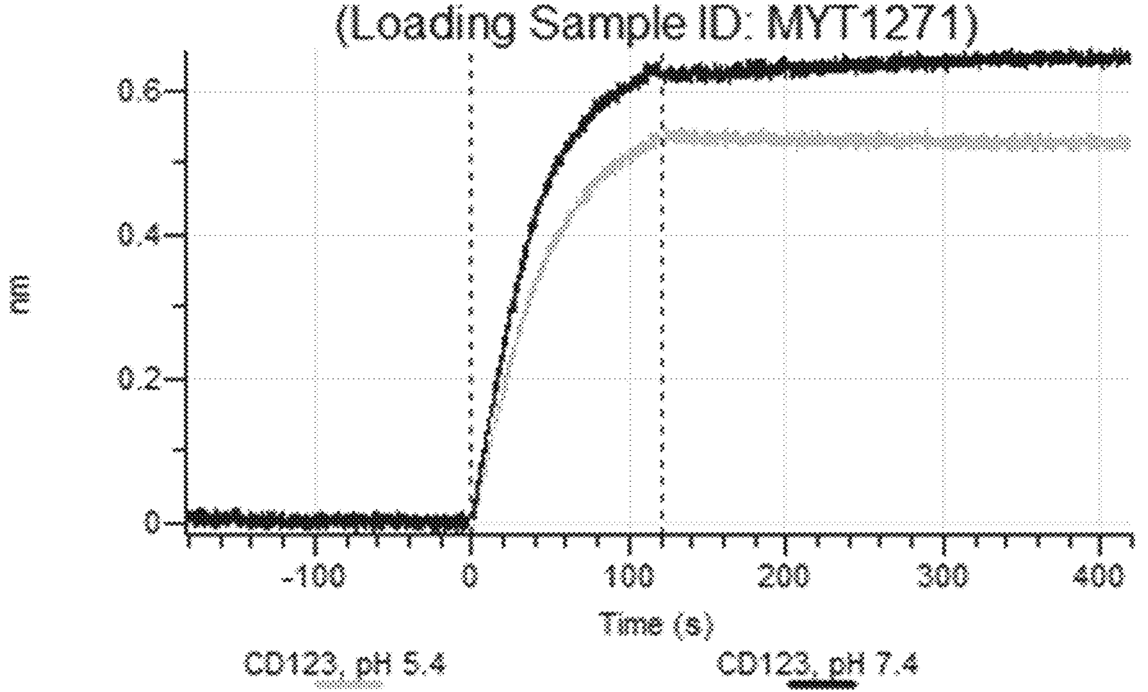
Figure 2V:
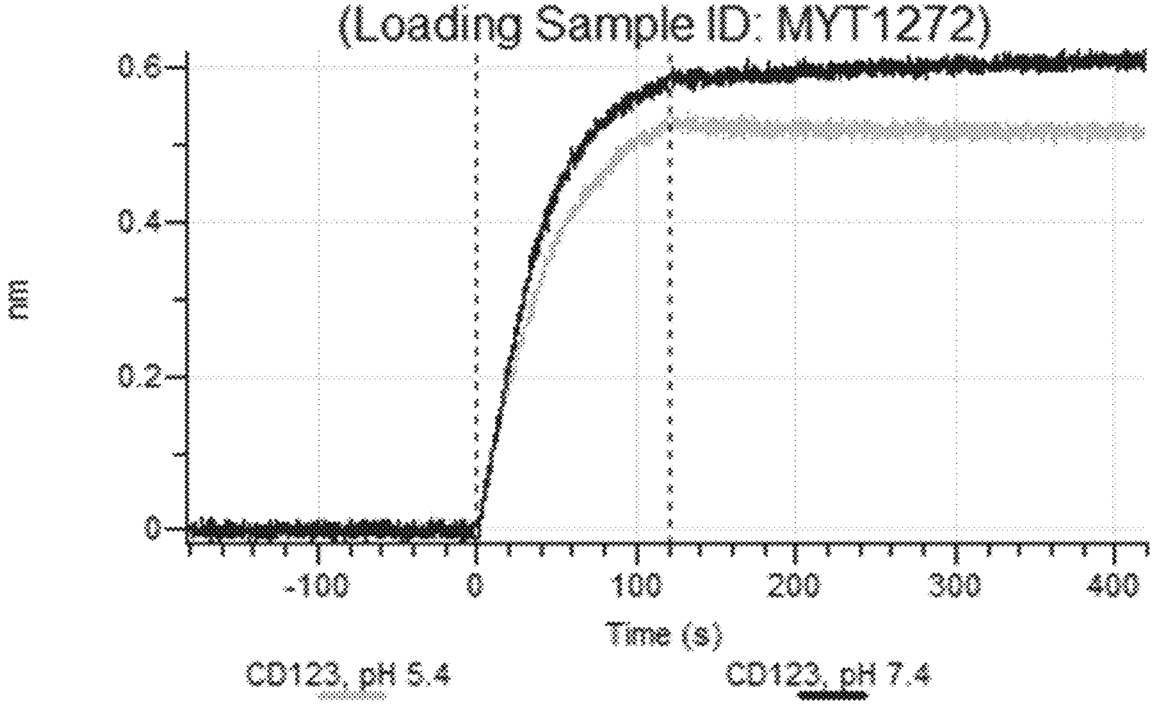
Figure 2W:
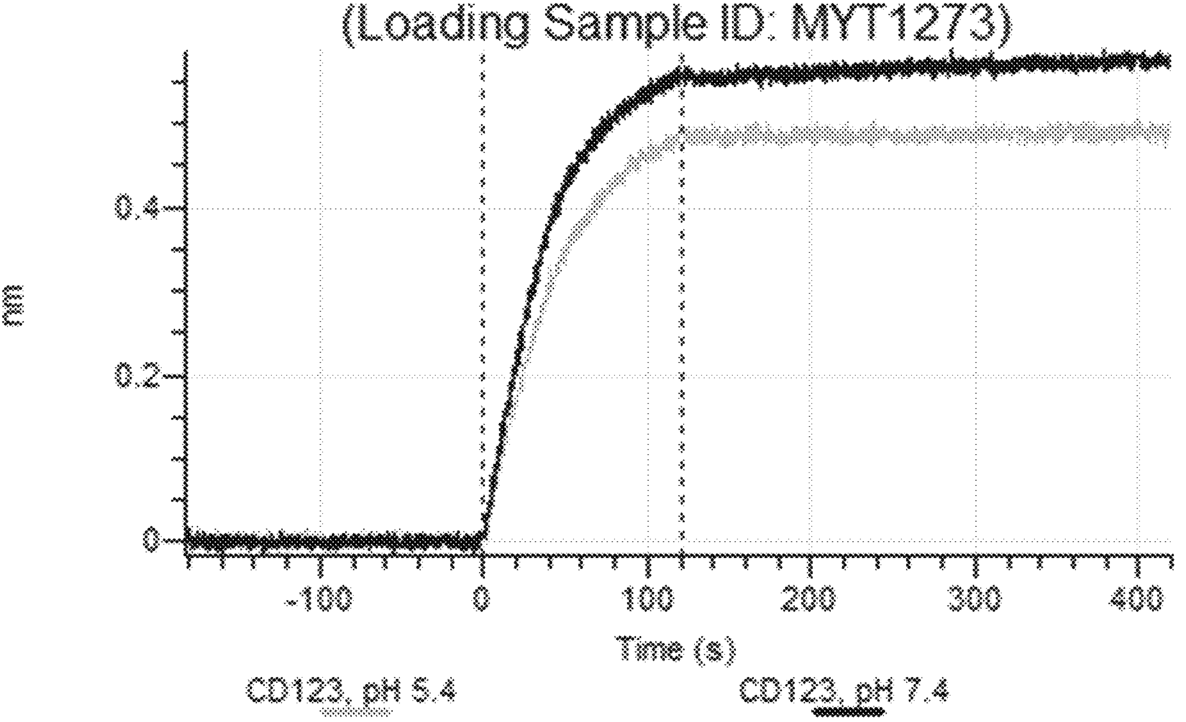
Figure 2X:
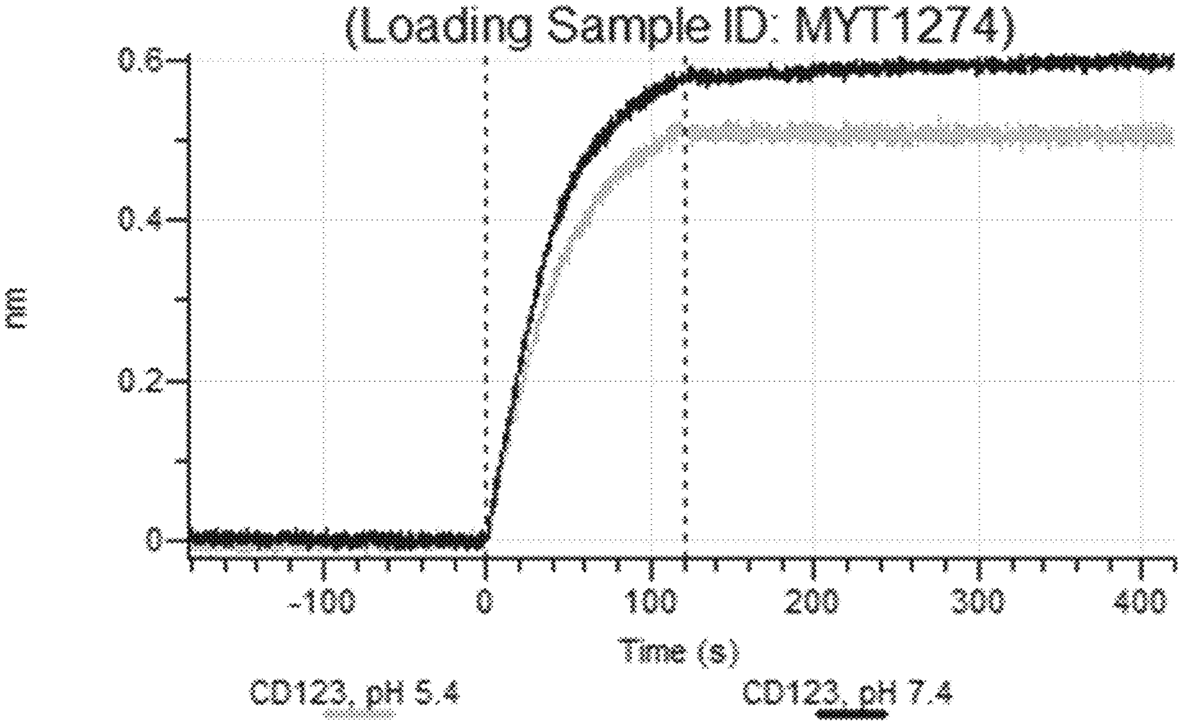
Figure 2Y:
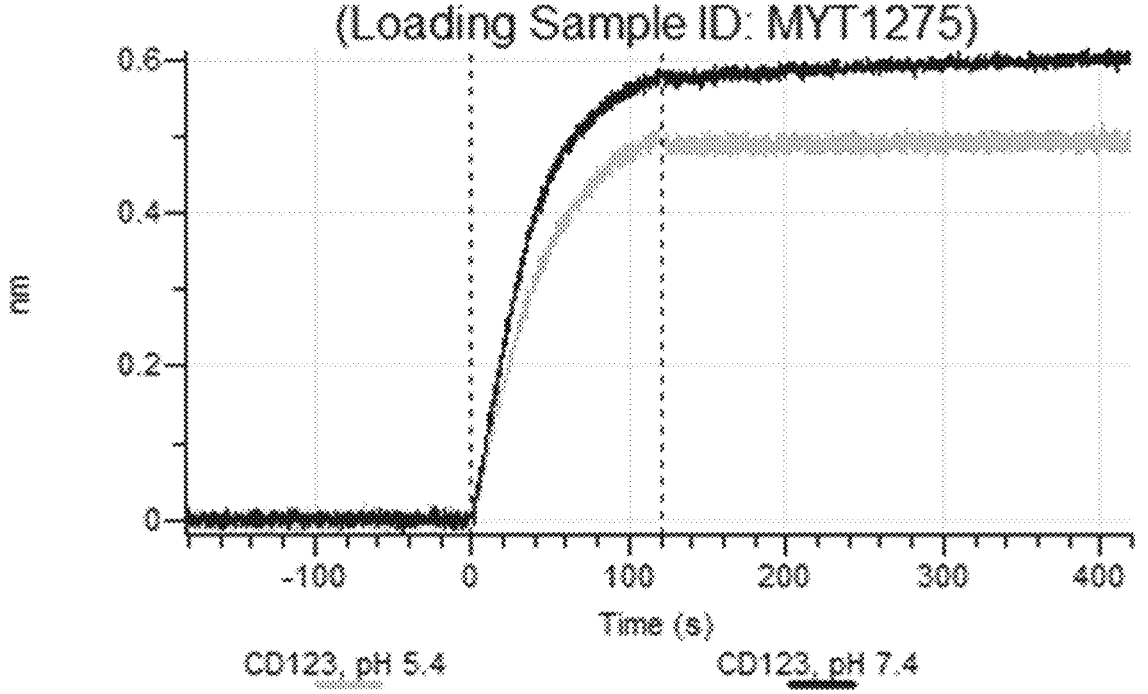
Figure 2Z:
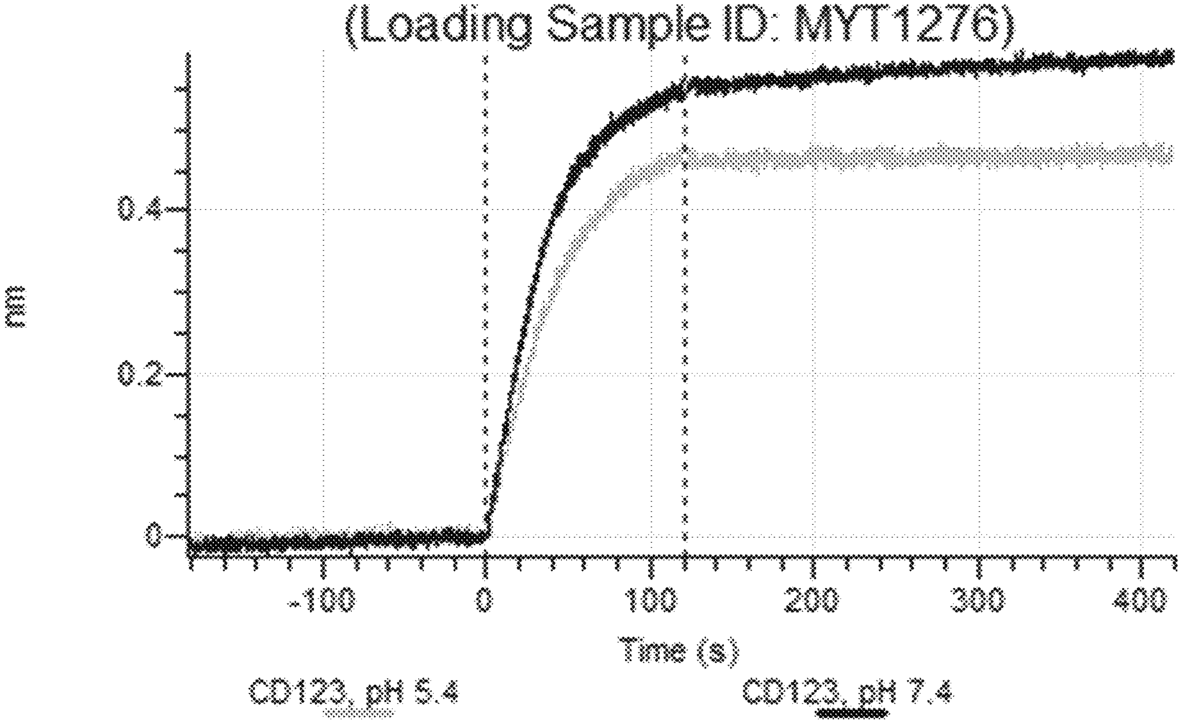
Figure 2A:
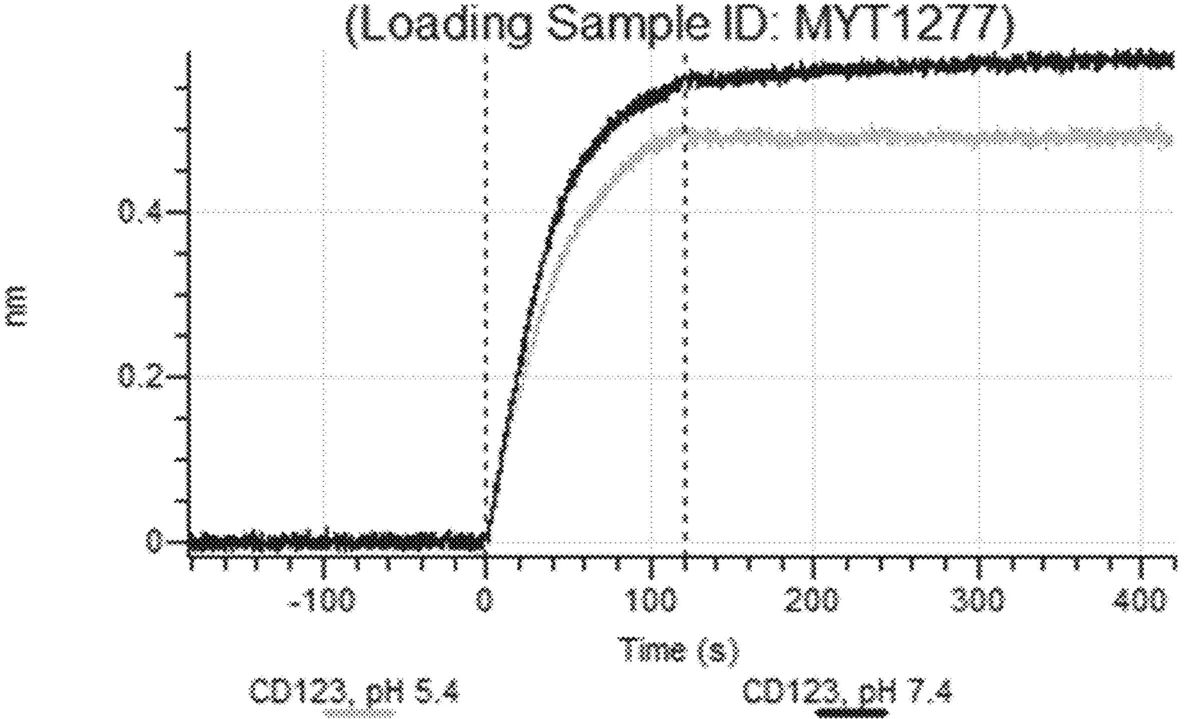
Figure 2A:
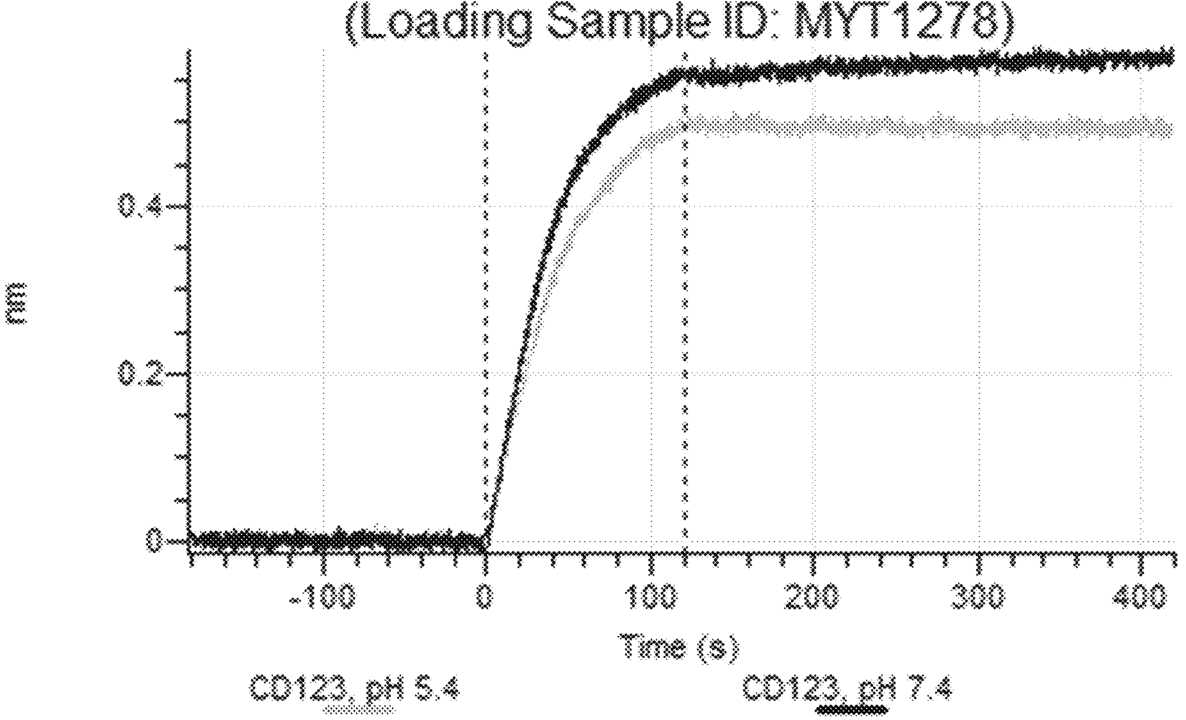
Figure 2A:
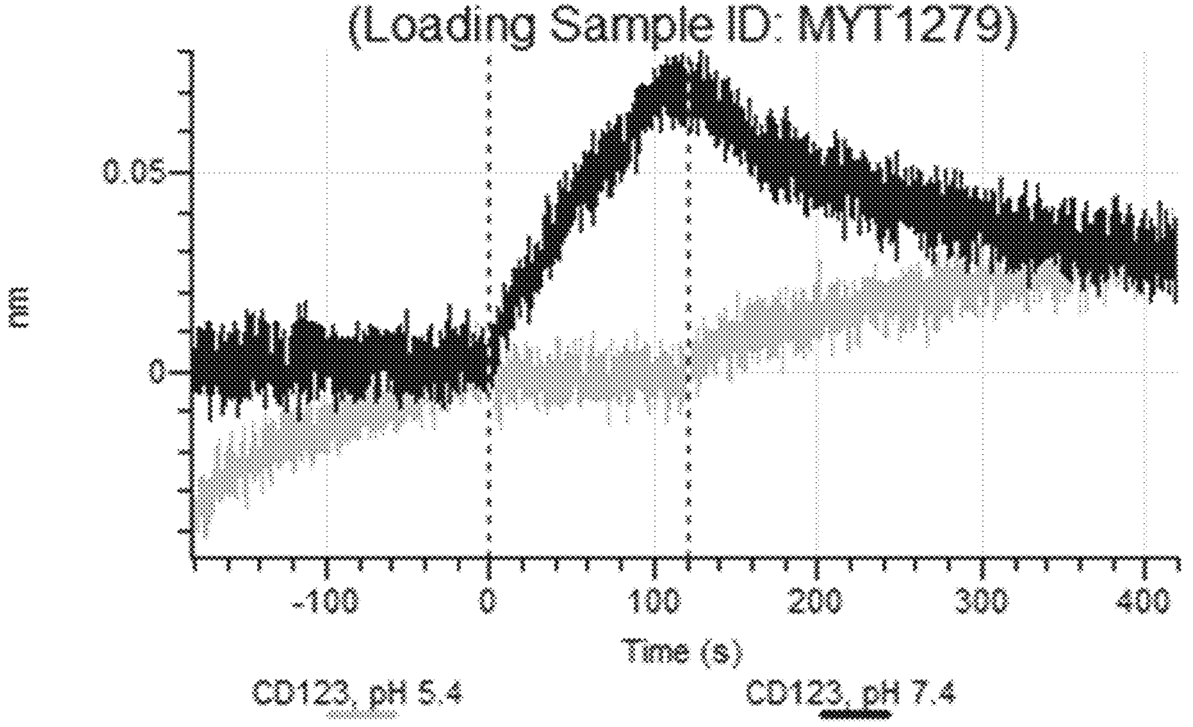
Figure 2A:
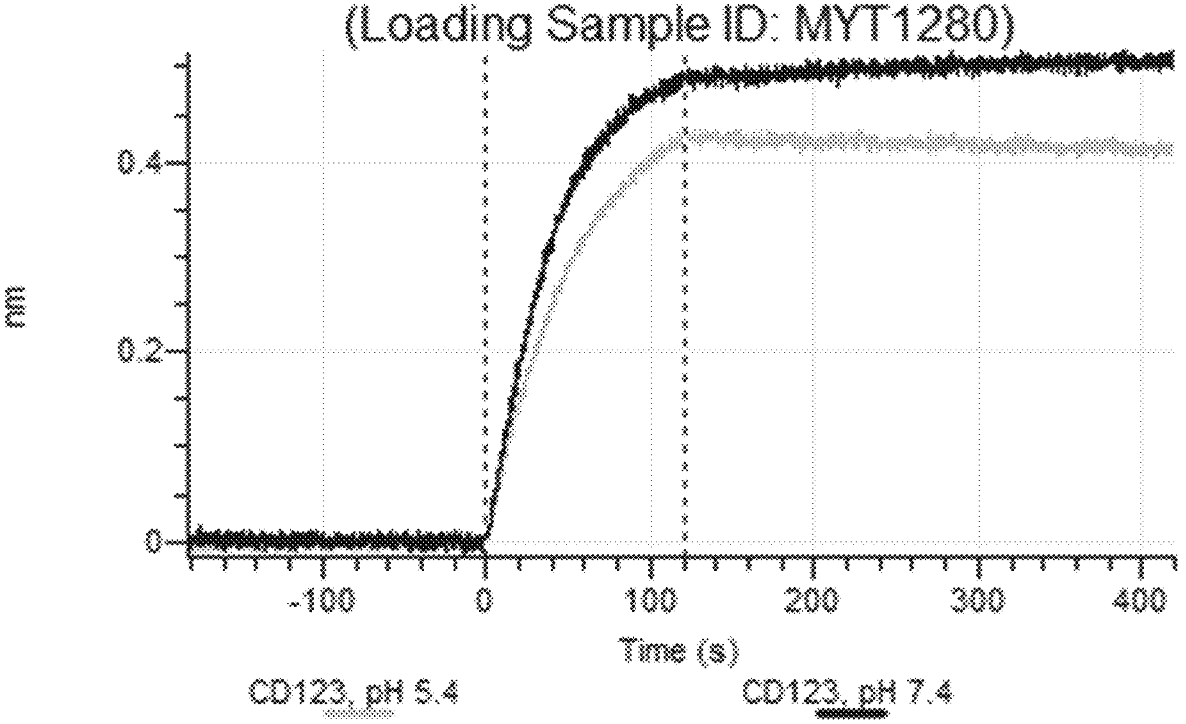
Figure 2A:
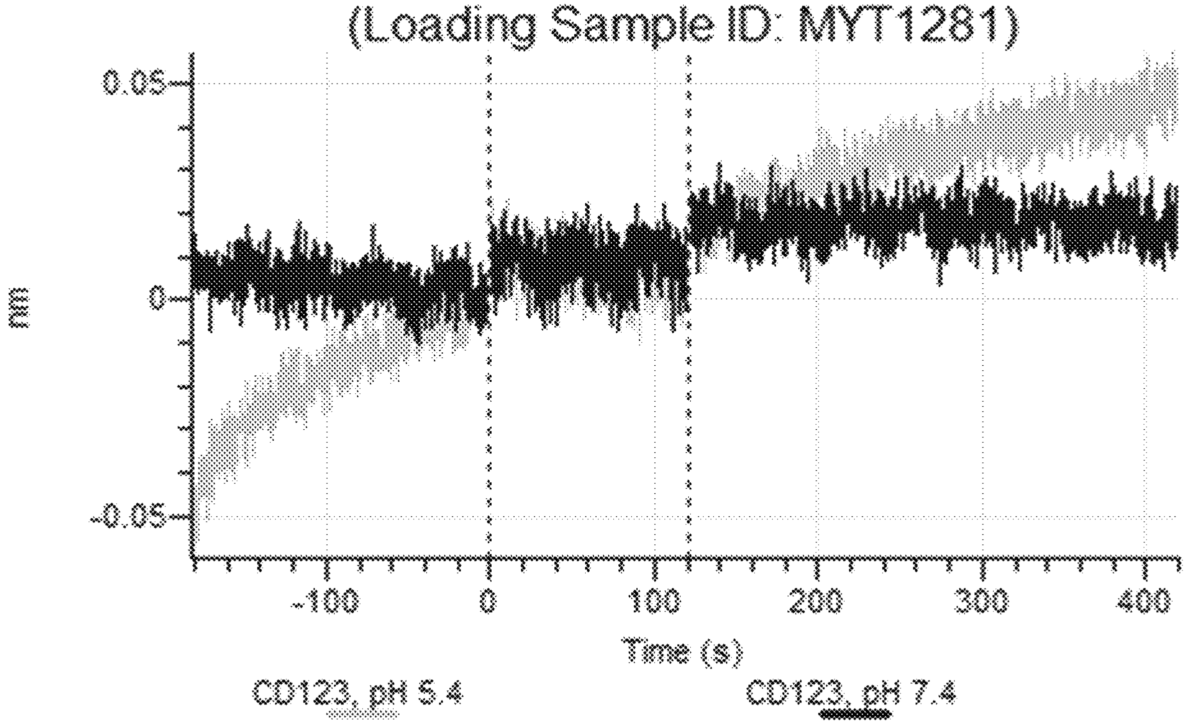
Figure 2A:
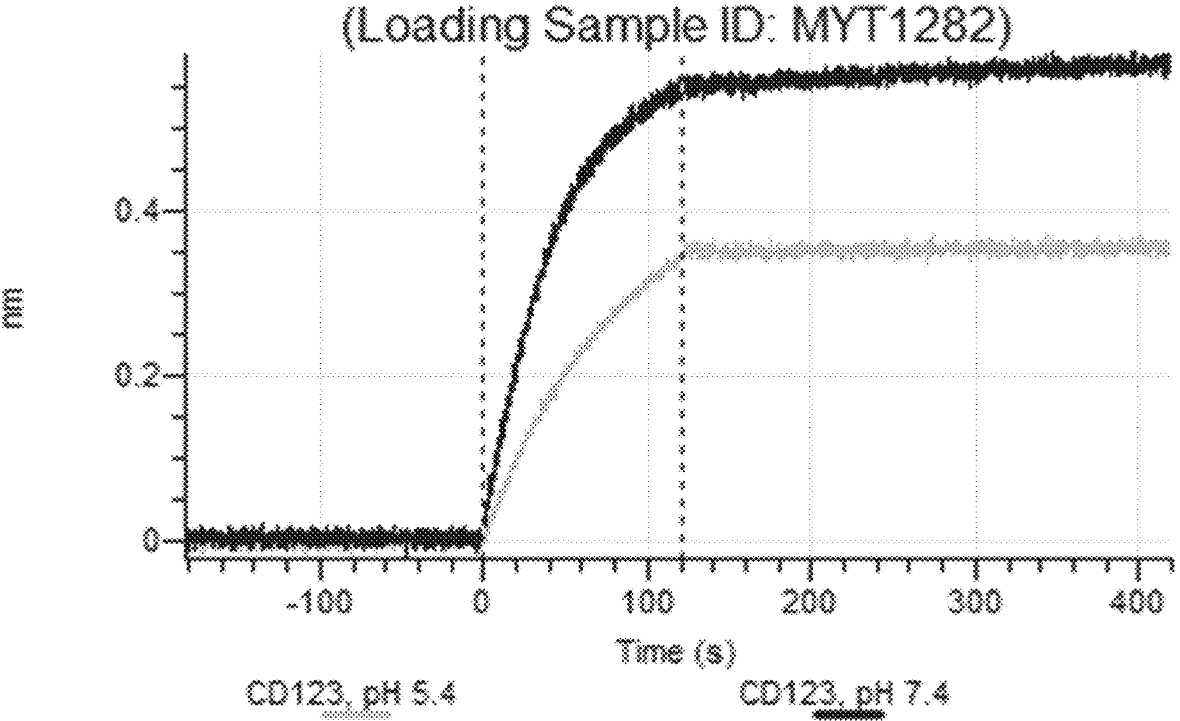
Figure 2A:
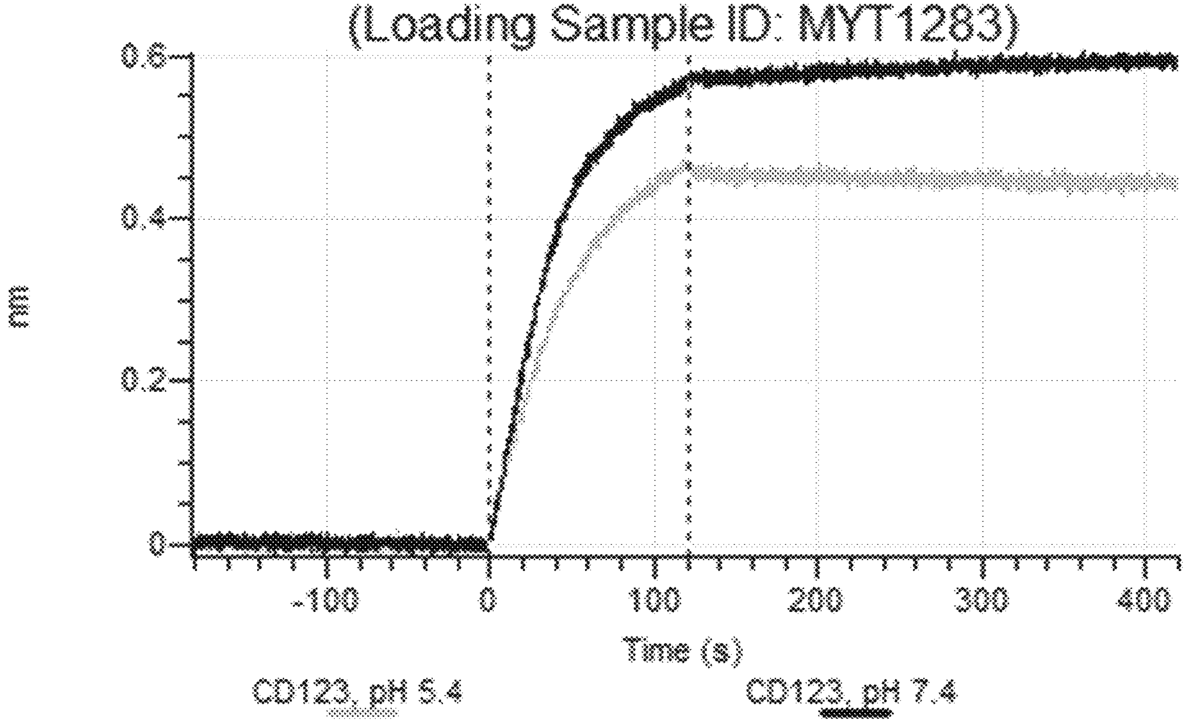
Figure 2A:
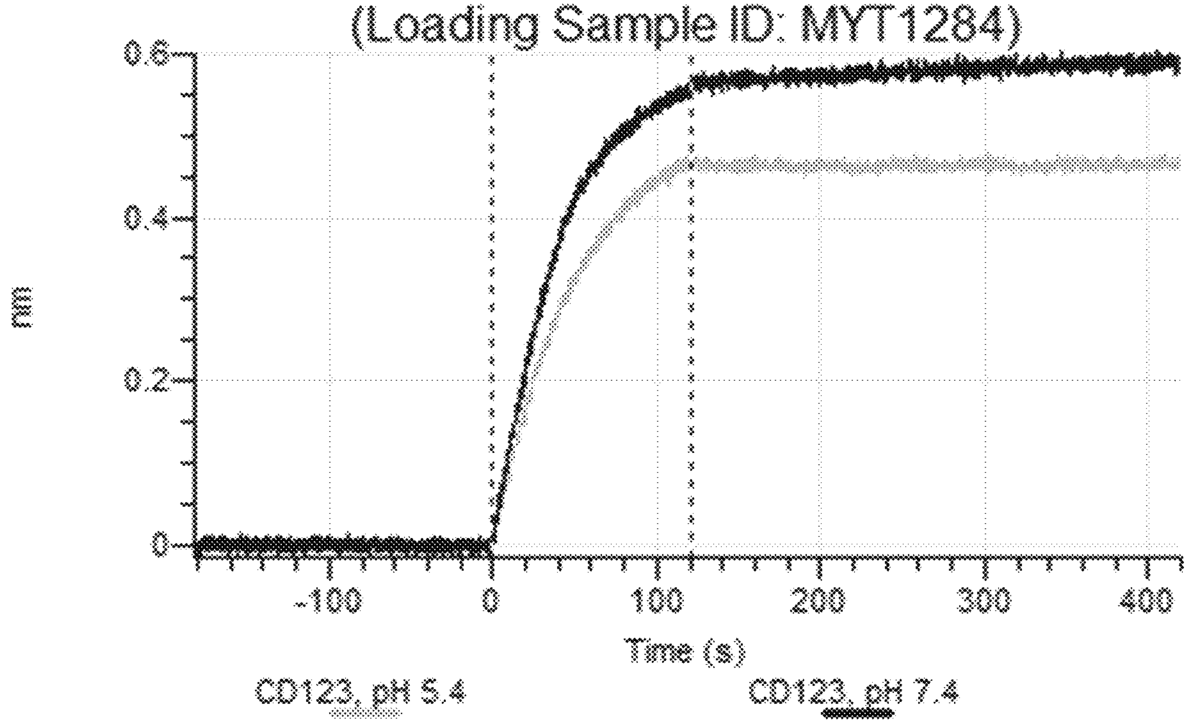
Figure 2A:
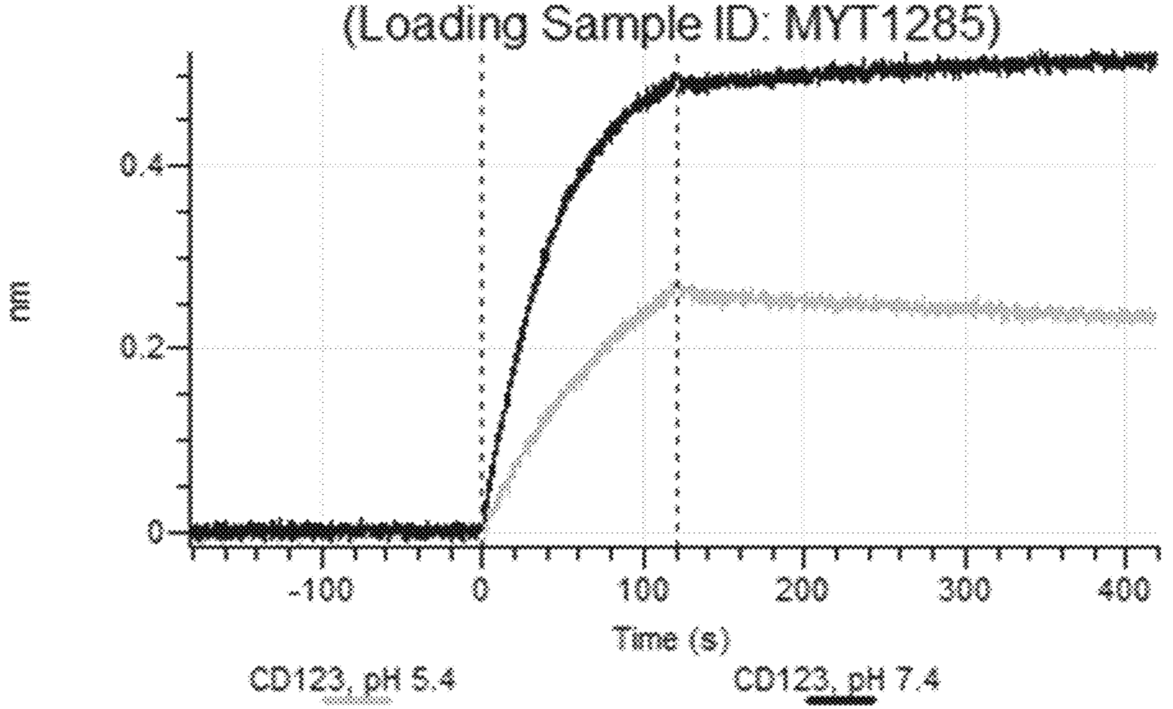
Figure 2A:
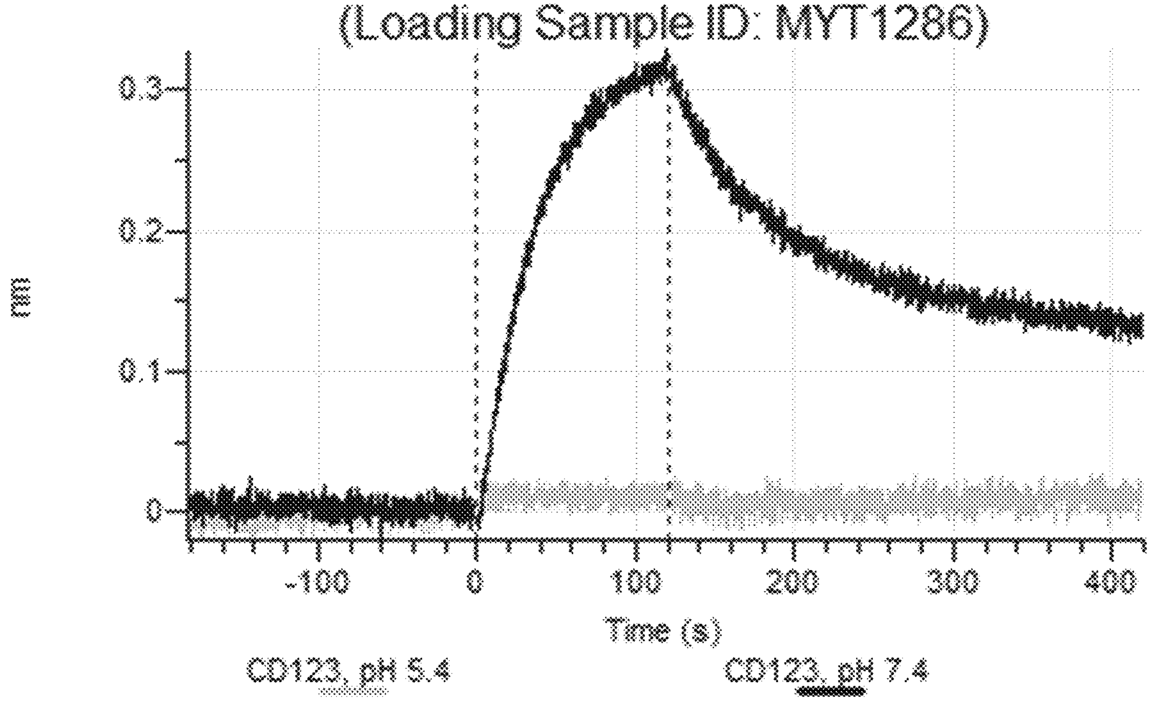
Figure 2A:
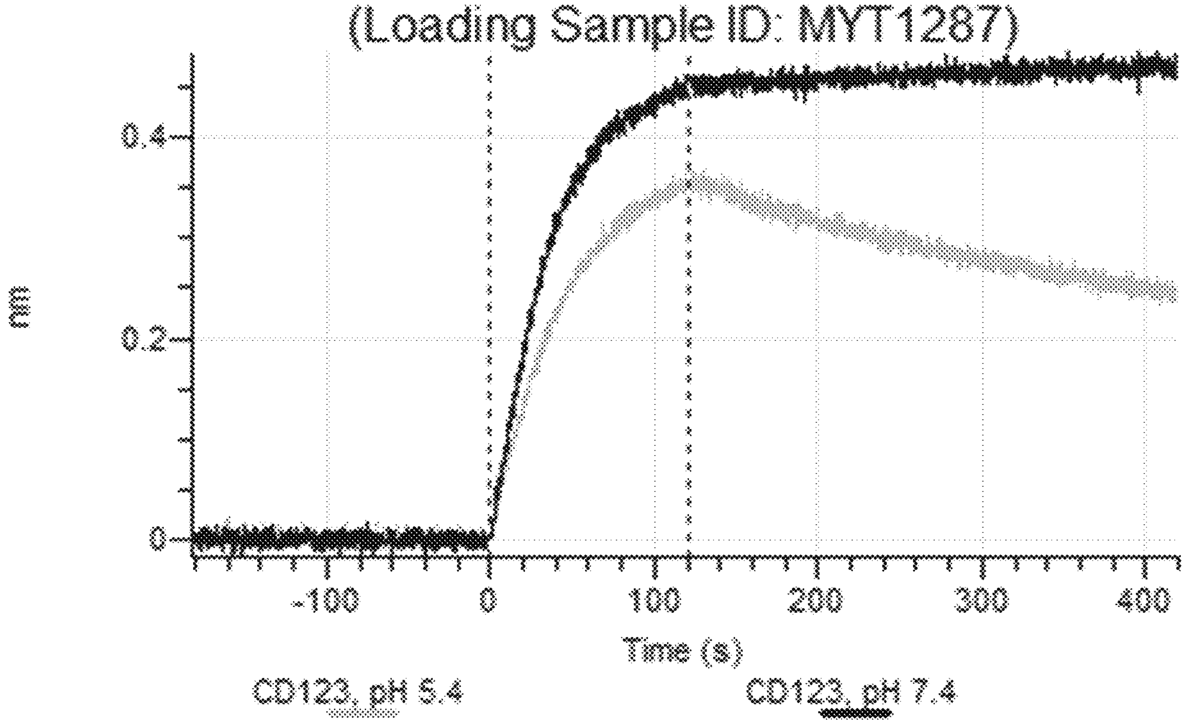
Figure 2A:
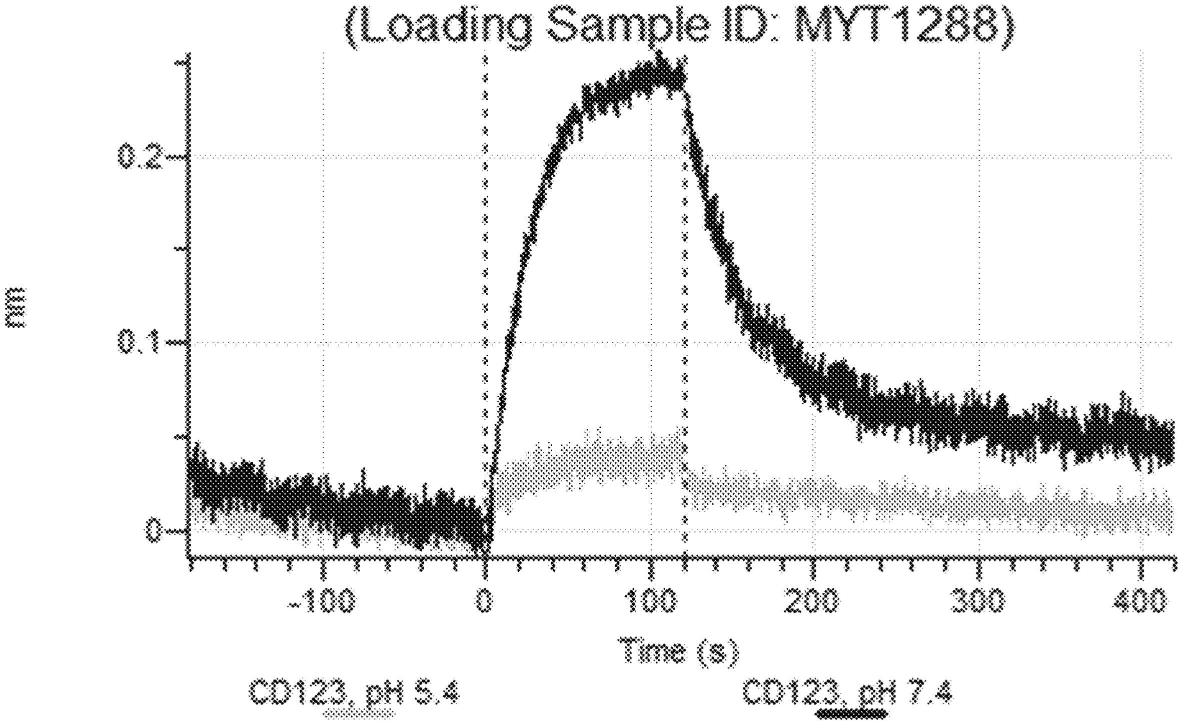
Figure 2A:
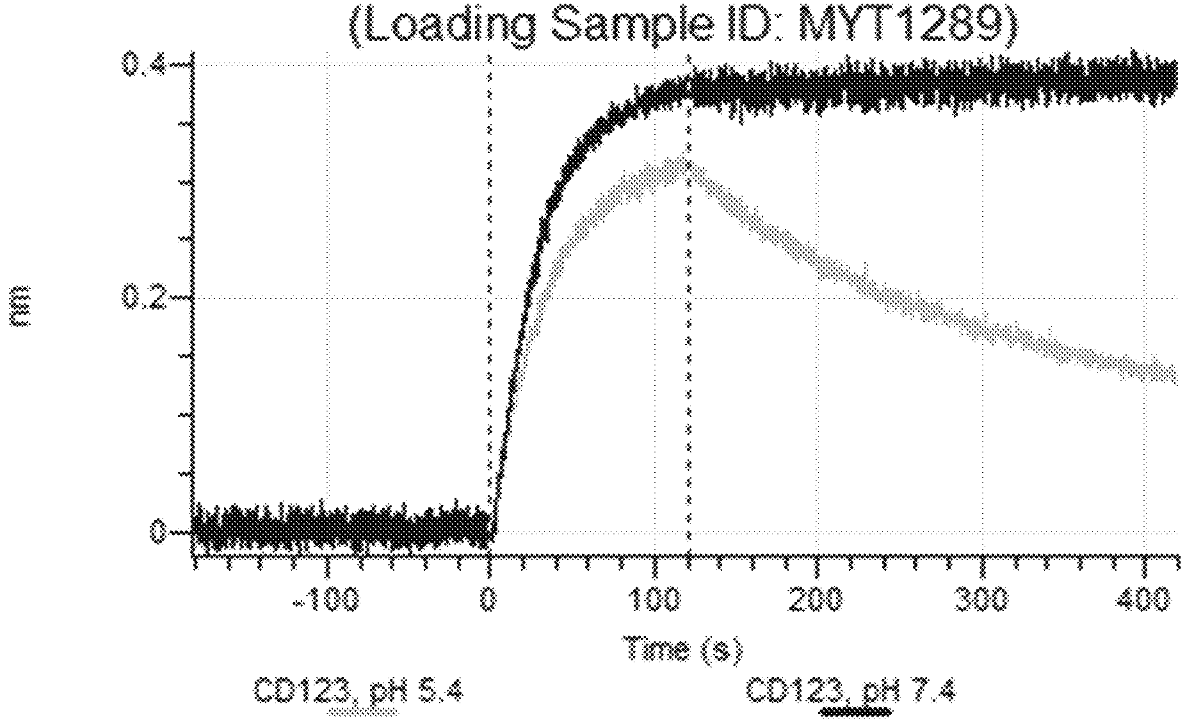
Figure 2A:
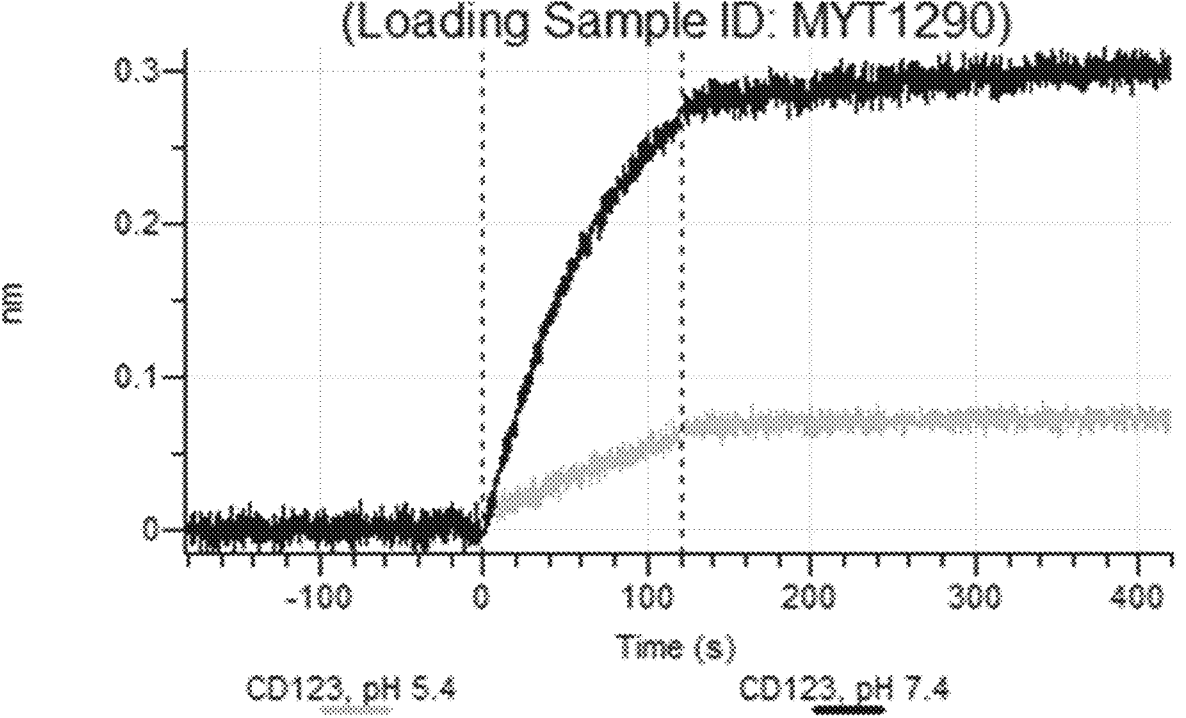
Figure 2A:
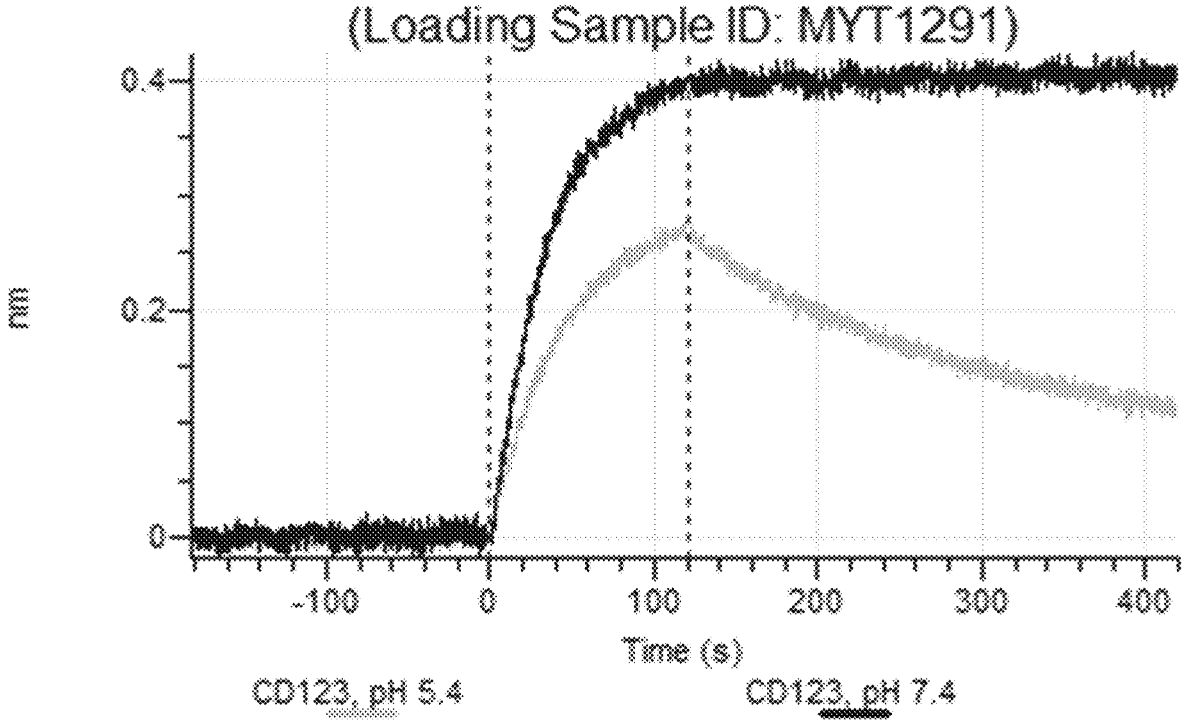
Figure 2A:
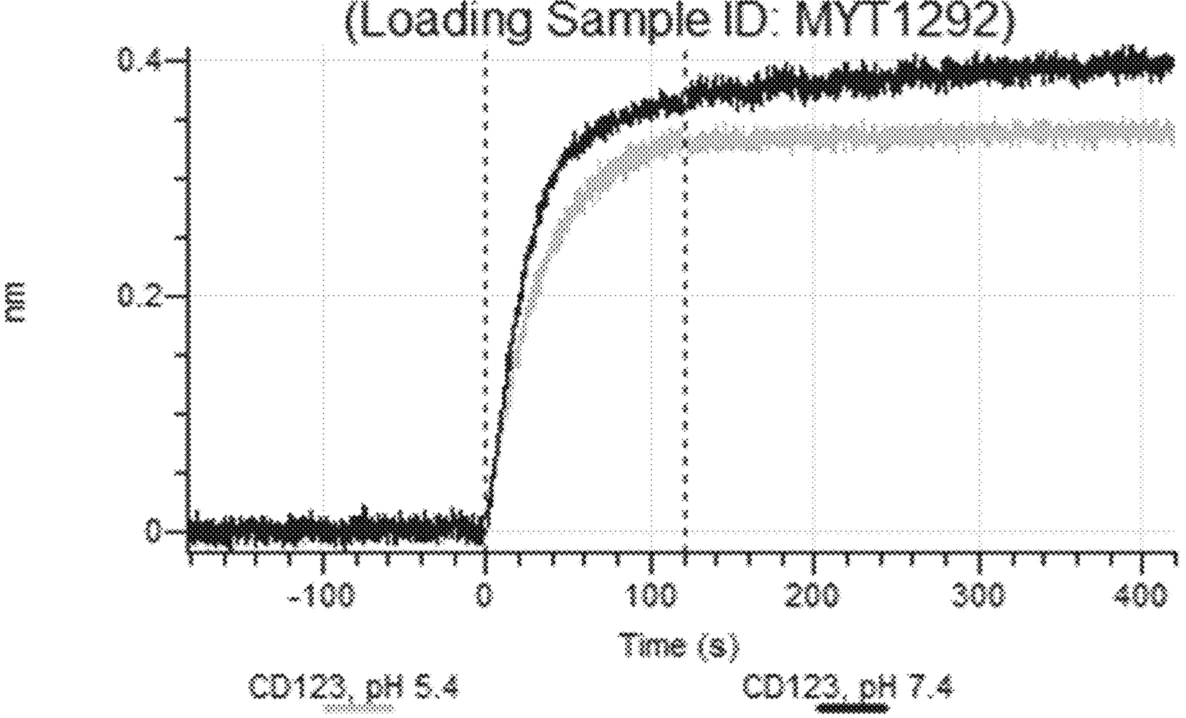

Provided herein are antigen-binding protein constructs (ABPCs) that include: a first antigen-binding domain that is capable of specifically binding CD123 or an epitope of CD123 presented on the surface of a target mammalian cell, where: (a) the dissociation rate of the first antigen-binding domain at a pH of about 4.0 to about 6.5 is faster than the dissociation rate at a pH of about 7.0 to about 8.0; and/or (b)

the dissociation constant ($K_D$) of the first antigen-binding domain at a pH of about 4.0 to about 6.5 is greater than the $K_D$ at a pH of about 7.0 to about 8.0. In some examples of these ABPCs, the ABPC is degraded in the target mammalian cell following internalization of the ABPC by the target mammalian cell. Some examples of any of the ABPCs described herein can further include a conjugated toxin, radioisotope, drug, or small molecule (e.g., a fluorophore or dye).

Also provided are antigen-binding protein constructs (ABPCs) that include: a first antigen-binding domain that is capable of specifically binding CD123 or an epitope of CD123 presented on the surface of a target mammalian cell; and a conjugated toxin, radioisotope, drug, or small molecule, where: (a) the dissociation rate of the first antigen-binding domain at a pH of about 4.0 to about 6.5 is faster than the dissociation rate at a pH of about 7.0 to about 8.0; and/or the dissociation constant ($K_D$) of the first antigen-binding domain at a pH of about 4.0 to about 6.5 is greater than the $K_D$ at a pH of about 7.0 to about 8.0; and (b) a composition including the ABPC provides for one or more (e.g., two or three) of: an increase (e.g., a detectable increase) in toxin liberation in the target mammalian cell as compared to a composition comprising the same amount of a control ABPC; an increase (e.g., a detectable increase) in target mammalian cell killing as compared to a composition comprising the same amount of a control ABPC; and an increase (e.g., a detectable increase) in endolysosomal delivery in the target mammalian cell as compared to a composition comprising the same amount of a control ABPC.

In some examples of any of the ABPCs described herein, the first antigen-binding domain includes a heavy chain variable domain of IMGN632 with one or more (e.g., one, two, three, four, five, six, seven, eight, nine, ten, eleven, twelve, thirteen, fourteen, fifteen, sixteen, seventeen, eighteen, nineteen, or twenty) amino acids substituted with a histidine. In some examples of any of the ABPCs described herein, the first antigen-binding domain includes a light chain variable domain of IMGN632 with one or more (e.g., one, two, three, four, five, six, seven, eight, nine, ten, eleven, twelve, thirteen, fourteen, fifteen, sixteen, seventeen, eighteen, nineteen, or twenty) amino acids substituted with a histidine. In some examples of any of the ABPCs described herein, the first antigen-binding domain includes a heavy chain variable domain of IMGN632 with one or more (e.g., one, two, three, four, five, six, seven, eight, nine, ten, eleven, twelve, thirteen, fourteen, fifteen, sixteen, seventeen, eighteen, nineteen, or twenty) amino acids substituted with a histidine; and a light chain variable domain of IMGN632 with one or more (e.g., one, two, three, four, five, six, seven, eight, nine, ten, eleven, twelve, thirteen, fourteen, fifteen, sixteen, seventeen, eighteen, nineteen, or twenty) amino acids substituted with a histidine. In some examples of any of the ABPCs described herein, the heavy chain variable domain of IMGN632 comprises SEQ ID NO: 1. In some examples of any of the ABPCs described herein, the light chain variable domain of IMGN632 comprises SEQ ID NO: 2.

In some examples of any of the ABPCs described herein, the first antigen-binding domain comprises a heavy chain variable domain comprising a CDR1, a CDR2, and a CDR3 of SEQ ID NO: 3, SEQ ID NO: 4, and SEQ ID NO: 5, respectively, with collectively a total of one or more (e.g., one, two, three, four, five, six, seven, eight, nine, or ten) amino acid positions in SEQ ID NOs: 3-5 substituted with a histidine. In some examples of any of the ABPCs described herein, the first antigen-binding domain comprises a light chain variable domain comprising a CDR1, a CDR2, and a CDR3 of SEQ ID NO: 6, SEQ ID NO: 7, and SEQ ID NO: 8, respectively, with collectively a total of one or more (e.g., one, two, three, four, five, six, seven, eight, nine, or ten) amino acid positions in SEQ ID NOs: 6-8 substituted with a histidine. In some examples of any of the ABPCs described herein, the first antigen-binding domain includes: a heavy chain variable domain comprising a CDR1, a CDR2, and a CDR3 of SEQ ID NO: 3, SEQ ID NO: 4, and SEQ ID NO: 5, respectively, with collectively a total of one or more (e.g., one, two, three, four, five, six, seven, eight, nine, or ten) amino acid positions in SEQ ID NOs: 3-5 substituted with a histidine; and a light chain variable domain comprising a CDR1, a CDR2, and a CDR3 of SEQ ID NO: 6, SEQ ID NO: 7, and SEQ ID NO: 8, respectively, with collectively a total of one or more (e.g., one, two, three, four, five, six, seven, eight, nine, or ten) amino acid positions in SEQ ID NOs: 6-8 substituted with a histidine.

In some examples of any of the ABPCs described herein, the first antigen-binding domain includes a heavy chain variable domain that is at least 90% (e.g., at least 92%, at least 94%, at least 96%, at least 98%, at least 99%, or 100%) identical to SEQ ID NO: 1, where the heavy chain variable domain includes a histidine at one or more (e.g., one, two, three, four, five, six, seven, eight, nine, ten, eleven, twelve, thirteen, fourteen, fifteen, sixteen, seventeen, eighteen, nineteen, or twenty) amino acid positions in SEQ ID NO: 1 selected from the group of: 27, 28, 29, 30, 33, 53, 97, 103, 104, 105, 106, 107, 108, or 109. In some examples of any of the ABPCs described herein, the first antigen-binding domain includes a light chain variable domain that is at least 90% (e.g., at least 92%, at least 94%, at least 96%, at least 98%, at least 99%, or 100%) identical to SEQ ID NO: 2, where the light chain variable domain includes a histidine at one or more (e.g., one, two, three, four, five, six, seven, eight, nine, ten, eleven, twelve, thirteen, fourteen, fifteen, sixteen, seventeen, eighteen, nineteen, or twenty) amino acid positions in SEQ ID NO: 2 selected from the group of: 34, 55, 91, 94, 95, and 96. In some examples of any of the ABPCs described herein the first antigen-binding domain includes: a heavy chain variable domain that is at least 90% (e.g., at least 92%, at least 94%, at least 96%, at least 98%, at least 99%, or 100%) identical to SEQ ID NO: 1, where the heavy chain variable domain includes a histidine at one or more (e.g., one, two, three, four, five, six, seven, eight, nine, ten, eleven, twelve, thirteen, fourteen, fifteen, sixteen, seventeen, eighteen, nineteen, or twenty) amino acid positions in SEQ ID NO: 1 selected from the group consisting of: 27, 28, 29, 30, 33, 53, 97, 103, 104, 105, 106, 107, 108, or 109, and a light chain variable domain that is at least 90% (e.g., at least 92%, at least 94%, at least 96%, at least 98%, at least 99%, or 100%) identical to SEQ ID NO: 2, where the light chain variable domain includes a histidine at one or more (e.g., one, two, three, four, five, six, seven, eight, nine, ten, eleven, twelve, thirteen, fourteen, fifteen, sixteen, seventeen, eighteen, nineteen, or twenty) amino acid positions in SEQ ID NO: 2 selected from the group consisting of: 34, 55, 91, 94, 95, and 96.

In some examples of any of the ABPCs described herein, a heavy chain variable domain includes a heavy chain variable domain that is at least 90% (e.g., at least 92%, at least 94%, at least 96%, at least 98%, at least 99%, or 100%) identical to SEQ ID NO: 1, where the heavy chain variable domain includes a histidine at any of the specific combinations of one or more amino acid positions in SEQ ID NO: 1 listed in Table 1.

In some examples of any of the ABPCs described herein, the first antigen-binding domain includes a heavy chain variable domain that is at least 90% (e.g., at least 92%, at least 94%, at least 96%, at least 98%, at least 99%, or 100%) identical to SEQ ID NO: 1, where the heavy chain variable domain includes an alanine at position 35 in SEQ ID NO: 1.

In some examples of any of the ABPCs described herein the first antigen-binding domain includes: a heavy chain variable domain that is at least 90% (e.g., at least 92%, at least 94%, at least 96%, at least 98%, at least 99%, or 100%) identical to SEQ ID NO: 1, where the heavy chain variable domain includes an alanine at position 35 in SEQ ID NO: 1, and a light chain variable domain that is at least 90% (e.g., at least 92%, at least 94%, at least 96%, at least 98%, at least 99%, or 100%) identical to SEQ ID NO: 2, where the light chain variable domain includes a histidine at one or more (e.g., one, two, three, four, five, six, seven, eight, nine, ten, eleven, twelve, thirteen, fourteen, fifteen, sixteen, seventeen, eighteen, nineteen, or twenty) amino acid positions in SEQ ID NO: 2 selected from the group consisting of: 34, 55, 91, 94, 95, and 96.

In some examples of any of the ABPCs described herein, the first antigen-binding domain includes a heavy chain variable domain that is at least 90% (e.g., at least 92%, at least 94%, at least 96%, at least 98%, at least 99%, or 100%) identical to SEQ ID NO: 1, where the heavy chain variable domain includes a histidine at one or more (e.g., one, two, three, four, five, six, seven, eight, nine, ten, eleven, twelve, thirteen, fourteen, fifteen, sixteen, seventeen, eighteen, nineteen, or twenty) amino acid positions in SEQ ID NO: 1 selected from the group consisting of: 27, 28, 29, 30, 33, 53, 97, 103, 104, 105, 106, 107, 108, or 109 and where the heavy chain variable domain includes an alanine at position 35 in SEQ ID NO: 1. In some examples of any of the ABPCs described herein the first antigen-binding domain includes: a heavy chain variable domain that is at least 90% (e.g., at least 92%, at least 94%, at least 96%, at least 98%, at least 99%, or 100%) identical to SEQ ID NO: 1, where the heavy chain variable domain includes a histidine at one or more (e.g., one, two, three, four, five, six, seven, eight, nine, ten, eleven, twelve, thirteen, fourteen, fifteen, sixteen, seventeen, eighteen, nineteen, or twenty) amino acid positions in SEQ ID NO: 1 selected from the group consisting of: 27, 28, 29, 30, 33, 53, 97, 103, 104, 105, 106, 107, 108, or 109 and where the heavy chain variable domain includes an alanine at position 35 in SEQ ID NO: 1, and a light chain variable domain that is at least 90% (e.g., at least 92%, at least 94%, at least 96%, at least 98%, at least 99%, or 100%) identical to SEQ ID NO: 2, where the light chain variable domain includes a histidine at one or more (e.g., one, two, three, four, five, six, seven, eight, nine, ten, eleven, twelve, thirteen, fourteen, fifteen, sixteen, seventeen, eighteen, nineteen, or twenty) amino acid positions in SEQ ID NO: 2 selected from the group consisting of: 34, 55, 91, 94, 95, and 96.

In some examples of any of the ABPCs described herein, a heavy chain variable domain includes a heavy chain variable domain that is at least 90% (e.g., at least 92%, at least 94%, at least 96%, at least 98%, at least 99%, or 100%) identical to SEQ ID NO: 1, where the heavy chain variable domain includes a histidine at any of the specific combinations of one or more amino acid positions in SEQ ID NO: 1 listed in Table 1 and where the heavy chain variable domain includes an alanine at position 35 of SEQ ID NO: 1.

TABLE 1

| Exemplary Combinations of Amino Acid Positions in SEQ ID NO: 1 that can be Substituted with Histidine |
| --- |
| 27 + 28, 27 + 29, 27 + 30, 27 + 33, 27 + 53, 27 + 97, 27 + 103, 27 + 104, 27 + 105, 27 + 106, 27 + 107, 27 + 108, 27 + 109, 28 + 29, 28 + 30, 28 + 33, 28 + 53, 28 + 97, 28 + 103, 28 + 104, 28 + 105, 28 + 106, 28 + 107, 28 + 108, 28 + 109, 29 + 30, 29 + 33, 29 + 53, 29 + 97, 29 + 103, 29 + 104, 29 + 105, 29 + 106, 29 + 107, 29 + 108, 29 + 109, 30 + 33, 30 + 53, 30 + 97, 30 + 103, 30 + 104, 30 + 105, 30 + 106, 30 + 107, 30 + 108, 30 + 109, 33 + 53, 33 + 97, 33 + 103, 33 + 104, 33 + 105, 33 + 106, 33 + 107, 33 + 108, 33 + 109, 53 + 97, 53 + 103, 53 + 104, 53 + 105, 53 + 106, 53 + 107, 53 + 108, 53 + 109, 97 + 103, 97 + 104, 97 + 105, 97 + 106, 97 + 107, 97 + 108, 97 + 109, 103 + 104, 103 + 105, 103 + 106, 103 + 107, 103 + 108, 103 + 109, 104 + 105, 104 + 106, 104 + 107, 104 + 108, 104 + 109, 105 + 106, 105 + 107, 105 + 108, 105 + 109, 106 + 107, 106 + 108, 106 + 109, 107 + 108, 107 + 109, 108 + 109, 27 + 28 + 29, 27 + 28 + 30, 27 + 28 + 33, 27 + 28 + 53, 27 + 28 + 97, 27 + 28 + 103, 27 + 28 + 104, 27 + 28 + 105, 27 + 28 + 106, 27 + 28 + 107, 27 + 28 + 108, 27 + 28 + 109, 27 + 29 + 30, 27 + 29 + 33, 27 + 29 + 53, 27 + 29 + 97, 27 + 29 + 103, 27 + 29 + 104, 27 + 29 + 105, 27 + 29 + 106, 27 + 29 + 107, 27 + 29 + 108, 27 + 29 + 109, 27 + 30 + 33, 27 + 30 + 53, 27 + 30 + 97, 27 + 30 + 103, 27 + 30 + 104, 27 + 30 + 105, 27 + 30 + 106, 27 + 30 + 107, 27 + 30 + 108, 27 + 30 + 109, 27 + 33 + 53, 27 + 33 + 97, 27 + 33 + 103, 27 + 33 + 104, 27 + 33 + 105, 27 + 33 + 106, 27 + 33 + 107, 27 + 33 + 108, 27 + 33 + 109, 27 + 53 + 97, 27 + 53 + 103, 27 + 53 + 104, 27 + 53 + 105, 27 + 53 + 106, 27 + 53 + 107, 27 + 53 + 108, 27 + 53 + 109, 27 + 97 + 103, 27 + 97 + 104, 27 + 97 + 105, 27 + 97 + 106, 27 + 97 + 107, 27 + 97 + 108, 27 + 97 + 109, 27 + 103 + 104, 27 + 103 + 105, 27 + 103 + 106, 27 + 103 + 107, 27 + 103 + 108, 27 + 103 + 109, 27 + 104 + 105, 27 + 104 + 106, 27 + 104 + 107, 27 + 104 + 108, 27 + 104 + 109, 27 + 105 + 106, 27 + 105 + 107, 27 + 105 + 108, 27 + 105 + 109, 27 + 106 + 107, 27 + 106 + 108, 27 + 106 + 109, 27 + 107 + 108, 27 + 107 + 109, 27 + 108 + 109, 28 + 29 + 30, 28 + 29 + 33, 28 + 29 + 53, 28 + 29 + 97, 28 + 29 + 103, 28 + 29 + 104, 28 + 29 + 105, 28 + 29 + 106, 28 + 29 + 107, 28 + 29 + 108, 28 + 29 + 109, 28 + 30 + 33, 28 + 30 + 53, 28 + 30 + 97, 28 + 30 + 103, 28 + 30 + 104, 28 + 30 + 105, 28 + 30 + 106, 28 + 30 + 107, 28 + 30 + 108, 28 + 30 + 109, 28 + 33 + 53, 28 + 33 + 97, 28 + 33 + 103, 28 + 33 + 104, 28 + 33 + 105, 28 + 33 + 106, 28 + 33 + 107, 28 + 33 + 108, 28 + 33 + 109, 28 + 53 + 97, 28 + 53 + 103, 28 + 53 + 104, 28 + 53 + 105, 28 + 53 + 106, 28 + 53 + 107, 28 + 53 + 108, 28 + 53 + 109, 28 + 97 + 103, 28 + 97 + 104, 28 + 97 + 105, 28 + 97 + 106, 28 + 97 + 107, 28 + 97 + 108, 28 + 97 + 109, 28 + 103 + 104, 28 + 103 + 105, 28 + 103 + 106, 28 + 103 + 107, 28 + 103 + 108, 28 + 103 + 109, 28 + 104 + 105, 28 + 104 + 106, 28 + 104 + 107, 28 + 104 + 108, 28 + 104 + 109, 28 + 105 + 106, 28 + 105 + 107, 28 + 105 + 108, 28 + 105 + 109, 28 + 106 + 107, 28 + 106 + 108, 28 + 106 + 109, 28 + 107 + 108, 28 + 107 + 109, 28 + 108 + 109, 29 + 30 + 33, 29 + 30 + 53, 29 + 30 + 97, 29 + 30 + 103, 29 + 30 + 104, 29 + 30 + 105, 29 + 30 + 106, 29 + 30 + 107, 29 + 30 + 108, 29 + 30 + 109, 29 + 33 + 53, 29 + 33 + 97, 29 + 33 + 103, 29 + 33 + 104, 29 + 33 + |

TABLE 1-continued

| Exemplary Combinations of Amino Acid Positions in SEQ ID NO: 1 that can be Substituted with Histidine |
| --- |
| 105, 29 + 33 + 106, 29 + 33 + 107, 29 + 33 + 108, 29 + 33 + 109, 29 + 53 + 97, 29 + 53 + 103, 29 + 53 + 104, 29 + 53 + 105, 29 + 53 + 106, 29 + 53 + 107, 29 + 53 + 108, 29 + 53 + 109, 29 + 97 + 103, 29 + 97 + 104, 29 + 97 + 105, 29 + 97 + 106, 29 + 97 + 107, 29 + 97 + 108, 29 + 97 + 109, 29 + 103 + 104, 29 + 103 + 105, 29 + 103 + 106, 29 + 103 + 107, 29 + 103 + 108, 29 + 103 + 109, 29 + 104 + 105, 29 + 104 + 106, 29 + 104 + 107, 29 + 104 + 108, 29 + 104 + 109, 29 + 105 + 106, 29 + 105 + 107, 29 + 105 + 108, 29 + 105 + 109, 29 + 106 + 107, 29 + 106 + 108, 29 + 106 + 109, 29 + 107 + 108, 29 + 107 + 109, 29 + 108 + 109, 30 + 33 + 53, 30 + 33 + 97, 30 + 33 + 103, 30 + 33 + 104, 30 + 33 + 105, 30 + 33 + 106, 30 + 33 + 107, 30 + 33 + 108, 30 + 33 + 109, 30 + 53 + 97, 30 + 53 + 103, 30 + 53 + 104, 30 + 53 + 105, 30 + 53 + 106, 30 + 53 + 107, 30 + 53 + 108, 30 + 53 + 109, 30 + 97 + 103, 30 + 97 + 104, 30 + 97 + 105, 30 + 97 + 106, 30 + 97 + 107, 30 + 97 + 108, 30 + 97 + 109, 30 + 103 + 104, 30 + 103 + 105, 30 + 103 + 106, 30 + 103 + 107, 30 + 103 + 108, 30 + 103 + 109, 30 + 104 + 105, 30 + 104 + 106, 30 + 104 + 107, 30 + 104 + 108, 30 + 104 + 109, 30 + 105 + 106, 30 + 105 + 107, 30 + 105 + 108, 30 + 105 + 109, 30 + 106 + 107, 30 + 106 + 108, 30 + 106 + 109, 30 + 107 + 108, 30 + 107 + 109, 30 + 108 + 109, 33 + 53 + 97, 33 + 53 + 103, 33 + 53 + 104, 33 + 53 + 105, 33 + 53 + 106, 33 + 53 + 107, 33 + 53 + 108, 33 + 53 + 109, 33 + 97 + 103, 33 + 97 + 104, 33 + 97 + 105, 33 + 97 + 106, 33 + 97 + 107, 33 + 97 + 108, 33 + 97 + 109, 33 + 103 + 104, 33 + 103 + 105, 33 + 103 + 106, 33 + 103 + 107, 33 + 103 + 108, 33 + 103 + 109, 33 + 104 + 105, 33 + 104 + 106, 33 + 104 + 107, 33 + 104 + 108, 33 + 104 + 109, 33 + 105 + 106, 33 + 105 + 107, 33 + 105 + 108, 33 + 105 + 109, 33 + 106 + 107, 33 + 106 + 108, 33 + 106 + 109, 33 + 107 + 108, 33 + 107 + 109, 33 + 108 + 109, 53 + 97 + 103, 53 + 97 + 104, 53 + 97 + 105, 53 + 97 + 106, 53 + 97 + 107, 53 + 97 + 108, 53 + 97 + 109, 53 + 103 + 104, 53 + 103 + 105, 53 + 103 + 106, 53 + 103 + 107, 53 + 103 + 108, 53 + 103 + 109, 53 + 104 + 105, 53 + 104 + 106, 53 + 104 + 107, 53 + 104 + 108, 53 + 104 + 109, 53 + 105 + 106, 53 + 105 + 107, 53 + 105 + 108, 53 + 105 + 109, 53 + 106 + 107, 53 + 106 + 108, 53 + 106 + 109, 53 + 107 + 108, 53 + 107 + 109, 53 + 108 + 109, 97 + 103 + 104, 97 + 103 + 105, 97 + 103 + 106, 97 + 103 + 107, 97 + 103 + 108, 97 + 103 + 109, 97 + 104 + 105, 97 + 104 + 106, 97 + 104 + 107, 97 + 104 + 108, 97 + 104 + 109, 97 + 105 + 106, 97 + 105 + 107, 97 + 105 + 108, 97 + 105 + 109, 97 + 106 + 107, 97 + 106 + 108, 97 + 106 + 109, 97 + 107 + 108, 97 + 107 + 109, 97 + 108 + 109, 103 + 104 + 105, 103 + 104 + 106, 103 + 104 + 107, 103 + 104 + 108, 103 + 104 + 109, 103 + 105 + 106, 103 + 105 + 107, 103 + 105 + 108, 103 + 105 + 109, 103 + 106 + 107, 103 + 106 + 108, 103 + 106 + 109, 103 + 107 + 108, 103 + 107 + 109, 103 + 108 + 109, 104 + 105 + 106, 104 + 105 + 107, 104 + 105 + 108, 104 + 105 + 109, 104 + 106 + 107, 104 + 106 + 108, 104 + 106 + 109, 104 + 107 + 108, 104 + 107 + 109, 104 + 108 + 109, 105 + 106 + 107, 105 + 106 + 108, 105 + 106 + 109, 105 + 107 + 108, 105 + 107 + 109, 105 + 108 + 109, 106 + 107 + 108, 106 + 107 + 109, 106 + 108 + 109, 107 + 108 + 109 |

In some examples of any of the ABPCs described herein, a light chain variable domain includes a light chain variable domain that is at least 90% (e.g., at least 92%, at least 94%, at least 96%, at least 98%, at least 99%, or 100%) identical to SEQ ID NO: 2, where the light chain variable domain includes a histidine at any of the specific combinations of one or more amino acid positions in SEQ ID NO: 2 listed in Table 2.

TABLE 2

| Exemplary Combinations of Amino Acid Positions in SEQ ID NO: 2 that can be Substituted with Histidine |
| --- |
| 34 + 55, 34 + 91, 34 + 94, 34 + 95, 34 + 96, 55 + 91, 55 + 94, 55 + 95, 55 + 96, 91 + 94, 91 + 95, 91 + 96, 94 + 95, 94 + 96, 95 + 96, 34 + 55 + 91, 34 + 55 + 94, 34 + 55 + 95, 34 + 55 + 96, 34 + 91 + 94, 34 + 91 + 95, 34 + 91 + 96, 34 + 94 + 95, 34 + 94 + 96, 34 + 95 + 96, 55 + 91 + 94, 55 + 91 + 95, 55 + 91 + 96, 55 + 94 + 95, 55 + 94 + 96, 55 + 95 + 96, 91 + 94 + 95, 91 + 94 + 96, 91 + 95 + 96, 94 + 95 + 96 |

In some examples of any of the ABPCs described herein, the first antigen-binding domain includes a heavy chain variable domain that is at least 90% (e.g., at least 92%, at least 94%, at least 96%, at least 98%, at least 99%, or 100%) identical to SEQ ID NO: 1, where the heavy chain variable domain includes a histidine at any of the specific combinations of one or more amino acid positions in SEQ ID NO: 1 listed in Table 1; and a light chain variable domain that that is at least 90% (e.g., at least 92%, at least 94%, at least 96%, at least 98%, at least 99%, or 100%) identical to SEQ ID NO: 2, where the light chain variable domain includes a histidine at any of the specific combinations of one or more amino acid positions in SEQ ID NO: 2 listed in Table 2.

In some examples of any of the ABPCs described herein, the first antigen-binding domain includes a heavy chain variable domain that is at least 90% (e.g., at least 92%, at least 94%, at least 96%, at least 98%, at least 99%, or 100%) identical to SEQ ID NO: 1, where the heavy chain variable domain includes a histidine at any of the specific combinations of one or more amino acid positions in SEQ ID NO: 1 listed in Table 1, and where the heavy chain variable domain includes an alanine at position 35 in SEQ ID NO: 1; and a light chain variable domain that that is at least 90% (e.g., at least 92%, at least 94%, at least 96%, at least 98%, at least 99%, or 100%) identical to SEQ ID NO: 2, where the light chain variable domain includes a histidine at any of the specific combinations of one or more amino acid positions in SEQ ID NO: 2 listed in Table 2.

In some examples of any of the ABPCs described herein, the first antigen-binding domain comprises a light chain variable domain comprising SEQ ID NO: 2, and a heavy chain variable domain that is at least 90% identical (e.g., at least 92%, at least 94%, at least 96%, at least 98%, at least 99%, or 100%) identical to SEQ ID NO: 1, where the heavy chain variable domain includes a histidine at any of the specific combinations of one or more (e.g., two, three, four, five, six, seven, eight, nine, or ten) amino acid positions in SEQ ID NO: 1 listed in Table 1.

In some examples of any of the ABPCs described herein, the first antigen-binding domain comprises a light chain variable domain that is at least 90% identical to SEQ ID NO: 2, wherein the light chain variable domain includes a histidine at position 34 in SEQ ID NO: 2; and a heavy chain variable domain that is at least 90% (e.g., at least 92%, at least 94%, at least 96%, at least 98%, at least 99%, or 100%) identical to SEQ ID NO: 1, where the heavy chain variable domain includes a histidine at any of the specific combinations of one or more amino acid positions in SEQ ID NO: 1 listed in Table 1.

In some examples of any of the ABPCs described herein, the first antigen-binding domain comprises a light chain variable domain that is at least 90% identical to SEQ ID NO: 2, wherein the light chain variable domain includes a histidine at position 55 in SEQ ID NO: 2; and a heavy chain variable domain that is at least 90% (e.g., at least 92%, at least 94%, at least 96%, at least 98%, at least 99%, or 100%) identical to SEQ ID NO: 1, where the heavy chain variable domain includes a histidine at any of the specific combinations of one or more amino acid positions in SEQ ID NO: 1 listed in Table 1.

In some examples of any of the ABPCs described herein, the first antigen-binding domain comprises a light chain variable domain that is at least 90% identical to SEQ ID NO: 2, wherein the light chain variable domain includes a histidine at position 91 in SEQ ID NO: 2; and a heavy chain variable domain that is at least 90% (e.g., at least 92%, at least 94%, at least 96%, at least 98%, at least 99%, or 100%) identical to SEQ ID NO: 1, where the heavy chain variable domain includes a histidine at any of the specific combinations of one or more amino acid positions in SEQ ID NO: 1 listed in Table 1.

In some examples of any of the ABPCs described herein, the first antigen-binding domain comprises a light chain variable domain that is at least 90% identical to SEQ ID NO: 2, wherein the light chain variable domain includes a histidine at position 94 in SEQ ID NO: 2; and a heavy chain variable domain that is at least 90% (e.g., at least 92%, at least 94%, at least 96%, at least 98%, at least 99%, or 100%) identical to SEQ ID NO: 1, where the heavy chain variable domain includes a histidine at any of the specific combinations of one or more amino acid positions in SEQ ID NO: 1 listed in Table 1.

In some examples of any of the ABPCs described herein, the first antigen-binding domain comprises a light chain variable domain that is at least 90% identical to SEQ ID NO: 2, wherein the light chain variable domain includes a histidine at position 95 in SEQ ID NO: 2; and a heavy chain variable domain that is at least 90% (e.g., at least 92%, at least 94%, at least 96%, at least 98%, at least 99%, or 100%) identical to SEQ ID NO: 1, where the heavy chain variable domain includes a histidine at any of the specific combinations of one or more amino acid positions in SEQ ID NO: 1 listed in Table 1.

In some examples of any of the ABPCs described herein, the first antigen-binding domain comprises a light chain variable domain that is at least 90% identical to SEQ ID NO: 2, wherein the light chain variable domain includes a histidine at position 96 in SEQ ID NO: 2; and a heavy chain variable domain that is at least 90% (e.g., at least 92%, at least 94%, at least 96%, at least 98%, at least 99%, or 100%) identical to SEQ ID NO: 1, where the heavy chain variable domain includes a histidine at any of the specific combinations of one or more amino acid positions in SEQ ID NO: 1 listed in Table 1.

In some examples of any of the ABPCs described herein, the first antigen-binding domain includes a heavy chain variable domain of IMGN632 with one or more (e.g., one, two, three, four, five, six, seven, eight, nine, ten, eleven, twelve, thirteen, fourteen, fifteen, sixteen, seventeen, eighteen, nineteen, or twenty) histidine(s) substituted with an alanine. In some examples of any of the ABPCs described herein, the first antigen-binding domain includes a light chain variable domain of IMGN632 with one or more (e.g., one, two, three, four, five, six, seven, eight, nine, ten, eleven, twelve, thirteen, fourteen, fifteen, sixteen, seventeen, eighteen, nineteen, or twenty) histidine(s) substituted with an alanine. In some examples of any of the ABPCs described herein, the first antigen-binding domain includes a heavy chain variable domain of IMGN632 with one or more (e.g., one, two, three, four, five, six, seven, eight, nine, ten, eleven, twelve, thirteen, fourteen, fifteen, sixteen, seventeen, eighteen, nineteen, or twenty) histidines substituted with an alanine; and a light chain variable domain of IMGN632 with one or more (e.g., one, two, three, four, five, six, seven, eight, nine, ten, eleven, twelve, thirteen, fourteen, fifteen, sixteen, seventeen, eighteen, nineteen, or twenty) histidine(s) substituted with an alanine. In some examples of any of the ABPCs described herein, the heavy chain variable domain of IMGN632 comprises SEQ ID NO: 1. In some examples of any of the ABPCs described herein, the light chain variable domain of IMGN632 comprises SEQ ID NO: 2.

In some examples of any of the ABPCs described herein, the first antigen-binding domain comprises a heavy chain variable domain comprising a CDR1, a CDR2, and a CDR3 of SEQ ID NO: 3, SEQ ID NO: 4, and SEQ ID NO: 5, respectively, with collectively a total of one or more (e.g., one, two, three, four, five, six, seven, eight, nine, or ten) histidine(s) in SEQ ID NOs: 3-5 substituted with an alanine. In some examples of any of the ABPCs described herein, the first antigen-binding domain comprises a light chain variable domain comprising a CDR1, a CDR2, and a CDR3 of SEQ ID NO: 6, SEQ ID NO: 7, and SEQ ID NO: 8, respectively, with collectively a total of one or more (e.g., one, two, three, four, five, six, seven, eight, nine, or ten) histidine(s) in SEQ ID NOs: 6-8 substituted with an alanine. In some examples of any of the ABPCs described herein, the first antigen-binding domain includes: a heavy chain variable domain comprising a CDR1, a CDR2, and a CDR3 of SEQ ID NO: 3, SEQ ID NO: 4, and SEQ ID NO: 5, respectively, with collectively a total of one or more (e.g., one, two, three, four, five, six, seven, eight, nine, or ten) histidine(s) in SEQ ID NOs: 3-5 substituted with an alanine; and a light chain variable domain comprising a CDR1, a CDR2, and a CDR3 of SEQ ID NO: 6, SEQ ID NO: 7, and SEQ ID NO: 8, respectively, with collectively a total of one or more (e.g., one, two, three, four, five, six, seven, eight, nine, or ten) histidine(s) in SEQ ID NOs: 6-8 substituted with an alanine.

In some examples of any of the ABPCs described herein, the first antigen-binding domain comprises a heavy chain variable domain of SEQ ID NO: 1, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53.

In some examples of any of the ABPCs described herein, the first antigen-binding domain includes a light chain variable domain of SEQ ID NO: 2, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, or SEQ ID NO: 80.

In some examples of any of the ABPCs described herein, the first antigen-binding domain includes a light chain variable domain comprising SEQ ID NO: 2, and a heavy chain variable domain comprising: SEQ ID NO: 1, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53.

In some examples of any of the ABPCs described herein, the first antigen-binding domain includes a light chain variable domain comprising SEQ ID NO: 54, and a heavy chain variable domain comprising: SEQ ID NO: 1, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53.

In some examples of any of the ABPCs described herein, the first antigen-binding domain includes a light chain variable domain comprising SEQ ID NO: 55, and a heavy chain variable domain comprising: SEQ ID NO: 1, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53.

In some examples of any of the ABPCs described herein, the first antigen-binding domain includes a light chain variable domain comprising SEQ ID NO: 56, and a heavy chain variable domain comprising: SEQ ID NO: 1, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53.

In some examples of any of the ABPCs described herein, the first antigen-binding domain includes a light chain variable domain comprising SEQ ID NO: 57, and a heavy chain variable domain comprising: SEQ ID NO: 1, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53.

In some examples of any of the ABPCs described herein, the first antigen-binding domain includes a light chain variable domain comprising SEQ ID NO: 58, and a heavy chain variable domain comprising: SEQ ID NO: 1, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53.

In some examples of any of the ABPCs described herein, the first antigen-binding domain includes a light chain variable domain comprising SEQ ID NO: 59, and a heavy chain variable domain comprising: SEQ ID NO: 1, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53.

In some examples of any of the ABPCs described herein, the first antigen-binding domain includes a light chain variable domain comprising SEQ ID NO: 60, and a heavy chain variable domain comprising: SEQ ID NO: 1, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53.

In some examples of any of the ABPCs described herein, the first antigen-binding domain includes a light chain variable domain comprising SEQ ID NO: 61, and a heavy chain variable domain comprising: SEQ ID NO: 1, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53.

In some examples of any of the ABPCs described herein, the first antigen-binding domain includes a light chain variable domain comprising SEQ ID NO: 62, and a heavy chain variable domain comprising: SEQ ID NO: 1, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53.

In some examples of any of the ABPCs described herein, the first antigen-binding domain includes a light chain variable domain comprising SEQ ID NO: 63, and a heavy chain variable domain comprising: SEQ ID NO: 1, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53.

In some examples of any of the ABPCs described herein, the first antigen-binding domain includes a light chain variable domain comprising SEQ ID NO: 64, and a heavy chain variable domain comprising: SEQ ID NO: 1, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53.

In some examples of any of the ABPCs described herein, the first antigen-binding domain includes a light chain variable domain comprising SEQ ID NO: 65, and a heavy chain variable domain comprising: SEQ ID NO: 1, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53.

In some examples of any of the ABPCs described herein, the first antigen-binding domain includes a light chain variable domain comprising SEQ ID NO: 66, and a heavy chain variable domain comprising: SEQ ID NO: 1, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53.

In some examples of any of the ABPCs described herein, the first antigen-binding domain includes a light chain variable domain comprising SEQ ID NO: 67, and a heavy chain variable domain comprising: SEQ ID NO: 1, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53.

In some examples of any of the ABPCs described herein, the first antigen-binding domain includes a light chain variable domain comprising SEQ ID NO: 68, and a heavy chain variable domain comprising: SEQ ID NO: 1, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53.

In some examples of any of the ABPCs described herein, the first antigen-binding domain includes a light chain variable domain comprising SEQ ID NO: 69, and a heavy chain variable domain comprising: SEQ ID NO: 1, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53.

In some examples of any of the ABPCs described herein, the first antigen-binding domain includes a light chain variable domain comprising SEQ ID NO: 70, and a heavy chain variable domain comprising: SEQ ID NO: 1, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53.

In some examples of any of the ABPCs described herein, the first antigen-binding domain includes a light chain variable domain comprising SEQ ID NO: 71, and a heavy chain variable domain comprising: SEQ ID NO: 1, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53.

In some examples of any of the ABPCs described herein, the first antigen-binding domain includes a light chain variable domain comprising SEQ ID NO: 72, and a heavy chain variable domain comprising: SEQ ID NO: 1, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53.

In some examples of any of the ABPCs described herein, the first antigen-binding domain includes a light chain variable domain comprising SEQ ID NO: 73, and a heavy chain variable domain comprising: SEQ ID NO: 1, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53.

In some examples of any of the ABPCs described herein, the first antigen-binding domain includes a light chain variable domain comprising SEQ ID NO: 74, and a heavy chain variable domain comprising: SEQ ID NO: 1, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53.

In some examples of any of the ABPCs described herein, the first antigen-binding domain includes a light chain variable domain comprising SEQ ID NO: 75, and a heavy chain variable domain comprising: SEQ ID NO: 1, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53.

In some examples of any of the ABPCs described herein, the first antigen-binding domain includes a light chain variable domain comprising SEQ ID NO: 76, and a heavy chain variable domain comprising: SEQ ID NO: 1, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53.

In some examples of any of the ABPCs described herein, the first antigen-binding domain includes a light chain variable domain comprising SEQ ID NO: 77, and a heavy chain variable domain comprising: SEQ ID NO: 1, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53.

In some examples of any of the ABPCs described herein, the first antigen-binding domain includes a light chain variable domain comprising SEQ ID NO: 78, and a heavy chain variable domain comprising: SEQ ID NO: 1, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53.

In some examples of any of the ABPCs described herein, the first antigen-binding domain includes a light chain variable domain comprising SEQ ID NO: 79, and a heavy chain variable domain comprising: SEQ ID NO: 1, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53.

In some examples of any of the ABPCs described herein, the first antigen-binding domain includes a light chain variable domain comprising SEQ ID NO: 80, and a heavy chain variable domain comprising: SEQ ID NO: 1, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, or SEQ ID NO: 53.

In some examples of any of the ABPCs described herein, the first antigen-binding domain includes a heavy chain variable domain of SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, or SEQ ID NO: 100.

In some examples of any of the ABPCs described herein, the first antigen-binding domain includes a heavy chain variable domain comprising SEQ ID NO: 81, and a light chain variable domain comprising SEQ ID NO: 2, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, or SEQ ID NO: 80.

In some examples of any of the ABPCs described herein, the first antigen-binding domain includes a heavy chain variable domain comprising SEQ ID NO: 82, and a light chain variable domain comprising SEQ ID NO: 2, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, or SEQ ID NO: 80.

In some examples of any of the ABPCs described herein, the first antigen-binding domain includes a heavy chain variable domain comprising SEQ ID NO: 83, and a light chain variable domain comprising SEQ ID NO: 2, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, or SEQ ID NO: 80.

In some examples of any of the ABPCs described herein, the first antigen-binding domain includes a heavy chain variable domain comprising SEQ ID NO: 84, and a light chain variable domain comprising SEQ ID NO: 2, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, or SEQ ID NO: 80.

In some examples of any of the ABPCs described herein, the first antigen-binding domain includes a heavy chain variable domain comprising SEQ ID NO: 85, and a light chain variable domain comprising SEQ ID NO: 2, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, or SEQ ID NO: 80.

In some examples of any of the ABPCs described herein, the first antigen-binding domain includes a heavy chain variable domain comprising SEQ ID NO: 86, and a light chain variable domain comprising SEQ ID NO: 2, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, or SEQ ID NO: 80.

In some examples of any of the ABPCs described herein, the first antigen-binding domain includes a heavy chain variable domain comprising SEQ ID NO: 87, and a light chain variable domain comprising SEQ ID NO: 2, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, or SEQ ID NO: 80.

In some examples of any of the ABPCs described herein, the first antigen-binding domain includes a heavy chain variable domain comprising SEQ ID NO: 88, and a light chain variable domain comprising SEQ ID NO: 2, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, or SEQ ID NO: 80.

In some examples of any of the ABPCs described herein, the first antigen-binding domain includes a heavy chain variable domain comprising SEQ ID NO: 89, and a light chain variable domain comprising SEQ ID NO: 2, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, or SEQ ID NO: 80.

In some examples of any of the ABPCs described herein, the first antigen-binding domain includes a heavy chain variable domain comprising SEQ ID NO: 90, and a light chain variable domain comprising SEQ ID NO: 2, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, or SEQ ID NO: 80.

In some examples of any of the ABPCs described herein, the first antigen-binding domain includes a heavy chain variable domain comprising SEQ ID NO: 91, and a light chain variable domain comprising SEQ ID NO: 2, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, or SEQ ID NO: 80.

In some examples of any of the ABPCs described herein, the first antigen-binding domain includes a heavy chain variable domain comprising SEQ ID NO: 92, and a light chain variable domain comprising SEQ ID NO: 2, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, or SEQ ID NO: 80.

In some examples of any of the ABPCs described herein, the first antigen-binding domain includes a heavy chain variable domain comprising SEQ ID NO: 93, and a light chain variable domain comprising SEQ ID NO: 2, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, or SEQ ID NO: 80.

In some examples of any of the ABPCs described herein, the first antigen-binding domain includes a heavy chain variable domain comprising SEQ ID NO: 94, and a light chain variable domain comprising SEQ ID NO: 2, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, or SEQ ID NO: 80.

In some examples of any of the ABPCs described herein, the first antigen-binding domain includes a heavy chain variable domain comprising SEQ ID NO: 95, and a light chain variable domain comprising SEQ ID NO: 2, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, or SEQ ID NO: 80.

In some examples of any of the ABPCs described herein, the first antigen-binding domain includes a heavy chain variable domain comprising SEQ ID NO: 96, and a light chain variable domain comprising SEQ ID NO: 2, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, or SEQ ID NO: 80.

In some examples of any of the ABPCs described herein, the first antigen-binding domain includes a heavy chain variable domain comprising SEQ ID NO: 97, and a light chain variable domain comprising SEQ ID NO: 2, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, or SEQ ID NO: 80.

In some examples of any of the ABPCs described herein, the first antigen-binding domain includes a heavy chain variable domain comprising SEQ ID NO: 98, and a light chain variable domain comprising SEQ ID NO: 2, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, or SEQ ID NO: 80.

In some examples of any of the ABPCs described herein, the first antigen-binding domain includes a heavy chain variable domain comprising SEQ ID NO: 99, and a light chain variable domain comprising SEQ ID NO: 2, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, or SEQ ID NO: 80.

In some examples of any of the ABPCs described herein, the first antigen-binding domain includes a heavy chain variable domain comprising SEQ ID NO: 100, and a light chain variable domain comprising SEQ ID NO: 2, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, or SEQ ID NO: 80.

In some examples of any of the ABPCs described herein, the first antigen-binding domain includes a heavy chain variable domain of a SGN-CD123A with one or more (e.g., one, two, three, four, five, six, seven, eight, nine, ten, eleven, twelve, thirteen, fourteen, fifteen, sixteen, seventeen, eighteen, nineteen, or twenty) amino acids substituted with a histidine. In some examples of any of the ABPCs described herein, the first antigen-binding domain includes a light chain variable domain of SGN-CD123A with one or more (e.g., one, two, three, four, five, six, seven, eight, nine, ten, eleven, twelve, thirteen, fourteen, fifteen, sixteen, seventeen, eighteen, nineteen, or twenty) amino acids substituted with a histidine. In some examples of any of the ABPCs described herein, the first antigen-binding domain includes a heavy chain variable domain of SGN-CD123A with one or more (e.g., one, two, three, four, five, six, seven, eight, nine, ten, eleven, twelve, thirteen, fourteen, fifteen, sixteen, seventeen, eighteen, nineteen, or twenty) amino acids substituted with a histidine; and a light chain variable domain of SGN-CD123A with one or more (e.g., one, two, three, four, five, six, seven, eight, nine, ten, eleven, twelve, thirteen, fourteen, fifteen, sixteen, seventeen, eighteen, nineteen, or twenty) amino acids substituted with a histidine. In some examples of any of the ABPCs described herein, the heavy chain variable domain of SGN-CD123A comprises SEQ ID NO: 101. In some examples of any of the ABPCs described herein, the light chain variable domain of SGN-CD123A comprises SEQ ID NO: 102.

In some examples of any of the ABPCs described herein, the first antigen-binding domain comprises a heavy chain variable domain comprising a CDR1, a CDR2, and a CDR3 of SEQ ID NO: 103, SEQ ID NO: 104, and SEQ ID NO: 105, respectively, with collectively a total of one or more (e.g., one, two, three, four, five, six, seven, eight, nine, or ten) amino acid positions in SEQ ID NOs: 103-105 substituted with a histidine. In some examples of any of the ABPCs described herein, the first antigen-binding domain comprises a light chain variable domain comprising a CDR1, a CDR2, and a CDR3 of SEQ ID NO: 106, SEQ ID NO: 107, and SEQ ID NO: 108, respectively, with collectively a total of one or more (e.g., one, two, three, four, five, six, seven, eight, nine, or ten) amino acid positions in SEQ ID NOs: 106-108 substituted with a histidine. In some examples of any of the ABPCs described herein, the first antigen-binding domain includes: a heavy chain variable domain comprising a CDR1, a CDR2, and a CDR3 of SEQ ID NO: 103, SEQ ID NO: 104, and SEQ ID NO: 105, respectively, with collectively a total of one or more (e.g., one, two, three, four, five, six, seven, eight, nine, or ten) amino acid positions in SEQ ID NOs: 103-105 substituted with a histidine; and a light chain variable domain comprising a CDR1, a CDR2, and a CDR3 of SEQ ID NO: 106, SEQ ID NO: 107, and SEQ ID NO: 108, respectively, with collectively a total of one or more (e.g., one, two, three, four, five, six, seven, eight, nine, or ten) amino acid positions in SEQ ID NOs: 106-108 substituted with a histidine.

In some examples of any of the ABPCs described herein, the first antigen-binding domain includes a heavy chain variable domain that is at least 90% (e.g., at least 92%, at least 94%, at least 96%, at least 98%, at least 99%, or 100%) identical to SEQ ID NO: 101, where the heavy chain variable domain includes a histidine at one or more (e.g., one, two, three, four, five, six, seven, eight, nine, ten, eleven, twelve, thirteen, fourteen, fifteen, sixteen, seventeen, eighteen, nineteen, or twenty) amino acid positions in SEQ ID NO: 101 selected from the group consisting of: 26, 27, 32, 33, 35, 52, 57, 58, 59, 104, and 105. In some examples of any of the ABPCs described herein, the first antigen-binding domain includes a light chain variable domain that is at least 90% (e.g., at least 92%, at least 94%, at least 96%, at least 98%, at least 99%, or 100%) identical to SEQ ID NO: 102. In some examples of any of the ABPCs described herein the first antigen-binding domain includes: a heavy chain variable domain that is at least 90% (e.g., at least 92%, at least 94%, at least 96%, at least 98%, at least 99%, or 100%) identical to SEQ ID NO: 101, where the heavy chain variable domain includes a histidine at one or more (e.g., one, two, three, four, five, six, seven, eight, nine, ten, eleven, twelve, thirteen, fourteen, fifteen, sixteen, seventeen, eighteen, nineteen, or twenty) amino acid positions in SEQ ID NO: 101 selected from the group consisting of: 26, 27, 32, 33, 35, 52, 57, 58, 59, 104, and 105, and a light chain variable domain that is at least 90% (e.g., at least 92%, at least 94%, at least 96%, at least 98%, at least 99%, or 100%) identical to SEQ ID NO: 102.

In some examples of any of the ABPCs described herein, a heavy chain variable domain includes a heavy chain variable domain that is at least 90% (e.g., at least 92%, at least 94%, at least 96%, at least 98%, at least 99%, or 100%) identical to SEQ ID NO: 101, where the heavy chain variable domain includes a histidine at any of the specific combinations of one or more amino acid positions in SEQ ID NO: 101 listed in Table 1.

101, wherein the heavy chain variable domain includes a histidine at position 32 in SEQ ID NO: 101; and a light chain variable domain that is at least 90% (e.g., at least 92%, at least 94%, at least 96%, at least 98%, at least 99%, or 100%) identical to SEQ ID NO: 102.

TABLE 3

| Exemplary Combinations of Amino Acid Positions in SEQ ID NO: 101 that can be Substituted with Histidine |
|---|
| 26 + 27, 26 + 32, 26 + 33, 26 + 35, 26 + 52, 26 + 57, 26 + 58, 26 + 59, 26 + 104, 26 + 105, 27 + 32, 27 + 33, 27 + 35, 27 + 52, 27 + 57, 27 + 58, 27 + 59, 27 + 104, 27 + 105, 32 + 33, 32 + 35, 32 + 52, 32 + 57, 32 + 58, 32 + 59, 32 + 104, 32 + 105, 33 + 35, 33 + 52, 33 + 57, 33 + 58, 33 + 59, 33 + 104, 33 + 105, 35 + 52, 35 + 57, 35 + 58, 35 + 59, 35 + 104, 35 + 105, 52 + 57, 52 + 58, 52 + 59, 52 + 104, 52 + 105, 57 + 58, 57 + 59, 57 + 104, 57 + 105, 58 + 59, 58 + 104, 58 + 105, 59 + 104, 59 + 105, 104 + 105, 26 + 27 + 32, 26 + 27 + 33, 26 + 27 + 35, 26 + 27 + 52, 26 + 27 + 57, 26 + 27 + 58, 26 + 27 + 59, 26 + 27 + 104, 26 + 27 + 105, 26 + 32 + 33, 26 + 32 + 35, 26 + 32 + 52, 26 + 32 + 57, 26 + 32 + 58, 26 + 32 + 59, 26 + 32 + 104, 26 + 32 + 105, 26 + 33 + 35, 26 + 33 + 52, 26 + 33 + 57, 26 + 33 + 58, 26 + 33 + 59, 26 + 33 + 104, 26 + 33 + 105, 26 + 35 + 52, 26 + 35 + 57, 26 + 35 + 58, 26 + 35 + 59, 26 + 35 + 104, 26 + 35 + 105, 26 + 52 + 57, 26 + 52 + 58, 26 + 52 + 59, 26 + 52 + 104, 26 + 52 + 105, 26 + 57 + 58, 26 + 57 + 59, 26 + 57 + 104, 26 + 57 + 105, 26 + 58 + 59, 26 + 58 + 104, 26 + 58 + 105, 26 + 59 + 104, 26 + 59 + 105, 26 + 104 + 105, 27 + 32 + 33, 27 + 32 + 35, 27 + 32 + 52, 27 + 32 + 57, 27 + 32 + 58, 27 + 32 + 59, 27 + 32 + 104, 27 + 32 + 105, 27 + 33 + 35, 27 + 33 + 52, 27 + 33 + 57, 27 + 33 + 58, 27 + 33 + 59, 27 + 33 + 104, 27 + 33 + 105, 27 + 35 + 52, 27 + 35 + 57, 27 + 35 + 58, 27 + 35 + 59, 27 + 35 + 104, 27 + 35 + 105, 27 + 52 + 57, 27 + 52 + 58, 27 + 52 + 59, 27 + 52 + 104, 27 + 52 + 105, 27 + 57 + 58, 27 + 57 + 59, 27 + 57 + 104, 27 + 57 + 105, 27 + 58 + 59, 27 + 58 + 104, 27 + 58 + 105, 27 + 59 + 104, 27 + 59 + 105, 27 + 104 + 105, 32 + 33 + 35, 32 + 33 + 52, 32 + 33 + 57, 32 + 33 + 58, 32 + 33 + 59, 32 + 33 + 104, 32 + 33 + 105, 32 + 35 + 52, 32 + 35 + 57, 32 + 35 + 58, 32 + 35 + 59, 32 + 35 + 104, 32 + 35 + 105, 32 + 52 + 57, 32 + 52 + 58, 32 + 52 + 59, 32 + 52 + 104, 32 + 52 + 105, 32 + 57 + 58, 32 + 57 + 59, 32 + 57 + 104, 32 + 57 + 105, 32 + 58 + 59, 32 + 58 + 104, 32 + 58 + 105, 32 + 59 + 104, 32 + 59 + 105, 32 + 104 + 105, 33 + 35 + 52, 33 + 35 + 57, 33 + 35 + 58, 33 + 35 + 59, 33 + 35 + 104, 33 + 35 + 105, 33 + 52 + 57, 33 + 52 + 58, 33 + 52 + 59, 33 + 52 + 104, 33 + 52 + 105, 33 + 57 + 58, 33 + 57 + 59, 33 + 57 + 104, 33 + 57 + 105, 33 + 58 + 59, 33 + 58 + 104, 33 + 58 + 105, 33 + 59 + 104, 33 + 59 + 105, 33 + 104 + 105, 35 + 52 + 57, 35 + 52 + 58, 35 + 52 + 59, 35 + 52 + 104, 35 + 52 + 105, 35 + 57 + 58, 35 + 57 + 59, 35 + 57 + 104, 35 + 57 + 105, 35 + 58 + 59, 35 + 58 + 104, 35 + 58 + 105, 35 + 59 + 104, 35 + 59 + 105, 35 + 104 + 105, 52 + 57 + 58, 52 + 57 + 59, 52 + 57 + 104, 52 + 57 + 105, 52 + 58 + 59, 52 + 58 + 104, 52 + 58 + 105, 52 + 59 + 104, 52 + 59 + 105, 52 + 104 + 105, 57 + 58 + 59, 57 + 58 + 104, 57 + 58 + 105, 57 + 59 + 104, 57 + 59 + 105, 57 + 104 + 105, 58 + 59 + 104, 58 + 59 + 105, 58 + 104 + 105, 59 + 104 + 105 |

In some examples of any of the ABPCs described herein, the first antigen-binding domain comprises a light chain variable domain comprising SEQ ID NO: 2, and a heavy chain variable domain that is at least 90% identical (e.g., at least 92%, at least 94%, at least 96%, at least 98%, at least 99%, or 100%) identical to SEQ ID NO: 101, where the heavy chain variable domain includes a histidine at any of the specific combinations of one or more (e.g., two, three, four, five, six, seven, eight, nine, or ten) amino acid positions in SEQ ID NO: 101 listed in Table 3.

In some examples of any of the ABPCs described herein, the first antigen-binding domain comprises a heavy chain variable domain that is at least 90% identical to SEQ ID NO: 101, wherein the heavy chain variable domain includes a histidine at position 26 in SEQ ID NO: 101; and a light chain variable domain that is at least 90% (e.g., at least 92%, at least 94%, at least 96%, at least 98%, at least 99%, or 100%) identical to SEQ ID NO: 102.

In some examples of any of the ABPCs described herein, the first antigen-binding domain comprises a heavy chain variable domain that is at least 90% identical to SEQ ID NO: 101, wherein the heavy chain variable domain includes a histidine at position 27 in SEQ ID NO: 101; and a light chain variable domain that is at least 90% (e.g., at least 92%, at least 94%, at least 96%, at least 98%, at least 99%, or 100%) identical to SEQ ID NO: 102.

In some examples of any of the ABPCs described herein, the first antigen-binding domain comprises a heavy chain variable domain that is at least 90% identical to SEQ ID NO:

In some examples of any of the ABPCs described herein, the first antigen-binding domain comprises a heavy chain variable domain that is at least 90% identical to SEQ ID NO: 101, wherein the heavy chain variable domain includes a histidine at position 33 in SEQ ID NO: 101; and a light chain variable domain that is at least 90% (e.g., at least 92%, at least 94%, at least 96%, at least 98%, at least 99%, or 100%) identical to SEQ ID NO: 102.

In some examples of any of the ABPCs described herein, the first antigen-binding domain comprises a heavy chain variable domain that is at least 90% identical to SEQ ID NO: 101, wherein the heavy chain variable domain includes a histidine at position 35 in SEQ ID NO: 101; and a light chain variable domain that is at least 90% (e.g., at least 92%, at least 94%, at least 96%, at least 98%, at least 99%, or 100%) identical to SEQ ID NO: 102.

In some examples of any of the ABPCs described herein, the first antigen-binding domain comprises a heavy chain variable domain that is at least 90% identical to SEQ ID NO: 101, wherein the heavy chain variable domain includes a histidine at position 52 in SEQ ID NO: 101; and a light chain variable domain that is at least 90% (e.g., at least 92%, at least 94%, at least 96%, at least 98%, at least 99%, or 100%) identical to SEQ ID NO: 102.

In some examples of any of the ABPCs described herein, the first antigen-binding domain comprises a heavy chain variable domain that is at least 90% identical to SEQ ID NO: 101, wherein the heavy chain variable domain includes a histidine at position 57 in SEQ ID NO: 101; and a light chain variable domain that is at least 90% (e.g., at least 92%, at least 94%, at least 96%, at least 98%, at least 99%, or 100%) identical to SEQ ID NO: 102.

In some examples of any of the ABPCs described herein, the first antigen-binding domain comprises a heavy chain variable domain that is at least 90% identical to SEQ ID NO: 101, wherein the heavy chain variable domain includes a histidine at position 58 in SEQ ID NO: 101; and a light chain variable domain that is at least 90% (e.g., at least 92%, at least 94%, at least 96%, at least 98%, at least 99%, or 100%) identical to SEQ ID NO: 102.

In some examples of any of the ABPCs described herein, the first antigen-binding domain comprises a heavy chain variable domain that is at least 90% identical to SEQ ID NO: 101, wherein the heavy chain variable domain includes a histidine at position 59 in SEQ ID NO: 101; and a light chain variable domain that is at least 90% (e.g., at least 92%, at least 94%, at least 96%, at least 98%, at least 99%, or 100%) identical to SEQ ID NO: 102.

In some examples of any of the ABPCs described herein, the first antigen-binding domain comprises a heavy chain variable domain that is at least 90% identical to SEQ ID NO: 101, wherein the heavy chain variable domain includes a histidine at position 104 in SEQ ID NO: 101; and a light chain variable domain that is at least 90% (e.g., at least 92%, at least 94%, at least 96%, at least 98%, at least 99%, or 100%) identical to SEQ ID NO: 102.

In some examples of any of the ABPCs described herein, the first antigen-binding domain comprises a heavy chain variable domain that is at least 90% identical to SEQ ID NO: 101, wherein the heavy chain variable domain includes a histidine at position 105 in SEQ ID NO: 101; and a light chain variable domain that is at least 90% (e.g., at least 92%, at least 94%, at least 96%, at least 98%, at least 99%, or 100%) identical to SEQ ID NO: 102.

In some examples of any of the ABPCs described herein, the first antigen-binding domain includes a heavy chain variable domain of SGN-CD123A with one or more (e.g., one, two, three, four, five, six, seven, eight, nine, ten, eleven, twelve, thirteen, fourteen, fifteen, sixteen, seventeen, eighteen, nineteen, or twenty) histidine(s) substituted with an alanine. In some examples of any of the ABPCs described herein, the first antigen-binding domain includes a light chain variable domain of SGN-CD123A with one or more (e.g., one, two, three, four, five, six, seven, eight, nine, ten, eleven, twelve, thirteen, fourteen, fifteen, sixteen, seventeen, eighteen, nineteen, or twenty) histidine(s) substituted with an alanine. In some examples of any of the ABPCs described herein, the first antigen-binding domain includes a heavy chain variable domain of SGN-CD123A with one or more (e.g., one, two, three, four, five, six, seven, eight, nine, ten, eleven, twelve, thirteen, fourteen, fifteen, sixteen, seventeen, eighteen, nineteen, or twenty) histidines substituted with an alanine; and a light chain variable domain of SGN-CD123A with one or more (e.g., one, two, three, four, five, six, seven, eight, nine, ten, eleven, twelve, thirteen, fourteen, fifteen, sixteen, seventeen, eighteen, nineteen, or twenty) histidine(s) substituted with an alanine. In some examples of any of the ABPCs described herein, the heavy chain variable domain of SGN-CD123A comprises SEQ ID NO: 101. In some examples of any of the ABPCs described herein, the light chain variable domain of SGN-CD123A comprises SEQ ID NO: 102.

In some examples of any of the ABPCs described herein, the first antigen-binding domain comprises a heavy chain variable domain comprising a CDR1, a CDR2, and a CDR3 of SEQ ID NO: 103, SEQ ID NO: 104, and SEQ ID NO: 105, respectively, with collectively a total of one or more (e.g., one, two, three, four, five, six, seven, eight, nine, or ten) histidine(s) in SEQ ID NOs: 103-105 substituted with an alanine. In some examples of any of the ABPCs described herein, the first antigen-binding domain comprises a light chain variable domain comprising a CDR1, a CDR2, and a CDR3 of SEQ ID NO: 106, SEQ ID NO: 107, and SEQ ID NO: 108, respectively, with collectively a total of one or more (e.g., one, two, three, four, five, six, seven, eight, nine, or ten) histidine(s) in SEQ ID NOs: 106-108 substituted with an alanine. In some examples of any of the ABPCs described herein, the first antigen-binding domain includes: a heavy chain variable domain comprising a CDR1, a CDR2, and a CDR3 of SEQ ID NO: 103, SEQ ID NO: 104, and SEQ ID NO: 105, respectively, with collectively a total of one or more (e.g., one, two, three, four, five, six, seven, eight, nine, or ten) histidine(s) in SEQ ID NOs: 103-105 substituted with an alanine; and a light chain variable domain comprising a CDR1, a CDR2, and a CDR3 of SEQ ID NO: 106, SEQ ID NO: 107, and SEQ ID NO: 108, respectively, with collectively a total of one or more (e.g., one, two, three, four, five, six, seven, eight, nine, or ten) histidine(s) in SEQ ID NOs: 106-108 substituted with an alanine.

In some examples of any of the ABPCs described herein, the first antigen-binding domain comprises a heavy chain variable domain of SEQ ID NO: 101, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, or SEQ ID NO: 148.

In some examples of any of the ABPCs described herein, the first antigen-binding domain includes a light chain variable domain of SEQ ID NO: 102.

In some examples of any of the ABPCs described herein, the first antigen-binding domain includes a light chain variable domain comprising SEQ ID NO: 102, and a heavy chain variable domain comprising: SEQ ID NO: 101, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, or SEQ ID NO: 148.

In some examples of any of the ABPCs described herein, the first antigen-binding domain includes a heavy chain variable domain of TPP-8988 with one or more (e.g., one, two, three, four, five, six, seven, eight, nine, ten, eleven, twelve, thirteen, fourteen, fifteen, sixteen, seventeen, eighteen, nineteen, or twenty) amino acids substituted with a histidine. In some examples of any of the ABPCs described herein, the first antigen-binding domain includes a light chain variable domain of TPP-8988 with one or more (e.g., one, two, three, four, five, six, seven, eight, nine, ten, eleven, twelve, thirteen, fourteen, fifteen, sixteen, seventeen, eighteen, nineteen, or twenty) amino acids substituted with a histidine. In some examples of any of the ABPCs described herein, the first antigen-binding domain includes a heavy chain variable domain of TPP-8988 with one or more (e.g., one, two, three, four, five, six, seven, eight, nine, ten, eleven, twelve, thirteen, fourteen, fifteen, sixteen, seventeen, eighteen, nineteen, or twenty) amino acids substituted with a histidine; and a light chain variable domain of TPP-8988 with one or more (e.g., one, two, three, four, five, six, seven, eight, nine, ten, eleven, twelve, thirteen, fourteen, fifteen, sixteen, seventeen, eighteen, nineteen, or twenty) amino acids substituted with a histidine. In some examples of any of the ABPCs described herein, the heavy chain variable domain of TPP-8988 comprises SEQ ID NO: 149. In some examples of any of the ABPCs described herein, the light chain variable domain of TPP-8988 comprises SEQ ID NO: 150.

In some examples of any of the ABPCs described herein, the first antigen-binding domain comprises a heavy chain variable domain comprising a CDR1, a CDR2, and a CDR3 of SEQ ID NO: 151, SEQ ID NO: 152, and SEQ ID NO: 153, respectively, with collectively a total of one or more (e.g., one, two, three, four, five, six, seven, eight, nine, or ten) amino acid positions in SEQ ID NOs: 151-153 substituted with a histidine. In some examples of any of the ABPCs described herein, the first antigen-binding domain comprises a light chain variable domain comprising a CDR1, a CDR2, and a CDR3 of SEQ ID NO: 154, SEQ ID NO: 155, and SEQ ID NO: 156, respectively, with collectively a total of one or more (e.g., one, two, three, four, five, six, seven, eight, nine, or ten) amino acid positions in SEQ ID NOs: 154-155 substituted with a histidine. In some examples of any of the ABPCs described herein, the first antigen-binding domain includes: a heavy chain variable domain comprising a CDR1, a CDR2, and a CDR3 of SEQ ID NO: 151, SEQ ID NO: 152, and SEQ ID NO: 153, respectively, with collectively a total of one or more (e.g., one, two, three, four, five, six, seven, eight, nine, or ten) amino acid positions in SEQ ID NOs: 151-153 substituted with a histidine; and a light chain variable domain comprising a CDR1, a CDR2, and a CDR3 of SEQ ID NO: 154, SEQ ID NO: 155, and SEQ ID NO: 156, respectively, with collectively a total of one or more (e.g., one, two, three, four, five, six, seven, eight, nine, or ten) amino acid positions in SEQ ID NOs: 154-156 substituted with a histidine.

In some examples of any of the ABPCs described herein, the first antigen-binding domain includes a heavy chain variable domain that is at least 90% (e.g., at least 92%, at least 94%, at least 96%, at least 98%, at least 99%, or 100%) identical to SEQ ID NO: 149, where the heavy chain variable domain includes a histidine at one or more (e.g., one, two, three, four, five, six, seven, eight, nine, ten, eleven, twelve, thirteen, fourteen, fifteen, sixteen, seventeen, eighteen, nineteen, or twenty) amino acid positions in SEQ ID NO: 149 selected from the group consisting of: 32, 34, 35, 36, 51, 53, 54, 98, 99, 100, 101, 103, and 104. In some examples of any of the ABPCs described herein, the first antigen-binding domain includes a light chain variable domain that is at least 90% (e.g., at least 92%, at least 94%, at least 96%, at least 98%, at least 99%, or 100%) identical to SEQ ID NO: 150, where the light chain variable domain includes a histidine at one or more (e.g., one, two, three, four, five, six, seven, eight, nine, ten, eleven, twelve, thirteen, fourteen, fifteen, sixteen, seventeen, eighteen, nineteen, or twenty) amino acid positions in SEQ ID NO: 150 selected from the group consisting of: 29, 30, 31, 32, 33, 34, 38, 56, 95, 96, 97, 101, and 102. In some examples of any of the ABPCs described herein the first antigen-binding domain includes: a heavy chain variable domain that is at least 90% (e.g., at least 92%, at least 94%, at least 96%, at least 98%, at least 99%, or 100%) identical to SEQ ID NO: 149, where the heavy chain variable domain includes a histidine at one or more (e.g., one, two, three, four, five, six, seven, eight, nine, ten, eleven, twelve, thirteen, fourteen, fifteen, sixteen, seventeen, eighteen, nineteen, or twenty) amino acid positions in SEQ ID NO: 149 selected from the group consisting of: 32, 34, 35, 36, 51, 53, 54, 98, 99, 100, 101, 103, and 104, and a light chain variable domain that is at least 90% (e.g., at least 92%, at least 94%, at least 96%, at least 98%, at least 99%, or 100%) identical to SEQ ID NO: 150, where the light chain variable domain includes a histidine at one or more (e.g., one, two, three, four, five, six, seven, eight, nine, ten, eleven, twelve, thirteen, fourteen, fifteen, sixteen, seventeen, eighteen, nineteen, or twenty) amino acid positions in SEQ ID NO: 150 selected from the group consisting of: 29, 30, 31, 32, 33, 34, 38, 56, 95, 96, 97, 101, and 102.

In some examples of any of the ABPCs described herein, a heavy chain variable domain includes a heavy chain variable domain that is at least 90% (e.g., at least 92%, at least 94%, at least 96%, at least 98%, at least 99%, or 100%) identical to SEQ ID NO: 149, where the heavy chain variable domain includes a histidine at any of the specific combinations of one or more amino acid positions in SEQ ID NO: 149 listed in Table 4.

TABLE 4

| Exemplary Combinations of Amino Acid Positions in SEQ ID NO: 149 that can be Substituted with Histidine |
|---|
| 32 + 34, 32 + 35, 32 + 36, 32 + 51, 32 + 53, 32 + 54, 32 + 98, 32 + 99, 32 + 100, 32 + 101, 32 + 103, 32 + 104, 34 + 35, 34 + 36, 34 + 51, 34 + 53, 34 + 54, 34 + 98, 34 + 99, 34 + 100, 34 + 101, 34 + 103, 34 + 104, 35 + 36, 35 + 51, 35 + 53, 35 + 54, 35 + 98, 35 + 99, 35 + 100, 35 + 101, 35 + 103, 35 + 104, 36 + 51, 36 + 53, 36 + 54, 36 + 98, 36 + 99, 36 + 100, 36 + 101, 36 + 103, 36 + 104, 51 + 53, 51 + 54, 51 + 98, 51 + 99, 51 + 100, 51 + 101, 51 + 103, 51 + 104, 53 + 54, 53 + 98, 53 + 99, 53 + 100, 53 + 101, 53 + 103, 53 + 104, 54 + 98, 54 + 99, 54 + 100, 54 + 101, 54 + 103, 54 + 104, 98 + 99, 98 + 100, 98 + 101, 98 + 103, 98 + 104, 99 + 100, 99 + 101, 99 + 103, 99 + 104, 100 + 101, 100 + 103, 100 + 104, 101 + 103, 101 + 104, 103 + 104, 32 + 34 + 35, 32 + 34 + 36, 32 + 34 + 51, 32 + 34 + 53, 32 + 34 + 54, 32 + 34 + 98, 32 + 34 + 99, 32 + 34 + 100, 32 + 34 + 101, 32 + 34 + 103, 32 + 34 + 104, 32 + 35 + 36, 32 + 35 + 51, 32 + 35 + 53, 32 + 35 + 54, 32 + 35 + 98, 32 + 35 + 99, 32 + 35 + 100, 32 + 35 + 101, 32 + 35 + 103, 32 + 35 + 104, 32 + 36 + 51, 32 + 36 + 53, 32 + 36 + 54, 32 + 36 + 98, 32 + 36 + 99, 32 + 36 + 100, 32 + 36 + 101, 32 + 36 + 103, 32 + 36 + 104, 32 + 51 + 53, 32 + 51 + 54, 32 + 51 + 98, 32 + 51 + 99, 32 + 51 + 100, 32 + 51 + 101, 32 + 51 + 103, 32 + 51 + 104, 32 + 53 + 54, 32 + 53 + 98, 32 + 53 + 99, 32 + 53 + 100, 32 + 53 + 101, 32 + 53 + 103, 32 + 53 + 104, |

TABLE 4-continued

| Exemplary Combinations of Amino Acid Positions in SEQ ID NO: 149 that can be Substituted with Histidine |
| --- |
| 32 + 54 + 98, 32 + 54 + 99, 32 + 54 + 100, 32 + 54 + 101, 32 + 54 + 103, 32 + 54 + 104, 32 + 98 + 99, 32 + 98 + 100, 32 + 98 + 101, 32 + 98 + 103, 32 + 98 + 104, 32 + 99 + 100, 32 + 99 + 101, 32 + 99 + 103, 32 + 99 + 104, 32 + 100 + 101, 32 + 100 + 103, 32 + 100 + 104, 32 + 101 + 103, 32 + 101 + 104, 32 + 103 + 104, 34 + 35 + 36, 34 + 35 + 51, 34 + 35 + 53, 34 + 35 + 54, 34 + 35 + 98, 34 + 35 + 99, 34 + 35 + 100, 34 + 35 + 101, 34 + 35 + 103, 34 + 35 + 104, 34 + 36 + 51, 34 + 36 + 53, 34 + 36 + 54, 34 + 36 + 98, 34 + 36 + 99, 34 + 36 + 100, 34 + 36 + 101, 34 + 36 + 103, 34 + 36 + 104, 34 + 51 + 53, 34 + 51 + 54, 34 + 51 + 98, 34 + 51 + 99, 34 + 51 + 100, 34 + 51 + 101, 34 + 51 + 103, 34 + 51 + 104, 34 + 53 + 54, 34 + 53 + 98, 34 + 53 + 99, 34 + 53 + 100, 34 + 53 + 101, 34 + 53 + 103, 34 + 53 + 104, 34 + 54 + 98, 34 + 54 + 99, 34 + 54 + 100, 34 + 54 + 101, 34 + 54 + 103, 34 + 54 + 104, 34 + 98 + 99, 34 + 98 + 100, 34 + 98 + 101, 34 + 98 + 103, 34 + 98 + 104, 34 + 99 + 100, 34 + 99 + 101, 34 + 99 + 103, 34 + 99 + 104, 34 + 100 + 101, 34 + 100 + 103, 34 + 100 + 104, 34 + 101 + 103, 34 + 101 + 104, 34 + 103 + 104, 35 + 36 + 51, 35 + 36 + 53, 35 + 36 + 54, 35 + 36 + 98, 35 + 36 + 99, 35 + 36 + 100, 35 + 36 + 101, 35 + 36 + 103, 35 + 36 + 104, 35 + 51 + 53, 35 + 51 + 54, 35 + 51 + 98, 35 + 51 + 99, 35 + 51 + 100, 35 + 51 + 101, 35 + 51 + 103, 35 + 51 + 104, 35 + 53 + 54, 35 + 53 + 98, 35 + 53 + 99, 35 + 53 + 100, 35 + 53 + 101, 35 + 53 + 103, 35 + 53 + 104, 35 + 54 + 98, 35 + 54 + 99, 35 + 54 + 100, 35 + 54 + 101, 35 + 54 + 103, 35 + 54 + 104, 35 + 98 + 99, 35 + 98 + 100, 35 + 98 + 101, 35 + 98 + 103, 35 + 98 + 104, 35 + 99 + 100, 35 + 99 + 101, 35 + 99 + 103, 35 + 99 + 104, 35 + 100 + 101, 35 + 100 + 103, 35 + 100 + 104, 35 + 101 + 103, 35 + 101 + 104, 35 + 103 + 104, 36 + 51 + 53, 36 + 51 + 54, 36 + 51 + 98, 36 + 51 + 99, 36 + 51 + 100, 36 + 51 + 101, 36 + 51 + 103, 36 + 51 + 104, 36 + 53 + 54, 36 + 53 + 98, 36 + 53 + 99, 36 + 53 + 100, 36 + 53 + 101, 36 + 53 + 103, 36 + 53 + 104, 36 + 54 + 98, 36 + 54 + 99, 36 + 54 + 100, 36 + 54 + 101, 36 + 54 + 103, 36 + 54 + 104, 36 + 98 + 99, 36 + 98 + 100, 36 + 98 + 101, 36 + 98 + 103, 36 + 98 + 104, 36 + 99 + 100, 36 + 99 + 101, 36 + 99 + 103, 36 + 99 + 104, 36 + 100 + 101, 36 + 100 + 103, 36 + 100 + 104, 36 + 101 + 103, 36 + 101 + 104, 36 + 103 + 104, 51 + 53 + 54, 51 + 53 + 98, 51 + 53 + 99, 51 + 53 + 100, 51 + 53 + 101, 51 + 53 + 103, 51 + 53 + 104, 51 + 54 + 98, 51 + 54 + 99, 51 + 54 + 100, 51 + 54 + 101, 51 + 54 + 103, 51 + 54 + 104, 51 + 98 + 99, 51 + 98 + 100, 51 + 98 + 101, 51 + 98 + 103, 51 + 98 + 104, 51 + 99 + 100, 51 + 99 + 101, 51 + 99 + 103, 51 + 99 + 104, 51 + 100 + 101, 51 + 100 + 103, 51 + 100 + 104, 51 + 101 + 103, 51 + 101 + 104, 51 + 103 + 104, 53 + 54 + 98, 53 + 54 + 99, 53 + 54 + 100, 53 + 54 + 101, 53 + 54 + 103, 53 + 54 + 104, 53 + 98 + 99, 53 + 98 + 100, 53 + 98 + 101, 53 + 98 + 103, 53 + 98 + 104, 53 + 99 + 100, 53 + 99 + 101, 53 + 99 + 103, 53 + 99 + 104, 53 + 100 + 101, 53 + 100 + 103, 53 + 100 + 104, 53 + 101 + 103, 53 + 101 + 104, 53 + 103 + 104, 54 + 98 + 99, 54 + 98 + 100, 54 + 98 + 101, 54 + 98 + 103, 54 + 98 + 104, 54 + 99 + 100, 54 + 99 + 101, 54 + 99 + 103, 54 + 99 + 104, 54 + 100 + 101, 54 + 100 + 103, 54 + 100 + 104, 54 + 101 + 103, 54 + 101 + 104, 54 + 103 + 104, 98 + 99 + 100, 98 + 99 + 101, 98 + 99 + 103, 98 + 99 + 104, 98 + 100 + 101, 98 + 100 + 103, 98 + 100 + 104, 98 + 101 + 103, 98 + 101 + 104, 98 + 103 + 104, 99 + 100 + 101, 99 + 100 + 103, 99 + 100 + 104, 99 + 101 + 103, 99 + 101 + 104, 99 + 103 + 104, 100 + 101 + 103, 100 + 101 + 104, 100 + 103 + 104, 101 + 103 + 104 |

In some examples of any of the ABPCs described herein, a light chain variable domain includes a light chain variable domain that is at least 90% (e.g., at least 92%, at least 94%, at least 96%, at least 98%, at least 99%, or 100%) identical to SEQ ID NO: 150, where the light chain variable domain includes a histidine at any of the specific combinations of one or more amino acid positions in SEQ ID NO: 150 listed in Table 5.

TABLE 5

| Exemplary Combinations of Amino Acid Positions in SEQ ID NO: 150 that can be Substituted with Histidine |
| --- |
| 29 + 30, 29 + 31, 29 + 32, 29 + 33, 29 + 34, 29 + 38, 29 + 56, 29 + 95, 29 + 96, 29 + 97, 29 + 101, 29 + 102, 30 + 31, 30 + 32, 30 + 33, 30 + 34, 30 + 38, 30 + 56, 30 + 95, 30 + 96, 30 + 97, 30 + 101, 30 + 102, 31 + 32, 31 + 33, 31 + 34, 31 + 38, 31 + 56, 31 + 95, 31 + 96, 31 + 97, 31 + 101, 31 + 102, 32 + 33, 32 + 34, 32 + 38, 32 + 56, 32 + 95, 32 + 96, 32 + 97, 32 + 101, 32 + 102, 33 + 34, 33 + 38, 33 + 56, 33 + 95, 33 + 96, 33 + 97, 33 + 101, 33 + 102, 34 + 38, 34 + 56, 34 + 95, 34 + 96, 34 + 97, 34 + 101, 34 + 102, 38 + 56, 38 + 95, 38 + 96, 38 + 97, 38 + 101, 38 + 102, 56 + 95, 56 + 96, 56 + 97, 56 + 101, 56 + 102, 95 + 96, 95 + 97, 95 + 101, 95 + 102, 96 + 97, 96 + 101, 96 + 102, 97 + 101, 97 + 102, 101 + 102, 29 + 30 + 31, 29 + 30 + 32, 29 + 30 + 33, 29 + 30 + 34, 29 + 30 + 38, 29 + 30 + 56, 29 + 30 + 95, 29 + 30 + 96, 29 + 30 + 97, 29 + 30 + 101, 29 + 30 + 102, 29 + 31 + 32, 29 + 31 + 33, 29 + 31 + 34, 29 + 31 + 38, 29 + 31 + 56, 29 + 31 + 95, 29 + 31 + 96, 29 + 31 + 97, 29 + 31 + 101, 29 + 31 + 102, 29 + 32 + 33, 29 + 32 + 34, 29 + 32 + 38, 29 + 32 + 56, 29 + 32 + 95, 29 + 32 + 96, 29 + 32 + 97, 29 + 32 + 101, 29 + 32 + 102, 29 + 33 + 34, 29 + 33 + 38, 29 + 33 + 56, 29 + 33 + 95, 29 + 33 + 96, 29 + 33 + 97, 29 + 33 + 101, 29 + 33 + 102, 29 + 34 + 38, 29 + 34 + 56, 29 + 34 + 95, 29 + 34 + 96, 29 + 34 + 97, 29 + 34 + 101, 29 + 34 + 102, 29 + 38 + 56, 29 + 38 + 95, 29 + 38 + 96, 29 + 38 + 97, 29 + 38 + 101, 29 + 38 + 102, 29 + 56 + 95, 29 + 56 + 96, 29 + 56 + 97, 29 + 56 + 101, 29 + 56 + 102, 29 + 95 + 96, 29 + 95 + 97, 29 + 95 + 101, 29 + 95 + 102, 29 + 96 + 97, 29 + 96 + 101, 29 + 96 + 102, 29 + 97 + 101, 29 + 97 + 102, 29 + 101 + 102, 30 + 31 + 32, 30 + 31 + 33, 30 + 31 + 34, 30 + 31 + 38, 30 + 31 + 56, 30 + 31 + 95, 30 + 31 + 96, 30 + 31 + 97, 30 + 31 + 101, 30 + 31 + 102, 30 + 32 + 33, 30 + 32 + 34, 30 + 32 + 38, 30 + 32 + 56, 30 + 32 + 95, 30 + 32 + 96, 30 + 32 + 97, 30 + 32 + 101, 30 + 32 + 102, 30 + 33 + 34, 30 + 33 + 38, 30 + 33 + 56, 30 + 33 + 95, 30 + 33 + 96, 30 + 33 + 97, 30 + 33 + 101, 30 + 33 + 102, 30 + 34 + 38, 30 + 34 + 56, 30 + 34 + 95, 30 + 34 + 96, 30 + 34 + 97, 30 + 34 + 101, 30 + |

TABLE 5-continued

| Exemplary Combinations of Amino Acid Positions in SEQ ID NO: 150 that can be Substituted with Histidine |
|---|
| 34 + 102, 30 + 38 + 56, 30 + 38 + 95, 30 + 38 + 96, 30 + 38 + 97, 30 + 38 + 101, 30 + 38 + 102, 30 + 56 + 95, 30 + 56 + 96, 30 + 56 + 97, 30 + 56 + 101, 30 + 56 + 102, 30 + 95 + 96, 30 + 95 + 97, 30 + 95 + 101, 30 + 95 + 102, 30 + 96 + 97, 30 + 96 + 101, 30 + 96 + 102, 30 + 97 + 101, 30 + 97 + 102, 30 + 101 + 102, 31 + 32 + 33, 31 + 32 + 34, 31 + 32 + 38, 31 + 32 + 56, 31 + 32 + 95, 31 + 32 + 96, 31 + 32 + 97, 31 + 32 + 101, 31 + 32 + 102, 31 + 33 + 34, 31 + 33 + 38, 31 + 33 + 56, 31 + 33 + 95, 31 + 33 + 96, 31 + 33 + 97, 31 + 33 + 101, 31 + 33 + 102, 31 + 34 + 38, 31 + 34 + 56, 31 + 34 + 95, 31 + 34 + 96, 31 + 34 + 97, 31 + 34 + 101, 31 + 34 + 102, 31 + 38 + 56, 31 + 38 + 95, 31 + 38 + 96, 31 + 38 + 97, 31 + 38 + 101, 31 + 38 + 102, 31 + 56 + 95, 31 + 56 + 96, 31 + 56 + 97, 31 + 56 + 101, 31 + 56 + 102, 31 + 95 + 96, 31 + 95 + 97, 31 + 95 + 101, 31 + 95 + 102, 31 + 96 + 97, 31 + 96 + 101, 31 + 96 + 102, 31 + 97 + 101, 31 + 97 + 102, 31 + 101 + 102, 32 + 33 + 34, 32 + 33 + 38, 32 + 33 + 56, 32 + 33 + 95, 32 + 33 + 96, 32 + 33 + 97, 32 + 33 + 101, 32 + 33 + 102, 32 + 34 + 38, 32 + 34 + 56, 32 + 34 + 95, 32 + 34 + 96, 32 + 34 + 97, 32 + 34 + 101, 32 + 34 + 102, 32 + 38 + 56, 32 + 38 + 95, 32 + 38 + 96, 32 + 38 + 97, 32 + 38 + 101, 32 + 38 + 102, 32 + 56 + 95, 32 + 56 + 96, 32 + 56 + 97, 32 + 56 + 101, 32 + 56 + 102, 32 + 95 + 96, 32 + 95 + 97, 32 + 95 + 101, 32 + 95 + 102, 32 + 96 + 97, 32 + 96 + 101, 32 + 96 + 102, 32 + 97 + 101, 32 + 97 + 102, 32 + 101 + 102, 33 + 34 + 38, 33 + 34 + 56, 33 + 34 + 95, 33 + 34 + 96, 33 + 34 + 97, 33 + 34 + 101, 33 + 34 + 102, 33 + 38 + 56, 33 + 38 + 95, 33 + 38 + 96, 33 + 38 + 97, 33 + 38 + 101, 33 + 38 + 102, 33 + 56 + 95, 33 + 56 + 96, 33 + 56 + 97, 33 + 56 + 101, 33 + 56 + 102, 33 + 95 + 96, 33 + 95 + 97, 33 + 95 + 101, 33 + 95 + 102, 33 + 96 + 97, 33 + 96 + 101, 33 + 96 + 102, 33 + 97 + 101, 33 + 97 + 102, 33 + 101 + 102, 34 + 38 + 56, 34 + 38 + 95, 34 + 38 + 96, 34 + 38 + 97, 34 + 38 + 101, 34 + 38 + 102, 34 + 56 + 95, 34 + 56 + 96, 34 + 56 + 97, 34 + 56 + 101, 34 + 56 + 102, 34 + 95 + 96, 34 + 95 + 97, 34 + 95 + 101, 34 + 95 + 102, 34 + 96 + 97, 34 + 96 + 101, 34 + 96 + 102, 34 + 97 + 101, 34 + 97 + 102, 34 + 101 + 102, 38 + 56 + 95, 38 + 56 + 96, 38 + 56 + 97, 38 + 56 + 101, 38 + 56 + 102, 38 + 95 + 96, 38 + 95 + 97, 38 + 95 + 101, 38 + 95 + 102, 38 + 96 + 97, 38 + 96 + 101, 38 + 96 + 102, 38 + 97 + 101, 38 + 97 + 102, 38 + 101 + 102, 56 + 95 + 96, 56 + 95 + 97, 56 + 95 + 101, 56 + 95 + 102, 56 + 96 + 97, 56 + 96 + 101, 56 + 96 + 102, 56 + 97 + 101, 56 + 97 + 102, 56 + 101 + 102, 95 + 96 + 97, 95 + 96 + 101, 95 + 96 + 102, 95 + 97 + 101, 95 + 97 + 102, 95 + 101 + 102, 96 + 97 + 101, 96 + 97 + 102, 96 + 101 + 102, 97 + 101 + 102 |

In some examples of any of the ABPCs described herein, the first antigen-binding domain includes a heavy chain variable domain that is at least 90% (e.g., at least 92%, at least 94%, at least 96%, at least 98%, at least 99%, or 100%) identical to SEQ ID NO: 149, where the heavy chain variable domain includes a histidine at any of the specific combinations of one or more amino acid positions in SEQ ID NO: 149 listed in Table 4; and a light chain variable domain that that is at least 90% (e.g., at least 92%, at least 94%, at least 96%, at least 98%, at least 99%, or 100%) identical to SEQ ID NO: 150, where the light chain variable domain includes a histidine at any of the specific combinations of one or more amino acid positions in SEQ ID NO: 2 listed in Table 5.

In some examples of any of the ABPCs described herein, the first antigen-binding domain comprises a light chain variable domain comprising SEQ ID NO: 150, and a heavy chain variable domain that is at least 90% identical (e.g., at least 92%, at least 94%, at least 96%, at least 98%, at least 99%, or 100%) identical to SEQ ID NO: 149, where the heavy chain variable domain includes a histidine at any of the specific combinations of one or more (e.g., two, three, four, five, six, seven, eight, nine, or ten) amino acid positions in SEQ ID NO: 149 listed in Table 4.

In some examples of any of the ABPCs described herein, the first antigen-binding domain comprises a light chain variable domain that is at least 90% identical to SEQ ID NO: 150, wherein the light chain variable domain includes a histidine at position 29 in SEQ ID NO: 150; and a heavy chain variable domain that is at least 90% (e.g., at least 92%, at least 94%, at least 96%, at least 98%, at least 99%, or 100%) identical to SEQ ID NO: 149, where the heavy chain variable domain includes a histidine at any of the specific combinations of one or more amino acid positions in SEQ ID NO: 149 listed in Table 4.

In some examples of any of the ABPCs described herein, the first antigen-binding domain comprises a light chain variable domain that is at least 90% identical to SEQ ID NO: 150, wherein the light chain variable domain includes a histidine at position 30 in SEQ ID NO: 150; and a heavy chain variable domain that is at least 90% (e.g., at least 92%, at least 94%, at least 96%, at least 98%, at least 99%, or 100%) identical to SEQ ID NO: 149, where the heavy chain variable domain includes a histidine at any of the specific combinations of one or more amino acid positions in SEQ ID NO: 149 listed in Table 4.

In some examples of any of the ABPCs described herein, the first antigen-binding domain comprises a light chain variable domain that is at least 90% identical to SEQ ID NO: 150, wherein the light chain variable domain includes a histidine at position 31 in SEQ ID NO: 150; and a heavy chain variable domain that is at least 90% (e.g., at least 92%, at least 94%, at least 96%, at least 98%, at least 99%, or 100%) identical to SEQ ID NO: 149, where the heavy chain variable domain includes a histidine at any of the specific combinations of one or more amino acid positions in SEQ ID NO: 149 listed in Table 4.

In some examples of any of the ABPCs described herein, the first antigen-binding domain comprises a light chain variable domain that is at least 90% identical to SEQ ID NO: 150, wherein the light chain variable domain includes a histidine at position 32 in SEQ ID NO: 150; and a heavy chain variable domain that is at least 90% (e.g., at least 92%, at least 94%, at least 96%, at least 98%, at least 99%, or 100%) identical to SEQ ID NO: 149, where the heavy chain variable domain includes a histidine at any of the specific combinations of one or more amino acid positions in SEQ ID NO: 149 listed in Table 4.

In some examples of any of the ABPCs described herein, the first antigen-binding domain comprises a light chain variable domain that is at least 90% identical to SEQ ID NO:

150, wherein the light chain variable domain includes a histidine at position 33 in SEQ ID NO: 150; and a heavy chain variable domain that is at least 90% (e.g., at least 92%, at least 94%, at least 96%, at least 98%, at least 99%, or 100%) identical to SEQ ID NO: 149, where the heavy chain variable domain includes a histidine at any of the specific combinations of one or more amino acid positions in SEQ ID NO: 149 listed in Table 4.

In some examples of any of the ABPCs described herein, the first antigen-binding domain comprises a light chain variable domain that is at least 90% identical to SEQ ID NO: 150, wherein the light chain variable domain includes a histidine at position 34 in SEQ ID NO: 150; and a heavy chain variable domain that is at least 90% (e.g., at least 92%, at least 94%, at least 96%, at least 98%, at least 99%, or 100%) identical to SEQ ID NO: 149, where the heavy chain variable domain includes a histidine at any of the specific combinations of one or more amino acid positions in SEQ ID NO: 149 listed in Table 4.

In some examples of any of the ABPCs described herein, the first antigen-binding domain comprises a light chain variable domain that is at least 90% identical to SEQ ID NO: 150, wherein the light chain variable domain includes a histidine at position 38 in SEQ ID NO: 150; and a heavy chain variable domain that is at least 90% (e.g., at least 92%, at least 94%, at least 96%, at least 98%, at least 99%, or 100%) identical to SEQ ID NO: 149, where the heavy chain variable domain includes a histidine at any of the specific combinations of one or more amino acid positions in SEQ ID NO: 149 listed in Table 4.

In some examples of any of the ABPCs described herein, the first antigen-binding domain comprises a light chain variable domain that is at least 90% identical to SEQ ID NO: 150, wherein the light chain variable domain includes a histidine at position 56 in SEQ ID NO: 150; and a heavy chain variable domain that is at least 90% (e.g., at least 92%, at least 94%, at least 96%, at least 98%, at least 99%, or 100%) identical to SEQ ID NO: 149, where the heavy chain variable domain includes a histidine at any of the specific combinations of one or more amino acid positions in SEQ ID NO: 149 listed in Table 4.

In some examples of any of the ABPCs described herein, the first antigen-binding domain comprises a light chain variable domain that is at least 90% identical to SEQ ID NO: 150, wherein the light chain variable domain includes a histidine at position 95 in SEQ ID NO: 150; and a heavy chain variable domain that is at least 90% (e.g., at least 92%, at least 94%, at least 96%, at least 98%, at least 99%, or 100%) identical to SEQ ID NO: 149, where the heavy chain variable domain includes a histidine at any of the specific combinations of one or more amino acid positions in SEQ ID NO: 149 listed in Table 4.

In some examples of any of the ABPCs described herein, the first antigen-binding domain comprises a light chain variable domain that is at least 90% identical to SEQ ID NO: 150, wherein the light chain variable domain includes a histidine at position 96 in SEQ ID NO: 150; and a heavy chain variable domain that is at least 90% (e.g., at least 92%, at least 94%, at least 96%, at least 98%, at least 99%, or 100%) identical to SEQ ID NO: 149, where the heavy chain variable domain includes a histidine at any of the specific combinations of one or more amino acid positions in SEQ ID NO: 149 listed in Table 4.

In some examples of any of the ABPCs described herein, the first antigen-binding domain comprises a light chain variable domain that is at least 90% identical to SEQ ID NO: 150, wherein the light chain variable domain includes a histidine at position 97 in SEQ ID NO: 150; and a heavy chain variable domain that is at least 90% (e.g., at least 92%, at least 94%, at least 96%, at least 98%, at least 99%, or 100%) identical to SEQ ID NO: 149, where the heavy chain variable domain includes a histidine at any of the specific combinations of one or more amino acid positions in SEQ ID NO: 149 listed in Table 4.

In some examples of any of the ABPCs described herein, the first antigen-binding domain comprises a light chain variable domain that is at least 90% identical to SEQ ID NO: 150, wherein the light chain variable domain includes a histidine at position 101 in SEQ ID NO: 150; and a heavy chain variable domain that is at least 90% (e.g., at least 92%, at least 94%, at least 96%, at least 98%, at least 99%, or 100%) identical to SEQ ID NO: 149, where the heavy chain variable domain includes a histidine at any of the specific combinations of one or more amino acid positions in SEQ ID NO: 149 listed in Table 4.

In some examples of any of the ABPCs described herein, the first antigen-binding domain comprises a light chain variable domain that is at least 90% identical to SEQ ID NO: 150, wherein the light chain variable domain includes a histidine at position 102 in SEQ ID NO: 150; and a heavy chain variable domain that is at least 90% (e.g., at least 92%, at least 94%, at least 96%, at least 98%, at least 99%, or 100%) identical to SEQ ID NO: 149, where the heavy chain variable domain includes a histidine at any of the specific combinations of one or more amino acid positions in SEQ ID NO: 149 listed in Table 4.

In some examples of any of the ABPCs described herein, the first antigen-binding domain includes a heavy chain variable domain of TPP-8988 with one or more (e.g., one, two, three, four, five, six, seven, eight, nine, ten, eleven, twelve, thirteen, fourteen, fifteen, sixteen, seventeen, eighteen, nineteen, or twenty) histidine(s) substituted with an alanine. In some examples of any of the ABPCs described herein, the first antigen-binding domain includes a light chain variable domain of TPP-8988 with one or more (e.g., one, two, three, four, five, six, seven, eight, nine, ten, eleven, twelve, thirteen, fourteen, fifteen, sixteen, seventeen, eighteen, nineteen, or twenty) histidine(s) substituted with an alanine. In some examples of any of the ABPCs described herein, the first antigen-binding domain includes a heavy chain variable domain of TPP-8988 with one or more (e.g., one, two, three, four, five, six, seven, eight, nine, ten, eleven, twelve, thirteen, fourteen, fifteen, sixteen, seventeen, eighteen, nineteen, or twenty) histidines substituted with an alanine; and a light chain variable domain of TPP-8988 with one or more (e.g., one, two, three, four, five, six, seven, eight, nine, ten, eleven, twelve, thirteen, fourteen, fifteen, sixteen, seventeen, eighteen, nineteen, or twenty) histidine(s) substituted with an alanine. In some examples of any of the ABPCs described herein, the heavy chain variable domain of TPP-8988 comprises SEQ ID NO: 149. In some examples of any of the ABPCs described herein, the light chain variable domain of TPP-8988 comprises SEQ ID NO: 150.

In some examples of any of the ABPCs described herein, the first antigen-binding domain comprises a heavy chain variable domain of SEQ ID NO: 149, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, SEQ ID NO: 183, SEQ ID NO: 184, SEQ ID NO: 185, SEQ ID NO: 186, SEQ ID NO: 187, SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, or SEQ ID NO: 197.

In some examples of any of the ABPCs described herein, the first antigen-binding domain includes a light chain variable domain of SEQ ID NO: 150, SEQ ID NO: 198, SEQ ID NO: 199, SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, SEQ ID NO: 212, SEQ ID NO: 213, SEQ ID NO: 214, SEQ ID NO: 215, SEQ ID NO: 216, SEQ ID NO: 217, SEQ ID NO: 218, SEQ ID NO: 219, SEQ ID NO: 220, SEQ ID NO: 221, SEQ ID NO: 222, SEQ ID NO: 223, SEQ ID NO: 224, SEQ ID NO: 225, SEQ ID NO: 226, or SEQ ID NO: 227.

In some examples of any of the ABPCs described herein, the first antigen-binding domain includes a light chain variable domain comprising SEQ ID NO: 150, and a heavy chain variable domain comprising: SEQ ID NO: 149, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, SEQ ID NO: 183, SEQ ID NO: 184, SEQ ID NO: 185, SEQ ID NO: 186, SEQ ID NO: 187, SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, or SEQ ID NO: 197.

In some examples of any of the ABPCs described herein, the first antigen-binding domain includes a light chain variable domain comprising SEQ ID NO: 198, and a heavy chain variable domain comprising: SEQ ID NO: 149, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, SEQ ID NO: 183, SEQ ID NO: 184, SEQ ID NO: 185, SEQ ID NO: 186, SEQ ID NO: 187, SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, or SEQ ID NO: 197.

In some examples of any of the ABPCs described herein, the first antigen-binding domain includes a light chain variable domain comprising SEQ ID NO: 199, and a heavy chain variable domain comprising: SEQ ID NO: 149, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, SEQ ID NO: 183, SEQ ID NO: 184, SEQ ID NO: 185, SEQ ID NO: 186, SEQ ID NO: 187, SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, or SEQ ID NO: 197.

In some examples of any of the ABPCs described herein, the first antigen-binding domain includes a light chain variable domain comprising SEQ ID NO: 200, and a heavy chain variable domain comprising: SEQ ID NO: 149, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, SEQ ID NO: 183, SEQ ID NO: 184, SEQ ID NO: 185, SEQ ID NO: 186, SEQ ID NO: 187, SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, or SEQ ID NO: 197.

In some examples of any of the ABPCs described herein, the first antigen-binding domain includes a light chain variable domain comprising SEQ ID NO: 201, and a heavy chain variable domain comprising: SEQ ID NO: 149, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, SEQ ID NO: 183, SEQ ID NO: 184, SEQ ID NO: 185, SEQ ID NO: 186, SEQ ID NO: 187, SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, or SEQ ID NO: 197.

In some examples of any of the ABPCs described herein, the first antigen-binding domain includes a light chain variable domain comprising SEQ ID NO: 202, and a heavy chain variable domain comprising: SEQ ID NO: 149, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, SEQ ID NO: 183, SEQ ID NO: 184, SEQ ID NO: 185, SEQ ID NO: 186, SEQ ID NO: 187, SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, or SEQ ID NO: 197.

In some examples of any of the ABPCs described herein, the first antigen-binding domain includes a light chain variable domain comprising SEQ ID NO: 203, and a heavy chain variable domain comprising: SEQ ID NO: 149, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, SEQ ID NO: 183, SEQ ID NO: 184, SEQ ID NO: 185, SEQ ID NO: 186, SEQ ID NO: 187, SEQ ID NO: 188, SEQ ID NO:

189, SEQ ID NO: 190, SEQ ID NO: 191, SEQ ID NO: 192, SEQ ID NO: 193, SEQ ID NO: 194, SEQ ID NO: 195, SEQ ID NO: 196, or SEQ ID NO: 197.

In some examples of any of the ABPCs described herein, the first antigen-binding domain includes a light chain variable domain comprising SEQ ID NO: 204, and a heavy chain variable domain comprising: SEQ ID NO: 149, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, SEQ ID NO: 183, SEQ ID NO: 184, SEQ ID NO: 185, SEQ ID NO: 186, SEQ ID NO: 187, SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, or SEQ ID NO: 197.

In some examples of any of the ABPCs described herein, the first antigen-binding domain includes a light chain variable domain comprising SEQ ID NO: 205, and a heavy chain variable domain comprising: SEQ ID NO: 149, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, SEQ ID NO: 183, SEQ ID NO: 184, SEQ ID NO: 185, SEQ ID NO: 186, SEQ ID NO: 187, SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, or SEQ ID NO: 197.

In some examples of any of the ABPCs described herein, the first antigen-binding domain includes a light chain variable domain comprising SEQ ID NO: 206, and a heavy chain variable domain comprising: SEQ ID NO: 149, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, SEQ ID NO: 183, SEQ ID NO: 184, SEQ ID NO: 185, SEQ ID NO: 186, SEQ ID NO: 187, SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, or SEQ ID NO: 197.

In some examples of any of the ABPCs described herein, the first antigen-binding domain includes a light chain variable domain comprising SEQ ID NO: 207, and a heavy chain variable domain comprising: SEQ ID NO: 149, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, SEQ ID NO: 183, SEQ ID NO: 184, SEQ ID NO: 185, SEQ ID NO: 186, SEQ ID NO: 187, SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, or SEQ ID NO: 197.

In some examples of any of the ABPCs described herein, the first antigen-binding domain includes a light chain variable domain comprising SEQ ID NO: 208, and a heavy chain variable domain comprising: SEQ ID NO: 149, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, SEQ ID NO: 183, SEQ ID NO: 184, SEQ ID NO: 185, SEQ ID NO: 186, SEQ ID NO: 187, SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, or SEQ ID NO: 197.

In some examples of any of the ABPCs described herein, the first antigen-binding domain includes a light chain variable domain comprising SEQ ID NO: 209, and a heavy chain variable domain comprising: SEQ ID NO: 149, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, SEQ ID NO: 183, SEQ ID NO: 184, SEQ ID NO: 185, SEQ ID NO: 186, SEQ ID NO: 187, SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, or SEQ ID NO: 197.

In some examples of any of the ABPCs described herein, the first antigen-binding domain includes a light chain variable domain comprising SEQ ID NO: 210, and a heavy chain variable domain comprising: SEQ ID NO: 149, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, SEQ ID NO: 183, SEQ ID NO: 184, SEQ ID NO: 185, SEQ ID NO: 186, SEQ ID NO: 187, SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, or SEQ ID NO: 197.

In some examples of any of the ABPCs described herein, the first antigen-binding domain includes a light chain variable domain comprising SEQ ID NO: 211, and a heavy chain variable domain comprising: SEQ ID NO: 149, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, SEQ ID NO: 183, SEQ ID NO: 184, SEQ ID NO: 185, SEQ ID NO: 186, SEQ ID NO: 187, SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, or SEQ ID NO: 197.

In some examples of any of the ABPCs described herein, the first antigen-binding domain includes a light chain variable domain comprising SEQ ID NO: 212, and a heavy chain variable domain comprising: SEQ ID NO: 149, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, SEQ ID NO: 183, SEQ ID NO: 184, SEQ ID NO: 185, SEQ ID NO: 186, SEQ ID NO: 187, SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, or SEQ ID NO: 197.

In some examples of any of the ABPCs described herein, the first antigen-binding domain includes a light chain variable domain comprising SEQ ID NO: 213, and a heavy chain variable domain comprising: SEQ ID NO: 149, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, SEQ ID NO: 183, SEQ ID NO: 184, SEQ ID NO: 185, SEQ ID NO: 186, SEQ ID NO: 187, SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, or SEQ ID NO: 197.

In some examples of any of the ABPCs described herein, the first antigen-binding domain includes a light chain variable domain comprising SEQ ID NO: 214, and a heavy chain variable domain comprising: SEQ ID NO: 149, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, SEQ ID NO: 183, SEQ ID NO: 184, SEQ ID NO: 185, SEQ ID NO: 186, SEQ ID NO: 187, SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, or SEQ ID NO: 197.

In some examples of any of the ABPCs described herein, the first antigen-binding domain includes a light chain variable domain comprising SEQ ID NO: 215, and a heavy chain variable domain comprising: SEQ ID NO: 149, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, SEQ ID NO: 183, SEQ ID NO: 184, SEQ ID NO: 185, SEQ ID NO: 186, SEQ ID NO: 187, SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, or SEQ ID NO: 197.

In some examples of any of the ABPCs described herein, the first antigen-binding domain includes a light chain variable domain comprising SEQ ID NO: 216, and a heavy chain variable domain comprising: SEQ ID NO: 149, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, SEQ ID NO: 183, SEQ ID NO: 184, SEQ ID NO: 185, SEQ ID NO: 186, SEQ ID NO: 187, SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, or SEQ ID NO: 197.

In some examples of any of the ABPCs described herein, the first antigen-binding domain includes a light chain variable domain comprising SEQ ID NO: 217, and a heavy chain variable domain comprising: SEQ ID NO: 149, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, SEQ ID NO: 183, SEQ ID NO: 184, SEQ ID NO: 185, SEQ ID NO: 186, SEQ ID NO: 187, SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, or SEQ ID NO: 197.

In some examples of any of the ABPCs described herein, the first antigen-binding domain includes a light chain variable domain comprising SEQ ID NO: 218, and a heavy chain variable domain comprising: SEQ ID NO: 149, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, SEQ ID NO: 183, SEQ ID NO: 184, SEQ ID NO: 185, SEQ ID NO: 186, SEQ ID NO: 187, SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, or SEQ ID NO: 197.

In some examples of any of the ABPCs described herein, the first antigen-binding domain includes a light chain variable domain comprising SEQ ID NO: 219, and a heavy chain variable domain comprising: SEQ ID NO: 149, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, SEQ ID NO:

176, SEQ ID NO: 177, SEQ ID NO: 178, SEQ ID NO: 179, SEQ ID NO: 180, SEQ ID NO: 181, SEQ ID NO: 182, SEQ ID NO: 183, SEQ ID NO: 184, SEQ ID NO: 185, SEQ ID NO: 186, SEQ ID NO: 187, SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, or SEQ ID NO: 197.

In some examples of any of the ABPCs described herein, the first antigen-binding domain includes a light chain variable domain comprising SEQ ID NO: 220, and a heavy chain variable domain comprising: SEQ ID NO: 149, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, SEQ ID NO: 183, SEQ ID NO: 184, SEQ ID NO: 185, SEQ ID NO: 186, SEQ ID NO: 187, SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, or SEQ ID NO: 197.

In some examples of any of the ABPCs described herein, the first antigen-binding domain includes a light chain variable domain comprising SEQ ID NO: 221, and a heavy chain variable domain comprising: SEQ ID NO: 149, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, SEQ ID NO: 183, SEQ ID NO: 184, SEQ ID NO: 185, SEQ ID NO: 186, SEQ ID NO: 187, SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, or SEQ ID NO: 197.

In some examples of any of the ABPCs described herein, the first antigen-binding domain includes a light chain variable domain comprising SEQ ID NO: 222, and a heavy chain variable domain comprising: SEQ ID NO: 149, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, SEQ ID NO: 183, SEQ ID NO: 184, SEQ ID NO: 185, SEQ ID NO: 186, SEQ ID NO: 187, SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, or SEQ ID NO: 197.

In some examples of any of the ABPCs described herein, the first antigen-binding domain includes a light chain variable domain comprising SEQ ID NO: 223, and a heavy chain variable domain comprising: SEQ ID NO: 149, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, SEQ ID NO: 183, SEQ ID NO: 184, SEQ ID NO: 185, SEQ ID NO: 186, SEQ ID NO: 187, SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, or SEQ ID NO: 197.

In some examples of any of the ABPCs described herein, the first antigen-binding domain includes a light chain variable domain comprising SEQ ID NO: 224, and a heavy chain variable domain comprising: SEQ ID NO: 149, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, SEQ ID NO: 183, SEQ ID NO: 184, SEQ ID NO: 185, SEQ ID NO: 186, SEQ ID NO: 187, SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, or SEQ ID NO: 197.

In some examples of any of the ABPCs described herein, the first antigen-binding domain includes a light chain variable domain comprising SEQ ID NO: 225, and a heavy chain variable domain comprising: SEQ ID NO: 149, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, SEQ ID NO: 183, SEQ ID NO: 184, SEQ ID NO: 185, SEQ ID NO: 186, SEQ ID NO: 187, SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, or SEQ ID NO: 197.

In some examples of any of the ABPCs described herein, the first antigen-binding domain includes a light chain variable domain comprising SEQ ID NO: 226, and a heavy chain variable domain comprising: SEQ ID NO: 149, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, SEQ ID NO: 183, SEQ ID NO: 184, SEQ ID NO: 185, SEQ ID NO: 186, SEQ ID NO: 187, SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, or SEQ ID NO: 197.

In some examples of any of the ABPCs described herein, the first antigen-binding domain includes a light chain variable domain comprising SEQ ID NO: 227, and a heavy chain variable domain comprising: SEQ ID NO: 149, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, SEQ ID NO: 183, SEQ ID NO: 184, SEQ ID NO: 185, SEQ ID NO: 186, SEQ ID NO: 187, SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, or SEQ ID NO: 197.

Also provided herein are pharmaceutical compositions including any of the ABPCs described herein. Also provided herein are methods of treating a subject in need thereof that include administering a therapeutically effective amount of any of the ABPCs described herein to the subject.

In some examples of any of the ABPCs described herein, a composition including the ABPC (e.g., any of the ABPCs described herein) can provide for an increase (e.g., a detectable increase) (e.g., at least a 1% increase, at least a 2% increase, at least a 5% increase, at least a 10% increase, at least a 15% increase, at least a 20% increase, at least a 25% increase, at least a 30% increase, at least a 35% increase, at least a 40% increase, at least a 45% increase, at least a 50% increase, at least a 55% increase, at least a 60% increase, at least a 65% increase, at least a 70% increase, at least a 75% increase, at least a 80% increase, at least a 85% increase, at least a 90% increase, at least a 95% increase, at least a 100% increase, at least a 120% increase, at least a 140% increase, at least a 160% increase, at least a 180% increase, at least a 200% increase, at least a 250% increase, at least a 300% increase, at least a 350% increase, at least a 400% increase, at least a 450% increase, at least a 500% increase, at least a 1,000% increase, at least a 2,000% increase, at least a 3,000% increase, at least a 4,000% increase, at least a 5,000% increase, at least a 6,000% increase, at least a 7,000% increase, at least a 8,000% increase, at a least a 9,000% increase, or at least a 10,000% increase, or about a 1% increase to about 10,000% increase, about a 1% increase to about a 9,000% increase, about a 1% increase to about a 8,000% increase, about a 1% increase to about a 7,000% increase, about a 1% increase to about a 6,000% increase, about a 1% increase to about a 5,000% increase, about a 1% increase to about a 4,000% increase, about a 1% increase to about a 3,000% increase, about a 1% increase to about a 2,000% increase, about a 1% increase to about a 1,000% increase, about a 1% increase to about a 500% increase, about a 1% increase to about a 450% increase, about a 1% increase to about a 400% increase, about a 1% increase to about a 350% increase, about a 1% increase to about a 300% increase, about a 1% increase to about a 250% increase, about a 1% increase to about a 200% increase, about a 1% increase to about a 180% increase, about a 1% increase to about a 160% increase, about a 1% increase to about a 140% increase, about a 1% increase to about a 120% increase, about a 1% increase to about a 100% increase, about a 1% increase to about a 95% increase, about a 1% increase to about a 90% increase, about a 1% increase to about a 85% increase, about a 1% increase to about a 80% increase, about a 1% increase to about a 75% increase, about a 1% increase to about a 70% increase, about a 1% increase to about a 65% increase, about a 1% increase to about a 60% increase, about a 1% increase to about a 55% increase, about a 1% increase to about a 50% increase, about a 1% increase to about a 45% increase, about a 1% increase to about a 40% increase, about a 1% increase to about a 35% increase, about a 1% increase to about a 25% increase, about a 1% increase to about a 20% increase, about a 1% increase to about a 15% increase, about a 1% increase to about a 10% increase, about a 1% increase to about a 5% increase, about a 2% increase to about 10,000% increase, about a 2% increase to about a 9,000% increase, about a 2% increase to about a 8,000% increase, about a 2% increase to about a 7,000% increase, about a 2% increase to about a 6,000% increase, about a 2% increase to about a 5,000% increase, about a 2% increase to about a 4,000% increase, about a 2% increase to about a 3,000% increase, about a 2% increase to about a 2,000% increase, about a 2% increase to about a 1,000% increase, about a 2% increase to about a 500% increase, about a 2% increase to about a 450% increase, about a 2% increase to about a 400% increase, about a 2% increase to about a 350% increase, about a 2% increase to about a 300% increase, about a 2% increase to about a 250% increase, about a 2% increase to about a 200% increase, about a 2% increase to about a 180% increase, about a 2% increase to about a 160% increase, about a 2% increase to about a 140% increase, about a 2% increase to about a 120% increase, about a 2% increase to about a 100% increase, about a 2% increase to about a 95% increase, about a 2% increase to about a 90% increase, about a 2% increase to about a 85% increase, about a 2% increase to about a 80% increase, about a 2% increase to about a 75% increase, about a 2% increase to about a 70% increase, about a 2% increase to about a 65% increase, about a 2% increase to about a 60% increase, about a 2% increase to about a 55% increase, about a 2% increase to about a 50% increase, about a 2% increase to about a 45% increase, about a 2% increase to about a 40% increase, about a 2% increase to about a 35% increase, about a 2% increase to about a 25% increase, about a 2% increase to about a 20% increase, about a 2% increase to about a 15% increase, about a 2% increase to about a 10% increase, about a 2% increase to about a 5% increase, about a 5% increase to about 10,000% increase, about a 5% increase to about a 9,000% increase, about a 5% increase to about a 8,000% increase, about a 5% increase to about a 7,000% increase, about a 5% increase to about a 6,000% increase, about a 5% increase to about a 5,000% increase, about a 5% increase to about a 4,000% increase, about a 5% increase to about a 3,000% increase, about a 5% increase to about a 2,000% increase, about a 5% increase to about a 1,000% increase, about a 5% increase to about a 500% increase, about a 5% increase to about a 450% increase, about a 5% increase to about a 400% increase, about a 5% increase to about a 350% increase, about a 5% increase to about a 300% increase, about a 5% increase to about a 250% increase, about a 5% increase to about a 200% increase, about a 5% increase to about a 180% increase, about a 5% increase to about a 160% increase, about a 5% increase to about a 140% increase, about a 5% increase to about a 120% increase, about a 5% increase to about a 100% increase, about a 5% increase to about a 95% increase, about a 5% increase to about a 90% increase, about a 5% increase to about a 85% increase, about a 5% increase to about a 80% increase, about a 5% increase to about a 75% increase, about a 5% increase to about a 70% increase, about a 5% increase to about a 65% increase, about a 5% increase to about a 60% increase, about a 5% increase to about a 55% increase, about a 5% increase to about a 50% increase, about a 5% increase to about a 45% increase, about a 5% increase to about a 40% increase, about a 5% increase to about a 35% increase, about a 5% increase to about a 25% increase, about a 5% increase to about a 20% increase, about a 5% increase to about a 15% increase, about a 5% increase to about a 10% increase, about a 10% increase to about 10,000% increase, about a 10% increase to about a 9,000% increase, about a 10% increase to about a 8,000% increase, about a 10% increase to about a 7,000% increase, about a 10% increase to about a 6,000% increase, about a 10% increase to about a 5,000% increase, about a 10% increase to about a 4,000% increase, about a 10% increase to about a 3,000% increase, about a 10% increase to about a 2,000% increase, about a 10% increase to about a 1,000% increase, about a 10% increase to about a 500% increase, about a 10% increase to about a 450% increase, about a 10% increase to about a 400% increase, about a 10% increase to about a 350% increase, about a 10% increase to about a 300% increase, about a 10% increase to about a 250% increase, about a 10% increase to about a 200% increase, about a 10% increase to about a 180% increase, about a 10% increase to about a 160% increase, about a 10% increase to about a 140% increase, about a 10% increase to about a 120% increase, about a 10% increase to about a 100% increase, about a 10% increase to about a 95% increase, about a 10% increase to about a 90% increase, about a 10% increase to about a 85% increase, about a 10% increase to about a 80% increase, about a 10% increase to about a 75% increase, about a 10% increase to about a 70% increase, about a 10% increase to about a 65% increase, about a 10% increase to about a 60% increase, about a 10% increase to about a 55% increase, about a 10% increase to about a 50% increase, about a 10% increase to about a 45% increase, about a 10% increase to about a 40% increase, about a 10% increase to about a 35% increase, about a 10% increase to about a 30% increase, about a 10% increase to about a 25% increase, about a 10% increase to about a 20% increase, about a 10% increase to about a 15% increase, about a 15% increase to about 10,000% increase, about a 15% increase to about a 9,000% increase, about a 15% increase to about a 8,000% increase, about a 15% increase to about a 7,000% increase, about a 15% increase to about a 6,000% increase, about a 15% increase to about a 5,000% increase, about a 15% increase to about a 4,000% increase, about a 15% increase to about a 3,000% increase, about a 15% increase to about a 2,000% increase, about a 15% increase to about a 1,000% increase, about a 15% increase to about a 500% increase, about a 15% increase to about a 450% increase, about a 15% increase to about a 400% increase, about a 15% increase to about a 350% increase, about a 15% increase to about a 300% increase, about a 15% increase to about a 250% increase, about a 15% increase to about a 200% increase, about a 15% increase to about a 180% increase, about a 15% increase to about a 160% increase, about a 15% increase to about a 140% increase, about a 15% increase to about a 120% increase, about a 15% increase to about a 100% increase, about a 15% increase to about a 95% increase, about a 15% increase to about a 90% increase, about a 15% increase to about a 85% increase, about a 15% increase to about a 80% increase, about a 15% increase to about a 75% increase, about a 15% increase to about a 70% increase, about a 15% increase to about a 65% increase, about a 15% increase to about a 60% increase, about a 15% increase to about a 55% increase, about a 15% increase to about a 50% increase, about a 15% increase to about a 45% increase, about a 15% increase to about a 40% increase, about a 15% increase to about a 35% increase, about a 15% increase to about a 30% increase, about a 15% increase to about a 25% increase, about a 15% increase to about a 20% increase, about a 20% increase to about 10,000% increase, about a 20% increase to about a 9,000% increase, about a 20% increase to about a 8,000% increase, about a 20% increase to about a 7,000% increase, about a 20% increase to about a 6,000% increase, about a 20% increase to about a 5,000% increase, about a 20% increase to about a 4,000% increase, about a 20% increase to about a 3,000% increase, about a 20% increase to about a 2,000% increase, about a 20% increase to about a 1,000% increase, about a 20% increase to about a 500% increase, about a 20% increase to about a 450% increase, about a 20% increase to about a 400% increase, about a 20% increase to about a 350% increase, about a 20% increase to about a 300% increase, about a 20% increase to about a 250% increase, about a 20% increase to about a 200% increase, about a 20% increase to about a 180% increase, about a 20% increase to about a 160% increase, about a 20% increase to about a 140% increase, about a 20% increase to about a 120% increase, about a 20% increase to about a 100% increase, about a 20% increase to about a 95% increase, about a 20% increase to about a 90% increase, about a 20% increase to about a 85% increase, about a 20% increase to about a 80% increase, about a 20% increase to about a 75% increase, about a 20% increase to about a 70% increase, about a 20% increase to about a 65% increase, about a 20% increase to about a 60% increase, about a 20% increase to about a 55% increase, about a 20% increase to about a 50% increase, about a 20% increase to about a 45% increase, about a 20% increase to about a 40% increase, about a 20% increase to about a 35% increase, about a 20% increase to about a 30% increase, about a 20% increase to about a 25% increase, about a 25% increase to about 10,000% increase, about a 25% increase to about a 9,000% increase, about a 25% increase to about a 8,000% increase, about a 25% increase to about a 7,000% increase, about a 25% increase to about a 6,000% increase, about a 25% increase to about a 5,000% increase, about a 25% increase to about a 4,000% increase, about a 25% increase to about a 3,000% increase, about a 25% increase to about a 2,000% increase, about a 25% increase to about a 1,000% increase, about a 25% increase to about a 500% increase, about a 25% increase to about a 450% increase, about a 25% increase to about a 400% increase, about a 25% increase to about a 350% increase, about a 25% increase to about a 300% increase, about a 25% increase to about a 250% increase, about a 25% increase to about a 200% increase, about a 25% increase to about a 180% increase, about a 25% increase to about a 160% increase, about a 25% increase to about a 140% increase, about a 25% increase to about a 120% increase, about a 25% increase to about a 100% increase, about a 25% increase to about a 95% increase, about a 25% increase to about a 90% increase, about a 25% increase to about a 85% increase, about a 25% increase to about a 80% increase, about a 25% increase to about a 75% increase, about a 25% increase to about a 70% increase, about a 25% increase to about a 65% increase, about a 25% increase to about a 60% increase, about a 25% increase to about a 55% increase, about a 25% increase to about a 50% increase, about a 25% increase to about a 45% increase, about a 25% increase to about a 40% increase, about a 25% increase to about a 35% increase, about a 25% increase to about a 30% increase, about a 30% increase to about 10,000% increase, about a 30% increase to about a 9,000% increase, about a 30% increase to about a 8,000% increase, about a 30% increase to about a 7,000% increase, about a 30% increase to about a 6,000% increase, about a 30% increase to about a 5,000% increase, about a 30% increase to about a 4,000% increase, about a 30% increase to about a 3,000% increase, about a 30% increase to about a 2,000% increase, about a 30% increase to about a 1,000% increase, about a 30% increase to about a 500% increase, about a 30% increase to about a 450% increase, about a 30% increase to about a 400% increase, about a 30% increase to about a 350% increase, about a 30% increase to about a 300% increase, about a 30% increase to about a 250% increase, about a 30% increase to about a 200% increase, about a 30% increase to about a 180% increase, about a 30% increase to about a 160% increase, about a 30% increase to about a 140% increase, about a 30% increase to about a 120% increase, about a 30% increase to about a 100% increase, about a 30% increase to about a 95% increase, about a 30% increase to about a 90% increase, about a 30% increase to about a 85% increase, about a 30% increase to about a 80% increase, about a 30% increase to about a 75% increase, about a 30% increase to about a 70% increase, about a 30% increase to about a 65% increase, about a 30% increase to about a 60% increase, about a 30% increase to about a 55% increase, about a 30% increase to about a 50% increase, about a 30% increase to about a 45% increase, about a 30% increase to about a 40% increase, about a 30% increase to about a 35% increase, about a 35% increase to about 10,000% increase, about a 35% increase to about a 9,000% increase, about a 35% increase to about a 8,000% increase, about a 35% increase to about a 7,000% increase, about a 35% increase to about a 6,000% increase, about a 35% increase to about a 5,000% increase, about a 35% increase to about a 4,000% increase, about a 35% increase to about a 3,000% increase, about a 35% increase to about a 2,000% increase, about a 35% increase to about a 1,000% increase, about a 35% increase to about a 500% increase, about a 35% increase to about a 450% increase, about a 35% increase to about a 400% increase, about a 35% increase to about a 350% increase, about a 35% increase to about a 300% increase, about a 35% increase to about a 250% increase, about a 35% increase to about a 200% increase, about a 35% increase to about a 180% increase, about a 35% increase to about a 160% increase, about a 35% increase to about a 140% increase, about a 35% increase to about a 120% increase, about a 35% increase to about a 100% increase, about a 35% increase to about a 95% increase, about a 35% increase to about a 90% increase, about a 35% increase to about a 85% increase, about a 35% increase to about a 80% increase, about a 35% increase to about a 75% increase, about a 35% increase to about a 70% increase, about a 35% increase to about a 65% increase, about a 35% increase to about a 60% increase, about a 35% increase to about a 55% increase, about a 35% increase to about a 50% increase, about a 35% increase to about a 45% increase, about a 35% increase to about a 40% increase, about a 40% increase to about 10,000% increase, about a 40% increase to about a 9,000% increase, about a 40% increase to about a 8,000% increase, about a 40% increase to about a 7,000% increase, about a 40% increase to about a 6,000% increase, about a 40% increase to about a 5,000% increase, about a 40% increase to about a 4,000% increase, about a 40% increase to about a 3,000% increase, about a 40% increase to about a 2,000% increase, about a 40% increase to about a 1,000% increase, about a 40% increase to about a 500% increase, about a 40% increase to about a 450% increase, about a 40% increase to about a 400% increase, about a 40% increase to about a 350% increase, about a 40% increase to about a 300% increase, about a 40% increase to about a 250% increase, about a 40% increase to about a 200% increase, about a 40% increase to about a 180% increase, about a 40% increase to about a 160% increase, about a 40% increase to about a 140% increase, about a 40% increase to about a 120% increase, about a 40% increase to about a 100% increase, about a 40% increase to about a 95% increase, about a 40% increase to about a 90% increase, about a 40% increase to about a 85% increase, about a 40% increase to about a 80% increase, about a 40% increase to about a 75% increase, about a 40% increase to about a 70% increase, about a 40% increase to about a 65% increase, about a 40% increase to about a 60% increase, about a 40% increase to about a 55% increase, about a 40% increase to about a 50% increase, about a 40% increase to about a 45% increase, about a 45% increase to about 10,000% increase, about a 45% increase to about a 9,000% increase, about a 45% increase to about a 8,000% increase, about a 45% increase to about a 7,000% increase, about a 45% increase to about a 6,000% increase, about a 45% increase to about a 5,000% increase, about a 45% increase to about a 4,000% increase, about a 45% increase to about a 3,000% increase, about a 45% increase to about a 2,000% increase, about a 45% increase to about a 1,000% increase, about a 45% increase to about a 500% increase, about a 45% increase to about a 450% increase, about a 45% increase to about a 400% increase, about a 45% increase to about a 350% increase, about a 45% increase to about a 300% increase, about a 45% increase to about a 250% increase, about a 45% increase to about a 200% increase, about a 45% increase to about a 180% increase, about a 45% increase to about a 160% increase, about a 45% increase to about a 140% increase, about a 45% increase to about a 120% increase, about a 45% increase to about a 100% increase, about a 45% increase to about a 95% increase, about a 45% increase to about a 90% increase, about a 45% increase to about a 85% increase, about a 45% increase to about a 80% increase, about a 45% increase to about a 75% increase, about a 45% increase to about a 70% increase, about a 45% increase to about a 65% increase, about a 45% increase to about a 60% increase, about a 45% increase to about a 55% increase, about a 45% increase to about a 50% increase, about a 50% increase to about 10,000% increase, about a 50% increase to about a 9,000% increase, about a 50% increase to about a 8,000% increase, about a 50% increase to about a 7,000% increase, about a 50% increase to about a 6,000% increase, about a 50% increase to about a 5,000% increase, about a 50% increase to about a 4,000% increase, about a 50% increase to about a 3,000% increase, about a 50% increase to about a 2,000% increase, about a 50% increase to about a 1,000% increase, about a 50% increase to about a 500% increase, about a 50% increase to about a 450% increase, about a 50% increase to about a 400% increase, about a 50% increase to about a 350% increase, about a 50% increase to about a 300% increase, about a 50% increase to about a 250% increase, about a 50% increase to about a 200% increase, about a 50% increase to about a 180% increase, about a 50% increase to about a 160% increase, about a 50% increase to about a 140% increase, about a 50% increase to about a 120% increase, about a 50% increase to about a 100% increase, about a 50% increase to about a 95% increase, about a 50% increase to about a 90% increase, about a 50% increase to about a 85% increase, about a 50% increase to about a 80% increase, about a 50% increase to about a 75% increase, about a 50% increase to about a 70% increase, about a 50% increase to about a 65% increase, about a 50% increase to about a 60% increase, about a 50% increase to about a 55% increase, about a 55% increase to about 10,000% increase, about a 55% increase to about a 9,000% increase, about a 55% increase to about a 8,000% increase, about a 55% increase to about a 7,000% increase, about a 55% increase to about a 6,000% increase, about a 55% increase to about a 5,000% increase, about a 55% increase to about a 4,000% increase, about a 55% increase to about a 3,000% increase, about a 55% increase to about a 2,000% increase, about a 55% increase to about a 1,000% increase, about a 55% increase to about a 500% increase, about a 55% increase to about a 450% increase, about a 55% increase to about a 400% increase, about a 55% increase to about a 350% increase, about a 55% increase to about a 300% increase, about a 55% increase to about a 250% increase, about a 55% increase to about a 200% increase, about a 55% increase to about a 180% increase, about a 55% increase to about a 160% increase, about a 55% increase to about a 140% increase, about a 55% increase to about a 120% increase, about a 55% increase to about a 100% increase, about a 55% increase to about a 95% increase, about a 55% increase to about a 90% increase, about a 55% increase to about a 85% increase, about a 55% increase to about a 80% increase, about a 55% increase to about a 75% increase, about a 55% increase to about a 70% increase, about a 55% increase to about a 65% increase, about a 55% increase to about a 60% increase, about a 60% increase to about 10,000% increase, about a 60% increase to about a 9,000% increase, about a 60% increase to about a 8,000% increase, about a 60% increase to about a 7,000% increase, about a 60% increase to about a 6,000% increase, about a 60% increase to about a 5,000% increase, about a 60% increase to about a 4,000% increase, about a 60% increase to about a 3,000% increase, about a 60% increase to about a 2,000% increase, about a 60% increase to about a 1,000% increase, about a 60% increase to about a 500% increase, about a 60% increase to about a 450% increase, about a 60% increase to about a 400% increase, about a 60% increase to about a 350% increase, about a 60% increase to about a 300% increase, about a 60% increase to about a 250% increase, about a 60% increase to about a 200% increase, about a 60% increase to about a 180% increase, about a 60% increase to about a 160% increase, about a 60% increase to about a 140% increase, about a 60% increase to about a 120% increase, about a 60% increase to about a 100% increase, about a 60% increase to about a 95% increase, about a 60% increase to about a 90% increase, about a 60% increase to about a 85% increase, about a 60% increase to about a 80% increase, about a 60% increase to about a 75% increase, about a 60% increase to about a 70% increase, about a 60% increase to about a 65% increase, about a 65% increase to about 10,000% increase, about a 65% increase to about a 9,000% increase, about a 65% increase to about a 8,000% increase, about a 65% increase to about a 7,000% increase, about a 65% increase to about a 6,000% increase, about a 65% increase to about a 5,000% increase, about a 65% increase to about a 4,000% increase, about a 65% increase to about a 3,000% increase, about a 65% increase to about a 2,000% increase, about a 65% increase to about a 1,000% increase, about a 65% increase to about a 500% increase, about a 65% increase to about a 450% increase, about a 65% increase to about a 400% increase, about a 65% increase to about a 350% increase, about a 65% increase to about a 300% increase, about a 65% increase to about a 250% increase, about a 65% increase to about a 200% increase, about a 65% increase to about a 180% increase, about a 65% increase to about a 160% increase, about a 65% increase to about a 140% increase, about a 65% increase to about a 120% increase, about a 65% increase to about a 100% increase, about a 65% increase to about a 95% increase, about a 65% increase to about a 90% increase, about a 65% increase to about a 85% increase, about a 65% increase to about a 80% increase, about a 65% increase to about a 75% increase, about a 65% increase to about a 70% increase, about a 70% increase to about 10,000% increase, about a 70% increase to about a 9,000% increase, about a 70% increase to about a 8,000% increase, about a 70% increase to about a 7,000% increase, about a 70% increase to about a 6,000% increase, about a 70% increase to about a 5,000% increase, about a 70% increase to about a 4,000% increase, about a 70% increase to about a 3,000% increase, about a 70% increase to about a 2,000% increase, about a 70% increase to about a 1,000% increase, about a 70% increase to about a 500% increase, about a 70% increase to about a 450% increase, about a 70% increase to about a 400% increase, about a 70% increase to about a 350% increase, about a 70% increase to about a 300% increase, about a 70% increase to about a 250% increase, about a 70% increase to about a 200% increase, about a 70% increase to about a 180% increase, about a 70% increase to about a 160% increase, about a 70% increase to about a 140% increase, about a 70% increase to about a 120% increase, about a 70% increase to about a 100% increase, about a 70% increase to about a 95% increase, about a 70% increase to about a 90% increase, about a 70% increase to about a 85% increase, about a 70% increase to about a 80% increase, about a 70% increase to about a 75% increase, about a 75% increase to about 10,000% increase, about a 75% increase to about a 9,000% increase, about a 75% increase to about a 8,000% increase, about a 75% increase to about a 7,000% increase, about a 75% increase to about a 6,000% increase, about a 75% increase to about a 5,000% increase, about a 75% increase to about a 4,000% increase, about a 75% increase to about a 3,000% increase, about a 75% increase to about a 2,000% increase, about a 75% increase to about a 1,000% increase, about a 75% increase to about a 500% increase, about a 75% increase to about a 450% increase, about a 75% increase to about a 400% increase, about a 75% increase to about a 350% increase, about a 75% increase to about a 300% increase, about a 75% increase to about a 250% increase, about a 75% increase to about a 200% increase, about a 75% increase to about a 180% increase, about a 75% increase to about a 160% increase, about a 75% increase to about a 140% increase, about a 75% increase to about a 120% increase, about a 75% increase to about a 100% increase, about a 75% increase to about a 95% increase, about a 75% increase to about a 90% increase, about a 75% increase to about a 85% increase, about a 75% increase to about a 80%, about a 80% increase to about 10,000% increase, about a 80% increase to about a 9,000% increase, about a 80% increase to about a 8,000% increase, about a 80% increase to about a 7,000% increase, about a 80% increase to about a 6,000% increase, about a 80% increase to about a 5,000% increase, about a 80% increase to about a 4,000% increase, about a 80% increase to about a 3,000% increase, about a 80% increase to about a 2,000% increase, about a 80% increase to about a 1,000% increase, increase, about a 80% increase to about a 500% increase, about a 80% increase to about a 450% increase, about a 80% increase to about a 400% increase, about a 80% increase to about a 350% increase, about a 80% increase to about a 300% increase, about a 80% increase to about a 250% increase, about a 80% increase to about a 200% increase, about a 80% increase to about a 180% increase, about a 80% increase to about a 160% increase, about a 80% increase to about a 140% increase, about a 80% increase to about a 120% increase, about a 80% increase to about a 100% increase, about a 80% increase to about a 95% increase, about a 80% increase to about a 90% increase, about a 80% increase to about a 85% increase, about a 85% increase to about 10,000% increase, about a 85% increase to about a 9,000% increase, about a 85% increase to about a 8,000% increase, about a 85% increase to about a 7,000% increase, about a 85% increase to about a 6,000% increase, about a 85% increase to about a 5,000% increase, about a 85% increase to about a 4,000% increase, about a 85% increase to about a 3,000% increase, about a 85% increase to about a 2,000% increase, about a 85% increase to about a 1,000% increase, about a 85% increase to about a 500% increase, about a 85% increase to about a 450% increase, about a 85% increase to about a 400% increase, about a 85% increase to about a 350% increase, about a 85% increase to about a 300% increase, about a 85% increase to about a 250% increase, about a 85% increase to about a 200% increase, about a 85% increase to about a 180% increase, about a 85% increase to about a 160% increase, about a 85% increase to about a 140% increase, about a 85% increase to about a 120% increase, about a 85% increase to about a 100% increase, about a 85% increase to about a 95% increase, about a 85% increase to about a 90% increase, about a 90% increase to about 10,000% increase, about a 90% increase to about a 9,000% increase, about a 90% increase to about a 8,000% increase, about a 90% increase to about a 7,000% increase, about a 90% increase to about a 6,000% increase, about a 90% increase to about a 5,000% increase, about a 90% increase to about a 4,000% increase, about a 90% increase to about a 3,000% increase, about a 90% increase to about a 2,000% increase, about a 90% increase to about a 1,000% increase, about a 90% increase to about a 500% increase, about a 90% increase to about a 450% increase, about a 90% increase to about a 400% increase, about a 90% increase to about a 350% increase, about a 90% increase to about a 300% increase, about a 90% increase to about a 250% increase, about a 90% increase to about a 200% increase, about a 90% increase to about a 180% increase, about a 90% increase to about a 160% increase, about a 90% increase to about a 140% increase, about a 90% increase to about a 120% increase, about a 90% increase to about a 100% increase, about a 90% increase to about a 95% increase, about a 95% increase to about 10,000% increase, about a 95% increase to about a 9,000% increase, about a 95% increase to about a 8,000% increase, about a 95% increase to about a 7,000% increase, about a 95% increase to about a 6,000% increase, about a 95% increase to about a 5,000% increase, about a 95% increase to about a 4,000% increase, about a 95% increase to about a 3,000% increase, about a 95% increase to about a 2,000% increase, about a 95% increase to about a 1,000% increase, about a 95% increase to about a 500% increase, about a 95% increase to about a 450% increase, about a 95% increase to about a 400% increase, about a 95% increase to about a 350% increase, about a 95% increase to about a 300% increase, about a 95% increase to about a 250% increase, about a 95% increase to about a 200% increase, about a 95% increase to about a 180% increase, about a 95% increase to about a 160% increase, about a 95% increase to about a 140% increase, about a 95% increase to about a 120% increase, about a 95% increase to about a 100% increase, about a 100% increase to about 10,000% increase, about a 100% increase to about a 9,000% increase, about a 100% increase to about a 8,000% increase, about a 100% increase to about a 7,000% increase, about a 100% increase to about a 6,000% increase, about a 100% increase to about a 5,000% increase, about a 100% increase to about a 4,000% increase, about a 100% increase to about a 3,000% increase, about a 100% increase to about a 2,000% increase, about a 100% increase to about a 1,000% increase, about a 100% increase to about a 500% increase, about a 100% increase to about a 450% increase, about a 100% increase to about a 400% increase, about a 100% increase to about a 350% increase, about a 100% increase to about a 300% increase, about a 100% increase to about a 250% increase, about a 100% increase to about a 200% increase, about a 100% increase to about a 180% increase, about a 100% increase to about a 160% increase, about a 100% increase to about a 140% increase, about a 100% increase to about a 120% increase, about a 120% increase to about 10,000% increase, about a 120% increase to about a 9,000% increase, about a 120% increase to about a 8,000% increase, about a 120% increase to about a 7,000% increase, about a 120% increase to about a 6,000% increase, about a 120% increase to about a 5,000% increase, about a 120% increase to about a 4,000% increase, about a 120% increase to about a 3,000% increase, about a 120% increase to about a 2,000% increase, about a 120% increase to about a 1,000% increase, about a 120% increase to about a 500% increase, about a 120% increase to about a 450% increase, about a 120% increase to about a 400% increase, about a 120% increase to about a 350% increase, about a 120% increase to about a 300% increase, about a 120% increase to about a 250% increase, about a 120% increase to about a 200% increase, about a 120% increase to about a 180% increase, about a 120% increase to about a 160% increase, about a 120% increase to about a 140% increase, about a 140% increase to about 10,000% increase, about a 140% increase to about a 9,000% increase, about a 140% increase to about a 8,000% increase, about a 140% increase to about a 7,000% increase, about a 140% increase to about a 6,000% increase, about a 140% increase to about a 5,000% increase, about a 140% increase to about a 4,000% increase, about a 140% increase to about a 3,000% increase, about a 140% increase to about a 2,000% increase, about a 140% increase to about a 1,000% increase, about a 140% increase to about a 500% increase, about a 140% increase to about a 450% increase, about a 140% increase to about a 400% increase, about a 140% increase to about a 350% increase, about a 140% increase to about a 300% increase, about a 140% increase to about a 250% increase, about a 140% increase to about a 200% increase, about a 140% increase to about a 180% increase, about a 140% increase to about a 160% increase, about a 160% increase to about 10,000% increase, about a 160% increase to about a 9,000% increase, about a 160% increase to about a 8,000% increase, about a 160% increase to about a 7,000% increase, about a 160% increase to about a 6,000% increase, about a 160% increase to about a 5,000% increase, about a 160% increase to about a 4,000% increase, about a 160% increase to about a 3,000% increase, about a 160% increase to about a 2,000% increase, about a 160% increase to about a 1,000% increase, about a 160% increase to about a 500% increase, about a 160% increase to about a 450% increase, about a 160% increase to about a 400% increase, about a 160% increase to about a 350% increase, about a 160% increase to about a 300% increase, about a 160% increase to about a 250% increase, about a 160% increase to about a 200% increase, about a 160% increase to about a 180% increase, about a 180% increase to about 10,000% increase, about a 180% increase to about a 9,000% increase, about a 180% increase to about a 8,000% increase, about a 180% increase to about a 7,000% increase, about a 180% increase to about a 6,000% increase, about a 180% increase to about a 5,000% increase, about a 180% increase to about a 4,000% increase, about a 180% increase to about a 3,000% increase, about a 180% increase to about a 2,000% increase, about a 180% increase to about a 1,000% increase, about a 180% increase to about a 500% increase, about a 180% increase to about a 450% increase, about a 180% increase to about a 400% increase, about a 180% increase to about a 350% increase, about a 180% increase to about a 300% increase, about a 180% increase to about a 250% increase, about a 180% increase to about a 200% increase, about a 200% increase to about 10,000% increase, about a 200% increase to about a 9,000% increase, about a 200% increase to about a 8,000% increase, about a 200% increase to about a 7,000% increase, about a 200% increase to about a 6,000% increase, about a 200% increase to about a 5,000% increase, about a 200% increase to about a 4,000% increase, about a 200% increase to about a 3,000% increase, about a 200% increase to about a 2,000% increase, about a 200% increase to about a 1,000% increase, about a 200% increase to about a 500% increase, about a 200% increase to about a 450% increase, about a 200% increase to about a 400% increase, about a 200% increase to about a 350% increase, about a 200% increase to about a 300% increase, about a 200% increase to about a 250% increase, about a 250% increase to about 10,000% increase, about a 250% increase to about a 9,000% increase, about a 250% increase to about a 8,000% increase, about a 250% increase to about a 7,000% increase, about a 250% increase to about a 6,000% increase, about a 250% increase to about a 5,000% increase, about a 250% increase to about a 4,000% increase, about a 250% increase to about a 3,000% increase, about a 250% increase to about a 2,000% increase, about a 250% increase to about a 1,000% increase, about a 250% increase to about a 500% increase, about a 250% increase to about a 450% increase, about a 250% increase to about a 400% increase, about a 250% increase to about a 350% increase, about a 250% increase to about a 300% increase, about a 300% increase to about 10,000% increase, about a 300% increase to about a 9,000% increase, about a 300% increase to about a 8,000% increase, about a 300% increase to about a 7,000% increase, about a 300% increase to about a 6,000% increase, about a 300% increase to about a 5,000% increase, about a 300% increase to about a 4,000% increase, about a 300% increase to about a 3,000% increase, about a 300% increase to about a 2,000% increase, about a 300% increase to about a 1,000% increase, about a 300% increase to about a 500% increase, about a 300% increase to about a 450% increase, about a 300% increase to about a 400% increase, about a 300% increase to about a 350% increase, about a 350% increase to about 10,000% increase, about a 350% increase to about a 9,000% increase, about a 350% increase to about a 8,000% increase, about a 350% increase to about a 7,000% increase, about a 350% increase to about a 6,000% increase, about a 350% increase to about a 5,000% increase, about a 350% increase to about a 4,000% increase, about a 350% increase to about a 3,000% increase, about a 350% increase to about a 2,000% increase, about a 350% increase to about a 1,000% increase, about a 350% increase to about a 500% increase, about a 350% increase to about a 450% increase, about a 350% increase to about a 400% increase, about a 400% increase to about 10,000% increase, about a 400% increase to about a 9,000% increase, about a 400% increase to about a 8,000% increase, about a 400% increase to about a 7,000% increase, about a 400% increase to about a 6,000% increase, about a 400% increase to about a 5,000% increase, about a 400% increase to about a 4,000% increase, about a 400% increase to about a 3,000% increase, about a 400% increase to about a 2,000% increase, about a 400% increase to about a 1,000% increase, about a 400% increase to about a 500% increase, about a 400% increase to about a 450% increase, about a 450% increase to about 10,000% increase, about a 450% increase to about a 9,000% increase, about a 450% increase to about a 8,000% increase, about a 450% increase to about a 7,000% increase, about a 450% increase to about a 6,000% increase, about a 450% increase to about a 5,000% increase, about a 450% increase to about a 4,000% increase, about a 450% increase to about a 3,000% increase, about a 450% increase to about a 2,000% increase, about a 450% increase to about a 1,000% increase, about a 450% increase to about a 500% increase, about a 500% increase to about 10,000% increase, about a 500% increase to about a 9,000% increase, about a 500% increase to about a 8,000% increase, about a 500% increase to about a 7,000% increase, about a 500% increase to about a 6,000% increase, about a 500% increase to about a 5,000% increase, about a 500% increase to about a 4,000% increase, about a 500% increase to about a 3,000% increase, about a 500% increase to about a 2,000% increase, about a 500% increase to about a 1,000% increase, about a 1,000% increase to about 10,000% increase, about a 1,000% increase to about a 9,000% increase, about a 1,000% increase to about a 8,000% increase, about a 1,000% increase to about a 7,000% increase, about a 1,000% increase to about a 6,000% increase, about a 1,000% increase to about a 5,000% increase, about a 1,000% increase to about a 4,000% increase, about a 1,000% increase to about a 3,000% increase, about a 1,000% increase to about a 2,000% increase, about a 2,000% increase to about 10,000% increase, about a 2,000% increase to about a 9,000% increase, about a 2,000% increase to about a 8,000% increase, about a 2,000% increase to about a 7,000% increase, about a 2,000% increase to about a 6,000% increase, about a 2,000% increase to about a 5,000% increase, about a 2,000% increase to about a 4,000% increase, about a 2,000% increase to about a 3,000% increase, about a 3,000% increase to about 10,000% increase, about a 3,000% increase to about a 9,000% increase, about a 3,000% increase to about a 8,000% increase, about a 3,000% increase to about a 7,000% increase, about a 3,000% increase to about a 6,000% increase, about a 3,000% increase to about a 5,000% increase, about a 3,000% increase to about a 4,000% increase, about a 4,000% increase to about 10,000% increase, about a 4,000% increase to about a 9,000% increase, about a 4,000% increase to about a 8,000% increase, about a 4,000% increase to about a 7,000% increase, about a 4,000% increase to about a 6,000% increase, about a 4,000% increase to about a 5,000% increase, about a 5,000% increase to about 10,000% increase, about a 5,000% increase to about a 9,000% increase, about a 5,000% increase to about a 8,000% increase, about a 5,000% increase to about a 7,000% increase, about a 5,000% increase to about a 6,000% increase, about a 6,000% increase to about 10,000% increase, about a 6,000% increase to about a 9,000% increase, about a 6,000% increase to about a 8,000% increase, about a 6,000% increase to about a 7,000% increase, about a 7,000% increase to about 10,000% increase, about a 7,000% increase to about a 9,000% increase, about a 7,000% increase to about a 8,000% increase, about a 8,000% increase to about 10,000% increase, about a 8,000% increase to about a 9,000% increase, or about a 9,000% increase to about 10,000%) in toxin liberation in the target mammalian cell (e.g., any of the target mammalian cells described herein) as compared to a composition including the same amount of a control ABPC (e.g., any of the exemplary control ABPCs described herein).

In some examples of any of the ABPCs described herein, a composition including the ABPC (e.g., any of the ABPCs described herein) can provide for an increase (e.g., a detectable increase) (e.g., at least a 0.1-fold increase, at least a 0.2-fold increase, at least a 0.3-fold increase, at least a 0.4-fold increase, at least a 0.5-fold increase, at least a 0.6-fold increase, at least a 0.7-fold increase, at least a 0.8-fold increase, at least a 0.9-fold increase, at least a 1.0-fold increase, at least a 1.2-fold increase, at least a 1.4-fold increase, at least a 1.5-fold increase, at least a 1.6-fold increase, at least a 1.8-fold increase, at least a 2.0-fold increase, at least a 2.2-fold increase, at least a 2.4-fold increase, at least a 2.5-fold increase, at least a 2.6-fold increase, at least a 2.8-fold increase, at least a 3.0-fold increase, at least a 3.5-fold increase, at least a 4.0-fold increase, at least a 4.5-fold increase, at least a 5.0-fold increase, at least a 5.5-fold increase, at least a 6.0-fold increase, at least a 6.5-fold increase, at least a 7.0-fold increase, at least a 7.5-fold increase, at least a 8.0-fold increase, at least a 8.5-fold increase, at least a 9.0-fold increase, at least a 9.5-fold increase, at least a 10-fold increase, at least a 15-fold increase, at least a 20-fold increase, at least a 25-fold increase, at least a 30-fold increase, at least a 35-fold increase, at least a 40-fold increase, at least a 45-fold increase, at least a 50-fold increase, at least a 55-fold increase, at least a 60-fold increase, at least a 65-fold increase, at least a 70-fold increase, at least a 75-fold increase, at least a 80-fold increase, at least a 85-fold increase, at least a 90-fold increase, at least a 95-fold increase, or at least a 100-fold increase, or about a 0.1-fold increase to about a 100-fold increase, about 0.1-fold increase to about a 90-fold increase, about 0.1-fold increase to about a 80-fold increase, about a 0.1-fold increase to about a 70-fold increase, about a 0.1-fold increase to about a 60-fold increase, about a 0.1-fold increase to about a 50-fold increase, about a 0.1-fold increase to about a 40-fold increase, about a 0.1-fold increase to about a 30-fold increase, about 0.1-fold increase to about 20-fold increase, about a 0.1-fold increase to about a 10-fold increase, about a 0.1-fold increase to about a 9.5-fold increase, about a 0.1-fold increase to about a 9.0-fold increase, about a 0.1-fold increase to about a 8.5-fold increase, about a 0.1-fold increase to about a 8.0-fold increase, about a 0.1-fold increase to about a 7.5-fold increase, about a 0.1-fold increase to about a 7.0-fold increase, about a 0.1-fold increase to about a 6.5-fold increase, about a 0.1-fold increase to about a 6.0-fold increase, about a 0.1-fold increase to about a 5.5-fold increase, about a 0.1-fold increase to about a 5.0-fold increase, about a 0.1-fold increase to about a 4.5-fold increase, about a 0.1-fold increase to about a 4.0-fold increase, about a 0.1-fold increase to about a 3.5-fold increase, about 0.1-fold increase to about a 3.0-fold increase, about a 0.1-fold increase to about a 2.8-fold increase, about a 0.1-fold increase to about a 2.6-fold increase, about a 0.1-fold increase to about a 2.5-fold increase, about a 0.1-fold increase to about a 2.4-fold increase, about a 0.1-fold increase to about a 2.2-fold increase, about a 0.1-fold increase to about a 2.0-fold increase, about a 0.1-fold increase to about a 1.8-fold increase, about a 0.1-fold increase to about a 1.6-fold increase, about a 0.1-fold increase to about a 1.5-fold increase, about a 0.1-fold increase to about a 1.4-fold increase, about a 0.1-fold increase to about a 1.2-fold increase, about a 0.1-fold increase to about a 1.0-fold increase, about a 0.1-fold increase to about a 0.9-fold increase, about a 0.1-fold increase to about a 0.8-fold increase, about a 0.1-fold increase to about a 0.7-fold increase, about a 0.1-fold increase to about a 0.6-fold increase, about a 0.1-fold increase to about a 0.5-fold increase, about a 0.1-fold increase to about a 0.4-fold increase, about a 0.1-fold increase to about a 0.3-fold increase, about a 0.2-fold increase to about a 100-fold increase, about 0.2-fold increase to about a 90-fold increase, about 0.2-fold increase to about a 80-fold increase, about a 0.2-fold increase to about a 70-fold increase, about a 0.2-fold increase to about a 60-fold increase, about a 0.2-fold increase to about a 50-fold increase, about a 0.2-fold increase to about a 40-fold increase, about a 0.2-fold increase to about a 30-fold increase, about 0.2-fold increase to about 20-fold increase, about a 0.2-fold increase to about a 10-fold increase, about a 0.2-fold increase to about a 9.5-fold increase, about a 0.2-fold increase to about a 9.0-fold increase, about a 0.2-fold increase to about a 8.5-fold increase, about a 0.2-fold increase to about a 8.0-fold increase, about a 0.2-fold increase to about a 7.5-fold increase, about a 0.2-fold increase to about a 7.0-fold increase, about a 0.2-fold increase to about a 6.5-fold increase, about a 0.2-fold increase to about a 6.0-fold increase, about a 0.2-fold increase to about a 5.5-fold increase, about a 0.2-fold increase to about a 5.0-fold increase, about a 0.2-fold increase to about a 4.5-fold increase, about a 0.2-fold increase to about a 4.0-fold increase, about a 0.2-fold increase to about a 3.5-fold increase, about 0.2-fold increase to about a 3.0-fold increase, about a 0.2-fold increase to about a 2.8-fold increase, about a 0.2-fold increase to about a 2.6-fold increase, about a 0.2-fold increase to about a 2.5-fold increase, about a 0.2-fold increase to about a 2.4-fold increase, about a 0.2-fold increase to about a 2.2-fold increase, about a 0.2-fold increase to about a 2.0-fold increase, about a 0.2-fold increase to about a 1.8-fold increase, about a 0.2-fold increase to about a 1.6-fold increase, about a 0.2-fold increase to about a 1.5-fold increase, about a 0.2-fold increase to about a 1.4-fold increase, about a 0.2-fold increase to about a 1.2-fold increase, about a 0.2-fold increase to about a 1.0-fold increase, about a 0.2-fold increase to about a 0.9-fold increase, about a 0.2-fold increase to about a 0.8-fold increase, about a 0.2-fold increase to about a 0.7-fold increase, about a 0.2-fold increase to about a 0.6-fold increase, about a 0.2-fold increase to about a 0.5-fold increase, about a 0.2-fold increase to about a 0.4-fold increase, about a 0.3-fold increase to about a 100-fold increase, about 0.3-fold increase to about a 90-fold increase, about 0.3-fold increase to about a 80-fold increase, about a 0.3-fold increase to about a 70-fold increase, about a 0.3-fold increase to about a 60-fold increase, about a 0.3-fold increase to about a 50-fold increase, about a 0.3-fold increase to about a 40-fold increase, about a 0.3-fold increase to about a 30-fold increase, about 0.3-fold increase to about 20-fold increase, about a 0.3-fold increase to about a 10-fold increase, about a 0.3-fold increase to about a 9.5-fold increase, about a 0.3-fold increase to about a 9.0-fold increase, about a 0.3-fold increase to about a 8.5-fold increase, about a 0.3-fold increase to about a 8.0-fold increase, about a 0.3-fold increase to about a 7.5-fold increase, about a 0.3-fold increase to about a 7.0-fold increase, about a 0.3-fold increase to about a 6.5-fold increase, about a 0.3-fold increase to about a 6.0-fold increase, about a 0.3-fold increase to about a 5.5-fold increase, about a 0.3-fold increase to about a 5.0-fold increase, about a 0.3-fold increase to about a 4.5-fold increase, about a 0.3-fold increase to about a 4.0-fold increase, about a 0.3-fold increase to about a 3.5-fold increase, about 0.3-fold increase to about a 3.0-fold increase, about a 0.3-fold increase to about a 2.8-fold increase, about a 0.3-fold increase to about a 2.6-fold increase, about a 0.3-fold increase to about a 2.5-fold increase, about a 0.3-fold increase to about a 2.4-fold increase, about a 0.3-fold increase to about a 2.2-fold increase, about a 0.3-fold increase to about a 2.0-fold increase, about a 0.3-fold increase to about a 1.8-fold increase, about a 0.3-fold increase to about a 1.6-fold increase, about a 0.3-fold increase to about a 1.5-fold increase, about a 0.3-fold increase to about a 1.4-fold increase, about a 0.3-fold increase to about a 1.2-fold increase, about a 0.3-fold increase to about a 1.0-fold increase, about a 0.3-fold increase to about a 0.9-fold increase, about a 0.3-fold increase to about a 0.8-fold increase, about a 0.3-fold increase to about a 0.7-fold increase, about a 0.3-fold increase to about a 0.6-fold increase, about a 0.3-fold increase to about a 0.5-fold increase, about a 0.4-fold increase to about a 100-fold increase, about 0.4-fold increase to about a 90-fold increase, about 0.4-fold increase to about a 80-fold increase, about a 0.4-fold increase to about a 70-fold increase, about a 0.4-fold increase to about a 60-fold increase, about a 0.4-fold increase to about a 50-fold increase, about a 0.4-fold increase to about a 40-fold increase, about a 0.4-fold increase to about a 30-fold increase, about 0.4-fold increase to about 20-fold increase, about a 0.4-fold increase to about a 10-fold increase, about a 0.4-fold increase to about a 9.5-fold increase, about a 0.4-fold increase to about a 9.0-fold increase, about a 0.4-fold increase to about a 8.5-fold increase, about a 0.4-fold increase to about a 8.0-fold increase, about a 0.4-fold increase to about a 7.5-fold increase, about a 0.4-fold increase to about a 7.0-fold increase, about a 0.4-fold increase to about a 6.5-fold increase, about a 0.4-fold increase to about a 6.0-fold increase, about a 0.4-fold increase to about a 5.5-fold increase, about a 0.4-fold increase to about a 5.0-fold increase, about a 0.4-fold increase to about a 4.5-fold increase, about a 0.4-fold increase to about a 4.0-fold increase, about a 0.4-fold increase to about a 3.5-fold increase, about 0.4-fold increase to about a 3.0-fold increase, about a 0.4-fold increase to about a 2.8-fold increase, about a 0.4-fold increase to about a 2.6-fold increase, about a 0.4-fold increase to about a 2.5-fold increase, about a 0.4-fold increase to about a 2.4-fold increase, about a 0.4-fold increase to about a 2.2-fold increase, about a 0.4-fold increase to about a 2.0-fold increase, about a 0.4-fold increase to about a 1.8-fold increase, about a 0.4-fold increase to about a 1.6-fold increase, about a 0.4-fold increase to about a 1.5-fold increase, about a 0.4-fold increase to about a 1.4-fold increase, about a 0.4-fold increase to about a 1.2-fold increase, about a 0.4-fold increase to about a 1.0-fold increase, about a 0.4-fold increase to about a 0.9-fold increase, about a 0.4-fold increase to about a 0.8-fold increase, about a 0.4-fold increase to about a 0.7-fold increase, about a 0.4-fold increase to about a 0.6-fold increase, about a 0.5-fold increase to about a 100-fold increase, about 0.5-fold increase to about a 90-fold increase, about 0.5-fold increase to about a 80-fold increase, about a 0.5-fold increase to about a 70-fold increase, about a 0.5-fold increase to about a 60-fold increase, about a 0.5-fold increase to about a 50-fold increase, about a 0.5-fold increase to about a 40-fold increase, about a 0.5-fold increase to about a 30-fold increase, about 0.5-fold increase to about 20-fold increase, about a 0.5-fold increase to about a 10-fold increase, about a 0.5-fold increase to about a 9.5-fold increase, about a 0.5-fold increase to about a 9.0-fold increase, about a 0.5-fold increase to about a 8.5-fold increase, about a 0.5-fold increase to about a 8.0-fold increase, about a 0.5-fold increase to about a 7.5-fold increase, about a 0.5-fold increase to about a 7.0-fold increase, about a 0.5-fold increase to about a 6.5-fold increase, about a 0.5-fold increase to about a 6.0-fold increase, about a 0.5-fold increase to about a 5.5-fold increase, about a 0.5-fold increase to about a 5.0-fold increase, about a 0.5-fold increase to about a 4.5-fold increase, about a 0.5-fold increase to about a 4.0-fold increase, about a 0.5-fold increase to about a 3.5-fold increase, about 0.5-fold increase to about a 3.0-fold increase, about a 0.5-fold increase to about a 2.8-fold increase, about a 0.5-fold increase to about a 2.6-fold increase, about a 0.5-fold increase to about a 2.5-fold increase, about a 0.5-fold increase to about a 2.4-fold increase, about a 0.5-fold increase to about a 2.2-fold increase, about a 0.5-fold increase to about a 2.0-fold increase, about a 0.5-fold increase to about a 1.8-fold increase, about a 0.5-fold increase to about a 1.6-fold increase, about a 0.5-fold increase to about a 1.5-fold increase, about a 0.5-fold increase to about a 1.4-fold increase, about a 0.5-fold increase to about a 1.2-fold increase, about a 0.5-fold increase to about a 1.0-fold increase, about a 0.5-fold increase to about a 0.9-fold increase, about a 0.5-fold increase to about a 0.8-fold increase, about a 0.5-fold increase to about a 0.7-fold increase, about a 0.6-fold increase to about a 100-fold increase, about 0.6-fold increase to about a 90-fold increase, about 0.6-fold increase to about a 80-fold increase, about a 0.6-fold increase to about a 70-fold increase, about a 0.6-fold increase to about a 60-fold increase, about a 0.6-fold increase to about a 50-fold increase, about a 0.6-fold increase to about a 40-fold increase, about a 0.6-fold increase to about a 30-fold increase, about 0.6-fold increase to about 20-fold increase, about a 0.6-fold increase to about a 10-fold increase, about a 0.6-fold increase to about a 9.5-fold increase, about a 0.6-fold increase to about a 9.0-fold increase, about a 0.6-fold increase to about a 8.5-fold increase, about a 0.6-fold increase to about a 8.0-fold increase, about a 0.6-fold increase to about a 7.5-fold increase, about a 0.6-fold increase to about a 7.0-fold increase, about a 0.6-fold increase to about a 6.5-fold increase, about a 0.6-fold increase to about a 6.0-fold increase, about a 0.6-fold increase to about a 5.5-fold increase, about a 0.6-fold increase to about a 5.0-fold increase, about a 0.6-fold increase to about a 4.5-fold increase, about a 0.6-fold increase to about a 4.0-fold increase, about a 0.6-fold increase to about a 3.5-fold increase, about 0.6-fold increase to about a 3.0-fold increase, about a 0.6-fold increase to about a 2.8-fold increase, about a 0.6-fold increase to about a 2.6-fold increase, about a 0.6-fold increase to about a 2.5-fold increase, about a 0.6-fold increase to about a 2.4-fold increase, about a 0.6-fold increase to about a 2.2-fold increase, about a 0.6-fold increase to about a 2.0-fold increase, about a 0.6-fold increase to about a 1.8-fold increase, about a 0.6-fold increase to about a 1.6-fold increase, about a 0.6-fold increase to about a 1.5-fold increase, about a 0.6-fold increase to about a 1.4-fold increase, about a 0.6-fold increase to about a 1.2-fold increase, about a 0.6-fold increase to about a 1.0-fold increase, about a 0.6-fold increase to about a 0.9-fold increase, about a 0.6-fold increase to about a 0.8-fold increase, about a 0.7-fold increase to about a 100-fold increase, about 0.7-fold increase to about a 90-fold increase, about 0.7-fold increase to about a 80-fold increase, about a 0.7-fold increase to about a 70-fold increase, about a 0.7-fold increase to about a 60-fold increase, about a 0.7-fold increase to about a 50-fold increase, about a 0.7-fold increase to about a 40-fold increase, about a 0.7-fold increase to about a 30-fold increase, about 0.7-fold increase to about 20-fold increase, about a 0.7-fold increase to about a 10-fold increase, about a 0.7-fold increase to about a 9.5-fold increase, about a 0.7-fold increase to about a 9.0-fold increase, about a 0.7-fold increase to about a 8.5-fold increase, about a 0.7-fold increase to about a 8.0-fold increase, about a 0.7-fold increase to about a 7.5-fold increase, about a 0.7-fold increase to about a 7.0-fold increase, about a 0.7-fold increase to about a 6.5-fold increase, about a 0.7-fold increase to about a 6.0-fold increase, about a 0.7-fold increase to about a 5.5-fold increase, about a 0.7-fold increase to about a 5.0-fold increase, about a 0.7-fold increase to about a 4.5-fold increase, about a 0.7-fold increase to about a 4.0-fold increase, about a 0.7-fold increase to about a 3.5-fold increase, about 0.7-fold increase to about a 3.0-fold increase, about a 0.7-fold increase to about a 2.8-fold increase, about a 0.7-fold increase to about a 2.6-fold increase, about a 0.7-fold increase to about a 2.5-fold increase, about a 0.7-fold increase to about a 2.4-fold increase, about a 0.7-fold increase to about a 2.2-fold increase, about a 0.7-fold increase to about a 2.0-fold increase, about a 0.7-fold increase to about a 1.8-fold increase, about a 0.7-fold increase to about a 1.6-fold increase, about a 0.7-fold increase to about a 1.5-fold increase, about a 0.7-fold increase to about a 1.4-fold increase, about a 0.7-fold increase to about a 1.2-fold increase, about a 0.7-fold increase to about a 1.0-fold increase, about a 0.7-fold increase to about a 0.9-fold increase, about a 0.8-fold increase to about a 100-fold increase, about 0.8-fold increase to about a 90-fold increase, about 0.8-fold increase to about a 80-fold increase, about a 0.8-fold increase to about a 70-fold increase, about a 0.8-fold increase to about a 60-fold increase, about a 0.8-fold increase to about a 50-fold increase, about a 0.8-fold increase to about a 40-fold increase, about a 0.8-fold increase to about a 30-fold increase, about 0.8-fold increase to about 20-fold increase, about a 0.8-fold increase to about a 10-fold increase, about a 0.8-fold increase to about a 9.5-fold increase, about a 0.8-fold increase to about a 9.0-fold increase, about a 0.8-fold increase to about a 8.5-fold increase, about a 0.8-fold increase to about a 8.0-fold increase, about a 0.8-fold increase to about a 7.5-fold increase, about a 0.8-fold increase to about a 7.0-fold increase, about a 0.8-fold increase to about a 6.5-fold increase, about a 0.8-fold increase to about a 6.0-fold increase, about a 0.8-fold increase to about a 5.5-fold increase, about a 0.8-fold increase to about a 5.0-fold increase, about a 0.8-fold increase to about a 4.5-fold increase, about a 0.8-fold increase to about a 4.0-fold increase, about a 0.8-fold increase to about a 3.5-fold increase, about 0.8-fold increase to about a 3.0-fold increase, about a 0.8-fold increase to about a 2.8-fold increase, about a 0.8-fold increase to about a 2.6-fold increase, about a 0.8-fold increase to about a 2.5-fold increase, about a 0.8-fold increase to about a 2.4-fold increase, about a 0.8-fold increase to about a 2.2-fold increase, about a 0.8-fold increase to about a 2.0-fold increase, about a 0.8-fold increase to about a 1.8-fold increase, about a 0.8-fold increase to about a 1.6-fold increase, about a 0.8-fold increase to about a 1.5-fold increase, about a 0.8-fold increase to about a 1.4-fold increase, about a 0.8-fold increase to about a 1.2-fold increase, about a 0.8-fold increase to about a 1.0-fold increase, about a 1.0-fold increase to about a 100-fold increase, about 1.0-fold increase to about a 90-fold increase, about 1.0-fold increase to about a 80-fold increase, about a 1.0-fold increase to about a 70-fold increase, about a 1.0-fold increase to about a 60-fold increase, about a 1.0-fold increase to about a 50-fold increase, about a 1.0-fold increase to about a 40-fold increase, about a 1.0-fold increase to about a 30-fold increase, about 1.0-fold increase to about 20-fold increase, about a 1.0-fold increase to about a 10-fold increase, about a 1.0-fold increase to about a 9.5-fold increase, about a 1.0-fold increase to about a 9.0-fold increase, about a 1.0-fold increase to about a 8.5-fold increase, about a 1.0-fold increase to about a 8.0-fold increase, about a 1.0-fold increase to about a 7.5-fold increase, about a 1.0-fold increase to about a 7.0-fold increase, about a 1.0-fold increase to about a 6.5-fold increase, about a 1.0-fold increase to about a 6.0-fold increase, about a 1.0-fold increase to about a 5.5-fold increase, about a 1.0-fold increase to about a 5.0-fold increase, about a 1.0-fold increase to about a 4.5-fold increase, about a 1.0-fold increase to about a 4.0-fold increase, about a 1.0-fold increase to about a 3.5-fold increase, about 1.0-fold increase to about a 3.0-fold increase, about a 1.0-fold increase to about a 2.8-fold increase, about a 1.0-fold increase to about a 2.6-fold increase, about a 1.0-fold increase to about a 2.5-fold increase, about a 1.0-fold increase to about a 2.4-fold increase, about a 1.0-fold increase to about a 2.2-fold increase, about a 1.0-fold increase to about a 2.0-fold increase, about a 1.0-fold increase to about a 1.8-fold increase, about a 1.0-fold increase to about a 1.6-fold increase, about a 1.0-fold increase to about a 1.5-fold increase, about a 1.0-fold increase to about a 1.4-fold increase, about a 1.0-fold increase to about a 1.2-fold increase, about a 1.2-fold increase to about a 100-fold increase, about 1.2-fold increase to about a 90-fold increase, about 1.2-fold increase to about a 80-fold increase, about a 1.2-fold increase to about a 70-fold increase, about a 1.2-fold increase to about a 60-fold increase, about a 1.2-fold increase to about a 50-fold increase, about a 1.2-fold increase to about a 40-fold increase, about a 1.2-fold increase to about a 30-fold increase, about 1.2-fold increase to about 20-fold increase, about a 1.2-fold increase to about a 10-fold increase, about a 1.2-fold increase to about a 9.5-fold increase, about a 1.2-fold increase to about a 9.0-fold increase, about a 1.2-fold increase to about a 8.5-fold increase, about a 1.2-fold increase to about a 8.0-fold increase, about a 1.2-fold increase to about a 7.5-fold increase, about a 1.2-fold increase to about a 7.0-fold increase, about a 1.2-fold increase to about a 6.5-fold increase, about a 1.2-fold increase to about a 6.0-fold increase, about a 1.2-fold increase to about a 5.5-fold increase, about a 1.2-fold increase to about a 5.0-fold increase, about a 1.2-fold increase to about a 4.5-fold increase, about a 1.2-fold increase to about a 4.0-fold increase, about a 1.2-fold increase to about a 3.5-fold increase, about 1.2-fold increase to about a 3.0-fold increase, about a 1.2-fold increase to about a 2.8-fold increase, about a 1.2-fold increase to about a 2.6-fold increase, about a 1.2-fold increase to about a 2.5-fold increase, about a 1.2-fold increase to about a 2.4-fold increase, about a 1.2-fold increase to about a 2.2-fold increase, about a 1.2-fold increase to about a 2.0-fold increase, about a 1.2-fold increase to about a 1.8-fold increase, about a 1.2-fold increase to about a 1.6-fold increase, about a 1.2-fold increase to about a 1.5-fold increase, about a 1.2-fold increase to about a 1.4-fold increase, about a 1.4-fold increase to about a 100-fold increase, about 1.4-fold increase to about a 90-fold increase, about 1.4-fold increase to about a 80-fold increase, about a 1.4-fold increase to about a 70-fold increase, about a 1.4-fold increase to about a 60-fold increase, about a 1.4-fold increase to about a 50-fold increase, about a 1.4-fold increase to about a 40-fold increase, about a 1.4-fold increase to about a 30-fold increase, about 1.4-fold increase to about 20-fold increase, about a 1.4-fold increase to about a 10-fold increase, about a 1.4-fold increase to about a 9.5-fold increase, about a 1.4-fold increase to about a 9.0-fold increase, about a 1.4-fold increase to about a 8.5-fold increase, about a 1.4-fold increase to about a 8.0-fold increase, about a 1.4-fold increase to about a 7.5-fold increase, about a 1.4-fold increase to about a 7.0-fold increase, about a 1.4-fold increase to about a 6.5-fold increase, about a 1.4-fold increase to about a 6.0-fold increase, about a 1.4-fold increase to about a 5.5-fold increase, about a 1.4-fold increase to about a 5.0-fold increase, about a 1.4-fold increase to about a 4.5-fold increase, about a 1.4-fold increase to about a 4.0-fold increase, about a 1.4-fold increase to about a 3.5-fold increase, about 1.4-fold increase to about a 3.0-fold increase, about a 1.4-fold increase to about a 2.8-fold increase, about a 1.4-fold increase to about a 2.6-fold increase, about a 1.4-fold increase to about a 2.5-fold increase, about a 1.4-fold increase to about a 2.4-fold increase, about a 1.4-fold increase to about a 2.2-fold increase, about a 1.4-fold increase to about a 2.0-fold increase, about a 1.4-fold increase to about a 1.8-fold increase, about a 1.4-fold increase to about a 1.6-fold increase, about a 1.6-fold increase to about a 10-fold increase, about a 1.6-fold increase to about a 100-fold increase, about 1.6-fold increase to about a 90-fold increase, about 1.6-fold increase to about a 80-fold increase, about a 1.6-fold increase to about a 70-fold increase, about a 1.6-fold increase to about a 60-fold increase, about a 1.6-fold increase to about a 50-fold increase, about a 1.6-fold increase to about a 40-fold increase, about a 1.6-fold increase to about a 30-fold increase, about 1.6-fold increase to about 20-fold increase, about a 1.6-fold increase to about a 9.5-fold increase, about a 1.6-fold increase to about a 9.0-fold increase, about a 1.6-fold increase to about a 8.5-fold increase, about a 1.6-fold increase to about a 8.0-fold increase, about a 1.6-fold increase to about a 7.5-fold increase, about a 1.6-fold increase to about a 7.0-fold increase, about a 1.6-fold increase to about a 6.5-fold increase, about a 1.6-fold increase to about a 6.0-fold increase, about a 1.6-fold increase to about a 5.5-fold increase, about a 1.6-fold increase to about a 5.0-fold increase, about a 1.6-fold increase to about a 4.5-fold increase, about a 1.6-fold increase to about a 4.0-fold increase, about a 1.6-fold increase to about a 3.5-fold increase, about 1.6-fold increase to about a 3.0-fold increase, about a 1.6-fold increase to about a 2.8-fold increase, about a 1.6-fold increase to about a 2.6-fold increase, about a 1.6-fold increase to about a 2.5-fold increase, about a 1.6-fold increase to about a 2.4-fold increase, about a 1.6-fold increase to about a 2.2-fold increase, about a 1.6-fold increase to about a 2.0-fold increase, about a 1.6-fold increase to about a 1.8-fold increase, about a 1.8-fold increase to about a 100-fold increase, about 1.8-fold increase to about a 90-fold increase, about 1.8-fold increase to about a 80-fold increase, about a 1.8-fold increase to about a 70-fold increase, about a 1.8-fold increase to about a 60-fold increase, about a 1.8-fold increase to about a 50-fold increase, about a 1.8-fold increase to about a 40-fold increase, about a 1.8-fold increase to about a 30-fold increase, about 1.8-fold increase to about 20-fold increase, about a 1.8-fold increase to about a 10-fold increase, about a 1.8-fold increase to about a 9.5-fold increase, about a 1.8-fold increase to about a 9.0-fold increase, about a 1.8-fold increase to about a 8.5-fold increase, about a 1.8-fold increase to about a 8.0-fold increase, about a 1.8-fold increase to about a 7.5-fold increase, about a 1.8-fold increase to about a 7.0-fold increase, about a 1.8-fold increase to about a 6.5-fold increase, about a 1.8-fold increase to about a 6.0-fold increase, about a 1.8-fold increase to about a 5.5-fold increase, about a 1.8-fold increase to about a 5.0-fold increase, about a 1.8-fold increase to about a 4.5-fold increase, about a 1.8-fold increase to about a 4.0-fold increase, about a 1.8-fold increase to about a 3.5-fold increase, about 1.8-fold increase to about a 3.0-fold increase, about a 1.8-fold increase to about a 2.8-fold increase, about a 1.8-fold increase to about a 2.6-fold increase, about a 1.8-fold increase to about a 2.5-fold increase, about a 1.8-fold increase to about a 2.4-fold increase, about a 1.8-fold increase to about a 2.2-fold increase, about a 1.8-fold increase to about a 2.0-fold increase, about a 2.0-fold increase to about a 100-fold increase, about 2.0-fold increase to about a 90-fold increase, about 2.0-fold increase to about a 80-fold increase, about a 2.0-fold increase to about a 70-fold increase, about a 2.0-fold increase to about a 60-fold increase, about a 2.0-fold increase to about a 50-fold increase, about a 2.0-fold increase to about a 40-fold increase, about a 2.0-fold increase to about a 30-fold increase, about 2.0-fold increase to about 20-fold increase, about a 2.0-fold increase to about a 10-fold increase, about a 2.0-fold increase to about a 9.5-fold increase, about a 2.0-fold increase to about a 9.0-fold increase, about a 2.0-fold increase to about a 8.5-fold increase, about a 2.0-fold increase to about a 8.0-fold increase, about a 2.0-fold increase to about a 7.5-fold increase, about a 2.0-fold increase to about a 7.0-fold increase, about a 2.0-fold increase to about a 6.5-fold increase, about a 2.0-fold increase to about a 6.0-fold increase, about a 2.0-fold increase to about a 5.5-fold increase, about a 2.0-fold increase to about a 5.0-fold increase, about a 2.0-fold increase to about a 4.5-fold increase, about a 2.0-fold increase to about a 4.0-fold increase, about a 2.0-fold increase to about a 3.5-fold increase, about 2.0-fold increase to about a 3.0-fold increase, about a 2.0-fold increase to about a 2.8-fold increase, about a 2.0-fold increase to about a 2.6-fold increase, about a 2.0-fold increase to about a 2.5-fold increase, about a 2.0-fold increase to about a 2.4-fold increase, about a 2.0-fold increase to about a 2.2-fold increase, about a 2.2-fold increase to about a 100-fold increase, about 2.2-fold increase to about a 90-fold increase, about 2.2-fold increase to about a 80-fold increase, about a 2.2-fold increase to about a 70-fold increase, about a 2.2-fold increase to about a 60-fold increase, about a 2.2-fold increase to about a 50-fold increase, about a 2.2-fold increase to about a 40-fold increase, about a 2.2-fold increase to about a 30-fold increase, about 2.2-fold increase to about 20-fold increase, about a 2.2-fold increase to about a 10-fold increase, about a 2.2-fold increase to about a 9.5-fold increase, about a 2.2-fold increase to about a 9.0-fold increase, about a 2.2-fold increase to about a 8.5-fold increase, about a 2.2-fold increase to about a 8.0-fold increase, about a 2.2-fold increase to about a 7.5-fold increase, about a 2.2-fold increase to about a 7.0-fold increase, about a 2.2-fold increase to about a 6.5-fold increase, about a 2.2-fold increase to about a 6.0-fold increase, about a 2.2-fold increase to about a 5.5-fold increase, about a 2.2-fold increase to about a 5.0-fold increase, about a 2.2-fold increase to about a 4.5-fold increase, about a 2.2-fold increase to about a 4.0-fold increase, about a 2.2-fold increase to about a 3.5-fold increase, about 2.2-fold increase to about a 3.0-fold increase, about a 2.2-fold increase to about a 2.8-fold increase, about a 2.2-fold increase to about a 2.6-fold increase, about a 2.2-fold increase to about a 2.5-fold increase, about a 2.2-fold increase to about a 2.4-fold increase, about a 2.4-fold increase to about a 100-fold increase, about 2.4-fold increase to about a 90-fold increase, about 2.4-fold increase to about a 80-fold increase, about a 2.4-fold increase to about a 70-fold increase, about a 2.4-fold increase to about a 60-fold increase, about a 2.4-fold increase to about a 50-fold increase, about a 2.4-fold increase to about a 40-fold increase, about a 2.4-fold increase to about a 30-fold increase, about 2.4-fold increase to about 20-fold increase, about a 2.4-fold increase to about a 10-fold increase, about a 2.4-fold increase to about a 9.5-fold increase, about a 2.4-fold increase to about a 9.0-fold increase, about a 2.4-fold increase to about a 8.5-fold increase, about a 2.4-fold increase to about a 8.0-fold increase, about a 2.4-fold increase to about a 7.5-fold increase, about a 2.4-fold increase to about a 7.0-fold increase, about a 2.4-fold increase to about a 6.5-fold increase, about a 2.4-fold increase to about a 6.0-fold increase, about a 2.4-fold increase to about a 5.5-fold increase, about a 2.4-fold increase to about a 5.0-fold increase, about a 2.4-fold increase to about a 4.5-fold increase, about a 2.4-fold increase to about a 4.0-fold increase, about a 2.4-fold increase to about a 3.5-fold increase, about 2.4-fold increase to about a 3.0-fold increase, about a 2.4-fold increase to about a 2.8-fold increase, about a 2.4-fold increase to about a 2.6-fold increase, about a 2.6-fold increase to about a 100-fold increase, about 2.6-fold increase to about a 90-fold increase, about 2.6-fold increase to about a 80-fold increase, about a 2.6-fold increase to about a 70-fold increase, about a 2.6-fold increase to about a 60-fold increase, about a 2.6-fold increase to about a 50-fold increase, about a 2.6-fold increase to about a 40-fold increase, about a 2.6-fold increase to about a 30-fold increase, about 2.6-fold increase to about 20-fold increase, about a 2.6-fold increase to about a 10-fold increase, about a 2.6-fold increase to about a 9.5-fold increase, about a 2.6-fold increase to about a 9.0-fold increase, about a 2.6-fold increase to about a 8.5-fold increase, about a 2.6-fold increase to about a 8.0-fold increase, about a 2.6-fold increase to about a 7.5-fold increase, about a 2.6-fold increase to about a 7.0-fold increase, about a 2.6-fold increase to about a 6.5-fold increase, about a 2.6-fold increase to about a 6.0-fold increase, about a 2.6-fold increase to about a 5.5-fold increase, about a 2.6-fold increase to about a 5.0-fold increase, about a 2.6-fold increase to about a 4.5-fold increase, about a 2.6-fold increase to about a 4.0-fold increase, about a 2.6-fold increase to about a 3.5-fold increase, about 2.6-fold increase to about a 3.0-fold increase, about a 2.6-fold increase to about a 2.8-fold increase, about a 2.8-fold increase to about a 100-fold increase, about 2.8-fold increase to about a 90-fold increase, about 2.8-fold increase to about a 80-fold increase, about a 2.8-fold increase to about a 70-fold increase, about a 2.8-fold increase to about a 60-fold increase, about a 2.8-fold increase to about a 50-fold increase, about a 2.8-fold increase to about a 40-fold increase, about a 2.8-fold increase to about a 30-fold increase, about 2.8-fold increase to about 20-fold increase, about a 2.8-fold increase to about a 10-fold increase, about a 2.8-fold increase to about a 9.5-fold increase, about a 2.8-fold increase to about a 9.0-fold increase, about a 2.8-fold increase to about a 8.5-fold increase, about a 2.8-fold increase to about a 8.0-fold increase, about a 2.8-fold increase to about a 7.5-fold increase, about a 2.8-fold increase to about a 7.0-fold increase, about a 2.8-fold increase to about a 6.5-fold increase, about a 2.8-fold increase to about a 6.0-fold increase, about a 2.8-fold increase to about a 5.5-fold increase, about a 2.8-fold increase to about a 5.0-fold increase, about a 2.8-fold increase to about a 4.5-fold increase, about a 2.8-fold increase to about a 4.0-fold increase, about a 2.8-fold increase to about a 3.5-fold increase, about 2.8-fold increase to about a 3.0-fold increase, about a 3.0-fold increase to about a 100-fold increase, about 3.0-fold increase to about a 90-fold increase, about 3.0-fold increase to about a 80-fold increase, about a 3.0-fold increase to about a 70-fold increase, about a 3.0-fold increase to about a 60-fold increase, about a 3.0-fold increase to about a 50-fold increase, about a 3.0-fold increase to about a 40-fold increase, about a 3.0-fold increase to about a 30-fold increase, about 3.0-fold increase to about 20-fold increase, about a 3.0-fold increase to about a 10-fold increase, about a 3.0-fold increase to about a 9.5-fold increase, about a 3.0-fold increase to about a 9.0-fold increase, about a 3.0-fold increase to about a 8.5-fold increase, about a 3.0-fold increase to about a 8.0-fold increase, about a 3.0-fold increase to about a 7.5-fold increase, about a 3.0-fold increase to about a 7.0-fold increase, about a 3.0-fold increase to about a 6.5-fold increase, about a 3.0-fold increase to about a 6.0-fold increase, about a 3.0-fold increase to about a 5.5-fold increase, about a 3.0-fold increase to about a 5.0-fold increase, about a 3.0-fold increase to about a 4.5-fold increase, about a 3.0-fold increase to about a 4.0-fold increase, about a 3.0-fold increase to about a 3.5-fold increase, about a 3.5-fold increase to about a 100-fold increase, about 3.5-fold increase to about a 90-fold increase, about 3.5-fold increase to about a 80-fold increase, about a 3.5-fold increase to about a 70-fold increase, about a 3.5-fold increase to about a 60-fold increase, about a 3.5-fold increase to about a 50-fold increase, about a 3.5-fold increase to about a 40-fold increase, about a 3.5-fold increase to about a 30-fold increase, about 3.5-fold increase to about 20-fold increase, about a 3.5-fold increase to about a 10-fold increase, about a 3.5-fold increase to about a 9.5-fold increase, about a 3.5-fold increase to about a 9.0-fold increase, about a 3.5-fold increase to about a 8.5-fold increase, about a 3.5-fold increase to about a 8.0-fold increase, about a 3.5-fold increase to about a 7.5-fold increase, about a 3.5-fold increase to about a 7.0-fold increase, about a 3.5-fold increase to about a 6.5-fold increase, about a 3.5-fold increase to about a 6.0-fold increase, about a 3.5-fold increase to about a 5.5-fold increase, about a 3.5-fold increase to about a 5.0-fold increase, about a 3.5-fold increase to about a 4.5-fold increase, about a 3.5-fold increase to about a 4.0-fold increase, about a 4.0-fold increase to about a 100-fold increase, about 4.0-fold increase to about a 90-fold increase, about 4.0-fold increase to about a 80-fold increase, about a 4.0-fold increase to about a 70-fold increase, about a 4.0-fold increase to about a 60-fold increase, about a 4.0-fold increase to about a 50-fold increase, about a 4.0-fold increase to about a 40-fold increase, about a 4.0-fold increase to about a 30-fold increase, about 4.0-fold increase to about 20-fold increase, about a 4.0-fold increase to about a 10-fold increase, about a 4.0-fold increase to about a 9.5-fold increase, about a 4.0-fold increase to about a 9.0-fold increase, about a 4.0-fold increase to about a 8.5-fold increase, about a 4.0-fold increase to about a 8.0-fold increase, about a 4.0-fold increase to about a 7.5-fold increase, about a 4.0-fold increase to about a 7.0-fold increase, about a 4.0-fold increase to about a 6.5-fold increase, about a 4.0-fold increase to about a 6.0-fold increase, about a 4.0-fold increase to about a 5.5-fold increase, about a 4.0-fold increase to about a 5.0-fold increase, about a 4.0-fold increase to about a 4.5-fold increase, about a 4.5-fold increase to about a 100-fold increase, about 4.5-fold increase to about a 90-fold increase, about 4.5-fold increase to about a 80-fold increase, about a 4.5-fold increase to about a 70-fold increase, about a 4.5-fold increase to about a 60-fold increase, about a 4.5-fold increase to about a 50-fold increase, about a 4.5-fold increase to about a 40-fold increase, about a 4.5-fold increase to about a 30-fold increase, about 4.5-fold increase to about 20-fold increase, about a 4.5-fold increase to about a 10-fold increase, about a 4.5-fold increase to about a 9.5-fold increase, about a 4.5-fold increase to about a 9.0-fold increase, about a 4.5-fold increase to about a 8.5-fold increase, about a 4.5-fold increase to about a 8.0-fold increase, about a 4.5-fold increase to about a 7.5-fold increase, about a 4.5-fold increase to about a 7.0-fold increase, about a 4.5-fold increase to about a 6.5-fold increase, about a 4.5-fold increase to about a 6.0-fold increase, about a 4.5-fold increase to about a 5.5-fold increase, about a 4.5-fold increase to about a 5.0-fold increase, about a 5.0-fold increase to about a 100-fold increase, about 5.0-fold increase to about a 90-fold increase, about 5.0-fold increase to about a 80-fold increase, about a 5.0-fold increase to about a 70-fold increase, about a 5.0-fold increase to about a 60-fold increase, about a 5.0-fold increase to about a 50-fold increase, about a 5.0-fold increase to about a 40-fold increase, about a 5.0-fold increase to about a 30-fold increase, about 5.0-fold increase to about 20-fold increase, about a 5.0-fold increase to about a 10-fold increase, about a 5.0-fold increase to about a 9.5-fold increase, about a 5.0-fold increase to about a 9.0-fold increase, about a 5.0-fold increase to about a 8.5-fold increase, about a 5.0-fold increase to about a 8.0-fold increase, about a 5.0-fold increase to about a 7.5-fold increase, about a 5.0-fold increase to about a 7.0-fold increase, about a 5.0-fold increase to about a 6.5-fold increase, about a 5.0-fold increase to about a 6.0-fold increase, about a 5.0-fold increase to about a 5.5-fold increase, about a 5.5-fold increase to about a 100-fold increase, about 5.5-fold increase to about a 90-fold increase, about 5.5-fold increase to about a 80-fold increase, about a 5.5-fold increase to about a 70-fold increase, about a 5.5-fold increase to about a 60-fold increase, about a 5.5-fold increase to about a 50-fold increase, about a 5.5-fold increase to about a 40-fold increase, about a 5.5-fold increase to about a 30-fold increase, about 5.5-fold increase to about 20-fold increase, about a 5.5-fold increase to about a 10-fold increase, about a 5.5-fold increase to about a 9.5-fold increase, about a 5.5-fold increase to about a 9.0-fold increase, about a 5.5-fold increase to about a 8.5-fold increase, about a 5.5-fold increase to about a 8.0-fold increase, about a 5.5-fold increase to about a 7.5-fold increase, about a 5.5-fold increase to about a 7.0-fold increase, about a 5.5-fold increase to about a 6.5-fold increase, about a 5.5-fold increase to about a 6.0-fold increase, about a 6.0-fold increase to about a 100-fold increase, about 6.0-fold increase to about a 90-fold increase, about 6.0-fold increase to about a 80-fold increase, about a 6.0-fold increase to about a 70-fold increase, about a 6.0-fold increase to about a 60-fold increase, about a 6.0-fold increase to about a 50-fold increase, about a 6.0-fold increase to about a 40-fold increase, about a 6.0-fold increase to about a 30-fold increase, about 6.0-fold increase to about 20-fold increase, about a 6.0-fold increase to about a 10-fold increase, about a 6.0-fold increase to about a 9.5-fold increase, about a 6.0-fold increase to about a 9.0-fold increase, about a 6.0-fold increase to about a 8.5-fold increase, about a 6.0-fold increase to about a 8.0-fold increase, about a 6.0-fold increase to about a 7.5-fold increase, about a 6.0-fold increase to about a 7.0-fold increase, about a 6.0-fold increase to about a 6.5-fold increase, about a 6.5-fold increase to about a 100-fold increase, about 6.5-fold increase to about a 90-fold increase, about 6.5-fold increase to about a 80-fold increase, about a 6.5-fold increase to about a 70-fold increase, about a 6.5-fold increase to about a 60-fold increase, about a 6.5-fold increase to about a 50-fold increase, about a 6.5-fold increase to about a 40-fold increase, about a 6.5-fold increase to about a 30-fold increase, about 6.5-fold increase to about 20-fold increase, about a 6.5-fold increase to about a 10-fold increase, about a 6.5-fold increase to about a 9.5-fold increase, about a 6.5-fold increase to about a 9.0-fold increase, about a 6.5-fold increase to about a 8.5-fold increase, about a 6.5-fold increase to about a 8.0-fold increase, about a 6.5-fold increase to about a 7.5-fold increase, about a 6.5-fold increase to about a 7.0-fold increase, about a 7.0-fold increase to about a 100-fold increase, about 7.0-fold increase to about a 90-fold increase, about 7.0-fold increase to about a 80-fold increase, about a 7.0-fold increase to about a 70-fold increase, about a 7.0-fold increase to about a 60-fold increase, about a 7.0-fold increase to about a 50-fold increase, about a 7.0-fold increase to about a 40-fold increase, about a 7.0-fold increase to about a 30-fold increase, about 7.0-fold increase to about 20-fold increase, about a 7.0-fold increase to about a 10-fold increase, about a 7.0-fold increase to about a 9.5-fold increase, about a 7.0-fold increase to about a 9.0-fold increase, about a 7.0-fold increase to about a 8.5-fold increase, about a 7.0-fold increase to about a 8.0-fold increase, about a 7.0-fold increase to about a 7.5-fold increase, about a 7.5-fold increase to about a 100-fold increase, about 7.5-fold increase to about a 90-fold increase, about 7.5-fold increase to about a 80-fold increase, about a 7.5-fold increase to about a 70-fold increase, about a 7.5-fold increase to about a 60-fold increase, about a 7.5-fold increase to about a 50-fold increase, about a 7.5-fold increase to about a 40-fold increase, about a 7.5-fold increase to about a 30-fold increase, about 7.5-fold increase to about 20-fold increase, about a 7.5-fold increase to about a 10-fold increase, about a 7.5-fold increase to about a 9.5-fold increase, about a 7.5-fold increase to about a 9.0-fold increase, about a 7.5-fold increase to about a 8.5-fold increase, about a 7.5-fold increase to about a 8.0-fold increase, about a 8.0-fold increase to about a 100-fold increase, about 8.0-fold increase to about a 90-fold increase, about 8.0-fold increase to about a 80-fold increase, about a 8.0-fold increase to about a 70-fold increase, about a 8.0-fold increase to about a 60-fold increase, about a 8.0-fold increase to about a 50-fold increase, about a 8.0-fold increase to about a 40-fold increase, about a 8.0-fold increase to about a 30-fold increase, about 8.0-fold increase to about 20-fold increase, about a 8.0-fold increase to about a 10-fold increase, about a 8.0-fold increase to about a 9.5-fold increase, about a 8.0-fold increase to about a 9.0-fold increase, about a 8.0-fold increase to about a 8.5-fold increase, about a 8.5-fold increase to about a 100-fold increase, about 8.5-fold increase to about a 90-fold increase, about 8.5-fold increase to about a 80-fold increase, about a 8.5-fold increase to about a 70-fold increase, about a 8.5-fold increase to about a 60-fold increase, about a 8.5-fold increase to about a 50-fold increase, about a 8.5-fold increase to about a 40-fold increase, about a 8.5-fold increase to about a 30-fold increase, about 8.5-fold increase to about 20-fold increase, about a 8.5-fold increase to about a 10-fold increase, about a 8.5-fold increase to about a 9.5-fold increase, about a 8.5-fold increase to about a 9.0-fold increase, about a 9.0-fold increase to about a 100-fold increase, about 9.0-fold increase to about a 90-fold increase, about 9.0-fold increase to about a 80-fold increase, about a 9.0-fold increase to about a 70-fold increase, about a 9.0-fold increase to about a 60-fold increase, about a 9.0-fold increase to about a 50-fold increase, about a 9.0-fold increase to about a 40-fold increase, about a 9.0-fold increase to about a 30-fold increase, about 9.0-fold increase to about 20-fold increase, about a 9.0-fold increase to about a 10-fold increase, about a 9.0-fold increase to about a 9.5-fold increase, about a 9.5-fold increase to about a 100-fold increase, about 9.5-fold increase to about a 90-fold increase, about 9.5-fold increase to about a 80-fold increase, about a 9.5-fold increase to about a 70-fold increase, about a 9.5-fold increase to about a 60-fold increase, about a 9.5-fold increase to about a 50-fold increase, about a 9.5-fold increase to about a 40-fold increase, about a 9.5-fold increase to about a 30-fold increase, about 9.5-fold increase to about 20-fold increase, about a 9.5-fold increase to about a 10-fold increase, about a 10-fold increase to about a 100-fold increase, about 10-fold increase to about a 90-fold increase, about 10-fold increase to about a 80-fold increase, about a 10-fold increase to about a 70-fold increase, about a 10-fold increase to about a 60-fold increase, about a 10-fold increase to about a 50-fold increase, about a 10-fold increase to about a 40-fold increase, about a 10-fold increase to about a 30-fold increase, about 10-fold increase to about 20-fold increase, about a 20-fold increase to about a 100-fold increase, about 20-fold increase to about a 90-fold increase, about 20-fold increase to about a 80-fold increase, about a 20-fold increase to about a 70-fold increase, about a 20-fold increase to about a 60-fold increase, about a 20-fold increase to about a 50-fold increase, about a 20-fold increase to about a 40-fold increase, about a 20-fold increase to about a 30-fold increase, about a 30-fold increase to about a 100-fold increase, about 30-fold increase to about a 90-fold increase, about 30-fold increase to about a 80-fold increase, about a 30-fold increase to about a 70-fold increase, about a 30-fold increase to about a 60-fold increase, about a 30-fold increase to about a 50-fold increase, about a 30-fold increase to about a 40-fold increase, about a 40-fold increase to about a 100-fold increase, about 40-fold increase to about a 90-fold increase, about 40-fold increase to about a 80-fold increase, about a 40-fold increase to about a 70-fold increase, about a 40-fold increase to about a 60-fold increase, about a 40-fold increase to about a 50-fold increase, about a 50-fold increase to about a 100-fold increase, about 50-fold increase to about a 90-fold increase, about 50-fold increase to about a 80-fold increase, about a 50-fold increase to about a 70-fold increase, about a 50-fold increase to about a 60-fold increase, about a 60-fold increase to about a 100-fold increase, about 60-fold increase to about a 90-fold increase, about 60-fold increase to about a 80-fold increase, about a 60-fold increase to about a 70-fold increase, about a 70-fold increase to about a 100-fold increase, about 70-fold increase to about a 90-fold increase, about 70-fold increase to about a 80-fold increase, about a 80-fold increase to about a 100-fold increase, about 80-fold increase to about a 90-fold increase, or about a 90-fold increase to about a 100-fold increase) in toxin liberation in the target mammalian cell (e.g., any of the target mammalian cells described herein) as compared to a composition including the same amount of a control ABPC (e.g., any of the exemplary control ABPCs described herein).

In some examples of any of the ABPCs described herein, a composition including the ABPC (e.g., any of the ABPCs described herein) can provide for an increase (e.g., a detectable increase) (e.g., at least a 1% increase, at least a 2% increase, at least a 5% increase, at least a 10% increase, at least a 15% increase, at least a 20% increase, at least a 25% increase, at least a 30% increase, at least a 35% increase, at least a 40% increase, at least a 45% increase, at least a 50% increase, at least a 55% increase, at least a 60% increase, at least a 65% increase, at least a 70% increase, at least a 75% increase, at least a 80% increase, at least a 85% increase, at least a 90% increase, at least a 95% increase, at least a 100% increase, at least a 120% increase, at least a 140% increase, at least a 160% increase, at least a 180% increase, at least a 200% increase, at least a 250% increase, at least a 300% increase, at least a 350% increase, at least a 400% increase, at least a 450% increase, at least a 500% increase, at least a 1,000% increase, at least a 2,000% increase, at least a 3,000% increase, at least a 4,000% increase, at least a 5,000% increase, at least a 6,000% increase, at least a 7,000% increase, at least a 8,000% increase, at a least a 9,000% increase, or at least a 10,000% increase, or about a 1% increase to about a 10,000% increase (e.g., or any of the subranges of this range described herein)) in target mammalian cell killing (e.g., any of the exemplary target mammalian cells described herein) as compared to a composition including the same amount of a control ABPC (e.g., any of the exemplary control ABPCs described herein).

In some examples of any of the ABPCs described herein, a composition including the ABPC (e.g., any of the ABPCs described herein) can provide for an increase (e.g., a detectable increase) (e.g., at least a 0.1-fold increase, at least a 0.2-fold increase, at least a 0.3-fold increase, at least a 0.4-fold increase, at least a 0.5-fold increase, at least a 0.6-fold increase, at least a 0.7-fold increase, at least a 0.8-fold increase, at least a 0.9-fold increase, at least a 1.0-fold increase, at least a 1.2-fold increase, at least a 1.4-fold increase, at least a 1.5-fold increase, at least a 1.6-fold increase, at least a 1.8-fold increase, at least a 2.0-fold increase, at least a 2.2-fold increase, at least a 2.4-fold increase, at least a 2.5-fold increase, at least a 2.6-fold increase, at least a 2.8-fold increase, at least a 3.0-fold increase, at least a 3.5-fold increase, at least a 4.0-fold increase, at least a 4.5-fold increase, at least a 5.0-fold increase, at least a 5.5-fold increase, at least a 6.0-fold increase, at least a 6.5-fold increase, at least a 7.0-fold increase, at least a 7.5-fold increase, at least a 8.0-fold increase, at least a 8.5-fold increase, at least a 9.0-fold increase, at least a 9.5-fold increase, at least a 10-fold increase, at least a 15-fold increase, at least a 20-fold increase, at least a 25-fold increase, at least a 30-fold increase, at least a 35-fold increase, at least a 40-fold increase, at least a 40-fold increase, at least a 45-fold increase, at least a 50-fold increase, at least a 55-fold increase, at least a 60-fold increase, at least a 65-fold increase, at least a 70-fold increase, at least a 80-fold increase, at least a 85-fold increase, at least a 90-fold increase, at least a 95-fold increase, or at least a 100-fold increase, or about a 0.1-fold increase to about a 100-fold increase (or any of the subranges of this range described herein)) in target mammalian cell killing (e.g., any of the exemplary target mammalian cells described herein) as compared to a composition including the same amount of a control ABPC (e.g., any of the exemplary control ABPCs described herein).

In some examples of any of the ABPCs described herein, a composition including any of the ABPCs described herein (e.g., upon contacting target mammalian cells presenting CD123 on their surface) results in decreased (e.g., at least a 1% decrease, at least a 5% decrease, at least a 10% decrease, at least a 15% decrease, at least a 20% decrease, at least a 25% decrease, at least a 30% decrease, at least a 35% decrease, at least a 40% decrease, at least a 45% decrease, at least a 50% decrease, at least a 55% decrease, at least a 60% decrease, at least a 65% decrease, at least a 70% decrease, at least a 75% decrease, at least a 80% decrease, at least a 85% decrease, at least a 90% decrease, at least a 95% decrease, or at least a 99% decrease, about a 1% decrease to about a 99% decrease, or any of the subranges of this range described herein) $IC_{50}$ (for target mammalian cell killing) as compared to the $IC_{50}$ for a composition including the same amount of a control ABPC (e.g., any of the control ABPCs described herein) (e.g., upon contacting the same target mammalian cells).

In some examples of any of the ABPCs described herein, a composition including any of the ABPCs described herein (e.g., upon contacting target mammalian cells presenting CD123 on their surface) can provide for an increase (e.g., at least a 0.1-fold increase, at least a 0.2-fold increase, at least a 0.4-fold increase, at least a 0.6-fold increase, at least a 0.8-fold increase, at least a 1-fold increase, at least a 2-fold increase, at least a 5-fold increase, at least a 10-fold increase, at least a 15-fold increase, at least a 20-fold increase, at least a 25-fold increase, at least a 30-fold increase, at least a 35-fold increase, at least a 40-fold increase, at least a 45-fold increase, at least a 50-fold increase, at least a 55-fold increase, at least a 60-fold increase, at least a 65-fold increase, at least a 70-fold increase, at least a 75-fold increase, at least a 80-fold increase, at least a 85-fold increase, at least a 90-fold increase, at least a 95-fold increase, or at least a 100-fold increase, or about a 0.1-fold increase to about 500-fold increase (or any of the subranges of this range described herein) in the ratio of $K_D$ on target mammalian cells presenting CD123 on their surface at a neutral pH (a pH of about 7.0 to about 8.0) to $IC_{50}$ at the neutral pH on the same target cells, e.g., as compared to a control ABPC (e.g., any of the exemplary control ABPCs described herein).

In some examples of any of the ABPCs described herein, a composition including the ABPC (e.g., any of the ABPCs described herein) can provide for an increase (e.g., a detectable increase) (e.g., at least a 1% increase, at least a 2% increase, at least a 5% increase, at least a 10% increase, at least a 15% increase, at least a 20% increase, at least a 25% increase, at least a 30% increase, at least a 35% increase, at least a 40% increase, at least a 45% increase, at least a 50% increase, at least a 55% increase, at least a 60% increase, at least a 65% increase, at least a 70% increase, at least a 75% increase, at least a 80% increase, at least a 85% increase, at least a 90% increase, at least a 95% increase, at least a 100% increase, at least a 120% increase, at least a 140% increase, at least a 160% increase, at least a 180% increase, at least a 200% increase, at least a 250% increase, at least a 300% increase, at least a 350% increase, at least a 400% increase, at least a 450% increase, at least a 500% increase, at least a 1,000% increase, at least a 2,000% increase, at least a 3,000% increase, at least a 4,000% increase, at least a 5,000% increase, at least a 6,000% increase, at least a 7,000% increase, at least a 8,000% increase, at least a 9,000% increase, or at least a 10,000% increase, or about a 1% increase to about a 10,000% increase (e.g., or any of the subranges of this range described herein)) in endolysosomal delivery in the target mammalian cell (e.g., any of the exemplary target mammalian cells described herein) as compared to a composition including the same amount of a control ABPC (e.g., any of the exemplary control ABPCs described herein).

In some examples of any of the ABPCs described herein, a composition including the ABPC (e.g., any of the ABPCs described herein) can provide for an increase (e.g., a detectable increase) (e.g., at least a 0.1-fold increase, at least a 0.2-fold increase, at least a 0.3-fold increase, at least a 0.4-fold increase, at least a 0.5-fold increase, at least a 0.6-fold increase, at least a 0.7-fold increase, at least a 0.8-fold increase, at least a 0.9-fold increase, at least a 1.0-fold increase, at least a 1.2-fold increase, at least a 1.4-fold increase, at least a 1.5-fold increase, at least a 1.6-fold increase, at least a 1.8-fold increase, at least a 2.0-fold increase, at least a 2.2-fold increase, at least a 2.4-fold increase, at least a 2.5-fold increase, at least a 2.6-fold increase, at least a 2.8-fold increase, at least a 3.0-fold increase, at least a 3.5-fold increase, at least a 4.0-fold increase, at least a 4.5-fold increase, at least a 5.0-fold increase, at least a 5.5-fold increase, at least a 6.0-fold increase, at least a 6.5-fold increase, at least a 7.0-fold increase, at least a 7.5-fold increase, at least a 8.0-fold increase, at least a 8.5-fold increase, at least a 9.0-fold increase, at least a 9.5-fold increase, at least a 10-fold increase, at least a 15-fold increase, at least a 20-fold increase, at least a 25-fold increase, at least a 30-fold increase, at least a 35-fold increase, at least a 40-fold increase, at least a 45-fold increase, at least a 50-fold increase, at least a 55-fold increase, at least a 60-fold increase, at least a 65-fold increase, at least a 70-fold increase, at least a 75-fold increase, at least a 80-fold increase, at least a 85-fold increase, at least a 90-fold increase, at least a 95-fold increase, or at least a 100-fold increase, or about a 0.1-fold increase to about a 100-fold increase (or any of the subranges of this range described herein)) in endolysosomal delivery in the target mammalian cell (e.g., any of the exemplary target mammalian cells described herein) as compared to a composition including the same amount of a control ABPC (e.g., any of the exemplary control ABPCs described herein).

In examples of any of the ABPCs described herein, the target mammalian cell does not express an FcRn receptor, or expresses a lower (e.g., a detectably lower) level (e.g., at least a 1% decreased, at least a 2% decreased, at least a 5% decreased, at least a 10% decrease, at least a 15% decreased, at least a 20% decreased, at least a 25% decreased, at least a 30% decreased, at least a 35% decreased, at least a 40% decreased, at least a 45% decreased, at least a 50% decreased, at least a 55% decreased, at least a 60% decreased, at least a 65% decreased, at least a 70% decreased, at least a 75% decreased, at least a 80% decreased, at least a 85% decreased, at least a 90% decreased, at least a 95% decreased, or at least a 99% decreased level) of FcRn receptor as compared to a FcRn expressing control cell (e.g., HUVEC—ThermoFisher #C0035C). In some examples of any of the ABPCs described herein, the target mammalian cell is a cancer cell. In some examples of any of the ABPCs described herein, the ABPC is cytotoxic or cytostatic to the target mammalian cell.

In some examples of any of the ABPCs described herein, a composition including any of the ABPCs described herein (e.g., upon administration to a subject) results in less (e.g., a 1% decrease to about a 99% decrease, or any of the subranges of this range described herein) of a reduction in the level of CD123 presented on the surface of the target cell as compared to a composition including the same amount of a control ABPC (e.g., any of the control ABPCs described herein). In some examples of any of the ABPCs described herein, the composition does not result in a detectable reduction in the level of the CD123 presented on the surface of the target mammalian cell.

In some examples of any of the ABPCs described herein, the ABPC is cross-reactive with a non-human primate CD123 and a human CD123. In some examples of any of the ABPCs described herein, the ABPC is cross-reactive with a non-human primate CD123, a human CD123, and one or both of rat CD123 and a mouse CD123. In some examples of any of the ABPCs described herein, the ABPC is cross-reactive with a non-human primate CD123, a human CD123, a rat CD123, and a mouse CD123. In some examples of any of the ABPCs described herein, the ABPC is cross-reactive with mouse CD123 and rat CD123. In some examples of any of the ABPCs described herein, the antigen-binding domain binds to an epitope of CD123 that is present on the surface of cells from an Old World Monkey.

Some examples of any of the ABPCs described herein can further include a second antigen-binding domain (e.g., any of the exemplary antigen-binding domains described herein). Non-limiting aspects of these methods are described below, and can be used in any combination without limitation. Additional aspects of these methods are known in the art.

CD123 or Epitope of CD123

Interleukin 3 receptor subunit alpha (CD123) is a tumor antigen that is known in the art, and is the target of therapeutic antibodies in oncology (Kovtun, Yelena, et al. (2018) "A CD123-Targeting Antibody-Drug Conjugate, IMGN632, Designed to Eradicate AML While Sparing Normal Bone Marrow Cells." Blood Advances, American Society of Hematology 2(8) 848-858). The sequence of the mature Human CD123 can be found in SEQ ID NO: 9. The sequence of the cDNA encoding the mature Human CD123 can be found in SEQ ID NO: 10. The sequence of the extracellular domain of CD123 can be found in SEQ ID NO: 11. The sequence of the cDNA encoding the extracellular domain of CD123 can be found in SEQ ID NO: 12.

Antigen-Binding Protein Constructs

Any of the antigen-binding protein constructs (ABPCs) described herein can be a single polypeptide, or can include two, three, four, five, six, seven, eight, nine, or ten (the same or different) polypeptides. In some embodiments where the ABPC is a single polypeptide, the ABPC can include a single antigen-binding domain or two antigen-binding domains. In some embodiments where the ABPC is a single polypeptide and includes two antigen-binding domains, the first and second antigen-binding domains can be identical or different from each other (and can specifically bind to the same or different antigens or epitopes).

In some embodiments where the ABPC is a single polypeptide, the first antigen-binding domain and the second antigen-binding domain (if present) can each be independently selected from the group of: a VH domain, a VHH domain, a VNAR domain, and a scFv. In some embodiments where the ABPC is a single polypeptide, the antigen-binding protein construct can be a BiTe, a (scFv)2, a nanobody, a nanobody-HSA, a DART, a TandAb, a scDiabody, a scDiabody-CH3, scFv-CH-CL-scFv, a HSAbody, scDiabody-HAS, a tandem-scFv, an Adnectin, a DARPin, a fibronectin, and a DEP conjugate. Additional examples of antigen-binding domains that can be used when the ABPC is a single polypeptide are known in the art.

A $V_H$H domain is a single monomeric variable antibody domain that can be found in camelids. A $V_{NAR}$ domain is a single monomeric variable antibody domain that can be found in cartilaginous fish. Non-limiting aspects of $V_H$H domains and $V_{NAR}$ domains are described in, e.g., Cromie et al., *Curr. Top. Med. Chem.* 15:2543-2557, 2016; De Genst et al., *Dev. Comp. Immunol.* 30:187-198, 2006; De Meyer et al., *Trends Biotechnol.* 32:263-270, 2014; Kijanka et al., *Nanomedicine* 10:161-174, 2015; Kovaleva et al., *Expert. Opin. Biol. Ther.* 14:1527-1539, 2014; Krah et al., *Immunopharmacol. Immunotoxicol.* 38:21-28, 2016; Mujic-Delic et al., *Trends Pharmacol. Sci.* 35:247-255, 2014; Muyldermans, *J. Biotechnol.* 74:277-302, 2001; Muyldermans et al., *Trends Biochem. Sci.* 26:230-235, 2001; Muyldermans, *Ann. Rev. Biochem.* 82:775-797, 2013; Rahbarizadeh et al., *Immunol. Invest.* 40:299-338, 2011; Van Audenhove et al., *EBioMedicine* 8:40-48, 2016; Van Bockstaele et al., *Curr Opin. Investig. Drugs* 10:1212-1224, 2009; Vincke et al., *Methods Mol. Biol.* 911:15-26, 2012; and Wesolowski et al., *Med. Microbiol. Immunol.* 198:157-174, 2009.

In some embodiments where the ABPC is a single polypeptide and includes two antigen-binding domains, the first antigen-binding domain and the second antigen-binding domain can both be VHH domains, or at least one antigen-binding domain can be a VHH domain. In some embodiments where the ABPC is a single polypeptide and includes two antigen-binding domains, the first antigen-binding domain and the second antigen-binding domain are both $V_{NAR}$ domains, or at least one antigen-binding domain is a $V_{NAR}$ domain. In some embodiments where the ABPC is a single polypeptide, the first antigen-binding domain is a scFv domain. In some embodiments where the ABPC is a single polypeptide and includes two antigen-binding domains, the first antigen-binding domain and the second antigen-binding domain can both be scFv domains, or at least one antigen-binding domain can be a scFv domain.

In some embodiments, the ABPC can include two or more polypeptides (e.g., two, three, four, five, six, seven, eight, nine, or ten polypeptides). In some embodiments where the ABPC includes two or more polypeptides, two, three, four, five or six of the polypeptides of the two or more polypeptides can be identical.

In some embodiments where the ABPC includes two or more polypeptides (e.g., two, three, four, five, six, seven, eight, nine, or ten polypeptides), two or more of the polypeptides of the ABPC can assemble (e.g., non-covalently assemble) to form one or more antigen-binding domains, e.g., an antigen-binding fragment of an antibody (e.g., any of the antigen-binding fragments of an antibody described herein), a VHH-scAb, a VHH-Fab, a Dual scFab, a F(ab')2, a diabody, a crossMab, a DAF (two-in-one), a DAF (four-in-one), a DutaMab, a DT-IgG, a knobs-in-holes common light chain, a knobs-in-holes assembly, a charge pair, a Fab-arm exchange, a SEEDbody, a LUZ-Y, a Fcab, a κλ-body, an orthogonal Fab, a DVD-IgG, a IgG(H)-scFv, a scFv-(H)IgG, IgG(L)-scFv, scFv-(L)IgG, IgG(L,H)-Fv, IgG (H)-V, V(H)-IgG, IgG(L)-V, V(L)-IgG, KIH IgG-scFab, 2scFv-IgG, IgG-2scFv, scFv4-Ig, Zybody, DVI-IgG, Diabody-CH3, a triple body, a miniantibody, a minibody, a TriBi minibody, scFv-CH3 KIH, Fab-scFv, a F(ab')2-scFv2, a scFv-KIH, a Fab-scFv-Fc, a tetravalent HCAb, a scDiabody-Fc, a Diabody-Fc, a tandem scFv-Fc, a VHH-Fc, a tandem VHH-Fc, a VHH-Fc KiH, a Fab-VHH-Fc, an Intrabody, a dock and lock, an ImmTAC, an IgG-IgG conjugate, a Cov-X-Body, a scFv1-PEG-scFv2, an Adnectin, a DARPin, a fibronectin, and a DEP conjugate. See, e.g., Spiess et al., Mol. Immunol. 67:95-106, 2015, incorporated in its entirety herewith, for a description of these elements. Non-limiting examples of an antigen-binding fragment of an antibody include an Fv fragment, a Fab fragment, a F(ab')2 fragment, and a Fab' fragment. Additional examples of an antigen-binding fragment of an antibody is an antigen-binding fragment of an IgG (e.g., an antigen-binding fragment of IgG1, IgG2, IgG3, or IgG4) (e.g., an antigen-binding fragment of a human or humanized IgG, e.g., human or humanized IgG1, IgG2, IgG3, or IgG4); an antigen-binding fragment of an IgA (e.g., an antigen-binding fragment of IgA1 or IgA2) (e.g., an antigen-binding fragment of a human or humanized IgA, e.g., a human or humanized IgA1 or IgA2); an antigen-binding fragment of an IgD (e.g., an antigen-binding fragment of a human or humanized IgD); an antigen-binding fragment of an IgE (e.g., an antigen-binding fragment of a human or humanized IgE); or an antigen-binding fragment of an IgM (e.g., an antigen-binding fragment of a human or humanized IgM).

A "Fv" fragment includes a non-covalently-linked dimer of one heavy chain variable domain and one light chain variable domain.

A "Fab" fragment includes, the constant domain of the light chain and the first constant domain ($C_{H1}$) of the heavy chain, in addition to the heavy and light chain variable domains of the Fv fragment.

A "F(ab')$_2$" fragment includes two Fab fragments joined, near the hinge region, by disulfide bonds.

A "dual variable domain immunoglobulin" or "DVD-Ig" refers to multivalent and multispecific binding proteins as described, e.g., in DiGiammarino et al., *Methods Mol. Biol.* 899:145-156, 2012; Jakob et al., *MABs* 5:358-363, 2013; and U.S. Pat. Nos. 7,612,181; 8,258,268; 8,586,714; 8,716,450; 8,722,855; 8,735,546; and 8,822,645, each of which is incorporated by reference in its entirety.

DARTs are described in, e.g., Garber, *Nature Reviews Drug Discovery* 13:799-801, 2014. Additional aspects of ABPCs are known in the art.

Antigen-Binding Domains

In some embodiments of any of the antigen-binding protein constructs (ABPCs) described herein, the dissociation rate of the first antigen-binding domain (and optionally the second antigen-binding domain, if present) at a pH of about 4.0 to about 6.5 (e.g., about 4.0 to about 6.4, about 4.0 to about 6.3, about 4.0 to about 6.2, about 4.0 to about 6.1, about 4.0 to about 6.0, about 4.0 to about 5.9, about 4.0 to about 5.8, about 4.0 to about 5.7, about 4.0 to about 5.6, about 4.0 to about 5.5, about 4.0 to about 5.4, about 4.0 to about 5.3, about 4.0 to about 5.2, about 4.0 to about 5.1, about 4.0 to about 5.0, about 4.0 to about 4.9, about 4.0 to about 4.8, about 4.0 to about 4.7, about 4.0 to about 4.6, about 4.0 to about 4.5, about 4.0 to about 4.4, about 4.0 to about 4.3, about 4.0 to about 4.2, about 4.0 to about 4.1, about 4.1 to about 6.5, about 4.1 to about 6.4, about 4.1 to about 6.3, about 4.1 to about 6.2, about 4.1 to about 6.1, about 4.1 to about 6.0, about 4.1 to about 5.9, about 4.1 to about 5.8, about 4.1 to about 5.7, about 4.1 to about 5.6, about 4.1 to about 5.5, about 4.1 to about 5.4, about 4.1 to about 5.3, about 4.1 to about 5.2, about 4.1 to about 5.1, about 4.1 to about 5.0, about 4.1 to about 4.9, about 4.1 to about 4.8, about 4.1 to about 4.7, about 4.1 to about 4.6, about 4.1 to about 4.5, about 4.1 to about 4.4, about 4.1 to about 4.3, about 4.1 to about 4.2, about 4.2 to about 6.5, about 4.2 to about 6.4, about 4.2 to about 6.3, about 4.2 to about 6.2, about 4.2 to about 6.1, about 4.2 to about 6.0, about 4.2 to about 5.9, about 4.2 to about 5.8, about 4.2 to about 5.7, about 4.2 to about 5.6, about 4.2 to about 5.5, about 4.2 to about 5.4, about 4.2 to about 5.3, about 4.2 to about 5.2, about 4.2 to about 5.1, about 4.2 to about 5.0, about 4.2 to about 4.9, about 4.2 to about 4.8, about 4.2 to about 4.7, about 4.2 to about 4.6, about 4.2 to about 4.5, about 4.2 to about 4.4, about 4.2 to about 4.3, about 4.3 to about 6.5, about 4.3 to about 6.4, about 4.3 to about 6.3, about 4.3 to about 6.2, about 4.3 to about 6.1, about 4.3 to about 6.0, about 4.3 to about 5.9, about 4.3 to about 5.8, about 4.3 to about 5.7, about 4.3 to about 5.6, about 4.3 to about 5.5, about 4.3 to about 5.4, about 4.3 to about 5.3, about 4.3 to about 5.2, about 4.3 to about 5.1, about 4.3 to about 5.0, about 4.3 to about 4.9, about 4.3 to about 4.8, about 4.3 to about 4.7, about 4.3 to about 4.6, about 4.3 to about 4.5, about 4.3 to about 4.4, about 4.4 to about 6.5, about 4.4 to about 6.4, about 4.4 to about 6.3, about 4.4 to about 6.2, about 4.4 to about 6.1, about 4.4 to about 6.0, about 4.4 to about 5.9, about 4.4 to about 5.8, about 4.4 to about 5.7, about 4.4 to about 5.6, about 4.4 to about 5.5, about 4.4 to about 5.4, about 4.4 to about 5.3, about 4.4 to about 5.2, about 4.4 to about 5.1, about 4.4 to about 5.0, about 4.4 to about 4.9, about 4.4 to about 4.8, about 4.4 to about 4.7, about 4.4 to about 4.6, about 4.4 to about 4.5, about 4.5 to about 6.5, about 4.5 to about 6.4, about 4.5 to about 6.3, about 4.5 to about 6.2, about 4.5 to about 6.1, about 4.5 to about 6.0, about 4.5 to about 5.9, about 4.5 to about 5.8, about 4.5 to about 5.7, about 4.5 to about 5.6, about 4.5 to about 5.5, about 4.5 to about 5.4, about 4.5 to about 5.3, about 4.5 to about 5.2, about 4.5 to about 5.1, about 4.5 to about 5.0, about 4.5 to about 4.9, about 4.5 to about 4.8, about 4.5 to about 4.7, about 4.5 to about 4.6, about 4.6 to about 6.5, about 4.6 to about 6.4, about 4.6 to about 6.3, about 4.6 to about 6.2, about 4.6 to about 6.1, about 4.6 to about 6.0, about 4.6 to about 5.9, about 4.6 to about 5.8, about 4.6 to about 5.7, about 4.6 to about 5.6, about 4.6 to about 5.5, about 4.6 to about 5.4, about 4.6 to about 5.3, about 4.6 to about 5.2, about 4.6 to about 5.1, about 4.6 to about 5.0, about 4.6 to about 4.9, about 4.6 to about 4.8, about 4.6 to about 4.7, about 4.7 to about 6.5, about 4.7 to about 6.4, about 4.7 to about 6.3, about 4.7 to about 6.2, about 4.7 to about 6.1, about 4.7 to about 6.0, about 4.7 to about 5.9, about 4.7 to about 5.8, about 4.7 to about 5.7, about 4.7 to about 5.6, about 4.7 to about 5.5, about 4.7 to about 5.4, about 4.7 to about 5.3, about 4.7 to about 5.2, about 4.7 to about 5.1, about 4.7 to about 5.0, about 4.7 to about 4.9, about 4.7 to about 4.8, about 4.8 to about 6.5, about 4.8 to about 6.4, about 4.8 to about 6.3, about 4.8 to about 6.2, about 4.8 to about 6.1, about 4.8 to about 6.0, about 4.8 to about 5.9, about 4.8 to about 5.8, about 4.8 to about 5.7, about 4.8 to about 5.6, about 4.8 to about 5.5, about 4.8 to about 5.4, about 4.8 to about 5.3, about 4.8 to about 5.2, about 4.8 to about 5.1, about 4.8 to about 5.0, about 4.8 to about 4.9, about 4.9 to about 6.5, about 4.9 to about 6.4, about 4.9 to about 6.3, about 4.9 to about 6.2, about 4.9 to about 6.1, about 4.9 to about 6.0, about 4.9 to about 5.9, about 4.9 to about 5.8, about 4.9 to about 5.7, about 4.9 to about 5.6, about 4.9 to about 5.5, about 4.9 to about 5.4, about 4.9 to about 5.3, about 4.9 to about 5.2, about 4.9 to about 5.1, about 4.9 to about 5.0, about 5.0 to about 6.5, about 5.0 to about 6.4, about 5.0 to about 6.3, about 5.0 to about 6.2, about 5.0 to about 6.1, about 5.0 to about 6.0, about 5.0 to about 5.9, about 5.0 to about 5.8, about 5.0 to about 5.7, about 5.0 to about 5.6, about 5.0 to about 5.5, about 5.0 to about 5.4, about 5.0 to about 5.3, about 5.0 to about 5.2, about 5.0 to about 5.1, about 5.1 to about 6.5, about 5.1 to about 6.4, about 5.1 to about 6.3, about 5.1 to about 6.2, about 5.1 to about 6.1, about 5.1 to about 6.0, about 5.1 to about 5.9, about 5.1 to about 5.8, about 5.1 to about 5.7, about 5.1 to about 5.6, about 5.1 to about 5.5, about 5.1 to about 5.4, about 5.1 to about 5.3, about 5.1 to about 5.2, about 5.2 to about 6.5, about 5.2 to about 6.4, about 5.2 to about 6.3, about 5.2 to about 6.2, about 5.2 to about 6.1, about 5.2 to about 6.0, about 5.2 to about 5.9, about 5.2 to about 5.8, about 5.2 to about 5.7, about 5.2 to about 5.6, about 5.2 to about 5.5, about 5.2 to about 5.4, about 5.2 to about 5.3, about 5.3 to about 6.5, about 5.3 to about 6.4, about 5.3 to about 6.3, about 5.3 to about 6.2, about 5.3 to about 6.1, about 5.3 to about 6.0, about 5.3 to about 5.9, about 5.3 to about 5.8, about 5.3 to about 5.7, about 5.3 to about 5.6, about 5.3 to about 5.5, about 5.3 to about 5.4, about 5.4 to about 6.5, about 5.4 to about 6.4, about 5.4 to about 6.3, about 5.4 to about 6.2, about 5.4 to about 6.1, about 5.4 to about 6.0, about 5.4 to about 5.9, about 5.4 to about 5.8, about 5.4 to about 5.7, about 5.4 to about 5.6, about 5.4 to about 5.5, about 5.5 to about 6.5, about 5.5 to about 6.4, about 5.5 to about 6.3, about 5.5 to about 6.2, about 5.5 to about 6.1, about 5.5 to about 6.0, about 5.5 to about 5.9, about 5.5 to about 5.8, about 5.5 to about 5.7, about 5.5 to about 5.6, about 5.6 to about 6.5, about 5.6 to about 6.4, about 5.6 to about 6.3, about 5.6 to about 6.2, about 5.6 to about 6.1, about 5.6 to about 6.0, about 5.6 to about 5.9, about 5.6 to about 5.8, about 5.6 to about 5.7, about 5.7 to about 6.5, about 5.7 to about 6.4, about 5.7 to about 6.3, about 5.7 to about 6.2, about 5.7 to about 6.1, about 5.7 to about 6.0, about 5.7 to about 5.9, about 5.7 to about 5.8, about 5.8 to about 6.5, about 5.8 to about 6.4, about 5.8 to about 6.3, about 5.8 to about 6.2, about 5.8 to about 6.1, about 5.8 to about 6.0, about 5.8 to about 5.9, about 5.9 to about 6.5, about 5.9 to about 6.4, about 5.9 to about 6.3, about 5.9 to about 6.2, about 5.9 to about 6.1, about 5.9 to about 6.0, about 6.0 to about 6.5, about 6.0 to about 6.4, about 6.0 to about 6.3, about 6.0 to about 6.2, about 6.0 to about 6.1, about 6.1 to about 6.5, about 6.1 to about 6.4, about 6.1 to about 6.3, about 6.1 to about 6.2, about 6.2 to about 6.5, about 6.2 to about 6.4, about 6.2 to about 6.3, about 6.3 to about 6.5, about 6.3 to about 6.4, or about 6.4 to about 6.5) is faster (e.g., (e.g., at least 5% faster, at least 10% faster, at least 15% faster, at least 20%, at least 25% faster, at least 30% faster, at least 35% faster, at least 40% faster, at least 45% faster, at least 50% faster, at least 55% faster, at least 60% faster, at least 65% faster, at least 70% faster, at least 75% faster, at least 80% faster, at least 85% faster, at least 90% faster, at least 95% faster, at least 100% faster, at least 120% faster, at least 140% faster, at least 160% faster, at least 180% faster, at least 200% faster, at least 220% faster at least 240% faster at least 260% faster at least 280% faster at least 300% faster at least 320% faster at least 340% faster at least 360% faster at least 380% faster at least 400% faster at least 420% faster at least 440% faster at least 460% faster at least 480% faster, at least 500% faster, at least 1,000% faster, at least 2,000% faster, at least 3,000% faster, at least 4,000% faster, at least 5,000%, at least 6,000% faster, at least 7,000% faster, at least 8,000% faster, at least 9,000% faster, or at least 10,000% faster, or about 5% faster to about 10,000% faster, about 5% faster to about 9,000% faster, about 5% faster to about 8,000% faster, about 5% faster to about 7,000% faster, about 5% faster to about 6,000% faster, about 5% faster to about 5,000% faster, about 5% faster to about 4,000% faster, about 5% faster to about 3,000% faster, about 5% faster to about 2,000% faster, about 5% faster to about 1,000% faster, about 5% faster to about 500% faster, about 5% faster to about 480% faster, about 5% faster to about 460% faster, about 5% faster to about 440% faster, about 5% faster to about 420% faster, about 5% faster to about 400% faster, about 5% faster to about 380% faster, about 5% faster to about 360% faster, about 5% faster to about 340% faster, about 5% faster to about 320% faster, about 5% faster to about 300% faster, about 5% faster to about 280% faster, about 5% faster to about 260% faster, about 5% faster to about 240% faster, about 5% faster to about 220% faster, about 5% faster to about 200% faster, about 5% faster to about 180% faster, about 5% faster to about 160% faster, about 5% faster to about 140% faster, about 5% faster to about 120% faster, about 5% faster to about 100% faster, about 5% faster to about 95% faster, about 5% faster to about 90% faster, about 5% faster to about 85% faster, about 5% faster to about 80% faster, about 5% faster to about 75% faster, about 5% faster to about 70% faster, about 5% faster to about 65% faster, about 5% faster to about 60% faster, about 5% faster to about 55% faster, about 5% faster to about 50% faster, about 5% faster to about 45% faster, about 5% faster to about 40% faster, about 5% faster to about 35% faster, about 5% faster to about 30% faster, about 5% faster to about 25% faster, about 5% faster to about 20% faster, about 5% faster to about 15% faster, about 5% faster to about 10% faster, about 10% faster to about 10,000% faster, about 10% faster to about 9,000% faster, about 10% faster to about 8,000% faster, about 10% faster to about 7,000% faster, about 10% faster to about 6,000% faster, about 10% faster to about 5,000% faster, about 10% faster to about 4,000% faster, about 10% faster to about 3,000% faster, about 10% faster to about 2,000% faster, about 10% faster to about 1,000% faster, about 10% faster to about 500% faster, about 10% faster to about 480% faster, about 10% faster to about 460% faster, about 10% faster to about 440% faster, about 10% faster to about 420% faster, about 10% faster to about 400% faster, about 10% faster to about 380% faster, about 10% faster to about 360% faster, about 10% faster to about 340% faster, about 10% faster to about 320% faster, about 10% faster to about 300% faster, about 10% faster to about 280% faster, about 10% faster to about 260% faster, about 10% faster to about 240% faster, about 10% faster to about 220% faster, about 10% faster to about 200% faster, about 10% faster to about 180% faster, about 10% faster to about 160% faster, about 10% faster to about 140% faster, about 10% faster to about 120% faster, about 10% faster to about 100% faster, about 10% faster to about 95% faster, about 10% faster to about 90% faster, about 10% faster to about 85% faster, about 10% faster to about 80% faster, about 10% faster to about 75% faster, about 10% faster to about 70% faster, about 10% faster to about 65% faster, about 10% faster to about 60% faster, about 10% faster to about 55% faster, about 10% faster to about 50% faster, about 10% faster to about 45% faster, about 10% faster to about 40% faster, about 10% faster to about 35% faster, about 10% faster to about 30% faster, about 10% faster to about 25% faster, about 10% faster to about 20% faster, about 10% faster to about 15% faster, about 15% faster to about 10,000% faster, about 15% faster to about 9,000% faster, about 15% faster to about 8,000% faster, about 15% faster to about 7,000% faster, about 15% faster to about 6,000% faster, about 15% faster to about 5,000% faster, about 15% faster to about 4,000% faster, about 15% faster to about 3,000% faster, about 15% faster to about 2,000% faster, about 15% faster to about 1,000% faster, about 15% faster to about 500% faster, about 15% faster to about 480% faster, about 15% faster to about 460% faster, about 15% faster to about 440% faster, about 15% faster to about 420% faster, about 15% faster to about 400% faster, about 15% faster to about 380% faster, about 15% faster to about 360% faster, about 15% faster to about 340% faster, about 15% faster to about 320% faster, about 15% faster to about 300% faster, about 15% faster to about 280% faster, about 15% faster to about 260% faster, about 15% faster to about 240% faster, about 15% faster to about 220% faster, about 15% faster to about 200% faster, about 15% faster to about 180% faster, about 15% faster to about 160% faster, about 15% faster to about 140% faster, about 15% faster to about 120% faster, about 15% faster to about 100% faster, about 15% faster to about 95% faster, about 15% faster to about 90% faster, about 15% faster to about 85% faster, about 15% faster to about 80% faster, about 15% faster to about 75% faster, about 15% faster to about 70% faster, about 15% faster to about 65% faster, about 15% faster to about 60% faster, about 15% faster to about 55% faster, about 15% faster to about 50% faster, about 15% faster to about 45% faster, about 15% faster to about 40% faster, about 15% faster to about 35% faster, about 15% faster to about 30% faster, about 15% faster to about 25% faster, about 15% faster to about 20% faster, about 20% faster to about 10,000% faster, about 20% faster to about 9,000% faster, about 20% faster to about 8,000% faster, about 20% faster to about 7,000% faster, about 20% faster to about 6,000% faster, about 20% faster to about 5,000% faster, about 20% faster to about 4,000% faster, about 20% faster to about 3,000% faster, about 20% faster to about 2,000% faster, about 20% faster to about 1,000% faster, about 20% faster to about 500% faster, about 20% faster to about 480% faster, about 20% faster to about 460% faster, about 20% faster to about 440% faster, about 20% faster to about 420% faster, about 20% faster to about 400% faster, about 20% faster to about 380% faster, about 20% faster to about 360% faster, about 20% faster to about 340% faster, about 20% faster to about 320% faster, about 20% faster to about 300% faster, about 20% faster to about 280% faster, about 20% faster to about 260% faster, about 20% faster to about 240% faster, about 20% faster to about 220% faster, about 20% faster to about 200% faster, about 20% faster to about 180% faster, about 20% faster to about 160% faster, about 20% faster to about 140% faster, about 20% faster to about 120% faster, about 20% faster to about 100% faster, about 20% faster to about 95% faster, about 20% faster to about 90% faster, about 20% faster to about 85% faster, about 20% faster to about 80% faster, about 20% faster to about 75% faster, about 20% faster to about 70% faster, about 20% faster to about 65% faster, about 20% faster to about 60% faster, about 20% faster to about 55% faster, about 20% faster to about 50% faster, about 20% faster to about 45% faster, about 20% faster to about 40% faster, about 20% faster to about 35% faster, about 20% faster to about 30% faster, about 20% faster to about 25% faster, about 25% faster to about 10,000% faster, about 25% faster to about 9,000% faster, about 25% faster to about 8,000% faster, about 25% faster to about 7,000% faster, about 25% faster to about 6,000% faster, about 25% faster to about 5,000% faster, about 25% faster to about 4,000% faster, about 25% faster to about 3,000% faster, about 25% faster to about 2,000% faster, about 25% faster to about 1,000% faster, about 25% faster to about 500% faster, about 25% faster to about 480% faster, about 25% faster to about 460% faster, about 25% faster to about 440% faster, about 25% faster to about 420% faster, about 25% faster to about 400% faster, about 25% faster to about 380% faster, about 25% faster to about 360% faster, about 25% faster to about 340% faster, about 25% faster to about 320% faster, about 25% faster to about 300% faster, about 25% faster to about 280% faster, about 25% faster to about 260% faster, about 25% faster to about 240% faster, about 25% faster to about 220% faster, about 25% faster to about 200% faster, about 25% faster to about 180% faster, about 25% faster to about 160% faster, about 25% faster to about 140% faster, about 25% faster to about 120% faster, about 25% faster to about 100% faster, about 25% faster to about 95% faster, about 25% faster to about 90% faster, about 25% faster to about 85% faster, about 25% faster to about 80% faster, about 25% faster to about 75% faster, about 25% faster to about 70% faster, about 25% faster to about 65% faster, about 25% faster to about 60% faster, about 25% faster to about 55% faster, about 25% faster to about 50% faster, about 25% faster to about 45% faster, about 25% faster to about 40% faster, about 25% faster to about 35% faster, about 25% faster to about 30% faster, about 30% faster to about 10,000% faster, about 30% faster to about 9,000% faster, about 30% faster to about 8,000% faster, about 30% faster to about 7,000% faster, about 30% faster to about 6,000% faster, about 30% faster to about 5,000% faster, about 30% faster to about 4,000% faster, about 30% faster to about 3,000% faster, about 30% faster to about 2,000% faster, about 30% faster to about 1,000% faster, about 30% faster to about 500% faster, about 30% faster to about 480% faster, about 30% faster to about 460% faster, about 30% faster to about 440% faster, about 30% faster to about 420% faster, about 30% faster to about 400% faster, about 30% faster to about 380% faster, about 30% faster to about 360% faster, about 30% faster to about 340% faster, about 30% faster to about 320% faster, about 30% faster to about 300% faster, about 30% faster to about 280% faster, about 30% faster to about 260% faster, about 30% faster to about 240% faster, about 30% faster to about 220% faster, about 30% faster to about 200% faster, about 30% faster to about 180% faster, about 30% faster to about 160% faster, about 30% faster to about 140% faster, about 30% faster to about 120% faster, about 30% faster to about 100% faster, about 30% faster to about 95% faster, about 30% faster to about 90% faster, about 30% faster to about 85% faster, about 30% faster to about 80% faster, about 30% faster to about 75% faster, about 30% faster to about 70% faster, about 30% faster to about 65% faster, about 30% faster to about 60% faster, about 30% faster to about 55% faster, about 30% faster to about 50% faster, about 30% faster to about 45% faster, about 30% faster to about 40% faster, about 30% faster to about 35% faster, about 35% faster to about 10,000% faster, about 35% faster to about 9,000% faster, about 35% faster to about 8,000% faster, about 35% faster to about 7,000% faster, about 35% faster to about 6,000% faster, about 35% faster to about 5,000% faster, about 35% faster to about 4,000% faster, about 35% faster to about 3,000% faster, about 35% faster to about 2,000% faster, about 35% faster to about 1,000% faster, about 35% faster to about 500% faster, about 35% faster to about 480% faster, about 35% faster to about 460% faster, about 35% faster to about 440% faster, about 35% faster to about 420% faster, about 35% faster to about 400% faster, about 35% faster to about 380% faster, about 35% faster to about 360% faster, about 35% faster to about 340% faster, about 35% faster to about 320% faster, about 35% faster to about 300% faster, about 35% faster to about 280% faster, about 35% faster to about 260% faster, about 35% faster to about 240% faster, about 35% faster to about 220% faster, about 35% faster to about 200% faster, about 35% faster to about 180% faster, about 35% faster to about 160% faster, about 35% faster to about 140% faster, about 35% faster to about 120% faster, about 35% faster to about 100% faster, about 35% faster to about 95% faster, about 35% faster to about 90% faster, about 35% faster to about 85% faster, about 35% faster to about 80% faster, about 35% faster to about 75% faster, about 35% faster to about 70% faster, about 35% faster to about 65% faster, about 35% faster to about 60% faster, about 35% faster to about 55% faster, about 35% faster to about 50% faster, about 35% faster to about 45% faster, about 35% faster to about 40% faster, about 40% faster to about 10,000% faster, about 40% faster to about 9,000% faster, about 40% faster to about 8,000% faster, about 40% faster to about 7,000% faster, about 40% faster to about 6,000% faster, about 40% faster to about 5,000% faster, about 40% faster to about 4,000% faster, about 40% faster to about 3,000% faster, about 40% faster to about 2,000% faster, about 40% faster to about 1,000% faster, about 40% faster to about 500% faster, about 40% faster to about 480% faster, about 40% faster to about 460% faster, about 40% faster to about 440% faster, about 40% faster to about 420% faster, about 40% faster to about 400% faster, about 40% faster to about 380% faster, about 40% faster to about 360% faster, about 40% faster to about 340% faster, about 40% faster to about 320% faster, about 40% faster to about 300% faster, about 40% faster to about 280% faster, about 40% faster to about 260% faster, about 40% faster to about 240% faster, about 40% faster to about 220% faster, about 40% faster to about 200% faster, about 40% faster to about 180% faster, about 40% faster to about 160% faster, about 40% faster to about 140% faster, about 40% faster to about 120% faster, about 40% faster to about 100% faster, about 40% faster to about 95% faster, about 40% faster to about 90% faster, about 40% faster to about 85% faster, about 40% faster to about 80% faster, about 40% faster to about 75% faster, about 40% faster to about 70% faster, about 40% faster to about 65% faster, about 40% faster to about 60% faster, about 40% faster to about 55% faster, about 40% faster to about 50% faster, about 40% faster to about 45% faster, about 45% faster to about 10,000% faster, about 45% faster to about 9,000% faster, about 45% faster to about 8,000% faster, about 45% faster to about 7,000% faster, about 45% faster to about 6,000% faster, about 45% faster to about 5,000% faster, about 45% faster to about 4,000% faster, about 45% faster to about 3,000% faster, about 45% faster to about 2,000% faster, about 45% faster to about 1,000% faster, about 45% faster to about 500% faster, about 45% faster to about 480% faster, about 45% faster to about 460% faster, about 45% faster to about 440% faster, about 45% faster to about 420% faster, about 45% faster to about 400% faster, about 45% faster to about 380% faster, about 45% faster to about 360% faster, about 45% faster to about 340% faster, about 45% faster to about 320% faster, about 45% faster to about 300% faster, about 45% faster to about 280% faster, about 45% faster to about 260% faster, about 45% faster to about 240% faster, about 45% faster to about 220% faster, about 45% faster to about 200% faster, about 45% faster to about 180% faster, about 45% faster to about 160% faster, about 45% faster to about 140% faster, about 45% faster to about 120% faster, about 45% faster to about 100% faster, about 45% faster to about 95% faster, about 45% faster to about 90% faster, about 45% faster to about 85% faster, about 45% faster to about 80% faster, about 45% faster to about 75% faster, about 45% faster to about 70% faster, about 45% faster to about 65% faster, about 45% faster to about 60% faster, about 45% faster to about 55% faster, about 45% faster to about 50% faster, about 50% faster to about 10,000% faster, about 50% faster to about 9,000% faster, about 50% faster to about 8,000% faster, about 50% faster to about 7,000% faster, about 50% faster to about 6,000% faster, about 50% faster to about 5,000% faster, about 50% faster to about 4,000% faster, about 50% faster to about 3,000% faster, about 50% faster to about 2,000% faster, about 50% faster to about 1,000% faster, about 50% faster to about 500% faster, about 50% faster to about 480% faster, about 50% faster to about 460% faster, about 50% faster to about 440% faster, about 50% faster to about 420% faster, about 50% faster to about 400% faster, about 50% faster to about 380% faster, about 50% faster to about 360% faster, about 50% faster to about 340% faster, about 50% faster to about 320% faster, about 50% faster to about 300% faster, about 50% faster to about 280% faster, about 50% faster to about 260% faster, about 50% faster to about 240% faster, about 50% faster to about 220% faster, about 50% faster to about 200% faster, about 50% faster to about 180% faster, about 50% faster to about 160% faster, about 50% faster to about 140% faster, about 50% faster to about 120% faster, about 50% faster to about 100% faster, about 50% faster to about 95% faster, about 50% faster to about 90% faster, about 50% faster to about 85% faster, about 50% faster to about 80% faster, about 50% faster to about 75% faster, about 50% faster to about 70% faster, about 50% faster to about 65% faster, about 50% faster to about 60% faster, about 50% faster to about 55% faster, about 55% faster to about 10,000% faster, about 55% faster to about 9,000% faster, about 55% faster to about 8,000% faster, about 55% faster to about 7,000% faster, about 55% faster to about 6,000% faster, about 55% faster to about 5,000% faster, about 55% faster to about 4,000% faster, about 55% faster to about 3,000% faster, about 55% faster to about 2,000% faster, about 55% faster to about 1,000% faster, about 55% faster to about 500% faster, about 55% faster to about 480% faster, about 55% faster to about 460% faster, about 55% faster to about 440% faster, about 55% faster to about 420% faster, about 55% faster to about 400% faster, about 55% faster to about 380% faster, about 55% faster to about 360% faster, about 55% faster to about 340% faster, about 55% faster to about 320% faster, about 55% faster to about 300% faster, about 55% faster to about 280% faster, about 55% faster to about 260% faster, about 55% faster to about 240% faster, about 55% faster to about 220% faster, about 55% faster to about 200% faster, about 55% faster to about 180% faster, about 55% faster to about 160% faster, about 55% faster to about 140% faster, about 55% faster to about 120% faster, about 55% faster to about 100% faster, about 55% faster to about 95% faster, about 55% faster to about 90% faster, about 55% faster to about 85% faster, about 55% faster to about 80% faster, about 55% faster to about 75% faster, about 55% faster to about 70% faster, about 55% faster to about 65% faster, about 55% faster to about 60% faster, about 60% faster to about 10,000% faster, about 60% faster to about 9,000% faster, about 60% faster to about 8,000% faster, about 60% faster to about 7,000% faster, about 60% faster to about 6,000% faster, about 60% faster to about 5,000% faster, about 60% faster to about 4,000% faster, about 60% faster to about 3,000% faster, about 60% faster to about 2,000% faster, about 60% faster to about 1,000% faster, about 60% faster to about 500% faster, about 60% faster to about 480% faster, about 60% faster to about 460% faster, about 60% faster to about 440% faster, about 60% faster to about 420% faster, about 60% faster to about 400% faster, about 60% faster to about 380% faster, about 60% faster to about 360% faster, about 60% faster to about 340% faster, about 60% faster to about 320% faster, about 60% faster to about 300% faster, about 60% faster to about 280% faster, about 60% faster to about 260% faster, about 60% faster to about 240% faster, about 60% faster to about 220% faster, about 60% faster to about 200% faster, about 60% faster to about 180% faster, about 60% faster to about 160% faster, about 60% faster to about 140% faster, about 60% faster to about 120% faster, about 60% faster to about 100% faster, about 60% faster to about 95% faster, about 60% faster to about 90% faster, about 60% faster to about 85% faster, about 60% faster to about 80% faster, about 60% faster to about 75% faster, about 60% faster to about 70% faster, about 60% faster to about 65% faster, about 65% faster to about 10,000% faster, about 65% faster to about 9,000% faster, about 65% faster to about 8,000% faster, about 65% faster to about 7,000% faster, about 65% faster to about 6,000% faster, about 65% faster to about 5,000% faster, about 65% faster to about 4,000% faster, about 65% faster to about 3,000% faster, about 65% faster to about 2,000% faster, about 65% faster to about 1,000% faster, about 65% faster to about 500% faster, about 65% faster to about 480% faster, about 65% faster to about 460% faster, about 65% faster to about 440% faster, about 65% faster to about 420% faster, about 65% faster to about 400% faster, about 65% faster to about 380% faster, about 65% faster to about 360% faster, about 65% faster to about 340% faster, about 65% faster to about 320% faster, about 65% faster to about 300% faster, about 65% faster to about 280% faster, about 65% faster to about 260% faster, about 65% faster to about 240% faster, about 65% faster to about 220% faster, about 65% faster to about 200% faster, about 65% faster to about 180% faster, about 65% faster to about 160% faster, about 65% faster to about 140% faster, about 65% faster to about 120% faster, about 65% faster to about 100% faster, about 65% faster to about 95% faster, about 65% faster to about 90% faster, about 65% faster to about 85% faster, about 65% faster to about 80% faster, about 65% faster to about 75% faster, about 65% faster to about 70% faster, about 70% faster to about 10,000% faster, about 70% faster to about 9,000% faster, about 70% faster to about 8,000% faster, about 70% faster to about 7,000% faster, about 70% faster to about 6,000% faster, about 70% faster to about 5,000% faster, about 70% faster to about 4,000% faster, about 70% faster to about 3,000% faster, about 70% faster to about 2,000% faster, about 70% faster to about 1,000% faster, about 70% faster to about 500% faster, about 70% faster to about 480% faster, about 70% faster to about 460% faster, about 70% faster to about 440% faster, about 70% faster to about 420% faster, about 70% faster to about 400% faster, about 70% faster to about 380% faster, about 70% faster to about 360% faster, about 70% faster to about 340% faster, about 70% faster to about 320% faster, about 70% faster to about 300% faster, about 70% faster to about 280% faster, about 70% faster to about 260% faster, about 70% faster to about 240% faster, about 70% faster to about 220% faster, about 70% faster to about 200% faster, about 70% faster to about 180% faster, about 70% faster to about 160% faster, about 70% faster to about 140% faster, about 70% faster to about 120% faster, about 70% faster to about 100% faster, about 70% faster to about 95% faster, about 70% faster to about 90% faster, about 70% faster to about 85% faster, about 70% faster to about 80% faster, about 70% faster to about 75% faster, about 75% faster to about 10,000% faster, about 75% faster to about 9,000% faster, about 75% faster to about 8,000% faster, about 75% faster to about 7,000% faster, about 75% faster to about 6,000% faster, about 75% faster to about 5,000% faster, about 75% faster to about 4,000% faster, about 75% faster to about 3,000% faster, about 75% faster to about 2,000% faster, about 75% faster to about 1,000% faster, about 75% faster to about 500% faster, about 75% faster to about 480% faster, about 75% faster to about 460% faster, about 75% faster to about 440% faster, about 75% faster to about 420% faster, about 75% faster to about 400% faster, about 75% faster to about 380% faster, about 75% faster to about 360% faster, about 75% faster to about 340% faster, about 75% faster to about 320% faster, about 75% faster to about 300% faster, about 75% faster to about 280% faster, about 75% faster to about 260% faster, about 75% faster to about 240% faster, about 75% faster to about 220% faster, about 75% faster to about 200% faster, about 75% faster to about 180% faster, about 75% faster to about 160% faster, about 75% faster to about 140% faster, about 75% faster to about 120% faster, about 75% faster to about 100% faster, about 75% faster to about 95% faster, about 75% faster to about 90% faster, about 75% faster to about 85% faster, about 75% faster to about 80% faster, about 80% faster to about 10,000% faster, about 80% faster to about 9,000% faster, about 80% faster to about 8,000% faster, about 80% faster to about 7,000% faster, about 80% faster to about 6,000% faster, about 80% faster to about 5,000% faster, about 80% faster to about 4,000% faster, about 80% faster to about 3,000% faster, about 80% faster to about 2,000% faster, about 80% faster to about 1,000% faster, about 80% faster to about 500% faster, about 80% faster to about 480% faster, about 80% faster to about 460% faster, about 80% faster to about 440% faster, about 80% faster to about 420% faster, about 80% faster to about 400% faster, about 80% faster to about 380% faster, about 80% faster to about 360% faster, about 80% faster to about 340% faster, about 80% faster to about 320% faster, about 80% faster to about 300% faster, about 80% faster to about 280% faster, about 80% faster to about 260% faster, about 80% faster to about 240% faster, about 80% faster to about 220% faster, about 80% faster to about 200% faster, about 80% faster to about 180% faster, about 80% faster to about 160% faster, about 80% faster to about 140% faster, about 80% faster to about 120% faster, about 80% faster to about 100% faster, about 80% faster to about 95% faster, about 80% faster to about 90% faster, about 80% faster to about 85% faster, about 85% faster to about 10,000% faster, about 85% faster to about 9,000% faster, about 85% faster to about 8,000% faster, about 85% faster to about 7,000% faster, about 85% faster to about 6,000% faster, about 85% faster to about 5,000% faster, about 85% faster to about 4,000% faster, about 85% faster to about 3,000% faster, about 85% faster to about 2,000% faster, about 85% faster to about 1,000% faster, about 85% faster to about 500% faster, about 85% faster to about 480% faster, about 85% faster to about 460% faster, about 85% faster to about 440% faster, about 85% faster to about 420% faster, about 85% faster to about 400% faster, about 85% faster to about 380% faster, about 85% faster to about 360% faster, about 85% faster to about 340% faster, about 85% faster to about 320% faster, about 85% faster to about 300% faster, about 85% faster to about 280% faster, about 85% faster to about 260% faster, about 85% faster to about 240% faster, about 85% faster to about 220% faster, about 85% faster to about 200% faster, about 85% faster to about 180% faster, about 85% faster to about 160% faster, about 85% faster to about 140% faster, about 85% faster to about 120% faster, about 85% faster to about 100% faster, about 85% faster to about 95% faster, about 85% faster to about 90% faster, about 90% faster to about 10,000% faster, about 90% faster to about 9,000% faster, about 90% faster to about 8,000% faster, about 90% faster to about 7,000% faster, about 90% faster to about 6,000% faster, about 90% faster to about 5,000% faster, about 90% faster to about 4,000% faster, about 90% faster to about 3,000% faster, about 90% faster to about 2,000% faster, about 90% faster to about 1,000% faster, about 90% faster to about 500% faster, about 90% faster to about 480% faster, about 90% faster to about 460% faster, about 90% faster to about 440% faster, about 90% faster to about 420% faster, about 90% faster to about 400% faster, about 90% faster to about 380% faster, about 90% faster to about 360% faster, about 90% faster to about 340% faster, about 90% faster to about 320% faster, about 90% faster to about 300% faster, about 90% faster to about 280% faster, about 90% faster to about 260% faster, about 90% faster to about 240% faster, about 90% faster to about 220% faster, about 90% faster to about 200% faster, about 90% faster to about 180% faster, about 90% faster to about 160% faster, about 90% faster to about 140% faster, about 90% faster to about 120% faster, about 90% faster to about 100% faster, about 90% faster to about 95% faster, about 95% faster to about 10,000% faster, about 95% faster to about 9,000% faster, about 95% faster to about 8,000% faster, about 95% faster to about 7,000% faster, about 95% faster to about 6,000% faster, about 95% faster to about 5,000% faster, about 95% faster to about 4,000% faster, about 95% faster to about 3,000% faster, about 95% faster to about 2,000% faster, about 95% faster to about 1,000% faster, about 95% faster to about 500% faster, about 95% faster to about 480% faster, about 95% faster to about 460% faster, about 95% faster to about 440% faster, about 95% faster to about 420% faster, about 95% faster to about 400% faster, about 95% faster to about 380% faster, about 95% faster to about 360% faster, about 95% faster to about 340% faster, about 95% faster to about 320% faster, about 95% faster to about 300% faster, about 95% faster to about 280% faster, about 95% faster to about 260% faster, about 95% faster to about 240% faster, about 95% faster to about 220% faster, about 95% faster to about 200% faster, about 95% faster to about 180% faster, about 95% faster to about 160% faster, about 95% faster to about 140% faster, about 95% faster to about 120% faster, about 95% faster to about 100% faster, about 100% faster to about 10,000% faster, about 100% faster to about 9,000% faster, about 100% faster to about 8,000% faster, about 100% faster to about 7,000% faster, about 100% faster to about 6,000% faster, about 100% faster to about 5,000% faster, about 100% faster to about 4,000% faster, about 100% faster to about 3,000% faster, about 100% faster to about 2,000% faster, about 100% faster to about 1,000% faster, about 100% faster to about 500% faster, about 100% faster to about 480% faster, about 100% faster to about 460% faster, about 100% faster to about 440% faster, about 100% faster to about 420% faster, about 100% faster to about 400% faster, about 100% faster to about 380% faster, about 100% faster to about 360% faster, about 100% faster to about 340% faster, about 100% faster to about 320% faster, about 100% faster to about 300% faster, about 100% faster to about 280% faster, about 100% faster to about 260% faster, about 100% faster to about 240% faster, about 100% faster to about 220% faster, about 100% faster to about 200% faster, about 100% faster to about 180% faster, about 100% faster to about 160% faster, about 100% faster to about 140% faster, about 100% faster to about 120% faster, about 120% faster to about 10,000% faster, about 120% faster to about 9,000% faster, about 120% faster to about 8,000% faster, about 120% faster to about 7,000% faster, about 120% faster to about 6,000% faster, about 120% faster to about 5,000% faster, about 120% faster to about 4,000% faster, about 120% faster to about 3,000% faster, about 120% faster to about 2,000% faster, about 120% faster to about 1,000% faster, about 120% faster to about 500% faster, about 120% faster to about 480% faster, about 120% faster to about 460% faster, about 120% faster to about 440% faster, about 120% faster to about 420% faster, about 120% faster to about 400% faster, about 120% faster to about 380% faster, about 120% faster to about 360% faster, about 120% faster to about 340% faster, about 120% faster to about 320% faster, about 120% faster to about 300% faster, about 120% faster to about 280% faster, about 120% faster to about 260% faster, about 120% faster to about 240% faster, about 120% faster to about 220% faster, about 120% faster to about 200% faster, about 120% faster to about 180% faster, about 120% faster to about 160% faster, about 120% faster to about 140% faster, about 140% faster to about 10,000% faster, about 140% faster to about 9,000% faster, about 140% faster to about 8,000% faster, about 140% faster to about 7,000% faster, about 140% faster to about 6,000% faster, about 140% faster to about 5,000% faster, about 140% faster to about 4,000% faster, about 140% faster to about 3,000% faster, about 140% faster to about 2,000% faster, about 140% faster to about 1,000% faster, about 140% faster to about 500% faster, about 140% faster to about 480% faster, about 140% faster to about 460% faster, about 140% faster to about 440% faster, about 140% faster to about 420% faster, about 140% faster to about 400% faster, about 140% faster to about 380% faster, about 140% faster to about 360% faster, about 140% faster to about 340% faster, about 140% faster to about 320% faster, about 140% faster to about 300% faster, about 140% faster to about 280% faster, about 140% faster to about 260% faster, about 140% faster to about 240% faster, about 140% faster to about 220% faster, about 140% faster to about 200% faster, about 140% faster to about 180% faster, about 140% faster to about 160% faster, about 160% faster to about 10,000% faster, about 160% faster to about 9,000% faster, about 160% faster to about 8,000% faster, about 160% faster to about 7,000% faster, about 160% faster to about 6,000% faster, about 160% faster to about 5,000% faster, about 160% faster to about 4,000% faster, about 160% faster to about 3,000% faster, about 160% faster to about 2,000% faster, about 160% faster to about 1,000% faster, about 160% faster to about 500% faster, about 160% faster to about 480% faster, about 160% faster to about 460% faster, about 160% faster to about 440% faster, about 160% faster to about 420% faster, about 160% faster to about 400% faster, about 160% faster to about 380% faster, about 160% faster to about 360% faster, about 160% faster to about 340% faster, about 160% faster to about 320% faster, about 160% faster to about 300% faster, about 160% faster to about 280% faster, about 160% faster to about 260% faster, about 160% faster to about 240% faster, about 160% faster to about 220% faster, about 160% faster to about 200% faster, about 160% faster to about 180% faster, about 180% faster to about 10,000% faster, about 180% faster to about 9,000% faster, about 180% faster to about 8,000% faster, about 180% faster to about 7,000% faster, about 180% faster to about 6,000% faster, about 180% faster to about 5,000% faster, about 180% faster to about 4,000% faster, about 180% faster to about 3,000% faster, about 180% faster to about 2,000% faster, about 180% faster to about 1,000% faster, about 180% faster to about 500% faster, about 180% faster to about 480% faster, about 180% faster to about 460% faster, about 180% faster to about 440% faster, about 180% faster to about 420% faster, about 180% faster to about 400% faster, about 180% faster to about 380% faster, about 180% faster to about 360% faster, about 180% faster to about 340% faster, about 180% faster to about 320% faster, about 180% faster to about 300% faster, about 180% faster to about 280% faster, about 180% faster to about 260% faster, about 180% faster to about 240% faster, about 180% faster to about 220% faster, about 180% faster to about 200% faster, about 200% faster to about 10,000% faster, about 200% faster to about 9,000% faster, about 200% faster to about 8,000% faster, about 200% faster to about 7,000% faster, about 200% faster to about 6,000% faster, about 200% faster to about 5,000% faster, about 200% faster to about 4,000% faster, about 200% faster to about 3,000% faster, about 200% faster to about 2,000% faster, about 200% faster to about 1,000% faster, about 200% faster to about 500% faster, about 200% faster to about 480% faster, about 200% faster to about 460% faster, about 200% faster to about 440% faster, about 200% faster to about 420% faster, about 200% faster to about 400% faster, about 200% faster to about 380% faster, about 200% faster to about 360% faster, about 200% faster to about 340% faster, about 200% faster to about 320% faster, about 200% faster to about 300% faster, about 200% faster to about 280% faster, about 200% faster to about 260% faster, about 200% faster to about 240% faster, about 200% faster to about 220% faster, about 220% faster to about 10,000% faster, about 220% faster to about 9,000% faster, about 220% faster to about 8,000% faster, about 220% faster to about 7,000% faster, about 220% faster to about 6,000% faster, about 220% faster to about 5,000% faster, about 220% faster to about 4,000% faster, about 220% faster to about 3,000% faster, about 220% faster to about 2,000% faster, about 220% faster to about 1,000% faster, about 220% faster to about 500% faster, about 220% faster to about 480% faster, about 220% faster to about 460% faster, about 220% faster to about 440% faster, about 220% faster to about 420% faster, about 220% faster to about 400% faster, about 220% faster to about 380% faster, about 220% faster to about 360% faster, about 220% faster to about 340% faster, about 220% faster to about 320% faster, about 220% faster to about 300% faster, about 220% faster to about 280% faster, about 220% faster to about 260% faster, about 220% faster to about 240% faster, about 240% faster to about 10,000% faster, about 240% faster to about 9,000% faster, about 240% faster to about 8,000% faster, about 240% faster to about 7,000% faster, about 240% faster to about 6,000% faster, about 240% faster to about 5,000% faster, about 240% faster to about 4,000% faster, about 240% faster to about 3,000% faster, about 240% faster to about 2,000% faster, about 240% faster to about 1,000% faster, about 240% faster to about 500% faster, about 240% faster to about 480% faster, about 240% faster to about 460% faster, about 240% faster to about 440% faster, about 240% faster to about 420% faster, about 240% faster to about 400% faster, about 240% faster to about 380% faster, about 240% faster to about 360% faster, about 240% faster to about 340% faster, about 240% faster to about 320% faster, about 240% faster to about 300% faster, about 240% faster to about 280% faster, about 240% faster to about 260% faster, about 260% faster to about 10,000% faster, about 260% faster to about 9,000% faster, about 260% faster to about 8,000% faster, about 260% faster to about 7,000% faster, about 260% faster to about 6,000% faster, about 260% faster to about 5,000% faster, about 260% faster to about 4,000% faster, about 260% faster to about 3,000% faster, about 260% faster to about 2,000% faster, about 260% faster to about 1,000% faster, about 260% faster to about 500% faster, about 260% faster to about 480% faster, about 260% faster to about 460% faster, about 260% faster to about 440% faster, about 260% faster to about 420% faster, about 260% faster to about 400% faster, about 260% faster to about 380% faster, about 260% faster to about 360% faster, about 260% faster to about 340% faster, about 260% faster to about 320% faster, about 260% faster to about 300% faster, about 260% faster to about 280% faster, about 280% faster to about 10,000% faster, about 280% faster to about 9,000% faster, about 280% faster to about 8,000% faster, about 280% faster to about 7,000% faster, about 280% faster to about 6,000% faster, about 280% faster to about 5,000% faster, about 280% faster to about 4,000% faster, about 280% faster to about 3,000% faster, about 280% faster to about 2,000% faster, about 280% faster to about 1,000% faster, about 280% faster to about 500% faster, about 280% faster to about 480% faster, about 280% faster to about 460% faster, about 280% faster to about 440% faster, about 280% faster to about 420% faster, about 280% faster to about 400% faster, about 280% faster to about 380% faster, about 280% faster to about 360% faster, about 280% faster to about 340% faster, about 280% faster to about 320% faster, about 280% faster to about 300% faster, about 300% faster to about 10,000% faster, about 300% faster to about 9,000% faster, about 300% faster to about 8,000% faster, about 300% faster to about 7,000% faster, about 300% faster to about 6,000% faster, about 300% faster to about 5,000% faster, about 300% faster to about 4,000% faster, about 300% faster to about 3,000% faster, about 300% faster to about 2,000% faster, about 300% faster to about 1,000% faster, about 300% faster to about 500% faster, about 300% faster to about 480% faster, about 300% faster to about 460% faster, about 300% faster to about 440% faster, about 300% faster to about 420% faster, about 300% faster to about 400% faster, about 300% faster to about 380% faster, about 300% faster to about 360% faster, about 300% faster to about 340% faster, about 300% faster to about 320% faster, about 320% faster to about 10,000% faster, about 320% faster to about 9,000% faster, about 320% faster to about 8,000% faster, about 320% faster to about 7,000% faster, about 320% faster to about 6,000% faster, about 320% faster to about 5,000% faster, about 320% faster to about 4,000% faster, about 320% faster to about 3,000% faster, about 320% faster to about 2,000% faster, about 320% faster to about 1,000% faster, about 320% faster to about 500% faster, about 320% faster to about 480% faster, about 320% faster to about 460% faster, about 320% faster to about 440% faster, about 320% faster to about 420% faster, about 320% faster to about 400% faster, about 320% faster to about 380% faster, about 320% faster to about 360% faster, about 320% faster to about 340% faster, about 340% faster to about 10,000% faster, about 340% faster to about 9,000% faster, about 340% faster to about 8,000% faster, about 340% faster to about 7,000% faster, about 340% faster to about 6,000% faster, about 340% faster to about 5,000% faster, about 340% faster to about 4,000% faster, about 340% faster to about 3,000% faster, about 340% faster to about 2,000% faster, about 340% faster to about 1,000% faster, about 340% faster to about 500% faster, about 340% faster to about 480% faster, about 340% faster to about 460% faster, about 340% faster to about 440% faster, about 340% faster to about 420% faster, about 340% faster to about 400% faster, about 340% faster to about 380% faster, about 340% faster to about 360% faster, about 360% faster to about 10,000% faster, about 360% faster to about 9,000% faster, about 360% faster to about 8,000% faster, about 360% faster to about 7,000% faster, about 360% faster to about 6,000% faster, about 360% faster to about 5,000% faster, about 360% faster to about 4,000% faster, about 360% faster to about 3,000% faster, about 360% faster to about 2,000% faster, about 360% faster to about 1,000% faster, about 360% faster to about 500% faster, about 360% faster to about 480% faster, about 360% faster to about 460% faster, about 360% faster to about 440% faster, about 360% faster to about 420% faster, about 360% faster to about 400% faster, about 360% faster to about 380% faster, about 380% faster to about 10,000% faster, about 380% faster to about 9,000% faster, about 380% faster to about 8,000% faster, about 380% faster to about 7,000% faster, about 380% faster to about 6,000% faster, about 380% faster to about 5,000% faster, about 380% faster to about 4,000% faster, about 380% faster to about 3,000% faster, about 380% faster to about 2,000% faster, about 380% faster to about 1,000% faster, about 380% faster to about 500% faster, about 380% faster to about 480% faster, about 380% faster to about 460% faster, about 380% faster to about 440% faster, about 380% faster to about 420% faster, about 380% faster to about 400% faster, about 400% faster to about 10,000% faster, about 400% faster to about 9,000% faster, about 400% faster to about 8,000% faster, about 400% faster to about 7,000% faster, about 400% faster to about 6,000% faster, about 400% faster to about 5,000% faster, about 400% faster to about 4,000% faster, about 400% faster to about 3,000% faster, about 400% faster to about 2,000% faster, about 400% faster to about 1,000% faster, about 400% faster to about 500% faster, about 400% faster to about 480% faster, about 400% faster to about 460% faster, about 400% faster to about 440% faster, about 400% faster to about 420% faster, about 420% faster to about 10,000% faster, about 420% faster to about 9,000% faster, about 420% faster to about 8,000% faster, about 420% faster to about 7,000% faster, about 420% faster to about 6,000% faster, about 420% faster to about 5,000% faster, about 420% faster to about 4,000% faster, about 420% faster to about 3,000% faster, about 420% faster to about 2,000% faster, about 420% faster to about 1,000% faster, about 420% faster to about 500% faster, about 420% faster to about 480% faster, about 420% faster to about 460% faster, about 420% faster to about 440% faster, about 440% faster to about 10,000% faster, about 440% faster to about 9,000% faster, about 440% faster to about 8,000% faster, about 440% faster to about 7,000% faster, about 440% faster to about 6,000% faster, about 440% faster to about 5,000% faster, about 440% faster to about 4,000% faster, about 440% faster to about 3,000% faster, about 440% faster to about 2,000% faster, about 440% faster to about 1,000% faster, about 440% faster to about 500% faster, about 440% faster to about 480% faster, about 440% faster to about 460% faster, about 460% faster to about 10,000% faster, about 460% faster to about 9,000% faster, about 460% faster to about 8,000% faster, about 460% faster to about 7,000% faster, about 460% faster to about 6,000% faster, about 460% faster to about 5,000% faster, about 460% faster to about 4,000% faster, about 460% faster to about 3,000% faster, about 460% faster to about 2,000% faster, about 460% faster to about 1,000% faster, about 460% faster to about 500% faster, about 460% faster to about 480% faster, about 480% faster to about 10,000% faster, about 480% faster to about 9,000% faster, about 480% faster to about 8,000% faster, about 480% faster to about 7,000% faster, about 480% faster to about 6,000% faster, about 480% faster to about 5,000% faster, about 480% faster to about 4,000% faster, about 480% faster to about 3,000% faster, about 480% faster to about 2,000% faster, about 480% faster to about 1,000% faster, about 480% faster to about 500% faster, about 500% faster to about 10,000% faster, about 500% faster to about 9,000% faster, about 500% faster to about 8,000% faster, about 500% faster to about 7,000% faster, about 500% faster to about 6,000% faster, about 500% faster to about 5,000% faster, about 500% faster to about 4,000% faster, about 500% faster to about 3,000% faster, about 500% faster to about 2,000% faster, about 500% faster to about 1,000% faster, about 1,000% faster to about 10,000% faster, about 1,000% faster to about 9,000% faster, about 1,000% faster to about 8,000% faster, about 1,000% faster to about 7,000% faster, about 1,000% faster to about 6,000% faster, about 1,000% faster to about 5,000% faster, about 1,000% faster to about 4,000% faster, about 1,000% faster to about 3,000% faster, about 1,000% faster to about 2,000% faster, about 2,000% faster to about 10,000% faster, about 2,000% faster to about 9,000% faster, about 2,000% faster to about 8,000% faster, about 2,000% faster to about 7,000% faster, about 2,000% faster to about 6,000% faster, about 2,000% faster to about 5,000% faster, about 2,000% faster to about 4,000% faster, about 2,000% faster to about 3,000% faster, about 3,000% faster to about 10,000% faster, about 3,000% faster to about 9,000% faster, about 3,000% faster to about 8,000% faster, about 3,000% faster to about 7,000% faster, about 3,000% faster to about 6,000% faster, about 3,000% faster to about 5,000% faster, about 3,000% faster to about 4,000% faster, about 4,000% faster to about 10,000% faster, about 4,000% faster to about 9,000% faster, about 4,000% faster to about 8,000% faster, about 4,000% faster to about 7,000% faster, about 4,000% faster to about 6,000% faster, about 4,000% faster to about 5,000% faster, about 5,000% faster to about 10,000% faster, about 5,000% faster to about 9,000% faster, about 5,000% faster to about 8,000% faster, about 5,000% faster to about 7,000% faster, about 5,000% faster to about 6,000% faster, about 6,000% faster to about 10,000% faster, about 6,000% faster to about 9,000% faster, about 6,000% faster to about 8,000% faster, about 6,000% faster to about 7,000% faster, about 7,000% faster to about 10,000% faster, about 7,000% faster to about 9,000% faster, about 7,000% faster to about 8,000% faster, about 8,000% faster to about 10,000% faster, about 8,000% faster to about 9,000% faster, or about 9,000% faster to about 10,000% faster) than the dissociation rate at a pH of about 7.0 to about 8.0 (e.g., about 7.0 to about 7.9, about 7.0 to about 7.8, about 7.0 to about 7.7, about 7.0 to about 7.6, about 7.0 to about 7.5, about 7.0 to about 7.4, about 7.0 to about 7.3, about 7.0 to about 7.2, about 7.0 to about 7.1, about 7.1 to about 8.0, about 7.1 to about 7.9, about 7.1 to about 7.8, about 7.1 to about 7.7, about 7.1 to about 7.6, about 7.1 to about 7.5, about 7.1 to about 7.4, about 7.1 to about 7.3, about 7.1 to about 7.2, about 7.2 to about 8.0, about 7.2 to about 7.9, about 7.2 to about 7.8, about 7.2 to about 7.7, about 7.2 to about 7.6, about 7.2 to about 7.5, about 7.2 to about 7.4, about 7.2 to about 7.3, about 7.3 to about 8.0, about 7.3 to about 7.9, about 7.3 to about 7.8, about 7.3 to about 7.7, about 7.3 to about 7.6, about 7.3 to about 7.5, about 7.3 to about 7.4, about 7.4 to about 8.0, about 7.4 to about 7.9, about 7.4 to about 7.8, about 7.4 to about 7.7, about 7.4 to about 7.6, about 7.4 to about 7.5, about 7.5 to about 8.0, about 7.5 to about 7.9, about 7.5 to about 7.8, about 7.5 to about 7.7, about 7.5 to about 7.6, about 7.6 to about 8.0, about 7.6 to about 7.9, about 7.6 to about 7.8, about 7.6 to about 7.7, about 7.7 to about 8.0, about 7.7 to about 7.9, about 7.7 to about 7.8, about 7.8 to about 8.0, about 7.8 to about 7.9, or about 7.9 to about 8.0).

In some embodiments of any of the antigen-binding protein constructs (ABPCs) described herein, the dissociation constant ($K_D$) of the first antigen-binding domain (and optionally the second antigen-binding domain, if present) at a pH of about 4.0 to about 6.5 (e.g., any of the subranges of this range described herein) is greater (e.g., detectably greater) (e.g., at least 5% greater, at least 10% greater, at least 15% greater, at least 20% greater, at least 25% greater, at least 30% greater, at least 35% greater, at least 40% greater, at least 45% greater, at least 50% greater, at least 55% greater, at least 60% greater, at least 65% greater, at least 70% greater, at least 80% greater, at least 85% greater, at least 90% greater, at least 95% greater, at least 100% greater, at least 120% greater, at least 140% greater, at least 160% greater, at least 180% greater, at least 200% greater, at least 220% greater, at least 240% greater, at least 260% greater, at least 280% greater, at least 300% greater, at least 320% greater, at least 340% greater, at least 360% greater, at least 380% greater, at least 400% greater, at least 420% greater, at least 440% greater, at least 460% greater, at least 480% greater, at least 500% greater, at least 1,000% greater, at least 2,000% greater, at least 3,000% greater, at least 4,000% greater, at least 5,000% greater, at least 6,000% greater, at least 7,000% greater, at least 8,000% greater, at least 9,000% greater, or at least 10,000% greater, or about 5% greater to about 10,000% greater, about 5% greater to about 9,000% greater, about 5% greater to about 8,000% greater, about 5% greater to about 7,000% greater, about 5% greater to about 6,000% greater, about 5% greater to about 5,000% greater, about 5% greater to about 4,000% greater, about 5% greater to about 3,000% greater, about 5% greater to about 2,000% greater, about 5% greater to about 1,000% greater, about 5% greater to about 500% greater, about 5% greater to about 480% greater, about 5% greater to about 460% greater, about 5% greater to about 440% greater, about 5% greater to about 420% greater, about 5% greater to about 400% greater, about 5% greater to about 380% greater, about 5% greater to about 360% greater, about 5% greater to about 340% greater, about 5% greater to about 320% greater, about 5% greater to about 300% greater, about 5% greater to about 280% greater, about 5% greater to about 260% greater, about 5% greater to about 240% greater, about 5% greater to about 220% greater, about 5% greater to about 200% greater, about 5% greater to about 180% greater, about 5% greater to about 160% greater, about 5% greater to about 140% greater, about 5% greater to about 120% greater, about 5% greater to about 100% greater, about 5% greater to about 95% greater, about 5% greater to about 90% greater, about 5% greater to about 85% greater, about 5% greater to about 80% greater, about 5% greater to about 75% greater, about 5% greater to about 70% greater, about 5% greater to about 65% greater, about 5% greater to about 60% greater, about 5% greater to about 55% greater, about 5% greater to about 50% greater, about 5% greater to about 45% greater, about 5% greater to about 40% greater, about 5% greater to about 35% greater, about 5% greater to about 30% greater, about 5% greater to about 25% greater, about 5% greater to about 20% greater, about 5% greater to about 15% greater, about 5% greater to about 10% greater, about 10% greater to about 10,000% greater, about 10% greater to about 9,000% greater, about 10% greater to about 8,000% greater, about 10% greater to about 7,000% greater, about 10% greater to about 6,000% greater, about 10% greater to about 5,000% greater, about 10% greater to about 4,000% greater, about 10% greater to about 3,000% greater, about 10% greater to about 2,000% greater, about 10% greater to about 1,000% greater, about 10% greater to about 500% greater, about 10% greater to about 480% greater, about 10% greater to about 460% greater, about 10% greater to about 440% greater, about 10% greater to about 420% greater, about 10% greater to about 400% greater, about 10% greater to about 380% greater, about 10% greater to about 360% greater, about 10% greater to about 340% greater, about 10% greater to about 320% greater, about 10% greater to about 300% greater, about 10% greater to about 280% greater, about 10% greater to about 260% greater, about 10% greater to about 240% greater, about 10% greater to about 220% greater, about 10% greater to about 200% greater, about 10% greater to about 180% greater, about 10% greater to about 160% greater, about 10% greater to about 140% greater, about 10% greater to about 120% greater, about 10% greater to about 100% greater, about 10% greater to about 95% greater, about 10% greater to about 90% greater, about 10% greater to about 85% greater, about 10% greater to about 80% greater, about 10% greater to about 75% greater, about 10% greater to about 70% greater, about 10% greater to about 65% greater, about 10% greater to about 60% greater, about 10% greater to about 55% greater, about 10% greater to about 50% greater, about 10% greater to about 45% greater, about 10% greater to about 40% greater, about 10% greater to about 35% greater, about 10% greater to about 30% greater, about 10% greater to about 25% greater, about 10% greater to about 20% greater, about 10% greater to about 15% greater, about 15% greater to about 10,000% greater, about 15% greater to about 9,000% greater, about 15% greater to about 8,000% greater, about 15% greater to about 7,000% greater, about 15% greater to about 6,000% greater, about 15% greater to about 5,000% greater, about 15% greater to about 4,000% greater, about 15% greater to about 3,000% greater, about 15% greater to about 2,000% greater, about 15% greater to about 1,000% greater, about 15% greater to about 500% greater, about 15% greater to about 480% greater, about 15% greater to about 460% greater, about 15% greater to about 440% greater, about 15% greater to about 420% greater, about 15% greater to about 400% greater, about 15% greater to about 380% greater, about 15% greater to about 360% greater, about 15% greater to about 340% greater, about 15% greater to about 320% greater, about 15% greater to about 300% greater, about 15% greater to about 280% greater, about 15% greater to about 260% greater, about 15% greater to about 240% greater, about 15% greater to about 220% greater, about 15% greater to about 200% greater, about 15% greater to about 180% greater, about 15% greater to about 160% greater, about 15% greater to about 140% greater, about 15% greater to about 120% greater, about 15% greater to about 100% greater, about 15% greater to about 95% greater, about 15% greater to about 90% greater, about 15% greater to about 85% greater, about 15% greater to about 80% greater, about 15% greater to about 75% greater, about 15% greater to about 70% greater, about 15% greater to about 65% greater, about 15% greater to about 60% greater, about 15% greater to about 55% greater, about 15% greater to about 50% greater, about 15% greater to about 45% greater, about 15% greater to about 40% greater, about 15% greater to about 35% greater, about 15% greater to about 30% greater, about 15% greater to about 25% greater, about 15% greater to about 20% greater, about 20% greater to about 10,000% greater, about 20% greater to about 9,000% greater, about 20% greater to about 8,000% greater, about 20% greater to about 7,000% greater, about 20% greater to about 6,000% greater, about 20% greater to about 5,000% greater, about 20% greater to about 4,000% greater, about 20% greater to about 3,000% greater, about 20% greater to about 2,000% greater, about 20% greater to about 1,000% greater, about 20% greater to about 500% greater, about 20% greater to about 480% greater, about 20% greater to about 460% greater, about 20% greater to about 440% greater, about 20% greater to about 420% greater, about 20% greater to about 400% greater, about 20% greater to about 380% greater, about 20% greater to about 360% greater, about 20% greater to about 340% greater, about 20% greater to about 320% greater, about 20% greater to about 300% greater, about 20% greater to about 280% greater, about 20% greater to about 260% greater, about 20% greater to about 240% greater, about 20% greater to about 220% greater, about 20% greater to about 200% greater, about 20% greater to about 180% greater, about 20% greater to about 160% greater, about 20% greater to about 140% greater, about 20% greater to about 120% greater, about 20% greater to about 100% greater, about 20% greater to about 95% greater, about 20% greater to about 90% greater, about 20% greater to about 85% greater, about 20% greater to about 80% greater, about 20% greater to about 75% greater, about 20% greater to about 70% greater, about 20% greater to about 65% greater, about 20% greater to about 60% greater, about 20% greater to about 55% greater, about 20% greater to about 50% greater, about 20% greater to about 45% greater, about 20% greater to about 40% greater, about 20% greater to about 35% greater, about 20% greater to about 30% greater, about 20% greater to about 25% greater, about 25% greater to about 10,000% greater, about 25% greater to about 9,000% greater, about 25% greater to about 8,000% greater, about 25% greater to about 7,000% greater, about 25% greater to about 6,000% greater, about 25% greater to about 5,000% greater, about 25% greater to about 4,000% greater, about 25% greater to about 3,000% greater, about 25% greater to about 2,000% greater, about 25% greater to about 1,000% greater, about 25% greater to about 500% greater, about 25% greater to about 480% greater, about 25% greater to about 460% greater, about 25% greater to about 440% greater, about 25% greater to about 420% greater, about 25% greater to about 400% greater, about 25% greater to about 380% greater, about 25% greater to about 360% greater, about 25% greater to about 340% greater, about 25% greater to about 320% greater, about 25% greater to about 300% greater, about 25% greater to about 280% greater, about 25% greater to about 260% greater, about 25% greater to about 240% greater, about 25% greater to about 220% greater, about 25% greater to about 200% greater, about 25% greater to about 180% greater, about 25% greater to about 160% greater, about 25% greater to about 140% greater, about 25% greater to about 120% greater, about 25% greater to about 100% greater, about 25% greater to about 95% greater, about 25% greater to about 90% greater, about 25% greater to about 85% greater, about 25% greater to about 80% greater, about 25% greater to about 75% greater, about 25% greater to about 70% greater, about 25% greater to about 65% greater, about 25% greater to about 60% greater, about 25% greater to about 55% greater, about 25% greater to about 50% greater, about 25% greater to about 45% greater, about 25% greater to about 40% greater, about 25% greater to about 35% greater, about 25% greater to about 30% greater, about 30% greater to about 10,000% greater, about 30% greater to about 9,000% greater, about 30% greater to about 8,000% greater, about 30% greater to about 7,000% greater, about 30% greater to about 6,000% greater, about 30% greater to about 5,000% greater, about 30% greater to about 4,000% greater, about 30% greater to about 3,000% greater, about 30% greater to about 2,000% greater, about 30% greater to about 1,000% greater, about 30% greater to about 500% greater, about 30% greater to about 480% greater, about 30% greater to about 460% greater, about 30% greater to about 440% greater, about 30% greater to about 420% greater, about 30% greater to about 400% greater, about 30% greater to about 380% greater, about 30% greater to about 360% greater, about 30% greater to about 340% greater, about 30% greater to about 320% greater, about 30% greater to about 300% greater, about 30% greater to about 280% greater, about 30% greater to about 260% greater, about 30% greater to about 240% greater, about 30% greater to about 220% greater, about 30% greater to about 200% greater, about 30% greater to about 180% greater, about 30% greater to about 160% greater, about 30% greater to about 140% greater, about 30% greater to about 120% greater, about 30% greater to about 100% greater, about 30% greater to about 95% greater, about 30% greater to about 90% greater, about 30% greater to about 85% greater, about 30% greater to about 80% greater, about 30% greater to about 75% greater, about 30% greater to about 70% greater, about 30% greater to about 65% greater, about 30% greater to about 60% greater, about 30% greater to about 55% greater, about 30% greater to about 50% greater, about 30% greater to about 45% greater, about 30% greater to about 40% greater, about 30% greater to about 35% greater, about 35% greater to about 10,000% greater, about 35% greater to about 9,000% greater, about 35% greater to about 8,000% greater, about 35% greater to about 7,000% greater, about 35% greater to about 6,000% greater, about 35% greater to about 5,000% greater, about 35% greater to about 4,000% greater, about 35% greater to about 3,000% greater, about 35% greater to about 2,000% greater, about 35% greater to about 1,000% greater, about 35% greater to about 500% greater, about 35% greater to about 480% greater, about 35% greater to about 460% greater, about 35% greater to about 440% greater, about 35% greater to about 420% greater, about 35% greater to about 400% greater, about 35% greater to about 380% greater, about 35% greater to about 360% greater, about 35% greater to about 340% greater, about 35% greater to about 320% greater, about 35% greater to about 300% greater, about 35% greater to about 280% greater, about 35% greater to about 260% greater, about 35% greater to about 240% greater, about 35% greater to about 220% greater, about 35% greater to about 200% greater, about 35% greater to about 180% greater, about 35% greater to about 160% greater, about 35% greater to about 140% greater, about 35% greater to about 120% greater, about 35% greater to about 100% greater, about 35% greater to about 95% greater, about 35% greater to about 90% greater, about 35% greater to about 85% greater, about 35% greater to about 80% greater, about 35% greater to about 75% greater, about 35% greater to about 70% greater, about 35% greater to about 65% greater, about 35% greater to about 60% greater, about 35% greater to about 55% greater, about 35% greater to about 50% greater, about 35% greater to about 45% greater, about 35% greater to about 40% greater, about 40% greater to about 10,000% greater, about 40% greater to about 9,000% greater, about 40% greater to about 8,000% greater, about 40% greater to about 7,000% greater, about 40% greater to about 6,000% greater, about 40% greater to about 5,000% greater, about 40% greater to about 4,000% greater, about 40% greater to about 3,000% greater, about 40% greater to about 2,000% greater, about 40% greater to about 1,000% greater, about 40% greater to about 500% greater, about 40% greater to about 480% greater, about 40% greater to about 460% greater, about 40% greater to about 440% greater, about 40% greater to about 420% greater, about 40% greater to about 400% greater, about 40% greater to about 380% greater, about 40% greater to about 360% greater, about 40% greater to about 340% greater, about 40% greater to about 320% greater, about 40% greater to about 300% greater, about 40% greater to about 280% greater, about 40% greater to about 260% greater, about 40% greater to about 240% greater, about 40% greater to about 220% greater, about 40% greater to about 200% greater, about 40% greater to about 180% greater, about 40% greater to about 160% greater, about 40% greater to about 140% greater, about 40% greater to about 120% greater, about 40% greater to about 100% greater, about 40% greater to about 95% greater, about 40% greater to about 90% greater, about 40% greater to about 85% greater, about 40% greater to about 80% greater, about 40% greater to about 75% greater, about 40% greater to about 70% greater, about 40% greater to about 65% greater, about 40% greater to about 60% greater, about 40% greater to about 55% greater, about 40% greater to about 50% greater, about 40% greater to about 45% greater, about 45% greater to about 10,000% greater, about 45% greater to about 9,000% greater, about 45% greater to about 8,000% greater, about 45% greater to about 7,000% greater, about 45% greater to about 6,000% greater, about 45% greater to about 5,000% greater, about 45% greater to about 4,000% greater, about 45% greater to about 3,000% greater, about 45% greater to about 2,000% greater, about 45% greater to about 1,000% greater, about 45% greater to about 500% greater, about 45% greater to about 480% greater, about 45% greater to about 460% greater, about 45% greater to about 440% greater, about 45% greater to about 420% greater, about 45% greater to about 400% greater, about 45% greater to about 380% greater, about 45% greater to about 360% greater, about 45% greater to about 340% greater, about 45% greater to about 320% greater, about 45% greater to about 300% greater, about 45% greater to about 280% greater, about 45% greater to about 260% greater, about 45% greater to about 240% greater, about 45% greater to about 220% greater, about 45% greater to about 200% greater, about 45% greater to about 180% greater, about 45% greater to about 160% greater, about 45% greater to about 140% greater, about 45% greater to about 120% greater, about 45% greater to about 100% greater, about 45% greater to about 95% greater, about 45% greater to about 90% greater, about 45% greater to about 85% greater, about 45% greater to about 80% greater, about 45% greater to about 75% greater, about 45% greater to about 70% greater, about 45% greater to about 65% greater, about 45% greater to about 60% greater, about 45% greater to about 55% greater, about 45% greater to about 50% greater, about 50% greater to about 10,000% greater, about 50% greater to about 9,000% greater, about 50% greater to about 8,000% greater, about 50% greater to about 7,000% greater, about 50% greater to about 6,000% greater, about 50% greater to about 5,000% greater, about 50% greater to about 4,000% greater, about 50% greater to about 3,000% greater, about 50% greater to about 2,000% greater, about 50% greater to about 1,000% greater, about 50% greater to about 500% greater, about 50% greater to about 480% greater, about 50% greater to about 460% greater, about 50% greater to about 440% greater, about 50% greater to about 420% greater, about 50% greater to about 400% greater, about 50% greater to about 380% greater, about 50% greater to about 360% greater, about 50% greater to about 340% greater, about 50% greater to about 320% greater, about 50% greater to about 300% greater, about 50% greater to about 280% greater, about 50% greater to about 260% greater, about 50% greater to about 240% greater, about 50% greater to about 220% greater, about 50% greater to about 200% greater, about 50% greater to about 180% greater, about 50% greater to about 160% greater, about 50% greater to about 140% greater, about 50% greater to about 120% greater, about 50% greater to about 100% greater, about 50% greater to about 95% greater, about 50% greater to about 90% greater, about 50% greater to about 85% greater, about 50% greater to about 80% greater, about 50% greater to about 75% greater, about 50% greater to about 70% greater, about 50% greater to about 65% greater, about 50% greater to about 60% greater, about 50% greater to about 55% greater, about 55% greater to about 10,000% greater, about 55% greater to about 9,000% greater, about 55% greater to about 8,000% greater, about 55% greater to about 7,000% greater, about 55% greater to about 6,000% greater, about 55% greater to about 5,000% greater, about 55% greater to about 4,000% greater, about 55% greater to about 3,000% greater, about 55% greater to about 2,000% greater, about 55% greater to about 1,000% greater, about 55% greater to about 500% greater, about 55% greater to about 480% greater, about 55% greater to about 460% greater, about 55% greater to about 440% greater, about 55% greater to about 420% greater, about 55% greater to about 400% greater, about 55% greater to about 380% greater, about 55% greater to about 360% greater, about 55% greater to about 340% greater, about 55% greater to about 320% greater, about 55% greater to about 300% greater, about 55% greater to about 280% greater, about 55% greater to about 260% greater, about 55% greater to about 240% greater, about 55% greater to about 220% greater, about 55% greater to about 200% greater, about 55% greater to about 180% greater, about 55% greater to about 160% greater, about 55% greater to about 140% greater, about 55% greater to about 120% greater, about 55% greater to about 100% greater, about 55% greater to about 95% greater, about 55% greater to about 90% greater, about 55% greater to about 85% greater, about 55% greater to about 80% greater, about 55% greater to about 75% greater, about 55% greater to about 70% greater, about 55% greater to about 65% greater, about 55% greater to about 60% greater, about 60% greater to about 10,000% greater, about 60% greater to about 9,000% greater, about 60% greater to about 8,000% greater, about 60% greater to about 7,000% greater, about 60% greater to about 6,000% greater, about 60% greater to about 5,000% greater, about 60% greater to about 4,000% greater, about 60% greater to about 3,000% greater, about 60% greater to about 2,000% greater, about 60% greater to about 1,000% greater, about 60% greater to about 500% greater, about 60% greater to about 480% greater, about 60% greater to about 460% greater, about 60% greater to about 440% greater, about 60% greater to about 420% greater, about 60% greater to about 400% greater, about 60% greater to about 380% greater, about 60% greater to about 360% greater, about 60% greater to about 340% greater, about 60% greater to about 320% greater, about 60% greater to about 300% greater, about 60% greater to about 280% greater, about 60% greater to about 260% greater, about 60% greater to about 240% greater, about 60% greater to about 220% greater, about 60% greater to about 200% greater, about 60% greater to about 180% greater, about 60% greater to about 160% greater, about 60% greater to about 140% greater, about 60% greater to about 120% greater, about 60% greater to about 100% greater, about 60% greater to about 95% greater, about 60% greater to about 90% greater, about 60% greater to about 85% greater, about 60% greater to about 80% greater, about 60% greater to about 75% greater, about 60% greater to about 70% greater, about 60% greater to about 65% greater, about 65% greater to about 10,000% greater, about 65% greater to about 9,000% greater, about 65% greater to about 8,000% greater, about 65% greater to about 7,000% greater, about 65% greater to about 6,000% greater, about 65% greater to about 5,000% greater, about 65% greater to about 4,000% greater, about 65% greater to about 3,000% greater, about 65% greater to about 2,000% greater, about 65% greater to about 1,000% greater, about 65% greater to about 500% greater, about 65% greater to about 480% greater, about 65% greater to about 460% greater, about 65% greater to about 440% greater, about 65% greater to about 420% greater, about 65% greater to about 400% greater, about 65% greater to about 380% greater, about 65% greater to about 360% greater, about 65% greater to about 340% greater, about 65% greater to about 320% greater, about 65% greater to about 300% greater, about 65% greater to about 280% greater, about 65% greater to about 260% greater, about 65% greater to about 240% greater, about 65% greater to about 220% greater, about 65% greater to about 200% greater, about 65% greater to about 180% greater, about 65% greater to about 160% greater, about 65% greater to about 140% greater, about 65% greater to about 120% greater, about 65% greater to about 100% greater, about 65% greater to about 95% greater, about 65% greater to about 90% greater, about 65% greater to about 85% greater, about 65% greater to about 80% greater, about 65% greater to about 75% greater, about 65% greater to about 70% greater, about 70% greater to about 10,000% greater, about 70% greater to about 9,000% greater, about 70% greater to about 8,000% greater, about 70% greater to about 7,000% greater, about 70% greater to about 6,000% greater, about 70% greater to about 5,000% greater, about 70% greater to about 4,000% greater, about 70% greater to about 3,000% greater, about 70% greater to about 2,000% greater, about 70% greater to about 1,000% greater, about 70% greater to about 500% greater, about 70% greater to about 480% greater, about 70% greater to about 460% greater, about 70% greater to about 440% greater, about 70% greater to about 420% greater, about 70% greater to about 400% greater, about 70% greater to about 380% greater, about 70% greater to about 360% greater, about 70% greater to about 340% greater, about 70% greater to about 320% greater, about 70% greater to about 300% greater, about 70% greater to about 280% greater, about 70% greater to about 260% greater, about 70% greater to about 240% greater, about 70% greater to about 220% greater, about 70% greater to about 200% greater, about 70% greater to about 180% greater, about 70% greater to about 160% greater, about 70% greater to about 140% greater, about 70% greater to about 120% greater, about 70% greater to about 100% greater, about 70% greater to about 95% greater, about 70% greater to about 90% greater, about 70% greater to about 85% greater, about 70% greater to about 80% greater, about 70% greater to about 75% greater, about 75% greater to about 10,000% greater, about 75% greater to about 9,000% greater, about 75% greater to about 8,000% greater, about 75% greater to about 7,000% greater, about 75% greater to about 6,000% greater, about 75% greater to about 5,000% greater, about 75% greater to about 4,000% greater, about 75% greater to about 3,000% greater, about 75% greater to about 2,000% greater, about 75% greater to about 1,000% greater, about 75% greater to about 500% greater, about 75% greater to about 480% greater, about 75% greater to about 460% greater, about 75% greater to about 440% greater, about 75% greater to about 420% greater, about 75% greater to about 400% greater, about 75% greater to about 380% greater, about 75% greater to about 360% greater, about 75% greater to about 340% greater, about 75% greater to about 320% greater, about 75% greater to about 300% greater, about 75% greater to about 280% greater, about 75% greater to about 260% greater, about 75% greater to about 240% greater, about 75% greater to about 220% greater, about 75% greater to about 200% greater, about 75% greater to about 180% greater, about 75% greater to about 160% greater, about 75% greater to about 140% greater, about 75% greater to about 120% greater, about 75% greater to about 100% greater, about 75% greater to about 95% greater, about 75% greater to about 90% greater, about 75% greater to about 85% greater, about 75% greater to about 80% greater, about 80% greater to about 10,000% greater, about 80% greater to about 9,000% greater, about 80% greater to about 8,000% greater, about 80% greater to about 7,000% greater, about 80% greater to about 6,000% greater, about 80% greater to about 5,000% greater, about 80% greater to about 4,000% greater, about 80% greater to about 3,000% greater, about 80% greater to about 2,000% greater, about 80% greater to about 1,000% greater, about 80% greater to about 500% greater, about 80% greater to about 480% greater, about 80% greater to about 460% greater, about 80% greater to about 440% greater, about 80% greater to about 420% greater, about 80% greater to about 400% greater, about 80% greater to about 380% greater, about 80% greater to about 360% greater, about 80% greater to about 340% greater, about 80% greater to about 320% greater, about 80% greater to about 300% greater, about 80% greater to about 280% greater, about 80% greater to about 260% greater, about 80% greater to about 240% greater, about 80% greater to about 220% greater, about 80% greater to about 200% greater, about 80% greater to about 180% greater, about 80% greater to about 160% greater, about 80% greater to about 140% greater, about 80% greater to about 120% greater, about 80% greater to about 100% greater, about 80% greater to about 95% greater, about 80% greater to about 90% greater, about 80% greater to about 85% greater, about 85% greater to about 10,000% greater, about 85% greater to about 9,000% greater, about 85% greater to about 8,000% greater, about 85% greater to about 7,000% greater, about 85% greater to about 6,000% greater, about 85% greater to about 5,000% greater, about 85% greater to about 4,000% greater, about 85% greater to about 3,000% greater, about 85% greater to about 2,000% greater, about 85% greater to about 1,000% greater, about 85% greater to about 500% greater, about 85% greater to about 480% greater, about 85% greater to about 460% greater, about 85% greater to about 440% greater, about 85% greater to about 420% greater, about 85% greater to about 400% greater, about 85% greater to about 380% greater, about 85% greater to about 360% greater, about 85% greater to about 340% greater, about 85% greater to about 320% greater, about 85% greater to about 300% greater, about 85% greater to about 280% greater, about 85% greater to about 260% greater, about 85% greater to about 240% greater, about 85% greater to about 220% greater, about 85% greater to about 200% greater, about 85% greater to about 180% greater, about 85% greater to about 160% greater, about 85% greater to about 140% greater, about 85% greater to about 120% greater, about 85% greater to about 100% greater, about 85% greater to about 95% greater, about 85% greater to about 90% greater, about 90% greater to about 10,000% greater, about 90% greater to about 9,000% greater, about 90% greater to about 8,000% greater, about 90% greater to about 7,000% greater, about 90% greater to about 6,000% greater, about 90% greater to about 5,000% greater, about 90% greater to about 4,000% greater, about 90% greater to about 3,000% greater, about 90% greater to about 2,000% greater, about 90% greater to about 1,000% greater, about 90% greater to about 500% greater, about 90% greater to about 480% greater, about 90% greater to about 460% greater, about 90% greater to about 440% greater, about 90% greater to about 420% greater, about 90% greater to about 400% greater, about 90% greater to about 380% greater, about 90% greater to about 360% greater, about 90% greater to about 340% greater, about 90% greater to about 320% greater, about 90% greater to about 300% greater, about 90% greater to about 280% greater, about 90% greater to about 260% greater, about 90% greater to about 240% greater, about 90% greater to about 220% greater, about 90% greater to about 200% greater, about 90% greater to about 180% greater, about 90% greater to about 160% greater, about 90% greater to about 140% greater, about 90% greater to about 120% greater, about 90% greater to about 100% greater, about 90% greater to about 95% greater, about 95% greater to about 10,000% greater, about 95% greater to about 9,000% greater, about 95% greater to about 8,000% greater, about 95% greater to about 7,000% greater, about 95% greater to about 6,000% greater, about 95% greater to about 5,000% greater, about 95% greater to about 4,000% greater, about 95% greater to about 3,000% greater, about 95% greater to about 2,000% greater, about 95% greater to about 1,000% greater, about 95% greater to about 500% greater, about 95% greater to about 480% greater, about 95% greater to about 460% greater, about 95% greater to about 440% greater, about 95% greater to about 420% greater, about 95% greater to about 400% greater, about 95% greater to about 380% greater, about 95% greater to about 360% greater, about 95% greater to about 340% greater, about 95% greater to about 320% greater, about 95% greater to about 300% greater, about 95% greater to about 280% greater, about 95% greater to about 260% greater, about 95% greater to about 240% greater, about 95% greater to about 220% greater, about 95% greater to about 200% greater, about 95% greater to about 180% greater, about 95% greater to about 160% greater, about 95% greater to about 140% greater, about 95% greater to about 120% greater, about 95% greater to about 100% greater, about 100% greater to about 10,000% greater, about 100% greater to about 9,000% greater, about 100% greater to about 8,000% greater, about 100% greater to about 7,000% greater, about 100% greater to about 6,000% greater, about 100% greater to about 5,000% greater, about 100% greater to about 4,000% greater, about 100% greater to about 3,000% greater, about 100% greater to about 2,000% greater, about 100% greater to about 1,000% greater, about 100% greater to about 500% greater, about 100% greater to about 480% greater, about 100% greater to about 460% greater, about 100% greater to about 440% greater, about 100% greater to about 420% greater, about 100% greater to about 400% greater, about 100% greater to about 380% greater, about 100% greater to about 360% greater, about 100% greater to about 340% greater, about 100% greater to about 320% greater, about 100% greater to about 300% greater, about 100% greater to about 280% greater, about 100% greater to about 260% greater, about 100% greater to about 240% greater, about 100% greater to about 220% greater, about 100% greater to about 200% greater, about 100% greater to about 180% greater, about 100% greater to about 160% greater, about 100% greater to about 140% greater, about 100% greater to about 120% greater, about 120% greater to about 10,000% greater, about 120% greater to about 9,000% greater, about 120% greater to about 8,000% greater, about 120% greater to about 7,000% greater, about 120% greater to about 6,000% greater, about 120% greater to about 5,000% greater, about 120% greater to about 4,000% greater, about 120% greater to about 3,000% greater, about 120% greater to about 2,000% greater, about 120% greater to about 1,000% greater, about 120% greater to about 500% greater, about 120% greater to about 480% greater, about 120% greater to about 460% greater, about 120% greater to about 440% greater, about 120% greater to about 420% greater, about 120% greater to about 400% greater, about 120% greater to about 380% greater, about 120% greater to about 360% greater, about 120% greater to about 340% greater, about 120% greater to about 320% greater, about 120% greater to about 300% greater, about 120% greater to about 280% greater, about 120% greater to about 260% greater, about 120% greater to about 240% greater, about 120% greater to about 220% greater, about 120% greater to about 200% greater, about 120% greater to about 180% greater, about 120% greater to about 160% greater, about 120% greater to about 140% greater, about 140% greater to about 10,000% greater, about 140% greater to about 9,000% greater, about 140% greater to about 8,000% greater, about 140% greater to about 7,000% greater, about 140% greater to about 6,000% greater, about 140% greater to about 5,000% greater, about 140% greater to about 4,000% greater, about 140% greater to about 3,000% greater, about 140% greater to about 2,000% greater, about 140% greater to about 1,000% greater, about 140% greater to about 500% greater, about 140% greater to about 480% greater, about 140% greater to about 460% greater, about 140% greater to about 440% greater, about 140% greater to about 420% greater, about 140% greater to about 400% greater, about 140% greater to about 380% greater, about 140% greater to about 360% greater, about 140% greater to about 340% greater, about 140% greater to about 320% greater, about 140% greater to about 300% greater, about 140% greater to about 280% greater, about 140% greater to about 260% greater, about 140% greater to about 240% greater, about 140% greater to about 220% greater, about 140% greater to about 200% greater, about 140% greater to about 180% greater, about 140% greater to about 160% greater, about 160% greater to about 10,000% greater, about 160% greater to about 9,000% greater, about 160% greater to about 8,000% greater, about 160% greater to about 7,000% greater, about 160% greater to about 6,000% greater, about 160% greater to about 5,000% greater, about 160% greater to about 4,000% greater, about 160% greater to about 3,000% greater, about 160% greater to about 2,000% greater, about 160% greater to about 1,000% greater, about 160% greater to about 500% greater, about 160% greater to about 480% greater, about 160% greater to about 460% greater, about 160% greater to about 440% greater, about 160% greater to about 420% greater, about 160% greater to about 400% greater, about 160% greater to about 380% greater, about 160% greater to about 360% greater, about 160% greater to about 340% greater, about 160% greater to about 320% greater, about 160% greater to about 300% greater, about 160% greater to about 280% greater, about 160% greater to about 260% greater, about 160% greater to about 240% greater, about 160% greater to about 220% greater, about 160% greater to about 200% greater, about 160% greater to about 180% greater, about 180% greater to about 10,000% greater, about 180% greater to about 9,000% greater, about 180% greater to about 8,000% greater, about 180% greater to about 7,000% greater, about 180% greater to about 6,000% greater, about 180% greater to about 5,000% greater, about 180% greater to about 4,000% greater, about 180% greater to about 3,000% greater, about 180% greater to about 2,000% greater, about 180% greater to about 1,000% greater, about 180% greater to about 500% greater, about 180% greater to about 480% greater, about 180% greater to about 460% greater, about 180% greater to about 440% greater, about 180% greater to about 420% greater, about 180% greater to about 400% greater, about 180% greater to about 380% greater, about 180% greater to about 360% greater, about 180% greater to about 340% greater, about 180% greater to about 320% greater, about 180% greater to about 300% greater, about 180% greater to about 280% greater, about 180% greater to about 260% greater, about 180% greater to about 240% greater, about 180% greater to about 220% greater, about 180% greater to about 200% greater, about 200% greater to about 10,000% greater, about 200% greater to about 9,000% greater, about 200% greater to about 8,000% greater, about 200% greater to about 7,000% greater, about 200% greater to about 6,000% greater, about 200% greater to about 5,000% greater, about 200% greater to about 4,000% greater, about 200% greater to about 3,000% greater, about 200% greater to about 2,000% greater, about 200% greater to about 1,000% greater, about 200% greater to about 500% greater, about 200% greater to about 480% greater, about 200% greater to about 460% greater, about 200% greater to about 440% greater, about 200% greater to about 420% greater, about 200% greater to about 400% greater, about 200% greater to about 380% greater, about 200% greater to about 360% greater, about 200% greater to about 340% greater, about 200% greater to about 320% greater, about 200% greater to about 300% greater, about 200% greater to about 280% greater, about 200% greater to about 260% greater, about 200% greater to about 240% greater, about 200% greater to about 220% greater, about 220% greater to about 10,000% greater, about 220% greater to about 9,000% greater, about 220% greater to about 8,000% greater, about 220% greater to about 7,000% greater, about 220% greater to about 6,000% greater, about 220% greater to about 5,000% greater, about 220% greater to about 4,000% greater, about 220% greater to about 3,000% greater, about 220% greater to about 2,000% greater, about 220% greater to about 1,000% greater, about 220% greater to about 500% greater, about 220% greater to about 480% greater, about 220% greater to about 460% greater, about 220% greater to about 440% greater, about 220% greater to about 420% greater, about 220% greater to about 400% greater, about 220% greater to about 380% greater, about 220% greater to about 360% greater, about 220% greater to about 340% greater, about 220% greater to about 320% greater, about 220% greater to about 300% greater, about 220% greater to about 280% greater, about 220% greater to about 260% greater, about 220% greater to about 240% greater, about 240% greater to about 10,000% greater, about 240% greater to about 9,000% greater, about 240% greater to about 8,000% greater, about 240% greater to about 7,000% greater, about 240% greater to about 6,000% greater, about 240% greater to about 5,000% greater, about 240% greater to about 4,000% greater, about 240% greater to about 3,000% greater, about 240% greater to about 2,000% greater, about 240% greater to about 1,000% greater, about 240% greater to about 500% greater, about 240% greater to about 480% greater, about 240% greater to about 460% greater, about 240% greater to about 440% greater, about 240% greater to about 420% greater, about 240% greater to about 400% greater, about 240% greater to about 380% greater, about 240% greater to about 360% greater, about 240% greater to about 340% greater, about 240% greater to about 320% greater, about 240% greater to about 300% greater, about 240% greater to about 280% greater, about 240% greater to about 260% greater, about 260% greater to about 10,000% greater, about 260% greater to about 9,000% greater, about 260% greater to about 8,000% greater, about 260% greater to about 7,000% greater, about 260% greater to about 6,000% greater, about 260% greater to about 5,000% greater, about 260% greater to about 4,000% greater, about 260% greater to about 3,000% greater, about 260% greater to about 2,000% greater, about 260% greater to about 1,000% greater, about 260% greater to about 500% greater, about 260% greater to about 480% greater, about 260% greater to about 460% greater, about 260% greater to about 440% greater, about 260% greater to about 420% greater, about 260% greater to about 400% greater, about 260% greater to about 380% greater, about 260% greater to about 360% greater, about 260% greater to about 340% greater, about 260% greater to about 320% greater, about 260% greater to about 300% greater, about 260% greater to about 280% greater, about 280% greater to about 10,000% greater, about 280% greater to about 9,000% greater, about 280% greater to about 8,000% greater, about 280% greater to about 7,000% greater, about 280% greater to about 6,000% greater, about 280% greater to about 5,000% greater, about 280% greater to about 4,000% greater, about 280% greater to about 3,000% greater, about 280% greater to about 2,000% greater, about 280% greater to about 1,000% greater, about 280% greater to about 500% greater, about 280% greater to about 480% greater, about 280% greater to about 460% greater, about 280% greater to about 440% greater, about 280% greater to about 420% greater, about 280% greater to about 400% greater, about 280% greater to about 380% greater, about 280% greater to about 360% greater, about 280% greater to about 340% greater, about 280% greater to about 320% greater, about 280% greater to about 300% greater, about 300% greater to about 10,000% greater, about 300% greater to about 9,000% greater, about 300% greater to about 8,000% greater, about 300% greater to about 7,000% greater, about 300% greater to about 6,000% greater, about 300% greater to about 5,000% greater, about 300% greater to about 4,000% greater, about 300% greater to about 3,000% greater, about 300% greater to about 2,000% greater, about 300% greater to about 1,000% greater, about 300% greater to about 500% greater, about 300% greater to about 480% greater, about 300% greater to about 460% greater, about 300% greater to about 440% greater, about 300% greater to about 420% greater, about 300% greater to about 400% greater, about 300% greater to about 380% greater, about 300% greater to about 360% greater, about 300% greater to about 340% greater, about 300% greater to about 320% greater, about 320% greater to about 10,000% greater, about 320% greater to about 9,000% greater, about 320% greater to about 8,000% greater, about 320% greater to about 7,000% greater, about 320% greater to about 6,000% greater, about 320% greater to about 5,000% greater, about 320% greater to about 4,000% greater, about 320% greater to about 3,000% greater, about 320% greater to about 2,000% greater, about 320% greater to about 1,000% greater, about 320% greater to about 500% greater, about 320% greater to about 480% greater, about 320% greater to about 460% greater, about 320% greater to about 440% greater, about 320% greater to about 420% greater, about 320% greater to about 400% greater, about 320% greater to about 380% greater, about 320% greater to about 360% greater, about 320% greater to about 340% greater, about 340% greater to about 10,000% greater, about 340% greater to about 9,000% greater, about 340% greater to about 8,000% greater, about 340% greater to about 7,000% greater, about 340% greater to about 6,000% greater, about 340% greater to about 5,000% greater, about 340% greater to about 4,000% greater, about 340% greater to about 3,000% greater, about 340% greater to about 2,000% greater, about 340% greater to about 1,000% greater, about 340% greater to about 500% greater, about 340% greater to about 480% greater, about 340% greater to about 460% greater, about 340% greater to about 440% greater, about 340% greater to about 420% greater, about 340% greater to about 400% greater, about 340% greater to about 380% greater, about 340% greater to about 360% greater, about 360% greater to about 10,000% greater, about 360% greater to about 9,000% greater, about 360% greater to about 8,000% greater, about 360% greater to about 7,000% greater, about 360% greater to about 6,000% greater, about 360% greater to about 5,000% greater, about 360% greater to about 4,000% greater, about 360% greater to about 3,000% greater, about 360% greater to about 2,000% greater, about 360% greater to about 1,000% greater, about 360% greater to about 500% greater, about 360% greater to about 480% greater, about 360% greater to about 460% greater, about 360% greater to about 440% greater, about 360% greater to about 420% greater, about 360% greater to about 400% greater, about 360% greater to about 380% greater, about 380% greater to about 10,000% greater, about 380% greater to about 9,000% greater, about 380% greater to about 8,000% greater, about 380% greater to about 7,000% greater, about 380% greater to about 6,000% greater, about 380% greater to about 5,000% greater, about 380% greater to about 4,000% greater, about 380% greater to about 3,000% greater, about 380% greater to about 2,000% greater, about 380% greater to about 1,000% greater, about 380% greater to about 500% greater, about 380% greater to about 480% greater, about 380% greater to about 460% greater, about 380% greater to about 440% greater, about 380% greater to about 420% greater, about 380% greater to about 400% greater, about 400% greater to about 10,000% greater, about 400% greater to about 9,000% greater, about 400% greater to about 8,000% greater, about 400% greater to about 7,000% greater, about 400% greater to about 6,000% greater, about 400% greater to about 5,000% greater, about 400% greater to about 4,000% greater, about 400% greater to about 3,000% greater, about 400% greater to about 2,000% greater, about 400% greater to about 1,000% greater, about 400% greater to about 500% greater, about 400% greater to about 480% greater, about 400% greater to about 460% greater, about 400% greater to about 440% greater, about 400% greater to about 420% greater, about 420% greater to about 10,000% greater, about 420% greater to about 9,000% greater, about 420% greater to about 8,000% greater, about 420% greater to about 7,000% greater, about 420% greater to about 6,000% greater, about 420% greater to about 5,000% greater, about 420% greater to about 4,000% greater, about 420% greater to about 3,000% greater, about 420% greater to about 2,000% greater, about 420% greater to about 1,000% greater, about 420% greater to about 500% greater, about 420% greater to about 480% greater, about 420% greater to about 460% greater, about 420% greater to about 440% greater, about 440% greater to about 10,000% greater, about 440% greater to about 9,000% greater, about 440% greater to about 8,000% greater, about 440% greater to about 7,000% greater, about 440% greater to about 6,000% greater, about 440% greater to about 5,000% greater, about 440% greater to about 4,000% greater, about 440% greater to about 3,000% greater, about 440% greater to about 2,000% greater, about 440% greater to about 1,000% greater, about 440% greater to about 500% greater, about 440% greater to about 480% greater, about 440% greater to about 460% greater, about 460% greater to about 10,000% greater, about 460% greater to about 9,000% greater, about 460% greater to about 8,000% greater, about 460% greater to about 7,000% greater, about 460% greater to about 6,000% greater, about 460% greater to about 5,000% greater, about 460% greater to about 4,000% greater, about 460% greater to about 3,000% greater, about 460% greater to about 2,000% greater, about 460% greater to about 1,000% greater, about 460% greater to about 500% greater, about 460% greater to about 480% greater, about 480% greater to about 10,000% greater, about 480% greater to about 9,000% greater, about 480% greater to about 8,000% greater, about 480% greater to about 7,000% greater, about 480% greater to about 6,000% greater, about 480% greater to about 5,000% greater, about 480% greater to about 4,000% greater, about 480% greater to about 3,000% greater, about 480% greater to about 2,000% greater, about 480% greater to about 1,000% greater, about 480% greater to about 500% greater about 500% greater to about 10,000% greater, about 500% greater to about 9,000% greater, about 500% greater to about 8,000% greater, about 500% greater to about 7,000% greater, about 500% greater to about 6,000% greater, about 500% greater to about 5,000% greater, about 500% greater to about 4,000% greater, about 500% greater to about 3,000% greater, about 500% greater to about 2,000% greater, about 500% greater to about 1,000% greater, about 1,000% greater to about 10,000% greater, about 1,000% greater to about 9,000% greater, about 1,000% greater to about 8,000% greater, about 1,000% greater to about 7,000% greater, about 1,000% greater to about 6,000% greater, about 1,000% greater to about 5,000% greater, about 1,000% greater to about 4,000% greater, about 1,000% greater to about 3,000% greater, about 1,000% greater to about 2,000% greater, about 2,000% greater to about 10,000% greater, about 2,000% greater to about 9,000% greater, about 2,000% greater to about 8,000% greater, about 2,000% greater to about 7,000% greater, about 2,000% greater to about 6,000% greater, about 2,000% greater to about 5,000% greater, about 2,000% greater to about 4,000% greater, about 2,000% greater to about 3,000% greater, about 3,000% greater to about 10,000% greater, about 3,000% greater to about 9,000% greater, about 3,000% greater to about 8,000% greater, about 3,000% greater to about 7,000% greater, about 3,000% greater to about 6,000% greater, about 3,000% greater to about 5,000% greater, about 3,000% greater to about 4,000% greater, about 4,000% greater to about 10,000% greater, about 4,000% greater to about 9,000% greater, about 4,000% greater to about 8,000% greater, about 4,000% greater to about 7,000% greater, about 4,000% greater to about 6,000% greater, about 4,000% greater to about 5,000% greater, about 5,000% greater to about 10,000% greater, about 5,000% greater to about 9,000% greater, about 5,000% greater to about 8,000% greater, about 5,000% greater to about 7,000% greater, about 5,000% greater to about 6,000% greater, about 6,000% greater to about 10,000% greater, about 6,000% greater to about 9,000% greater, about 6,000% greater to about 8,000% greater, about 6,000% greater to about 7,000% greater, about 7,000% greater to about 10,000% greater, about 7,000% greater to about 9,000% greater, about 7,000% greater to about 8,000% greater, about 8,000% greater to about 10,000% greater, about 8,000% greater to about 9,000% greater, or about 9,000% greater to about 10,000% greater) than the $K_D$ at a pH of about 7.0 to about 8.0 (e.g., any of the subranges of this range described herein).

In some embodiments of any of the antigen-binding protein constructs (ABPCs) described herein, the dissociation rate of the first antigen-binding domain (and optionally the second antigen-binding domain, if present) at a pH of about 4.0 to about 6.5 (e.g., any of the subranges of this range described herein) is faster (e.g., at least 0.2-fold faster, at least 0.3-fold, at least 0.4-fold, at least 0.5-fold, at least 0.6-fold, at least 0.7-fold, at least 0.8-fold, at least 0.9-fold, at least 1.0-fold, at least 1.5-fold, at least 2.0-fold, at least 2.5-fold, at least 3.0 fold, at least 3.5-fold, at least 4.0-fold, at least 4.5-fold, at least 5.0-fold, at least 5.5-fold, at least 6.0-fold, at least 6.5-fold, at least 7.0-fold, at least 7.5-fold, at least 8.0-fold, at least 8.5-fold, at least 9.0-fold, at least 9.5-fold, at least 10.0-fold, at least 10.5-fold, at least 11.0-fold, at least 11.5-fold, at least 12.0-fold, at least 12.5-fold, at least 13.0-fold, at least 13.5-fold, at least 14.0-fold, at least 14.5-fold, at least 15.0-fold, at least 15.5-fold, at least 16.0-fold, at least 16.5-fold, at least 17.0-fold, at least 17.5-fold, at least 18.0-fold, at least 18.5-fold, at least 19.0-fold, at least 19.5-fold, at least 20-fold, at least 25-fold, at least 30-fold, at least 35-fold, at least 40-fold, at least 45-fold, at least 50-fold, at least 55-fold, at least 60-fold, at least 65-fold, at least 70-fold, at least 75-fold, at least 80-fold, at least 85-fold, at least 90-fold, at least 95-fold, or at least 100-fold faster or about 0.2-fold to about 100-fold faster, about 0.2-fold to about 90-fold faster, about 0.2-fold to about 80-fold faster, about 0.2-fold to about 70-fold faster, about 0.2-fold to about 60-fold faster, about 0.2-fold to about 50-fold faster, about 0.2-fold to about 40-fold faster, about 0.2-fold to about 30-fold faster, about 0.2-fold to about 20-fold faster, about 0.2-fold to about 15-fold faster, about 0.2-fold to about 10-fold faster, about 0.2-fold to about 5-fold, about 0.2-fold to about 2-fold faster, about 0.2-fold to about 1-fold faster, about 0.2-fold to about 0.5-fold faster, about 0.5-fold to about 100-fold faster, about 0.5-fold to about 90-fold faster, about 0.5-fold to about 80-fold faster, about 0.5-fold to about 70-fold faster, about 0.5-fold to about 60-fold faster, about 0.5-fold to about 50-fold faster, about 0.5-fold to about 40-fold faster, about 0.5-fold to about 30-fold faster, about 0.5-fold to about 20-fold faster, about 0.5-fold to about 15-fold faster, about 0.5-fold to about 10-fold faster, about 0.5-fold to about 5-fold, about 0.5-fold to about 2-fold faster, about 0.5-fold to about 1-fold faster, about 1-fold to about 100-fold faster, about 1-fold to about 90-fold faster, about 1-fold to about 80-fold faster, about 1-fold to about 70-fold faster, about 1-fold to about 60-fold faster, about 1-fold to about 50-fold faster, about 1-fold to about 40-fold faster, about 1-fold to about 30-fold faster, about 1-fold to about 20-fold faster, about 1-fold to about 15-fold faster, about 1-fold to about 10-fold faster, about 1-fold to about 5-fold, about 1-fold to about 2-fold faster, about 2-fold to about 100-fold faster, about 2-fold to about 90-fold faster, about 2-fold to about 80-fold faster, about 2-fold to about 70-fold faster, about 2-fold to about 60-fold faster, about 2-fold to about 50-fold faster, about 2-fold to about 40-fold faster, about 2-fold to about 30-fold faster, about 2-fold to about 20-fold faster, about 2-fold to about 15-fold faster, about 2-fold to about 10-fold faster, about 2-fold to about 5-fold, about 5-fold to about 100-fold faster, about 5-fold to about 90-fold faster, about 5-fold to about 80-fold faster, about 5-fold to about 70-fold faster, about 5-fold to about 60-fold faster, about 5-fold to about 50-fold faster, about 5-fold to about 40-fold faster, about 5-fold to about 30-fold faster, about 5-fold to about 20-fold faster, about 5-fold to about 15-fold faster, about 5-fold to about 10-fold faster, about 10-fold to about 100-fold faster, about 10-fold to about 90-fold faster, about 10-fold to about 80-fold faster, about 10-fold to about 70-fold faster, about 10-fold to about 60-fold faster, about 10-fold to about 50-fold faster, about 10-fold to about 40-fold faster, about 10-fold to about 30-fold faster, about 10-fold to about 20-fold faster, about 10-fold to about 15-fold faster, about 15-fold to about 100-fold faster, about 15-fold to about 90-fold faster, about 15-fold to about 80-fold faster, about 15-fold to about 70-fold faster, about 15-fold to about 60-fold faster, about 15-fold to about 50-fold faster, about 15-fold to about 40-fold faster, about 15-fold to about 30-fold faster, about 15-fold to about 20-fold faster, about 20-fold to about 100-fold faster, about 20-fold to about 90-fold faster, about 20-fold to about 80-fold faster, about 20-fold to about 70-fold faster, about 20-fold to about 60-fold faster, about 20-fold to about 50-fold faster, about 20-fold to about 40-fold faster, about 20-fold to about 30-fold faster, about 30-fold to about 100-fold faster, about 30-fold to about 90-fold faster, about 30-fold to about 80-fold faster, about 30-fold to about 70-fold faster, about 30-fold to about 60-fold faster, about 30-fold to about 50-fold faster, about 30-fold to about 40-fold faster, about 40-fold to about 100-fold faster, about 40-fold to about 90-fold faster, about 40-fold to about 80-fold faster, about 40-fold to about 70-fold faster, about 40-fold to about 60-fold faster, about 40-fold to about 50-fold faster, about 50-fold to about 100-fold faster, about 50-fold to about 90-fold faster, about 50-fold to about 80-fold faster, about 50-fold to about 70-fold faster, about 50-fold to about 60-fold faster, about 60-fold to about 100-fold faster, about 60-fold to about 90-fold faster, about 60-fold to about 80-fold faster, about 60-fold to about 70-fold faster, about 70-fold to about 100-fold faster, about 70-fold to about 90-fold faster, about 70-fold to about 80-fold faster, about 80-fold to about 100-fold faster, about 80-fold to about 90-fold faster, or about 90-fold to about 100-fold faster) than the dissociation rate at a pH of about 7.0 to about 8.0 (e.g., or any of the subranges of this range described herein).

In some embodiments of any of the antigen-binding protein constructs (ABPCs) described herein, the dissociation constant ($K_D$) of the first antigen-binding domain (and optionally the second antigen-binding domain, if present) at a pH of about 4.0 to about 6.5 (e.g., any of the subranges of this range described herein) is greater (e.g., detectably greater) (e.g., at least 0.2-fold greater, at least 0.3-fold, at least 0.4-fold, at least 0.5-fold, at least 0.6-fold, at least 0.7-fold, at least 0.8-fold, at least 0.9-fold, at least 1.0-fold, at least 1.5-fold, at least 2.0-fold, at least 2.5-fold, at least 3.0 fold, at least 3.5-fold, at least 4.0-fold, at least 4.5-fold, at least 5.0-fold, at least 5.5-fold, at least 6.0-fold, at least 6.5-fold, at least 7.0-fold, at least 7.5-fold, at least 8.0-fold, at least 8.5-fold, at least 9.0-fold, at least 9.5-fold, at least 10.0-fold, at least 10.5-fold, at least 11.0-fold, at least 11.5-fold, at least 12.0-fold, at least 12.5-fold, at least 13.0-fold, at least 13.5-fold, at least 14.0-fold, at least 14.5-fold, at least 15.0-fold, at least 15.5-fold, at least 16.0-fold, at least 16.5-fold, at least 17.0-fold, at least 17.5-fold, at least 18.0-fold, at least 18.5-fold, at least 19.0-fold, at least 19.5-fold, at least 20-fold greater, at least 25-fold greater, at least 30-fold greater, at least 35-fold greater, at least 40-fold greater, at least 45-fold greater, at least 50-fold greater, at least 55-fold greater, at least 60-fold greater, at least 65-fold greater, at least 70-fold greater, at least 75-fold greater, at least 80-fold greater, at least 85-fold greater, at least 90-fold greater, at least 95-fold greater, or at least 100-fold greater, or about 0.2-fold to about 100-fold greater, about 0.2-fold to about 90-fold greater, about 0.2-fold to about 80-fold greater, about 0.2-fold to about 70-fold greater, about 0.2-fold to about 60-fold greater, about 0.2-fold to about 50-fold greater, about 0.2-fold to about 40-fold greater, about 0.2-fold to about 30-fold greater, about 0.2-fold to about 25-fold greater, about 0.2-fold to about 20-fold greater, about 0.2-fold to about 15-fold greater, about 0.2-fold to about 10-fold greater, about 0.2-fold to about 8-fold greater, about 0.2-fold to about 5-fold greater, about 0.2-fold to about 2-fold greater, about 0.2-fold to about 1-fold greater, about 0.2-fold to about 0.5-fold greater, about 0.5-fold to about 100-fold greater, about 0.5-fold to about 90-fold greater, about 0.5-fold to about 80-fold greater, about 0.5-fold to about 70-fold greater, about 0.5-fold to about 60-fold greater, about 0.5-fold to about 50-fold greater, about 0.5-fold to about 40-fold greater, about 0.5-fold to about 30-fold greater, about 0.5-fold to about 25-fold greater, about 0.5-fold to about 20-fold greater, about 0.5-fold to about 15-fold greater, about 0.5-fold to about 10-fold greater, about 0.5-fold to about 8-fold greater, about 0.5-fold to about 5-fold greater, about 0.5-fold to about 2-fold greater, about 0.5-fold to about 1-fold greater, about 1-fold to about 100-fold greater, about 1-fold to about 90-fold greater, about 1-fold to about 80-fold greater, about 1-fold to about 70-fold greater, about 1-fold to about 60-fold greater, about 1-fold to about 50-fold greater, about 1-fold to about 40-fold greater, about 1-fold to about 30-fold greater, about 1-fold to about 25-fold greater, about 1-fold to about 20-fold greater, about 1-fold to about 15-fold greater, about 1-fold to about 10-fold greater, about 1-fold to about 8-fold greater, about 1-fold to about 5-fold greater, about 1-fold to about 2-fold greater, about 2-fold to about 100-fold greater, about 2-fold to about 90-fold greater, about 2-fold to about 80-fold greater, about 2-fold to about 70-fold greater, about 2-fold to about 60-fold greater, about 2-fold to about 50-fold greater, about 2-fold to about 40-fold greater, about 2-fold to about 30-fold greater, about 2-fold to about 25-fold greater, about 2-fold to about 20-fold greater, about 2-fold to about 15-fold greater, about 2-fold to about 10-fold greater, about 2-fold to about 8-fold greater, about 2-fold to about 5-fold greater, about 5-fold to about 100-fold greater, about 5-fold to about 90-fold greater, about 5-fold to about 80-fold greater, about 5-fold to about 70-fold greater, about 5-fold to about 60-fold greater, about 5-fold to about 50-fold greater, about 5-fold to about 40-fold greater, about 5-fold to about 30-fold greater, about 5-fold to about 25-fold greater, about 5-fold to about 20-fold greater, about 5-fold to about 15-fold greater, about 5-fold to about 10-fold greater, about 5-fold to about 8-fold greater, about 8-fold to about 100-fold greater, about 8-fold to about 90-fold greater, about 8-fold to about 80-fold greater, about 8-fold to about 70-fold greater, about 8-fold to about 60-fold greater, about 8-fold to about 50-fold greater, about 8-fold to about 40-fold greater, about 8-fold to about 30-fold greater, about 8-fold to about 25-fold greater, about 8-fold to about 20-fold greater, about 8-fold to about 15-fold greater, about 8-fold to about 10-fold greater, about 10-fold to about 100-fold greater, about 10-fold to about 90-fold greater, about 10-fold to about 80-fold greater, about 10-fold to about 70-fold greater, about 10-fold to about 60-fold greater, about 10-fold to about 50-fold greater, about 10-fold to about 40-fold greater, about 10-fold to about 30-fold greater, about 10-fold to about 25-fold greater, about 10-fold to about 20-fold greater, about 10-fold to about 15-fold greater, about 15-fold to about 100-fold greater, about 15-fold to about 90-fold greater, about 15-fold to about 80-fold greater, about 15-fold to about 70-fold greater, about 15-fold to about 60-fold greater, about 15-fold to about 50-fold greater, about 15-fold to about 40-fold greater, about 15-fold to about 30-fold greater, about 15-fold to about 25-fold greater, about 15-fold to about 20-fold greater, about 20-fold to about 100-fold greater, about 20-fold to about 90-fold greater, about 20-fold to about 80-fold greater, about 20-fold to about 70-fold greater, about 20-fold to about 60-fold greater, about 20-fold to about 50-fold greater, about 20-fold to about 40-fold greater, about 20-fold to about 30-fold greater, about 20-fold to about 25-fold greater, about 25-fold to about 100-fold greater, about 25-fold to about 90-fold greater, about 25-fold to about 80-fold greater, about 25-fold to about 70-fold greater, about 25-fold to about 60-fold greater, about 25-fold to about 50-fold greater, about 25-fold to about 40-fold greater, about 25-fold to about 30-fold greater, about 30-fold to about 100-fold greater, about 30-fold to about 90-fold greater, about 30-fold to about 80-fold greater, about 30-fold to about 70-fold greater, about 30-fold to about 60-fold greater, about 30-fold to about 50-fold greater, about 30-fold to about 40-fold greater, about 40-fold to about 100-fold greater, about 40-fold to about 90-fold greater, about 40-fold to about 80-fold greater, about 40-fold to about 70-fold greater, about 40-fold to about 60-fold greater, about 40-fold to about 50-fold greater, about 50-fold to about 100-fold greater, about 50-fold to about 90-fold greater, about 50-fold to about 80-fold greater, about 50-fold to about 70-fold greater, about 50-fold to about 60-fold greater, about 60-fold to about 100-fold greater, about 60-fold to about 90-fold greater, about 60-fold to about 80-fold greater, about 60-fold to about 70-fold greater, about 70-fold to about 100-fold greater, about 70-fold to about 90-fold greater, about 70-fold to about 80-fold greater, about 80-fold to about 100-fold greater, about 80-fold to about 90-fold greater, or about 90-fold to about 100-fold greater), than the $K_D$ at a pH of about 7.0 to about 8.0 (e.g., any of the subranges of this range described herein).

In some embodiments of the ABPCs that include a first antigen-binding domain and a second antigen-binding domain, the first and second antigen-binding domains are identical or are at least 80% identical (e.g., at least 82%, at least 84%, at least 86%, at least 88%, at least 90%, at least 91%, at least 92%, at least 93%, at least 94%, at least 95%, at least 96%, at least 97%, at least 98%, or at least 99% identical) in amino acid sequence to each other. In some embodiments, the ABPCs that include a first antigen-binding domain and a second antigen-binding domain, the first antigen-binding domain and the second antigen-binding domain have a sequence that is less than 80% identical (e.g., less than 75% identical, less than 70% identical, less than 65% identical, less than 60% identical, less than 55% identical, less than 50% identical, less than 45% identical, less than 40% identical, less than 35% identical, less than 30% identical, less than 25% identical, less than 20% identical, less than 15% identical, less than 10% identical, or less than 5% identical) to each other. In some embodiments of ABPCs that include a first and a second antigen-binding domain, the first and second antigen-binding domain binds two different epitopes (e.g., two different epitopes on CD123 or the first antigen-binding domain binding specifically to CD123 and the second antigen-binding domain binding to an antigen other than CD123).

In some embodiments of any of the ABPCs described herein, the $K_D$ of the first antigen-binding domain (and optionally, the second antigen-binding domain if present) at a pH of about 7.0 to about 8.0 (e.g., any of the subranges of this range described herein) is between about 1 pM to about 5 μM (e.g., about 1 pM to about 2 μM, about 1 pM to about 1 μM, about 1 pM to about 500 nM, about 1 pM to about 250 nM, about 1 pM to about 240 nM, about 1 pM to about 230 nM, about 1 pM to about 220 nM, about 1 pM to about 210 nM, about 1 pM to about 200 nM, about 1 pM to about 190 nM, about 1 pM to about 180 nM, about 1 pM to about 170 nM, about 1 pM to about 160 nM, about 1 pM to about 150 nM, about 1 pM to about 140 nM, about 1 pM to about 130 nM, about 1 pM to about 120 nM, about 1 pM to about 110 nM, about 1 pM to about 100 nM, about 1 pM to about 95 nM, about 1 pM to about 90 nM, about 1 pM to about 85 nM, about 1 pM to about 80 nM, about 1 pM to about 75 nM, about 1 pM to about 70 nM, about 1 pM to about 65 nM, about 1 pM to about 60 nM, about 1 pM to about 55 nM, about 1 pM to about 50 nM, about 1 pM to about 45 nM, about 1 pM to about 40 nM, about 1 pM to about 35 nM, about 1 pM to about 30 nM, about 1 pM to about 25 nM, about 1 pM to about 20 nM, about 1 pM to about 15 nM, about 1 pM to about 10 nM, about 1 pM to about 5 nM, about 1 pM to about 2 nM, about 1 pM to about 1 nM, about 1 pM to about 950 pM, about 1 pM to about 900 pM, about 1 pM to about 850 pM, about 1 pM to about 800 pM, about 1 pM to about 750 pM, about 1 pM to about 700 pM, about 1 pM to about 650 pM, about 1 pM to about 600 pM, about 1 pM to about 550 pM, about 1 pM to about 500 pM, about 1 pM to about 450 pM, about 1 pM to about 400 pM, about 1 pM to about 350 pM, about 1 pM to about 300 pM, about 1 pM to about 250 pM, about 1 pM to about 200 pM, about 1 pM to about 150 pM, about 1 pM to about 100 pM, about 1 pM to about 90 pM, about 1 pM to about 80 pM, about 1 pM to about 70 pM, about 1 pM to about 60 pM, about 1 pM to about 50 pM, about 1 pM to about 40 pM, about 1 pM to about 30 pM, about 1 pM to about 20 pM, about 1 pM to about 10 pM, about 1 pM to about 5 pM, about 1 pM to about 4 pM, about 1 pM to about 3 pM, about 1 pM to about 2 pM, about 2 pM to about 5 μM, about 2 pM to about 2 μM, about 2 pM to about 1 μM, about 2 pM to about 500 nM, about 2 pM to about 250 nM, about 2 pM to about 240 nM, about 2 pM to about 230 nM, about 2 pM to about 220 nM, about 2 pM to about 210 nM, about 2 pM to about 200 nM, about 2 pM to about 190 nM, about 2 pM to about 180 nM, about 2 pM to about 170 nM, about 2 pM to about 160 nM, about 2 pM to about 150 nM, about 2 pM to about 140 nM, about 2 pM to about 130 nM, about 2 pM to about 120 nM, about 2 pM to about 110 nM, about 2 pM to about 100 nM, about 2 pM to about 95 nM, about 2 pM to about 90 nM, about 2 pM to about 85 nM, about 2 pM to about 80 nM, about 2 pM to about 75 nM, about 2 pM to about 70 nM, about 2 pM to about 65 nM, about 2 pM to about 60 nM, about 2 pM to about 55 nM, about 2 pM to about 50 nM, about 2 pM to about 45 nM, about 2 pM to about 40 nM, about 2 pM to about 35 nM, about 2 pM to about 30 nM, about 2 pM to about 25 nM, about 2 pM to about 20 nM, about 2 pM to about 15 nM, about 2 pM to about 10 nM, about 2 pM to about 5 nM, about 2 pM to about 2 nM, about 2 pM to about 1 nM, about 2 pM to about 950 pM, about 2 pM to about 900 pM, about 2 pM to about 850 pM, about 2 pM to about 800 pM, about 2 pM to about 750 pM, about 2 pM to about 700 pM, about 2 pM to about 650 pM, about 2 pM to about 600 pM, about 2 pM to about 550 pM, about 2 pM to about 500 pM, about 2 pM to about 450 pM, about 2 pM to about 400 pM, about 2 pM to about 350 pM, about 2 pM to about 300 pM, about 2 pM to about 250 pM, about 2 pM to about 200 pM, about 2 pM to about 150 pM, about 2 pM to about 100 pM, about 2 pM to about 90 pM, about 2 pM to about 80 pM, about 2 pM to about 70 pM, about 2 pM to about 60 pM, about 2 pM to about 50 pM, about 2 pM to about 40 pM, about 2 pM to about 30 pM, about 2 pM to about 20 pM, about 2 pM to about 10 pM, about 2 pM to about 5 pM, about 2 pM to about 4 pM, about 2 pM to about 3 pM, about 5 pM to about 5 μM, about 5 pM to about 2 μM, about 5 pM to about 1 μM, about 5 pM to about 500 nM, about 5 pM to about 250 nM, about 5 pM to about 240 nM, about 5 pM to about 230 nM, about 5 pM to about 220 nM, about 5 pM to about 210 nM, about 5 pM to about 200 nM, about 5 pM to about 190 nM, about 5 pM to about 180 nM, about 5 pM to about 170 nM, about 5 pM to about 160 nM, about 5 pM to about 150 nM, about 5 pM to about 140 nM, about 5 pM to about 130 nM, about 5 pM to about 120 nM, about 5 pM to about 110 nM, about 5 pM to about 100 nM, about 5 pM to about 95 nM, about 5 pM to about 90 nM, about 5 pM to about 85 nM, about 5 pM to about 80 nM, about 5 pM to about 75 nM, about 5 pM to about 70 nM, about 5 pM to about 65 nM, about 5 pM to about 60 nM, about 5 pM to about 55 nM, about 5 pM to about 50 nM, about 5 pM to about 45 nM, about 5 pM to about 40 nM, about 5 pM to about 35 nM, about 5 pM to about 30 nM, about 5 pM to about 25 nM, about 5 pM to about 20 nM, about 5 pM to about 15 nM, about 5 pM to about 10 nM, about 5 pM to about 5 nM, about 5 pM to about 2 nM, about 5 pM to about 1 nM, about 5 pM to about 950 pM, about 5 pM to about 900 pM, about 5 pM to about 850 pM, about 5 pM to about 800 pM, about 5 pM to about 750 pM, about 5 pM to about 700 pM, about 5 pM to about 650 pM, about 5 pM to about 600 pM, about 5 pM to about 550 pM, about 5 pM to about 500 pM, about 5 pM to about 450 pM, about 5 pM to about 400 pM, about 5 pM to about 350 pM, about 5 pM to about 300 pM, about 5 pM to about 250 pM, about 5 pM to about 200 pM, about 5 pM to about 150 pM, about 5 pM to about 100 pM, about 5 pM to about 90 pM, about 5 pM to about 80 pM, about 5 pM to about 70 pM, about 5 pM to about 60 pM, about 5 pM to about 50 pM, about 5 pM to about 40 pM, about 5 pM to about 30 pM, about 5 pM to about 20 pM, about 5 pM to about 10 pM, about 10 pM to about 5 μM, about 10 pM to about 2 μM, about 10 pM to about 1 μM, about 10 pM to about 500 nM, about 10 pM to about 250 nM, about 10 pM to about 240 nM, about 10 pM to about 230 nM, about 10 pM to about 220 nM, about 10 pM to about 210 nM, about 10 pM to about 200 nM, about 10 pM to about 190 nM, about 10 pM to about 180 nM, about 10 pM to about 170 nM, about 10 pM to about 160 nM, about 10 pM to about 150 nM, about 10 pM to about 140 nM, about 10 pM to about 130 nM, about 10 pM to about 120 nM, about 10 pM to about 110 nM, about 10 pM to about 100 nM, about 10 pM to about 95 nM, about 10 pM to about 90 nM, about 10 pM to about 85 nM, about 10 pM to about 80 nM, about 10 pM to about 75 nM, about 10 pM to about 70 nM, about 10 pM to about 65 nM, about 10 pM to about 60 nM, about 10 pM to about 55 nM, about 10 pM to about 50 nM, about 10 pM to about 45 nM, about 10 pM to about 40 nM, about 10 pM to about 35 nM, about 10 pM to about 30 nM, about 10 pM to about 25 nM, about 10 pM to about 20 nM, about 10 pM to about 15 nM, about 10 pM to about 10 nM, about 10 pM to about 5 nM, about 10 pM to about 2 nM, about 10 pM to about 1 nM, about 10 pM to about 950 pM, about 10 pM to about 900 pM, about 10 pM to about 850 pM, about 10 pM to about 800 pM, about 10 pM to about 750 pM, about 10 pM to about 700 pM, about 10 pM to about 650 pM, about 10 pM to about 600 pM, about 10 pM to about 550 pM, about 10 pM to about 500 pM, about 10 pM to about 450 pM, about 10 pM to about 400 pM, about 10 pM to about 350 pM, about 10 pM to about 300 pM, about 10 pM to about 250 pM, about 10 pM to about 200 pM, about 10 pM to about 150 pM, about 10 pM to about 100 pM, about 10 pM to about 90 pM, about 10 pM to about 80 pM, about 10 pM to about 70 pM, about 10 pM to about 60 pM, about 10 pM to about 50 pM, about 10 pM to about 40 pM, about 10 pM to about 30 pM, about 10 pM to about 20 pM, about 15 pM to about 5 μM, about 15 pM to about 2 μM, about 15 pM to about 1 μM, about 15 pM to about 500 nM, about 15 pM to about 250 nM, about 15 pM to about 240 nM, about 15 pM to about 230 nM, about 15 pM to about 220 nM, about 15 pM to about 210 nM, about 15 pM to about 200 nM, about 15 pM to about 190 nM, about 15 pM to about 180 nM, about 15 pM to about 170 nM, about 15 pM to about 160 nM, about 15 pM to about 150 nM, about 15 pM to about 140 nM, about 15 pM to about 130 nM, about 15 pM to about 120 nM, about 15 pM to about 110 nM, about 15 pM to about 100 nM, about 15 pM to about 95 nM, about 15 pM to about 90 nM, about 15 pM to about 85 nM, about 15 pM to about 80 nM, about 15 pM to about 75 nM, about 15 pM to about 70 nM, about 15 pM to about 65 nM, about 15 pM to about 60 nM, about 15 pM to about 55 nM, about 15 pM to about 50 nM, about 15 pM to about 45 nM, about 15 pM to about 40 nM, about 15 pM to about 35 nM, about 15 pM to about 30 nM, about 15 pM to about 25 nM, about 15 pM to about 20 nM, about 15 pM to about 15 nM, about 15 pM to about 10 nM, about 15 pM to about 5 nM, about 15 pM to about 2 nM, about 15 pM to about 1 nM, about 15 pM to about 950 pM, about 15 pM to about 900 pM, about 15 pM to about 850 pM, about 15 pM to about 800 pM, about 15 pM to about 750 pM, about 15 pM to about 700 pM, about 15 pM to about 650 pM, about 15 pM to about 600 pM, about 15 pM to about 550 pM, about 15 pM to about 500 pM, about 15 pM to about 450 pM, about 15 pM to about 400 pM, about 15 pM to about 350 pM, about 15 pM to about 300 pM, about 15 pM to about 250 pM, about 15 pM to about 200 pM, about 15 pM to about 150 pM, about 15 pM to about 100 pM, about 15 pM to about 90 pM, about 15 pM to about 80 pM, about 15 pM to about 70 pM, about 15 pM to about 60 pM, about 15 pM to about 50 pM, about 15 pM to about 40 pM, about 15 pM to about 30 pM, about 15 pM to about 20 pM, about 20 pM to about 5 μM, about 20 pM to about 2 μM, about 20 pM to about 1 μM, about 20 pM to about 500 nM, about 20 pM to about 250 nM, about 20 pM to about 240 nM, about 20 pM to about 230 nM, about 20 pM to about 220 nM, about 20 pM to about 210 nM, about 20 pM to about 200 nM, about 20 pM to about 190 nM, about 20 pM to about 180 nM, about 20 pM to about 170 nM, about 20 pM to about 160 nM, about 20 pM to about 150 nM, about 20 pM to about 140 nM, about 20 pM to about 130 nM, about 20 pM to about 120 nM, about 20 pM to about 110 nM, about 20 pM to about 100 nM, about 20 pM to about 95 nM, about 20 pM to about 90 nM, about 20 pM to about 85 nM, about 20 pM to about 80 nM, about 20 pM to about 75 nM, about 20 pM to about 70 nM, about 20 pM to about 65 nM, about 20 pM to about 60 nM, about 20 pM to about 55 nM, about 20 pM to about 50 nM, about 20 pM to about 45 nM, about 20 pM to about 40 nM, about 20 pM to about 35 nM, about 20 pM to about 30 nM, about 20 pM to about 25 nM, about 20 pM to about 20 nM, about 20 pM to about 15 nM, about 20 pM to about 10 nM, about 20 pM to about 5 nM, about 20 pM to about 2 nM, about 20 pM to about 1 nM, about 20 pM to about 950 pM, about 20 pM to about 900 pM, about 20 pM to about 850 pM, about 20 pM to about 800 pM, about 20 pM to about 750 pM, about 20 pM to about 700 pM, about 20 pM to about 650 pM, about 20 pM to about 600 pM, about 20 pM to about 550 pM, about 20 pM to about 500 pM, about 20 pM to about 450 pM, about 20 pM to about 400 pM, about 20 pM to about 350 pM, about 20 pM to about 300 pM, about 20 pM to about 250 pM, about 20 pM to about 20 pM, about 200 pM to about 150 pM, about 20 pM to about 100 pM, about 20 pM to about 90 pM, about 20 pM to about 80 pM, about 20 pM to about 70 pM, about 20 pM to about 60 pM, about 20 pM to about 50 pM, about 20 pM to about 40 pM, about 20 pM to about 30 pM, about 30 pM to about 5 μM, about 30 pM to about 2 μM, about 30 pM to about 1 μM, about 30 pM to about 500 nM, about 30 pM to about 250 nM, about 30 pM to about 240 nM, about 30 pM to about 230 nM, about 30 pM to about 220 nM, about 30 pM to about 210 nM, about 30 pM to about 200 nM, about 30 pM to about 190 nM, about 30 pM to about 180 nM, about 30 pM to about 170 nM, about 30 pM to about 160 nM, about 30 pM to about 150 nM, about 30 pM to about 140 nM, about 30 pM to about 130 nM, about 30 pM to about 120 nM, about 30 pM to about 110 nM, about 30 pM to about 100 nM, about 30 pM to about 95 nM, about 30 pM to about 90 nM, about 30 pM to about 85 nM, about 30 pM to about 80 nM, about 30 pM to about 75 nM, about 30 pM to about 70 nM, about 30 pM to about 65 nM, about 30 pM to about 60 nM, about 30 pM to about 55 nM, about 30 pM to about 50 nM, about 30 pM to about 45 nM, about 30 pM to about 40 nM, about 30 pM to about 35 nM, about 30 pM to about 30 nM, about 30 pM to about 25 nM, about 30 pM to about 20 nM, about 30 pM to about 15 nM, about 30 pM to about 10 nM, about 30 pM to about 5 nM, about 30 pM to about 2 nM, about 30 pM to about 1 nM, about 30 pM to about 950 pM, about 30 pM to about 900 pM, about 30 pM to about 850 pM, about 30 pM to about 800 pM, about 30 pM to about 750 pM, about 30 pM to about 700 pM, about 30 pM to about 650 pM, about 30 pM to about 600 pM, about 30 pM to about 550 pM, about 30 pM to about 500 pM, about 30 pM to about 450 pM, about 30 pM to about 400 pM, about 30 pM to about 350 pM, about 30 pM to about 300 pM, about 30 pM to about 250 pM, about 30 pM to about 200 pM, about 30 pM to about 150 pM, about 30 pM to about 100 pM, about 30 pM to about 90 pM, about 30 pM to about 80 pM, about 30 pM to about 70 pM, about 30 pM to about 60 pM, about 30 pM to about 50 pM, about 30 pM to about 40 pM, about 40 pM to about 5 μM, about 40 pM to about 2 μM, about 40 pM to about 1 μM, about 40 pM to about 500 nM, about 40 pM to about 250 nM, about 40 pM to about 240 nM, about 40 pM to about 230 nM, about 40 pM to about 220 nM, about 40 pM to about 210 nM, about 40 pM to about 200 nM, about 40 pM to about 190 nM, about 40 pM to about 180 nM, about 40 pM to about 170 nM, about 40 pM to about 160 nM, about 40 pM to about 150 nM, about 40 pM to about 140 nM, about 40 pM to about 130 nM, about 40 pM to about 120 nM, about 40 pM to about 110 nM, about 40 pM to about 100 nM, about 40 pM to about 95 nM, about 40 pM to about 90 nM, about 40 pM to about 85 nM, about 40 pM to about 80 nM, about 40 pM to about 75 nM, about 40 pM to about 70 nM, about 40 pM to about 65 nM, about 40 pM to about 60 nM, about 40 pM to about 55 nM, about 40 pM to about 50 nM, about 40 pM to about 45 nM, about 40 pM to about 40 nM, about 40 pM to about 35 nM, about 40 pM to about 30 nM, about 40 pM to about 25 nM, about 40 pM to about 30 nM, about 40 pM to about 15 nM, about 40 pM to about 10 nM, about 40 pM to about 5 nM, about 40 pM to about 2 nM, about 40 pM to about 1 nM, about 40 pM to about 950 pM, about 40 pM to about 900 pM, about 40 pM to about 850 pM, about 40 pM to about 800 pM, about 40 pM to about 750 pM, about 40 pM to about 700 pM, about 40 pM to about 650 pM, about 40 pM to about 600 pM, about 40 pM to about 550 pM, about 40 pM to about 500 pM, about 40 pM to about 450 pM, about 40 pM to about 400 pM, about 40 pM to about 350 pM, about 40 pM to about 300 pM, about 40 pM to about 250 pM, about 40 pM to about 200 pM, about 40 pM to about 150 pM, about 40 pM to about 100 pM, about 40 pM to about 90 pM, about 40 pM to about 80 pM, about 40 pM to about 70 pM, about 40 pM to about 60 pM, about 40 pM to about 50 pM, about 50 pM to about 5 μM, about 50 pM to about 2 μM, about 50 pM to about 1 μM, about 50 pM to about 500 nM, about 50 pM to about 250 nM, about 50 pM to about 240 nM, about 50 pM to about 230 nM, about 50 pM to about 220 nM, about 50 pM to about 210 nM, about 50 pM to about 200 nM, about 50 pM to about 190 nM, about 50 pM to about 180 nM, about 50 pM to about 170 nM, about 50 pM to about 160 nM, about 50 pM to about 150 nM, about 50 pM to about 140 nM, about 50 pM to about 130 nM, about 50 pM to about 120 nM, about 50 pM to about 110 nM, about 50 pM to about 100 nM, about 50 pM to about 95 nM, about 50 pM to about 90 nM, about 50 pM to about 85 nM, about 50 pM to about 80 nM, about 50 pM to about 75 nM, about 50 pM to about 70 nM, about 50 pM to about 65 nM, about 50 pM to about 60 nM, about 50 pM to about 55 nM, about 50 pM to about 50 nM, about 50 pM to about 45 nM, about 50 pM to about 40 nM, about 50 pM to about 35 nM, about 50 pM to about 30 nM, about 50 pM to about 25 nM, about 50 pM to about 30 nM, about 50 pM to about 15 nM, about 50 pM to about 10 nM, about 50 pM to about 5 nM, about 50 pM to about 2 nM, about 50 pM to about 1 nM, about 50 pM to about 950 pM, about 50 pM to about 900 pM, about 50 pM to about 850 pM, about 50 pM to about 800 pM, about 50 pM to about 750 pM, about 50 pM to about 700 pM, about 50 pM to about 650 pM, about 50 pM to about 600 pM, about 50 pM to about 550 pM, about 50 pM to about 500 pM, about 50 pM to about 450 pM, about 50 pM to about 400 pM, about 50 pM to about 350 pM, about 50 pM to about 300 pM, about 50 pM to about 250 pM, about 50 pM to about 200 pM, about 50 pM to about 150 pM, about 50 pM to about 100 pM, about 50 pM to about 90 pM, about 50 pM to about 80 pM, about 50 pM to about 70 pM, about 50 pM to about 60 pM, about 60 pM to about 5 μM, about 60 pM to about 2 μM, about 60 pM to about 1 μM, about 60 pM to about 500 nM, about 60 pM to about 250 nM, about 60 pM to about 240 nM, about 60 pM to about 230 nM, about 60 pM to about 220 nM, about 60 pM to about 210 nM, about 60 pM to about 200 nM, about 60 pM to about 190 nM, about 60 pM to about 180 nM, about 60 pM to about 170 nM, about 60 pM to about 160 nM, about 60 pM to about 150 nM, about 60 pM to about 140 nM, about 60 pM to about 130 nM, about 60 pM to about 120 nM, about 60 pM to about 110 nM, about 60 pM to about 100 nM, about 60 pM to about 95 nM, about 60 pM to about 90 nM, about 60 pM to about 85 nM, about 60 pM to about 80 nM, about 60 pM to about 75 nM, about 60 pM to about 70 nM, about 60 pM to about 65 nM, about 60 pM to about 60 nM, about 60 pM to about 55 nM, about 60 pM to about 50 nM, about 60 pM to about 45 nM, about 60 pM to about 40 nM, about 60 pM to about 35 nM, about 60 pM to about 30 nM, about 60 pM to about 25 nM, about 60 pM to about 20 nM, about 60 pM to about 15 nM, about 60 pM to about 10 nM, about 60 pM to about 5 nM, about 60 pM to about 2 nM, about 60 pM to about 1 nM, about 60 pM to about 950 pM, about 60 pM to about 900 pM, about 60 pM to about 850 pM, about 60 pM to about 800 pM, about 60 pM to about 750 pM, about 60 pM to about 700 pM, about 60 pM to about 650 pM, about 60 pM to about 600 pM, about 60 pM to about 550 pM, about 60 pM to about 500 pM, about 60 pM to about 450 pM, about 60 pM to about 400 pM, about 60 pM to about 350 pM, about 60 pM to about 300 pM, about 60 pM to about 250 pM, about 60 pM to about 200 pM, about 60 pM to about 150 pM, about 60 pM to about 100 pM, about 60 pM to about 90 pM, about 60 pM to about 80 pM, about 60 pM to about 70 pM, about 70 pM to about 5 μM, about 70 pM to about 2 μM, about 70 pM to about 1 μM, about 70 pM to about 500 nM, about 70 pM to about 250 nM, about 70 pM to about 240 nM, about 70 pM to about 230 nM, about 70 pM to about 220 nM, about 70 pM to about 210 nM, about 70 pM to about 200 nM, about 70 pM to about 190 nM, about 70 pM to about 180 nM, about 70 pM to about 170 nM, about 70 pM to about 160 nM, about 70 pM to about 150 nM, about 70 pM to about 140 nM, about 70 pM to about 130 nM, about 70 pM to about 120 nM, about 70 pM to about 110 nM, about 70 pM to about 100 nM, about 70 pM to about 95 nM, about 70 pM to about 90 nM, about 70 pM to about 85 nM, about 70 pM to about 80 nM, about 70 pM to about 75 nM, about 70 pM to about 70 nM, about 70 pM to about 65 nM, about 70 pM to about 60 nM, about 70 pM to about 55 nM, about 70 pM to about 50 nM, about 70 pM to about 45 nM, about 70 pM to about 40 nM, about 70 pM to about 35 nM, about 70 pM to about 30 nM, about 70 pM to about 25 nM, about 70 pM to about 20 nM, about 70 pM to about 15 nM, about 70 pM to about 10 nM, about 70 pM to about 5 nM, about 70 pM to about 2 nM, about 70 pM to about 1 nM, about 70 pM to about 950 pM, about 70 pM to about 900 pM, about 70 pM to about 850 pM, about 70 pM to about 800 pM, about 70 pM to about 750 pM, about 70 pM to about 700 pM, about 70 pM to about 650 pM, about 70 pM to about 600 pM, about 70 pM to about 550 pM, about 70 pM to about 500 pM, about 70 pM to about 450 pM, about 70 pM to about 400 pM, about 70 pM to about 350 pM, about 70 pM to about 300 pM, about 70 pM to about 250 pM, about 70 pM to about 200 pM, about 70 pM to about 150 pM, about 70 pM to about 100 pM, about 70 pM to about 90 pM, about 70 pM to about 80 pM, about 80 pM to about 5 μM, about 80 pM to about 2 μM, about 80 pM to about 1 μM, about 80 pM to about 500 nM, about 80 pM to about 250 nM, about 80 pM to about 240 nM, about 80 pM to about 230 nM, about 80 pM to about 220 nM, about 80 pM to about 210 nM, about 80 pM to about 200 nM, about 80 pM to about 190 nM, about 80 pM to about 180 nM, about 80 pM to about 170 nM, about 80 pM to about 160 nM, about 80 pM to about 150 nM, about 80 pM to about 140 nM, about 80 pM to about 130 nM, about 80 pM to about 120 nM, about 80 pM to about 110 nM, about 80 pM to about 100 nM, about 80 pM to about 95 nM, about 80 pM to about 90 nM, about 80 pM to about 85 nM, about 80 pM to about 80 nM, about 80 pM to about 75 nM, about 80 pM to about 70 nM, about 80 pM to about 65 nM, about 80 pM to about 60 nM, about 80 pM to about 55 nM, about 80 pM to about 50 nM, about 80 pM to about 45 nM, about 80 pM to about 40 nM, about 80 pM to about 35 nM, about 80 pM to about 30 nM, about 80 pM to about 25 nM, about 80 pM to about 20 nM, about 80 pM to about 15 nM, about 80 pM to about 10 nM, about 80 pM to about 5 nM, about 80 pM to about 2 nM, about 80 pM to about 1 nM, about 80 pM to about 950 pM, about 80 pM to about 900 pM, about 80 pM to about 850 pM, about 80 pM to about 800 pM, about 80 pM to about 750 pM, about 80 pM to about 700 pM, about 80 pM to about 650 pM, about 80 pM to about 600 pM, about 80 pM to about 550 pM, about 80 pM to about 500 pM, about 80 pM to about 450 pM, about 80 pM to about 400 pM, about 80 pM to about 350 pM, about 80 pM to about 300 pM, about 80 pM to about 250 pM, about 80 pM to about 200 pM, about 80 pM to about 150 pM, about 80 pM to about 100 pM, about 80 pM to about 90 pM, about 90 pM to about 5 μM, about 90 pM to about 2 μM, about 90 pM to about 1 μM, about 90 pM to about 500 nM, about 90 pM to about 250 nM, about 90 pM to about 240 nM, about 90 pM to about 230 nM, about 90 pM to about 220 nM, about 90 pM to about 210 nM, about 90 pM to about 200 nM, about 90 pM to about 190 nM, about 90 pM to about 180 nM, about 90 pM to about 170 nM, about 90 pM to about 160 nM, about 90 pM to about 150 nM, about 90 pM to about 140 nM, about 90 pM to about 130 nM, about 90 pM to about 120 nM, about 90 pM to about 110 nM, about 90 pM to about 100 nM, about 90 pM to about 95 nM, about 90 pM to about 90 nM, about 90 pM to about 85 nM, about 90 pM to about 80 nM, about 90 pM to about 75 nM, about 90 pM to about 70 nM, about 90 pM to about 65 nM, about 90 pM to about 60 nM, about 90 pM to about 55 nM, about 90 pM to about 50 nM, about 90 pM to about 45 nM, about 90 pM to about 40 nM, about 90 pM to about 35 nM, about 90 pM to about 30 nM, about 90 pM to about 25 nM, about 90 pM to about 30 nM, about 90 pM to about 15 nM, about 90 pM to about 10 nM, about 90 pM to about 5 nM, about 90 pM to about 2 nM, about 90 pM to about 1 nM, about 90 pM to about 950 pM, about 90 pM to about 900 pM, about 90 pM to about 850 pM, about 90 pM to about 800 pM, about 90 pM to about 750 pM, about 90 pM to about 700 pM, about 90 pM to about 650 pM, about 90 pM to about 600 pM, about 90 pM to about 550 pM, about 90 pM to about 500 pM, about 90 pM to about 450 pM, about 90 pM to about 400 pM, about 90 pM to about 350 pM, about 90 pM to about 300 pM, about 90 pM to about 250 pM, about 90 pM to about 200 pM, about 90 pM to about 150 pM, about 90 pM to about 100 pM, about 100 pM to about 30 nM, about 100 pM to about 25 nM, about 100 pM to about 5 μM, about 100 pM to about 2 μM, about 100 pM to about 1 μM, about 100 pM to about 500 nM, about 100 pM to about 250 nM, about 100 pM to about 240 nM, about 100 pM to about 230 nM, about 100 pM to about 220 nM, about 100 pM to about 210 nM, about 100 pM to about 200 nM, about 100 pM to about 190 nM, about 100 pM to about 180 nM, about 100 pM to about 170 nM, about 100 pM to about 160 nM, about 100 pM to about 150 nM, about 100 pM to about 140 nM, about 100 pM to about 130 nM, about 100 pM to about 120 nM, about 100 pM to about 110 nM, about 100 pM to about 100 nM, about 100 pM to about 95 nM, about 100 pM to about 90 nM, about 100 pM to about 85 nM, about 100 pM to about 80 nM, about 100 pM to about 75 nM, about 100 pM to about 70 nM, about 100 pM to about 65 nM, about 100 pM to about 60 nM, about 100 pM to about 55 nM, about 100 pM to about 50 nM, about 100 pM to about 45 nM, about 100 pM to about 40 nM, about 100 pM to about 35 nM, about 100 pM to about 30 nM, about 100 pM to about 15 nM, about 100 pM to about 10 nM, about 100 pM to about 5 nM, about 100 pM to about 2 nM, about 100 pM to about 1 nM, about 100 pM to about 950 pM, about 100 pM to about 900 pM, about 100 pM to about 850 pM, about 100 pM to about 800 pM, about 100 pM to about 750 pM, about 100 pM to about 700 pM, about 100 pM to about 650 pM, about 100 pM to about 600 pM, about 100 pM to about 550 pM, about 100 pM to about 500 pM, about 100 pM to about 450 pM, about 100 pM to about 400 pM, about 100 pM to about 350 pM, about 100 pM to about 300 pM, about 100 pM to about 250 pM, about 100 pM to about 200 pM, about 100 pM to about 150 pM, about 150 pM to about 5 μM, about 150 pM to about 2 μM, about 150 pM to about 1 μM, about 150 pM to about 500 nM, about 150 pM to about 250 nM, about 150 pM to about 240 nM, about 150 pM to about 230 nM, about 150 pM to about 220 nM, about 150 pM to about 210 nM, about 150 pM to about 200 nM, about 150 pM to about 190 nM, about 150 pM to about 180 nM, about 150 pM to about 170 nM, about 150 pM to about 160 nM, about 150 pM to about 150 nM, about 150 pM to about 140 nM, about 150 pM to about 130 nM, about 150 pM to about 120 nM, about 150 pM to about 110 nM, about 150 pM to about 100 nM, about 150 pM to about 95 nM, about 150 pM to about 90 nM, about 150 pM to about 85 nM, about 150 pM to about 80 nM, about 150 pM to about 75 nM, about 150 pM to about 70 nM, about 150 pM to about 65 nM, about 150 pM to about 60 nM, about 150 pM to about 55 nM, about 150 pM to about 50 nM, about 150 pM to about 45 nM, about 150 pM to about 40 nM, about 150 pM to about 35 nM, about 150 pM to about 30 nM, about 150 pM to about 25 nM, about 150 pM to about 30 nM, about 150 pM to about 15 nM, about 150 pM to about 10 nM, about 150 pM to about 5 nM, about 150 pM to about 2 nM, about 150 pM to about 1 nM, about 150 pM to about 950 pM, about 150 pM to about 900 pM, about 150 pM to about 850 pM, about 150 pM to about 800 pM, about 150 pM to about 750 pM, about 150 pM to about 700 pM, about 150 pM to about 650 pM, about 150 pM to about 600 pM, about 150 pM to about 550 pM, about 150 pM to about 500 pM, about 150 pM to about 450 pM, about 150 pM to about 400 pM, about 150 pM to about 350 pM, about 150 pM to about 300 pM, about 150 pM to about 250 pM, about 150 pM to about 200 pM, about 200 pM to about 5 μM, about 200 pM to about 2 μM, about 200 pM to about 1 μM, about 200 pM to about 500 nM, about 200 pM to about 250 nM, about 200 pM to about 240 nM, about 200 pM to about 230 nM, about 200 pM to about 220 nM, about 200 pM to about 210 nM, about 200 pM to about 200 nM, about 200 pM to about 190 nM, about 200 pM to about 180 nM, about 200 pM to about 170 nM, about 200 pM to about 160 nM, about 200 pM to about 150 nM, about 200 pM to about 140 nM, about 200 pM to about 130 nM, about 200 pM to about 120 nM, about 200 pM to about 110 nM, about 200 pM to about 100 nM, about 200 pM to about 95 nM, about 200 pM to about 90 nM, about 200 pM to about 85 nM, about 200 pM to about 80 nM, about 200 pM to about 75 nM, about 200 pM to about 70 nM, about 200 pM to about 65 nM, about 200 pM to about 60 nM, about 200 pM to about 55 nM, about 200 pM to about 50 nM, about 200 pM to about 45 nM, about 200 pM to about 40 nM, about 200 pM to about 35 nM, about 200 pM to about 30 nM, about 200 pM to about 25 nM, about 200 pM to about 30 nM, about 200 pM to about 15 nM, about 200 pM to about 10 nM, about 200 pM to about 5 nM, about 200 pM to about 2 nM, about 200 pM to about 1 nM, about 200 pM to about 950 pM, about 200 pM to about 900 pM, about 200 pM to about 850 pM, about 200 pM to about 800 pM, about 200 pM to about 750 pM, about 200 pM to about 700 pM, about 200 pM to about 650 pM, about 200 pM to about 600 pM, about 200 pM to about 550 pM, about 200 pM to about 500 pM, about 200 pM to about 450 pM, about 200 pM to about 400 pM, about 200 pM to about 350 pM, about 200 pM to about 300 pM, about 200 pM to about 250 pM, about 300 pM to about 30 nM, about 300 pM to about 25 nM, about 300 pM to about 5 μM, about 300 pM to about 2 μM, about 300 pM to about 1 μM, about 300 pM to about 500 nM, about 300 pM to about 250 nM, about 300 pM to about 240 nM, about 300 pM to about 230 nM, about 300 pM to about 220 nM, about 300 pM to about 210 nM, about 300 pM to about 200 nM, about 300 pM to about 190 nM, about 300 pM to about 180 nM, about 300 pM to about 170 nM, about 300 pM to about 160 nM, about 300 pM to about 150 nM, about 300 pM to about 140 nM, about 300 pM to about 130 nM, about 300 pM to about 120 nM, about 300 pM to about 110 nM, about 300 pM to about 100 nM, about 300 pM to about 95 nM, about 300 pM to about 90 nM, about 300 pM to about 85 nM, about 300 pM to about 80 nM, about 300 pM to about 75 nM, about 300 pM to about 70 nM, about 300 pM to about 65 nM, about 300 pM to about 60 nM, about 300 pM to about 55 nM, about 300 pM to about 50 nM, about 300 pM to about 45 nM, about 300 pM to about 40 nM, about 300 pM to about 35 nM, about 300 pM to about 30 nM, about 300 pM to about 15 nM, about 300 pM to about 10 nM, about 300 pM to about 5 nM, about 300 pM to about 2 nM, about 300 pM to about 1 nM, about 300 pM to about 950 pM, about 300 pM to about 900 pM, about 300 pM to about 850 pM, about 300 pM to about 800 pM, about 300 pM to about 750 pM, about 300 pM to about 700 pM, about 300 pM to about 650 pM, about 300 pM to about 600 pM, about 300 pM to about 550 pM, about 300 pM to about 500 pM, about 300 pM to about 450 pM, about 300 pM to about 400 pM, about 300 pM to about 350 pM, about 400 pM to about 5 μM, about 400 pM to about 2 μM, about 400 pM to about 1 μM, about 400 pM to about 500 nM, about 400 pM to about 250 nM, about 400 pM to about 240 nM, about 400 pM to about 230 nM, about 400 pM to about 220 nM, about 400 pM to about 210 nM, about 400 pM to about 200 nM, about 400 pM to about 190 nM, about 400 pM to about 180 nM, about 400 pM to about 170 nM, about 400 pM to about 160 nM, about 400 pM to about 150 nM, about 400 pM to about 140 nM, about 400 pM to about 130 nM, about 400 pM to about 120 nM, about 400 pM to about 110 nM, about 400 pM to about 100 nM, about 400 pM to about 95 nM, about 400 pM to about 90 nM, about 400 pM to about 85 nM, about 400 pM to about 80 nM, about 400 pM to about 75 nM, about 400 pM to about 70 nM, about 400 pM to about 65 nM, about 400 pM to about 60 nM, about 400 pM to about 55 nM, about 400 pM to about 50 nM, about 400 pM to about 45 nM, about 400 pM to about 40 nM, about 400 pM to about 35 nM, about 400 pM to about 30 nM, about 400 pM to about 25 nM, about 400 pM to about 20 nM, about 400 pM to about 15 nM, about 400 pM to about 10 nM, about 400 pM to about 5 nM, about 400 pM to about 2 nM, about 400 pM to about 1 nM, about 400 pM to about 950 pM, about 400 pM to about 900 pM, about 400 pM to about 850 pM, about 400 pM to about 800 pM, about 400 pM to about 750 pM, about 400 pM to about 700 pM, about 400 pM to about 650 pM, about 400 pM to about 600 pM, about 400 pM to about 550 pM, about 400 pM to about 500 pM, about 500 pM to about 5 μM, about 500 pM to about 2 μM, about 500 pM to about 1 μM, about 500 pM to about 500 nM, about 500 pM to about 250 nM, about 500 pM to about 240 nM, about 500 pM to about 230 nM, about 500 pM to about 220 nM, about 500 pM to about 210 nM, about 500 pM to about 200 nM, about 500 pM to about 190 nM, about 500 pM to about 180 nM, about 500 pM to about 170 nM, about 500 pM to about 160 nM, about 500 pM to about 150 nM, about 500 pM to about 140 nM, about 500 pM to about 130 nM, about 500 pM to about 120 nM, about 500 pM to about 110 nM, about 500 pM to about 100 nM, about 500 pM to about 95 nM, about 500 pM to about 90 nM, about 500 pM to about 85 nM, about 500 pM to about 80 nM, about 500 pM to about 75 nM, about 500 pM to about 70 nM, about 500 pM to about 65 nM, about 500 pM to about 60 nM, about 500 pM to about 55 nM, about 500 pM to about 50 nM, about 500 pM to about 45 nM, about 500 pM to about 40 nM, about 500 pM to about 35 nM, about 500 pM to about 30 nM, about 500 pM to about 25 nM, about 500 pM to about 20 nM, about 500 pM to about 15 nM, about 500 pM to about 10 nM, about 500 pM to about 5 nM, about 500 pM to about 2 nM, about 500 pM to about 1 nM, about 500 pM to about 950 pM, about 500 pM to about 900 pM, about 500 pM to about 850 pM, about 500 pM to about 800 pM, about 500 pM to about 750 pM, about 500 pM to about 700 pM, about 500 pM to about 650 pM, about 500 pM to about 600 pM, about 500 pM to about 550 pM, about 600 pM to about 5 μM, about 600 pM to about 2 μM, about 600 pM to about 1 μM, about 600 pM to about 500 nM, about 600 pM to about 250 nM, about 600 pM to about 240 nM, about 600 pM to about 230 nM, about 600 pM to about 220 nM, about 600 pM to about 210 nM, about 600 pM to about 200 nM, about 600 pM to about 190 nM, about 600 pM to about 180 nM, about 600 pM to about 170 nM, about 600 pM to about 160 nM, about 600 pM to about 150 nM, about 600 pM to about 140 nM, about 600 pM to about 130 nM, about 600 pM to about 120 nM, about 600 pM to about 110 nM, about 600 pM to about 100 nM, about 600 pM to about 95 nM, about 600 pM to about 90 nM, about 600 pM to about 85 nM, about 600 pM to about 80 nM, about 600 pM to about 75 nM, about 600 pM to about 70 nM, about 600 pM to about 65 nM, about 600 pM to about 60 nM, about 600 pM to about 55 nM, about 600 pM to about 50 nM, about 600 pM to about 45 nM, about 600 pM to about 40 nM, about 600 pM to about 35 nM, about 600 pM to about 30 nM, about 600 pM to about 25 nM, about 600 pM to about 20 nM, about 600 pM to about 15 nM, about 600 pM to about 10 nM, about 600 pM to about 5 nM, about 600 pM to about 2 nM, about 600 pM to about 1 nM, about 600 pM to about 950 pM, about 600 pM to about 900 pM, about 600 pM to about 850 pM, about 600 pM to about 800 pM, about 600 pM to about 750 pM, about 600 pM to about 700 pM, about 600 pM to about 650 pM, about 700 pM to about 5 μM, about 700 pM to about 2 μM, about 700 pM to about 1 μM, about 700 pM to about 500 nM, about 700 pM to about 250 nM, about 700 pM to about 240 nM, about 700 pM to about 230 nM, about 700 pM to about 220 nM, about 700 pM to about 210 nM, about 700 pM to about 200 nM, about 700 pM to about 190 nM, about 700 pM to about 180 nM, about 700 pM to about 170 nM, about 700 pM to about 160 nM, about 700 pM to about 150 nM, about 700 pM to about 140 nM, about 700 pM to about 130 nM, about 700 pM to about 120 nM, about 700 pM to about 110 nM, about 700 pM to about 100 nM, about 700 pM to about 95 nM, about 700 pM to about 90 nM, about 700 pM to about 85 nM, about 700 pM to about 80 nM, about 700 pM to about 75 nM, about 700 pM to about 70 nM, about 700 pM to about 65 nM, about 700 pM to about 60 nM, about 700 pM to about 55 nM, about 700 pM to about 50 nM, about 700 pM to about 45 nM, about 700 pM to about 40 nM, about 700 pM to about 35 nM, about 700 pM to about 30 nM, about 700 pM to about 25 nM, about 700 pM to about 20 nM, about 700 pM to about 15 nM, about 700 pM to about 10 nM, about 700 pM to about 5 nM, about 700 pM to about 2 nM, about 700 pM to about 1 nM, about 700 pM to about 950 pM, about 700 pM to about 900 pM, about 700 pM to about 850 pM, about 700 pM to about 800 pM, about 700 pM to about 750 pM, about 800 pM to about 5 μM, about 800 pM to about 2 μM, about 800 pM to about 1 μM, about 800 pM to about 500 nM, about 800 pM to about 250 nM, about 800 pM to about 240 nM, about 800 pM to about 230 nM, about 800 pM to about 220 nM, about 800 pM to about 210 nM, about 800 pM to about 200 nM, about 800 pM to about 190 nM, about 800 pM to about 180 nM, about 800 pM to about 170 nM, about 800 pM to about 160 nM, about 800 pM to about 150 nM, about 800 pM to about 140 nM, about 800 pM to about 130 nM, about 800 pM to about 120 nM, about 800 pM to about 110 nM, about 800 pM to about 100 nM, about 800 pM to about 95 nM, about 800 pM to about 90 nM, about 800 pM to about 85 nM, about 800 pM to about 80 nM, about 800 pM to about 75 nM, about 800 pM to about 70 nM, about 800 pM to about 65 nM, about 800 pM to about 60 nM, about 800 pM to about 55 nM, about 800 pM to about 50 nM, about 800 pM to about 45 nM, about 800 pM to about 40 nM, about 800 pM to about 35 nM, about 800 pM to about 30 nM, about 800 pM to about 25 nM, about 800 pM to about 20 nM, about 800 pM to about 15 nM, about 800 pM to about 10 nM, about 800 pM to about 5 nM, about 800 pM to about 2 nM, about 800 pM to about 1 nM, about 800 pM to about 950 pM, about 800 pM to about 900 pM, about 800 pM to about 850 pM, about 900 pM to about 5 μM, about 900 pM to about 2 μM, about 900 pM to about 1 μM, about 900 pM to about 500 nM, about 900 pM to about 250 nM, about 900 pM to about 240 nM, about 900 pM to about 230 nM, about 900 pM to about 220 nM, about 900 pM to about 210 nM, about 900 pM to about 200 nM, about 900 pM to about 190 nM, about 900 pM to about 180 nM, about 900 pM to about 170 nM, about 900 pM to about 160 nM, about 900 pM to about 150 nM, about 900 pM to about 140 nM, about 900 pM to about 130 nM, about 900 pM to about 120 nM, about 900 pM to about 110 nM, about 900 pM to about 100 nM, about 900 pM to about 95 nM, about 900 pM to about 90 nM, about 900 pM to about 85 nM, about 900 pM to about 80 nM, about 900 pM to about 75 nM, about 900 pM to about 70 nM, about 900 pM to about 65 nM, about 900 pM to about 60 nM, about 900 pM to about 55 nM, about 900 pM to about 50 nM, about 900 pM to about 45 nM, about 900 pM to about 40 nM, about 900 pM to about 35 nM, about 900 pM to about 30 nM, about 900 pM to about 25 nM, about 900 pM to about 20 nM, about 900 pM to about 15 nM, about 900 pM to about 10 nM, about 900 pM to about 5 nM, about 900 pM to about 2 nM, about 900 pM to about 1 nM, about 900 pM to about 950 pM, about 1 nM to about 5 μM, about 1 nM to about 2 μM, about 1 nM to about 1 μM, about 1 nM to about 500 nM, about 1 nM to about 250 nM, about 1 nM to about 240 nM, about 1 nM to about 230 nM, about 1 nM to about 220 nM, about 1 nM to about 210 nM, about 1 nM to about 200 nM, about 1 nM to about 190 nM, about 1 nM to about 180 nM, about 1 nM to about 170 nM, about 1 nM to about 160 nM, about 1 nM to about 150 nM, about 1 nM to about 140 nM, about 1 nM to about 130 nM, about 1 nM to about 120 nM, about 1 nM to about 110 nM, about 1 nM to about 100 nM, about 1 nM to about 95 nM, about 1 nM to about 90 nM, about 1 nM to about 85 nM, about 1 nM to about 80 nM, about 1 nM to about 75 nM, about 1 nM to about 70 nM, about 1 nM to about 65 nM, about 1 nM to about 60 nM, about 1 nM to about 55 nM, about 1 nM to about 50 nM, about 1 nM to about 45 nM, about 1 nM to about 40 nM, about 1 nM to about 35 nM, about 1 nM to about 30 nM, about 1 nM to about 25 nM, about 1 nM to about 20 nM, about 1 nM to about 15 nM, about 1 nM to about 10 nM, about 1 nM to about 5 nM, about 2 nM to about 5 μM, about 2 nM to about 2 μM, about 2 nM to about 1 μM, about 2 nM to about 500 nM, about 2 nM to about 250 nM, about 2 nM to about 240 nM, about 2 nM to about 230 nM, about 2 nM to about 220 nM, about 2 nM to about 210 nM, about 2 nM to about 200 nM, about 2 nM to about 190 nM, about 2 nM to about 180 nM, about 2 nM to about 170 nM, about 2 nM to about 160 nM, about 2 nM to about 150 nM, about 2 nM to about 140 nM, about 2 nM to about 130 nM, about 2 nM to about 120 nM, about 2 nM to about 110 nM, about 2 nM to about 100 nM, about 2 nM to about 95 nM, about 2 nM to about 90 nM, about 2 nM to about 85 nM, about 2 nM to about 80 nM, about 2 nM to about 75 nM, about 2 nM to about 70 nM, about 2 nM to about 65 nM, about 2 nM to about 60 nM, about 2 nM to about 55 nM, about 2 nM to about 50 nM, about 2 nM to about 45 nM, about 2 nM to about 40 nM, about 2 nM to about 35 nM, about 2 nM to about 30 nM, about 2 nM to about 25 nM, about 2 nM to about 20 nM, about 2 nM to about 15 nM, about 2 nM to about 10 nM, about 2 nM to about 5 nM, about 4 nM to about 5 μM, about 4 nM to about 2 μM, about 4 nM to about 1 μM, about 4 nM to about 500 nM, about 4 nM to about 250 nM, about 4 nM to about 240 nM, about 4 nM to about 230 nM, about 4 nM to about 220 nM, about 4 nM to about 210 nM, about 4 nM to about 200 nM, about 4 nM to about 190 nM, about 4 nM to about 180 nM, about 4 nM to about 170 nM, about 4 nM to about 160 nM, about 4 nM to about 150 nM, about 4 nM to about 140 nM, about 4 nM to about 130 nM, about 4 nM to about 120 nM, about 4 nM to about 110 nM, about 4 nM to about 100 nM, about 4 nM to about 95 nM, about 4 nM to about 90 nM, about 4 nM to about 85 nM, about 4 nM to about 80 nM, about 4 nM to about 75 nM, about 4 nM to about 70 nM, about 4 nM to about 65 nM, about 4 nM to about 60 nM, about 4 nM to about 55 nM, about 4 nM to about 50 nM, about 4 nM to about 45 nM, about 4 nM to about 40 nM, about 4 nM to about 35 nM, about 4 nM to about 30 nM, about 4 nM to about 25 nM, about 4 nM to about 20 nM, about 4 nM to about 15 nM, about 4 nM to about 10 nM, about 4 nM to about 5 nM, about 5 nM to about 5 μM, about 5 nM to about 2 μM, about 5 nM to about 1 μM, about 5 nM to about 500 nM, about 5 nM to about 250 nM, about 5 nM to about 240 nM, about 5 nM to about 230 nM, about 5 nM to about 220 nM, about 5 nM to about 210 nM, about 5 nM to about 200 nM, about 5 nM to about 190 nM, about 5 nM to about 180 nM, about 5 nM to about 170 nM, about 5 nM to about 160 nM, about 5 nM to about 150 nM, about 5 nM to about 140 nM, about 5 nM to about 130 nM, about 5 nM to about 120 nM, about 5 nM to about 110 nM, about 5 nM to about 100 nM, about 5 nM to about 95 nM, about 5 nM to about 90 nM, about 5 nM to about 85 nM, about 5 nM to about 80 nM, about 5 nM to about 75 nM, about 5 nM to about 70 nM, about 5 nM to about 65 nM, about 5 nM to about 60 nM, about 5 nM to about 55 nM, about 5 nM to about 50 nM, about 5 nM to about 45 nM, about 5 nM to about 40 nM, about 5 nM to about 35 nM, about 5 nM to about 30 nM, about 5 nM to about 25 nM, about 5 nM to about 20 nM, about 5 nM to about 15 nM, about 5 nM to about 10 nM, about 10 nM to about 5 μM, about 10 nM to about 2 μM, about 10 nM to about 1 μM, about 10 nM to about 500 nM, about 10 nM to about 250 nM, about 10 nM to about 240 nM, about 10 nM to about 230 nM, about 10 nM to about 220 nM, about 10 nM to about 210 nM, about 10 nM to about 200 nM, about 10 nM to about 190 nM, about 10 nM to about 180 nM, about 10 nM to about 170 nM, about 10 nM to about 160 nM, about 10 nM to about 150 nM, about 10 nM to about 140 nM, about 10 nM to about 130 nM, about 10 nM to about 120 nM, about 10 nM to about 110 nM, about 10 nM to about 100 nM, about 10 nM to about 95 nM, about 10 nM to about 90 nM, about 10 nM to about 85 nM, about 10 nM to about 80 nM, about 10 nM to about 75 nM, about 10 nM to about 70 nM, about 10 nM to about 65 nM, about 10 nM to about 60 nM, about 10 nM to about 55 nM, about 10 nM to about 50 nM, about 10 nM to about 45 nM, about 10 nM to about 40 nM, about 10 nM to about 35 nM, about 10 nM to about 30 nM, about 10 nM to about 25 nM, about 10 nM to about 20 nM, about 10 nM to about 15 nM, about 15 nM to about 5 μM, about 15 nM to about 2 μM, about 15 nM to about 1 μM, about 15 nM to about 500 nM, about 15 nM to about 250 nM, about 15 nM to about 240 nM, about 15 nM to about 230 nM, about 15 nM to about 220 nM, about 15 nM to about 210 nM, about 15 nM to about 200 nM, about 15 nM to about 190 nM, about 15 nM to about 180 nM, about 15 nM to about 170 nM, about 15 nM to about 160 nM, about 15 nM to about 150 nM, about 15 nM to about 140 nM, about 15 nM to about 130 nM, about 15 nM to about 120 nM, about 15 nM to about 110 nM, about 15 nM to about 100 nM, about 15 nM to about 95 nM, about 15 nM to about 90 nM, about 15 nM to about 85 nM, about 15 nM to about 80 nM, about 15 nM to about 75 nM, about 15 nM to about 70 nM, about 15 nM to about 65 nM, about 15 nM to about 60 nM, about 15 nM to about 55 nM, about 15 nM to about 50 nM, about 15 nM to about 45 nM, about 15 nM to about 40 nM, about 15 nM to about 35 nM, about 15 nM to about 30 nM, about 15 nM to about 25 nM, about 15 nM to about 20 nM, about 20 nM to about 5 μM, about 20 nM to about 2 μM, about 20 nM to about 1 μM, about 20 nM to about 500 nM, about 20 nM to about 250 nM, about 20 nM to about 240 nM, about 20 nM to about 230 nM, about 20 nM to about 220 nM, about 20 nM to about 210 nM, about 20 nM to about 200 nM, about 20 nM to about 190 nM, about 20 nM to about 180 nM, about 20 nM to about 170 nM, about 20 nM to about 160 nM, about 20 nM to about 150 nM, about 20 nM to about 140 nM, about 20 nM to about 130 nM, about 20 nM to about 120 nM, about 20 nM to about 110 nM, about 20 nM to about 100 nM, about 20 nM to about 95 nM, about 20 nM to about 90 nM, about 20 nM to about 85 nM, about 20 nM to about 80 nM, about 20 nM to about 75 nM, about 20 nM to about 70 nM, about 20 nM to about 65 nM, about 20 nM to about 60 nM, about 20 nM to about 55 nM, about 20 nM to about 50 nM, about 20 nM to about 45 nM, about 20 nM to about 40 nM, about 20 nM to about 35 nM, about 20 nM to about 30 nM, about 20 nM to about 25 nM, about 25 nM to about 5 μM, about 25 nM to about 2 μM, about 25 nM to about 1 μM, about 25 nM to about 500 nM, about 25 nM to about 250 nM, about 25 nM to about 240 nM, about 25 nM to about 230 nM, about 25 nM to about 220 nM, about 25 nM to about 210 nM, about 25 nM to about 200 nM, about 25 nM to about 190 nM, about 25 nM to about 180 nM, about 25 nM to about 170 nM, about 25 nM to about 160 nM, about 25 nM to about 150 nM, about 25 nM to about 140 nM, about 25 nM to about 130 nM, about 25 nM to about 120 nM, about 25 nM to about 110 nM, about 25 nM to about 100 nM, about 25 nM to about 95 nM, about 25 nM to about 90 nM, about 25 nM to about 85 nM, about 25 nM to about 80 nM, about 25 nM to about 75 nM, about 25 nM to about 70 nM, about 25 nM to about 65 nM, about 25 nM to about 60 nM, about 25 nM to about 55 nM, about 25 nM to about 50 nM, about 25 nM to about 45 nM, about 25 nM to about 40 nM, about 25 nM to about 35 nM, about 25 nM to about 30 nM, about 30 nM to about 5 μM, about 30 nM to about 2 μM, about 30 nM to about 1 μM, about 30 nM to about 500 nM, about 30 nM to about 250 nM, about 30 nM to about 240 nM, about 30 nM to about 230 nM, about 30 nM to about 220 nM, about 30 nM to about 210 nM, about 30 nM to about 200 nM, about 30 nM to about 190 nM, about 30 nM to about 180 nM, about 30 nM to about 170 nM, about 30 nM to about 160 nM, about 30 nM to about 150 nM, about 30 nM to about 140 nM, about 30 nM to about 130 nM, about 30 nM to about 120 nM, about 30 nM to about 110 nM, about 30 nM to about 100 nM, about 30 nM to about 95 nM, about 30 nM to about 90 nM, about 30 nM to about 85 nM, about 30 nM to about 80 nM, about 30 nM to about 75 nM, about 30 nM to about 70 nM, about 30 nM to about 65 nM, about 30 nM to about 60 nM, about 30 nM to about 55 nM, about 30 nM to about 50 nM, about 30 nM to about 45 nM, about 30 nM to about 40 nM, about 30 nM to about 35 nM, about 40 nM to about 5 μM, about 40 nM to about 2 μM, about 40 nM to about 1 μM, about 40 nM to about 500 nM, about 40 nM to about 250 nM, about 40 nM to about 240 nM, about 40 nM to about 230 nM, about 40 nM to about 220 nM, about 40 nM to about 210 nM, about 40 nM to about 200 nM, about 40 nM to about 190 nM, about 40 nM to about 180 nM, about 40 nM to about 170 nM, about 40 nM to about 160 nM, about 40 nM to about 150 nM, about 40 nM to about 140 nM, about 40 nM to about 130 nM, about 40 nM to about 120 nM, about 40 nM to about 110 nM, about 40 nM to about 100 nM, about 40 nM to about 95 nM, about 40 nM to about 90 nM, about 40 nM to about 85 nM, about 40 nM to about 80 nM, about 40 nM to about 75 nM, about 40 nM to about 70 nM, about 40 nM to about 65 nM, about 40 nM to about 60 nM, about 40 nM to about 55 nM, about 40 nM to about 50 nM, about 40 nM to about 45 nM, about 50 nM to about 5 μM, about 50 nM to about 2 μM, about 50 nM to about 1 μM, about 50 nM to about 500 nM, about 50 nM to about 250 nM, about 50 nM to about 240 nM, about 50 nM to about 230 nM, about 50 nM to about 220 nM, about 50 nM to about 210 nM, about 50 nM to about 200 nM, about 50 nM to about 190 nM, about 50 nM to about 180 nM, about 50 nM to about 170 nM, about 50 nM to about 160 nM, about 50 nM to about 150 nM, about 50 nM to about 140 nM, about 50 nM to about 130 nM, about 50 nM to about 120 nM, about 50 nM to about 110 nM, about 50 nM to about 100 nM, about 50 nM to about 95 nM, about 50 nM to about 90 nM, about 50 nM to about 85 nM, about 50 nM to about 80 nM, about 50 nM to about 75 nM, about 50 nM to about 70 nM, about 50 nM to about 65 nM, about 50 nM to about 60 nM, about 50 nM to about 55 nM, about 60 nM to about 5 μM, about 60 nM to about 2 μM, about 60 nM to about 1 μM, about 60 nM to about 500 nM, about 60 nM to about 250 nM, about 60 nM to about 240 nM, about 60 nM to about 230 nM, about 60 nM to about 220 nM, about 60 nM to about 210 nM, about 60 nM to about 200 nM, about 60 nM to about 190 nM, about 60 nM to about 180 nM, about 60 nM to about 170 nM, about 60 nM to about 160 nM, about 60 nM to about 150 nM, about 60 nM to about 140 nM, about 60 nM to about 130 nM, about 60 nM to about 120 nM, about 60 nM to about 110 nM, about 60 nM to about 100 nM, about 60 nM to about 95 nM, about 60 nM to about 90 nM, about 60 nM to about 85 nM, about 60 nM to about 80 nM, about 60 nM to about 75 nM, about 60 nM to about 70 nM, about 60 nM to about 65 nM, about 70 nM to about 5 μM, about 70 nM to about 2 μM, about 70 nM to about 1 μM, about 70 nM to about 500 nM, about 70 nM to about 250 nM, about 70 nM to about 240 nM, about 70 nM to about 230 nM, about 70 nM to about 220 nM, about 70 nM to about 210 nM, about 70 nM to about 200 nM, about 70 nM to about 190 nM, about 70 nM to about 180 nM, about 70 nM to about 170 nM, about 70 nM to about 160 nM, about 70 nM to about 150 nM, about 70 nM to about 140 nM, about 70 nM to about 130 nM, about 70 nM to about 120 nM, about 70 nM to about 110 nM, about 70 nM to about 100 nM, about 70 nM to about 95 nM, about 70 nM to about 90 nM, about 70 nM to about 85 nM, about 70 nM to about 80 nM, about 70 nM to about 75 nM, about 80 nM to about 5 μM, about 80 nM to about 2 μM, about 80 nM to about 1 μM, about 80 nM to about 500 nM, about 80 nM to about 250 nM, about 80 nM to about 240 nM, about 80 nM to about 230 nM, about 80 nM to about 220 nM, about 80 nM to about 210 nM, about 80 nM to about 200 nM, about 80 nM to about 190 nM, about 80 nM to about 180 nM, about 80 nM to about 170 nM, about 80 nM to about 160 nM, about 80 nM to about 150 nM, about 80 nM to about 140 nM, about 80 nM to about 130 nM, about 80 nM to about 120 nM, about 80 nM to about 110 nM, about 80 nM to about 100 nM, about 80 nM to about 95 nM, about 80 nM to about 90 nM, about 80 nM to about 85 nM, about 90 nM to about 5 μM, about 90 nM to about 2 μM, about 90 mM to about 1 μM, about 90 nM to about 500 nM, about 90 nM to about 250 nM, about 90 nM to about 240 nM, about 90 nM to about 230 nM, about 90 nM to about 220 nM, about 90 nM to about 210 nM, about 90 nM to about 200 nM, about 90 nM to about 190 nM, about 90 nM to about 180 nM, about 90 nM to about 170 nM, about 90 nM to about 160 nM, about 90 nM to about 150 nM, about 90 nM to about 140 nM, about 90 nM to about 130 nM, about 90 nM to about 120 nM, about 90 nM to about 110 nM, about 90 nM to about 100 nM, about 90 nM to about 95 nM, about 100 nM to about 5 μM, about 100 nM to about 2 μM, about 100 nM to about 1 μM, about 100 nM to about 500 nM, about 100 nM to about 250 nM, about 100 nM to about 240 nM, about 100 nM to about 230 nM, about 100 nM to about 220 nM, about 100 nM to about 210 nM, about 100 nM to about 200 nM, about 100 nM to about 190 nM, about 100 nM to about 180 nM, about 100 nM to about 170 nM, about 100 nM to about 160 nM, about 100 nM to about 150 nM, about 100 nM to about 140 nM, about 100 nM to about 130 nM, about 100 nM to about 120 nM, about 100 nM to about 110 nM, about 110 nM to about 5 μM, about 110 nM to about 2 μM, about 110 nM to about 1 μM, about 110 nM to about 500 nM, about 110 nM to about 250 nM, about 110 nM to about 240 nM, about 110 nM to about 230 nM, about 110 nM to about 220 nM, about 110 nM to about 210 nM, about 110 nM to about 200 nM, about 110 nM to about 190 nM, about 110 nM to about 180 nM, about 110 nM to about 170 nM, about 110 nM to about 160 nM, about 110 nM to about 150 nM, about 110 nM to about 140 nM, about 110 nM to about 130 nM, about 110 nM to about 120 nM, about 120 nM to about 5 μM, about 120 nM to about 2 μM, about 120 nM to about 1 μM, about 120 nM to about 500 nM, about 120 nM to about 250 nM, about 120 nM to about 240 nM, about 120 nM to about 230 nM, about 120 nM to about 220 nM, about 120 nM to about 210 nM, about 120 nM to about 200 nM, about 120 nM to about 190 nM, about 120 nM to about 180 nM, about 120 nM to about 170 nM, about 120 nM to about 160 nM, about 120 nM to about 150 nM, about 120 nM to about 140 nM, about 120 nM to about 130 nM, about 130 nM to about 5 μM, about 130 nM to about 2 μM, about 130 nM to about 1 μM, about 130 nM to about 500 nM, about 130 nM to about 250 nM, about 130 nM to about 240 nM, about 130 nM to about 230 nM, about 130 nM to about 220 nM, about 130 nM to about 210 nM, about 130 nM to about 200 nM, about 130 nM to about 190 nM, about 130 nM to about 180 nM, about 130 nM to about 170 nM, about 130 nM to about 160 nM, about 130 nM to about 150 nM, about 130 nM to about 140 nM, about 140 nM to about 5 μM, about 140 nM to about 2 μM, about 140 nM to about 1 μM, about 140 nM to about 500 nM, about 140 nM to about 250 nM, about 140 nM to about 240 nM, about 140 nM to about 230 nM, about 140 nM to about 220 nM, about 140 nM to about 210 nM, about 140 nM to about 200 nM, about 140 nM to about 190 nM, about 140 nM to about 180 nM, about 140 nM to about 170 nM, about 140 nM to about 160 nM, about 140 nM to about 150 nM, about 150 nM to about 5 μM, about 150 nM to about 2 μM, about 150 nM to about 1 μM, about 150 nM to about 500 nM, about 150 nM to about 250 nM, about 150 nM to about 240 nM, about 150 nM to about 230 nM, about 150 nM to about 220 nM, about 150 nM to about 210 nM, about 150 nM to about 200 nM, about 150 nM to about 190 nM, about 150 nM to about 180 nM, about 150 nM to about 170 nM, about 150 nM to about 160 nM, about 160 nM to about 5 μM, about 160 nM to about 2 μM, about 160 nM to about 1 μM, about 160 nM to about 500 nM, about 160 nM to about 250 nM, about 160 nM to about 240 nM, about 160 nM to about 230 nM, about 160 nM to about 220 nM, about 160 nM to about 210 nM, about 160 nM to about 200 nM, about 160 nM to about 190 nM, about 160 nM to about 180 nM, about 160 nM to about 170 nM, about 170 nM to about 5 μM, about 170 nM to about 2 μM, about 170 nM to about 1 μM, about 170 nM to about 500 nM, about 170 nM to about 250 nM, about 170 nM to about 240 nM, about 170 nM to about 230 nM, about 170 nM to about 220 nM, about 170 nM to about 210 nM, about 170 nM to about 200 nM, about 170 nM to about 190 nM, about 170 nM to about 180 nM, about 180 nM to about 5 μM, about 180 nM to about 2 μM, about 180 nM to about 1 μM, about 180 nM to about 500 nM, about 180 nM to about 250 nM, about 180 nM to about 240 nM, about 180 nM to about 230 nM, about 180 nM to about 220 nM, about 180 nM to about 210 nM, about 180 nM to about 200 nM, about 180 nM to about 190 nM, about 190 nM to about 5 μM, about 190 nM to about 2 μM, about 190 nM to about 1 μM, about 190 nM to about 500 nM, about 190 nM to about 250 nM, about 190 nM to about 240 nM, about 190 nM to about 230 nM, about 190 nM to about 220 nM, about 190 nM to about 210 nM, about 190 nM to about 200 nM, about 200 nM to about 5 μM, about 200 nM to about 2 μM, about 200 nM to about 1 μM, about 200 nM to about 500 nM, about 200 nM to about 250 nM, about 200 nM to about 240 nM, about 200 nM to about 230 nM, about 200 nM to about 220 nM, about 200 nM to about 210 nM, about 210 nM to about 5 μM, about 210 nM to about 2 μM, about 210 nM to about 1 μM, about 210 nM to about 500 nM, about 210 nM to about 250 nM, about 210 nM to about 240 nM, about 210 nM to about 230 nM, about 210 nM to about 220 nM, about 220 nM to about 5 μM, about 220 nM to about 2 μM, about 220 nM to about 1 μM, about 220 nM to about 500 nM, about 220 nM to about 250 nM, about 220 nM to about 240 nM, about 220 nM to about 230 nM, about 230 nM to about 5 μM, about 230 nM to about 2 μM, about 230 nM to about 1 μM, about 230 nM to about 500 nM, about 230 nM to about 250 nM, about 230 nM to about 240 nM, about 240 nM to about 5 μM, about 240 nM to about 2 μM, about 240 nM to about 1 μM, about 240 nM to about 500 nM, about 240 nM to about 250 nM, about 250 nM to about 5 μM, about 250 nM to about 2 μM, about 250 nM to about 1 μM, about 250 nM to about 500 nM, about 500 nM to about 5 μM, about 500 nM to about 2 μM, about 500 nM to about 1 μM, about 1 μM to about 5 μM, about 1 to about 2 μM, or about 2 μM to about 5 μM).

In some embodiments of any of the ABPCs described herein, the $K_D$ of the first antigen-binding domain (and optionally, the second antigen-binding domain, if present) at a pH of about 4.0 to about 6.5 (e.g., any of the subranges of this range described herein) can be greater than 1 nM (e.g., between about 1 nM to about 1 mM, about 1 nM to about 900 μM, about 1 nM to about 800 μM, about 1 nM to about 700 μM, about 1 nM to about 600 μM, about 1 nM to about 500 μM, about 1 nM to about 400 μM, about 1 nM to about 300 μM, about 1 nM to about 200 μM, about 1 nM to about 100 μM, about 1 nM to about 90 μM, about 1 nM to about 80 μM, about 1 nM to about 70 μM, about 1 nM to about 60 μM, about 1 nM to about 50 μM, about 1 nM to about 40 μM, about 1 nM to about 30 μM, about 1 nM to about 20 μM, about 1 nM to about 10 μM, about 1 nM to about 5 μM, about 1 nM to about 4 μM, about 1 nM to about 2 μM, about 1 nM to about 1 μM, about 1 nM to about 900 nM, about 1 nM to about 800 nM, about 1 nM to about 700 nM, about 1 nM to about 600 nM, about 1 nM to about 500 nM, about 1 nM to about 400 nM, about 1 nM to about 300 nM, about 1 nM to about 200 nM, about 1 nM to about 100 nM, about 1 nM to about 90 nM, about 1 nM to about 80 nM, about 1 nM to about 70 nM, about 1 nM to about 60 nM, about 1 nM to about 50 nM, about 1 nM to about 40 nM, about 1 nM to about 30 nM, about 2 nM to about 1 mM, about 2 nM to about 900 μM, about 2 nM to about 800 μM, about 2 nM to about 700 μM, about 2 nM to about 600 μM, about 2 nM to about 500 μM, about 2 nM to about 400 μM, about 2 nM to about 300 μM, about 2 nM to about 200 μM, about 2 nM to about 100 μM, about 2 nM to about 90 μM, about 2 nM to about 80 μM, about 2 nM to about 70 μM, about 2 nM to about 60 μM, about 2 nM to about 50 μM, about 2 nM to about 40 μM, about 2 nM to about 30 μM, about 2 nM to about 20 μM, about 2 nM to about 10 μM, about 2 nM to about 5 μM, about 2 nM to about 4 μM, about 2 nM to about 2 μM, about 2 nM to about 1 μM, about 2 nM to about 900 nM, about 2 nM to about 800 nM, about 2 nM to about 700 nM, about 2 nM to about 600 nM, about 2 nM to about 500 nM, about 2 nM to about 400 nM, about 2 nM to about 300 nM, about 2 nM to about 200 nM, about 2 nM to about 100 nM, about 2 nM to about 90 nM, about 2 nM to about 80 nM, about 2 nM to about 70 nM, about 2 nM to about 60 nM, about 2 nM to about 50 nM, about 2 nM to about 40 nM, about 2 nM to about 30 nM, about 5 nM to about 1 mM, about 5 nM to about 900 μM, about 5 nM to about 800 μM, about 5 nM to about 700 μM, about 5 nM to about 600 μM, about 5 nM to about 500 μM, about 5 nM to about 400 μM, about 5 nM to about 300 μM, about 5 nM to about 200 μM, about 5 nM to about 100 μM, about 5 nM to about 90 μM, about 5 nM to about 80 μM, about 5 nM to about 70 μM, about 5 nM to about 60 μM, about 5 nM to about 50 μM, about 5 nM to about 40 μM, about 5 nM to about 30 μM, about 5 nM to about 20 μM, about 5 nM to about 10 μM, about 5 nM to about 5 μM, about 5 nM to about 4 μM, about 5 nM to about 2 μM, about 5 nM to about 1 μM, about 5 nM to about 900 nM, about 5 nM to about 800 nM, about 5 nM to about 700 nM, about 5 nM to about 600 nM, about 5 nM to about 500 nM, about 5 nM to about 400 nM, about 5 nM to about 300 nM, about 5 nM to about 200 nM, about 5 nM to about 100 nM, about 5 nM to about 90 nM, about 5 nM to about 80 nM, about 5 nM to about 70 nM, about 5 nM to about 60 nM, about 5 nM to about 50 nM, about 5 nM to about 40 nM, about 5 nM to about 30 nM, about 10 nM to about 1 mM, about 10 nM to about 900 μM, about 10 nM to about 800 μM, about 10 nM to about 700 μM, about 10 nM to about 600 μM, about 10 nM to about 500 μM, about 10 nM to about 400 μM, about 10 nM to about 300 μM, about 10 nM to about 200 μM, about 10 nM to about 100 μM, about 10 nM to about 90 μM, about 10 nM to about 80 μM, about 10 nM to about 70 μM, about 10 nM to about 60 μM, about 10 nM to about 50 μM, about 10 nM to about 40 μM, about 10 nM to about 30 μM, about 10 nM to about 20 μM, about 10 nM to about 10 μM, about 10 nM to about 5 μM, about 10 nM to about 4 μM, about 10 nM to about 2 μM, about 10 nM to about 1 μM, about 10 nM to about 900 nM, about 10 nM to about 800 nM, about 10 nM to about 700 nM, about 10 nM to about 600 nM, about 10 nM to about 500 nM, about 10 nM to about 400 nM, about 10 nM to about 300 nM, about 10 nM to about 200 nM, about 10 nM to about 100 nM, about 10 nM to about 90 nM, about 10 nM to about 80 nM, about 10 nM to about 70 nM, about 10 nM to about 60 nM, about 10 nM to about 50 nM, about 10 nM to about 40 nM, about 10 nM to about 30 nM, about 20 nM to about 1 mM, about 20 nM to about 900 μM, about 20 nM to about 800 μM, about 20 nM to about 700 μM, about 20 nM to about 600 μM, about 20 nM to about 500 μM, about 20 nM to about 400 μM, about 20 nM to about 300 μM, about 20 nM to about 200 μM, about 20 nM to about 100 μM, about 20 nM to about 90 μM, about 20 nM to about 80 μM, about 20 nM to about 70 μM, about 20 nM to about 60 μM, about 20 nM to about 50 μM, about 20 nM to about 40 μM, about 20 nM to about 30 μM, about 20 nM to about 20 μM, about 20 nM to about 10 μM, about 20 nM to about 5 μM, about 20 nM to about 4 μM, about 20 nM to about 2 μM, about 20 nM to about 1 μM, about 20 nM to about 900 nM, about 20 nM to about 800 nM, about 20 nM to about 700 nM, about 20 nM to about 600 nM, about 20 nM to about 500 nM, about 20 nM to about 400 nM, about 20 nM to about 300 nM, about 20 nM to about 200 nM, about 20 nM to about 100 nM, about 20 nM to about 90 nM, about 20 nM to about 80 nM, about 20 nM to about 70 nM, about 20 nM to about 60 nM, about 20 nM to about 50 nM, about 20 nM to about 40 nM, about 20 nM to about 30 nM; about 1 μM to about 1 mM, about 1 μM to about 900 μM, about 1 μM to about 800 μM, about 1 μM to about 700 μM, about 1 μM to about 600 μM, about 1 μM to about 500 μM, about 1 μM to about 400 μM, about 1 μM to about 300 μM, about 1 μM to about 200 μM, about 1 μM to about 100 μM, about 1 μM to about 90 μM, about 1 μM to about 80 μM, about 1 μM to about 70 μM, about 1 μM to about 60 μM, about 1 μM to about 50 μM, about 1 μM to about 40 μM, about 1 μM to about 30 μM, about 1 μM to about 20 μM, about 1 μM to about 10 μM, about 1 μM to about 5 μM, about 1 μM to about 4 μM, about 1 μM to about 3 μM, about 1 μM to about 2 μM, about 2 μM to about 1 mM, about 2 μM to about 900 μM, about 2 μM to about 800 μM, about 2 μM to about 700 μM, about 2 μM to about 600 μM, about 2 μM to about 500 μM, about 2 μM to about 400 μM, about 2 μM to about 300 μM, about 2 μM to about 200 μM, about 2 μM to about 100 μM, about 2 μM to about 90 μM, about 2 μM to about 80 μM, about 2 μM to about 70 μM, about 2 μM to about 60 μM, about 2 μM to about 50 μM, about 2 μM to about 40 μM, about 2 μM to about 30 μM, about 2 μM to about 20 μM, about 2 μM to about 10 μM, about 2 μM to about 5 μM, about 2 μM to about 4 μM, about 2 μM to about 3 μM, about 5 μM to about 1 mM, about 5 μM to about 900 μM, about 5 μM to about 800 μM, about 5 μM to about 700 μM, about 5 μM to about 600 μM, about 5 μM to about 500 μM, about 5 μM to about 400 μM, about 5 μM to about 300 μM, about 5 μM to about 200 μM, about 5 μM to about 100 μM, about 5 μM to about 90 μM, about 5 μM to about 80 μM, about 5 μM to about 70 μM, about 5 μM to about 60 μM, about 5 μM to about 50 μM, about 5 μM to about 40 μM, about 5 μM to about 30 μM, about 5 μM to about 20 μM, about 5 μM to about 10 μM, about 10 μM to about 1 mM, about 10 μM to about 900 μM, about 10 μM to about 800 μM, about 10 μM to about 700 μM, about 10 μM to about 600 μM, about 10 μM to about 500 μM, about 10 μM to about 400 μM, about 10 μM to about 300 μM, about 10 μM to about 200 μM, about 10 μM to about 100 μM, about 10 μM to about 90 μM, about 10 μM to about 80 μM, about 10 μM to about 70 μM, about 10 μM to about 60 μM, about 10 μM to about 50 μM, about 10 μM to about 40 μM, about 10 μM to about 30 μM, about 10 μM to about 20 μM, about 20 μM to about 1 mM, about 20 μM to about 900 μM, about 20 μM to about 800 μM, about 20 μM to about 700 μM, about 20 μM to about 600 μM, about 20 μM to about 500 μM, about 20 μM to about 400 μM, about 20 μM to about 300 μM, about 20 μM to about 200 μM, about 20 μM to about 100 μM, about 20 μM to about 90 μM, about 20 μM to about 80 μM, about 20 μM to about 70 μM, about 20 μM to about 60 μM, about 20 μM to about 50 μM, about 20 μM to about 40 μM, about 20 μM to about 30 μM, about 30 μM to about 1 mM, about 30 μM to about 900 μM, about 30 μM to about 800 μM, about 30 μM to about 700 μM, about 30 μM to about 600 μM, about 30 μM to about 500 μM, about 30 μM to about 400 μM, about 30 μM to about 300 μM, about 30 μM to about 200 μM, about 30 μM to about 100 μM, about 30 μM to about 90 μM, about 30 μM to about 80 μM, about 30 μM to about 70 μM, about 30 μM to about 60 μM, about 30 μM to about 50 μM, about 30 μM to about 40 μM, about 40 μM to about 1 mM, about 40 μM to about 900 μM, about 40 μM to about 800 μM, about 40 μM to about 700 μM, about 40 μM to about 600 μM, about 40 μM to about 500 μM, about 40 μM to about 400 μM, about 40 μM to about 300 μM, about 40 μM to about 200 μM, about 40 μM to about 100 μM, about 40 μM to about 90 μM, about 40 μM to about 80 μM, about 40 μM to about 70 μM, about 40 μM to about 60 μM, about 40 μM to about 50 μM, about 50 μM to about 1 mM, about 50 μM to about 900 μM, about 50 μM to about 800 μM, about 50 μM to about 700 μM, about 50 μM to about 600 μM, about 50 μM to about 500 μM, about 50 μM to about 400 μM, about 50 μM to about 300 μM, about 50 μM to about 200 μM, about 50 μM to about 100 μM, about 50 μM to about 90 μM, about 50 μM to about 80 μM, about 50 μM to about 70 μM, about 50 μM to about 60 μM, about 60 μM to about 1 mM, about 60 μM to about 900 μM, about 60 μM to about 800 μM, about 60 μM to about 700 μM, about 60 μM to about 600 μM, about 60 μM to about 500 μM, about 60 μM to about 400 μM, about 60 μM to about 300 μM, about 60 μM to about 200 μM, about 60 μM to about 100 μM, about 60 μM to about 90 μM, about 60 μM to about 80 μM, about 60 μM to about 70 μM, about 70 μM to about 1 mM, about 70 μM to about 900 μM, about 70 μM to about 800 μM, about 70 μM to about 700 μM, about 70 μM to about 600 μM, about 70 μM to about 500 μM, about 70 μM to about 400 μM, about 70 μM to about 300 μM, about 70 μM to about 200 μM, about 70 μM to about 100 μM, about 70 μM to about 90 μM, about 70 μM to about 80 μM, about 80 μM to about 1 mM, about 80 μM to about 900 μM, about 80 μM to about 800 μM, about 80 μM to about 700 μM, about 80 μM to about 600 μM, about 80 μM to about 500 μM, about 80 μM to about 400 μM, about 80 μM to about 300 μM, about 80 μM to about 200 μM, about 80 μM to about 100 μM, about 80 μM to about 90 μM, about 90 μM to about 1 mM, about 90 μM to about 900 μM, about 90 μM to about 800 μM, about 90 μM to about 700 μM, about 90 μM to about 600 μM, about 90 μM to about 500 μM, about 90 μM to about 400 μM, about 90 μM to about 300 μM, about 90 μM to about 200 μM, about 90 μM to about 100 μM, about 100 μM to about 1 mM, about 100 μM to about 900 μM, about 100 μM to about 800 μM, about 100 μM to about 700 μM, about 100 μM to about 600 μM, about 100 μM to about 500 μM, about 100 μM to about 400 μM, about 100 μM to about 300 μM, about 100 μM to about 200 μM, about 200 μM to about 1 mM, about 200 μM to about 900 μM, about 200 μM to about 800 μM, about 200 μM to about 700 μM, about 200 μM to about 600 μM, about 200 μM to about 500 μM, about 200 μM to about 400 μM, about 200 μM to about 300 μM, about 300 μM to about 1 mM, about 300 μM to about 900 μM, about 300 μM to about 800 μM, about 300 μM to about 700 μM, about 300 μM to about 600 μM, about 300 μM to about 500 μM, about 300 μM to about 400 μM, about 400 μM to about 1 mM, about 400 μM to about 900 μM, about 400 μM to about 800 μM, about 400 μM to about 700 μM, about 400 μM to about 600 μM, about 400 μM to about 500 μM, about 500 μM to about 1 mM, about 500 μM to about 900 μM, about 500 μM to about 800 μM, about 500 μM to about 700 μM, about 500 μM to about 600 μM, about 600 μM to about 1 mM, about 600 μM to about 900 μM, about 600 μM to about 800 μM, about 600 μM to about 700 μM, about 700 μM to about 1 mM, about 700 μM to about 900 μM, about 700 μM to about 800 μM, about 800 μM to about 1 mM, about 800 μM to about 900 μM, or about 900 μM to about 1 mM).

A variety of different methods known in the art can be used to determine the $K_D$ values of any of the antigen-binding protein constructs described herein (e.g., an electrophoretic mobility shift assay, a filter binding assay, surface plasmon resonance, a biomolecular binding kinetics assay, in vitro binding assay on antigen-expressing cells, etc.).

In some examples of any of the ABPCs described herein, the half-life of the ABPC in vivo is decreased (e.g., a detectable decrease) (e.g., at least a 1% decrease, at least a 5% decrease, at least a 10% decrease, at least a 15% decrease, at least a 20% decrease, at least a 25% decrease, at least a 30% decrease, at least a 35% decrease, at least a 40% decrease, at least a 45% decrease, at least a 50% decrease, at least a 55% decrease, at least a 60% decrease, at least a 65% decrease, at least a 70% decrease, at least a 75% decrease, at least a 80% decrease, at least a 85% decrease, at least a 90% decrease, at least a 95% decrease, or at least a 99% decrease, or about a 1% decrease to about a 99% decrease, about a 1% decrease to about a 95% decrease, about a 1% decrease to about a 90% decrease, about a 1% decrease to about a 85% decrease, about a 1% decrease to about a 80% decrease, about a 1% decrease to about a 75% decrease, about a 1% decrease to about a 70% decrease, about a 1% decrease to about a 65% decrease, about a 1% decrease to about a 60% decrease, about a 1% decrease to about a 55% decrease, about a 1% decrease to about a 50% decrease, about a 1% decrease to about a 45% decrease, about a 1% decrease to about a 40% decrease, about a 1% decrease to about a 35% decrease, about a 1% decrease to about a 30% decrease, about a 1% decrease to about a 25% decrease, about a 1% decrease to about a 20% decrease, about a 1% decrease to about a 15% decrease, about a 1% decrease to about a 10% decrease, about a 1% decrease to about a 5% decrease, about a 5% decrease to about a 99% decrease, about a 5% decrease to about a 95% decrease, about a 5% decrease to about a 90% decrease, about a 5% decrease to about a 85% decrease, about a 5% decrease to about a 80% decrease, about a 5% decrease to about a 75% decrease, about a 5% decrease to about a 70% decrease, about a 5% decrease to about a 65% decrease, about a 5% decrease to about a 60% decrease, about a 5% decrease to about a 55% decrease, about a 5% decrease to about a 50% decrease, about a 5% decrease to about a 45% decrease, about a 5% decrease to about a 40% decrease, about a 5% decrease to about a 35% decrease, about a 5% decrease to about a 30% decrease, about a 5% decrease to about a 25% decrease, about a 5% decrease to about a 20% decrease, about a 5% decrease to about a 15% decrease, about a 5% decrease to about a 10% decrease, about a 10% decrease to about a 99% decrease, about a 10% decrease to about a 95% decrease, about a 10% decrease to about a 90% decrease, about a 10% decrease to about a 85% decrease, about a 10% decrease to about a 80% decrease, about a 10% decrease to about a 75% decrease, about a 10% decrease to about a 70% decrease, about a 10% decrease to about a 65% decrease, about a 10% decrease to about a 60% decrease, about a 10% decrease to about a 55% decrease, about a 10% decrease to about a 50% decrease, about a 10% decrease to about a 45% decrease, about a 10% decrease to about a 40% decrease, about a 10% decrease to about a 35% decrease, about a 10% decrease to about a 30% decrease, about a 10% decrease to about a 25% decrease, about a 10% decrease to about a 20% decrease, about a 10% decrease to about a 15% decrease, about a 15% decrease to about a 99% decrease, about a 15% decrease to about a 95% decrease, about a 15% decrease to about a 90% decrease, about a 15% decrease to about a 85% decrease, about a 15% decrease to about a 80% decrease, about a 15% decrease to about a 75% decrease, about a 15% decrease to about a 70% decrease, about a 15% decrease to about a 65% decrease, about a 15% decrease to about a 60% decrease, about a 15% decrease to about a 55% decrease, about a 15% decrease to about a 50% decrease, about a 15% decrease to about a 45% decrease, about a 15% decrease to about a 40% decrease, about a 15% decrease to about a 35% decrease, about a 15% decrease to about a 30% decrease, about a 15% decrease to about a 25% decrease, about a 15% decrease to about a 20% decrease, about a 20% decrease to about a 99% decrease, about a 20% decrease to about a 95% decrease, about a 20% decrease to about a 90% decrease, about a 20% decrease to about a 85% decrease, about a 20% decrease to about a 80% decrease, about a 20% decrease to about a 75% decrease, about a 20% decrease to about a 70% decrease, about a 20% decrease to about a 65% decrease, about a 20% decrease to about a 60% decrease, about a 20% decrease to about a 55% decrease, about a 20% decrease to about a 50% decrease, about a 20% decrease to about a 45% decrease, about a 20% decrease to about a 40% decrease, about a 20% decrease to about a 35% decrease, about a 20% decrease to about a 30% decrease, about a 20% decrease to about a 25% decrease, about a 25% decrease to about a 99% decrease, about a 25% decrease to about a 95% decrease, about a 25% decrease to about a 90% decrease, about a 25% decrease to about a 85% decrease, about a 25% decrease to about a 80% decrease, about a 25% decrease to about a 75% decrease, about a 25% decrease to about a 70% decrease, about a 25% decrease to about a 65% decrease, about a 25% decrease to about a 60% decrease, about a 25% decrease to about a 55% decrease, about a 25% decrease to about a 50% decrease, about a 25% decrease to about a 45% decrease, about a 25% decrease to about a 40% decrease, about a 25% decrease to about a 35% decrease, about a 25% decrease to about a 30% decrease, about a 30% decrease to about a 99% decrease, about a 30% decrease to about a 95% decrease, about a 30% decrease to about a 90% decrease, about a 30% decrease to about a 85% decrease, about a 30% decrease to about a 80% decrease, about a 30% decrease to about a 75% decrease, about a 30% decrease to about a 70% decrease, about a 30% decrease to about a 65% decrease, about a 30% decrease to about a 60% decrease, about a 30% decrease to about a 55% decrease, about a 30% decrease to about a 50% decrease, about a 30% decrease to about a 45% decrease, about a 30% decrease to about a 40% decrease, about a 30% decrease to about a 35% decrease, about a 35% decrease to about a 99% decrease, about a 35% decrease to about a 95% decrease, about a 35% decrease to about a 90% decrease, about a 35% decrease to about a 85% decrease, about a 35% decrease to about a 80% decrease, about a 35% decrease to about a 75% decrease, about a 35% decrease to about a 70% decrease, about a 35% decrease to about a 65% decrease, about a 35% decrease to about a 60% decrease, about a 35% decrease to about a 55% decrease, about a 35% decrease to about a 50% decrease, about a 35% decrease to about a 45% decrease, about a 35% decrease to about a 40% decrease, about a 40% decrease to about a 99% decrease, about a 40% decrease to about a 95% decrease, about a 40% decrease to about a 90% decrease, about a 40% decrease to about a 85% decrease, about a 40% decrease to about a 80% decrease, about a 40% decrease to about a 75% decrease, about a 40% decrease to about a 70% decrease, about a 40% decrease to about a 65% decrease, about a 40% decrease to about a 60% decrease, about a 40% decrease to about a 55% decrease, about a 40% decrease to about a 50% decrease, about a 40% decrease to about a 45% decrease, about a 45% decrease to about a 99% decrease, about a 45% decrease to about a 95% decrease, about a 45% decrease to about a 90% decrease, about a 45% decrease to about a 85% decrease, about a 45% decrease to about a 80% decrease, about a 45% decrease to about a 75% decrease, about a 45% decrease to about a 70% decrease, about a 45% decrease to about a 65% decrease, about a 45% decrease to about a 60% decrease, about a 45% decrease to about a 55% decrease, about a 45% decrease to about a 50% decrease, about a 50% decrease to about a 99% decrease, about a 50% decrease to about a 95% decrease, about a 50% decrease to about a 90% decrease, about a 50% decrease to about a 85% decrease, about a 50% decrease to about a 80% decrease, about a 50% decrease to about a 75% decrease, about a 50% decrease to about a 70% decrease, about a 50% decrease to about a 65% decrease, about a 50% decrease to about a 60% decrease, about a 50% decrease to about a 55% decrease, about a 55% decrease to about a 99% decrease, about a 55% decrease to about a 95% decrease, about a 55% decrease to about a 90% decrease, about a 55% decrease to about a 85% decrease, about a 55% decrease to about a 80% decrease, about a 55% decrease to about a 75% decrease, about a 55% decrease to about a 70% decrease, about a 55% decrease to about a 65% decrease, about a 55% decrease to about a 60% decrease, about a 60% decrease to about a 99% decrease, about a 60% decrease to about a 95% decrease, about a 60% decrease to about a 90% decrease, about a 60% decrease to about a 85% decrease, about a 60% decrease to about a 80% decrease, about a 60% decrease to about a 75% decrease, about a 60% decrease to about a 70% decrease, about a 60% decrease to about a 65% decrease, about a 65% decrease to about a 99% decrease, about a 65% decrease to about a 95% decrease, about a 65% decrease to about a 90% decrease, about a 65% decrease to about a 85% decrease, about a 65% decrease to about a 80% decrease, about a 65% decrease to about a 75% decrease, about a 65% decrease to about a 70% decrease, about a 70% decrease to about a 99% decrease, about a 70% decrease to about a 95% decrease, about a 70% decrease to about a 90% decrease, about a 70% decrease to about a 85% decrease, about a 70% decrease to about a 80% decrease, about a 70% decrease to about a 75% decrease, about a 75% decrease to about a 99% decrease, about a 75% decrease to about a 95% decrease, about a 75% decrease to about a 90% decrease, about a 75% decrease to about a 85% decrease, about a 75% decrease to about a 80% decrease, about a 80% decrease to about a 99% decrease, about a 80% decrease to about a 95% decrease, about a 80% decrease to about a 90% decrease, about a 80% decrease to about a 85% decrease, about a 85% decrease to about a 99% decrease, about a 85% decrease to about a 95% decrease, about a 85% decrease to about a 90% decrease, about a 90% decrease to about a 99% decrease, about a 90% decrease to about a 95% decrease, or about a 95% decrease to about a 99% decrease) as compared to the half-life of a control ABPC (e.g., any of the exemplary control ABPCs described herein).

Conjugation

In some embodiments, the ABPCs provided herein can be conjugated to a drug (e.g., a chemotherapeutic drug, a small molecule), a toxin, or a radioisotope. Non-limiting examples of drugs, toxins, and radioisotopes (e.g., known to be useful for the treatment of cancer) are known in the art.

In some embodiments, at least one polypeptide of any of the ABPCs described herein is conjugated to the toxin, the radioisotope, or the drug via a cleavable linker. In some embodiments, the cleavable linker includes a protease cleavage site. In some embodiments, the cleavable linker is cleaved on the ABPC once it is transported to the lysosome or late endosome by the target mammalian cell. In some embodiments, cleavage of the linker functionally activates the drug or toxin.

In some embodiments, at least one polypeptide of any of the ABPCs described herein is conjugated to the toxin, the radioisotope, or the drug via a non-cleavable linker. In some embodiments, the conjugated toxin, radioisotope, or drug is released during lysosomal and/or late endosomal degradation of the ABPC.

Non-limiting examples of cleavable linkers include: hydrazone linkers, peptide linkers, disulfide linkers, and thioether linkers. See, e.g., Carter et al., *Cancer J.* 14(3): 154-169, 2008; Sanderson et al., *Clin. Cancer Res.* 11(2 Pt1):843-852, 2005; Chari et al., *Acc. Chem. Res.* 41(1):98-107, 2008; Oflazoglu et al., *Clin. Cancer Res.* 14(19): 6171-6180, 2008; and Lu et al., *Int. J. Mol. Sci.* 17(4): 561, 2016.

Non-limiting examples of non-cleavable linkers include: maleimide alkane-linkers and meleimide cyclohexane linker (MMC) (see, e.g., those described in McCombs et al., AAPS 17(2):339-351, 2015).

In some embodiments, any of the ABPCs described herein is cytotoxic or cytostatic to the target mammalian cell.

Expression of an Antigen-Binding Protein Construct in a Cell

Also provided herein are methods of generating a recombinant cell that expresses an ABPC (e.g., any of the ABPCs described herein) that include: introducing into a cell a nucleic acid encoding the ABPC to produce a recombinant cell; and culturing the recombinant cell under conditions sufficient for the expression of the ABPC. In some embodiments, the introducing step includes introducing into a cell an expression vector including a nucleic acid encoding the ABPC to produce a recombinant cell.

Any of the ABPCs described herein can be produced by any cell, e.g., a eukaryotic cell or a prokaryotic cell. As used herein, the term "eukaryotic cell" refers to a cell having a distinct, membrane-bound nucleus. Such cells may include, for example, mammalian (e.g., rodent, non-human primate, or human), insect, fungal, or plant cells. In some embodiments, the eukaryotic cell is a yeast cell, such as *Saccharomyces cerevisiae*. In some embodiments, the eukaryotic cell is a higher eukaryote, such as mammalian, avian, plant, or insect cells. As used herein, the term "prokaryotic cell" refers to a cell that does not have a distinct, membrane-bound nucleus. In some embodiments, the prokaryotic cell is a bacterial cell.

Methods of culturing cells are well known in the art. Cells can be maintained in vitro under conditions that favor proliferation, differentiation, and growth. Briefly, cells can be cultured by contacting a cell (e.g., any cell) with a cell culture medium that includes the necessary growth factors and supplements to support cell viability and growth.

Methods of introducing nucleic acids and expression vectors into a cell (e.g., a eukaryotic cell) are known in the art. Non-limiting examples of methods that can be used to introduce a nucleic acid into a cell include lipofection, transfection, electroporation, microinjection, calcium phosphate transfection, dendrimer-based transfection, cationic polymer transfection, cell squeezing, sonoporation, optical transfection, impalection, hydrodynamic delivery, magnetofection, viral transduction (e.g., adenoviral and lentiviral transduction), and nanoparticle transfection.

Provided herein are methods that further include isolation of the ABPCs from a cell (e.g., a eukaryotic cell) using techniques well-known in the art (e.g., ammonium sulfate precipitation, polyethylene glycol precipitation, ion-exchange chromatography (anion or cation), chromatography based on hydrophobic interaction, metal-affinity chromatography, ligand-affinity chromatography, and size exclusion chromatography).

Methods of Treatment

Provided herein are methods of treating a cancer characterized by having a population of cancer cells that have CD123 or an epitope of CD123 presented on their surface, that include: administering a therapeutically effective amount of any of the pharmaceutical compositions described herein or any of the ABPCs described herein to a subject identified as having a cancer characterized by having the population of cancer cells.

Also provided herein are methods of reducing the volume of a tumor in a subject, wherein the tumor is characterized by having a population of cancer cells that have CD123 or an epitope of CD123 presented on their surface, that include: administering a therapeutically effective amount of any of the pharmaceutical compositions described herein or any of the ABPCs described herein to a subject identified as having a cancer characterized by having the population of cancer cells. In some embodiments of any of the methods described herein, the volume of at least one (e.g., 1, 2, 3, 4, or 5) tumor (e.g., solid tumor) or tumor location (e.g., a site of metastasis) is reduced (e.g., a detectable reduction) by at least 1%, at least 2%, at least 3%, at least 4%, at least 5%, at least 6%, at least 8%, at least 10%, at least 12%, at least 14%, at least 16%, at least 18%, at least 20%, at least 22%, at least 24%, at least 26%, at least 28%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%) reduced as compared to the size of the at least one tumor (e.g., solid tumor) before administration of the ABPC.

Also provided herein are methods of inducing cell death in a cancer cell in a subject, wherein the cancer cell has CD123 or an epitope of CD123 presented on its surface, that include: administering a therapeutically effective amount of any of the pharmaceutical compositions of described herein or any of the ABPCs described herein to a subject identified as having a cancer characterized as having the population of cancer cells. In some embodiments, the cell death that is induced is necrosis. In some embodiments, the cell death that is induced is apoptosis.

In some embodiments of any of the methods described herein, the cancer is a primary tumor.

In some embodiments of any of the methods described herein, the cancer is a metastasis.

In some embodiments of any of the methods described herein, the cancer is a non-T-cell-infiltrating tumor. In some embodiments of any of the methods described herein, the cancer is a T-cell-infiltrating tumor.

Provided herein are methods of decreasing the risk of developing a metastasis or decreasing the risk of developing an additional metastasis in a subject having a cancer, wherein the cancer is characterized by having a population of cancer cells that have CD123 or an epitope of CD123 presented on their surface, that include: administering a therapeutically effective amount of any of the pharmaceutical compositions of described herein or any of the ABPCs described herein to a subject identified as having a cancer characterized as having the population of cancer cells. In some embodiments, the risk of developing a metastasis or the risk of developing an additional metastasis is decreased (e.g., a detectable decrease) by at least 1%, by at least 2%, at least 3%, at least 4%, at least 5%, at least 6%, at least 8%, at least 10%, at least 12%, at least 14%, at least 16%, at least 18%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% in the subject as compared to the risk of a subject having a similar cancer, but administered no treatment or a treatment that does not include the administration of any of the ABPCs described herein.

In some embodiments of any of the methods described herein, the cancer is a non-T-cell-infiltrating tumor. In some embodiments of any of the methods described herein, the cancer is a T-cell-infiltrating tumor. In some embodiments of any of the methods described herein, the cellular compartment is part of the endosomal/lysosomal pathway. In some embodiments of any of the methods described herein, the cellular compartment is an endosome.

The term "subject" refers to any mammal. In some embodiments, the subject or "subject suitable for treatment" may be a canine (e.g., a dog), feline (e.g., a cat), equine (e.g., a horse), ovine, bovine, porcine, caprine, primate, e.g., a simian (e.g., a monkey (e.g., marmoset, baboon), or an ape (e.g., a gorilla, chimpanzee, orangutan, or gibbon) or a human; or rodent (e.g., a mouse, a guinea pig, a hamster, or a rat). In some embodiments, the subject or "subject suitable for treatment" may be a non-human mammal, especially mammals that are conventionally used as models for demonstrating therapeutic efficacy in humans (e.g., murine, lapine, porcine, canine or primate animals) may be employed.

As used herein, treating includes reducing the number, frequency, or severity of one or more (e.g., two, three, four, or five) signs or symptoms of a cancer in a patient having a cancer (e.g., any of the cancers described herein). For example, treatment can reducing cancer progression, reduce the severity of a cancer, or reduce the risk of re-occurrence of a cancer in a subject having the cancer.

Provided herein are methods of inhibiting the growth of a solid tumor in a subject (e.g., any of the subjects described herein) that include administering to the subject a therapeutically effective amount of any of the ABPCs described herein or any of the pharmaceutical compositions described herein (e.g., as compared to the growth of the solid tumor in the subject prior to treatment or the growth of a similar solid tumor in a different subject receiving a different treatment or receiving no treatment).

In some embodiments of any of the methods described herein, the growth of a solid tumor is primary growth of a solid tumor. In some embodiments of any of the methods described herein, the growth of a solid tumor is recurrent growth of a solid tumor. In some embodiments of any of the methods described herein, the growth of a solid tumor is metastatic growth of a solid tumor. In some embodiments, treatment results in about a 1% decrease to about 99% decrease (or any of the subranges of this range described herein) in the growth of a solid tumor in the subject (e.g., as compared to the growth of the solid tumor in the subject prior to treatment or the growth of a similar solid tumor in a different subject receiving a different treatment or receiving no treatment). The growth of a solid tumor in a subject can be assessed by a variety of different imaging methods, e.g., positron emission tomograph, X-ray computed tomography, computed axial tomography, and magnetic resonance imaging.

Also provided herein are methods of decreasing the risk of developing a metastasis or developing an additional metastasis over a period of time in a subject identified as having a cancer (e.g., any of the exemplary cancers described herein) that include administering to the subject a therapeutically effective amount of any of the proteins described herein or any of the pharmaceutical compositions described herein (e.g., as compared to a subject having a similar cancer and receiving a different treatment or receiving no treatment). In some embodiments of any of the methods described herein, the metastasis or additional metastasis is one or more to a bone, lymph nodes, brain, lung, liver, skin, chest wall including bone, cartilage and soft tissue, abdominal cavity, contralateral breast, soft tissue, muscle, bone marrow, ovaries, adrenal glands, and pancreas.

In some embodiments of any of the methods described herein, the period of time is about 1 month to about 3 years (e.g., about 1 month to about 2.5 years, about 1 month to about 2 years, about 2 months to about 1.5 years, about 1 month to about 1 year, about 1 month to about 10 months, about 1 month to about 8 months, about 1 month to about 6 months, about 1 month to about 5 months, about 1 month to about 4 months, about 1 month to about 3 months, about 1 month to about 2 months, about 2 months to about 3 years, about 2 months to about 2.5 years, about 2 months to about 2 years, about 2 months to about 1.5 years, about 2 months to about 1 year, about 2 months to about 10 months, about 2 months to about 8 months, about 2 months to about 6 months, about 2 months to about 5 months, about 2 months to about 4 months, about 2 months to about 3 months, about 3 months to about 3 years, about 3 months to about 2.5 years, about 3 months to about 2 years, about 3 months to about 1.5 years, about 3 months to about 1 year, about 3 months to about 10 months, about 3 months to about 8 months, about 3 months to about 6 months, about 3 months to about 5 months, about 3 months to about 4 months, about 4 months to about 3 years, about 4 months to about 2.5 years, about 4 months to about 2 years, about 4 months to about 1.5 years, about 4 months to about 1 year, about 4 months to about 10 months, about 4 months to about 8 months, about 4 months to about 6 months, about 4 months to about 5 months, about 5 months to about 3 years, about 5 months to about 2.5 years, about 5 months to about 2 years, about 5 months to about 1.5 years, about 5 months to about 1 year, about 5 months to about 10 months, about 5 months to about 8 months, about 5 months to about 6 months, about 6 months to about 3 years, about 6 months to about 2.5 years, about 6 months to about 2 years, about 6 months to about 1.5 years, about 6 months to about 1 year, about 6 months to about 10 months, about 6 months to about 8 months, about 8 months to about 3 years, about 8 months to about 2.5 years, about 8 months to about 2 years, about 8 months to about 1.5 years, about 8 months to about 1 year, about 8 months to about 10 months, about 10 months to about 3 years, about 10 months to about 2.5 years, about 10 months to about 2 years, about 10 months to about 1.5 years, about 10 months to about 1 year, about 1 year to about 3 years, about 1 year to about 2.5 years, about 1 year to about 2 years, about 1 year to about 1.5 years, about 1.5 years to about 3 years, about 1.5 years to about 2.5 years, about 1.5 years to about 2 years, about 2 years to about 3 years, about 2 years to about 2.5 years, or about 2.5 years to about 3 years).

In some embodiments, the risk of developing a metastasis or developing an additional metastasis over a period of time in a subject identified as having a cancer is decreased by about 1% to about 99% (e.g., or any of the subranges of this range described herein), e.g., as compared to the risk in a subject having a similar cancer receiving a different treatment or receiving no treatment.

Non-limiting examples of cancer include: acute lymphoblastic leukemia (ALL), acute myeloid leukemia (AML), adrenocortical carcinoma, anal cancer, appendix cancer, astrocytoma, basal cell carcinoma, brain tumor, bile duct cancer, bladder cancer, bone cancer, breast cancer, bronchial tumor, Burkitt Lymphoma, carcinoma of unknown primary origin, cardiac tumor, cervical cancer, chordoma, chronic lymphocytic leukemia (CLL), chronic myelogenous leukemia (CML), chronic myeloproliferative neoplasm, colon cancer, colorectal cancer, craniopharyngioma, cutaneous T-cell lymphoma, ductal carcinoma, embryonal tumor, endometrial cancer, ependymoma, esophageal cancer, esthesioneuroblastoma, fibrous histiocytoma, Ewing sarcoma, eye cancer, germ cell tumor, gallbladder cancer, gastric cancer, gastrointestinal carcinoid tumor, gastrointestinal stromal tumor, gestational trophoblastic disease, glioma, head and neck cancer, hairy cell leukemia, hepatocellular cancer, histiocytosis, Hodgkin lymphoma, hypopharyngeal cancer, intraocular melanoma, islet cell tumor, Kaposi sarcoma, kidney cancer, Langerhans cell histiocytosis, laryngeal cancer, leukemia, lip and oral cavity cancer, liver cancer, lobular carcinoma in situ, lung cancer, lymphoma, macroglobulinemia, malignant fibrous histiocytoma, melanoma, Merkel cell carcinoma, mesothelioma, metastatic squamous neck cancer with occult primary, midline tract carcinoma involving NUT gene, mouth cancer, multiple endocrine neoplasia syndrome, multiple myeloma, mycosis fungoides, myelodysplastic syndrome, myelodysplastic/myeloproliferative neoplasm, nasal cavity and para-nasal sinus cancer, nasopharyngeal cancer, neuroblastoma, non-Hodgkin lymphoma, non-small cell lung cancer, oropharyngeal cancer, osteosarcoma, ovarian cancer, pancreatic cancer, papillomatosis, paraganglioma, parathyroid cancer, penile cancer, pharyngeal cancer, pheochromocytomas, pituitary tumor, pleuropulmonary blastoma, primary central nervous system lymphoma, prostate cancer, rectal cancer, renal cell cancer, renal pelvis and ureter cancer, retinoblastoma, rhabdoid tumor, salivary gland cancer, Sezary syndrome, skin cancer, small cell lung cancer, small intestine cancer, soft tissue sarcoma, spinal cord tumor, stomach cancer, T-cell lymphoma, teratoid tumor, testicular cancer, throat cancer, thymoma and thymic carcinoma, thyroid cancer, urethral cancer, uterine cancer, vaginal cancer, vulvar cancer, and Wilms' tumor. Additional examples of cancer are known in the art.

In some embodiments, the patient is further administered one or more additional therapeutic agents (e.g., one or more of a chemotherapeutic agent, a recombinant cytokine or interleukin protein, a kinase inhibitor, and a checkpoint inhibitor). In some embodiments, the one or more additional therapeutic agents is administered to the patient at approximately the same time as any of the ABPCs described herein are administered to the patient. In some embodiments, the one or more additional therapeutic agents are administered to the patient after the administration of any of the ABPCs described herein to the patient. In some embodiments, the one or more additional therapeutic agents are administered to the patient before the administration of any of the ABPCs described herein to the patient.

In some embodiments of any of the methods described herein, the cancer is a solid cancer (e.g., breast cancer, prostate cancer, or non-small cell lung cancer).

Compositions

Also provided herein are compositions (e.g., pharmaceutical compositions) that include at least one of any of the ABPCs described herein. In some embodiments, the compositions (e.g., pharmaceutical compositions) can be disposed in a sterile vial or a pre-loaded syringe.

In some embodiments, the compositions (e.g., pharmaceutical compositions) are formulated for different routes of administration (e.g., intravenous, subcutaneous, intramuscular, or intratumoral). In some embodiments, the compositions (e.g., pharmaceutical compositions) can include a pharmaceutically acceptable carrier (e.g., phosphate buffered saline). Single or multiple administrations of any of the pharmaceutical compositions described herein can be given to a subject depending on, for example: the dosage and frequency as required and tolerated by the patient. A dosage of the pharmaceutical composition should provide a sufficient quantity of the ABPC to effectively treat or ameliorate conditions, diseases, or symptoms. Also provided herein are methods of treating a subject having a cancer (e.g., any of the cancers described herein) that include administering a therapeutically effective amount of at least one of any of the compositions or pharmaceutical compositions provided herein.

Kits

Also provided herein are kits that include any of the ABPCs described herein, any of the compositions described herein, or any of the pharmaceutical compositions described herein. In some embodiments, the kits can include instructions for performing any of the methods described herein. In some embodiments, the kits can include at least one dose of any of the compositions (e.g., pharmaceutical compositions) described herein. In some embodiments, the kits can provide a syringe for administering any of the pharmaceutical compositions described herein.

Protein Constructs

Also provided are protein constructs (PCs) that include: a first antigen-binding domain that is capable of specifically binding CD123 or an epitope of CD123 presented on the surface of a target mammalian cell, where: (a) the dissociation rate of the first antigen-binding domain at a pH of about 7.0 to about 8.0 (or any of the subranges of this range described herein) is faster than the dissociation rate at a pH of about 4.0 to about 6.5 (or any of the subranges of this range described herein); and/or (b) the dissociation constant ($K_D$) of the first antigen-binding domain at a pH of about 7.0 to about 8.0 (or any of the subranges of this range) is greater than the $K_D$ at a pH of about 4.0 to about 6.5.

Also provided herein are pharmaceutical compositions including any of the PCs described herein. Also provided herein are methods of treating a subject in need thereof that include administering a therapeutically effective amount of any of the PCs described herein to the subject.

Methods of Improving pH Dependence of an Antigen-Binding Protein Construct

Also provided herein are methods of improving pH dependence of an antigen-binding protein construct, the method comprises providing a starting antigen-binding protein construct comprising an antigen-binding domain and introducing one or more histidine amino acid substitutions into one or more CDRs of the antigen-binding domain in the starting antigen-binding protein construct, wherein the method results in the generation of an antigen-binding protein construct having one or both of: (a) an increased (e.g., at least a 0.1-fold increase to about a 100-fold increase, or any of the subranges of this range described herein) ratio of the dissociation rate of the antigen-binding domain at a pH of about 4.0 to about 6.5 to the dissociation rate at a pH of about 7.0 to about 8.0, as compared to the starting antigen-binding protein construct, and (b) an increased (e.g., at least a 0.1-fold increase to about a 100-fold increase, or any of the subranges of this range described herein) ratio the dissociation constant ($K_D$) of the antigen-binding domain at a pH of about 4.0 to about 6.5 to the $K_D$ at a pH of about 7.0 to about 8.0, as compared to the starting antigen-binding protein construct.

The invention is further described in the following examples, which do not limit the scope of the invention described in the claims.

EXAMPLES

Example 1. Generation of CD123 Binders and Engineering of pH Binding Dependence pH-engineered ABPCs specific for CD123 are generated using two methods. In the first approach, published monoclonal antibodies against CD123 were used as a starting template for introduction of additional mutations that allow engineering of pH-dependent binding to CD123 and i) enhanced endolysosomal accumulation of a conjugated toxin, as well as ii) enhanced CD123 recycling to the cell surface. The second approach involves discovery of de novo ABPCs specific for CD123 via antibody display methods from naive libraries or libraries with defined CDR compositions and screening under conditions designed for selection of pH-engineered ABPCs specific for CD123. In either case, histidine residues play an important role in engineering pH-dependent binding proteins.

Histidine residues are at least partially protonated at a pH below 6.5 owing to its pKa of 6.0. Therefore, if a histidine side chain in an antigen-binding domain participates in an electrostatic binding interaction with its antigen it will start to turn positively charged at a pH at or below 6.5. This could either weaken or enhance the binding affinity of the interaction at a pH below 6.5, based on the corresponding charge of and interactions with the antigen epitope. Thus, systematic introduction of histidines into antibody complementarity determining regions (CDRs) in an antibody or other binder library (e.g., an scFv library) can be used to identify substitutions that will affect an antigen-binding domain's interaction with an antigen at lower pH values. The first approach therefore involves histidine-scanning of variable region sequences of published monoclonal antibodies to identify pH-dependent variants.

Multiple CD123-binding monoclonal antibodies have been described in the literature and can be used as a template for engineering pH-dependent binding [Kovtun, Yelena, et al. (2018) "A CD123-Targeting Antibody-Drug Conjugate, IMGN632, Designed to Eradicate AML While Sparing Normal Bone Marrow Cells." Blood Advances, American Society of Hematology 2(8) 848-858.]. Briefly, for a subset of the antibody sequences, CDRs in each chain are identified using the methods described by Kabat et al (Kabat et al. (1992) Sequences of Proteins of Immunological Interest (DIANE publishing) and IMGT (Lefranc M P (1999) "The IMGT unique numbering for Immunoglobulins, T cell receptors and Ig-like domains" The Immunologist 7, 132-136), and for each CDR, residues falling under either or both Kabat and IMGT CDR definitions were called as CDR residues. To engineer pH-dependent sequence variants, individual amino acid residues within the heavy chain and/or light chain CDRs are systematically substituted with a histidine, one at a time. In cases where the starting CDR residue is a histidine, it is mutated to an alanine. Antibody variants with only one histidine or alanine mutation in a heavy/light chain CDR are generated by co-transfection of Expi293 cells with a) one heavy chain or light chain sequence variant, and b) the corresponding starting ABPC (e.g., the starting CD123-binding monoclonal antibody) light chain or heavy chain, respectively, using methods known to the art. After allowing for a period of protein expression, cell culture supernatants are collected, quantified, and the pH dependence of the variant is evaluated using biolayer interferometry (BLI) or other methods known to the art. Briefly, cell culture supernatants are normalized to an antibody expression level of 50 μg/mL, and captured on an anti-human Fc sensor (Forte Bio). A baseline is established using 1× kinetics buffer (Forte Bio), and the sensor is associated with 100 nM of CD123 in 1×PBS at pH 7.4 for 300 sec to generate an association curve. In the dissociation phase, the antibody-antigen complex on the sensor is exposed to 1×PBS at either pH 5.5 or pH 7.4 for 300-500 sec. Association and dissociation phase curves are examined for the starting ABPC antibody and each corresponding antibody variant at pH 5.5 and pH 7.4 to inform on two criteria: a) enhanced dissociation (i.e., higher koff values) at pH 5.5 due to histidine or alanine substitution compared to the starting ABPC, and b) reduced dissociation at pH 7.4 (i.e., lower koff values) compared to pH 5.5 in the antibody variant itself and with the starting ABPC. Variants that show either enhanced dissociation at pH 5.5 or reduced dissociation at pH 7.4 or both are selected for further analysis. It is also noted that while some histidine and alanine mutations obliterate CD123 binding, others are tolerated with little (e.g., less than 1-fold change in $K_D$ or dissociation rate) or no change in CD123 binding kinetics. Especially because histidine is a large, positively charged amino acid, these histidine variants and alanine variants with no change are noted as positions that may tolerate a wide range of mutations and lead to antibodies with different sequence but similar binding properties, a designation that is not otherwise apparent. The variants selected for further analysis are expressed at a larger scale and purified using protein A affinity chromatography. Binding kinetics (kon and koff) of the purified starting ABPC and variant antibodies are measured at pH 5.5 and pH 7.4 using Biacore (GE Healthcare). The ratio of the antibody's rate of dissociation (koff at pH 7.4 divided by koff at pH 5.5) is also used as a quantitative assessment of pH-dependent binding; similarly, the dissociation constant $K_D$ is calculated at both pH 5.5 and pH 7.4 as koff divided by kon and the ratio of the antibody's dissociation constant ($K_D$ at pH 7.4 divided by $K_D$ at pH 5.5) is also used as a quantitative assessment of pH-dependent binding. Antibodies with a rate of dissociation ratio less than that of the starting ABPC and/or a dissociation constant ratio less than that of the starting ABPC are selected for further assessment of combinatorial substitutions. Favorable histidine and/or alanine amino acid positions can also be combined to enhance pH dependence; this can be done by, e.g., combinatorially or rationally combining histidine and/or alanine substitutions on a given heavy or light chain that individually improve pH dependence, by, e.g., combinatorially or rationally combining modified heavy and light chains such that histidine and/or alanine substitutions are present on both chains, or combinations thereof. Such combinatorial variants are generated and tested/analyzed for differential pH dependence using the methods and protocols described herein, or others known to the art. Antibody variants that have the lowest rate of dissociation ratios and/or dissociation constant ratios are selected as candidates for further analysis (hereafter referred to as "pH-engineered ABPCs specific for CD123").

The second method for selection of pH-engineered ABPCs specific for CD123 involves either screening libraries to identify de novo pH-dependent ABPCs specific for CD123 or ABPCs that could serve as templates for engineering pH-dependent binding as described herein. Two types of libraries can be used for these selections: naive phage/yeast display antibody libraries (e.g., Fab, scFv, VHH, VL, or others known to the art) or phage/yeast display libraries where CDRs have been mutated to express a subset of amino acid residues. Libraries are screened against soluble recombinant CD123 extracellular domains using methods known to the art with positive selection for variants that bind weakly (e.g., are eluted from beads) at pH 5.0 and bind strongly (e.g., are bound to beads) at pH 7.4. Three rounds of selections are performed. The final round of binders are screened using ELISA for binding to human CD123 and cyno CD123 and mouse CD123 or via mean fluorescence intensity in flow cytometric analysis. If more binders with cyno or murine cross-reactivity are desired, the final selection round can instead be performed on cyno CD123 or murine CD123. Selected binding proteins are subcloned into mammalian expression vectors and expressed as either full IgG proteins or Fc fusions in Expi293 cells. BLI analysis is performed as described herein for selection of pH-dependent binder variants and confirmed using Biacore.

Example 2. In Vitro Demonstration of pH-Dependent Binding to CD123, pH-Dependent Release of CD123, Enhanced Endolysosomal Delivery in CD123+ Cells, and Increased CD123 Antigen Density in CD123+ Cells after Exposure to pH-Engineered ABPCs Specific for CD123 as Compared to Control ABPCs Specific for CD123

As discussed herein, pH-engineered ABPCs specific for CD123 exhibit the desirable property of decreased CD123 binding at acidic pH (e.g., pH 5.0, pH 5.5), but enhanced binding at higher pH (e.g., pH 7.4), which enhances their accumulation in endolysosomes under physiological conditions.

pH-Dependent Binding to CD123 on Cells

To demonstrate that pH-engineered ABPCs specific for CD123 binds cell surface CD123 at neutral pH, a cell surface binding assay is performed. A panel of human cells that are CD123+ is assembled (e.g., MOLM-13 Cat #ACC 554, Kasumi-3 ATCC Cat #CRL-2725, EOL-1 DSMZ Cat #ACC-386). Methods of identifying and quantifying gene expression (e.g., CD123) for a given cell line are known to the art, and include, e.g., consulting the Cancer Cell Line Encyclopedia (CCLE; https://portals.broadinstitute.org/ccle) to ascertain the expression level and/or mutation status of a given gene in a tumor cell line), rtPCR, microarray, or RNA-Seq analysis, or cell staining with antibodies known in the art (e.g. R&D Systems Human IL-3R alpha/CD123 antibody, MAB301-SP, or Biolegend Purified anti-human CD123 Antibody, Cat #306002 for CD123). Cells are seeded at approximately 5-10,000 per well in 150 μL of pH 7.4 culture medium and incubated at 37° C. for 5 minutes at several doses (e.g., a two-fold dilution series) from 1 pM to 1 μM with one of the following antibodies: a known, control ABPC specific for CD123 (e.g., an antibody, IMGN632, or SGN-CD123A, or TPP8988), the pH-engineered ABPC specific for CD123, and an appropriate negative isotype control mAb (e.g., Biolegend Purified Human IgG1 Isotype Control Recombinant Antibody, Cat #403501). Prior to the onset of the experiment, the binding properties of all antibodies are validated using methods known to the art. Following the 5 minute incubation, cells are fixed with 4% formaldehyde (20 min at room temperature) and incubated with an appropriate fluorophore-labeled secondary antibody (e.g., ThermoFisher Mouse anti-Human IgG1 Fc Secondary Antibody, Alexa Fluor 488, Cat #A-10631) for 60 minutes. Unbound reagents are washed with a series of PBS washes, and the cell panels are imaged using confocal microscopy. Upon analysis of the images, significant fluorescence can be observed on the surface of cells bound with the known, control ABPC specific for CD123 as well as the pH-engineered ABPC specific for CD123, but little surface binding can be observed for the isotype negative control. To isolate the effect of pH on surface binding, the same experiment is repeated twice, with the primary antibody incubation taking place at sequentially lower pH (e.g., pH 6.5 and 5.5 and 5.0). Analysis of the resulting confocal microscopy images can show significant fluorescence on the surface of cells bound with all mAbs tested, excepting the isotype negative control, and that this fluorescence decreases for the pH-engineered ABPC specific for CD123 as the pH decreases. Alternatively, cells are analyzed for mean fluorescent intensity by flow cytometry using methods known in the art. A dissociation constant $K_D$ on cells at neutral pH of the antibodies analyzed is determined by nonlinear regression methods known in the art (e.g., a Scatchard plot). Taken together, the results can show that the pH engineering process results in the creation of a pH-engineered ABPC specific for CD123 that is pH-dependent in its binding properties and that it more effectively binds at neutral pH as compared to more acidic pH. Other methods of assessing the pH dependence of the pH-engineered ABPCs specific for CD123 are known in the art and include, e.g., using flow cytometry to measure ABPC surface binding.

pH-Dependent Release of CD123 on Cells

To demonstrate that pH-engineered ABPCs specific for CD123 are capable of releasing CD123 at low pH after binding at a neutral pH, a variant of the cell surface binding assay described above is performed using methods known to the art (e.g., as generally described in Gera N. (2012) PLoS ONE 7(11): e48928). Briefly, an appropriate CD123+ cell line (passage number less than 25) is harvested and 50,000 cells per well are plated in a U-Bottomed 96-well microplate. Three conditions are tested; binding and secondary staining at pH 7.4, binding and secondary staining at pH 5.0, and binding at pH 7.4 followed by release at pH 5.0 for 30 minutes and secondary staining at pH 7.4. Both pH-engineered ABPCs specific for CD123 as well as a control ABPC specific for CD123 are tested. The cells are washed two times with 200 μL of FACS buffer (1×PBS containing 3% Fetal Bovine Serum) at either pH 7.4 or 5.0 depending on the condition being tested. The purified protein samples are diluted into FACS buffer of the appropriate pH and added to the cells and allowed to bind for one hour on ice. After incubation with the primary antibodies the pH 7.4 and pH 5.0 conditions are washed twice as before, and then 100 μl of secondary rat anti-human Fc AF488 (BioLegend 410706) or other appropriate antibody, diluted 1:50, or anti Myc-Tag mouse mAb-AF488 (Cell Signaling Technologies 2279S) diluted 1:50 is added in FACS buffer of the appropriate pH, and incubated for 30 minutes on ice. The pH 5.0 release condition is washed twice with FACS buffer pH 7.4 and then resuspended in 100 μl of FACS buffer pH 5.0 and incubated on ice for 30 minutes, followed by secondary staining in FACS buffer pH 7.4 as described for the other conditions. The plates are washed twice as before and resuspended in 1% paraformaldehyde in the appropriate FACS buffer to fix them for flow cytometry analysis. All conditions are read on a flow cytometer (Accuri C6, BD Biosciences). Binding is observed as a shift in the FL1 signal (as a mean fluorescence intensity) versus secondary alone. Upon analysis of the data, it can be determined that both the pH-engineered ABPC specific for CD123 as well as the control ABPC specific for CD123 effectively bind the surface of CD123+ cells at neutral pH, but the pH-engineered ABPC specific for CD123 binds poorly at pH 5.0; similarly, it can be determined that the pH-engineered ABPC specific for CD123 binds effectively at pH 7.4, but then releases/unbinds CD123 at pH 5.0.

Enhanced Endolysosomal Delivery in CD123+ Cells of pH-Engineered ABPCs Specific for CD123 as Compared to Control ABPCs Specific for CD123 (pHrodo)

To verify and demonstrate that ABPCs specific for CD123 achieve endolysosomal localization following cellular uptake, an internalization assay is performed using methods known to the art (e.g., Mahmutefendic et al., Int. J. Biochem. Cell Bio. 2011). Briefly, as described herein, a panel of human cells that express CD123 highly is assembled using methods known to the art. Cells are plated, washed three times with PBS, and incubated at 37 degrees C. for 60 minutes in media at neutral pH, with added concentrations of 2 micrograms per milliliter of a known, control ABPC specific for CD123 (e.g., as described herein), the pH-engineered ABPC specific for CD123, and an appropriate negative isotype control mAb (e.g., as described herein). In a subset of cells, validation of antibody internalization and endosomal localization is performed using methods known to the art; e.g., cells are fixed in 4% formaldehyde as described herein, permeabilized using TWEEN 20 or other methods known to the art (Jamur M C et al (2010) Permeabilization of cell membranes, Methods Mol Biol. 588:63-6), additionally stained with an endosomal marker, e.g., a fluorescent RAB11 antibody (RAB11 Antibody, Alexa Fluor 488, 3H18L5, ABfinity™ Rabbit Monoclonal), stained with an appropriate fluorescently labeled anti-human secondary antibody (e.g., as described herein), and imaged using confocal fluorescence microscopy, as described herein. Analysis of the confocal images can be used to show that both the pH-engineered ABPC specific for CD123 as well as the control ABPC specific for CD123 are internalized and accumulate in the endolysosomes.

To demonstrate that pH-engineered ABPCs specific for CD123 achieve enhanced endolysosomal accumulation relative to a control ABPC specific for CD123, a pHrodo-based internalization assay is performed using both a known, control ABPC specific for CD123 (e.g., as described herein) as well as the pH-engineered ABPC specific for CD123. The assay makes use of pHrodo™ iFL (P36014, ThermoFisher), a dye whose fluorescence increases with decreasing pH, such that its level of fluorescence outside the cell at neutral pH is lower than its level of fluorescence inside the acidic pH environment of endolysosomes. Briefly, an appropriate CD123+ cell line (less than passage 25) is suspended in its recommended media (e.g., by cell banks or cell bank databases ATCC, DSMZ, or ExPASy Cellosaurus) and plated in a 24-well plate at a density of 2,000,000 cells/mL, 1 mL per well. While keeping the cells on ice, 1 mL of 2× pHrodo iFL-labeled antibody (prepared in accordance with the manufacturer's instructions) is added to each well, the well is pipetted/mixed five times, and the plate is incubated in a light-protected environment for 45 minutes, on ice. An identical but separate plate is also incubated on ice that is meant as a no-internalization negative control. Following this incubation, the experimental plate is moved to a 37 degree C. incubator, the negative control plate is kept on ice to slow or block internalization, and samples are taken at designated time points to create an internalization time course. Samples are placed into a U-bottom 96-well plate, and internalization is quenched via addition of 200 μL/well of ice-cold FACS buffer. The plates are spun down at 2000×g for 2 minutes, resuspended in 200 μL ice-cold FACS buffer, spun down again, and resuspended in FACS buffer a second time. Finally, the samples are loaded into a flow cytometer for read-out of cellular pHrodo fluorescence using excitation and emission wavelengths consistent with the excitation and emission maxima of the pHrodo iFL Red dye (566 nm and 590 nm, respectively). Upon completion of the flow cytometry experiment and analysis of the data, it can be observed that cells treated with the pH-engineered ABPC specific for CD123 have a higher pHrodo iFL signal relative to a known, control ABPC specific for CD123, indicating that pH-engineered ABPCs specific for CD123 achieve enhanced endolysosomal accumulation relative to a control ABPC specific for CD123.

Alternatively, to demonstrate that pH-engineered ABPCs specific for CD123 achieve enhanced endolysosomal accumulation relative to a control ABPC specific for CD123, a variation of the above-described experiment is performed. CD123+ cells are plated, washed three times with PBS, and incubated at 37 degrees C. for 60 minutes in media at neutral pH with added concentrations of 2 μg/mL of either pH-engineered ABPC specific for CD123 or control ABPC specific for CD123. Following incubation, cells are washed three times with PBS, fixed and permeabilized, and stained with a panel of appropriately selected antibodies that bind late endosomal markers as well as lysosomes (e.g., RAB7, and LAMP1; Cell Signaling Technology, Endosomal Marker Antibody Sampler Kit #12666; AbCam, Anti-LAMP2 antibody [GL2A7], ab13524). After primary antibody staining, cells are stained with an appropriate mixture of fluorescently labeled secondary antibodies (e.g., Goat Anti-Human IgG (H&L) Secondary Antibody (Alexa Fluor 647) Cat #A-21445, and Abcam Goat Anti-Rabbit IgG H&L (Alexa Fluor 488), Cat #ab150077), imaged using confocal fluorescence microscopy, and regions of co-localization of signal from CD123-specific antibodies and endosomal markers are visualized and quantified. Upon analysis of the data, it can be revealed that there is increased co-localization of endolysosmal and CD123-specific antibody signal in wells treated with the pH-engineered ABPCs specific for CD123 as compared to wells treated with control ABPC specific for CD123, and can thereby demonstrate that pH-engineered ABPCs specific for CD123 achieve enhanced endolysosomal accumulation relative to control ABPC specific for CD123.

Increased CD123 Antigen Density in CD123+ Cells after Exposure to pH-Engineered ABPCs Specific for CD123 as Compared to Control ABPCs Specific for CD123

To demonstrate that treatment of cells with the pH-engineered ABPCs specific for CD123 does not result in a detectable reduction of the level of CD123 on the surface of cells exposed to the pH-engineered ABPCs specific for CD123, or that said treatment results in less of a reduction of the level of CD123 on the surface of cells exposed to the pH-engineered ABPC specific for CD123 versus a control ABPC specific for CD123, an antigen density study is performed using flow cytometry. Briefly, 4.0×10^5 cells that express CD123 are plated per well in a 96-well plate in 100 μL media. Cells are treated with a titration from 1 pM to 1 μM of i) pH-engineered ABPCs specific for CD123, ii) a first control ABPC specific for CD123, iii) an appropriate isotype control, and iv) an untreated control. Cells are incubated for 2 hours at 37° C., at which point all cells are incubated with 200 nM of a fluorophore-labeled second control ABPC specific for CD123 (e.g., as described herein) which has a different epitope (as determined by, e.g., competitive binding studies on cells) than either the first control ABPC specific for CD123 or the pH-engineered ABPCs specific for CD123 for 30 minutes at 4° C. Following this 30-minute incubation, the mean fluorescence intensity (MFI) of all cells is read out using, e.g., flow cytometry, using methods known to one of ordinary skill in the art. In parallel, a quantitative standard curve that can be used to quantify the presence of CD123 on the surface of treated cells as a function of MFI is generated using a commercially available quantification kit (e.g., BD Biosciences PE Phycoerythrin Fluorescence Quantitation Kit, catalog #340495); the quantitative standard curve is created by following the manufacturer's instructions. Other methods of determining the absolute number of CD123 on the cell surface are known in the art and include, e.g., use of radioisotopically labeled reagents. Upon analysis of the data, it can be revealed that at least one antibody concentration, cells treated with a control ABPC specific for CD123 experience a reduction of the level of CD123 on their surface, whereas cells treated with pH-engineered ABPCs specific for CD123 experience a significantly smaller reduction or no reduction at all, both relative to the isotype and untreated controls.

Example 3. Conjugation of pH-Engineered and Control ABPCs Specific for CD123 to Cytotoxic Drugs An antigen-binding protein construct conjugate (ADC) is made comprising the CD123-binding IgG (hereafter, CD123-IgG) described herein linked to monomethyl auristatin E (MMAE) via a valine-citrulline (vc) linker (hereafter, CD123-IgG-DC). Conjugation of the antigen-binding protein construct with vcMMAE begins with a partial reduction of the CD123-IgG followed by reaction with maleimidocaproyl-Val-Cit-PABC-MMAE (vcMMAE). The CD123-IgG (20 mg/mL) is partially reduced by addition of TCEP (molar equivalents of TCEP:mAb is 2:1) followed by incubation at 0° C. overnight. The reduction reaction is then warmed to 20° C. To conjugate all of the thiols, vcMMAE is added to a final vcMMAE:reduced Cys molar ratio of 1:15. The conjugation reaction is carried out in the presence of 10% v/v of DMSO and allowed to proceed at 20° C. for 60 minutes.

After the conjugation reaction, excess free N(acetyl)-Cysteine (2 equivalents vs. vcMMAE charge) is added to quench unreacted vcMMAE to produce the Cys-Val-Cit-MMAE adduct. The Cys quenching reaction is allowed to proceed at 20° C. for approximately 30 minutes. The Cys-quenched reaction mixture is purified as per below. The above conjugation method can also be used to conjugate maleimidocaproyl monomethylauristatin F (mcMMAF) to an antigen-binding protein construct.

The CD123-IgG-DC is purified using a batch purification method. The reaction mixture is treated with the appropriate amount of water washed Bu-HIC resin (ToyoPearl; Tosoh Biosciences), i.e., seven weights of resin is added to the mixture. The resin/reaction mixture is stirred for the appropriate time, and monitored by analytical hydrophobic interaction chromatography for removal of drug conjugate products, filtered through a coarse polypropylene filter, and washed by two bed volumes of a buffer (0.28 M sodium chloride, 7 mM potassium phosphate, pH 7). The combined filtrate and rinses are combined and analyzed for product profile by HIC HPLC. The combined filtrate and rinses are buffer exchanged by ultrafiltration/diafiltration (UF/DF) to 15 mM histidine, pH 6 with 10 diavolumes 15 nM histidine buffer.

A similar protocol can be used to conjugate DNA toxins such as SG3249 and SGD-1910 to CD123-IgG (see Tiberghien A C et al (2016) Design and Synthesis of Tesirine, a Clinical Antibody—Drug Conjugate Pyrrolobenzodiazepine Dimer Payload, ACS Med Chem Lett 7:983-987). Briefly, for SG3249, CD123-IgG (15 mg, 100 nanomoles) is diluted into 13.5 mL of a reduction buffer containing 10 mM sodium borate pH 8.4, 2.5 mM EDTA and a final antibody concentration of 1.11 mg/mL. A 10 mM solution of TCEP is added (1.5 molar equivalent/antibody, 150 nanomoles, 15 microliters) and the reduction mixture is heated at +37° C. for 1.5 hours in an incubator. After cooling down to room temperature, SG3249 is added as a DMSO solution (5 molar equivalent/antibody, 500 nanomoles, in 1.5 mL DMSO). The solution is mixed for 1.25 hours at room temperature, then the conjugation is quenched by addition of N-acetyl cysteine (1 micromole, 100 microliters at 10 mM), and injected into an AKTA™ Pure FPLC using a GE Healthcare HiLoad™ 26/600 column packed with Superdex 200 PG, and eluted with 2.6 mL/min of sterile-filtered phosphate-buffered saline (PBS). Fractions corresponding to the CD123-IgG-DC monomer peak are pooled, concentrated using a 15 mL Amicon Ultracell 50 KDa MWCO spin filter, analysed and sterile-filtered. UHPLC analysis on a Shimadzu Prominence system using a Phenomenex Aeris 3.6u XB-C18 150×2.1 mm column eluting with a gradient of water and acetonitrile on a reduced sample of CD123-IgG-DC at 280 nm and 330 nm (SG3249 specific) can show a mixture of light and heavy chains attached to several molecules of SG3249, consistent with a drug-per-antibody ratio (DAR) of 1 to 4 molecules of SG3249 per antibody. UHPLC analysis on a Shimadzu Prominence system using a Phenomenex Yarra 3u SEC-3000 300 mm×4.60 mm column eluting with sterile-filtered SEC buffer containing 200 mM potassium phosphate pH 6.95, 250 mM potassium chloride and 10% isopropanol (v/v) on a sample of CD123-IgG-DC at 280 nm can show a monomer purity of over 90% with no impurity detected. UHPLC SEC analysis allows determination of final CD123-IgG-DC yield of greater than 30%.

Alternatively, methods to conjugate toxins to antibodies via lysine residues are known in the art (e.g., see Catcott K C et al (2016) Microscale screening of antibody libraries as maytansinoid antibody-drug conjugates, MAbs 8:513-23). In addition, similar methods to the above can be used to conjugate drugs and toxins to non-IgG formats with disulfide bonds, such as Vh-Fcs.

Example 4. Demonstration of Enhanced Cytotoxicity of pH-Engineered ABPC ADCs Specific for CD123 in CD123+ Cells as Compared to a Control ABPC ADC Specific for CD123

The cytotoxic activity of both pH-engineered ADCs specific for CD123 (e.g., a pH-engineered CD123-IgG-DC) and control ABPC ADCs specific for CD123 (e.g., a control ABPC CD123-IgG-DC) are separately evaluated on a panel of CD123+ cell lines expressing a variety of antigen densities (e.g., as described herein) and a CD123-cell line (e.g., Namalwa ATCC Cat #CRL-1432), selected using the methods described herein, and, optionally, cells expressing transgenic CD123, e.g., HEK293 cells transfected with CD123 using methods known in the art (e.g., Expi293™ Expression System Kit ThermoFisher Catalog number: A14635). For purposes of validation, prior to use, all cell lines are tested for expression of CD123 using methods known to the art, e.g., qPCR, flow cytometry, mRNA RPKM, and antibody staining using anti-CD123 antibodies known to the art (e.g., as described herein) followed by visualization of the stain using fluorescence microscopy, immunohistochemistry, flow cytometry, ELISA, or other methods known to the art. To evaluate the cytotoxicity of compounds, cells are seeded at approximately 10-40,000 per well in 150 microliters of culture medium, then treated with graded doses of compounds from 1 pM to 1 μM in quadruplicates at the initiation of the assay. Cytotoxicity assays are carried out for 96 hours after addition of test compounds. Fifty microliters of resazurin dye are added to each well during the last 4 to 6 hours of the incubation to assess viable cells at the end of culture. Dye reduction is determined by fluorescence spectrometry using the excitation and emission wavelengths of 535 nm and 590 nm, respectively. For analysis, the extent of resazurin reduction by the treated cells is compared to that of untreated control cells, and percent cytotoxicity is determined. Alternatively, a WST-8 kit is used to measure cytotoxicity per the manufacturer's instructions (e.g., Dojindo Molecular Technologies Catalog #CCK-8). IC50, the concentration at which half-maximal killing is observed, is calculated using curve-fitting methods known in the art. Upon analysis of the data, it can be determined that pH-engineered and control ABPC ADCs specific for CD123 are substantially cytotoxic to one or more CD123+ cell line, but less toxic to CD123-cells. It also can be determined that pH-engineered ADCs specific for CD123 are more cytotoxic to one or more CD123+ cell lines than control ABPC ADCs specific for CD123 because: a) they show greater depth of killing at one or more concentrations or, b) they show lower IC50 or, c) they show a greater ratio of their dissociation constant $K_D$ on cells at neutral pH (as described herein) divided by their IC50 on those same cells.

Additionally, the cytotoxic activity of ABPCs specific for CD123 can be measured in a secondary ADC assay. Secondary ADC assays are known in the art (e.g., Moradec Cat #αHFc-NC-MMAF and Cat #αHFc-CL-MMAE, and associated manufacturer's instructions). Briefly, the assay is carried out as in the previous paragraph, except the ABPC specific for CD123 is substituted for the ADC specific for CD123, and to evaluate the cytotoxicity of compounds, cells are seeded at approximately 10-40,000 per well in 150 microliters of culture medium, then treated with graded doses of ABPC specific for CD123 from 1 pM to 1 μM (final concentration in culture medium, having been pre-mixed with 100 nM, final concentration in culture medium, of Moradec Cat #αHFc-NC-MMAF secondary ADC reagent and pre-incubated at 37° C. for 30 min before addition of the mixture to the culture medium) in quadruplicates at the initiation of the assay.

The cytotoxic activity of pH-engineered ADCs specific for CD123 and control ABPC ADCs specific for CD123 conjugates, as well as ABPCs specific for CD123 in a secondary ADC assay, are additionally measured by a cell proliferation assay employing the following protocol (Promega Corp. Technical Bulletin TB288; Mendoza et al., Cancer Res. 62:5485-5488, 2002):

1. An aliquot of 100 microliters of cell culture containing about 104 cells (e.g., CD123+ cells as described herein) in medium is deposited in each well of a 96-well, opaque-walled plate.
2. Control wells are prepared containing medium and without cells.
3. ADC specific for CD123 is added to the experimental wells at a range of concentrations from 1 pM-1 uM and incubated for 1-5 days. Alternatively, in a secondary ADC assay, 100 nM secondary ADC reagent (final concentration in culture medium, Moradec Cat #αHFc-NC-MMAF) and ABPC specific for CD123 at a range of concentrations from 1 pM-1 uM (final concentration in culture medium) are pre-mixed and pre-incubated at 37° C. for 30 min before addition of the mixture to the culture medium, and incubated for 1-5 days.
4. The plates are equilibrated to room temperature for approximately 30 minutes.
5. A volume of CellTiter-Glo Reagent equal to the volume of cell culture medium present in each well is added.
6. The contents are mixed for 2 minutes on an orbital shaker to induce cell lysis.
7. The plate is incubated at room temperature for 10 minutes to stabilize the luminescence signal.
8. Luminescence is recorded and reported in graphs as RLU=relative luminescence units.

Example 5. Demonstration of Enhanced Toxin Liberation of pH-Engineered ABPC ADCs Specific for CD123 in CD123+ Cells as Compared to a Control ABPC ADC Specific for CD123

The pH-engineered ADCs specific for CD123 (e.g., a pH-engineered CD123-IgG-DC) can also demonstrate increased toxin liberation in CD123+ cells as compared to a control ABPC ADC specific for CD123 (e.g., a control ABPC CD123-IgG-DC). After treatment of CD123+ cells with pH-engineered and control ABPC ADCs specific for CD123 as described herein, an LC-MS/MS method is used to quantify unconjugated (i.e., liberated) MMAE in treated CD123+ cells (Singh, A. P. and Shah, D. K. Drug Metabolism and Disposition 45.11 (2017): 1120-1132.) An LC-MS/MS system with electrospray interphase and triple quadrupole mass spectrometer is used. For the detection of MMAE, a XBridge BEH Amide column (Waters, Milford, MA) is used with mobile phase A as water (with 5 mM ammonium formate and 0.1% formic acid) and mobile phase B as 95:5 acetonitrile/water (with 0.1% formic acid and 1 mM ammonium formate), using a gradient at a flow rate of 0.25 mL/min at 40° C. The total duration of the chromatographic run is 12 minutes, where two MRM scans (718.5/686.5 and 718.5/152.1 amu) are monitored. Deuterated (d8) MMAE (MCE MedChem Express, Monmouth Junction, NJ) is used as an internal standard. First, an equation for quantifying unconjugated MMAE in a biological sample is derived by dividing the peak area for each drug standard by the peak area obtained for the internal standard. The resultant peak area ratios are then plotted as a function of the standard concentrations, and data points are fitted to the curve using linear regression. Three QC samples are included in the low, middle, and upper ranges of the standard curve to assess the predictive capability of the developed standard curve. The standard curves obtained are then used to deduce the observed concentrations of MMAE in a biologic sample. For measurement of MMAE concentration, treated cell samples are pelleted and reconstituted in fresh media to a final concentration of 0.25 million cells/100 μL. Samples are spiked with d8-MMAE (1 ng/mL) before performing cell lysis by the addition of a 2-fold volume of ice-cold methanol followed by freeze-thaw cycle of 45 minutes at −20° C. The final cell lysate is obtained by centrifuging the samples at 13,000 rpm for 15 minutes at 4° C. followed by collection of supernatant. For the preparation of standards and QC samples, a fresh cell suspension (0.25 million/100 μl) is spiked with known concentrations of MMAE and internal standard (d8-MMAE) before a procedure similar to the cell lysis mentioned above. The resulting cell lysates are then evaporated and reconstituted in mobile phase B before injection into LC-MS/MS. The concentration of unconjugated MMAE in lysates of CD123+ cells treated with pH-engineered ADCs specific for CD123 is observed to be greater than that in CD123+ cells treated with control ABPC ADC specific for CD123.

For tubulin-inhibiting toxins, toxin liberation is also assessed by monitoring of cell viability and cell cycle phase. ~2.0×10^5 CD123+ cells are plated in a 96-well flat bottom plate and treated with pH-engineered and control ABPC ADCs specific for CD123 as described herein. After treatment, cells are transferred to a 96-round bottom plate, and the plate is centrifuged at 400 rcf for 2 min to decant supernatant. Decanted cells are stained with Live/Dead eFluor 660. Cells are then centrifuged and washed with FACS buffer (PBS with 2% FBS), after which cell cycle distribution is analyzed with a BD Cycletest™ Plus DNA Kit (cat #340242). Briefly, cells are re-suspended in 76 ul Solution A and incubated for 10 min at room temperature. 61 μL Solution B is then added, and cells are incubated for another 10 min at room temperature. Finally, 61 μL of cold Solution C is added, and cells are again incubated for 10 min at room temp. Immediately after the last incubation step, cells are analyzed by flow cytometry (without washing) at a flow rate of 10 μL/sec. Increased G2/M-phase arrest can be observed with exposure to pH-engineered ADCs specific for CD123 as compared to control ABPC ADC specific for CD123.

For DNA-damaging toxins (e.g., pyrrolobenzodiazepine or "PBD"), DNA damage is assessed by measuring the phosphorylated histone H2AX (γH2AX). H2AX is normally phosphorylated in response to double-strand breaks in DNA; however, increased levels γH2AX may also be observed as a result of treatment with DNA-cross-linking toxins such as PBD or cisplatin (Huang, X. et al. 2004, Cytometry Part A 58A, 99-110). CD123+ cells are treated with pH-engineered and control ABPC ADCs specific for CD123 as described herein. After treatment, cells are rinsed with PBS, and then fixed in suspension in 1% methanol-free formaldehyde (Polysciences, Warrington, PA) in PBS at 0° C. for 15 min. Cells are resuspended in 70% ethanol for at least 2 h at −20° C. Cells are then washed twice in PBS and suspended in 0.2% Triton X-100 (Sigma) in a 1% (w/v) solution of BSA (Sigma) in PBS for 30 min to suppress nonspecific Ab binding. Cells are centrifuged again (200 g, 5 min) and the cell pellet is suspended in 100 μL of 1% BSA containing 1:800 diluted anti-histone γH2AX polyclonal Ab (Trevigen, Gaithersburg, MD). The cells are then incubated overnight at 4° C., washed twice with PBS, and resuspended in 100 μL of 1:30 diluted FITC-conjugated F(ab')2 fragment of swine anti-rabbit immunoglobulin (DAKO, Carpinteria, CA) for 30 min at room temperature in the dark. The cells are then counterstained with 5 μg/mL of PI (Molecular Probes, Eugene, OR) dissolved in PBS containing 100 μg/mL of DNase-free RNase A (Sigma), for 20 min at room temperature. Cellular fluorescence of the FITC γH2AX signal and the PI counterstain are measured using flow cytometry using methods known in the art. When comparing cells within the same stage of the cell cycle (based on total DNA content), treated CD123+ cells can be observed to have an increased FITC γH2AX signal relative to untreated CD123+ cells (which serve as a baseline). Furthermore, CD123+ cells treated with pH-engineered ADCs specific for CD123 can be observed to have a greater increase in levels of γH2AX over baseline than cells treated with a control ABPC ADC specific for CD123. In addition to the γH2AX assay, DNA cross-linking can be more directly assessed with a Comet assay (Chandna, S. (2004) Cytometry 61A, 127-133).

In addition, as disclosed herein, pH-engineered and control ABPCs can be assayed using the methods in this example without direct conjugation by performing a secondary ADC assay instead of using primary conjugated ADCs.

Example 6. Demonstration of Decreased Half-Life of pH-Engineered ABPCs Specific for CD123 as Compared to a Control ABPC Specific for CD123

One of the surprising aspects of the pH-engineered ABPCs specific for CD123 described by the invention can be their ability to facilitate increased dissociation of ABPCs from the CD123 within the endosome or lysosome resulting in a decreased serum half-life relative to control ABPCs specific for CD123 or ABPCs that are not specific for CD123. This decreased serum half-life is due to the enhanced frequency with which pH-engineered ABPCs specific for CD123 are cleared from circulation due to their enhanced cellular internalization once bound to CD123, which over time can be observed through a decrease in serum concentration of unbound pH-engineered ABPC specific for CD123. To demonstrate these properties, a series of animal studies in mice and/or monkeys is performed using pH-engineered ABPC specific for CD123 and control ABPC specific for CD123 using methods known to the art (e.g., Gupta, P., et al. (2016), mAbs, 8:5, 991-997). Briefly, to conduct mouse studies, a single intravenous bolus (e.g., 5 mg/kg) of either pH-engineered ABPC specific for CD123 or control ABPC specific for CD123 is administered via tail vein to two groups of NOD SCID mice (e.g. Jackson Labs NOD.CB17-Prkdcscid/J Stock No: 001303) xenografted with a CD123+ cell line (e.g., as described herein). Xenografted mice are prepared by growing 1-5 million CD123+ cells in vitro and inoculating subcutaneously into the right flank of the mouse. Tumors are size matched at 300 mm3. Measurements of the length (L) and width (W) of the tumors are taken via electronic caliper and the volume is calculated according to the following equation: $V=L\times W^2/2$. Blood samples are collected via retro-orbital bleeds from each group at each of the following time points: 15 m, 30 m, 1 h, 8 h, 24 h, and 3 d, 7 d, 10 d, 14 d, 17 d, 21 d, and 28 d. Samples are processed to collect serum, and antibody concentrations are quantified using ELISA or other methods known to the art (e.g., PAC assay or MAC assay; Fischer, S. K. et al. (2012), mAbs, 4:5, 623-631, utilizing, e.g., anti-human Fc antibody Jackson ImmunoResearch Labs, Cat #109-006-006). Antibody concentrations of pH-engineered ABPC specific for CD123 and control ABPC specific for CD123 are plotted as a function of time. Upon analysis of the data, it can be observed that the pH-engineered ABPC specific for CD123 has a significantly shorter serum half-life relative to control ABPC specific for CD123, thereby demonstrating the ability of the pH-engineered ABPC specific for CD123's pH dependence to facilitate an enhanced dissociation within the endosome or lysosome relative to other, similar binders (e.g., control ABPC specific for CD123) that bind the same antigen but that differ in their pH dependence. If the pH-engineered and control ABPCs specific for CD123 are cross-reactive with the mouse homolog of CD123, a similar experiment can be repeated with non-xenografted mice.

Optionally, if the pH-engineered and control ABPCs specific for CD123 are cross-reactive with the cynomolgus monkey homolog of CD123, a similar experiment can be performed on monkeys (e.g., cynomolgus monkeys). An equal number of male and female monkeys (e.g., n=1-2 each) are administered a bolus of either pH-engineered ABPC specific for CD123 or control ABPC specific for CD123 at a dose of, e.g., 1 mg/kg via saphenous vein injection. Alternatively, several different doses of CD123-binding protein are administered across a group of several monkeys. Blood samples are collected via the peripheral vein or femoral vein at intervals similar to those described above, and analyzed for the presence of either pH-engineered ABPC specific for CD123 or control ABPC specific for CD123 using methods known to the art (e.g., ELISA). Upon analysis of the data, it can be observed that pH-engineered ABPC specific for CD123 has a significantly shorter serum half-life relative to control ABPC specific for CD123, thereby demonstrating the ability of pH-engineered ABPC specific for CD123 to facilitate an enhanced dissociation within the endosome or lysosome relative to other, similar binders (e.g., control ABPC specific for CD123) that bind the same antigen but that differ in their pH dependence. In some cases, this effect is observed only in certain doses, whereas in others it is observed across doses.

In addition, the half life of pH-engineered and control ABPC ADCs specific for CD123 can be assessed using the above methods by substituting pH-engineered and control ABPC ADCs specific for CD123 for the pH-engineered and control ABPCs specific for CD123 (i.e., studying the ABPCs after conjugation to a drug or toxin, as described herein).

Example 7. Increased Potency of pH-Engineered ADCs Specific for CD123 vs. A Control ABPC ADC Specific for CD123 in Mouse Xenograft Models The enhanced anti-tumor activity of the pH-engineered ADCs specific for CD123 against CD123+ tumors can be demonstrated in a subcutaneous xenograft model of CD123+ cells. For the experiments, 1-5 million CD123+ cells are grown in vitro and inoculated subcutaneously per mouse into the right flank of female immunodeficient (e.g., SCID-Beige or NOD scid) mice.

Tumors are size matched at 100-200 mm3, and dosed intraperitoneally (IP) (1 dose given every ~4-7 days for a total of ~2-6 doses). Measurements of the length (L) and width (W) of the tumors are taken via electronic caliper and the volume is calculated according to the following equation: V=L×W^2/2. A bolus (e.g., 5 mg/kg) of either pH-engineered ADC specific for CD123 or control ABPC ADC specific for CD123 is administered via tail vein. Tumor growth inhibition (TGI) and tumor growth delay (TGD) and survival are significantly improved with administration of pH-engineered ADC specific for CD123 compared to administration of control ABPC ADC specific for CD123 at the same regimen.

Optionally, spread of tumor cells into the various tissues is determined in sacrificed animals. Metastasis is measured according to Schneider, T., et al., Clin. Exp. Metas. 19 (2002) 571-582. Briefly, tissues are harvested and human Alu sequences are quantified by real-time PCR. Higher human DNA levels, quantified by real-time PCR, correspond to higher levels of metastasis. Levels of human Alu sequences (correlating to invasion of tumor cells into secondary tissue) are significantly lower in animals treated with pH-engineered ADC specific for CD123, corresponding to reduced metastasis, compared to mice treated with control ABPC ADC specific for CD123 at the same regimen. Alternatively, the enhanced anti-tumor activity of the pH-engineered ADC specific for CD123 can be shown in CD123+ patient-derived xenograft models (e.g., available from Champions Oncology).

Example 8. Creation of a pH-Engineered Bispecific CD123 Bispecific ABPC and Demonstration of Exemplary Properties as Compared to a Control Bispecific ABPC To create a pH-engineered ABPC specific for CD123 with modified toxicity and internalization properties, a bispecific antibody that binds two different epitopes on CD123 is constructed. It is known in the art that biparatopic antibodies can show increased antigen-dependent internalization, and are therefore useful for applications such as antibody-drug conjugates (e.g., see Li et al (2016) A Biparatopic HER2-Targeting Antibody-Drug Conjugate Induces Tumor Regression in Primary Models Refractory to or Ineligible for HER2-Targeted Therapy, Cancer Cell 29:117-29). Briefly, a pH-engineered CD123×CD123 bispecific, biparatopic ABPC specific for CD123 is assembled using light chain/heavy chain pairs from two different pH-engineered ABPCs specific for CD123, each of which binds a distinct epitope on CD123 that does not overlap with the other epitope. A set of pH-engineered ABPCs specific for CD123 that bind non-overlapping epitopes are discovered, e.g., using the methods described herein, or others known to one of ordinary skill in the art. Briefly, two binders are selected on the basis that they bind substantially different epitopes on CD123, as determined by, e.g., a binding competition assay as in Abdiche Y N et al (2009) Exploring blocking assays using Octet, ProteOn, and Biacore biosensors, Anal Biochem 386:172-80. Alternatively, briefly, as described herein, cell culture supernatants of cells transfected with a first ABPC specific for CD123 are normalized to an antibody expression level of 50 μg/mL, and captured on an anti-human Fc sensor (Forte Bio). A baseline is established using 1× kinetics buffer (Forte Bio), and the sensor is associated with 50 nM of CD123 in 1×PBS (that has been mixed and pre-incubated for 30 min at 37 degrees C. with a second ABPC specific for CD123 transfection supernatant or the first ABPC specific for CD123 transfection supernatant, both normalized to 50 ug/mL) at pH 7.4 for 300 sec to generate an association curve. If the association rate in the presence of the second ABPC specific for CD123 is significantly faster (as calculated by the instrument software, or as seen by an elevated level of association over time) than the association rate in the presence of the first ABPC specific for CD123, then the second ABPC specific for CD123 is deemed to bind a non-overlapping epitope of CD123. Optionally, each antibody is screened for its internazation properties when bound to its epitope on a cell expressing CD123, and well-internalizing antibodies are selected. Assays for determining the internalization rate of a molecule present on the surface of a cell are known to the art. See, e.g., Wiley et al. (1991) J. Biol. Chem. 266: 11083-11094; and Sorkin and Duex (2010) Curr. Protoc. Cell Biol. Chapter, Unit-15.14; Vainshtein et al. (2015) Pharm Res. 32: 286-299. Once selected, heavy and light chain constructs with engineered mutations for heavy and light chain pairing (Spiess et al., "Alternative molecular formats and therapeutic applications of bispecific antibodies," 2015) are synthesized for both arms. Bispecific ABPCs specific for CD123 are produced by co-expression of corresponding heavy and light chain plasmids in, e.g., Expi293 cells. Cell culture supernatants are harvested and subjected to Protein A purification. Heterodimeric ABPCs specific for CD123 are separated from homodimeric species via additional purification steps such as ion exchange chromatography, hydrophobic interaction chromatography, and mixed mode chromatography. The purified pH-engineered CD123×CD123 bispecific, biparatopic ABPCs specific for CD123 are characterized via mass spectrometry to confirm the purity and absence of homodimeric species and size exclusion chromatography to confirm the presence of monomeric antigen-binding protein construct species. For the product antibody, binding to the CD123 is confirmed via Biacore analysis. Other methods of bispecific antibody production are known to the art and could also be used to create a bispecific antibody, e.g., the CD123×CD123 bispecific, biparatopic ABPCs specific for CD123 described herein (e.g., Labrijn et al (2014) "Controlled Fab-arm exchange for the generation of stable bispecific IgG1" Nature Protcols 9:2450-2463, accessed at http://www.nature.com/nprot/journal/v9/n10/abs/nprot.2014.169.html), as would be apparent to one of ordinary skill in the art. Alternatively, instead of a CD123×CD123 ABPC specific for CD123, a pH-engineered CD123× BINDER ABPC specific for CD123 can be constructed using similar methods apparent to one skilled in the art, where BINDER is any antibody that has been published in the art or discovered using methods like those herein or those known in the art (e.g., display-based or immunization-based methods).

Next, exemplary properties of pH-engineered CD123×CD123 ABPCs specific for CD123 can be demonstrated using the methods described herein, with the appropriate control being a control ABPC monospecific or bispecific ABPC specific for CD123. Briefly, it can be shown that, as compared to a control, the pH-engineered CD123×CD123 ABPCs specific for CD123: a) bind in a pH-dependent manner to cells, e.g., bind at a neutral pH but not an acidic pH and b) release from cells in a pH-dependent manner, e.g. bind at a neutral pH and release at an acidic pH and c) show enhanced endolysosomal accumulation in CD123+ cells and d) show increased CD123 antigen density after exposure to CD123+ cells and e) when conjugated to a toxin, show increased cytotoxicity to CD123+ cells and f) when conjugated to a toxin, show increased toxin liberation when incubated with CD123+ cells and g) show decreased half life when exposed to CD123 antigen in a relevant animal model and h) when conjugated to a toxin, show increased efficacy in a mouse xenograft model of CD123+ cells. Similarly, the exemplary properties of pH-engineered CD123× BINDER ABPCs specific for CD123 can be demonstrated using the methods described herein, with the appropriate control being a control ABPC CD123× BINDER bispecific ABPC specific for CD123.

Example 9. Construction and Screening of pH-Engineered CD123 ABPCs

Multiple CD123-binding monoclonal antibodies have been described in the literature and can be used as a template for engineering pH-dependent binding [Kovtun, Yelena, et al. (2018) "A CD123-Targeting Antibody-Drug Conjugate, IMGN632, Designed to Eradicate AML While Sparing Normal Bone Marrow Cells." Blood Advances, American Society of Hematology 2(8) 848-858]. We selected IMGN632 (Heavy chain SEQ ID NO: 1, Light chain SEQ ID NO: 2) as a CD123-binding monoclonal antibody for pH engineering via histidine scanning. Briefly, CDRs in the heavy chain were identified using the methods described by Kabat et al (Kabat et al. (1992) Sequences of Proteins of Immunological Interest, DIANE publishing) and IMGT (Lefranc M P (1999) "The IMGT unique numbering for Immunoglobulins, T cell receptors and Ig-like domains" The Immunologist 7, 132-136), and for each CDR, residues falling under either or both Kabat and IMGT CDR definitions were called as CDR residues. To generate pH-dependent sequence variants, individual amino acid residues within the heavy chain CDRs were systematically substituted with a histidine, one at a time (MYT1252-MYT1292). In cases where the starting CDR residue was a histidine, it was mutated to an alanine. Antibody variants with only one histidine or alanine mutation in a heavy chain CDR were generated by co-transfection of Expi293 cells with a) one heavy chain sequence variant, and b) the corresponding starting ABPC light chain using methods known to the art. After allowing for four days of protein expression, cell culture supernatants were collected, quantified by SDS-PAGE analysis (FIG. 1), and the pH dependence of the variant was evaluated using biolayer interferometry (BLI) on an Octet RED 384 instrument. For constructs MYT1252, MYT1254-MYT1287, and MYT1289-1292, 104, of cell culture supernatant was diluted into 1904, of 1×PBST pH 7.4. For MYT1253 and MYT1288 254, and 504, of cell culture supernatant was diluted into 1754, and 1504, respectively. This resulted in a high concentration of 68 μg/mL, a low concentration of 17 μg/mL and an average concentration of 33 μg/mL. The resulting diluted supernatants were then captured on an anti-human Fc sensor (Forte Bio). A baseline was established using 1×PBST (50 mM Potassium Phosphate Buffer+150 mM NaCl+0.05% Tween 20) pH 7.4, and the sensor was associated with 50 nM of CD123 (CD123 Protein, His Tag, Acro Biosciences Cat. No. ILA-H52H6, Lot No. 1741d-89CF1-KB) in 1×PBST pH 7.4 for 120 sec to generate an association curve. In the dissociation phase, the antibody-antigen complex on the sensor was exposed to 1×PBST pH 7.4 for 300-600 sec. Baseline, association, and dissociation were repeated using 1×PBST pH 5.4 throughout in a separate condition. Association and dissociation phase curves were examined for the starting ABPC antibody (with no substitutions) and each corresponding antibody variant at pH 5.4 and pH 7.4 to inform on two criteria: a) enhanced dissociation (i.e., higher koff values) at pH 5.4 due to histidine or alanine substitution compared to the starting ABPC, (with no substitutions), and b) reduced dissociation at pH 7.4 (i.e., lower koff values) compared to pH 5.4 in the antibody variant itself and with the starting ABPC (with no substitutions). Heavy chain variants that showed either enhanced dissociation at pH 5.4 or reduced dissociation at pH 7.4 or both (as compared to the starting ABPC), as shown in FIG. 2 were selected for further analysis (e.g., MYT1253, MYT1254, MYT1255, MYT1256, MYT1259, MYT1261, MYT1265, MYT1279, MYT1285, MYT1286, MYT1287, MYT1288, MYT1289, MYT1290, MYT1291). It was also noted that while some histidine and alanine mutations obliterated CD123 binding (e.g., MYT1281), others were tolerated with little (e.g., less than 1-fold change in dissociation constant $K_D$ or dissociation rate) or no change in CD123 binding kinetics (e.g., MYT1252, MYT1257, MYT1258, MYT1260, MYT1262, MYT1263, MYT1266, MYT1267, MYT1268, MYT1269, MYT1270, MYT1271, MYT1272, MYT1273, MYT1274, MYT1275, MYT1276, MYT1277, MYT1278, MYT1280, MYT1282, MYT1283, MYT1284, MYT1292).

Especially because histidine is a large, positively charged amino acid, these variants with no change were noted as positions in the heavy chain that may tolerate a wide range of mutations and lead to antibodies with different sequence but similar binding properties, a designation that is not otherwise apparent.

Example 10. Construction and Screening of pH-Engineered CD123 ABPCs

Figure 4:
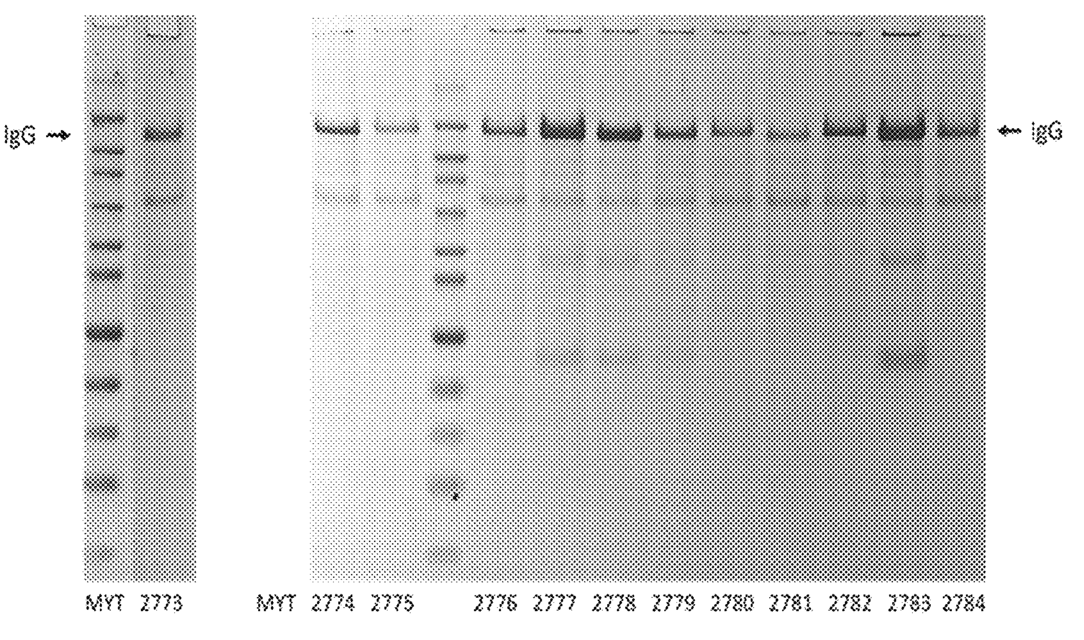
FIG. 4: SDS PAGE for IMGN632 histidine scanning and alanine scanning. Expi293 cell culture supernatants post-harvest were loaded on non-reduced SDS PAGE gels to confirm expression of IMGN632 and histidine scanning and alanine scanning variants. Arrows show the corresponding size for an IgG on a non-reduced SDS PAGE gel. MYT2773-MYT2799 are IMGN632 light chain histidine scanning and alanine scanning variants.
Figure 4:
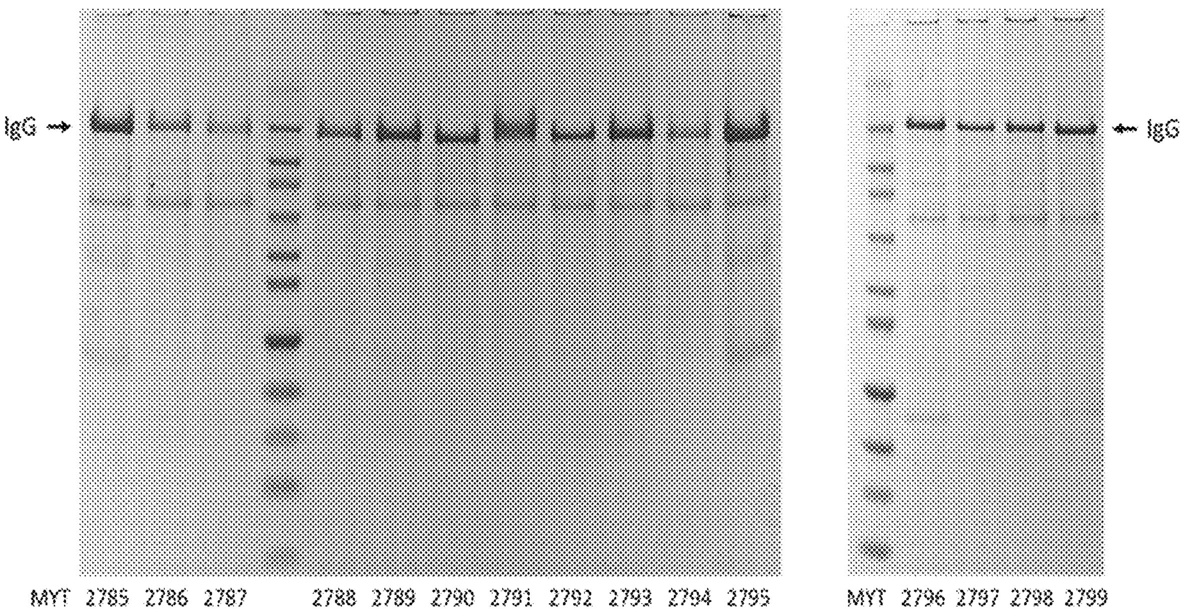
Figure 5A:
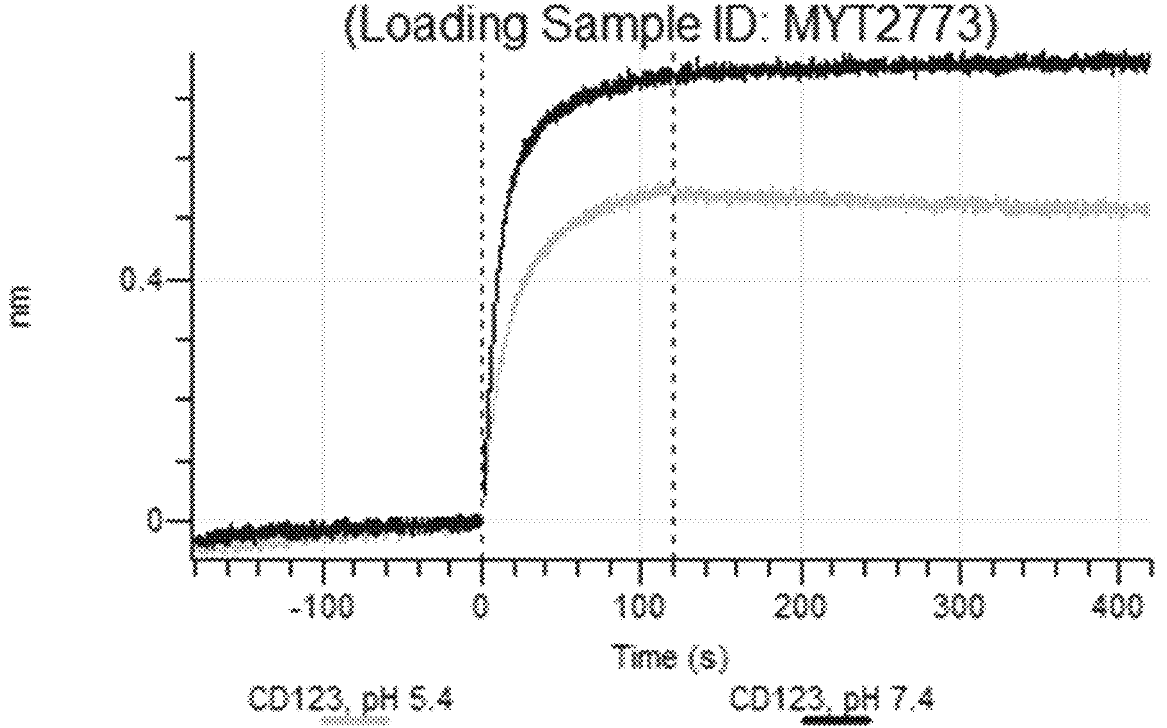
FIGS. 5*a* to 5*aa*: Binding of IMGN632 starting ABPC and histidine scanning and alanine scanning variants to CD123 by biolayer interferometry. MYT2773-MYT2799, light chain histidine scanning and alanine scanning variants of IMGN632, were captured on anti-human Fc biosensors and associated with CD123 at low pH or high pH, as specified in the figures.
Figure 5B:
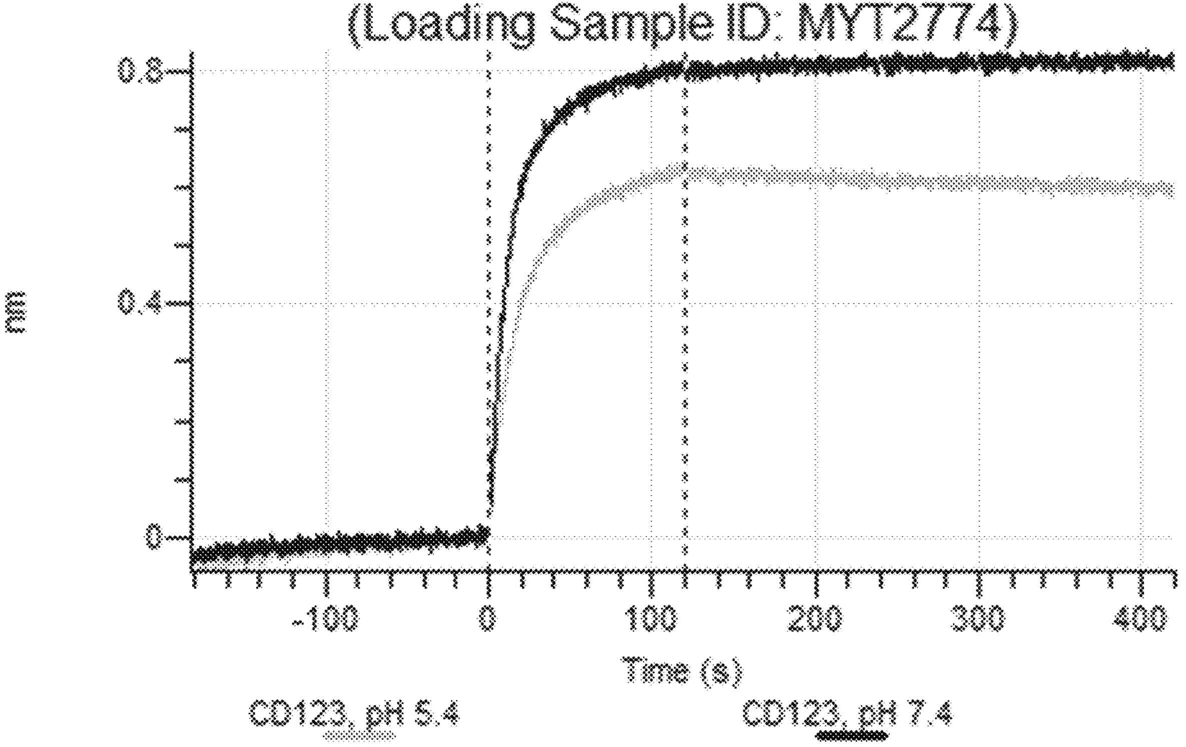
Figure 5C:
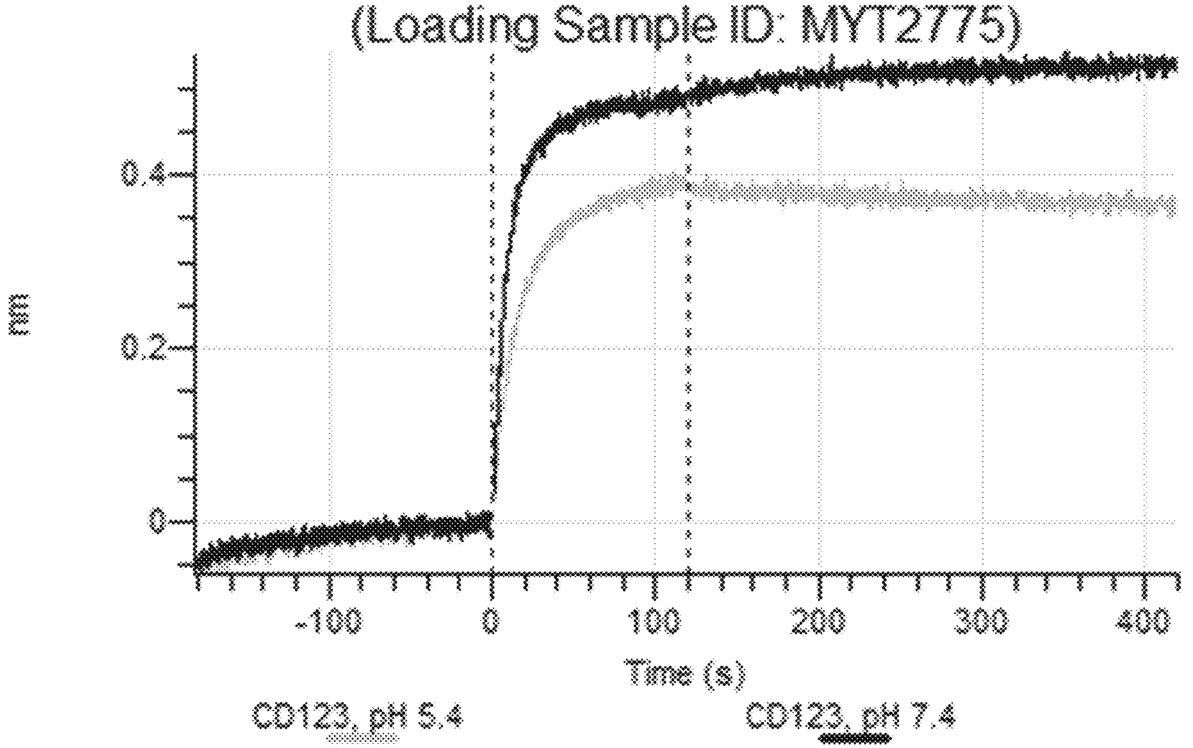
Figure 5D:
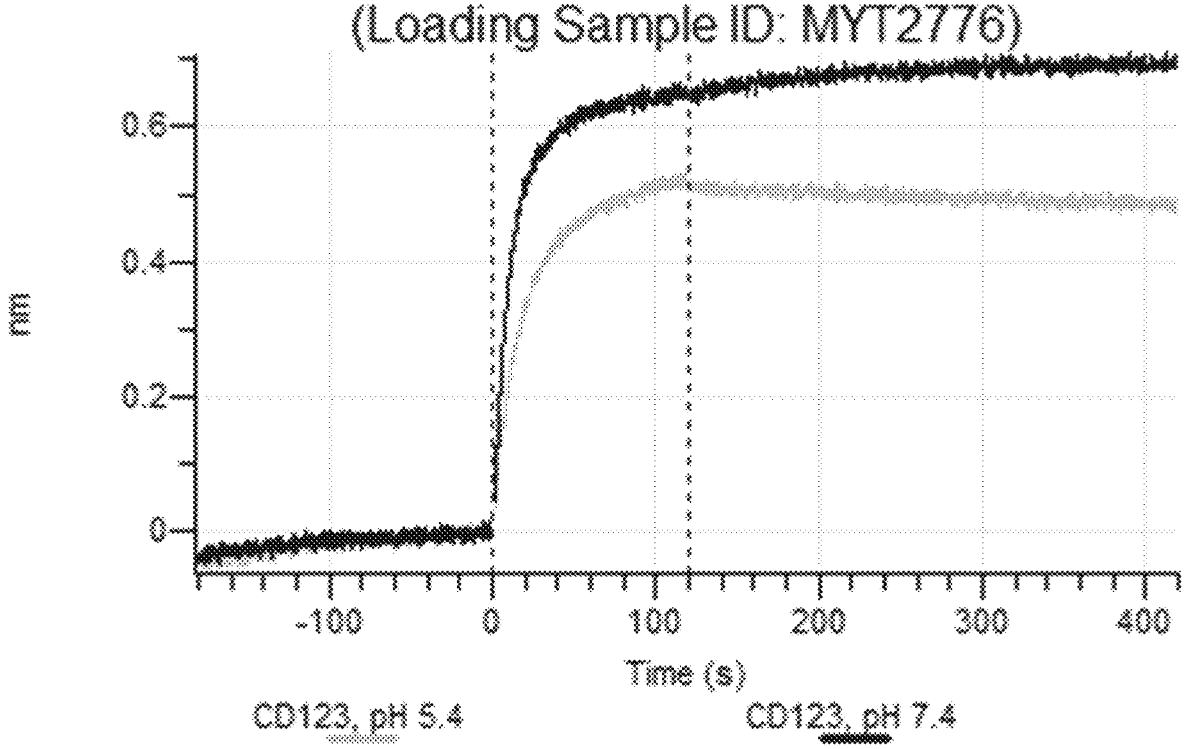
Figure 5E:
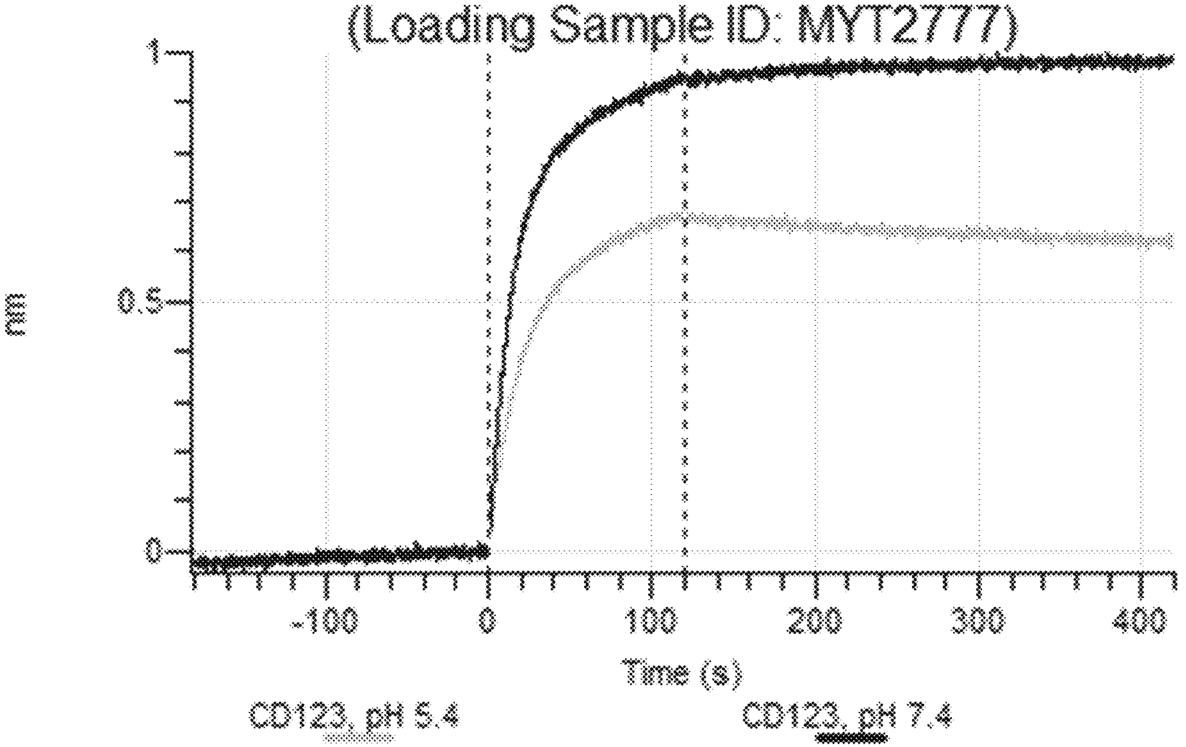
Figure 5F:
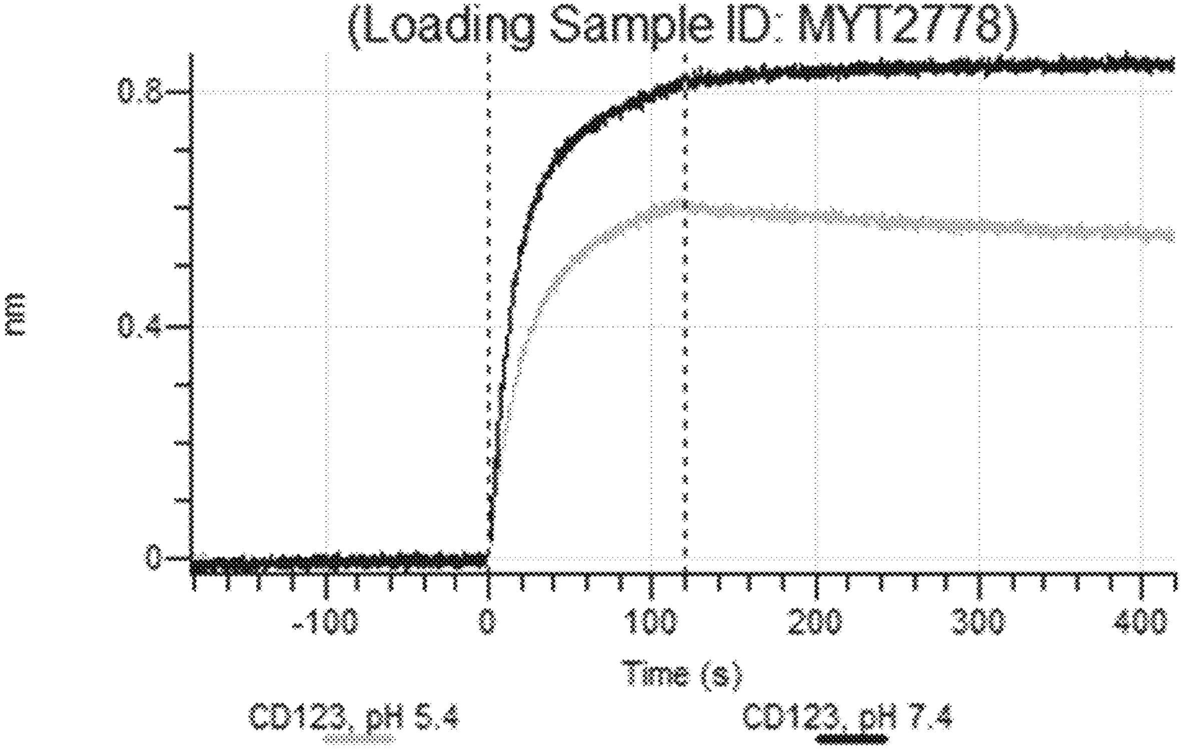
Figure 5G:
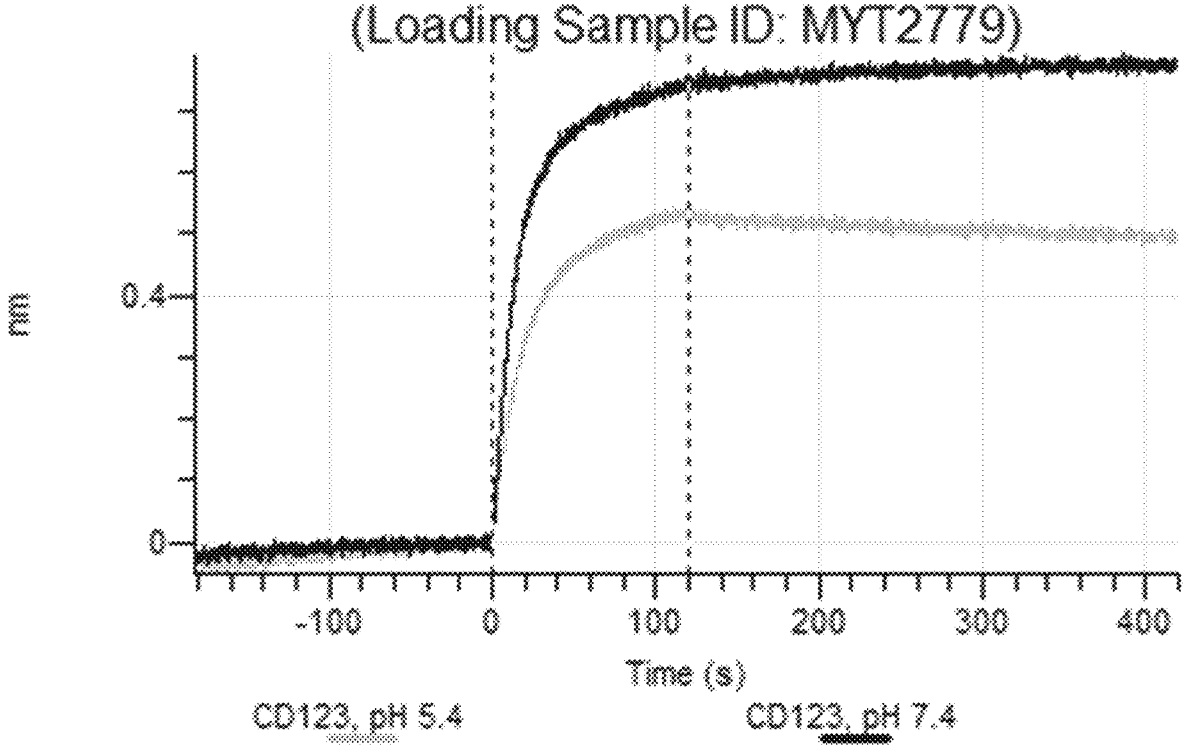
Figure 5H:
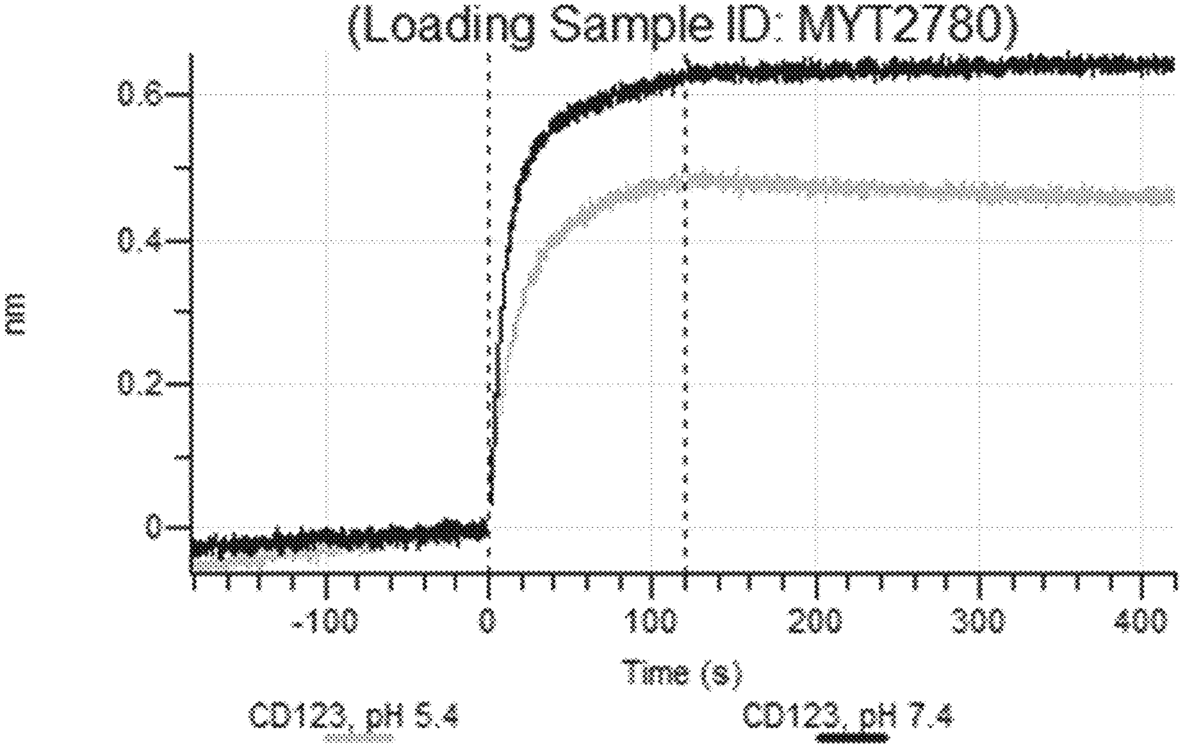
Figure 5I:
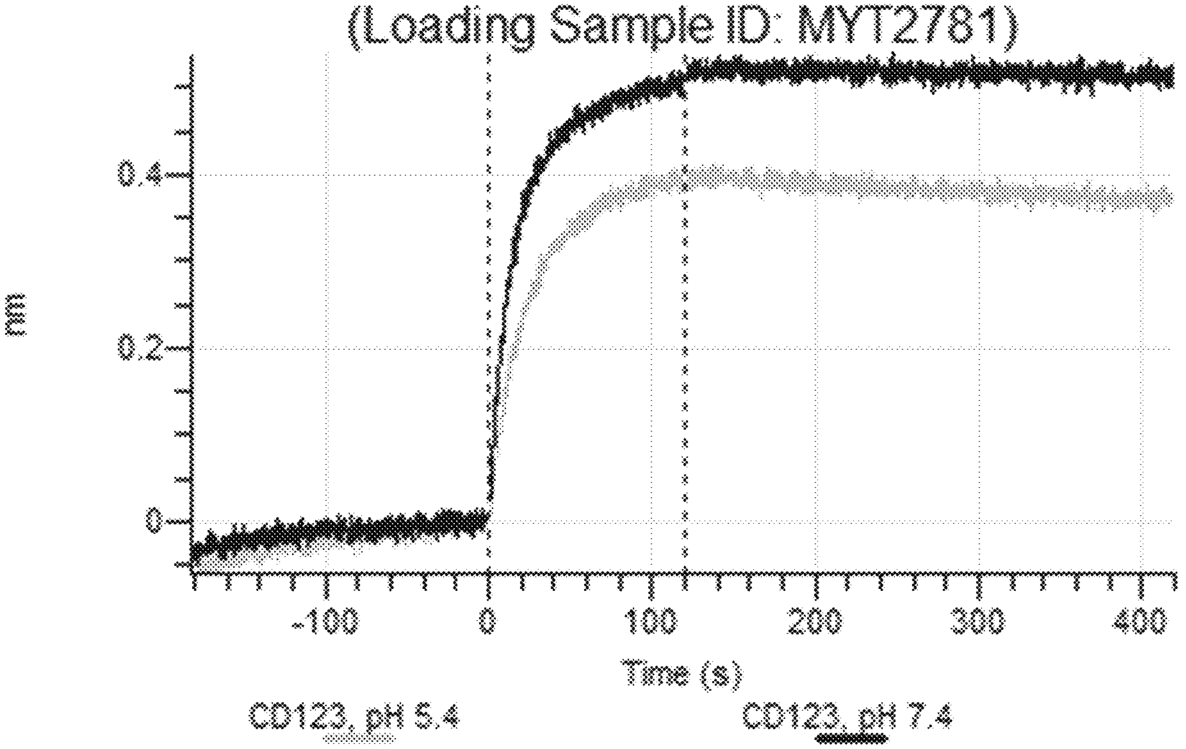
Figure 5J:
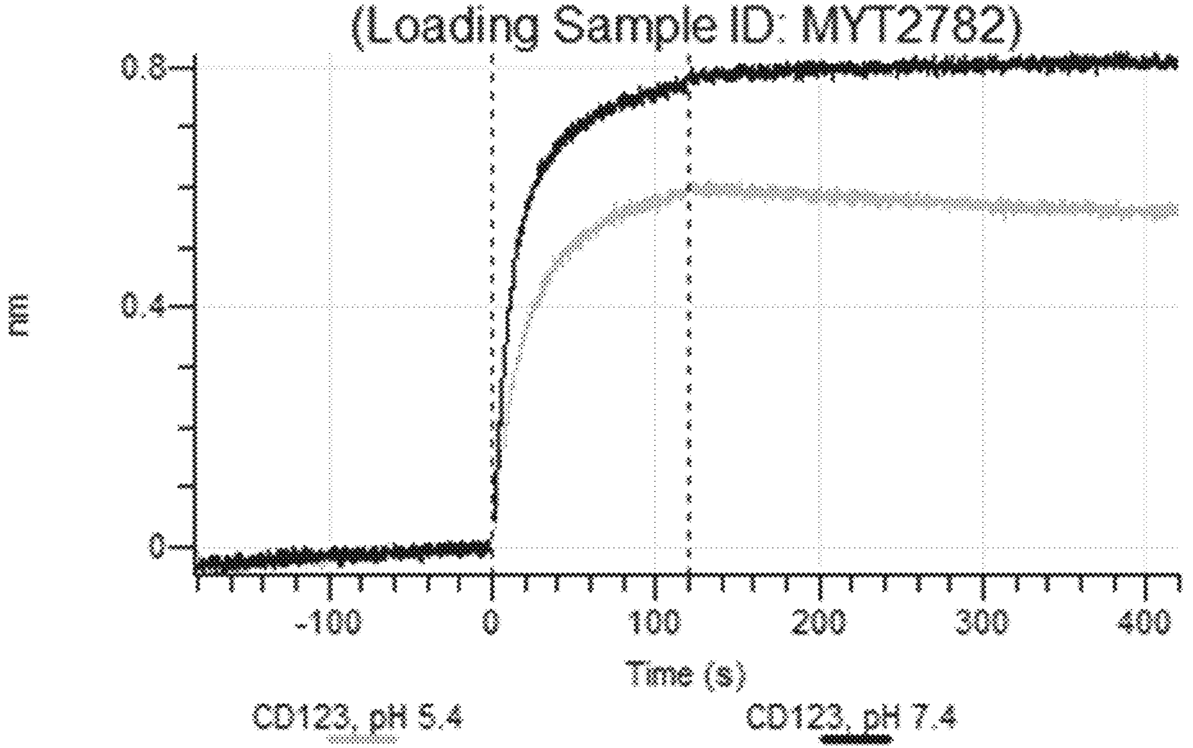
Figure 5K:
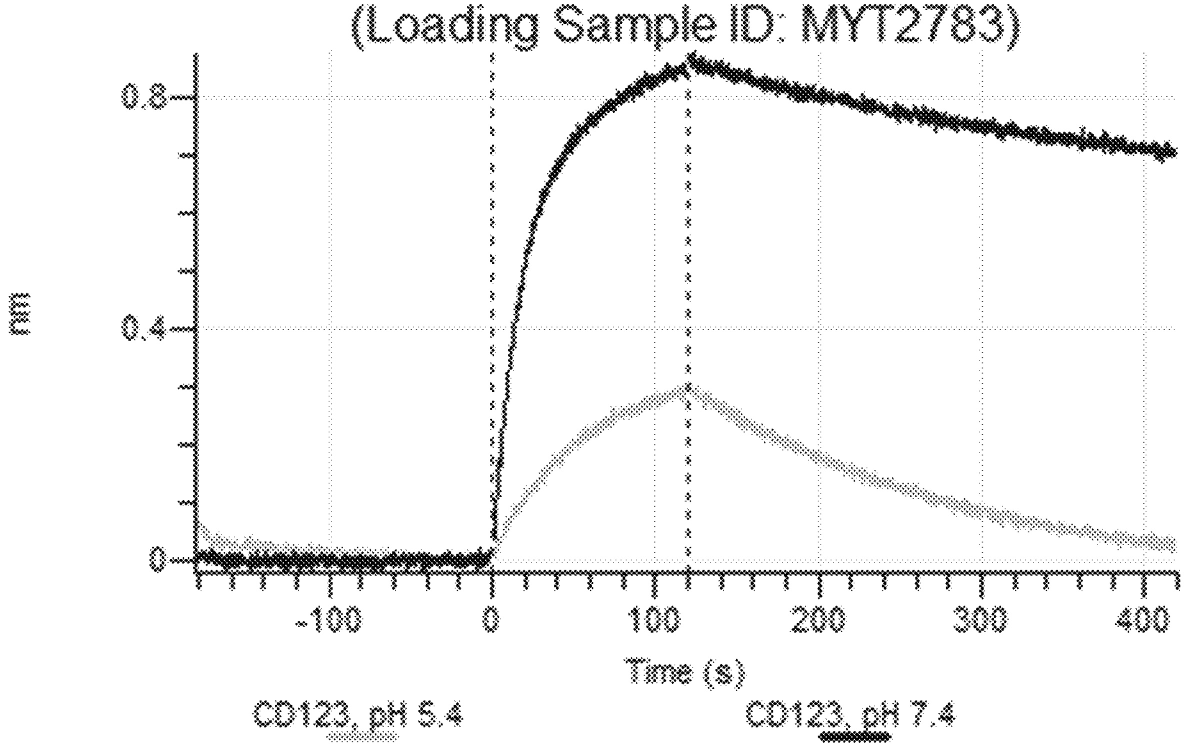
Figure 5L:
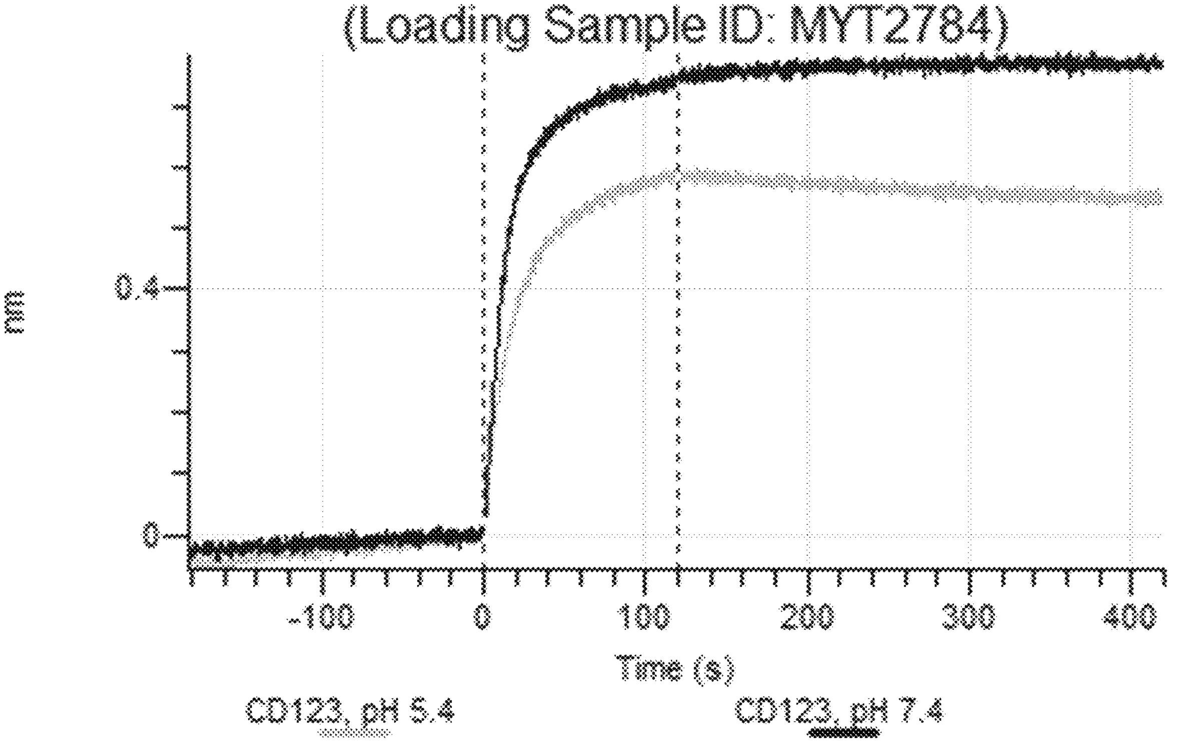
Figure 5M:
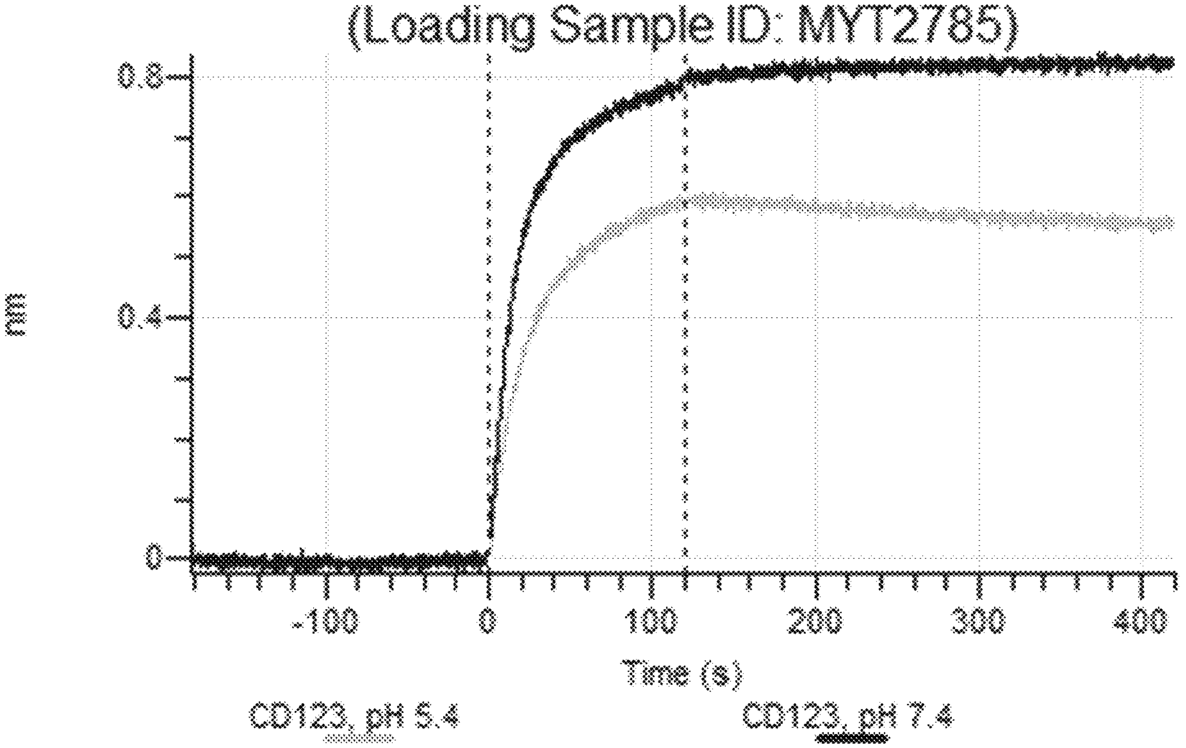
Figure 5N:
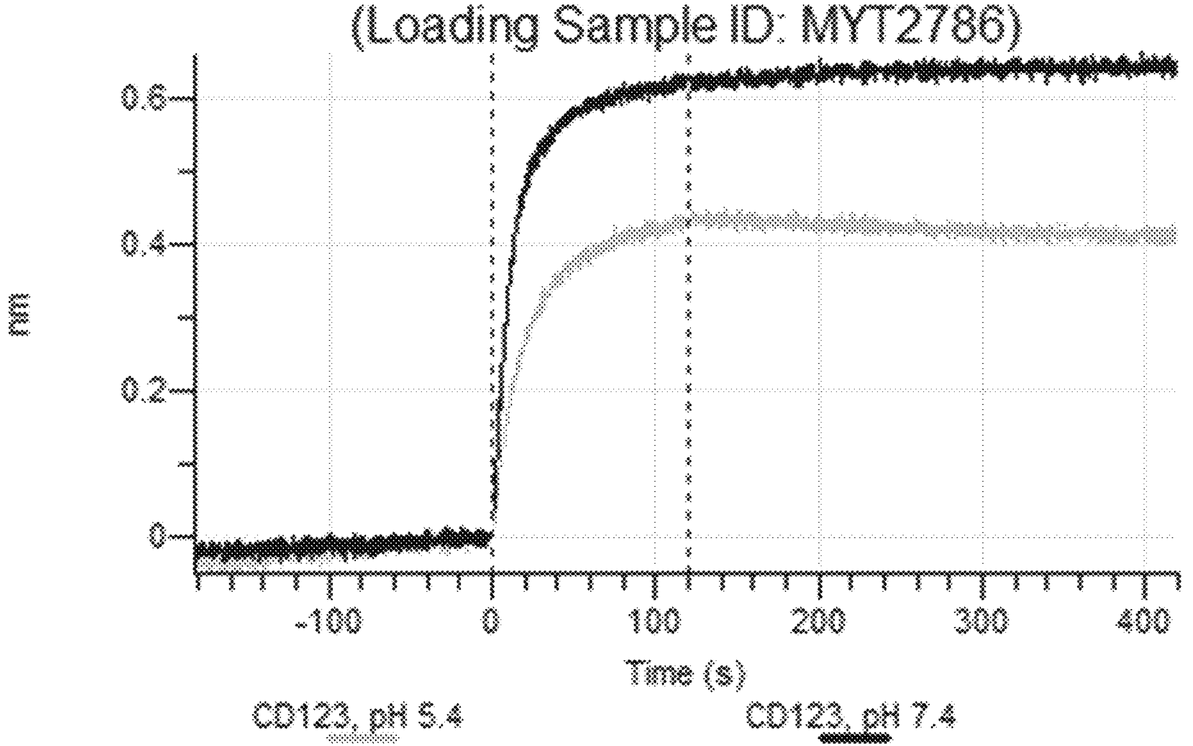
Figure 5O:
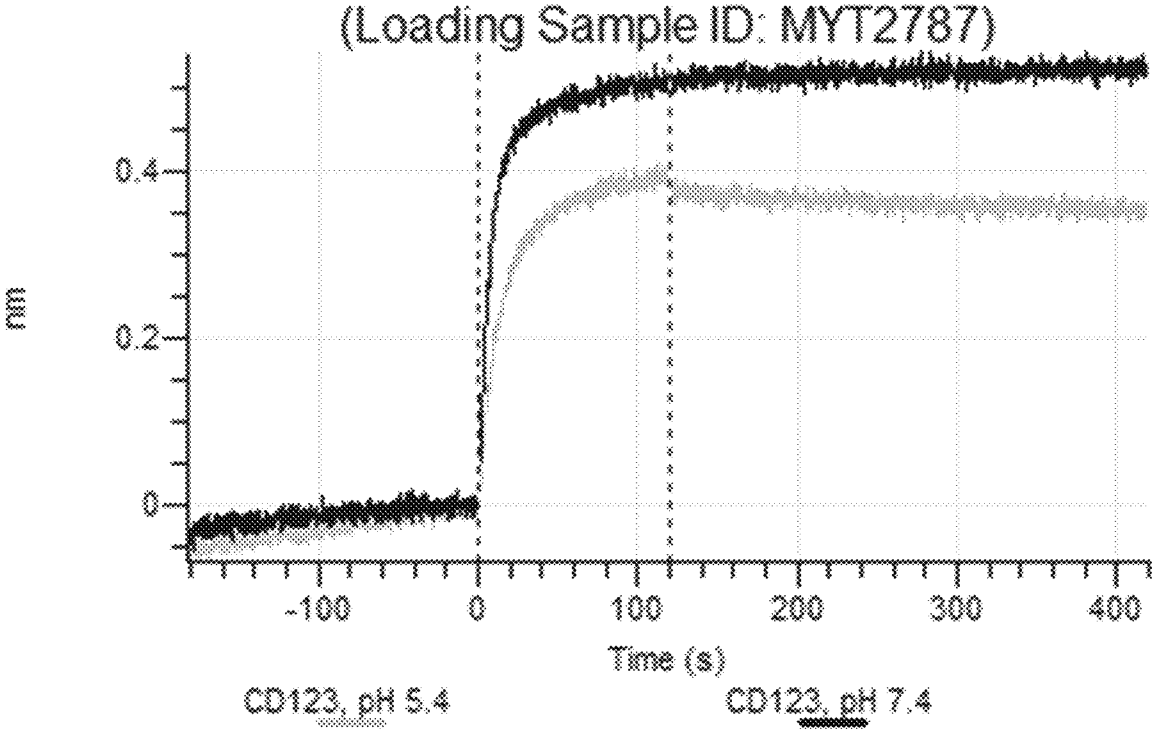
Figure 5P:
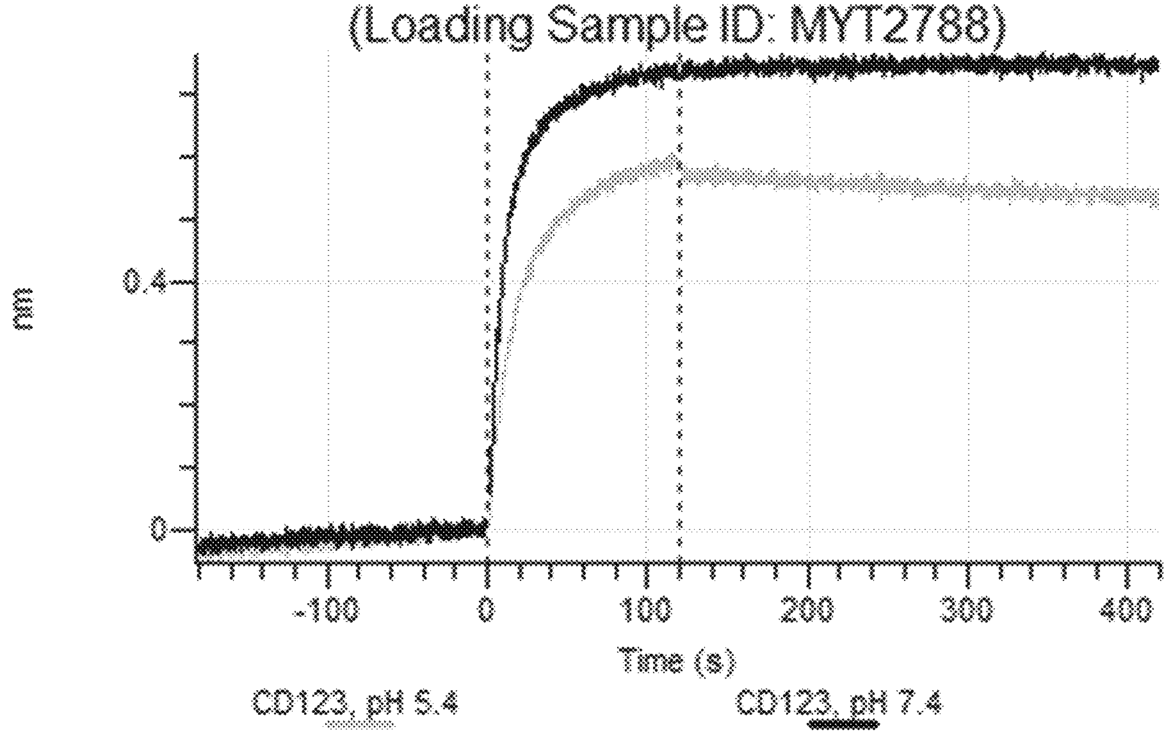
Figure 5Q:
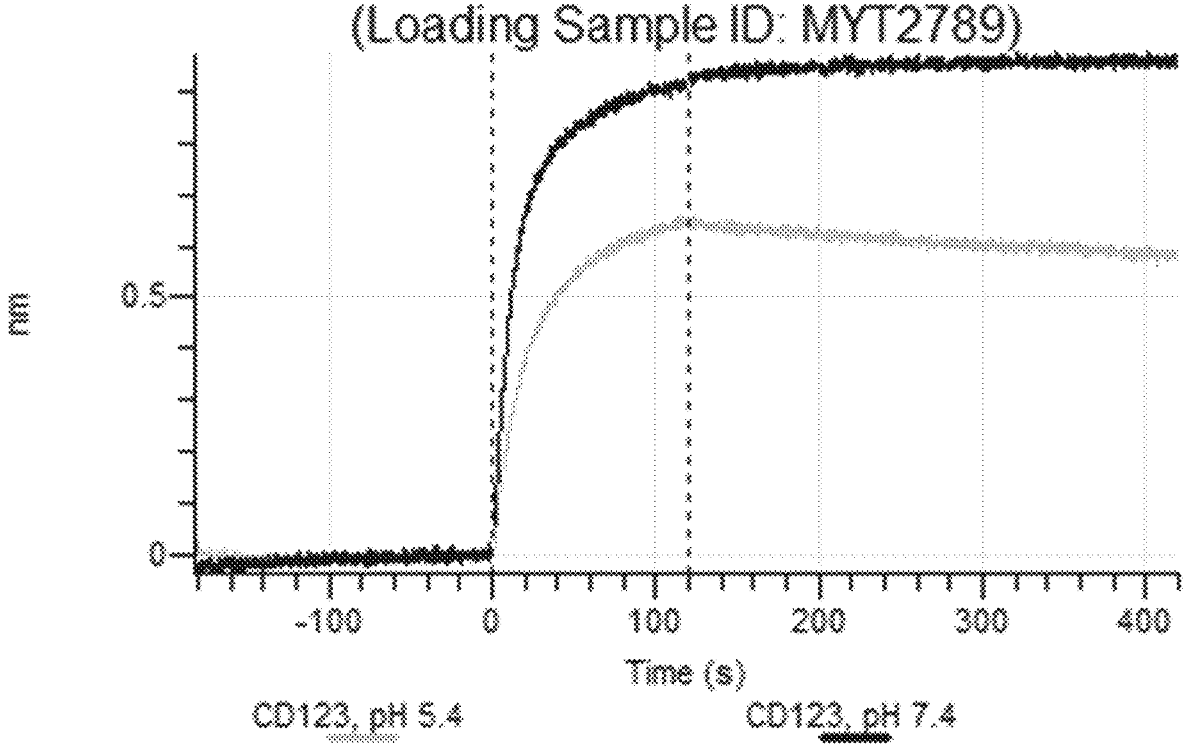
Figure 5R:
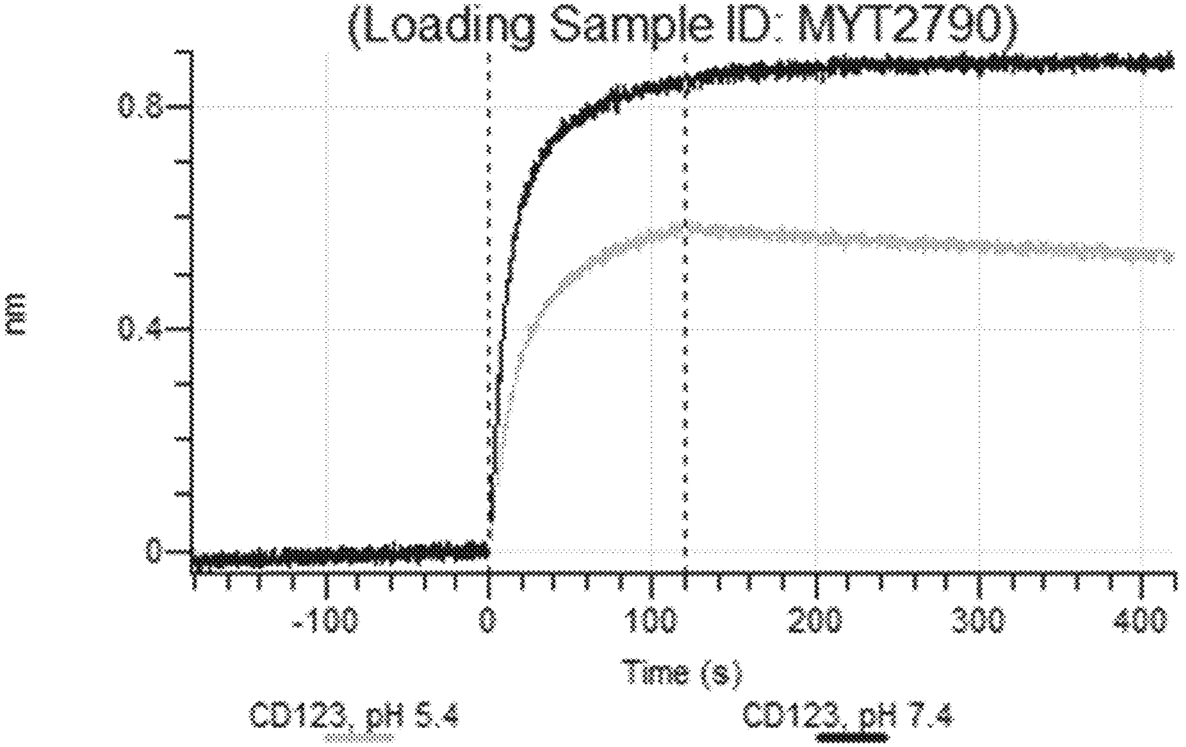
Figure 5S:
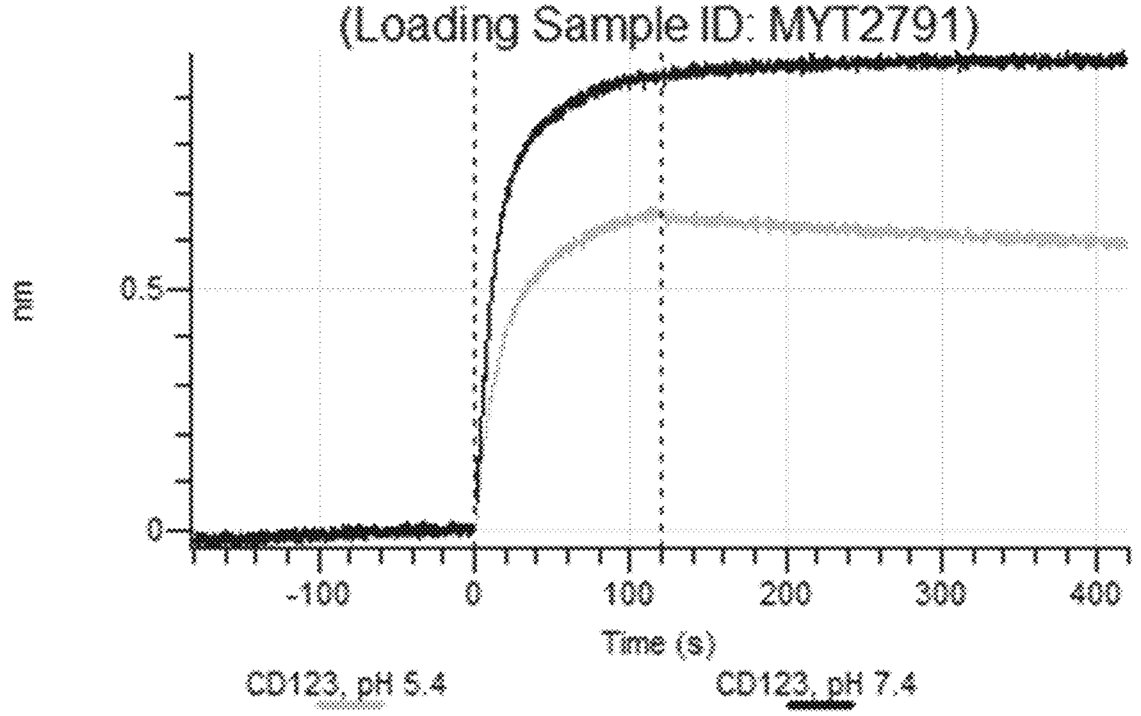
Figure 5T:
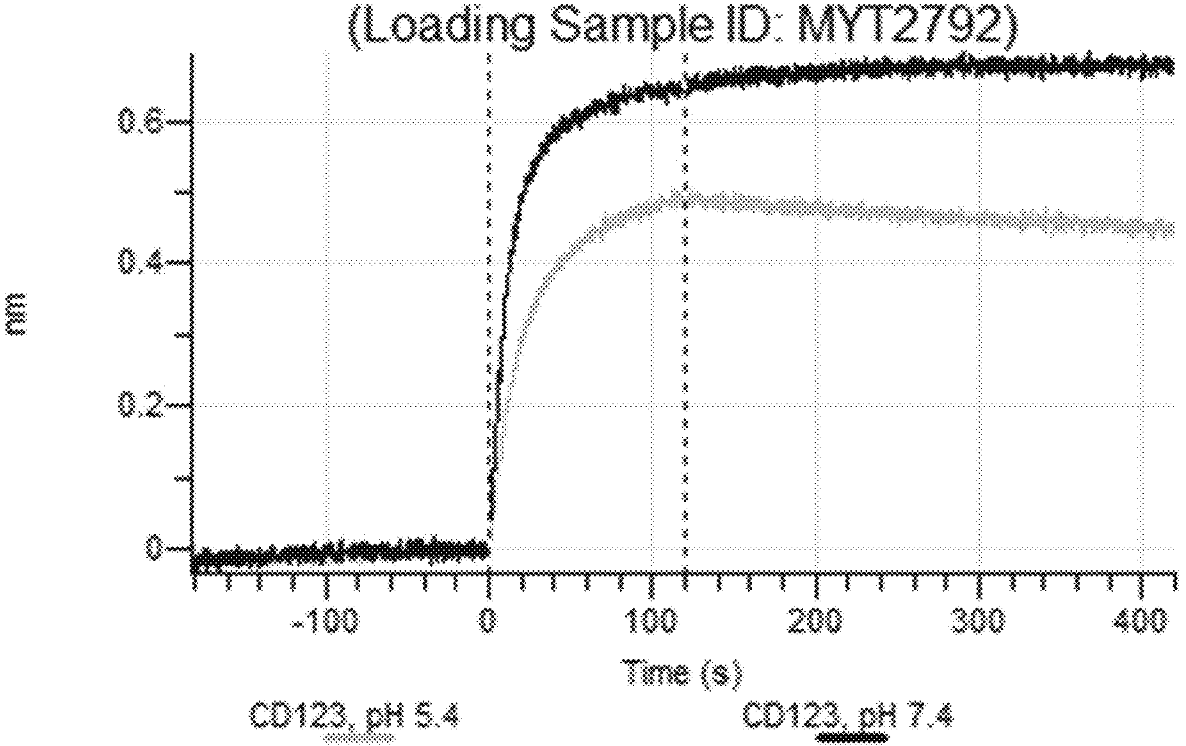
Figure 5U:
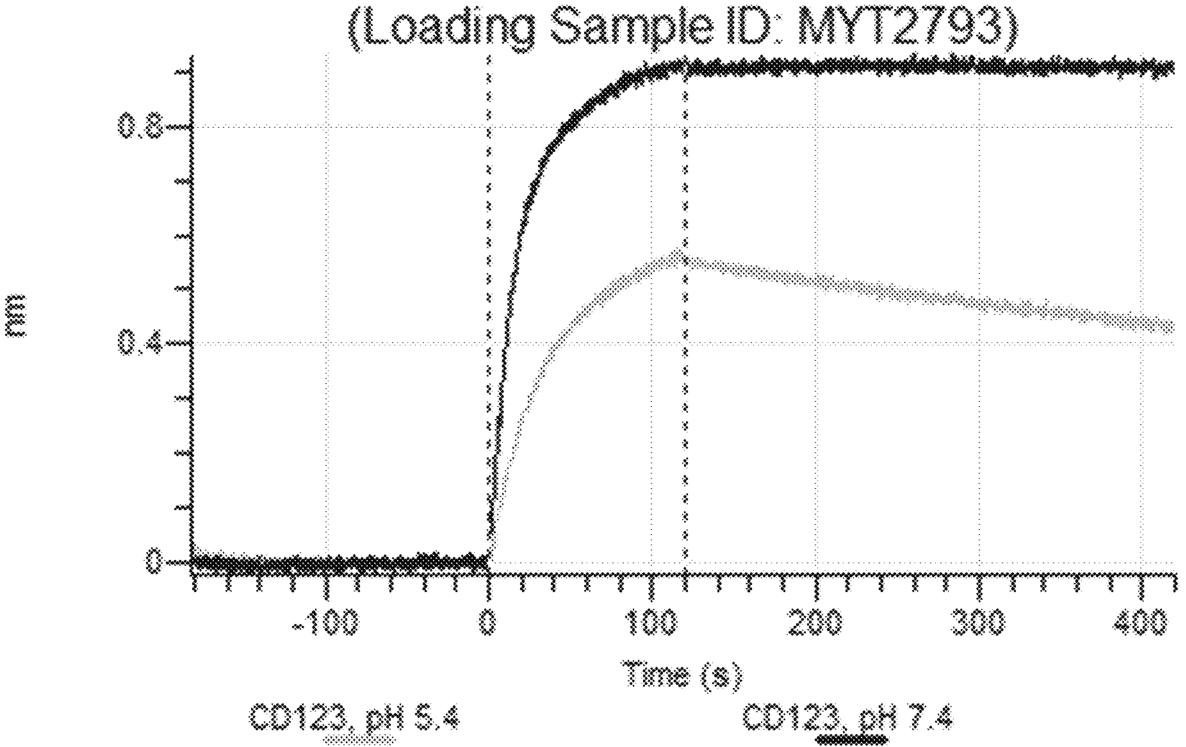
Figure 5V:
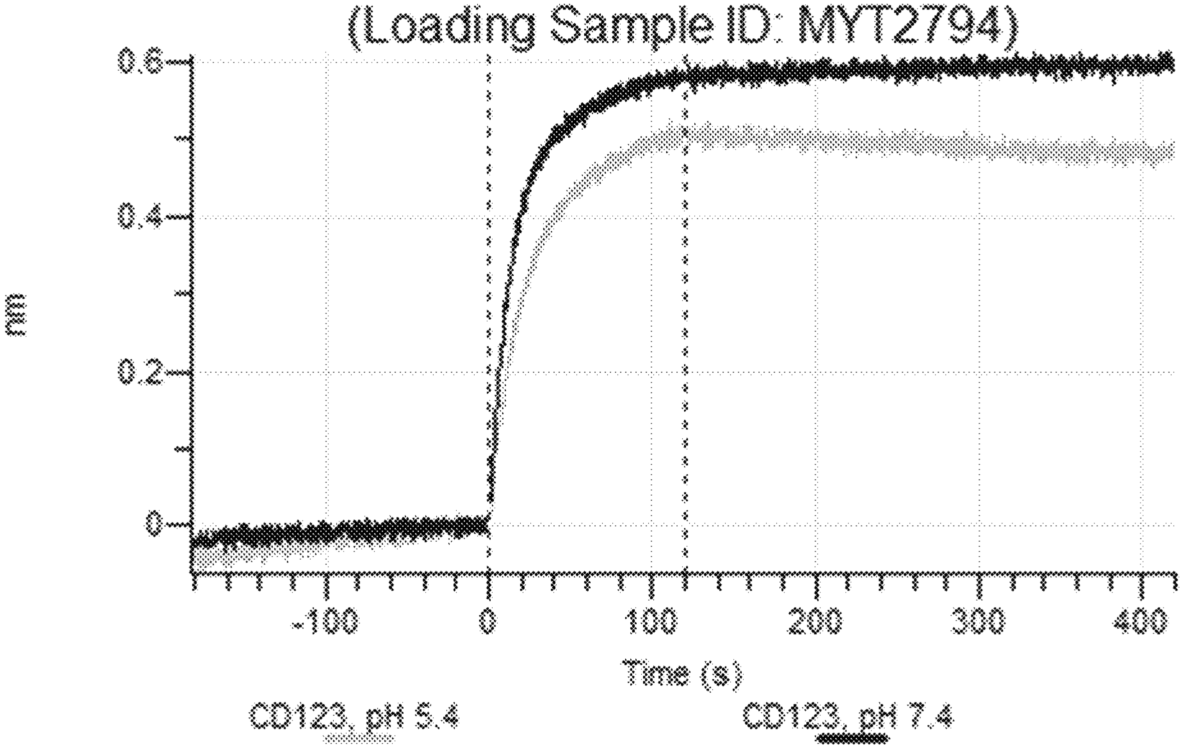
Figure 5W:
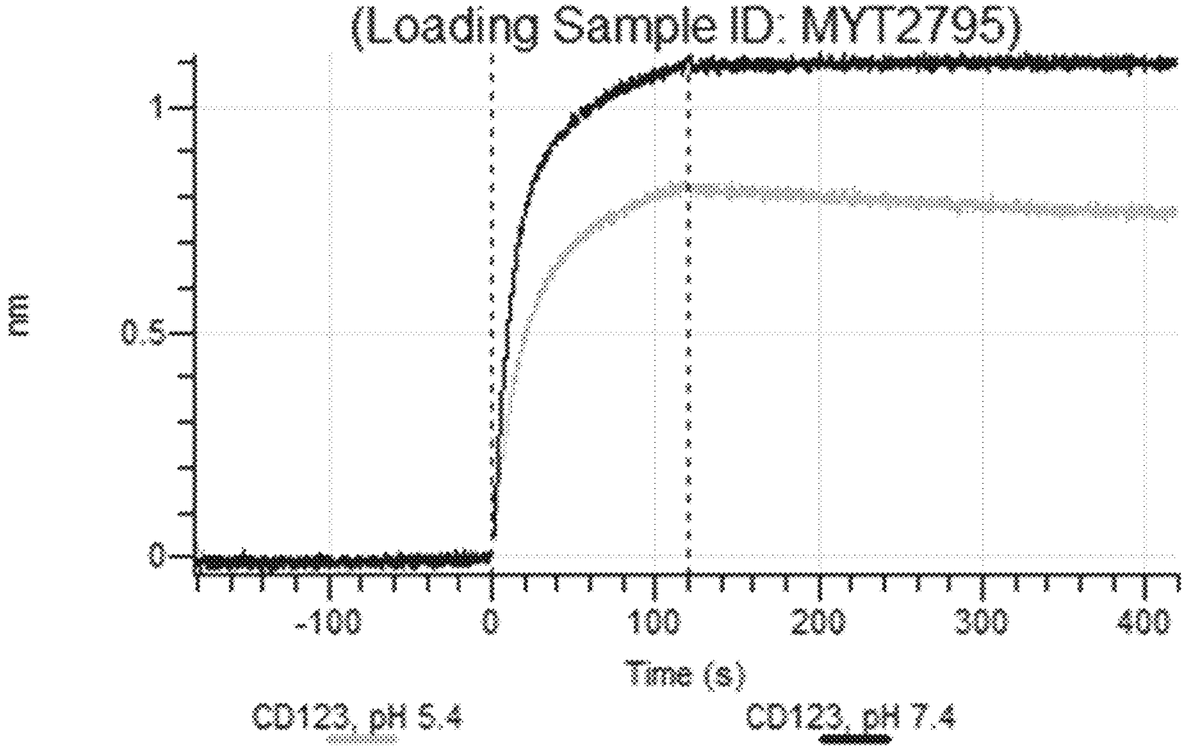
Figure 5X:
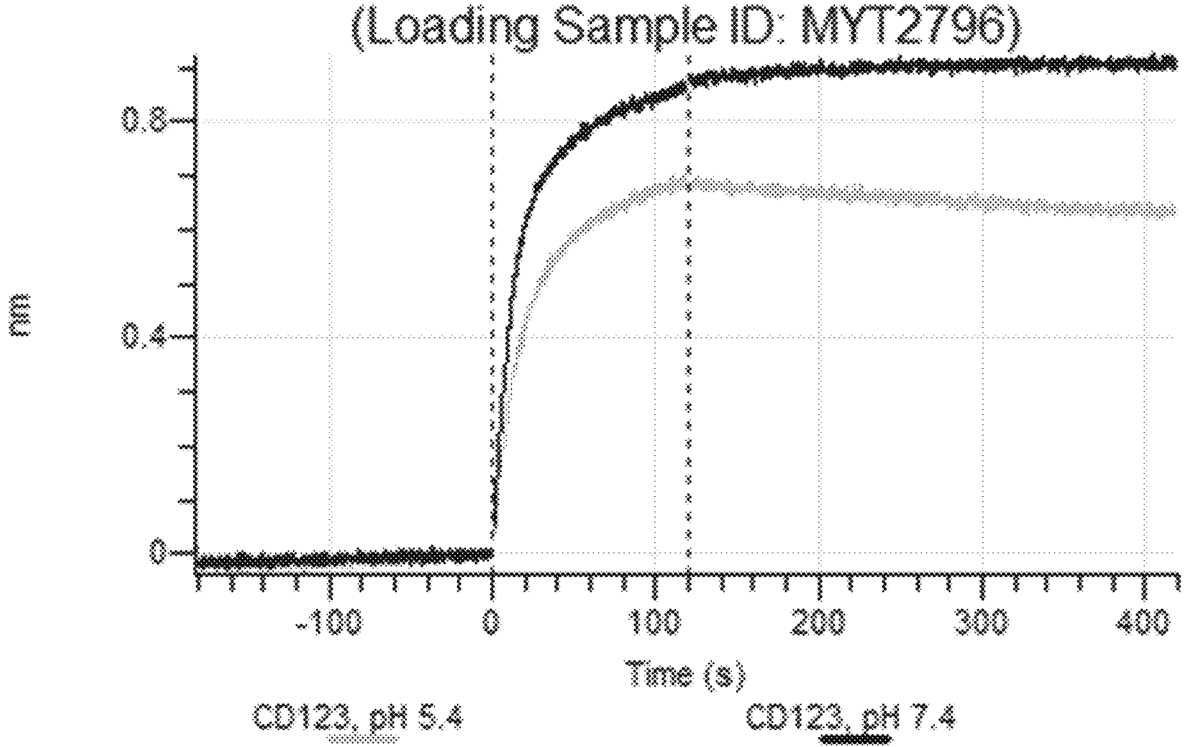
Figure 5Y:
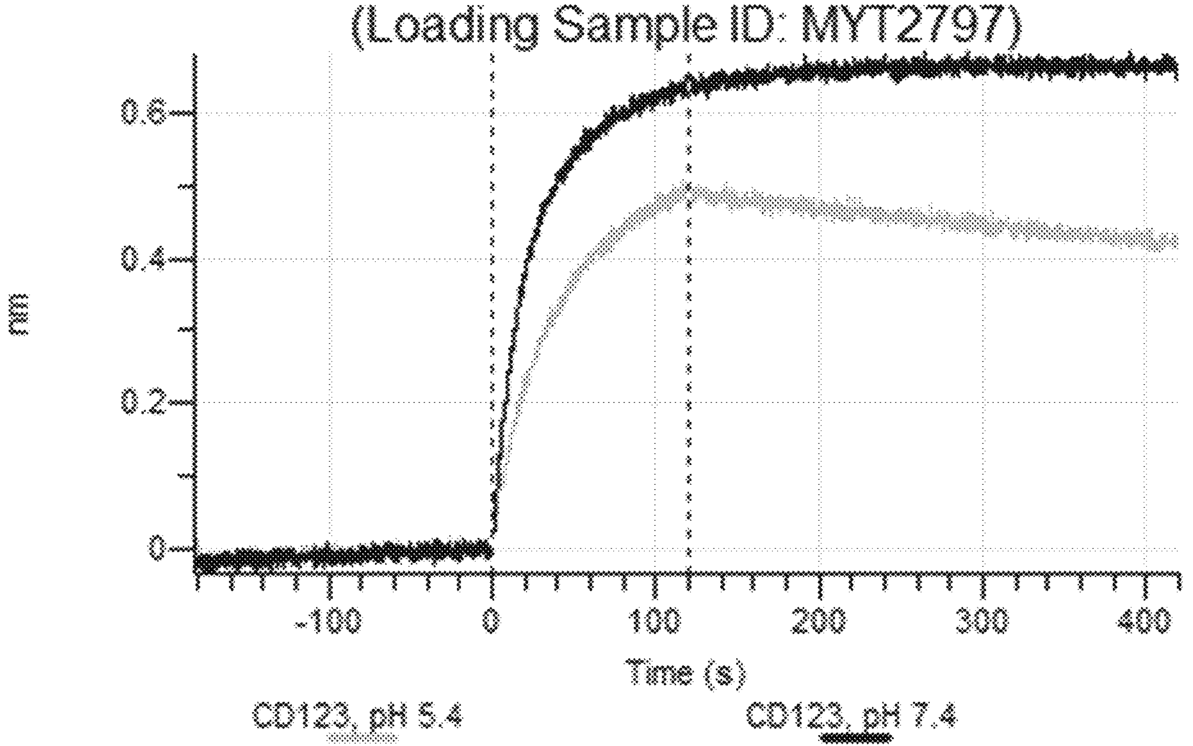
Figure 5Z:
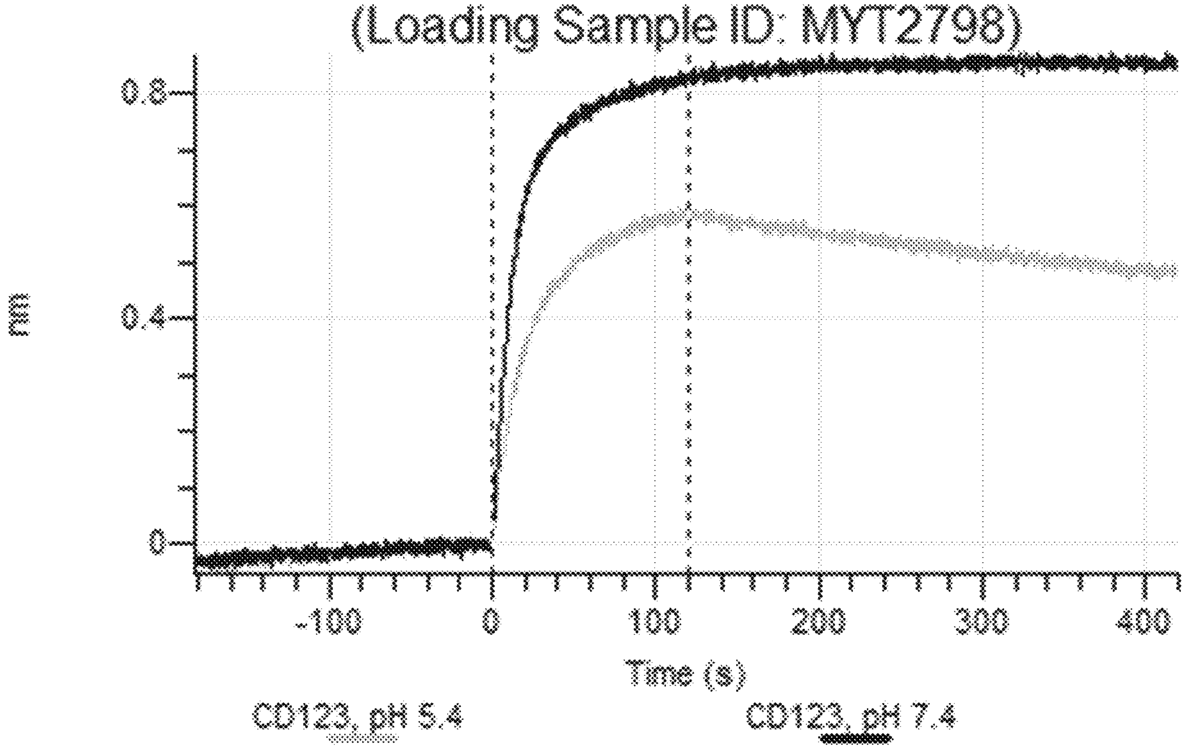
Figure 5A:
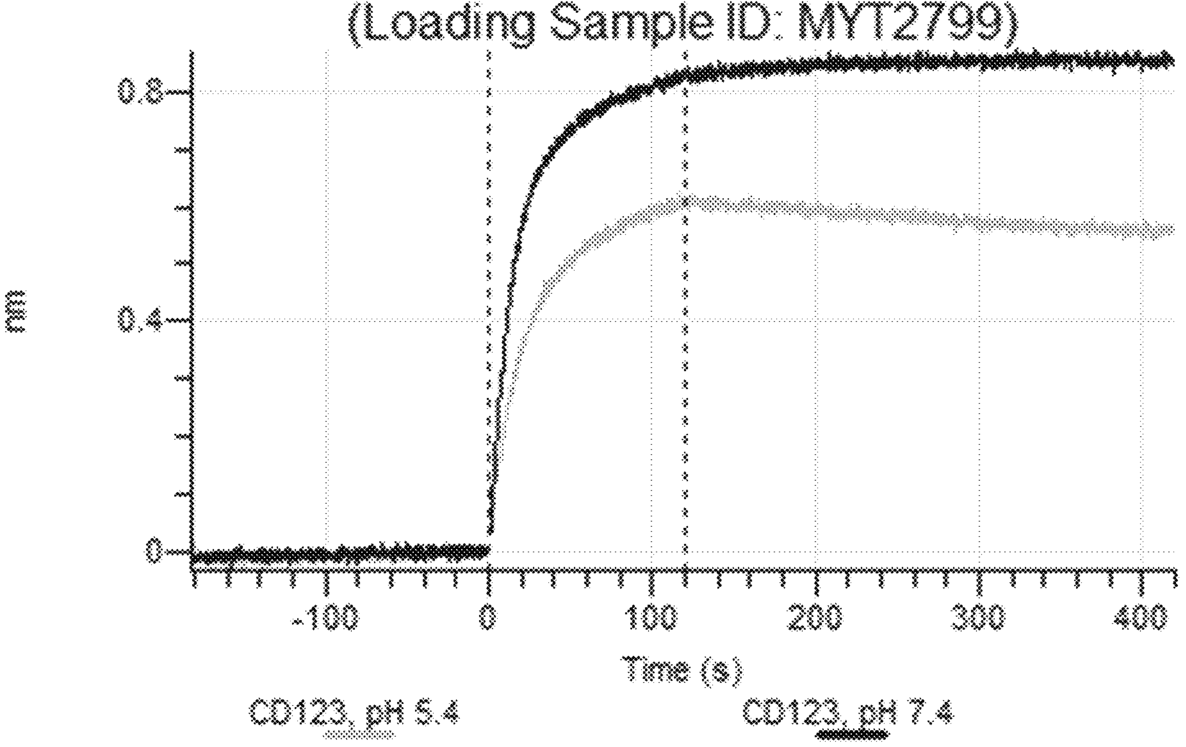

Multiple CD123-binding monoclonal antibodies have been described in the literature and can be used as a template for engineering pH-dependent binding [Kovtun, Yelena, et al. (2018) "A CD123-Targeting Antibody-Drug Conjugate, IMGN632, Designed to Eradicate AML While Sparing Normal Bone Marrow Cells." Blood Advances, American Society of Hematology 2(8) 848-858]. We selected IMGN632 (Heavy chain SEQ ID NO: 1, Light chain SEQ ID NO: 2) as a CD123-binding monoclonal antibody for pH engineering via histidine scanning. Briefly, CDRs in the light chain were identified using the methods described by Kabat et al (Kabat et al. (1992) Sequences of Proteins of Immunological Interest, DIANE publishing) and IMGT (Lefranc M P (1999) "The IMGT unique numbering for Immunoglobulins, T cell receptors and Ig-like domains" The Immunologist 7, 132-136), and for each CDR, residues falling under either or both Kabat and IMGT CDR definitions were called as CDR residues. To generate pH-dependent sequence variants, individual amino acid residues within the light chain CDRs were systematically substituted with a histidine, one at a time (MYT2773-MYT2799). In cases where the starting CDR residue was a histidine, it was mutated to an alanine. Antibody variants with only one histidine or alanine mutation in a light chain CDR were generated by co-transfection of Expi293 cells with a) one light chain sequence variant, and b) the corresponding starting ABPC heavy chain using methods known to the art. After allowing for four days of protein expression, cell culture supernatants were collected, quantified by SDS-PAGE analysis (FIG. 4), and the pH dependence of the variant was evaluated using biolayer interferometry (BLI) on an Octet RED 96e instrument. Briefly, cell culture supernatants were diluted based on qualitative expression level of the variant determined by visual examination of SDS-PAGE gels, 5 μL of cell culture supernatant was diluted into 195 μL of 1×PBST, pH 7.4 for high expressors, 25 μL of cell culture supernatant was diluted into 175 μL of 1×PBST, pH 7.4 for medium expressors and 100 μL of cell culture supernatant was diluted into 100 μL of 1×PBST, pH 7.4 for low expressors for loading onto the sensor tips. Diluted supernatants were then captured on an anti-human Fc sensor (Forte Bio). A baseline was established using 1×PBST (50 mM Potassium Phosphate Buffer+150 mM NaCl+0.05% Tween 20) pH 7.4, and the sensor was associated with 50 nM of CD123 protein (Acro Biosciences Cat. No. ILA-H52H6, Lot No. 1741d-89CF1-KB) in 1×PBST pH 7.4 for 120 sec to generate an association curve. In the dissociation phase, the antibody-antigen complex on the sensor was exposed to 1×PBST pH 7.4 for 300-600 sec. Baseline, association, and dissociation were repeated using 1×PBST pH 5.4 throughout in a separate condition. Association and dissociation phase curves were examined for the starting ABPC antibody (with no substitutions) and each corresponding antibody variant at pH 5.4 and pH 7.4 to inform on two criteria: a) enhanced dissociation (i.e., higher koff values) at pH 5.4 due to histidine or alanine substitution compared to the starting ABPC (with no substitutions), and b) reduced dissociation at pH 7.4 (i.e., lower koff values) compared to pH 5.4 in the antibody variant itself and with the starting ABPC (with no substitutions). Light chain variants that showed either enhanced dissociation at pH 5.4 or reduced dissociation at pH 7.4 or both (as compared to the starting ABPC), as shown in FIG. 5 were selected for further analysis (e.g., MYT2783, MYT2789, MYT2793, MYT2796, MYT2797, and MYT2798). It was also noted that some histidine and alanine mutations were tolerated with little (e.g., less than 1-fold change in dissociation constant $K_D$ or dissociation rate) or no change in MET binding kinetics (e.g., MYT2773, MYT2774, MYT2775, MYT2776, MYT2777, MYT2778, MYT2779, MYT2780, MYT2781, MYT2782, MYT2784, MYT2785, MYT2786, MYT2787, MYT2788, MYT2790, MYT2791, MYT2792, MYT2794, MYT2795, and MYT2799).

Especially because histidine is a large, positively charged amino acid, these variants with no change were noted as positions in the light chain that may tolerate a wide range of mutations and lead to antibodies with different sequence but similar binding properties, a designation that is not otherwise apparent.

Example 11. Construction and Screening of pH-Engineered CD123 ABPCs

Figure 7:
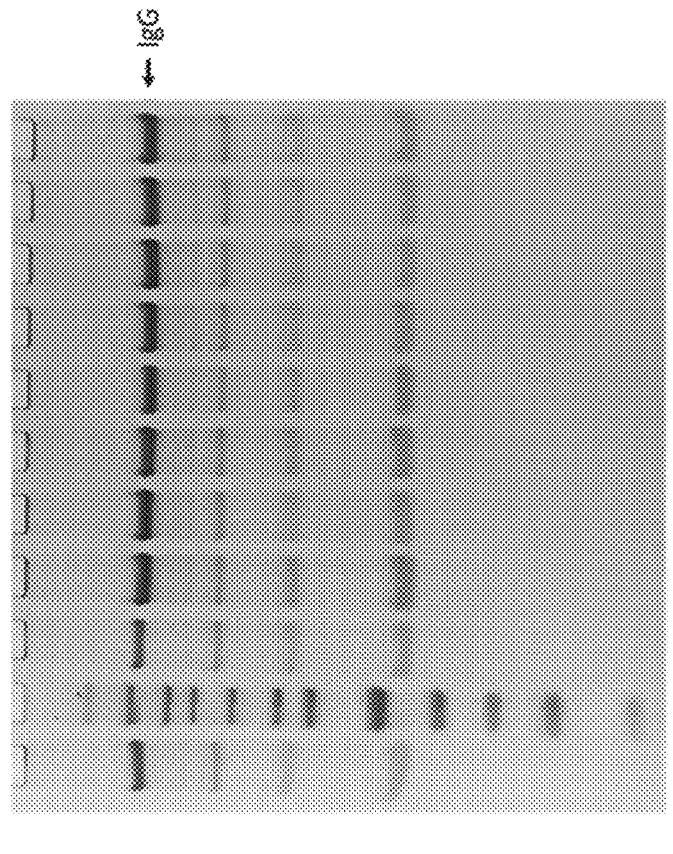
FIG. 7: SDS PAGE for IMGN632 histidine scanning and alanine scanning. Expi293 cell culture supernatants post-harvest were loaded on non-reduced SDS PAGE gels to confirm expression of IMGN632 histidine scanning and alanine scanning variants. Arrows show the corresponding size for an IgG on a non-reduced SDS PAGE gel. MYT2753 to MYT2772 are IMGN632 heavy chain combinations histidine scanning and alanine scanning variants.
Figure 7:
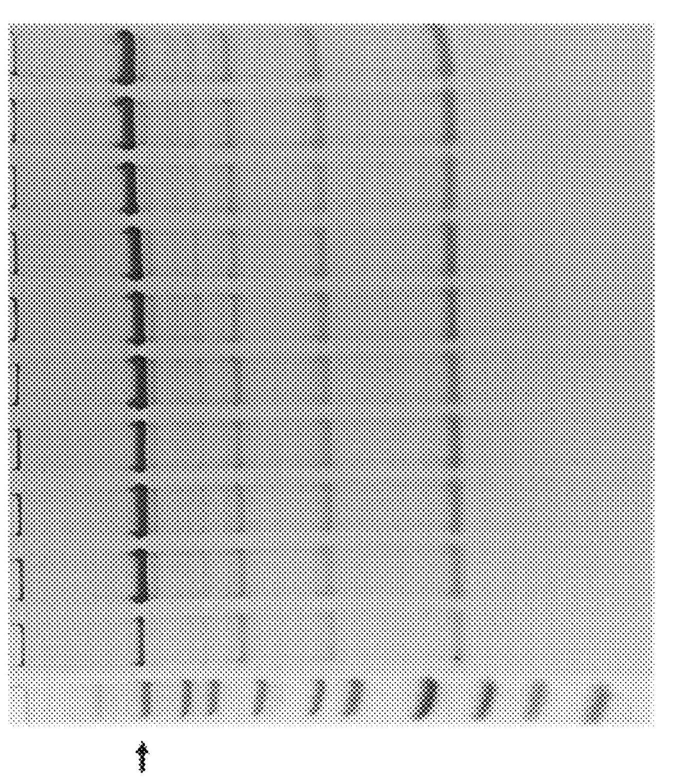
Figure 8A:
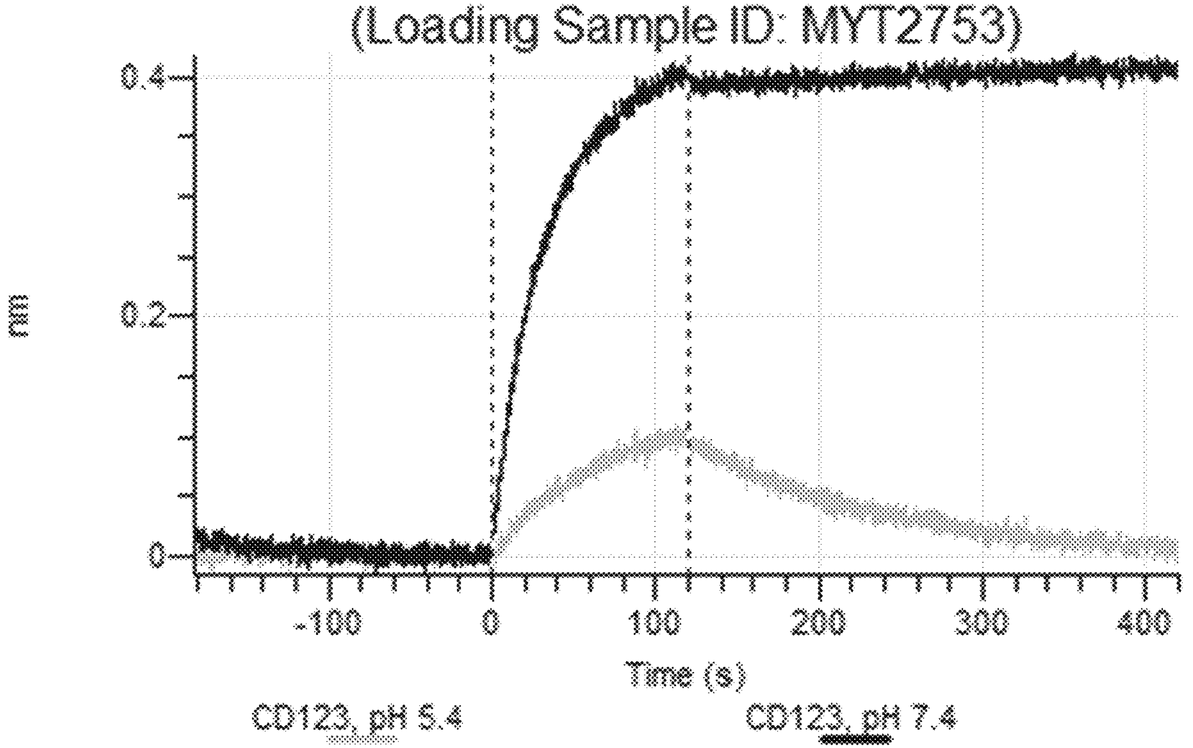
FIGS. 8*a* to 8*t*: Binding of histidine scanning and alanine scanning variants of IMGN632 to CD123 by biolayer interferometry. MYT2753 to MYT2772, heavy chain combination histidine scanning and alanine scanning variants, were captured on anti-human Fc biosensors and associated with CD123 at low pH or high pH, as specified in the figures.
Figure 8B:
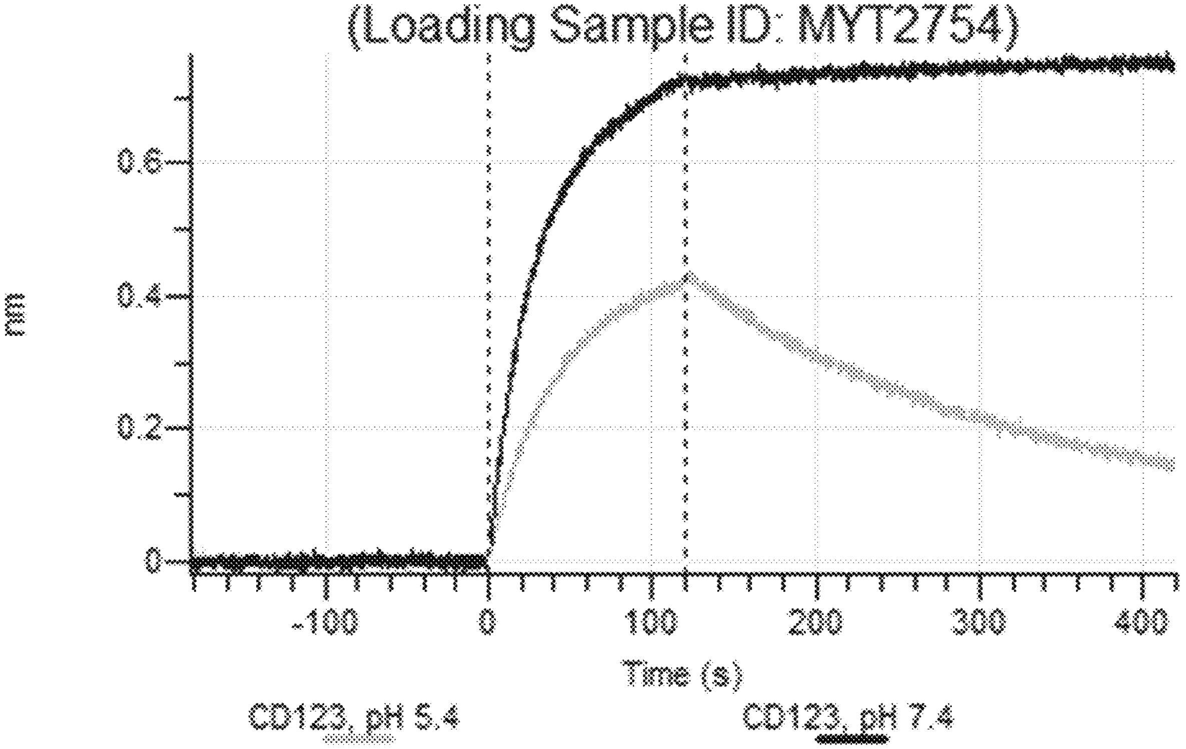
Figure 8C:
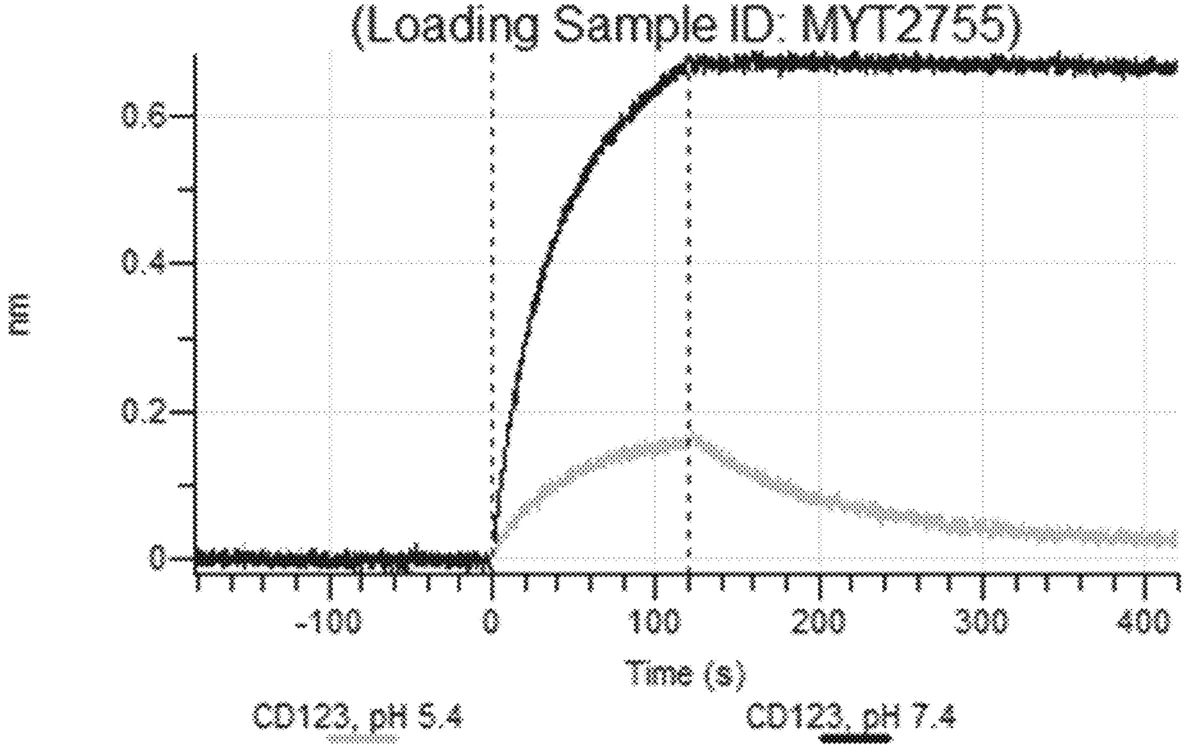
Figure 8D:
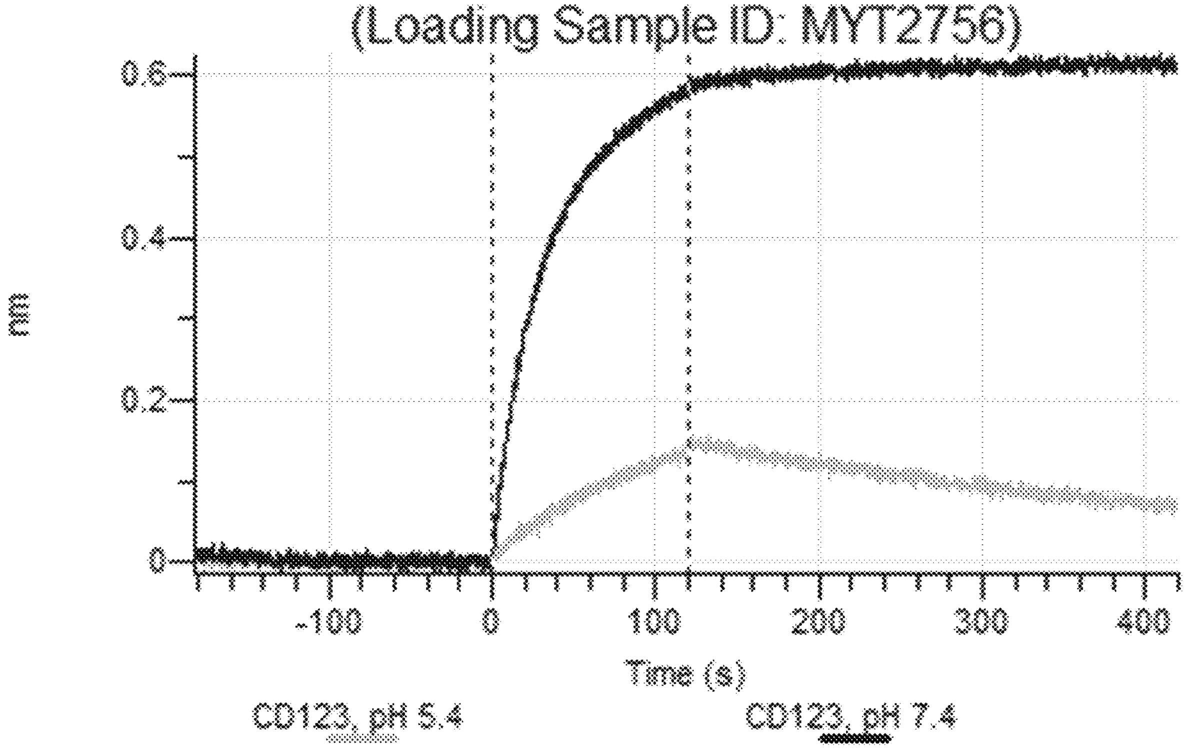
Figure 8E:
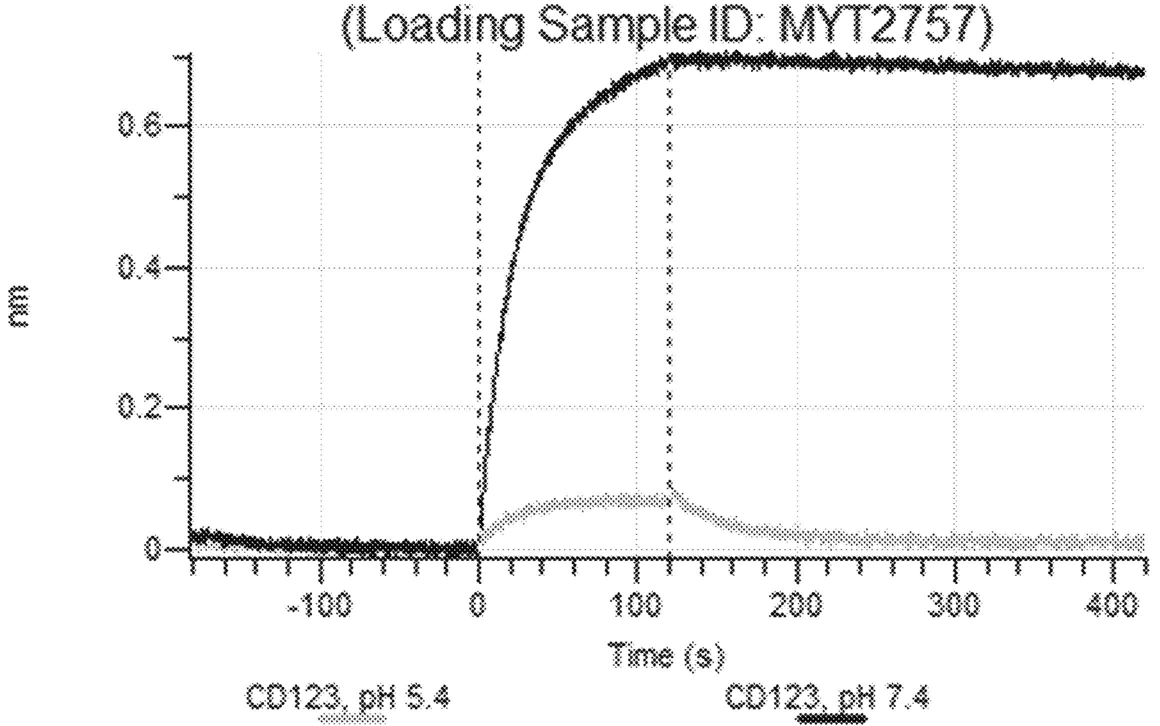
Figure 8F:
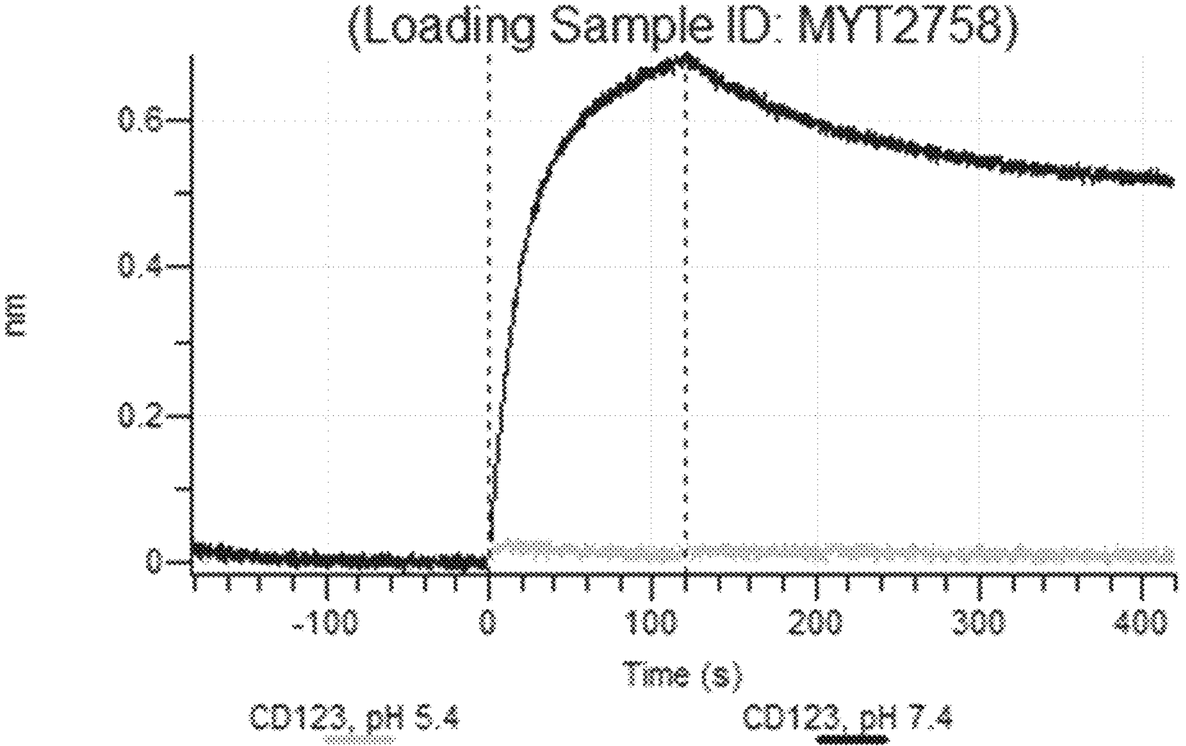
Figure 8G:
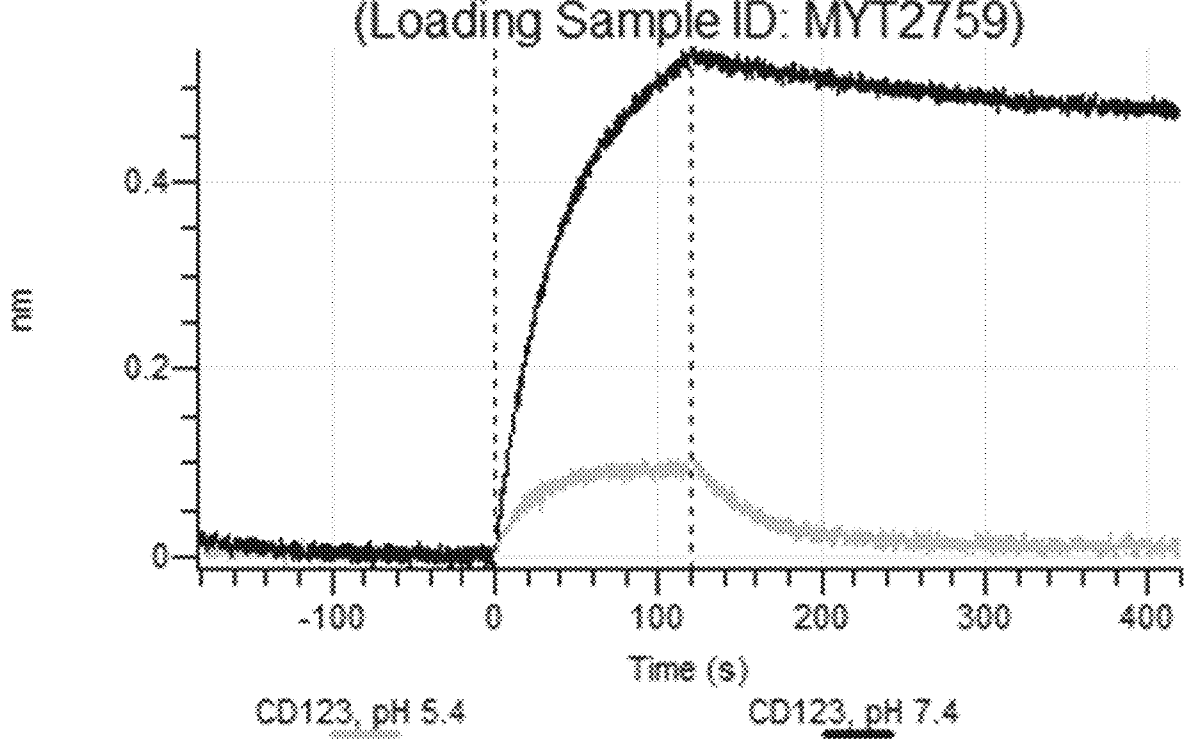
Figure 8H:
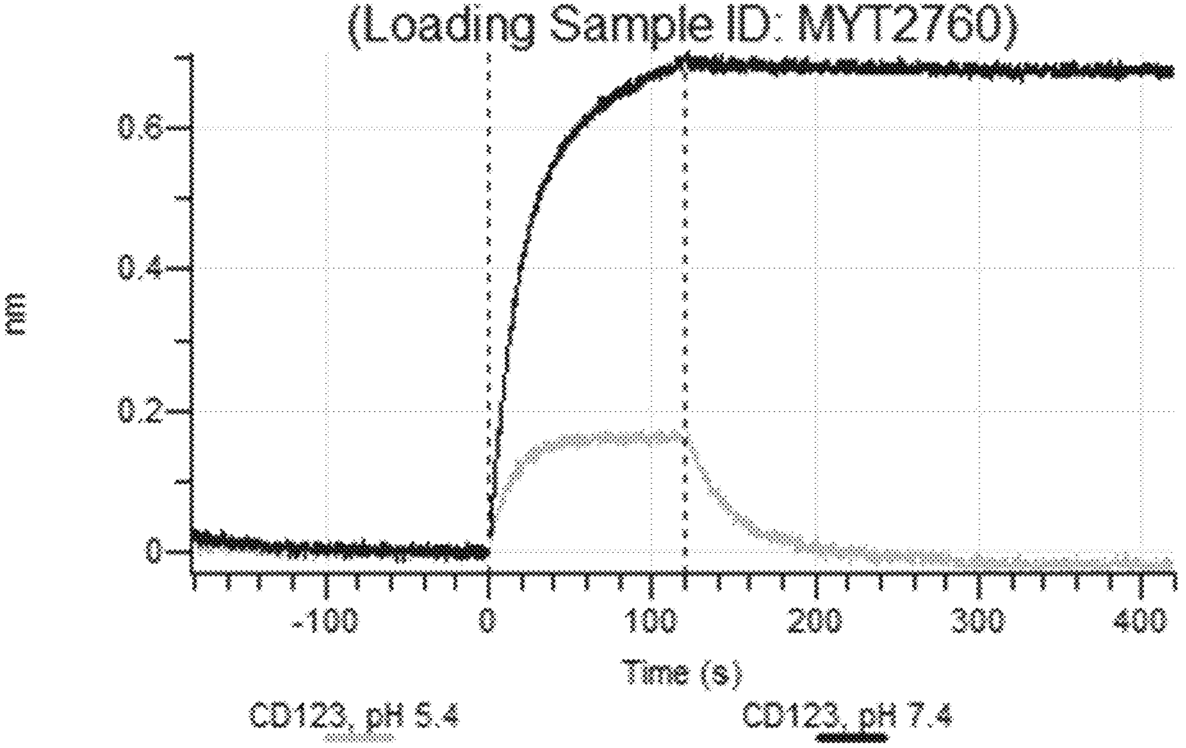
Figure 8I:
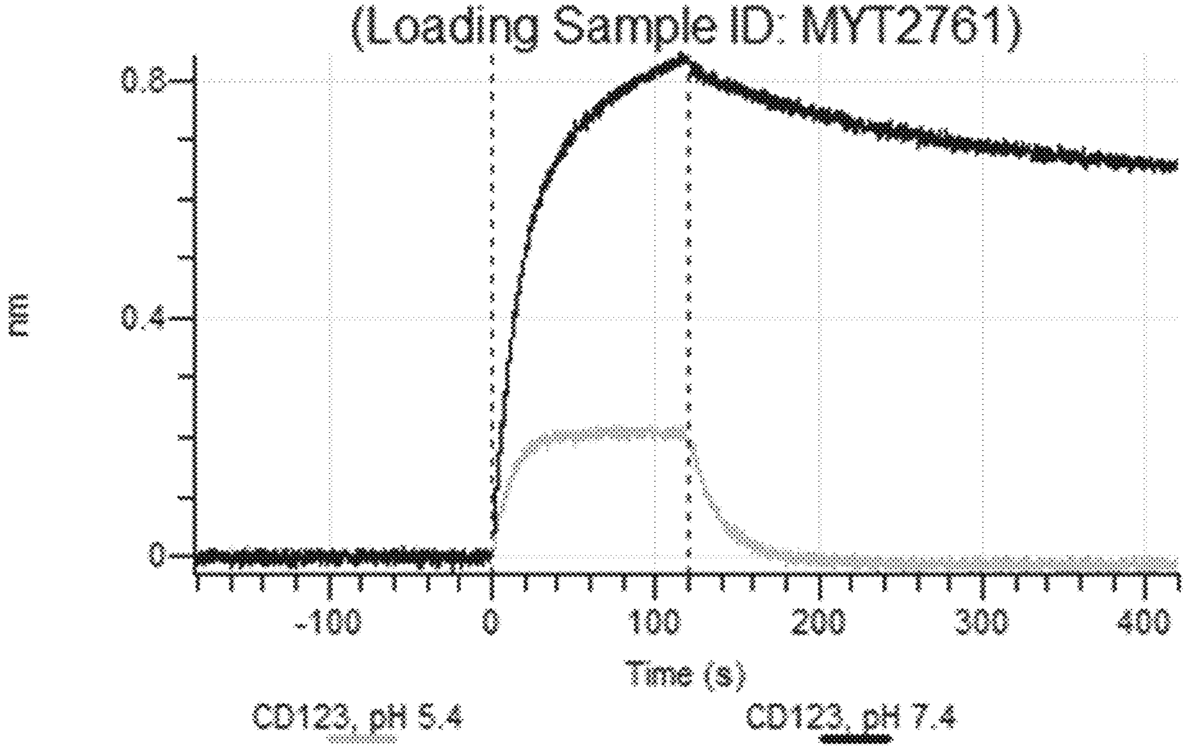
Figure 8J:
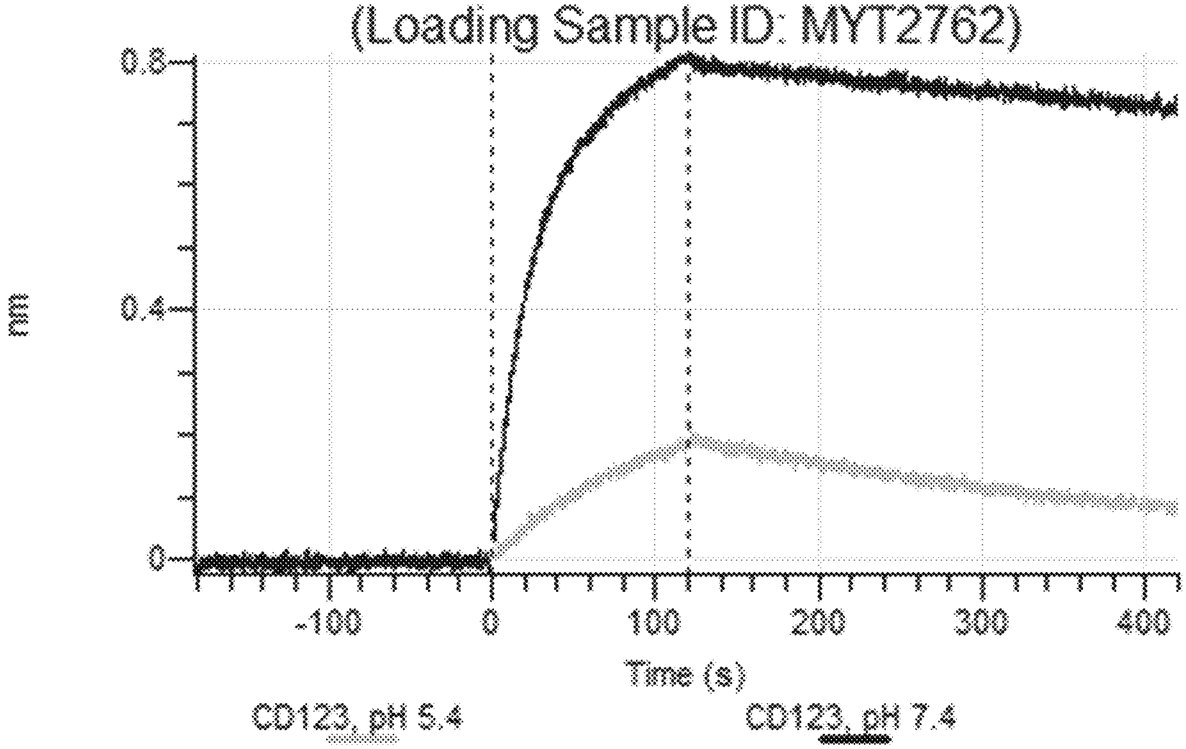
Figure 8K:
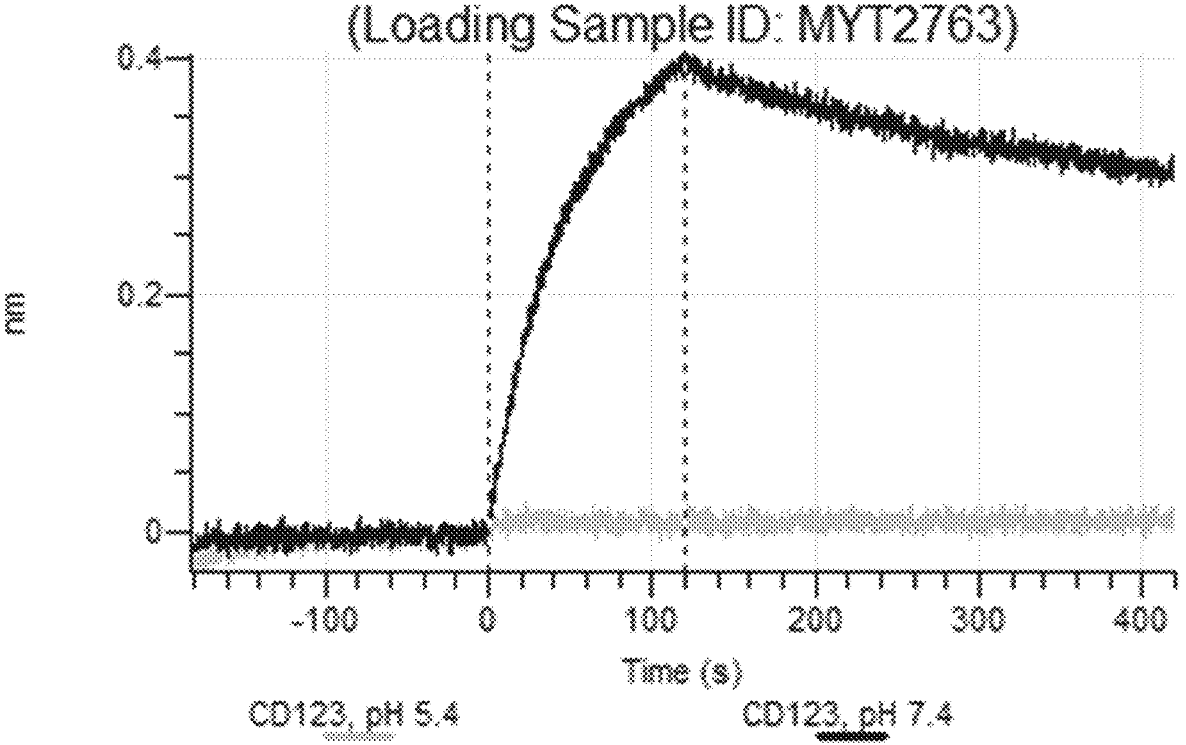
Figure 8L:
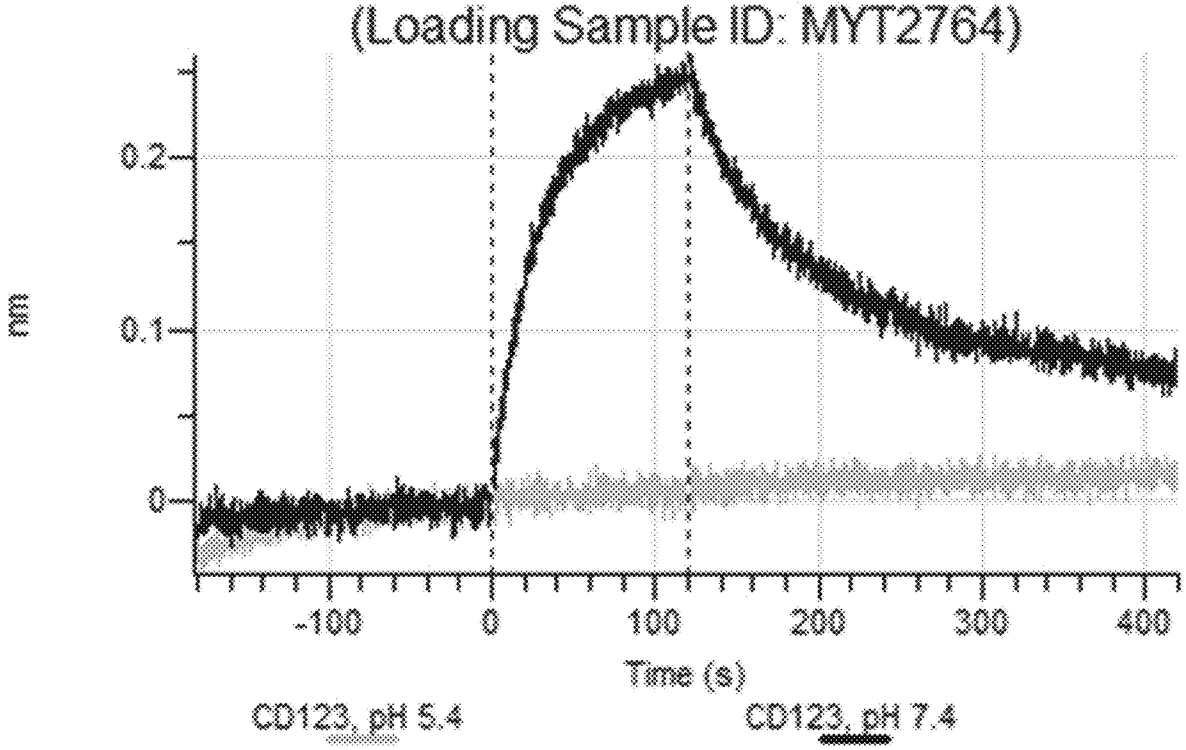
Figure 8M:
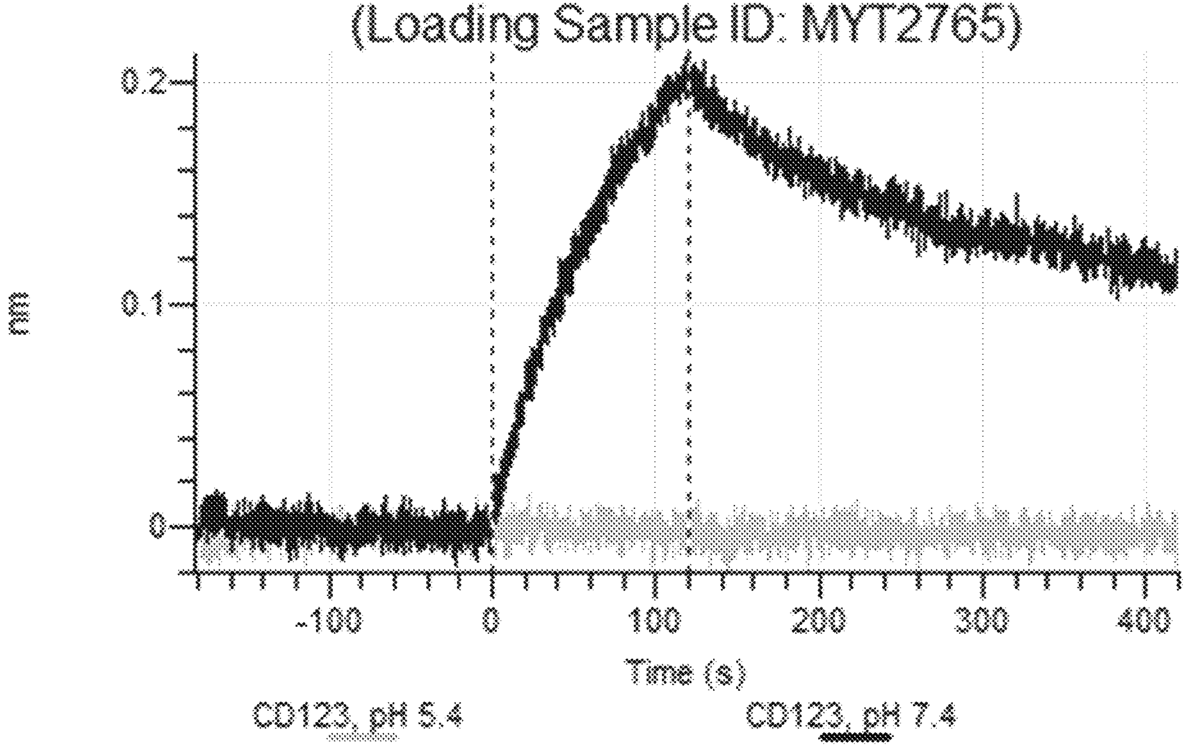
Figure 8N:
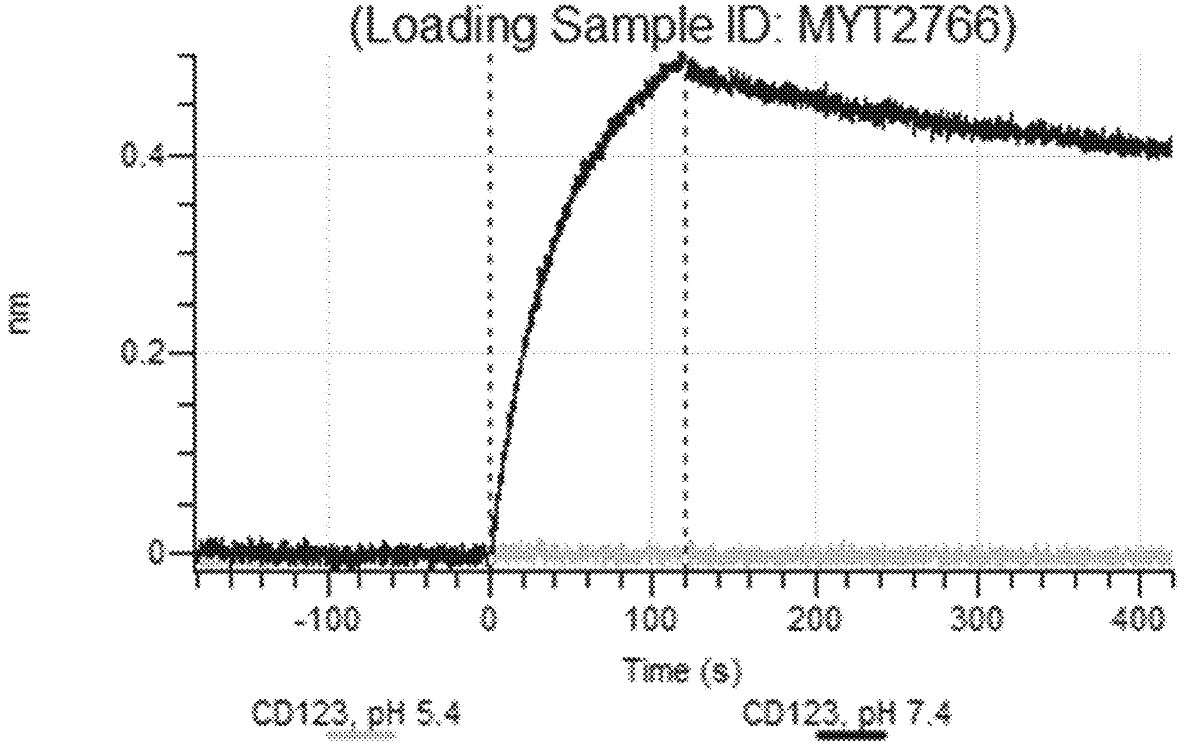
Figure 8O:
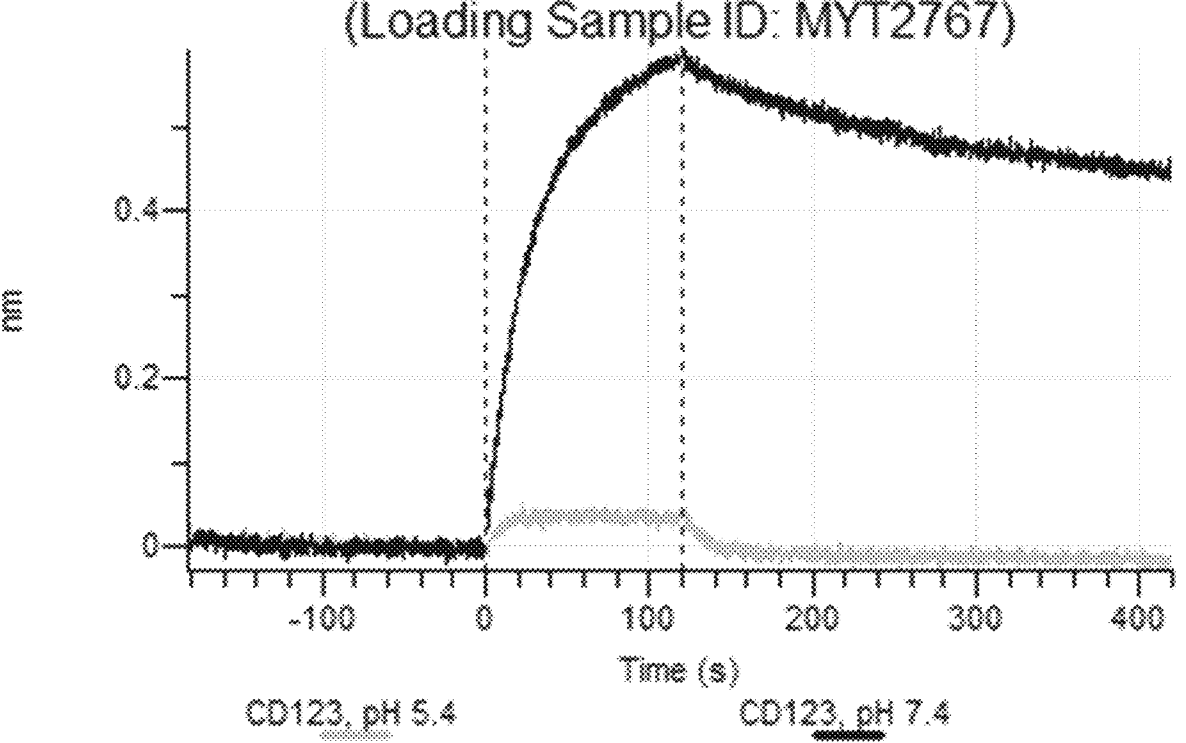
Figure 8P:
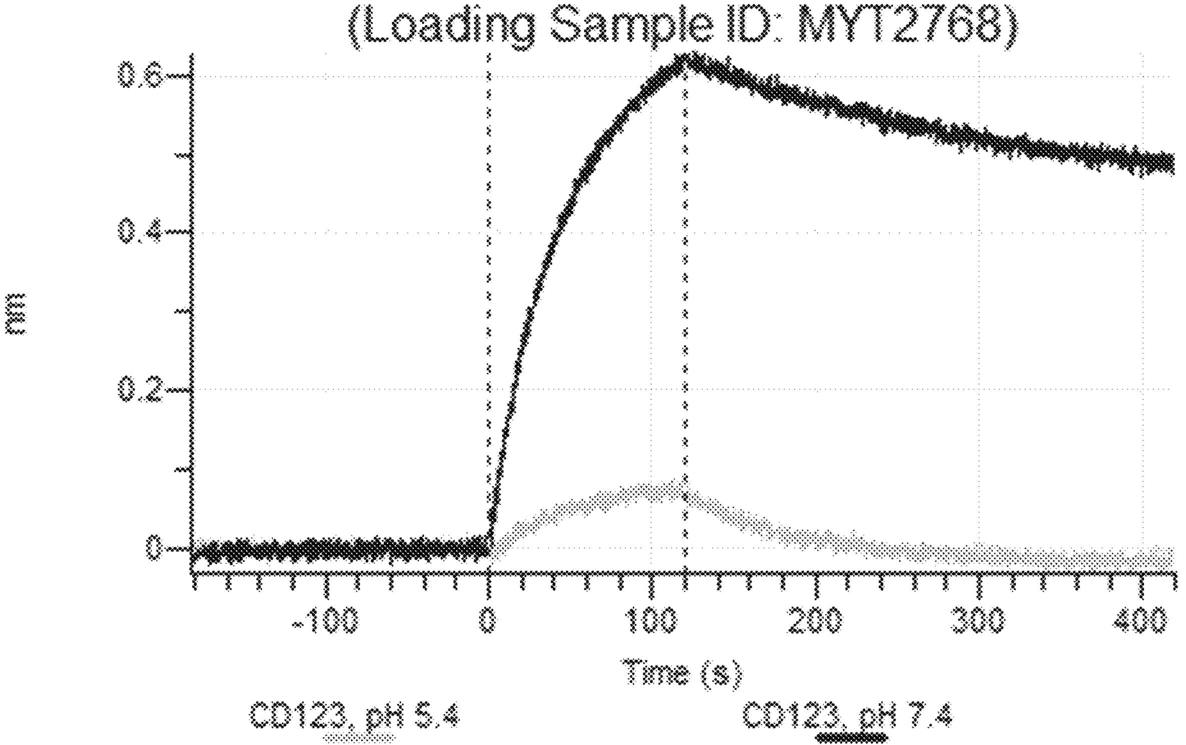
Figure 8Q:
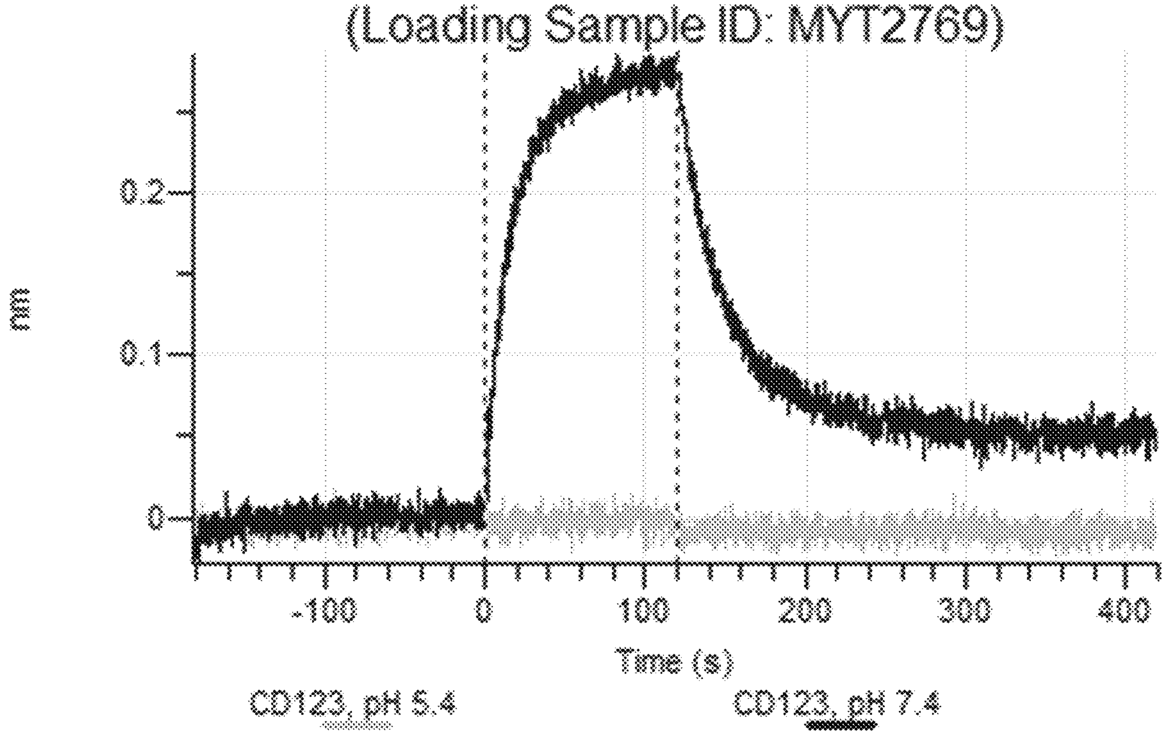
Figure 8R:
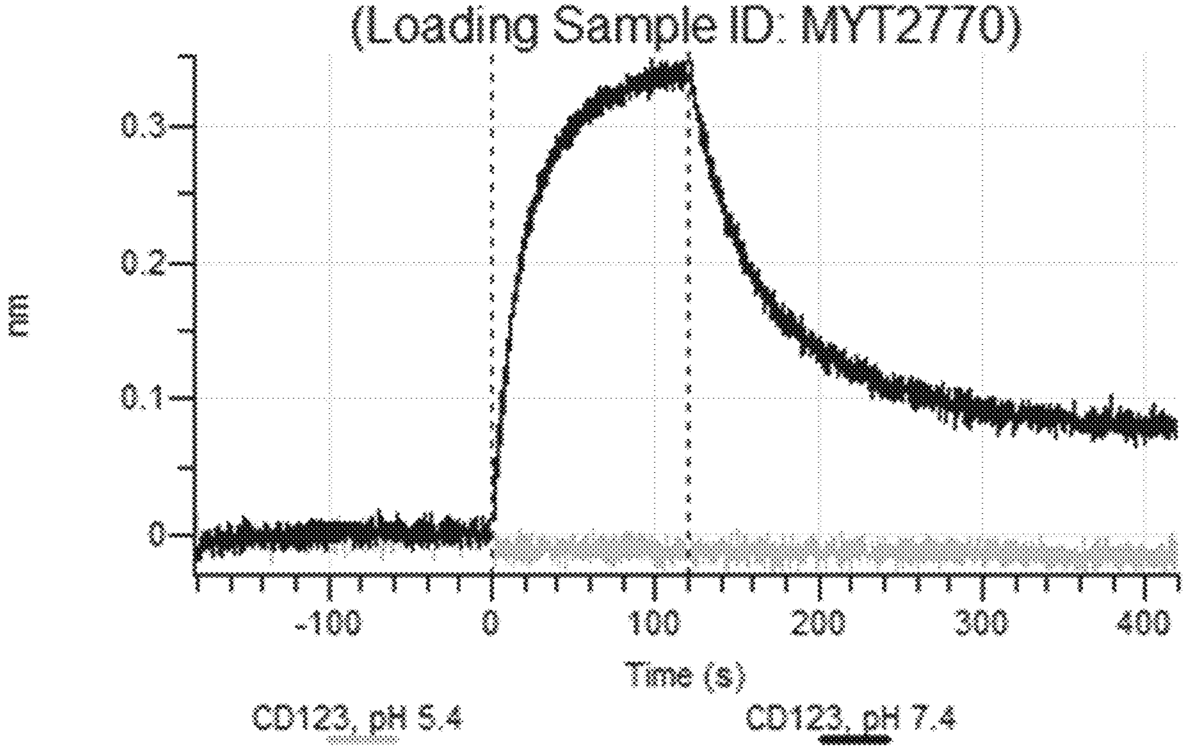
Figure 8S:
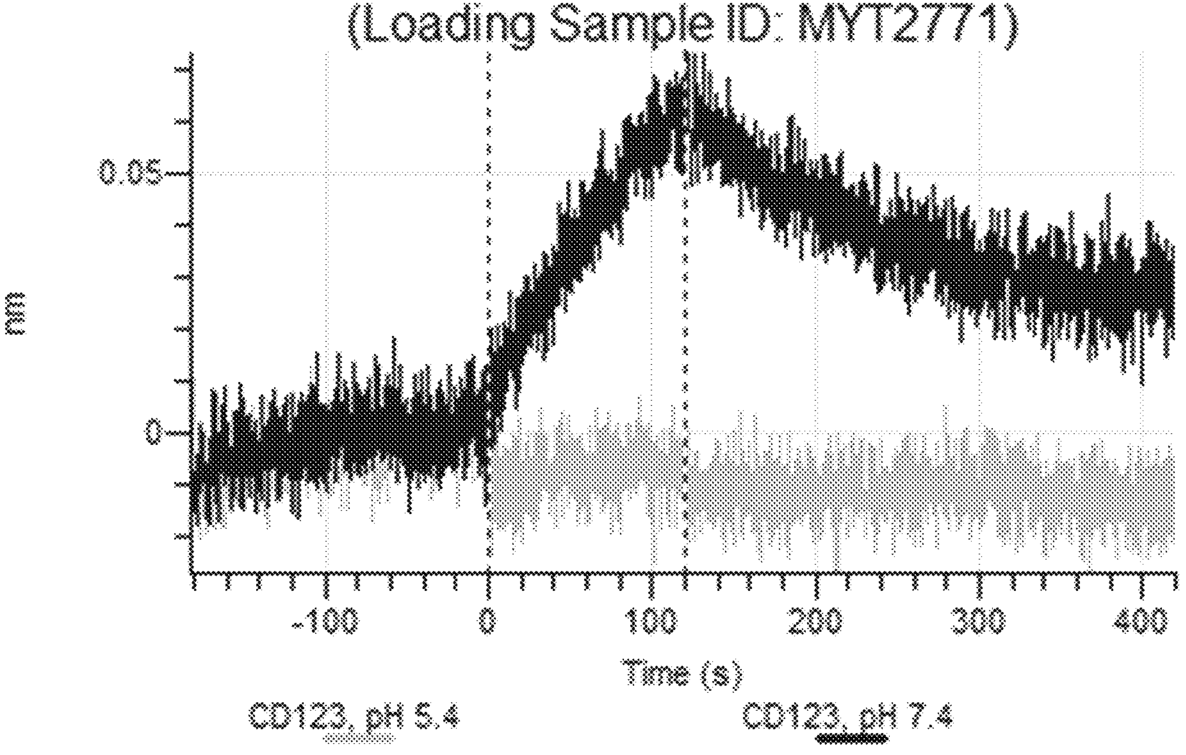
Figure 8T:
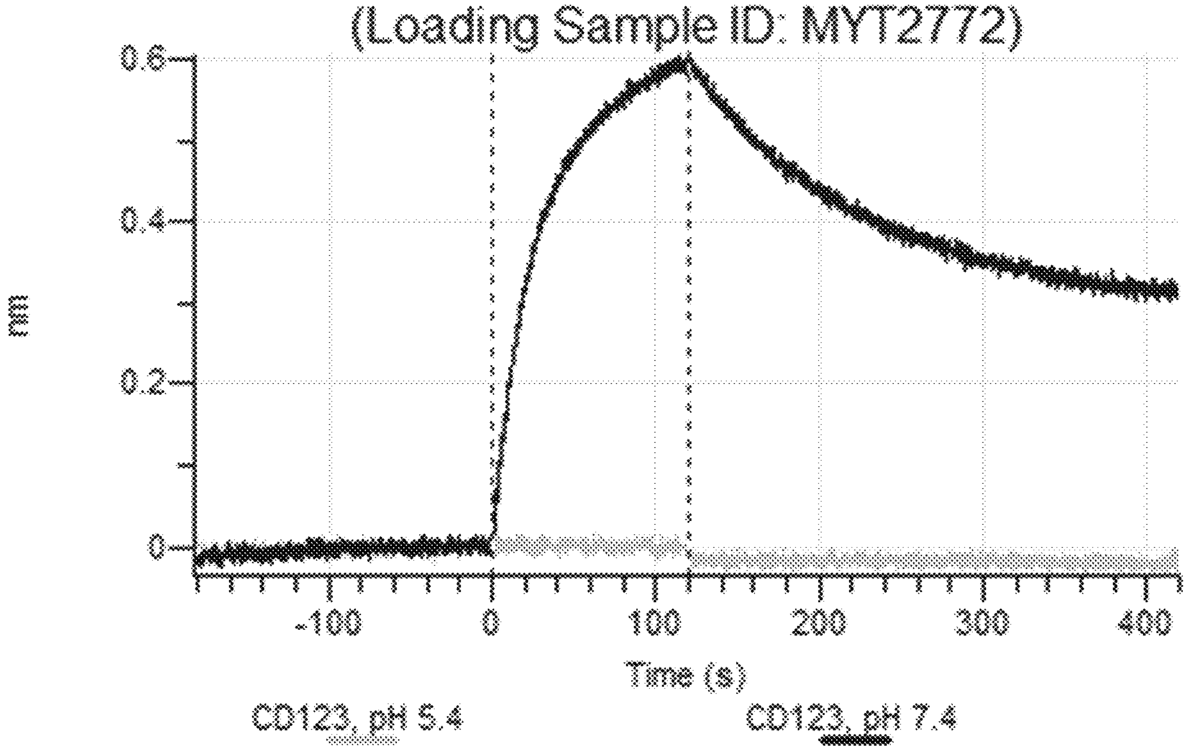

Multiple CD123-binding monoclonal antibodies have been described in the literature and can be used as a template for engineering pH-dependent binding [Kovtun, Yelena, et al. (2018) "A CD123-Targeting Antibody-Drug Conjugate, IMGN632, Designed to Eradicate AML While Sparing Normal Bone Marrow Cells." Blood Advances, American Society of Hematology 2(8) 848-858]. We selected IMGN632 (Heavy chain SEQ ID NO: 1, Light chain SEQ ID NO: 2) as a CD123-binding monoclonal antibody for pH engineering via histidine scanning. Briefly, CDRs in the heavy chain were identified using the methods described by Kabat et al (Kabat et al. (1992) Sequences of Proteins of Immunological Interest, DIANE publishing) and IMGT (Lefranc M P (1999) "The IMGT unique numbering for Immunoglobulins, T cell receptors and Ig-like domains" The Immunologist 7, 132-136), and for each CDR, residues falling under either or both Kabat and IMGT CDR definitions were called as CDR residues. To generate pH-dependent sequence variants, individual amino acid mutations within the heavy chain CDRs that had been previously selected for further analysis in Example 9 were systematically combined two or more at a time (MYT2753-MYT2772). In cases where the starting CDR residue was a histidine, it was mutated to an alanine. Antibody variants with two or more histidine or alanine mutations in the heavy chain CDRs were generated by co-transfection of Expi293 cells with a) one heavy chain combinations sequence variant, and b) the corresponding starting ABPC light chain using methods known to the art. After allowing for four days of protein expression, cell culture supernatants were collected, quantified by SDS-PAGE analysis (FIG. 7), and the pH dependence of the variant was evaluated using biolayer interferometry (BLI) on an Octet RED 96e instrument. Briefly, cell culture supernatants were diluted based on qualitative expression level of the variant determined by visual examination of SDS-PAGE gels, 5 μL of cell culture supernatant was diluted into 195 μL of 1×PBST, pH 7.4 for high expressors, 25 μL of cell culture supernatant was diluted into 175 μL of 1×PBST, pH 7.4 for medium expressors and 100 μL it of cell culture supernatant was diluted into 100 μL of 1×PBST, pH 7.4 for low expressors for loading onto the sensor tips. Diluted supernatants were then captured on an anti-human Fc sensor (Forte Bio). A baseline was established using 1×PBST (50 mM Potassium Phosphate Buffer+150 mM NaCl+0.05% Tween 20) pH 7.4, and the sensor was associated with 50 nM of CD123 protein (Acro Biosciences Cat. No. ILA-H52H6, Lot No. 1741d-89CF1-KB) in 1×PBST pH 7.4 for 120 sec to generate an association curve. In the dissociation phase, the antibody-antigen complex on the sensor was exposed to 1×PBST pH 7.4 for 300-600 sec. Baseline, association, and dissociation were repeated using 1×PBST pH 5.4 throughout in a separate condition. Association and dissociation phase curves were examined for the starting ABPC antibody (with no substitutions) and each corresponding antibody variant at pH 5.4 and pH 7.4 to inform on two criteria: a) enhanced dissociation (i.e., higher koff values) at pH 5.4 due to histidine or alanine substitution compared to the starting ABPC (with no substitutions), and b) reduced dissociation at pH 7.4 (i.e., lower koff values) compared to pH 5.4 in the antibody variant itself and with the starting ABPC (with no substitutions). Heavy chain combinations variants that showed either enhanced dissociation at pH 5.4 or reduced dissociation at pH 7.4 or both (as compared to the starting ABPC), as shown in FIG. 8 were selected for further analysis (e.g, MYT2753, MYT2754, MYT2755, MYT2756, MYT2757, MYT2758, MYT2759, MYT2760, MYT2761, MYT2762, MYT2763, MYT2764, MYT2765, MYT2766, MYT2767, MYT2768, MYT2769, MYT2770, MYT2771, MYT2772).

Example 12. Construction and Screening of pH-Engineered CD123 ABPCs

Figure 10:
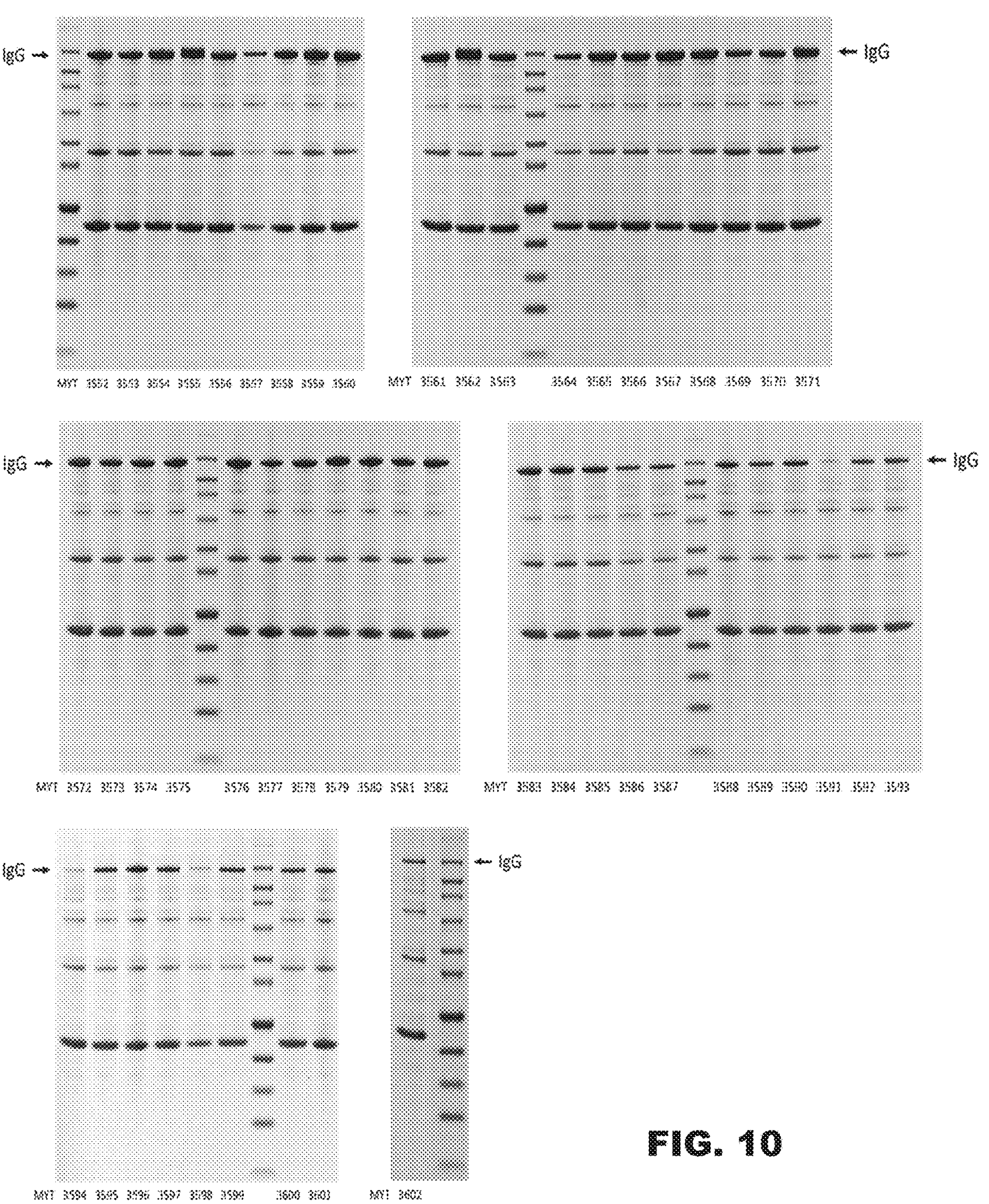
FIG. 10: SDS PAGE for IMGN632 histidine scanning and alanine scanning. Expi293 cell culture supernatants post-harvest were loaded on non-reduced SDS PAGE gels to confirm expression of IMGN632 histidine scanning and alanine scanning variants. Arrows show the corresponding size for an IgG on a non-reduced SDS PAGE gel. MYT3552-MYT3602 are IMGN632 paired heavy and light chain variants, combining light chain histidine and alanine scanning variants with heavy chain histidine and alanine scanning variants or heavy chain combination histidine scanning and alanine scanning variants.
Figure 11A:
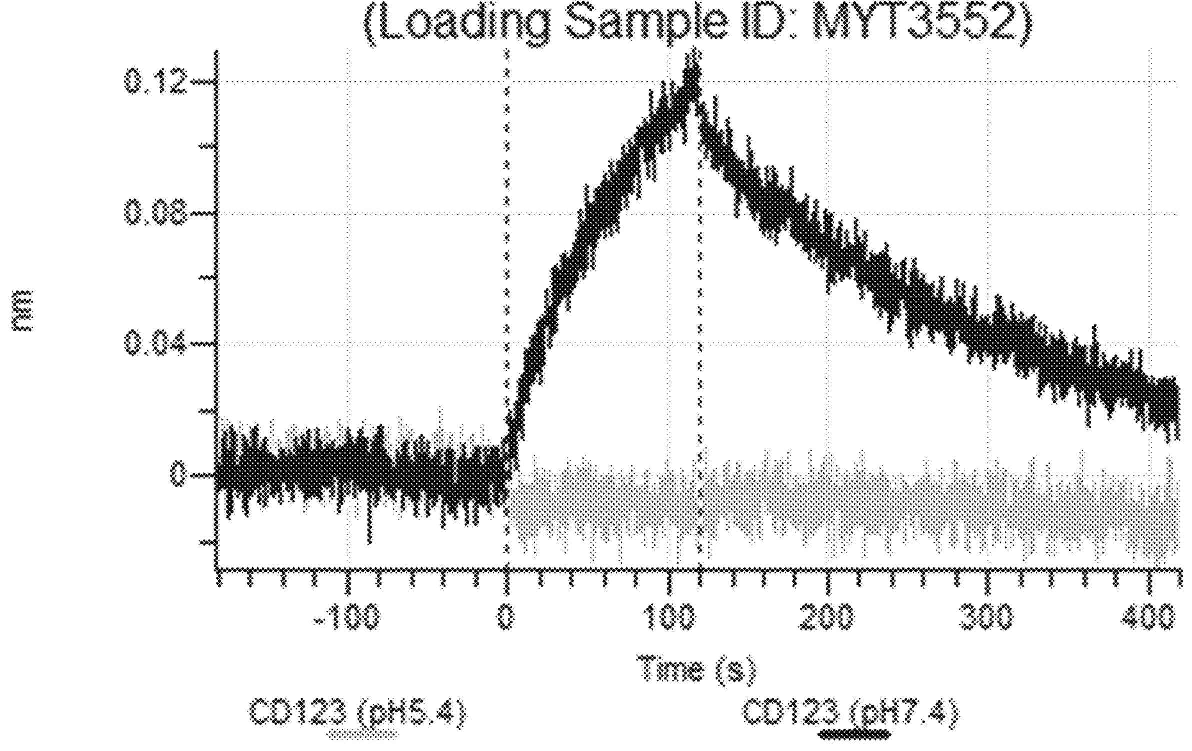
FIGS. 11*a* to 11*ay*: Binding of histidine scanning and alanine scanning variants of IMGN632 to CD123 by biolayer interferometry. MYT3552-MYT3602, paired heavy and light chain variants, combining light chain histidine and alanine scanning variants with heavy chain histidine and alanine scanning variants or heavy chain combination histidine scanning and alanine scanning variants, were captured on anti-human Fc biosensors and associated with CD123 at low pH or high pH, as specified in the figures.
Figure 11B:
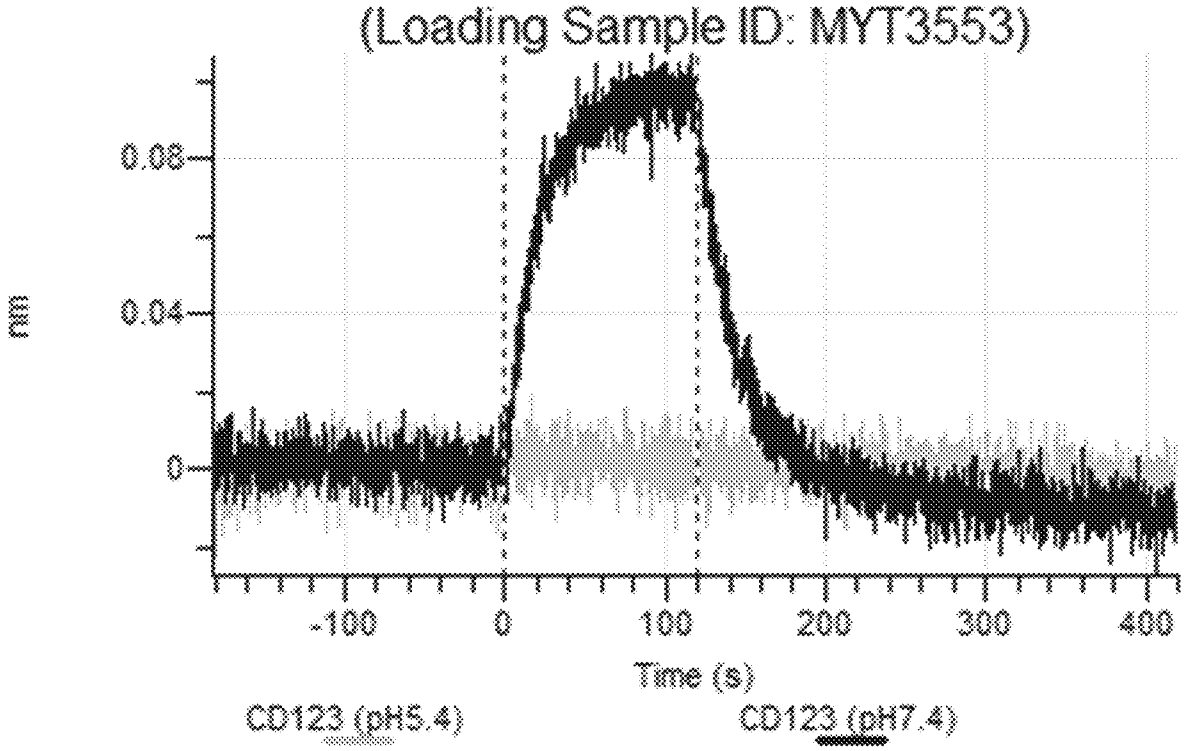
Figure 11C:
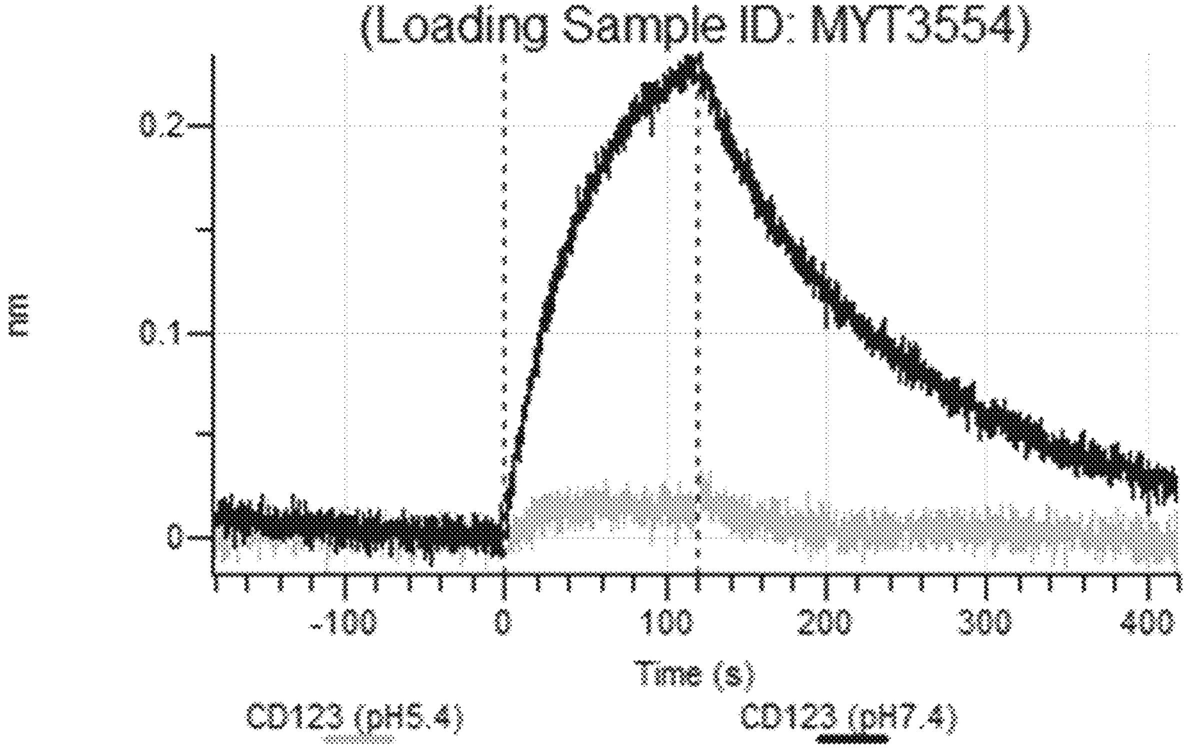
Figure 11D:
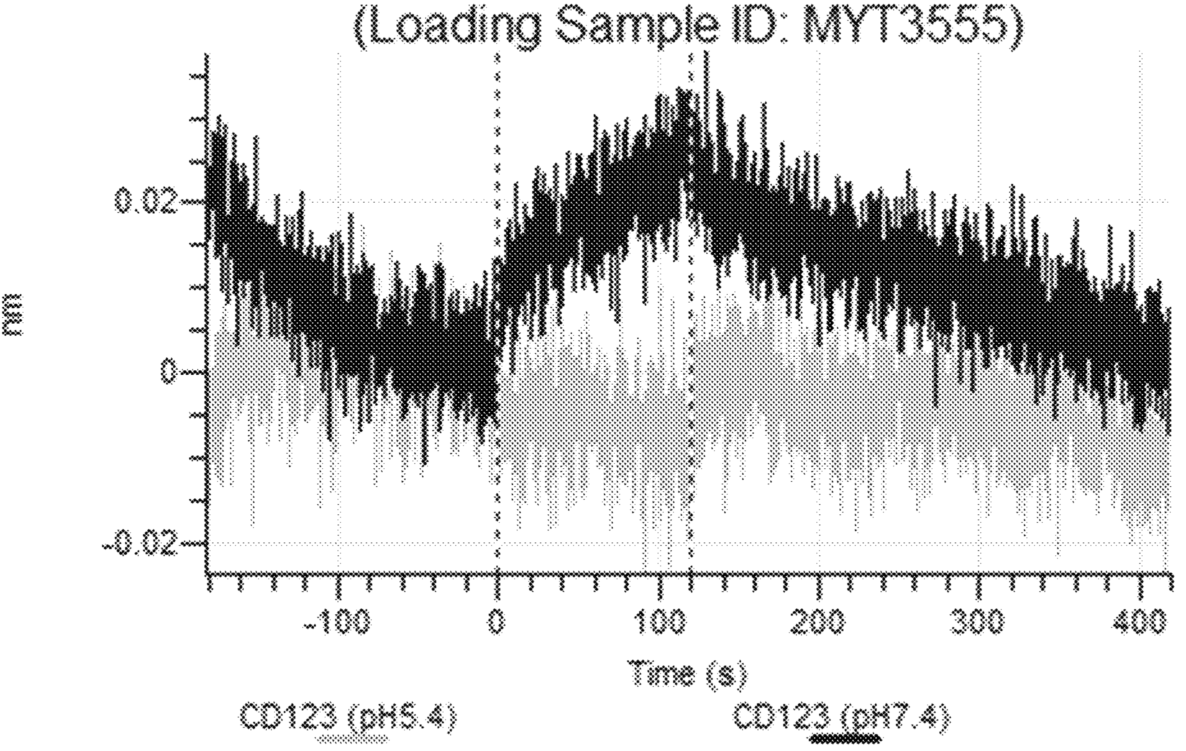
Figure 11E:
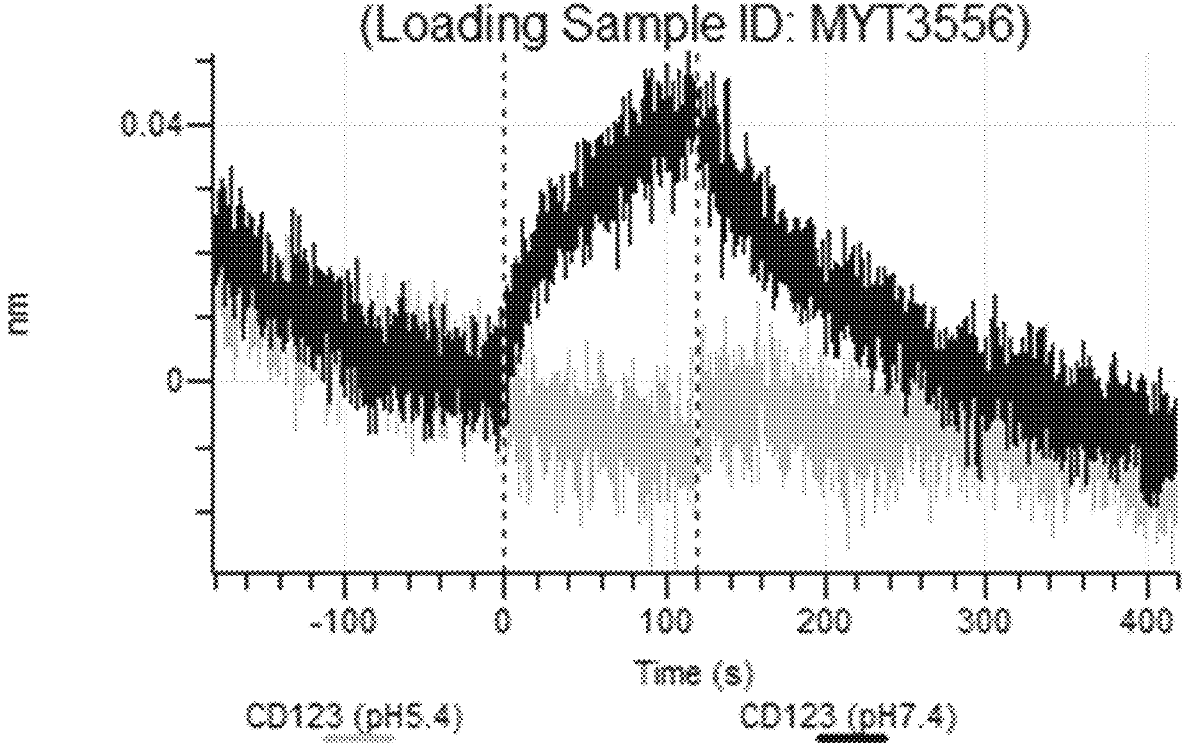
Figure 11F:
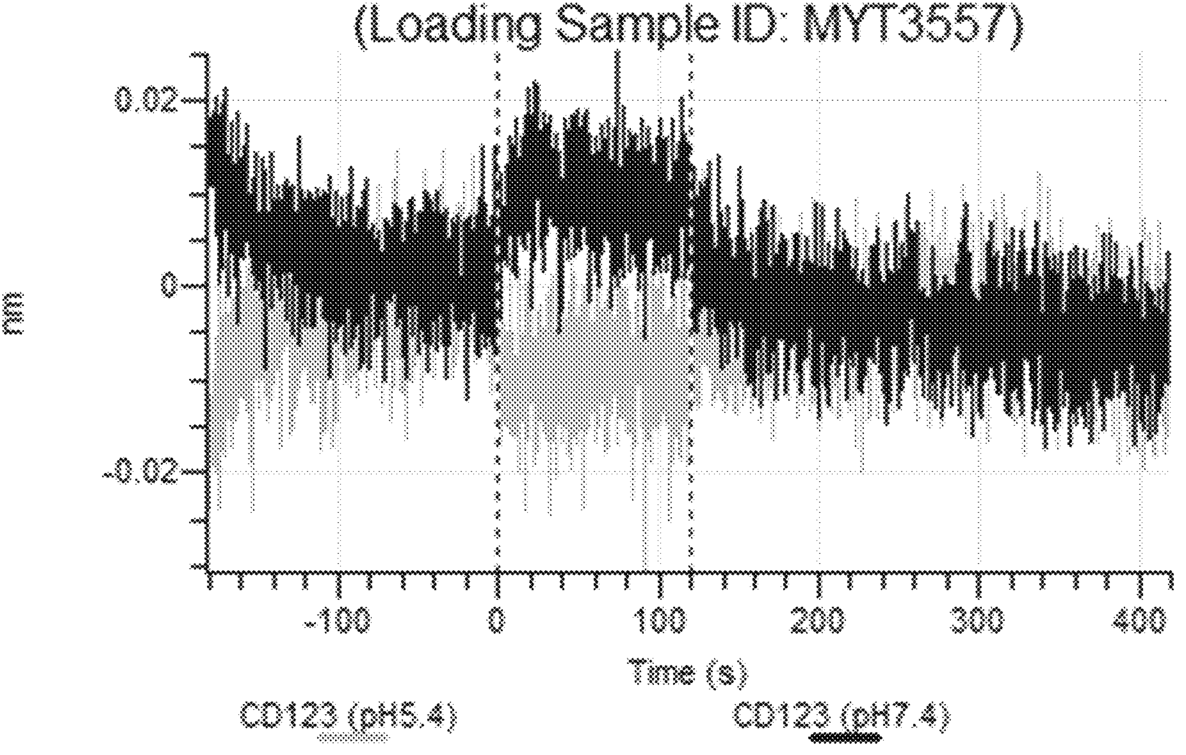
Figure 11G:
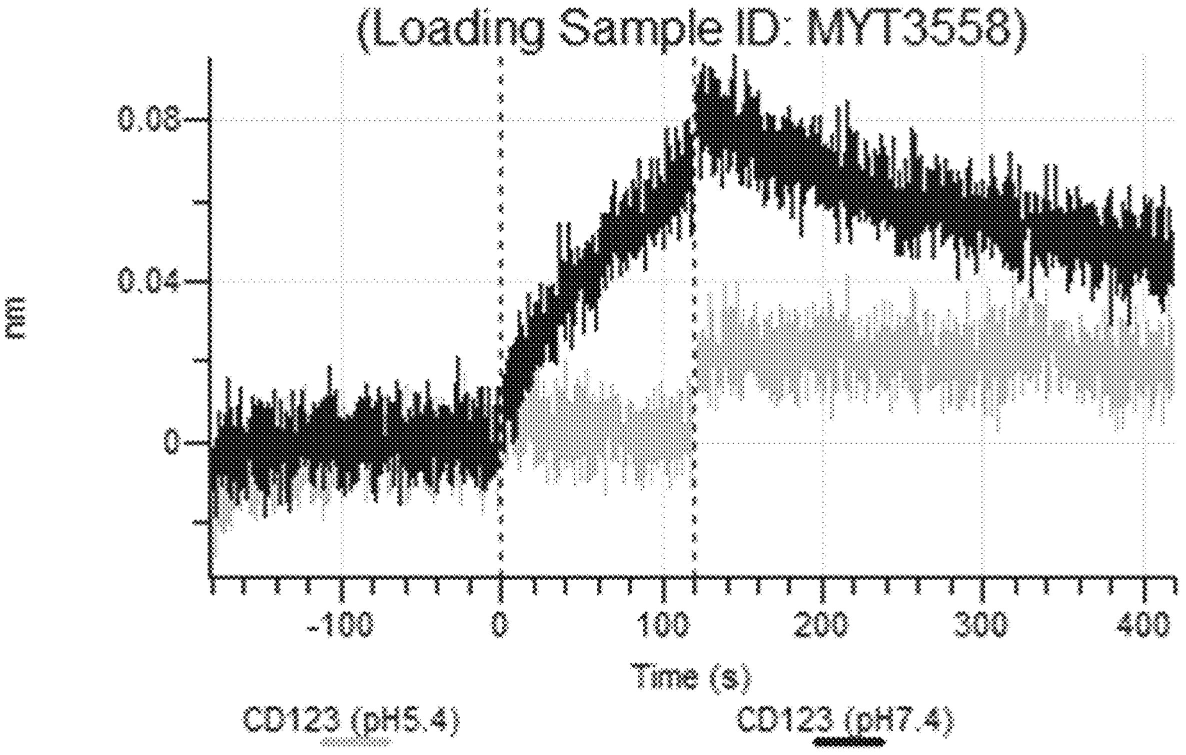
Figure 11H:
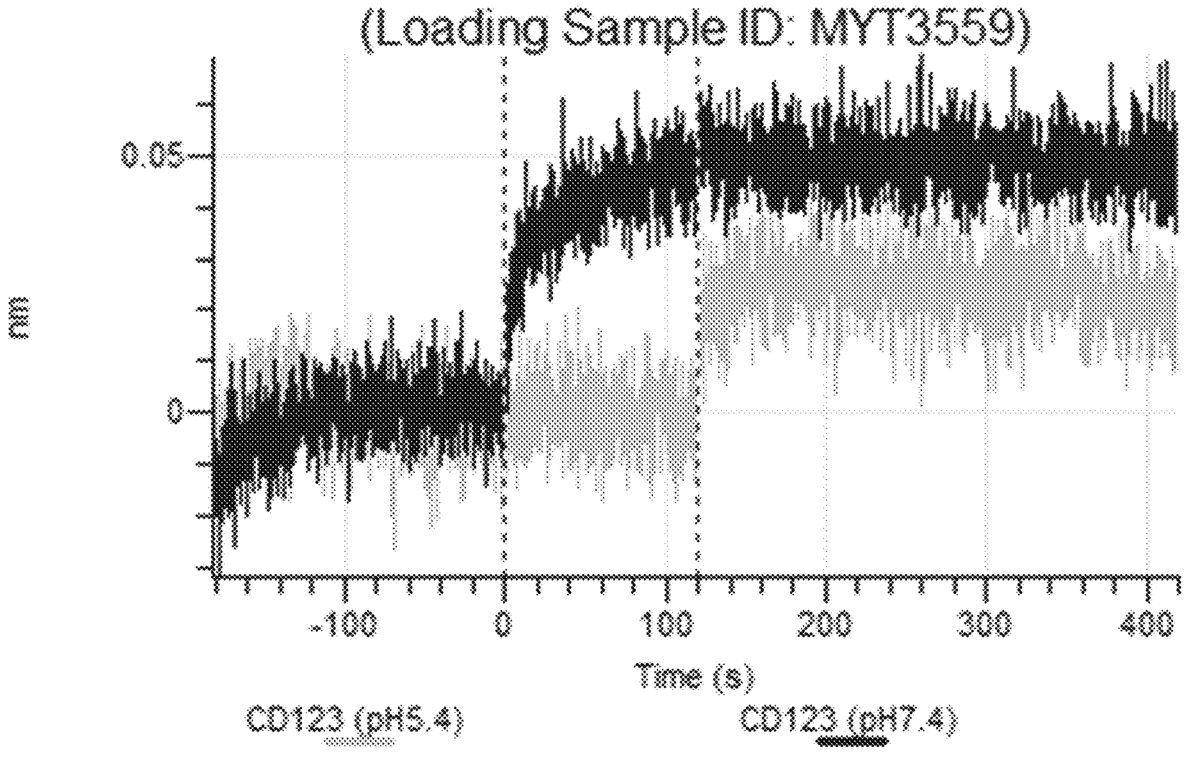
Figure 11I:
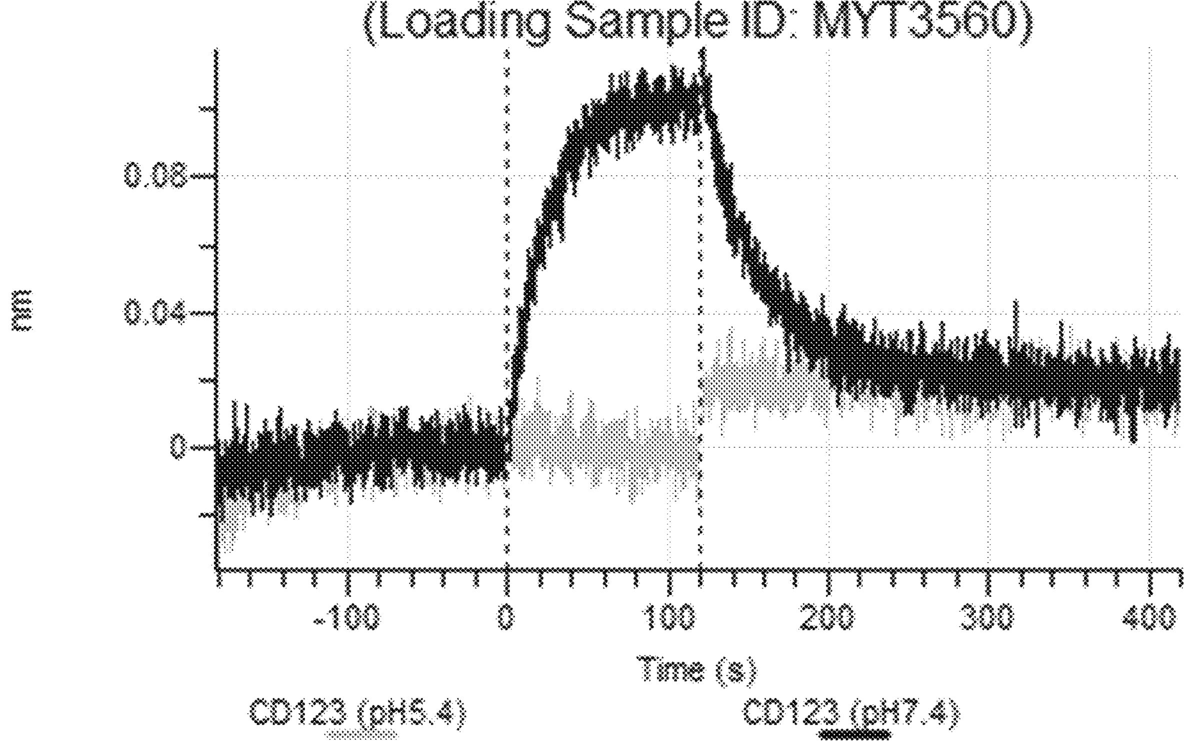
Figure 11J:
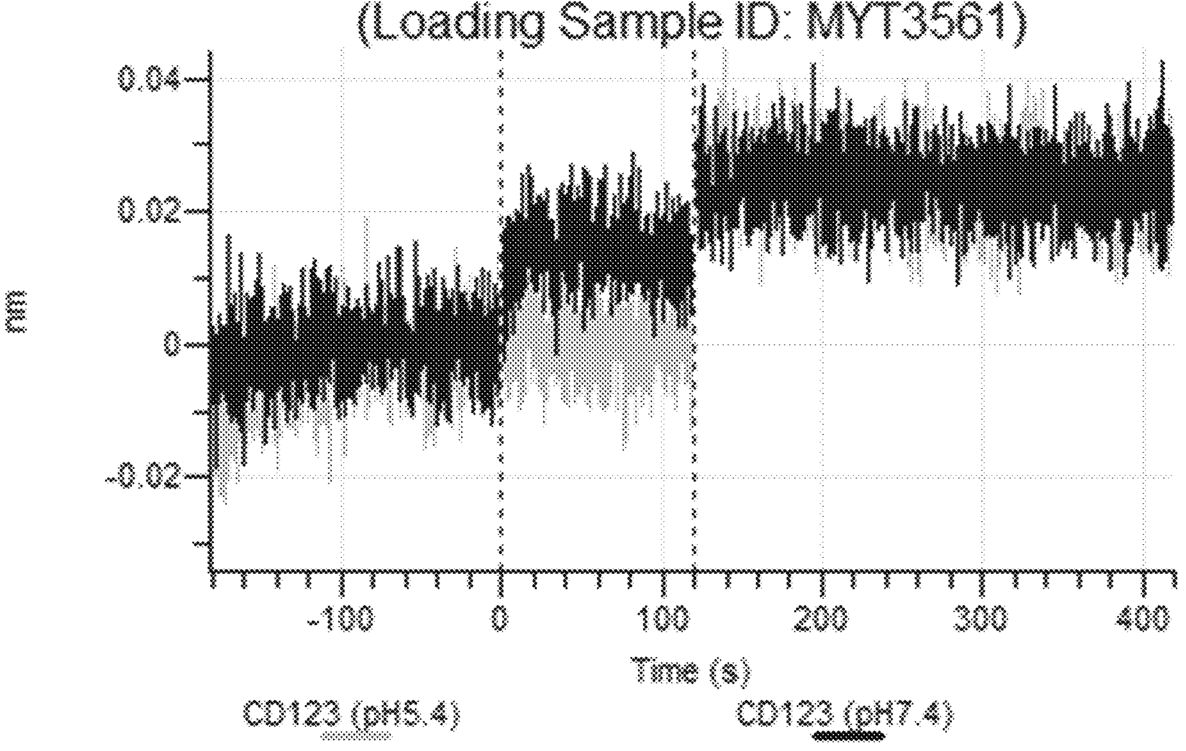
Figure 11K:
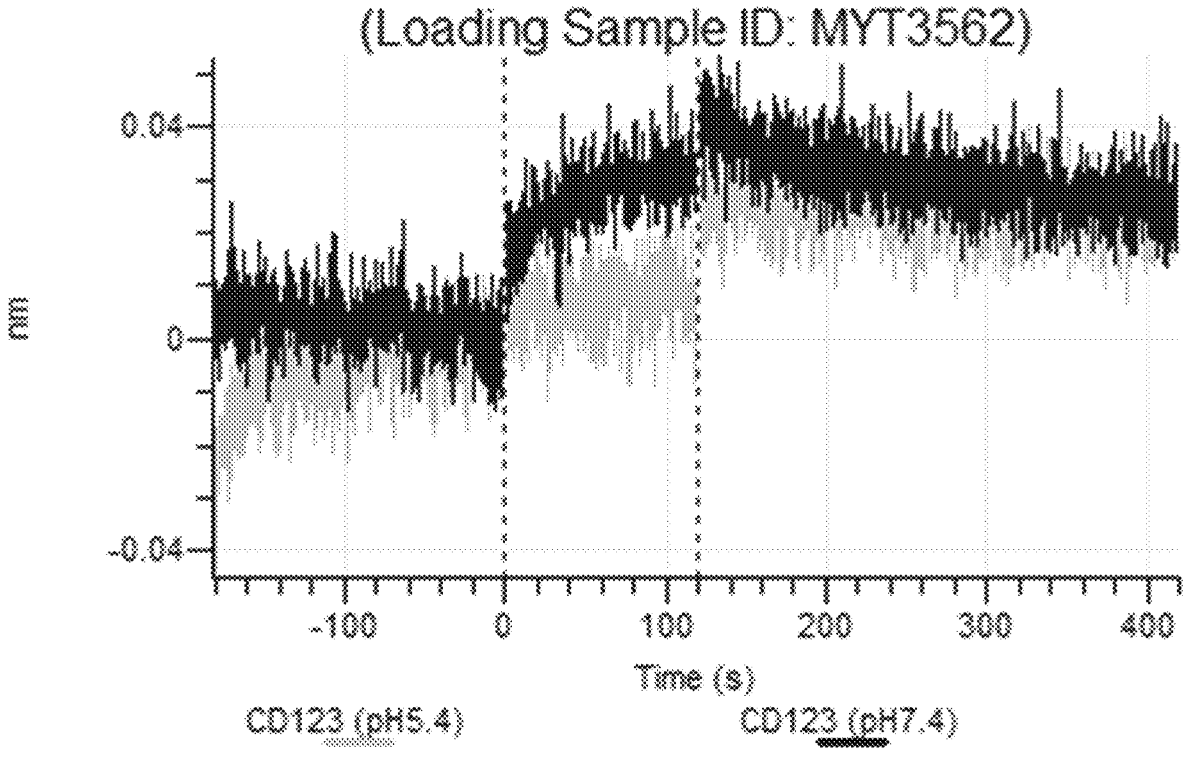
Figure 11L:
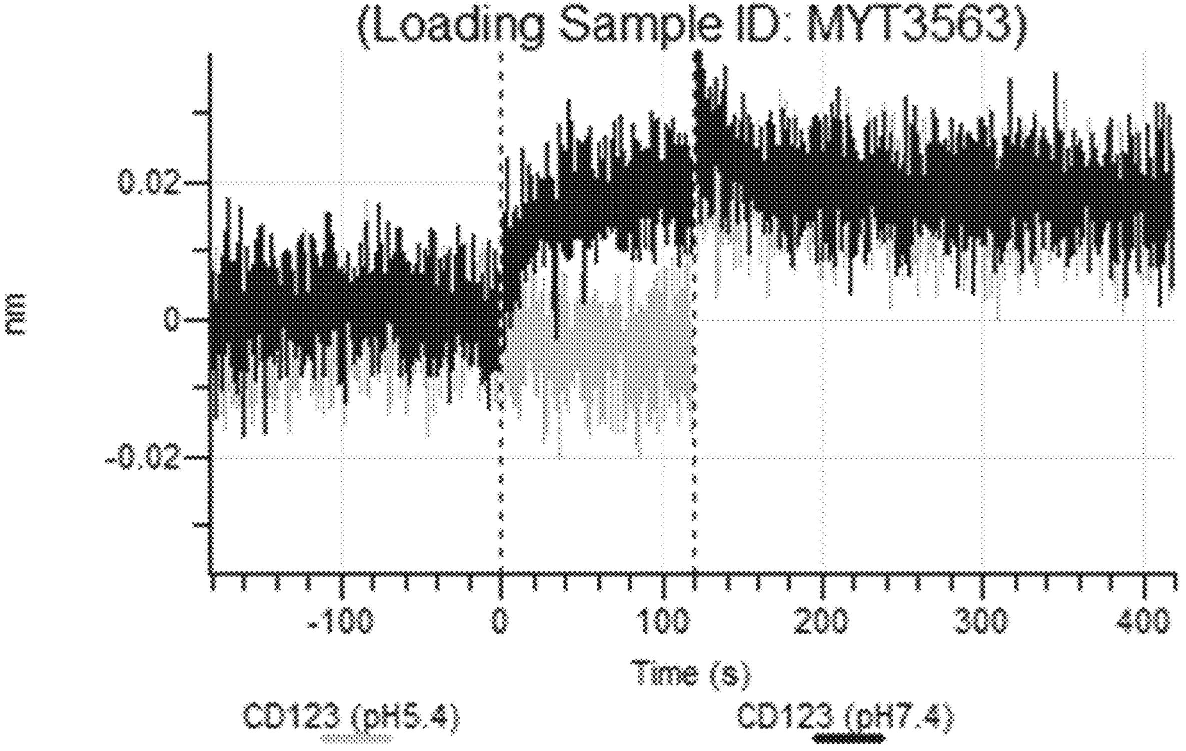
Figure 11M:
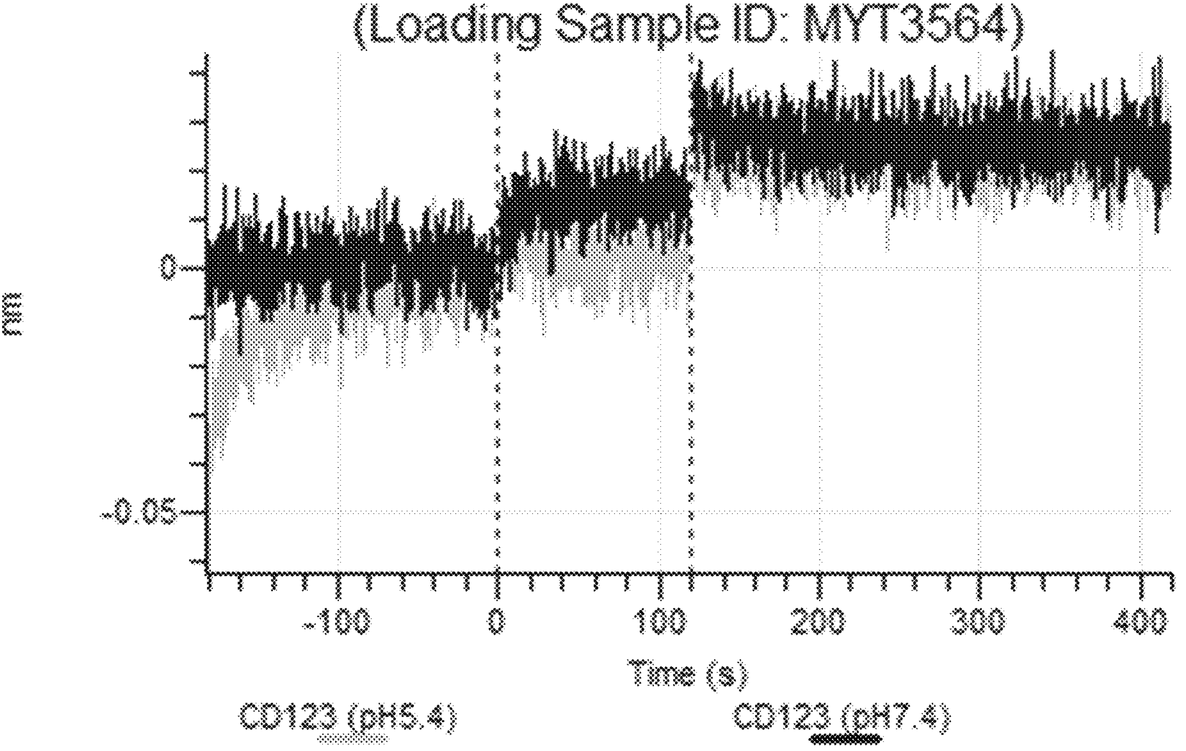
Figure 11N:
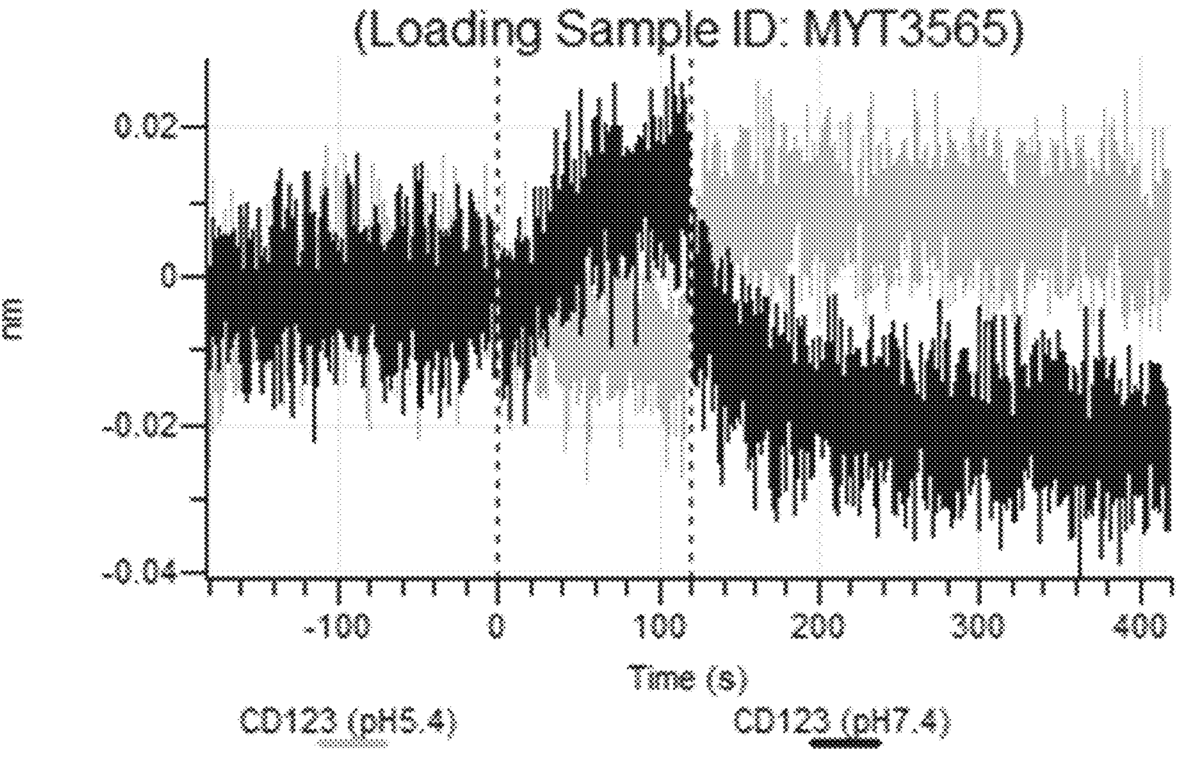
Figure 11O:
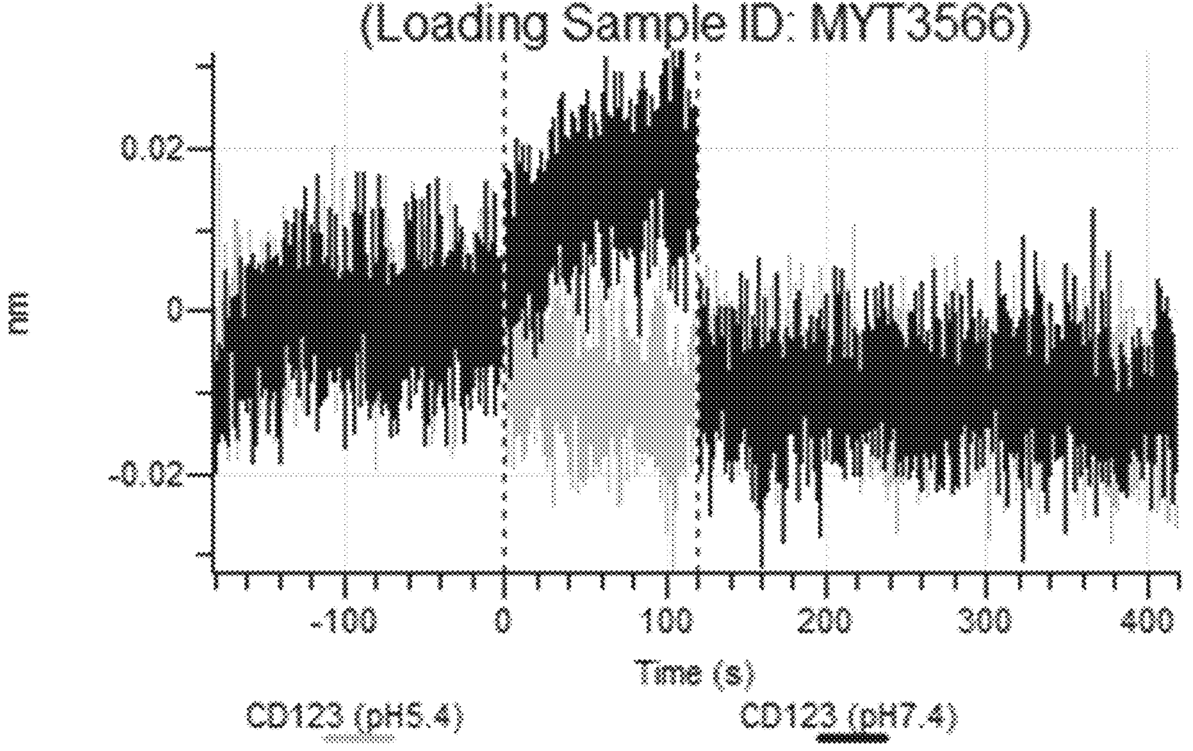
Figure 11P:
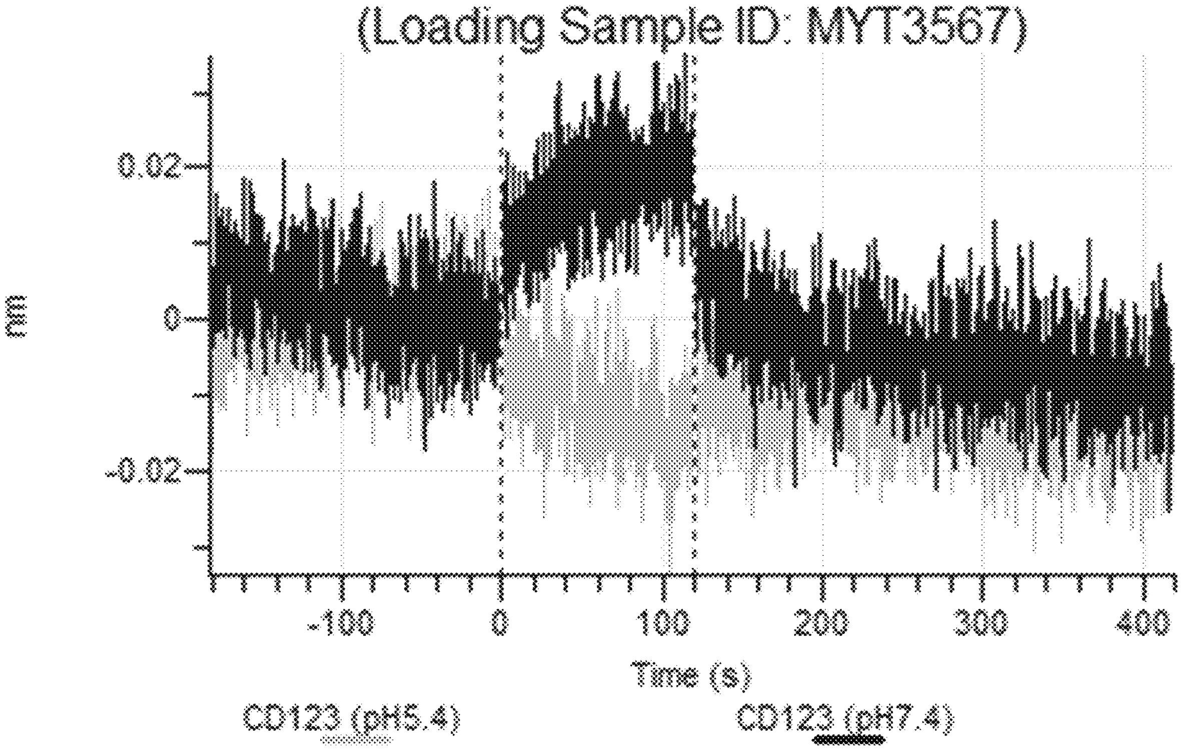
Figure 11Q:
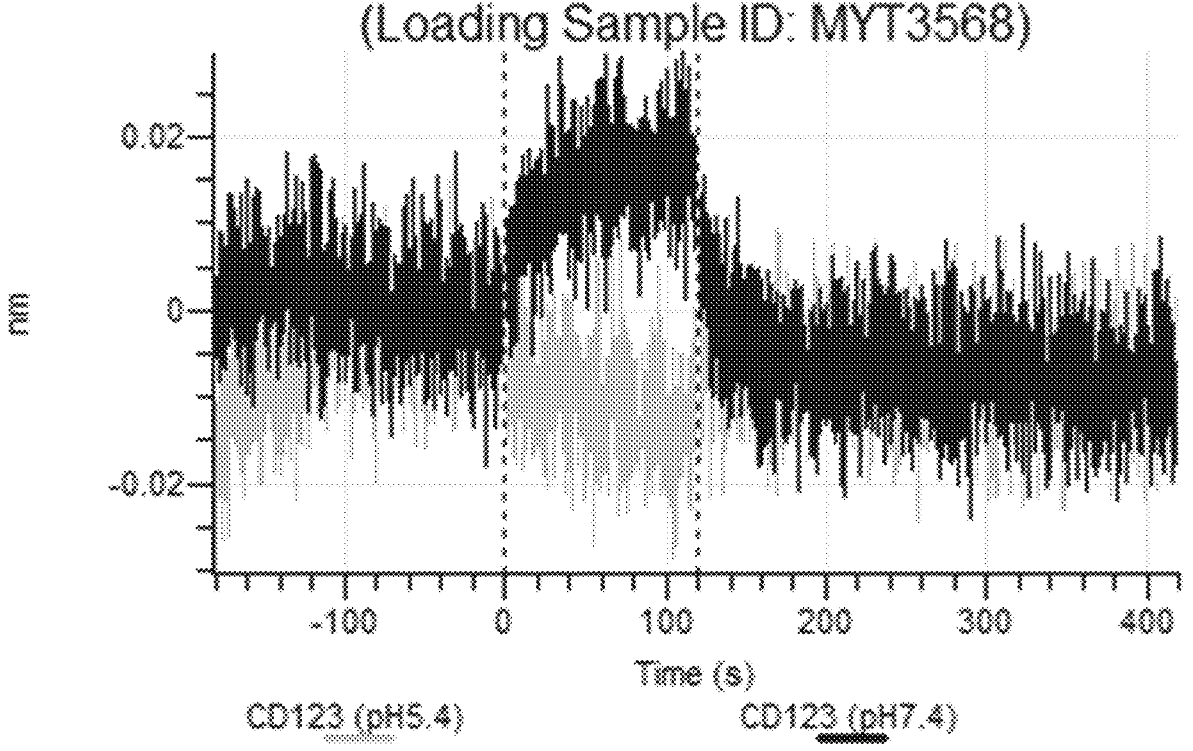
Figure 11R:
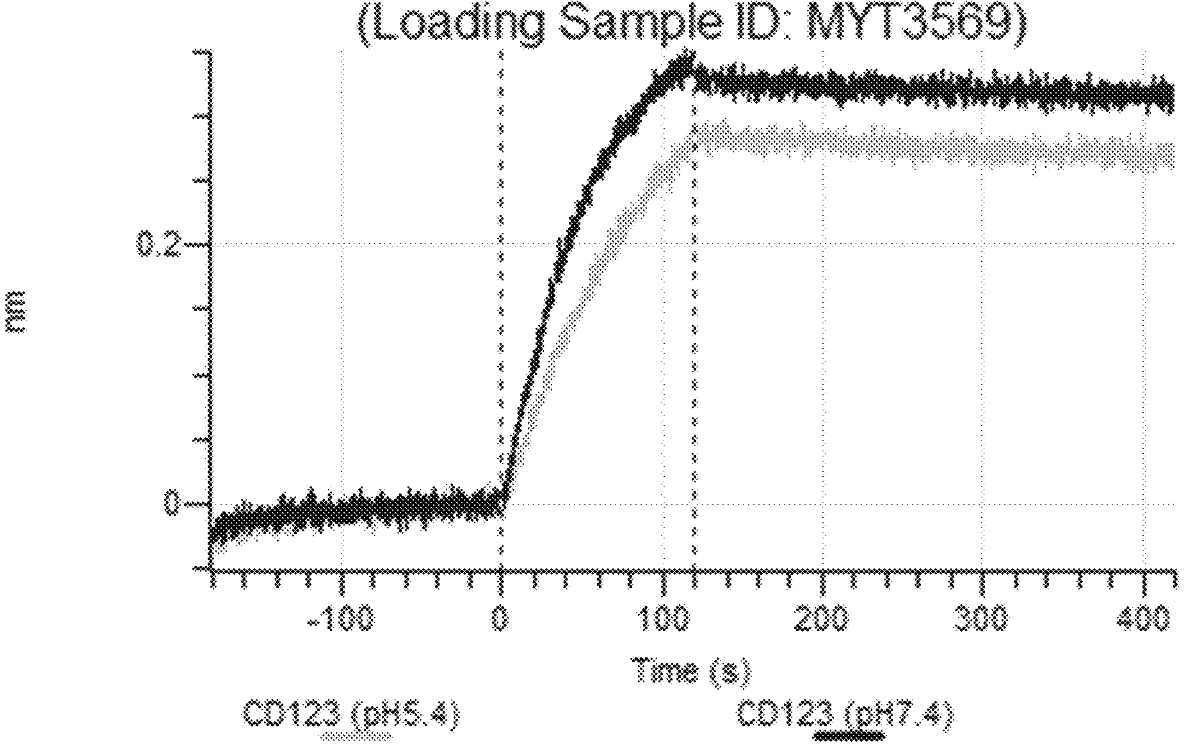
Figure 11S:
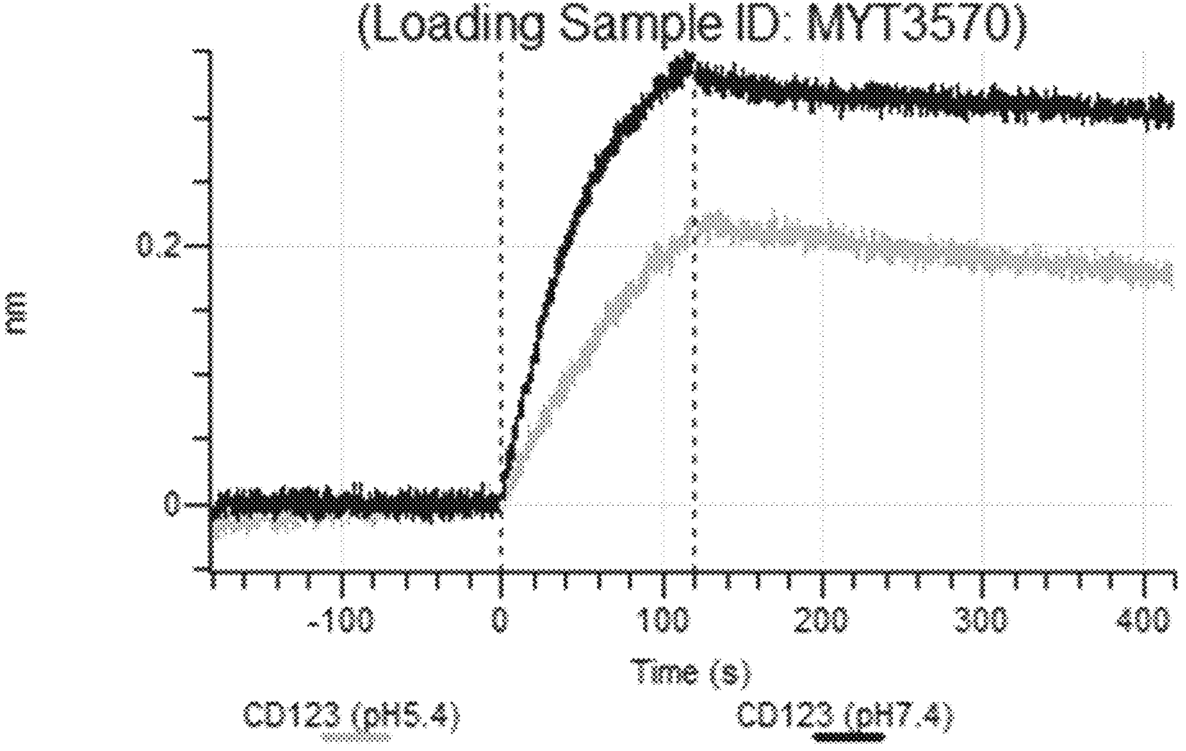
Figure 11T:
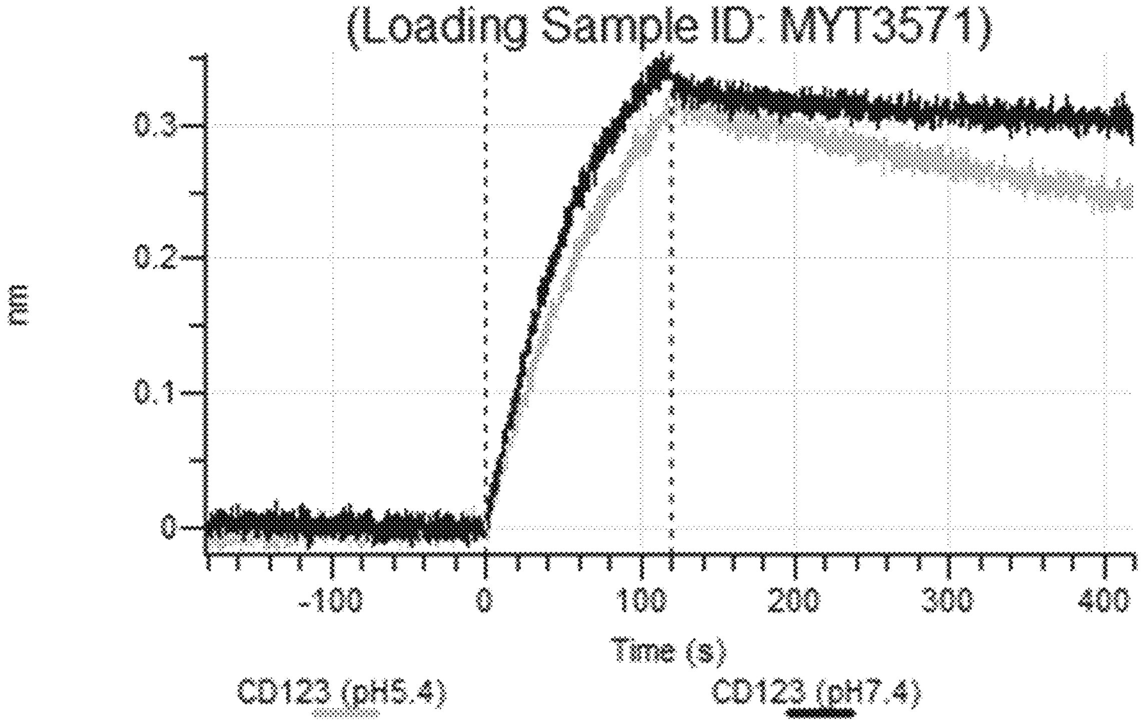
Figure 11U:
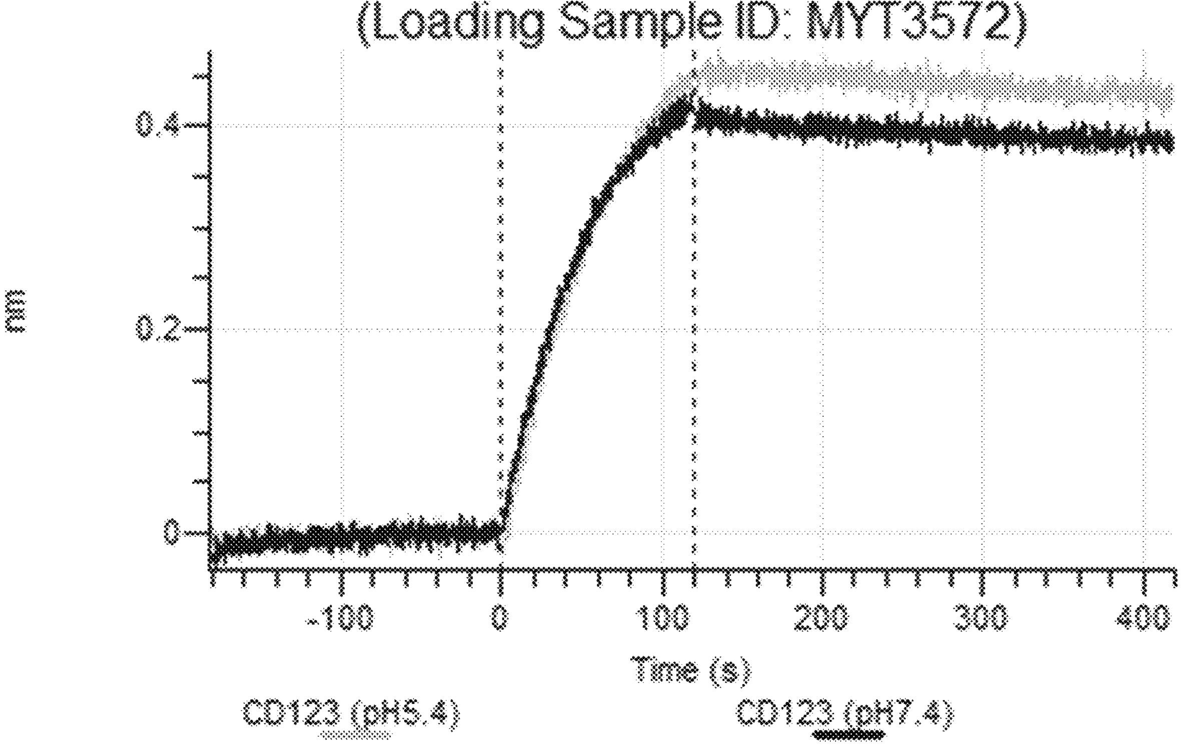
Figure 11V:
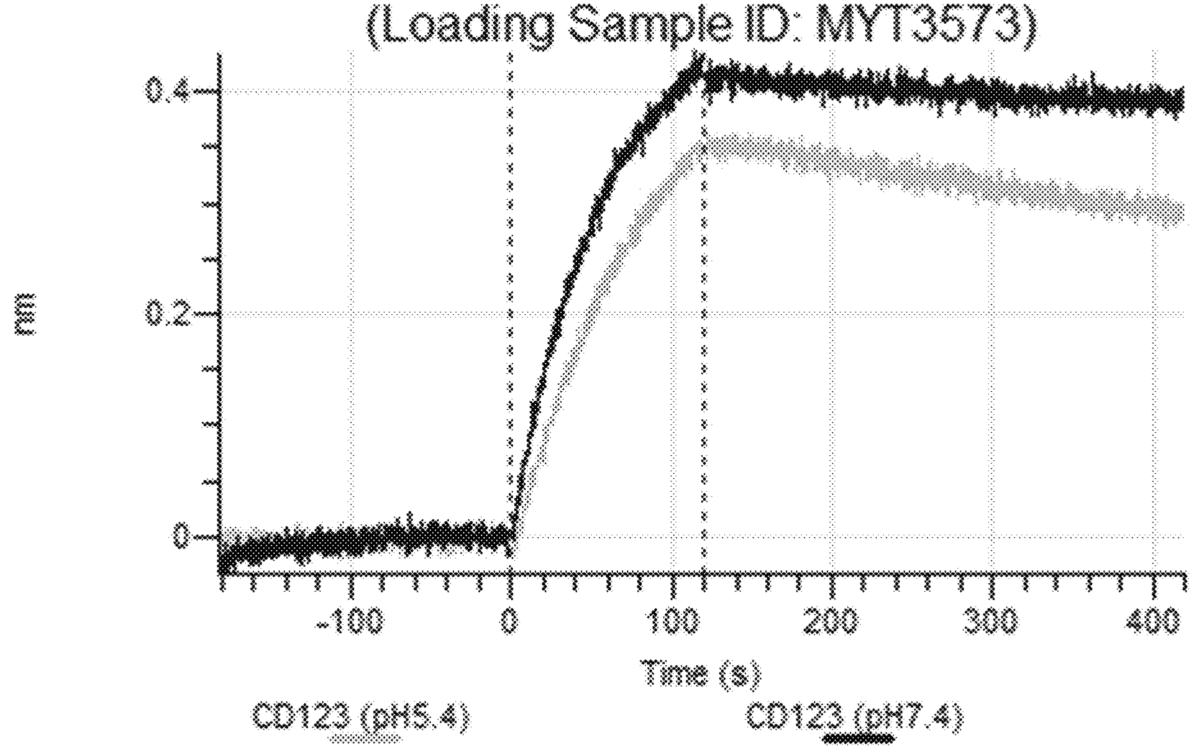
Figure 11W:
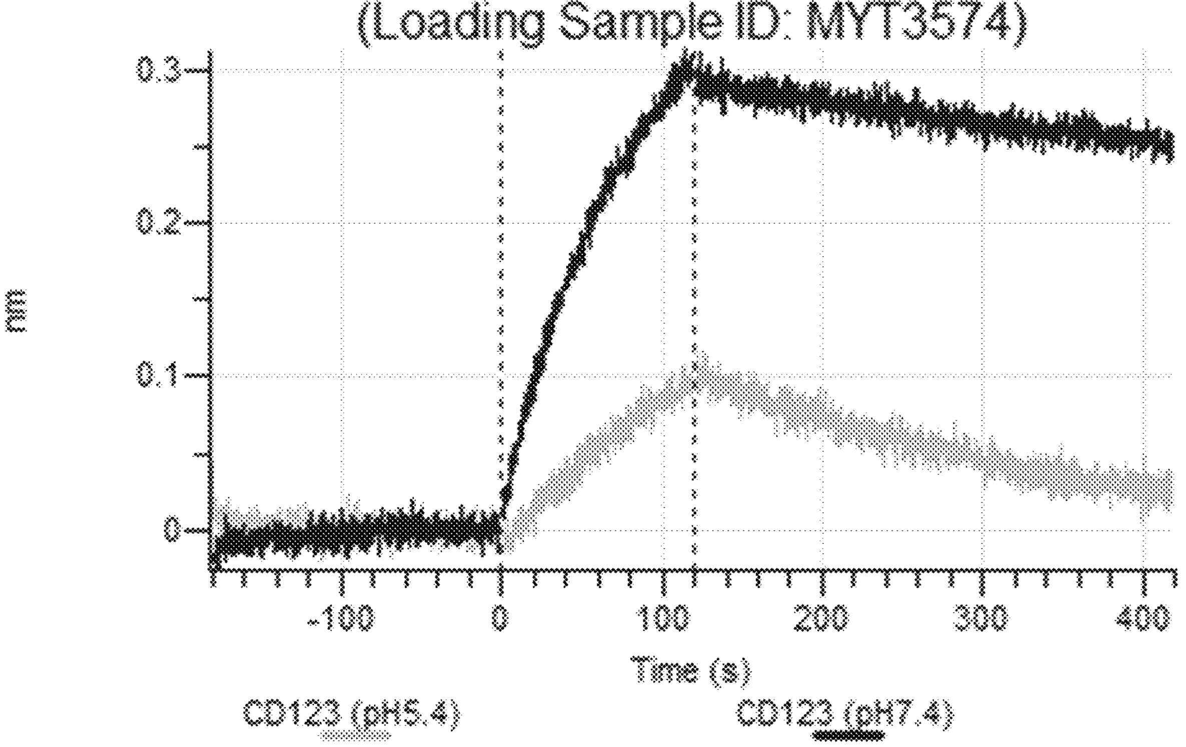
Figure 11X:
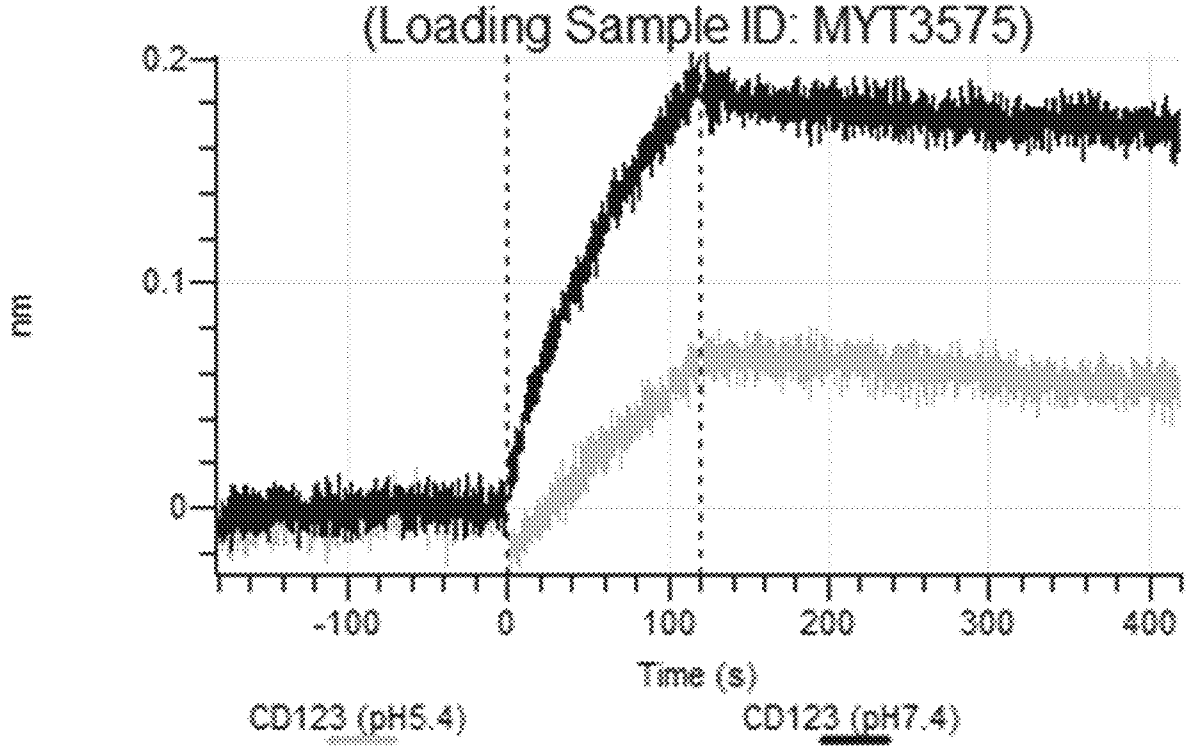
Figure 11Y:
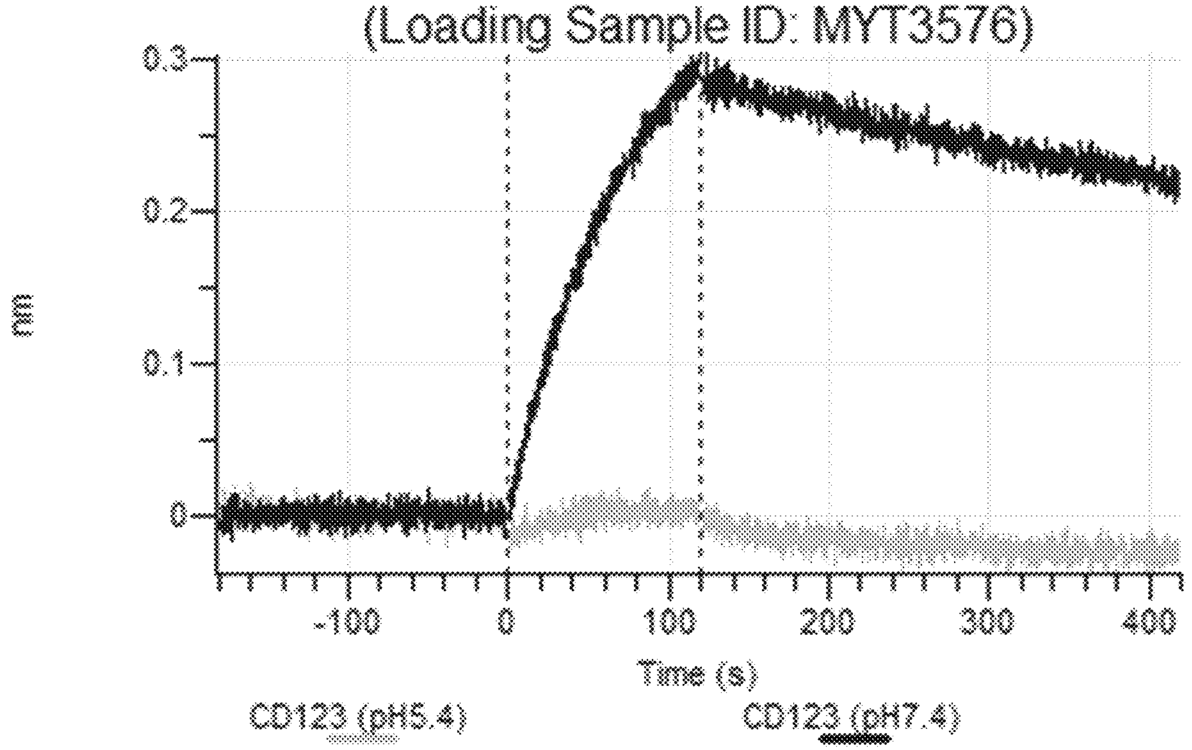
Figure 11Z:
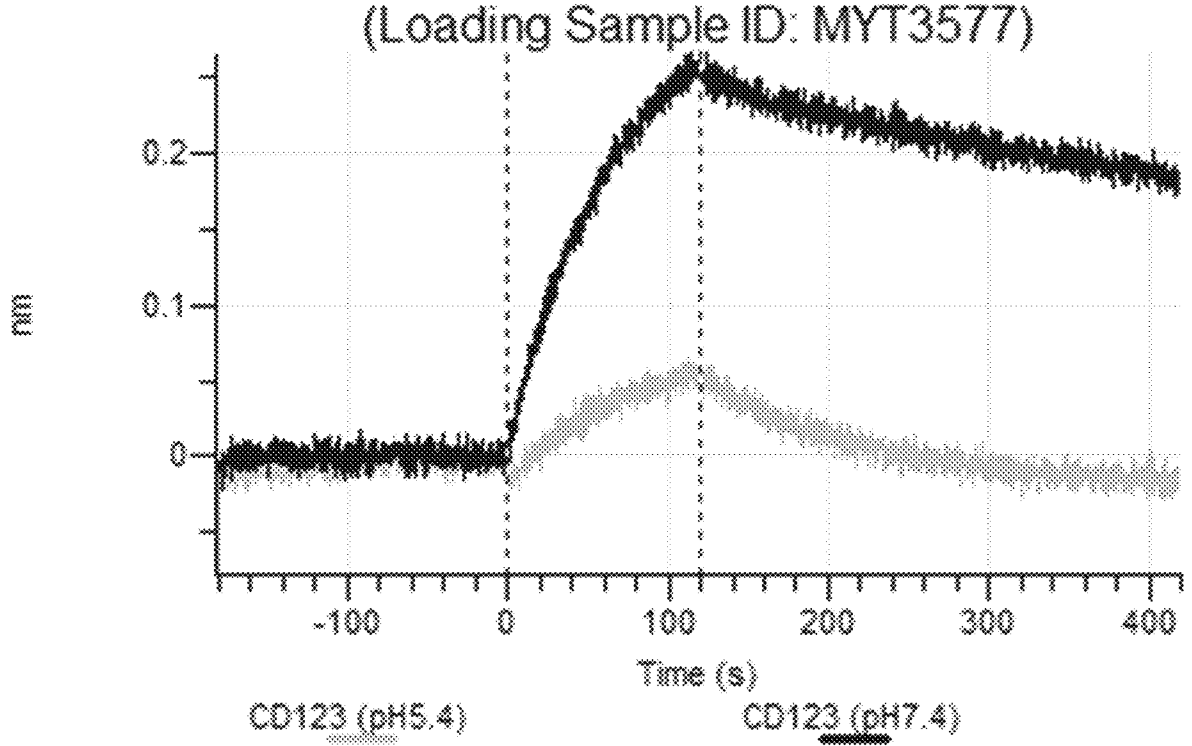
Figure 11A:
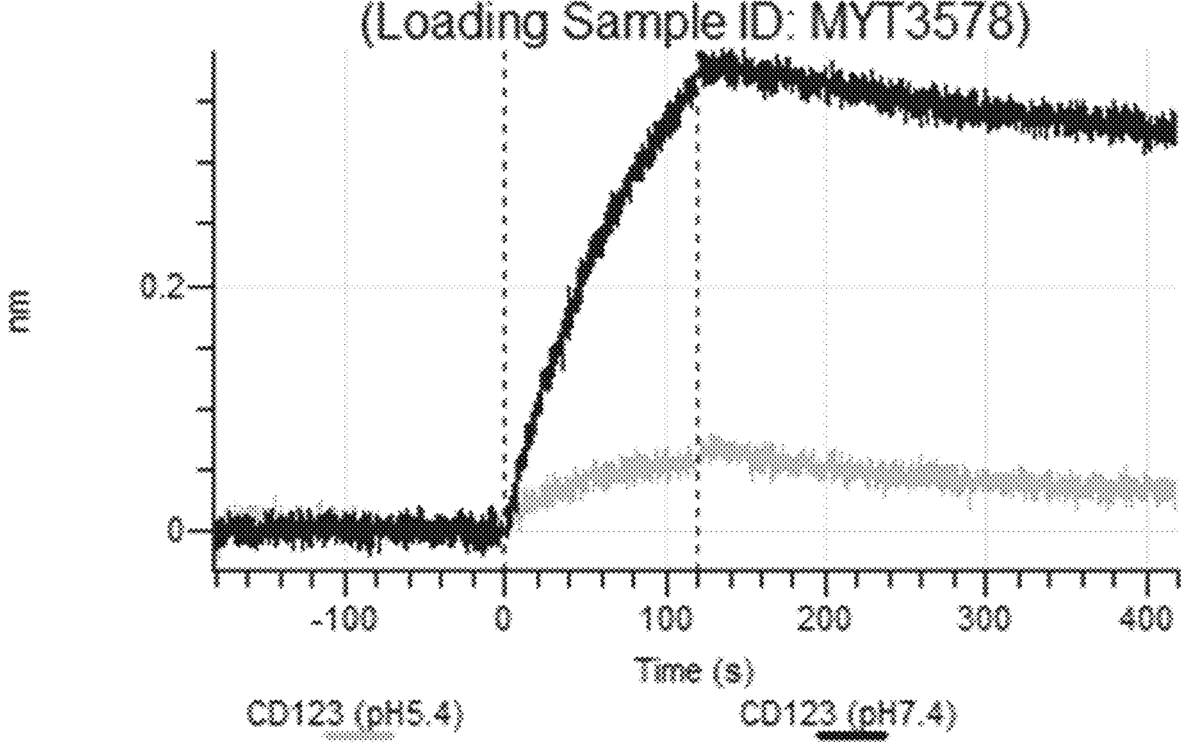
Figure 11A:
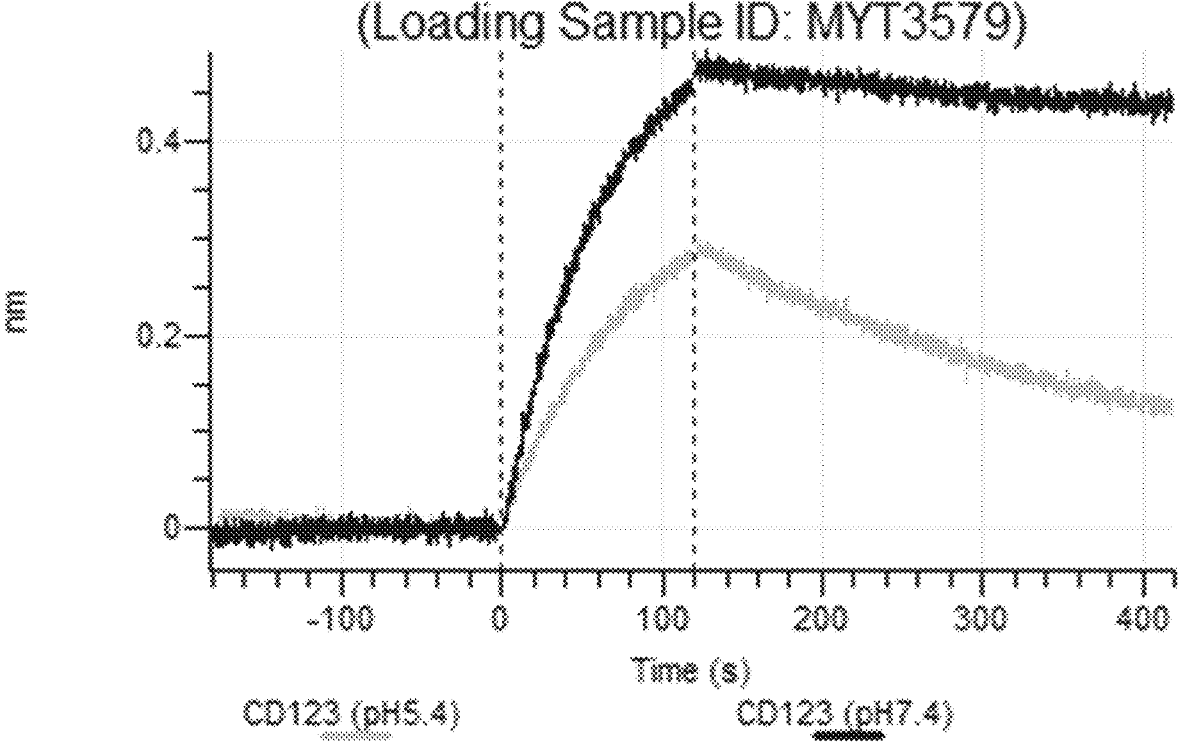
Figure 11A:
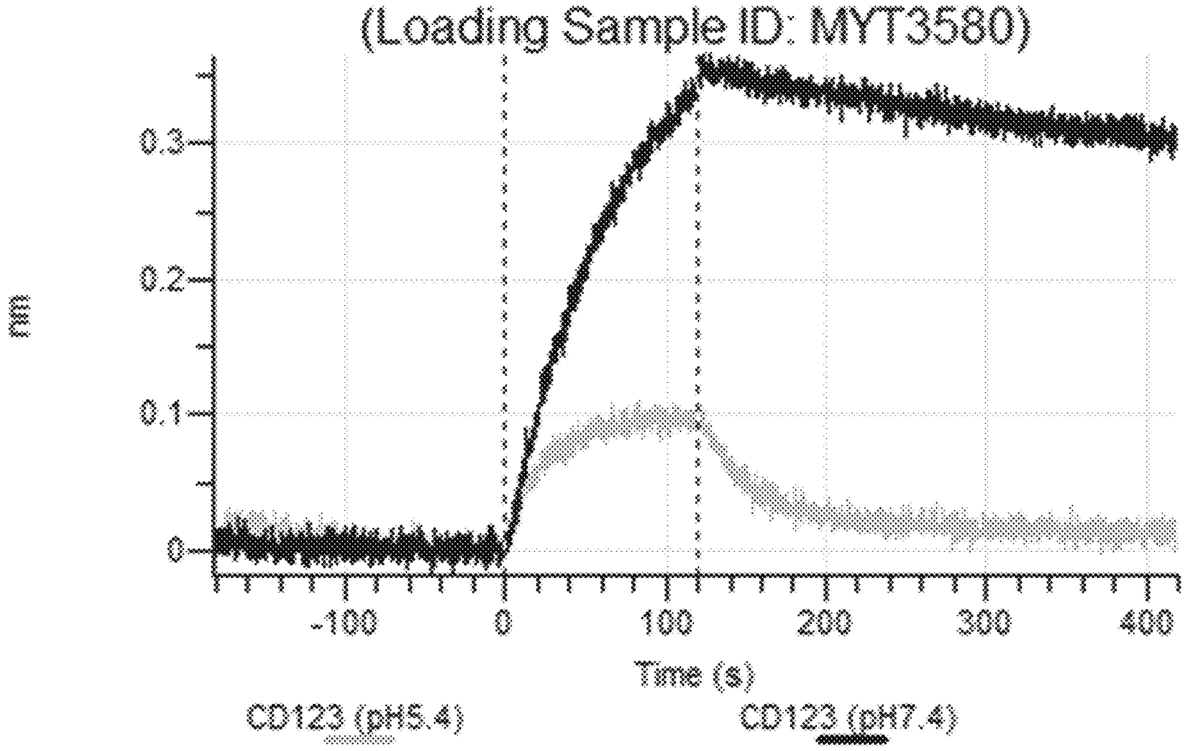
Figure 11A:
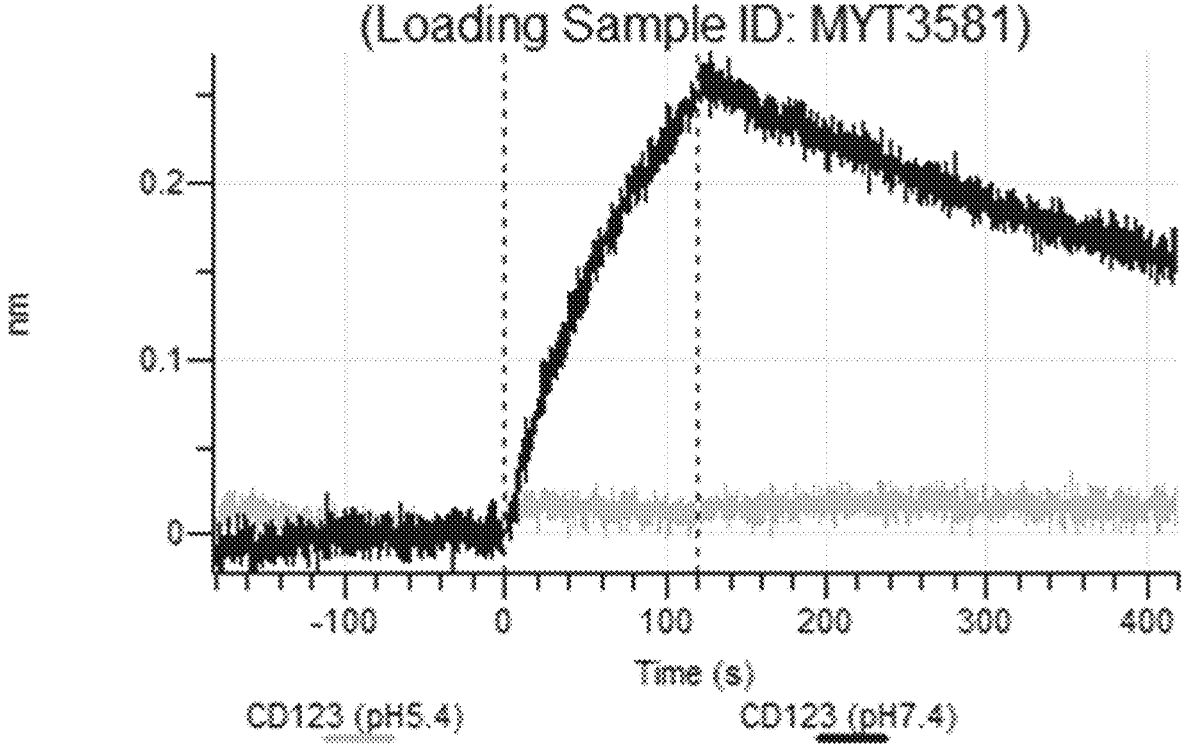
Figure 11A:
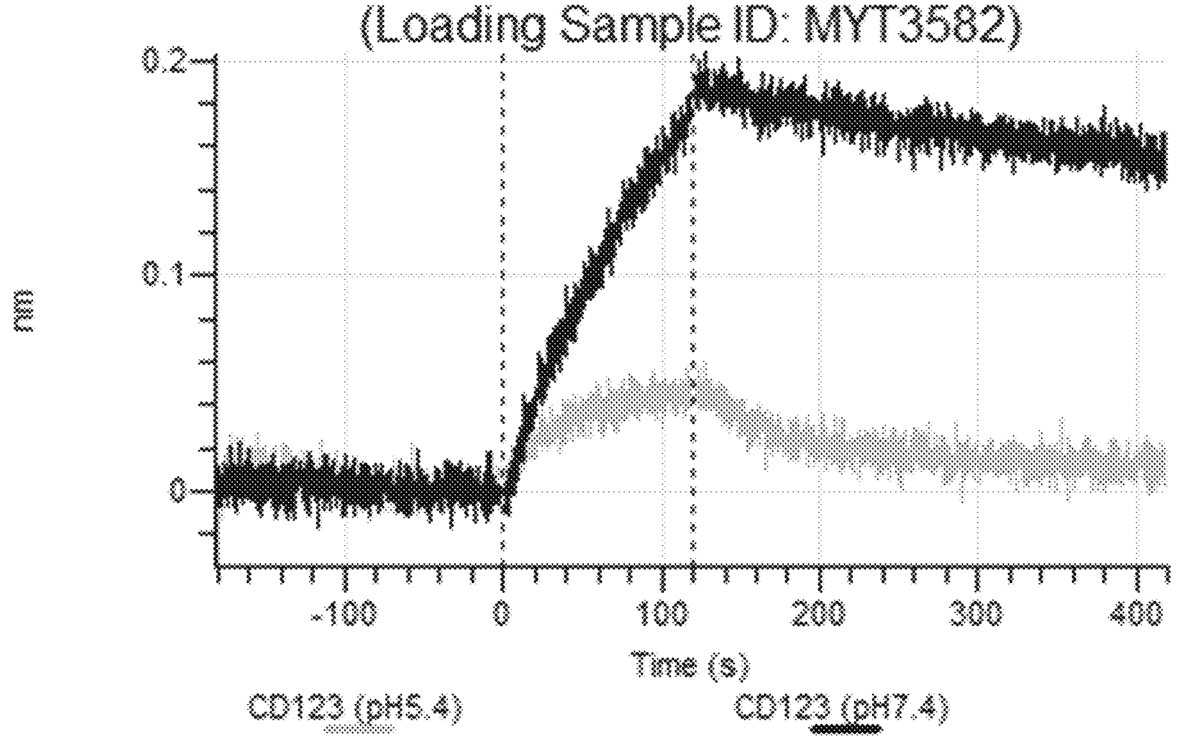
Figure 11A:
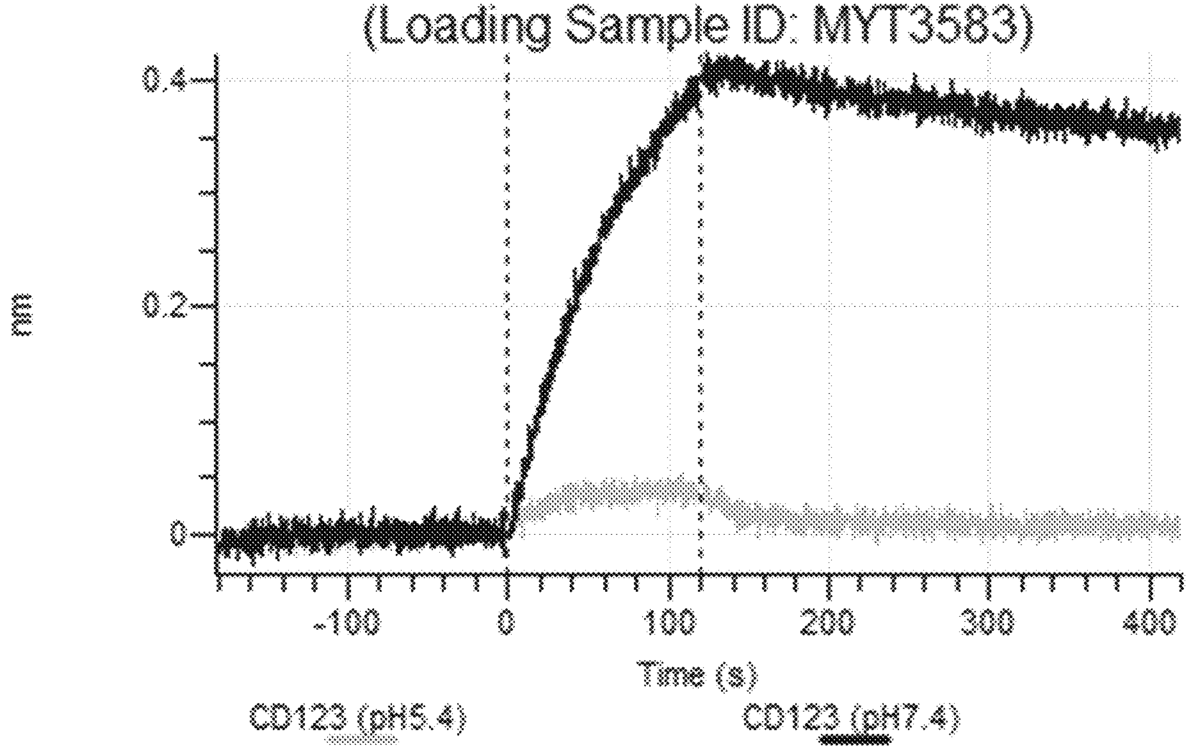
Figure 11A:
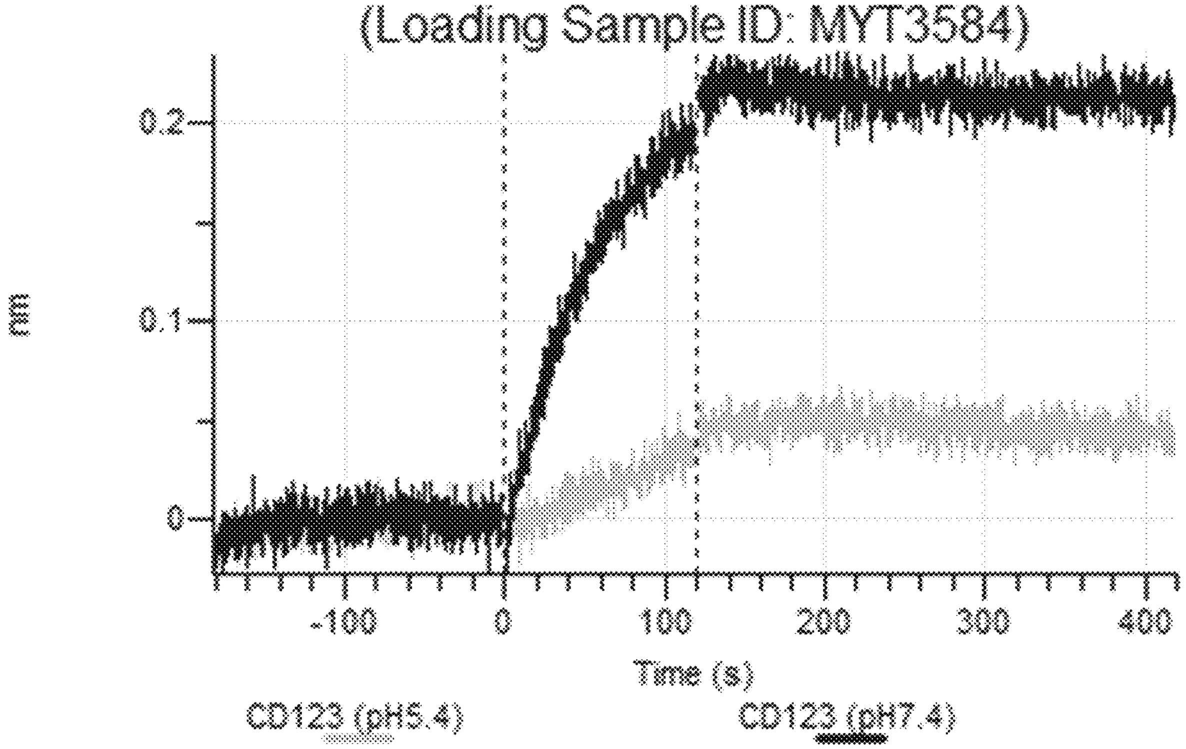
Figure 11A:
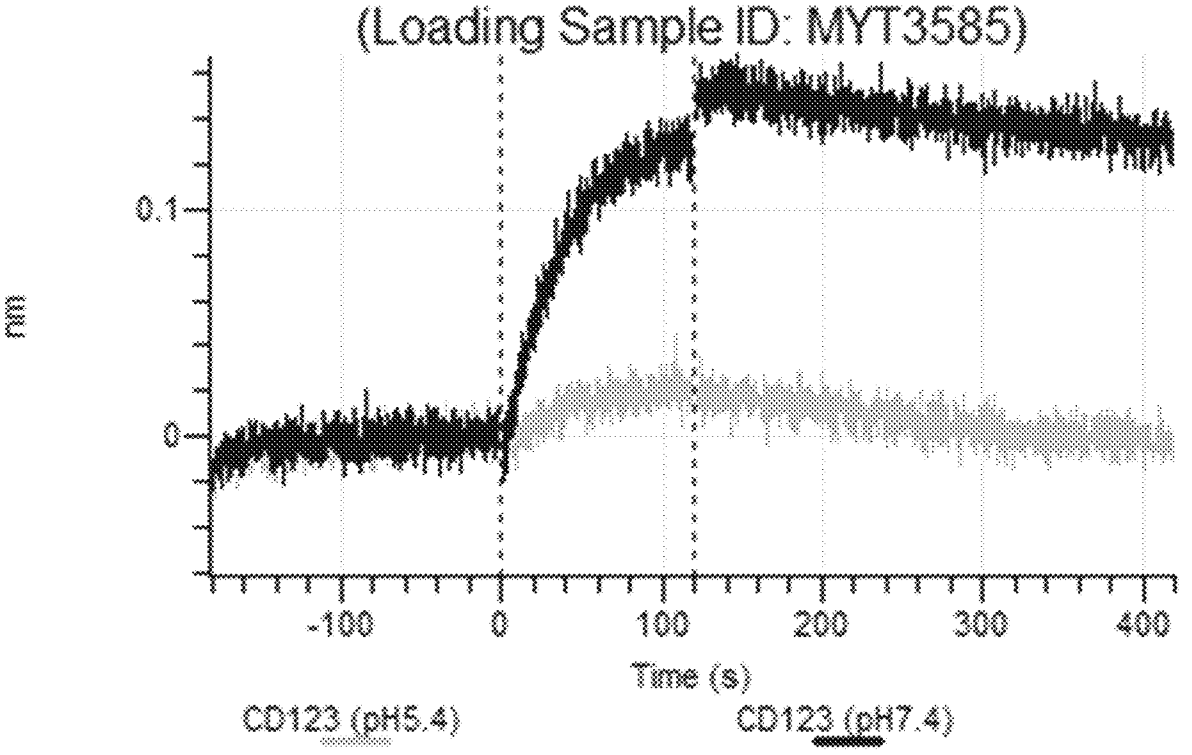
Figure 11A:
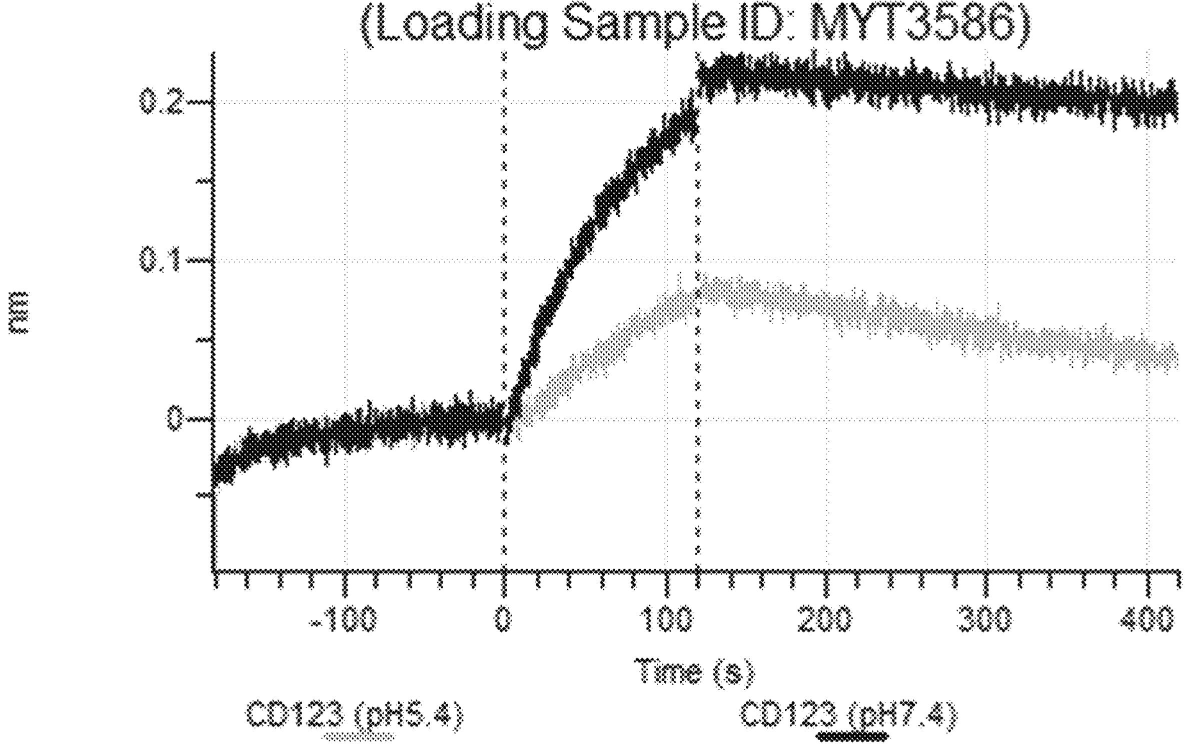
Figure 11A:
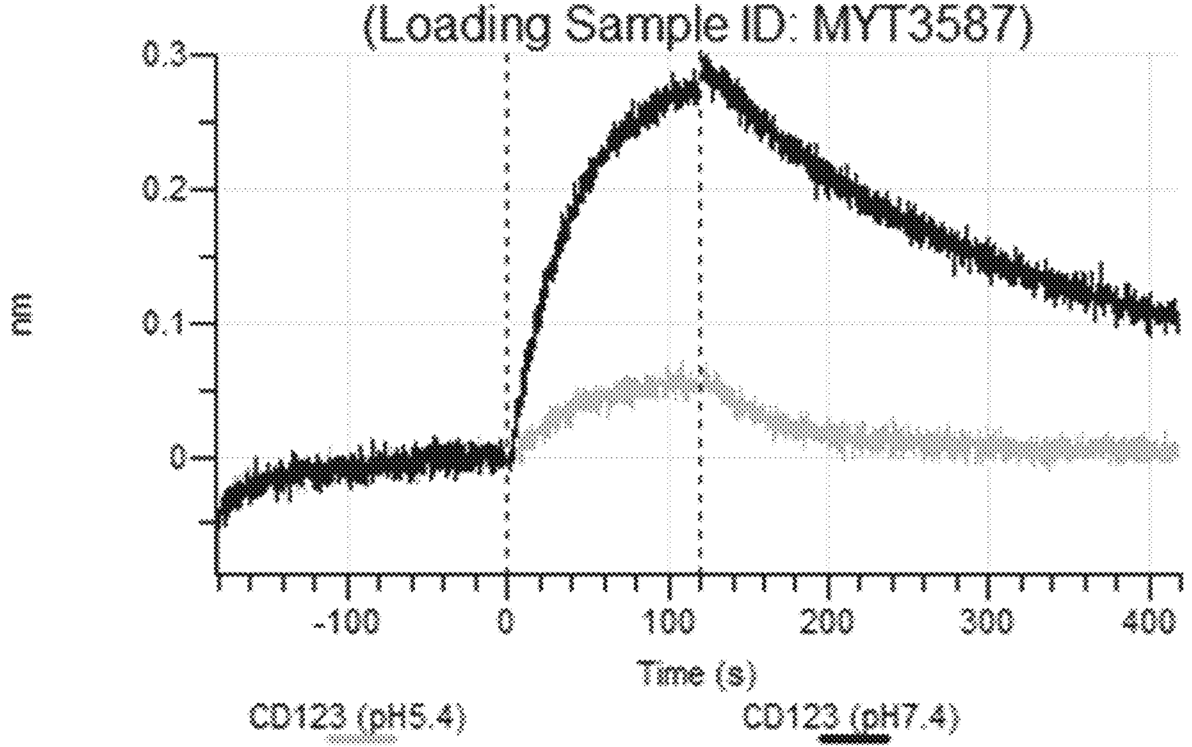
Figure 11A:
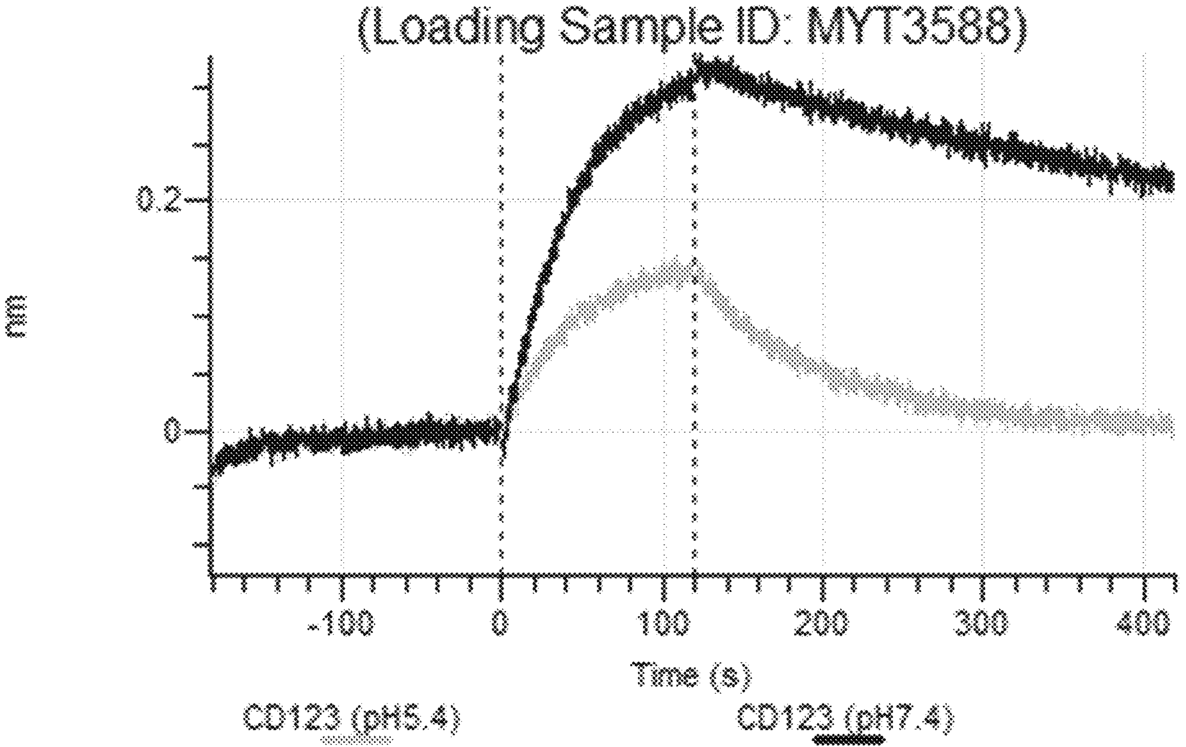
Figure 11A:
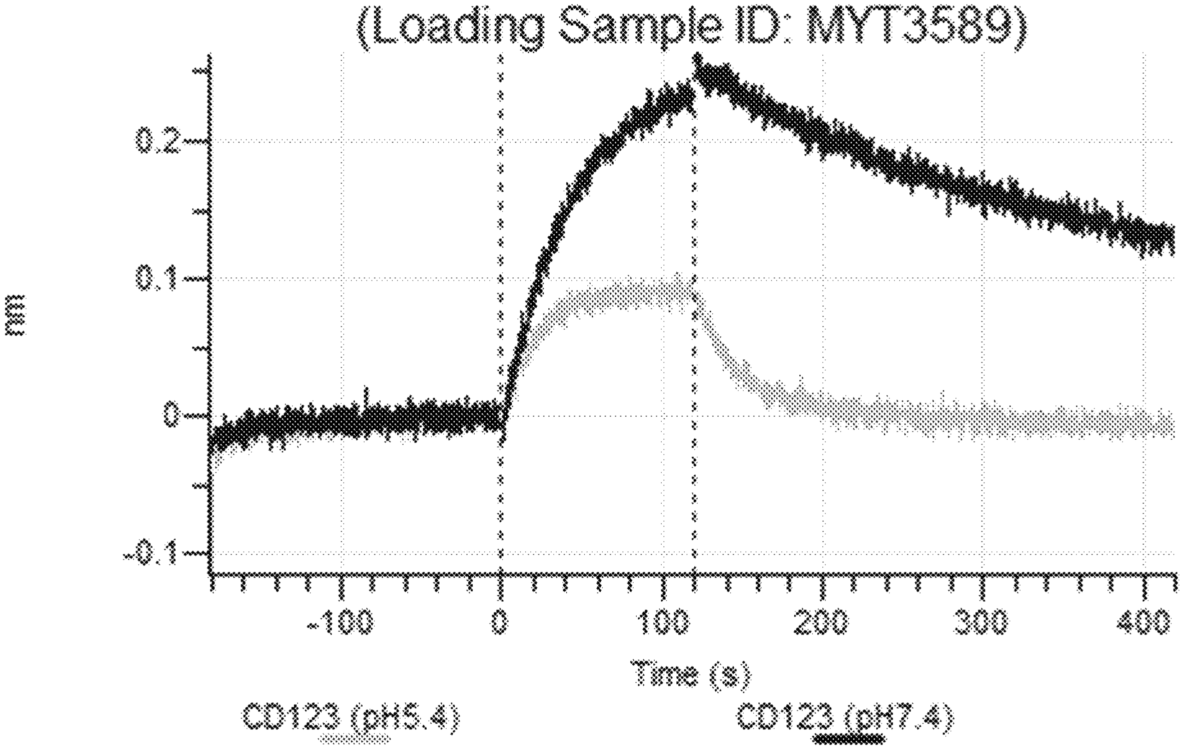
Figure 11A:
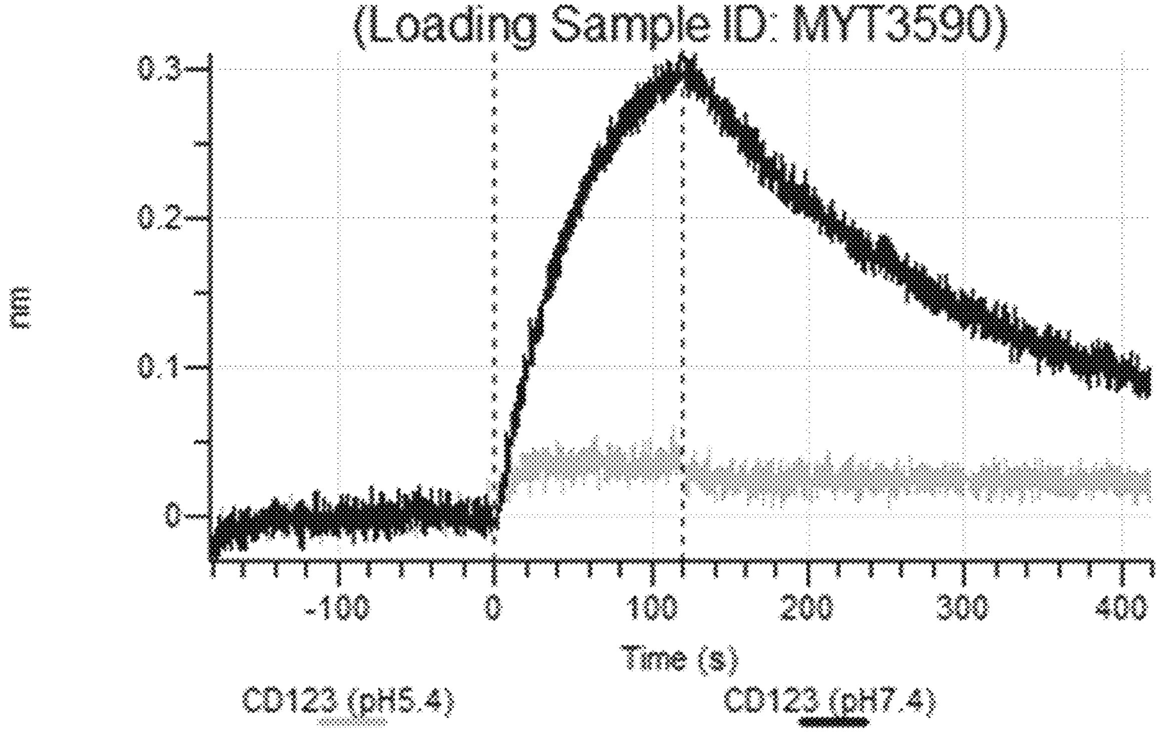
Figure 11A:
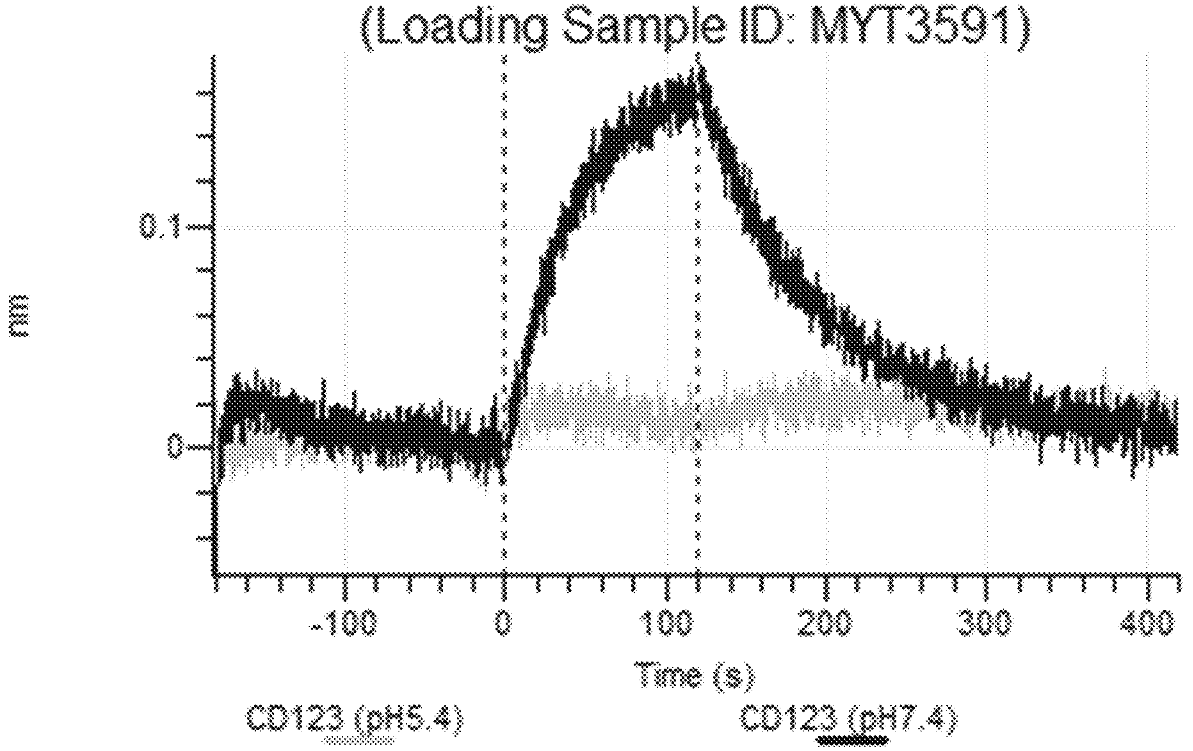
Figure 11A:
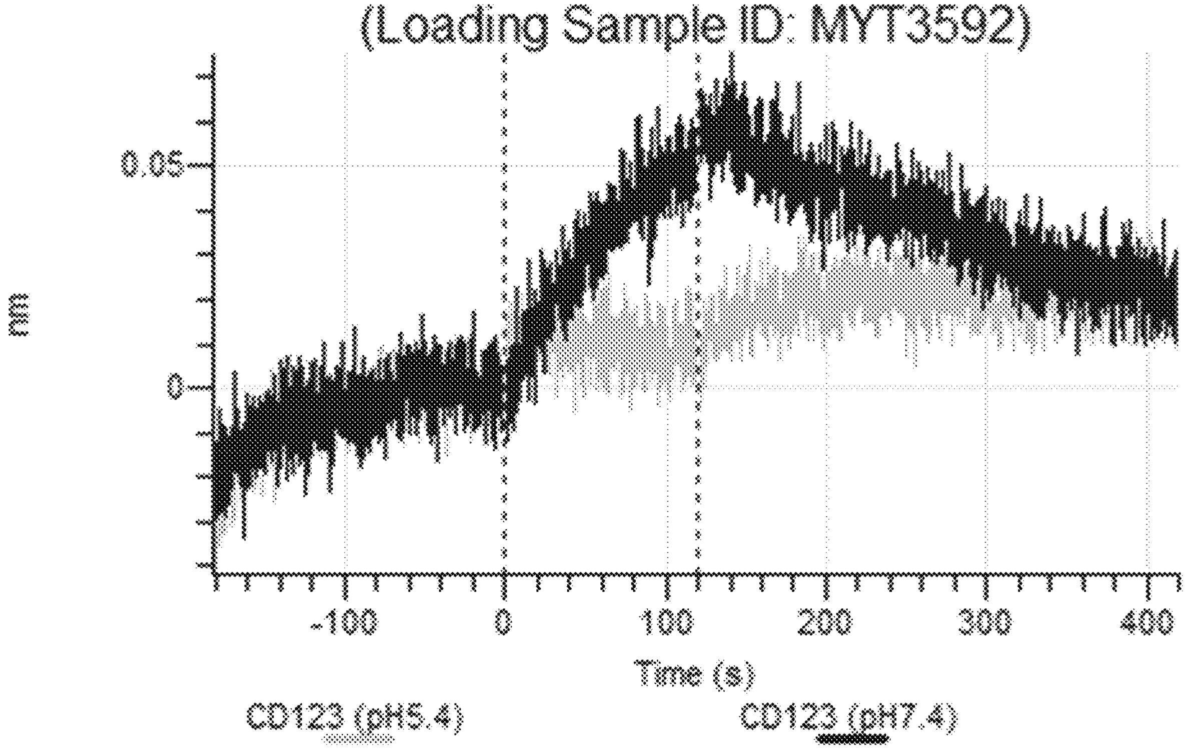
Figure 11A:
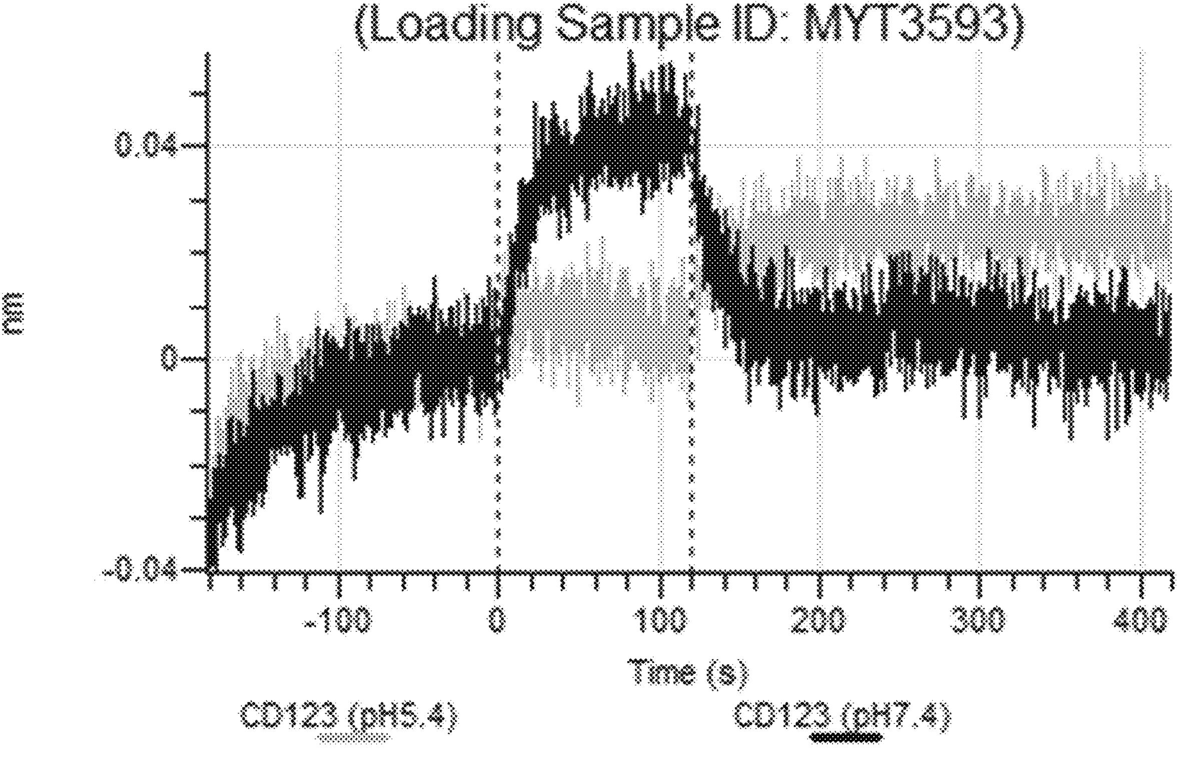
Figure 11A:
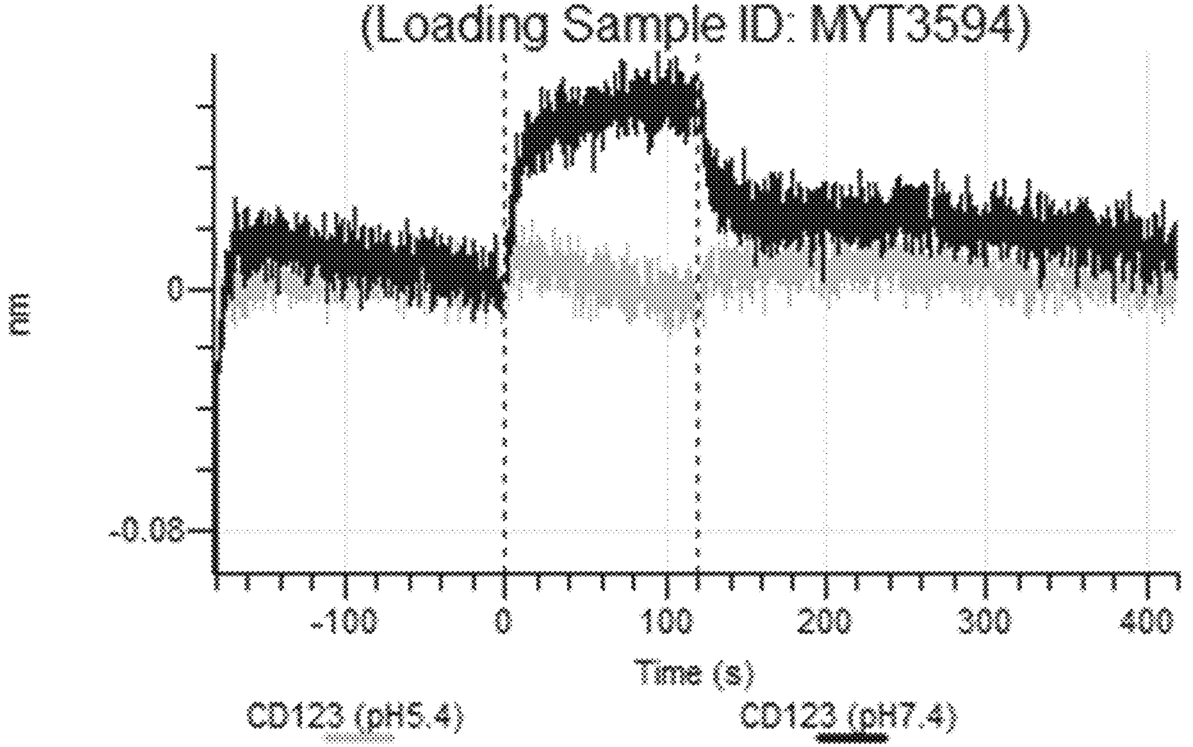
Figure 11A:
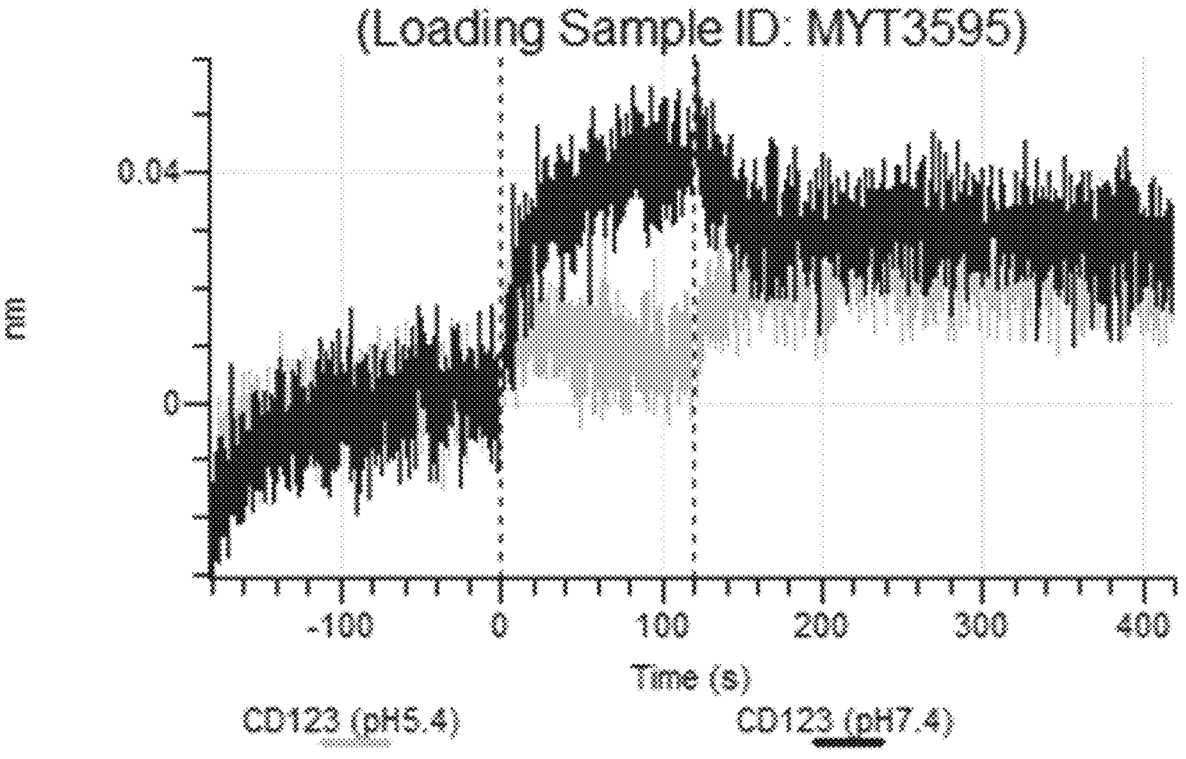
Figure 11A:
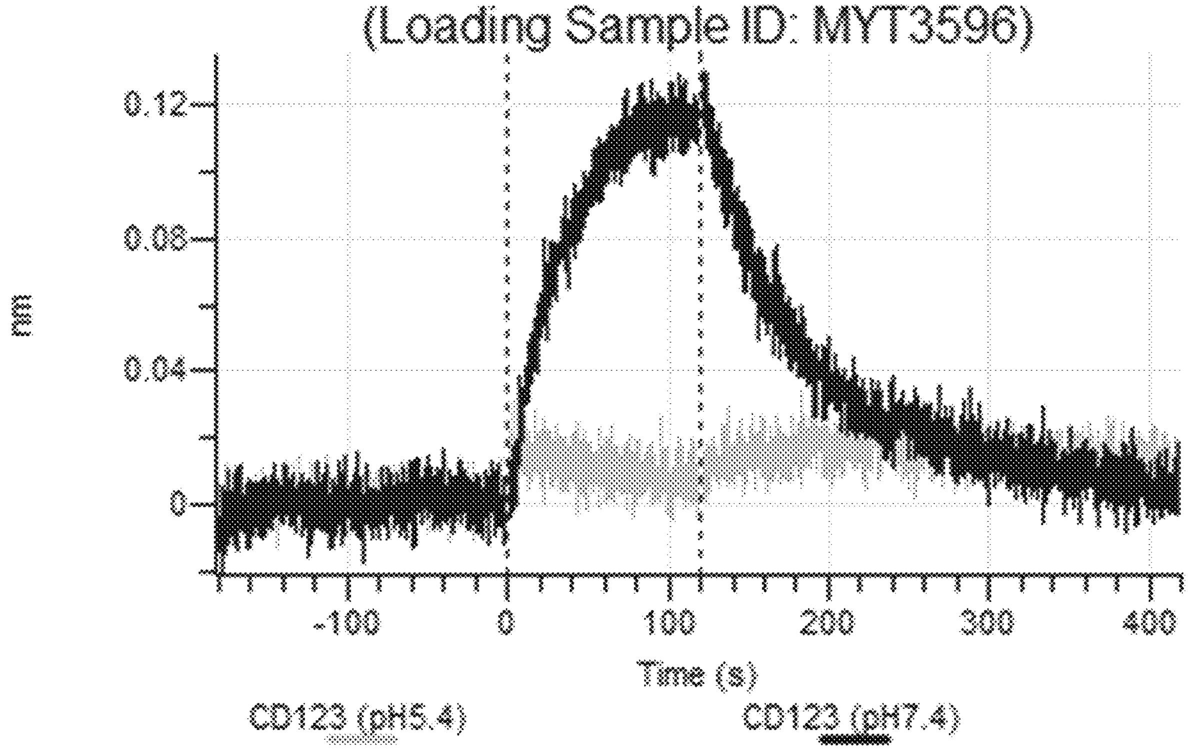
Figure 11A:
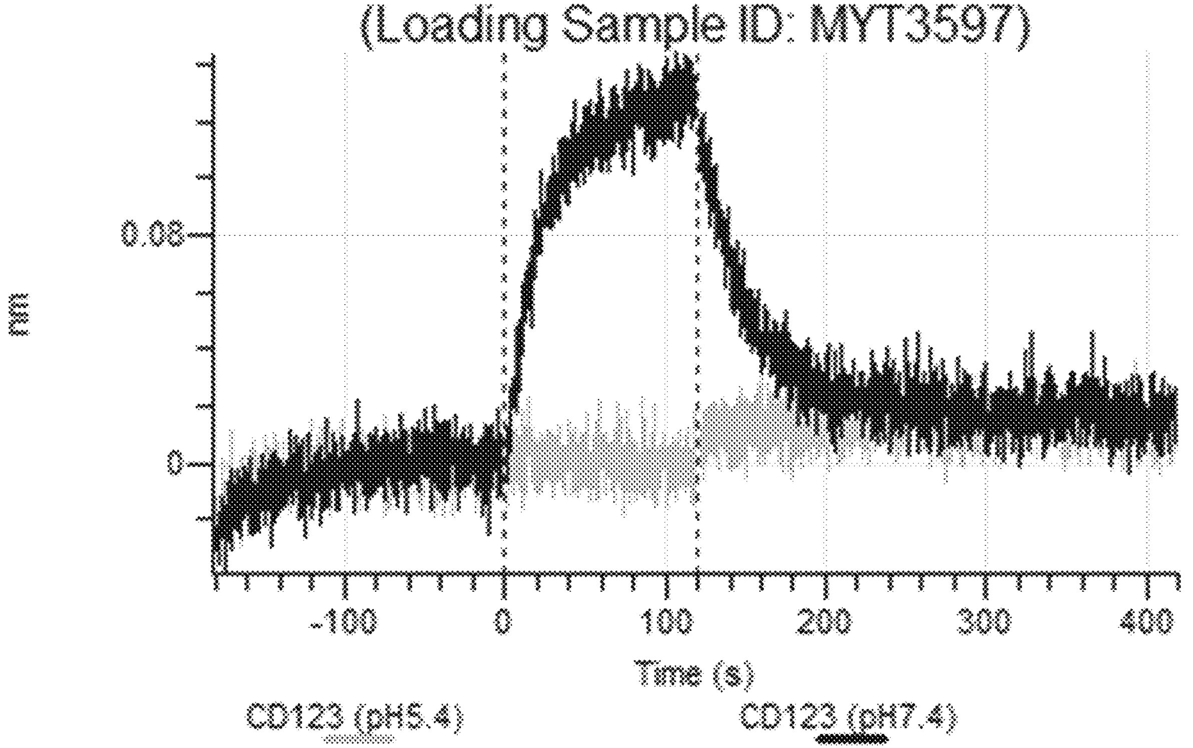
Figure 11A:
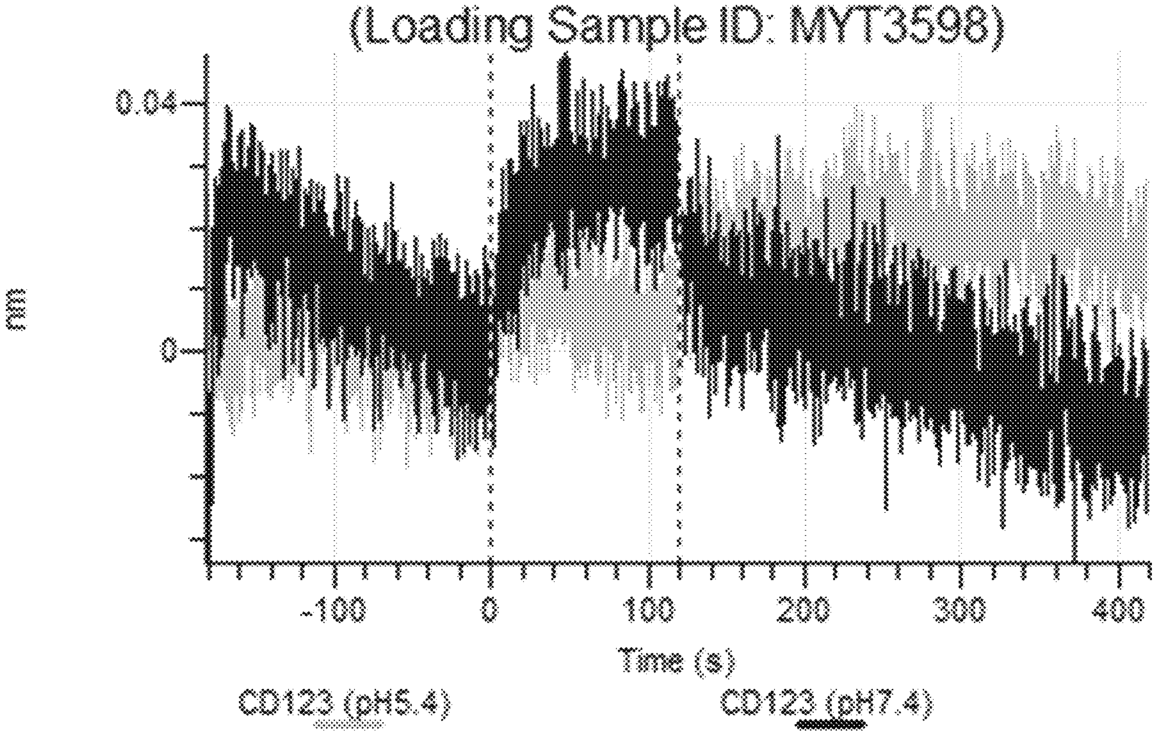
Figure 11A:
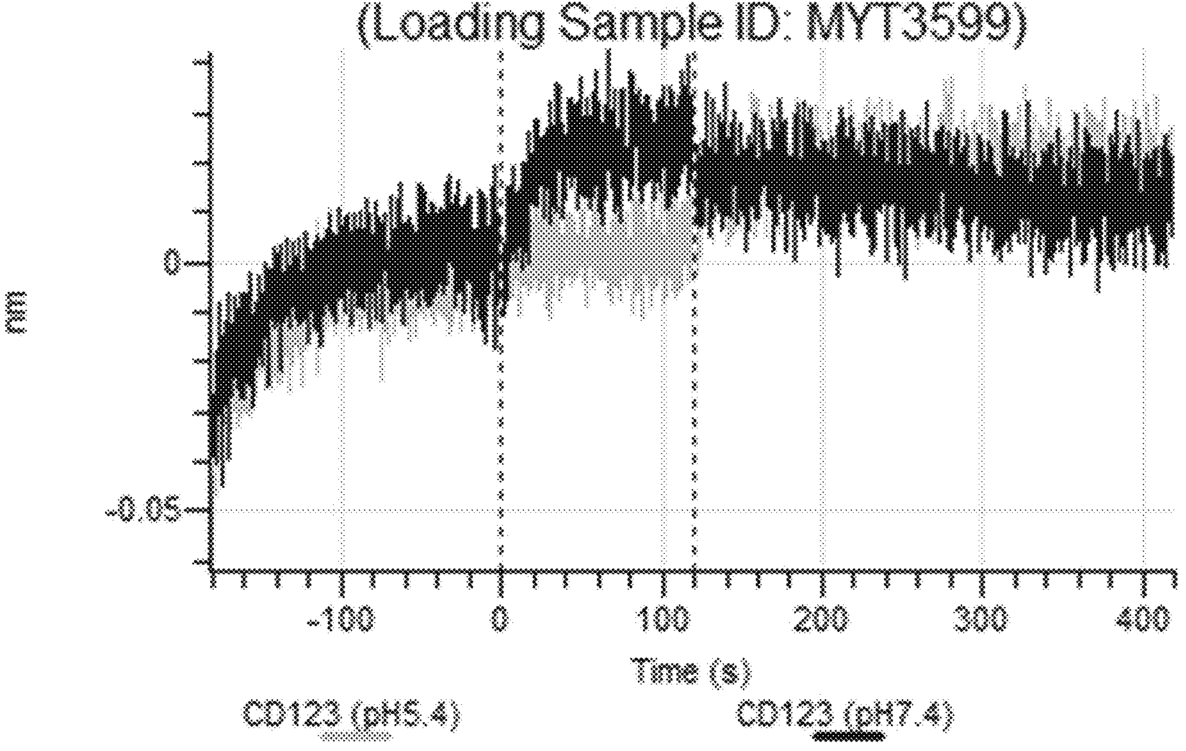
Figure 11A:
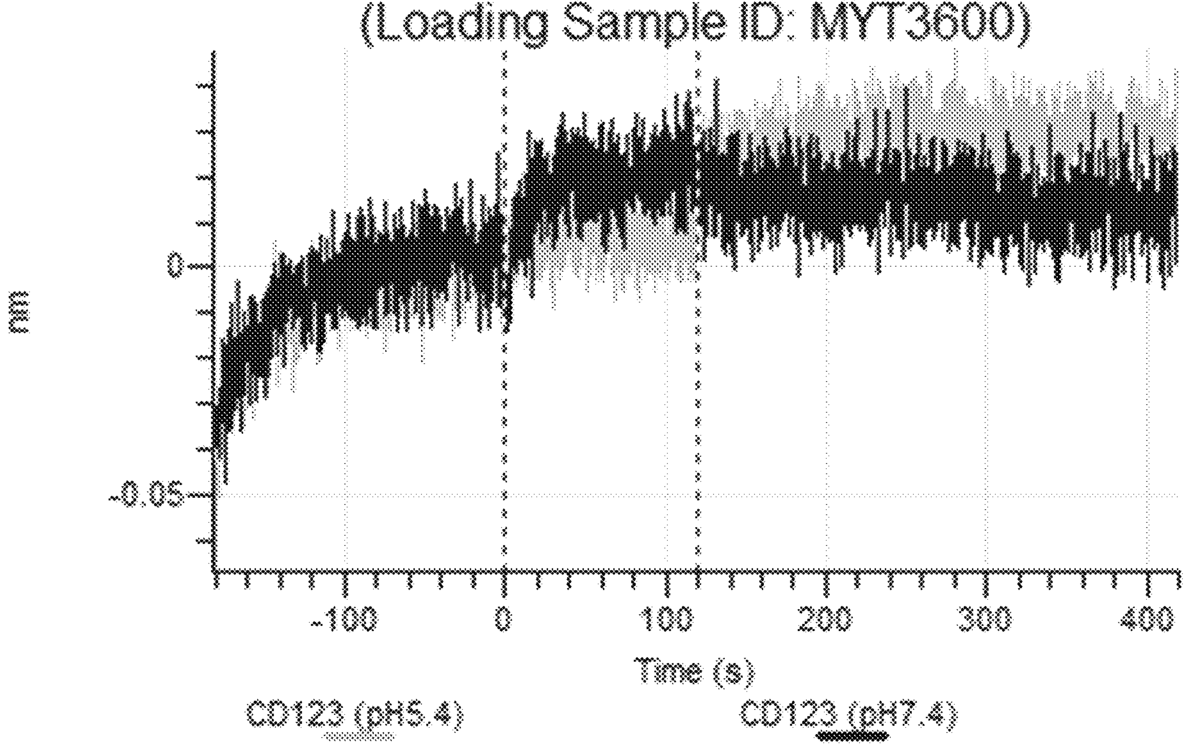
Figure 11A:
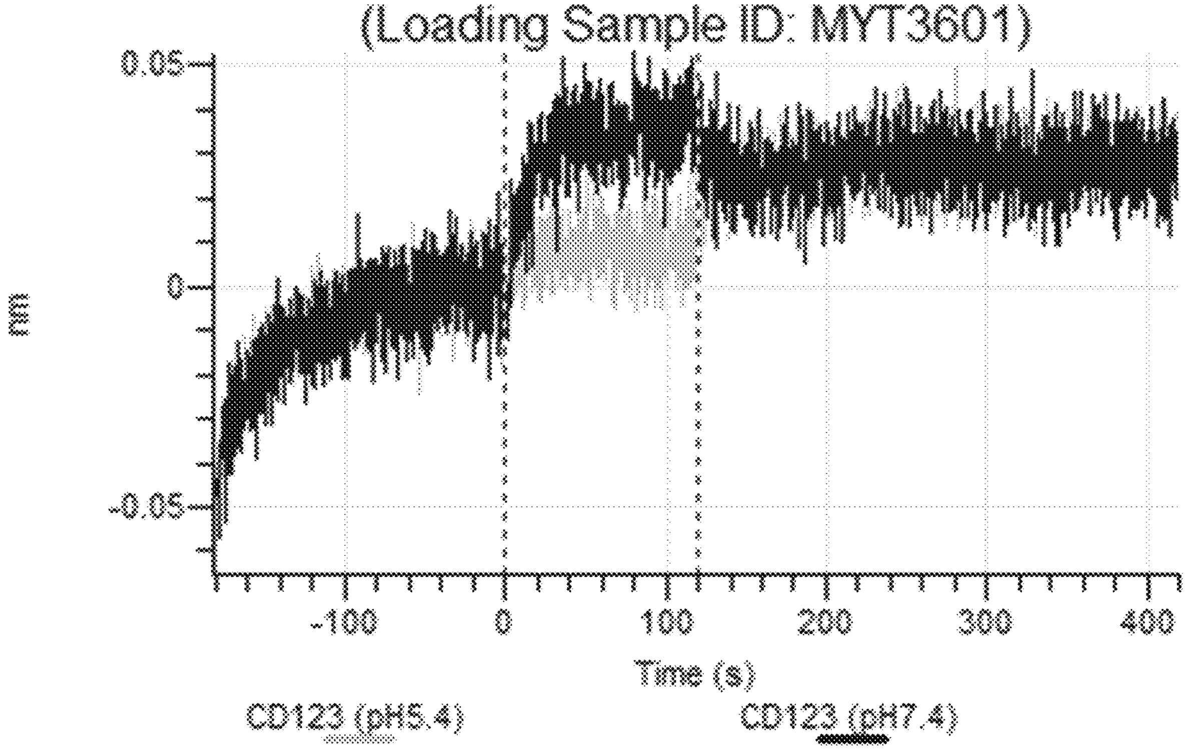
Figure 11A:
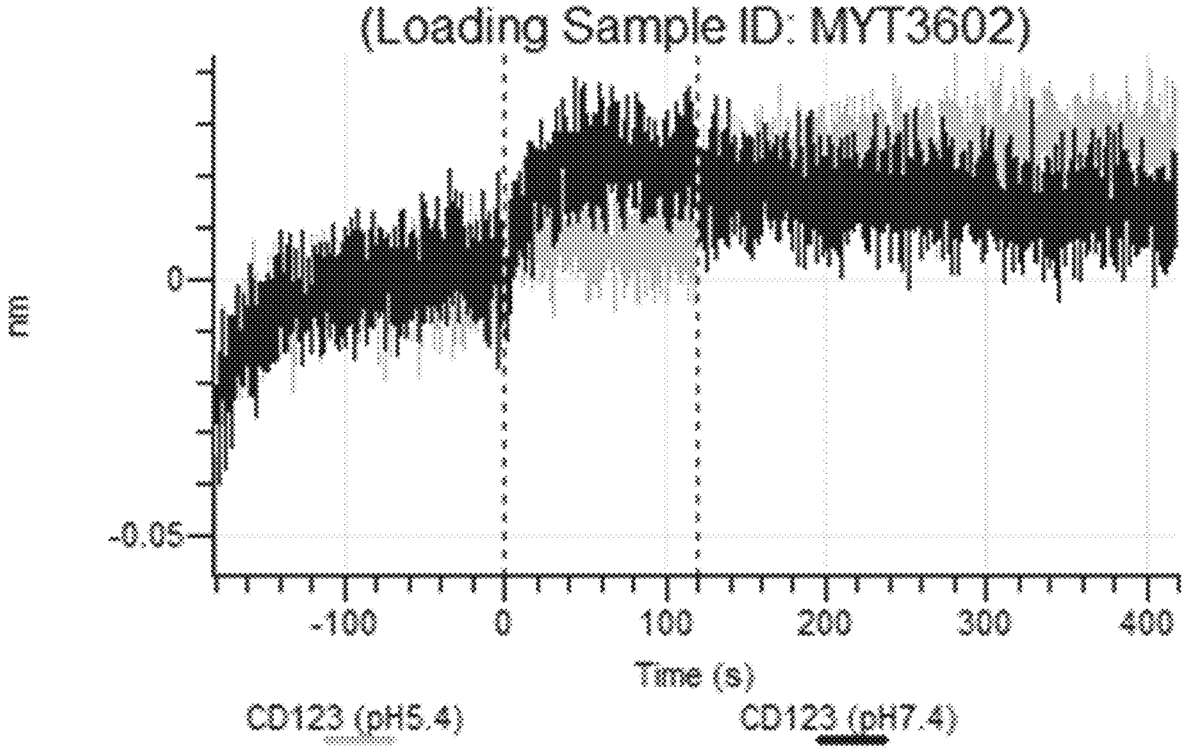

Multiple CD123-binding monoclonal antibodies have been described in the literature and can be used as a template for engineering pH-dependent binding [Kovtun, Yelena, et al. (2018) "A CD123-Targeting Antibody-Drug Conjugate, IMGN632, Designed to Eradicate AML While Sparing Normal Bone Marrow Cells." Blood Advances, American Society of Hematology 2(8) 848-858]. We selected IMGN632 (Heavy chain SEQ ID NO: 1, Light chain SEQ ID NO: 2) as a CD123-binding monoclonal antibody for pH engineering via histidine scanning. Briefly, CDRs in the heavy and light chains were identified using the methods described by Kabat et al (Kabat et al. (1992) Sequences of Proteins of Immunological Interest, DIANE publishing) and IMGT (Lefranc M P (1999) "The IMGT unique numbering for Immunoglobulins, T cell receptors and Ig-like domains" The Immunologist 7, 132-136), and for each CDR, residues falling under either or both Kabat and IMGT CDR definitions were called as CDR residues. To generate pH-dependent sequence variants, individual amino acid mutations within the heavy and light chain CDRs that had been previously selected for further analysis in Examples 9-11 were systematically combined two or more at a time (MYT3552-MYT3602). In cases where the starting CDR residue was a histidine, it was mutated to an alanine. Antibody variants with two or more histidine or alanine mutations were generated by co-transfection of Expi293 cells with a) one light chain sequence variant, and b) one heavy chain sequence variant or heavy chain combinations sequence variant using methods known to the art. After allowing for four days of protein expression, cell culture supernatants were collected, quantified by SDS-PAGE analysis (FIG. 10), and the pH dependence of the variant was evaluated using biolayer interferometry (BLI) on an Octet RED 96e instrument. Briefly, cell culture supernatants were diluted based on qualitative expression level of the variant determined by visual examination of SDS-PAGE gels, 5 μL of cell culture supernatant was diluted into 195 μL of 1×PBST, pH 7.4 for high expressors, 25 μL of cell culture supernatant was diluted into 175 μL of 1×PBST, pH 7.4 for medium expressors and 100 μL of cell culture supernatant was diluted into 100 μL of 1×PBST, pH 7.4 for low expressors for loading onto the sensor tips. Diluted supernatants were then captured on an anti-human Fc sensor (Forte Bio). A baseline was established using 1×PBST (50 mM Potassium Phosphate Buffer+150 mM NaCl+0.05% Tween 20), pH 7.4, and the sensor was associated with 50 nM of CD123 protein (R&D Systems Catalog No. 301-R3-025/CF) in 1× PBST, pH 7.4, for 120 sec to generate an association curve. In the dissociation phase, the antibody-antigen complex on the sensor was exposed to 1×PBST, pH 7.4, for 300-600 sec. Baseline, association, and dissociation were repeated using 1×PBST, pH 5.4, throughout in a separate condition. Association and dissociation phase curves were examined for the starting ABPC antibody (with no substitutions) and each corresponding antibody variant at pH 5.4 and pH 7.4 to inform on two criteria: a) enhanced dissociation (e.g., higher koff values) at pH 5.4 due to histidine or alanine substitution compared to the starting ABPC (with no substitutions), and b) reduced dissociation at pH 7.4 (e.g., lower koff values) compared to pH 5.4 in the antibody variant itself and with the starting ABPC (with no substitutions). Paired heavy and light chain variants that showed either enhanced dissociation at pH 5.4 or reduced dissociation at pH 7.4 or both (as compared to the starting ABPC), as shown in FIG. 11, were selected for further analysis (MYT3552, MYT3553, MYT3554, MYT3555, MYT3556, MYT3558, MYT3559, MYT3560, MYT3565, MYT3566, MYT3567, MYT3568, MYT3570, MYT3571, MYT3573, MYT3574, MYT3575, MYT3576, MYT3577, MYT3578, MYT3579, MYT3580, MYT3581, MYT3582, MYT3583, MYT3584, MYT3585, MYT3586, MYT3587, MYT3588, MYT3589, MYT3590, MYT3591, MYT3592, MYT3593, MYT3594, MYT3595, MYT3596, and MYT3597).

Example 13. Construction and Screening of pH-Engineered CD123 ABPCs

Figure 13:
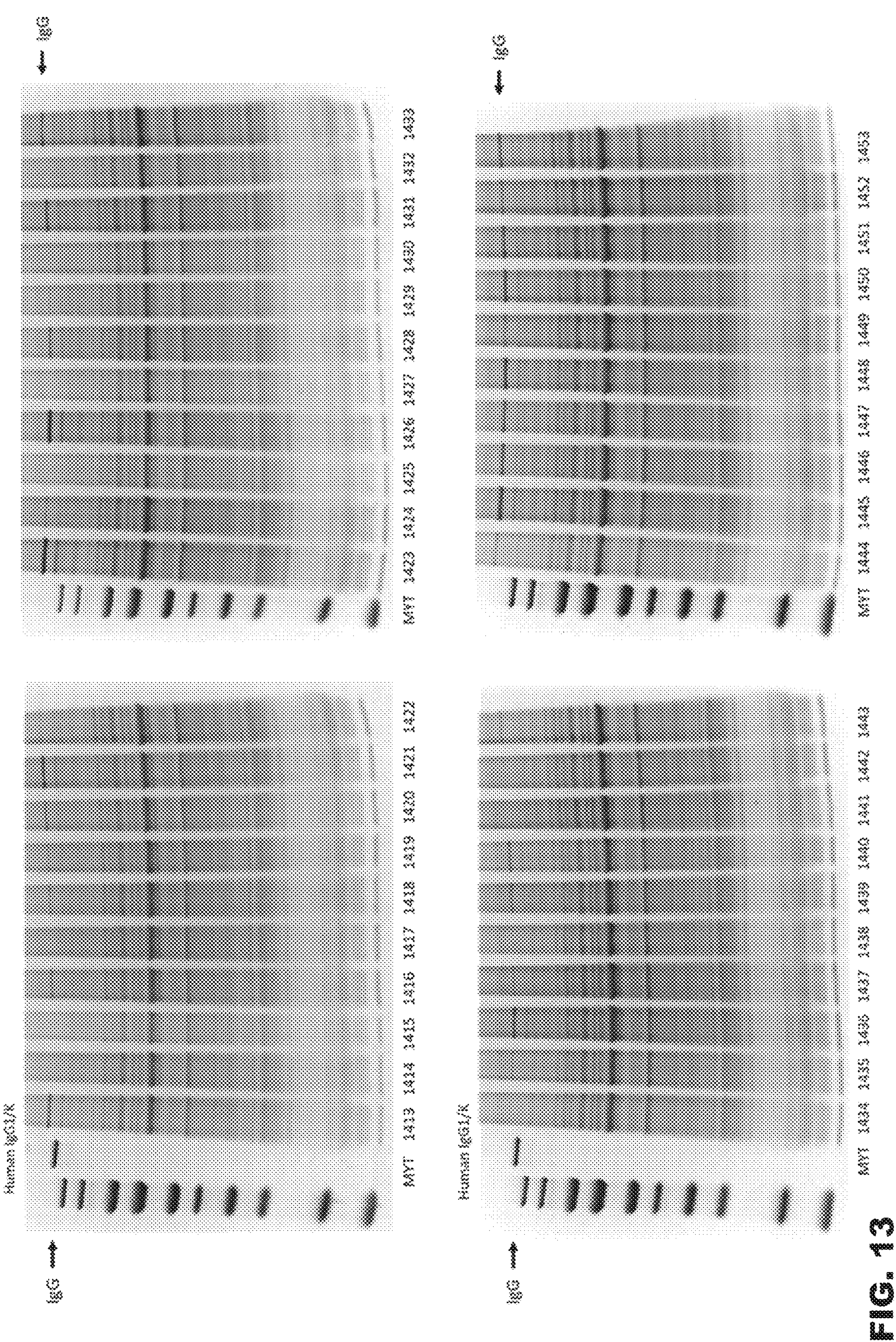
FIG. 13: SDS PAGE for SGN-CD123A histidine scanning and alanine scanning. Expi293 cell culture supernatants post-harvest were loaded on non-reduced SDS PAGE gels to confirm expression of SGN-CD123A and histidine scanning and alanine scanning variants. Arrows show the corresponding size for an IgG on a non-reduced SDS PAGE gel. MYT1413 is SGN-CD123A and the rest of the lanes (MYT1414-MYT1453) are SGN-CD123A heavy chain histidine scanning and alanine scanning variants.
Figure 14A:
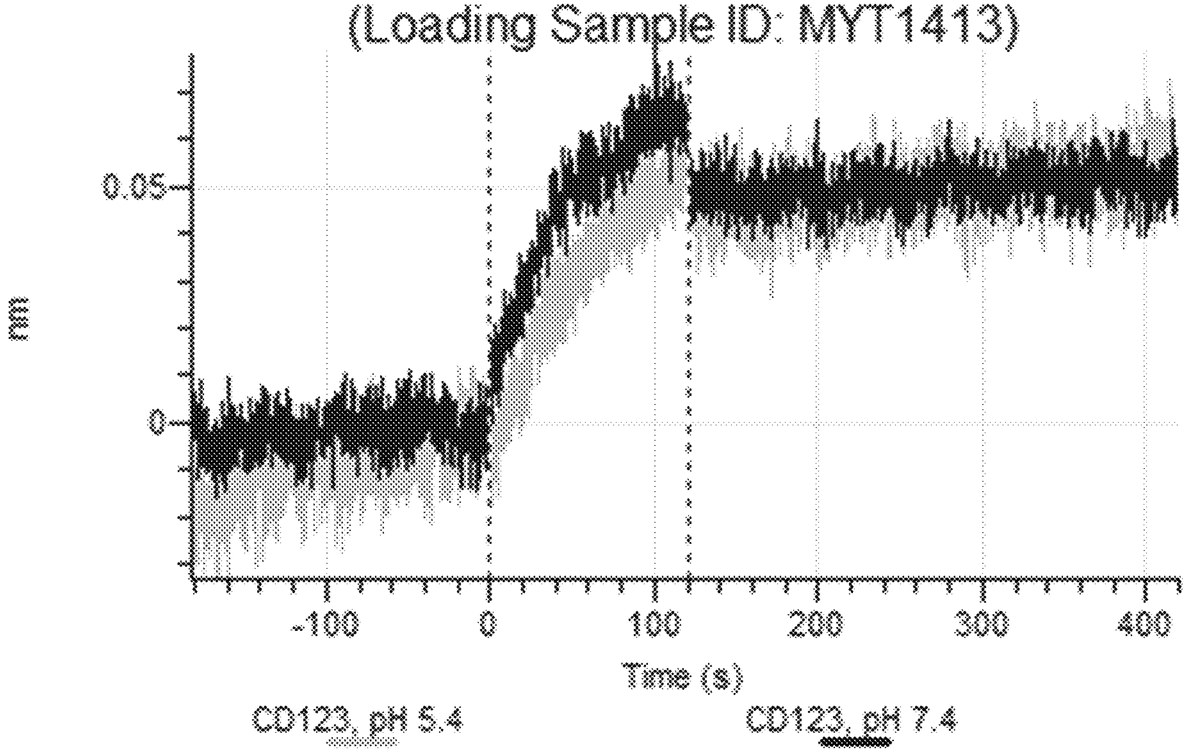
FIGS. 14*a* to 14*ao*: Binding of SGN-CD123A starting ABPC and histidine scanning and alanine scanning variants to CD123 by biolayer interferometry. MYT1413 (SGN-CD123A) and MYT1414-MYT1453, heavy chain histidine scanning and alanine scanning variants, were captured on anti-human Fc biosensors and associated with CD123 at low pH or high pH, as specified in the figures.
Figure 14B:
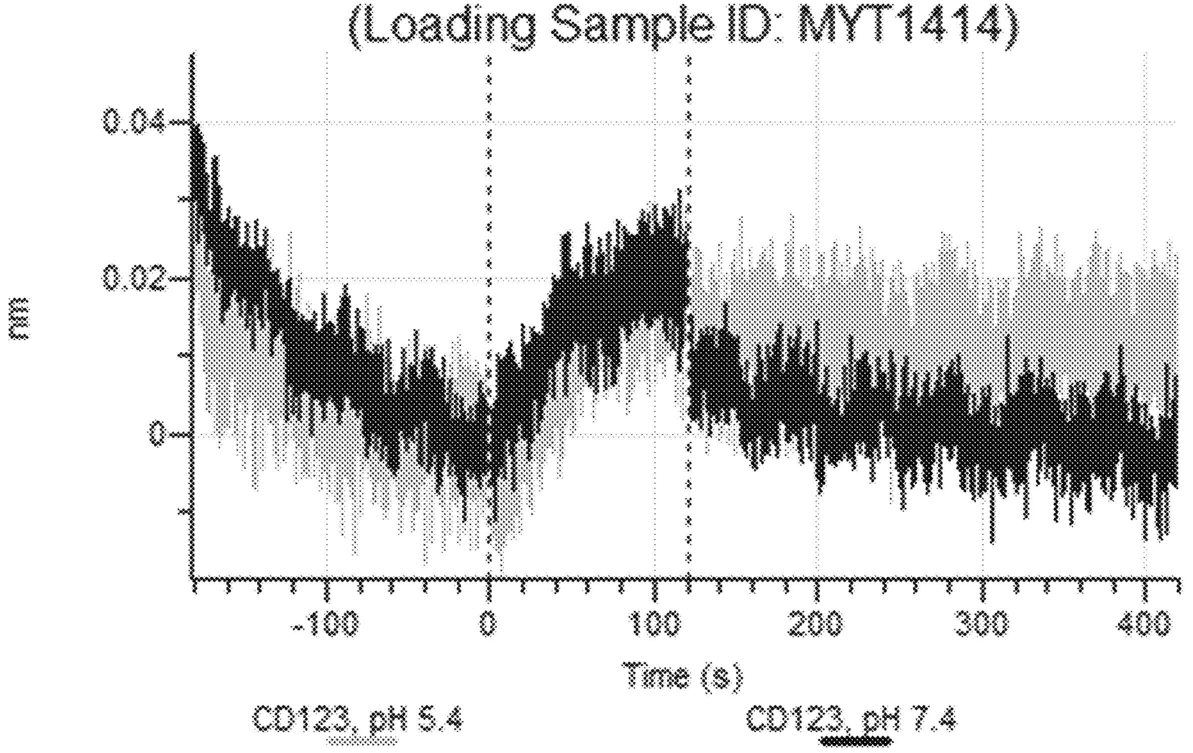
Figure 14C:
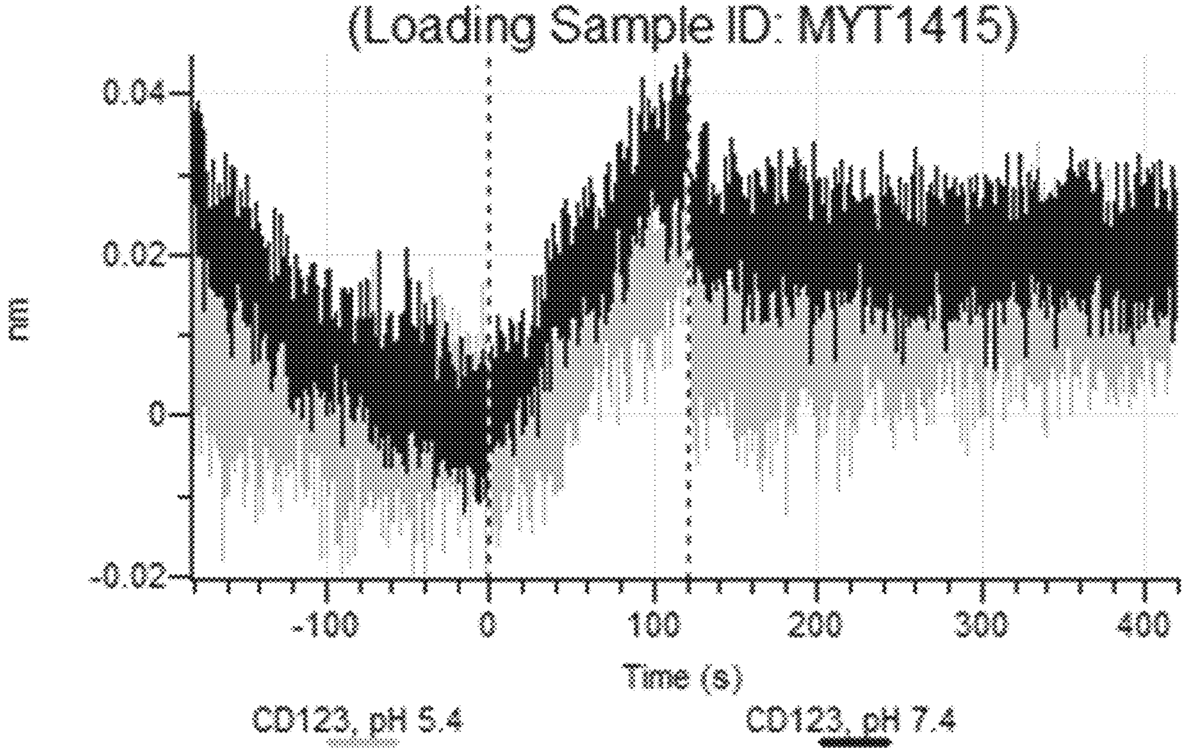
Figure 14D:
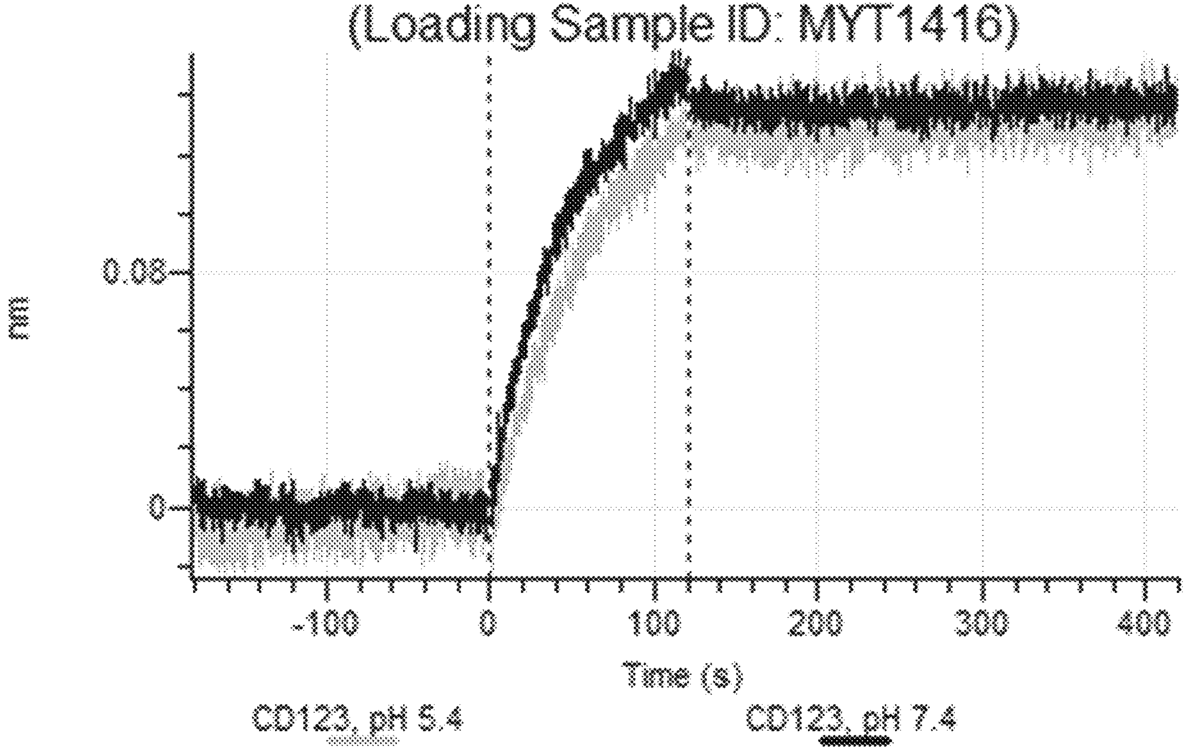
Figure 14E:
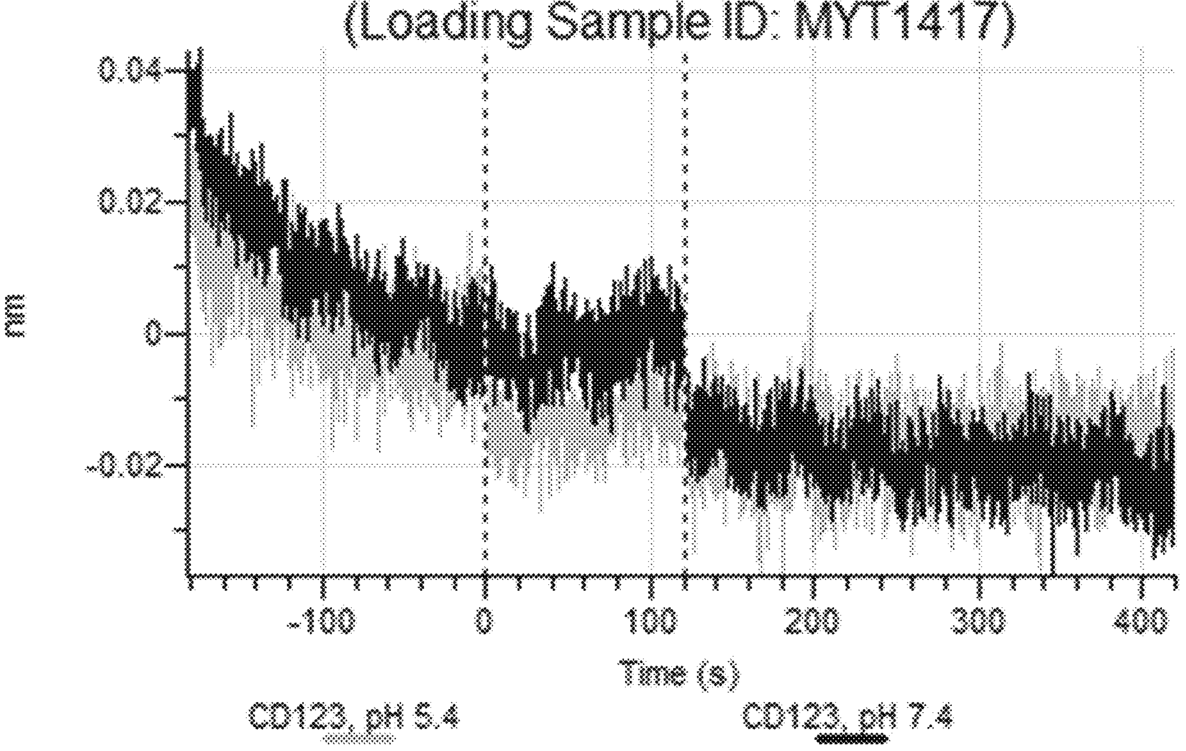
Figure 14F:
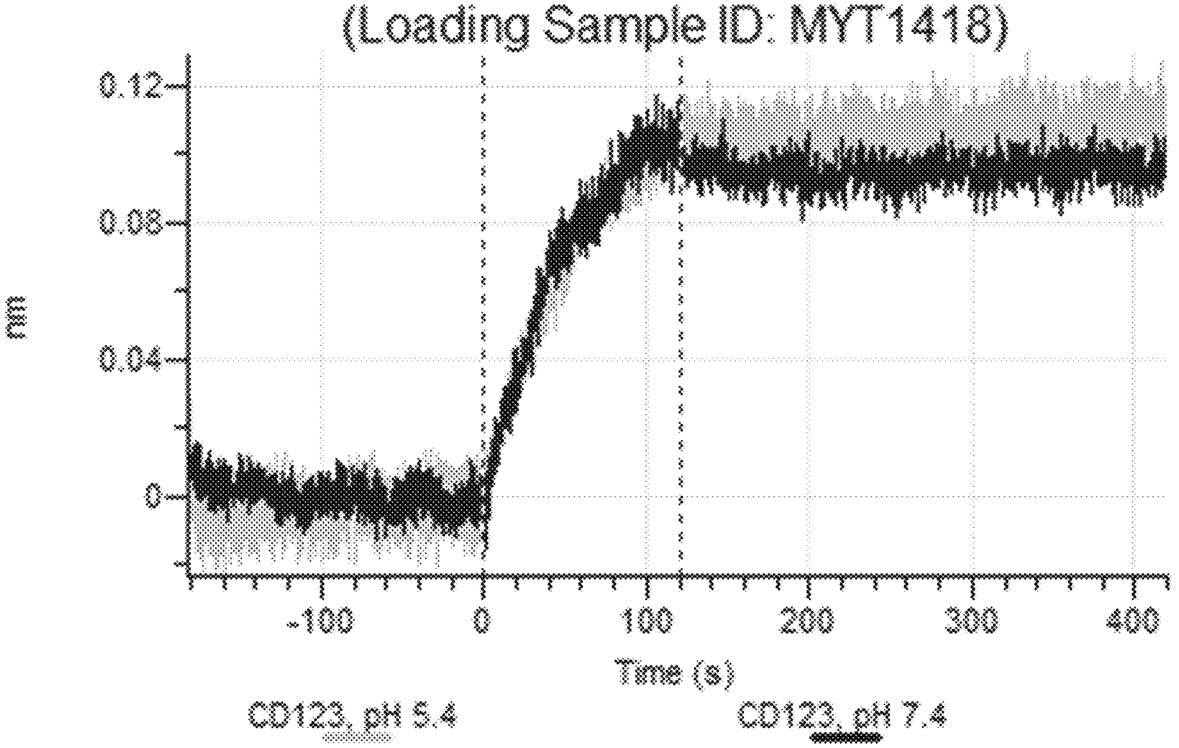
Figure 14G:
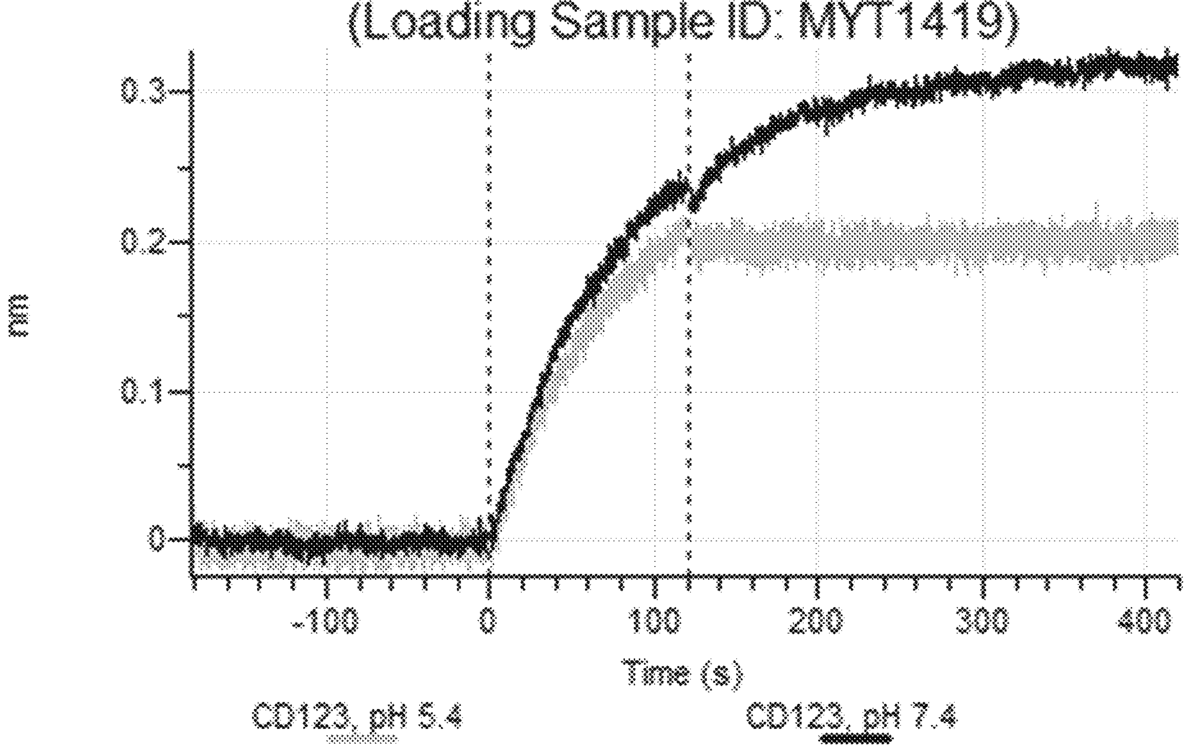
Figure 14H:
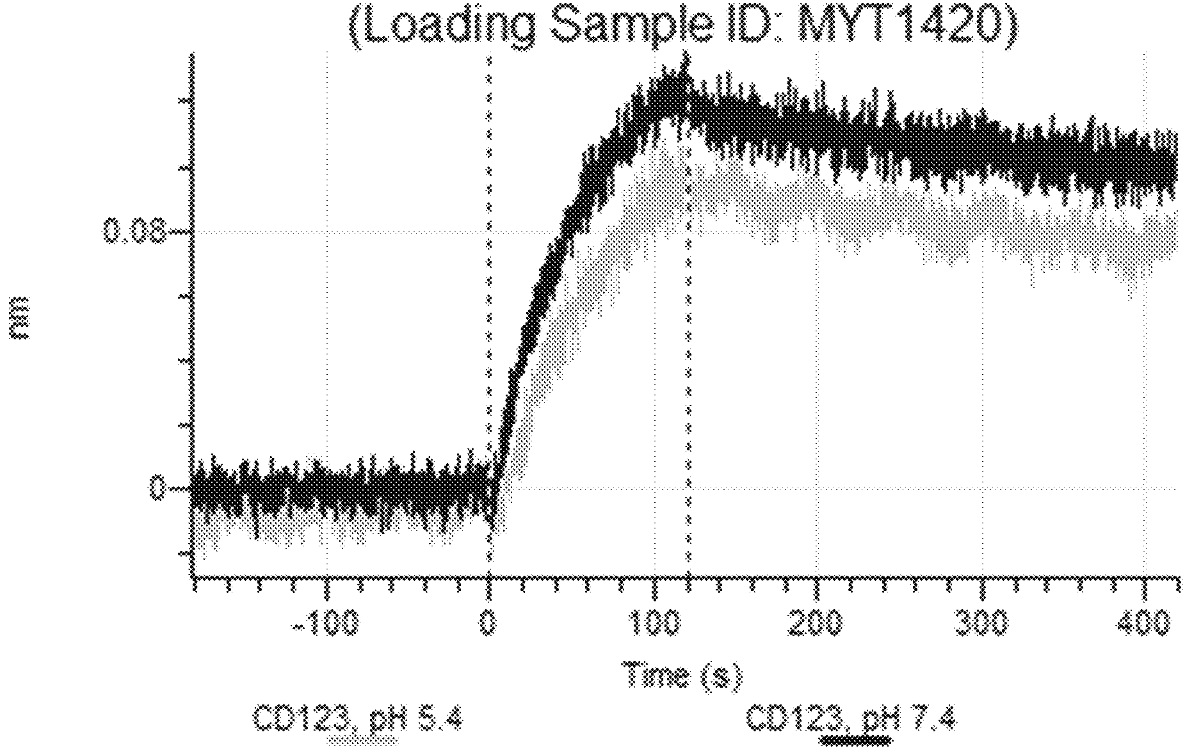
Figure 14I:
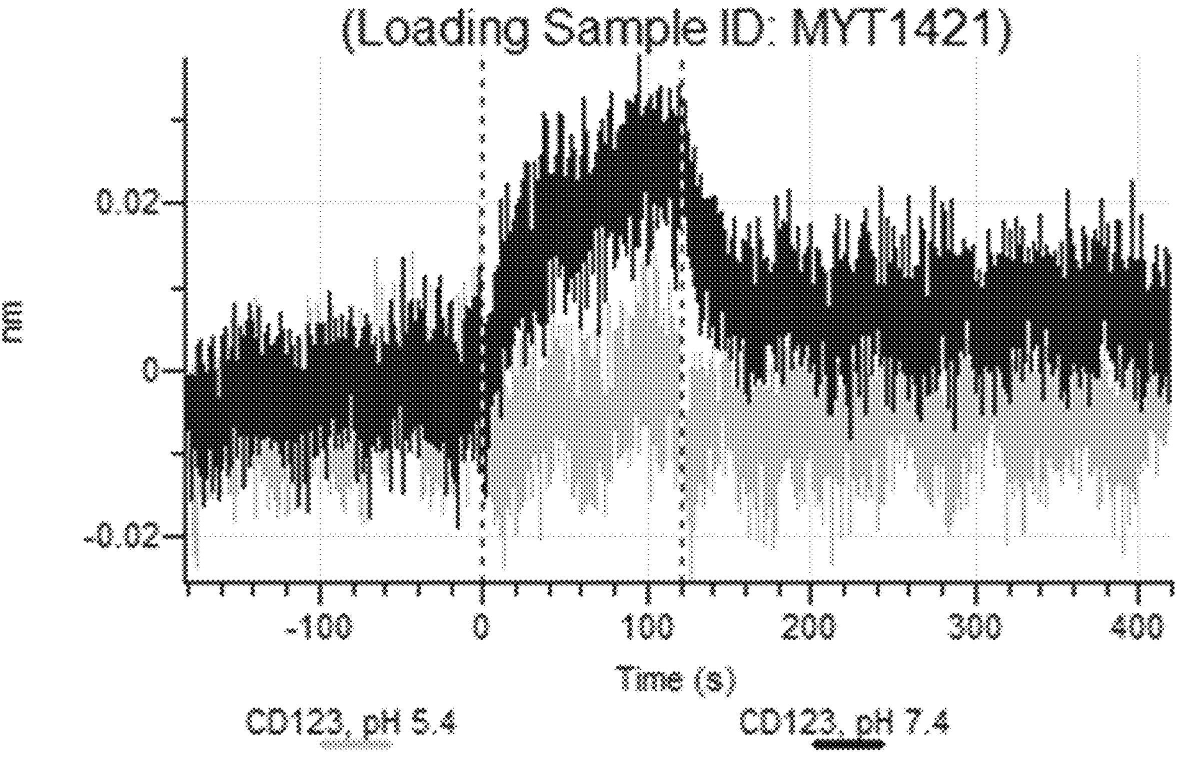
Figure 14J:
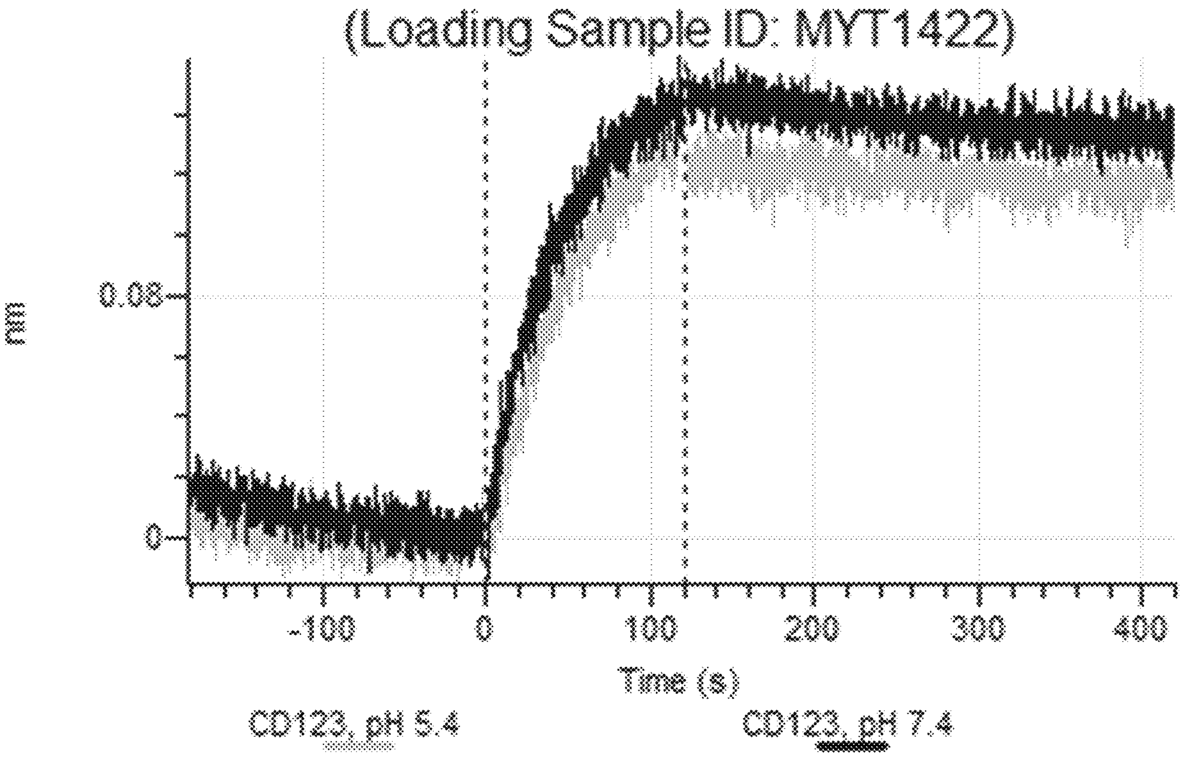
Figure 14K:
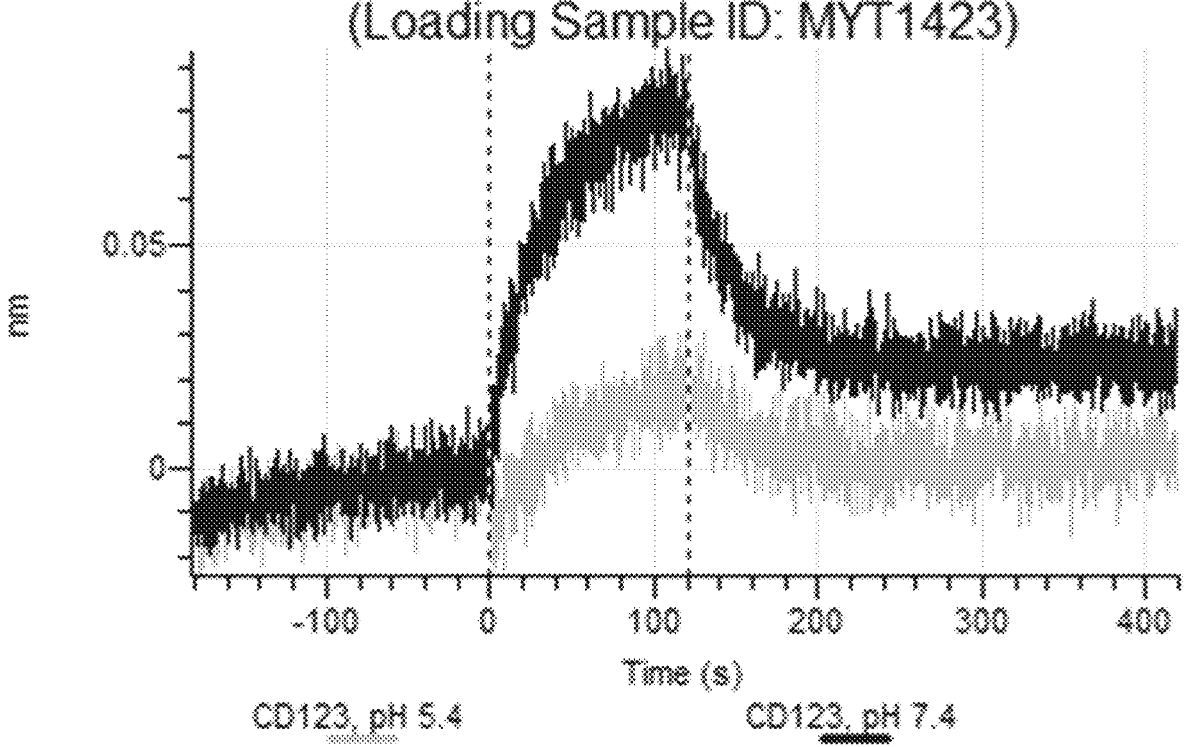
Figure 14L:
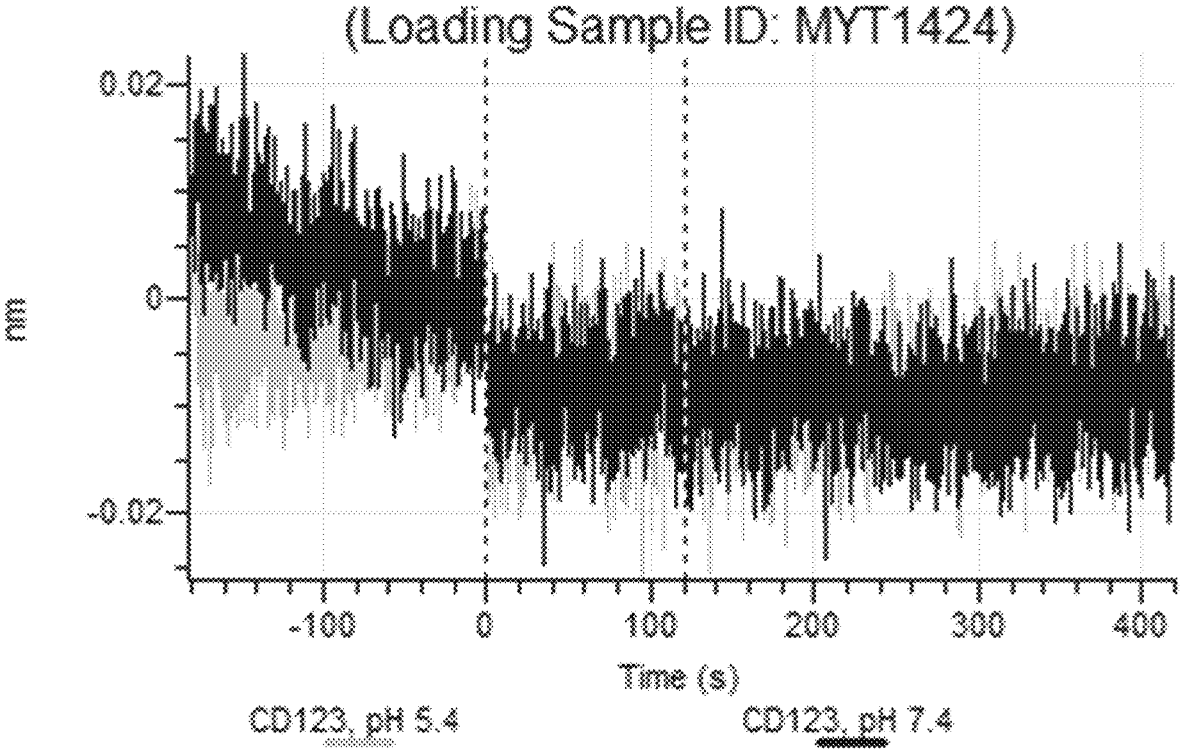
Figure 14M:
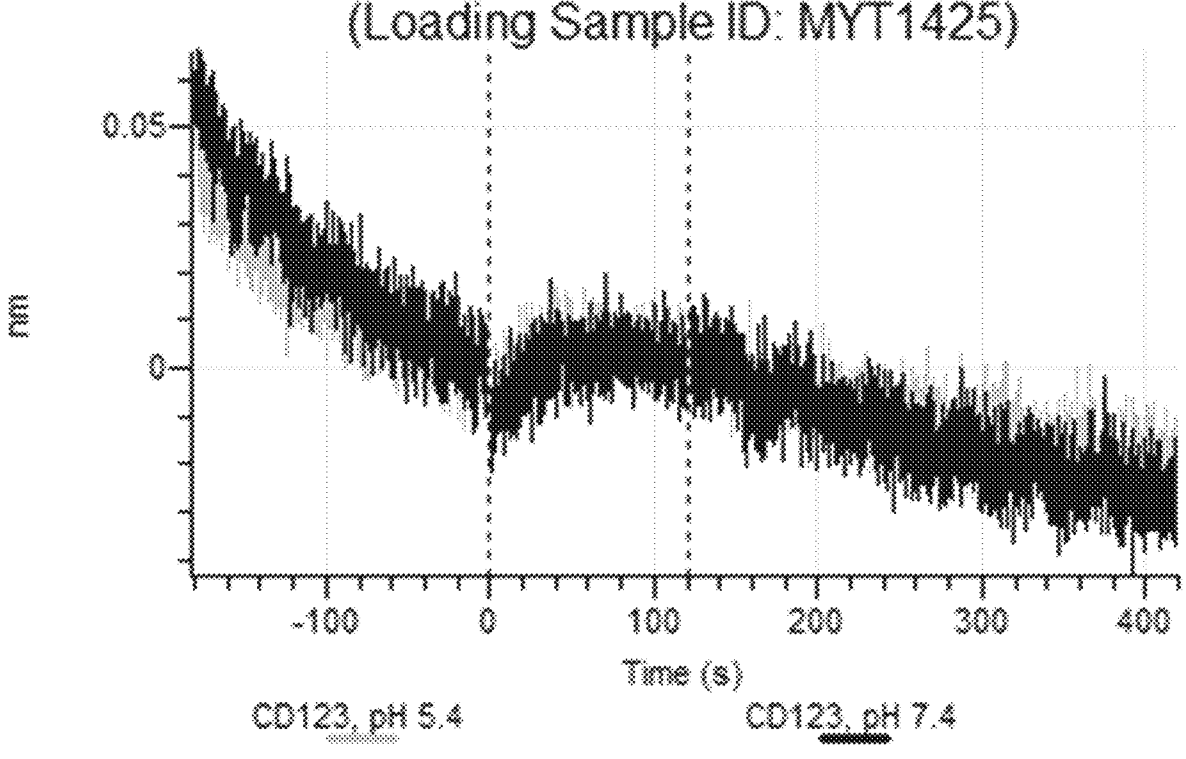
Figure 14N:
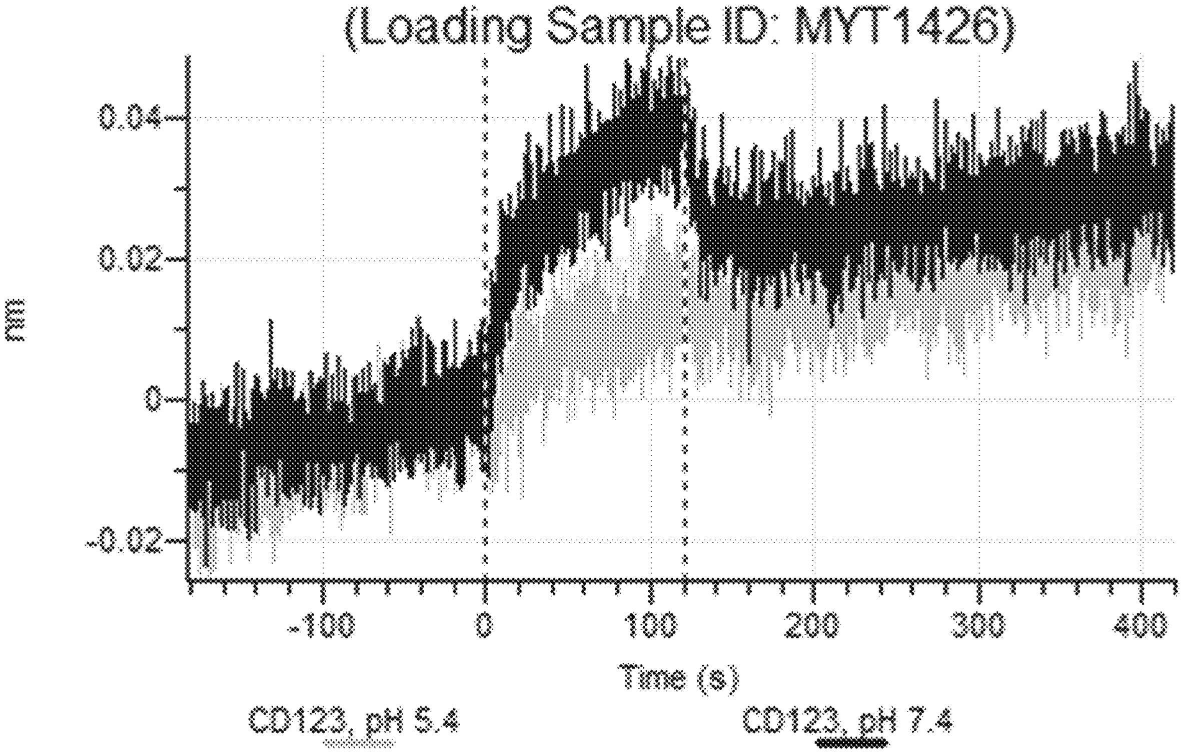
Figure 14O:
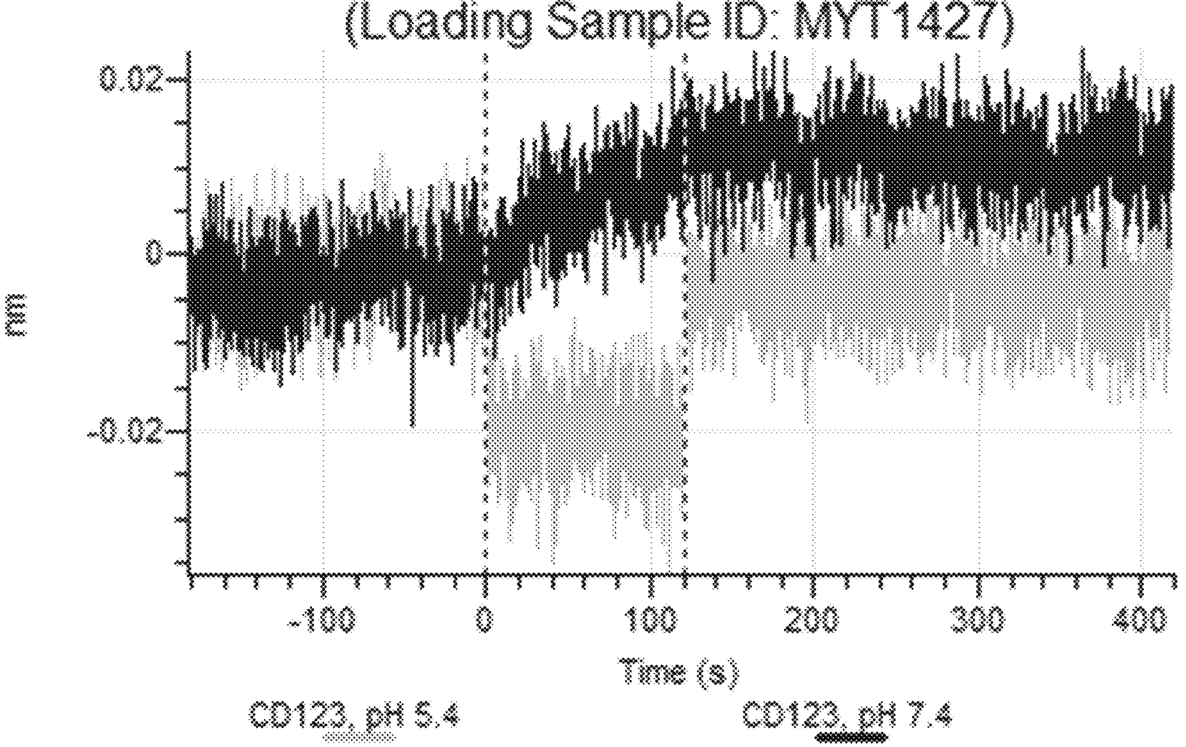
Figure 14P:
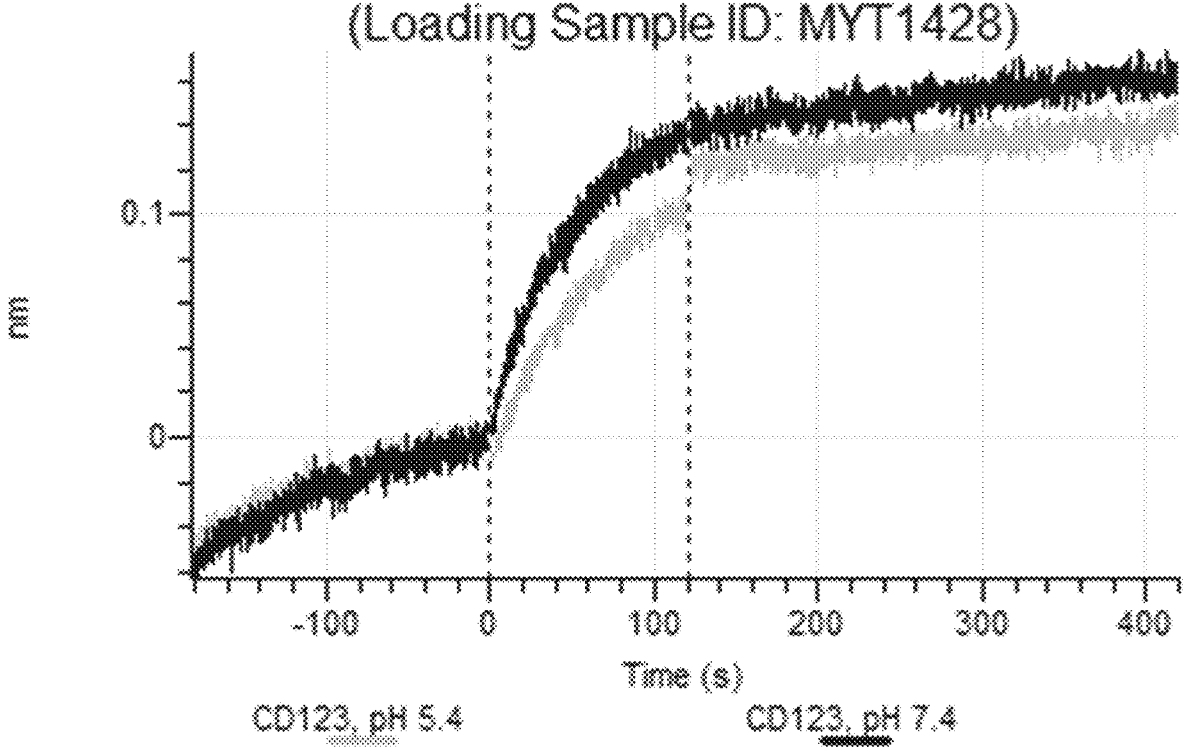
Figure 14Q:
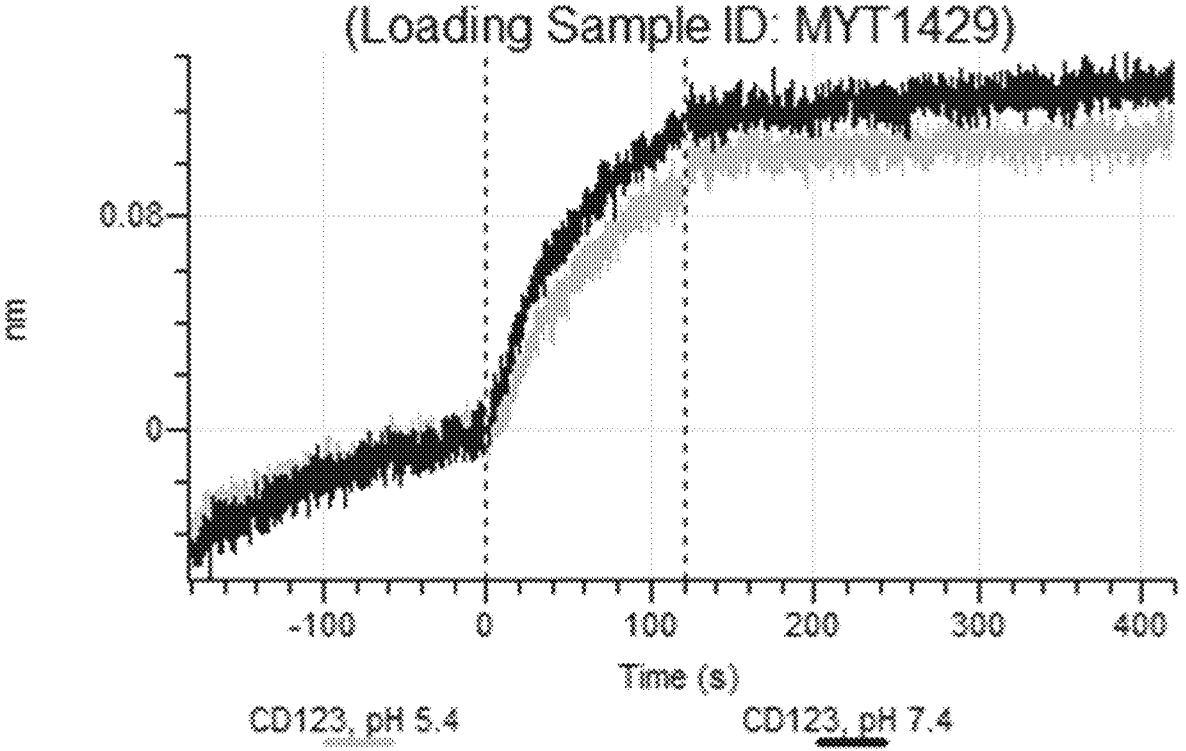
Figure 14R:
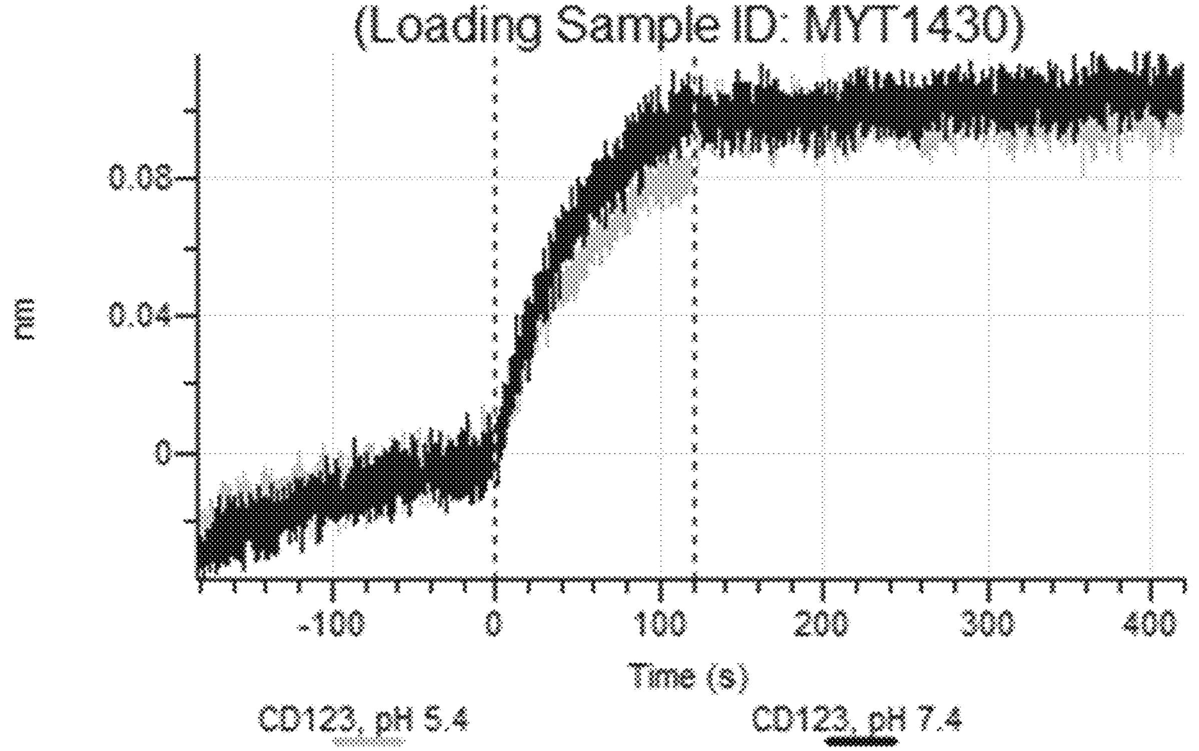
Figure 14S:
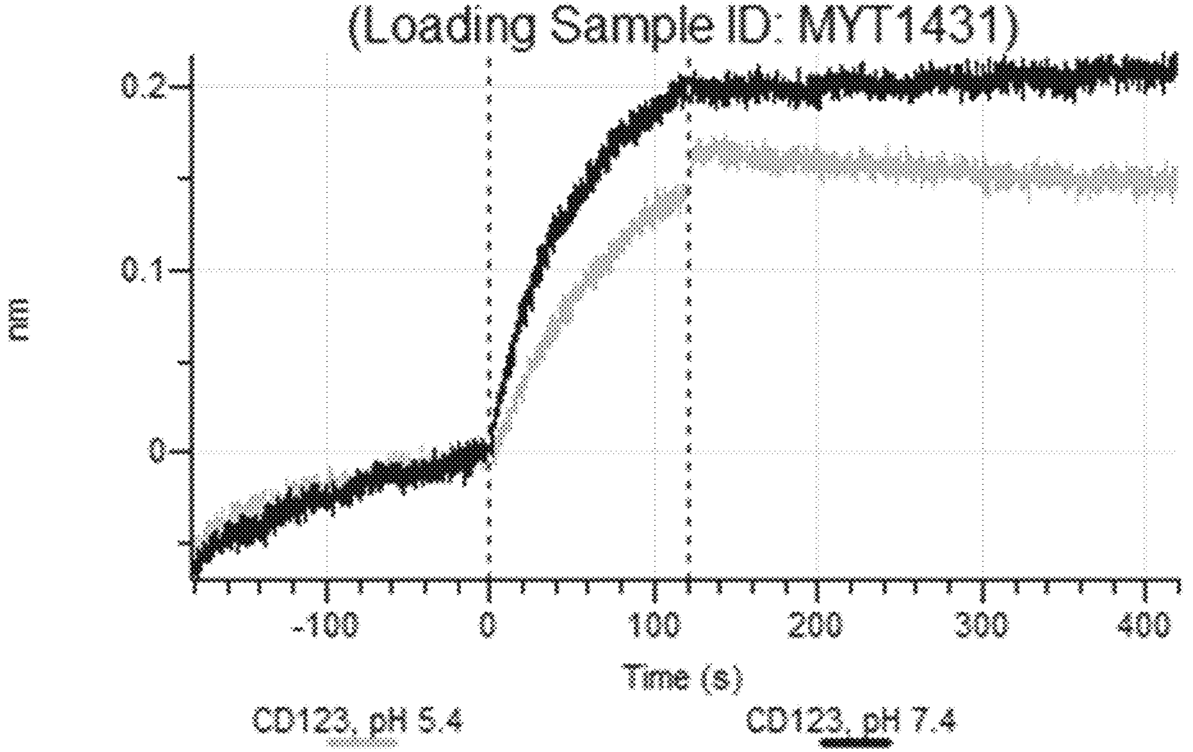
Figure 14T:
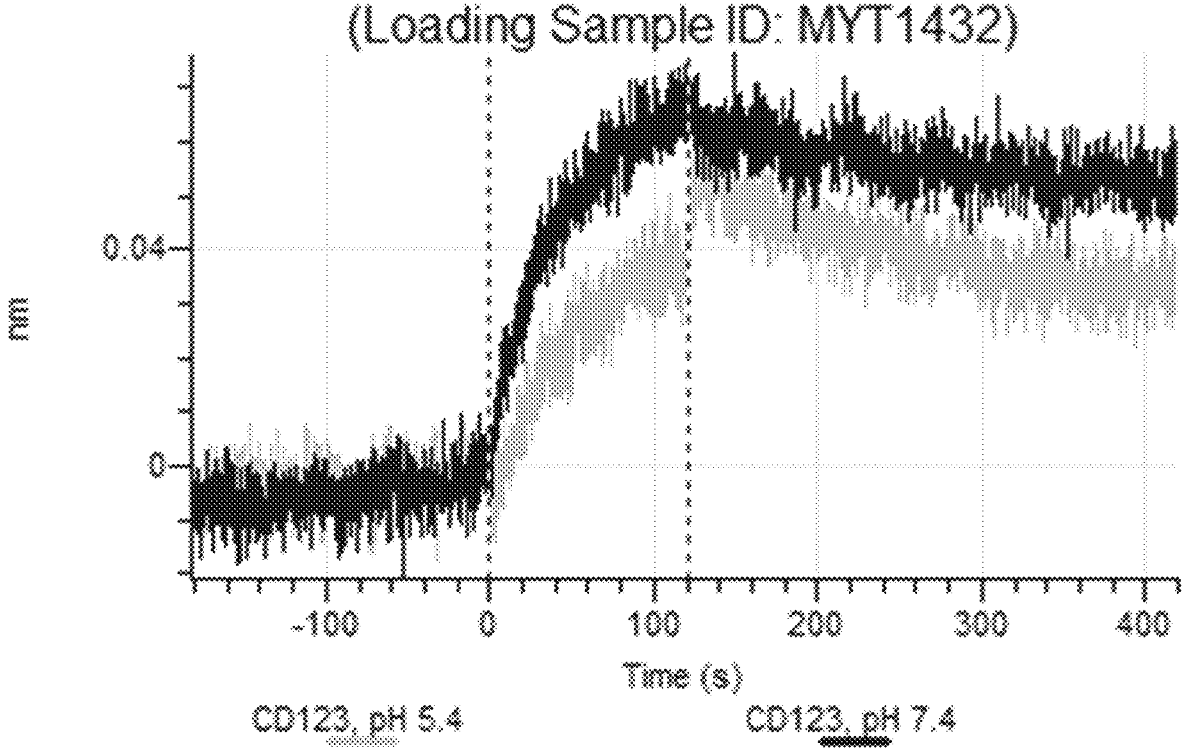
Figure 14U:
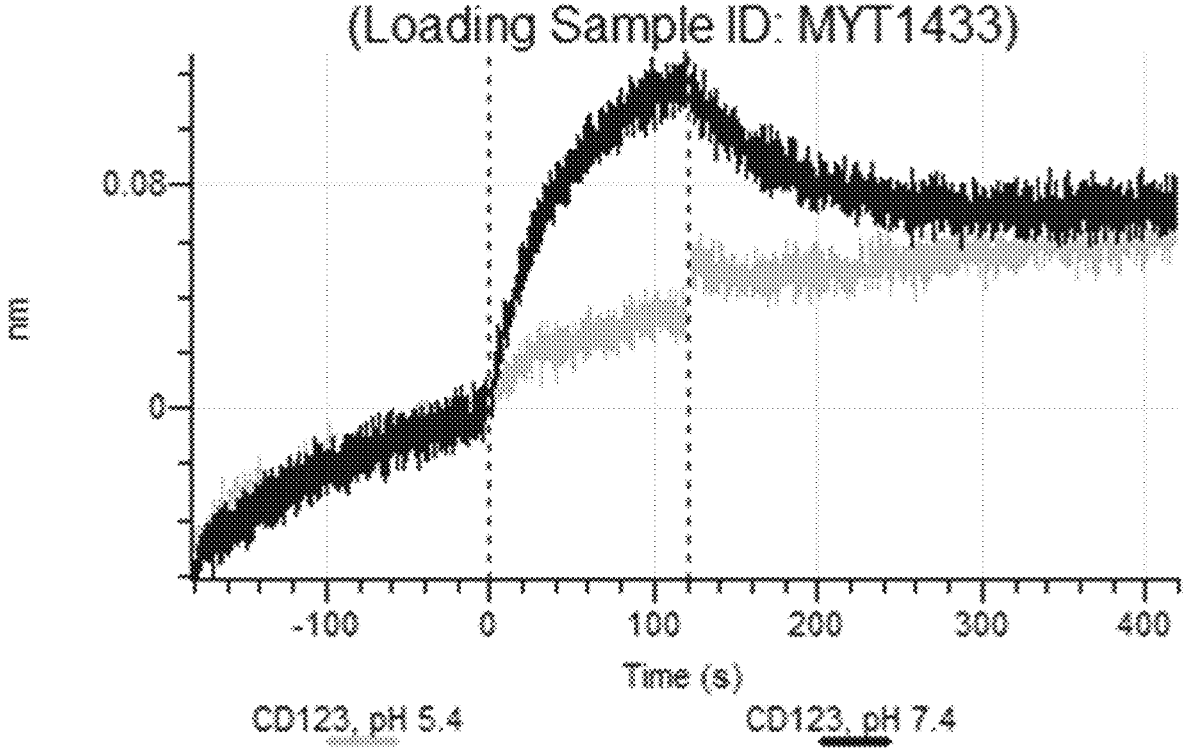
Figure 14V:
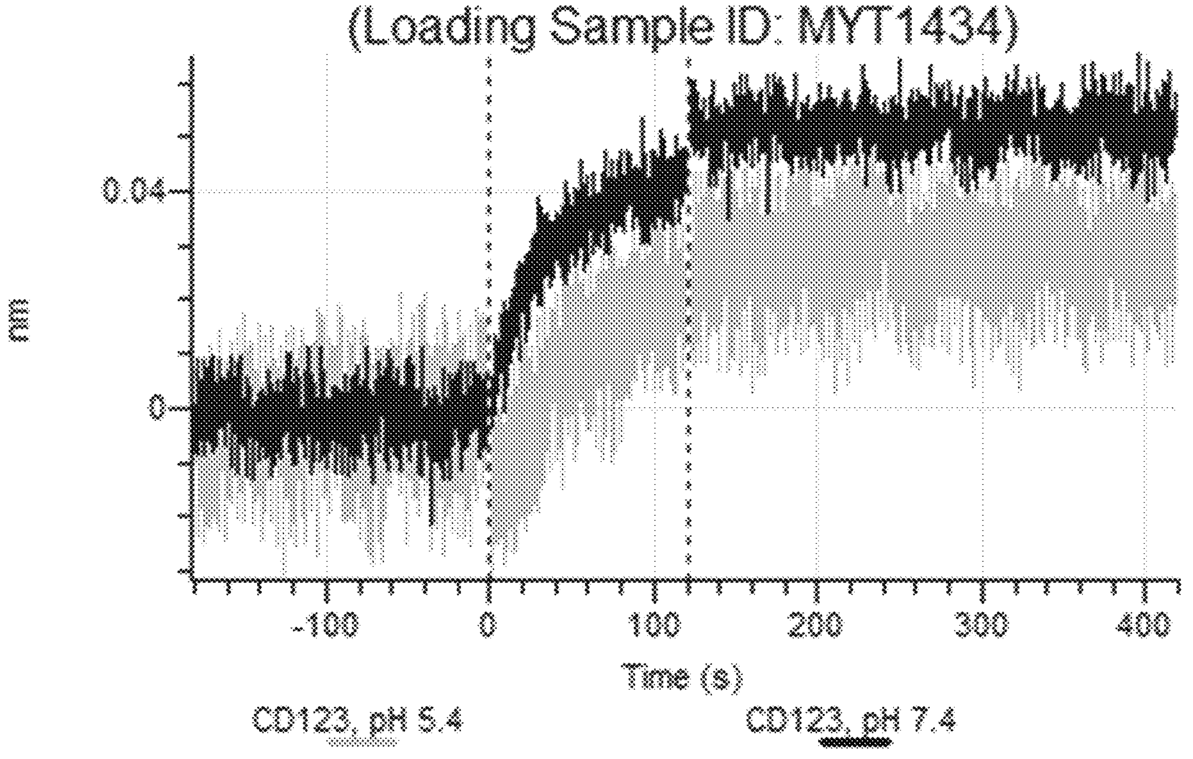
Figure 14W:
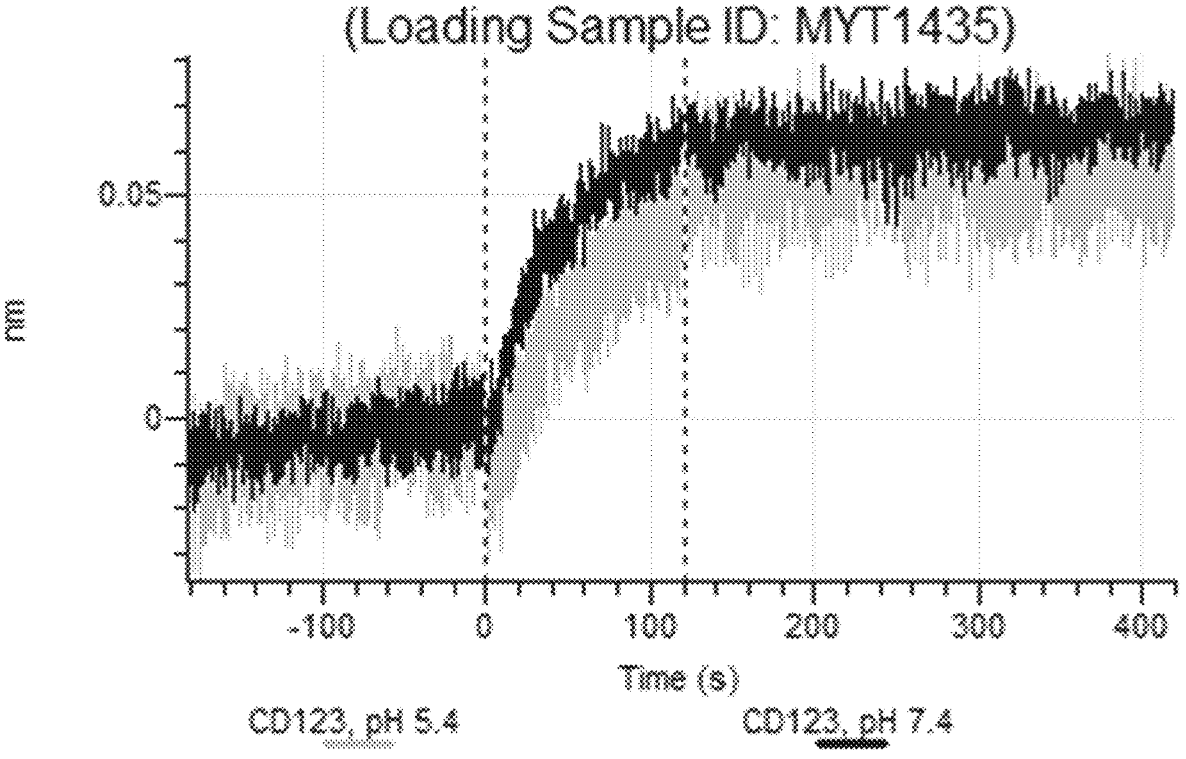
Figure 14X:
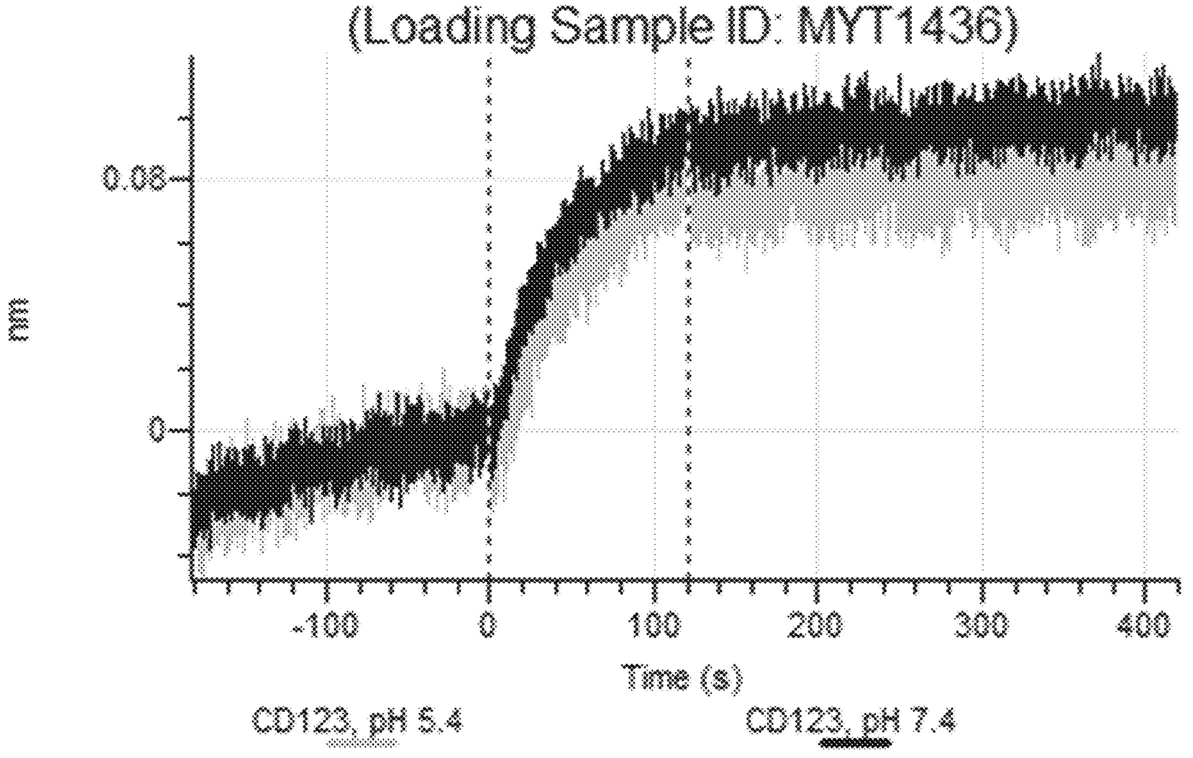
Figure 14Y:
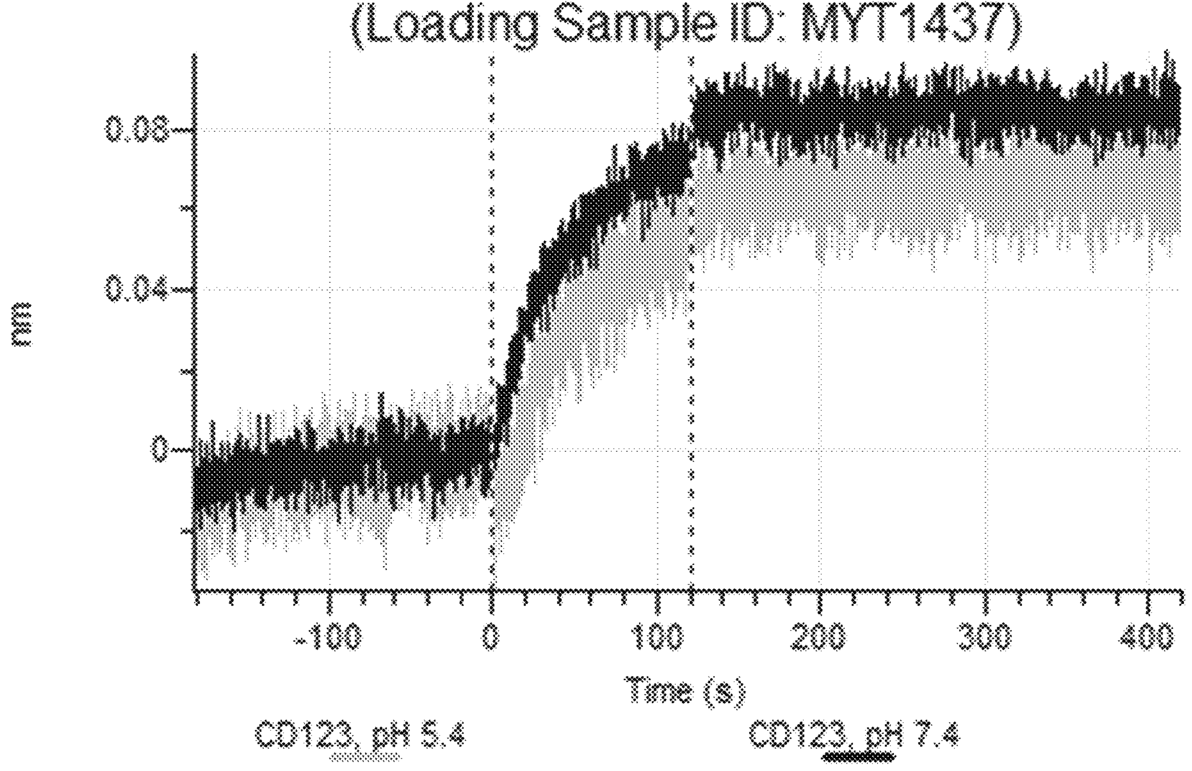
Figure 14Z:
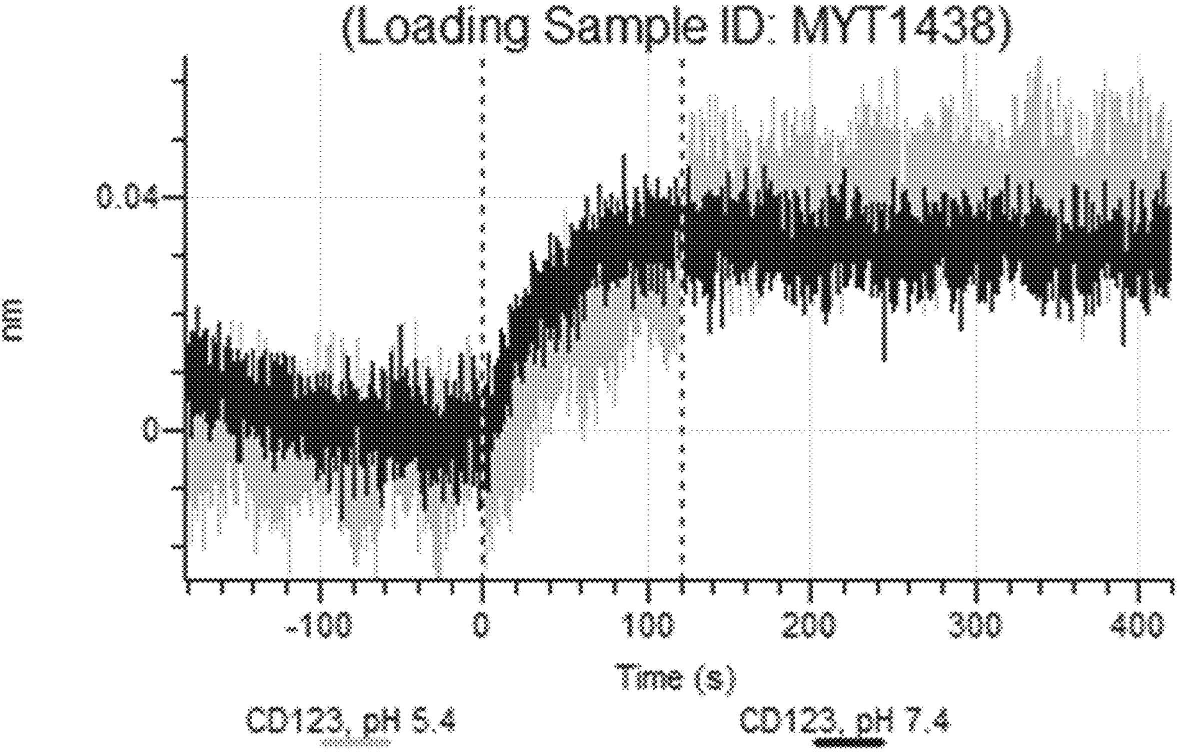
Figure 14A:
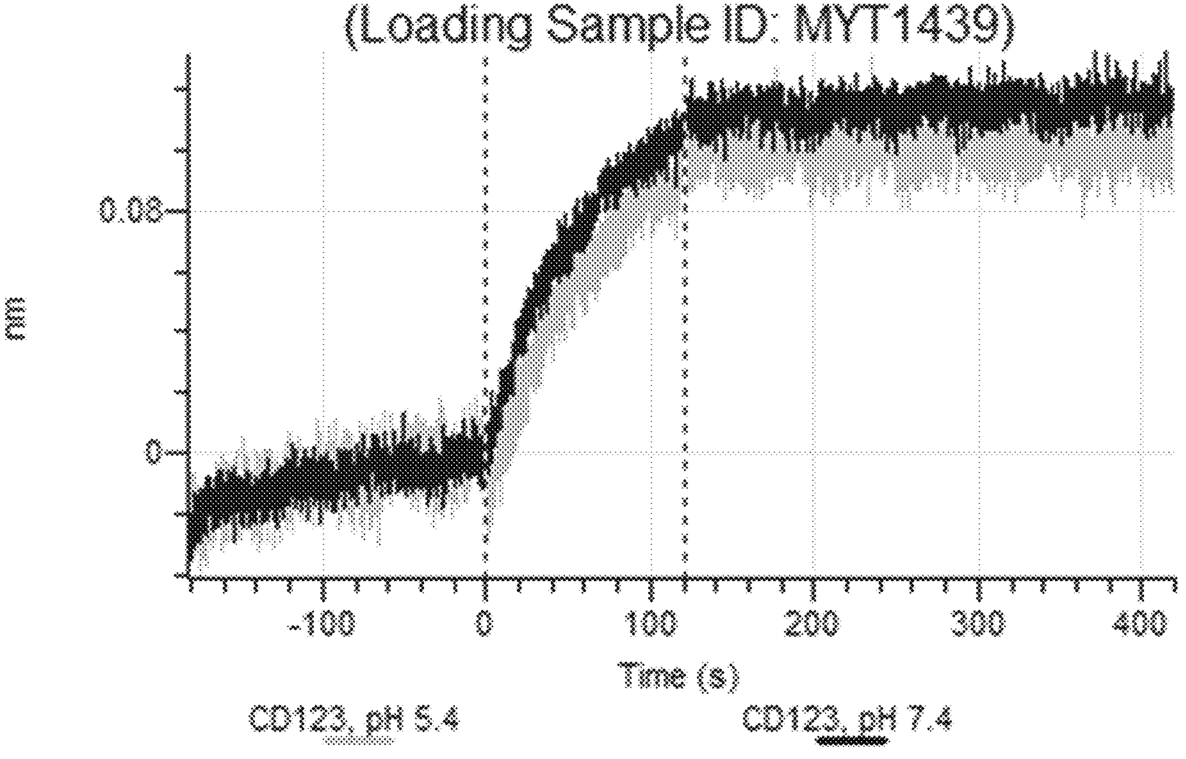
Figure 14A:
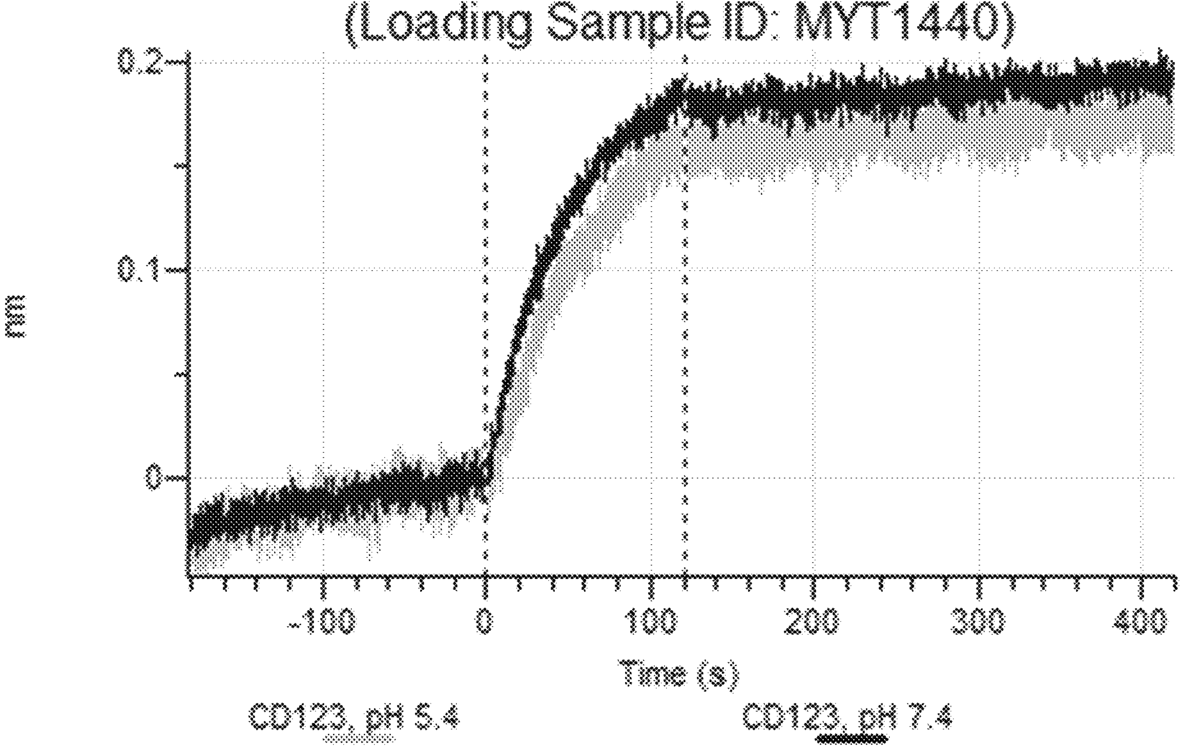
Figure 14A:
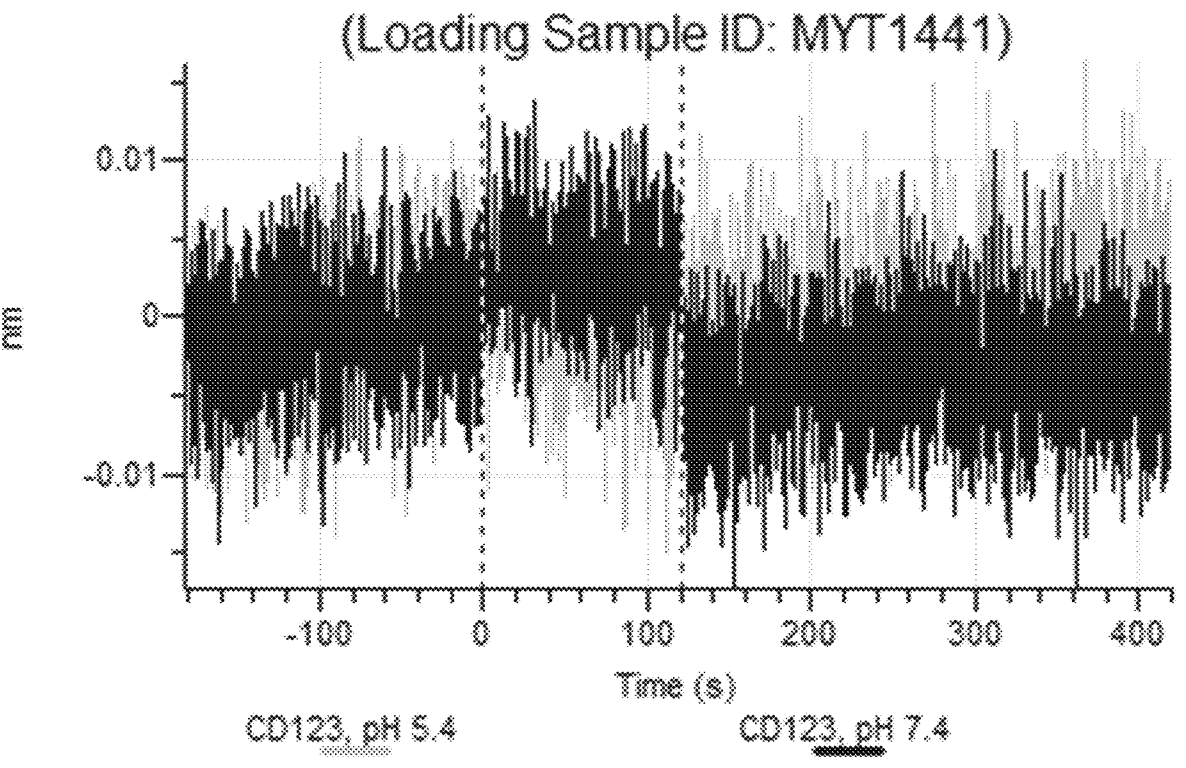
Figure 14A:
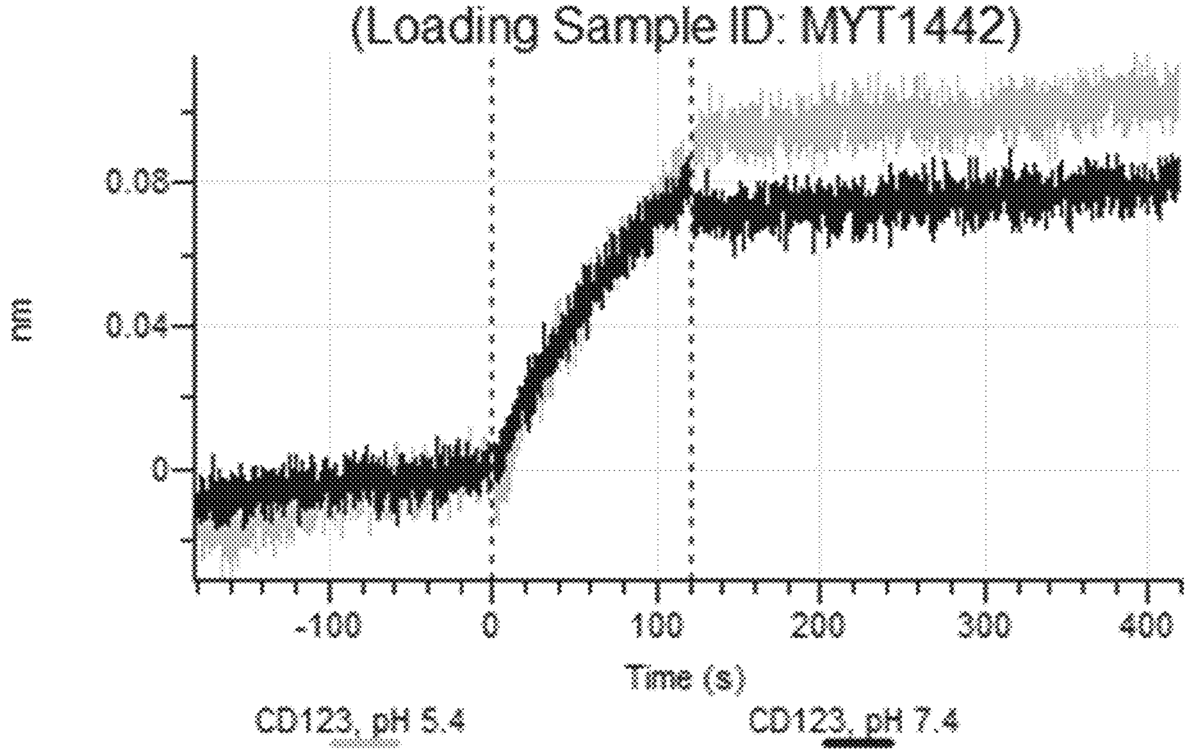
Figure 14A:
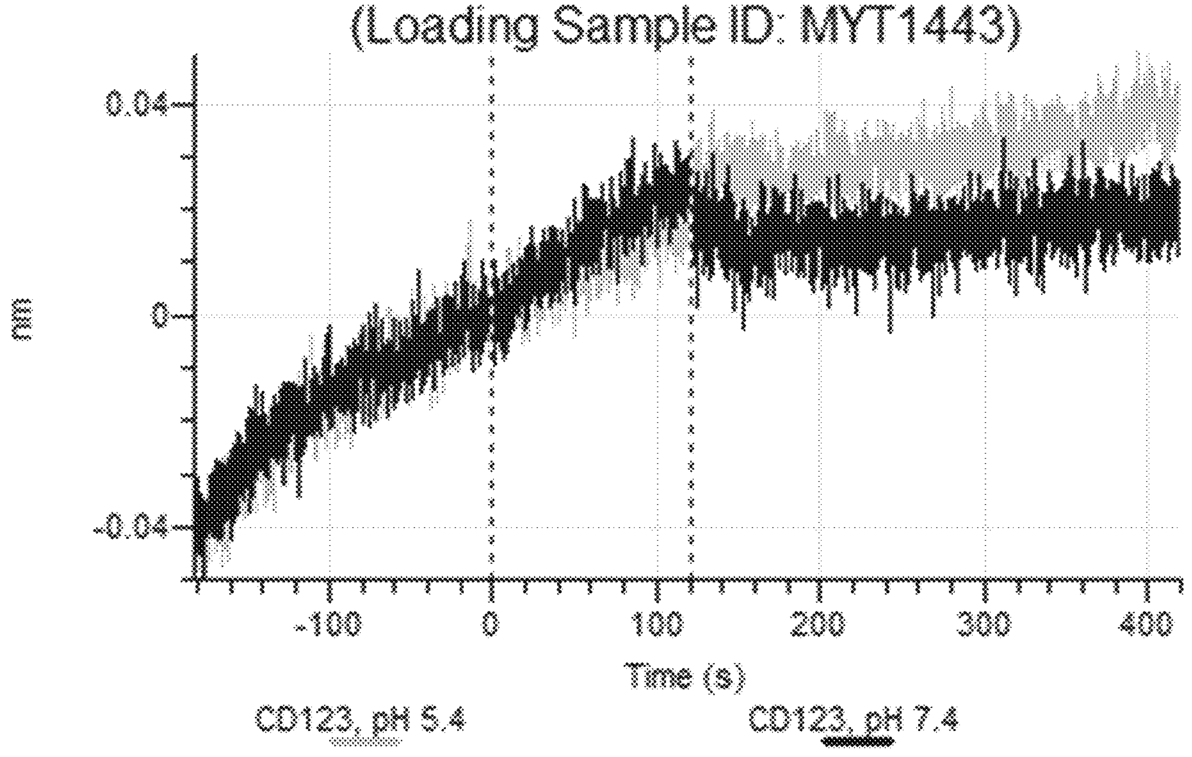
Figure 14A:
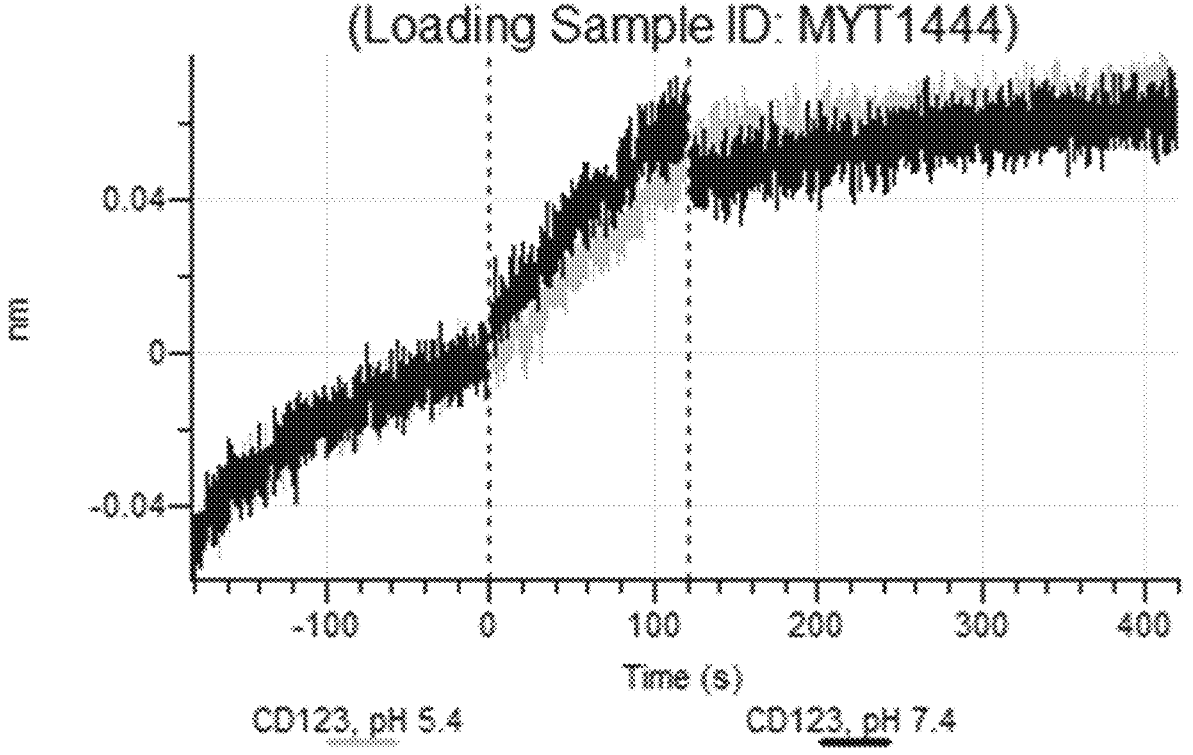
Figure 14A:
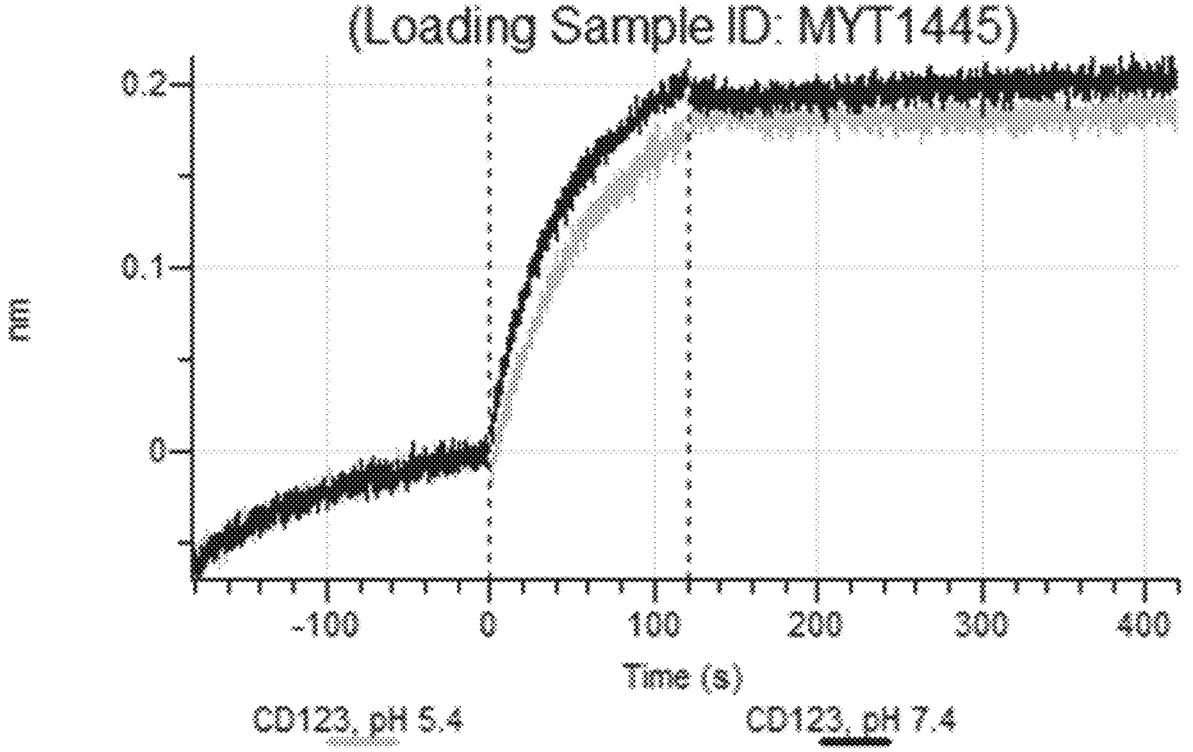
Figure 14A:
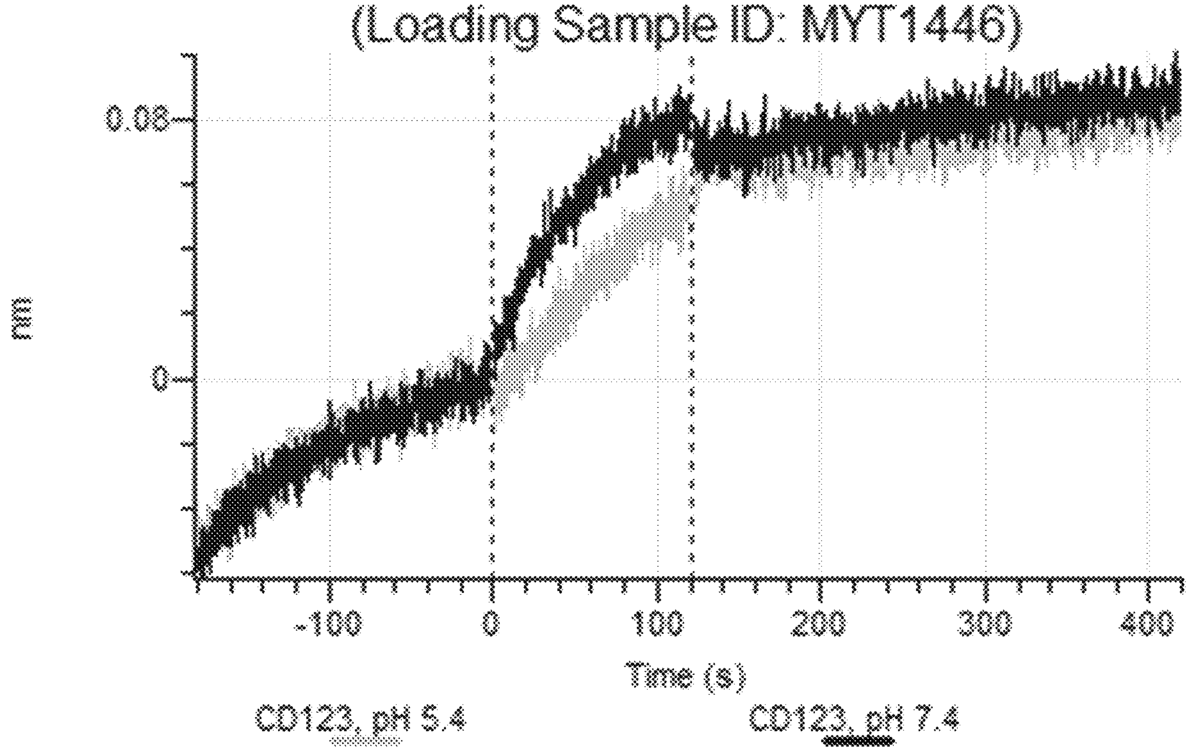
Figure 14A:
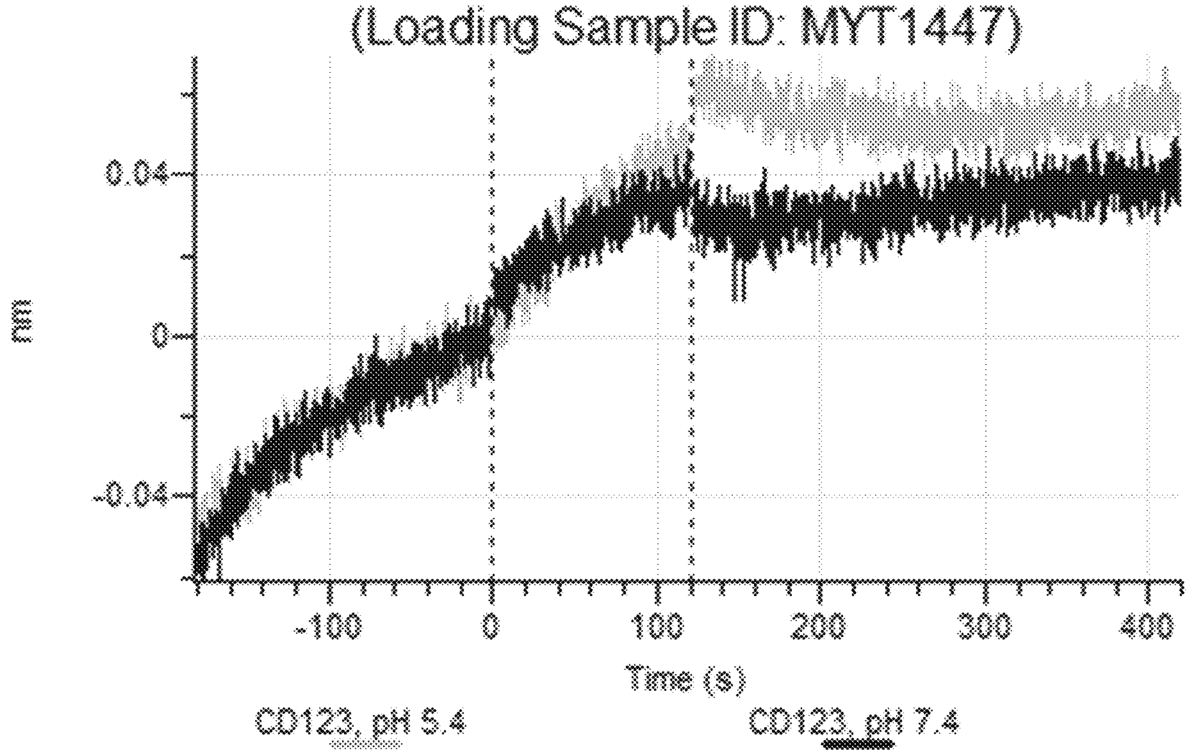
Figure 14A:
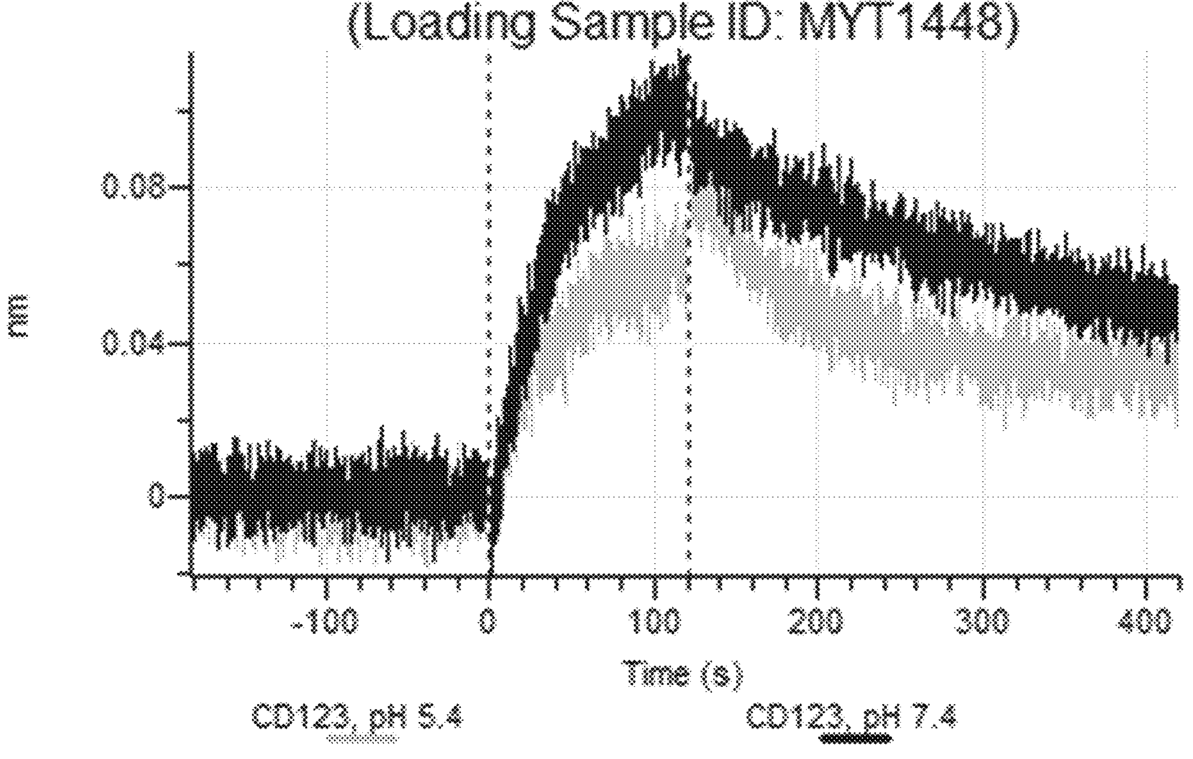
Figure 14A:
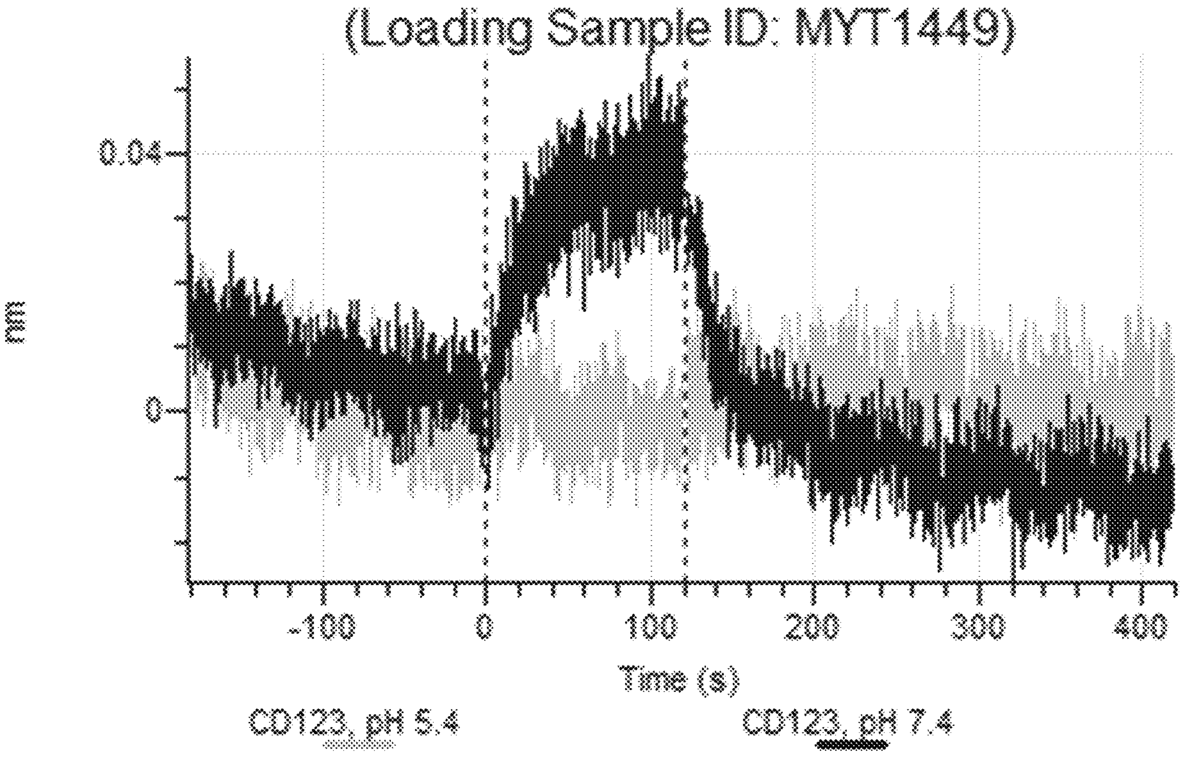
Figure 14A:
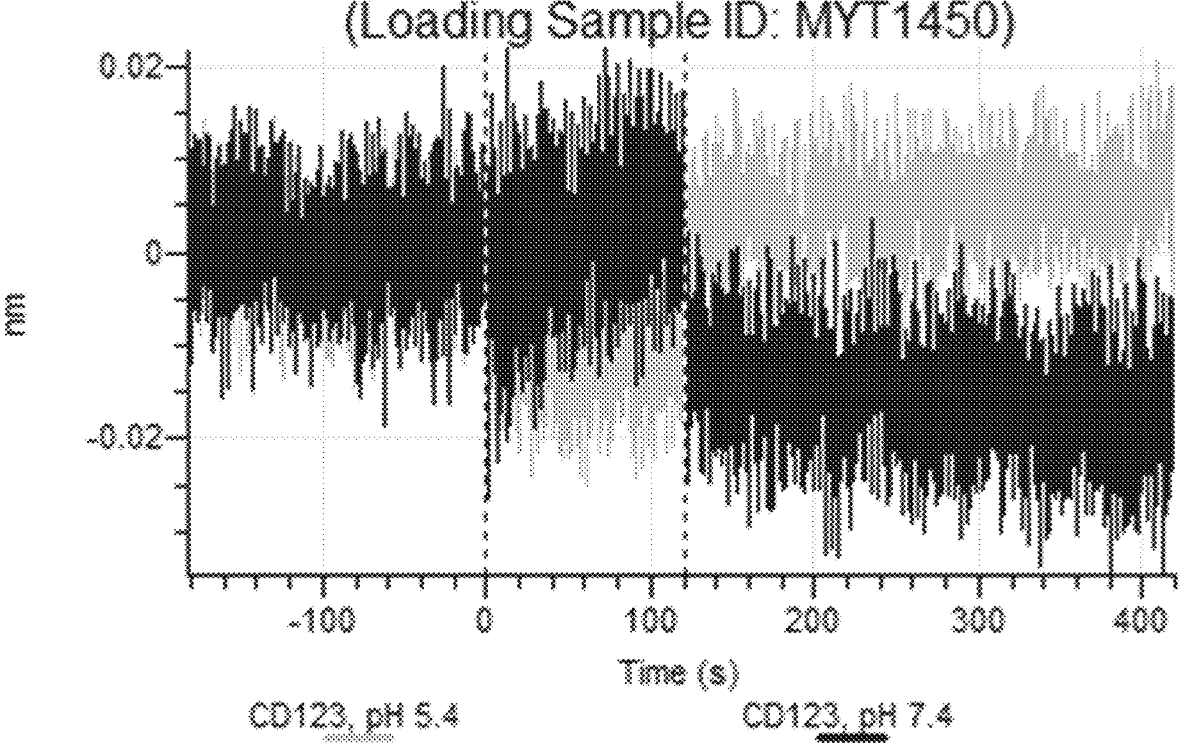
Figure 14A:
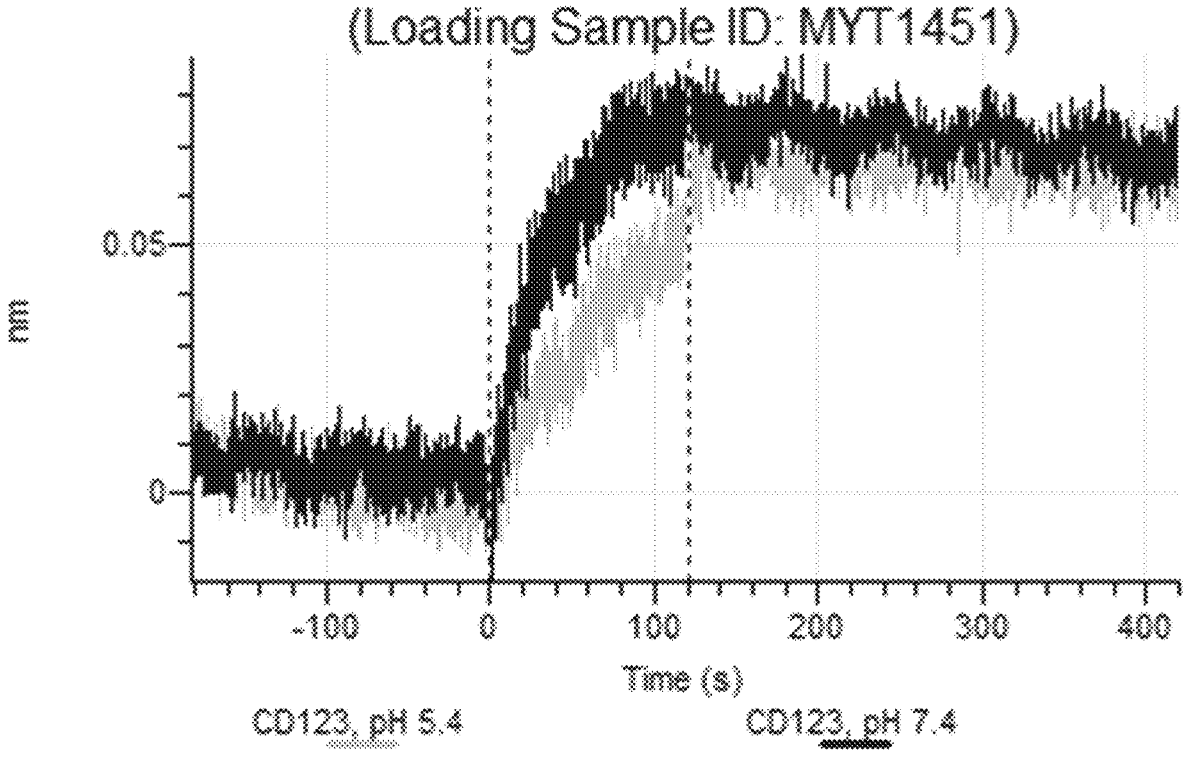
Figure 14A:
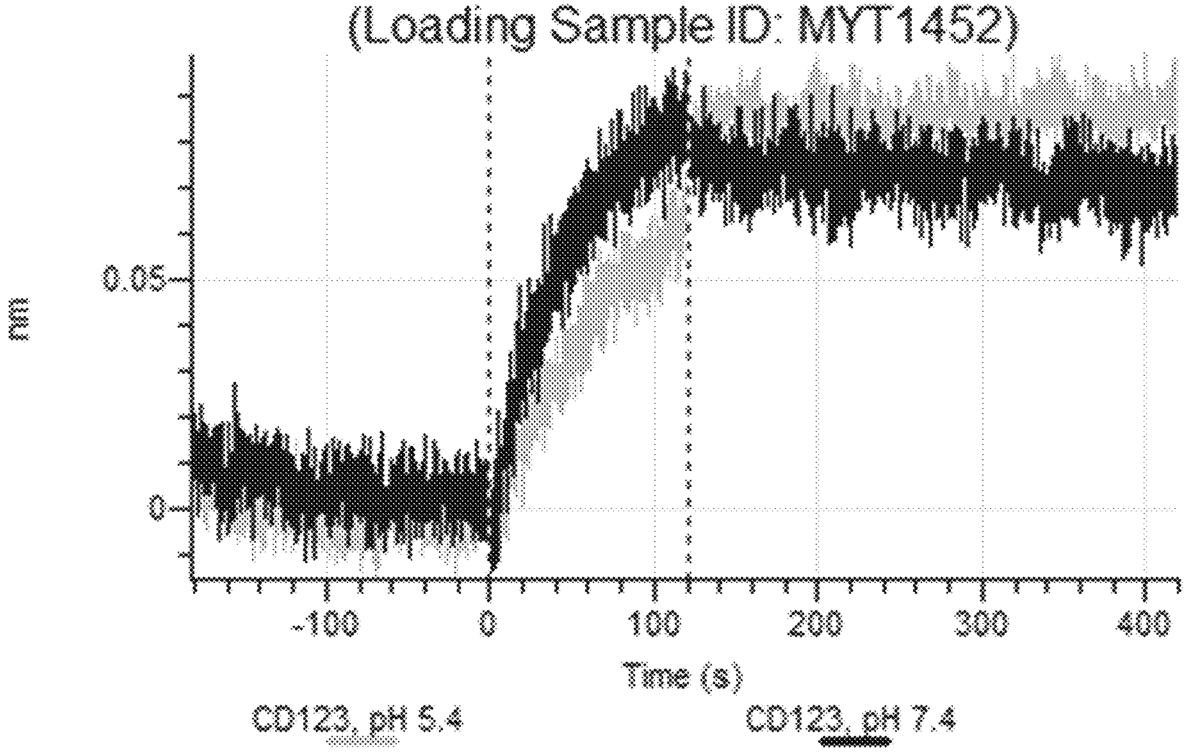
Figure 14A:
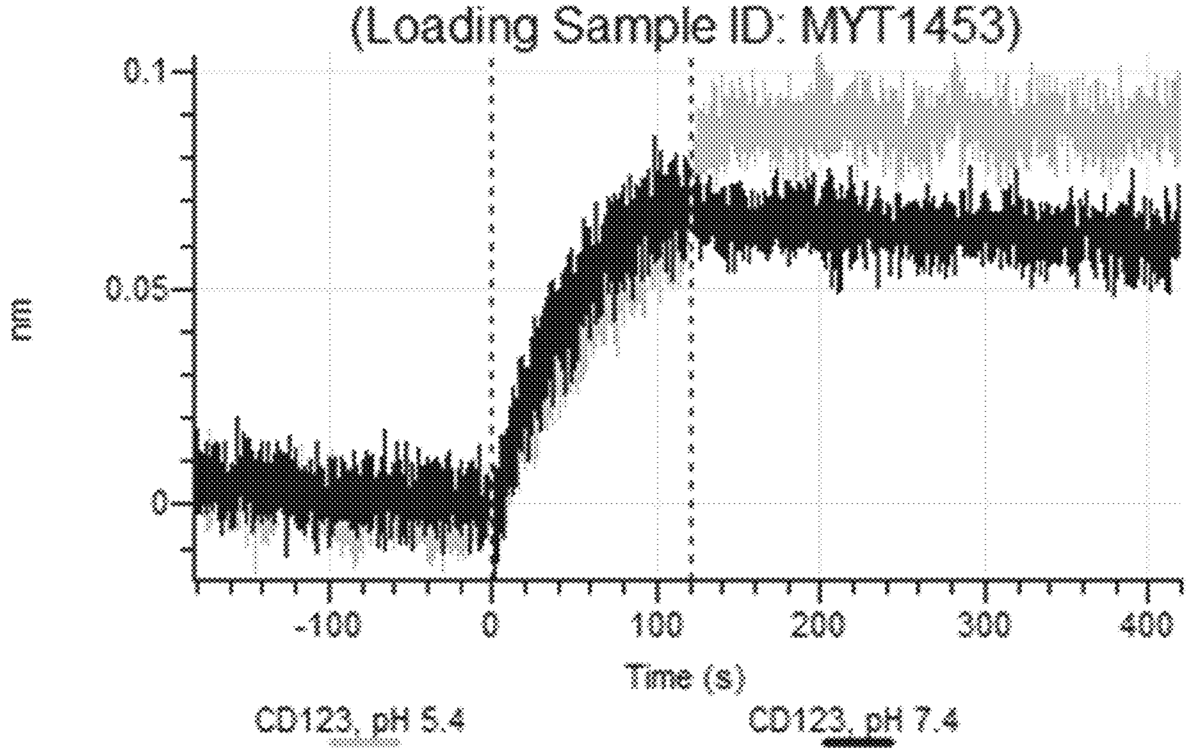

Multiple CD123-binding monoclonal antibodies have been described in the literature and can be used as a template for engineering pH-dependent binding [Li F, Sutherland M K, Yu C, et al. Characterization of SGN-CD123A, A Potent CD123-directed antibody-drug conjugate for acute myeloid leukemia. Mol Cancer Ther. 2018; 17(2):554-564]. We selected SGN-CD123A (Heavy chain SEQ ID NO: 101, Light chain SEQ ID NO: 102) as a CD123-binding monoclonal antibody for pH engineering via histidine scanning. Briefly, CDRs in the heavy chain were identified using the methods described by Kabat et al (Kabat et al. (1992) Sequences of Proteins of Immunological Interest, DIANE publishing) and IMGT (Lefranc M P (1999) "The IMGT unique numbering for Immunoglobulins, T cell receptors and Ig-like domains" The Immunologist 7, 132-136), and for each CDR, residues falling under either or both Kabat and IMGT CDR definitions were called as CDR residues. To generate pH-dependent sequence variants, individual amino acid residues within the heavy chain CDRs were systematically substituted with a histidine, one at a time (MYT1414-MYT1453). In cases where the starting CDR residue was a histidine, it was mutated to an alanine. Antibody variants with only one histidine or alanine mutation in a heavy chain CDR were generated by co-transfection of Expi293 cells with a) one heavy chain sequence variant, and b) the corresponding starting ABPC light chain using methods known to the art. After allowing for four days of protein expression, cell culture supernatants were collected, quantified by SDS-PAGE analysis (FIG. 13), and the pH dependence of the variant was evaluated using biolayer interferometry (BLI) on an Octet RED 96e instrument. Briefly, cell culture supernatants were diluted based on qualitative expression level of the variant determined by visual examination of SDS-PAGE gels, 5 μL of cell culture supernatant was diluted into 195 μL of 1×PBST, pH 7.4 for very high expressors, 15 μL of cell culture supernatant was diluted into 185 μL of 1×PBST, pH 7.4 for high expressors, 25 μL of cell culture supernatant was diluted into 175 μL of 1×PBST, pH 7.4 for medium expressors, 50 of cell culture supernatant was diluted into 175 μL of 1×PBST, pH 7.4 for low expressors and 100 μL of cell culture supernatant was diluted into 100 μL of 1×PBST, pH 7.4 for very low expressors for loading onto the sensor tips. The resulting diluted supernatants were then captured on an anti-human Fc sensor (Forte Bio). A baseline was established using 1×PBST (50 mM Potassium Phosphate Buffer+150 mM NaCl+0.05% Tween 20) pH 7.4, and the sensor was associated with 50 nM of CD123 (CD123 Protein, His Tag, Acro Biosciences Cat. No. ILA-H52H6, Lot No. 1741d-89CF1-KB) in 1×PBST pH 7.4 for 120 sec to generate an association curve. In the dissociation phase, the antibody-antigen complex on the sensor was exposed to 1× PBST pH 7.4 for 300-600 sec. Baseline, association, and dissociation were repeated using 1×PBST pH 5.4 throughout in a separate condition. Association and dissociation phase curves were examined for the starting ABPC antibody (with no substitutions) and each corresponding antibody variant at pH 5.4 and pH 7.4 to inform on two criteria: a) enhanced dissociation (i.e., higher koff values) at pH 5.4 due to histidine or alanine substitution compared to the starting ABPC, (with no substitutions), and b) reduced dissociation at pH 7.4 (i.e., lower koff values) compared to pH 5.4 in the antibody variant itself and with the starting ABPC (with no substitutions). Heavy chain variants that showed either enhanced dissociation at pH 5.4 or reduced dissociation at pH 7.4 or both (as compared to the starting ABPC), as shown in FIG. 14 were selected for further analysis (e.g, MYT1414, MYT1415, MYT1420, MYT1421, MYT1423, MYT1426, MYT1431, MYT1432, MYT1433, MYT1448, MYT1449). It was also noted that while some histidine and alanine mutations obliterated CD123 binding (e.g., MYT1417, MYT1424, MYT1425, MYT1427, MYT1441, MYT1443, MYT1444, MYT1447, MYT1450), others were tolerated with little (e.g., less than 1-fold change in dissociation constant $K_D$ or dissociation rate) or no change in CD123 binding kinetics (e.g., MYT1416, MYT1418, MYT1419, MYT1422, MYT1428, MYT1429, MYT1430, MYT1434, MYT1435, MYT1436, MYT1437, MYT1438, MYT1439, MYT1440, MYT1442, MYT1445, MYT1446, MYT1451, MYT1452, MYT1453).

Especially because histidine is a large, positively charged amino acid, these variants with no change were noted as positions in the heavy chain that may tolerate a wide range of mutations and lead to antibodies with different sequence but similar binding properties, a designation that is not otherwise apparent.

Example 14. Construction and Screening of pH-Engineered CD123 ABPCs

Figure 16:
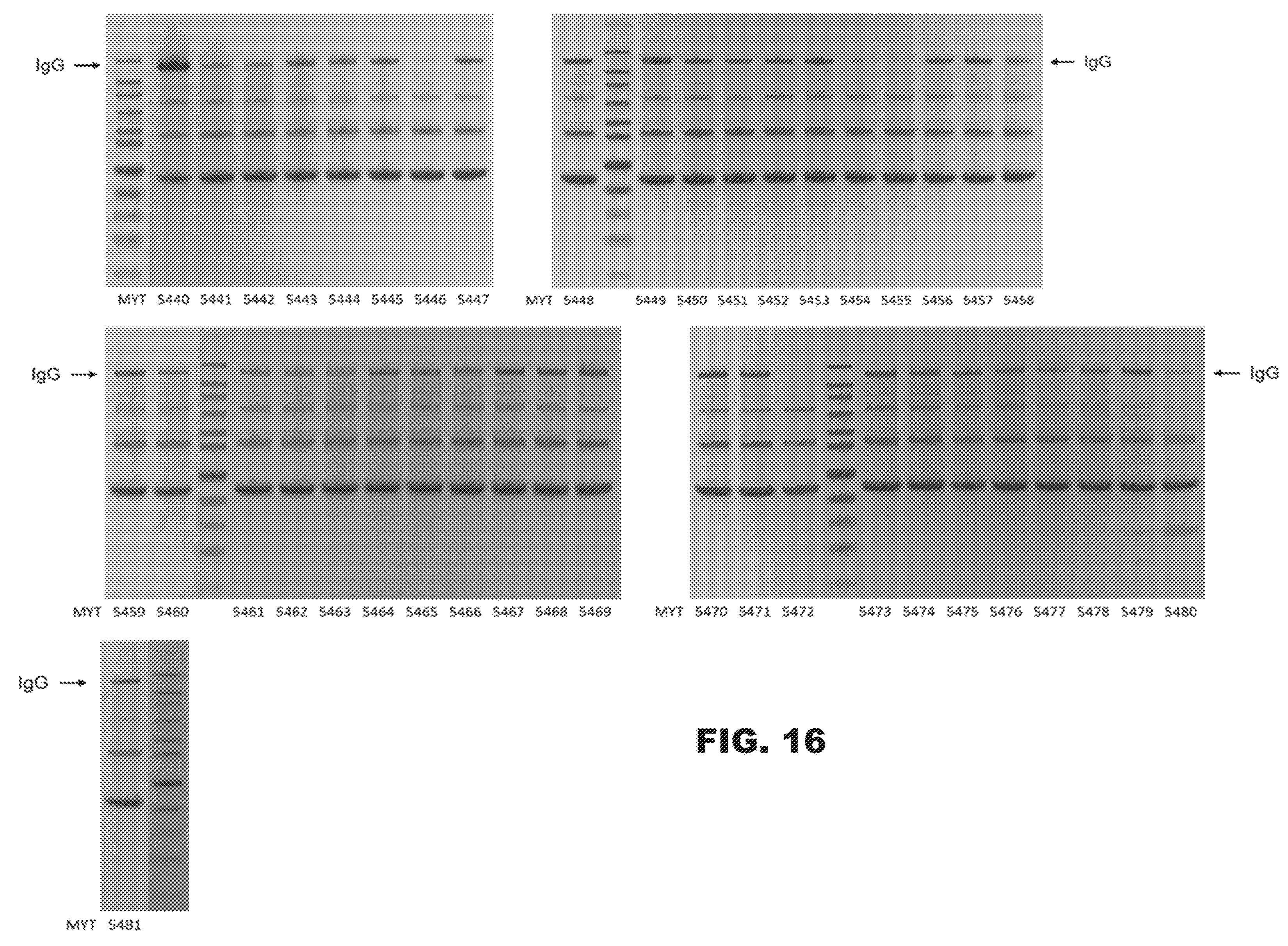
FIG. 16: SDS PAGE for TPP-8988 histidine scanning and alanine scanning. Expi293 cell culture supernatants post-harvest were loaded on non-reduced SDS PAGE gels to confirm expression of TPP-8988 and histidine scanning and alanine scanning variants. Arrows show the corresponding size for an IgG on a non-reduced SDS PAGE gel. MYT5440 is TPP-8988 and the rest of the lanes (MYT5441-MYT5481) are TPP-8988 heavy chain histidine scanning and alanine scanning variants.
Figure 17A:
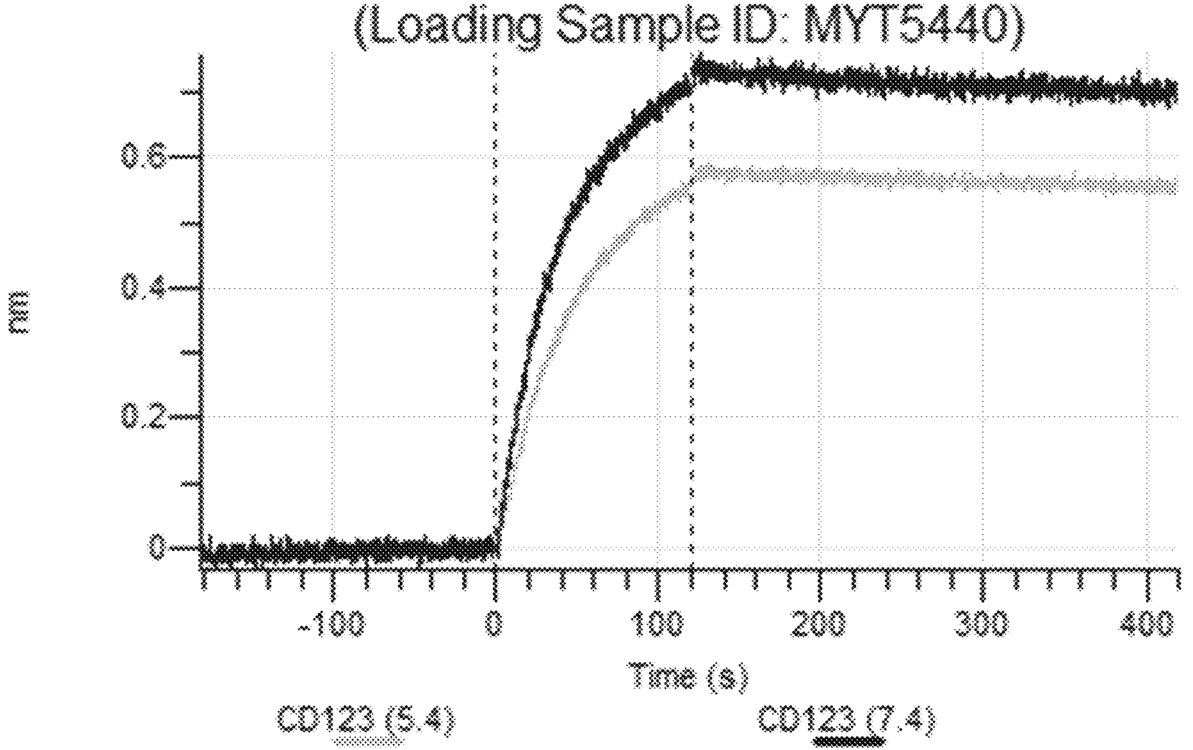
FIGS. 17*a* to 17*ap*: Binding of TPP-8988 starting ABPC and histidine scanning and alanine scanning variants to CD123 by biolayer interferometry. MYT5440 (TPP-8988) and MYT5441-MYT5481, heavy chain histidine scanning and alanine scanning variants, were captured on anti-human Fc biosensors and associated with CD123 at low pH or high pH, as specified in the figures.
Figure 17B:
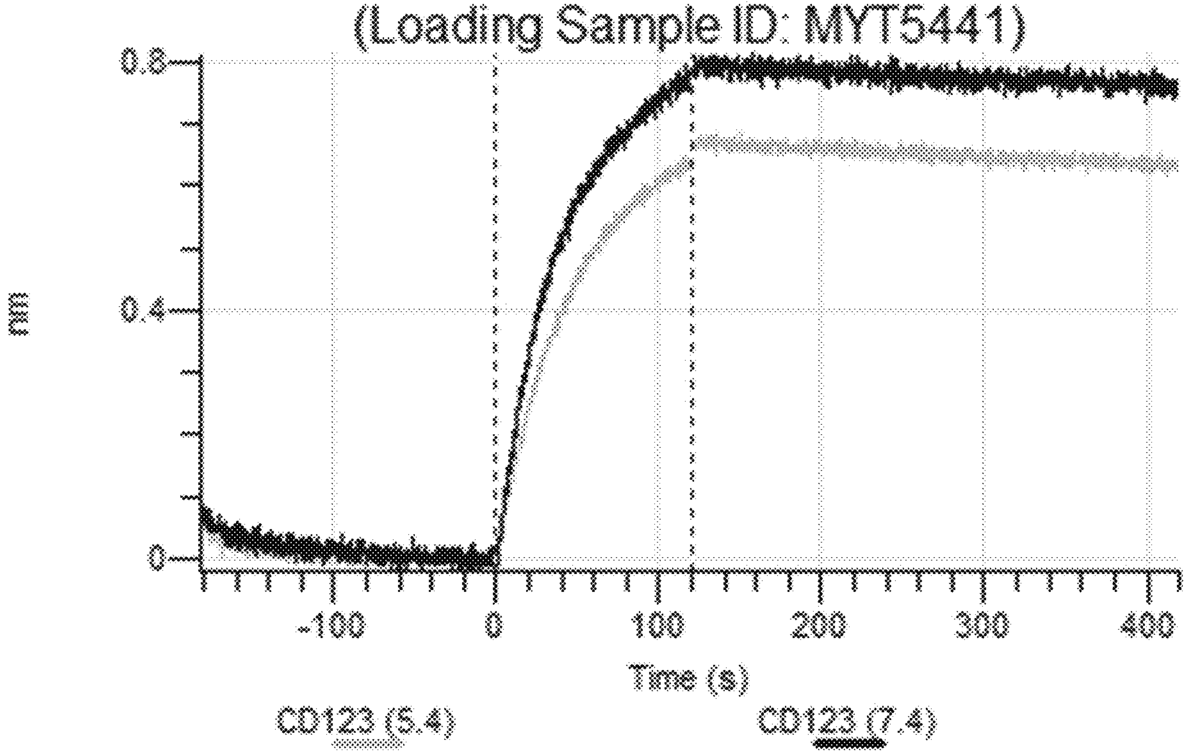
Figure 17C:
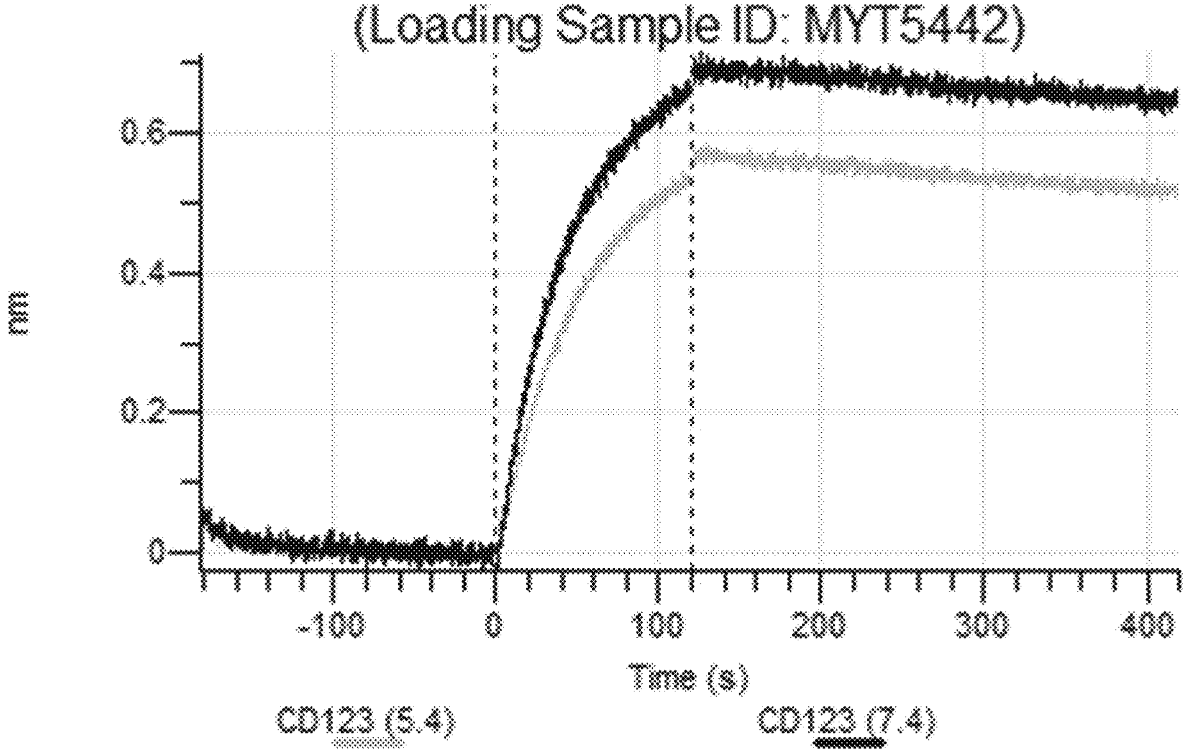
Figure 17D:
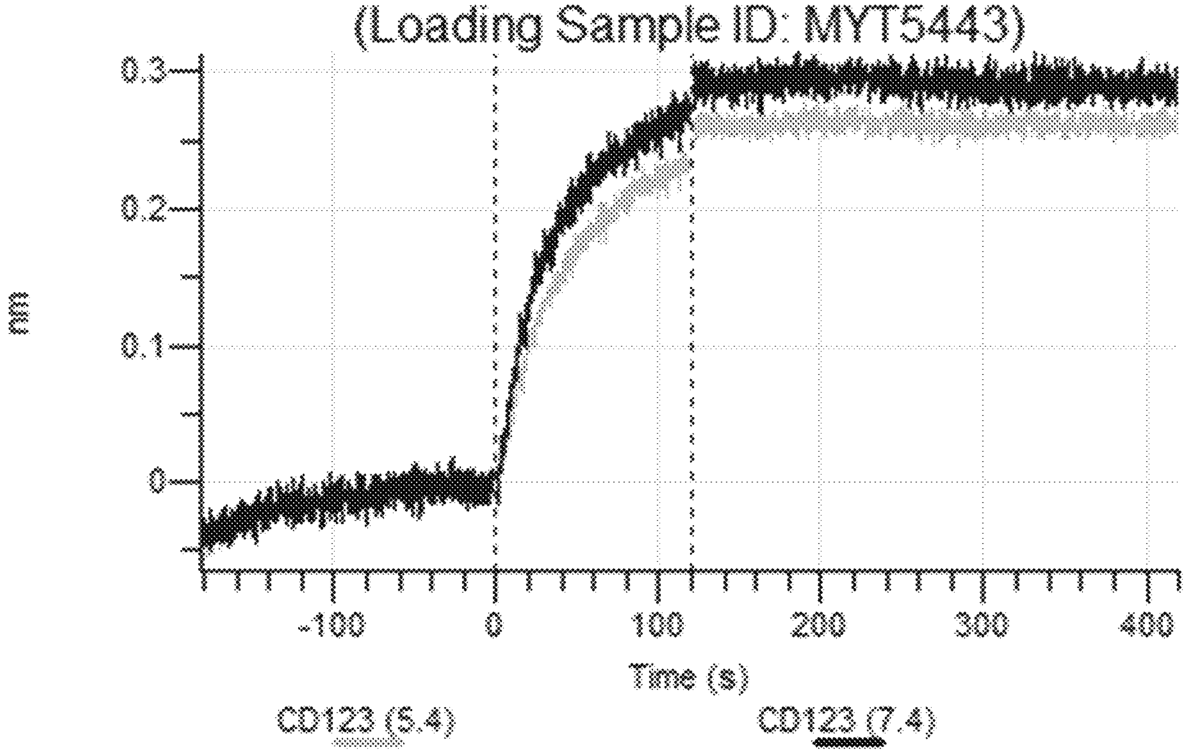
Figure 17E:
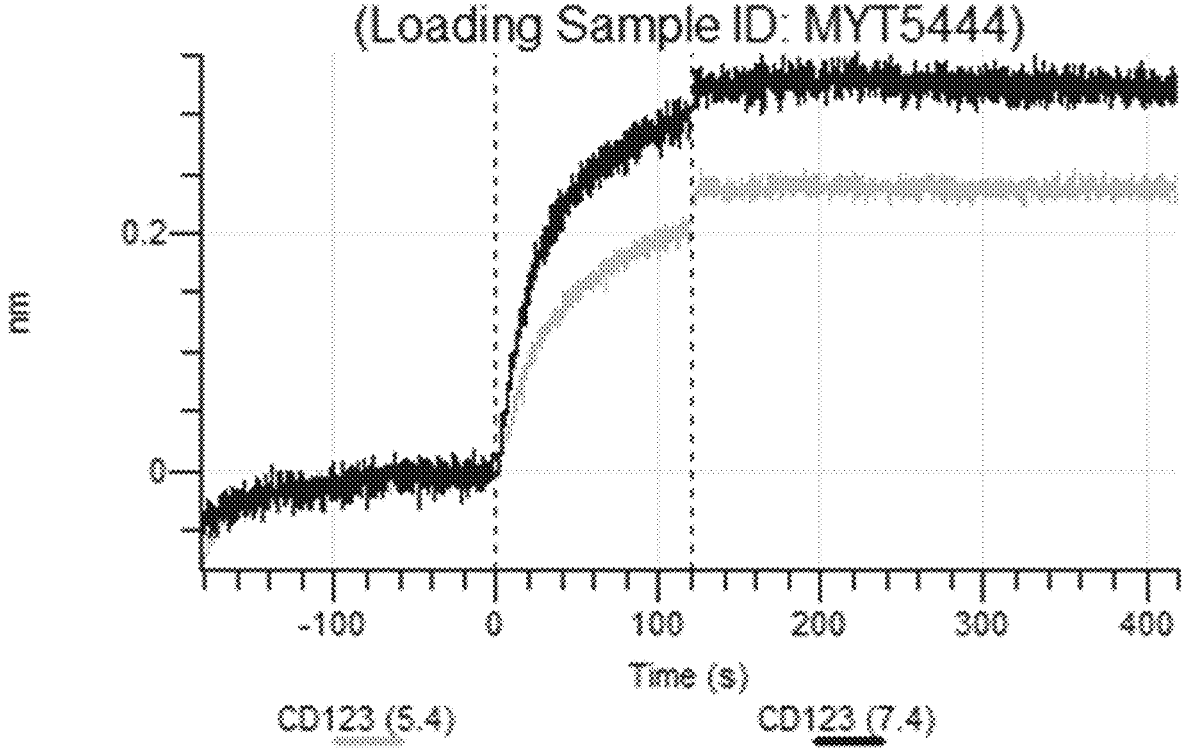
Figure 17F:
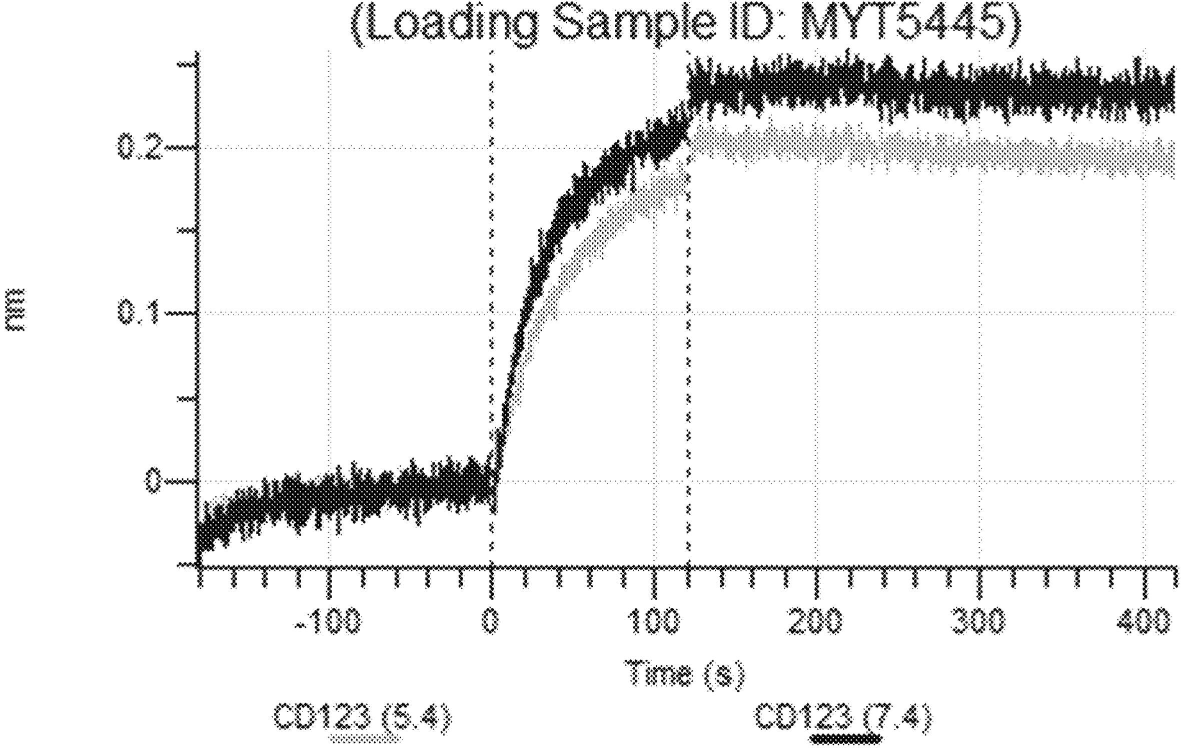
Figure 17G:
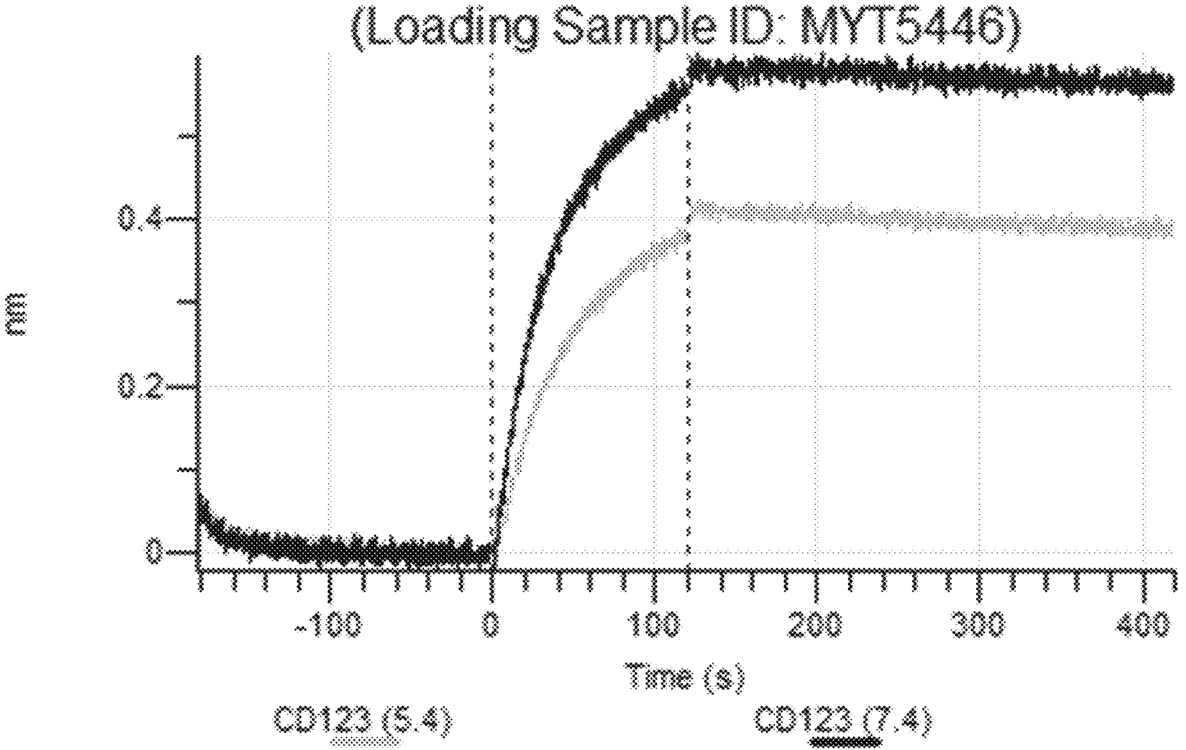
Figure 17H:
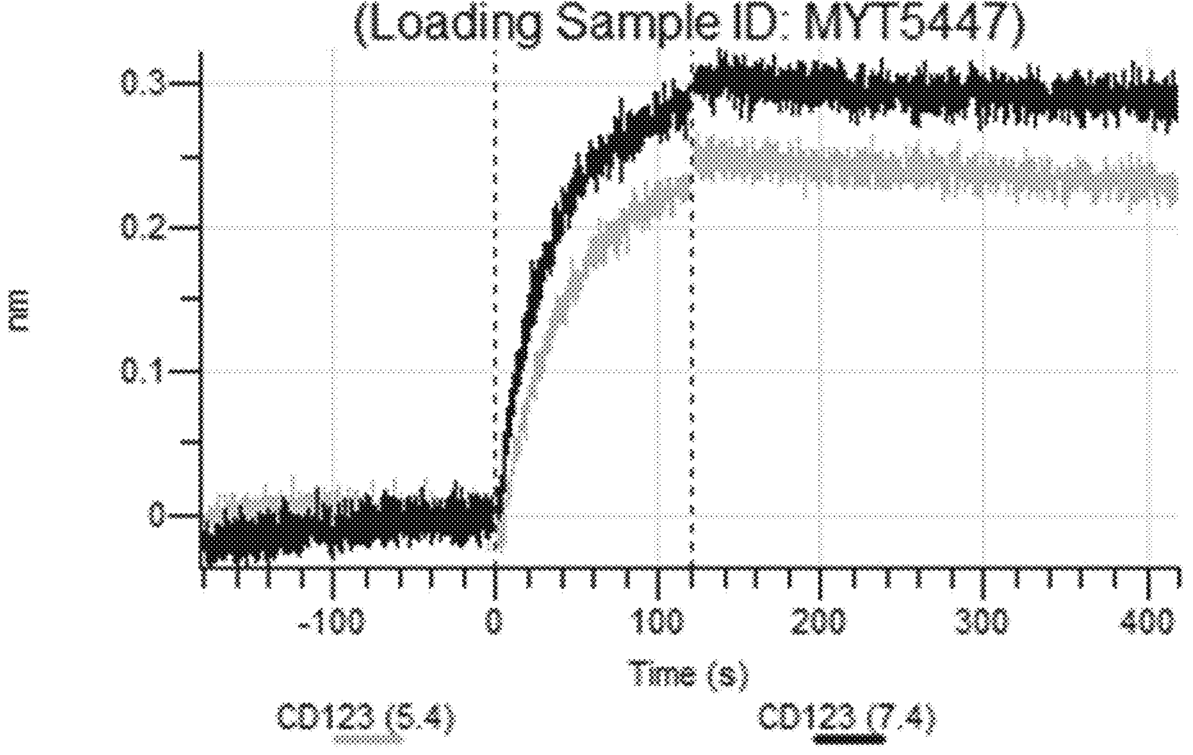
Figure 17I:
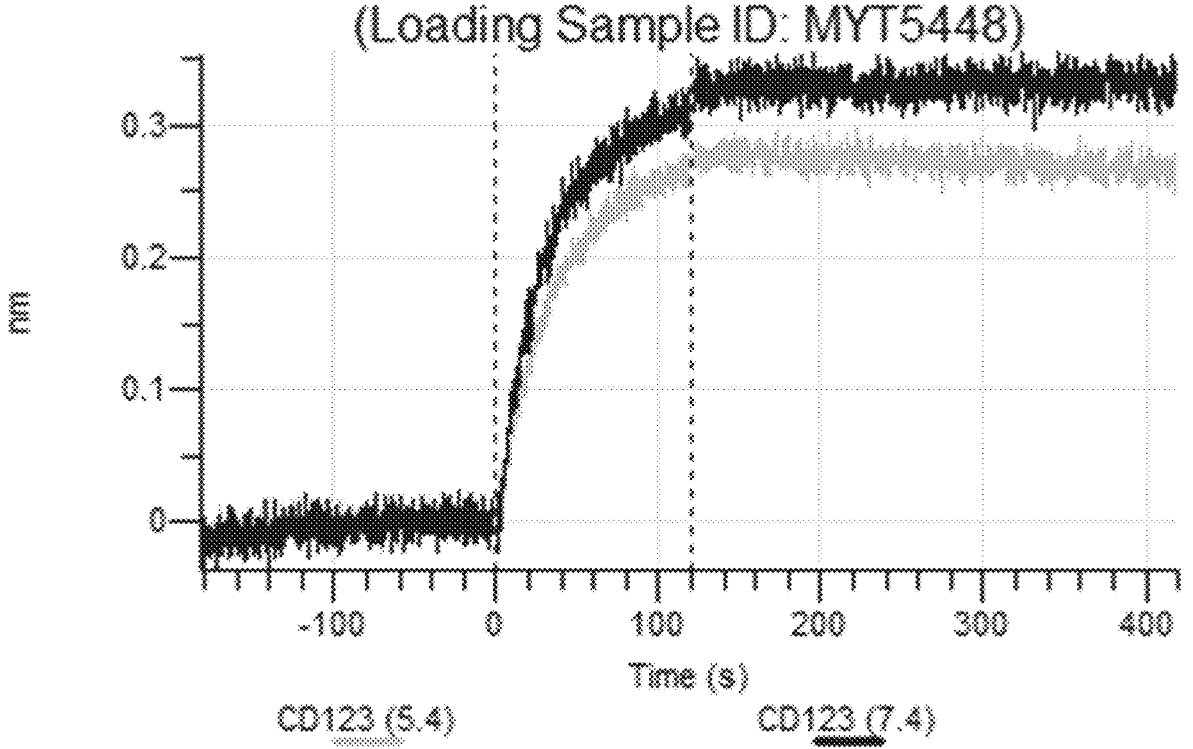
Figure 17J:
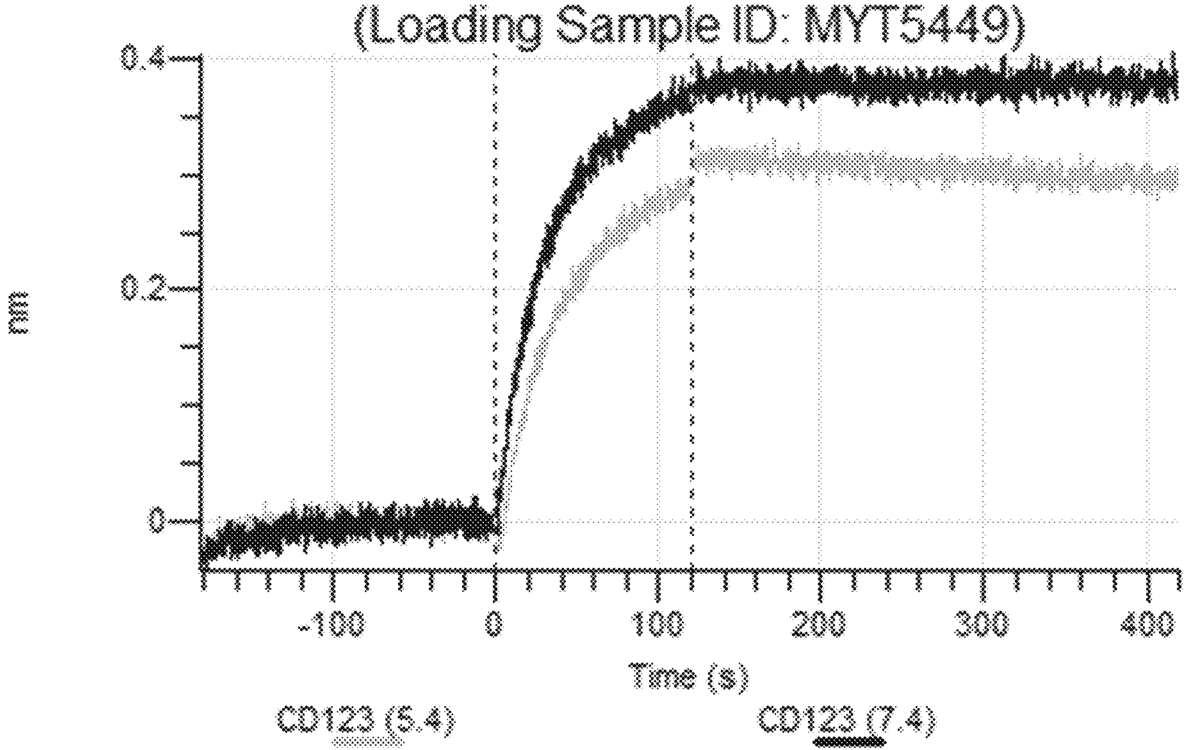
Figure 17K:
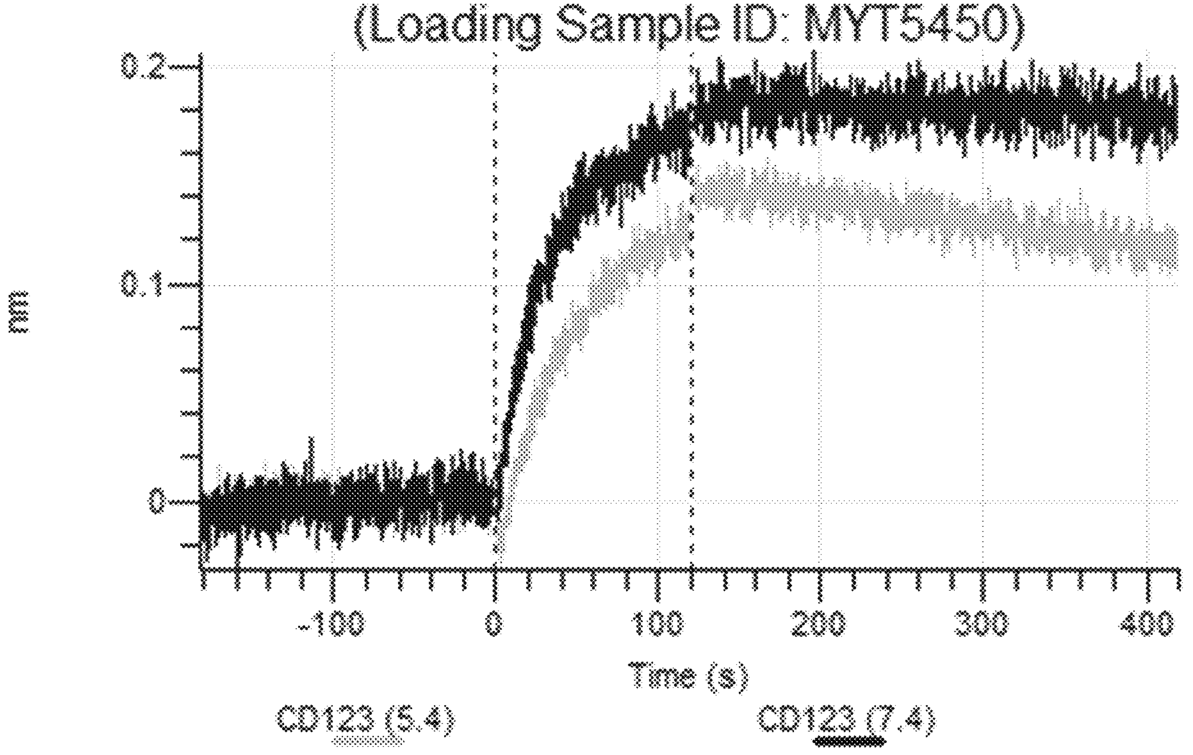
Figure 17L:
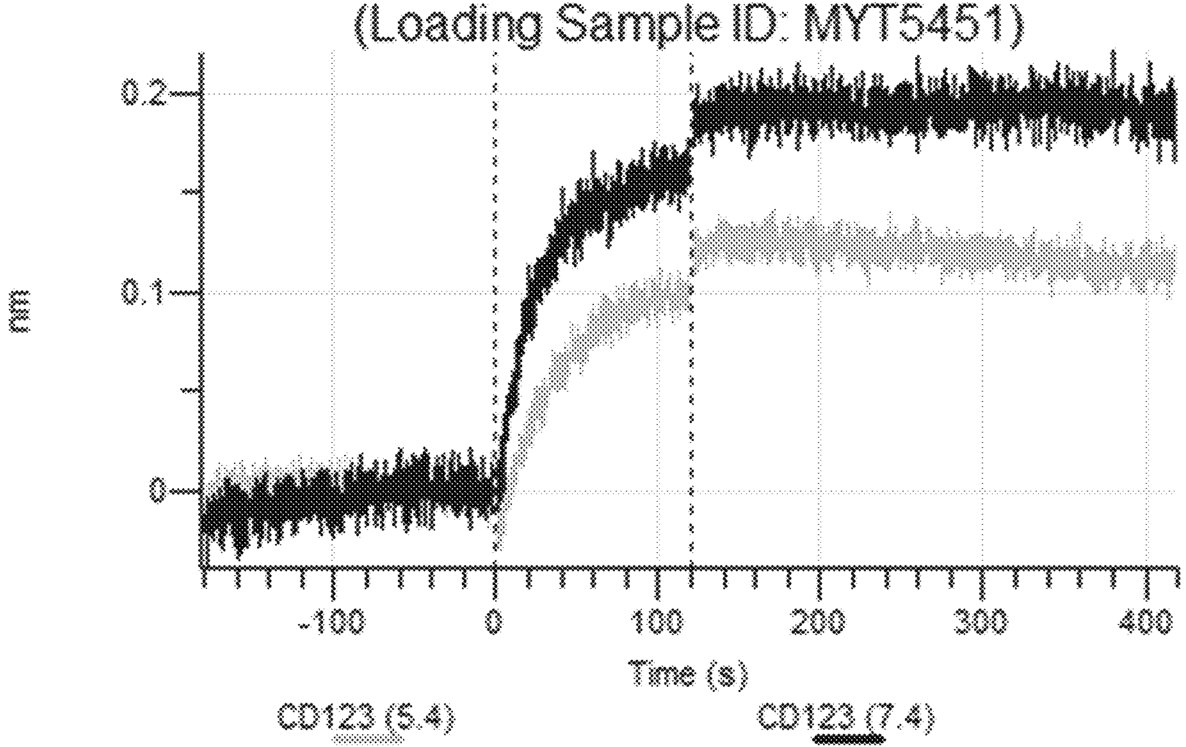
Figure 17M:
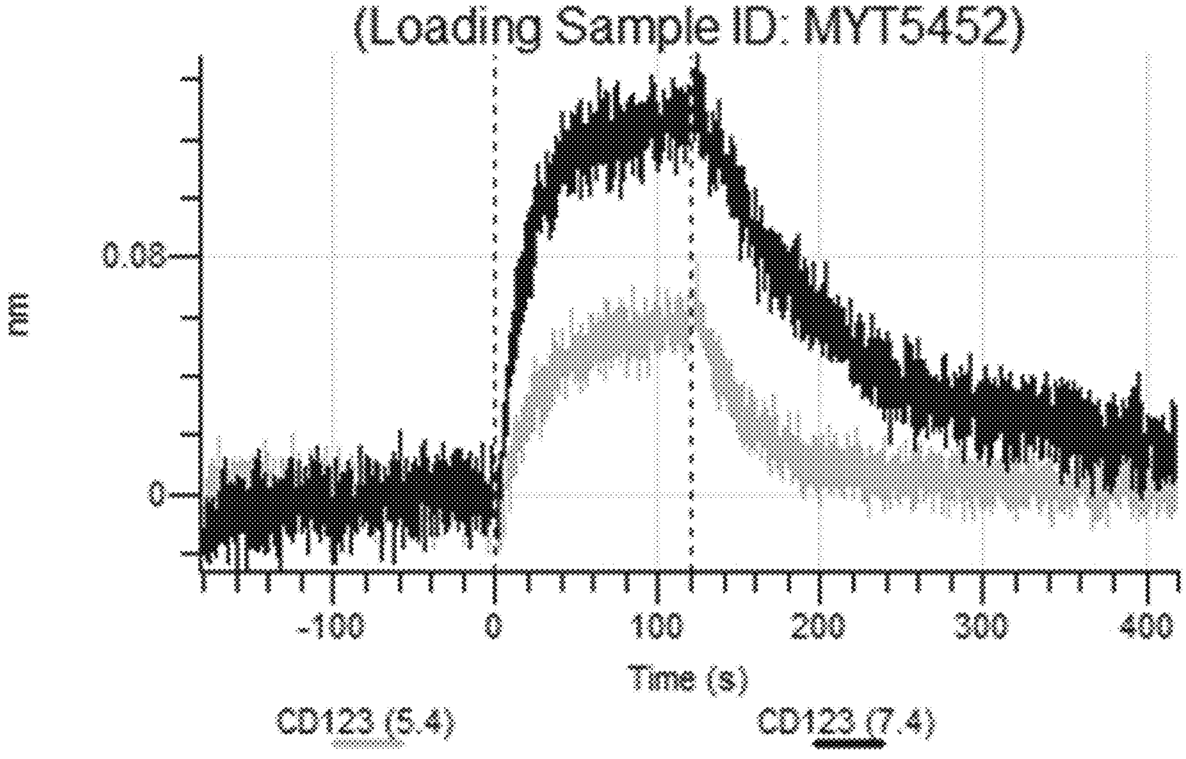
Figure 17N:
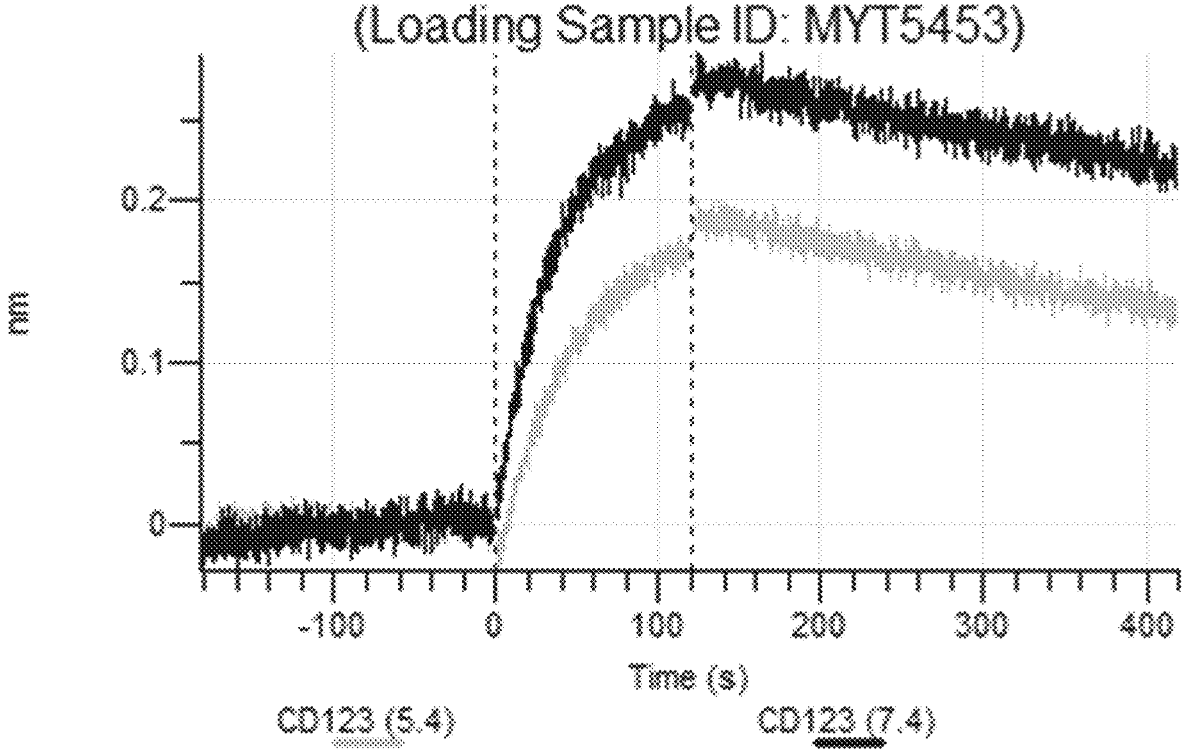
Figure 17O:
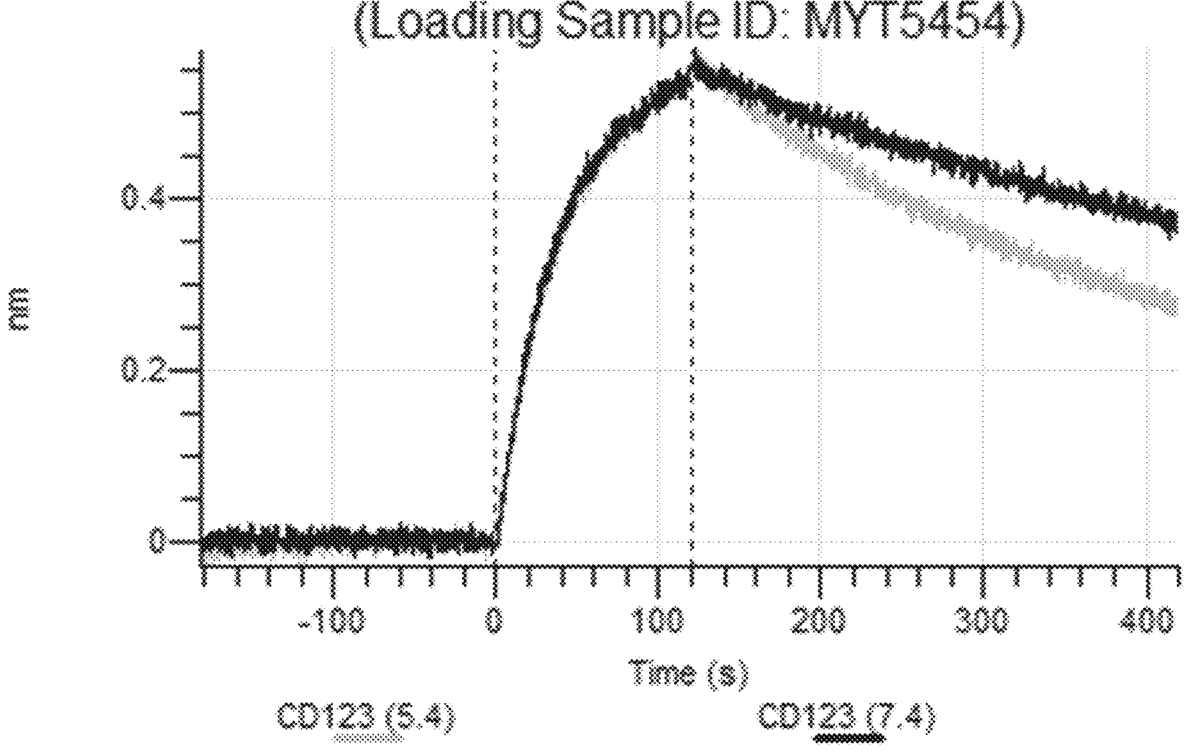
Figure 17P:
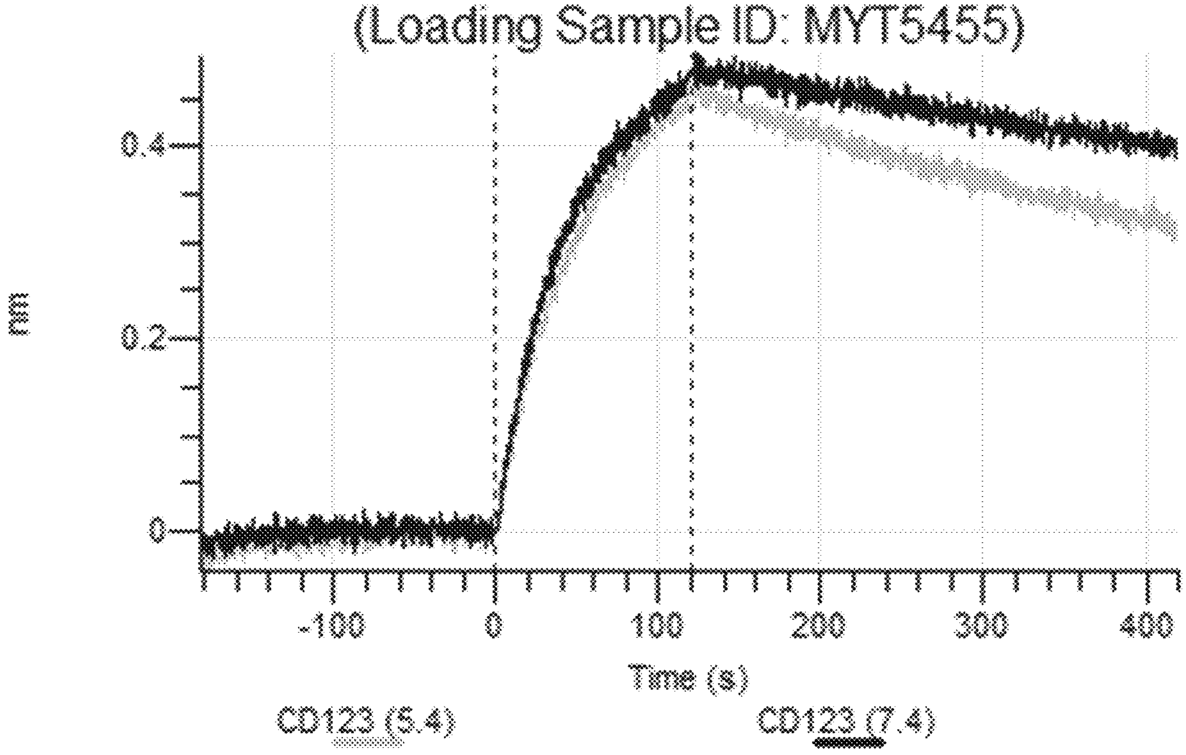
Figure 17Q:
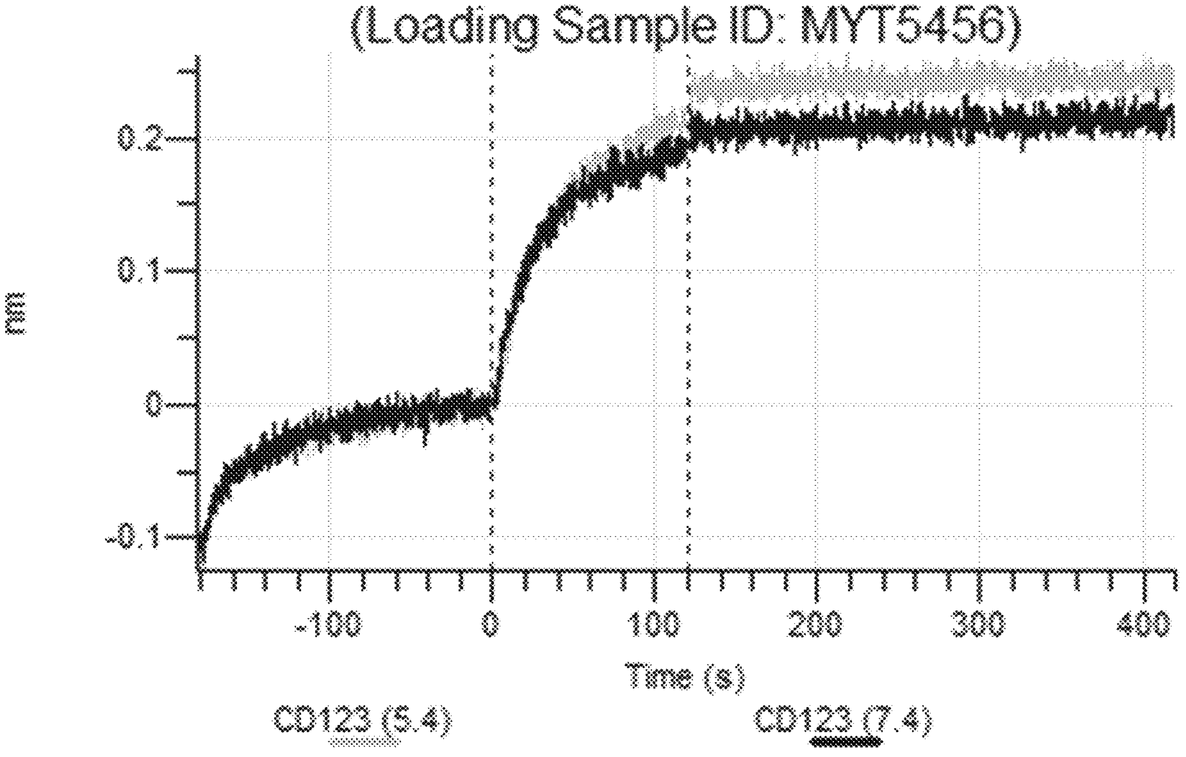
Figure 17R:
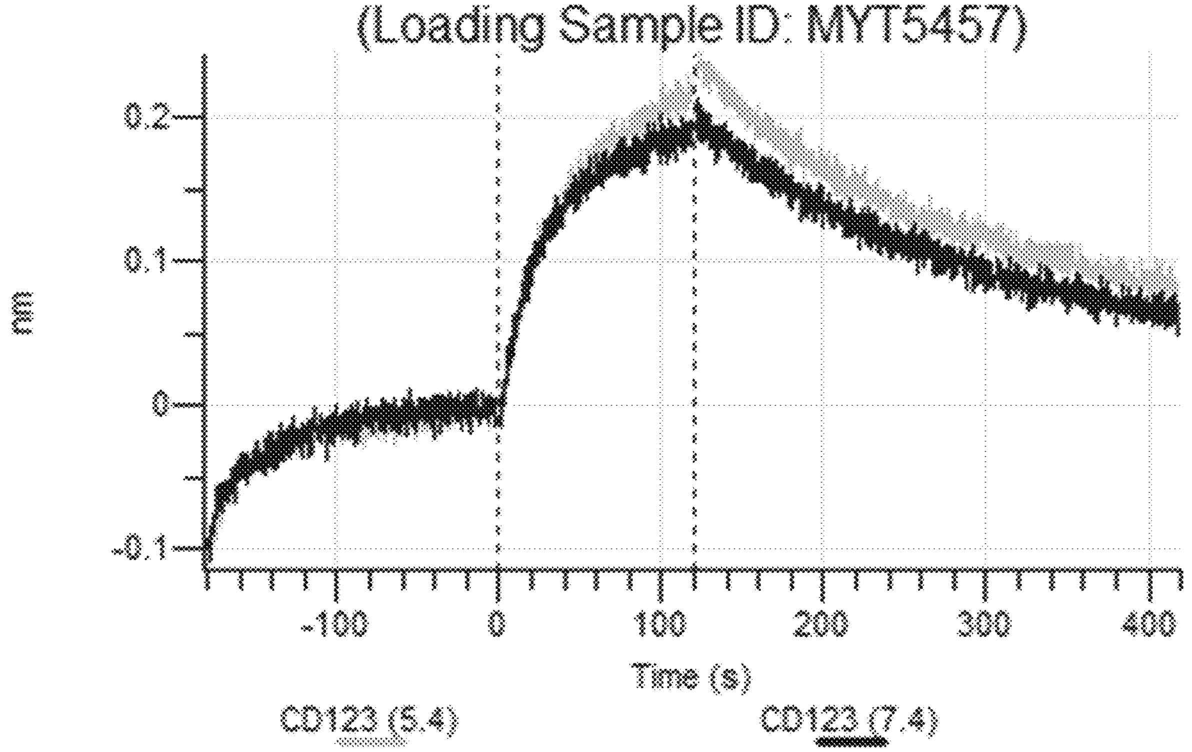
Figure 17S:
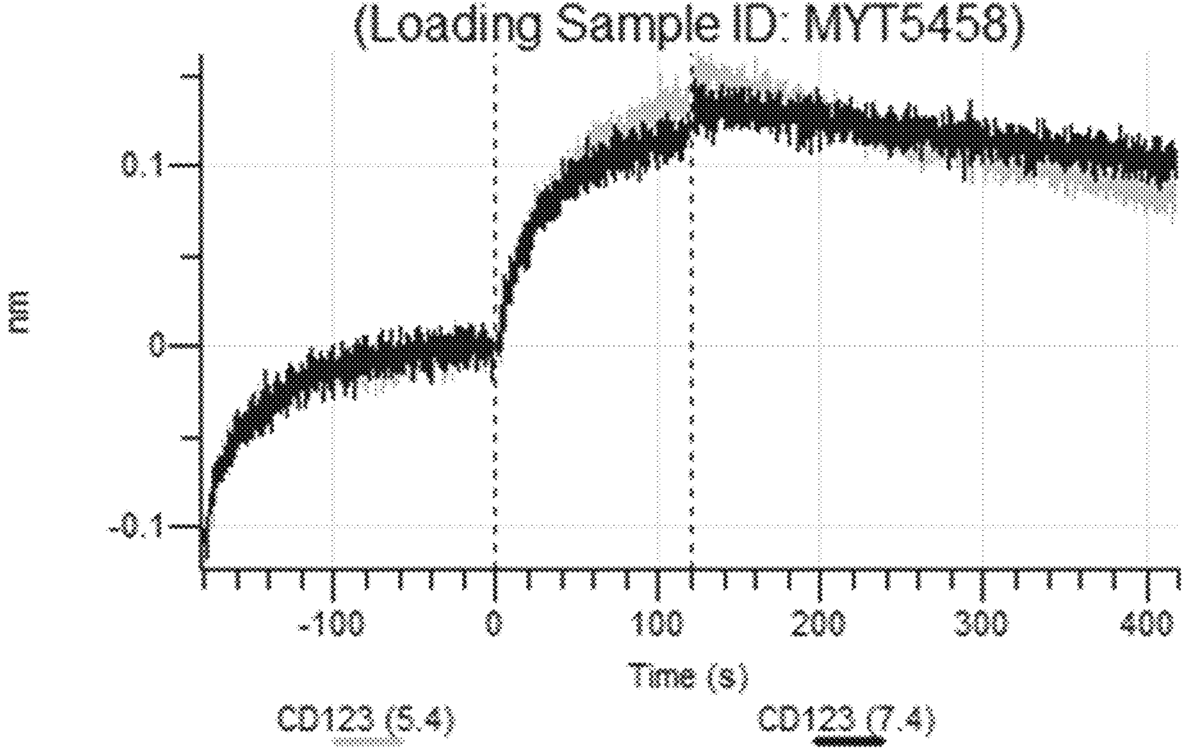
Figure 17T:
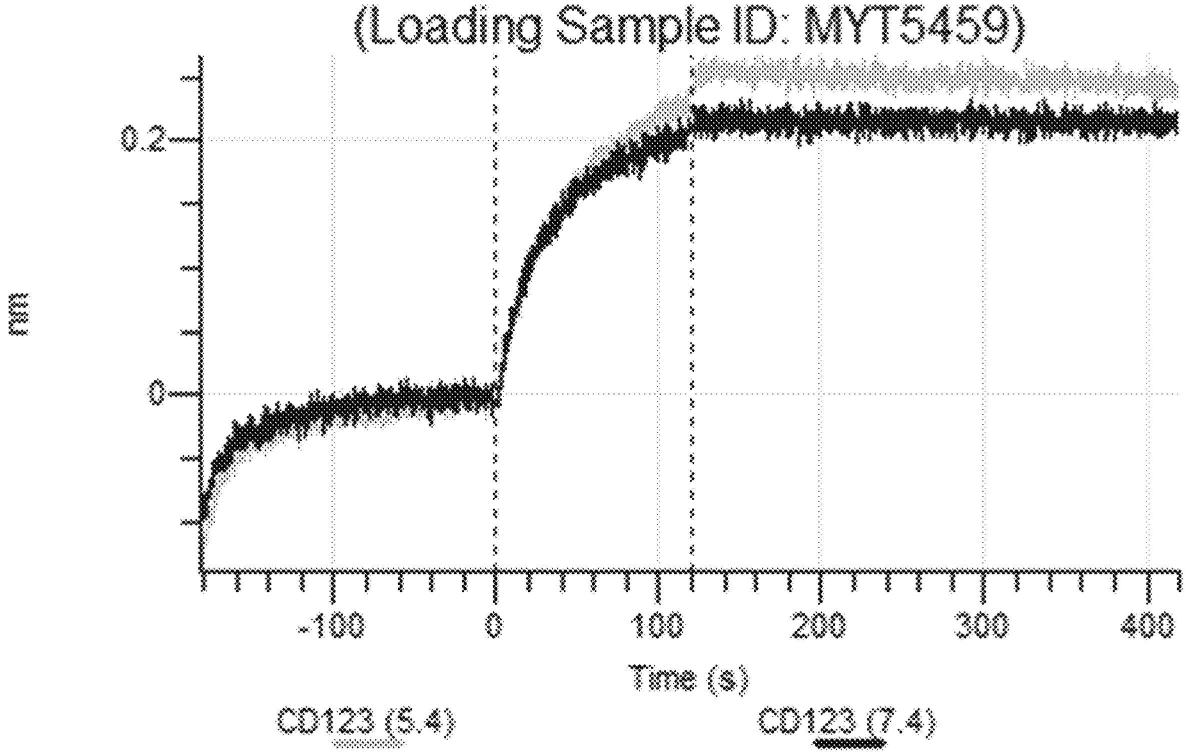
Figure 17U:
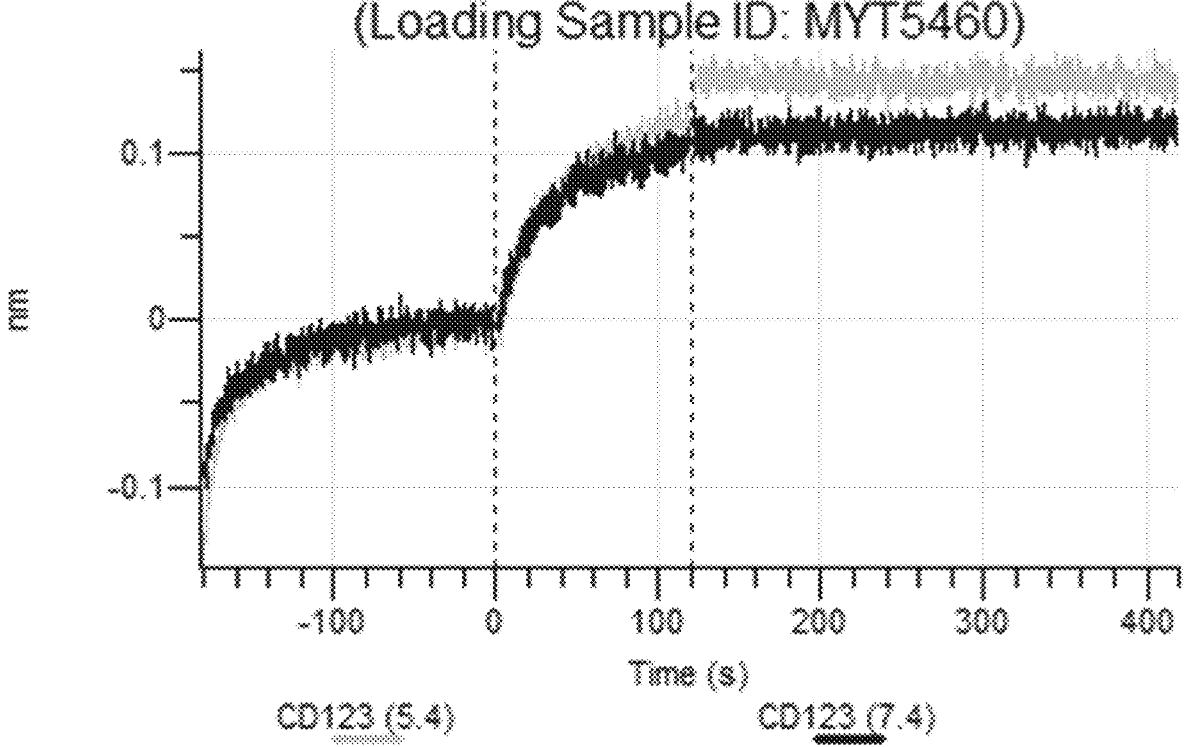
Figure 17V:
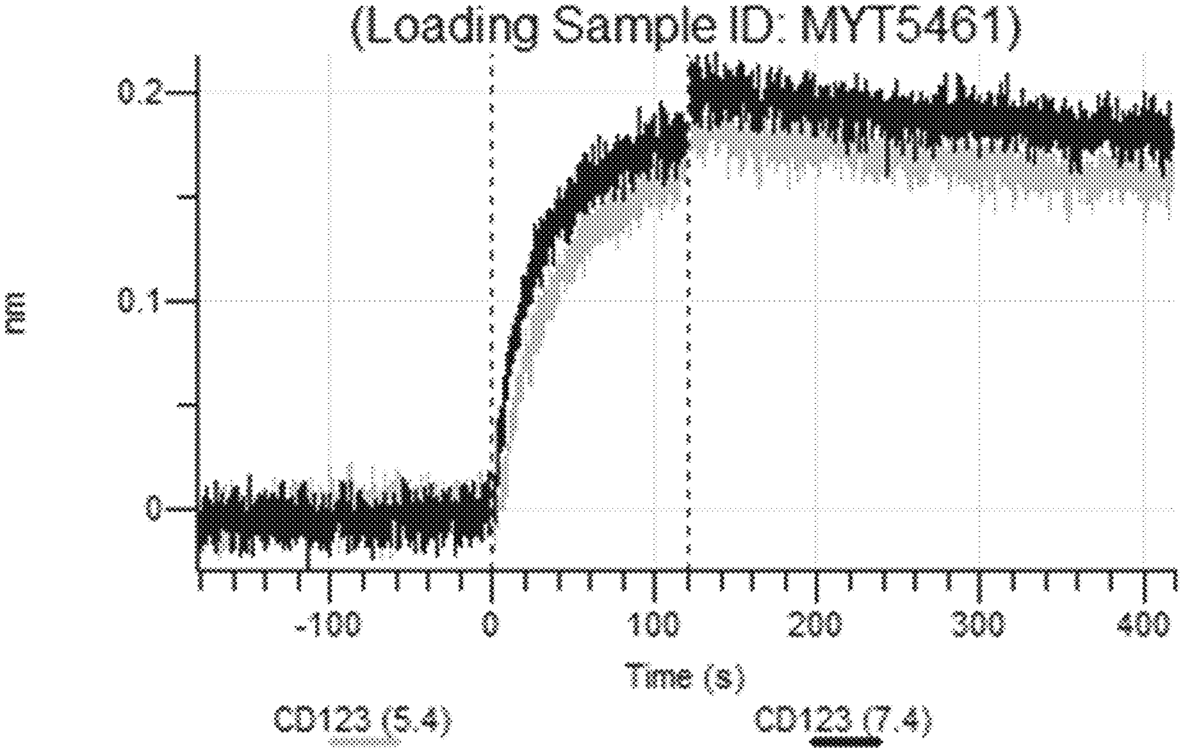
Figure 17W:
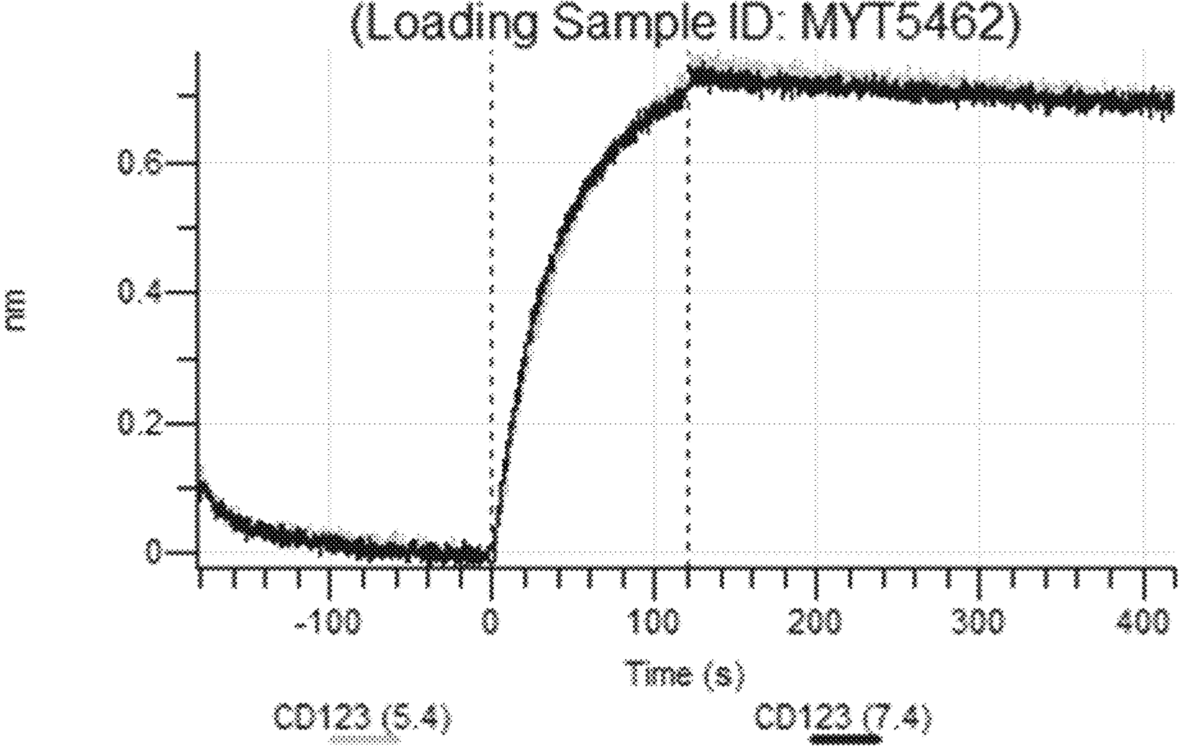
Figure 17X:
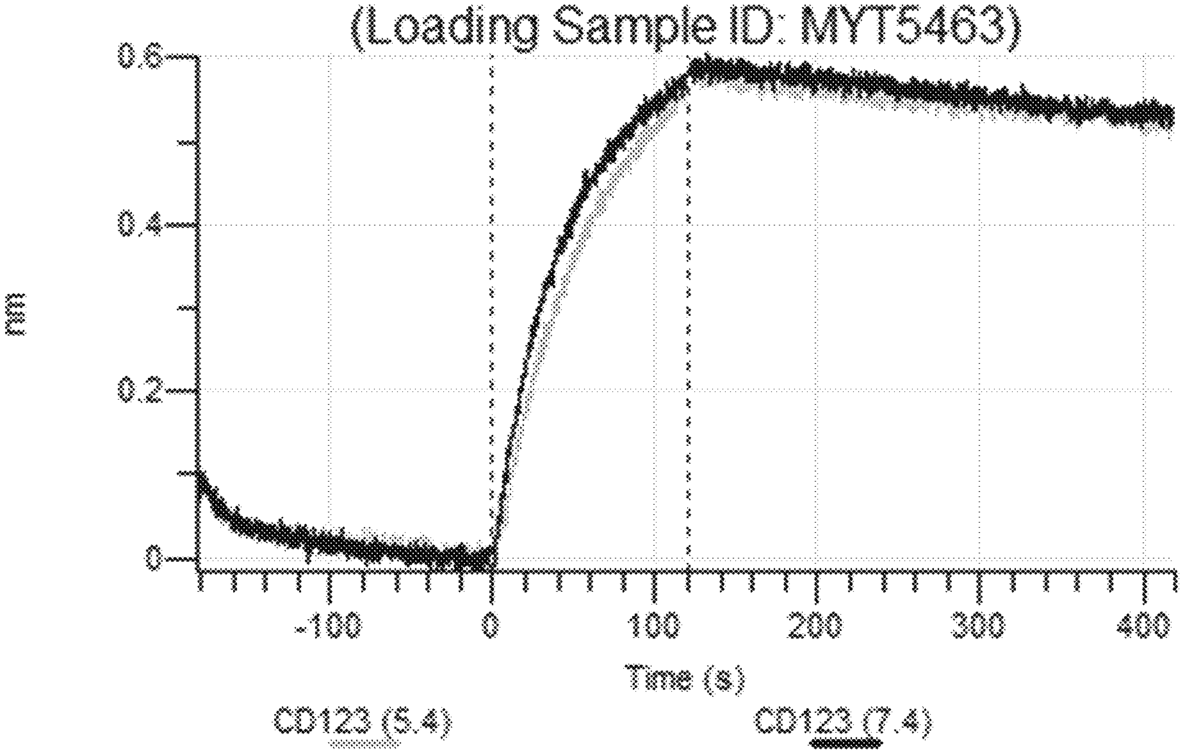
Figure 17Y:
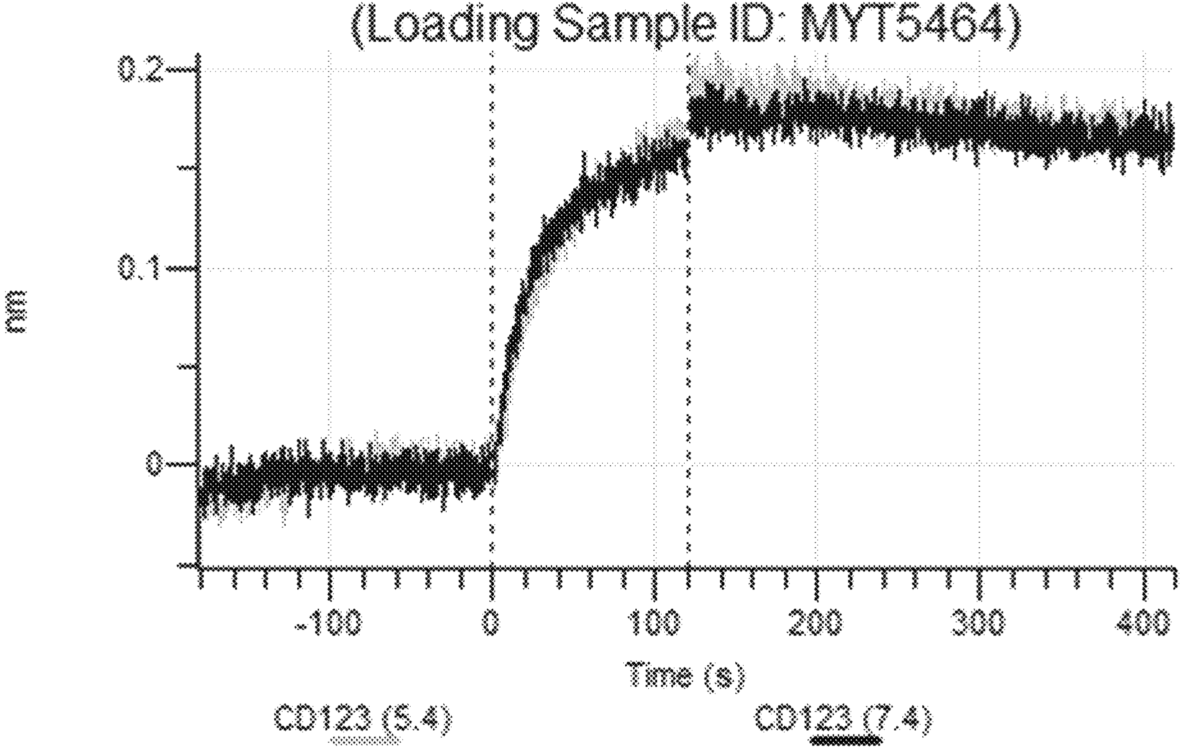
Figure 17Z:
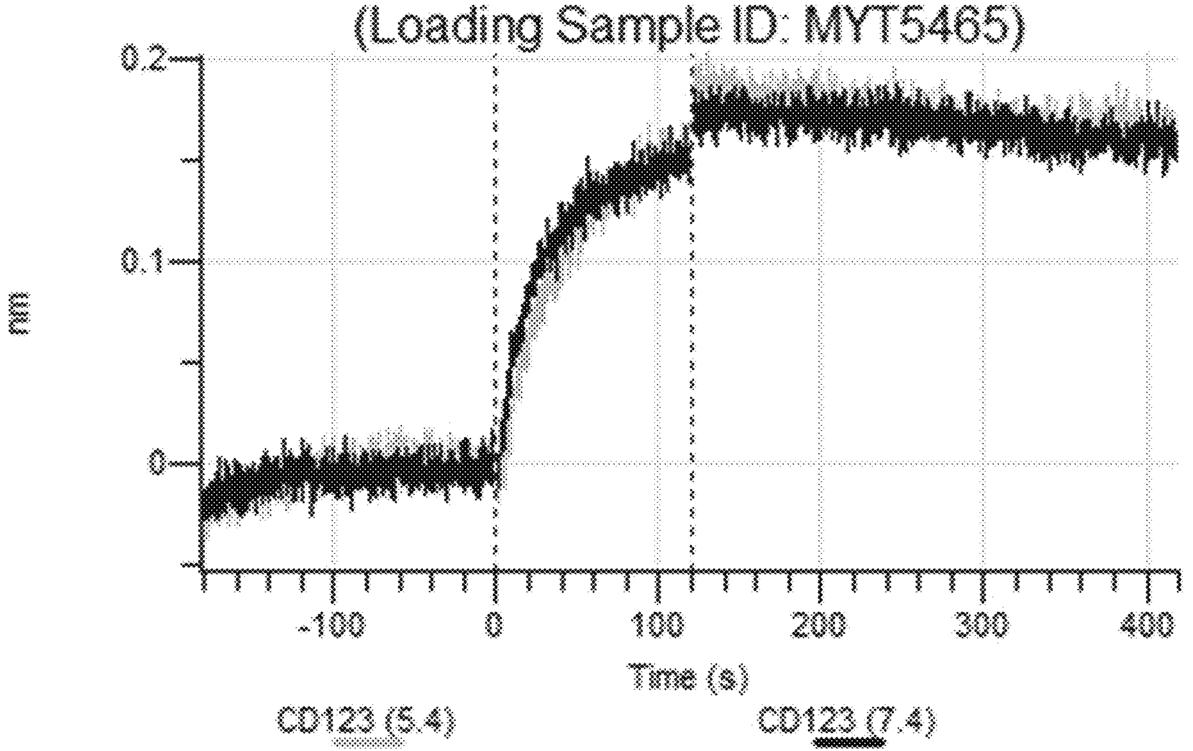
Figure 17A:
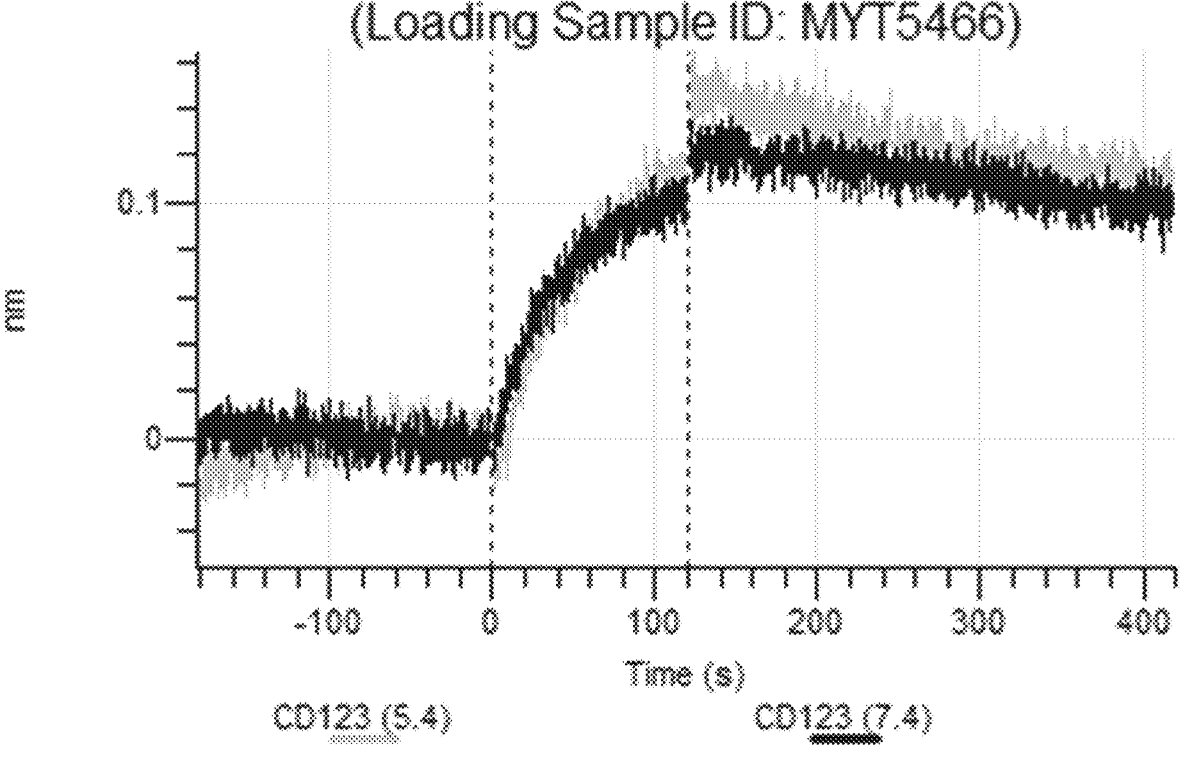
Figure 17A:
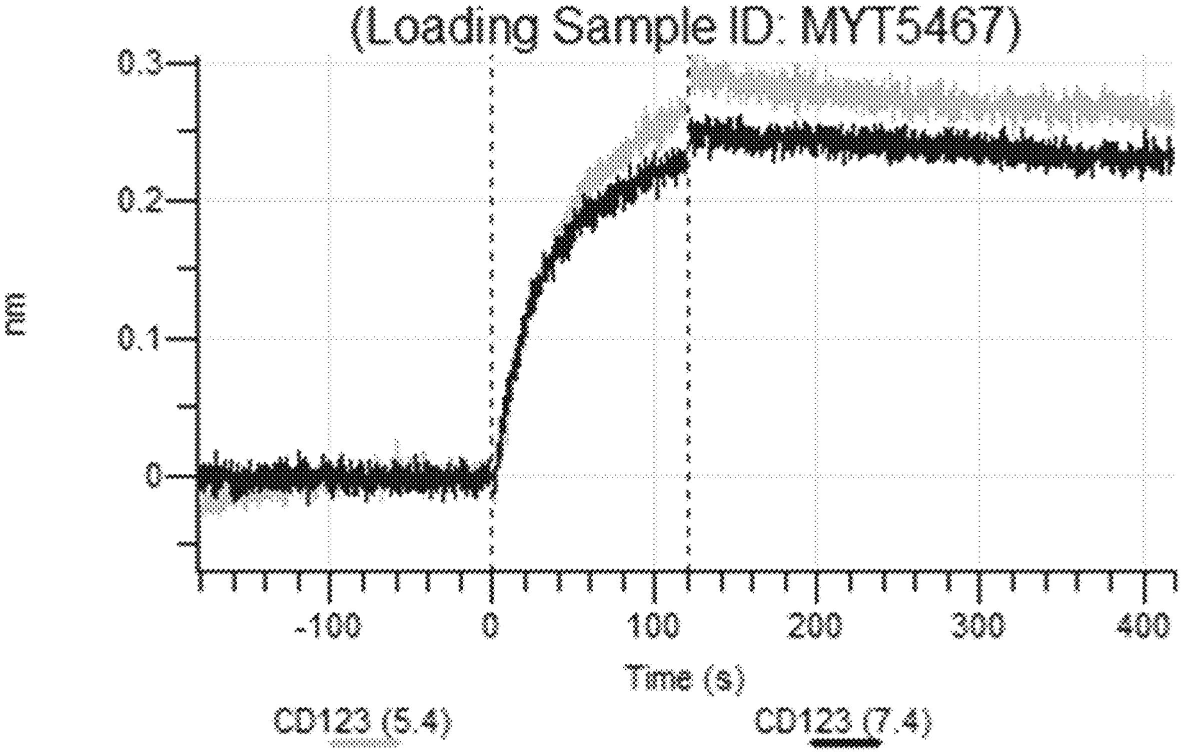
Figure 17A:
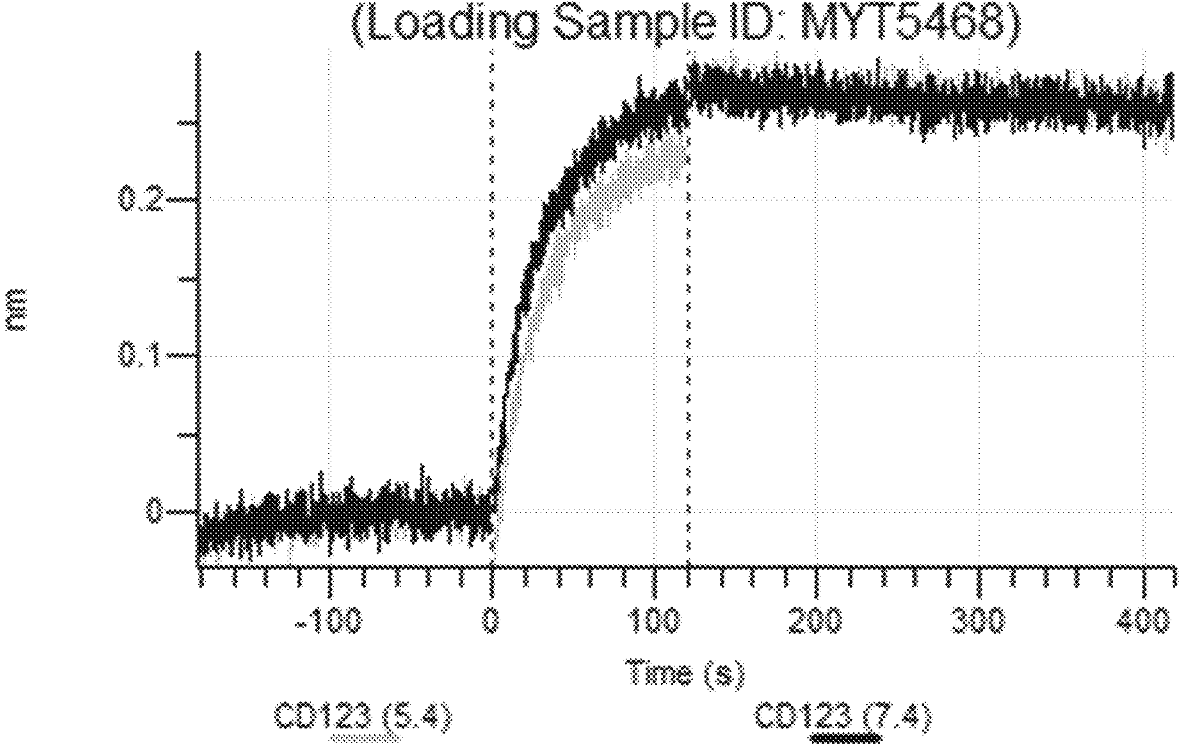
Figure 17A:
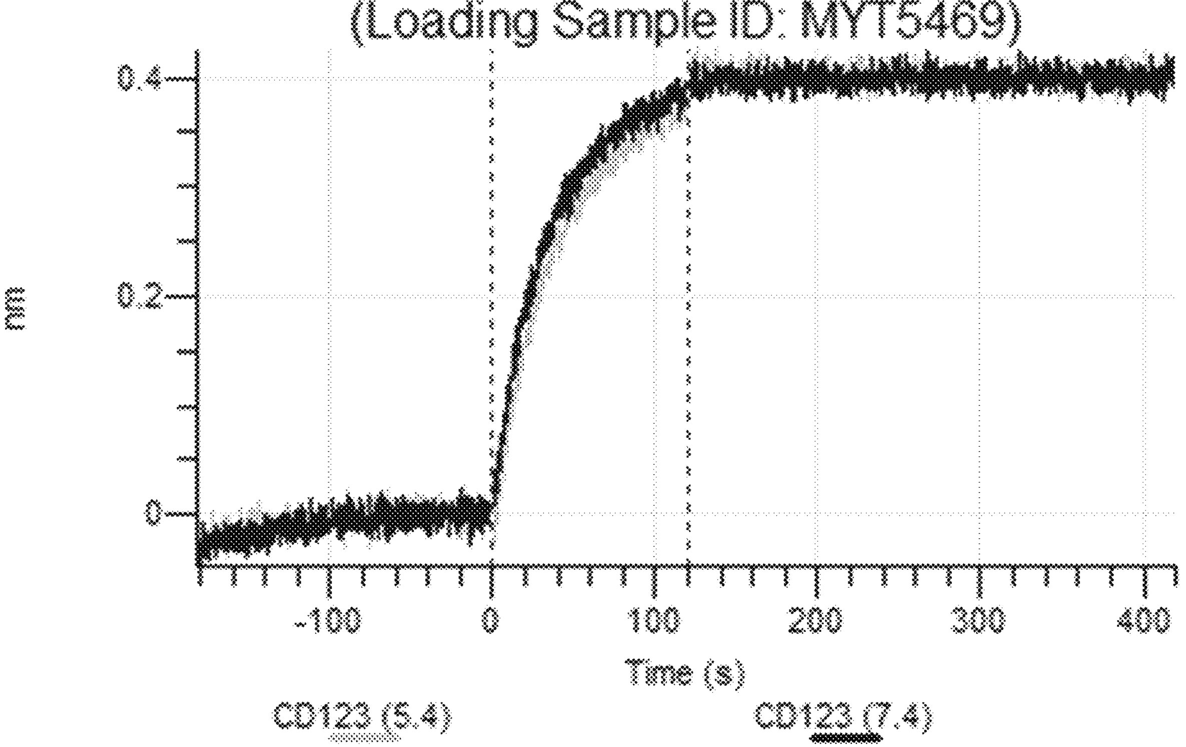
Figure 17A:
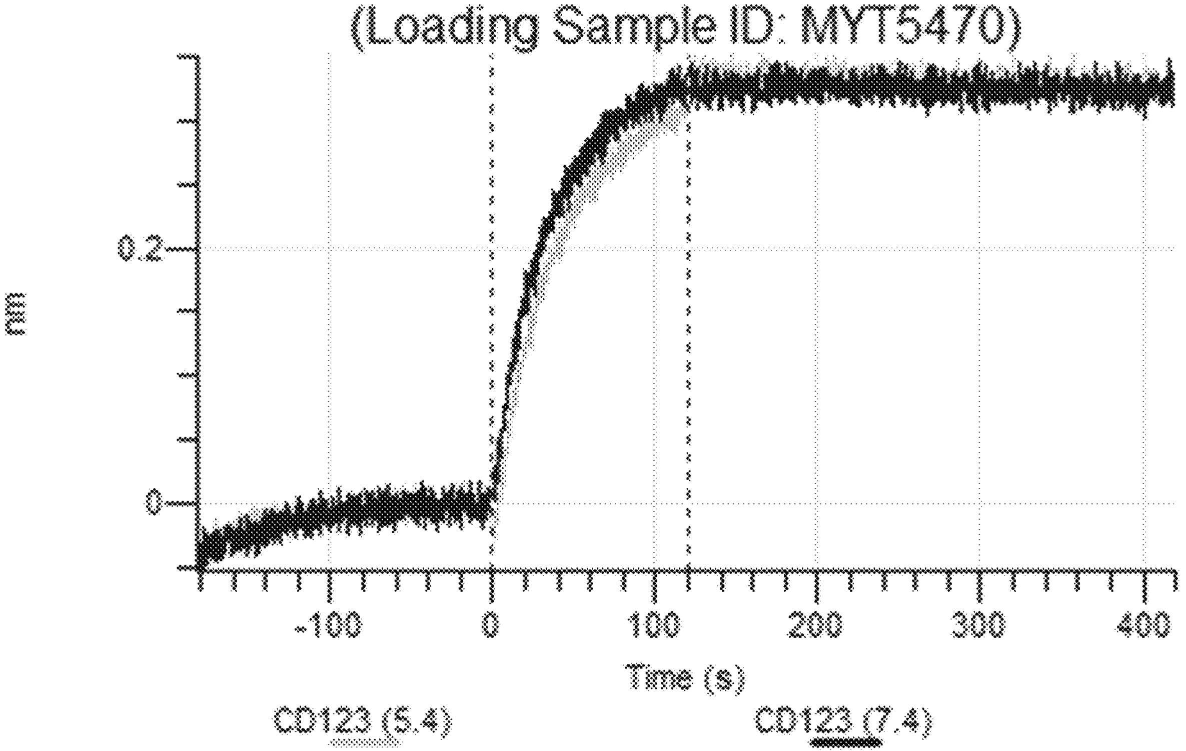
Figure 17A:
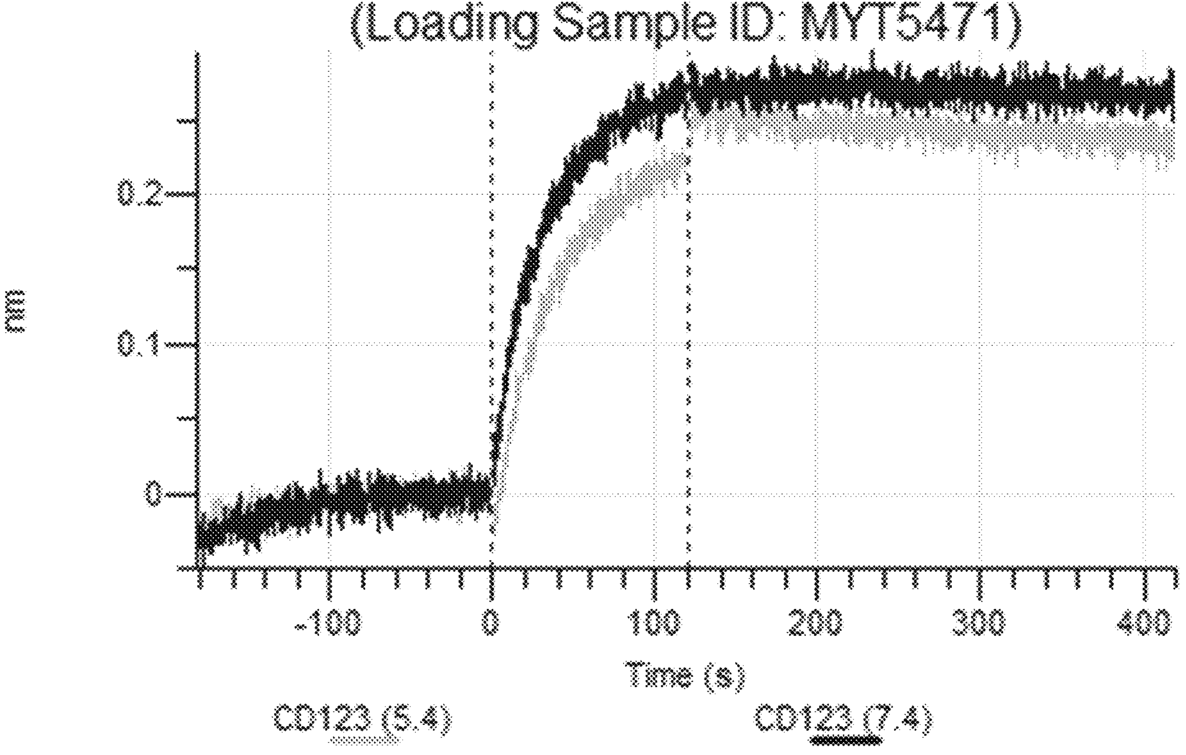
Figure 17A:
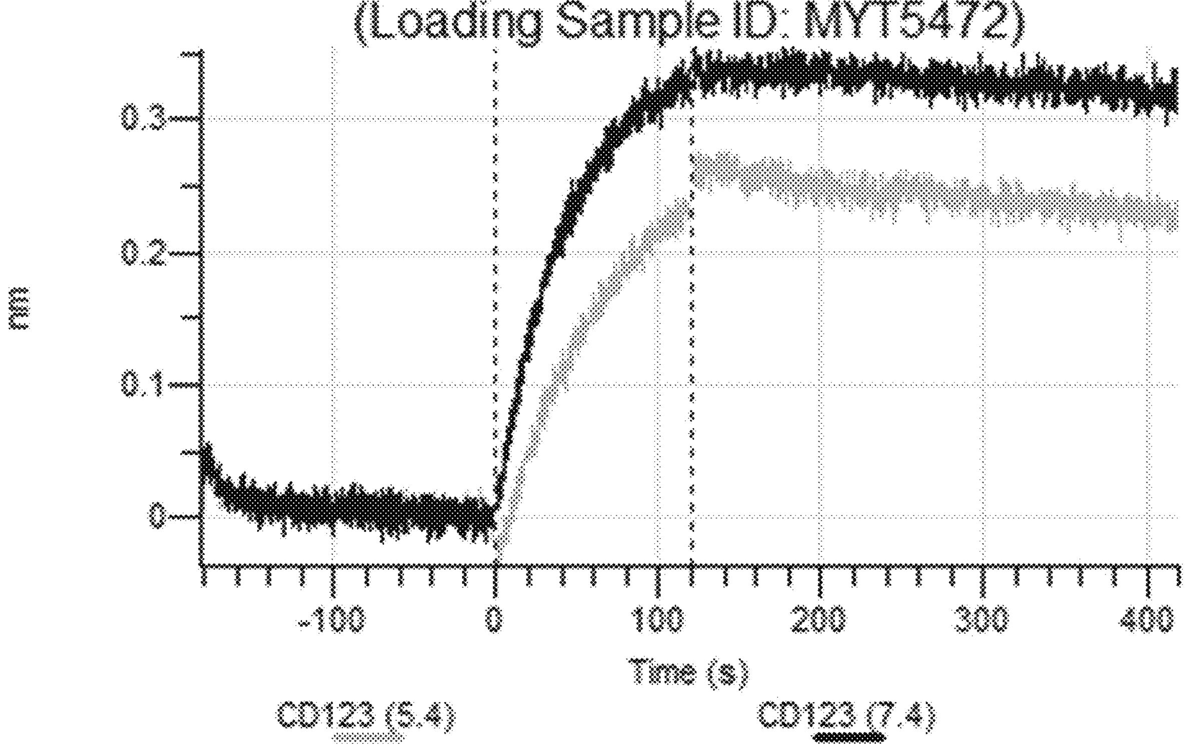
Figure 17A:
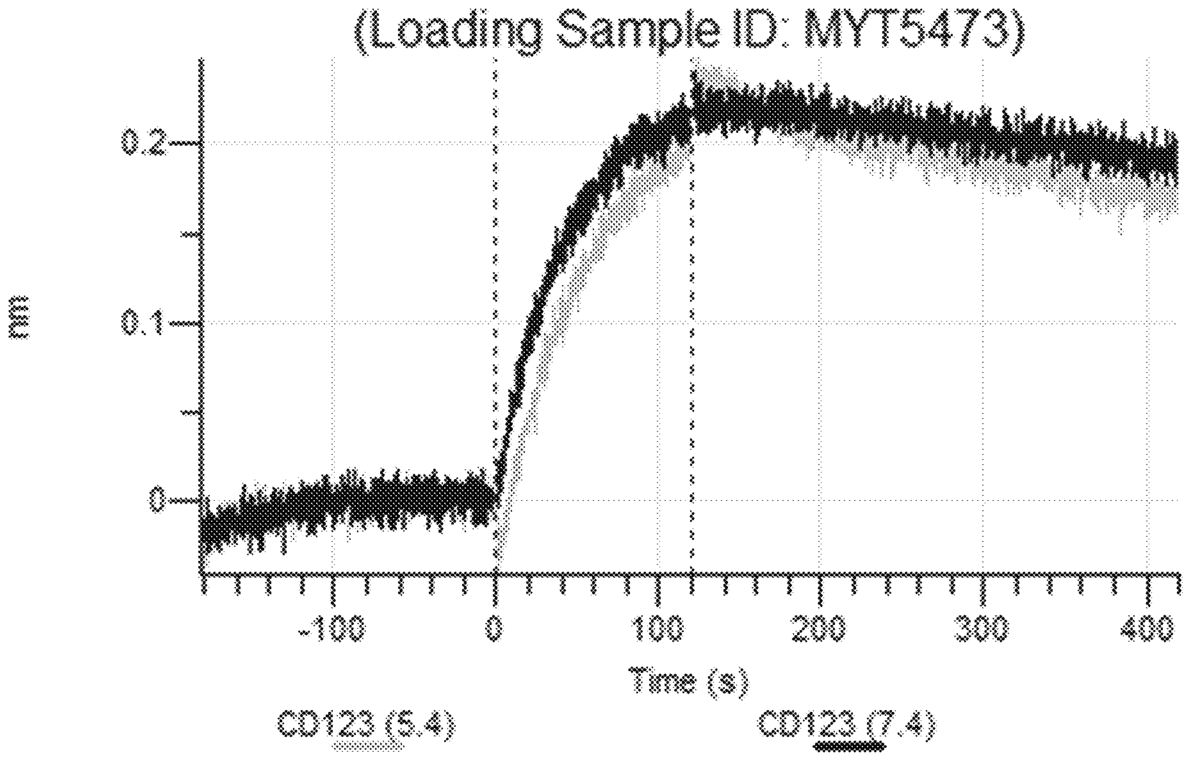
Figure 17A:
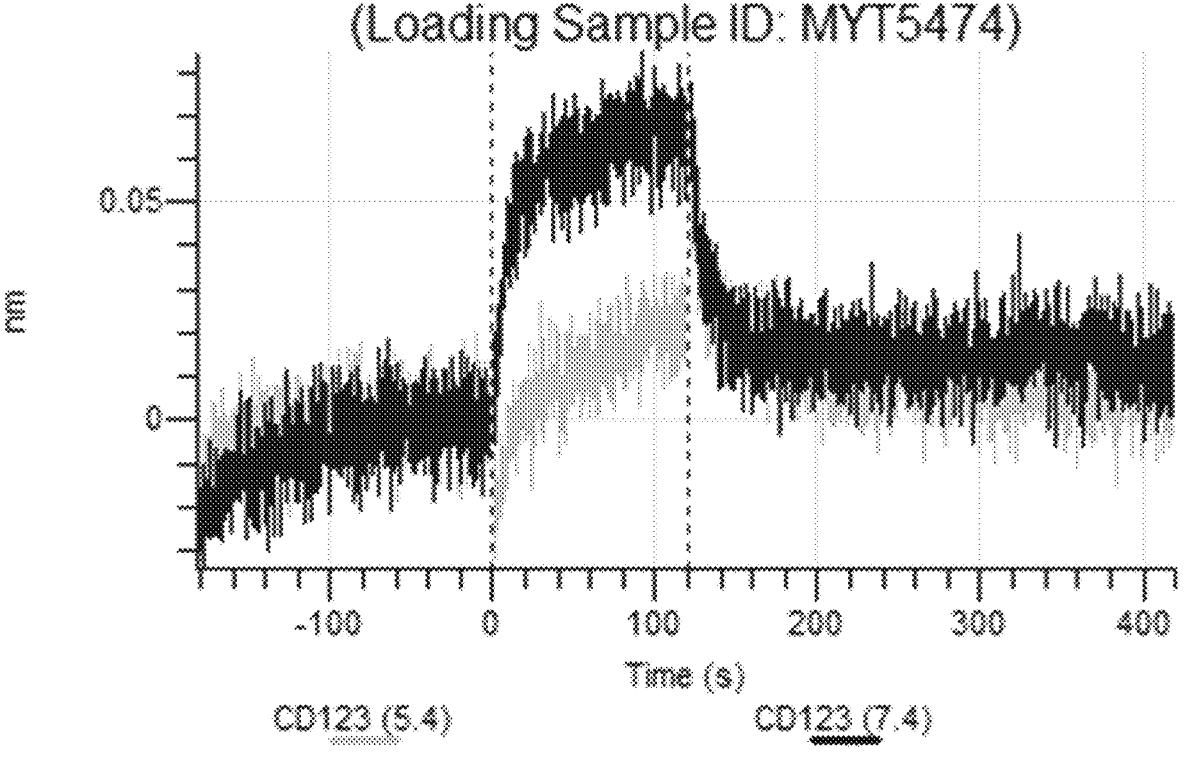
Figure 17A:
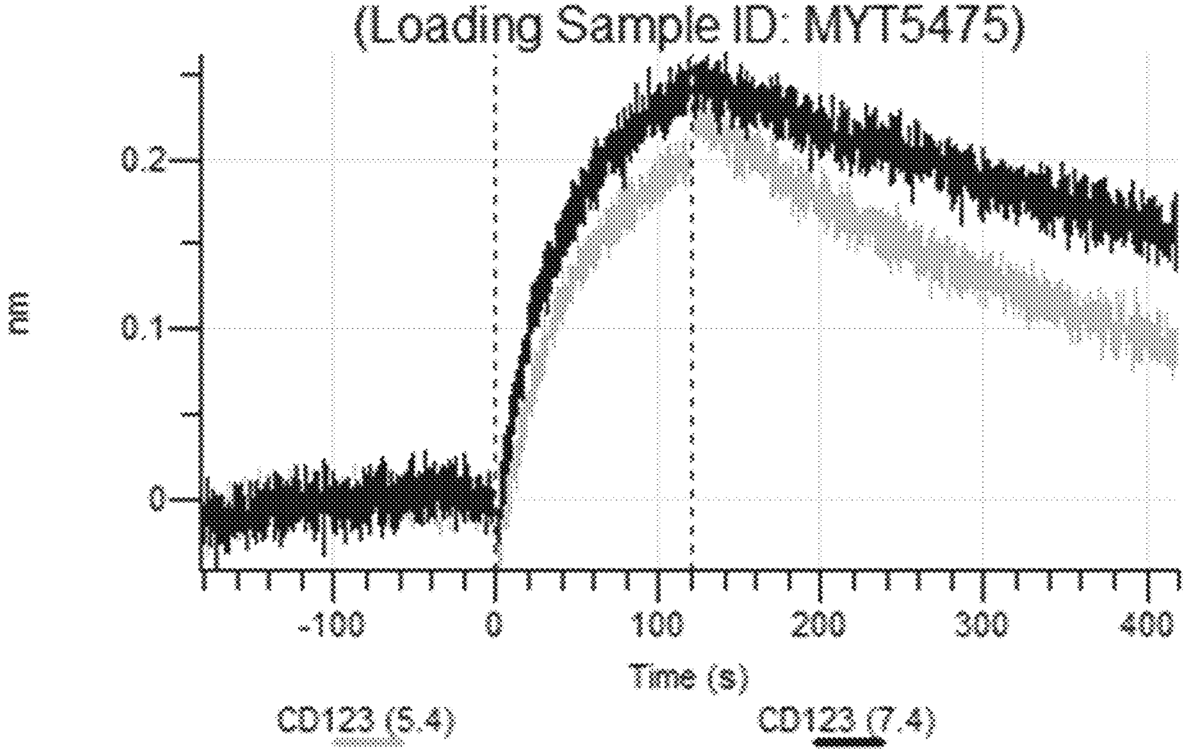
Figure 17A:
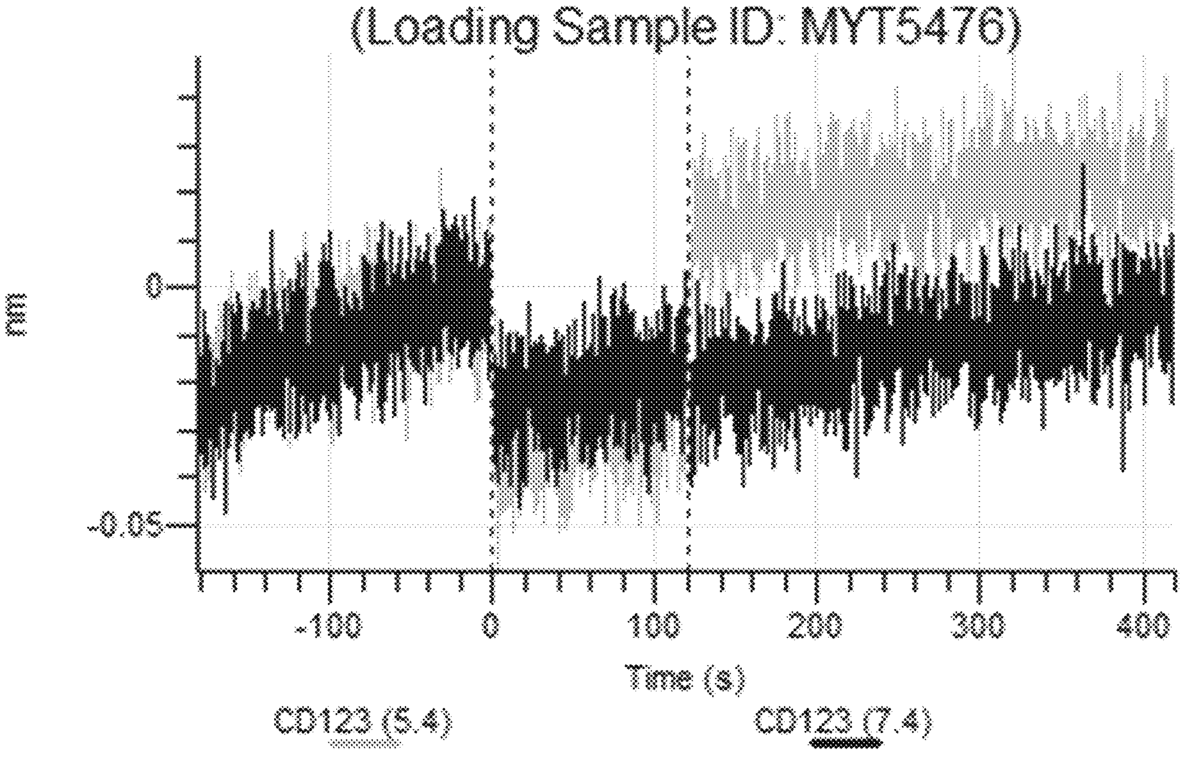
Figure 17A:
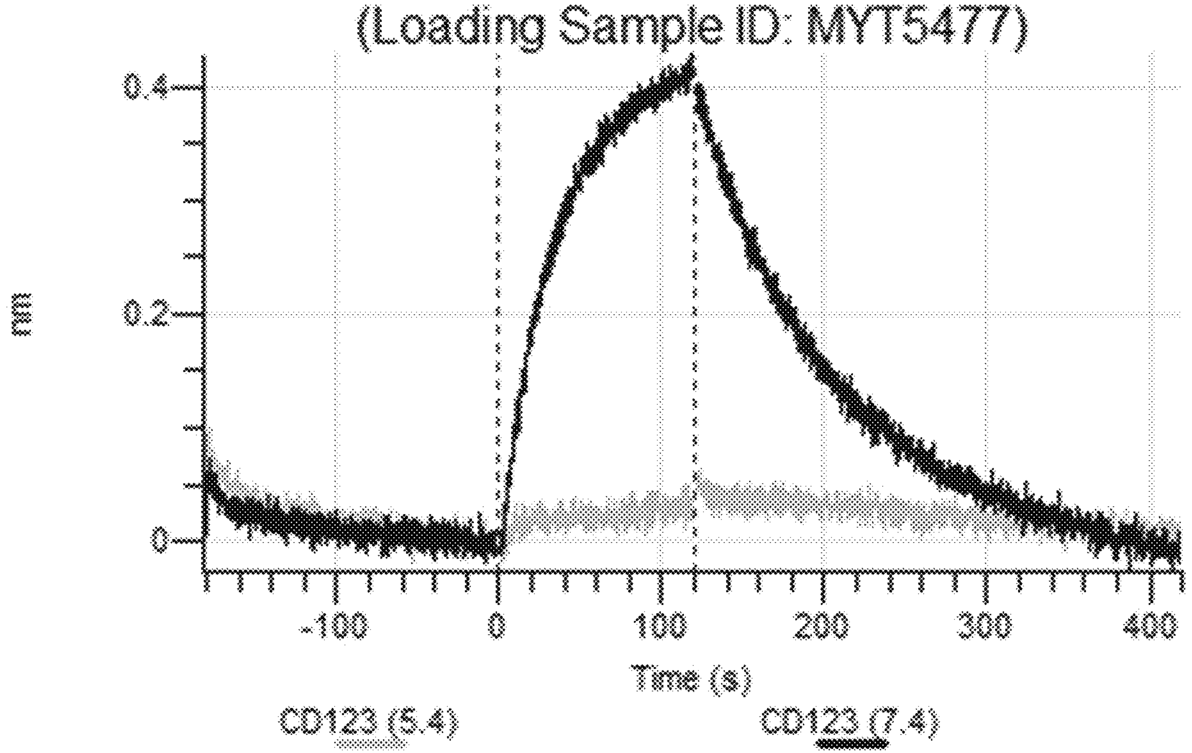
Figure 17A:
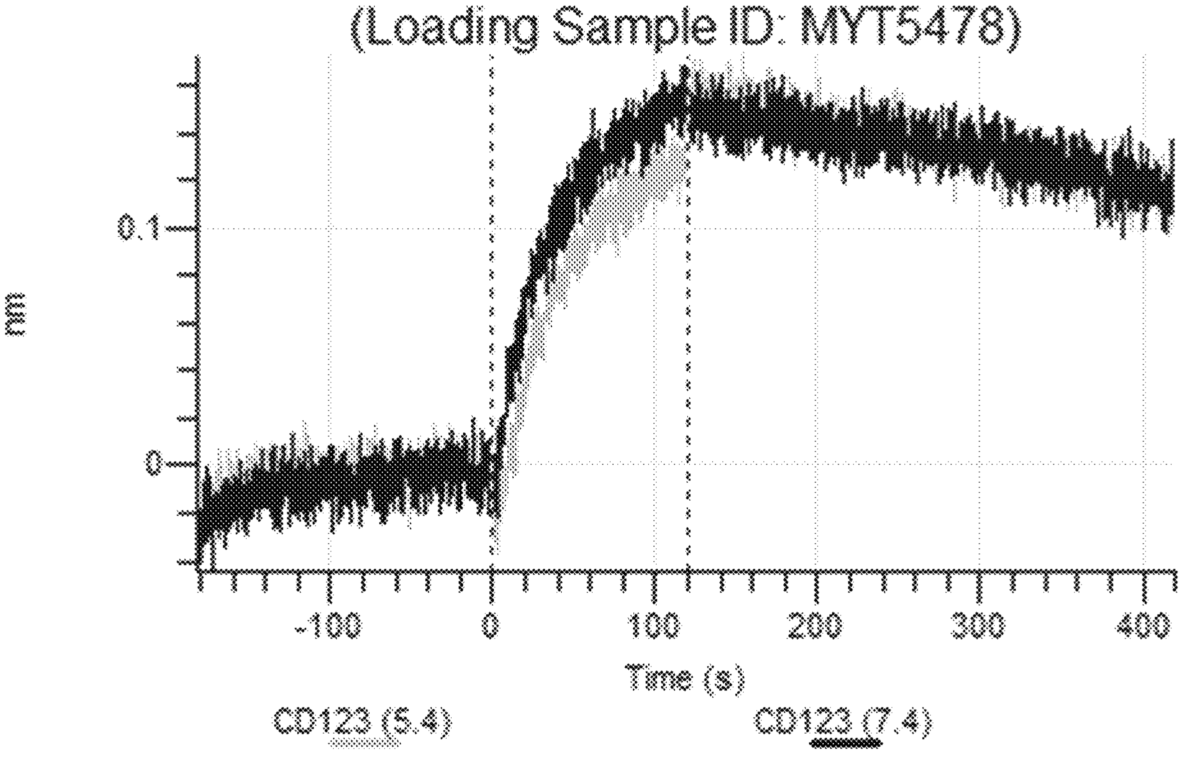
Figure 17A:
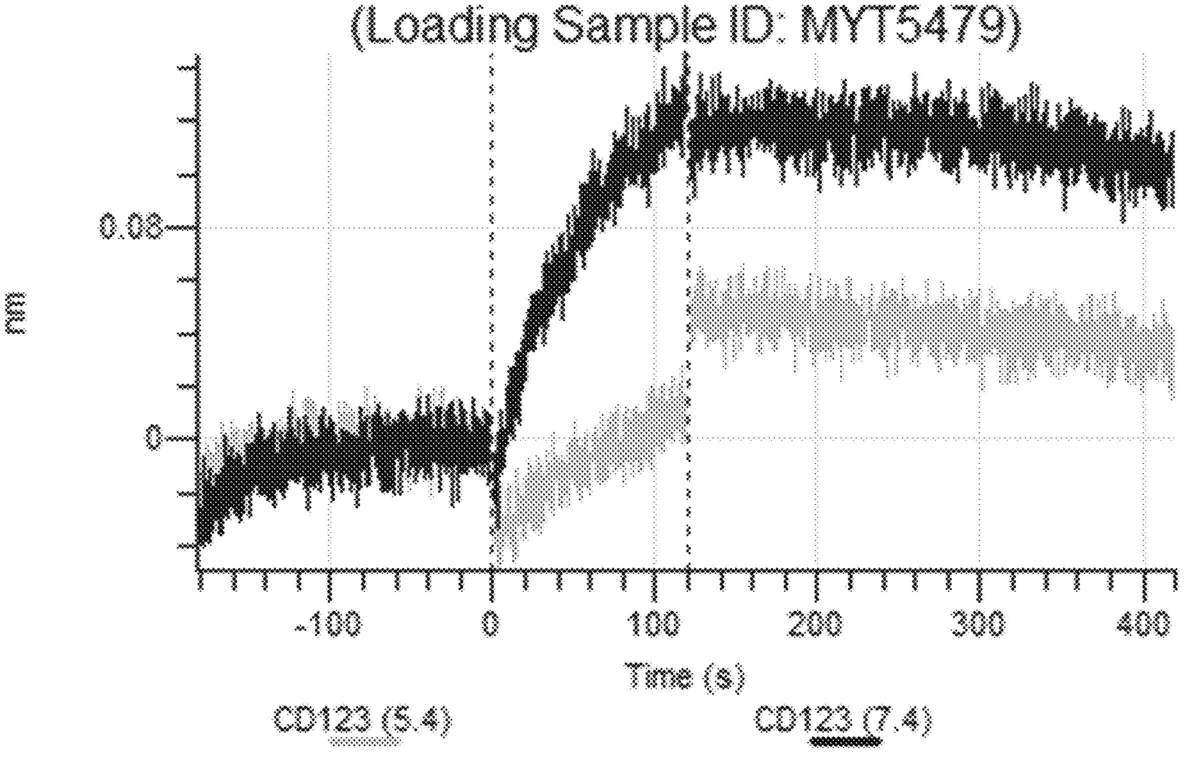
Figure 17A:
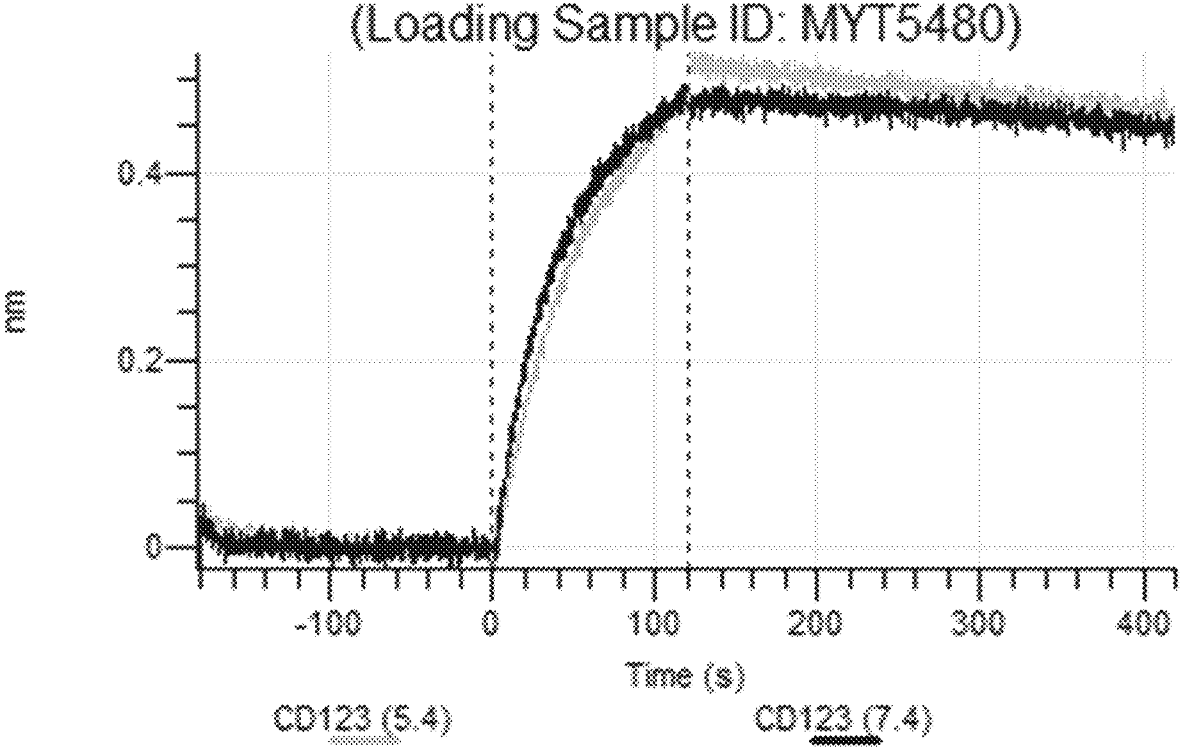
Figure 17A:
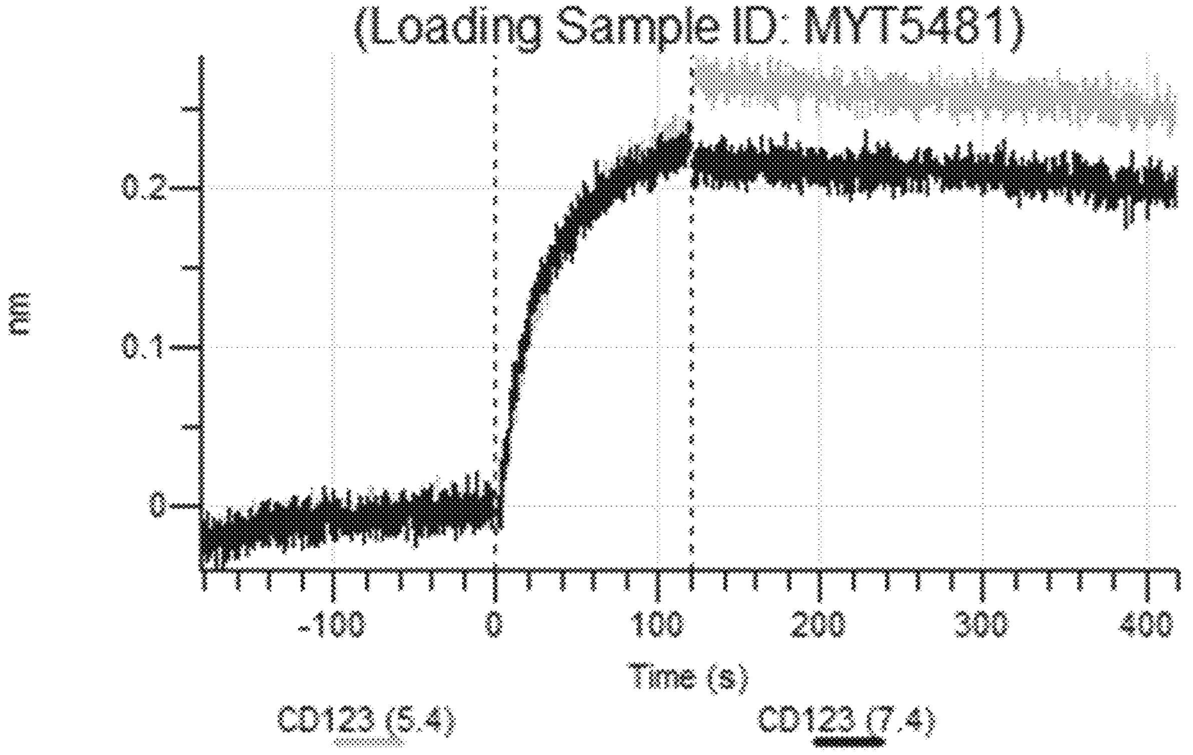
Figure 20A:
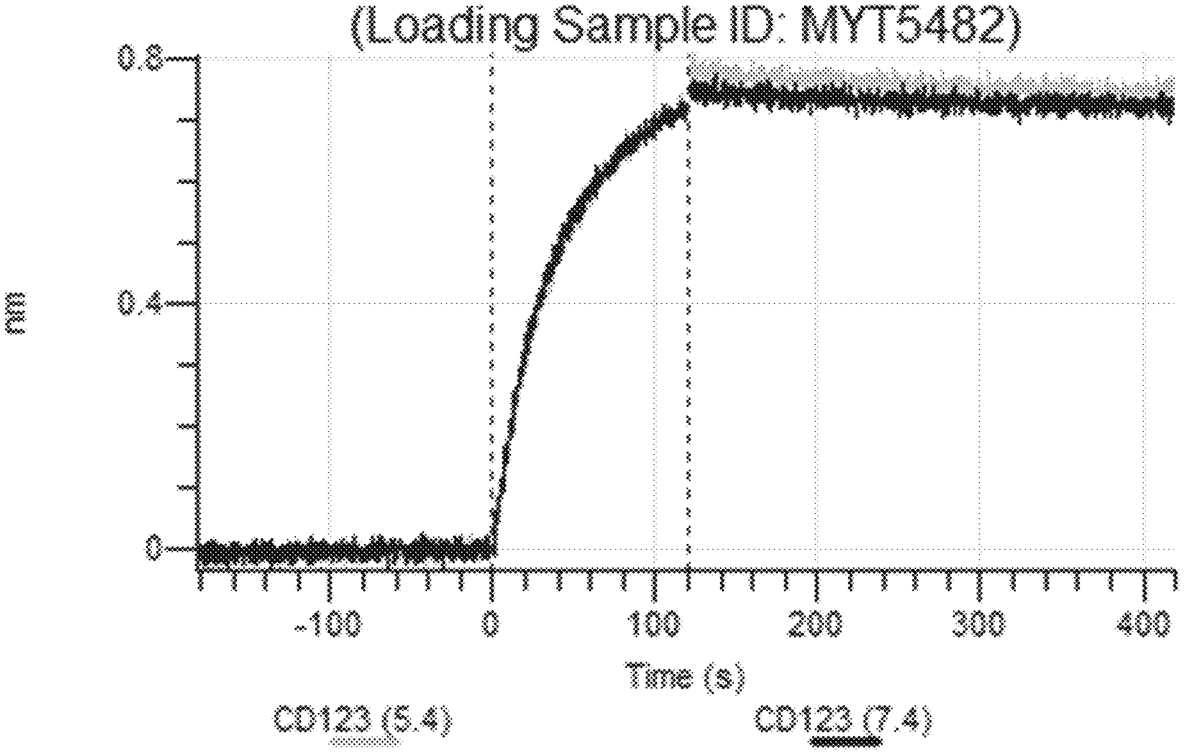
FIGS. 20*a* to 20*ad*: Binding of TPP-8988 starting ABPC and histidine scanning and alanine scanning variants to CD123 by biolayer interferometry. MYT5482-MYT5511, light chain histidine scanning and alanine scanning variants, were captured on anti-human Fc biosensors and associated with CD123 at low pH or high pH, as specified in the figures.
Figure 20B:
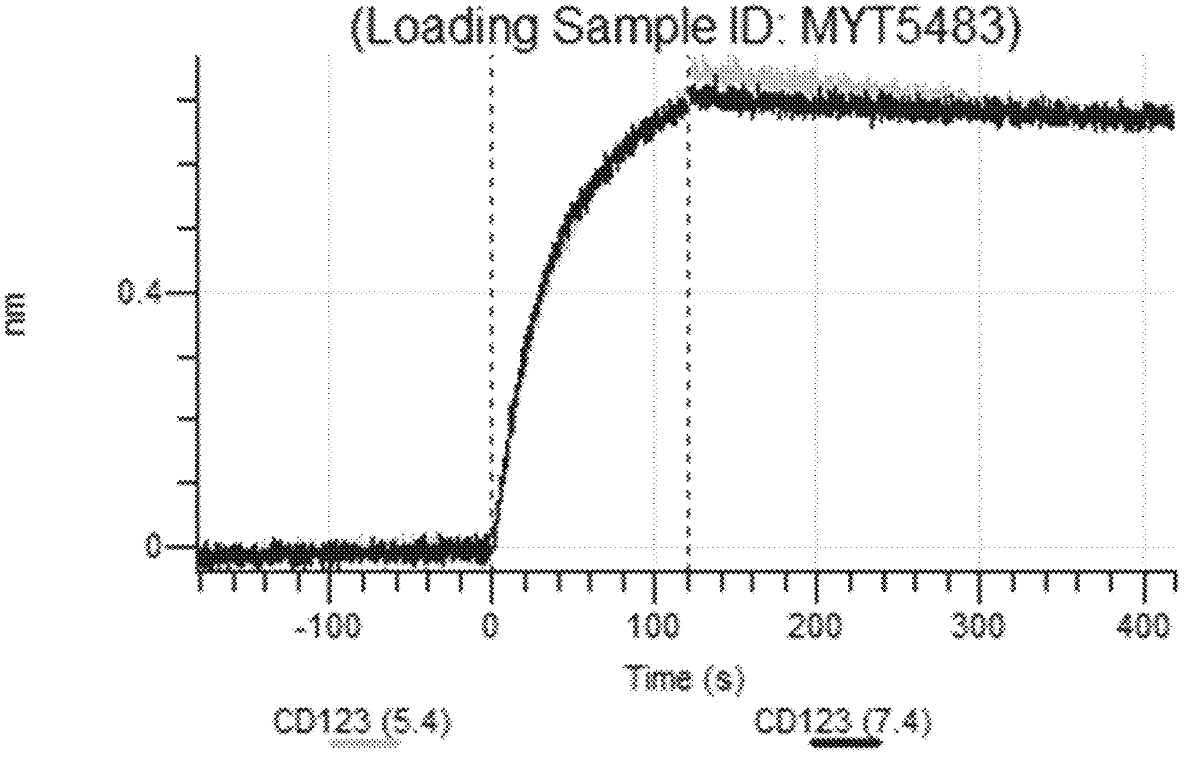
Figure 20C:
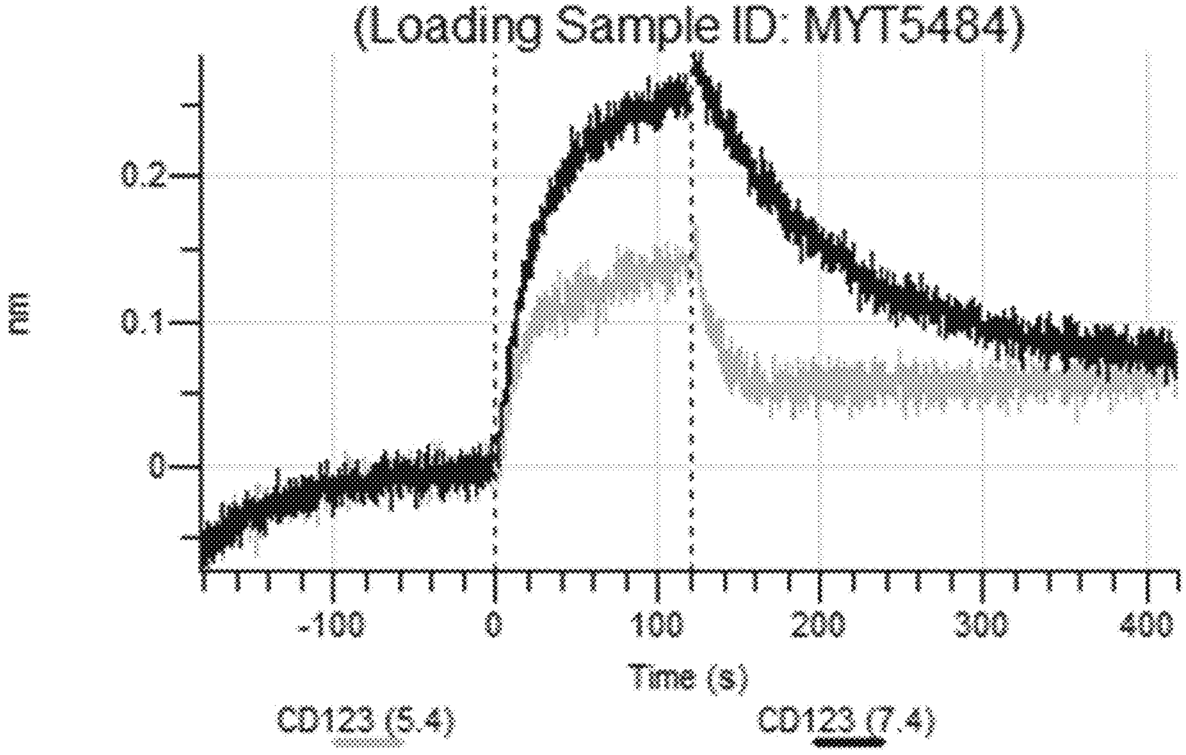
Figure 20D:
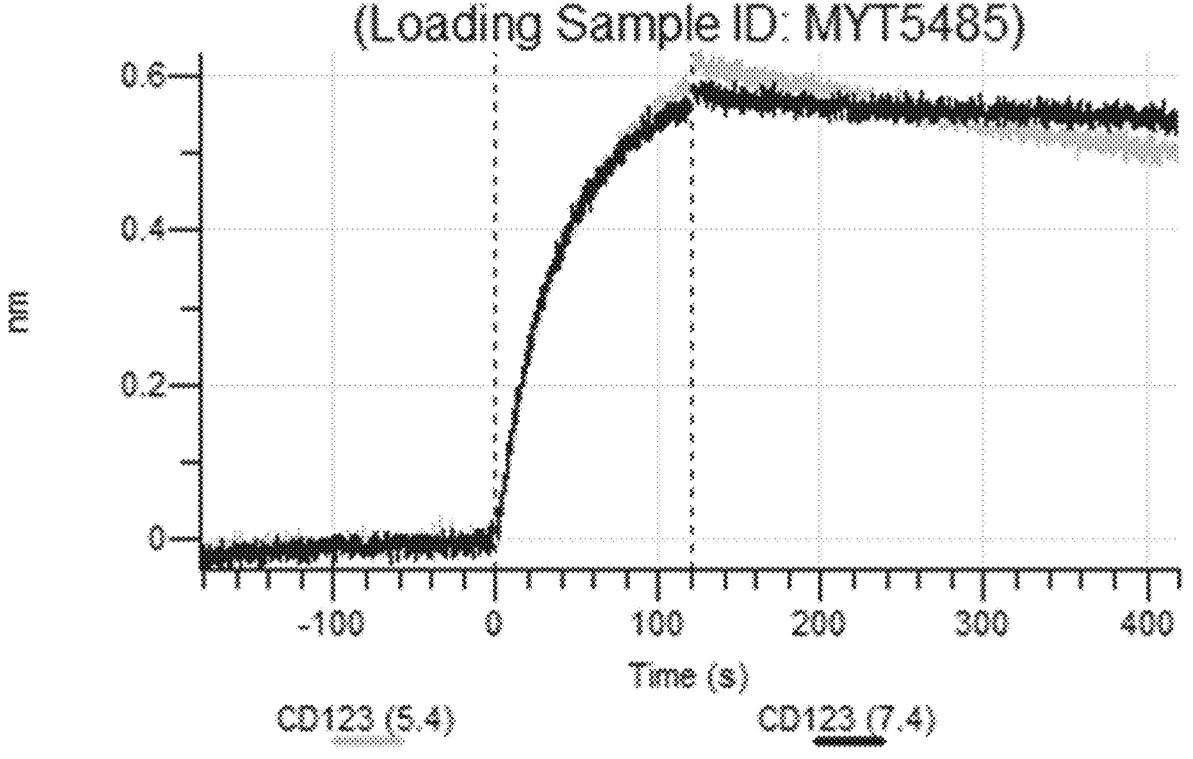
Figure 20E:
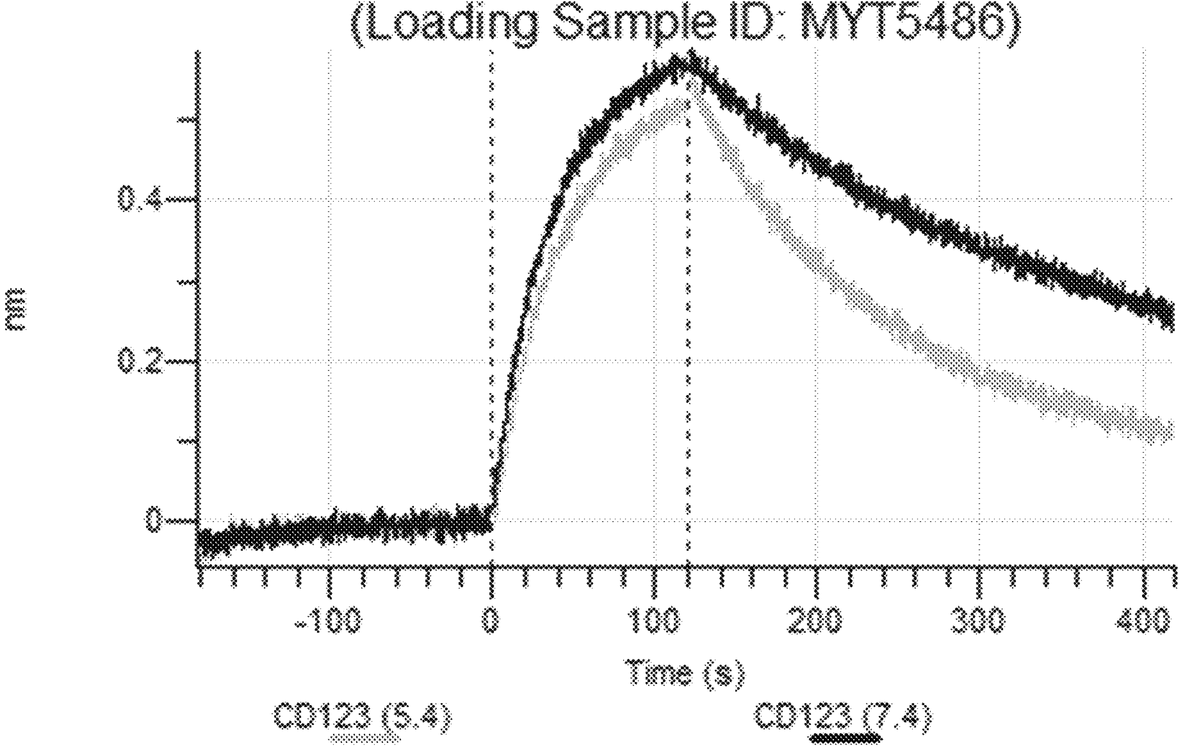
Figure 20F:
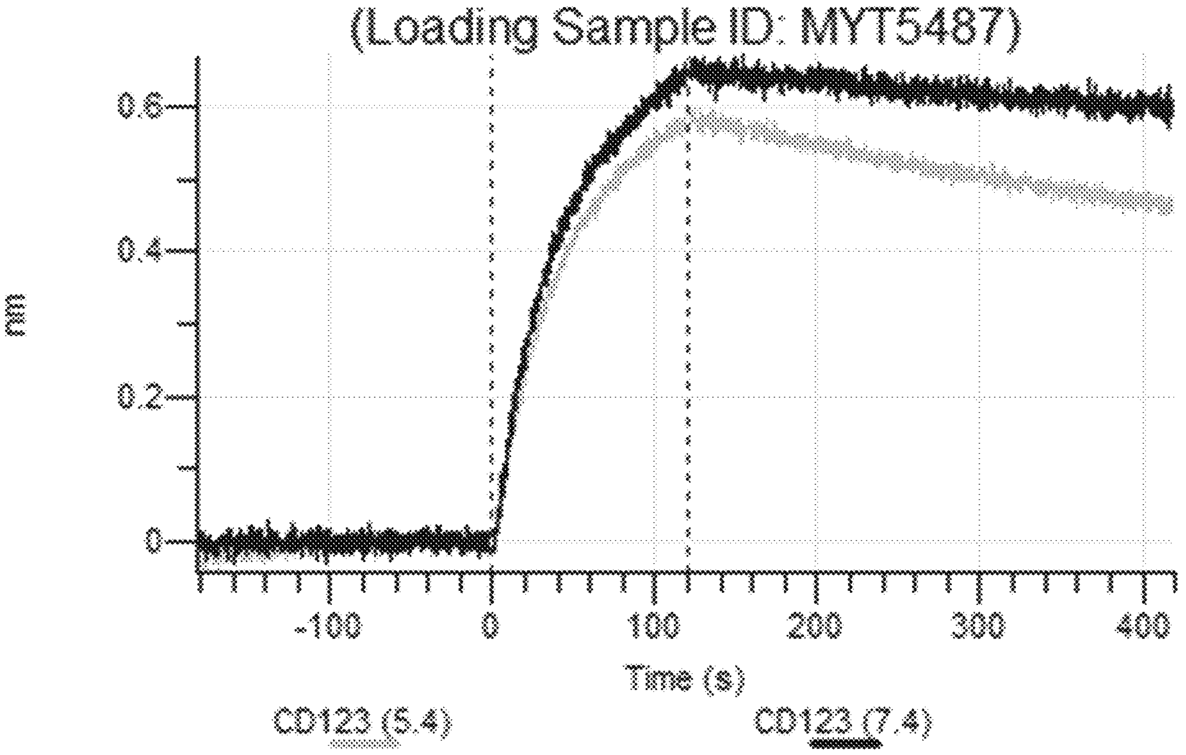
Figure 20G:
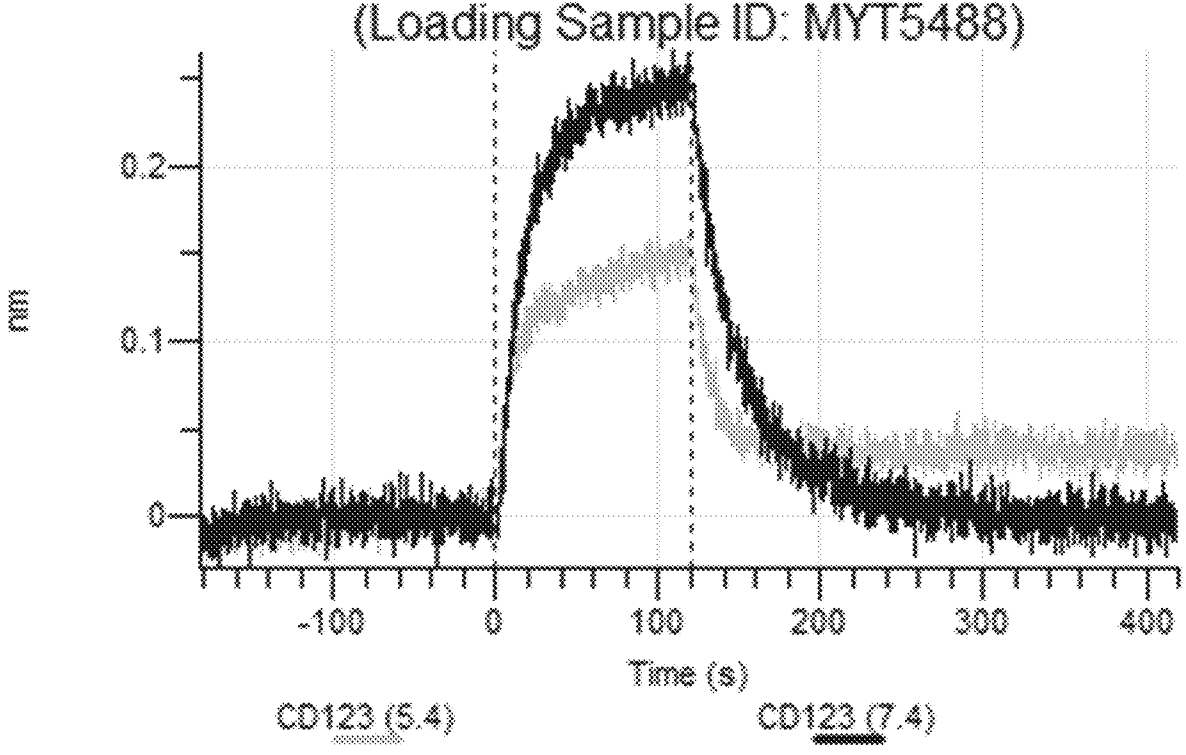
Figure 20H:
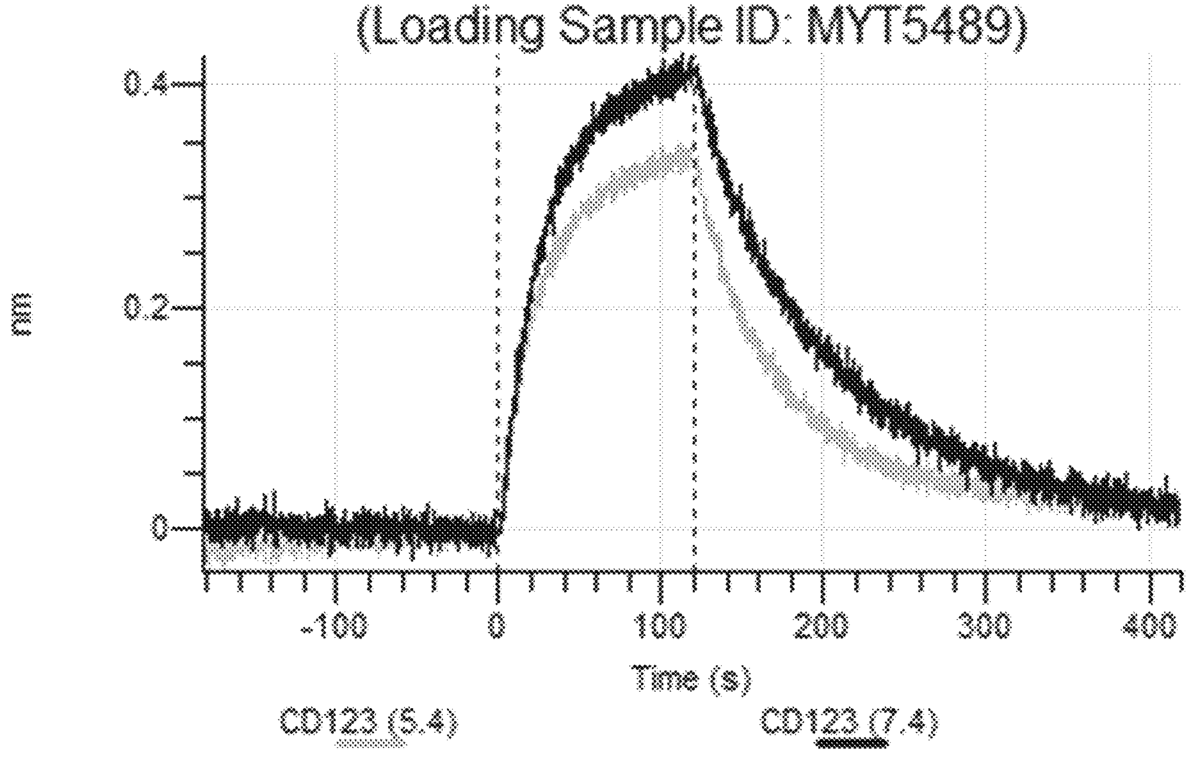
Figure 20I:
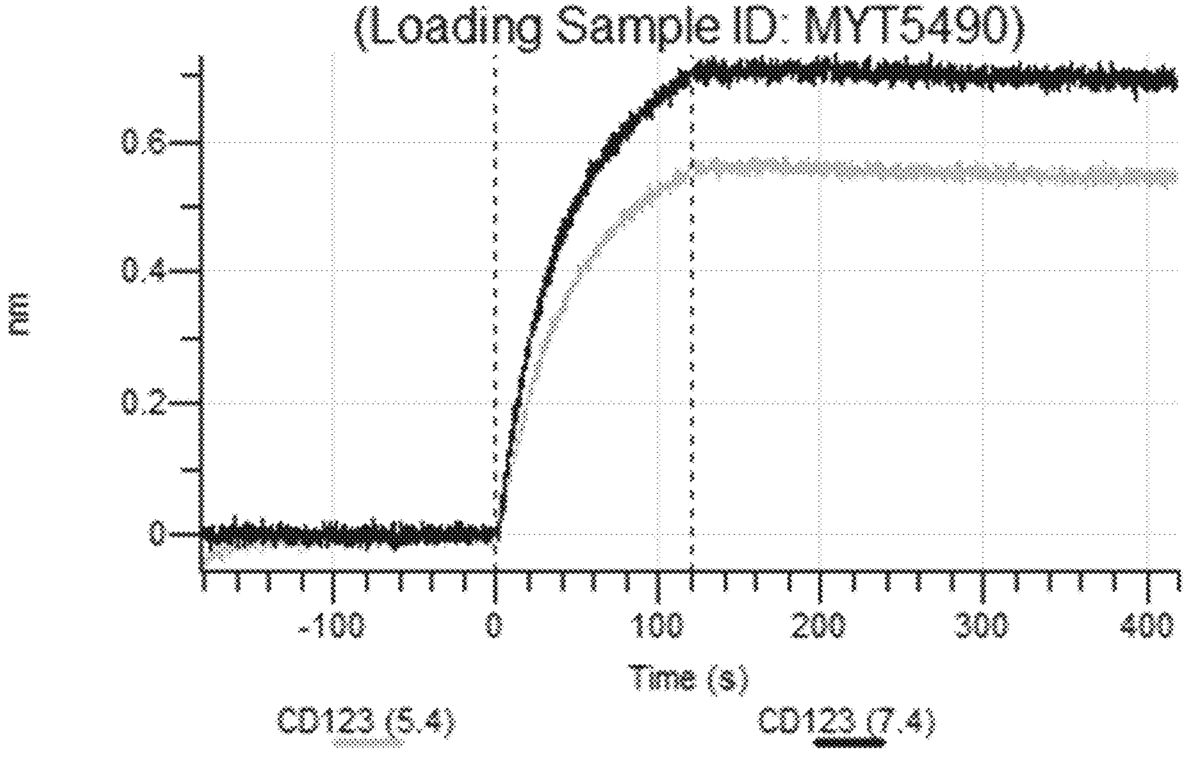
Figure 20J:
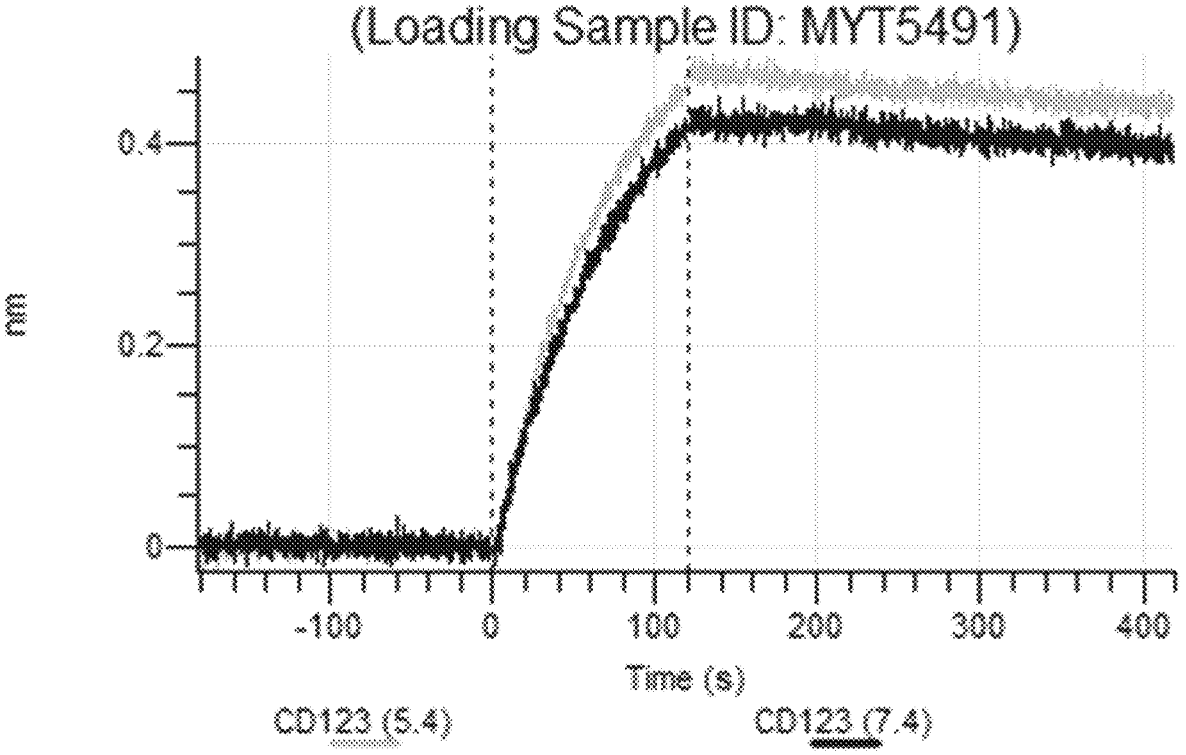
Figure 20K:
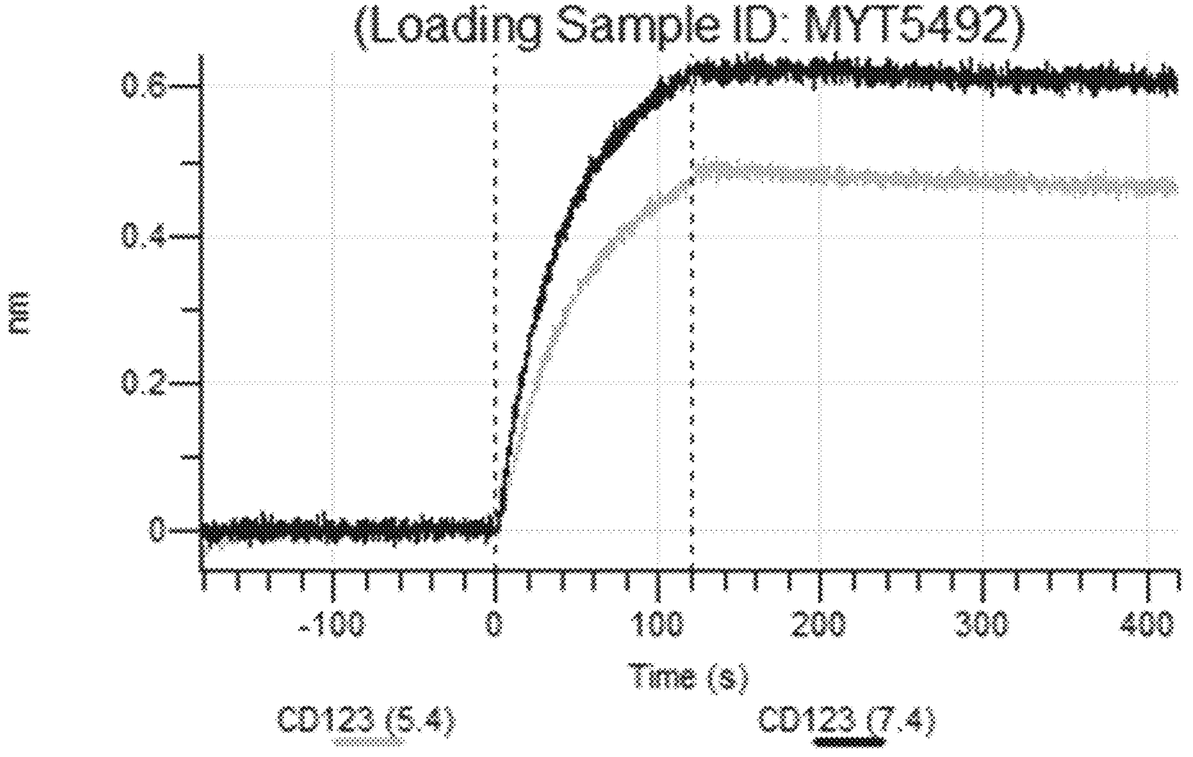
Figure 20L:
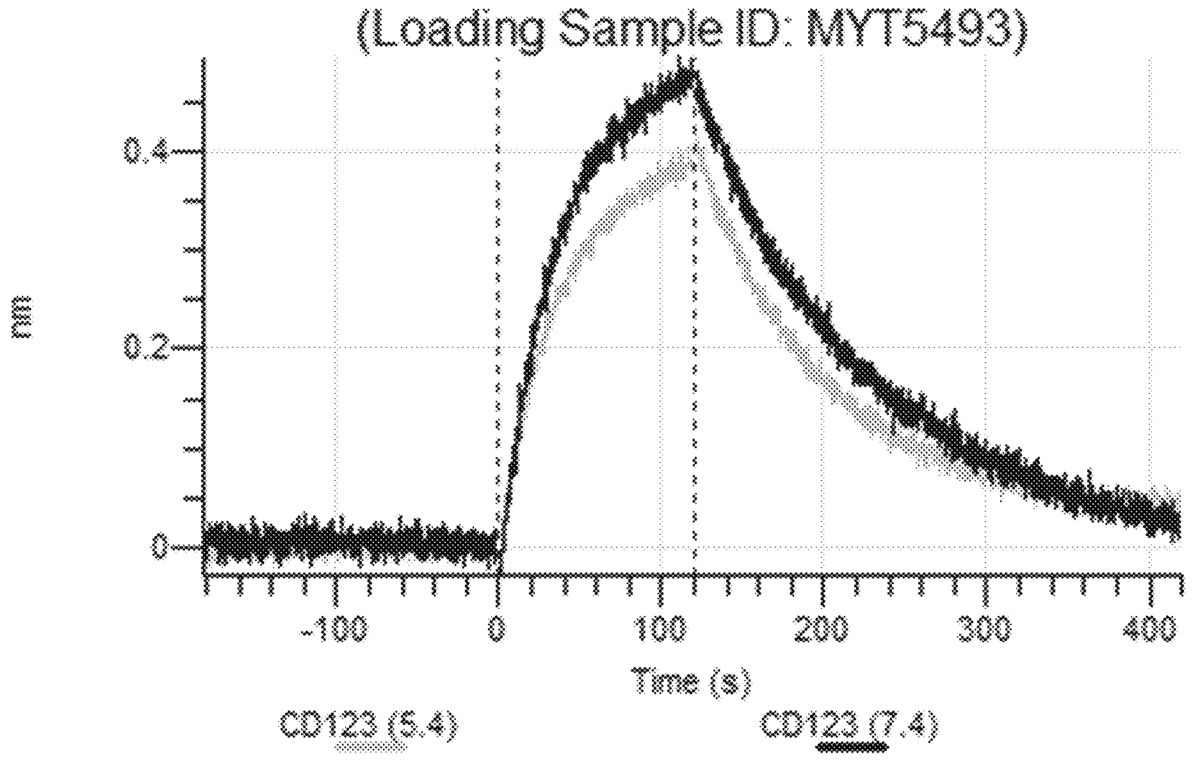
Figure 20M:
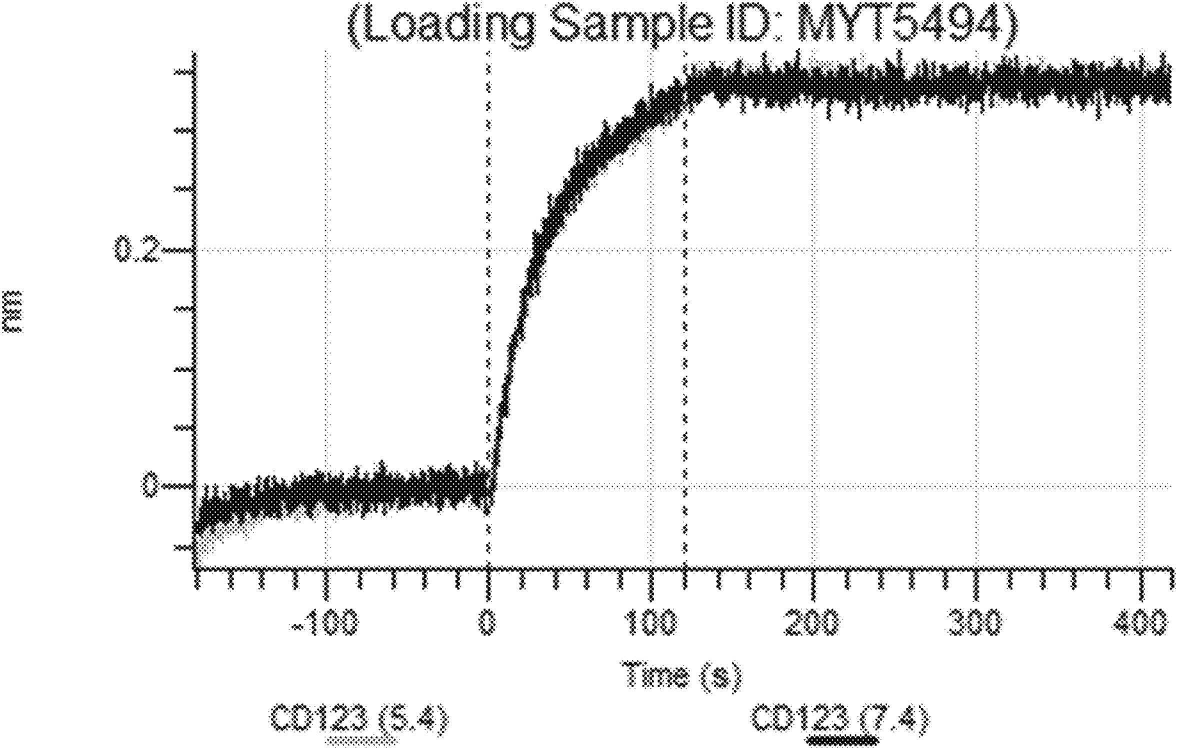
Figure 20N:
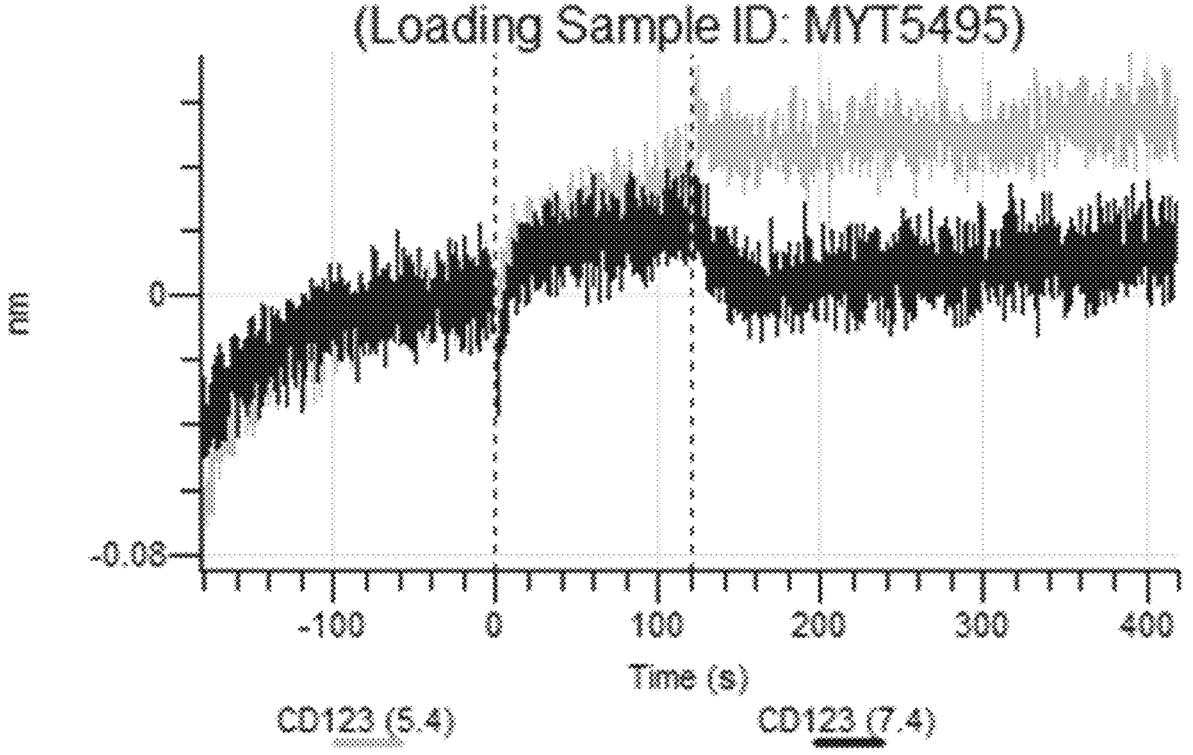
Figure 20O:
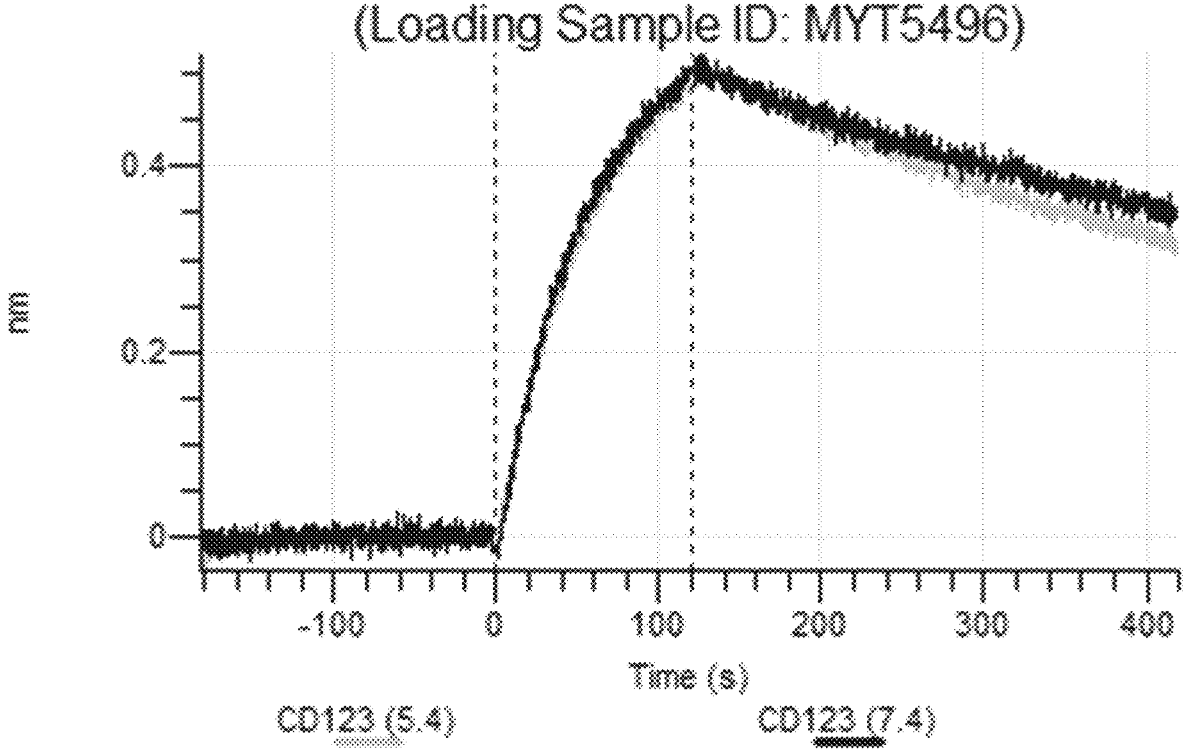
Figure 20P:
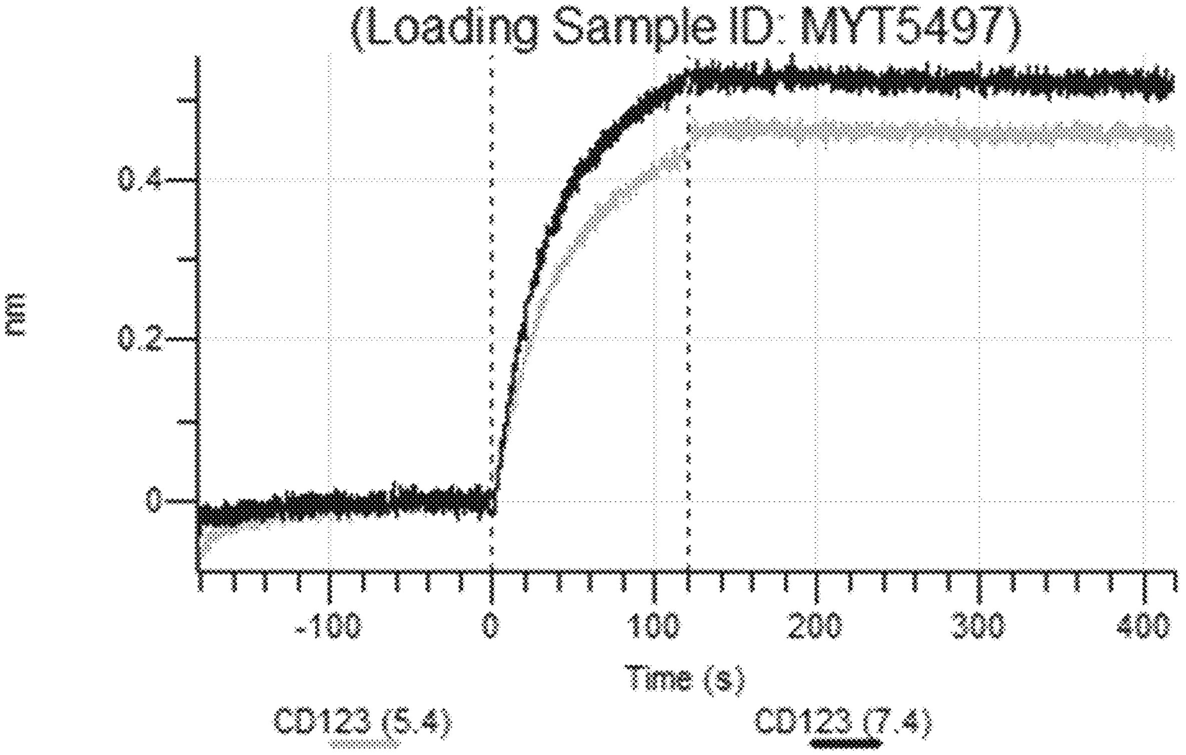
Figure 20Q:
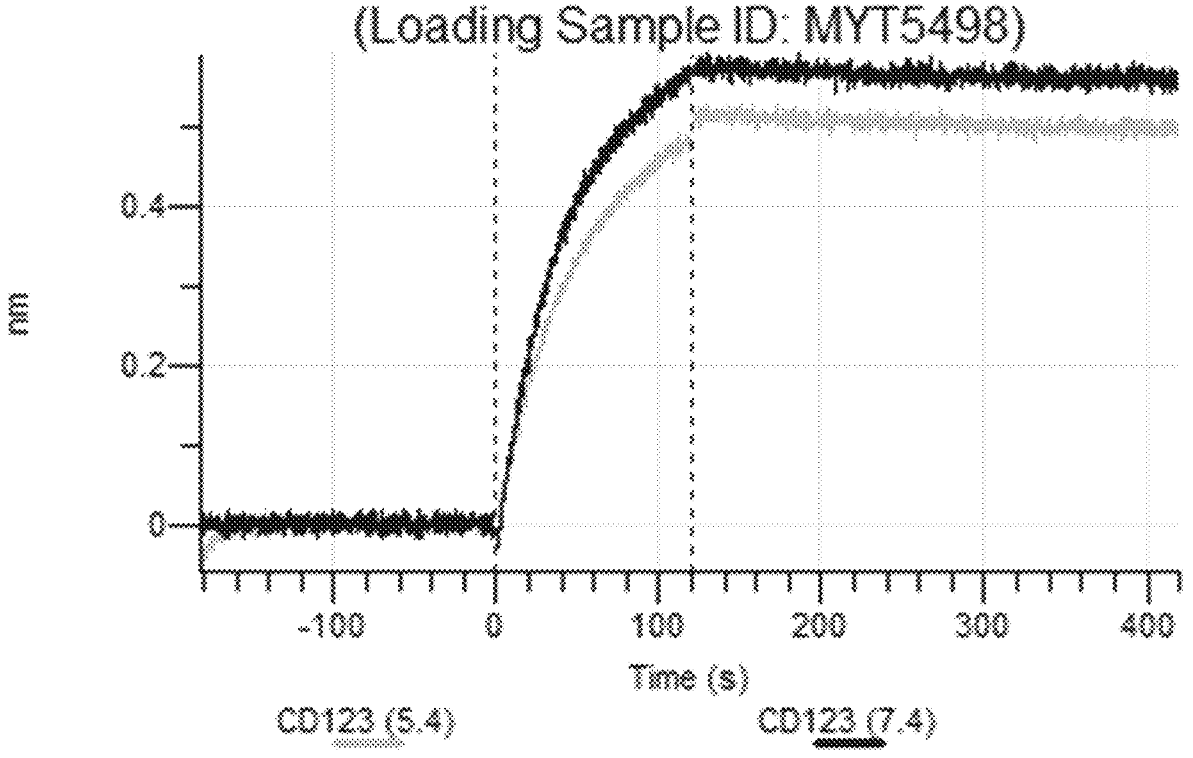
Figure 20R:
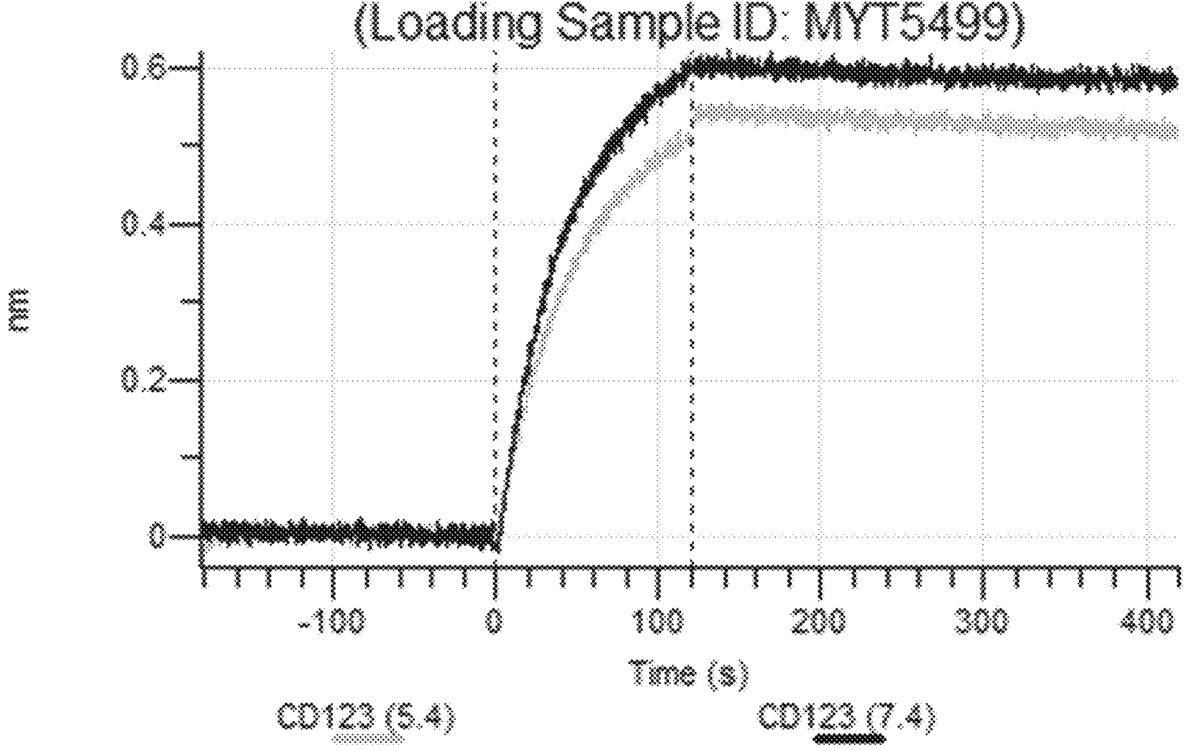
Figure 20S:
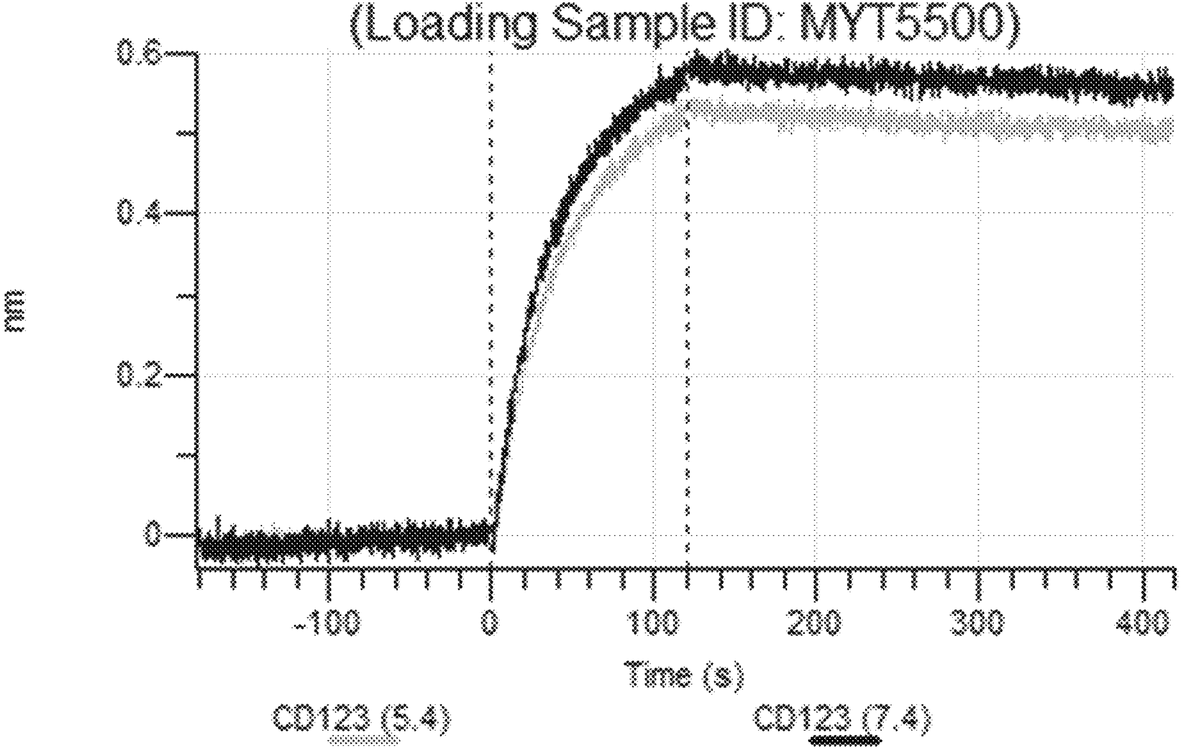
Figure 20T:
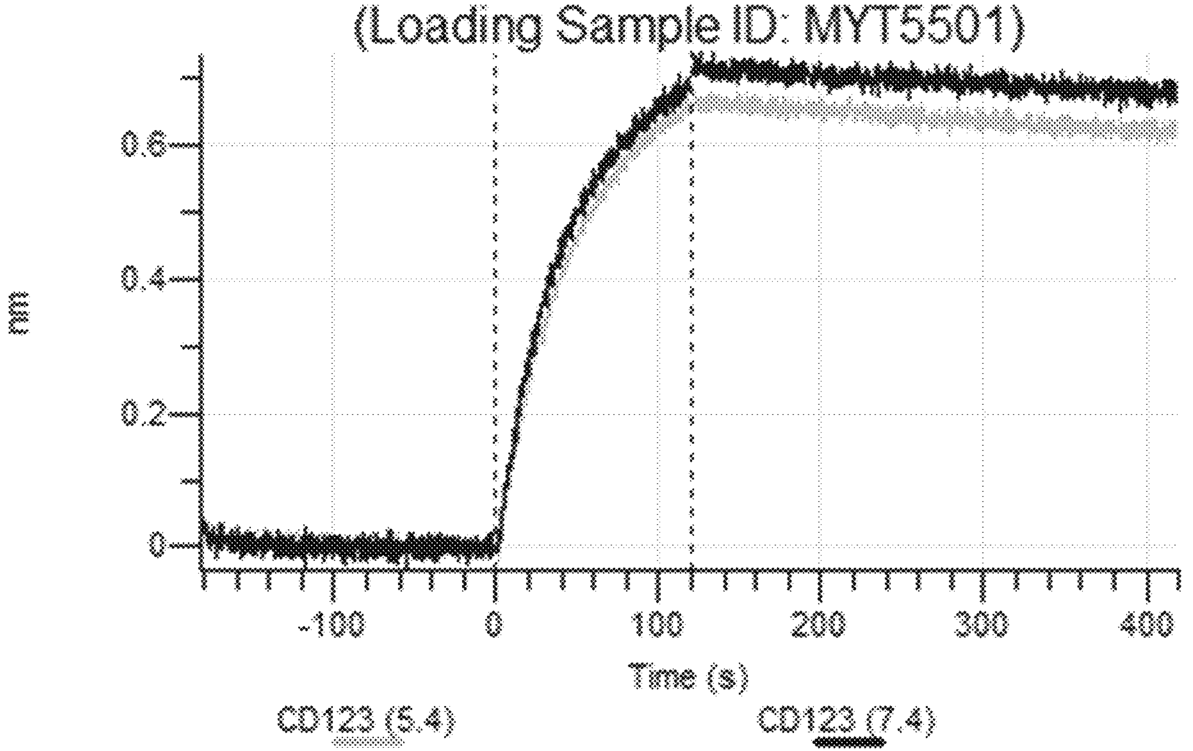
Figure 20U:
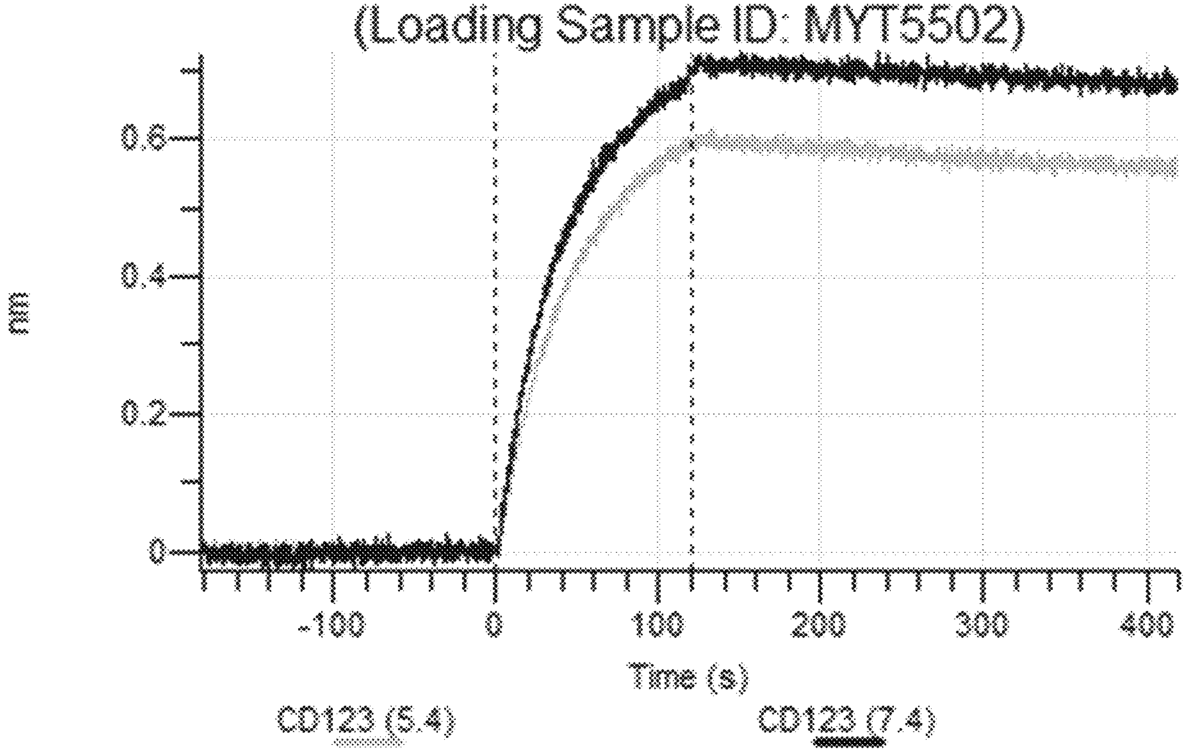
Figure 20V:
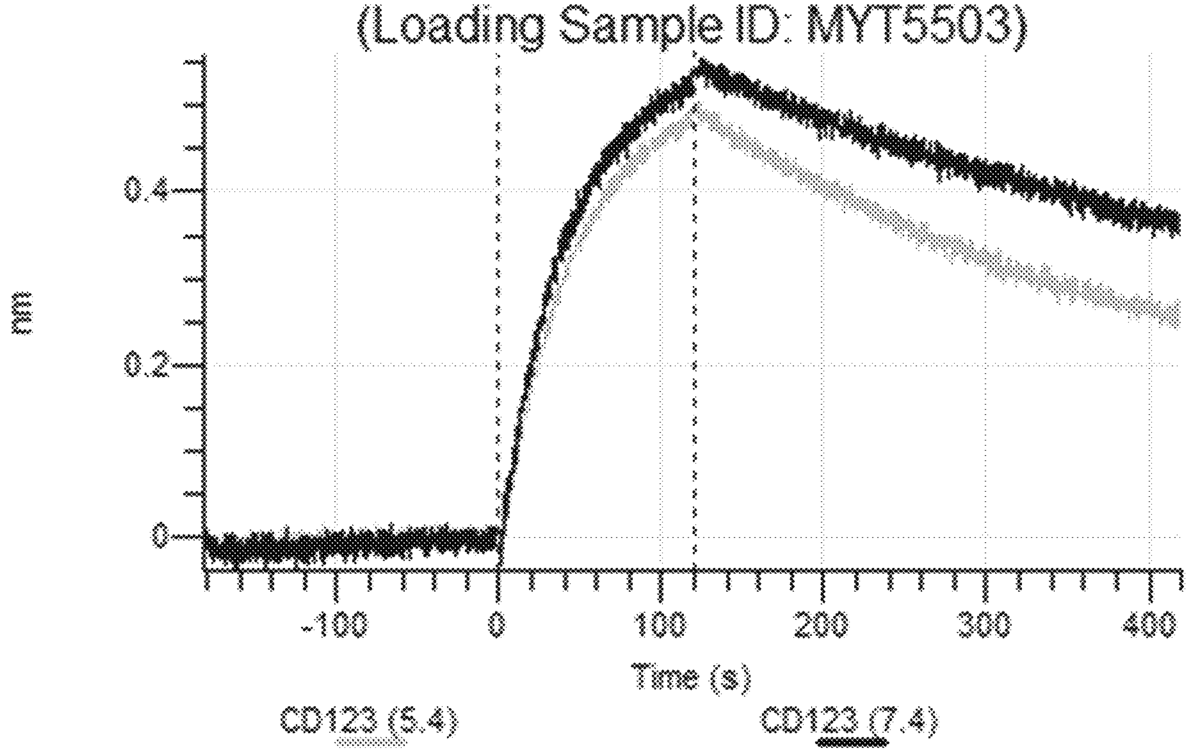
Figure 20W:
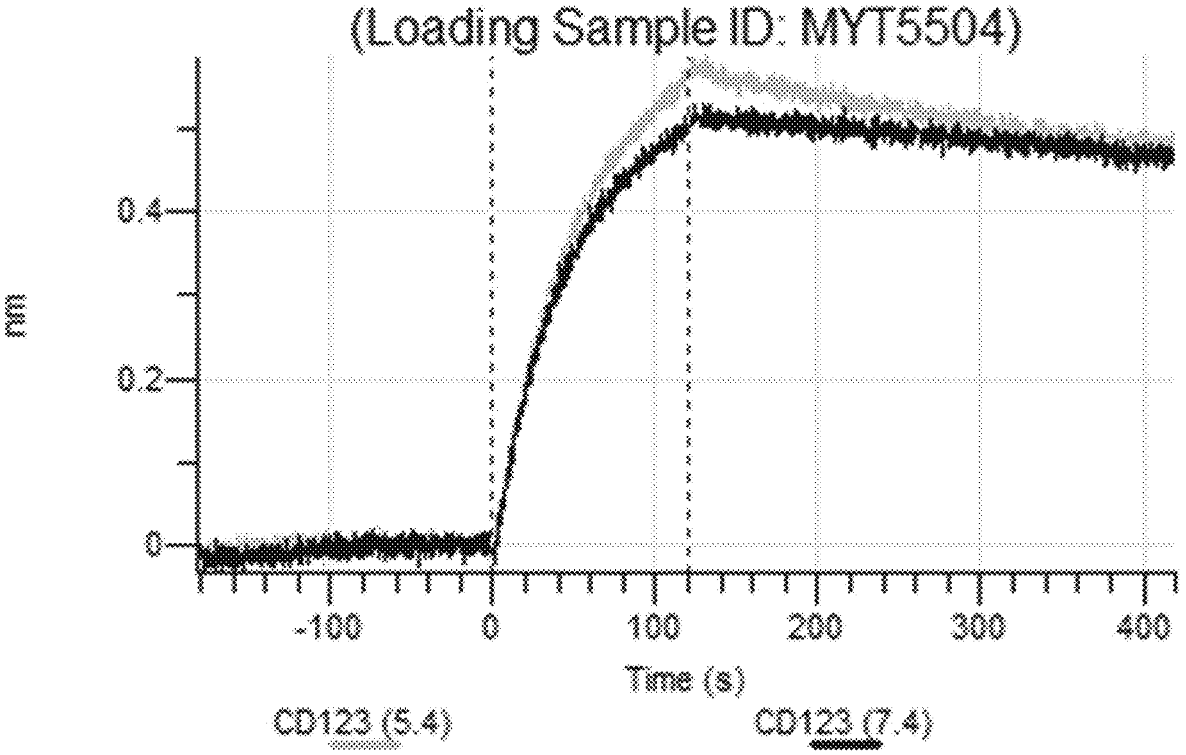
Figure 20X:
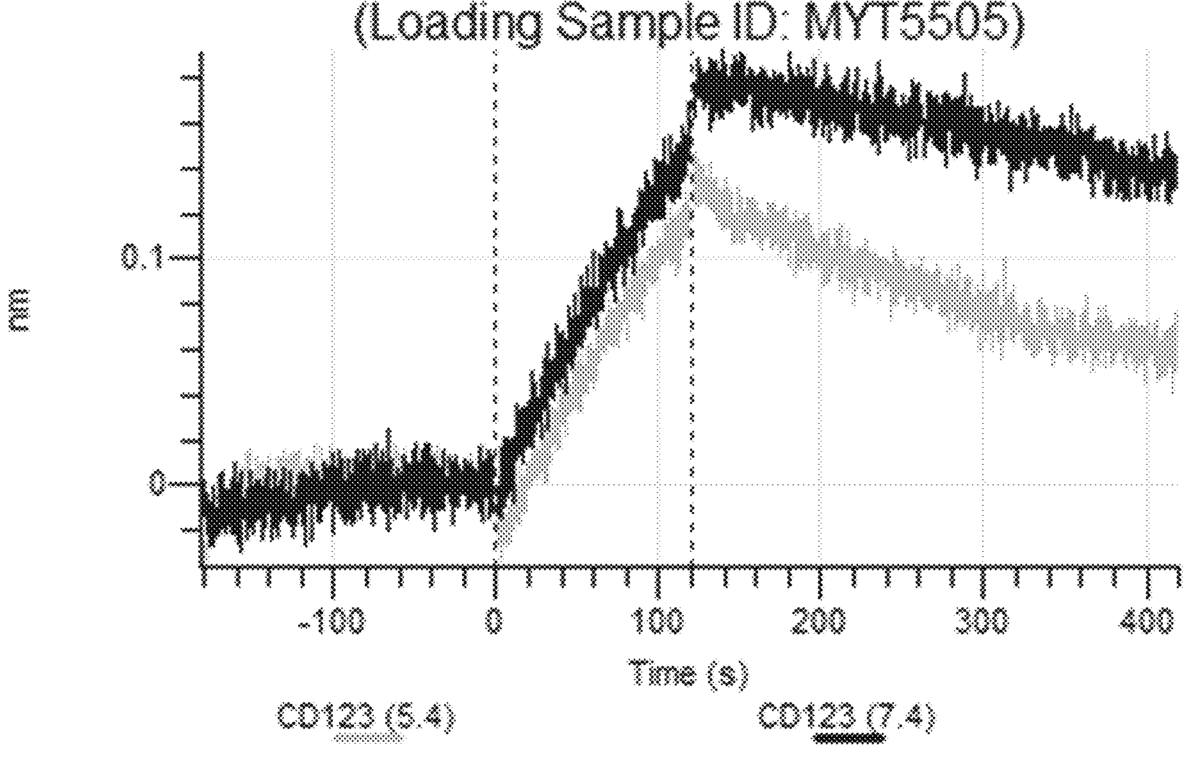
Figure 20Y:
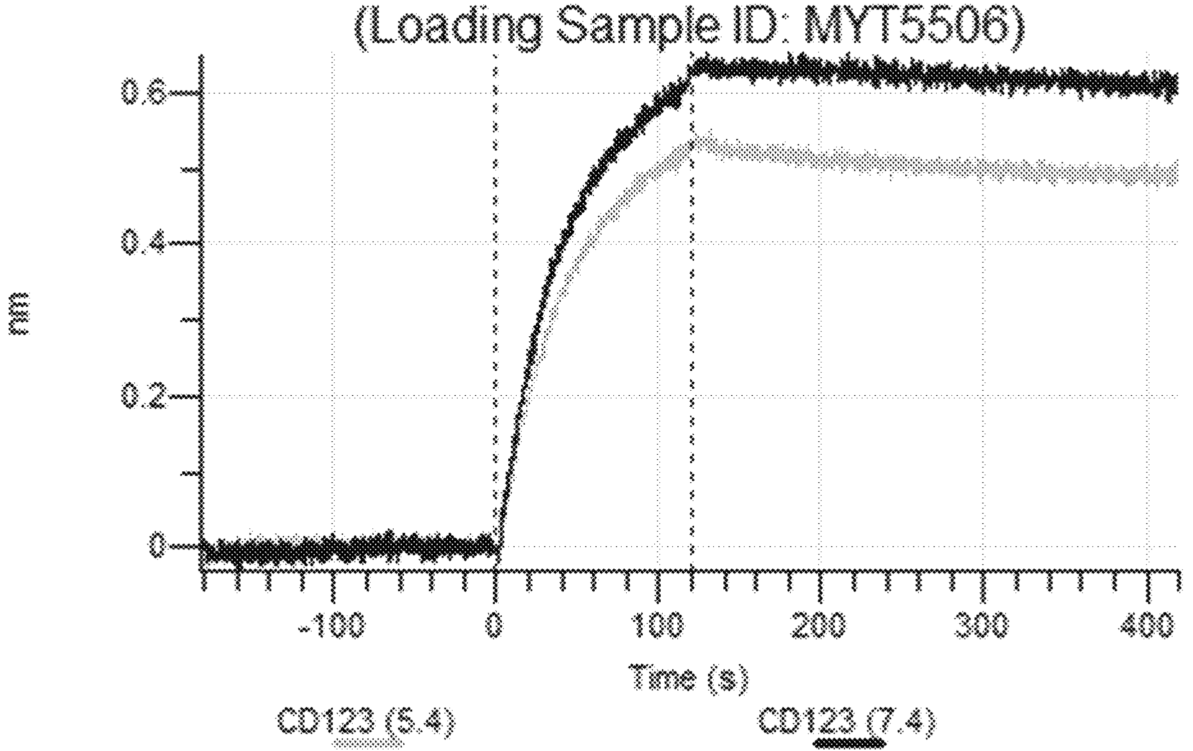
Figure 20Z:
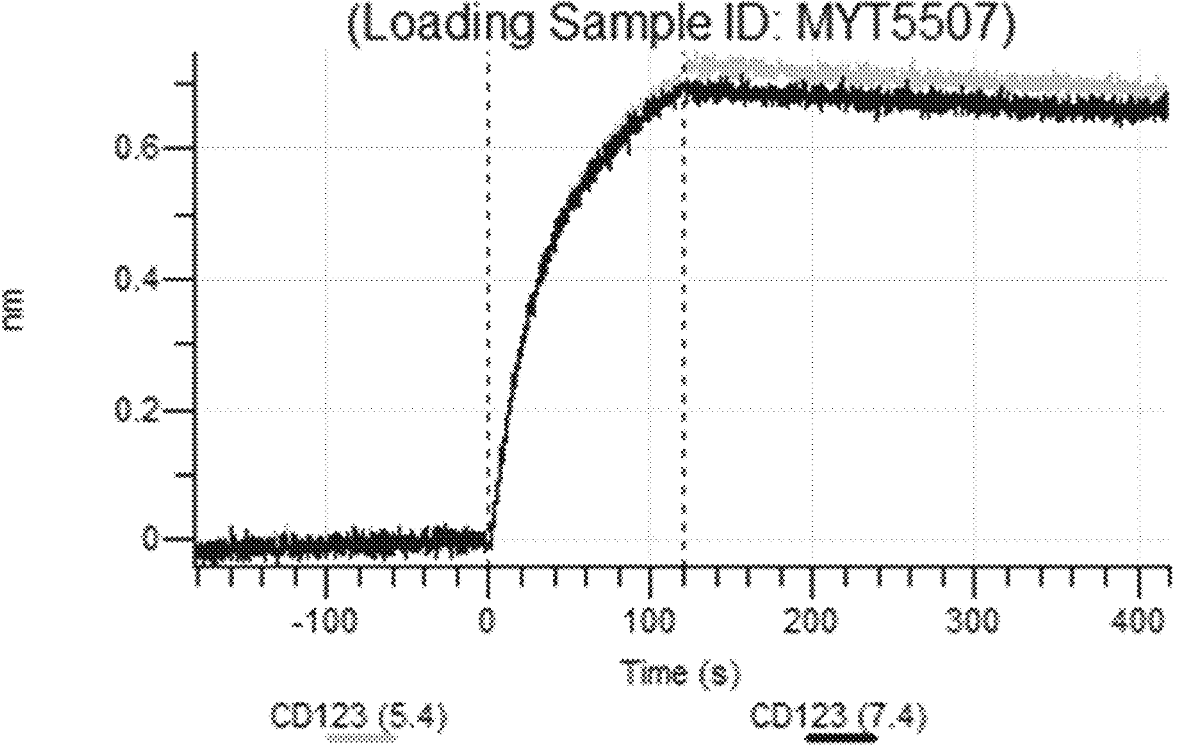
Figure 20A:
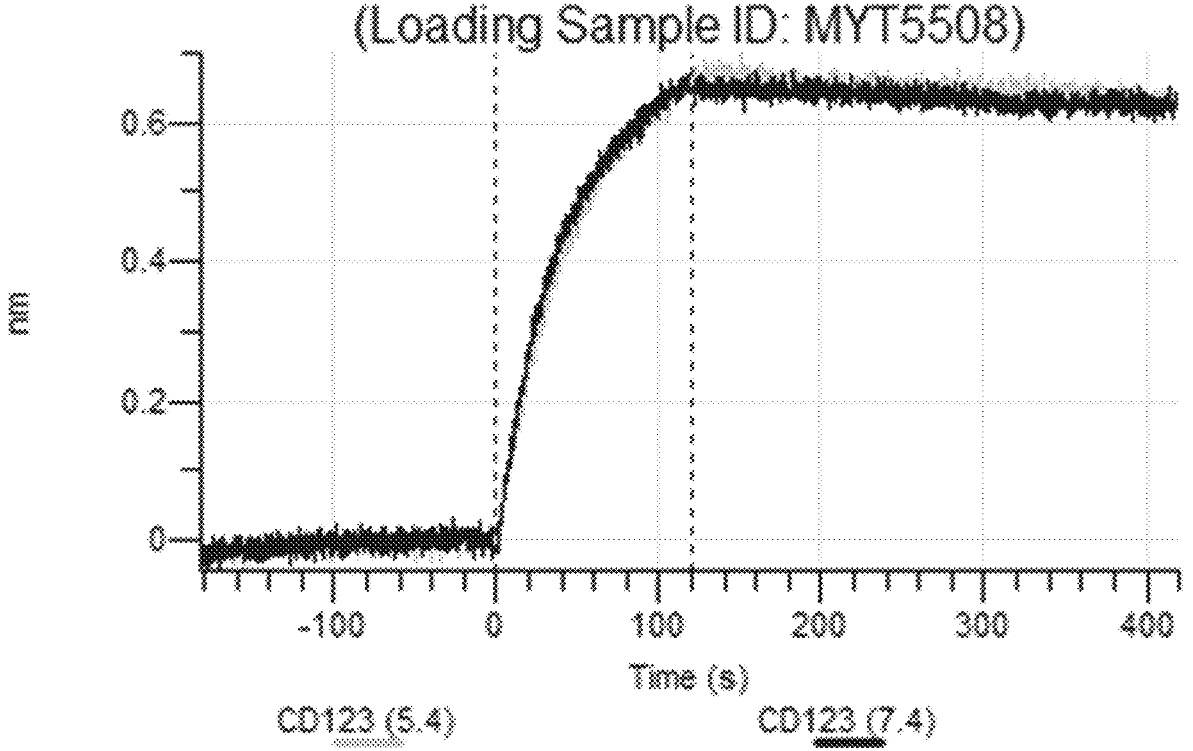
Figure 20A:
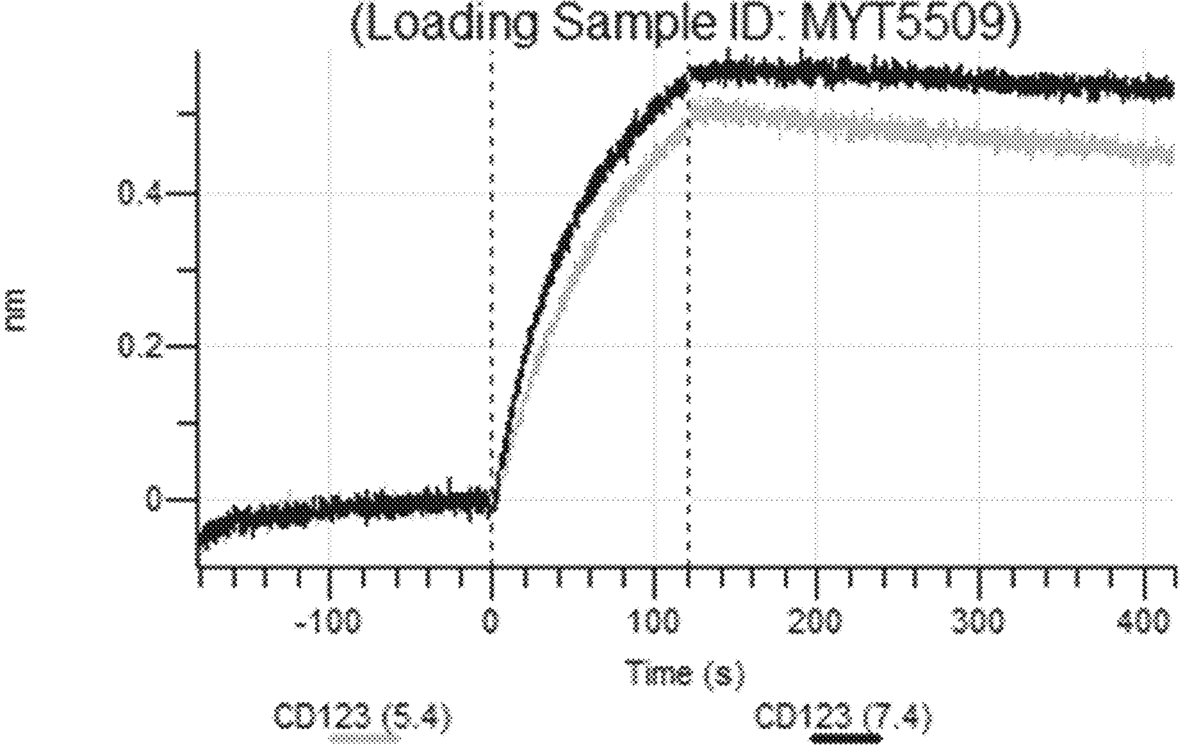
Figure 20A:
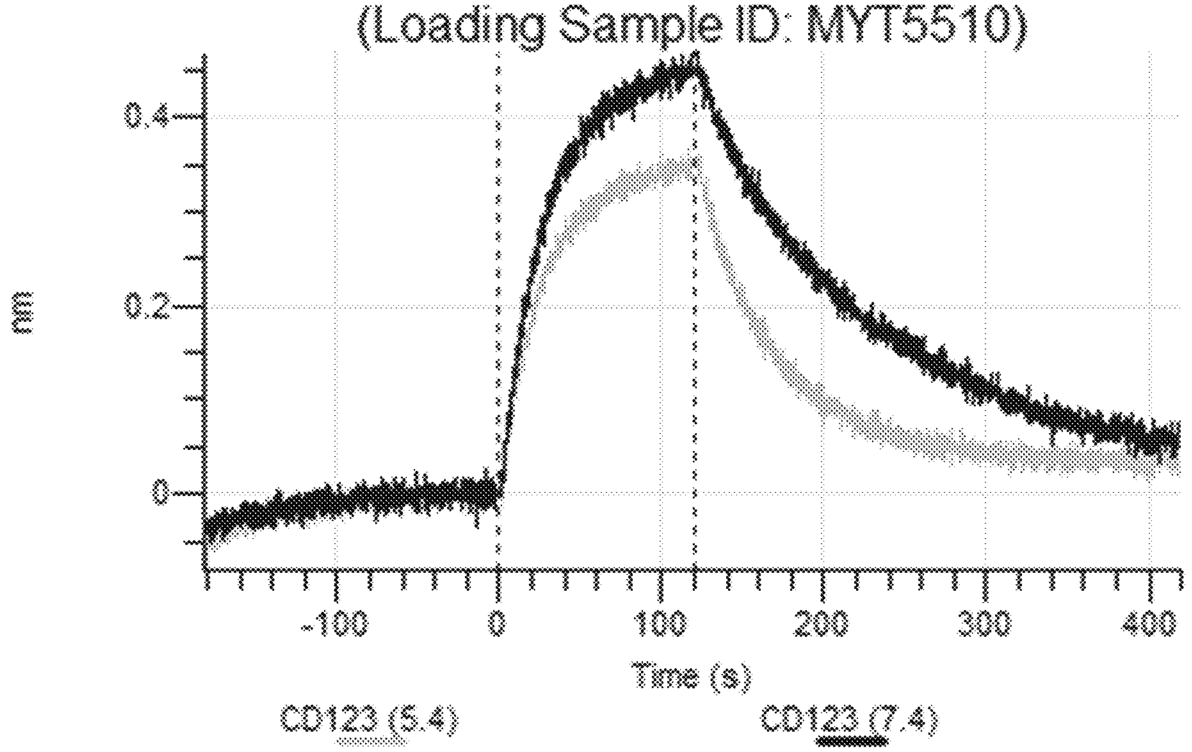
Figure 20A:
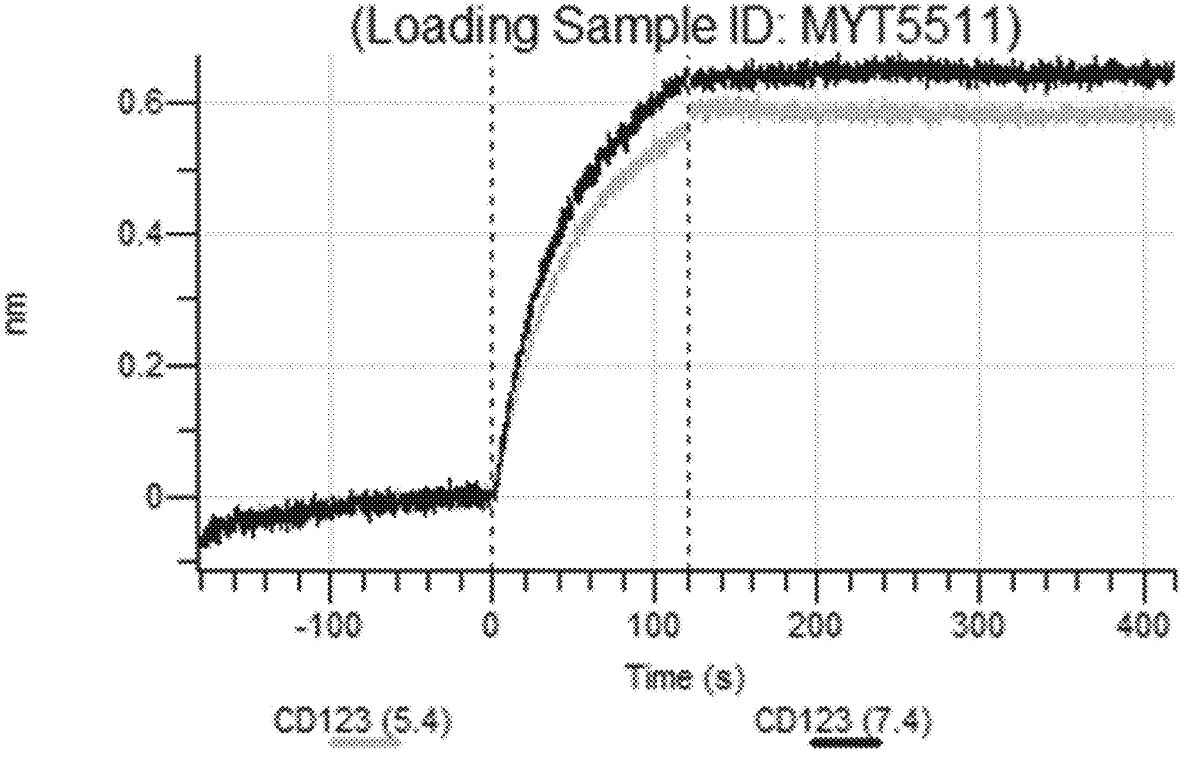

Multiple CD123-binding monoclonal antibodies have been described in the literature and can be used as a template for engineering pH-dependent binding (Lerchen H et al. "Specific Antibody-Drug-Conjugates (ADCS) with KSP Inhibitors and Anti-CD123-Antibodies" US Patent Application US 2019/0330357 A1 (2019). We selected TPP-8988 (Heavy chain SEQ ID NO: 149, Light chain SEQ ID NO: 150) as a CD123-binding monoclonal antibody for pH engineering via histidine scanning. Briefly, CDRs in the heavy chain were identified using the methods described by Kabat et al (Kabat et al. (1992) Sequences of Proteins of Immunological Interest, DIANE publishing) and IMGT (Lefranc M P (1999) "The IMGT unique numbering for Immunoglobulins, T cell receptors and Ig-like domains" The Immunologist 7, 132-136), and for each CDR, residues falling under either or both Kabat and IMGT CDR definitions were called as CDR residues. To generate pH-dependent sequence variants, individual amino acid residues within the heavy chain CDRs were systematically substituted with a histidine, one at a time (MYT5441-MYT5481). In cases where the starting CDR residue was a histidine, it was mutated to an alanine. Antibody variants with only one histidine or alanine mutation in a heavy chain CDR were generated by co-transfection of Expi293 cells with a) one heavy chain sequence variant, and b) the corresponding starting ABPC light chain using methods known to the art. After allowing for four days of protein expression, cell culture supernatants were collected, quantified by SDS-PAGE analysis (FIG. 16), and the pH dependence of the variant was evaluated using biolayer interferometry (BLI) on an Octet RED 96e instrument. Briefly, cell culture supernatants were diluted based on qualitative expression level of the variant determined by visual examination of SDS-PAGE gels, 5 μL of cell culture supernatant was diluted into 195 μL of 1×PBST, pH 7.4 for high expressors, 25 μL of cell culture supernatant was diluted into 175 μL of 1×PBST, pH 7.4 for medium expressors and 100 μL of cell culture supernatant was diluted into 100 μL of 1×PBST, pH 7.4 for low expressors for loading onto the sensor tips. The resulting diluted supernatants were then captured on an anti-human Fc sensor (Forte Bio). A baseline was established using 1×PBST (50 mM Potassium Phosphate Buffer+150 mM NaCl+0.05% Tween 20) pH 7.4, and the sensor was associated with 50 nM of CD123 (R&D Systems Catalog No. 301-R3-025/CF) in 1×PBST pH 7.4 for 120 sec to generate an association curve. In the dissociation phase, the antibody-antigen complex on the sensor was exposed to 1× PBST pH 7.4 for 300-600 sec. Baseline, association, and dissociation were repeated using 1×PBST pH 5.4 throughout in a separate condition. Association and dissociation phase curves were examined for the starting ABPC antibody (with no substitutions) and each corresponding antibody variant at pH 5.4 and pH 7.4 to inform on two criteria: a) enhanced dissociation (i.e., higher koff values) at pH 5.4 due to histidine or alanine substitution compared to the starting ABPC, (with no substitutions), and b) reduced dissociation at pH 7.4 (i.e., lower koff values) compared to pH 5.4 in the antibody variant itself and with the starting ABPC (with no substitutions). Heavy chain variants that showed either enhanced dissociation at pH 5.4 or reduced dissociation at pH 7.4 or both (as compared to the starting ABPC), as shown in FIG. 17 were selected for further analysis (e.g, MYT5450, MYT5452, MYT5453, MYT5454, MYT5455, MYT5457, MYT5458, MYT5472, MYT5473, MYT5474, MYT5475, MYT5477, and MYT5478). It was also noted that while some histidine and alanine mutations obliterated CD123 binding (e.g., MYT5476), others were tolerated with little (e.g., less than 1-fold change in dissociation constant $K_D$ or dissociation rate) or no change in CD123 binding kinetics (e.g., MYT5441, MYT5442, MYT5443, MYT5444, MYT5445, MYT5446, MYT5447, MYT5448, MYT5449, MYT5451, MYT5456, MYT5459, MYT5460, MYT5461, MYT5462, MYT5463, MYT5464, MYT5465, MYT5466, MYT5467, MYT5468, MYT5469, MYT5470, MYT5471, MYT5479, MYT5480, and MYT5481).

Especially because histidine is a large, positively charged amino acid, these variants with no change were noted as positions in the heavy chain that may tolerate a wide range of mutations and lead to antibodies with different sequence but similar binding properties, a designation that is not otherwise apparent.

Example 15. Construction and Screening of pH-Engineered CD123 ABPCs

Multiple CD123-binding monoclonal antibodies have been described in the literature and can be used as a template for engineering pH-dependent binding (Lerchen H et al. "Specific Antibody-Drug-Conjugates (ADCS) with KSP Inhibitors and Anti-CD123-Antibodies" US Patent Application US 2019/0330357 A1 (2019)). We selected TPP-8988 (Heavy chain SEQ ID NO: 149, Light chain SEQ ID NO: 150) as a CD123-binding monoclonal antibody for pH engineering via histidine scanning. Briefly, CDRs in the light chain were identified using the methods described by Kabat et al (Kabat et al. (1992) Sequences of Proteins of Immunological Interest, DIANE publishing) and IMGT (Lefranc M P (1999) "The IMGT unique numbering for Immunoglobulins, T cell receptors and Ig-like domains" The Immunologist 7, 132-136), and for each CDR, residues falling under either or both Kabat and IMGT CDR definitions were called as CDR residues. To generate pH-dependent sequence variants, individual amino acid residues within the light chain CDRs were systematically substituted with a histidine, one at a time (MYT5482-MYT5511). In cases where the starting CDR residue was a histidine, it was mutated to an alanine. Antibody variants with only one histidine or alanine mutation in a light chain CDR were generated by co-transfection of Expi293 cells with a) one light chain sequence variant, and b) the corresponding starting ABPC heavy chain using methods known to the art. After allowing for four days of protein expression, cell culture supernatants were collected, quantified by SDS-PAGE analysis (FIG. 19), and the pH dependence of the variant was evaluated using biolayer interferometry (BLI) on an Octet RED 96e instrument. Briefly, cell culture supernatants were diluted based on qualitative expression level of the variant determined by visual examination of SDS-PAGE gels, 5 μL of cell culture supernatant was diluted into 195 of 1×PBST, pH 7.4 for high expressors, 25 μL of cell culture supernatant was diluted into 175 μL of 1×PBST, pH 7.4 for medium expressors and 100 μL of cell culture supernatant was diluted into 100 μL of 1×PBST, pH 7.4 for low expressors for loading onto the sensor tips. Diluted supernatants were then captured on an anti-human Fc sensor (Forte Bio). A baseline was established using 1×PBST (50 mM Potassium Phosphate Buffer+150 mM NaCl+0.05% Tween 20) pH 7.4, and the sensor was associated with 50 nM of CD123 protein (R&D Systems Catalog No. 301-R3-025/CF) in 1×PBST pH 7.4 for 120 sec to generate an association curve. In the dissociation phase, the antibody-antigen complex on the sensor was exposed to 1× PBST pH 7.4 for 300-600 sec. Baseline, association, and dissociation were repeated using 1×PBST pH 5.4 throughout in a separate condition. Association and dissociation phase curves were examined for the starting ABPC antibody (with no substitutions) and each corresponding antibody variant at pH 5.4 and pH 7.4 to inform on two criteria: a) enhanced dissociation (i.e., higher koff values) at pH 5.4 due to histidine or alanine substitution compared to the starting ABPC (with no substitutions), and b) reduced dissociation at pH 7.4 (i.e., lower koff values) compared to pH 5.4 in the antibody variant itself and with the starting ABPC (with no substitutions). Light chain variants that showed either enhanced dissociation at pH 5.4 or reduced dissociation at pH 7.4 or both (as compared to the starting ABPC), as shown in FIG. 20 were selected for further analysis (e.g, MYT5484, MYT5485, MYT5486, MYT5487, MYT5488, MYT5489, MYT5493, MYT5496, MYT5503, MYT5504, MYT5505, MYT5509, and MYT5510). It was also noted that while some histidine and alanine mutations obliterated CD123 binding (e.g., MYT5495), others were tolerated with little (e.g., less than 1-fold change in dissociation constant $K_D$ or dissociation rate) or no change in MET binding kinetics (e.g., MYT5482, MYT5483, MYT5490, MYT5491, MYT5492, MYT5494, MYT5497, MYT5498, MYT5499, MYT5500, MYT5501, MYT5502, MYT5506, MYT5507, MYT5508, and MYT5511).

Especially because histidine is a large, positively charged amino acid, these variants with no change were noted as positions in the light chain that may tolerate a wide range of mutations and lead to antibodies with different sequence but similar binding properties, a designation that is not otherwise apparent.

Example 16. Characterization of Binding Affinity for Anti-CD123 mAbs

Figure 22A:
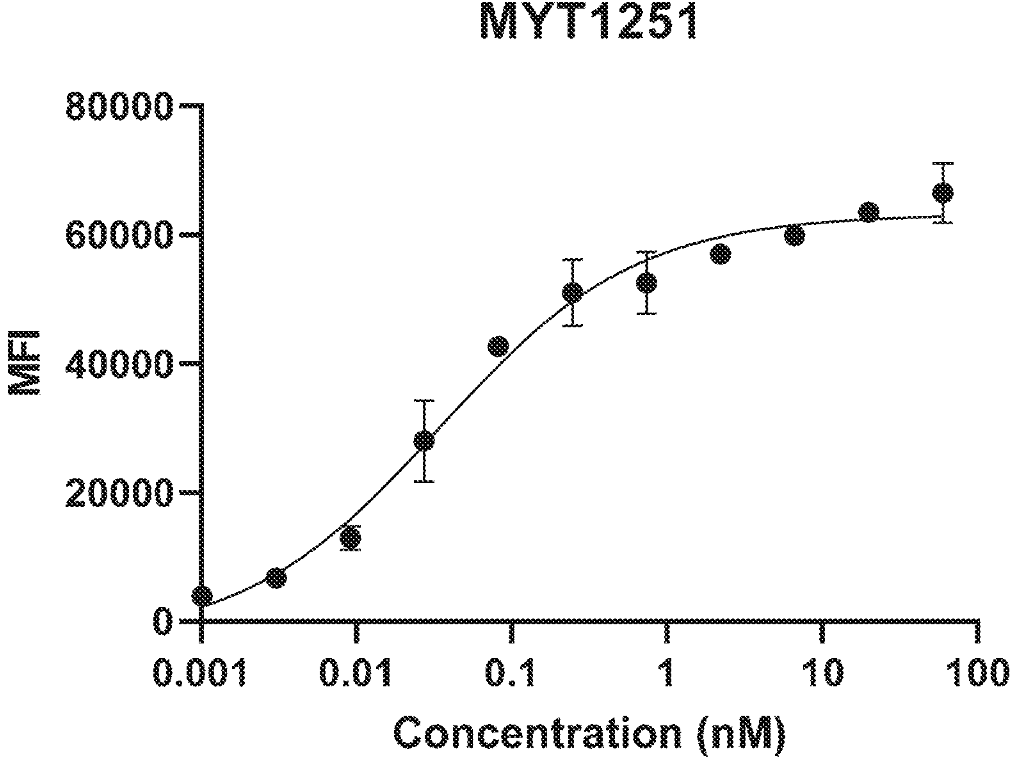
FIG. 22*a*-22*b*: Characterization of binding affinity for anti-CD123 mAbs. Anti-CD123 mAbs were assayed for their binding to EOL-1 (CD123+) cells.
Figure 22B:
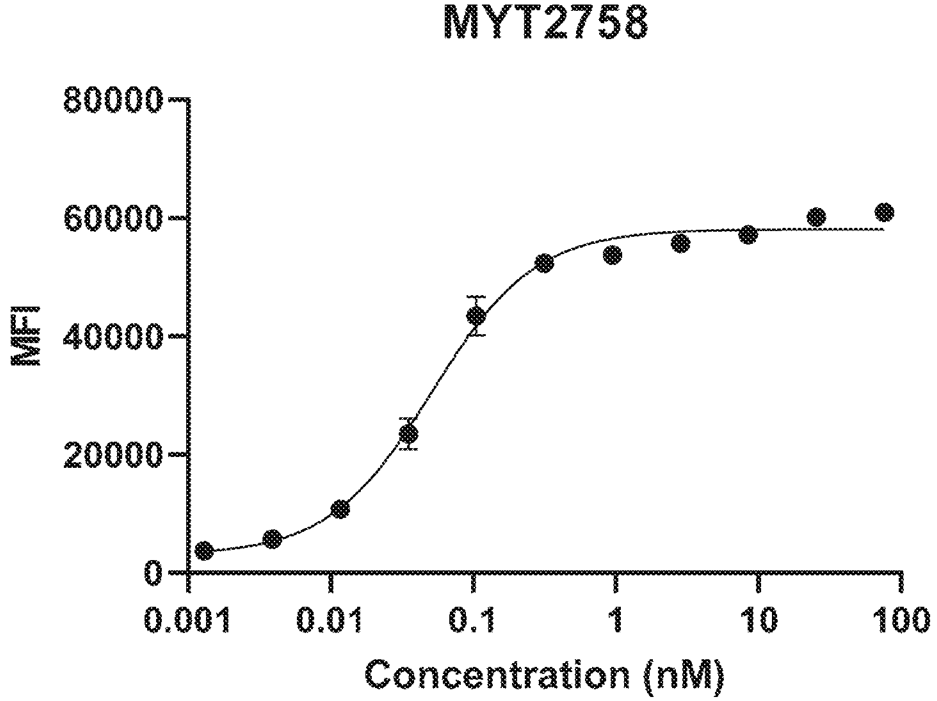

Binding affinity of selected CD-123 pH engineered antibody variants from Example 11 were measured on EOL-1 cells (CD123+) cells. 100,000 EOL-1 cells (DSMZ ACC 386) were seeded per well in a 96 well deep well plate. IMGN632 and a pH engineered antibody variant were serially diluted at a 1:3 dilution in ice cold FC buffer (phosphate buffered saline (PBS), pH 7.4+2 mM ethylenediaminetetraacetic acid (EDTA)+2% (v/v) HI FBS). The plates were spun at 2,000 RPM for 2 minuets, the supernatant was removed, and 100 μL of diluted antibody was added to each well with final concentration ranging from 60 nM to 1 pM and incubated for 2 hours at 4° C. Post incubation, the cells were spun at 2000 rpm for 2 min and supernatant was discarded. Cells were washed twice with 500 μL of ice-cold FC buffer and resuspended with 100 of FC buffer. The cells were then transferred from the deep well plate to 96 well round bottom plate, spun at 2000 rpm for 2 min and incubated with 100 μL of 10 μg/mL Alexa Fluor 488 conjugated goat anti-human IgG secondary antibody (ThermoFisher Scientific, A11013) for 30 min. Post incubation, cells were washed with FC buffer and resuspended in 100 μL of FC buffer to read on a BD Accuri C6 flow cytometer. Mean fluorescence intensity at each concentration per sample was background subtracted and plotted as shown in FIG. 22. Binding affinity was measured as a dissociation constant $K_D$ by GraphPad Prism assuming Michaelis-Menten binding kinetics. MYT2758 shows high affinity binding to cell surface CD123 on EOL-1 cells in the pM range confirming that variants created through pH engineering can retain functionally appropriate affinities as compared to their corresponding starting ABPCs (e.g., IMGN632). Variants with dissociation constants $K_D$ less than 100 nM were selected for further analysis.

Example 17. Characterization of Cellular Internalization and Endolysosomal Delivery of pH Engineered Anti-CD123 ABPCs Selected anti-CD123 pH engineered antibody variants from Examples 9 and 11 were analyzed for internalization and endolysosomal delivery in EOL-1 cells (CD123+).

Figure 23A:
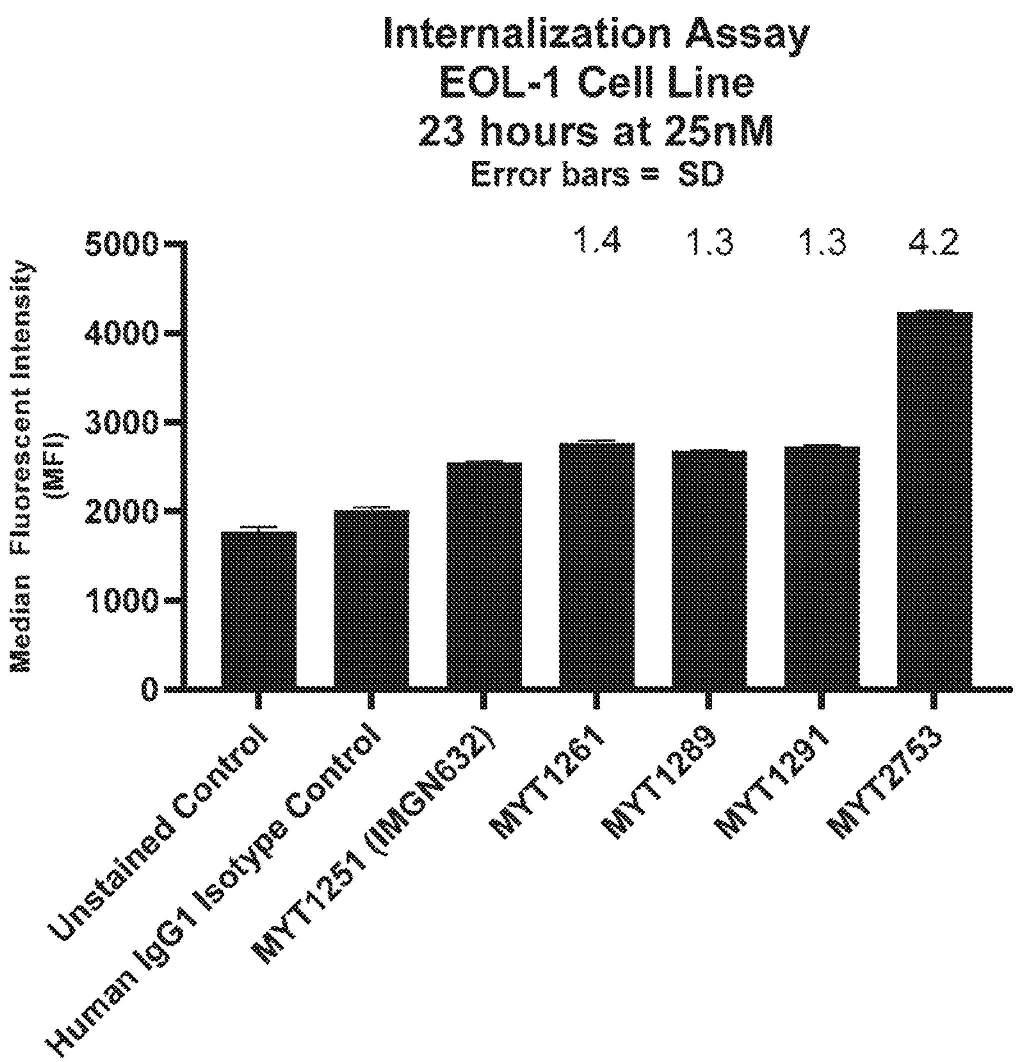
FIG. 23*a*-23*b*: Internalization of anti-CD123 mAbs in cells. Anti-CD123 pH engineered antibody variants, corresponding starting ABPC antibody, control IgG1 isotype control (BP0297, Bioxcell), along with a vehicle control, as specified in FIG. 23 were assayed for internalization and endolysosomal delivery as measured by mean fluorescence intensity on cells, conditions are specified in the figures. Error bars represent standard deviation. Numbers above the bars represent fold change over the corresponding starting ABPC.
Figure 23B:
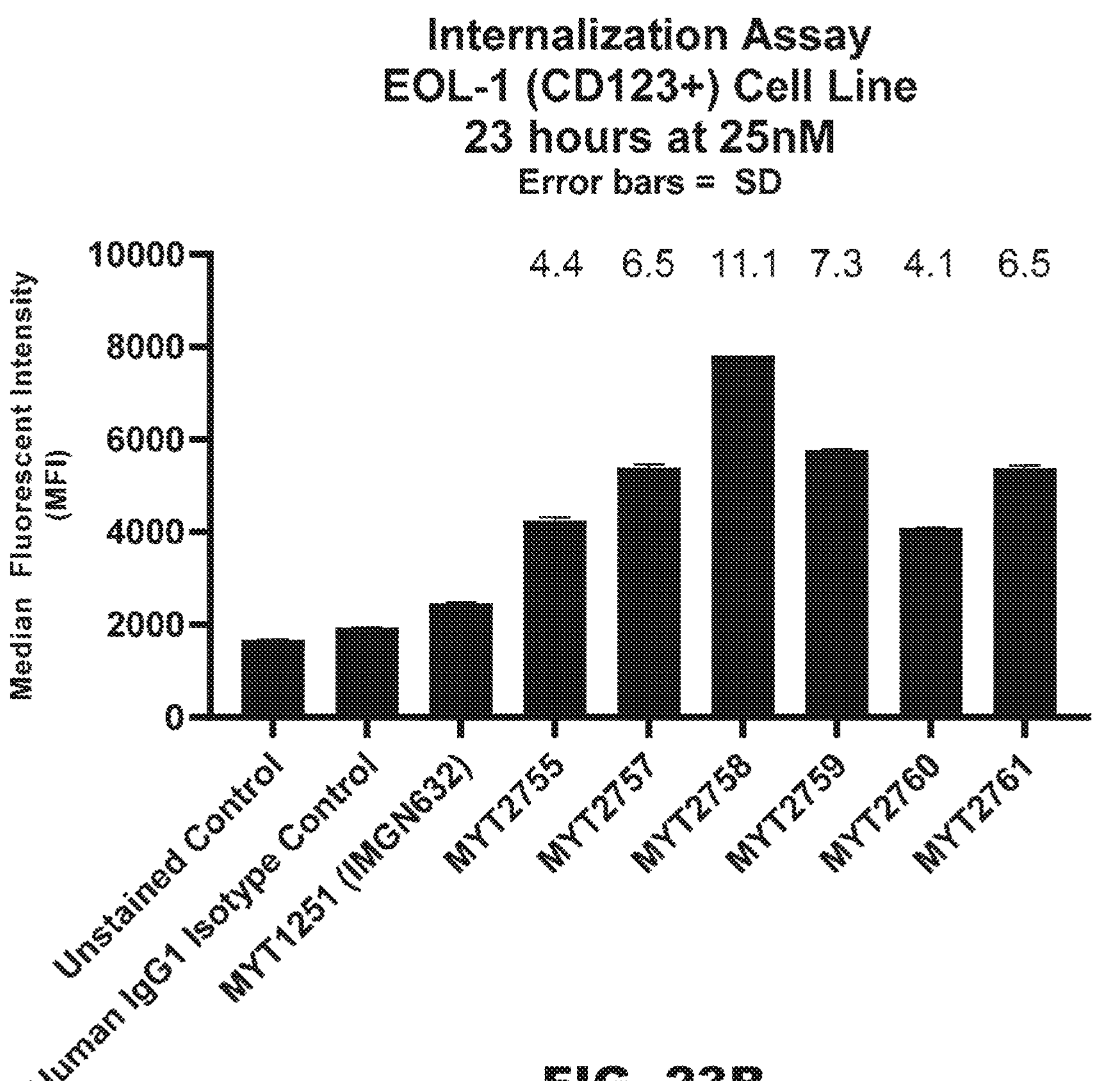

EOL-1 cells (DSMZ ACC386) were collected and resuspended in RPMI medium (ATCC 30-2001) plus 10% GenClone heat inactivated fetal bovine serum (HI FBS) (Genesee Scientific; 25-514H). Cell counts were determined using trypan blue staining and the Countess II FL Automated Cell Counter (Thermofisher; AMQAF1000). Cells were then diluted to 2,000,000 cells/mL and 50 μL/well was seeded into 96-well flat bottom cell culture plates (Genesee Scientific; 25-109). Anti-CD123 pH engineered antibody variants, starting ABPC antibodies, control IgG1 isotype control (BP0297, Bioxcell), and vehicle control were diluted in native culture media, and then mixed 1:1 with a 3× molar ratio Zenon pHrodo iFL Human IgG Labeling Reagent (ThermoFisher; Z25611). The mixture was incubated for 20 minutes at room temperature, followed by a 1:1 addition of cells for a final volume of 100 μL. The mixture of cells, anti-CD123 antibody variants, and Zenon pHrodo iFL Human IgG Labeling Reagent was incubated at 37° C., 5% CO2 for 1-24 hours. Following incubation, 100 μL of ice cold Flow Cytometry (FC) buffer (phosphate buffered saline (PBS), pH 7.4+2 mM ethylenediaminetetraacetic acid (EDTA)+2% (v/v) HI FBS is added to each well. Cells were then spun down at 4° C. for 2 min at 2000 rpm, washed with 200 μL ice cold FC buffer and resuspended in 100 μL ice cold FC buffer. Mean green fluorescence intensity was detected using a BD Accuri C6 flow cytometer. Data was analyzed using Flowjo analysis software. pHrodo green is a PH sensitive dye that fluoresces in the low pH environment of the endosomes and lysosomes and therefore can be used to quantify antibody internalization and endolysosomal delivery. Internalization and endolysosomal delivery of anti-CD123 starting ABPC's and variants at concentrations specified in the figures in EOL-1 (CD123+) cells (FIG. 23) as measured by pHrodo green mean fluorescence intensity. Several pH engineered anti-CD123 antibody variants showed increased mean fluorescence intensity relative to their corresponding starting ABPC antibodies demonstrating that increased dissociation at lower pH leads to enhanced internalization and endolysosomal delivery inside cells as shown by increased fluorescence or increased fluorescence as compared to IgG1 isotype control. Increased endolysosomal delivery is quantitated for each pH engineered anti-CD123 antibody variant on the top of each bar as a ratio of: the variant's mean fluorescence intensity minus the mean fluorescence intensity of the IgG control, then all divided by the variant's corresponding starting ABPC's mean fluorescence intensity minus the mean fluorescence intensity of the IgG control. For example, MYT1261, MYT1289, MYT1291, MYT2753, MYT2755, MYT2757, MYT2758, MYT2759, MYT2760, and MYT2761, antibody variants of IMGN632 showed increased internalization and endolysosomal delivery relative to IMGN632 (MYT1251). Such pH engineered anti-CD123 antibody variants with increased mean fluorescence intensity relative to their starting ABPC antibodies were selected for further analysis.

Figure 24A:
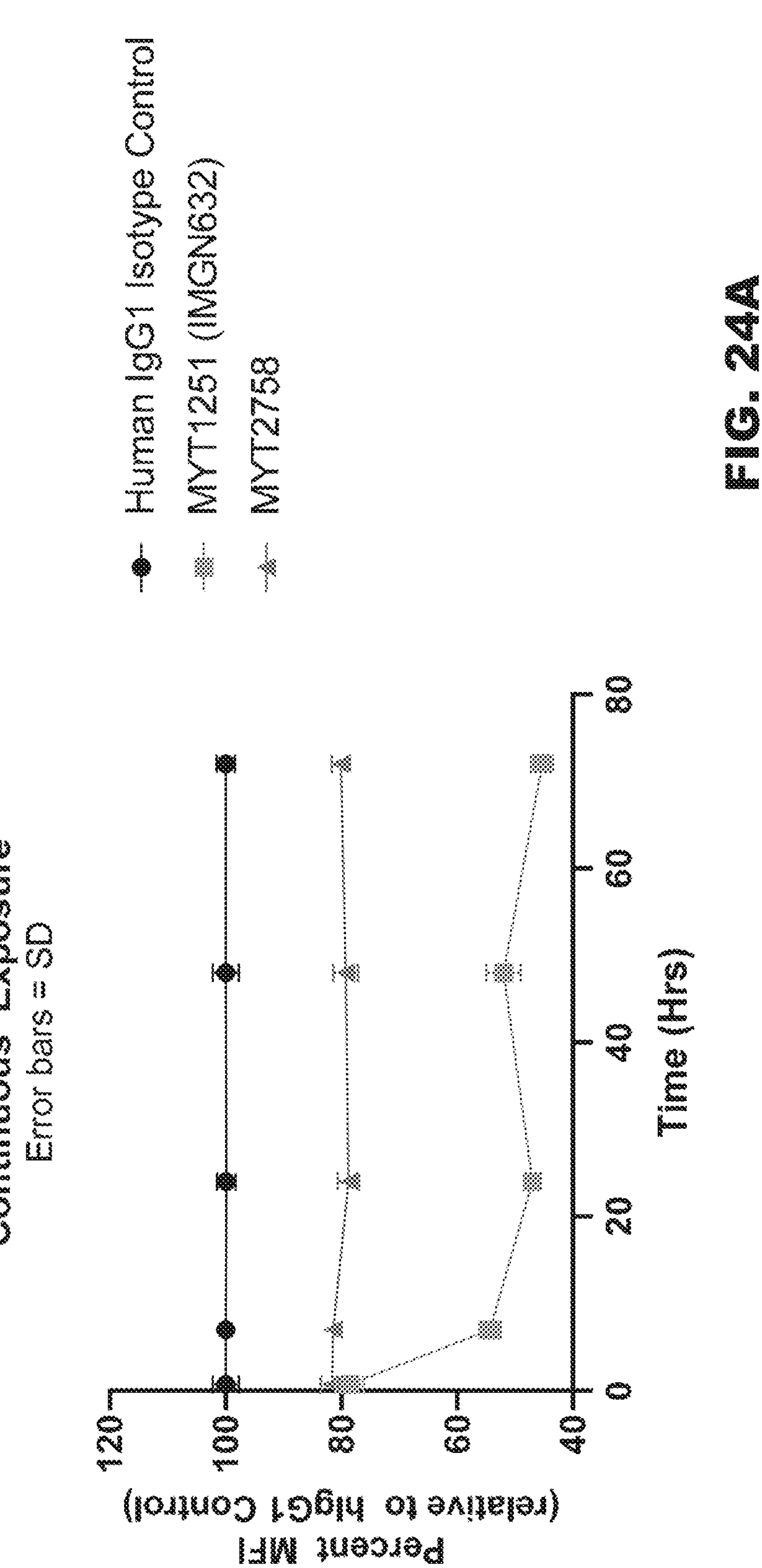
Figure 24B:
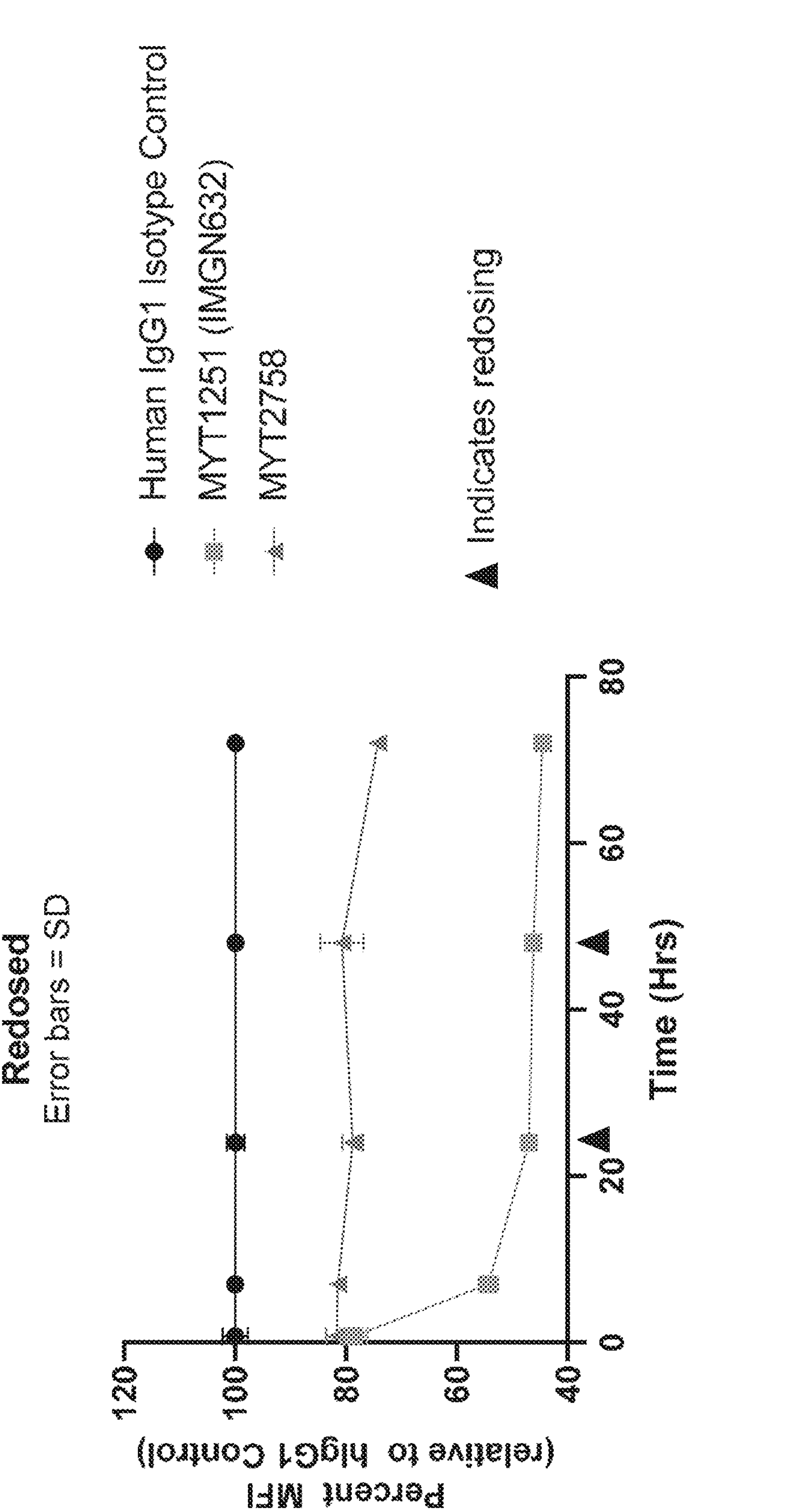
FIG. 24*b* shows the same assay redosed at 24 and 48 hours.

Example 18. Downregulation of CD123 Expression by pH-Engineered Anti-CD123 ABPCs Selected anti-CD123 pH-engineered variants and starting ABPCs from Example 11 were analyzed for downregulation of CD123 in EOL-1 cells (CD123+). 100,000 EOL-1 cells (DSMZ ACC 386) were seeded in 50 μL in a flat-bottom 96-well plate. 2× antibody mixtures were prepared in cell culture media and added to 50 μL of cells. Cells were incubated at 37° C. with 5% CO2 for 0.75, 7, 24, 48 and 72 hours, with either no additional antibody added (continuous exposure) or additional antibody added at 24 and 48 hours as indicated in the figures (redosed). Redosing was done by spinning the plates down at 1200 RPM for 5 minutes, removing the supernatant, and adding a 1× antibody mixture directly to the cells. After incubation with antibodies cells were transferred to a 96-well U-bottom plate and spun down at 1200 RPM for 5 minutes. The supernatant was removed and the cells were washed twice with 200 μL of ice cold flow cytometry (FC) buffer (PBS pH 7.4+2 mM EDTA+2? HI FBS))). After washing the cells were stained with a non-competing anti-CD123 antibody (data not shown, FITC anti-hCD123 antibody, Biolegend Cat #306014) in ice-cold FC buffer at 4° C. for 30 minutes. After staining the cells were washed twice with 200 μL of cold Flow Cytometry Buffer, resuspend in 100 uL Flow Cytometry Buffer and read immediately on a flow cytometer. Cells dosed with MYT2758 showed little to no decrease in CD123 cell surface expression over time (FIG. 24) while cells dosed with MYT1251 (IMGN632) showed a decrease over the same period.

Example 19. Conjugation of pH-Engineered and Control ABPCs Specific for CD123 to Cytotoxic Drugs Selected anti-CD123 pH-engineered variants and starting ABPCs from Examples 9-15 are selected for payload conjugation to form antigen-binding protein construct-drug conjugates (ADCs) using methods known in the art. Some selected examples of methods known in the art include, but are not limited to [Tiberghien A C et al (2016) Design and Synthesis of Tesirine, a Clinical Antibody—Drug Conjugate Pyrrolobenzodiazepine Dimer Payload, ACS Med Chem Lett 7:983-987], [Kovtun, Yelena, et al. (2018) "A CD123-Targeting Antibody-Drug Conjugate, IMGN632, Designed to Eradicate AML While Sparing Normal Bone Marrow Cells." Blood Advances, American Society of Hematology 2(8) 848-858], [Catcott K C et al (2016) Microscale screening of antibody libraries as maytansinoid antibody-drug conjugates, MAbs 8:513-23], (Liu, Fang and Li, Xinfang, "Separation of triple-light chain antibodies using cation exchange chromatography", WO2019060718A1), (Hilderbrand, Scott A and Hutchins, Benjamin M, "Selective sulfonation of benzodiazepine derivatives", WO2018098258A2), and (Chari, Ravi Nit et al, "Cytotoxic benzodiazepine derivatives", US20160082114A1). These pH-engineered and starting ADCs, including those comprising MYT2758 and MYT1251 (IMGN632), are subjected to antigen binding assays at different pHs, cell binding assays, and internalization assays similar to those described in Examples 11, 16, and 17, respectively. One or more ADCs comprising MYT2758 is selected for further analysis.

Example 20. Increased Potency of pH-Engineered ADCs Specific for CD123 vs. A Control ABPC ADC Specific for CD123 in Mouse Xenograft Models Selected anti-CD123 pH-engineered ADCs from Example 19, including one or more comprising MYT2758, one or more matched ADCs (i.e. with the same payload and conjugation method and design) comprising MYT1251 (IMGN632), and a non-binding matched ADC comprising an antibody comprising a variable region that does not bind CD123 or the target cancer cells, are selected to evaluate their efficacy in a mouse xenograft study using methods known in the art. One example of such a method known in the art is, without limitation, [Kovtun, Yelena, et al. (2018) "A CD123-Targeting Antibody-Drug Conjugate, IMGN632, Designed to Eradicate AML While Sparing Normal Bone Marrow Cells." Blood Advances, American Society of Hematology 2(8) 848-858.] Briefly EOL-1 cells (CD123+) are implanted subcutaneously into female athymic nude mice and the resulting tumors are monitored until they reach 80-120 $mm^3$. At this point (day 1), mice are randomized into groups of six to ten with similar tumor sizes. Mice are then dosed on day 1, 6 and 11 with IgG isotype control at 200 mg/kg (day 1) and 50 mg/kg (day 6 and 11). On day 3 the mice are dosed with either vehicle control, 200 ug/kg of non-binding matched ADC, 300 ug/kg of non-binding matched ADC, or select ADCs from Example 19 and matched ADCs comprising MYT1251 at either 300 ug/kg of ADC, 250 ug/kg of ADC, 250 ug/kg of ADC plus 750 ug/kg of the corresponding ABPC (e.g., MYT2758 or MYT1251), 200 μg/kg of ADC, 80 μg/kg of ADC, or 30 μg/kg of ADC, depending on the treatment group. Animals are monitored for tumor volume and body weight twice a week for 44 days and blood is collected from some mice in some groups to measure the presence of human IgG1 on days 5, 9 and 16. Alternatively, a similar experiment is performed with KG-1 cell xenografts using methods known in the art. It is observed that pH-engineered ADCs, including those comprising MYT2758, show greater tumor growth delay and tumor growth inhibition than matched ADCs comprising MYT1251 at the same dose of ADC.

The discoveries herein are in contrast to similar engineering on other antigens such as CLEC12a and two other targets wherein multiple variants per target showed enhanced dissociation at low pH, however, despite the favorable pH-dependent binding properties of these variants (which specifically bound CLEC12a and the two other targets), they had less than 10% increase in cell internalization and endolysosomal delivery as compared to the corresponding starting ABPC (e.g., the starting antibody). These variants (which specifically bound CLEC12a and the two other targets) also had similar biophysical characteristics (e.g., antibody expression, thermal stability, affinity at pH 7.4 etc.) to the corresponding starting ABPC (e.g., the starting antibody) confirming that this was not specific to the biophysical properties of the tested variant (i.e. the biophysical properties unrelated to enhanced dissociation at pH 5.4).

Exemplary Embodiments

Embodiment 1 is a pharmaceutical composition comprising an effective amount of an antigen-binding protein construct (ABPC) comprising: a first antigen-binding domain that is capable of specifically binding CD123 or an epitope of CD123 presented on the surface of a target mammalian cell, wherein: (a) the dissociation rate of the first antigen-binding domain at a pH of about 4.0 to about 6.5 is faster than the dissociation rate at a pH of about 7.0 to about 8.0; or (b) the dissociation constant ($K_D$) of the first antigen-binding domain at a pH of about 4.0 to about 6.5 is greater than the $K_D$ at a pH of about 7.0 to about 8.0.

Embodiment 2 is the pharmaceutical composition of embodiment 1, wherein the first antigen-binding domain comprises a heavy chain variable domain of IMGN632 with one or more amino acids substituted with a histidine.

Embodiment 3 is the pharmaceutical composition of embodiment 1, wherein the first antigen-binding domain comprises a light chain variable domain of IMGN632 with one or more amino acids substituted with a histidine.

Embodiment 4 is the pharmaceutical composition of embodiment 1, wherein the first antigen-binding domain comprises: a heavy chain variable domain of IMGN632 with one or more amino acids substituted with a histidine; and a light chain variable domain of IMGN632 with one or more amino acids substituted with a histidine.

Embodiment 5 is the pharmaceutical composition of embodiment 2 or 4, wherein the heavy chain variable domain of IMGN632 comprises SEQ ID NO: 1.

Embodiment 6 is the pharmaceutical composition of embodiment 3 or 4, wherein the light chain variable domain of IMGN632 comprises SEQ ID NO: 2.

Embodiment 7 is the pharmaceutical composition of embodiment 1, wherein the first antigen-binding domain comprises a heavy chain variable domain comprising a CDR1, a CDR2, and a CDR3 of SEQ ID NOs: 3-5, respectively, with collectively a total of one or more amino acid positions in SEQ ID NOs: 3-5 substituted with a histidine.

Embodiment 8 is the pharmaceutical composition of embodiment 1, wherein the first CD123-binding domain comprises a light chain variable domain comprising a CDR1, a CDR2, and a CDR3 of SEQ ID NOs: 6-8, respectively, with collectively a total of one or more amino acid positions in SEQ ID NOs: 6-8 substituted with a histidine.

Embodiment 9 is the pharmaceutical composition of embodiment 1, wherein the first CD123-binding domain comprises: a heavy chain variable domain comprising a CDR1, a CDR2, and a CDR3 of SEQ ID NOs: 3-5, respectively, with collectively a total of one or more amino acid positions in SEQ ID NOs: 3-5 substituted with a histidine; and a light chain variable domain comprising a CDR1, a CDR2, and a CDR3 of SEQ ID NOs: 6-8, respectively, with collectively a total of one or more amino acid positions in SEQ ID NOs: 6-8 substituted with a histidine.

Embodiment 10 is the pharmaceutical composition of embodiment 1, 2, or 7, wherein the first antigen-binding domain comprises a heavy chain variable domain that is at least 90% identical to SEQ ID NO: 1, wherein the heavy chain variable domain includes a histidine at one or more positions in SEQ ID NO: 1 selected from the group consisting of: 27, 28, 29, 30, 33, 53, 54, 97, 100, 103, 104, 105, 106, 107, 108, or 109.

Embodiment 11 is the pharmaceutical composition of embodiment 1, 3, or 8, wherein the first antigen-binding domain comprises a light chain variable domain that is at least 90% identical to SEQ ID NO: 2, wherein the light chain variable domain includes a histidine at one or more positions in SEQ ID NO: 2.

Embodiment 12 is the pharmaceutical composition of embodiment 1, 2, or 7, wherein the first antigen-binding domain comprises a heavy chain variable domain that is at least 90% identical to SEQ ID NO: 1, wherein the heavy chain variable domain includes a histidine at two or more positions in SEQ ID NO: 1.

Embodiment 13 is the pharmaceutical composition of embodiment 1, 4, or 9, wherein the first antigen-binding domain comprises: a heavy chain variable domain that is at least 90% identical to SEQ ID NO: 1, wherein the heavy chain variable domain includes a histidine at one or more positions in SEQ ID NO: 1 selected from the group consisting of: 27, 28, 29, 30, 33, 53, 54, 97, 100, 103, 104, 105, 106, 107, 108, or 109; and a light chain variable domain that is at least 90% identical to SEQ ID NO: 2.

Embodiment 14 is the pharmaceutical composition of embodiment 1, wherein the first antigen-binding domain comprises a heavy chain variable domain of SEQ ID NO: 14, SEQ ID NO: 15, SEQ ID NO: 16, SEQ ID NO: 17, SEQ ID NO: 20, SEQ ID NO: 22, SEQ ID NO: 26, SEQ ID NO: 27, SEQ ID NO: 40, SEQ ID NO: 43, SEQ ID NO: 46, SEQ ID NO: 47, SEQ ID NO: 48, SEQ ID NO: 49, SEQ ID NO: 50, SEQ ID NO: 51, or SEQ ID NO: 52.

Embodiment 15 is the pharmaceutical composition of embodiment 1 or 14, wherein the first antigen-binding domain comprises a light chain variable domain of SEQ ID NO: 2.

Embodiment 16 is the pharmaceutical composition of embodiment 1, wherein the first antigen-binding domain comprises a heavy chain variable domain.

Embodiment 17 is the pharmaceutical composition of embodiment 16, wherein the first antigen-binding domain comprises a light chain variable domain of SEQ ID NO: 2.

Embodiment 18 is the pharmaceutical composition of any one of embodiments 1-17, wherein the ABPC is degraded in the target mammalian cell following internalization of the ABPC by the target mammalian cell.

Embodiment 19 is the pharmaceutical composition of any one of embodiments 1-18, wherein the ABPC further comprises a conjugated toxin, radioisotope, drug, or small molecule.

Embodiment 20 is the pharmaceutical composition of embodiment 19, wherein the composition provides for an increase in toxin liberation in the target mammalian cell as compared to a composition comprising the same amount of a control ABPC.

Embodiment 21 is the pharmaceutical composition of embodiment 20, wherein the composition provides for at least a 20% increase in toxin liberation in the target mammalian cell as compared to a composition comprising the same amount of a control ABPC.

Embodiment 22 is the pharmaceutical composition of embodiment 21, wherein the composition provides for at least a 50% increase in toxin liberation in the target mammalian cell as compared to a composition comprising the same amount of a control ABPC.

Embodiment 23 is the pharmaceutical composition of embodiment 20, wherein the composition provides for at least a 2-fold increase in toxin liberation in the target mammalian cell as compared to a composition comprising the same amount of a control ABPC.

Embodiment 24 is the pharmaceutical composition of embodiment 23, wherein the composition provides for at least a 5-fold increase in toxin liberation in the target mammalian cell as compared to a composition comprising the same amount of a control ABPC.

Embodiment 25 is the pharmaceutical composition of any one of embodiments 19-24, wherein the composition provides for an increase in target mammalian cell killing as compared to a composition comprising the same amount of a control ABPC.

Embodiment 26 is the pharmaceutical composition of embodiment 25, wherein the composition provides for at least a 20% increase in target mammalian cell killing as compared to a composition comprising the same amount of a control ABPC.

Embodiment 27 is the pharmaceutical composition of embodiment 26, wherein the composition provides for at least a 50% increase in target mammalian cell killing as compared to a composition comprising the same amount of a control ABPC.

Embodiment 28 is the pharmaceutical composition of embodiment 25, wherein the composition provides for at least a 2-fold increase in target mammalian cell killing as compared to a composition comprising the same amount of a control ABPC.

Embodiment 29 is the pharmaceutical composition of embodiment 28, wherein the composition provides for at least a 5-fold increase in target mammalian cell killing as compared to a composition comprising the same amount of a control ABPC.

Embodiment 30 is the pharmaceutical composition of any one of embodiments 1-29, wherein the composition provides for an increase in endolysosomal delivery in the target mammalian cell as compared to a composition comprising the same amount of a control ABPC.

Embodiment 31 is the pharmaceutical composition of embodiment 30, wherein the composition provides for at least a 20% increase in endolysosomal delivery in the target mammalian cell as compared to a composition comprising the same amount of a control ABPC.

Embodiment 32 is the pharmaceutical composition of embodiment 31, wherein the composition provides for at least a 50% increase in endolysosomal delivery in the target mammalian cell as compared to a composition comprising the same amount of a control ABPC.

Embodiment 33 is the pharmaceutical composition of embodiment 30, wherein the composition provides for at least a 2-fold increase in endolysosomal delivery in the target mammalian cell as compared to a composition comprising the same amount of a control ABPC.

Embodiment 34 is the pharmaceutical composition of embodiment 33, wherein the composition provides for at least a 5-fold increase in endolysosomal delivery in the target mammalian cell as compared to a composition comprising the same amount of a control ABPC.

Embodiment 35 is the pharmaceutical composition of any one of embodiments 1-34, wherein the composition results in a less of a reduction in the level of CD123 presented on the surface of the target mammalian cell as compared to a composition comprising the same amount of a control ABPC.

Embodiment 36 is the pharmaceutical composition of any one of embodiments 1-34, wherein the composition does not result in a detectable reduction in the level of the CD123 presented on the surface of the target mammalian cell.

Embodiment 37 is a pharmaceutical composition comprising an effective amount of an antigen-binding protein construct (ABPC) comprising: a first antigen-binding domain that is capable of specifically binding CD123 or an epitope of CD123 presented on the surface of a target mammalian cell; and a conjugated toxin, radioisotope, drug, or small molecule, wherein: (a) the dissociation rate of the first antigen-binding domain at a pH of about 4.0 to about 6.5 is faster than the dissociation rate at a pH of about 7.0 to about 8.0; or the dissociation constant ($K_D$) of the first antigen-binding domain at a pH of about 4.0 to about 6.5 is greater than the $K_D$ at a pH of about 7.0 to about 8.0; and (b) the composition provides for one or more of: an increase in toxin liberation in the target mammalian cell as compared to a composition comprising the same amount of a control ABPC; an increase in target mammalian cell killing as compared to a composition comprising the same amount of a control ABPC; and an increase in endolysosomal delivery in the target mammalian cell as compared to a composition comprising the same amount of a control ABPC.

Embodiment 38 is the pharmaceutical composition of embodiment 37, wherein the first antigen-binding domain comprises a heavy chain variable domain of IMGN632 with one or more amino acids substituted with a histidine.

Embodiment 39 is the pharmaceutical composition of embodiment 37, wherein the first antigen-binding domain comprises a light chain variable domain of IMGN632 with one or more amino acids substituted with a histidine.

Embodiment 40 is the pharmaceutical composition of embodiment 37, wherein the first antigen-binding domain comprises: a heavy chain variable domain of IMGN632 with one or more amino acids substituted with a histidine; and a light chain variable domain of IMGN632 with one or more amino acids substituted with a histidine.

Embodiment 41 is the pharmaceutical composition of embodiment 38 or 40, wherein the heavy chain variable domain of IMGN632 comprises SEQ ID NO: 1.

Embodiment 42 is the pharmaceutical composition of embodiment 39 or 40, wherein the light chain variable domain of IMGN632 comprises SEQ ID NO: 2.

Embodiment 43 is the pharmaceutical composition of embodiment 37, wherein the first antigen-binding domain comprises a heavy chain variable domain comprising a CDR1, a CDR2, and a CDR3 of SEQ ID NOs: 3-5, respectively, with collectively a total of one or more amino acid positions in SEQ ID NOs: 3-5 substituted with a histidine.

Embodiment 44 is the pharmaceutical composition of embodiment 37, wherein the first CD123-binding domain comprises a light chain variable domain comprising a CDR1, a CDR2, and a CDR3 of SEQ ID NOs: 6-8, respectively, with collectively a total of one or more amino acid positions in SEQ ID NOs: 6-8 substituted with a histidine.

Embodiment 45 is the pharmaceutical composition of embodiment 37, wherein the first CD123-binding domain comprises: a heavy chain variable domain comprising a CDR1, a CDR2, and a CDR3 of SEQ ID NOs: 3-5, respectively, with collectively a total of one or more amino acid positions in SEQ ID NOs: 3-5 substituted with a histidine; and a light chain variable domain comprising a CDR1, a CDR2, and a CDR3 of SEQ ID NOs: 6-8, respectively, with collectively a total of one or more amino acid positions in SEQ ID NOs: 6-8 substituted with a histidine.

Embodiment 46 is the pharmaceutical composition of embodiment 37, 38, or 43, wherein the first antigen-binding domain comprises a heavy chain variable domain that is at least 90% identical to SEQ ID NO: 1, wherein the heavy chain variable domain includes a histidine at one or more positions in SEQ ID NO: 1 selected from the group consisting of: 27, 28, 29, 30, 33, 53, 54, 97, 100, 103, 104, 105, 106, 107, 108, or 109.

Embodiment 47 is the pharmaceutical composition of embodiment 37, 39, or 44, wherein the first antigen-binding domain comprises a light chain variable domain that is at least 90% identical to SEQ ID NO: 2, wherein the light chain variable domain includes a histidine at one or more positions in SEQ ID NO: 2.

Embodiment 48 is the pharmaceutical composition of embodiment 37, 38, or 43, wherein the first antigen-binding domain comprises a heavy chain variable domain that is at least 90% identical to SEQ ID NO: 1, wherein the heavy chain variable domain includes a histidine at two or more positions in SEQ ID NO: 1.

Embodiment 49 is the pharmaceutical composition of embodiment 37, 40, or 45, wherein the first antigen-binding domain comprises: a heavy chain variable domain that is at least 90% identical to SEQ ID NO: 1, wherein the heavy chain variable domain includes a histidine at one or more positions in SEQ ID NO: 1 selected from the group consisting of: 27, 28, 29, 30, 33, 53, 54, 97, 100, 103, 104, 105, 106, 107, 108, or 109; and a light chain variable domain that is at least 90% identical to SEQ ID NO: 2, wherein the light chain variable domain includes a histidine at one or more positions in SEQ ID NO: 2.

Embodiment 50 is the pharmaceutical composition of embodiment 37, wherein the first antigen-binding domain comprises a heavy chain variable domain SEQ ID NO: 14, SEQ ID NO: 15, SEQ ID NO: 16, SEQ ID NO: 17, SEQ ID NO: 20, SEQ ID NO: 22, SEQ ID NO: 26, SEQ ID NO: 27, SEQ ID NO: 40, SEQ ID NO: 43, SEQ ID NO: 46, SEQ ID NO: 47, SEQ ID NO: 48, SEQ ID NO: 49, SEQ ID NO: 50, SEQ ID NO: 51, or SEQ ID NO: 52.

Embodiment 51 is the pharmaceutical composition of embodiment 37 or 50, wherein the first antigen-binding domain comprises a light chain variable domain of SEQ ID NO: 2.

Embodiment 52 is the pharmaceutical composition of embodiment 37, wherein the first antigen-binding domain comprises a heavy chain variable domain of SEQ ID NO: 1.

Embodiment 53 is the pharmaceutical composition of embodiment 52, wherein the first antigen-binding domain comprises a light chain variable domain of SEQ ID NO: 2.

Embodiment 54 is the pharmaceutical composition of any one of embodiments 37-53, wherein the composition provides for an increase in toxin liberation in the target mammalian cell as compared to a composition comprising the same amount of a control ABPC.

Embodiment 55 is the pharmaceutical composition of embodiment 54, wherein the composition provides for at least a 20% increase in toxin liberation in the target mammalian cell as compared to a composition comprising the same amount of a control ABPC.

Embodiment 56 is the pharmaceutical composition of embodiment 55, wherein the composition provides for at least a 50% increase in toxin liberation in the target mammalian cell as compared to a composition comprising the same amount of a control ABPC.

Embodiment 57 is the pharmaceutical composition of embodiment 54, wherein the composition provides for at least a 2-fold increase in toxin liberation in the target mammalian cell as compared to a composition comprising the same amount of a control ABPC.

Embodiment 58 is the pharmaceutical composition of embodiment 57, wherein the composition provides for at least a 5-fold increase in toxin liberation in the target mammalian cell as compared to a composition comprising the same amount of a control ABPC.

Embodiment 59 is the pharmaceutical composition of any one of embodiments 37-58, wherein the composition provides for an increase in target mammalian cell killing as compared to a composition comprising the same amount of a control ABPC.

Embodiment 60 is the pharmaceutical composition of embodiment 59, wherein the composition provides for at least a 20% increase in target mammalian cell killing as compared to a composition comprising the same amount of a control ABPC.

Embodiment 61 is the pharmaceutical composition of embodiment 60, wherein the composition provides for at least a 50% increase in target mammalian cell killing as compared to a composition comprising the same amount of a control ABPC.

Embodiment 62 is the pharmaceutical composition of embodiment 59, wherein the composition provides for at least a 2-fold increase in target mammalian cell killing as compared to a composition comprising the same amount of a control ABPC.

Embodiment 63 is the pharmaceutical composition of embodiment 62, wherein the composition provides for at least a 5-fold increase in target mammalian cell killing as compared to a composition comprising the same amount of a control ABPC.

Embodiment 64 is the pharmaceutical composition of any one of embodiments 37-63, wherein the composition provides for an increase in endolysosomal delivery in the target mammalian cell as compared to a composition comprising the same amount of a control ABPC.

Embodiment 65 is the pharmaceutical composition of embodiment 64, wherein the composition provides for at least a 20% increase in endolysosomal delivery in the target mammalian cell as compared to a composition comprising the same amount of a control ABPC.

Embodiment 66 is the pharmaceutical composition of embodiment 65, wherein the composition provides for at least a 50% increase in endolysosomal delivery in the target mammalian cell as compared to a composition comprising the same amount of a control ABPC.

Embodiment 67 is the pharmaceutical composition of embodiment 64, wherein the composition provides for at least a 2-fold increase in endolysosomal delivery in the target mammalian cell as compared to a composition comprising the same amount of a control ABPC.

Embodiment 68 is the pharmaceutical composition of embodiment 67, wherein the composition provides for at least a 5-fold increase in endolysosomal delivery in the target mammalian cell as compared to a composition comprising the same amount of a control ABPC.

Embodiment 69 is the pharmaceutical composition of any one of embodiments 37-68, wherein the composition results in a less of a reduction in the level of CD123 presented on the surface of the target mammalian cell as compared to a composition comprising the same amount of a control ABPC.

Embodiment 70 is the pharmaceutical composition of any one of embodiments 37-68, wherein the composition does not result in a detectable reduction in the level of the CD123 presented on the surface of the target mammalian cell.

Embodiment 71 is the pharmaceutical composition of any one of embodiments 1-70, wherein the target mammalian cell is a cancer cell.

Embodiment 72 is the pharmaceutical composition of any one of embodiments 1-71, wherein the dissociation rate of the antigen-binding domain at a pH of about 4.0 to about 6.5 is at least 10% faster than the dissociation rate of the antigen-binding domain at a pH of about 7.0 to about 8.0.

Embodiment 73 is the pharmaceutical composition of any one of embodiments 1-71, wherein the dissociation rate of the antigen-binding domain at a pH of about 4.0 to about 6.5 is at least 3-fold faster than the dissociation rate of the antigen-binding domain at a pH of about 7.0 to about 8.0.

Embodiment 74 is the pharmaceutical composition of any one of embodiments 1-71, wherein the dissociation rate of the antigen-binding domain at a pH of about 4.0 to about 6.5 is at least 10-fold faster than the dissociation rate of the antigen-binding domain at a pH of about 7.0 to about 8.0.

Embodiment 75 is the pharmaceutical composition of any one of embodiments 1-74, wherein the $K_D$ of the antigen-binding domain at a pH of about 4.0 to about 6.5 is at least 10% greater than the $K_D$ of the antigen-binding domain at a pH of about 7.0 to about 8.0.

Embodiment 76 is the pharmaceutical composition of any one of embodiments 1-74, wherein the $K_D$ of the antigen-binding domain at a pH of about 4.0 to about 6.5 is at least 3-fold greater than the $K_D$ of the antigen-binding domain at a pH of about 7.0 to about 8.0.

Embodiment 77 is the pharmaceutical composition of any one of embodiments 1-74, wherein the $K_D$ of the antigen-binding domain at a pH of about 4.0 to about 6.5 is at least 10-fold greater than the $K_D$ of the antigen-binding domain at a pH of about 7.0 to about 8.0.

Embodiment 78 is the pharmaceutical composition of any one of embodiments 1-77, wherein the ABPC is cytotoxic or cytostatic to the target mammalian cell.

Embodiment 79 is the pharmaceutical composition of any one of embodiments 1-78, wherein the ABPC is cross-reactive with a non-human primate CD123 and human CD123.

Embodiment 80 is the pharmaceutical composition of any one of embodiments 1-78, wherein the ABPC is cross-reactive with a non-human primate CD123, a human CD123, and one or both of rat CD123 and a mouse CD123.

Embodiment 81 is the pharmaceutical composition of embodiment 80, wherein the ABPC is cross-reactive with a non-human primate CD123, a human CD123, a rat CD123, and a mouse CD123.

Embodiment 82 is the pharmaceutical composition of any one of embodiments 1-81, wherein the antigen-binding domain binds to an epitope of CD123 that is present on the surface of cells from an Old World Monkey.

Embodiment 83 is the pharmaceutical composition of any one of embodiments 1-82, wherein the ABPC comprises a single polypeptide.

Embodiment 84 is the pharmaceutical composition of embodiment 83, wherein the antigen-binding domain is selected from the group consisting of: a VH domain, a VHH domain, a VNAR domain, and a scFv.

Embodiment 85 is the pharmaceutical composition of embodiment 83 or 84, wherein the ABPC is a BiTe, a $(scFv)_2$, a nanobody, a nanobody-HSA, a DART, a TandAb, a scDiabody, a scDiabody-CH3, scFv-CH-CL-scFv, a HSA-body, scDiabody-HSA, or a tandem-scFv.

Embodiment 86 is the pharmaceutical composition of any one of embodiments 1-82, wherein the ABPC comprises two or more polypeptides.

Embodiment 87 is the pharmaceutical composition of embodiment 86, wherein the ABPC is selected from the group of an antibody, a VHH-scAb, a VHH-Fab, a Dual scFab, a F(ab')2, a diabody, a crossMab, a DAF (two-in-one), a DAF (four-in-one), a DutaMab, a DT-IgG, a knobs-in-holes common light chain, a knobs-in-holes assembly, a charge pair, a Fab-arm exchange, a SEEDbody, a LUZ-Y, a Fcab, a κλ-body, an orthogonal Fab, a DVD-IgG, a IgG(H)-scFv, a scFv-(H)IgG, IgG(L)-scFv, scFv-(L)IgG, IgG(L,H)-Fv, IgG(H)-V, V(H)-IgG, IgG(L)-V, V(L)-IgG, KIH IgG-scFab, 2scFv-IgG, IgG-2scFv, scFv4-Ig, Zybody, DVI-IgG, Diabody-CH3, a triple body, a miniantibody, a minibody, a TriBi minibody, scFv-CH3 KIH, Fab-scFv, a F(ab')2-scFv2, a scFv-KIH, a Fab-scFv-Fc, a tetravalent HCAb, a scDiabody-Fc, a Diabody-Fc, a tandem scFv-Fc, a VHH-Fc, a tandem VHH-Fc, a VHH-Fc KiH, a Fab-VHH-Fc, an Intrabody, a dock and lock, an ImmTAC, an IgG-IgG conjugate, a Cov-X-Body, a scFv1-PEG-scFv2, an Adnectin, a DARPin, a fibronectin, and a DEP conjugate.

Embodiment 88 is the pharmaceutical composition of any one of embodiments 19-87, wherein at least one polypeptide of the ABPC is conjugated to the toxin, the radioisotope, the drug, or the small molecule via a cleavable linker.

Embodiment 89 is the pharmaceutical composition of any one of embodiments 19-87, wherein at least one polypeptide of the ABPC is conjugated to the toxin, the radioisotope, the drug, or the small molecule via a non-cleavable linker.

Embodiment 90 is the pharmaceutical composition of any of embodiments 1-89, wherein the half-life of the ABPC in vivo is decreased as compared to the half-life of a control ABPC in vivo.

Embodiment 91 is the pharmaceutical composition of embodiment 90, wherein the half-life of the ABPC in vivo is decreased about 5% to about 95% as compared to the half-life of a control ABPC in vivo.

Embodiment 92 is the pharmaceutical composition of embodiment 90, wherein the half-life of the ABPC in vivo is decreased about 10% to about 95% as compared to the half-life of a control ABPC in vivo.

Embodiment 93 is the pharmaceutical composition of embodiment 90, wherein the half-life of the ABPC in vivo is decreased about 30% to about 95% as compared to the half-life of a control ABPC in vivo.

Embodiment 94 is the pharmaceutical composition of embodiment 90, wherein the half-life of the ABPC in vivo is decreased about 50% to about 95% as compared to the half-life of a control ABPC in vivo.

Embodiment 95 is the pharmaceutical composition of embodiment 90, wherein the half-life of the ABPC in vivo is decreased about 70% to about 95% as compared to the half-life of a control ABPC in vivo.

Embodiment 96 is the pharmaceutical composition of any one of embodiments 20-95, wherein the control ABPC is capable of specifically binding to CD123 or an epitope of CD123 presented on the surface of a target mammalian cell, wherein: (a) the control ABPC comprises a first antigen-binding domain: (b) the dissociation rate of the first antigen-binding domain of the control ABPC at a pH of about 4.0 to about 6.5 is no more than 3-fold faster than the dissociation rate at a pH of about 7.0 to about 8.0; and (c) the dissociation constant ($K_D$) of the first antigen-binding domain of the control ABPC at a pH of about 4.0 to about 6.5 is no more than 3-fold greater than the $K_D$ at a pH of about 7.0 to about 8.0.

Embodiment 97 is the pharmaceutical composition of any one of embodiments 20-95, wherein the control ABPC is capable of specifically binding to CD123 or an epitope of CD123 presented on the surface of a target mammalian cell, wherein: (a) the control ABPC comprises a first antigen-binding domain; (b) the dissociation rate of the first antigen-binding domain of the control ABPC at a pH of about 4.0 to about 6.5 is no more than 2-fold faster than the dissociation rate at a pH of about 7.0 to about 8.0; and (c) the dissociation constant ($K_D$) of the first antigen-binding domain of the control ABPC at a pH of about 4.0 to about 6.5 is no more than 2-fold greater than the $K_D$ at a pH of about 7.0 to about 8.0.

Embodiment 98 is the pharmaceutical composition of any one of embodiments 20-95, wherein the control ABPC is capable of specifically binding to CD123 or an epitope of CD123 presented on the surface of a target mammalian cell, wherein: (a) the control ABPC comprises a first antigen-binding domain; (b) the dissociation rate of the first antigen-binding domain of the control ABPC at a pH of about 4.0 to about 6.5 is no more than 1-fold faster than the dissociation rate at a pH of about 7.0 to about 8.0; and (c) the dissociation constant ($K_D$) of the first antigen-binding domain of the control ABPC at a pH of about 4.0 to about 6.5 is no more than 1-fold greater than the $K_D$ at a pH of about 7.0 to about 8.0.

Embodiment 99 is the pharmaceutical composition of any one of embodiments 20-95, wherein the control ABPC is IMGN632.

Embodiment 100 is the pharmaceutical composition of any one of embodiments 1-99, wherein the ABPC further comprises a second antigen-binding domain.

Embodiment 101 is a kit comprising at least one dose of the pharmaceutical composition of any one of embodiments 1-100.

Embodiment 102 is an antigen-binding protein construct (ABPC) comprising: a first antigen-binding domain that is capable of specifically binding CD123 or an epitope of CD123 presented on the surface of a target mammalian cell, wherein: (a) the dissociation rate of the first antigen-binding domain at a pH of about 4.0 to about 6.5 is faster than the dissociation rate at a pH of about 7.0 to about 8.0; or (b) the dissociation constant ($K_D$) of the first antigen-binding domain at a pH of about 4.0 to about 6.5 is greater than the $K_D$ at a pH of about 7.0 to about 8.0.

Embodiment 103 is the ABPC of embodiment 102, wherein the first antigen-binding domain comprises a heavy chain variable domain of IMGN632 with one or more amino acids substituted with a histidine.

Embodiment 104 is the ABPC of embodiment 102, wherein the first antigen-binding domain comprises a light chain variable domain of IMGN632 with one or more amino acids substituted with a histidine.

Embodiment 105 is the ABPC of embodiment 102, wherein the first antigen-binding domain comprises: a heavy chain variable domain of IMGN632 with one or more amino acids substituted with a histidine; and a light chain variable domain of IMGN632 with one or more amino acids substituted with a histidine.

Embodiment 106 is the ABPC of embodiment 103 or 105, wherein the heavy chain variable domain of IMGN632 comprises SEQ ID NO: 1.

Embodiment 107 is the ABPC of embodiment 104 or 105, wherein the light chain variable domain of IMGN632 comprises SEQ ID NO: 2.

Embodiment 108 is the ABPC of embodiment 102, wherein the first antigen-binding domain comprises a heavy chain variable domain comprising a CDR1, a CDR2, and a CDR3 of SEQ ID NOs: 3-5, respectively, with collectively a total of one or more amino acid positions in SEQ ID NOs: 3-5 substituted with a histidine.

Embodiment 109 is the ABPC of embodiment 102, wherein the first CD123-binding domain comprises a light chain variable domain comprising a CDR1, a CDR2, and a CDR3 of SEQ ID NOs: 6-8, respectively, with collectively a total of one or more amino acid positions in SEQ ID NOs: 6-8 substituted with a histidine.

Embodiment 110 is the ABPC of embodiment 102, wherein the first CD123-binding domain comprises: a heavy chain variable domain comprising a CDR1, a CDR2, and a CDR3 of SEQ ID NOs: 3-5, respectively, with collectively a total of one or more amino acid positions in SEQ ID NOs: 3-5 substituted with a histidine; and a light chain variable domain comprising a CDR1, a CDR2, and a CDR3 of SEQ ID NOs: 6-8, respectively, with collectively a total of one or more amino acid positions in SEQ ID NOs: 6-8 substituted with a histidine.

Embodiment 111 is the ABPC of embodiment 102, 103, or 108, wherein the first antigen-binding domain comprises a heavy chain variable domain that is at least 90% identical to SEQ ID NO: 1, wherein the heavy chain variable domain includes a histidine at one or more positions in SEQ ID NO: 1 selected from the group consisting of: 27, 28, 29, 30, 33, 53, 54, 97, 100, 103, 104, 105, 106, 107, 108, or 109.

Embodiment 112 is the ABPC of embodiment 102, 104, or 109, wherein the first antigen-binding domain comprises a light chain variable domain that is at least 90% identical to SEQ ID NO: 2, wherein the light chain variable domain includes a histidine at one or more positions in SEQ ID NO: 2.

Embodiment 113 is the ABPC of embodiment 102, 103, or 108, wherein the first antigen-binding domain comprises a heavy chain variable domain that is at least 90% identical to SEQ ID NO: 1, wherein the heavy chain variable domain includes a histidine at two or more positions in SEQ ID NO: 1.

Embodiment 114 is the ABPC of embodiment 102, 105, or 110, wherein the first antigen-binding domain comprises: a heavy chain variable domain that is at least 90% identical to SEQ ID NO: 1, wherein the heavy chain variable domain includes a histidine at one or more positions in SEQ ID NO: 1 selected from the group consisting of: 27, 28, 29, 30, 33, 53, 54, 97, 100, 103, 104, 105, 106, 107, 108, or 109; and a light chain variable domain that is at least 90% identical to SEQ ID NO: 2, wherein the light chain variable domain includes a histidine at one or more positions in SEQ ID NO: 2.

Embodiment 115 is the ABPC of embodiment 102, wherein the first antigen-binding domain comprises a heavy chain variable domain of SEQ ID NO: 14, SEQ ID NO: 15, SEQ ID NO: 16, SEQ ID NO: 17, SEQ ID NO: 20, SEQ ID NO: 22, SEQ ID NO: 26, SEQ ID NO: 27, SEQ ID NO: 40, SEQ ID NO: 43, SEQ ID NO: 46, SEQ ID NO: 47, SEQ ID NO: 48, SEQ ID NO: 49, SEQ ID NO: 50, SEQ ID NO: 51, or SEQ ID NO: 52.

Embodiment 116 is the ABPC of embodiment 102 or 115, wherein the first antigen-binding domain comprises a light chain variable domain of SEQ ID NO: 2.

Embodiment 117 is the ABPC of embodiment 102, wherein the first antigen-binding domain comprises a heavy chain variable domain of SEQ ID NO: 1.

Embodiment 118 is the ABPC of embodiment 117, wherein the first antigen-binding domain comprises a light chain variable domain of SEQ ID NO: 2.

Embodiment 119 is the ABPC of any one of embodiments 102-118, wherein the ABPC is degraded in the target mammalian cell following internalization of the ABPC by the target mammalian cell.

Embodiment 120 is the ABPC of any one of embodiments 102-119, wherein the ABPC further comprises a conjugated toxin, radioisotope, drug, or small molecule.

Embodiment 121 is the ABPC of embodiment 120, wherein a composition comprising the ABPC provides for an increase in toxin liberation in the target mammalian cell as compared to a composition comprising the same amount of a control ABPC.

Embodiment 122 is the ABPC of embodiment 121, wherein a composition comprising the ABPC provides for at least a 20% increase in toxin liberation in the target mammalian cell as compared to a composition comprising the same amount of a control ABPC.

Embodiment 123 is the ABPC of embodiment 122, wherein a composition comprising the ABPC provides for at least a 50% increase in toxin liberation in the target mammalian cell as compared to a composition comprising the same amount of a control ABPC.

Embodiment 124 is the ABPC of embodiment 121, wherein a composition comprising the ABPC provides for at least a 2-fold increase in toxin liberation in the target mammalian cell as compared to a composition comprising the same amount of a control ABPC.

Embodiment 125 is the ABPC of embodiment 124, wherein a composition comprising the ABPC provides for at least a 5-fold increase in toxin liberation in the target mammalian cell as compared to a composition comprising the same amount of a control ABPC.

Embodiment 126 is the ABPC of any one of embodiments 120-125, wherein a composition comprising the ABPC provides for an increase in target mammalian cell killing as compared to a composition comprising the same amount of a control ABPC.

Embodiment 127 is the ABPC of embodiment 126, wherein a composition comprising the ABPC provides for at least a 20% increase in target mammalian cell killing as compared to a composition comprising the same amount of a control ABPC.

Embodiment 128 is the ABPC of embodiment 127, wherein a composition comprising the ABPC provides for at least a 50% increase in target mammalian cell killing as compared to a composition comprising the same amount of a control ABPC.

Embodiment 129 is the ABPC of embodiment 126, wherein a composition comprising the ABPC provides for at least a 2-fold increase in target mammalian cell killing as compared to a composition comprising the same amount of a control ABPC.

Embodiment 130 is the ABPC of embodiment 129, wherein a composition comprising the ABPC provides for at least a 5-fold increase in target mammalian cell killing as compared to a composition comprising the same amount of a control ABPC.

Embodiment 131 is the ABPC of any one of embodiments 102-130, wherein a composition comprising the ABPC provides for an increase in endolysosomal delivery in the target mammalian cell as compared to a composition comprising the same amount of a control ABPC.

Embodiment 132 is the ABPC of embodiment 131, wherein a composition comprising the ABPC provides for at least a 20% increase in endolysosomal delivery in the target mammalian cell as compared to a composition comprising the same amount of a control ABPC.

Embodiment 133 is the ABPC of embodiment 132, wherein a composition comprising the ABPC provides for at least a 50% increase in endolysosomal delivery in the target mammalian cell as compared to a composition comprising the same amount of a control ABPC.

Embodiment 134 is the ABPC of embodiment 131, wherein a composition comprising the ABPC provides for at least a 2-fold increase in endolysosomal delivery in the target mammalian cell as compared to a composition comprising the same amount of a control ABPC.

Embodiment 135 is the ABPC of embodiment 134, wherein a composition comprising the ABPC provides for at least a 5-fold increase in endolysosomal delivery in the target mammalian cell as compared to a composition comprising the same amount of a control ABPC.

Embodiment 136 is the ABPC of any one of embodiments 102-135, wherein a composition comprising the ABPC results in a less of a reduction in the level of CD123 presented on the surface of the target mammalian cell as compared to a composition comprising the same amount of a control ABPC.

Embodiment 137 is the ABPC of any one of embodiments 102-135, wherein a composition comprising the ABPC does not result in a detectable reduction in the level of the CD123 presented on the surface of the target mammalian cell.

Embodiment 138 is an antigen-binding protein construct (ABPC) comprising: a first antigen-binding domain that is capable of specifically binding CD123 or an epitope of CD123 presented on the surface of a target mammalian cell;

and a conjugated toxin, radioisotope, drug, or small molecule, wherein: (a) the dissociation rate of the first antigen-binding domain at a pH of about 4.0 to about 6.5 is faster than the dissociation rate at a pH of about 7.0 to about 8.0; or the dissociation constant ($K_D$) of the first antigen-binding domain at a pH of about 4.0 to about 6.5 is greater than the $K_D$ at a pH of about 7.0 to about 8.0; and (b) the composition provides for one or more of: an increase in toxin liberation in the target mammalian cell as compared to a composition comprising the same amount of a control ABPC; an increase in target mammalian cell killing as compared to a composition comprising the same amount of a control ABPC; and an increase in endolysosomal delivery in the target mammalian cell as compared to a composition comprising the same amount of a control ABPC.

Embodiment 139 is the ABPC of embodiment 138, wherein the first antigen-binding domain comprises a heavy chain variable domain of IMGN632 with one or more amino acids substituted with a histidine.

Embodiment 140 is the ABPC of embodiment 138, wherein the first antigen-binding domain comprises a light chain variable domain of IMGN632 with one or more amino acids substituted with a histidine.

Embodiment 141 is the ABPC of embodiment 138, wherein the first antigen-binding domain comprises: a heavy chain variable domain of IMGN632 with one or more amino acids substituted with a histidine; and a light chain variable domain of IMGN632 with one or more amino acids substituted with a histidine.

Embodiment 142 is the ABPC of embodiment 139 or 141, wherein the heavy chain variable domain of IMGN632 comprises SEQ ID NO: 1.

Embodiment 143 is the ABPC of embodiment 140 or 141, wherein the light chain variable domain of IMGN632 comprises SEQ ID NO: 2.

Embodiment 144 is the ABPC of embodiment 138, wherein the first antigen-binding domain comprises a heavy chain variable domain comprising a CDR1, a CDR2, and a CDR3 of SEQ ID NOs: 3-5, respectively, with collectively a total of one or more amino acid positions in SEQ ID NOs: 3-5 substituted with a histidine.

Embodiment 145 is the ABPC of embodiment 138, wherein the first CD123-binding domain comprises a light chain variable domain comprising a CDR1, a CDR2, and a CDR3 of SEQ ID NOs: 6-8, respectively, with collectively a total of one or more amino acid positions in SEQ ID NOs: 6-8 substituted with a histidine.

Embodiment 146 is the ABPC of embodiment 138, wherein the first CD123-binding domain comprises: a heavy chain variable domain comprising a CDR1, a CDR2, and a CDR3 of SEQ ID NOs: 3-5, respectively, with collectively a total of one or more amino acid positions in SEQ ID NOs: 3-5 substituted with a histidine; and a light chain variable domain comprising a CDR1, a CDR2, and a CDR3 of SEQ ID NOs: 6-8, respectively, with collectively a total of one or more amino acid positions in SEQ ID NOs: 6-8 substituted with a histidine.

Embodiment 147 is the ABPC of embodiment 138, 139, or 144, wherein the first antigen-binding domain comprises a heavy chain variable domain that is at least 90% identical to SEQ ID NO: 1, wherein the heavy chain variable domain includes a histidine at one or more positions in SEQ ID NO: 1 selected from the group consisting of: 27, 28, 29, 30, 33, 53, 54, 97, 100, 103, 104, 105, 106, 107, 108, or 109.

Embodiment 148 is the ABPC of embodiment 138, 140, or 145, wherein the first antigen-binding domain comprises a light chain variable domain that is at least 90% identical to SEQ ID NO: 2, wherein the light chain variable domain includes a histidine at one or more positions in SEQ ID NO: 2.

Embodiment 149 is the ABPC of embodiment 138, 139, or 144, wherein the first antigen-binding domain comprises a heavy chain variable domain that is at least 90% identical to SEQ ID NO: 1, wherein the heavy chain variable domain includes a histidine at two more positions in SEQ ID NO: 1.

Embodiment 150 is the ABPC of embodiment 138, 141, or 146, wherein the first antigen-binding domain comprises: a heavy chain variable domain that is at least 90% identical to SEQ ID NO: 1, wherein the heavy chain variable domain includes a histidine at one or more positions in SEQ ID NO: 1 selected from the group consisting of: 27, 28, 29, 30, 33, 53, 54, 97, 100, 103, 104, 105, 106, 107, 108, or 109; and a light chain variable domain that is at least 90% identical to SEQ ID NO: 2, wherein the light chain variable domain includes a histidine at one or more positions in SEQ ID NO: 2.

Embodiment 151 is the ABPC of embodiment 138, wherein the first antigen-binding domain comprises a heavy chain variable domain of SEQ ID NO: 14, SEQ ID NO: 15, SEQ ID NO: 16, SEQ ID NO: 17, SEQ ID NO: 20, SEQ ID NO: 22, SEQ ID NO: 26, SEQ ID NO: 27, SEQ ID NO: 40, SEQ ID NO: 43, SEQ ID NO: 46, SEQ ID NO: 47, SEQ ID NO: 48, SEQ ID NO: 49, SEQ ID NO: 50, SEQ ID NO: 51, or SEQ ID NO: 52.

Embodiment 152 is the ABPC of embodiment 138 or 151, wherein the first antigen-binding domain comprises a light chain variable domain of SEQ ID NO: 2.

Embodiment 153 is the ABPC of embodiment 138, wherein the first antigen-binding domain comprises a heavy chain variable domain of SEQ ID NO: 1.

Embodiment 154 is the ABPC of embodiment 153, wherein the first antigen-binding domain comprises a light chain variable domain of SEQ ID NO: 2.

Embodiment 155 is the ABPC of any one of embodiments 138-154, wherein a composition comprising the ABPC provides for an increase in toxin liberation in the target mammalian cell as compared to a composition comprising the same amount of a control ABPC.

Embodiment 156 is the ABPC of embodiment 155, wherein a composition comprising the ABPC provides for at least a 20% increase in toxin liberation in the target mammalian cell as compared to a composition comprising the same amount of a control ABPC.

Embodiment 157 is the ABPC of embodiment 156, wherein a composition comprising the ABPC provides for at least a 50% increase in toxin liberation in the target mammalian cell as compared to a composition comprising the same amount of a control ABPC.

Embodiment 158 is the ABPC of embodiment 155, wherein a composition comprising the ABPC provides for at least a 2-fold increase in toxin liberation in the target mammalian cell as compared to a composition comprising the same amount of a control ABPC.

Embodiment 159 is the ABPC of embodiment 158, wherein a composition comprising the ABPC provides for at least a 5-fold increase in toxin liberation in the target mammalian cell as compared to a composition comprising the same amount of a control ABPC.

Embodiment 160 is the ABPC of any one of embodiments 138-159, wherein a composition comprising the ABPC provides for an increase in target mammalian cell killing as compared to a composition comprising the same amount of a control ABPC.

Embodiment 161 is the ABPC of embodiment 160, wherein a composition comprising the ABPC provides for at least a 20% increase in target mammalian cell killing as compared to a composition comprising the same amount of a control ABPC.

Embodiment 162 is the ABPC of embodiment 161, wherein a composition comprising the ABPC provides for at least a 50% increase in target mammalian cell killing as compared to a composition comprising the same amount of a control ABPC.

Embodiment 163 is the ABPC of embodiment 160, wherein a composition comprising the ABPC provides for at least a 2-fold increase in target mammalian cell killing as compared to a composition comprising the same amount of a control ABPC.

Embodiment 164 is the ABPC of embodiment 163, wherein a composition comprising the ABPC provides for at least a 5-fold increase in target mammalian cell killing as compared to a composition comprising the same amount of a control ABPC.

Embodiment 165 is the ABPC of any one of embodiments 138-164, wherein a composition comprising the ABPC provides for an increase in endolysosomal delivery in the target mammalian cell as compared to a composition comprising the same amount of a control ABPC.

Embodiment 166 is the ABPC of embodiment 165, wherein a composition comprising the ABPC provides for at least a 20% increase in endolysosomal delivery in the target mammalian cell as compared to a composition comprising the same amount of a control ABPC.

Embodiment 167 is the ABPC of embodiment 166, wherein a composition comprising the ABPC provides for at least a 50% increase in endolysosomal delivery in the target mammalian cell as compared to a composition comprising the same amount of a control ABPC.

Embodiment 168 is the ABPC of embodiment 165, wherein a composition comprising the ABPC provides for at least a 2-fold increase in endolysosomal delivery in the target mammalian cell as compared to a composition comprising the same amount of a control ABPC.

Embodiment 169 is the ABPC of embodiment 168, wherein a composition comprising the ABPC provides for at least a 5-fold increase in endolysosomal delivery in the target mammalian cell as compared to a composition comprising the same amount of a control ABPC.

Embodiment 170 is the ABPC of any one of embodiments 138-169, wherein a composition comprising the ABPC results in a less of a reduction in the level of CD123 presented on the surface of the target mammalian cell as compared to a composition comprising the same amount of a control ABPC.

Embodiment 171 is the ABPC of any one of embodiments 138-169, wherein a composition comprising the ABPC does not result in a detectable reduction in the level of the CD123 presented on the surface of the target mammalian cell.

Embodiment 172 is the ABPC of any one of embodiments 102-171, wherein the target mammalian cell is a cancer cell.

Embodiment 173 is the ABPC of any one of embodiments 102-172, wherein the dissociation rate of the antigen-binding domain at a pH of about 4.0 to about 6.5 is at least 10% faster than the dissociation rate of the antigen-binding domain at a pH of about 7.0 to about 8.0.

Embodiment 174 is the ABPC of any one of embodiments 102-172, wherein the dissociation rate of the antigen-binding domain at a pH of about 4.0 to about 6.5 is at least 3-fold faster than the dissociation rate of the antigen-binding domain at a pH of about 7.0 to about 8.0.

Embodiment 175 is the ABPC of any one of embodiments 102-172, wherein the dissociation rate of the antigen-binding domain at a pH of about 4.0 to about 6.5 is at least 10-fold faster than the dissociation rate of the antigen-binding domain at a pH of about 7.0 to about 8.0.

Embodiment 176 is the ABPC of any one of embodiments 102-175, wherein the $K_D$ of the antigen-binding domain at a pH of about 4.0 to about 6.5 is at least 10% greater than the $K_D$ of the antigen-binding domain at a pH of about 7.0 to about 8.0.

Embodiment 177 is the ABPC of any one of embodiments 102-175, wherein the $K_D$ of the antigen-binding domain at a pH of about 4.0 to about 6.5 is at least 3-fold greater than the $K_D$ of the antigen-binding domain at a pH of about 7.0 to about 8.0.

Embodiment 178 is the ABPC of any one of embodiments 102-175, wherein the $K_D$ of the antigen-binding domain at a pH of about 4.0 to about 6.5 is at least 10-fold greater than the $K_D$ of the antigen-binding domain at a pH of about 7.0 to about 8.0.

Embodiment 179 is the ABPC of any one of embodiments 102-178, wherein the ABPC is cytotoxic or cytostatic to the target mammalian cell.

Embodiment 180 is the ABPC of any one of embodiments 102-179, wherein the ABPC is cross-reactive with a non-human primate CD123 and human CD123.

Embodiment 181 is the pharmaceutical composition of any one of embodiments 102-179, wherein the ABPC is cross-reactive with a non-human primate CD123, a human CD123, and one or both of rat CD123 and a mouse CD123.

Embodiment 182 is the pharmaceutical composition of embodiment 181, wherein the ABPC is cross-reactive with a non-human primate CD123, a human CD123, a rat CD123, and a mouse CD123.

Embodiment 183 is the ABPC of any one of embodiments 102-182, wherein the antigen-binding domain binds to an epitope of CD123 that is present on the surface of cells from an Old World Monkey.

Embodiment 184 is the ABPC of any one of embodiments 102-183, wherein the ABPC comprises a single polypeptide.

Embodiment 185 is the ABPC of embodiment 184, wherein the antigen-binding domain is selected from the group consisting of: a VH domain, a VHH domain, a VNAR domain, and a scFv.

Embodiment 186 is the ABPC of embodiment 184 or 185, wherein the ABPC is a BiTe, a $(scFv)_2$, a nanobody, a nanobody-HSA, a DART, a TandAb, a scDiabody, a scDiabody-CH3, scFv-CH-CL-scFv, a HSAbody, scDiabody-HSA, or a tandem-scFv.

Embodiment 187 is the ABPC of any one of embodiments 102-183, wherein the ABPC comprises two or more polypeptides.

Embodiment 188 is the ABPC of embodiment 187, wherein the ABPC is selected from the group of an antibody, a VHH-scAb, a VHH-Fab, a Dual scFab, a $F(ab')_2$, a diabody, a crossMab, a DAF (two-in-one), a DAF (four-in-one), a DutaMab, a DT-IgG, a knobs-in-holes common light chain, a knobs-in-holes assembly, a charge pair, a Fab-arm exchange, a SEEDbody, a LUZ-Y, a Fcab, a ick-body, an orthogonal Fab, a DVD-IgG, a IgG(H)-scFv, a scFv-(H)IgG, IgG(L)-scFv, scFv-(L)IgG, IgG(L,H)-Fv, IgG(H)-V, V(H)-IgG, IgG(L)-V, V(L)-IgG, KIH IgG-scFab, 2scFv-IgG, IgG-2scFv, scFv4-Ig, Zybody, DVI-IgG, Diabody-CH3, a triple body, a miniantibody, a minibody, a TriBi minibody, scFv-CH3 KIH, Fab-scFv, a F(ab')2-scFv2, a scFv-KIH, a Fab-scFv-Fc, a tetravalent HCAb, a scDiabody-Fc, a Diabody-Fc, a tandem scFv-Fc, a VHH-Fc, a tandem VHH-Fc, a VHH-Fc KiH, a Fab-VHH-Fc, an Intrabody, a dock and lock, an ImmTAC, an IgG-IgG conjugate, a Cov-X-Body, a scFv1-PEG-scFv2, an Adnectin, a DARPin, a fibronectin, and a DEP conjugate.

Embodiment 189 is the ABPC of any one of embodiments 120-188, wherein at least one polypeptide of the ABPC is conjugated to the toxin, the radioisotope, the drug, or the small molecule via a cleavable linker.

Embodiment 190 is the ABPC of any one of embodiments 120-188, wherein at least one polypeptide of the ABPC is conjugated to the toxin, the radioisotope, the drug, or the small molecule via a non-cleavable linker.

Embodiment 191 is the ABPC of any of embodiments 102-190, wherein the half-life of the ABPC in vivo is decreased as compared to the half-life of a control ABPC in vivo.

Embodiment 192 is the ABPC of embodiment 191, wherein the half-life of the ABPC in vivo is decreased about 5% to about 95% as compared to the half-life of a control ABPC in vivo.

Embodiment 193 is the ABPC of embodiment 191, wherein the half-life of the ABPC in vivo is decreased about 10% to about 95% as compared to the half-life of a control ABPC in vivo.

Embodiment 194 is the ABPC of embodiment 191, wherein the half-life of the ABPC in vivo is decreased about 30% to about 95% as compared to the half-life of a control ABPC in vivo.

Embodiment 195 is the ABPC of embodiment 191, wherein the half-life of the ABPC in vivo is decreased about 50% to about 95% as compared to the half-life of a control ABPC in vivo.

Embodiment 196 is the ABPC of embodiment 191, wherein the half-life of the ABPC in vivo is decreased about 70% to about 95% as compared to the half-life of a control ABPC in vivo.

Embodiment 197 is the ABPC of any one of embodiments 121-196, wherein the control ABPC is capable of specifically binding to CD123 or an epitope of CD123 presented on the surface of a target mammalian cell, wherein: (a) the control ABPC comprises a first antigen-1c:1 binding domain; (b) the dissociation rate of the first antigen-binding domain of the control ABPC at a pH of about 4.0 to about 6.5 is no more than 3-fold faster than the dissociation rate at a pH of about 7.0 to about 8.0; and (c) the dissociation constant ($K_D$) of the first antigen-binding domain of the control ABPC at a pH of about 4.0 to about 6.5 is no more than 3-fold greater than the $K_D$ at a pH of about 7.0 to about 8.0.

Embodiment 198 is the ABPC of any one of embodiments 121-196, wherein the control ABPC is capable of specifically binding to CD123 or an epitope of CD123 presented on the surface of a target mammalian cell, wherein: (a) the control ABPC comprises a first antigen-binding domain; (b) the dissociation rate of the first antigen-binding domain of the control ABPC at a pH of about 4.0 to about 6.5 is no more than 2-fold faster than the dissociation rate at a pH of about 7.0 to about 8.0; and (c) the dissociation constant ($K_D$) of the first antigen-binding domain of the ABPC at a pH of about 4.0 to about 6.5 is no more than 2-fold greater than the $K_D$ at a pH of about 7.0 to about 8.0.

Embodiment 199 is the ABPC of any one of embodiments 121-196, wherein the control ABPC is capable of specifically binding to CD123 or an epitope of CD123 presented on the surface of a target mammalian cell, wherein: (a) the control ABPC comprises a first antigen-binding domain; (b) the dissociation rate of the first antigen-binding domain of the control ABPC at a pH of about 4.0 to about 6.5 is no more than 1-fold faster than the dissociation rate at a pH of about 7.0 to about 8.0; and (c) the dissociation constant ($K_D$) of the first antigen-binding domain of the control ABPC at a pH of about 4.0 to about 6.5 is no more than 1-fold greater than the $K_D$ at a pH of about 7.0 to about 8.0.

Embodiment 200 is the ABPC of any one of embodiments 121-196, wherein the control ABPC is IMGN632.

Embodiment 201 is the ABPC of any one of embodiments 102-200, wherein the ABPC further comprises a second antigen-binding domain.

Embodiment 202 is a kit comprising at least one dose of the ABPC of any one of embodiments 102-201.

Embodiment 203 is a method of treating a cancer characterized by having a population of cancer cells that have CD123 or an epitope of CD123 presented on their surface, the method comprising: administering a therapeutically effective amount of the pharmaceutical composition of any one of embodiments 1-100 or the ABPC of any one of embodiments 102-201 to a subject identified as having a cancer characterized by having the population of cancer cells.

Embodiment 204 is a method of reducing the volume of a tumor in a subject, wherein the tumor is characterized by having a population of cancer cells that have CD123 or an epitope of CD123 presented on their surface, the method comprising: administering a therapeutically effective amount of the pharmaceutical composition of any one of embodiments 1-100 or the ABPC of any one of embodiments 102-201 to a subject identified as having a cancer characterized by having the population of cancer cells.

Embodiment 205 is a method of inducing cell death in a cancer cell in a subject, wherein the cancer cell has CD123 or an epitope of CD123 presented on its surface, wherein the method comprises: administering a therapeutically effective amount of the pharmaceutical composition of any one of embodiments 1-98 or the ABPC of any one of embodiments 102-201 to a subject identified as having a cancer characterized by having a population of the cancer cells.

Embodiment 206 is the method of any one of embodiments 203-205, wherein the cancer is a primary tumor.

Embodiment 207 is the method of any one of embodiments 203-205, wherein the cancer is a metastasis.

Embodiment 208 is the method of any one of embodiments 203-207, wherein the cancer is a non-T-cell-infiltrating tumor.

Embodiment 209 is the method of any one of embodiments 203-207, wherein the cancer is a T-cell infiltrating tumor.

Embodiment 210 is a method of decreasing the risk of developing a metastasis or decreasing the risk of developing an additional metastasis in a subject having a cancer, wherein the cancer is characterized by having a population of cancer cells that have CD123 or an epitope of CD123 presented on their surface the method comprising: administering a therapeutically effective amount of the pharmaceutical composition of any one of embodiments 1-100 or the ABPC of any one of embodiments 102-201 to a subject identified as having a cancer characterized by having the population of cancer cells.

Embodiment 211 is the method of embodiment 210, wherein the cancer is a non-T-cell-infiltrating tumor.

Embodiment 212 is the method of embodiment 210, wherein the cancer is a T-cell infiltrating tumor.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

Sequence Appendix

>Heavy Chain of IMGN632 IgG (SEQ ID NO: 1)
QVQLVQSGAEVKKPGASVKVSCKASGYIFTSSIMHWVRQAPGQGLEWIGYIKPYNDGT
KYNEKFKGRATLTSDRSTSTAYMELSSLRSEDTAVYYCAREGGNDYYDTMDYWGQGT
LVTVSS >Light Chain of IMGN632 IgG (SEQ ID NO: 2)
DIQMTQSPSSLSASVGDRVTITCRASQDINSYLSWFQQKPGKAPKTLIYRVNRLVDGVPS
RFSGSGSGNDYTLTISSLQPEDFATYYCLQYDAFPYTFGQGTKVEIK >Heavy Chain CDR1 of IMGN632 (SEQ ID NO: 3)
GYIFTSSIMH >Heavy Chain CDR2 of IMGN632 (SEQ ID NO: 4)
YIKPYNDGTKYNEKFKG >Heavy Chain CDR3 of IMGN632 (SEQ ID NO: 5)
AREGGNDYYDTMDY >Light Chain CDR1 of IMGN632 (SEQ ID NO: 6)
RASQDINSYLS >Light Chain CDR2 of IMGN632 (SEQ ID NO: 7)
RVNRLVD >Light Chain CDR3 of IMGN632 (SEQ ID NO: 8)
LQYDAFPYT >Mature Human CD123 (SEQ ID NO: 9)
TKEDPNPPITNLRMKAKAQQLTWDLNRNVTDIECVKDADYSMPAVNNSYCQFGAISLC
EVTNYTVRVANPPFSTWILFPENSGKPWAGAENLTCWIHDVDFLSCSWAVGPGAPADV
QYDLYLNVANRRQQYECLHYKTDAQGTRIGCRFDDISRLSSGSQSSHILVRGRSAAFGIP
CTDKFVVFSQIEILTPPNMTAKCNKTHSFMHWKMRSHFNRKFRYELQIQKRMQPVITEQ
VRDRTSFQLLNPGTYTVQIRARERVYEFLSAWSTPQRFECDQEEGANTRAWRTSLLIAL
GTLLALVCVFVICRRYLVMQRLFPRIPHMKDPIGDSFQNDKLVVWEAGKAGLEECLVTE
VQVVQKT >cDNA Encoding Mature Human CD123 (SEQ ID NO: 10)
ACGAAGGAAGATCCAAACCCACCAATCACGAACCTAAGGATGAAAGCAAAGGCTC
AGCAGTTGACCTGGGACCTTAACAGAAATGTGACCGATATCGAGTGTGTTAAAGAC
GCCGACTATTCTATGCCGGCAGTGAACAATAGCTATTGCCAGTTTGGAGCAATTTCC
TTATGTGAAGTGACCAACTACACCGTCCGAGTGGCCAACCCACCATTCTCCACGTGG
ATCCTCTTCCCTGAGAACAGTGGGAAGCCTTGGGCAGGTGCGGAGAATCTGACCTGC
TGGATTCATGACGTGGATTTCTTGAGCTGCAGCTGGGCGGTAGGCCCGGGGGCCCCC
GCGGACGTCCAGTACGACCTGTACTTGAACGTTGCCAACAGGCGTCAACAGTACGA
GTGTCTTCACTACAAAACGGATGCTCAGGGAACACGTATCGGGTGTCGTTTCGATGA
CATCTCTCGACTCTCCAGCGGTTCTCAAAGTTCCCACATCCTGGTGCGGGGCAGGAG
CGCAGCCTTCGGTATCCCCTGCACAGATAAGTTTGTCGTCTTTTCACAGATTGAGAT
ATTAACTCCACCCAACATGACTGCAAAGTGTAATAAGACACATTCCTTTATGCACTG
GAAAATGAGAAGTCATTTCAATCGCAAATTTCGCTATGAGCTTCAGATACAAAAGA
GAATGCAGCCTGTAATCACAGAACAGGTCAGAGACAGAACCTCCTTCCAGCTACTC
AATCCTGGAACGTACACAGTACAAATAAGAGCCCGGGAAAGAGTGTATGAATTCTT
GAGCGCCTGGAGCACCCCCCAGCGCTTCGAGTGCGACCAGGAGGAGGGCGCAAACA
CACGTGCCTGGCGGACGTCGCTGCTGATCGCGCTGGGGACGCTGCTGGCCCTGGTCT
GTGTCTTCGTGATCTGCAGAAGGTATCTGGTGATGCAGAGACTCTTTCCCCGCATCC
CTCACATGAAAGACCCCATCGGTGACAGCTTCCAAAACGACAAGCTGGTGGTCTGG
GAGGCGGGCAAAGCCGGCCTGGAGGAGTGTCTGGTGACTGAAGTACAGGTCGTGCA
GAAAACT >Extracellular Domain of CD123 (SEQ ID NO: 11)
TKEDPNPPITNLRMKAKAQQLTWDLNRNVTDIECVKDADYSMPAVNNSYCQFGAISLC
EVTNYTVRVANPPFSTWILFPENSGKPWAGAENLTCWIHDVDFLSCSWAVGPGAPADV
QYDLYLNVANRRQQYECLHYKTDAQGTRIGCRFDDISRLSSGSQSSHILVRGRSAAFGIP
CTDKFVVFSQIEILTPPNMTAKCNKTHSFMHWKNRSHFNRKFRYELQIQKRMQPVITEQ
VRDRTSFQLLNPGTYTVQIRARERVYEFLSAWSTPQRFECDQEEGANTRAWR >cDNA Encoding Extracellular Domain of CD123 (SEQ ID NO: 12)
ACGAAGGAAGATCCAAACCCACCAATCACGAACCTAAGGATGAAAGCAAAGGCTC
AGCAGTTGACCTGGGACCTTAACAGAAATGTGACCGATATCGAGTGTGTTAAAGAC
GCCGACTATTCTATGCCGGCAGTGAACAATAGCTATTGCCAGTTTGGAGCAATTTCC
TTATGTGAAGTGACCAACTACACCGTCCGAGTGGCCAACCCACCATTCTCCACGTGG
ATCCTCTTCCCTGAGAACAGTGGGAAGCCTTGGGCAGGTGCGGAGAATCTGACCTGC
TGGATTCATGACGTGGATTTCTTGAGCTGCAGCTGGGCGGTAGGCCCGGGGGCCCCC
GCGGACGTCCAGTACGACCTGTACTTGAACGTTGCCAACAGGCGTCAACAGTACGA
GTGTCTTCACTACAAAACGGATGCTCAGGGAACACGTATCGGGTGTCGTTTCGATGA
CATCTCTCGACTCTCCAGCGGTTCTCAAAGTTCCCACATCCTGGTGCGGGGCAGGAG
CGCAGCCTTCGGTATCCCCTGCACAGATAAGTTTGTCGTCTTTTCACAGATTGAGAT
ATTAACTCCACCCAACATGACTGCAAAGTGTAATAAGACACATTCCTTTATGCACTG
GAAAATGAGAAGTCATTTCAATCGCAAATTTCGCTATGAGCTTCAGATACAAAAGA
GAATGCAGCCTGTAATCACAGAACAGGTCAGAGACAGAACCTCCTTCCAGCTACTC -continued Sequence Appendix AATCCTGGAACGTACACAGTACAAATAAGAGCCCGGGAAAGAGTGTATGAATTCTT
GAGCGCCTGGAGCACCCCCCAGCGCTTCGAGTGCGACCAGGAGGAGGGCGCAAACA
CACGTGCCTGGCGG >Heavy Chain of IMGN632 IgG histidine scanning variant #1 (SEQ ID NO: 13)
QVQLVQSGAEVKKPGASVKVSCKASHYIFTSSIMHWVRQAPGQGLEWIGYIKPYNDGT
KYNEKFKGRATLTSDRSTSTAYMELSSLRSEDTAVYYCAREGGNDYYDTMDYWGQGT
LVTVSS >Heavy Chain of IMGN632 IgG histidine scanning variant #2 (SEQ ID NO: 14)
QVQLVQSGAEVKKPGASVKVSCKASGHIFTSSIMHWVRQAPGQGLEWIGYIKPYNDGT
KYNEKFKGRATLTSDRSTSTAYMELSSLRSEDTAVYYCAREGGNDYYDTMDYWGQGT
LVTVSS >Heavy Chain of IMGN632 IgG histidine scanning variant #3 (SEQ ID NO: 15)
QVQLVQSGAEVKKPGASVKVSCKASGYHFTSSIMHWVRQAPGQGLEWIGYIKPYNDGT
KYNEKFKGRATLTSDRSTSTAYMELSSLRSEDTAVYYCAREGGNDYYDTMDYWGQGT
LVTVSS >Heavy Chain of IMGN632 IgG histidine scanning variant #4 (SEQ ID NO: 16)
QVQLVQSGAEVKKPGASVKVSCKASGYIHTSSIMHWVRQAPGQGLEWIGYIKPYNDGT
KYNEKFKGRATLTSDRSTSTAYMELSSLRSEDTAVYYCAREGGNDYYDTMDYWGQGT
LVTVSS >Heavy Chain of IMGN632 IgG histidine scanning variant #5 (SEQ ID NO: 17)
QVQLVQSGAEVKKPGASVKVSCKASGYIFHSSIMHWVRQAPGQGLEWIGYIKPYNDGT
KYNEKFKGRATLTSDRSTSTAYMELSSLRSEDTAVYYCAREGGNDYYDTMDYWGQGT
LVTVSS >Heavy Chain of IMGN632 IgG histidine scanning variant #6 (SEQ ID NO: 18)
QVQLVQSGAEVKKPGASVKVSCKASGYIFTHSIMHWVRQAPGQGLEWIGYIKPYNDGT
KYNEKFKGRATLTSDRSTSTAYMELSSLRSEDTAVYYCAREGGNDYYDTMDYWGQGT
LVTVSS >Heavy Chain of IMGN632 IgG histidine scanning variant #7 (SEQ ID NO: 19)
QVQLVQSGAEVKKPGASVKVSCKASGYIFTSHIMHWVRQAPGQGLEWIGYIKPYNDGT
KYNEKFKGRATLTSDRSTSTAYMELSSLRSEDTAVYYCAREGGNDYYDTMDYWGQGT
LVTVSS >Heavy Chain of IMGN632 IgG histidine scanning variant #8 (SEQ ID NO: 20)
QVQLVQSGAEVKKPGASVKVSCKASGYIFTSSHMHWVRQAPGQGLEWIGYIKPYNDGT
KYNEKFKGRATLTSDRSTSTAYMELSSLRSEDTAVYYCAREGGNDYYDTMDYWGQGT
LVTVSS >Heavy Chain of IMGN632 IgG histidine scanning variant #9 (SEQ ID NO: 21)
QVQLVQSGAEVKKPGASVKVSCKASGYIFTSSIHHWVRQAPGQGLEWIGYIKPYNDGT
KYNEKFKGRATLTSDRSTSTAYMELSSLRSEDTAVYYCAREGGNDYYDTMDYWGQGT
LVTVSS >Heavy Chain of IMGN632 IgG histidine scanning variant #10 (SEQ ID NO: 22)
QVQLVQSGAEVKKPGASVKVSCKASGYIFTSSIMAWVRQAPGQGLEWIGYIKPYNDGT
KYNEKFKGRATLTSDRSTSTAYMELSSLRSEDTAVYYCAREGGNDYYDTMDYWGQGT
LVTVSS >Heavy Chain of IMGN632 IgG histidine scanning variant #11 (SEQ ID NO: 23)
QVQLVQSGAEVKKPGASVKVSCKASGYIFTSSIMHWVRQAPGQGLEWIGHIKPYNDGT
KYNEKFKGRATLTSDRSTSTAYMELSSLRSEDTAVYYCAREGGNDYYDTMDYWGQGT
LVTVSS >Heavy Chain of IMGN632 IgG histidine scanning variant #12 (SEQ ID NO: 24)
QVQLVQSGAEVKKPGASVKVSCKASGYIFTSSIMHWVRQAPGQGLEWIGYHKPYNDGT
KYNEKFKGRATLTSDRSTSTAYMELSSLRSEDTAVYYCAREGGNDYYDTMDYWGQGT
LVTVSS >Heavy Chain of IMGN632 IgG histidine scanning variant #13 (SEQ ID NO: 25)
QVQLVQSGAEVKKPGASVKVSCKASGYIFTSSIMHWVRQAPGQGLEWIGYIHPYNDGT
KYNEKFKGRATLTSDRSTSTAYMELSSLRSEDTAVYYCAREGGNDYYDTMDYWGQGT
LVTVSS >Heavy Chain of IMGN632 IgG histidine scanning variant #14 (SEQ ID NO: 26)
QVQLVQSGAEVKKPGASVKVSCKASGYIFTSSIMHWVRQAPGQGLEWIGYIKHYNDGT
KYNEKFKGRATLTSDRSTSTAYMELSSLRSEDTAVYYCAREGGNDYYDTMDYWGQGT
LVTVSS Sequence Appendix >Heavy Chain of IMGN632 IgG histidine scanning variant #15 (SEQ ID NO: 27)
QVQLVQSGAEVKKPGASVKVSCKASGYIFTSSIMHWVRQAPGQGLEWIGYIKPHNDGT
KYNEKFKGRATLTSDRSTSTAYMELSSLRSEDTAVYYCAREGGNDYYDTMDYWGQGT
LVTVSS >Heavy Chain of IMGN632 IgG histidine scanning variant #16 (SEQ ID NO: 28)
QVQLVQSGAEVKKPGASVKVSCKASGYIFTSSIMHWVRQAPGQGLEWIGYIKPYHDGT
KYNEKFKGRATLTSDRSTSTAYMELSSLRSEDTAVYYCAREGGNDYYDTMDYWGQGT
LVTVSS >Heavy Chain of IMGN632 IgG histidine scanning variant #17 (SEQ ID NO: 29)
QVQLVQSGAEVKKPGASVKVSCKASGYIFTSSIMHWVRQAPGQGLEWIGYIKPYNHGT
KYNEKFKGRATLTSDRSTSTAYMELSSLRSEDTAVYYCAREGGNDYYDTMDYWGQGT
LVTVSS >Heavy Chain of IMGN632 IgG histidine scanning variant #18 (SEQ ID NO: 30)
QVQLVQSGAEVKKPGASVKVSCKASGYIFTSSIMHWVRQAPGQGLEWIGYIKPYNDHT
KYNEKFKGRATLTSDRSTSTAYMELSSLRSEDTAVYYCAREGGNDYYDTMDYWGQGT
LVTVSS >Heavy Chain of IMGN632 IgG histidine scanning variant #19 (SEQ ID NO: 31)
QVQLVQSGAEVKKPGASVKVSCKASGYIFTSSIMHWVRQAPGQGLEWIGYIKPYNDGH
KYNEKFKGRATLTSDRSTSTAYMELSSLRSEDTAVYYCAREGGNDYYDTMDYWGQGT
LVTVSS >Heavy Chain of IMGN632 IgG histidine scanning variant #20 (SEQ ID NO: 32)
QVQLVQSGAEVKKPGASVKVSCKASGYIFTSSIMHWVRQAPGQGLEWIGYIKPYNDGT
HYNEKFKGRATLTSDRSTSTAYMELSSLRSEDTAVYYCAREGGNDYYDTMDYWGQGT
LVTVSS >Heavy Chain of IMGN632 IgG histidine scanning variant #21 (SEQ ID NO: 33)
QVQLVQSGAEVKKPGASVKVSCKASGYIFTSSIMHWVRQAPGQGLEWIGYIKPYNDGT
KHNEKFKGRATLTSDRSTSTAYMELSSLRSEDTAVYYCAREGGNDYYDTMDYWGQGT
LVTVSS >Heavy Chain of IMGN632 IgG histidine scanning variant #22 (SEQ ID NO: 34)
QVQLVQSGAEVKKPGASVKVSCKASGYIFTSSIMHWVRQAPGQGLEWIGYIKPYNDGT
KYHEKFKGRATLTSDRSTSTAYMELSSLRSEDTAVYYCAREGGNDYYDTMDYWGQGT
LVTVSS >Heavy Chain of IMGN632 IgG histidine scanning variant #23 (SEQ ID NO: 35)
QVQLVQSGAEVKKPGASVKVSCKASGYIFTSSIMHWVRQAPGQGLEWIGYIKPYNDGT
KYNHKFKGRATLTSDRSTSTAYMELSSLRSEDTAVYYCAREGGNDYYDTMDYWGQGT
LVTVSS >Heavy Chain of IMGN632 IgG histidine scanning variant #24 (SEQ ID NO: 36)
QVQLVQSGAEVKKPGASVKVSCKASGYIFTSSIMHWVRQAPGQGLEWIGYIKPYNDGT
KYNEHFKGRATLTSDRSTSTAYMELSSLRSEDTAVYYCAREGGNDYYDTMDYWGQGT
LVTVSS >Heavy Chain of IMGN632 IgG histidine scanning variant #25 (SEQ ID NO: 37)
QVQLVQSGAEVKKPGASVKVSCKASGYIFTSSIMHWVRQAPGQGLEWIGYIKPYNDGT
KYNEKHKGRATLTSDRSTSTAYMELSSLRSEDTAVYYCAREGGNDYYDTMDYWGQGT
LVTVSS >Heavy Chain of IMGN632 IgG histidine scanning variant #26 (SEQ ID NO: 38)
QVQLVQSGAEVKKPGASVKVSCKASGYIFTSSIMHWVRQAPGQGLEWIGYIKPYNDGT
KYNEKFHGRATLTSDRSTSTAYMELSSLRSEDTAVYYCAREGGNDYYDTMDYWGQGT
LVTVSS >Heavy Chain of IMGN632 IgG histidine scanning variant #27 (SEQ ID NO: 39)
QVQLVQSGAEVKKPGASVKVSCKASGYIFTSSIMHWVRQAPGQGLEWIGYIKPYNDGT
KYNEKFKHRATLTSDRSTSTAYMELSSLRSEDTAVYYCAREGGNDYYDTMDYWGQGT
LVTVSS >Heavy Chain of IMGN632 IgG histidine scanning variant #28 (SEQ ID NO: 40)
QVQLVQSGAEVKKPGASVKVSCKASGYIFTSSIMHWVRQAPGQGLEWIGYIKPYNDGT
KYNEKFKGRATLTSDRSTSTAYMELSSLRSEDTAVYYCHREGGNDYYDTMDYWGQGT
LVTVSS >Heavy Chain of IMGN632 IgG histidine scanning variant #29 (SEQ ID NO: 41)
QVQLVQSGAEVKKPGASVKVSCKASGYIFTSSIMHWVRQAPGQGLEWIGYIKPYNDGT
KYNEKFKGRATLTSDRSTSTAYMELSSLRSEDTAVYYCAHEGGNDYYDTMDYWGQGT
LVTVSS Sequence Appendix >Heavy Chain of IMGN632 IgG histidine scanning variant #30 (SEQ ID NO: 42)
QVQLVQSGAEVKKPGASVKVSCKASGYIFTSSIMHWVRQAPGQGLEWIGYIKPYNDGT
KYNEKFKGRATLTSDRSTSTAYMELSSLRSEDTAVYYCARHGGNDYYDTMDYWGQGT
LVTVSS >Heavy Chain of IMGN632 IgG histidine scanning variant #31 (SEQ ID NO: 43)
QVQLVQSGAEVKKPGASVKVSCKASGYIFTSSIMHWVRQAPGQGLEWIGYIKPYNDGT
KYNEKFKGRATLTSDRSTSTAYMELSSLRSEDTAVYYCAREHGNDYYDTMDYWGQGT
LVTVSS >Heavy Chain of IMGN632 IgG histidine scanning variant #32 (SEQ ID NO: 44)
QVQLVQSGAEVKKPGASVKVSCKASGYIFTSSIMHWVRQAPGQGLEWIGYIKPYNDGT
KYNEKFKGRATLTSDRSTSTAYMELSSLRSEDTAVYYCAREGHNDYYDTMDYWGQGT
LVTVSS >Heavy Chain of IMGN632 IgG histidine scanning variant #33 (SEQ ID NO: 45)
QVQLVQSGAEVKKPGASVKVSCKASGYIFTSSIMHWVRQAPGQGLEWIGYIKPYNDGT
KYNEKFKGRATLTSDRSTSTAYMELSSLRSEDTAVYYCAREGGHDYYDTMDYWGQGT
LVTVSS >Heavy Chain of IMGN632 IgG histidine scanning variant #34 (SEQ ID NO: 46)
QVQLVQSGAEVKKPGASVKVSCKASGYIFTSSIMHWVRQAPGQGLEWIGYIKPYNDGT
KYNEKFKGRATLTSDRSTSTAYMELSSLRSEDTAVYYCAREGGNHYYDTMDYWGQGT
LVTVSS >Heavy Chain of IMGN632 IgG histidine scanning variant #35 (SEQ ID NO: 47)
QVQLVQSGAEVKKPGASVKVSCKASGYIFTSSIMHWVRQAPGQGLEWIGYIKPYNDGT
KYNEKFKGRATLTSDRSTSTAYMELSSLRSEDTAVYYCAREGGNDHYDTMDYWGQGT
LVTVSS >Heavy Chain of IMGN632 IgG histidine scanning variant #36 (SEQ ID NO: 48)
QVQLVQSGAEVKKPGASVKVSCKASGYIFTSSIMHWVRQAPGQGLEWIGYIKPYNDGT
KYNEKFKGRATLTSDRSTSTAYMELSSLRSEDTAVYYCAREGGNDYHDTMDYWGQGT
LVTVSS >Heavy Chain of IMGN632 IgG histidine scanning variant #37 (SEQ ID NO: 49)
QVQLVQSGAEVKKPGASVKVSCKASGYIFTSSIMHWVRQAPGQGLEWIGYIKPYNDGT
KYNEKFKGRATLTSDRSTSTAYMELSSLRSEDTAVYYCAREGGNDYYHTMDYWGQGT
LVTVSS >Heavy Chain of IMGN632 IgG histidine scanning variant #38 (SEQ ID NO: 50)
QVQLVQSGAEVKKPGASVKVSCKASGYIFTSSIMHWVRQAPGQGLEWIGYIKPYNDGT
KYNEKFKGRATLTSDRSTSTAYMELSSLRSEDTAVYYCAREGGNDYYDHMDYWGQGT
LVTVSS >Heavy Chain of IMGN632 IgG histidine scanning variant #39 (SEQ ID NO: 51)
QVQLVQSGAEVKKPGASVKVSCKASGYIFTSSIMHWVRQAPGQGLEWIGYIKPYNDGT
KYNEKFKGRATLTSDRSTSTAYMELSSLRSEDTAVYYCAREGGNDYYDTHDYWGQGT
LVTVSS >Heavy Chain of IMGN632 IgG histidine scanning variant #40 (SEQ ID NO: 52)
QVQLVQSGAEVKKPGASVKVSCKASGYIFTSSIMHWVRQAPGQGLEWIGYIKPYNDGT
KYNEKFKGRATLTSDRSTSTAYMELSSLRSEDTAVYYCAREGGNDYYDTMHYWGQGT
LVTVSS >Heavy Chain of IMGN632 IgG histidine scanning variant #41 (SEQ ID NO: 53)
QVQLVQSGAEVKKPGASVKVSCKASGYIFTSSIMHWVRQAPGQGLEWIGYIKPYNDGT
KYNEKFKGRATLTSDRSTSTAYMELSSLRSEDTAVYYCAREGGNDYYDTMDHWGQGT
LVTVSS >Light Chain of IMGN632 IgG histidine scanning variant #1 (SEQ ID NO: 54)
DIQMTQSPSSLSASVGDRVTITCHASQDINSYLSWFQQKPGKAPKTLIYRVNRLVDGVPS
RFSGSGSGNDYTLTISSLQPEDFATYYCLQYDAFPYTFGQGTKVEIK >Light Chain of IMGN632 IgG histidine scanning variant #2 (SEQ ID NO: 55)
DIQMTQSPSSLSASVGDRVTITCRHSQDINSYLSWFQQKPGKAPKTLIYRVNRLVDGVPS
RFSGSGSGNDYTLTISSLQPEDFATYYCLQYDAFPYTFGQGTKVEIK >Light Chain of IMGN632 IgG histidine scanning variant #3 (SEQ ID NO: 56)
DIQMTQSPSSLSASVGDRVTITCRAHQDINSYLSWFQQKPGKAPKTLIYRVNRLVDGVPS
RFSGSGSGNDYTLTISSLQPEDFATYYCLQYDAFPYTFGQGTKVEIK >Light Chain of IMGN632 IgG histidine scanning variant #4 (SEQ ID NO: 57)
DIQMTQSPSSLSASVGDRVTITCRASHDINSYLSWFQQKPGKAPKTLIYRVNRLVDGVPS
RFSGSGSGNDYTLTISSLQPEDFATYYCLQYDAFPYTFGQGTKVEIK

| Sequence Appendix |
|---|

>Light Chain of IMGN632 IgG histidine scanning variant #5 (SEQ ID NO: 58)
DIQMTQSPSSLSASVGDRVTITCRASQHINSYLSWFQQKPGKAPKTLIYRVNRLVDGVPS
RFSGSGSGNDYTLTISSLQPEDFATYYCLQYDAFPYTFGQGTKVEIK >Light Chain of IMGN632 IgG histidine scanning variant #6 (SEQ ID NO: 59)
DIQMTQSPSSLSASVGDRVTITCRASQDHNSYLSWFQQKPGKAPKTLIYRVNRLVDGVP
SRFSGSGSGNDYTLTISSLQPEDFATYYCLQYDAFPYTFGQGTKVEIK >Light Chain of IMGN632 IgG histidine scanning variant #7 (SEQ ID NO: 60)
DIQMTQSPSSLSASVGDRVTITCRASQDIHSYLSWFQQKPGKAPKTLIYRVNRLVDGVPS
RFSGSGSGNDYTLTISSLQPEDFATYYCLQYDAFPYTFGQGTKVEIK >Light Chain of IMGN632 IgG histidine scanning variant #8 (SEQ ID NO: 61)
DIQMTQSPSSLSASVGDRVTITCRASQDINHYLSWFQQKPGKAPKTLIYRVNRLVDGVPS
RFSGSGSGNDYTLTISSLQPEDFATYYCLQYDAFPYTFGQGTKVEIK >Light Chain of IMGN632 IgG histidine scanning variant #9 (SEQ ID NO: 62)
DIQMTQSPSSLSASVGDRVTITCRASQDINSHLSWFQQKPGKAPKTLIYRVNRLVDGVPS
RFSGSGSGNDYTLTISSLQPEDFATYYCLQYDAFPYTFGQGTKVEIK >Light Chain of IMGN632 IgG histidine scanning variant #10 (SEQ ID NO: 63)
DIQMTQSPSSLSASVGDRVTITCRASQDINSYHSWFQQKPGKAPKTLIYRVNRLVDGVPS
RFSGSGSGNDYTLTISSLQPEDFATYYCLQYDAFPYTFGQGTKVEIK >Light Chain of IMGN632 IgG histidine scanning variant #11 (SEQ ID NO: 64)
DIQMTQSPSSLSASVGDRVTITCRASQDINSYLHWFQQKPGKAPKTLIYRVNRLVDGVPS
RFSGSGSGNDYTLTISSLQPEDFATYYCLQYDAFPYTFGQGTKVEIK >Light Chain of IMGN632 IgG histidine scanning variant #12 (SEQ ID NO: 65)
DIQMTQSPSSLSASVGDRVTITCRASQDINSYLSWFQQKPGKAPKTLIYHVNRLVDGVPS
RFSGSGSGNDYTLTISSLQPEDFATYYCLQYDAFPYTFGQGTKVEIK >Light Chain of IMGN632 IgG histidine scanning variant #13 (SEQ ID NO: 66)
DIQMTQSPSSLSASVGDRVTITCRASQDINSYLSWFQQKPGKAPKTLIYRHNRLVDGVPS
RFSGSGSGNDYTLTISSLQPEDFATYYCLQYDAFPYTFGQGTKVEIK >Light Chain of IMGN632 IgG histidine scanning variant #14 (SEQ ID NO: 67)
DIQMTQSPSSLSASVGDRVTITCRASQDINSYLSWFQQKPGKAPKTLIYRVHRLVDGVPS
RFSGSGSGNDYTLTISSLQPEDFATYYCLQYDAFPYTFGQGTKVEIK >Light Chain of IMGN632 IgG histidine scanning variant #15 (SEQ ID NO: 68)
DIQMTQSPSSLSASVGDRVTITCRASQDINSYLSWFQQKPGKAPKTLIYRVNHLVDGVPS
RFSGSGSGNDYTLTISSLQPEDFATYYCLQYDAFPYTFGQGTKVEIK >Light Chain of IMGN632 IgG histidine scanning variant #16 (SEQ ID NO: 69)
DIQMTQSPSSLSASVGDRVTITCRASQDINSYLSWFQQKPGKAPKTLIYRVNRHVDGVPS
RFSGSGSGNDYTLTISSLQPEDFATYYCLQYDAFPYTFGQGTKVEIK >Light Chain of IMGN632 IgG histidine scanning variant #17 (SEQ ID NO: 70)
DIQMTQSPSSLSASVGDRVTITCRASQDINSYLSWFQQKPGKAPKTLIYRVNRLHDGVPS
RFSGSGSGNDYTLTISSLQPEDFATYYCLQYDAFPYTFGQGTKVEIK >Light Chain of IMGN632 IgG histidine scanning variant #18 (SEQ ID NO: 71)
DIQMTQSPSSLSASVGDRVTITCRASQDINSYLSWFQQKPGKAPKTLIYRVNRLVHGVPS
RFSGSGSGNDYTLTISSLQPEDFATYYCLQYDAFPYTFGQGTKVEIK >Light Chain of IMGN632 IgG histidine scanning variant #19 (SEQ ID NO: 72)
DIQMTQSPSSLSASVGDRVTITCRASQDINSYLSWFQQKPGKAPKTLIYRVNRLVDGVPS
RFSGSGSGNDYTLTISSLQPEDFATYYCHQYDAFPYTFGQGTKVEIK >Light Chain of IMGN632 IgG histidine scanning variant #20 (SEQ ID NO: 73)
DIQMTQSPSSLSASVGDRVTITCRASQDINSYLSWFQQKPGKAPKTLIYRVNRLVDGVPS
RFSGSGSGNDYTLTISSLQPEDFATYYCLHYDAFPYTFGQGTKVEIK >Light Chain of IMGN632 IgG histidine scanning variant #21 (SEQ ID NO: 74)
DIQMTQSPSSLSASVGDRVTITCRASQDINSYLSWFQQKPGKAPKTLIYRVNRLVDGVPS
RFSGSGSGNDYTLTISSLQPEDFATYYCLQHDAFPYTFGQGTKVEIK >Light Chain of IMGN632 IgG histidine scanning variant #22 (SEQ ID NO: 75)
DIQMTQSPSSLSASVGDRVTITCRASQDINSYLSWFQQKPGKAPKTLIYRVNRLVDGVPS
RFSGSGSGNDYTLTISSLQPEDFATYYCLQYHAFPYTFGQGTKVEIK >Light Chain of IMGN632 IgG histidine scanning variant #23 (SEQ ID NO: 76)
DIQMTQSPSSLSASVGDRVTITCRASQDINSYLSWFQQKPGKAPKTLIYRVNRLVDGVPS
RFSGSGSGNDYTLTISSLQPEDFATYYCLQYDHFPYTFGQGTKVEIK -continued Sequence Appendix >Light Chain of IMGN632 IgG histidine scanning variant #24 (SEQ ID NO: 77)
DIQMTQSPSSLSASVGDRVTITCRASQDINSYLSWFQQKPGKAPKTLIYRVNRLVDGVPS
RFSGSGSGNDYTLTISSLQPEDFATYYCLQYDAHPYTFGQGTKVEIK >Light Chain of IMGN632 IgG histidine scanning variant #25 (SEQ ID NO: 78)
DIQMTQSPSSLSASVGDRVTITCRASQDINSYLSWFQQKPGKAPKTLIYRVNRLVDGVPS
RFSGSGSGNDYTLTISSLQPEDFATYYCLQYDAFHYTFGQGTKVEIK >Light Chain of IMGN632 IgG histidine scanning variant #26 (SEQ ID NO: 79)
DIQMTQSPSSLSASVGDRVTITCRASQDINSYLSWFQQKPGKAPKTLIYRVNRLVDGVPS
RFSGSGSGNDYTLTISSLQPEDFATYYCLQYDAFPHTFGQGTKVEIK >Light Chain of IMGN632 IgG histidine scanning variant #27 (SEQ ID NO: 80)
DIQMTQSPSSLSASVGDRVTITCRASQDINSYLSWFQQKPGKAPKTLIYRVNRLVDGVPS
RFSGSGSGNDYTLTISSLQPEDFATYYCLQYDAFPYHFGQGTKVEIK >Heavy Chain Combinations of IMGN632 IgG histidine scanning variant #1 (SEQ ID NO: 81)
QVQLVQSGAEVKKPGASVKVSCKASGHIFTSSIMAWVRQAPGQGLEWIGYIKPYNDGT
KYNEKFKGRATLTSDRSTSTAYMELSSLRSEDTAVYYCAREGGNDYYDTMDYWGQGT
LVTVSS >Heavy Chain Combinations of IMGN632 IgG histidine scanning variant #2 (SEQ ID NO: 82)
QVQLVQSGAEVKKPGASVKVSCKASGHIFTSSIMHWVRQAPGQGLEWIGYIKPYNDGT
KYNEKFKGRATLTSDRSTSTAYMELSSLRSEDTAVYYCAREGGNDYHDTMDYWGQGT
LVTVSS >Heavy Chain Combinations of IMGN632 IgG histidine scanning variant #3 (SEQ ID NO: 83)
QVQLVQSGAEVKKPGASVKVSCKASGHIFTSSIMHWVRQAPGQGLEWIGYIKPYNDGT
KYNEKFKGRATLTSDRSTSTAYMELSSLRSEDTAVYYCAREGGNDYYDHMDYWGQGT
LVTVSS >Heavy Chain Combinations of IMGN632 IgG histidine scanning variant #4 (SEQ ID NO: 84)
QVQLVQSGAEVKKPGASVKVSCKASGHIFTSSIMHWVRQAPGQGLEWIGYIKPYNDGT
KYNEKFKGRATLTSDRSTSTAYMELSSLRSEDTAVYYCAREGGNDYYDTMHYWGQGT
LVTVSS >Heavy Chain Combinations of IMGN632 IgG histidine scanning variant #5 (SEQ ID NO: 85)
QVQLVQSGAEVKKPGASVKVSCKASGYIFTSSIMAWVRQAPGQGLEWIGYIKPYNDGT
KYNEKFKGRATLTSDRSTSTAYMELSSLRSEDTAVYYCAREGGNDYHDTMDYWGQGT
LVTVSS >Heavy Chain Combinations of IMGN632 IgG histidine scanning variant #6 (SEQ ID NO: 86)
QVQLVQSGAEVKKPGASVKVSCKASGYIFTSSIMAWVRQAPGQGLEWIGYIKPYNDGT
KYNEKFKGRATLTSDRSTSTAYMELSSLRSEDTAVYYCAREGGNDYYDHMDYWGQGT
LVTVSS >Heavy Chain Combinations of IMGN632 IgG histidine scanning variant #7 (SEQ ID NO: 87)
QVQLVQSGAEVKKPGASVKVSCKASGYIFTSSIMAWVRQAPGQGLEWIGYIKPYNDGT
KYNEKFKGRATLTSDRSTSTAYMELSSLRSEDTAVYYCAREGGNDYYDTMHYWGQGT
LVTVSS >Heavy Chain Combinations of IMGN632 IgG histidine scanning variant #8 (SEQ ID NO: 88)
QVQLVQSGAEVKKPGASVKVSCKASGYIFTSSIMHWVRQAPGQGLEWIGYIKPYNDGT
KYNEKFKGRATLTSDRSTSTAYMELSSLRSEDTAVYYCAREGGNDYHDHMDYWGQGT
LVTVSS >Heavy Chain Combinations of IMGN632 IgG histidine scanning variant #9 (SEQ ID NO: 89)
QVQLVQSGAEVKKPGASVKVSCKASGYIFTSSIMHWVRQAPGQGLEWIGYIKPYNDGT
KYNEKFKGRATLTSDRSTSTAYMELSSLRSEDTAVYYCAREGGNDYHDTMHYWGQGT
LVTVSS >Heavy Chain Combinations of IMGN632 IgG histidine scanning variant #10 (SEQ ID NO: 90)
QVQLVQSGAEVKKPGASVKVSCKASGYIFTSSIMIHWVRQAPGQGLEWIGYIKPYNDGT
KYNEKFKGRATLTSDRSTSTAYMELSSLRSEDTAVYYCAREGGNDYYDHMIRYWGQGT
LVTVSS >Heavy Chain Combinations of IMGN632 IgG histidine scanning variant #11 (SEQ ID NO: 91)
QVQLVQSGAEVKKPGASVKVSCKASGHIFTSSIMAWVRQAPGQGLEWIGYIKPYNDGT
KYNEKFKGRATLTSDRSTSTAYMELSSLRSEDTAVYYCAREGGNDYHDTMDYWGQGT
LVTVSS >Heavy Chain Combinations of IMGN632 IgG histidine scanning variant #12 (SEQ ID NO: 92)
QVQLVQSGAEVKKPGASVKVSCKASGHIFTSSIMAWVRQAPGQGLEWIGYIKPYNDGT
KYNEKFKGRATLTSDRSTSTAYMELSSLRSEDTAVYYCAREGGNDYYDHMDYWGQGT
LVTVSS -continued Sequence Appendix >Heavy Chain Combinations of IMGN632 IgG histidine scanning variant #13 (SEQ ID NO: 93)
QVQLVQSGAEVKKPGASVKVSCKASGHIFTSSIMAWVRQAPGQGLEWIGYIKPYNDGT
KYNEKFKGRATLTSDRSTSTAYMELSSLRSEDTAVYYCAREGGNDYYDTMHYWGQGT
LVTVSS >Heavy Chain Combinations of IMGN632 IgG histidine scanning variant #14 (SEQ ID NO: 94)
QVQLVQSGAEVKKPGASVKVSCKASGHIFTSSIMIHWVRQAPGQGLEWIGYIKPYNDGT
KYNEKFKGRATLTSDRSTSTAYMELSSLRSEDTAVYYCAREGGNDYHDHMDYWGQGT
LVTVSS >Heavy Chain Combinations of IMGN632 IgG histidine scanning variant #15 (SEQ ID NO: 95)
QVQLVQSGAEVKKPGASVKVSCKASGHIFTSSIMHWVRQAPGQGLEWIGYIKPYNDGT
KYNEKFKGRATLTSDRSTSTAYMELSSLRSEDTAVYYCAREGGNDYHDTMHYWGQGT
LVTVSS >Heavy Chain Combinations of IMGN632 IgG histidine scanning variant #16 (SEQ ID NO: 96)
QVQLVQSGAEVKKPGASVKVSCKASGHIFTSSIMHWVRQAPGQGLEWIGYIKPYNDGT
KYNEKFKGRATLTSDRSTSTAYMELSSLRSEDTAVYYCAREGGNDYYDHMHYWGQGT
LVTVSS >Heavy Chain Combinations of IMGN632 IgG histidine scanning variant #17 (SEQ ID NO: 97)
QVQLVQSGAEVKKPGASVKVSCKASGYIFTSSIMAWVRQAPGQGLEWIGYIKPYNDGT
KYNEKFKGRATLTSDRSTSTAYMELSSLRSEDTAVYYCAREGGNDYHDHMDYWGQGT
LVTVSS >Heavy Chain Combinations of IMGN632 IgG histidine scanning variant #18 (SEQ ID NO: 98)
QVQLVQSGAEVKKPGASVKVSCKASGYIFTSSIMAWVRQAPGQGLEWIGYIKPYNDGT
KYNEKFKGRATLTSDRSTSTAYMELSSLRSEDTAVYYCAREGGNDYHDTMHYWGQGT
LVTVSS >Heavy Chain Combinations of IMGN632 IgG histidine scanning variant #19 (SEQ ID NO: 99)
QVQLVQSGAEVKKPGASVKVSCKASGYIFTSSIMAWVRQAPGQGLEWIGYIKPYNDGT
KYNEKFKGRATLTSDRSTSTAYMELSSLRSEDTAVYYCAREGGNDYYDHMHYWGQGT
LVTVSS >Heavy Chain Combinations of IMGN632 IgG histidine scanning variant #20 (SEQ ID NO: 100)
QVQLVQSGAEVKKPGASVKVSCKASGYIFTSSIMHWVRQAPGQGLEWIGYIKPYNDGT
KYNEKFKGRATLTSDRSTSTAYMELSSLRSEDTAVYYCAREGGNDYHDHMHYWGQGT
LVTVSS >Heavy Chain of SGN-CD123A IgG (SEQ ID NO: 101)
QVQLVQSGAEVKKPGASVKMSCKASGYTFTDYYMKWVKQAPGQGLEWIGDIIPSNGA
TFYNQKFKGKATLTVDRSISTAYMHLNRLRSDDTAVYYCTRSHLLRASWFAYWGQGT
LVTVSS >Light Chain of SGN-CD123A IgG (SEQ ID NO: 102)
DFVMTQSPDSLAVSLGERATINCKSSQSLLNSGNQKNYLTWYLQKPGQPPKLLIYWAST
RESGVPDRFSGSGSGTDFTLTISSLQAEDVAVYYCQNDYSYPYTFGQGTKLEIK >Heavy Chain CDR1 of SGN-CD123A (SEQ ID NO: 103)
GYTFTDYYMK >Heavy Chain CDR2 of SGN-CD123A (SEQ ID NO: 104)
DIIPSNGATFYNQKFKG >Heavy Chain CDR3 of SGN-CD123A (SEQ ID NO: 105)
TRSHLLRASWFAY >Light Chain CDR1 of SGN-CD123A (SEQ ID NO: 106)
KSSQSLLNSGNQKNYLT >Light Chain CDR2 of SGN-CD123A (SEQ ID NO: 107)
WASTRES >Light Chain CDR3 of SGN-CD123A (SEQ ID NO: 108)
QNDYSYPYT >Heavy Chain of SGN-CD123A IgG histidine scanning variant #1 (SEQ ID NO: 109)
QVQLVQSGAEVKKPGASVKMSCKASHYTFTDYYMKWVKQAPGQGLEWIGDIIPSNGA
TFYNQKFKGKATLTVDRSISTAYMHLNRLRSDDTAVYYCTRSHLLRASWFAYWGQGT
LVTVSS >Heavy Chain of SGN-CD123A IgG histidine scanning variant #2 (SEQ ID NO: 110)
QVQLVQSGAEVKKPGASVKMSCKASGHTFTDYYMKWVKQAPGQGLEWIGDIIPSNGA
TFYNQKFKGKATLTVDRSISTAYMHLNRLRSDDTAVYYCTRSHLLRASWFAYWGQGT
LVTVSS Sequence Appendix >Heavy Chain of SGN-CD123A IgG histidine scanning variant #3 (SEQ ID NO: 111)
QVQLVQSGAEVKKPGASVKMSCKASGYHFTDYYMKWVKQAPGQGLEWIGDIIPSNGA
TFYNQKFKGKATLTVDRSISTAYMHLNRLRSDDTAVYYCTRSHLLRASWFAYWGQGT
LVTVSS >Heavy Chain of SGN-CD123A IgG histidine scanning variant #4 (SEQ ID NO: 112)
QVQLVQSGAEVKKPGASVKMSCKASGYTHTDYYMKWVKQAPGQGLEWIGDIIPSNGA
TFYNQKFKGKATLTVDRSISTAYMHLNRLRSDDTAVYYCTRSHLLRASWFAYWGQGT
LVTVSS >Heavy Chain of SGN-CD123A IgG histidine scanning variant #5 (SEQ ID NO: 113)
QVQLVQSGAEVKKPGASVKMSCKASGYTFHDYYMKWVKQAPGQGLEWIGDIIPSNGA
TFYNQKFKGKATLTVDRSISTAYMHLNRLRSDDTAVYYCTRSHLLRASWFAYWGQGT
LVTVSS >Heavy Chain of SGN-CD123A IgG histidine scanning variant #6 (SEQ ID NO: 114)
QVQLVQSGAEVKKPGASVKMSCKASGYTFTHYYMKWVKQAPGQGLEWIGDIIPSNGA
TFYNQKFKGKATLTVDRSISTAYMHLNRLRSDDTAVYYCTRSHLLRASWFAYWGQGT
LVTVSS >Heavy Chain of SGN-CD123A IgG histidine scanning variant #7 (SEQ ID NO: 115)
QVQLVQSGAEVKKPGASVKMSCKASGYTFTDHYMKWVKQAPGQGLEWIGDIIPSNGA
TFYNQKFKGKATLTVDRSISTAYMHLNRLRSDDTAVYYCTRSHLLRASWFAYWGQGT
LVTVSS >Heavy Chain of SGN-CD123A IgG histidine scanning variant #8 (SEQ ID NO: 116)
QVQLVQSGAEVKKPGASVKMSCKASGYTFTDYHMKWVKQAPGQGLEWIGDIIPSNGA
TFYNQKFKGKATLTVDRSISTAYMHLNRLRSDDTAVYYCTRSHLLRASWFAYWGQGT
LVTVSS >Heavy Chain of SGN-CD123A IgG histidine scanning variant #9 (SEQ ID NO: 117)
QVQLVQSGAEVKKPGASVKMSCKASGYTFTDYYHKWVKQAPGQGLEWIGDIIPSNGAT
FYNQKFKGKATLTVDRSISTAYMHLNRLRSDDTAVYYCTRSHLLRASWFAYWGQGTL
VTVSS >Heavy Chain of SGN-CD123A IgG histidine scanning variant #10 (SEQ ID NO: 118)
QVQLVQSGAEVKKPGASVKMSCKASGYTFTDYYMHWVKQAPGQGLEWIGDIIPSNGA
TFYNQKFKGKATLTVDRSISTAYMHLNRLRSDDTAVYYCTRSHLLRASWFAYWGQGT
LVTVSS >Heavy Chain of SGN-CD123A IgG histidine scanning variant #11 (SEQ ID NO: 119)
QVQLVQSGAEVKKPGASVKMSCKASGYTFTDYYMKWVKQAPGQGLEWIGHIIPSNGA
TFYNQKFKGKATLTVDRSISTAYMHLNRLRSDDTAVYYCTRSHLLRASWFAYWGQGT
LVTVSS >Heavy Chain of SGN-CD123A IgG histidine scanning variant #12 (SEQ ID NO: 120)
QVQLVQSGAEVKKPGASVKMSCKASGYTFTDYYMKWVKQAPGQGLEWIGDHIPSNGA
TFYNQKFKGKATLTVDRSISTAYMHLNRLRSDDTAVYYCTRSHLLRASWFAYWGQGT
LVTVSS >Heavy Chain of SGN-CD123A IgG histidine scanning variant #13 (SEQ ID NO: 121)
QVQLVQSGAEVKKPGASVKMSCKASGYTFTDYYMKWVKQAPGQGLEWIGDIHPSNGA
TFYNQKFKGKATLTVDRSISTAYMHLNRLRSDDTAVYYCTRSHLLRASWFAYWGQGT
LVTVSS >Heavy Chain of SGN-CD123A IgG histidine scanning variant #14 (SEQ ID NO: 122)
QVQLVQSGAEVKKPGASVKMSCKASGYTFTDYYMKWVKQAPGQGLEWIGDIIHSNGA
TFYNQKFKGKATLTVDRSISTAYMHLNRLRSDDTAVYYCTRSHLLRASWFAYWGQGT
LVTVSS >Heavy Chain of SGN-CD123A IgG histidine scanning variant #15 (SEQ ID NO: 123)
QVQLVQSGAEVKKPGASVKMSCKASGYTFTDYYMKWVKQAPGQGLEWIGDIIPHNGA
TFYNQKFKGKATLTVDRSISTAYMHLNRLRSDDTAVYYCTRSHLLRASWFAYWGQGT
LVTVSS >Heavy Chain of SGN-CD123A IgG histidine scanning variant #16 (SEQ ID NO: 124)
QVQLVQSGAEVKKPGASVKMSCKASGYTFTDYYMKWVKQAPGQGLEWIGDIIPSHGA
TFYNQKFKGKATLTVDRSISTAYMHLNRLRSDDTAVYYCTRSHLLRASWFAYWGQGT
LVTVSS >Heavy Chain of SGN-CD123A IgG histidine scanning variant #17 (SEQ ID NO: 125)
QVQLVQSGAEVKKPGASVKMSCKASGYTFTDYYMKWVKQAPGQGLEWIGDIIPSNHA
TFYNQKFKGKATLTVDRSISTAYMHLNRLRSDDTAVYYCTRSHLLRASWFAYWGQGT
LVTVSS Sequence Appendix >Heavy Chain of SGN-CD123A IgG histidine scanning variant #18 (SEQ ID NO: 126)
QVQLVQSGAEVKKPGASVKMSCKASGYTFTDYYMKWVKQAPGQGLEWIGDIIPSNGH
TFYNQKFKGKATLTVDRSISTAYMHLNRLRSDDTAVYYCTRSHLLRASWFAYWGQGT
LVTVSS >Heavy Chain of SGN-CD123A IgG histidine scanning variant #19 (SEQ ID NO: 127)
QVQLVQSGAEVKKPGASVKMSCKASGYTFTDYYMKWVKQAPGQGLEWIGDIIPSNGA
HFYNQKFKGKATLTVDRSISTAYMHLNRLRSDDTAVYYCTRSHLLRASWFAYWGQGT
LVTVSS >Heavy Chain of SGN-CD123A IgG histidine scanning variant #20 (SEQ ID NO: 128)
QVQLVQSGAEVKKPGASVKMSCKASGYTFTDYYMKWVKQAPGQGLEWIGDIIPSNGA
THYNQKFKGKATLTVDRSISTAYMHLNRLRSDDTAVYYCTRSHLLRASWFAYWGQGT
LVTVSS >Heavy Chain of SGN-CD123A IgG histidine scanning variant #21 (SEQ ID NO: 129)
QVQLVQSGAEVKKPGASVKMSCKASGYTFTDYYMKWVKQAPGQGLEWIGDIIPSNGA
TFHNQKFKGKATLTVDRSISTAYMHLNRLRSDDTAVYYCTRSHLLRASWFAYWGQGT
LVTVSS >Heavy Chain of SGN-CD123A IgG histidine scanning variant #22 (SEQ ID NO: 130)
QVQLVQSGAEVKKPGASVKMSCKASGYTFTDYYMKWVKQAPGQGLEWIGDIIPSNGA
TFYHQKFKGKATLTVDRSISTAYMHLNRLRSDDTAVYYCTRSHLLRASWFAYWGQGT
LVTVSS >Heavy Chain of SGN-CD123A IgG histidine scanning variant #23 (SEQ ID NO: 131)
QVQLVQSGAEVKKPGASVKMSCKASGYTFTDYYMKWVKQAPGQGLEWIGDIIPSNGA
TFYNHKFKGKATLTVDRSISTAYMHLNRLRSDDTAVYYCTRSHLLRASWFAYWGQGT
LVTVSS >Heavy Chain of SGN-CD123A IgG histidine scanning variant #24 (SEQ ID NO: 132)
QVQLVQSGAEVKKPGASVKMSCKASGYTFTDYYMKWVKQAPGQGLEWIGDIIPSNGA
TFYNQHFKGKATLTVDRSISTAYMHLNRLRSDDTAVYYCTRSHLLRASWFAYWGQGT
LVTVSS >Heavy Chain of SGN-CD123A IgG histidine scanning variant #25 (SEQ ID NO: 133)
QVQLVQSGAEVKKPGASVKMSCKASGYTFTDYYMKWVKQAPGQGLEWIGDIIPSNGA
TFYNQKHKGKATLTVDRSISTAYMHLNRLRSDDTAVYYCTRSHLLRASWFAYWGQGT
LVTVSS >Heavy Chain of SGN-CD123A IgG histidine scanning variant #26 (SEQ ID NO: 134)
QVQLVQSGAEVKKPGASVKMSCKASGYTFTDYYMKWVKQAPGQGLEWIGDIIPSNGA
TFYNQKFHGKATLTVDRSISTAYMHLNRLRSDDTAVYYCTRSHLLRASWFAYWGQGT
LVTVSS >Heavy Chain of SGN-CD123A IgG histidine scanning variant #27 (SEQ ID NO: 135)
QVQLVQSGAEVKKPGASVKMSCKASGYTFTDYYMKWVKQAPGQGLEWIGDIIPSNGA
TFYNQKFKHKATLTVDRSISTAYMHLNRLRSDDTAVYYCTRSHLLRASWFAYWGQGT
LVTVSS >Heavy Chain of SGN-CD123A IgG histidine scanning variant #28 (SEQ ID NO: 136)
QVQLVQSGAEVKKPGASVKMSCKASGYTFTDYYMKWVKQAPGQGLEWIGDIIPSNGA
TFYNQKFKGKATLTVDRSISTAYMHLNRLRSDDTAVYYCHRSHLLRASWFAYWGQGT
LVTVSS >Heavy Chain of SGN-CD123A IgG histidine scanning variant #29 (SEQ ID NO: 137)
QVQLVQSGAEVKKPGASVKMSCKASGYTFTDYYMKWVKQAPGQGLEWIGDIIPSNGA
TFYNQKFKGKATLTVDRSISTAYMHLNRLRSDDTAVYYCTHSHLLRASWFAYWGQGT
LVTVSS >Heavy Chain of SGN-CD123A IgG histidine scanning variant #30 (SEQ ID NO: 138)
QVQLVQSGAEVKKPGASVKMSCKASGYTFTDYYMKWVKQAPGQGLEWIGDIIPSNGA
TFYNQKFKGKATLTVDRSISTAYMHLNRLRSDDTAVYYCTRHHLLRASWFAYWGQGT
LVTVSS >Heavy Chain of SGN-CD123A IgG histidine scanning variant #31 (SEQ ID NO: 139)
QVQLVQSGAEVKKPGASVKMSCKASGYTFTDYYMKWVKQAPGQGLEWIGDIIPSNGA
TFYNQKFKGKATLTVDRSISTAYMHLNRLRSDDTAVYYCTRSALLRASWFAYWGQGT
LVTVSS >Heavy Chain of SGN-CD123A IgG histidine scanning variant #32 (SEQ ID NO: 140)
QVQLVQSGAEVKKPGASVKMSCKASGYTFTDYYMKWVKQAPGQGLEWIGDIIPSNGA
TFYNQKFKGKATLTVDRSISTAYMHLNRLRSDDTAVYYCTRSHHLRASWFAYWGQGT
LVTVSS

| Sequence Appendix |
| --- |

>Heavy Chain of SGN-CD123A IgG histidine scanning variant #33 (SEQ ID NO: 141)
QVQLVQSGAEVKKPGASVKMSCKASGYTFTDYYMKWVKQAPGQGLEWIGDIIPSNGA
TFYNQKFKGKATLTVDRSISTAYMHLNRLRSDDTAVYYCTRSHLHRASWFAYWGQGT
LVTVSS >Heavy Chain of SGN-CD123A IgG histidine scanning variant #34 (SEQ ID NO: 142)
QVQLVQSGAEVKKPGASVKMSCKASGYTFTDYYMKWVKQAPGQGLEWIGDIIPSNGA
TFYNQKFKGKATLTVDRSISTAYMHLNRLRSDDTAVYYCTRSHLLHASWFAYWGQGT
LVTVSS >Heavy Chain of SGN-CD123A IgG histidine scanning variant #35 (SEQ ID NO: 143)
QVQLVQSGAEVKKPGASVKMSCKASGYTFTDYYMKWVKQAPGQGLEWIGDIIPSNGA
TFYNQKFKGKATLTVDRSISTAYMHLNRLRSDDTAVYYCTRSHLLRHSWFAYWGQGT
LVTVSS >Heavy Chain of SGN-CD123A IgG histidine scanning variant #36 (SEQ ID NO: 144)
QVQLVQSGAEVKKPGASVKMSCKASGYTFTDYYMKWVKQAPGQGLEWIGDIIPSNGA
TFYNQKFKGKATLTVDRSISTAYMHLNRLRSDDTAVYYCTRSHLLRAHWFAYWGQGT
LVTVSS >Heavy Chain of SGN-CD123A IgG histidine scanning variant #37 (SEQ ID NO: 145)
QVQLVQSGAEVKKPGASVKMSCKASGYTFTDYYMKWVKQAPGQGLEWIGDIIPSNGA
TFYNQKFKGKATLTVDRSISTAYMHLNRLRSDDTAVYYCTRSHLLRASHFAYWGQGTL
VTVSS >Heavy Chain of SGN-CD123A IgG histidine scanning variant #38 (SEQ ID NO: 146)
QVQLVQSGAEVKKPGASVKMSCKASGYTFTDYYMKWVKQAPGQGLEWIGDIIPSNGA
TFYNQKFKGKATLTVDRSISTAYMHLNRLRSDDTAVYYCTRSHLLRASWHAYWGQGT
LVTVSS >Heavy Chain of SGN-CD123A IgG histidine scanning variant #39 (SEQ ID NO: 147)
QVQLVQSGAEVKKPGASVKMSCKASGYTFTDYYMKWVKQAPGQGLEWIGDIIPSNGA
TFYNQKFKGKATLTVDRSISTAYMHLNRLRSDDTAVYYCTRSHLLRASWFHYWGQGT
LVTVSS >Heavy Chain of SGN-CD123A IgG histidine scanning variant #40 (SEQ ID NO: 148)
QVQLVQSGAEVKKPGASVKMSCKASGYTFTDYYMKWVKQAPGQGLEWIGDIIPSNGA
TFYNQKFKGKATLTVDRSISTAYMHLNRLRSDDTAVYYCTRSHLLRASWFAHWGQGT
LVTVSS >Heavy Chain of TPP-8988 IgG (SEQ ID NO: 149)
EVQLLESGGGLVQPGGSLRLSCAVSDYSITSGYYWNWIRQAPGKKLEWMGYISYDGSN
NYNPSLKNGRITISRDTSKNTFYLQMNSLRAEDTAVYYCARGEGFYFDSWGQGTLVTVS
S >Light Chain of TPP-8988 IgG (SEQ ID NO: 150)
EIVLTQSPGTLSLSPGERATLSCKSSQSLFFGSTQKNYLAWYQQKPGQAPRLLIYWASTR
ESGIPDRFSGSGSGTDFTLTISRLEPEDFAVYYCQQYYNYPWTFGQGTKLEIK >Heavy Chain CDR1 of TPP-8988 (SEQ ID NO: 151)
AVSDYSITSGYYWN >Heavy Chain CDR2 of TPP-8988 (SEQ ID NO: 152)
YISYDGSNNYNPSLKNG >Heavy Chain CDR3 of TPP-8988 (SEQ ID NO: 153)
ARGEGFYFDS >Light Chain CDR1 of TPP-8988 (SEQ ID NO: 154)
QSLFFGSTQKNYLA >Light Chain CDR2 of TPP-8988 (SEQ ID NO: 155)
WASTRES >Light Chain CDR3 of TPP-8988 (SEQ ID NO: 156)
QQYYNYPWT >Heavy Chain of TPP-8988 IgG histidine scanning variant #1 (SEQ ID NO: 157)
EVQLLESGGGLVQPGGSLRLSCHVSDYSITSGYYWNWIRQAPGKKLEWMGYISYDGSN
NYNPSLKNGRITISRDTSKNTFYLQMNSLRAEDTAVYYCARGEGFYFDSWGQGTLVTVS
S >Heavy Chain of TPP-8988 IgG histidine scanning variant #2 (SEQ ID NO: 158)
EVQLLESGGGLVQPGGSLRLSCAHSDYSITSGYYWNWIRQAPGKKLEWMGYISYDGSN
NYNPSLKNGRITISRDTSKNTFYLQMNSLRAEDTAVYYCARGEGFYFDSWGQGTLVTVS
S Sequence Appendix >Heavy Chain of TPP-8988 IgG histidine scanning variant #3 (SEQ ID NO: 159)
EVQLLESGGGLVQPGGSLRLSCAVHDYSITSGYYWNWIRQAPGKKLEWMGYISYDGSN
NYNPSLKNGRITISRDTSKNTFYLQMNSLRAEDTAVYYCARGEGFYFDSWGQGTLVTVS
S >Heavy Chain of TPP-8988 IgG histidine scanning variant #4 (SEQ ID NO: 160)
EVQLLESGGGLVQPGGSLRLSCAVSHYSITSGYYWNWIRQAPGKKLEWMGYISYDGSN
NYNPSLKNGRITISRDTSKNTFYLQMNSLRAEDTAVYYCARGEGFYFDSWGQGTLVTVS
S >Heavy Chain of TPP-8988 IgG histidine scanning variant #5 (SEQ ID NO: 161)
EVQLLESGGGLVQPGGSLRLSCAVSDHSITSGYYWNWIRQAPGKKLEWMGYISYDGSN
NYNPSLKNGRITISRDTSKNTFYLQMNSLRAEDTAVYYCARGEGFYFDSWGQGTLVTVS
S >Heavy Chain of TPP-8988 IgG histidine scanning variant #6 (SEQ ID NO: 162)
EVQLLESGGGLVQPGGSLRLSCAVSDYHITSGYYWNWIRQAPGKKLEWMGYISYDGSN
NYNPSLKNGRITISRDTSKNTFYLQMNSLRAEDTAVYYCARGEGFYFDSWGQGTLVTVS
S >Heavy Chain of TPP-8988 IgG histidine scanning variant #7 (SEQ ID NO: 163)
EVQLLESGGGLVQPGGSLRLSCAVSDYSHTSGYYWNWIRQAPGKKLEWMGYISYDGS
NNYNPSLKNGRITISRDTSKNTFYLQMNSLRAEDTAVYYCARGEGFYFDSWGQGTLVT
VSS >Heavy Chain of TPP-8988 IgG histidine scanning variant #8 (SEQ ID NO: 164)
EVQLLESGGGLVQPGGSLRLSCAVSDYSIHSGYYWNWIRQAPGKKLEWMGYISYDGSN
NYNPSLKNGRITISRDTSKNTFYLQMNSLRAEDTAVYYCARGEGFYFDSWGQGTLVTVS
S >Heavy Chain of TPP-8988 IgG histidine scanning variant #9 (SEQ ID NO: 165)
EVQLLESGGGLVQPGGSLRLSCAVSDYSITHGYYWNWIRQAPGKKLEWMGYISYDGSN
NYNPSLKNGRITISRDTSKNTFYLQMNSLRAEDTAVYYCARGEGFYFDSWGQGTLVTVS
S >Heavy Chain of TPP-8988 IgG histidine scanning variant #10 (SEQ ID NO: 166)
EVQLLESGGGLVQPGGSLRLSCAVSDYSITSHYYWNWIRQAPGKKLEWMGYISYDGSN
NYNPSLKNGRITISRDTSKNTFYLQMNSLRAEDTAVYYCARGEGFYFDSWGQGTLVTVS
S >Heavy Chain of TPP-8988 IgG histidine scanning variant #11 (SEQ ID NO: 167)
EVQLLESGGGLVQPGGSLRLSCAVSDYSITSGAYWNWIRQAPGKKLEWMGYISYDGSN
NYNPSLKNGRITISRDTSKNTFYLQMNSLRAEDTAVYYCARGEGFYFDSWGQGTLVTVS
S >Heavy Chain of TPP-8988 IgG histidine scanning variant #12 (SEQ ID NO: 168)
EVQLLESGGGLVQPGGSLRLSCAVSDYSITSGYHWNWIRQAPGKKLEWMGYISYDGSN
NYNPSLKNGRITISRDTSKNTFYLQMNSLRAEDTAVYYCARGEGFYFDSWGQGTLVTVS
S >Heavy Chain of TPP-8988 IgG histidine scanning variant #13 (SEQ ID NO: 169)
EVQLLESGGGLVQPGGSLRLSCAVSDYSITSGYYHNWIRQAPGKKLEWMGYISYDGSN
NYNPSLKNGRITISRDTSKNTFYLQMNSLRAEDTAVYYCARGEGFYFDSWGQGTLVTVS
S >Heavy Chain of TPP-8988 IgG histidine scanning variant #14 (SEQ ID NO: 170)
EVQLLESGGGLVQPGGSLRLSCAVSDYSITSGYYWHWIRQAPGKKLEWMGYISYDGSN
NYNPSLKNGRITISRDTSKNTFYLQMNSLRAEDTAVYYCARGEGFYFDSWGQGTLVTVS
S >Heavy Chain of TPP-8988 IgG histidine scanning variant #15 (SEQ ID NO: 171)
EVQLLESGGGLVQPGGSLRLSCAVSDYSITSGYYWNWIRQAPGKKLEWMGHISYDGSN
NYNPSLKNGRITISRDTSKNTFYLQMNSLRAEDTAVYYCARGEGFYFDSWGQGTLVTVS
S >Heavy Chain of TPP-8988 IgG histidine scanning variant #16 (SEQ ID NO: 172)
EVQLLESGGGLVQPGGSLRLSCAVSDYSITSGYYWNWIRQAPGKKLEWMGYHSYDGS
NNYNPSLKNGRITISRDTSKNTFYLQMNSLRAEDTAVYYCARGEGFYFDSWGQGTLVT
VSS >Heavy Chain of TPP-8988 IgG histidine scanning variant #17 (SEQ ID NO: 173)
EVQLLESGGGLVQPGGSLRLSCAVSDYSITSGYYWNWIRQAPGKKLEWMGYIHYDGSN
NYNPSLKNGRITISRDTSKNTFYLQMNSLRAEDTAVYYCARGEGFYFDSWGQGTLVTVS
S -continued Sequence Appendix >Heavy Chain of TPP-8988 IgG histidine scanning variant #18 (SEQ ID NO: 174)
EVQLLESGGGLVQPGGSLRLSCAVSDYSITSGYYWNWIRQAPGKKLEWMGYISHDGSN
NYNPSLKNGRITISRDTSKNTFYLQMNSLRAEDTAVYYCARGEGFYFDSWGQGTLVTVS
S >Heavy Chain of TPP-8988 IgG histidine scanning variant #19 (SEQ ID NO: 175)
EVQLLESGGGLVQPGGSLRLSCAVSDYSITSGYYWNWIRQAPGKKLEWMGYISYHGSN
NYNPSLKNGRITISRDTSKNTFYLQMNSLRAEDTAVYYCARGEGFYFDSWGQGTLVTVS
S >Heavy Chain of TPP-8988 IgG histidine scanning variant #20 (SEQ ID NO: 176)
EVQLLESGGGLVQPGGSLRLSCAVSDYSITSGYYWNWIRQAPGKKLEWMGYISYDHSN
NYNPSLKNGRITISRDTSKNTFYLQMNSLRAEDTAVYYCARGEGFYFDSWGQGTLVTVS
S >Heavy Chain of TPP-8988 IgG histidine scanning variant #21 (SEQ ID NO: 177)
EVQLLESGGGLVQPGGSLRLSCAVSDYSITSGYYWNWIRQAPGKKLEWMGYISYDGHN
NYNPSLKNGRITISRDTSKNTFYLQMNSLRAEDTAVYYCARGEGFYFDSWGQGTLVTVS
S >Heavy Chain of TPP-8988 IgG histidine scanning variant #22 (SEQ ID NO: 178)
EVQLLESGGGLVQPGGSLRLSCAVSDYSITSGYYWNWIRQAPGKKLEWMGYISYDGSH
NYNPSLKNGRITISRDTSKNTFYLQMNSLRAEDTAVYYCARGEGFYFDSWGQGTLVTVS
S >Heavy Chain of TPP-8988 IgG histidine scanning variant #23 (SEQ ID NO: 179)
EVQLLESGGGLVQPGGSLRLSCAVSDYSITSGYYWNWIRQAPGKKLEWMGYISYDGSN
HYNPSLKNGRITISRDTSKNTFYLQMNSLRAEDTAVYYCARGEGFYFDSWGQGTLVTVS
S >Heavy Chain of TPP-8988 IgG histidine scanning variant #24 (SEQ ID NO: 180)
EVQLLESGGGLVQPGGSLRLSCAVSDYSITSGYYWNWIRQAPGKKLEWMGYISYDGSN
NHNPSLKNGRITISRDTSKNTFYLQMNSLRAEDTAVYYCARGEGFYFDSWGQGTLVTVS
S >Heavy Chain of TPP-8988 IgG histidine scanning variant #25 (SEQ ID NO: 181)
EVQLLESGGGLVQPGGSLRLSCAVSDYSITSGYYWNWIRQAPGKKLEWMGYISYDGSN
NYHPSLKNGRITISRDTSKNTFYLQMNSLRAEDTAVYYCARGEGFYFDSWGQGTLVTVS
S >Heavy Chain of TPP-8988 IgG histidine scanning variant #26 (SEQ ID NO: 182)
EVQLLESGGGLVQPGGSLRLSCAVSDYSITSGYYWNWIRQAPGKKLEWMGYISYDGSN
NYNHSLKNGRITISRDTSKNTFYLQMNSLRAEDTAVYYCARGEGFYFDSWGQGTLVTV
SS >Heavy Chain of TPP-8988 IgG histidine scanning variant #27 (SEQ ID NO: 183)
EVQLLESGGGLVQPGGSLRLSCAVSDYSITSGYYWNWIRQAPGKKLEWMGYISYDGSN
NYNPHLKNGRITISRDTSKNTFYLQMNSLRAEDTAVYYCARGEGFYFDSWGQGTLVTV
SS >Heavy Chain of TPP-8988 IgG histidine scanning variant #28 (SEQ ID NO: 184)
EVQLLESGGGLVQPGGSLRLSCAVSDYSITSGYYWNWIRQAPGKKLEWMGYISYDGSN
NYNPSHKNGRITISRDTSKNTFYLQMNSLRAEDTAVYYCARGEGFYFDSWGQGTLVTV
SS >Heavy Chain of TPP-8988 IgG histidine scanning variant #29 (SEQ ID NO: 185)
EVQLLESGGGLVQPGGSLRLSCAVSDYSITSGYYWNWIRQAPGKKLEWMGYISYDGSN
NYNPSLHNGRITISRDTSKNTFYLQMNSLRAEDTAVYYCARGEGFYFDSWGQGTLVTVS
S >Heavy Chain of TPP-8988 IgG histidine scanning variant #30 (SEQ ID NO: 186)
EVQLLESGGGLVQPGGSLRLSCAVSDYSITSGYYWNWIRQAPGKKLEWMGYISYDGSN
NYNPSLKHGRITISRDTSKNTFYLQMNSLRAEDTAVYYCARGEGFYFDSWGQGTLVTVS
S >Heavy Chain of TPP-8988 IgG histidine scanning variant #31 (SEQ ID NO: 187)
EVQLLESGGGLVQPGGSLRLSCAVSDYSITSGYYWNWIRQAPGKKLEWMGYISYDGSN
NYNPSLKNHRITISRDTSKNTFYLQMNSLRAEDTAVYYCARGEGFYFDSWGQGTLVTVS
S >Heavy Chain of TPP-8988 IgG histidine scanning variant #32 (SEQ ID NO: 188)
EVQLLESGGGLVQPGGSLRLSCAVSDYSITSGYYWNWIRQAPGKKLEWMGYISYDGSN
NYNPSLKNGRITISRDTSKNTFYLQMNSLRAEDTAVYYCHRGEGFYFDSWGQGTLVTVS
S -continued Sequence Appendix >Heavy Chain of TPP-8988 IgG histidine scanning variant #33 (SEQ ID NO: 189)
EVQLLESGGGLVQPGGSLRLSCAVSDYSITSGYYWNWIRQAPGKKLEWMGYISYDGSN
NYNPSLKNGRITISRDTSKNTFYLQMNSLRAEDTAVYYCAHGEGFYFDSWGQGTLVTV
SS >Heavy Chain of TPP-8988 IgG histidine scanning variant #34 (SEQ ID NO: 190)
EVQLLESGGGLVQPGGSLRLSCAVSDYSITSGYYWNWIRQAPGKKLEWMGYISYDGSN
NYNPSLKNGRITISRDTSKNTFYLQMNSLRAEDTAVYYCARHEGFYFDSWGQGTLVTVS
S >Heavy Chain of TPP-8988 IgG histidine scanning variant #35 (SEQ ID NO: 191)
EVQLLESGGGLVQPGGSLRLSCAVSDYSITSGYYWNWIRQAPGKKLEWMGYISYDGSN
NYNPSLKNGRITISRDTSKNTFYLQMNSLRAEDTAVYYCARGHGFYFDSWGQGTLVTV
SS >Heavy Chain of TPP-8988 IgG histidine scanning variant #36 (SEQ ID NO: 192)
EVQLLESGGGLVQPGGSLRLSCAVSDYSITSGYYWNWIRQAPGKKLEWMGYISYDGSN
NYNPSLKNGRITISRDTSKNTFYLQMNSLRAEDTAVYYCARGEHFYFDSWGQGTLVTVS
S >Heavy Chain of TPP-8988 IgG histidine scanning variant #37 (SEQ ID NO: 193)
EVQLLESGGGLVQPGGSLRLSCAVSDYSITSGYYWNWIRQAPGKKLEWMGYISYDGSN
NYNPSLKNGRITISRDTSKNTFYLQMNSLRAEDTAVYYCARGEGHYFDSWGQGTLVTV
SS >Heavy Chain of TPP-8988 IgG histidine scanning variant #38 (SEQ ID NO: 194)
EVQLLESGGGLVQPGGSLRLSCAVSDYSITSGYYWNWIRQAPGKKLEWMGYISYDGSN
NYNPSLKNGRITISRDTSKNTFYLQMNSLRAEDTAVYYCARGEGFHFDSWGQGTLVTVS
S >Heavy Chain of TPP-8988 IgG histidine scanning variant #39 (SEQ ID NO: 195)
EVQLLESGGGLVQPGGSLRLSCAVSDYSITSGYYWNWIRQAPGKKLEWMGYISYDGSN
NYNPSLKNGRITISRDTSKNTFYLQMNSLRAEDTAVYYCARGEGFYHDSWGQGTLVTV
SS >Heavy Chain of TPP-8988 IgG histidine scanning variant #40 (SEQ ID NO: 196)
EVQLLESGGGLVQPGGSLRLSCAVSDYSITSGYYWNWIRQAPGKKLEWMGYISYDGSN
NYNPSLKNGRITISRDTSKNTFYLQMNSLRAEDTAVYYCARGEGFYFHSWGQGTLVTVS
S >Heavy Chain of TPP-8988 IgG histidine scanning variant #41 (SEQ ID NO: 197)
EVQLLESGGGLVQPGGSLRLSCAVSDYSITSGYYWNWIRQAPGKKLEWMGYISYDGSN
NYNPSLKNGRITISRDTSKNTFYLQMNSLRAEDTAVYYCARGEGFYFDHWGQGTLVTV
SS >Light Chain of TPP-8988 IgG histidine scanning variant #1 (SEQ ID NO: 198)
EIVLTQSPGTLSLSPGERATLSCKSSHSLFFGSTQKNYLAWYQQKPGQAPRLLIYWASTR
ESGIPDRFSGSGSGTDFTLTISRLEPEDFAVYYCQQYYNYPWTFGQGTKLEIK >Light Chain of TPP-8988 IgG histidine scanning variant #2 (SEQ ID NO: 199)
EIVLTQSPGTLSLSPGERATLSCKSSQHLFFGSTQKNYLAWYQQKPGQAPRLLIYWASTR
ESGIPDRFSGSGSGTDFTLTISRLEPEDFAVYYCQQYYNYPWTFGQGTKLEIK >Light Chain of TPP-8988 IgG histidine scanning variant #3 (SEQ ID NO: 200)
EIVLTQSPGTLSLSPGERATLSCKSSQSHFFGSTQKNYLAWYQQKPGQAPRLLIYWASTR
ESGIPDRFSGSGSGTDFTLTISRLEPEDFAVYYCQQYYNYPWTFGQGTKLEIK >Light Chain of TPP-8988 IgG histidine scanning variant #4 (SEQ ID NO: 201)
EIVLTQSPGTLSLSPGERATLSCKSSQSLHFGSTQKNYLAWYQQKPGQAPRLLIYWASTR
ESGIPDRFSGSGSGTDFTLTISRLEPEDFAVYYCQQYYNYPWTFGQGTKLEIK >Light Chain of TPP-8988 IgG histidine scanning variant #5 (SEQ ID NO: 202)
EIVLTQSPGTLSLSPGERATLSCKSSQSLFHGSTQKNYLAWYQQKPGQAPRLLIYWASTR
ESGIPDRFSGSGSGTDFTLTISRLEPEDFAVYYCQQYYNYPWTFGQGTKLEIK >Light Chain of TPP-8988 IgG histidine scanning variant #6 (SEQ ID NO: 203)
EIVLTQSPGTLSLSPGERATLSCKSSQSLFFHSTQKNYLAWYQQKPGQAPRLLIYWASTR
ESGIPDRFSGSGSGTDFTLTISRLEPEDFAVYYCQQYYNYPWTFGQGTKLEIK >Light Chain of TPP-8988 IgG histidine scanning variant #7 (SEQ ID NO: 204)
EIVLTQSPGTLSLSPGERATLSCKSSQSLFFGHTQKNYLAWYQQKPGQAPRLLIYWASTR
ESGIPDRFSGSGSGTDFTLTISRLEPEDFAVYYCQQYYNYPWTFGQGTKLEIK >Light Chain of TPP-8988 IgG histidine scanning variant #8 (SEQ ID NO: 205)
EIVLTQSPGTLSLSPGERATLSCKSSQSLFFGSHQKNYLAWYQQKPGQAPRLLIYWASTR
ESGIPDRFSGSGSGTDFTLTISRLEPEDFAVYYCQQYYNYPWTFGQGTKLEIK -continued Sequence Appendix >Light Chain of TPP-8988 IgG histidine scanning variant #9 (SEQ ID NO: 206)
EIVLTQSPGTLSLSPGERATLSCKSSQSLFFGSTHKNYLAWYQQKPGQAPRLLIYWASTR
ESGIPDRFSGSGSGTDFTLTISRLEPEDFAVYYCQQYYNYPWTFGQGTKLEIK >Light Chain of TPP-8988 IgG histidine scanning variant #10 (SEQ ID NO: 207)
EIVLTQSPGTLSLSPGERATLSCKSSQSLFFGSTQHNYLAWYQQKPGQAPRLLIYWASTR
ESGIPDRFSGSGSGTDFTLTISRLEPEDFAVYYCQQYYNYPWTFGQGTKLEIK >Light Chain of TPP-8988 IgG histidine scanning variant #11 (SEQ ID NO: 208)
EIVLTQSPGTLSLSPGERATLSCKSSQSLFFGSTQKHYLAWYQQKPGQAPRLLIYWASTR
ESGIPDRFSGSGSGTDFTLTISRLEPEDFAVYYCQQYYNYPWTFGQGTKLEIK >Light Chain of TPP-8988 IgG histidine scanning variant #12 (SEQ ID NO: 209)
EIVLTQSPGTLSLSPGERATLSCKSSQSLFFGSTQKNHLAWYQQKPGQAPRLLIYWASTR
ESGIPDRFSGSGSGTDFTLTISRLEPEDFAVYYCQQYYNYPWTFGQGTKLEIK >Light Chain of TPP-8988 IgG histidine scanning variant #13 (SEQ ID NO: 210)
EIVLTQSPGTLSLSPGERATLSCKSSQSLFFGSTQKNYHAWYQQKPGQAPRLLIYWASTR
ESGIPDRFSGSGSGTDFTLTISRLEPEDFAVYYCQQYYNYPWTFGQGTKLEIK >Light Chain of TPP-8988 IgG histidine scanning variant #14 (SEQ ID NO: 211)
EIVLTQSPGTLSLSPGERATLSCKSSQSLFFGSTQKNYLHWYQQKPGQAPRLLIYWASTR
ESGIPDRFSGSGSGTDFTLTISRLEPEDFAVYYCQQYYNYPWTFGQGTKLEIK >Light Chain of TPP-8988 IgG histidine scanning variant #15 (SEQ ID NO: 212)
EIVLTQSPGTLSLSPGERATLSCKSSQSLFFGSTQKNYLAWYQQKPGQAPRLLIYHASTR
ESGIPDRFSGSGSGTDFTLTISRLEPEDFAVYYCQQYYNYPWTFGQGTKLEIK >Light Chain of TPP-8988 IgG histidine scanning variant #16 (SEQ ID NO: 213)
EIVLTQSPGTLSLSPGERATLSCKSSQSLFFGSTQKNYLAWYQQKPGQAPRLLIYWHSTR
ESGIPDRFSGSGSGTDFTLTISRLEPEDFAVYYCQQYYNYPWTFGQGTKLEIK >Light Chain of TPP-8988 IgG histidine scanning variant #17 (SEQ ID NO: 214)
EIVLTQSPGTLSLSPGERATLSCKSSQSLFFGSTQKNYLAWYQQKPGQAPRLLIYWAHTR
ESGIPDRFSGSGSGTDFTLTISRLEPEDFAVYYCQQYYNYPWTFGQGTKLEIK >Light Chain of TPP-8988 IgG histidine scanning variant #18 (SEQ ID NO: 215)
EIVLTQSPGTLSLSPGERATLSCKSSQSLFFGSTQKNYLAWYQQKPGQAPRLLIYWASHR
ESGIPDRFSGSGSGTDFTLTISRLEPEDFAVYYCQQYYNYPWTFGQGTKLEIK >Light Chain of TPP-8988 IgG histidine scanning variant #19 (SEQ ID NO: 216)
EIVLTQSPGTLSLSPGERATLSCKSSQSLFFGSTQKNYLAWYQQKPGQAPRLLIYWASTH
ESGIPDRFSGSGSGTDFTLTISRLEPEDFAVYYCQQYYNYPWTFGQGTKLEIK >Light Chain of TPP-8988 IgG histidine scanning variant #20 (SEQ ID NO: 217)
EIVLTQSPGTLSLSPGERATLSCKSSQSLFFGSTQKNYLAWYQQKPGQAPRLLIYWASTR
HSGIPDRFSGSGSGTDFTLTISRLEPEDFAVYYCQQYYNYPWTFGQGTKLEIK >Light Chain of TPP-8988 IgG histidine scanning variant #21 (SEQ ID NO: 218)
EIVLTQSPGTLSLSPGERATLSCKSSQSLFFGSTQKNYLAWYQQKPGQAPRLLIYWASTR
EHGIPDRFSGSGSGTDFTLTISRLEPEDFAVYYCQQYYNYPWTFGQGTKLEIK >Light Chain of TPP-8988 IgG histidine scanning variant #22 (SEQ ID NO: 219)
EIVLTQSPGTLSLSPGERATLSCKSSQSLFFGSTQKNYLAWYQQKPGQAPRLLIYWASTR
ESGIPDRFSGSGSGTDFTLTISRLEPEDFAVYYCHQYYNYPWTFGQGTKLEIK >Light Chain of TPP-8988 IgG histidine scanning variant #23 (SEQ ID NO: 220)
EIVLTQSPGTLSLSPGERATLSCKSSQSLFFGSTQKNYLAWYQQKPGQAPRLLIYWASTR
ESGIPDRFSGSGSGTDFTLTISRLEPEDFAVYYCQHYYNYPWTFGQGTKLEIK >Light Chain of TPP-8988 IgG histidine scanning variant #24 (SEQ ID NO: 221)
EIVLTQSPGTLSLSPGERATLSCKSSQSLFFGSTQKNYLAWYQQKPGQAPRLLIYWASTR
ESGIPDRFSGSGSGTDFTLTISRLEPEDFAVYYCQQHYNYPWTFGQGTKLEIK >Light Chain of TPP-8988 IgG histidine scanning variant #25 (SEQ ID NO: 222)
EIVLTQSPGTLSLSPGERATLSCKSSQSLFFGSTQKNYLAWYQQKPGQAPRLLIYWASTR
ESGIPDRFSGSGSGTDFTLTISRLEPEDFAVYYCQQYHNYPWTFGQGTKLEIK >Light Chain of TPP-8988 IgG histidine scanning variant #26 (SEQ ID NO: 223)
EIVLTQSPGTLSLSPGERATLSCKSSQSLFFGSTQKNYLAWYQQKPGQAPRLLIYWASTR
ESGIPDRFSGSGSGTDFTLTISRLEPEDFAVYYCQQYYHYPWTFGQGTKLEIK >Light Chain of TPP-8988 IgG histidine scanning variant #27 (SEQ ID NO: 224)
EIVLTQSPGTLSLSPGERATLSCKSSQSLFFGSTQKNYLAWYQQKPGQAPRLLIYWASTR
ESGIPDRFSGSGSGTDFTLTISRLEPEDFAVYYCQQYYNHPWTFGQGTKLEIK

| Sequence Appendix |
|---|
| >Light Chain of TPP-8988 IgG histidine scanning variant #28 (SEQ ID NO: 225)<br>EIVLTQSPGTLSLSPGERATLSCKSSQSLFFGSTQKNYLAWYQQKPGQAPRLLIYWASTR<br>ESGIPDRFSGSGSGTDFTLTISRLEPEDFAVYYCQQYYNYHWTFGQGTKLEIK |
| >Light Chain of TPP-8988 IgG histidine scanning variant #29 (SEQ ID NO: 226)<br>EIVLTQSPGTLSLSPGERATLSCKSSQSLFFGSTQKNYLAWYQQKPGQAPRLLIYWASTR<br>ESGIPDRFSGSGSGTDFTLTISRLEPEDFAVYYCQQYYNYPHTFGQGTKLEIK |
| >Light Chain of TPP-8988 IgG histidine scanning variant #30 (SEQ ID NO: 227)<br>EIVLTQSPGTLSLSPGERATLSCKSSQSLFFGSTQKNYLAWYQQKPGQAPRLLIYWASTR<br>ESGIPDRFSGSGSGTDFTLTISRLEPEDFAVYYCQQYYNYPWHFGQGTKLEIK |

What is claimed is:

1. A pharmaceutical composition comprising an effective amount of an antigen-binding protein construct (ABPC) comprising:

a first antigen-binding domain that is capable of specifically binding CD123 or an epitope of CD123 presented on the surface of a target mammalian cell, wherein the first antigen-binding domain comprises:

a heavy chain variable domain of SEQ ID NO: 1 and a light chain variable domain of SEQ ID NO: 64, SEQ ID NO: 70, SEQ ID NO: 74, SEQ ID NO: 77, SEQ ID NO: 78, or SEQ ID NO: 79; or a heavy chain variable domain of SEQ ID NO: 14, SEQ ID NO: 15, SEQ ID NO: 16, SEQ ID NO: 17, SEQ ID NO: 20, SEQ ID NO: 22, SEQ ID NO: 26, SEQ ID NO: 40, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, or SEQ ID NO: 100 and a light chain variable domain of SEQ ID NO: 2;

and wherein:

(i) the dissociation rate of the first antigen-binding domain at a pH of about 4.0 to about 6.5 is faster than the dissociation rate at a pH of about 7.0 to about 8.0; or (ii) the dissociation constant ($K_D$) of the first antigen-binding domain at a pH of about 4.0 to about 6.5 is greater than the Kp at a pH of about 7.0 to about 8.0.

2. The pharmaceutical composition of claim 1, wherein the ABPC is degraded in the target mammalian cell following internalization of the ABPC by the target mammalian cell.

3. The pharmaceutical composition of claim 1, wherein the ABPC further comprises a conjugated toxin, radioisotope, drug, or small molecule.

4. A pharmaceutical composition comprising an effective amount of an antigen-binding protein construct (ABPC) comprising:

a first antigen-binding domain that is capable of specifically binding CD123 or an epitope of CD123 presented on the surface of a target mammalian cell; and a conjugated toxin, radioisotope, drug, or small molecule, wherein the first antigen-binding domain comprises:

a heavy chain variable domain of SEQ ID NO: 1 and a light chain variable domain of SEQ ID NO: 64, SEQ ID NO: 70, SEQ ID NO: 74, SEQ ID NO: 77, SEQ ID NO: 78, or SEQ ID NO: 79; or a heavy chain variable domain of SEQ ID NO: 14, SEQ ID NO: 15, SEQ ID NO: 16, SEQ ID NO: 17, SEQ ID NO: 20, SEQ ID NO: 22, SEQ ID NO: 26, SEQ ID NO: 40, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, or SEQ ID NO: 100 and a light chain variable domain of SEQ ID NO: 2;

and wherein:

(i) the dissociation rate of the first antigen-binding domain at a pH of about 4.0 to about 6.5 is faster than the dissociation rate at a pH of about 7.0 to about 8.0; or the dissociation constant ($K_D$) of the first antigen-binding domain at a pH of about 4.0 to about 6.5 is greater than the $K_D$ at a pH of about 7.0 to about 8.0; and (ii) the composition provides for one or more of:

an increase in toxin liberation in the target mammalian cell as compared to a composition comprising the same amount of a control ABPC comprising a heavy chain variable domain of SEQ ID NO: 1 and a light chain variable domain of SEQ ID NO: 2;

an increase in target mammalian cell killing as compared to a composition comprising the same amount of the control ABPC; and an increase in endolysosomal delivery in the target mammalian cell as compared to a composition comprising the same amount of the control ABPC.

5. The pharmaceutical composition of claim 4, wherein the composition provides for:

an increase in toxin liberation in the target mammalian cell as compared to a composition comprising the same amount of the control ABPC; and/or an increase in target mammalian cell killing as compared to a composition comprising the same amount of the control ABPC.

6. The pharmaceutical composition of claim 1, wherein the composition provides for an increase in endolysosomal delivery in the target mammalian cell as compared to a composition comprising the same amount of a control ABPC.

7. The pharmaceutical composition of claim 1, wherein the composition:

results in less of a reduction in the level of CD123 presented on the surface of the target mammalian cell as compared to a composition comprising the same amount of a control ABPC comprising a heavy chain variable domain of SEQ ID NO: 1 and a light chain variable domain of SEQ ID NO: 2; or does not result in a detectable reduction in the level of CD123 presented on the surface of the target mammalian cell.

8. The pharmaceutical composition of claim 1, wherein the target mammalian cell is a cancer cell.

9. The pharmaceutical composition of claim 1, wherein the ABPC is cytotoxic or cytostatic to the target mammalian cell.

10. The pharmaceutical composition of claim 1, wherein the ABPC comprises a single polypeptide.

11. The pharmaceutical composition of claim 10, wherein the antigen-binding domain is an scFv.

12. The pharmaceutical composition of claim 1, wherein the ABPC comprises two or more polypeptides.

13. The pharmaceutical composition of claim 12, wherein the ABPC is an antibody.

14. The pharmaceutical composition of claim 1, wherein the ABPC further comprises a second antigen-binding domain.

15. An antigen-binding protein construct (ABPC) comprising:

a first antigen-binding domain that is capable of specifically binding CD123 or an epitope of CD123 presented on the surface of a target mammalian cell, wherein the first antigen-binding domain comprises:

a heavy chain variable domain of SEQ ID NO: 1 and a light chain variable domain of SEQ ID NO: 64, SEQ ID NO: 70, SEQ ID NO: 74, SEQ ID NO: 77, SEQ ID NO: 78, or SEQ ID NO: 79; or a heavy chain variable domain of SEQ ID NO: 14, SEQ ID NO: 15, SEQ ID NO: 16, SEQ ID NO: 17, SEQ ID NO: 20, SEQ ID NO: 22, SEQ ID NO: 26, SEQ ID NO: 40, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, or SEQ ID NO: 100 and a light chain variable domain of SEQ ID NO: 2;

and wherein:

(i) the dissociation rate of the first antigen-binding domain at a pH of about 4.0 to about 6.5 is faster than the dissociation rate at a pH of about 7.0 to about 8.0; or (ii) the dissociation constant ($K_D$) of the first antigen-binding domain at a pH of about 4.0 to about 6.5 is greater than the Kp at a pH of about 7.0 to about 8.0.

16. An antigen-binding protein construct (ABPC) comprising:

a first antigen-binding domain that is capable of specifically binding CD123 or an epitope of CD123 presented on the surface of a target mammalian cell; and a conjugated toxin, radioisotope, drug, or small molecule, wherein the first antigen-binding domain comprises:

a heavy chain variable domain of SEQ ID NO: 1 and a light chain variable domain of SEQ ID NO: 64, SEQ ID NO: 70, SEQ ID NO: 74, SEQ ID NO: 77, SEQ ID NO: 78, or SEQ ID NO: 79; or a heavy chain variable domain of SEQ ID NO: 14, SEQ ID NO: 15, SEQ ID NO: 16, SEQ ID NO: 17, SEQ ID NO: 20, SEQ ID NO: 22, SEQ ID NO: 26, SEQ ID NO: 40, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, or SEQ ID NO: 100 and a light chain variable domain of SEQ ID NO: 2;

and wherein:

(i) the dissociation rate of the first antigen-binding domain at a pH of about 4.0 to about 6.5 is faster than the dissociation rate at a pH of about 7.0 to about 8.0; or the dissociation constant ($K_D$) of the first antigen-binding domain at a pH of about 4.0 to about 6.5 is greater than the $K_D$ at a pH of about 7.0 to about 8.0; and (ii) the composition provides for one or more of:

an increase in toxin liberation in the target mammalian cell as compared to a composition comprising the same amount of a control ABPC comprising a heavy chain variable domain of SEQ ID NO: 1 and a light chain variable domain of SEQ ID NO: 2;

an increase in target mammalian cell killing as compared to a composition comprising the same amount of the control ABPC; and an increase in endolysosomal delivery in the target mammalian cell as compared to a composition comprising the same amount of the control ABPC.

17. A kit comprising at least one dose of the pharmaceutical composition of claim 1.

18. A method of treating a cancer characterized by having a population of cancer cells that have CD123 or an epitope of CD123 presented on their surface, the method comprising:

administering a therapeutically effective amount of the pharmaceutical composition of claim 1 to a subject identified as having a cancer characterized by having the population of cancer cells.

19. A method of reducing the volume of a tumor in a subject, wherein the tumor is characterized by having a population of cancer cells that have CD123 or an epitope of CD123 presented on their surface, the method comprising:

administering a therapeutically effective amount of the pharmaceutical composition of claim 1 to a subject identified as having a cancer characterized by having the population of cancer cells.

20. A method of inducing cell death in a cancer cell in a subject, wherein the cancer cell has CD123 or an epitope of CD123 presented on its surface, wherein the method comprises:

administering a therapeutically effective amount of the pharmaceutical composition of claim 1 to a subject identified as having a cancer characterized by having a population of the cancer cells.

21. A method of decreasing the risk of developing a metastasis or decreasing the risk of developing an additional metastasis in a subject having a cancer, wherein the cancer is characterized by having a population of cancer cells that have CD123 or an epitope of CD123 presented on their surface the method comprising:

administering a therapeutically effective amount of the pharmaceutical composition of claim 1 to a subject identified as having a cancer characterized by having the population of cancer cells.

* * * * *